(12) United States Patent
Steeneck et al.

(10) Patent No.: US 8,835,441 B2
(45) Date of Patent: *Sep. 16, 2014

(54) HETEROBICYCLIC METALLOPROTEASE INHIBITORS

(75) Inventors: Christoph Steeneck, Dossenheim (DE); Christian Gege, Mauer (DE); Frank Richter, HD-Handschuhsheim (DE); Heiko Kroth, Stadecken-Elsheim (DE); Matthias Hochgürtel, Schriesheim (DE); Michael Essers, Bergisch Gladbach (DE); Joshua van Veldhuizen, Seattle, WA (US); Bert Nolte, Aachen (DE); Brian M. Gallagher, Jr., Merrimac, MA (US); Tim Feuerstein, Neckargemeund (DE); Matthias Schneider, Dossenheim (DE); Torsten Arndt, Bensheim (DE); Hongbo Deng, Southborough, MA (US); Ralf Biesinger, Ludwigshafen (DE); Xinyuan Wu, Newton, MA (US); Harald Bluhm, Arnsberg-Neheim (DE); Irving Sucholeiki, Winchester, MA (US); Arthur G. Taveras, Southborough, MA (US)

(73) Assignee: Amgen Inc., Thousand Oaks, CA (US)

( * ) Notice: Subject to any disclaimer, the term of this patent is extended or adjusted under 35 U.S.C. 154(b) by 400 days.

This patent is subject to a terminal disclaimer.

(21) Appl. No.: 13/163,457

(22) Filed: Jun. 17, 2011

(65) Prior Publication Data

US 2012/0015920 A1    Jan. 19, 2012

Related U.S. Application Data

(63) Continuation of application No. 12/370,418, filed on Feb. 12, 2009, now abandoned, which is a continuation of application No. 11/602,140, filed on Nov. 20, 2006, now abandoned, which is a continuation-in-part of application No. 11/440,087, filed on May 22, 2006, now abandoned.

(60) Provisional application No. 60/734,991, filed on Nov. 9, 2005, provisional application No. 60/706,465, filed on Aug. 8, 2005, provisional application No. 60/683,470, filed on May 20, 2005.

(51) Int. Cl.
*A01N 43/90* (2006.01)
*A61K 31/519* (2006.01)
*C07D 487/00* (2006.01)

(52) U.S. Cl.
USPC ..................................... 514/259.3; 544/281

(58) Field of Classification Search
USPC ....................................................... 514/259.3
See application file for complete search history.

(56) References Cited

U.S. PATENT DOCUMENTS

| | | | |
|---|---|---|---|
| 4,497,814 A | 2/1985 | Witkowski |
| 4,801,516 A | 1/1989 | Ishikawa et al. |
| 4,861,784 A | 8/1989 | Rauber et al. |
| 4,874,391 A | 10/1989 | Reinert |
| 4,895,851 A | 1/1990 | Rauber et al. |
| 4,954,505 A | 9/1990 | Rauber et al. |
| 4,956,462 A | 9/1990 | Shimizu et al. |
| 4,958,019 A | 9/1990 | Shimizu et al. |
| 4,987,129 A | 1/1991 | Shimizu et al. |
| 5,234,818 A | 8/1993 | Zimmermann et al. |

(Continued)

FOREIGN PATENT DOCUMENTS

| | | |
|---|---|---|
| CA | 2065106 | 10/1992 |
| EP | 0 127 847 | 12/1984 |
| EP | 0 286 145 | 10/1988 |
| EP | 0 380 223 | 8/1990 |
| EP | 1 340 621 | 9/2003 |
| EP | 1505068 A1 | 2/2005 |
| EP | 1 505 068 | 9/2005 |
| FR | 2 638 161 | 4/1990 |
| GB | 2 153 818 | 8/1985 |
| GB | 2 307 177 | 5/1997 |

(Continued)

OTHER PUBLICATIONS

Wolff et. al., "Burger's Medicinal Chemistry and Drug Discovery," 5th Ed. Part 1, pp. 975-977 (1995).*
Banker, et. al., (1996), Modern Pharmaceuticals, p. 596.*
Chawla et. al. Current Research & Information on Pharmaceutical Science, 2004, 5(1), p. 9-12.*

(Continued)

*Primary Examiner* — Jeffrey H Murray
(74) *Attorney, Agent, or Firm* — Elsa D. Lemione

(57) ABSTRACT

The present invention relates generally to amide containing heterobicyclic compounds having the following formulas:

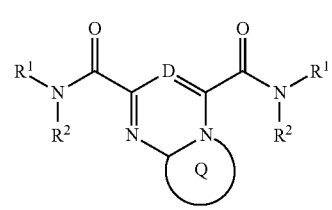

Formula (II)

wherein $R^1$, $R^2$, D, and Q are as defined in the specification. More particularly, the present invention provides a new class of amide containing heterobicyclic compounds, that exhibit an increased potency in relation to currently known MMP-13 and MMP-3 inhibitors.

10 Claims, No Drawings

(56) References Cited

U.S. PATENT DOCUMENTS

| | | |
|---|---|---|
| 5,236,917 A | 8/1993 | Dunlap et al. |
| 5,302,586 A | 4/1994 | Cordi et al. |
| 5,360,796 A | 11/1994 | Hansen, Jr. et al. |
| 5,371,074 A | 12/1994 | Dunlap et al. |
| 5,420,138 A | 5/1995 | Corbier et al. |
| 5,435,991 A | 7/1995 | Golman et al. |
| 5,445,943 A | 8/1995 | Hoenes |
| 5,457,200 A | 10/1995 | Zimmermann et al. |
| 5,464,843 A | 11/1995 | Hansen, Jr. et al. |
| 5,464,861 A | 11/1995 | Dobrusin et al. |
| 5,468,757 A | 11/1995 | Jakubowski et al. |
| 5,480,876 A | 1/1996 | Cordi et al. |
| 5,482,933 A | 1/1996 | Cordi et al. |
| 5,484,708 A | 1/1996 | Hoenes et al. |
| 5,486,512 A | 1/1996 | Gregor |
| 5,556,874 A | 9/1996 | Dobrusin et al. |
| 5,596,012 A | 1/1997 | Dunlap et al. |
| 5,633,237 A | 5/1997 | Hansen, Jr. et al. |
| 5,650,414 A | 7/1997 | Corbier et al. |
| 5,650,422 A | 7/1997 | Dunlap et al. |
| 5,658,857 A | 8/1997 | Andree et al. |
| 5,691,347 A | 11/1997 | Corbier et al. |
| 5,716,964 A | 2/1998 | Hansen, Jr. et al. |
| 5,721,223 A | 2/1998 | Hansen, Jr. et al. |
| 5,760,028 A | 6/1998 | Jadhav et al. |
| 5,827,857 A | 10/1998 | Riedl et al. |
| 5,874,432 A | 2/1999 | Dunlap et al. |
| 5,902,773 A | 5/1999 | Benoit et al. |
| 5,912,246 A | 6/1999 | Tenbrink |
| 5,955,252 A | 9/1999 | Goto et al. |
| 5,955,470 A | 9/1999 | Gittos |
| 5,958,904 A | 9/1999 | Cordi et al. |
| 5,968,725 A | 10/1999 | Katoh et al. |
| 5,973,148 A | 10/1999 | Ringer et al. |
| 6,013,654 A | 1/2000 | TenBrink |
| 6,054,587 A | 4/2000 | Reddy et al. |
| 6,110,944 A | 8/2000 | Chen et al. |
| 6,114,580 A | 9/2000 | Ringer et al. |
| 6,187,777 B1 | 2/2001 | Norman et al. |
| 6,190,848 B1 | 2/2001 | Boff et al. |
| 6,214,834 B1 | 4/2001 | Jadhav et al. |
| 6,232,320 B1 | 5/2001 | Stewart et al. |
| 6,294,672 B1 | 9/2001 | Reddy et al. |
| 6,303,622 B1 | 10/2001 | Guarna et al. |
| 6,319,660 B1 | 11/2001 | Allway et al. |
| 6,379,649 B1 | 4/2002 | Katsifis et al. |
| 6,403,588 B1 | 6/2002 | Hayakawa et al. |
| 6,455,242 B1 | 9/2002 | Allway et al. |
| 6,461,538 B2 | 10/2002 | Taguchi |
| 6,498,166 B1 | 12/2002 | Campbell et al. |
| 6,514,912 B1 | 2/2003 | Guarna et al. |
| 6,552,034 B2 | 4/2003 | Guarna et al. |
| 6,555,549 B2 | 4/2003 | Guarna et al. |
| 6,572,664 B2 | 6/2003 | Breton et al. |
| 6,579,882 B2 | 6/2003 | Stewart et al. |
| 6,583,154 B1 | 6/2003 | Norman et al. |
| 6,653,320 B2 | 11/2003 | Hayakawa et al. |
| 6,673,928 B2 | 1/2004 | Taguchi |
| 6,685,767 B2 | 2/2004 | Noro et al. |
| 6,730,789 B1 | 5/2004 | Birault et al. |
| 6,740,649 B2 | 5/2004 | Ott et al. |
| 6,756,498 B2 | 6/2004 | Fitzgerald et al. |
| 6,770,666 B2 | 8/2004 | Hashimoto et al. |
| 6,806,268 B2 | 10/2004 | Gall |
| 6,855,719 B1 | 2/2005 | Thomas et al. |
| 6,861,436 B2 | 3/2005 | Koya et al. |
| 6,919,352 B2 | 7/2005 | Chamberlain et al. |
| 7,795,245 B2 * | 9/2010 | Steeneck et al. ......... 514/210.02 |
| 2001/0015614 A1 | 8/2001 | Taguchi |
| 2001/0020030 A1 | 9/2001 | Stewart et al. |
| 2001/0044542 A1 | 11/2001 | Guarna et al. |
| 2001/0047098 A1 | 11/2001 | Guarna et al. |
| 2002/0002749 A1 | 1/2002 | Breton et al. |
| 2002/0041880 A1 | 4/2002 | DeFeo-Jones et al. |
| 2002/0042033 A1 | 4/2002 | Allway et al. |
| 2002/0046680 A1 | 4/2002 | Noro et al. |
| 2002/0068744 A1 | 6/2002 | Schmitt et al. |
| 2002/0091124 A1 | 7/2002 | Beckers et al. |
| 2002/0151549 A1 | 10/2002 | Hayakawa et al. |
| 2002/0170121 A9 | 11/2002 | Breton et al. |
| 2002/0193376 A1 | 12/2002 | Gall |
| 2003/0027820 A1 | 2/2003 | Gall |
| 2003/0050320 A1 | 3/2003 | Hashimoto et al. |
| 2003/0050476 A1 | 3/2003 | Taguchi |
| 2003/0139388 A1 | 7/2003 | Ott et al. |
| 2003/0153759 A1 | 8/2003 | Koya et al. |
| 2003/0158216 A1 | 8/2003 | Beckers et al. |
| 2003/0204090 A1 | 10/2003 | Ono et al. |
| 2003/0207885 A1 | 11/2003 | Hutchison et al. |
| 2003/0212275 A1 | 11/2003 | Fitzgerald et al. |
| 2003/0220322 A1 | 11/2003 | Gerlach et al. |
| 2003/0220365 A1 | 11/2003 | Stewart et al. |
| 2003/0229104 A1 | 12/2003 | Gerlach et al. |
| 2004/0023803 A1 | 2/2004 | Jäger et al. |
| 2004/0038993 A1 | 2/2004 | Shipps et al. |
| 2004/0063580 A1 | 4/2004 | Kuragano et al. |
| 2004/0072853 A1 | 4/2004 | Chamberlain et al. |
| 2004/0082635 A1 | 4/2004 | Hashimoto et al. |
| 2004/0097438 A1 | 5/2004 | Hashimoto et al. |
| 2004/0106574 A1 | 6/2004 | Berg et al. |
| 2004/0110763 A1 | 6/2004 | Akahane et al. |
| 2004/0116462 A1 | 6/2004 | Ono et al. |
| 2004/0176396 A1 | 9/2004 | Biftu et al. |
| 2004/0204402 A1 | 10/2004 | Venkatesan et al. |
| 2004/0214834 A1 | 10/2004 | Gudmunsson et al. |
| 2004/0214850 A1 | 10/2004 | Kova et al. |
| 2004/0248903 A1 | 12/2004 | Gudmundsson et al. |
| 2005/0004162 A1 | 1/2005 | Venkatesan et al. |
| 2005/0014754 A1 | 1/2005 | Ono et al. |
| 2005/0020593 A1 | 1/2005 | Mailliet et al. |
| 2005/0031588 A1 | 2/2005 | Sommadossi et al. |
| 2005/0049419 A1 | 3/2005 | Wallace et al. |
| 2005/0054701 A1 | 3/2005 | Wallace et al. |
| 2005/0059677 A1 | 3/2005 | Alberti et al. |
| 2005/0096256 A1 | 5/2005 | Sinclair |
| 2005/0107436 A1 | 5/2005 | Xie et al. |
| 2005/0113397 A1 | 5/2005 | Takemura et al. |
| 2005/0136065 A1 | 6/2005 | Valiante, Jr. |
| 2005/0136537 A1 | 6/2005 | Sinclair et al. |
| 2005/0148633 A1 | 7/2005 | Xie et al. |
| 2005/0165232 A1 | 7/2005 | Beresis et al. |
| 2006/0173183 A1 | 8/2006 | Powers et al. |
| 2006/0293345 A1 | 12/2006 | Steeneck et al. |
| 2007/0155737 A1 | 7/2007 | Gallagher, Jr. et al. |
| 2007/0155738 A1 | 7/2007 | Steeneck et al. |
| 2007/0155739 A1 | 7/2007 | Sucholeiki et al. |

FOREIGN PATENT DOCUMENTS

| | | |
|---|---|---|
| JP | 02-233684 | 9/1990 |
| JP | 02-247257 | 10/1990 |
| JP | 02-281203 | 11/1990 |
| JP | 05-011394 | 1/1993 |
| JP | 05-188537 | 7/1993 |
| JP | 06-009638 | 1/1994 |
| JP | 06-161063 | 6/1994 |
| JP | 06-256187 | 9/1994 |
| JP | 07-101958 | 4/1995 |
| JP | 07-133280 | 5/1995 |
| JP | 08-041451 | 2/1996 |
| JP | 08-171168 | 7/1996 |
| JP | 10-036375 | 2/1998 |
| JP | 10-110108 | 4/1998 |
| JP | 10-120680 | 5/1998 |
| JP | 11-116481 | 4/1999 |
| JP | 2001-006877 | 1/2001 |
| JP | 2001-057292 | 2/2001 |
| JP | 2001-139575 | 5/2001 |
| JP | 2001-152065 | 6/2001 |
| JP | 2001-30266 | 10/2001 |
| JP | 2002-072460 | 3/2002 |
| JP | 2002-080821 | 3/2002 |
| JP | 2004-002826 | 1/2004 |
| JP | 2004-091369 | 3/2004 |

(56) References Cited

FOREIGN PATENT DOCUMENTS

| WO | WO 93/02710 | 2/1993 |
|---|---|---|
| WO | WO 96/21662 | 7/1996 |
| WO | WO 97/23480 | 7/1997 |
| WO | WO 97/29107 | 8/1997 |
| WO | WO 98/25926 | 6/1998 |
| WO | WO 00/38638 | 7/2000 |
| WO | WO 01/82909 | 11/2001 |
| WO | WO 02/12236 | 2/2002 |
| WO | WO 02/34748 | 5/2002 |
| WO | WO 02/064568 | 8/2002 |
| WO | WO 02/064571 | 8/2002 |
| WO | WO 02/064595 | 8/2002 |
| WO | WO 02/076416 | 10/2002 |
| WO | WO 02/076417 | 10/2002 |
| WO | WO 02/076418 | 10/2002 |
| WO | WO 02/076419 | 10/2002 |
| WO | WO 02/088107 | 11/2002 |
| WO | WO 03/004497 | 1/2003 |
| WO | WO 03/037861 | 5/2003 |
| WO | WO 03/045950 | 6/2003 |
| WO | WO 03/049738 | 6/2003 |
| WO | WO 03/062392 | 7/2003 |
| WO | WO 03/064397 A1 | 8/2003 |
| WO | WO 03/091256 | 11/2003 |
| WO | WO 03/101993 | 12/2003 |
| WO | WO 2004/014354 | 2/2004 |
| WO | WO 2004/014916 | 2/2004 |
| WO | WO 2004/017950 | 3/2004 |
| WO | WO 2004/021989 | 3/2004 |
| WO | WO 2004/022054 | 3/2004 |
| WO | WO 2004/033454 | 4/2004 |
| WO | WO 2004/035579 | 4/2004 |
| WO | WO 2004/041788 | 5/2004 |
| WO | WO 2004/052315 | 6/2004 |
| WO | WO 2004/000608 | 7/2004 |
| WO | WO 2004/058203 | 7/2004 |
| WO | WO 2004/108722 | 12/2004 |
| WO | WO 2005/014543 | 2/2005 |
| WO | WO 2005/105760 | 11/2005 |
| WO | WO 2006/083454 | 8/2006 |
| WO | WO 2006/001281 | 11/2006 |

OTHER PUBLICATIONS

Newman et. al.; Drug Discovery Today; 2003, 8(19) p. 898-905.*
Salmon, et al., Encyclopedia of Regents for Organic Synthesis, *Preparation of Carboxylic Acid Chlorides (and Anhydrides)* pp. 1-8 (2001).
Wolff, et al., "Burger's Medicinal Chemistry and Drug Discovery", 5th Ed. vol. 1, pp. 975-977 (1995).
Banker, et al., Modern Pharmaceuticals, 3rd Ed. p. 956 (1996).
Dorwald, F., "Side Reactions in Organic Synthesis", Wiley: VCH, Weinheim p. IX of Preface (2005).
Borisy, et al., "Systematic discovery of multicomponent therapeutics", PNAS 100(13) pp. 7977-7982 (2003).
Goebel et al., J. Med Chem., (1982) 25, 1334-1338.

* cited by examiner

HETEROBICYCLIC METALLOPROTEASE INHIBITORS

CROSS REFERENCE TO RELATED APPLICATIONS

This application is a continuation of U.S. application Ser. No. 12/370,418, filed Feb. 12, 2009, now abandoned which is a continuation of U.S. application Ser. No. 11/602,140, filed Nov. 20, 2006, abandoned, which is a continuation in part of U.S. application Ser. No. 11/440,087, filed May 22, 2006, abandoned, which claims the benefit of U.S. Provisional Application No. 60/734,991, filed Nov. 9, 2005, U.S. Provisional Application No. 60/706,465, filed Aug. 8, 2005, and U.S. Provisional Application No. 60/683,470, filed May 20, 2005, the contents of each of which are hereby incorporated by reference.

FIELD OF THE INVENTION

The present invention relates generally to amide containing heterobicyclic metalloprotease inhibiting compounds, and more particularly to heterobicyclic MMP-13 inhibiting compounds.

BACKGROUND OF THE INVENTION

Matrix metalloproteinases (MMPs) and aggrecanases (ADAMTS=a disintegrin and metalloproteinase with thrombospondin motif) are a family of structurally related zinc-containing enzymes that have been reported to mediate the breakdown of connective tissue in normal physiological processes such as embryonic development, reproduction, and tissue remodelling. Over-expression of MMPs and aggrecanases or an imbalance between extracellular matrix synthesis and degradation has been suggested as factors in inflammatory, malignant and degenerative disease processes. MMPs and aggrecanases are, therefore, targets for therapeutic inhibitors in several inflammatory, malignant and degenerative diseases such as rheumatoid arthritis, osteoarthritis, osteoporosis, periodontitis, multiple sclerosis, gingivitis, corneal epidermal and gastric ulceration, atherosclerosis, neointimal proliferation (which leads to restenosis and ischemic heart failure) and tumor metastasis.

The ADAMTSs are a group of proteases that are encoded in 19 ADAMTS genes in humans. The ADAMTSs are extracellular, multidomain enzymes whose functions include collagen processing, cleavage of the matrix proteoglycans, inhibition of angiogenesis and blood coagulation homoeostasis (*Biochem. J.* 2005, 386, 15-27; *Arthritis Res. Ther.* 2005, 7, 160-169; *Curr. Med. Chem. Anti-Inflammatory Anti-Allergy Agents* 2005, 4, 251-264).

The mammalian MMP family has been reported to include at least 20 enzymes, (*Chem. Rev.* 1999, 99, 2735-2776). Collagenase-3 (MMP-13) is among three collagenases that have been identified. Based on identification of domain structures for individual members of the MMP family, it has been determined that the catalytic domain of the MMPs contains two zinc atoms; one of these zinc atoms performs a catalytic function and is coordinated with three histidines contained within the conserved amino acid sequence of the catalytic domain. MMP-13 is over-expressed in rheumatoid arthritis, osteoarthritis, abdominal aortic aneurysm, breast carcinoma, squamous cell carcinomas of the head and neck, and vulvar squamous cell carcinoma. The principal substrates of MMP-13 are fibrillar collagens (types I, II, III) and gelatins, proteoglycans, cytokines and other components of ECM (extracellular matrix).

The activation of the MMPs involves the removal of a propeptide, which features an unpaired cysteine residue complexes the catalytic zinc (II) ion. X-ray crystal structures of the complex between MMP-3 catalytic domain and TIMP-1 and MMP-14 catalytic domain and TIMP-2 also reveal ligation of the catalytic zinc (II) ion by the thiol of a cysteine residue. The difficulty in developing effective MMP inhibiting compounds comprises several factors, including choice of selective versus broad-spectrum MMP inhibitors and rendering such compounds bioavailable via an oral route of administration.

MMP-3 (stromelysin-1; transin-1) is another member of the MMP family (Woesner; FASEB J. 1991; 5:2145-2154). Human MMP-3 was initially isolated from cultured human synoviocytes. It is also expressed by chondrocytes and has been localized in OA cartilage and synovial tissues (Case; Am. J. Pathol. 1989 December; 135(6):1055-64).

MMP-3 is produced by basal keratinocytes in a variety of chronic ulcers. MMP-3 mRNA and Protein were detected in basal keratinocytes adjacent to but distal from the wound edge in what probably represents the sites of proliferating epidermis. MMP-3 may this prevent the epidermis from healing (Saarialho-Kere, J. Clin. Invest. 1994 July; 94(1):79-88)).

MMP-3 serum protein levels are significantly elevated in patients with early and long-term rheumatoid arthritis (Yamanaka; Arthritis Rheum. 2000 April; 43(4):852-8) and in osteoarthritis patients (Bramono; Clin Orthop Relat Res. 2004 November; (428):272-85) as well as in other inflammatory diseases like systemic lupus erythematosis and ankylosing spondylitis (Chen, Rheumatology 2006 April; 45(4):414-20.).

MMP-3 acts on components of the ECM as aggrecan, fibronectin, gelatine, laminin, elastin, fibrillin and others and on collagens of type III, IV, V, VII, KX, X (Bramono; Clin Orthop Relat Res. 2004 November; (428):272-85). On collagens of type II and IX, MMP-3 exhibits telopeptidase activity (Sandell, Arthritis Res. 2001; 3(2):107-13; Eyre, Clin Orthop Relat Res. 2004 October; (427 Suppl):S118-22.). MMP-3 can activate other MMP family members as MMP-1; MMP-7; MMP-8; MMP-9 and MMP-13 (Close, Ann Rheum Dis 2001 November; 60 Suppl 3:iii62-7).

MMP-3 is involved in the regulation of cytokines and chemokines by releasing TGFβ1 from the ECM, activating TNFα, inactivation of IL-1β and release of IGF (Parks, Nat Rev Immunol. 2004 August; 4(8):617-29). A potential role for MMP-3 in the regulation of macrophate infiltration is based on the ability of the enzyme to converse active MCP species into antagonistic peptides (McQuibban, Blood. 2002 Aug. 15; 100(4):1160-7.).

SUMMARY OF THE INVENTION

The present invention relates to a new class of heterobicyclic amide containing pharmaceutical agents which inhibits metalloproteases. In particular, the present invention provides a new class of metalloprotease inhibiting compounds that exhibit potent MMP-13 inhibiting activity and/or activity towards MMP-3, MMP-8, MMP-12, ADAMTS-4, and ADAMTS-5.

The present invention provides several new classes of amide containing heterobicyclic metalloprotease compounds, of which some are represented by the following general formulas:

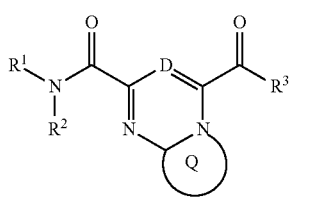

Formula (I)

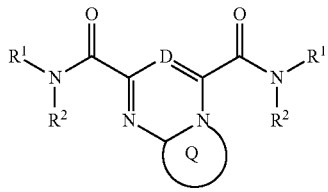

Formula (II)

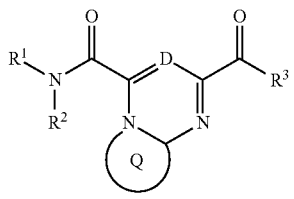

Formula (III)

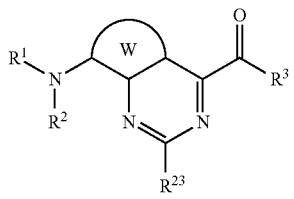

Formula (IV)

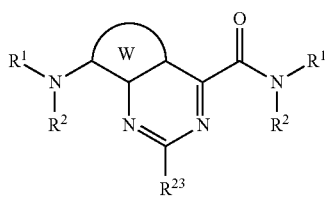

Formula (V)

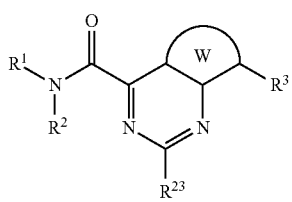

Formula (VI)

wherein all variables in the preceding Formulas (I) to (VI) are as defined hereinbelow.

The heterobicyclic metalloprotease inhibiting compounds of the present invention may be used in the treatment of metalloprotease mediated diseases, such as rheumatoid arthritis, osteoarthritis, abdominal aortic aneurysm, cancer (e.g. but not limited to melanoma, gastric carcinoma or non-small cell lung carcinoma), inflammation, atherosclerosis, multiple sclerosis, chronic obstructive pulmonary disease, ocular diseases (e.g. but not limited to ocular inflammation, retinopathy of prematurity, macular degeneration with the wet type preferred and corneal neovascularization), neurologic diseases, psychiatric diseases, thrombosis, bacterial infection, Parkinson's disease, fatigue, tremor, diabetic retinopathy, vascular diseases of the retina, aging, dementia, cardiomyopathy, renal tubular impairment, diabetes, psychosis, dyskinesia, pigmentary abnormalities, deafness, inflammatory and fibrotic syndromes, intestinal bowel syndrome, allergies, Alzheimers disease, arterial plaque formation, oncology, periodontal, viral infection, stroke, atherosclerosis, cardiovascular disease, reperfusion injury, trauma, chemical exposure or oxidative damage to tissues, chronic wound healing, wound healing, hemorroid, skin beautifying, pain, inflammatory pain, bone pain and joint pain, acne, acute alcoholic hepatitis, acute inflammation, acute pancreatitis, acute respiratory distress syndrome, adult respiratory disease, airflow obstruction, airway hyperresponsiveness, alcoholic liver disease, allograft rejections, angiogenesis, angiogenic ocular disease, arthritis, asthma, atopic dermatitis, bronchiectasis, bronchiolitis, bronchiolitis obliterans, burn therapy, cardiac and renal reperfusion injury, celiac disease, cerebral and cardiac ischemia, CNS tumors, CNS vasculitis, colds, contusions, cor pulmonae, cough, Crohn's disease, chronic bronchitis, chronic inflammation, chronic pancreatitis, chronic sinusitis, crystal induced arthritis, cystic fibrosis, delayted type hypersensitivity reaction, duodenal ulcers, dyspnea, early transplantation rejection, emphysema, encephalitis, endotoxic shock, esophagitis, gastric ulcers, gingivitis, glomerulonephritis, glossitis, gout, graft vs. host reaction, gram negative sepsis, granulocytic ehrlichiosis, hepatitis viruses, herpes, herpes viruses, HIV, hypercapnea, hyperinflation, hyperoxia-induced inflammation, hypoxia, hypersensitivity, hypoxemia, inflammatory bowel disease, interstitial pneumonitis, ischemia reperfusion injury, kaposi's sarcoma associated virus, liver fibrosis, lupus, malaria, meningitis, multi-organ dysfunction, necrotizing enterocolitis, osteoporosis, periodontitis, chronic periodontitis, peritonitis associated with continous ambulatory peritoneal dialysis (CAPD), pre-term labor, polymyositis, post surgical trauma, pruritis, psoriasis, psoriatic arthritis, pulmatory fibrosis, pulmatory hypertension, renal reperfusion injury, respiratory viruses, restinosis, right ventricular hypertrophy, sarcoidosis, septic shock, small airway disease, sprains, strains, subarachnoid hemorrhage, surgical lung volume reduction, thrombosis, toxic shock syndrome, transplant reperfusion injury, traumatic brain injury, ulcerative colitis, vasculitis, ventilation-perfusion mismatching, and wheeze.

In particular, the heterobicyclic metalloprotease inhibiting compounds of the present invention may be used in the treatment of MMP-13 mediated osteoarthritis and may be used for other MMP-13 mediated symptoms, inflammatory, malignant and degenerative diseases characterized by excessive extracellular matrix degradation and/or remodelling, such as cancer, and chronic inflammatory diseases such as arthritis, rheumatoid arthritis, osteoarthritis atherosclerosis, abdominal aortic aneurysm, inflammation, multiple sclerosis, and chronic obstructive pulmonary disease, and pain, such as inflammatory pain, bone pain and joint pain.

The present invention also provides heterobicyclic metalloprotease inhibiting compounds that are useful as active ingredients in pharmaceutical compositions for treatment or prevention of metalloprotease—especially MMP-13—mediated diseases. The present invention also contemplates use of such compounds in pharmaceutical compositions for oral or parenteral administration, comprising one or more of the heterobicyclic metalloprotease inhibiting compounds disclosed herein.

The present invention further provides methods of inhibiting metalloproteases, by administering formulations, including, but not limited to, oral, rectal, topical, intravenous, parenteral (including, but not limited to, intramuscular, intravenous), ocular (ophthalmic), transdermal, inhalative (including, but not limited to, pulmonary, aerosol inhalation), nasal, sublingual, subcutaneous or intraarticular formulations, comprising the heterobicyclic metalloprotease inhibiting compounds by standard methods known in medical practice, for the treatment of diseases or symptoms arising from or associated with metalloprotease, especially MMP-13, including prophylactic and therapeutic treatment. Although the most suitable route in any given case will depend on the nature and severity of the conditions being treated and on the nature of the active ingredient. The compounds from this invention are conveniently presented in unit dosage form and prepared by any of the methods well-known in the art of pharmacy.

The heterobicyclic metalloprotease inhibiting compounds of the present invention may be used in combination with a disease modifying antirheumatic drug, a nonsteroidal anti-inflammatory drug, a COX-2 selective inhibitor, a COX-1 inhibitor, an immunosuppressive, a steroid, a biological response modifier or other anti-inflammatory agents or therapeutics useful for the treatment of chemokines mediated diseases.

DETAILED DESCRIPTION OF THE INVENTION

The terms "alkyl" or "alk", as used herein alone or as part of another group, denote optionally substituted, straight and branched chain saturated hydrocarbon groups, preferably having 1 to 10 carbons in the normal chain, most preferably lower alkyl groups. Exemplary unsubstituted such groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl and the like. Exemplary substituents may include, but are not limited to, one or more of the following groups: halo, alkoxy, alkylthio, alkenyl, alkynyl, aryl (e.g., to form a benzyl group), cycloalkyl, cycloalkenyl, hydroxy or protected hydroxy, carboxyl (—COOH), alkyloxycarbonyl, alkylcarbonyloxy, alkylcarbonyl, carbamoyl (NH$_2$—CO—), substituted carbamoyl ((e)(R$^{11}$)N—CO— wherein R$^{10}$ or R$^{11}$ are as defined below, except that at least one of R$^{10}$ or R$^{11}$ is not hydrogen), amino, heterocyclo, mono- or dialkylamino, or thiol (—SH).

The terms "lower alk" or "lower alkyl" as used herein, denote such optionally substituted groups as described above for alkyl having 1 to 4 carbon atoms in the normal chain.

The term "alkoxy" denotes an alkyl group as described above bonded through an oxygen linkage (—O—).

The term "alkenyl", as used herein alone or as part of another group, denotes optionally substituted, straight and branched chain hydrocarbon groups containing at least one carbon to carbon double bond in the chain, and preferably having 2 to 10 carbons in the normal chain. Exemplary unsubstituted such groups include ethenyl, propenyl, isobutenyl, butenyl, pentenyl, hexenyl, heptenyl, octenyl, nonenyl, decenyl, and the like. Exemplary substituents may include, but are not limited to, one or more of the following groups: halo, alkoxy, alkylthio, alkyl, alkynyl, aryl, cycloalkyl, cycloalkenyl, hydroxy or protected hydroxy, carboxyl (—COOH), alkyloxycarbonyl, alkylcarbonyloxy, alkylcarbonyl, carbamoyl (NH$_2$—CO—), substituted carbamoyl ((R$^{10}$)(R$^{11}$)N—CO— wherein R$^{10}$ or R$^{11}$ are as defined below, except that at least one of R$^{10}$ or R$^{11}$ is not hydrogen), amino, heterocyclo, mono- or dialkylamino, or thiol (—SH).

The term "alkynyl", as used herein alone or as part of another group, denotes optionally substituted, straight and branched chain hydrocarbon groups containing at least one carbon to carbon triple bond in the chain, and preferably having 2 to 10 carbons in the normal chain. Exemplary unsubstituted such groups include, but are not limited to, ethynyl, propynyl, butynyl, pentynyl, hexynyl, heptynyl, octynyl, nonynyl, decynyl, and the like. Exemplary substituents may include, but are not limited to, one or more of the following groups: halo, alkoxy, alkylthio, alkyl, alkenyl, aryl, cycloalkyl, cycloalkenyl, hydroxy or protected hydroxy, carboxyl (—COOH), alkyloxycarbonyl, alkylcarbonyloxy, alkylcarbonyl, carbamoyl (NH$_2$—CO—), substituted carbamoyl ((R$^{10}$)(R$^{11}$)N—CO— wherein R$^{10}$ or R$^{11}$ are as defined below, except that at least one of R$^{10}$ or R$^{11}$ is not hydrogen), amino, heterocyclo, mono- or dialkylamino, or thiol (—SH).

The term "cycloalkyl", as used herein alone or as part of another group, denotes optionally substituted, saturated cyclic hydrocarbon ring systems, containing one ring with 3 to 9 carbons. Exemplary unsubstituted such groups include, but are not limited to, cyclopropyl, cyclobutyl, cyclopentyl, cyclohexyl, cycloheptyl, cyclooctyl, cyclodecyl, and cyclododecyl. Exemplary substituents include, but are not limited to, one or more alkyl groups as described above, or one or more groups described above as alkyl substituents.

The term "bicycloalkyl", as used herein alone or as part of another group, denotes optionally substituted, saturated cyclic bridged hydrocarbon ring systems, desirably containing 2 or 3 rings and 3 to 9 carbons per ring. Exemplary unsubstituted such groups include, but are not limited to, adamantyl, bicyclo[2.2.2]octane, bicyclo[2.2.1]heptane and cubane. Exemplary substituents include, but are not limited to, one or more alkyl groups as described above, or one or more groups described above as alkyl substituents.

The term "spiroalkyl", as used herein alone or as part of another group, denotes optionally substituted, saturated hydrocarbon ring systems, wherein two rings of 3 to 9 carbons per ring are bridged via one carbon atom. Exemplary unsubstituted such groups include, but are not limited to, spiro[3.5]nonane, spiro[4.5]decane or spiro[2.5]octane. Exemplary substituents include, but are not limited to, one or more alkyl groups as described above, or one or more groups described above as alkyl substituents.

The term "spiroheteroalkyl", as used herein alone or as part of another group, denotes optionally substituted, saturated hydrocarbon ring systems, wherein two rings of 3 to 9 carbons per ring are bridged via one carbon atom and at least one carbon atom is replaced by a heteroatom independently selected from N, O and S. The nitrogen and sulfur heteroatoms may optionally be oxidized. Exemplary unsubstituted such groups include, but are not limited to, 1,3-diaza-spiro[4.5]decane-2,4-dione. Exemplary substituents include, but are not limited to, one or more alkyl groups as described above, or one or more groups described above as alkyl substituents.

The terms "ar" or "aryl", as used herein alone or as part of another group, denote optionally substituted, homocyclic aromatic groups, preferably containing 1 or 2 rings and 6 to 12 ring carbons. Exemplary unsubstituted such groups include, but are not limited to, phenyl, biphenyl, and naphthyl. Exemplary substituents include, but are not limited to, one or more nitro groups, alkyl groups as described above or groups described above as alkyl substituents.

The term "heterocycle" or "heterocyclic system" denotes a heterocyclyl, heterocyclenyl, or heteroaryl group as described herein, which contains carbon atoms and from 1 to 4 heteroatoms independently selected from N, O and S and including any bicyclic or tricyclic group in which any of the above-defined heterocyclic rings is fused to one or more heterocycle, aryl or cycloalkyl groups. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolinyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isatinoyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, oxindolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl.

Further examples of heterocycles include, but are not limited to, "heterobicycloalkyl" groups such as 7-oxa-bicyclo[2.2.1]heptane, 7-aza-bicyclo[2.2.1]heptane, and 1-aza-bicyclo[2.2.2]octane.

"Heterocyclenyl" denotes a non-aromatic monocyclic or multicyclic hydrocarbon ring system of about 3 to about 10 atoms, desirably about 4 to about 8 atoms, in which one or more of the carbon atoms in the ring system is/are hetero element(s) other than carbon, for example nitrogen, oxygen or sulfur atoms, and which contains at least one carbon-carbon double bond or carbon-nitrogen double bond. Ring sizes of rings of the ring system may include 5 to 6 ring atoms. The designation of the aza, oxa or thia as a prefix before heterocyclenyl define that at least a nitrogen, oxygen or sulfur atom is present respectively as a ring atom. The heterocyclenyl may be optionally substituted by one or more substituents as defined herein. The nitrogen or sulphur atom of the heterocyclenyl may also be optionally oxidized to the corresponding N-oxide, S-oxide or S,S-dioxide. "Heterocyclenyl" as used herein includes by way of example and not limitation those described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and "J. Am. Chem. Soc.", 82:5566 (1960), the contents all of which are incorporated by reference herein. Exemplary monocyclic azaheterocyclenyl groups include, but are not limited to, 1,2,3,4-tetrahydrohydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, and the like. Exemplary oxaheterocyclenyl groups include, but are not limited to, 3,4-dihydro-2H-pyran, dihydrofuranyl, and fluorodihydrofuranyl. An exemplary multicyclic oxaheterocyclenyl group is 7-oxabicyclo[2.2.1]heptenyl.

"Heterocyclyl," or "heterocycloalkyl," denotes a non-aromatic saturated monocyclic or multicyclic ring system of about 3 to about 10 carbon atoms, desirably 4 to 8 carbon atoms, in which one or more of the carbon atoms in the ring system is/are hetero element(s) other than carbon, for example nitrogen, oxygen or sulfur. Ring sizes of rings of the ring system may include 5 to 6 ring atoms. The designation of the aza, oxa or thia as a prefix before heterocyclyl define that at least a nitrogen, oxygen or sulfur atom is present respectively as a ring atom. The heterocyclyl may be optionally substituted by one or more substituents which may be the same or different, and are as defined herein. The nitrogen or sulphur atom of the heterocyclyl may also be optionally oxidized to the corresponding N-oxide, S-oxide or S,S-dioxide.

"Heterocyclyl" as used herein includes by way of example and not limitation those described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and "J. Am. Chem. Soc.", 82:5566 (1960). Exemplary monocyclic heterocyclyl rings include, but are not limited to, piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Heteroaryl" denotes an aromatic monocyclic or multicyclic ring system of about 5 to about 10 atoms, in which one or more of the atoms in the ring system is/are hetero element(s) other than carbon, for example nitrogen, oxygen or sulfur. Ring sizes of rings of the ring system include 5 to 6 ring atoms. The "heteroaryl" may also be substituted by one or more substituents which may be the same or different, and are as defined herein. The designation of the aza, oxa or thia as a prefix before heteroaryl define that at least a nitrogen, oxygen or sulfur atom is present respectively as a ring atom. A nitrogen atom of a heteroaryl may be optionally oxidized to the corresponding N-oxide. Heteroaryl as used herein includes by way of example and not limitation those described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and "J. Am. Chem. Soc.", 82:5566 (1960). Exemplary heteroaryl and substituted heteroaryl groups include, but are not limited to, pyrazinyl, thienyl, isothiazolyl, oxazolyl, pyrazolyl, furazanyl, pyrrolyl, 1,2,4-thiadiazolyl, pyridazinyl, quinoxalinyl, phthalazinyl, imidazo[1,2-a]pyridine, imidazo[2,1-b]thiazolyl, benzofurazanyl, azaindolyl, benzimidazolyl, benzothienyl, thienopyridyl, thienopyrimidyl, pyrrolopyridyl, imidazopyridyl, benzoazaindole, 1,2,3-triazinyl, 1,2,4-triazinyl, 1,3,5-triazinyl, benzthiazolyl, dioxolyl, furanyl, imidazolyl, indolyl, indolizinyl, isoxazolyl, isoquinolinyl, isothiazolyl, oxadiazolyl, oxazinyl, oxiranyl, piperazinyl, piperidinyl, pyranyl, pyrazinyl, pyridazinyl, pyrazolyl, pyridyl, pyrimidinyl, pyrrolyl, pyrrolidinyl, quinazolinyl, quinolinyl, tetrazinyl, tetrazolyl, 1,3,4-thiadiazolyl, 1,2,3-thiadiazolyl, 1,2,4-thiadiazolyl, 1,2,5-thiadiazolyl, thiatriazolyl, thiazinyl, thiazolyl, thienyl, 5-thioxo-1,2,4-diazolyl, thiomorpholino, thiophenyl, thiopyranyl, triazolyl and triazolonyl.

The phrase "fused" means, that the group, mentioned before "fused" is connected via two adjacent atoms to the ring system mentioned after "fused" to form a bicyclic system. For example, "heterocycloalkyl fused aryl" includes, but is not limited to, 2,3-dihydro-benzo[1,4]dioxine, 4H-benzo[1,4]oxazin-3-one, 3H-Benzooxazol-2-one and 3,4-dihydro-2H-benzo[f][1,4]oxazepin-5-one.

The term "amino" denotes the radical —$NH_2$ wherein one or both of the hydrogen atoms may be replaced by an optionally substituted hydrocarbon group. Exemplary amino groups include, but are not limited to, n-butylamino, tert-butylamino, methylpropylamino and ethyldimethylamino.

The term "cycloalkylalkyl" denotes a cycloalkyl-alkyl group wherein a cycloalkyl as described above is bonded through an alkyl, as defined above. Cycloalkylalkyl groups may contain a lower alkyl moiety. Exemplary cycloalkylalkyl groups include, but are not limited to, cyclopropylmethyl, cyclopentylmethyl, cyclohexylmethyl, cyclopropylethyl, cyclopentylethyl, cyclohexylpropyl, cyclopropylpropyl, cyclopentylpropyl, and cyclohexylpropyl.

The term "arylalkyl" denotes an aryl group as described above bonded through an alkyl, as defined above.

The term "heteroarylalkyl" denotes a heteroaryl group as described above bonded through an alkyl, as defined above.

The term "heterocyclylalkyl," or "heterocycloalkylalkyl," denotes a heterocyclyl group as described above bonded through an alkyl, as defined above.

The terms "halogen", "halo", or "hal", as used herein alone or as part of another group, denote chlorine, bromine, fluorine, and iodine.

The term "haloalkyl" denotes a halo group as described above bonded though an alkyl, as defined above. Fluoroalkyl is an exemplary group.

The term "aminoalkyl" denotes an amino group as defined above bonded through an alkyl, as defined above.

The phrase "bicyclic fused ring system wherein at least one ring is partially saturated" denotes an 8- to 13-membered fused bicyclic ring group in which at least one of the rings is non-aromatic. The ring group has carbon atoms and optionally 1-4 heteroatoms independently selected from N, O and S. Illustrative examples include, but are not limited to, indanyl, tetrahydronaphthyl, tetrahydroquinolyl and benzocycloheptyl.

The phrase "tricyclic fused ring system wherein at least one ring is partially saturated" denotes a 9- to 18-membered fused tricyclic ring group in which at least one of the rings is non-aromatic. The ring group has carbon atoms and optionally 1-7 heteroatoms independently selected from N, O and S. Illustrative examples include, but are not limited to, fluorene, 10,11-dihydro-5H-dibenzo[a,d]cycloheptene and 2,2a,7,7a-tetrahydro-1H-cyclobuta[a]indene.

The term "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. Examples therefore may be, but are not limited to, sodium, potassium, choline, lysine, arginine or N-methyl-glucamine salts, and the like.

The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as, but not limited to, hydrochloric, hydrobromic, sulfuric, sulfamic, phosphoric, nitric and the like; and the salts prepared from organic acids such as, but not limited to, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Organic solvents include, but are not limited to, nonaqueous media like ethers, ethyl acetate, ethanol, isopropanol, or acetonitrile. Lists of suitable salts are found in *Remington's Pharmaceutical Sciences,* 18th ed., Mack Publishing Company, Easton, Pa., 1990, p. 1445, the disclosure of which is hereby incorporated by reference.

The phrase "pharmaceutically acceptable" denotes those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

The phrase "pharmaceutically acceptable carrier" denotes media generally accepted in the art for the delivery of biologically active agents to mammals, e.g., humans. Such carriers are generally formulated according to a number of factors well within the purview of those of ordinary skill in the art to determine and account for. These include, without limitation: the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, well known to those of ordinary skill in the art. Non-limiting examples of a pharmaceutically acceptable carrier are hyaluronic acid and salts thereof, and microspheres (including, but not limited to poly(D,L)-lactide-co-glycolic acid copolymer (PLGA), poly(L-lactic acid) (PLA), poly(caprolactone (PCL) and bovine serum albumin (BSA)). Descriptions of suitable pharmaceutically acceptable carriers, and factors involved in their selection, are found in a variety of readily available sources, e.g., Remington's Pharmaceutical Sciences, 17th ed., Mack Publishing Company, Easton, Pa., 1985, the contents of which are incorporated herein by reference.

Pharmaceutically acceptable carriers particularly suitable for use in conjunction with tablets include, for example, inert diluents, such as celluloses, calcium or sodium carbonate, lactose, calcium or sodium phosphate; disintegrating agents, such as croscarmellose sodium, cross-linked povidone, maize starch, or alginic acid; binding agents, such as povidone, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

The compositions of the invention may also be formulated as suspensions including a compound of the present invention in admixture with at least one pharmaceutically acceptable excipient suitable for the manufacture of a suspension. In yet another embodiment, pharmaceutical compositions of the invention may be formulated as dispersible powders and granules suitable for preparation of a suspension by the addition of suitable excipients.

Carriers suitable for use in connection with suspensions include suspending agents, such as sodium carboxymethylcellulose, methylcellulose, hydroxypropyl methylcelluose, sodium alginate, polyvinylpyrrolidone, gum tragacanth, gum acacia, dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate); and thickening agents, such as carbomer, beeswax, hard paraffin or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

Cyclodextrins may be added as aqueous solubility enhancers. Preferred cyclodextrins include hydroxypropyl, hydroxyethyl, glucosyl, maltosyl and maltotriosyl derivatives of α-, β-, and γ-cyclodextrin. The amount of solubility enhancer employed will depend on the amount of the compound of the present invention in the composition.

The term "formulation" denotes a product comprising the active ingredient(s) and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical formulations of the present invention encompass any composition made by admixing a compound of the present invention and a pharmaceutical carrier.

The term "N-oxide" denotes compounds that can be obtained in a known manner by reacting a compound of the present invention including a nitrogen atom (such as in a pyridyl group) with hydrogen peroxide or a peracid, such as 3-chloroperoxy-benzoic acid, in an inert solvent, such as dichloromethane, at a temperature between about −10-80° C., desirably about 0° C.

The term "polymorph" denotes a form of a chemical compound in a particular crystalline arrangement. Certain polymorphs may exhibit enhanced thermodynamic stability and may be more suitable than other polymorphic forms for inclusion in pharmaceutical formulations.

The compounds of the invention can contain one or more chiral centers and/or double bonds and, therefore, exist as stereoisomers, such as double-bond isomers (i.e., geometric isomers), enantiomers, or diastereomers. According to the invention, the chemical structures depicted herein, and therefore the compounds of the invention, encompass all of the corresponding enantiomers and stereoisomers, that is, both the stereomerically pure form (e.g., geometrically pure, enantiomerically pure, or diastereomerically pure) and enantiomeric and stereoisomeric mixtures.

The term "racemic mixture" denotes a mixture that is about 50% of one enantiomer and about 50% of the corresponding enantiomer relative to all chiral centers in the molecule. Thus, the invention encompasses all enantiomerically-pure, enantiomerically-enriched, and racemic mixtures of compounds of Formulas (I) through (VI).

Enantiomeric and stereoisomeric mixtures of compounds of the invention can be resolved into their component enantiomers or stereoisomers by well-known methods. Examples include, but are not limited to, the formation of chiral salts and the use of chiral or high performance liquid chromatography "HPLC" and the formation and crystallization of chiral salts. See, e.g., Jacques, J., et al., Enantiomers, Racemates and Resolutions (Wiley-Interscience, New York, 1981); Wilen, S. H., et al., Tetrahedron 33:2725 (1977); Eliel, E. L., Stereochemistry of Carbon Compounds (McGraw-Hill, NY, 1962); Wilen, S. H., Tables of Resolving Agents and Optical Resolutions p. 268 (E. L. Eliel, Ed., Univ. of Notre Dame Press, Notre Dame, Ind., 1972); Stereochemistry of Organic Compounds, Ernest L. Eliel, Samuel H. Wilen and Lewis N. Manda (1994 John Wiley & Sons, Inc.), and Stereoselective Synthesis A Practical Approach, Mihaly Nogradi (1995 VCH Publishers, Inc., NY, N.Y.). Enantiomers and stereoisomers can also be obtained from stereomerically- or enantiomerically-pure intermediates, reagents, and catalysts by well-known asymmetric synthetic methods.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced.

Unless moieties of a compound of the present invention are defined as being unsubstituted, the moieties of the compound may be substituted. In addition to any substituents provided above, the moieties of the compounds of the present invention may be optionally substituted with one or more groups independently selected from:

$C_1$-$C_4$ alkyl;
$C_2$-$C_4$ alkenyl;
$C_2$-$C_4$ alkynyl;
$CF_3$;
halo;
OH;
O—($C_1$-$C_4$ alkyl);
$OCH_2F$;
$OCHF_2$;
$OCF_3$;
$ONO_2$;
OC(O)—($C_1$-$C_4$ alkyl);
OC(O)—($C_1$-$C_4$ alkyl);
OC(O)NH—($C_1$-$C_4$ alkyl);
OC(O)N($C_1$-$C_4$ alkyl)$_2$;

OC(S)NH—(C$_1$-C$_4$ alkyl);
OC(S)N(C$_1$-C$_4$ alkyl)$_2$;
SH;
S—(C$_1$-C$_4$ alkyl);
S(O)—(C$_1$-C$_4$ alkyl);
S(O)$_2$—(C$_1$-C$_4$ alkyl);
SC(O)—(C$_1$-C$_4$ alkyl);
SC(O)O—(C$_1$-C$_4$ alkyl);
NH$_2$;
N(H)—(C$_1$-C$_4$ alkyl);
N(C$_1$-C$_4$ alkyl)$_2$;
N(H)C(O)—(C$_1$-C$_4$ alkyl);
N(CH$_3$)C(O)—(C$_1$-C$_4$ alkyl);
N(H)C(O)—CF$_3$;
N(CH$_3$)C(O)—CF$_3$;
N(H)C(S)—(C$_1$-C$_4$ alkyl);
N(CH$_3$)C(S)—(C$_1$-C$_4$ alkyl);
N(H)S(O)$_2$—(C$_1$-C$_4$ alkyl);
N(H)C(O)NH$_2$;
N(H)C(O)NH—(C$_1$-C$_4$ alkyl);
N(CH$_3$)C(O)NH—(C$_1$-C$_4$ alkyl);
N(H)C(O)N(C$_1$-C$_4$ alkyl)$_2$;
N(CH$_3$)C(O)N(C$_1$-C$_4$ alkyl)$_2$;
N(H)S(O)$_2$NH$_2$;
N(H)S(O)$_2$NH—(C$_1$-C$_4$ alkyl);
N(CH$_3$)S(O)$_2$NH—(C$_1$-C$_4$ alkyl);
N(H)S(O)$_2$N(C$_1$-C$_4$ alkyl)$_2$;
N(CH$_3$)S(O)$_2$N(C$_1$-C$_4$ alkyl)$_2$;
N(H)C(O)O—(C$_1$-C$_4$ alkyl);
N(CH$_3$)C(O)O—(C$_1$-C$_4$ alkyl);
N(H)S(O)$_2$O—(C$_1$-C$_4$ alkyl);
N(CH$_3$)S(O)$_2$O—(C$_1$-C$_4$ alkyl);
N(CH$_3$)C(S)NH—(C$_1$-C$_4$ alkyl);
N(CH$_3$)C(S)N(C$_1$-C$_4$ alkyl)$_2$;
N(CH$_3$)C(S)O—(C$_1$-C$_4$ alkyl);
N(H)C(S)NH$_2$;
NO$_2$;
CO$_2$H;
CO$_2$—(C$_1$-C$_4$ alkyl);
C(O)N(H)OH;
C(O)N(CH$_3$)OH:
C(O)N(CH$_3$)OH;
C(O)N(CH$_3$)O—(C$_1$-C$_4$ alkyl);
C(O)N(H)—(C$_1$-C$_4$ alkyl);
C(O)N(C$_1$-C$_4$ alkyl)$_2$;
C(S)N(H)—(C$_1$-C$_4$ alkyl);
C(S)N(C$_1$-C$_4$ alkyl)$_2$;
C(NH)N(H)—(C$_1$-C$_4$ alkyl);
C(NH)N(C$_1$-C$_4$ alkyl)$_2$;
C(NCH$_3$)N(H)—(C$_1$-C$_4$ alkyl);
C(NCH$_3$)N(C$_1$-C$_4$ alkyl)$_2$;
C(O)—(C$_1$-C$_4$ alkyl);
C(NH)—(C$_1$-C$_4$ alkyl);
C(NCH$_3$)—(C$_1$-C$_4$ alkyl);
C(NOH)—(C$_1$-C$_4$ alkyl);
C(NOCH$_3$)—(C$_1$-C$_4$ alkyl);
CN;
CHO;
CH$_2$OH;
CH$_2$O—(C$_1$-C$_4$ alkyl);
CH$_2$NH$_2$;
CH$_2$N(H)—(C$_1$-C$_4$ alkyl);
CH$_2$N(C$_1$-C$_4$ alkyl)$_2$;
aryl;
heteroaryl;
cycloalkyl; and
heterocyclyl.

In some cases, a ring substituent may be shown as being connected to the ring by a bond extending from the center of the ring. The number of such substituents present on a ring is indicated in subscript by a number. Moreover, the substituent may be present on any available ring atom, the available ring atom being any ring atom which bears a hydrogen which the ring substituent may replace. For illustrative purposes, if variable R$^x$ were defined as being:

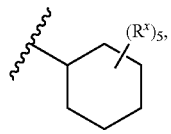

this would indicate a cyclohexyl ring bearing five R$^x$ substituents. The R$^x$ substituents may be bonded to any available ring atom. For example, among the configurations encompassed by this are configurations such as:

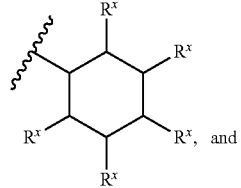 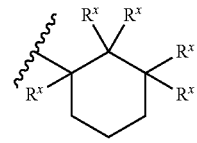

These configurations are illustrative and are not meant to limit the scope of the invention in any way.

In one embodiment of the present invention, the amide containing heterobicyclic metalloprotease compounds may be represented by the general Formula (I):

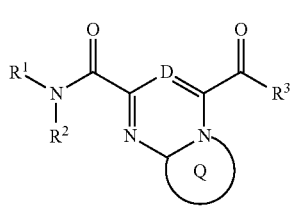

Formula (I)

wherein:
R$^1$ is selected from the group consisting of hydrogen, alkyl, alkenyl, alkynyl, cycloalkyl, heterocycloalkyl, bicycloalkyl, heterobicycloalkyl, spiroalkyl, spiroheteroalkyl, aryl, heteroaryl, cycloalkyl fused aryl, heterocycloalkyl fused aryl, cycloalkyl fused heteroaryl, heterocycloalkyl fused heteroaryl, cycloalkylalkyl, heterocycloalkylalkyl, bicycloalkylalkyl, heterobicycloalkylalkyl, spiroalkylalkyl, spiroheteroalkylalkyl, arylalkyl, heteroarylalkyl, cycloalkyl fused arylalkyl, heterocycloalkyl fused arylalkyl, cycloalkyl fused heteroarylalkyl, and heterocycloalkyl fused heteroarylalkyl,
wherein R$^1$ is optionally substituted one or more times, or
wherein R$^1$ is optionally substituted by one R$^{16}$ group and optionally substituted by one or more R$^9$ groups;
R$^2$ is selected from the group consisting of hydrogen and alkyl, wherein alkyl is optionally substituted one or more times or R$^1$ and R$^2$ when taken together with the nitrogen to which they are attached complete a 3- to 8-membered ring containing carbon atoms and optionally containing a heteroatom selected from O, S(O)$_x$, or NR$^{50}$ and which is optionally substituted one or more times;

R$^3$ is NR$^{20}$R$^{21}$;

R$^4$ in each occurrence is independently selected from the group consisting of R$^{10}$, hydrogen, alkyl, cycloalkyl, heterocycloalkyl, aryl, heteroaryl, halo, haloalkyl, CF$_3$, (C$_0$-C$_6$)-alkyl-COR$^{10}$, (C$_0$-C$_6$)-alkyl-OR$^{10}$, (C$_0$-C$_6$)-alkyl-NR$^{10}$R$^{11}$, (C$_0$-C$_6$)-alkyl-NO$_2$, (C$_0$-C$_6$)-alkyl-CN, (C$_0$-C$_6$)-alkyl-S(O)$_y$OR$^{10}$, (C$_0$-C$_6$)-alkyl-S(O)$_y$NR$^{10}$R$^{11}$, (C$_0$-C$_6$)-alkyl-NR$^{10}$CONR$^{11}$SO$_2$R$^{30}$, (C$_0$-C$_6$)-alkyl-S(O)$_x$R$^{10}$, (C$_0$-C$_6$)-alkyl-OC(O)R$^{10}$, (C$_0$-C$_6$)-alkyl-OC(O)NR$^{10}$R$^{11}$, (C$_0$-C$_6$)-alkyl-C(=NR$^{10}$)NR$^{10}$R$^{11}$, (C$_0$-C$_6$)-alkyl-NR$^{10}$C(=NR$^{11}$)NR$^{10}$R$^{11}$, (C$_0$-C$_6$)-alkyl-C(O)OR$^{10}$, (C$_0$-C$_6$)-alkyl-C(O)NR$^{10}$R$^{11}$, (C$_0$-C$_6$)-alkyl-C(O)NR$^{10}$SO$_2$R$^{11}$, (C$_0$-C$_6$)-alkyl-C(O)—NR$^{11}$—CN, O—(C$_0$-C$_6$)-alkyl-C(O)NR$^{10}$R$^{11}$, S(O)$_x$—(C$_0$-C$_6$)-alkyl-C(O)OR$^{10}$, S(O)$_x$—(C$_0$-C$_6$)-alkyl-C(O)NR$^{10}$R$^{11}$, (C$_0$-C$_6$)-alkyl-C(O)NR$^{10}$—(C$_0$-C$_6$)-alkyl-NR$^{10}$R$^{11}$, (C$_0$-C$_6$)-alkyl-NR$^{10}$—C(O)R$^{10}$, (C$_0$-C$_6$)-alkyl-NR$^{10}$—C(O)OR$^{10}$, (C$_0$-C$_6$)-alkyl-NR$^{10}$—C(O)—NR$^{10}$R$^{11}$, (C$_0$-C$_6$)-alkyl-NR$^{10}$—S(O)$_y$NR$^{10}$R$^{11}$, (C$_0$-C$_6$)-alkyl-NR$^{10}$—S(O)$_y$R$^{10}$, O—(C$_0$-C$_6$)-alkyl-aryl and O—(C$_0$-C$_6$)-alkyl-heteroaryl, wherein each R$^4$ group is optionally substituted one or more times, or wherein each R$^4$ group is optionally substituted by one or more R$^{14}$ groups;

R$^5$ in each occurrence is independently selected from the group consisting of hydrogen, alkyl, C(O)NR$^{10}$R$^{11}$, aryl, arylalkyl, SO$_2$NR$^{10}$R$^{11}$ and C(O)OR$^{10}$, wherein alkyl, aryl and arylalkyl are optionally substituted one or more times;

R$^9$ in each occurrence is independently selected from the group consisting of R$^{10}$, hydrogen, alkyl, cycloalkyl, heterocycloalkyl, aryl, heteroaryl, halo, CHF$_2$, CF$_3$, OR$^{10}$, SR$^{10}$, COOR$^{10}$, CH(CH$_3$)CO$_2$H, (C$_0$-C$_6$)-alkyl-COR$^{10}$, (C$_0$-C$_6$)-alkyl-OR$^{10}$, (C$_0$-C$_6$)-alkyl-NR$^{10}$R$^{11}$, (C$_0$-C$_6$)-alkyl-NO$_2$, (C$_0$-C$_6$)-alkyl-CN, (C$_0$-C$_6$)-alkyl-S(O)$_y$OR$^{10}$, (C$_0$-C$_6$)-alkyl-P(O)$_2$OH, (C$_0$-C$_6$)-alkyl-S(O)$_y$NR$^{10}$R$^{11}$, (C$_0$-C$_6$)-alkyl-NR$^{10}$CONR$^{11}$SO$_2$R$^{30}$, (C$_0$-C$_6$)-alkyl-S(O)$_x$R$^{10}$, (C$_0$-C$_6$)-alkyl-OC(O)R$^{10}$, (C$_0$-C$_6$)-alkyl-OC(O)NR$^{10}$R$^{11}$, (C$_0$-C$_6$)-alkyl-C(=NR$^{10}$)NR$^{10}$R$^{11}$, (C$_0$-C$_6$)-alkyl-NR$^{10}$C(=NR$^{11}$)NR$^{10}$R$^{11}$, (C$_0$-C$_6$)-alkyl-NR$^{10}$C(=N—CN)NR$^{10}$R$^{11}$, (C$_0$-C$_6$)-alkyl-C(=N—CN)NR$^{10}$R$^{11}$, (C$_0$-C$_6$)-alkyl-NR$^{10}$C(=N—NO$_2$)NR$^{10}$R$^{11}$, (C$_0$-C$_6$)-alkyl-C(=N—NO$_2$)NR$^{10}$R$^{11}$, (C$_0$-C$_6$)-alkyl-C(O)OR$^{10}$, (C$_0$-C$_6$)-alkyl-C(O)NR$^{10}$R$^{11}$, (C$_0$-C$_6$)-alkyl-C(O)NR$^{10}$SO$_2$R$^{11}$, C(O)NR$^{10}$—(C$_0$-C$_6$)-alkyl-heteroaryl, C(O)NR$^{10}$—(C$_0$-C$_6$)-alkyl-aryl, S(O)$_2$NR$^{10}$—(C$_0$-C$_6$)-alkyl-aryl, S(O)$_2$NR$^{10}$—(C$_0$-C$_6$)-alkyl-heteroaryl, S(O)$_2$NR$^{10}$-alkyl, S(O)$_2$—(C$_0$-C$_6$)-alkyl-aryl, S(O)$_2$—(C$_0$-C$_6$)-alkyl-heteroaryl, (C$_0$-C$_6$)-alkyl-C(O)—NR$^{11}$—CN, O—(C$_0$-C$_6$)-alkyl-C(O)NR$^{10}$R$^{11}$, S(O)$_x$—(C$_0$-C$_6$)-alkyl-C(O)OR$^{10}$, S(O)$_x$—(C$_0$-C$_6$)-alkyl-C(O)NR$^{10}$R$^{11}$, (C$_0$-C$_6$)-alkyl-C(O)NR$^{10}$—(C$_0$-C$_6$)-alkyl-NR$^{10}$R$^{11}$, (C$_0$-C$_6$)-alkyl-NR$^{10}$—C(O)R$^{10}$, (C$_0$-C$_6$)-alkyl-NR$^{10}$—C(O)OR$^{10}$, (C$_0$-C$_6$)-alkyl-NR$^{10}$—C(O)—NR$^{10}$R$^{11}$, (C$_0$-C$_6$)-alkyl-NR$^{10}$—S(O)$_y$NR$^{10}$R$^{11}$, (C$_0$-C$_6$)-alkyl-NR$^{10}$—S(O)$_y$R$^{11}$, O—(C$_0$-C$_6$)-alkyl-aryl and O—(C$_0$-C$_6$)-alkyl-heteroaryl, wherein each R$^9$ group is optionally substituted, or wherein each R$^9$ group is optionally substituted by one or more R$^{14}$ groups;

R$^{10}$ and R$^{11}$ in each occurrence are independently selected from the group consisting of hydrogen, alkyl, alkenyl, alkynyl, cycloalkyl, cycloalkylalkyl, heterocycloalkyl, bicycloalkyl, heterobicycloalkyl, spiroalkyl, spiroheteroalkyl, fluoroalkyl, heterocycloalkylalkyl, haloalkyl, alkenyl, alkynyl, aryl, heteroaryl, arylalkyl, heteroarylalkyl and aminoalkyl, wherein alkyl, cycloalkyl, cycloalkylalkyl, bicycloalkyl, heterobicycloalkyl, spiroalkyl, spiroheteroalkyl, heterocycloalkyl, fluoroalkyl, heterocycloalkylalkyl, alkenyl, alkynyl, aryl, heteroaryl, arylalkyl, heteroarylalkyl and aminoalkyl are optionally substituted one or more times, or R$^{10}$ and R$^{11}$ when taken together with the nitrogen to which they are attached complete a 3- to 8-membered ring containing carbon atoms and optionally containing a heteroatom selected from O, S(O)$_x$, or NR$^{50}$ and which is optionally substituted one or more times;

R$^{14}$ is independently selected from the group consisting of hydrogen, alkyl, arylalkyl, cycloalkylalkyl, heteroarylalkyl, heterocyclylalkyl and halo, wherein alkyl, arylalkyl, cycloalkylalkyl, heteroarylalkyl and heterocyclylalkyl are optionally substituted one or more times;

R$^{16}$ is selected from the group consisting of cycloalkyl, heterocycloalkyl, bicycloalkyl, heterobicycloalkyl, spiroalkyl, spiroheteroalkyl, aryl, heteroaryl, cycloalkyl fused aryl, heterocycloalkyl fused aryl, cycloalkyl fused heteroaryl, heterocycloalkyl fused heteroaryl, cycloalkylalkyl, heterocycloalkylalkyl, bicycloalkylalkyl, heterobicycloalkylalkyl, spiroalkylalkyl, spiroheteroalkylalkyl, arylalkyl, heteroarylalkyl, cycloalkyl fused arylalkyl, heterocycloalkyl fused arylalkyl, cycloalkyl fused heteroarylalkyl, heterocycloalkyl fused heteroarylalkyl, (i) and (ii):

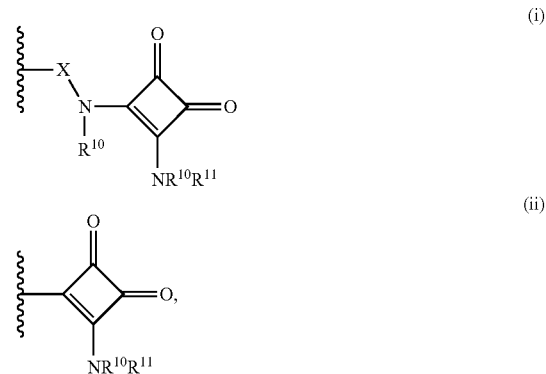

wherein cycloalkyl, heterocycloalkyl, bicycloalkyl, heterobicycloalkyl, spiroalkyl, spiroheteroalkyl, aryl, heteroaryl, cycloalkyl fused aryl, heterocycloalkyl fused aryl, cycloalkyl fused heteroaryl, heterocycloalkyl fused heteroaryl, cycloalkylalkyl, heterocycloalkylalkyl, bicycloalkylalkyl, heterobicycloalkylalkyl, spiroalkylalkyl, spiroheteroalkylalkyl, arylalkyl, heteroarylalkyl, cycloalkyl fused arylalkyl, heterocycloalkyl fused arylalkyl, cycloalkyl fused heteroarylalkyl, and heterocycloalkyl fused heteroarylalkyl are optionally substituted one or more times;

R$^{20}$ is selected from the group consisting of hydrogen and alkyl, wherein alkyl is optionally substituted one or more times;

R$^{21}$ is a bicyclic or tricyclic fused ring system, wherein at least one ring is partially saturated, and wherein R$^{21}$ is optionally substituted one or more times, or wherein R$^{21}$ is optionally substituted by one or more R$^9$ groups;

R$^{22}$ is selected from the group consisting of hydrogen, hydroxy, halo, alkyl, cycloalkyl, alkoxy, alkenyl, alkynyl, NO$_2$, NR$^{10}$R$^{11}$, CN, SR$^{10}$, SSR$^{10}$, PO$_3$R$^{10}$, NR$^{10}$NR$^{10}$R$^{11}$, NR$^{10}$N=CR$^{10}$R$^{11}$, NR$^{10}$SO$_2$R$^{11}$, C(O)OR$^{10}$, C(O)NR$^{10}$R$^{11}$, SO$_2$R$^{10}$, SO$_2$NR$^{10}$R$^{11}$ and fluoroalkyl, wherein alkyl, cycloalkyl, alkoxy, alkenyl, alkynyl, and fluoroalkyl are optionally substituted one or more times;

$R^{30}$ is selected from the group consisting of alkyl and ($C_0$-$C_6$)-alkyl-aryl, wherein alkyl and aryl are optionally substituted;

$R^{50}$ in each occurrence is independently selected from the group consisting of hydrogen, alkyl, aryl, heteroaryl, C(O)$R^{80}$, C(O)NR$^{80}$R$^{81}$, SO$_2$R$^{80}$ and SO$_2$NR$^{80}$R$^{81}$, wherein alkyl, aryl, and heteroaryl are optionally substituted one or more times;

$R^{80}$ and $R^{81}$ in each occurrence are independently selected from the group consisting of hydrogen, alkyl, cycloalkyl, cycloalkylalkyl, heterocycloalkyl, fluoroalkyl, heterocycloalkylalkyl, haloalkyl, alkenyl, alkynyl, aryl, heteroaryl, arylalkyl, heteroarylalkyl and aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl and aminoalkyl are optionally substituted, or $R^{80}$ and $R^{81}$ when taken together with the nitrogen to which they are attached complete a 3- to 8-membered ring containing carbon atoms and optionally a heteroatom selected from O, S(O)$_x$, —NH, and —N(alkyl) and which is optionally substituted one or more times;

E is selected from the group consisting of a bond, CR$^{10}$R$^{11}$, O, NR$^5$, S, S=O, S(=O)$_2$, C(=O), N(R$^{10}$)(C=O), (C=O)N(R$^{10}$), N(R$^{10}$)S(=O)$_2$, S(=O)$_2$N(R$^{10}$), C=N—OR$^{11}$, —C(R$^{10}$R$^{11}$)C(R$^{10}$R$^{11}$)—, —CH$_2$—W$^1$— and

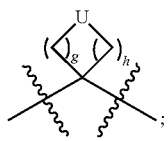

Q is a 5- or 6-membered ring selected from the group consisting of aryl and heteroaryl, wherein aryl and heteroaryl are optionally substituted one or more times with R$^4$;

D is a member selected from the group consisting of CR$^{22}$ and N;

U is selected from the group consisting of C(R$^5$R$^{10}$), NR$^5$, O, S, S=O and S(=O)$_2$;

W$^1$ is selected from the group consisting of O, NR$^5$, S, S=O, S(=O)$_2$, N(R$^{10}$)(C=O), N(R$^{10}$)S(=O)$_2$ and S(=O)$_2$N(R$^{10}$);

X is selected from the group consisting of a bond and (CR$^{10}$R$^{11}$)$_w$E(CR$^{10}$R$^{11}$)$_w$;

g and h are independently selected from 0-2;
w is independently selected from 0-4;
x is selected from 0 to 2;
y is selected from 1 and 2; and N-oxides, pharmaceutically acceptable salts, prodrugs, formulation, polymorphs, racemic mixtures and stereoisomers thereof.

In another embodiment, compounds of Formula (I) may be selected from Group I(a):

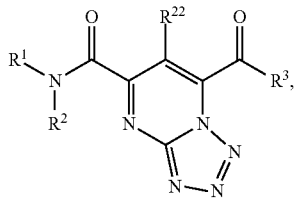

-continued

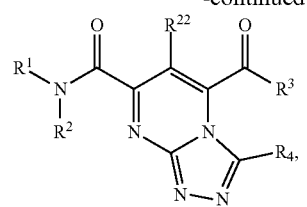

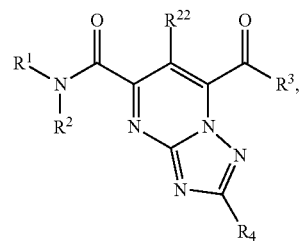

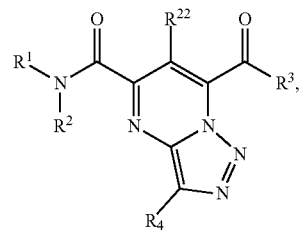

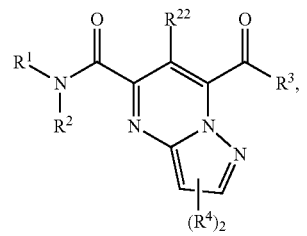

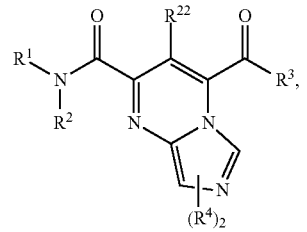

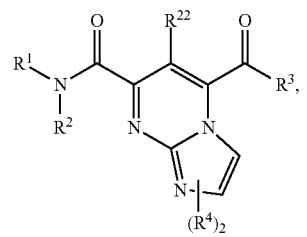

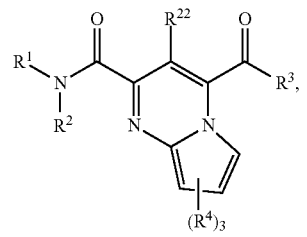

-continued

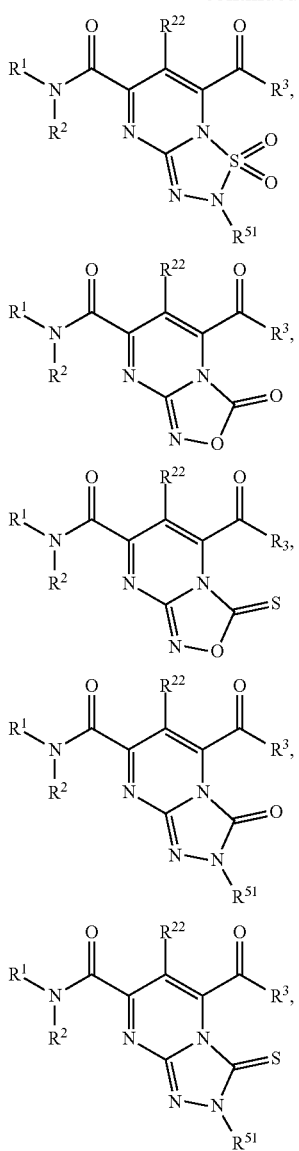

wherein:

R$^{51}$ is independently selected from the group consisting of hydrogen, alkyl, aryl, heteroaryl, arylalkyl, cycloalkylalkyl, heteroarylalkyl and haloalkyl, wherein alkyl, aryl, heteroaryl, arylalkyl, cycloalkylalkyl, heteroarylalkyl and haloalkyl are optionally substituted one or more times.

In still another embodiment, compounds of Formula (I) may be selected from:

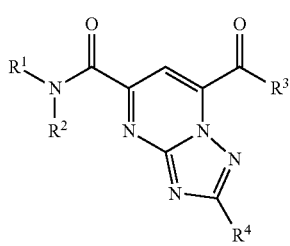

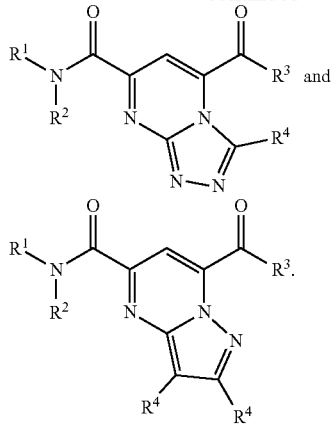

In yet another embodiment, compounds of Formula (I) may be selected from:

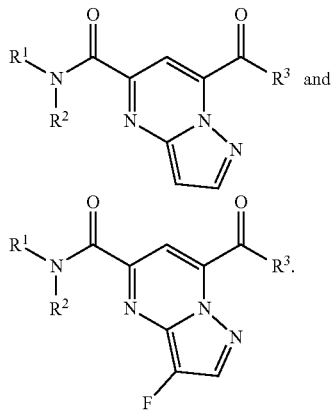

In some embodiments, R$^3$ of the compounds of Formula (I) may be selected from Substituent Group 1:

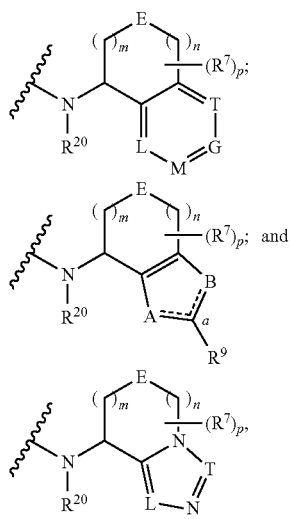

wherein:

R$^7$ is independently selected from the group consisting of hydrogen, alkyl, cycloalkyl, halo, R$^4$ and NR$^{10}$R$^{11}$, wherein alkyl and cycloalkyl are optionally substituted one or more times, or optionally two $R^7$ groups together at the same carbon atom form =O, =S or =NR$^{10}$;

A and B are independently selected from the group consisting of CR$^9$, CR$^9$R$^{10}$, NR$^{10}$, N, O and S(O)$_x$;

G, L, M and T are independently selected from the group consisting of CR$^9$ and N;

m and n are independently selected from 0-3, provided that:

(1) when E is present, m and n are not both 3;

(2) when E is —CH$_2$—W$^1$—, m and n are not 3; and (3) when E is a bond, m and n are not 0; and p is selected from 0-6;

wherein the dotted line represents a double bond between one of: carbon "a" and A, or carbon "a" and B.

For example, in some embodiments, $R^3$ of the compounds of Group 1(a) may be selected from Substituent Group 1 as defined hereinabove.

In some embodiments, $R^3$ of Formula (I) may be selected from Substituent Group I(2):

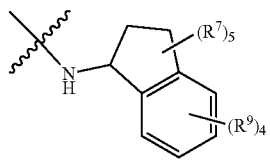

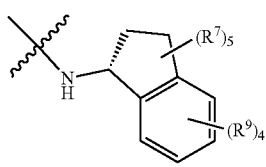

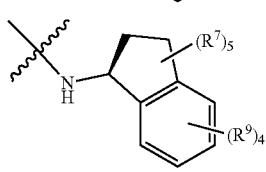

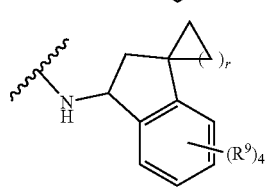

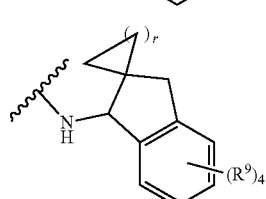

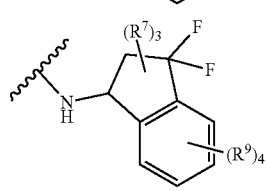

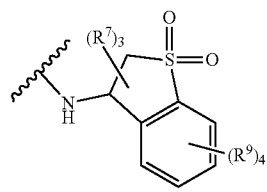

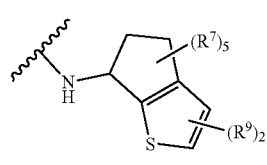

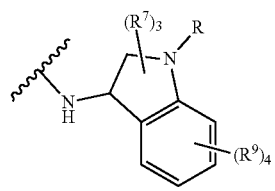

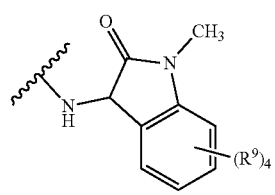

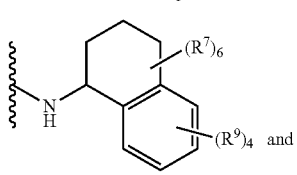 and

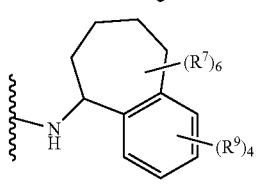

wherein:

R is selected from the group consisting of C(O)NR$^{10}$R$^{11}$, COR$^{10}$, SO$_2$NR$^{10}$R$^{11}$, SO$_2$R$^{10}$, CONHCH$_3$ and CON(CH$_3$)$_2$, wherein C(O)NR$^{10}$R$^{11}$, COR$^{10}$, SO$_2$NR$^{10}$R$^{11}$, SO$_2$R$^{10}$, CONHCH$_3$ and CON(CH$_3$)$_2$ are optionally substituted one or more times; and r is selected from 1-4.

For example, in some embodiments, $R^3$ of the compounds of Group I(a) may be selected from Substituent Group 2, as defined hereinabove.

In yet a further embodiment, $R^3$ of Formula (I) may be selected from Substituent Group 3:

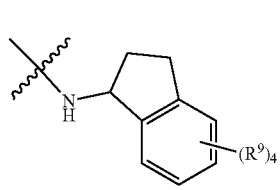

-continued
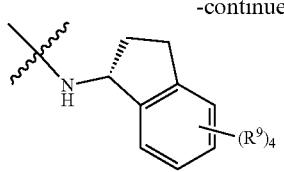
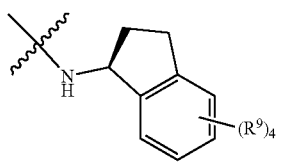
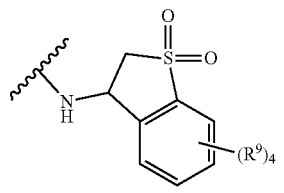
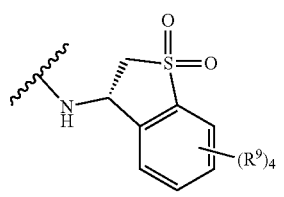
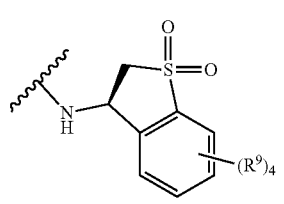
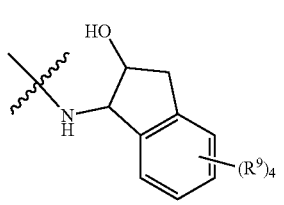
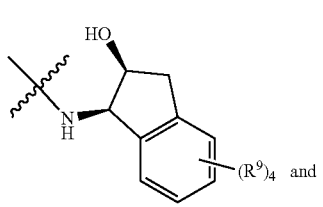
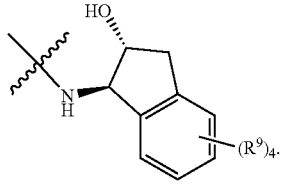
For example, in some embodiments, $R^3$ of the structures of Group I(a) may be selected from Substituent Group 3 as defined hereinabove.
In another embodiment, $R^9$ may be selected from Substituent Group 4:
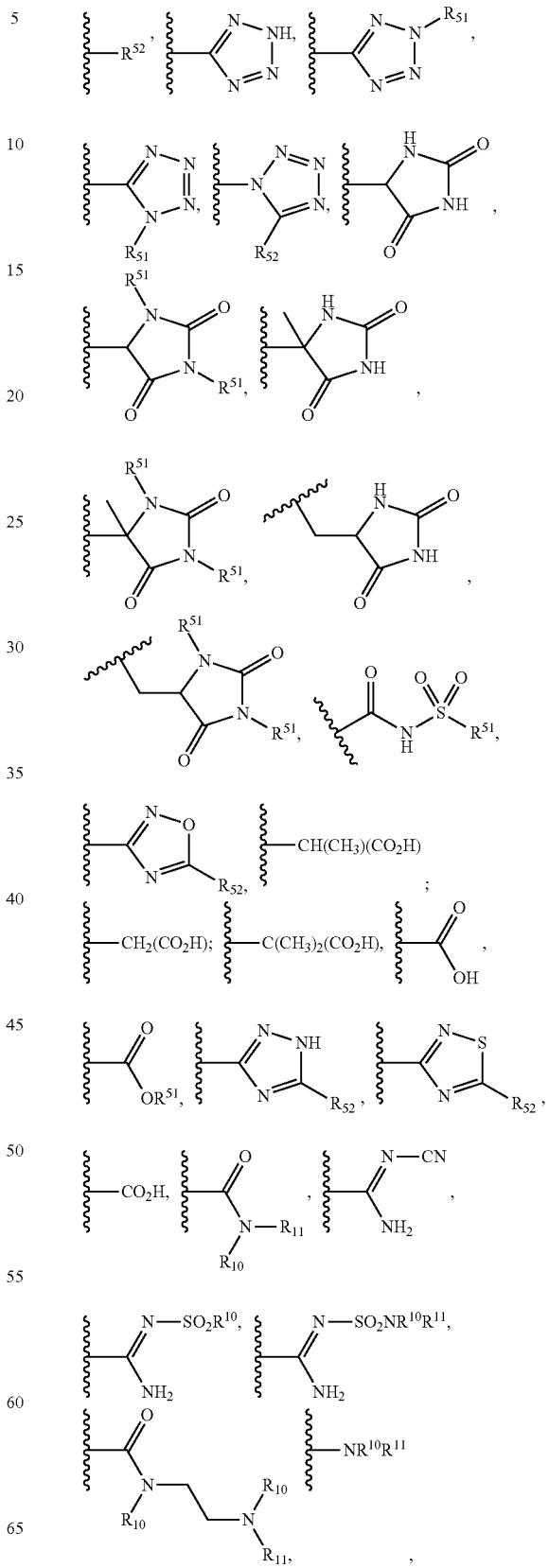

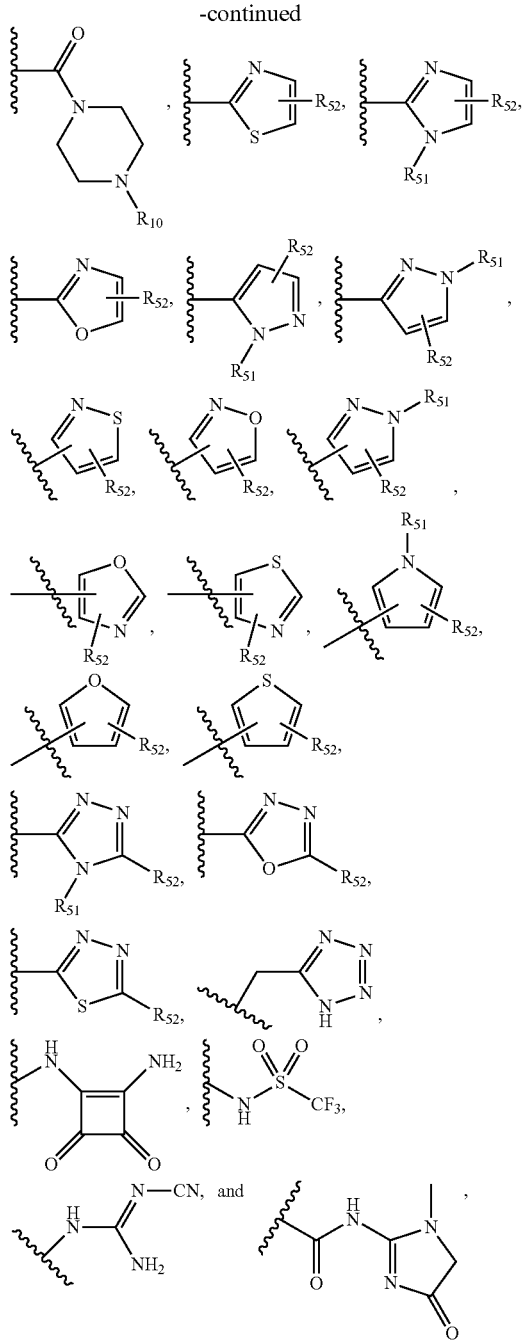

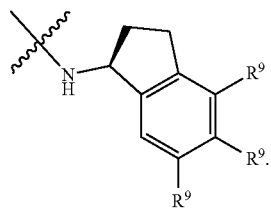

For example, in some embodiments, $R^3$ of the structures of Group I(a) may be selected from Substituent Group 16 as defined hereinabove.

In still a further embodiment, $R^3$ of Formula (I) may be selected from Substituent Group 5:

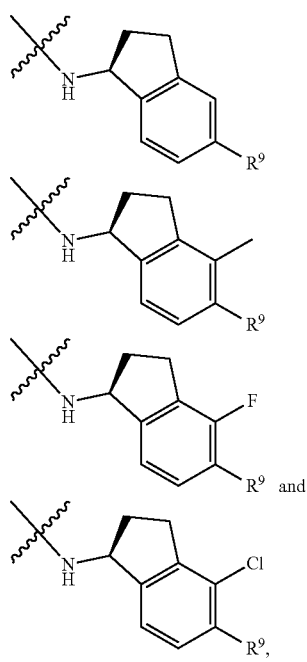

wherein:

$R^9$ is selected from the group consisting of hydrogen, fluoro, halo, CN, alkyl, $CO_2H$,

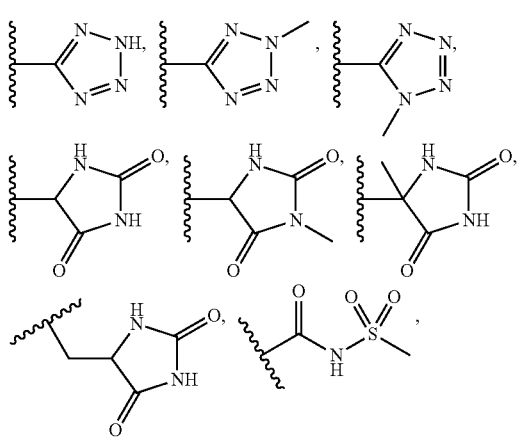

wherein:

$R^{52}$ is selected from the group consisting of hydrogen, halo, CN, hydroxy, alkoxy, fluoroalkoxy, alkyl, aryl, heteroaryl, arylalkyl, cycloalkylalkyl, heteroarylalkyl, haloalkyl, $C(O)NR^{10}R^{11}$ and $SO_2NR^{10}R^{11}$, wherein alkoxy, fluoroalkoxy, alkyl, aryl, heteroaryl, arylalkyl, cycloalkylalkyl, heteroarylalkyl, and haloalkyl are optionally substituted one or more times.

For example, in some embodiments, $R^9$ of Substituent Group 3 may be selected from Substituent Group 4 as defined hereinabove.

In yet a further embodiment, $R^3$ of the structures of Formula (I) may be Substituent Group 16:

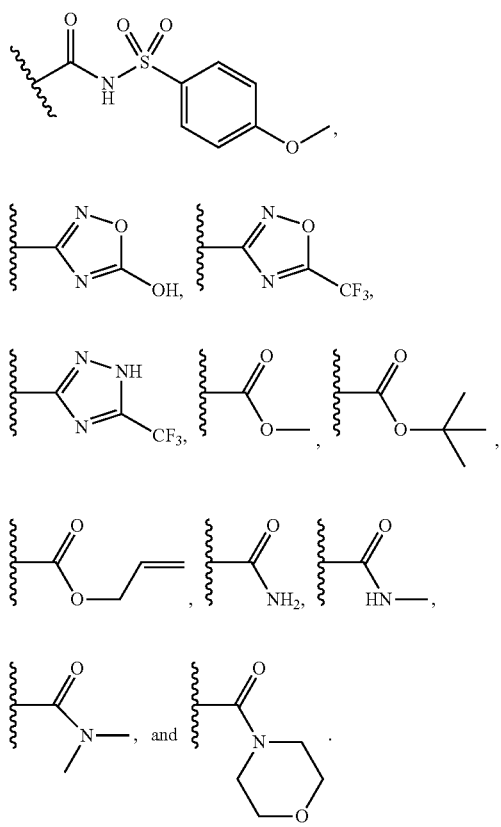

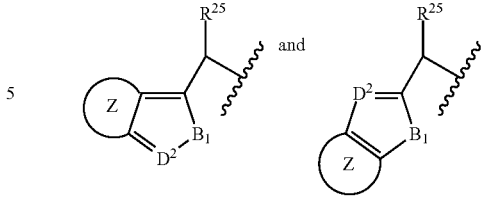

For example, in some embodiments, R³ of the structures of Group I(a) may be selected from Substituent Group 5 as defined hereinabove.

In another embodiment, R¹ of Formula (I) may be selected from Substituent Group 6:

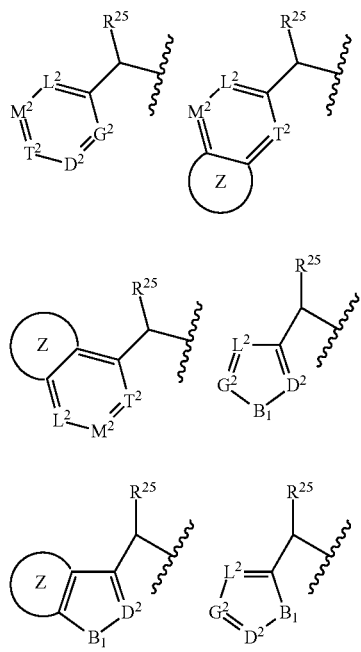

wherein:

R$^{18}$ is independently selected from the group consisting of hydrogen, alkyl, haloalkyl, cycloalkyl, heterocycloalkyl, alkynyl, aryl, heteroaryl, OH, halo, CN, C(O)NR$^{10}$R$^{11}$, CO$_2$R$^{10}$, OR$^{10}$, OCF$_3$, OCHF$_2$, NR$^{19}$CONR$^{10}$R$^{11}$, NR$^{10}$COR$^{11}$, NR$^{10}$SO$_2$R$^{11}$, NR$^{10}$SO$_2$NR$^{10}$R$^{11}$, SO$_2$NR$^{10}$R$^{11}$ and NR$^{10}$R$^{11}$, wherein alkyl, haloalkyl, cycloalkyl, heterocycloalkyl, alkynyl, aryl, heteroaryl are optionally substituted one or more times;

R$^{25}$ is selected from the group consisting of hydrogen, alkyl, cycloalkyl, CO$_2$R$^{10}$, C(O)NR$^{10}$R$^{11}$ and haloalkyl, wherein alkyl, cycloalkyl, and haloalkyl are optionally substituted one or more times;

B$_1$ is selected from the group consisting of NR$^{10}$, O and S(O)$_x$;

D$^2$, G$^2$, L$^2$, M$^2$ and T$^2$ are independently selected from the group consisting of CR$^{18}$ and N; and Z is a 5- to 8-membered ring selected from the group consisting of cycloalkyl, heterocycloalkyl, or a 5- to 6-membered ring selected from the group consisting of aryl and heteroaryl, wherein cycloalkyl, heterocycloalkyl, aryl and heteroaryl are optionally substituted one or more times.

For example, in another embodiment, R¹ of the structures of Group I(a) may be selected from Substituent Group 6 as defined hereinabove.

In yet another embodiment, R¹ of the structures of Group I(a) may be selected from Substituent Group 7:

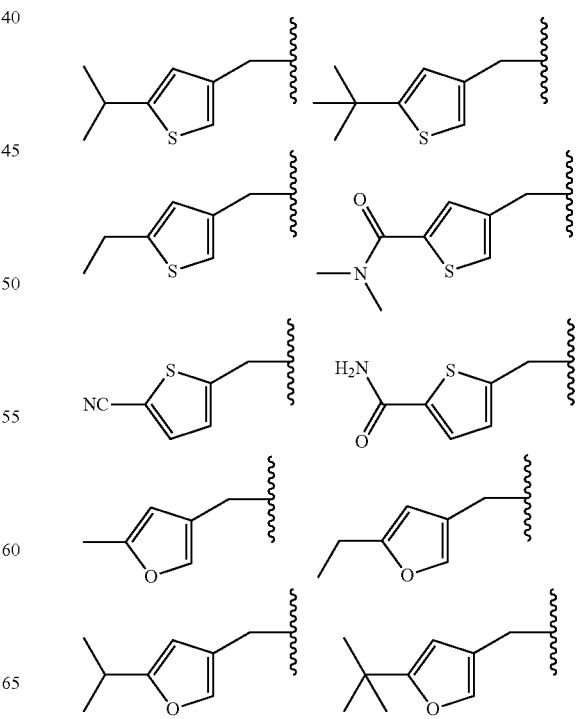

-continued
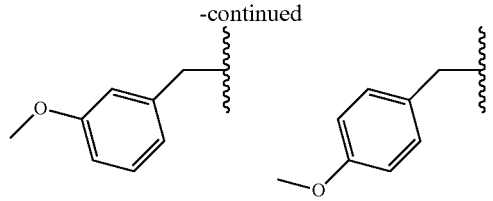
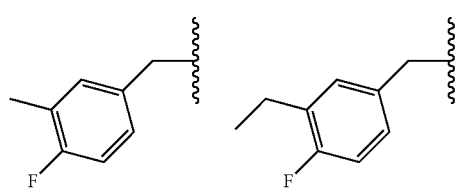
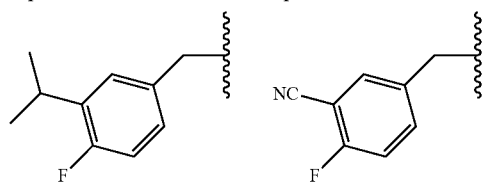
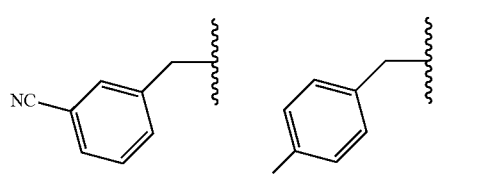

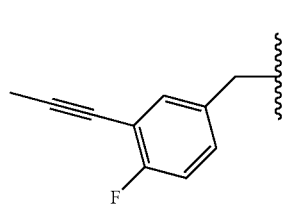
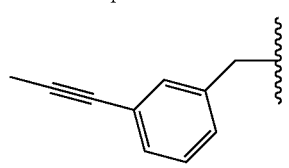
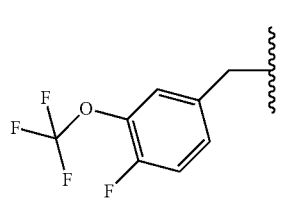
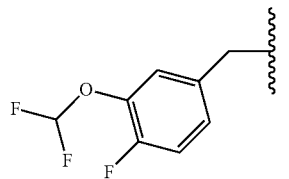
-continued
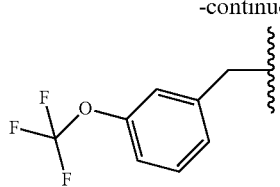
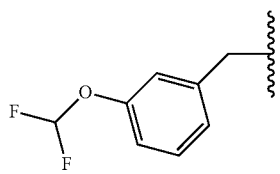
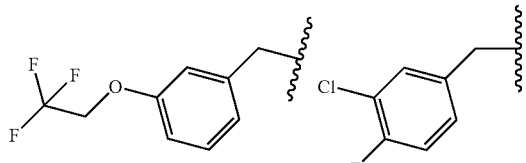
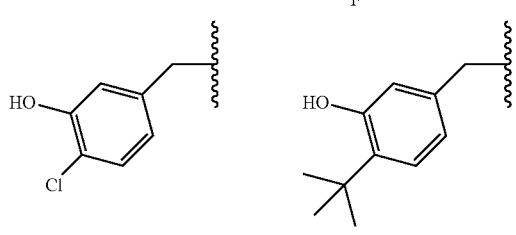
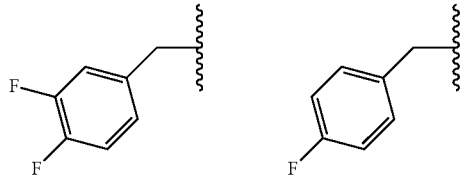
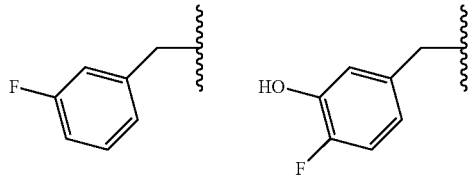
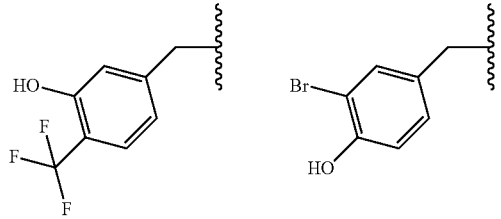
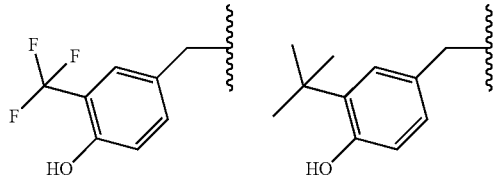
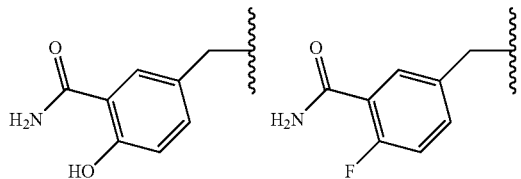

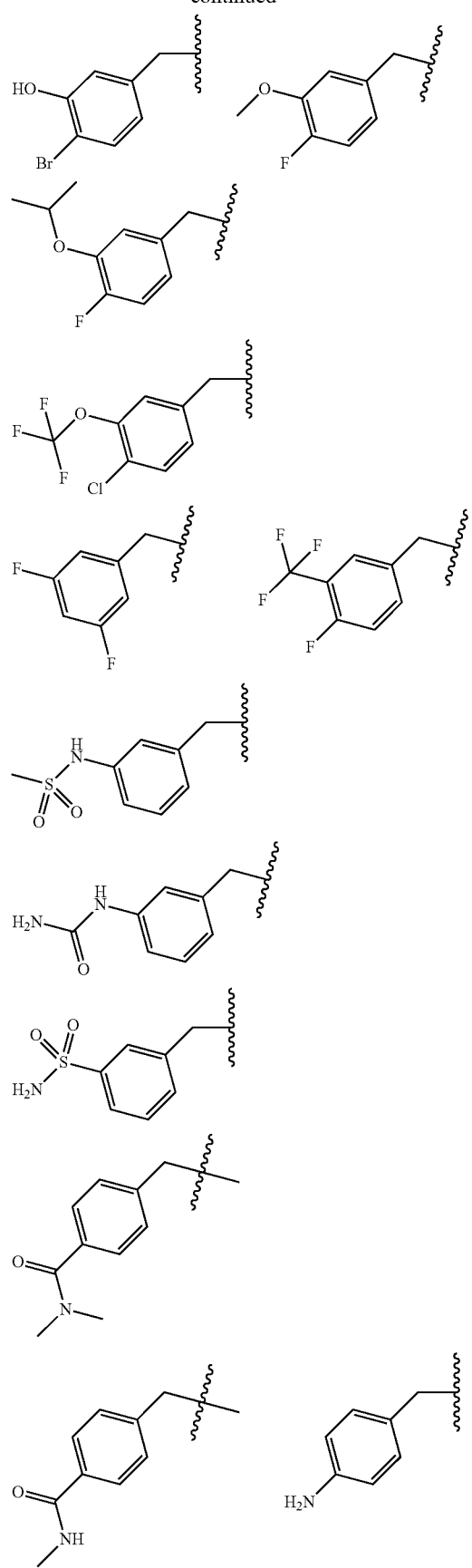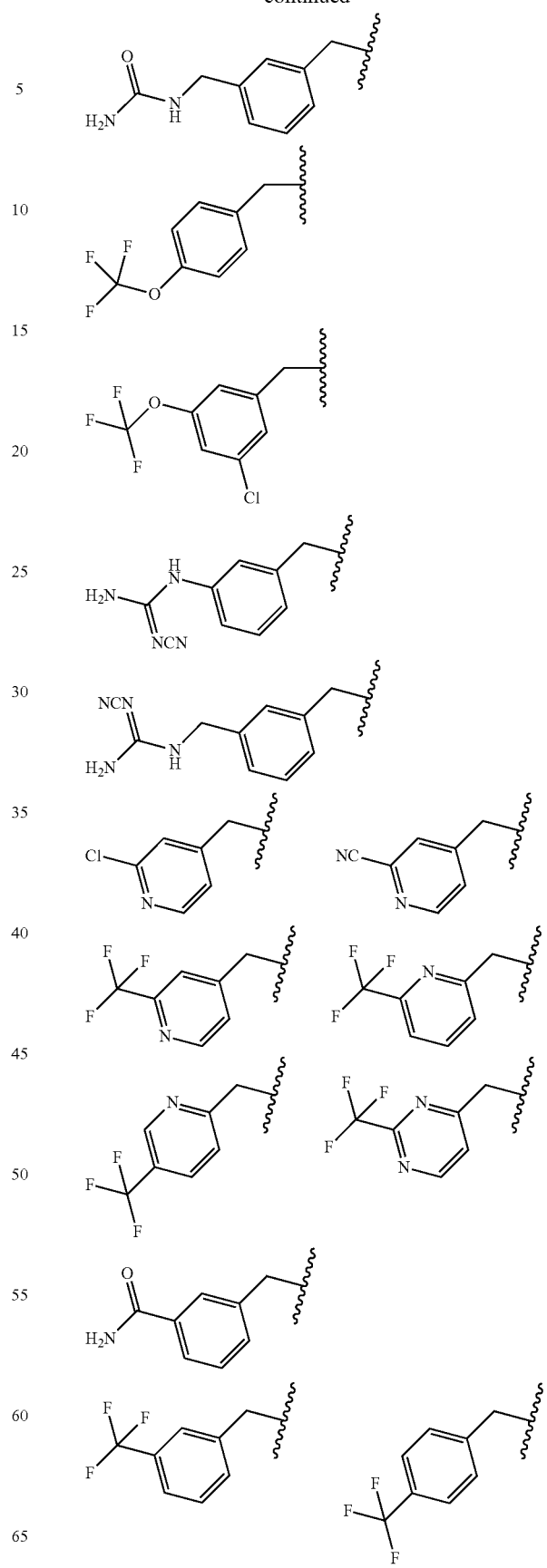

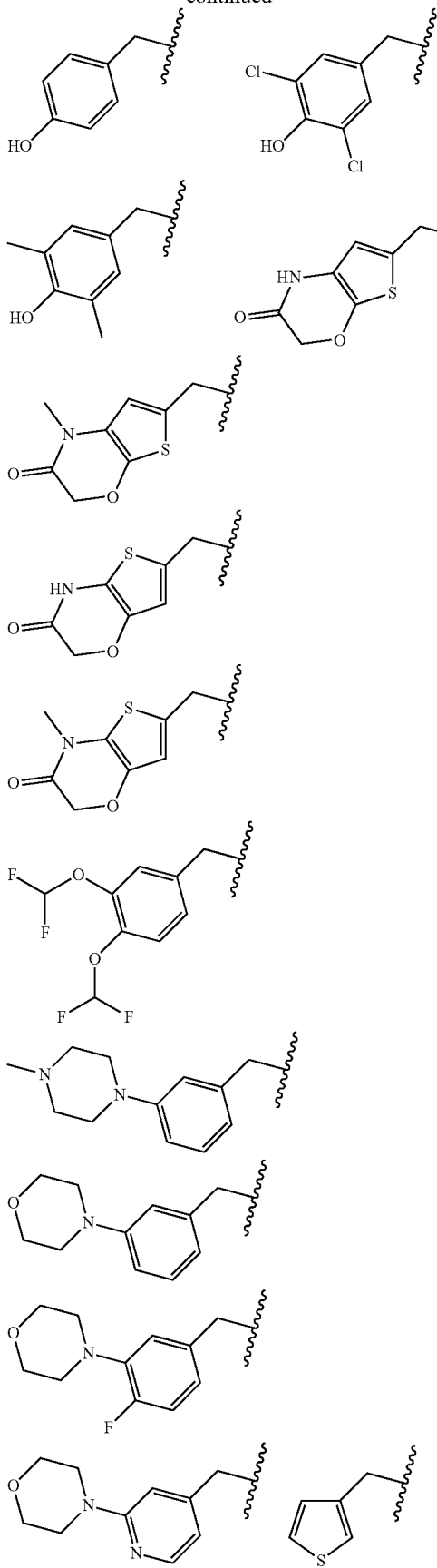
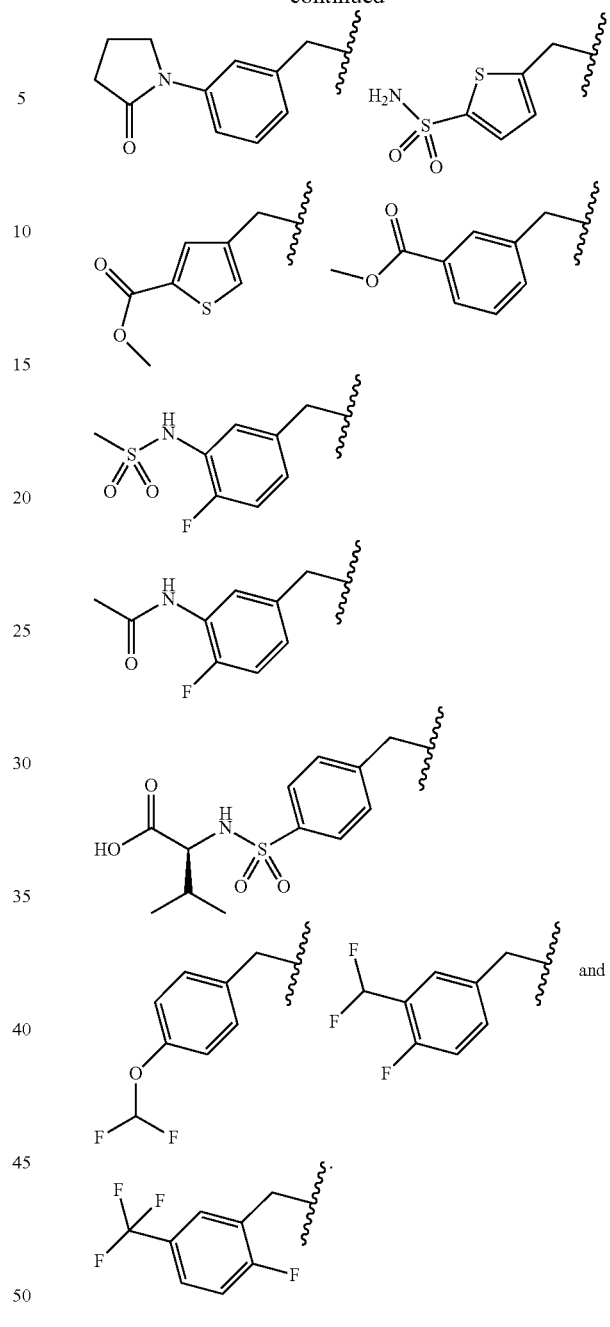
For example, in some embodiments, $R^1$ of the structures of Group I(a) may be selected from Substituent Group 7 as defined hereinabove.
In still another embodiment, $R^1$ of Formula (I) may be selected from Substituent Group 8:
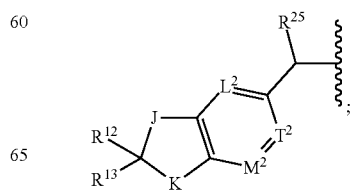

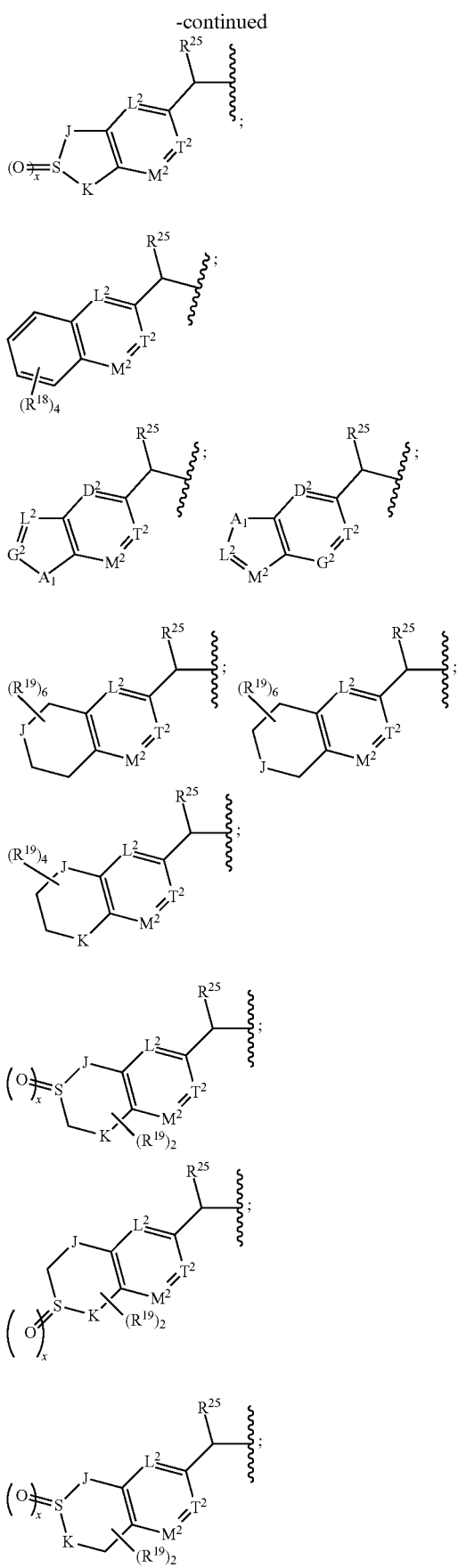
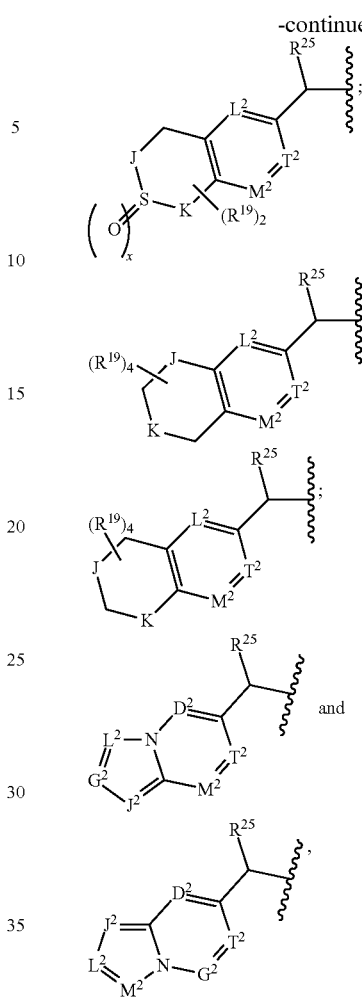

wherein:

$R^{12}$ and $R^{13}$ are independently selected from the group consisting of hydrogen, alkyl and halo, wherein alkyl is optionally substituted one or more times, or optionally $R^{12}$ and $R^{13}$ together form =O, =S or =NR$^{10}$;

$R^{18}$ is independently selected from the group consisting of hydrogen, alkyl, haloalkyl, cycloalkyl, heterocycloalkyl, alkynyl, aryl, heteroaryl, OH, halo, CN, C(O)NR$^{10}$R$^{11}$, CO$_2$R$^{10}$, OR$^{10}$, OCF$_3$, OCHF$_2$, NR$^{10}$CONR$^{10}$R$^{11}$, NR$^{10}$SO$_2$NR$^{10}$R$^{11}$, SO$_2$NR$^{10}$R$^{11}$ and NR$^{10}$R$^{11}$, wherein alkyl, haloalkyl, cycloalkyl, heterocycloalkyl, alkynyl, aryl, and heteroaryl are optionally substituted one or more times;

$R^{19}$ is independently selected from the group consisting of hydrogen, alkyl, haloalkyl, cycloalkyl, heterocycloalkyl, alkynyl, aryl, heteroaryl, OH, halo, CN, C(O)NR$^{10}$R$^{11}$, CO$_2$R$^{10}$, OR$^{10}$, OCF$_3$, OCHF$_2$, NR$^{10}$CONR$^{10}$R$^{11}$, NR$^{10}$COR$^{11}$, NR$^{10}$SO$_2$R$^{11}$, NR$^{10}$SO$_2$NR$^{10}$R$^{11}$, SO$_2$NR$^{10}$R$^{11}$ and NR$^{10}$R$^{11}$, wherein alkyl, haloalkyl, cycloalkyl, heterocycloalkyl, alkynyl, aryl, and heteroaryl are optionally substituted one or more times, or optionally two $R^{19}$ groups together at one carbon atom form =O, =S or =NR$^{10}$;

$R^{25}$ is selected from the group consisting of hydrogen, alkyl, cycloalkyl, CO$_2$R$^{10}$, C(O)NR$^{10}$R$^{11}$ and haloalkyl, wherein alkyl, cycloalkyl, and haloalkyl are optionally substituted one or more times;

J and K are independently selected from the group consisting of CR$^{10}$R$^{18}$, NR$^{10}$, O and S(O)$_x$;

$A_1$ is selected from the group consisting of $NR^{10}$, O and $S(O)_x$; and $D^2$, $G^2$, $J^2$, $L^2$, $M^2$ and $T^2$ are independently selected from the group consisting of $CR^{18}$ and N.

For example, some embodiments, $R^1$ of the structures of Group I(a) may be selected from Substituent Group 8 as defined hereinabove.

In a further embodiment, $R^1$ of Formula (I) may be selected from Substituent Group 9:

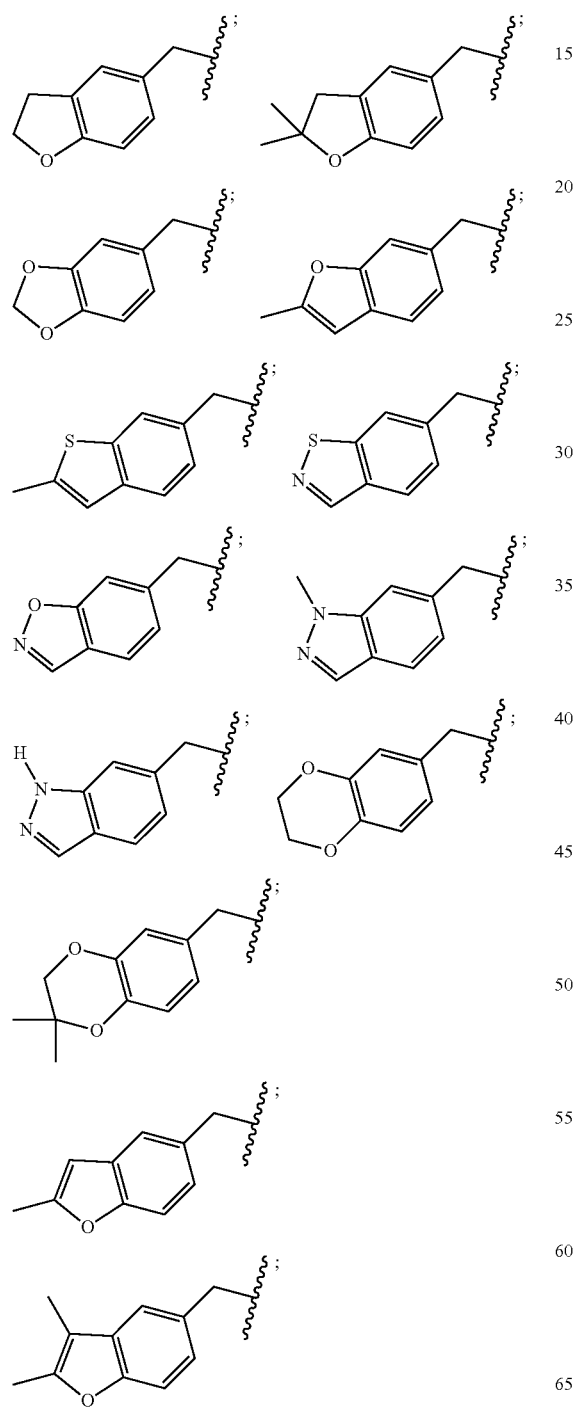

-continued

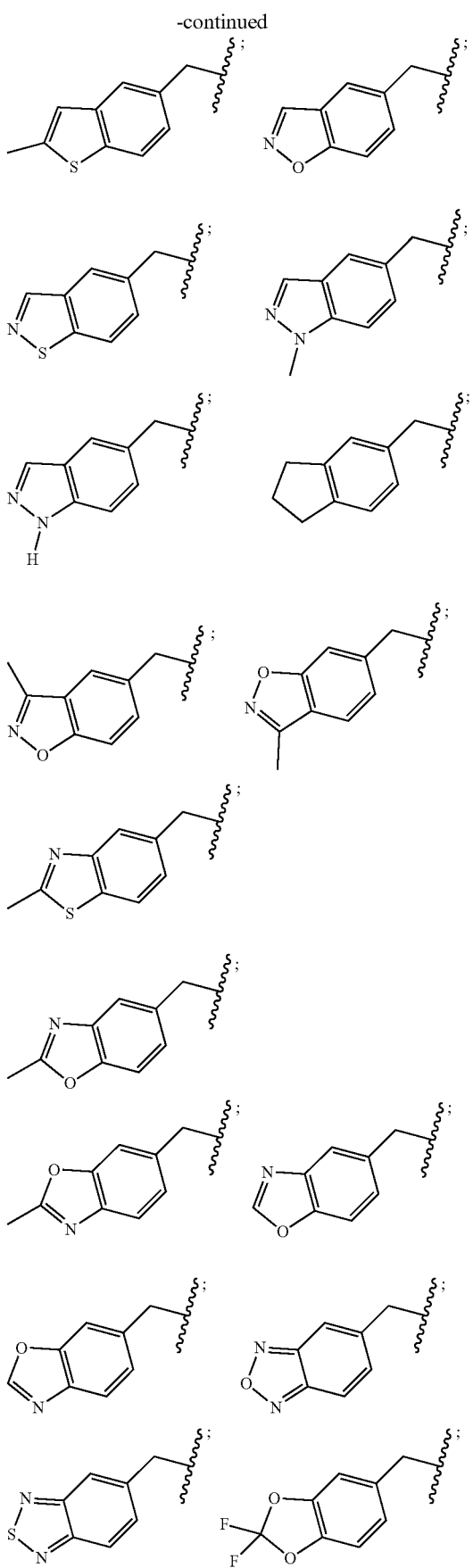

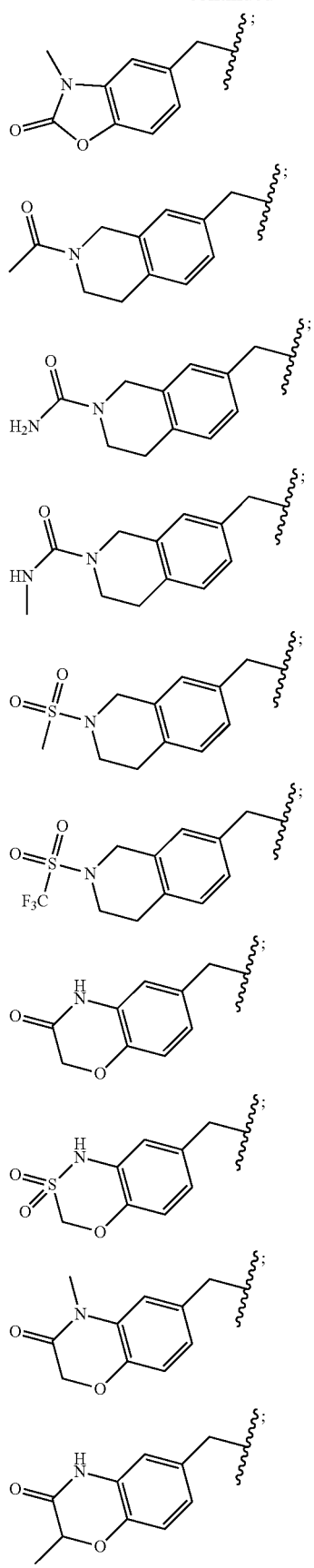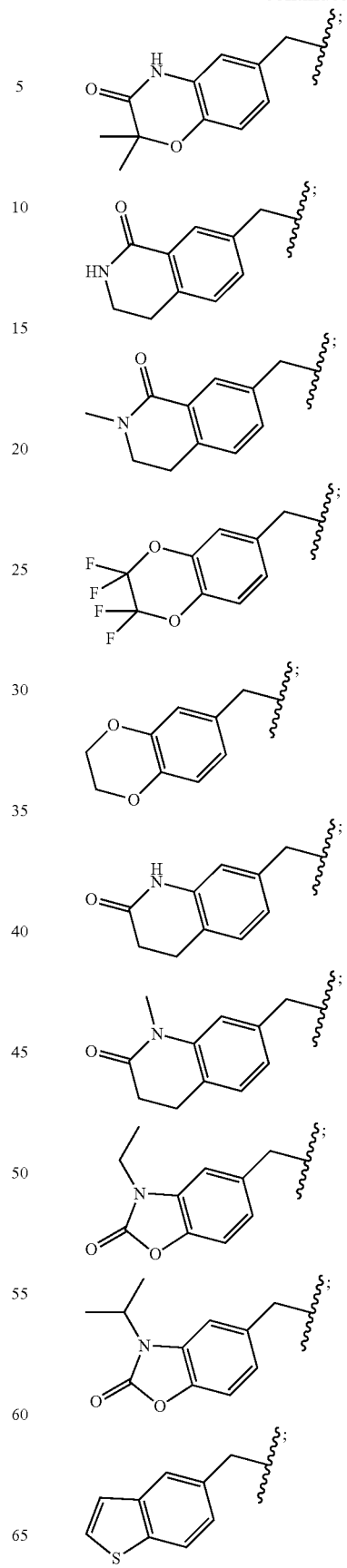

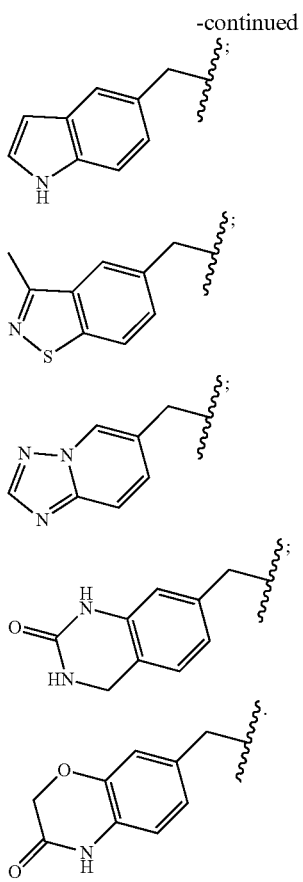

For example, in some embodiments, $R^1$ of the structures of Group I(a) may be selected from Substituent Group 9 as defined hereinabove.

In yet a further embodiment, $R^1$ of Formula (I) may be selected from Substituent Group 10:

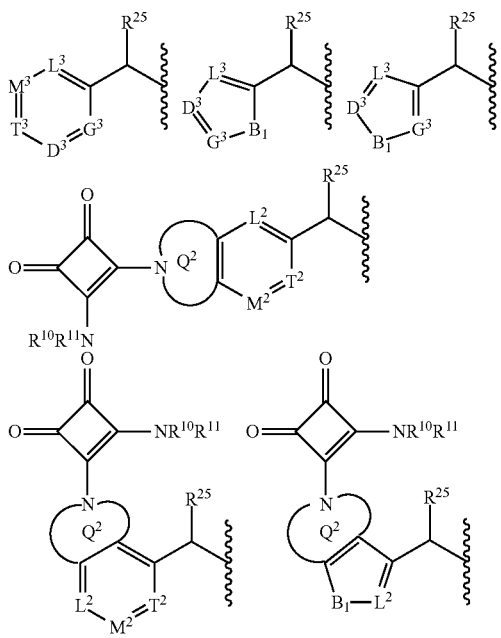

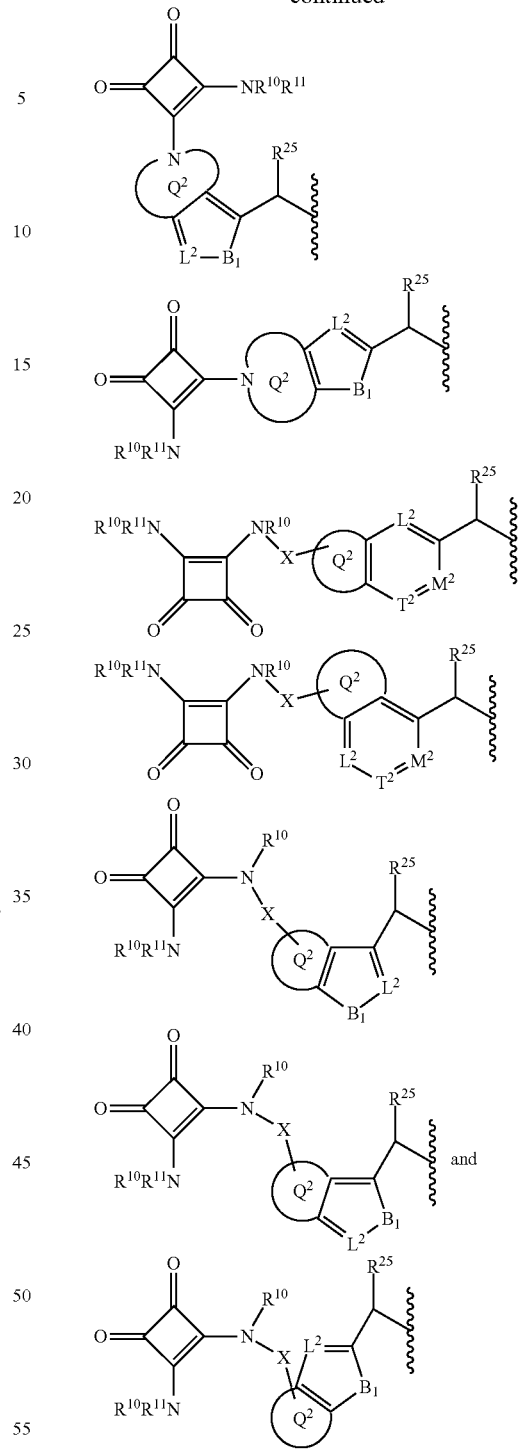

wherein:

$R^{18}$ is independently selected from the group consisting of hydrogen, alkyl, haloalkyl, cycloalkyl, heterocycloalkyl, alkynyl, aryl, heteroaryl, OH, halo, CN, $C(O)NR^{10}R^{11}$, $CO_2R^{10}$, $OR^{10}$, $OCF_3$, $OCHF_2$, $NR^{10}CONR^{10}R^{11}$, $NR^{10}COR^{11}$, $NR^{10}SO_2R^{11}$, $NR^{10}SO_2NR^{10}R^{11}$, $SO_2NR^{10}R^{11}$ and $NR^{10}R^{11}$, wherein alkyl, haloalkyl, cycloalkyl, heterocycloalkyl, alkynyl, aryl, and heteroaryl are optionally substituted one or more times;

$R^{19}$ is independently selected from the group consisting of hydrogen, alkyl, haloalkyl, cycloalkyl, heterocycloalkyl, alkynyl, aryl, heteroaryl, OH, halo, CN, C(O)NR$^{10}$R$^{11}$, CO$_2$R$^{10}$, OR$^{10}$, OCF$_3$, OCHF$_2$, NR$^{10}$CONR$^{10}$R$^{11}$, NR$^{10}$COR$^{11}$, NR$^{10}$SO$_2$R$^{11}$, NR$^{10}$SO$_2$NR$^{10}$R$^{11}$, SO$_2$NR$^{10}$R$^{11}$ and NR$^{10}$R$^{11}$, wherein alkyl, haloalkyl, cycloalkyl, heterocycloalkyl, alkynyl, aryl, and heteroaryl are optionally substituted one or more times, or optionally two $R^{10}$ groups together at one carbon atom form =O, =S or =NR$^{10}$;

$R^{25}$ is selected from the group consisting of hydrogen, alkyl, cycloalkyl, CONR$^{10}$R$^{11}$ and haloalkyl, wherein alkyl, cycloalkyl and haloalkyl are optionally substituted one or more times;

$L^2$, $M^2$, and $T^2$ are independently selected from the group consisting of CR$^{18}$ and N;

$D^3$, $G^3$, $L^3$, $M^3$, and $T^3$ are independently selected from N, CR$^{18}$, (i), or (ii),

with the proviso that one of $L^3$, $M^3$, $T^3$, $D^3$, and $G^3$ is (i) or (ii)

$B_1$ is selected from the group consisting of NR$^{10}$, O and S(O)$_x$; and $Q^2$ is a 5- to 8-membered ring selected from the group consisting of cycloalkyl, heterocycloalkyl, aryl, and heteroaryl, which is optionally substituted one or more times with R$^{19}$.

For example, in some embodiments, R$^1$ of the structures of Group I(a) may be selected from Substituent Group 10 as defined herinabove.

In still a further embodiment, R$^1$ of Formula (I) may be selected from Substituent Group 11:

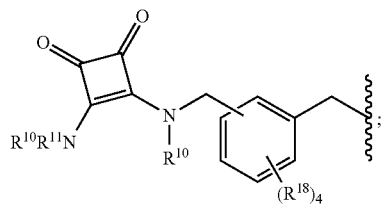

-continued

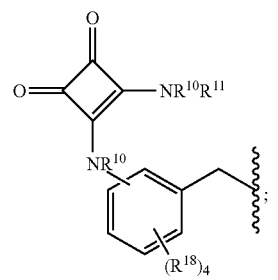

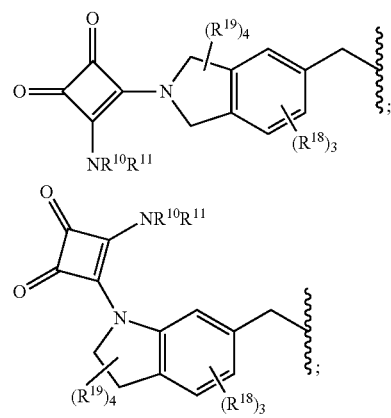

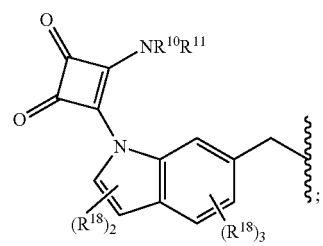

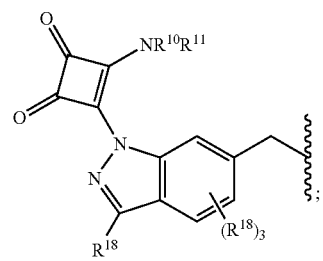

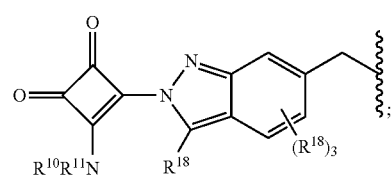

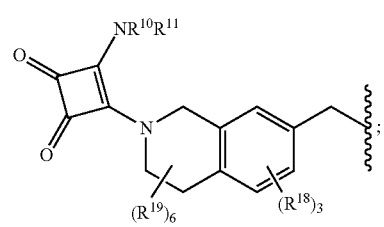

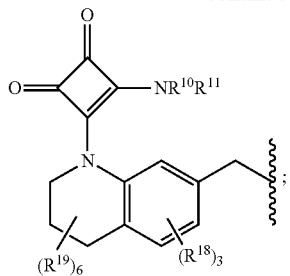
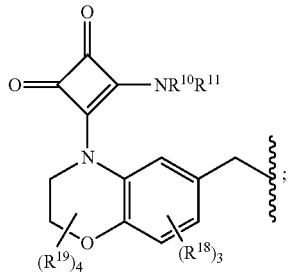
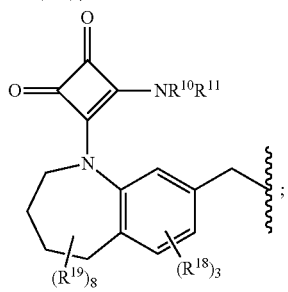
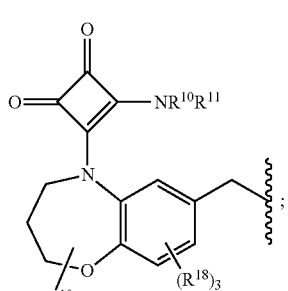
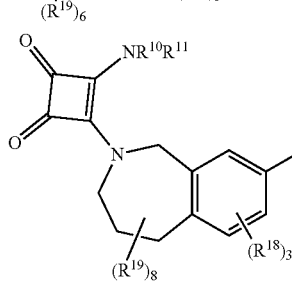
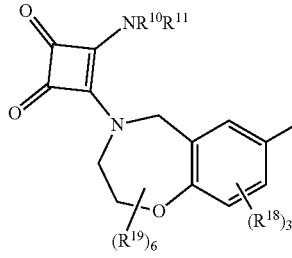
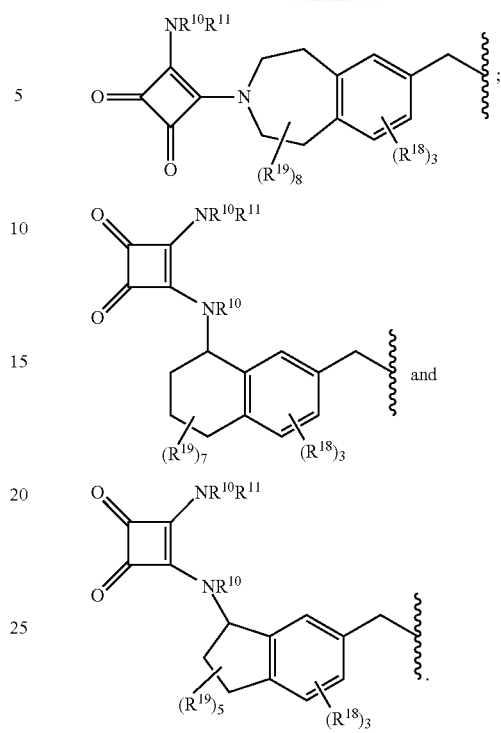
For example, in some embodiments, $R^1$ of the structures of Group I(a) may be selected from Substituent Group 11 as defined hereinabove.
In another embodiment, $R^1$ of Formula (I) may be selected from Substituent Group 12:
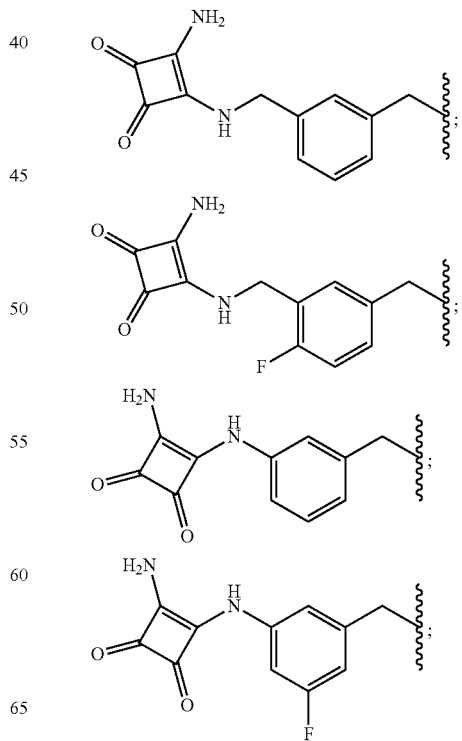

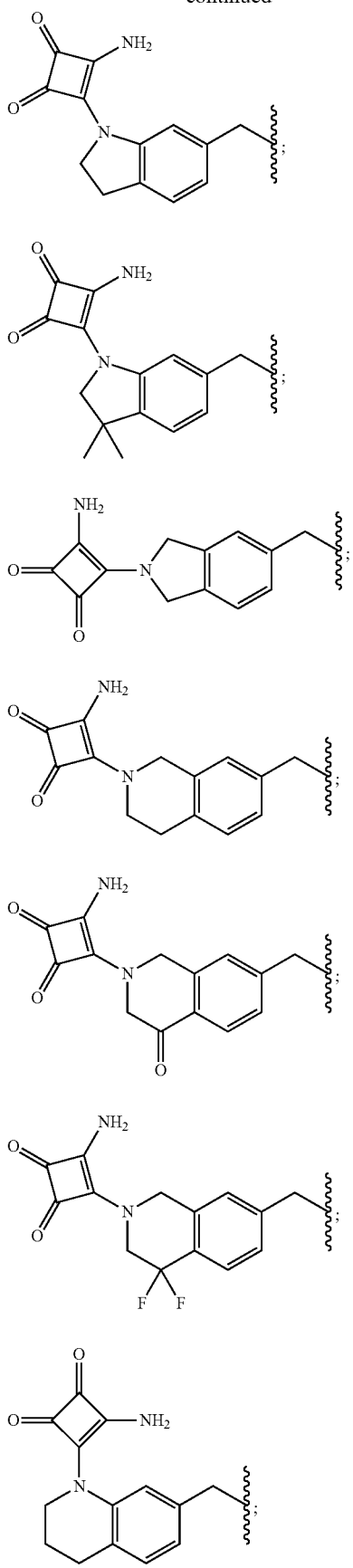
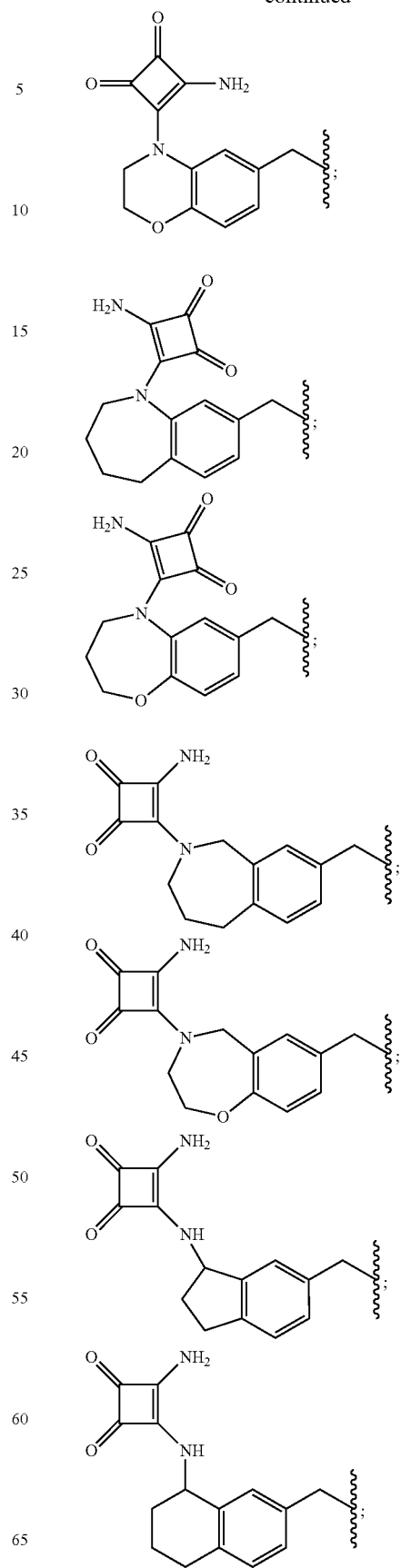

-continued

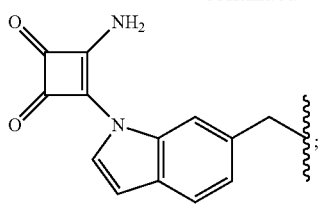

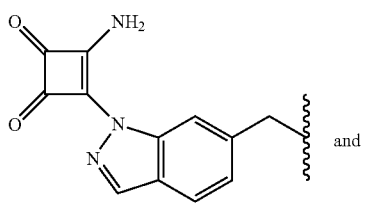 and

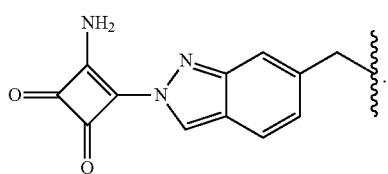

For example, in some embodiments, $R^1$ of the structures of Group I(a) may be selected from Substituent Group 12 as defined hereinabove.

In yet another embodiment, the amide containing heterobicyclic metalloprotease compounds may be represented by the general Formula (II):

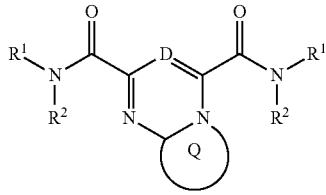

Formula (II)

and N-oxides, pharmaceutically acceptable salts, prodrugs, formulation, polymorphs, racemic mixtures and stereoisomers thereof, wherein:

$R^1$ in each occurrence may be the same or different and is as defined hereinabove;

$R^2$ in each occurrence may be the same or different and is as defined hereinabove; and all remaining variables are as defined hereinabove.

In still another embodiment, the compound of Formula (II) may be selected from Group II(a):

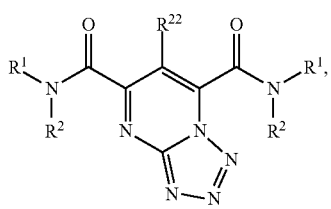

-continued



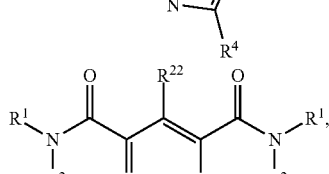

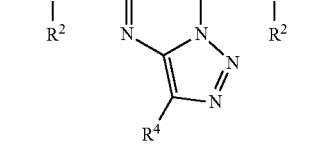

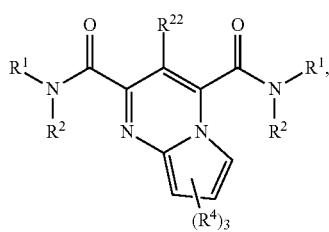

-continued
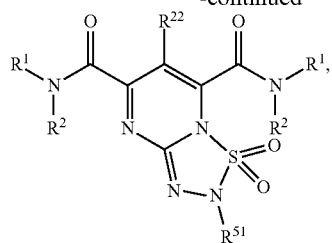
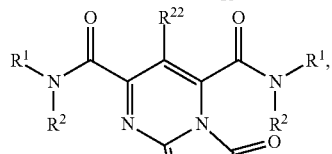
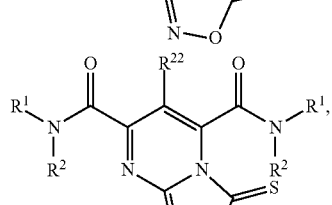
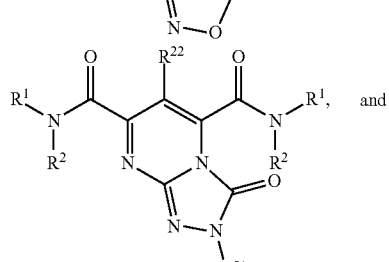
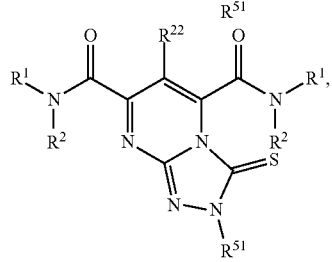
wherein all variables are as defined hereinabove.
In a further embodiment, the compound of Formula (II) may be selected from:
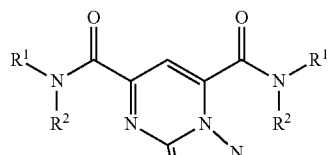
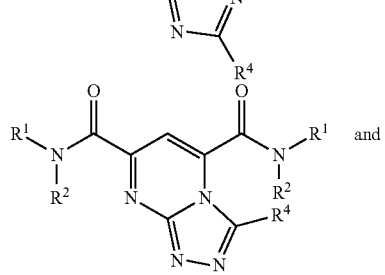
-continued
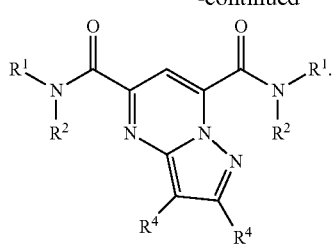
In yet a further embodiment, the compound of Formula (II) may be selected from:
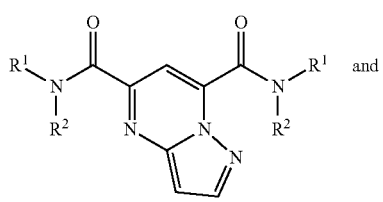
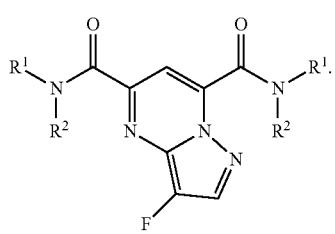
In still a further embodiment, at least one $R^1$ of Formula (II) may be selected from Substituent Group 13:
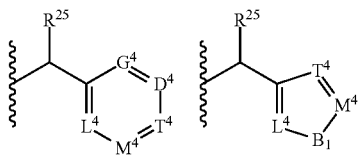
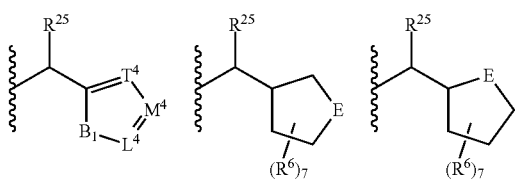
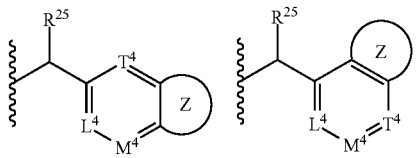
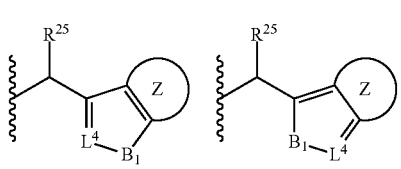

-continued

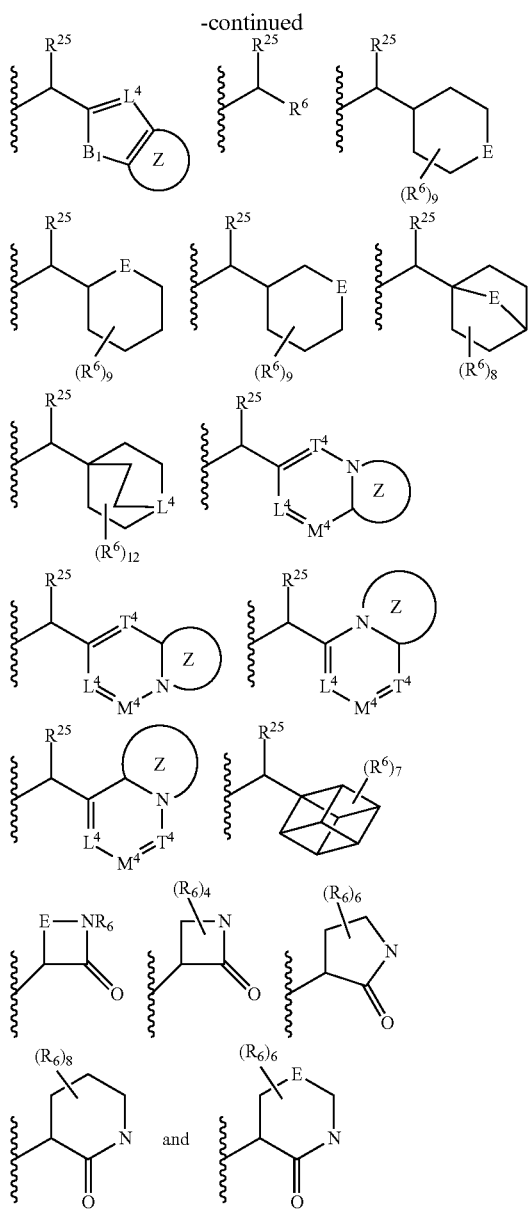

wherein:

$R^6$ is independently selected from the group consisting of $R^9$, alkenyl, alkynyl, cycloalkyl, heterocycloalkyl, bicycloalkyl, heterobicycloalkyl, spiroalkyl, spiroheteroalkyl, aryl, heteroaryl, $C(O)OR^{10}$, $CH(CH_3)CO_2H$, $(C_0\text{-}C_6)$-alkyl-$COR^{10}$, $(C_0\text{-}C_6)$-alkyl-$OR^{10}$, $(C_0\text{-}C_6)$-alkyl-$NR^{10}R^{11}$, $(C_0\text{-}C_6)$-alkyl-$NO_2$, $(C_0\text{-}C_6)$-alkyl-CN, $(C_0\text{-}C_6)$-alkyl-$S(O)_yOR^{10}$, $(C_0\text{-}C_6)$-alkyl-$P(O)_2OH$, $(C_0\text{-}C_6)$-alkyl-$S(O)_yNR^{10}R^{11}$, $(C_0\text{-}C_6)$-alkyl-$NR^{10}CONR^{11}SO_2R^{30}$, $(C_0\text{-}C_6)$-alkyl-$S(O)_xR^{10}$, $(C_0\text{-}C_6)$-alkyl-$OC(O)R^{10}$, $(C_0\text{-}C_6)$-alkyl-$OC(O)NR^{10}R^{11}$, $(C_0\text{-}C_6)$-alkyl-$C(=NR^{10})NR^{10}R^{11}$, $(C_0\text{-}C_6)$-alkyl-$NR^{10}C(=NR^{11})NR^{10}R^{11}$, $(C_0\text{-}C_6)$-alkyl-$NR^{10}C(=N\text{-}CN)NR^{10}R^{11}$, $(C_0\text{-}C_6)$-alkyl-$C(=N\text{-}CN)NR^{10}R^{11}$, $(C_0\text{-}C_6)$-alkyl-$NR^{10}C(=N\text{-}NO_2)NR^{10}R^{11}$, $(C_0\text{-}C_6)$-alkyl-$C(=N\text{-}NO_2)NR^{10}R^{11}$, $(C_0\text{-}C_6)$-alkyl-$C(O)OR^{10}$, $(C_0\text{-}C_6)$-alkyl-$C(O)NR^{10}R^{11}$, $(C_0\text{-}C_6)$-alkyl-$C(O)NR^{10}SO_2R^{11}$, $C(O)NR^{10}\text{---}(C_0\text{-}C_6)$-alkyl-heteroaryl, $C(O)NR^{10}\text{---}(C_0\text{-}C_6)$-alkyl-aryl, $S(O)_2NR^{10}\text{---}(C_0\text{-}C_6)$-alkyl-aryl, $S(O)_2NR^{10}\text{---}(C_0\text{-}C_6)$-alkyl-heteroaryl, $S(O)_2NR^{10}$-alkyl, $S(O)_2\text{---}(C_0\text{-}C_6)$-alkyl-aryl, $S(O)_2\text{---}(C_0\text{-}C_6)$-alkyl-heteroaryl, $(C_0\text{-}C_6)$-alkyl-$C(O)\text{---}NR^{11}\text{---}CN$, $O\text{---}(C_0\text{-}C_6)$-alkyl-$C(O)NR^{10}R^{11}$, $S(O)_x\text{---}(C_0\text{-}C_6)$-alkyl-$C(O)OR^{10}$, $S(O)_x\text{---}(C_0\text{-}C_6)$-alkyl-$C(O)NR^{10}R^{11}$, $(C_0\text{-}C_6)$-alkyl-$C(O)NR^{10}\text{---}(C_0\text{-}C_6)$-alkyl-$NR^{10}R^{11}$, $(C_0\text{-}C_6)$-alkyl-$NR^{10}\text{---}C(O)OR^{10}$, $(C_0\text{-}C_6)$-alkyl-$NR^{10}\text{---}C(O)\text{---}NR^{10}R^{11}$, $(C_0\text{-}C_6)$-alkyl-$NR^{10}\text{---}S(O)_yNR^{10}R^{11}$, $(C_0\text{-}C_6)$-alkyl-$NR^{10}\text{---}S(O)_yR^{11}$, $O\text{---}(C_0\text{-}C_6)$-alkyl-aryl and $O\text{---}(C_0\text{-}C_6)$-alkyl-heteroaryl, wherein each $R^6$ group is optionally substituted by one or more $R^{14}$ groups;

$R^9$ is independently selected from the group consisting of hydrogen, alkyl, halo, $CHF_2$, $CF_3$, $OR^{10}$, $NR^{10}R^{11}$, $NO_2$, and CN, wherein alkyl is optionally substituted one or more times;

$D^4$, $G^4$, $L^4$, $M^4$, and $T^4$ are independently selected from $CR^6$ and N; and all remaining variables are as defined hereinabove.

For example, in some embodiments, at least one $R^1$ of the structures of Group II(a) may independently be selected from Substituent Group 13 as defined hereinabove.

In another embodiment, at least one $R^1$ of Formula (II) may be selected from Substituent Group 14:

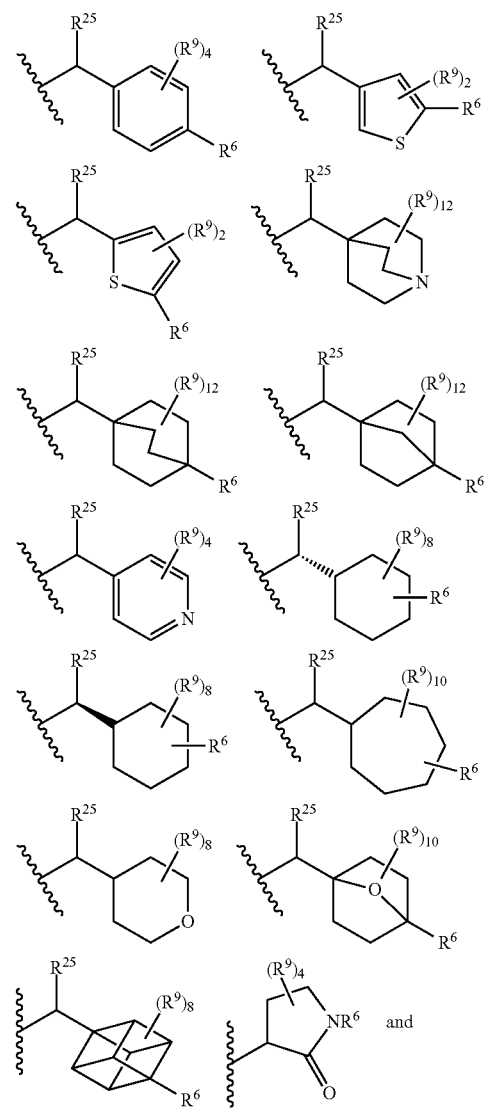

-continued

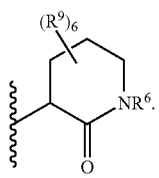

For example, in some embodiments, at least one $R^1$ of Group II(a) may independently be selected from Substituent Group 14 as defined hereinabove.

In yet another embodiment, $R^6$ of Substituent Group 14 may be selected from hydrogen, halo, CN, OH, $CH_2OH$, $CF_3$, $CHF_2$, $OCF_3$, $OCHF_2$, $COCH_3$, $SO_2CH_3$, $SO_2CF_3$, $SO_2NH_2$, $SO_2NHCH_3$, $SO_2N(CH_3)_2$, $NH_2$, $NHCOCH_3$, $N(COCH_3)_2$, $NHCONH_2$, $NHSO_2CH_3$, alkoxy, alkyl, cycloalkyl, heterocycloalkyl, bicycloalkyl, $CO_2H$,

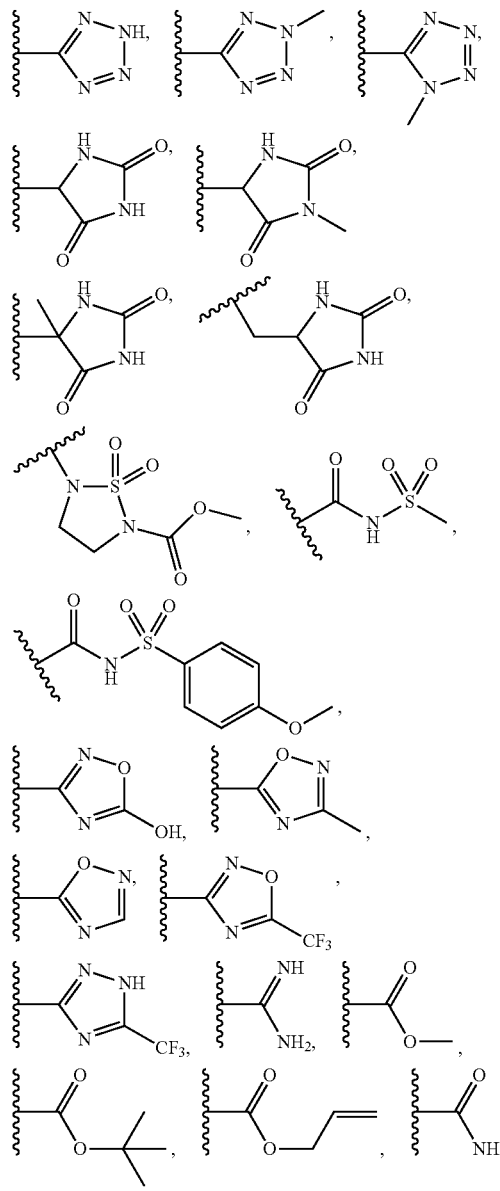

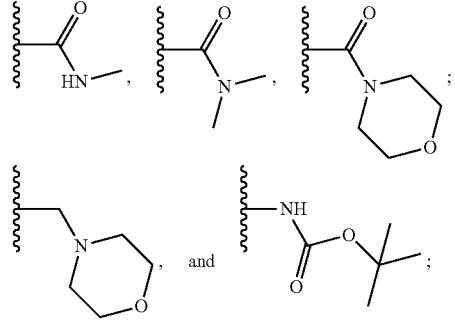

$R^9$ is independently selected from the group consisting of hydrogen, fluoro, chloro, $CH_3$, $CF_3$, $CHF_2$, $OCF_3$, and $OCHF_2$;

$R^{25}$ is selected from the group consisting of hydrogen, $CH_3$, $COOCH_3$, $COOH$, and $CONH_2$.

In yet another embodiment, at least one $R^1$ of Formula (II) may be selected from Substituent Group 15:

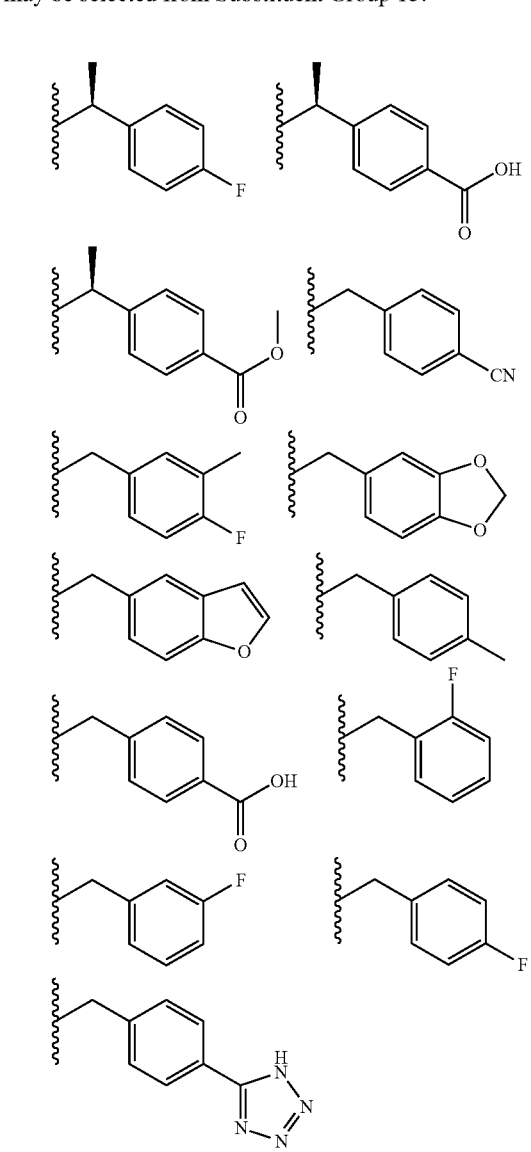

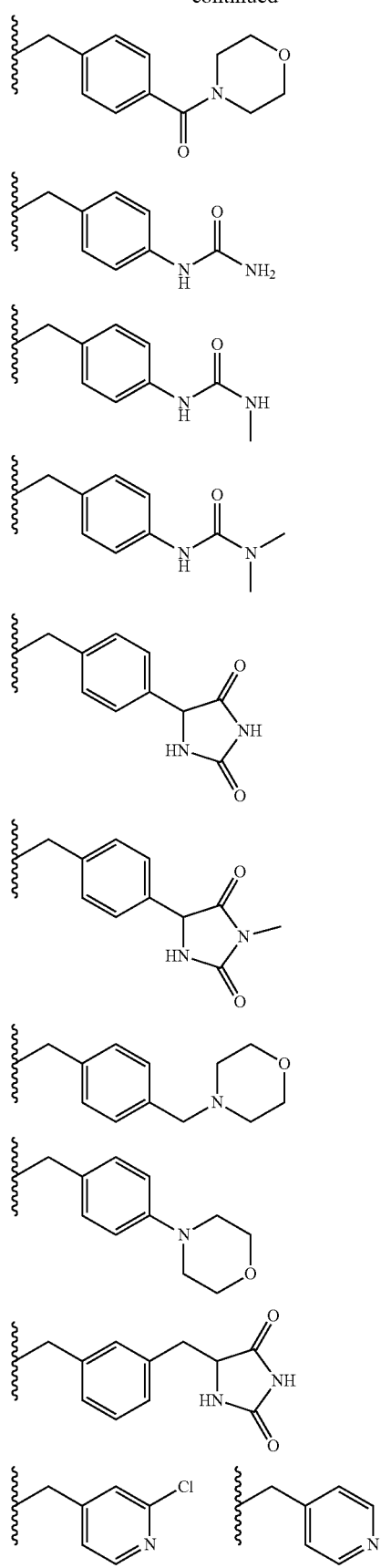
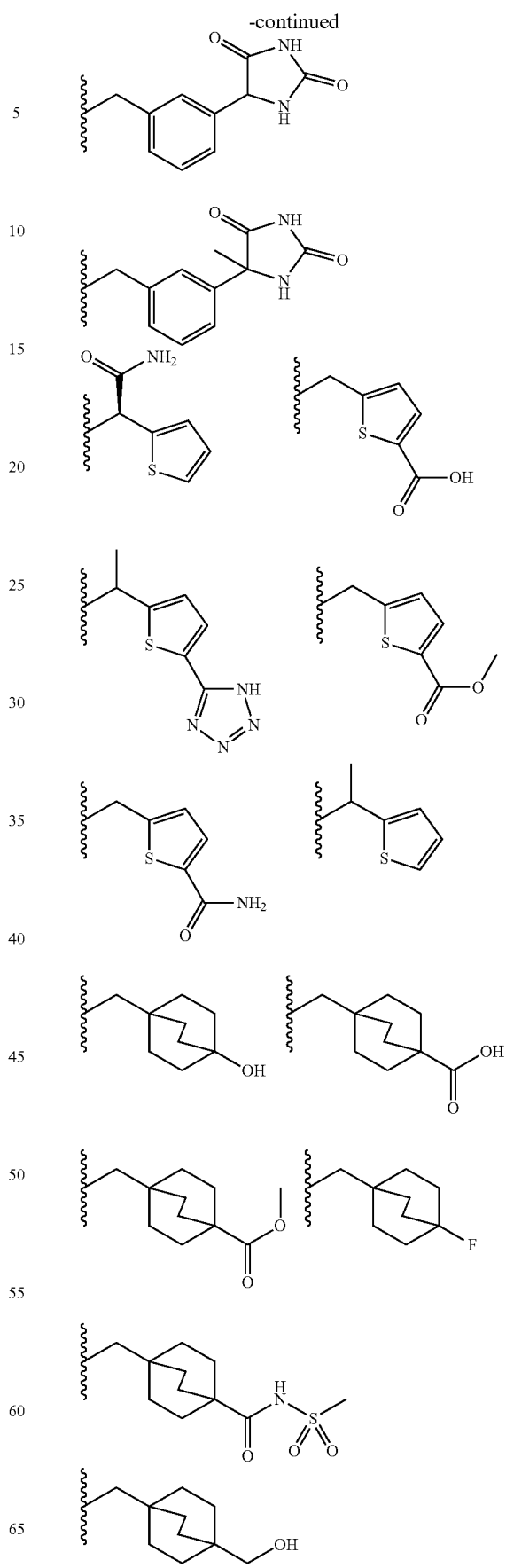

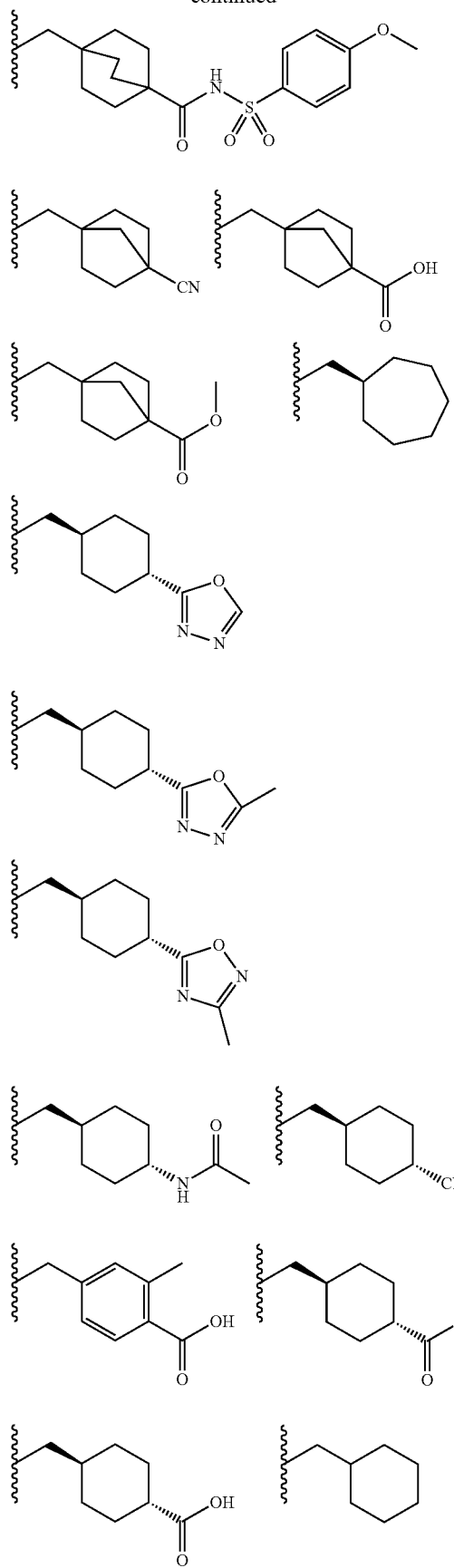
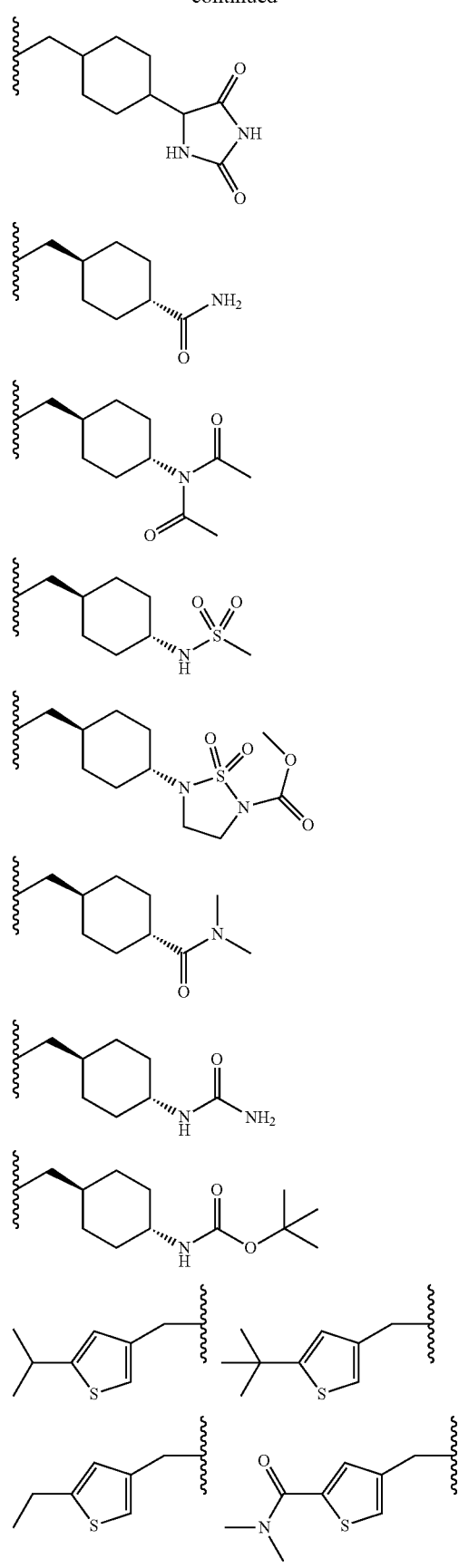

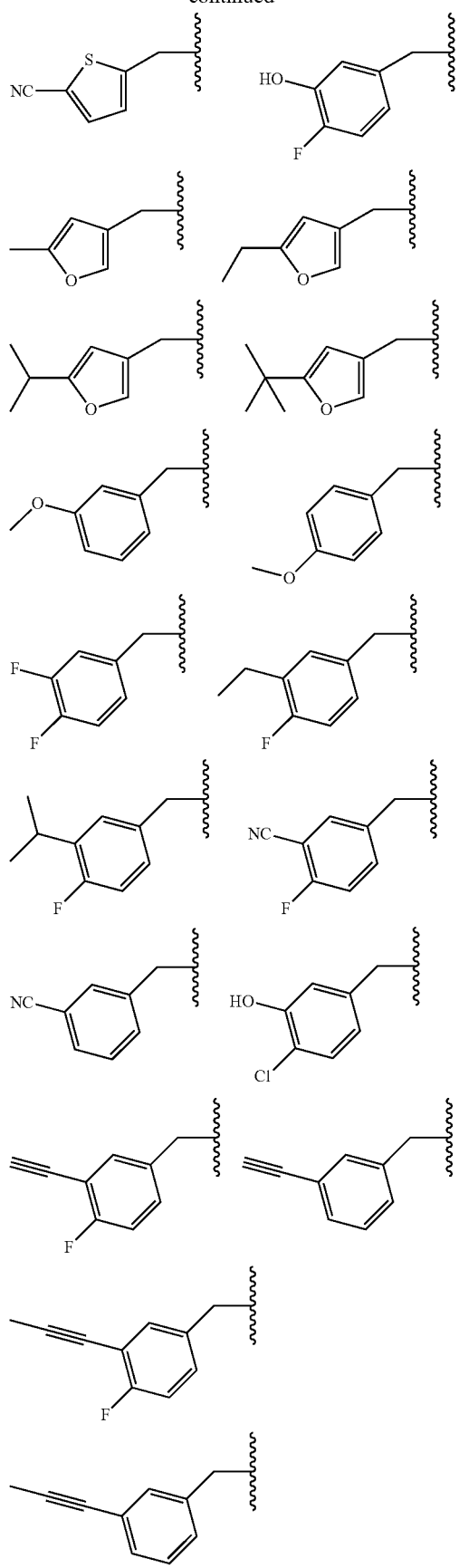
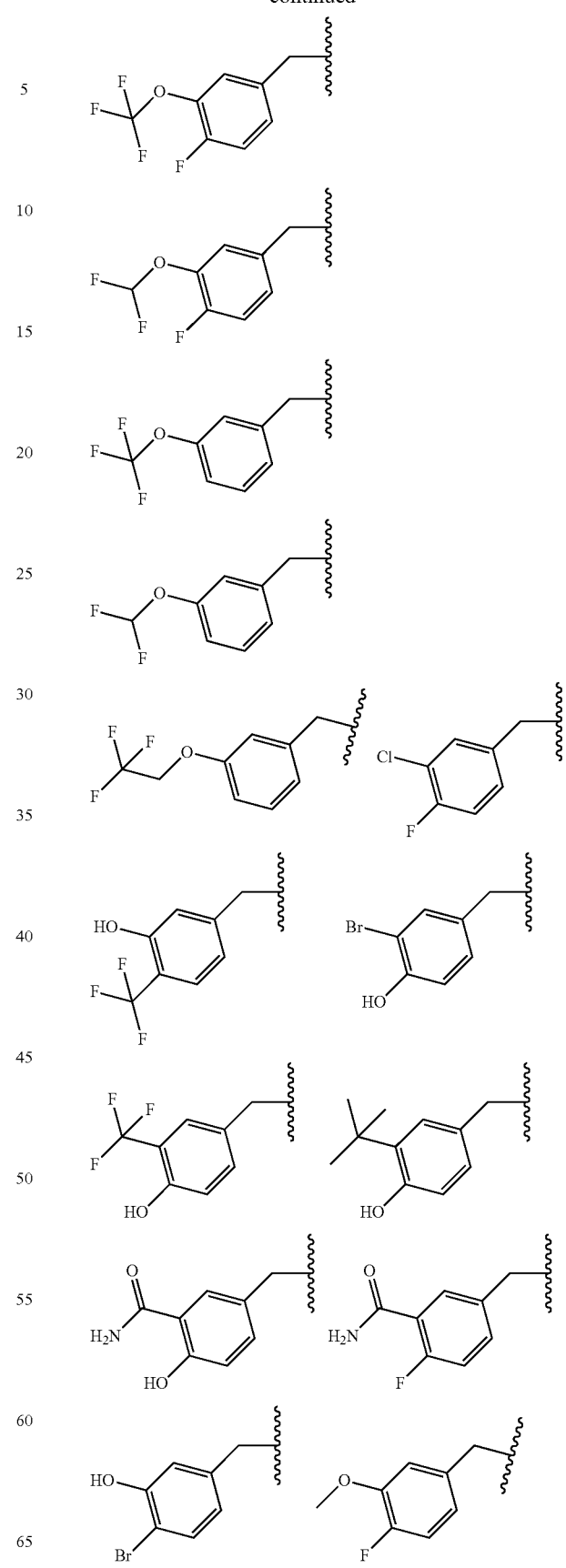

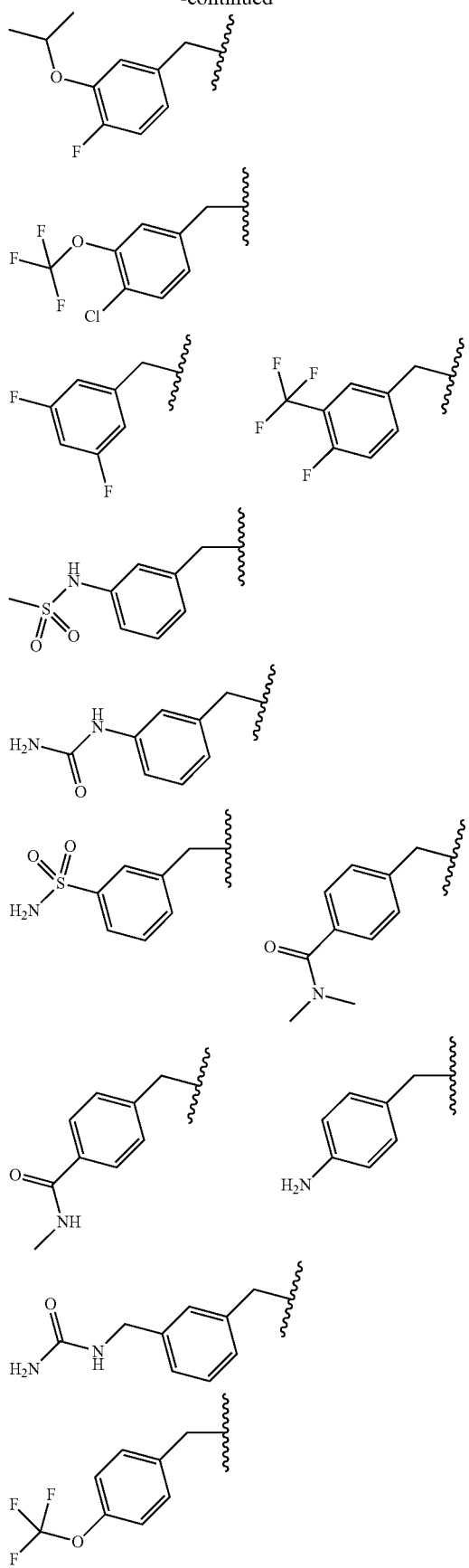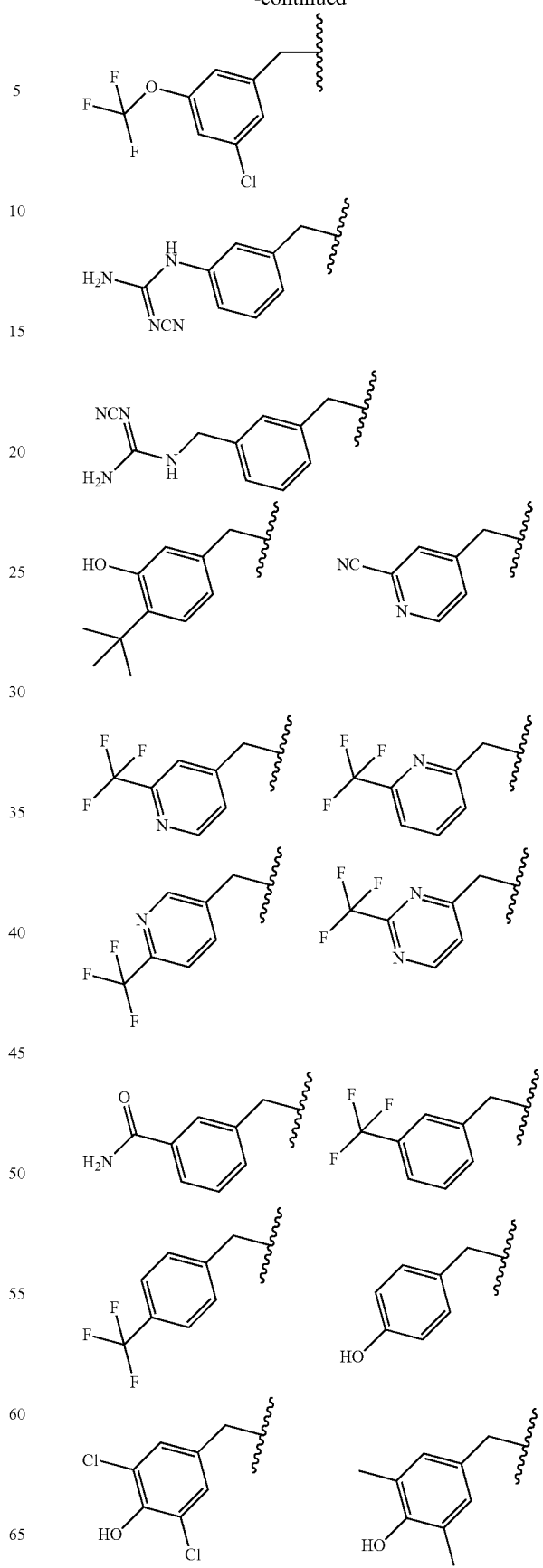

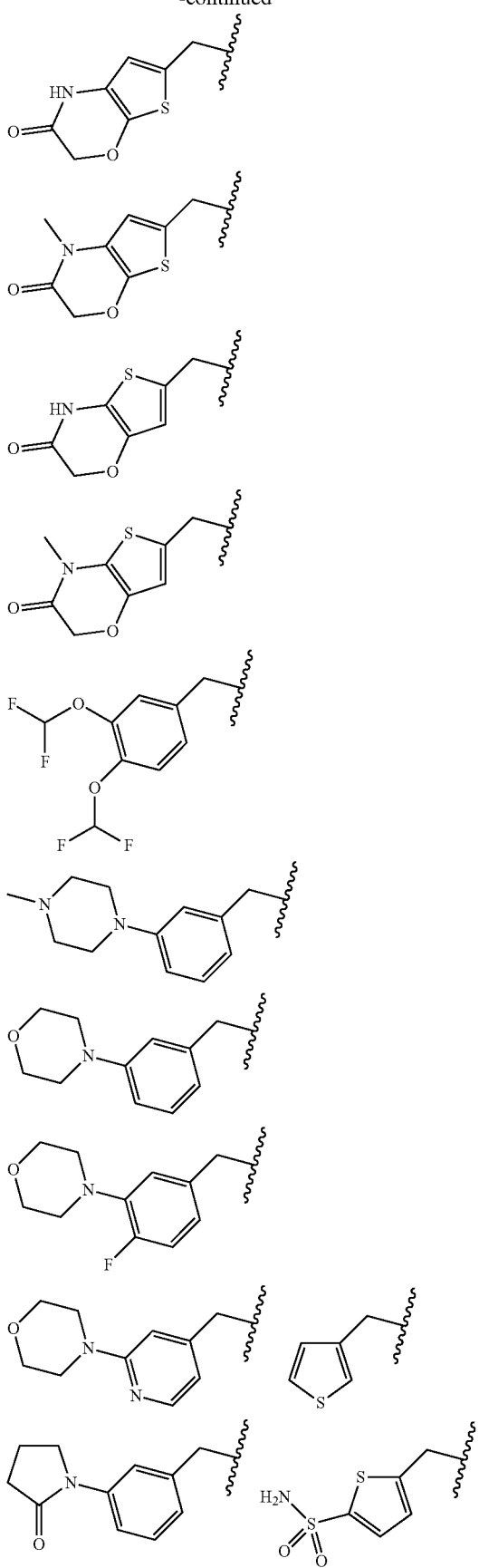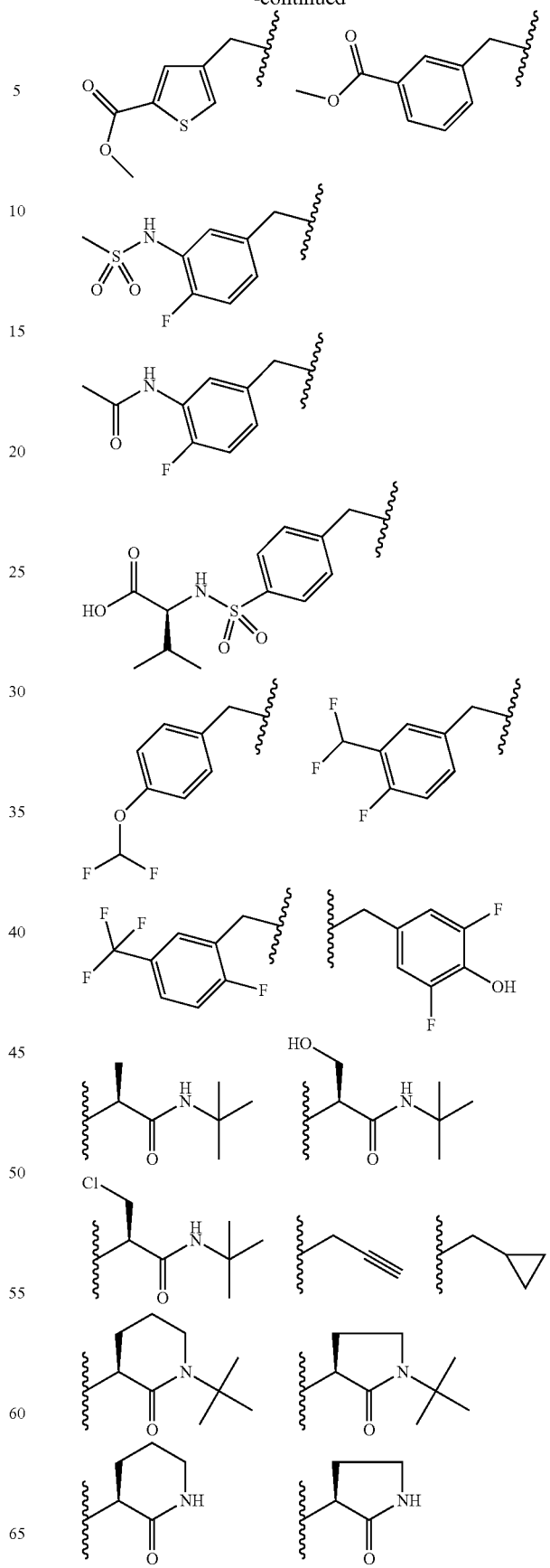

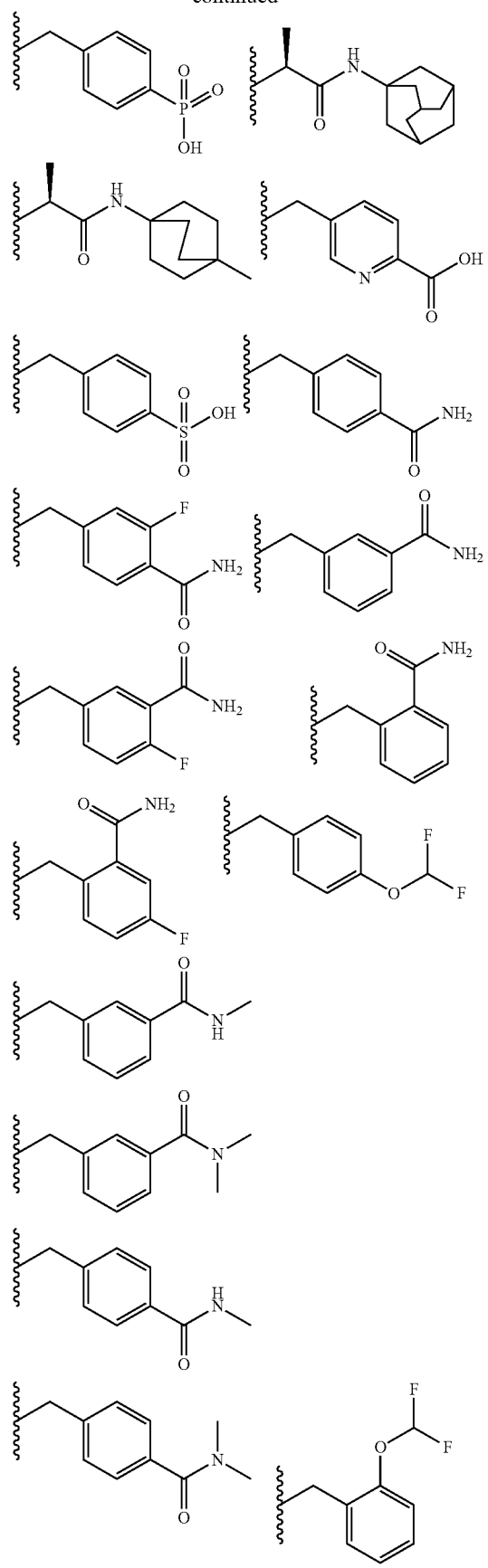
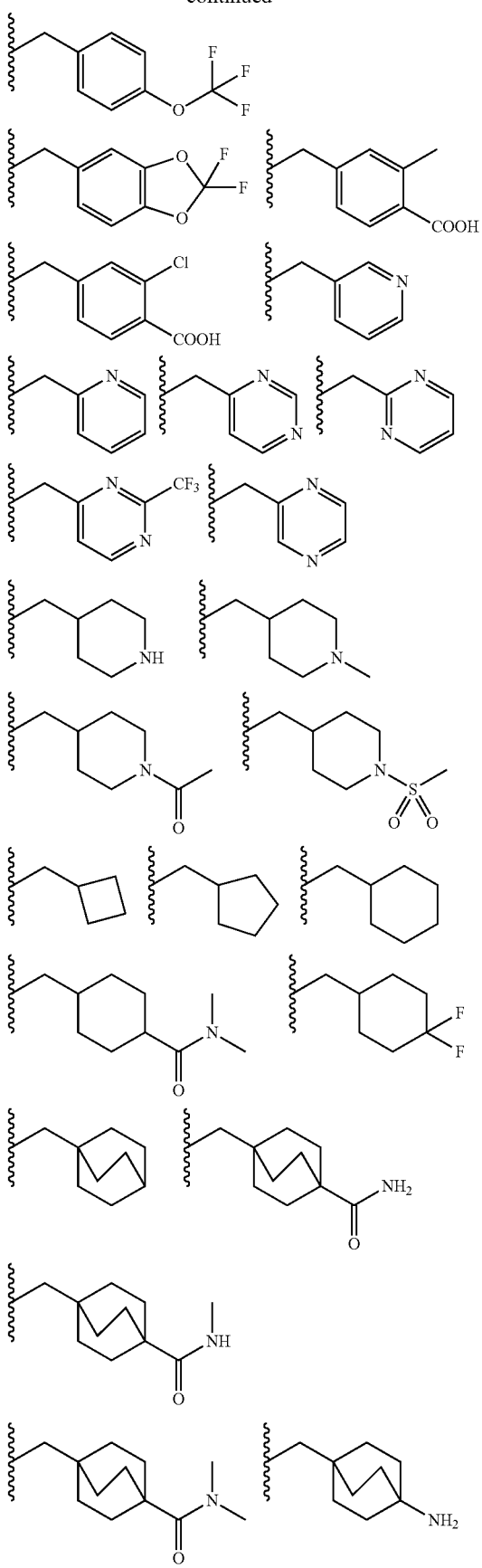

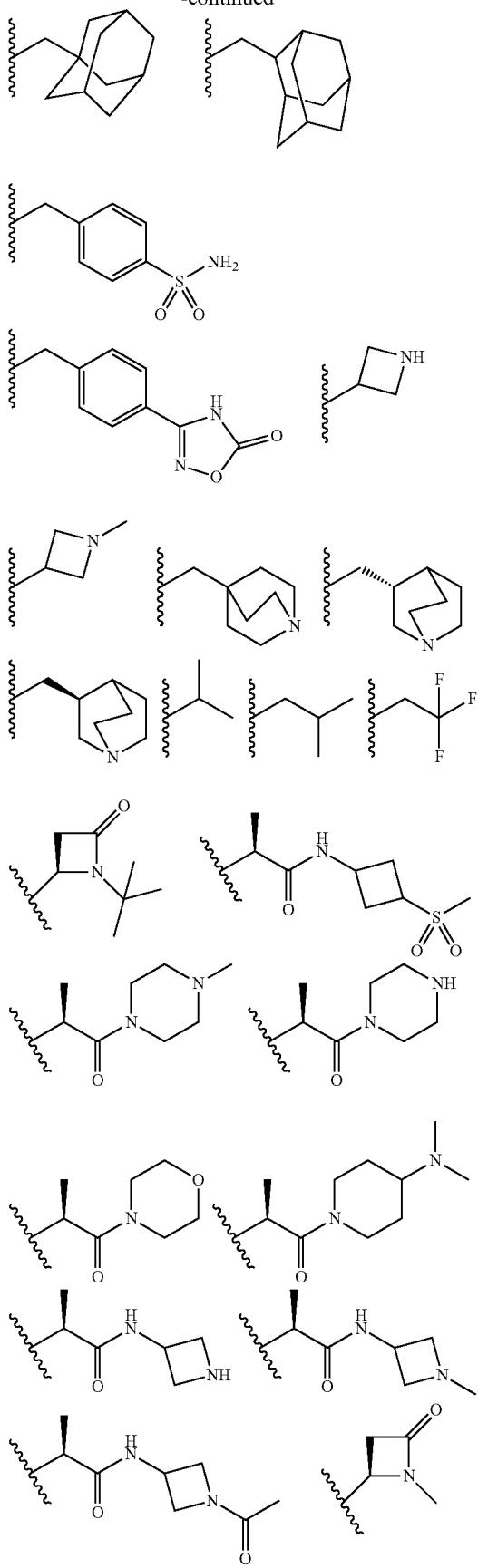
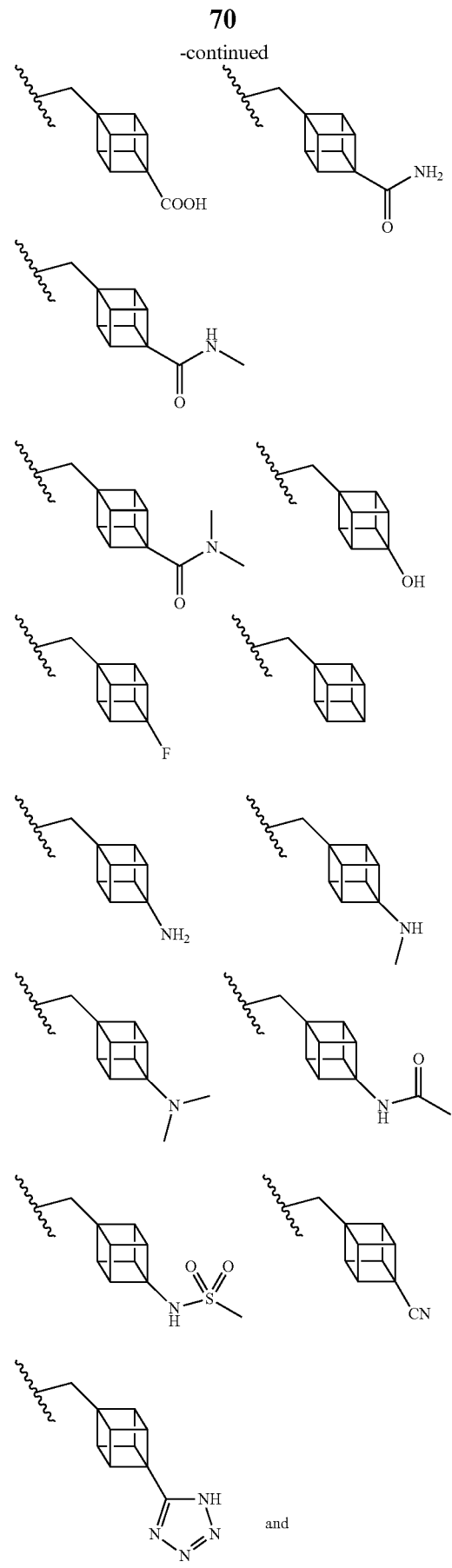

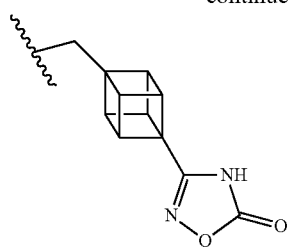

For example, in some embodiments, at least one $R^1$ of Group II(a) may be selected from Substituent Group 15 as defined hereinabove.

In still another embodiment, at least one $R^1$ of Formula (II) may be selected from Substituent Group 8:

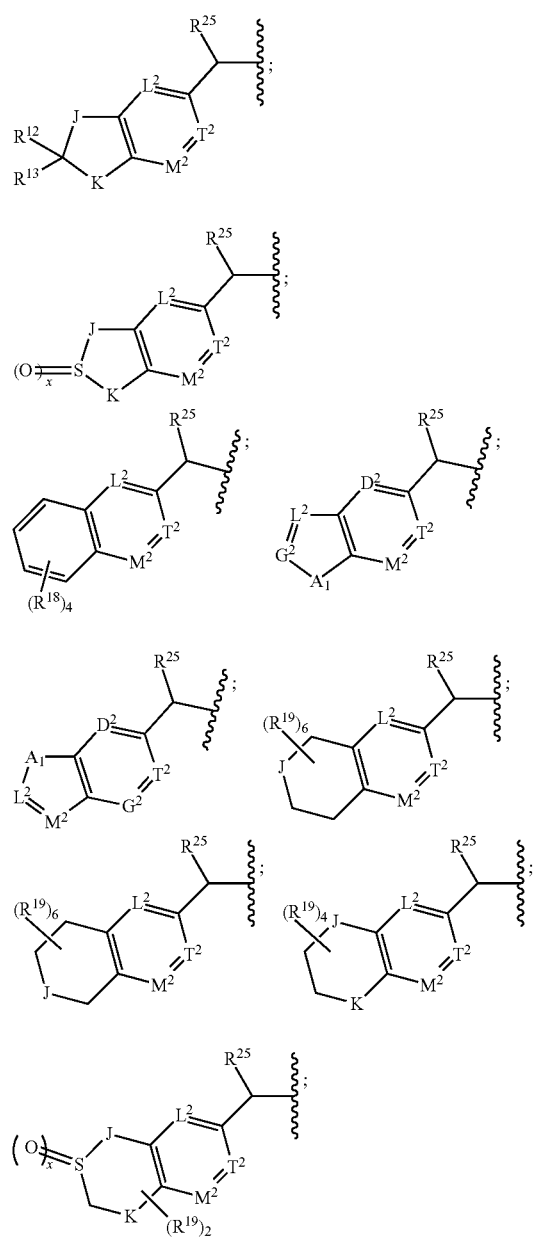

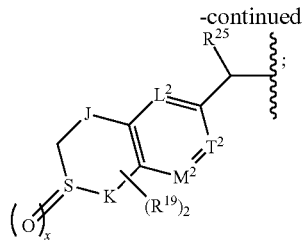

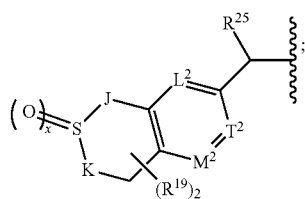

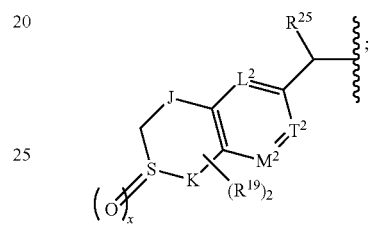

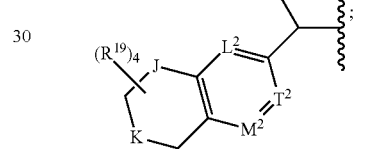

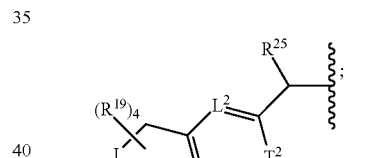

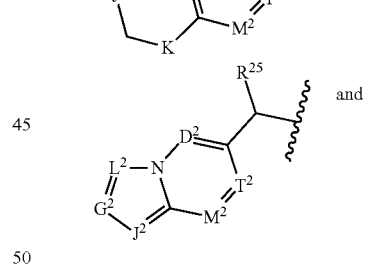 and 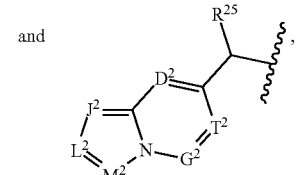

wherein all variables are as defined hereinabove.

For example, in some embodiments, at least one $R^1$ of Group II(a) may be selected from Substituent Group 8 as defined hereinabove.

In a further embodiment, at least one $R^1$ of Formula (II) may be selected from Substituent Group 9:

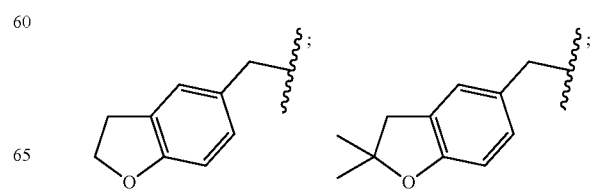

-continued
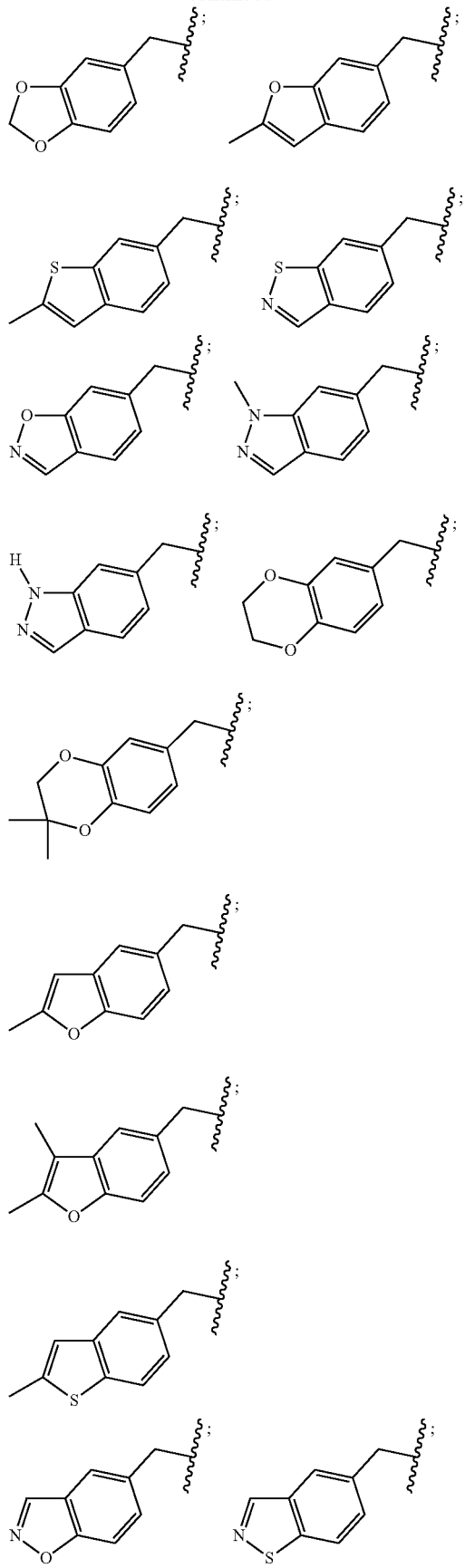
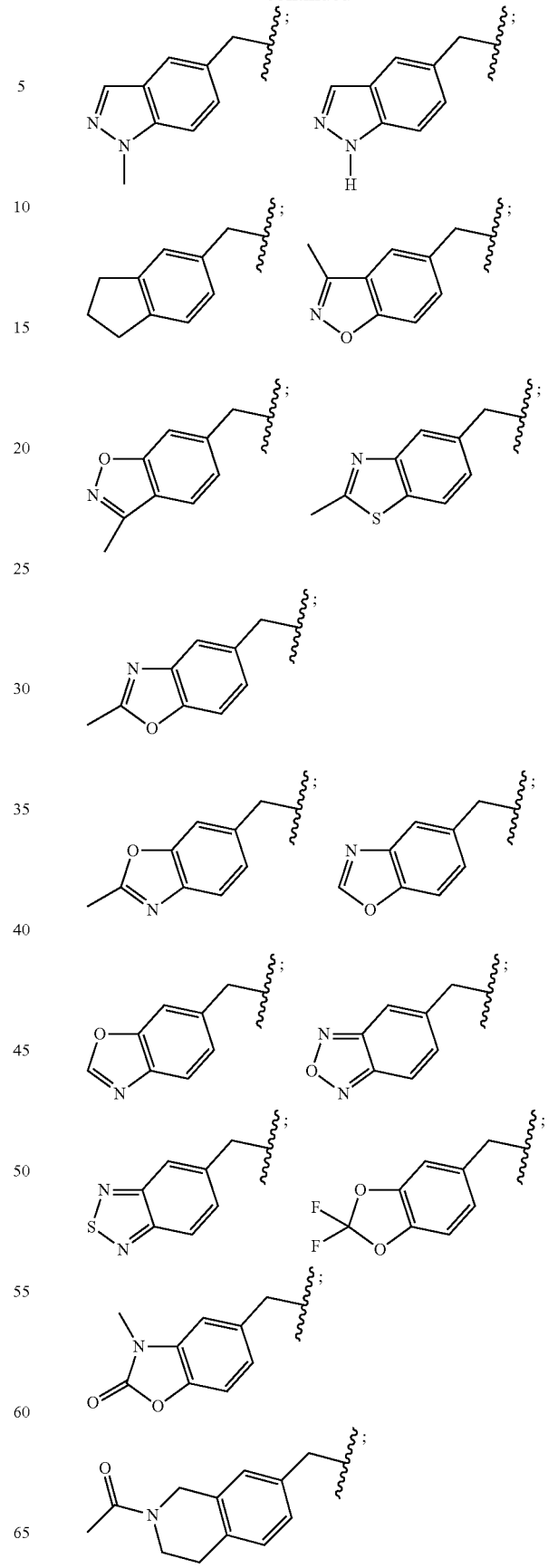

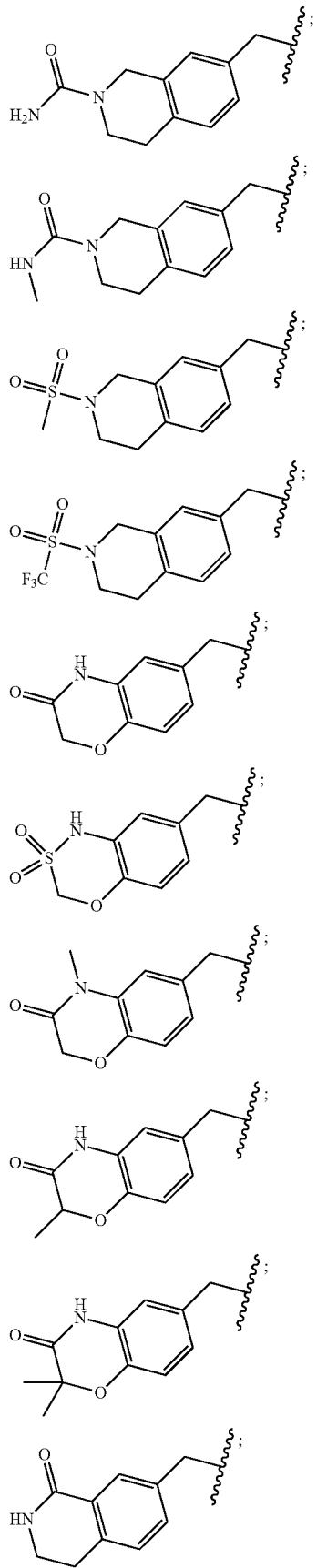
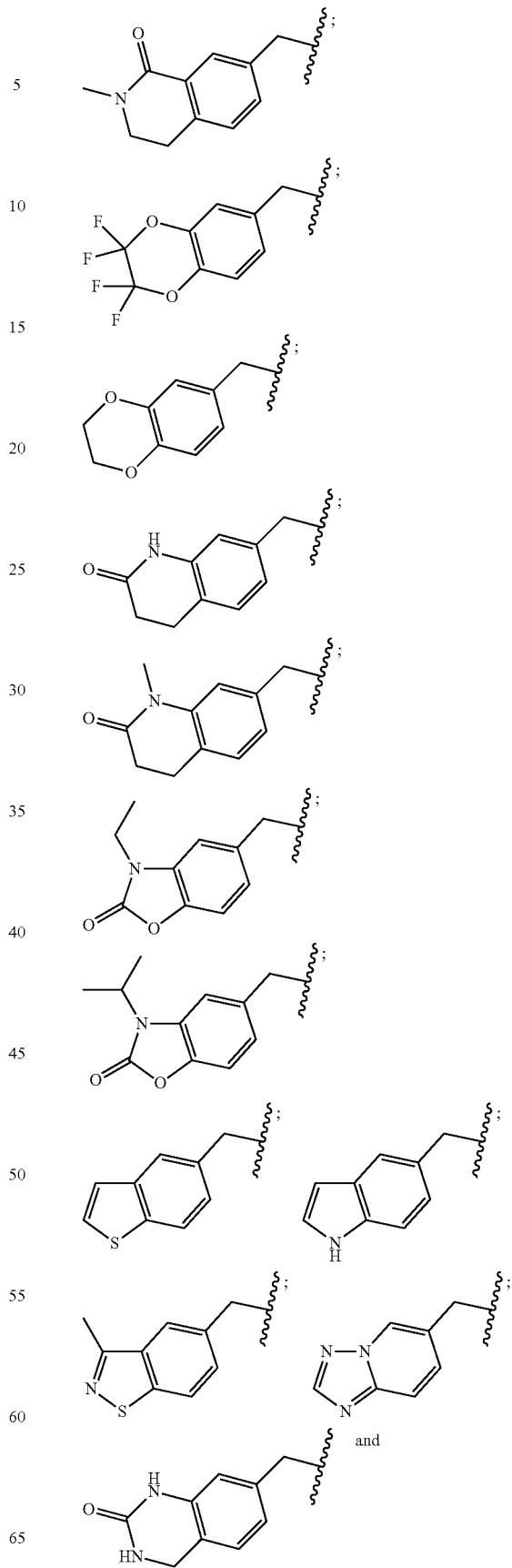

-continued

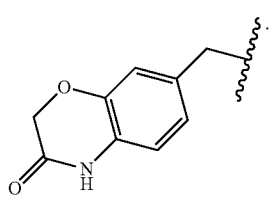

For example, in some embodiments, at least one R¹ of Group II(a) may be selected from Substituent Group 9 as defined hereinabove.

In yet a further embodiment, one R¹ of Formula (II) may be selected from Substituent Group 10:

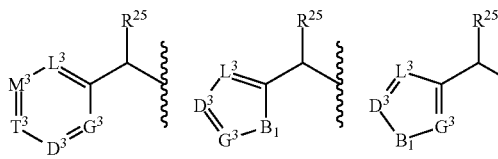

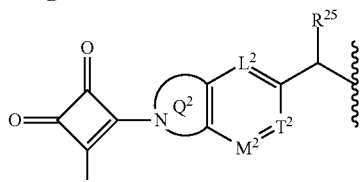

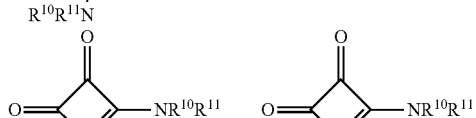

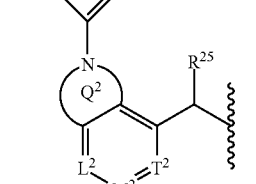

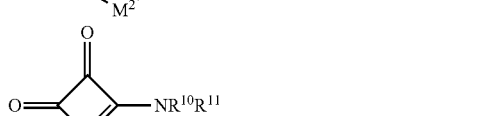

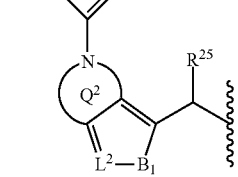

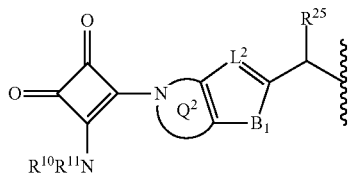

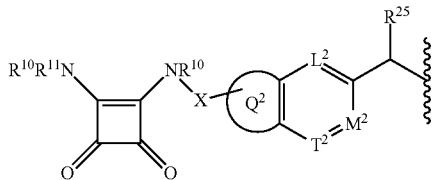

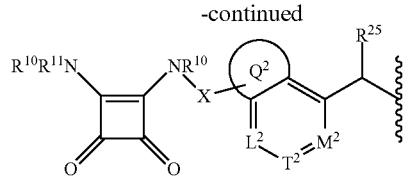

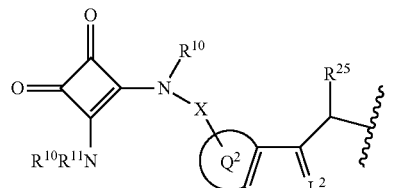

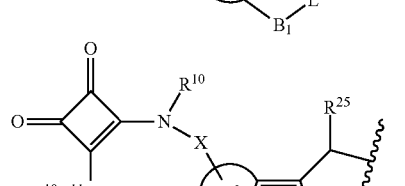

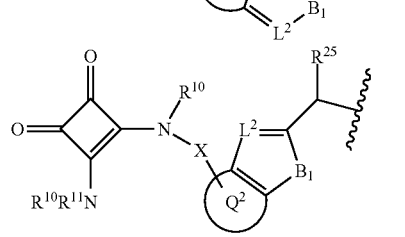

and

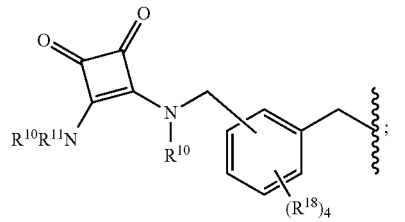

wherein all variables are as defined hereinabove.

For example, in some embodiments, one R¹ of Group II(a) may be selected from Substituent Group 10 as defined hereinabove.

In still a further embodiment, one R¹ of Formula (II) may independently be selected from Substituent Group 11:

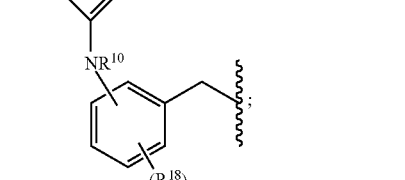

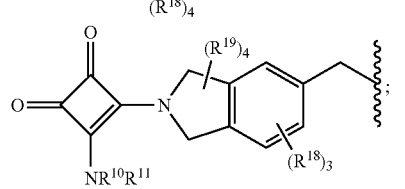

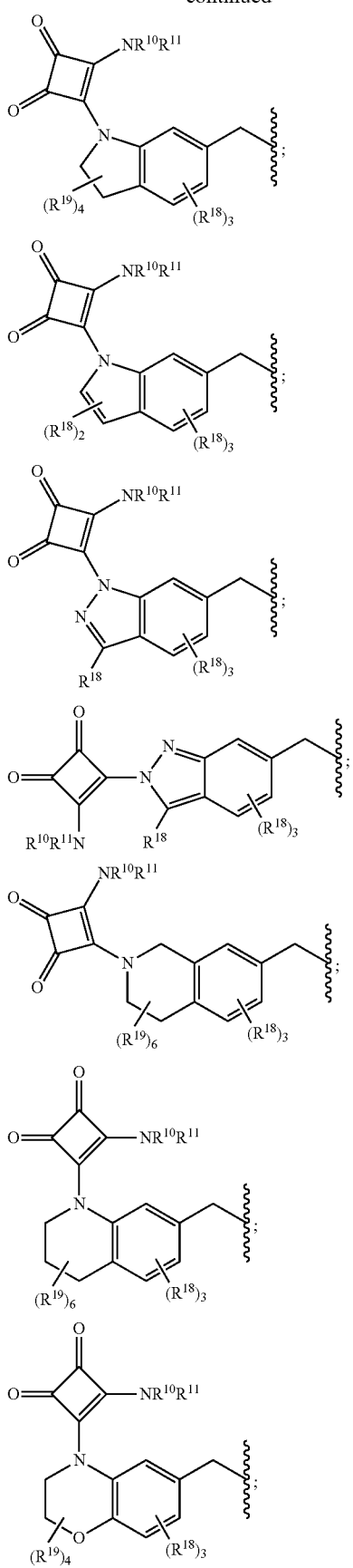
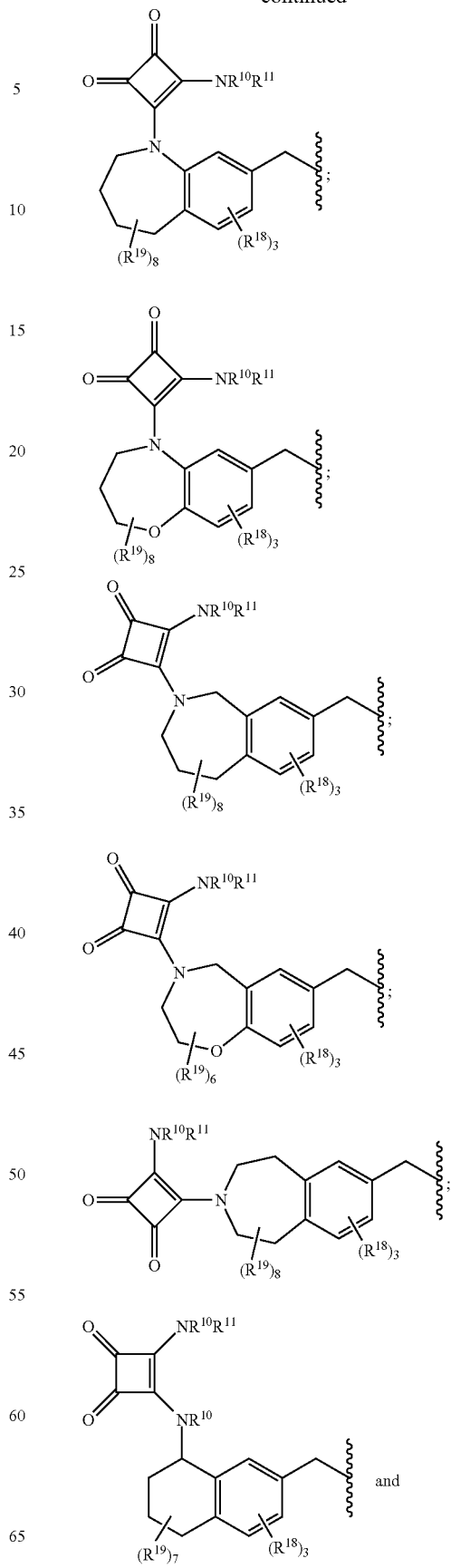

-continued
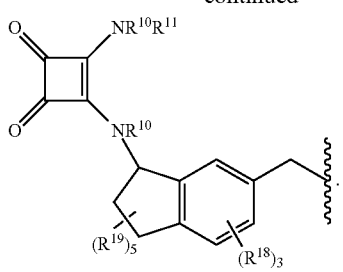
For example, in some embodiments, one R¹ of Group II(a) may be selected from Substituent Group 11 as defined hereinabove.
In one embodiment, one R¹ of Formula (II) may be selected from Substituent Group 12:
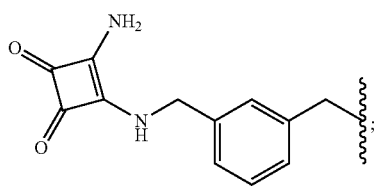
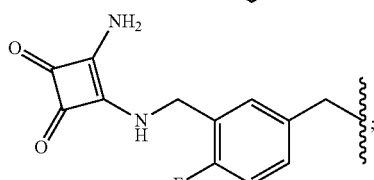
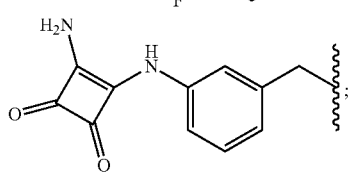
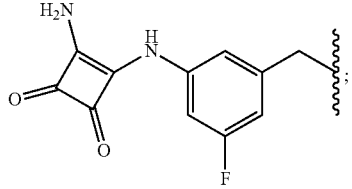
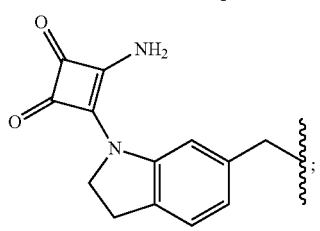
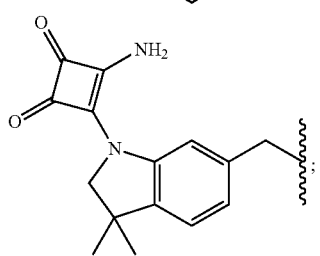
-continued
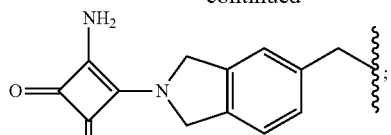
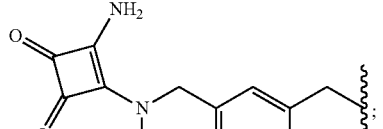
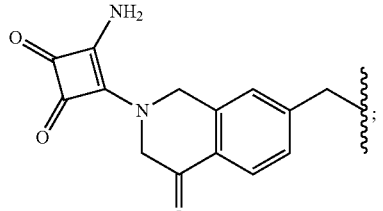
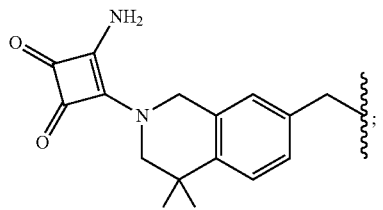
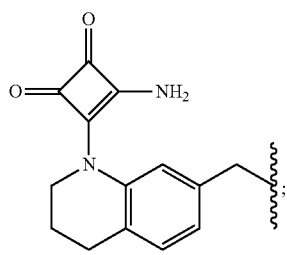
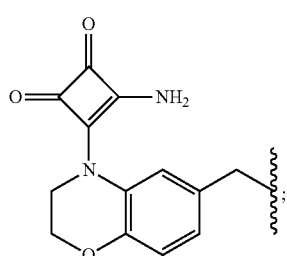
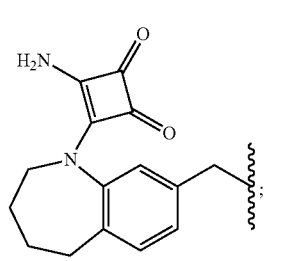

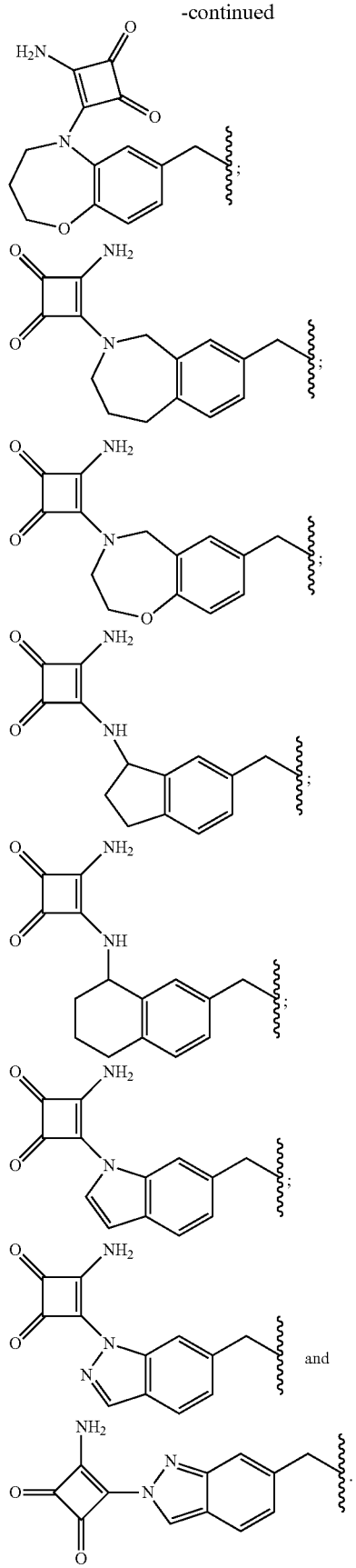
For example, in some embodiments, one R¹ of Group II(a) may be selected from Substituent Group 12 as defined hereinabove.
In some embodiments:
A) the first occurrence of R¹ of Formula (II) is selected from Substituent Group 13:

-continued
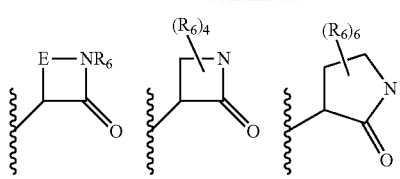
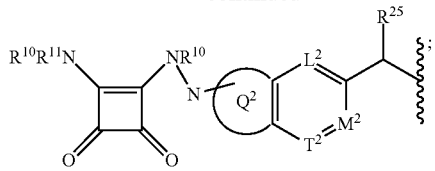
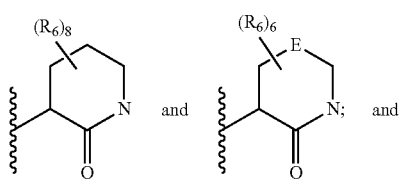
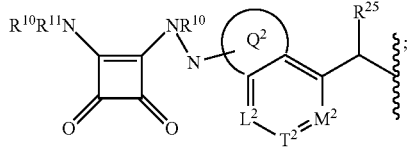
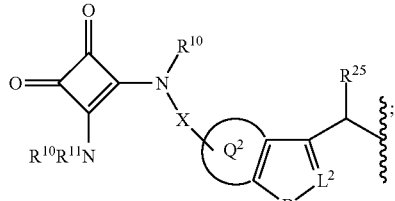
B) the second occurrence $R^1$ of Formula (II) is selected from Substituent Group 8 and Substituent Group 10:
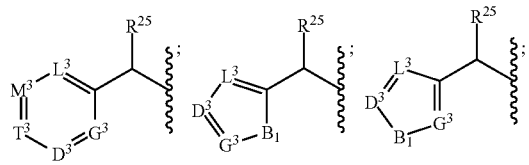
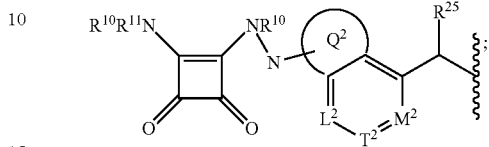
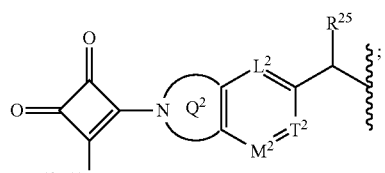
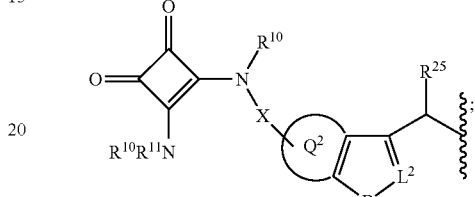
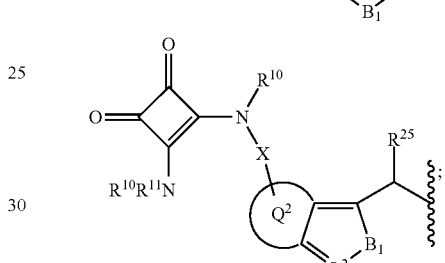
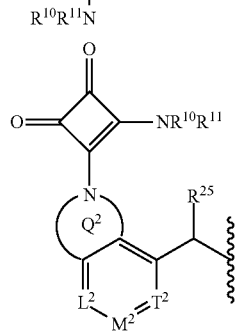
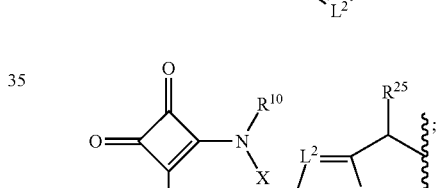
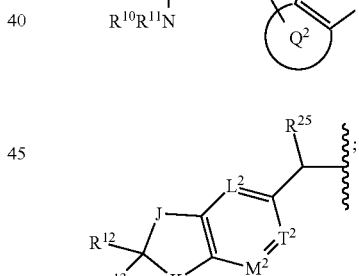
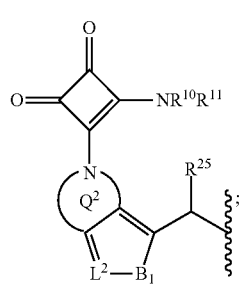
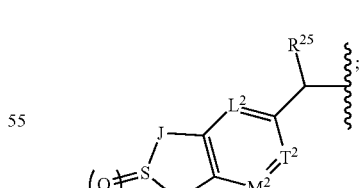
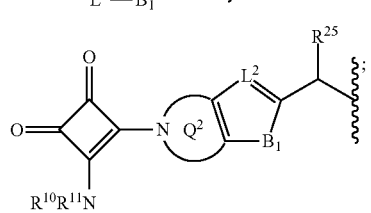
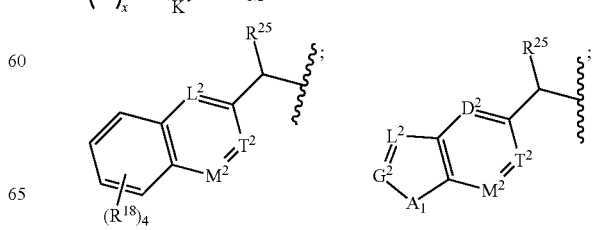

-continued

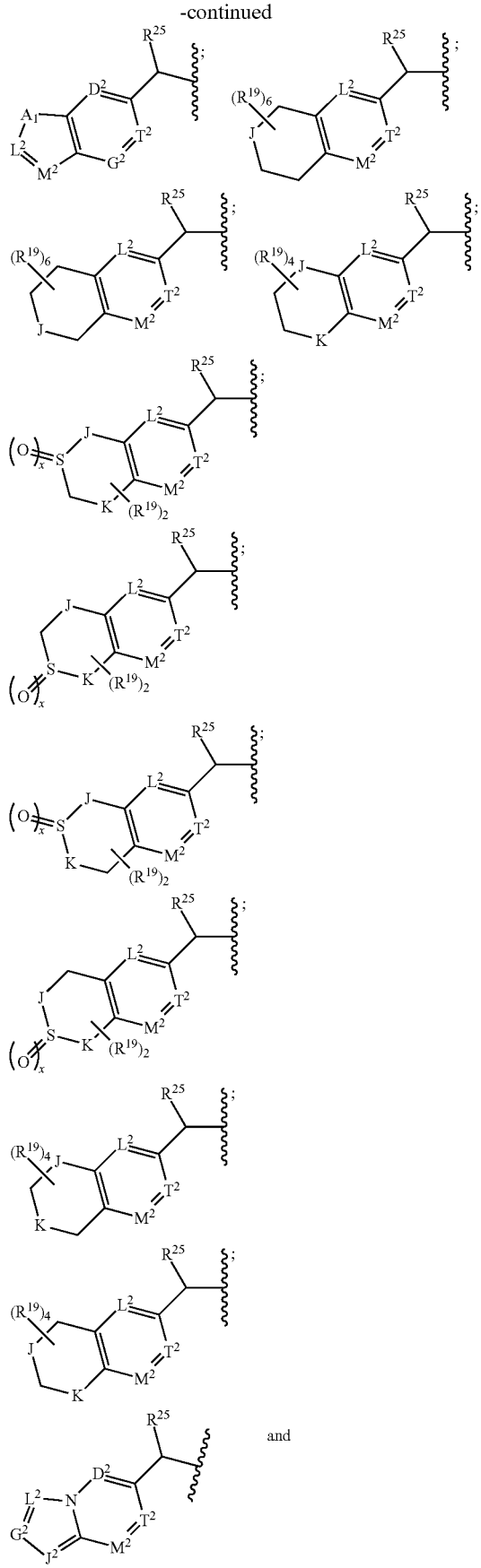

-continued

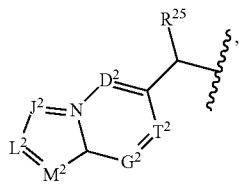

wherein all variables are as defined hereinabove.

For example in some embodiments, the first occurrence of $R^1$ of the structures of Group II(a) may be selected from Substituent Group 13 as defined hereinabove, and the second occurrence of $R^1$ may be selected from Substituent Group 10 as defined hereinabove.

In another embodiment of the present invention, the amide containing heterobicyclic metalloprotease compounds may be represented by the general Formula (III):

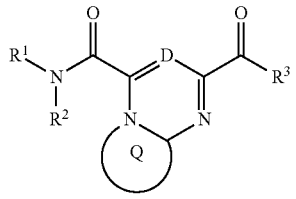

Formula (III)

and N-oxides, pharmaceutically acceptable salts, prodrugs, formulation, polymorphs, racemic mixtures and stereoisomers thereof, wherein all variables are as defined hereinabove.

In yet another embodiment, the compounds of Formula (III) may be selected from Group III(a):

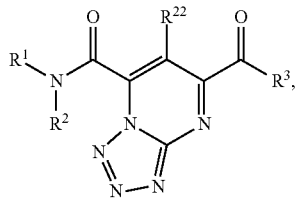

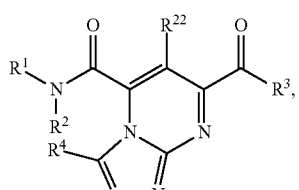

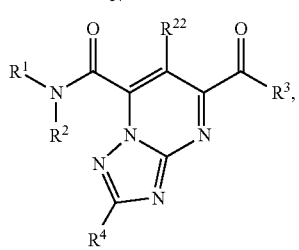

-continued
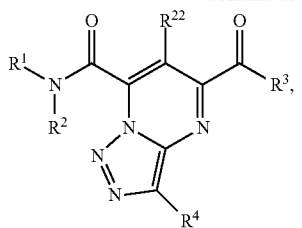
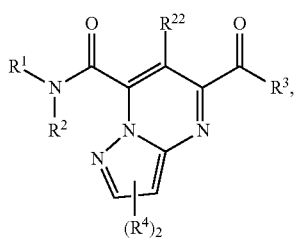
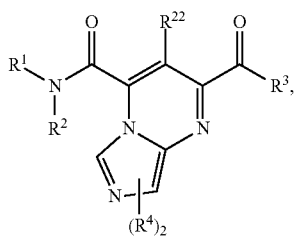
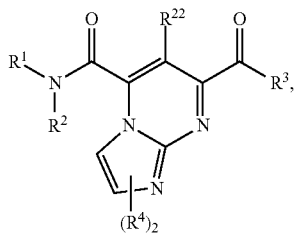
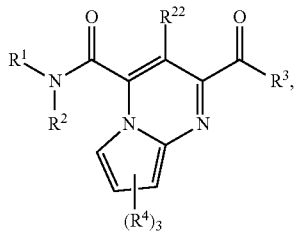
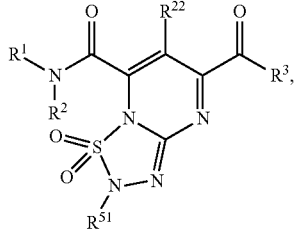
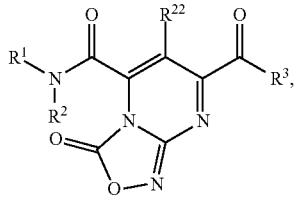
-continued
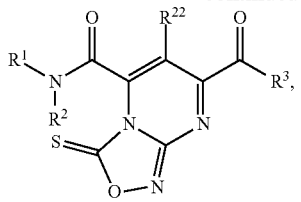
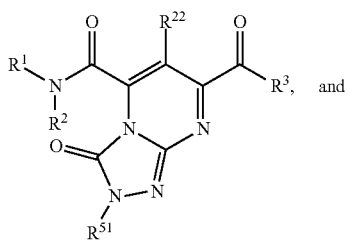 and
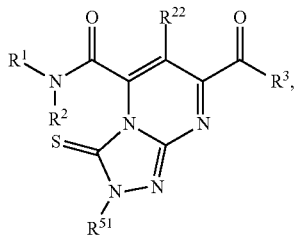
wherein all variables are as defined hereinabove.
In still another embodiment, the compounds of Formula (III) may be selected from:
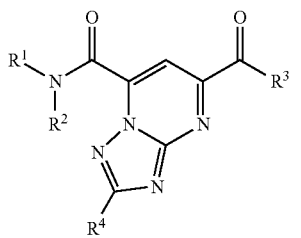
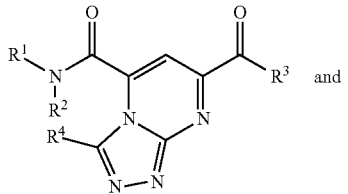 and
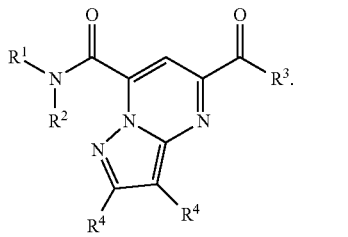
In a further embodiment, the compounds of Formula (III) may be selected from:

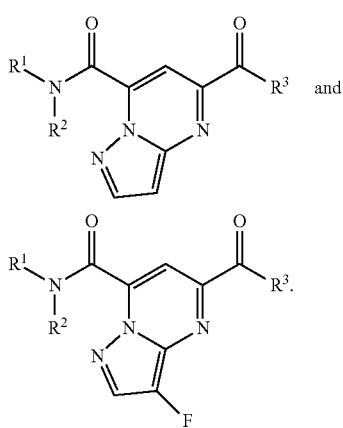
In yet a further embodiment, R³ of Formula (III) may be selected from Substituent Group 1:
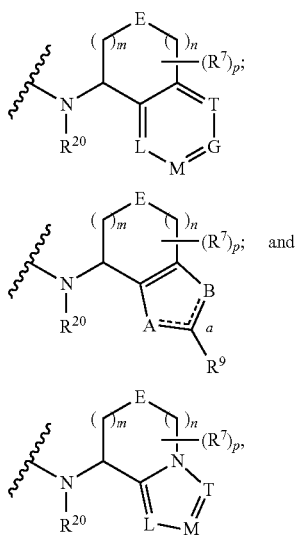
wherein all variables are as defined hereinabove.
For example, in some embodiments, R³ of the structures of Group III(a) may be selected from Substituent Group 1 as defined hereinabove.
In still a further embodiment, R³ of Formula (III) may be selected from Substituent Group 2:
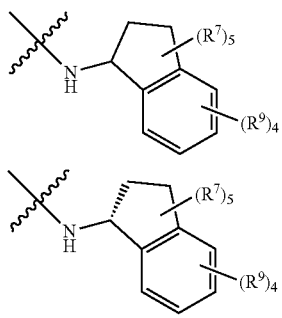
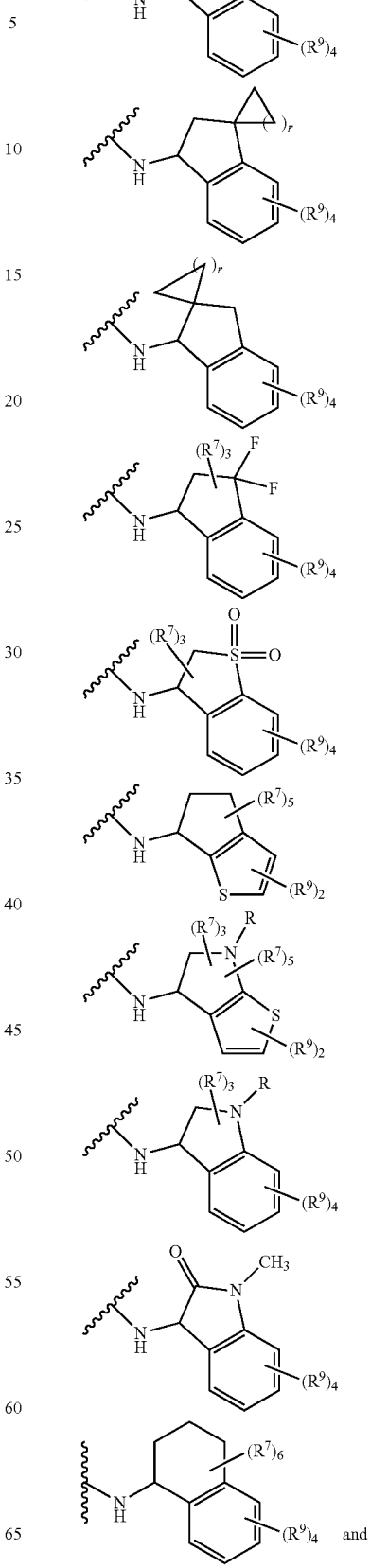

-continued

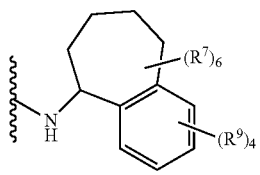

wherein all variables are as defined hereinabove.

In still a further embodiment, $R^3$ of the structures of Group III(a) may be selected from Substituent Group 2 as defined hereinabove.

In one embodiment, $R^3$ of Formula (III) may be selected from Substituent Group 3:

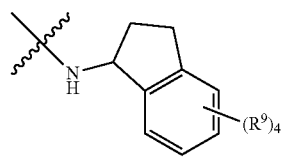
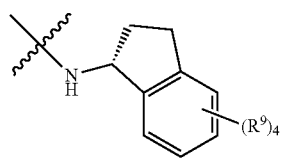
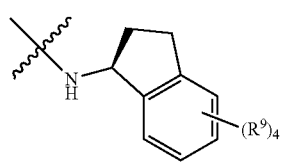
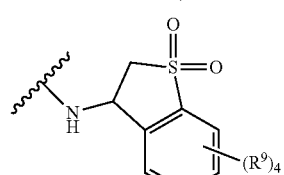
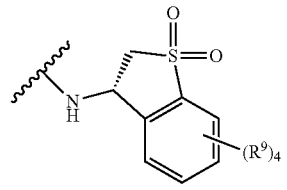
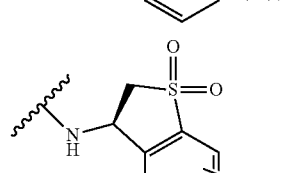
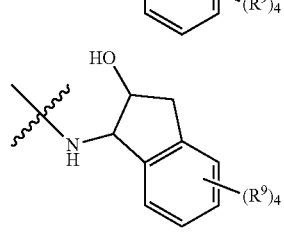

-continued

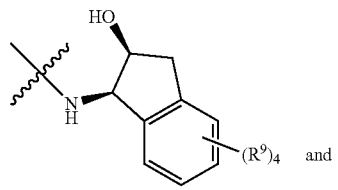
and
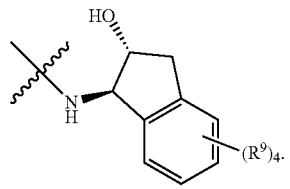

For example, in some embodiments, $R^3$ of the structures of Group III(a) may be selected from Substituent Group 3 as defined hereinabove.

In one embodiment, $R^9$ of the structures of Substituent Group 3 may be selected from:

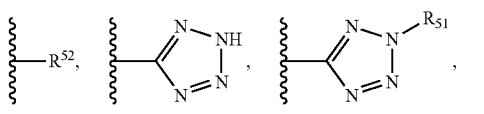
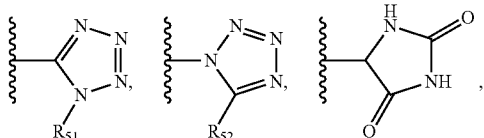
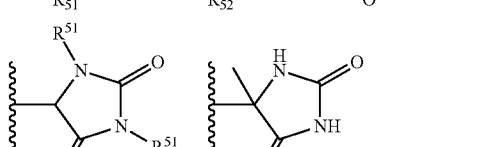
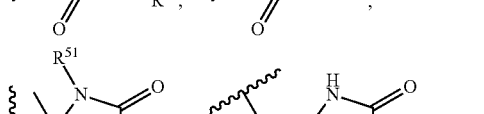
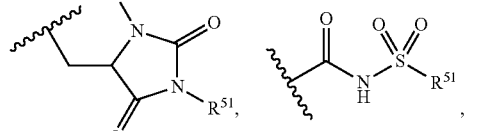
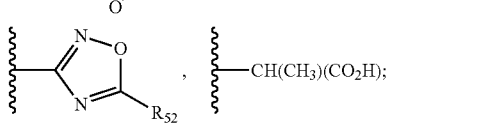
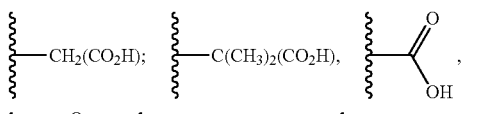
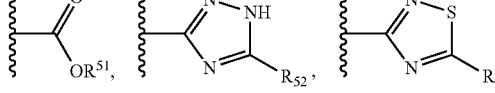

-continued

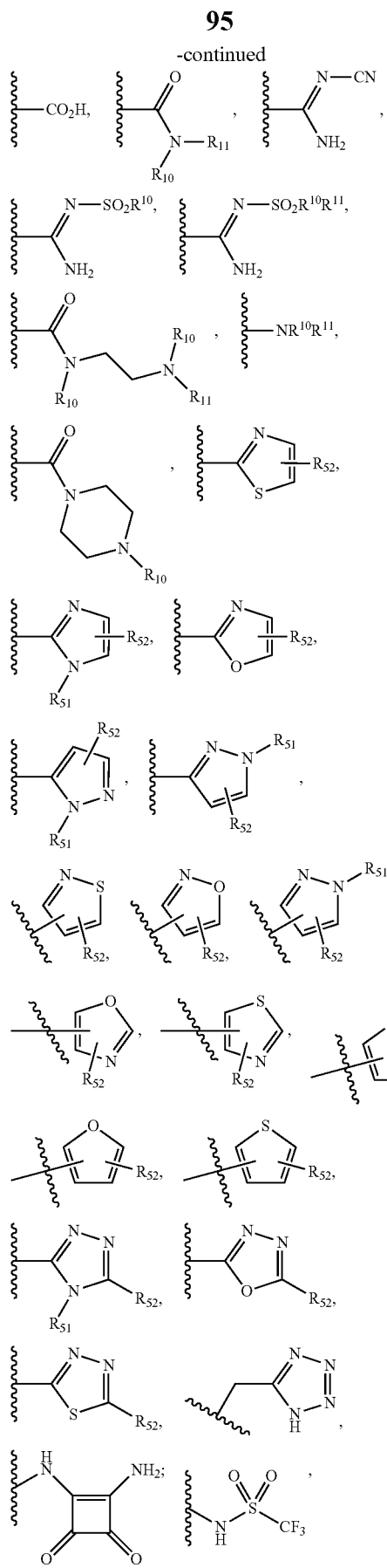

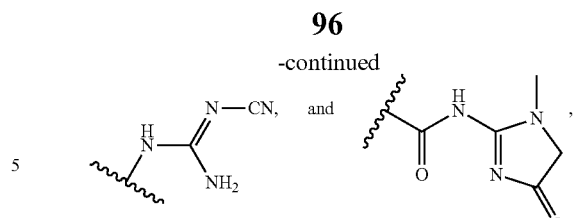

wherein all variables are as defined hereinabove.

In another embodiment, $R^3$ of Formula (III) may be Substituent Group 16:

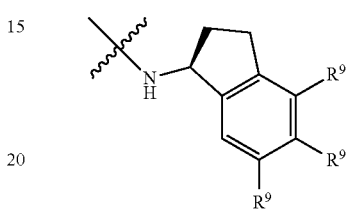

For example, in some embodiments, $R^3$ of the structures of Group III(a) may be Substituent Group 16 as defined hereinabove.

In yet another embodiment, $R^3$ of Formula (III) may be selected from Substituent Group 5:

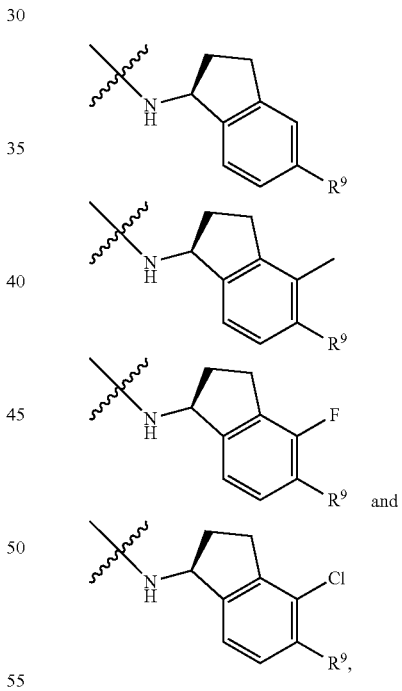

wherein:

$R^9$ is selected from hydrogen, fluoro, halo, CN, alkyl, $CO_2H$,

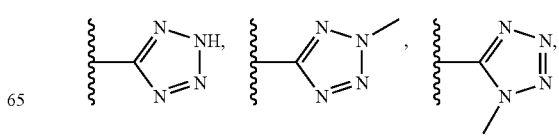

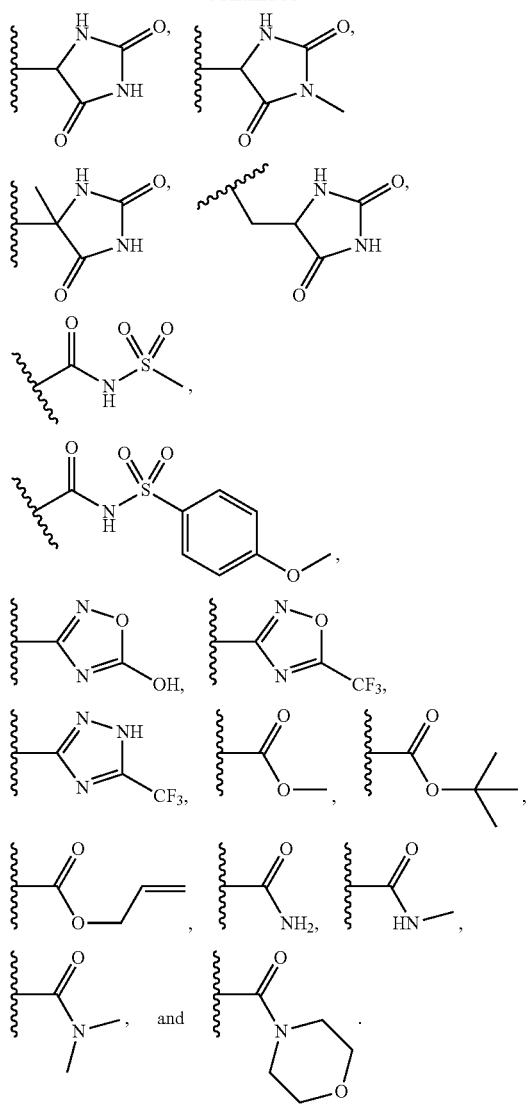

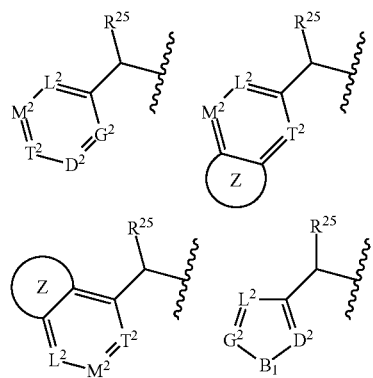

For example, in some embodiments, R³ of the structures of Group III(a) may be selected from Substituent Group 5 as defined hereinabove.

In still another embodiment, R¹ of the structures of Formula (III) may be selected from Substituent Group 6:

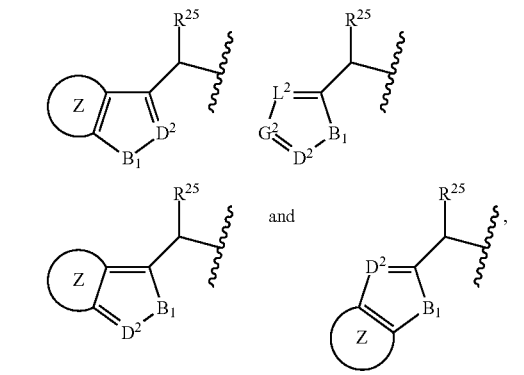

wherein all variables are as defined hereinabove.

For example, in some embodiments, R¹ of the structures of Group III(a) may be selected from Substituent Group 6 as defined hereinabove.

In a further embodiment, R¹ of Formula (III) may be selected from Substituent Group 7:

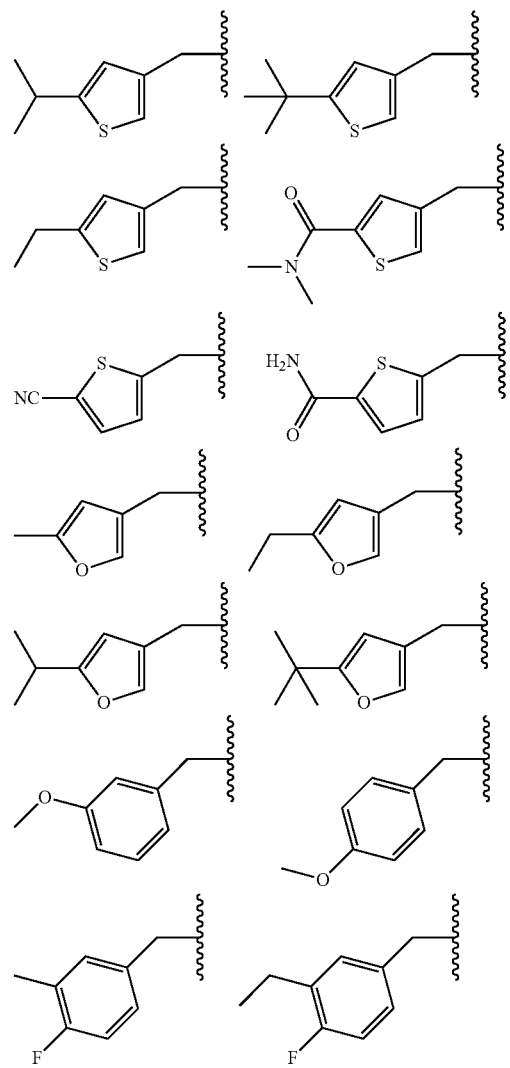

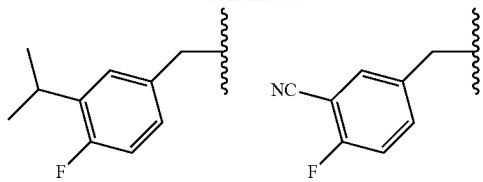
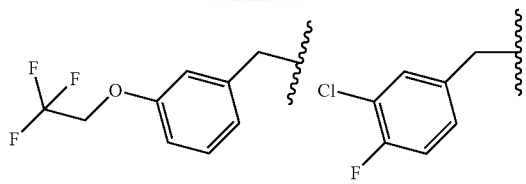

101
-continued
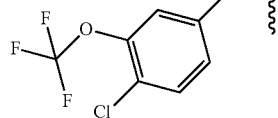
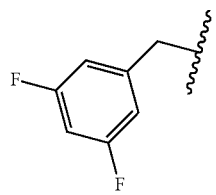
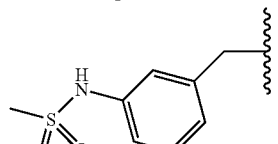
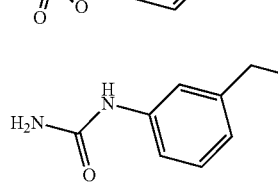
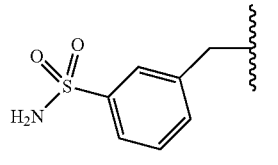
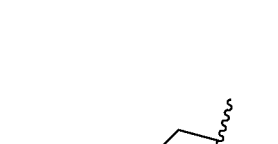
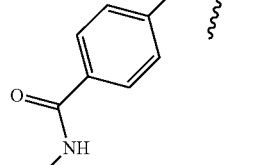
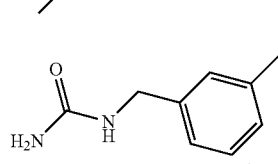
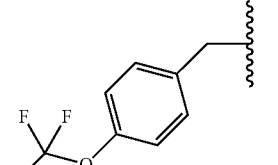
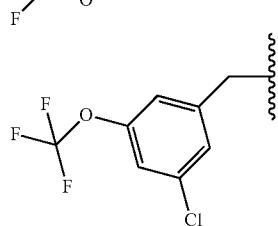
102
-continued
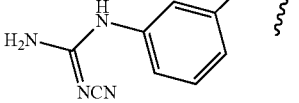
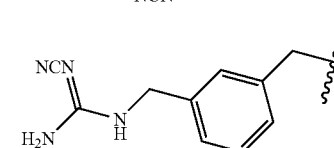
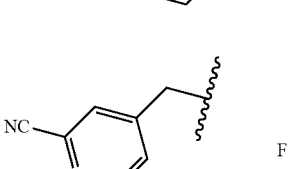
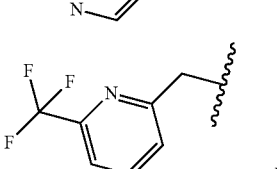
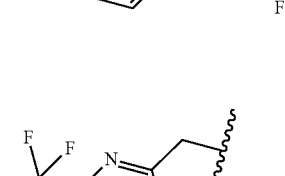
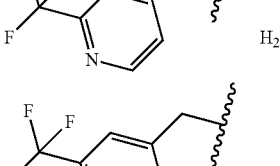
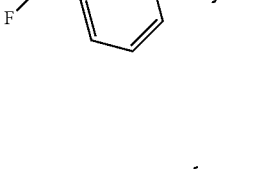
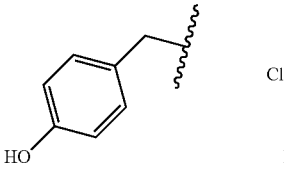
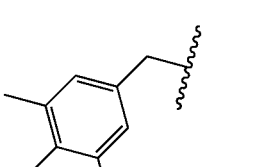
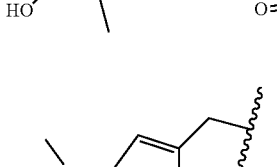
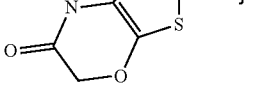

103
-continued
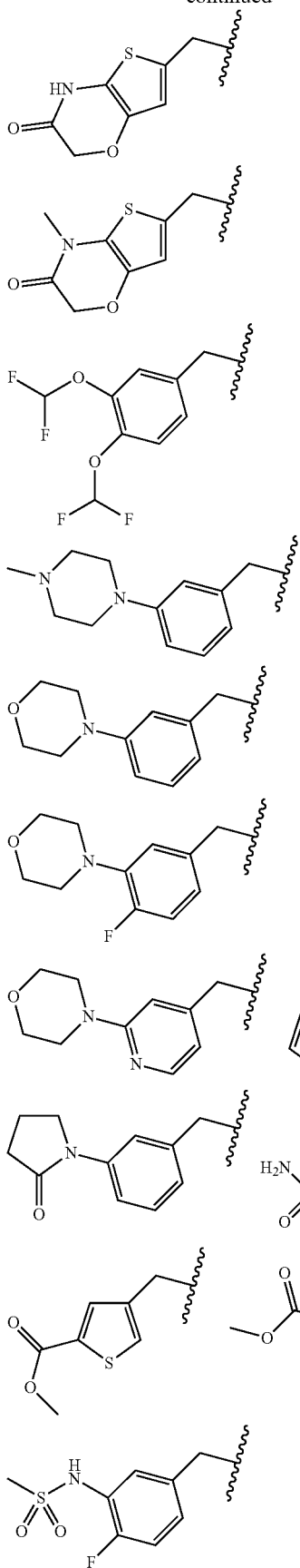
104
-continued
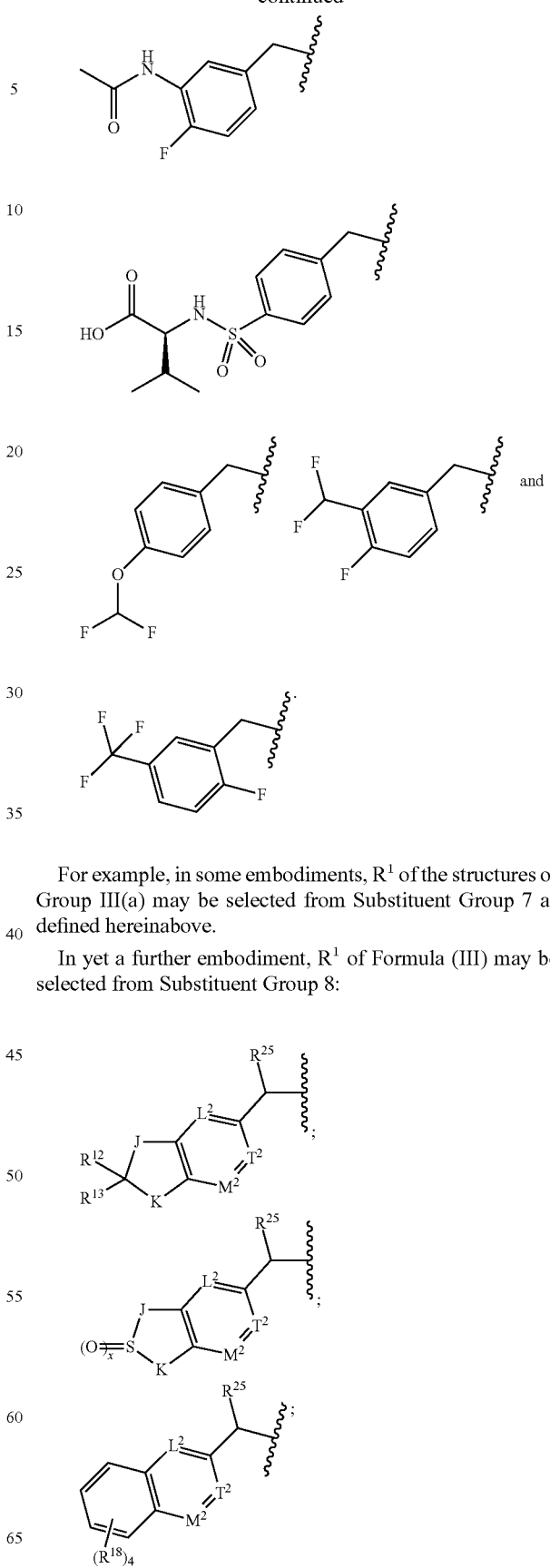
For example, in some embodiments, R¹ of the structures of Group III(a) may be selected from Substituent Group 7 as defined hereinabove.
In yet a further embodiment, R¹ of Formula (III) may be selected from Substituent Group 8:

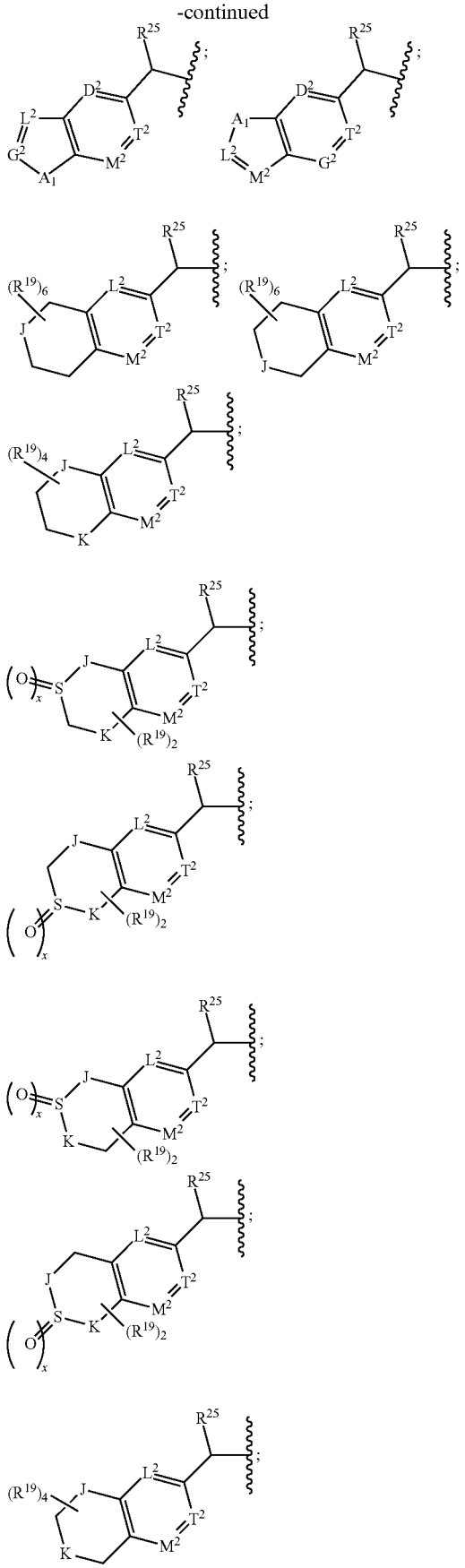
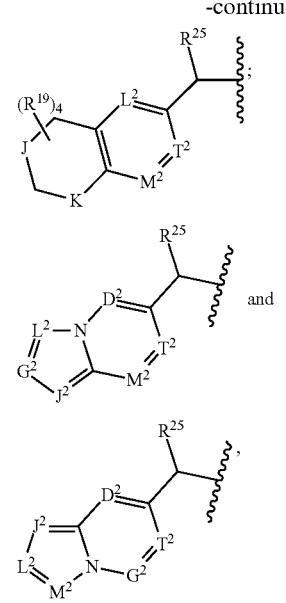
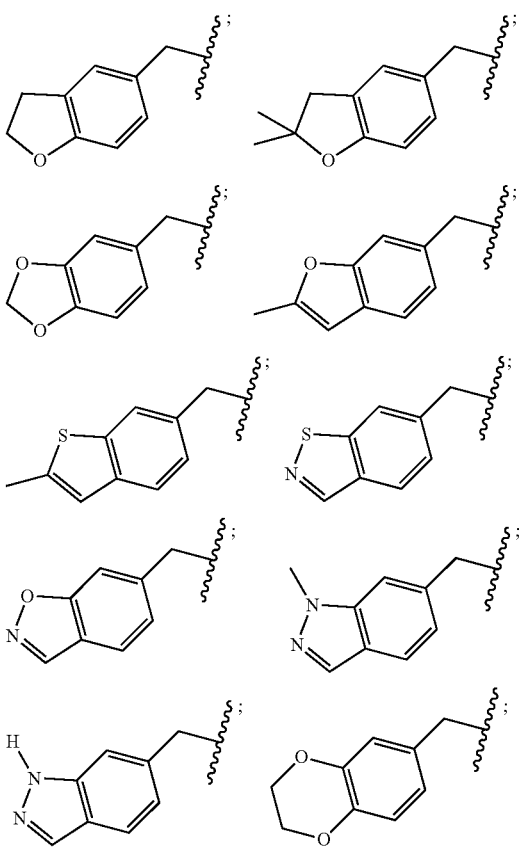
wherein all variables are as defined hereinabove.
For example, in some embodiments, R¹ of the structures of Group III(a) may be selected from Substituent Group 8 as defined hereinabove.
In still a further embodiment, R¹ of Formula (III) may be selected from Substituent Group 9:

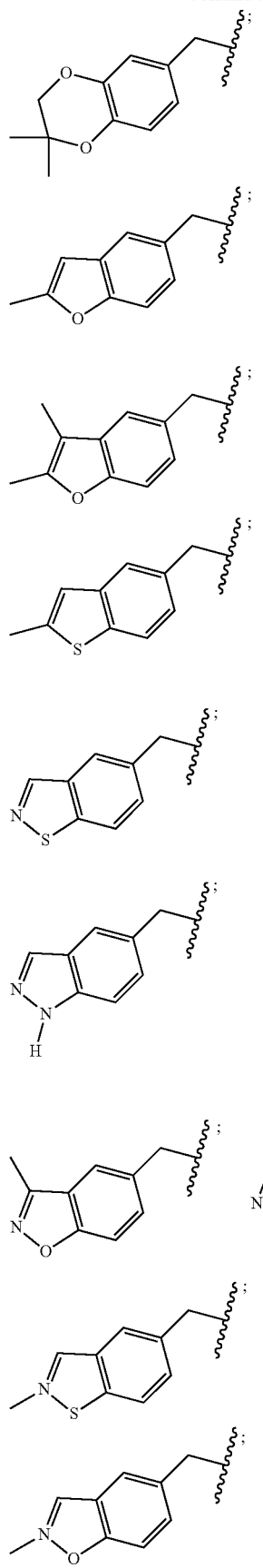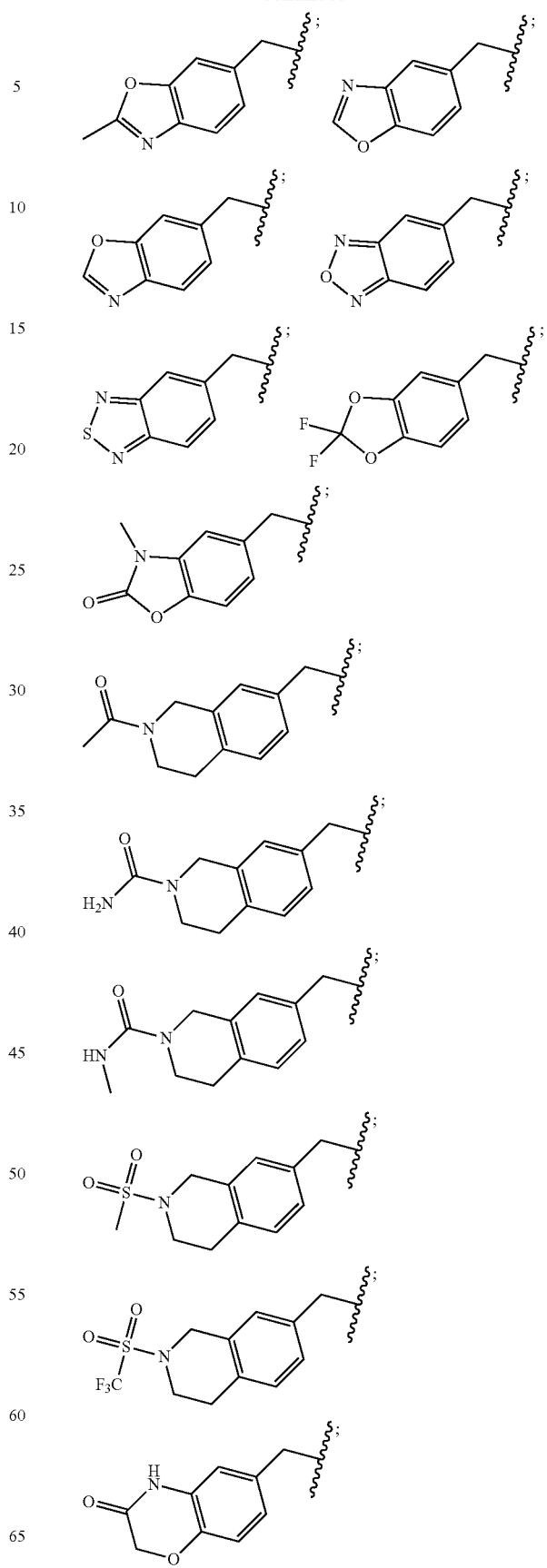

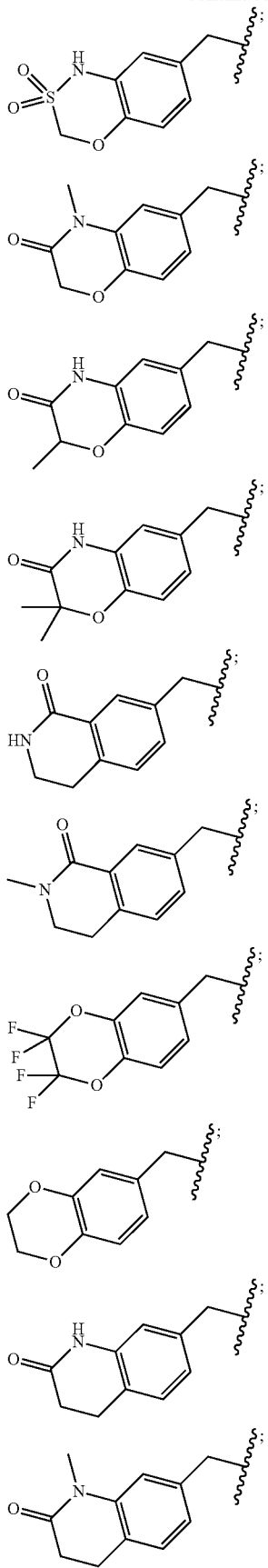
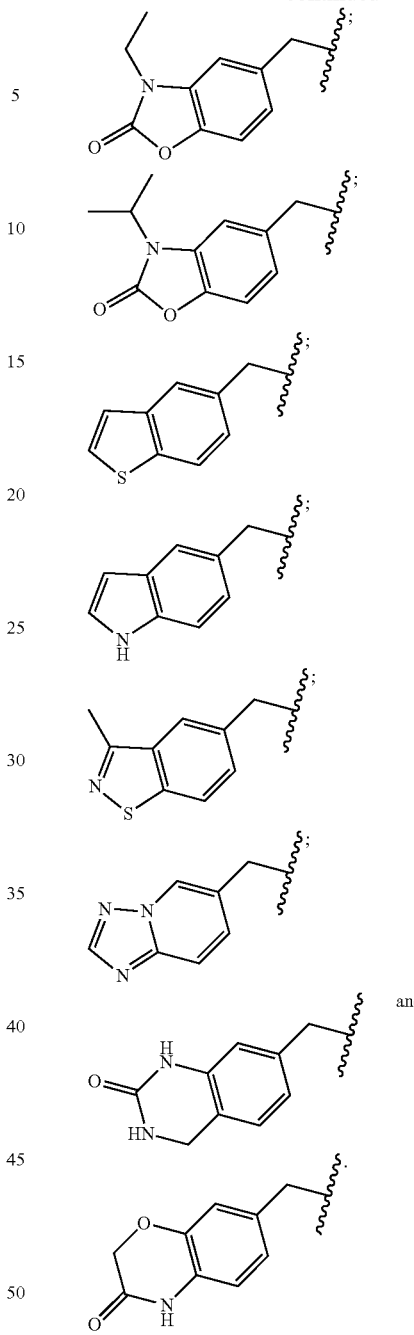
For example, in some embodiments, $R^1$ of the structures of Group III(a) may be selected from Substituent Group 9 as defined hereinabove.
In one embodiment, $R^1$ of Group III(a) may be selected from Substituent Group 10.
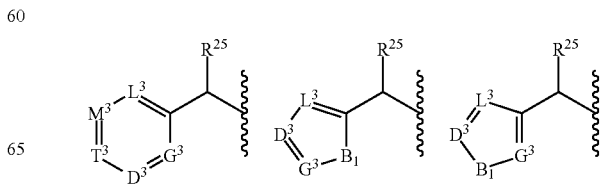

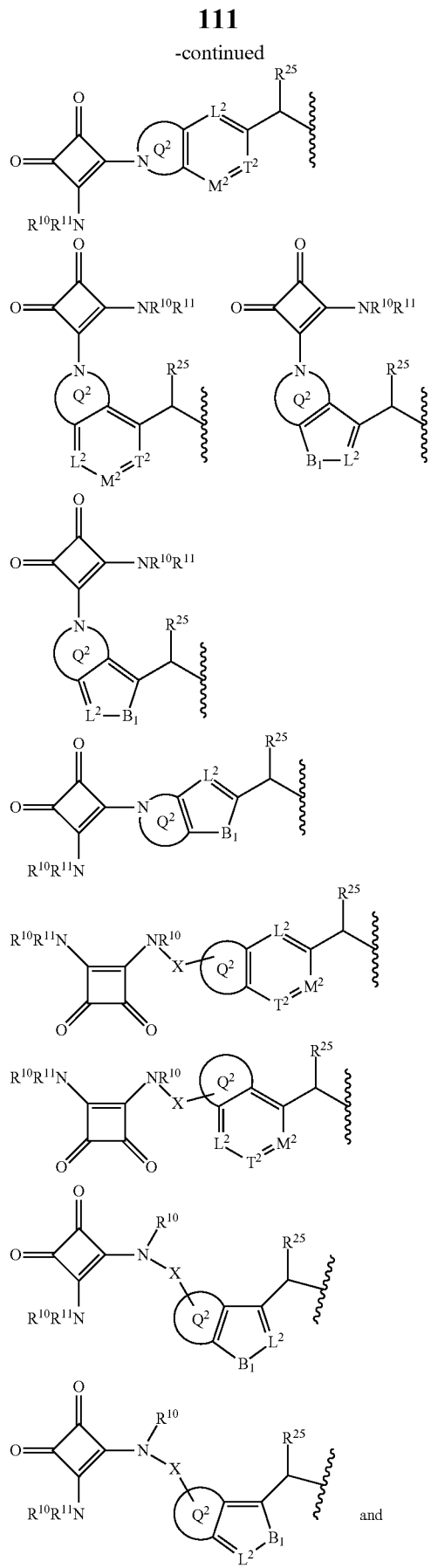
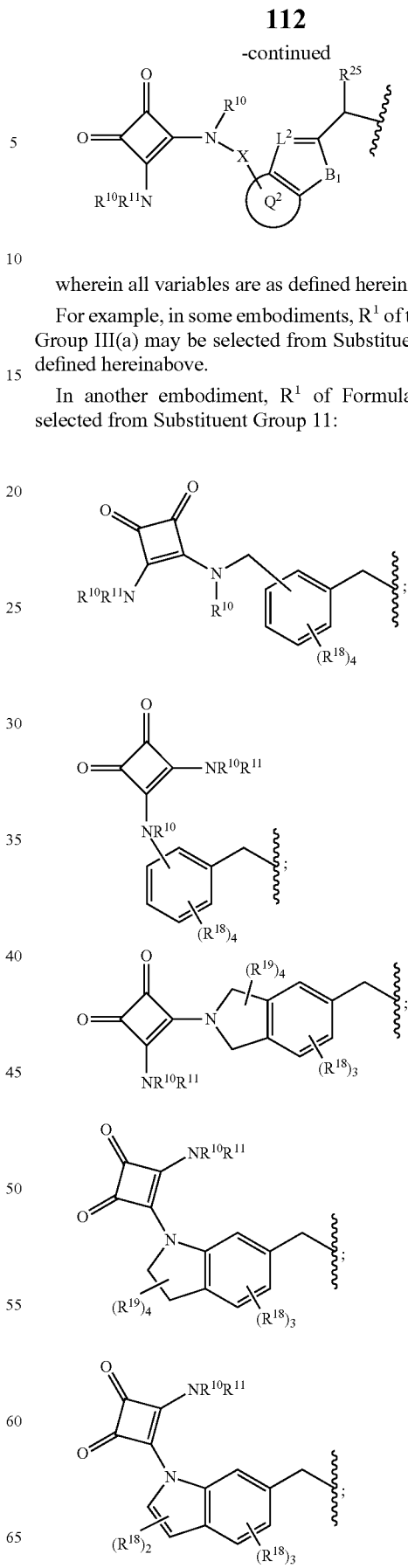
wherein all variables are as defined hereinabove.
For example, in some embodiments, $R^1$ of the structures of Group III(a) may be selected from Substituent Group 10 as defined hereinabove.
In another embodiment, $R^1$ of Formula (III) may be selected from Substituent Group 11:

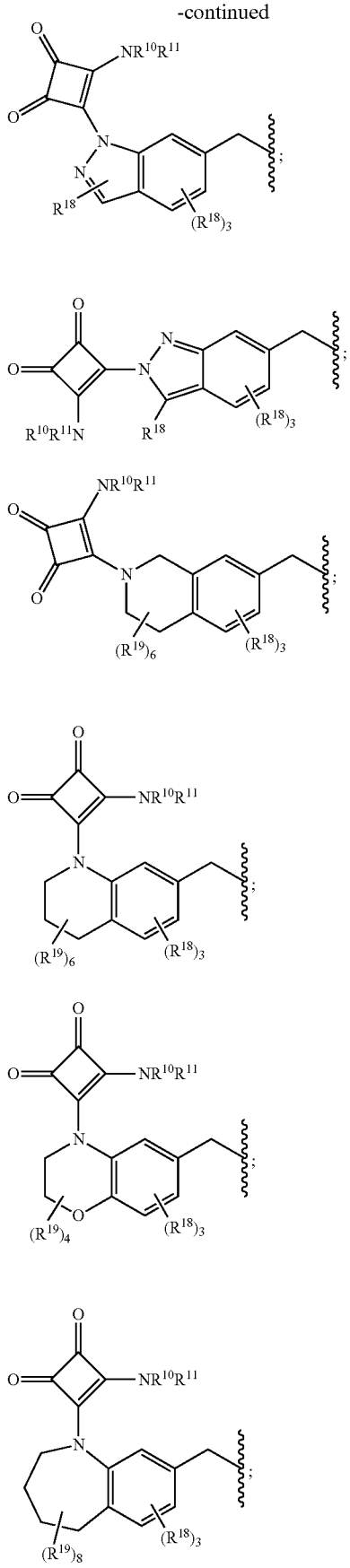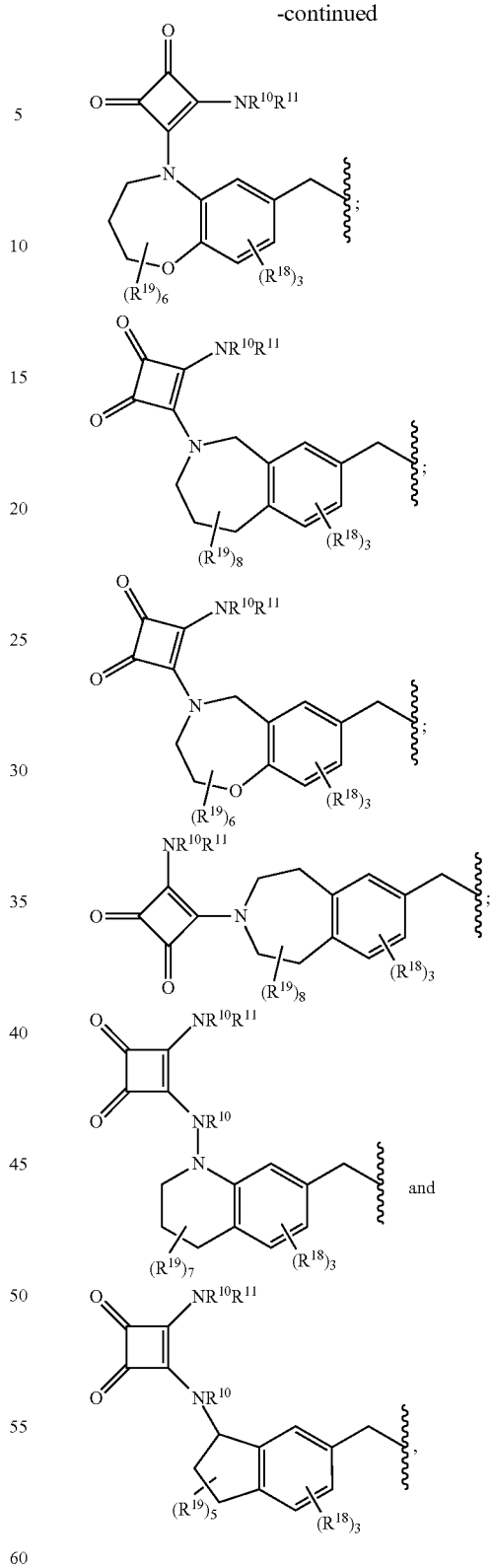
wherein all variables are as defined hereinabove.
For example, in some embodiments, R¹ of the structures of Group III(a) may be selected from Substituent Group 11 as defined hereinabove.
In yet another embodiment, R¹ of Formula (III) may be selected from Substituent Group 12:

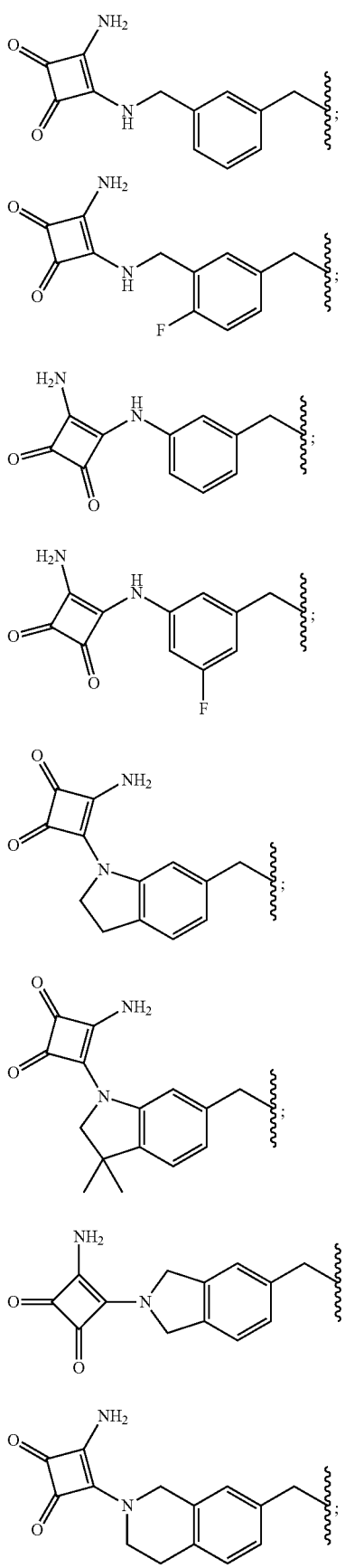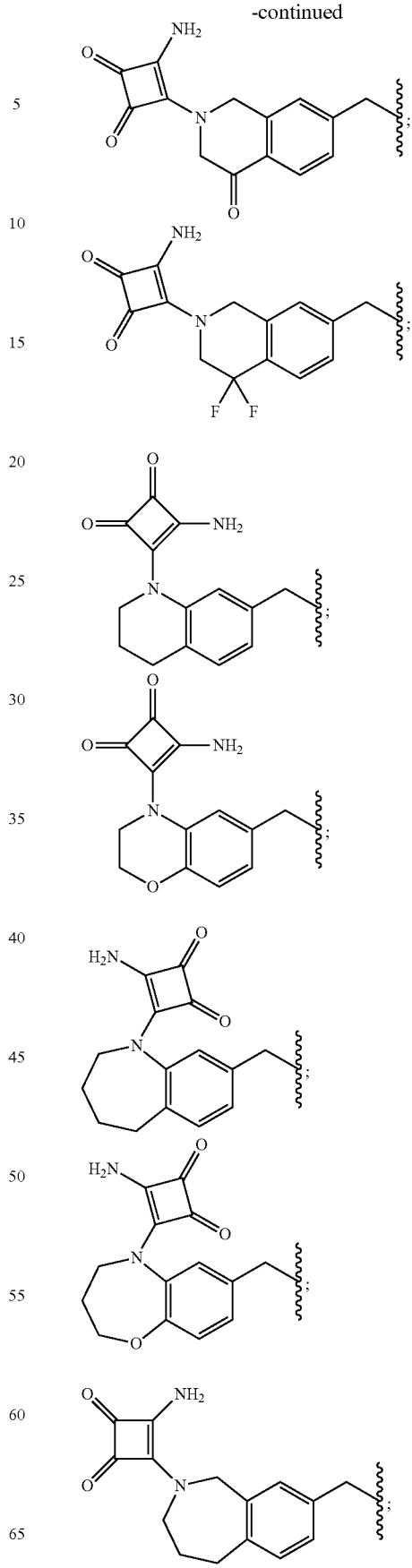

-continued

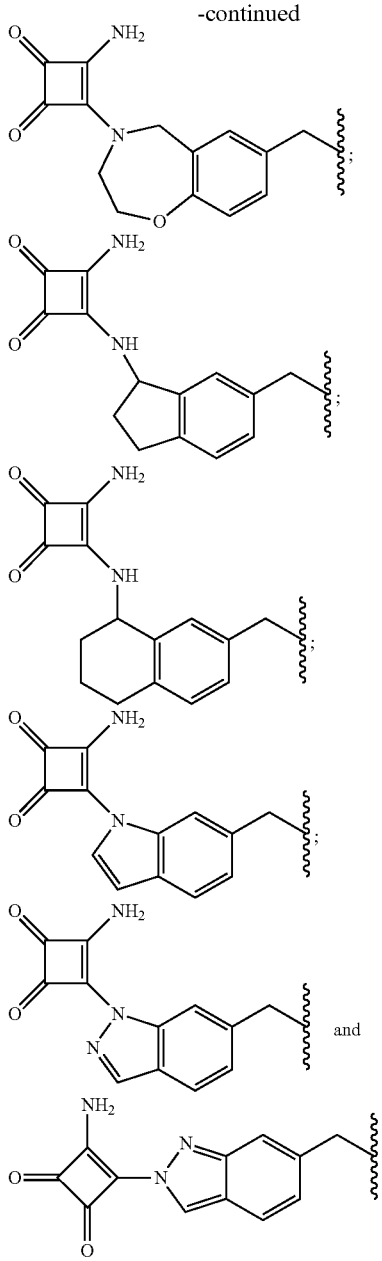

For example, in some embodiments, R¹ of the structures of Group III(a) may be selected from Substituent Group 12 as defined hereinabove.

In one embodiment of the present invention, the amide containing heterobicyclic metalloprotease compounds may be represented by the general Formula (IV):

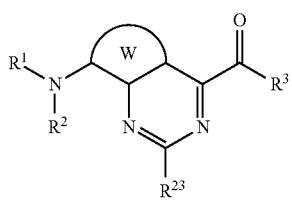

Formula (IV)

and N-oxides, pharmaceutically acceptable salts, prodrugs, formulation, polymorphs, racemic mixtures and stereoisomers thereof, wherein:

$R^{23}$ is selected from the group consisting of hydrogen, hydroxy, halo, alkyl, cycloalkyl, alkoxy, alkenyl, alkynyl, $NO_2$, $NR^{10}R^{11}$, CN, $SR^{10}$, $SSR^{10}$, $PO_3R^{10}$, $NR^{10}NR^{10}R^{11}$, $NR^{10}N=CR^{10}R^{11}$, $NR^{10}SO_2R^{11}$, $C(O)OR^{10}$, and fluoroalkyl, wherein alkyl, cycloalkyl, alkoxy, alkenyl, alkynyl, and fluoroalkyl are optionally substituted one or more times;

W is a 5- or 6-membered ring selected from the group consisting of aryl and heteroaryl, wherein aryl and heteroaryl are optionally substituted one or more times with $R^4$; and all remaining variables are as defined herein above.

In another embodiment, the compounds of Formula (IV) may be selected from Group IV(a):

wherein:

$R^{51}$ is independently selected from the group consisting of hydrogen, alkyl, aryl, heteroaryl, arylalkyl, cycloalkylalkyl, heteroarylalkyl and haloalkyl, wherein alkyl, aryl, heteroaryl, arylalkyl, cycloalkylalkyl, heteroarylalkyl and haloalkyl are optionally substituted one or more times;

$K^1$ is O, $S(O)_x$, or $NR^{51}$; and all remaining variables are as defined hereinabove.

In yet another embodiment, the compounds of Formula (IV) may be selected from Group IV(b):

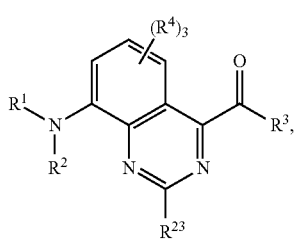
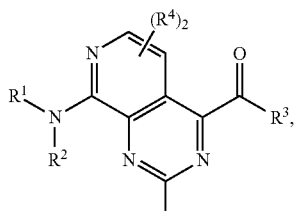
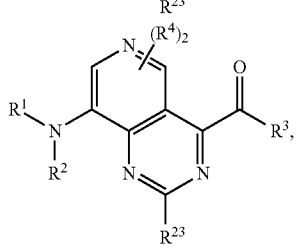
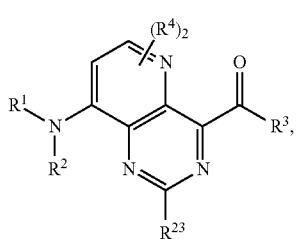
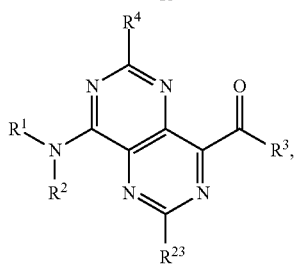
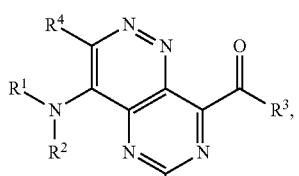
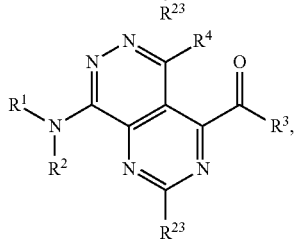
-continued
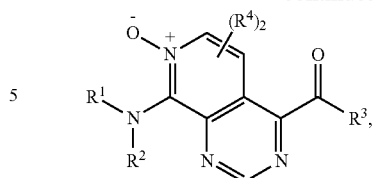
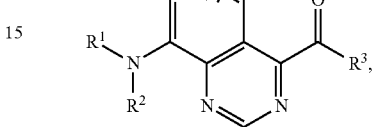
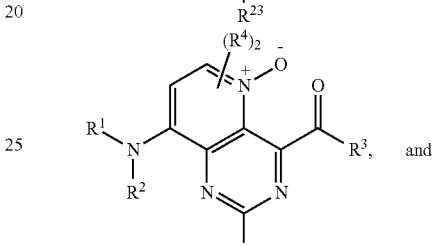
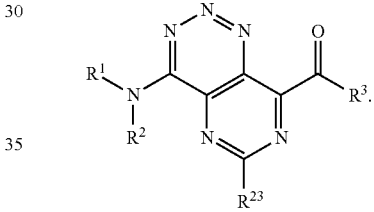
, and
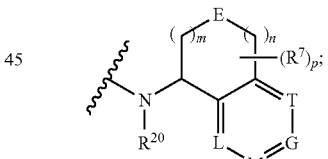
.
In still another embodiment, $R^3$ of Formula (IV) may be selected from Substituent Group 1:
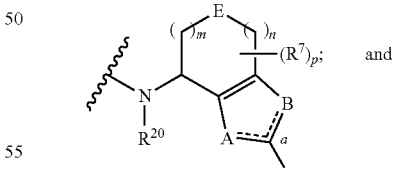
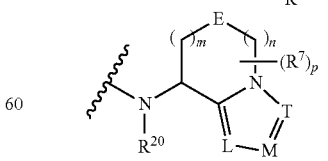
; and
wherein all variables are as defined hereinabove.
For example, in some embodiments, $R^3$ of the structures of Groups IV(a) and (b) may be selected from Substituent Group 1 as defined hereinabove.

In a further embodiment, $R^3$ of Formula (IV) may be selected from Substituent Group 2:
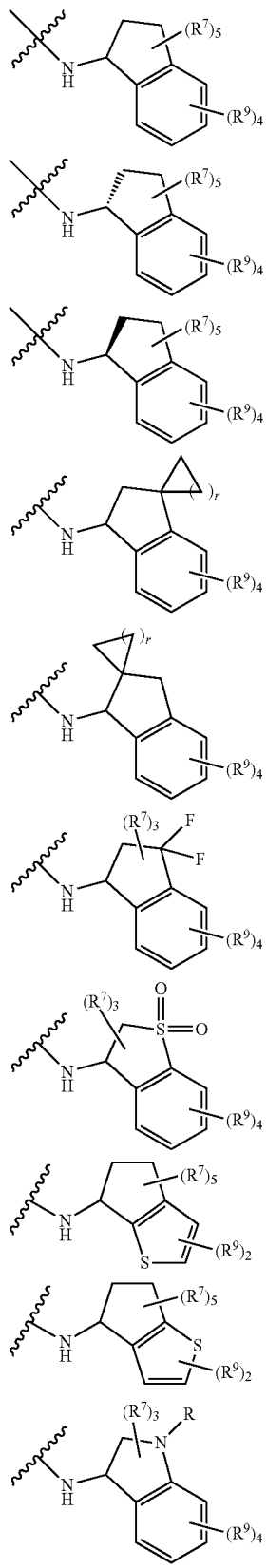
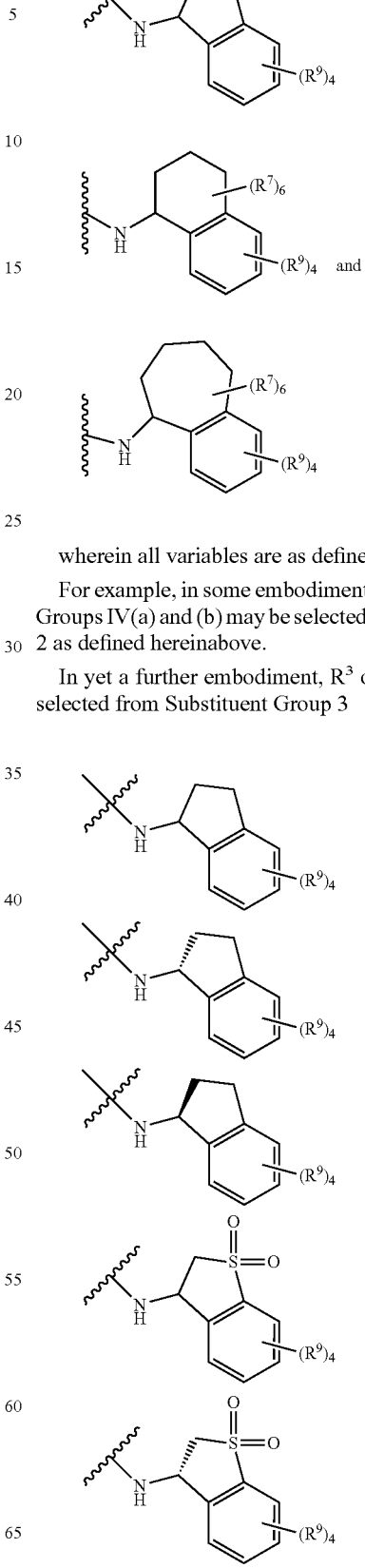
wherein all variables are as defined hereinabove.
For example, in some embodiments, $R^3$ of the structures of Groups IV(a) and (b) may be selected from Substituent Group 2 as defined hereinabove.
In yet a further embodiment, $R^3$ of Formula (IV) may be selected from Substituent Group 3
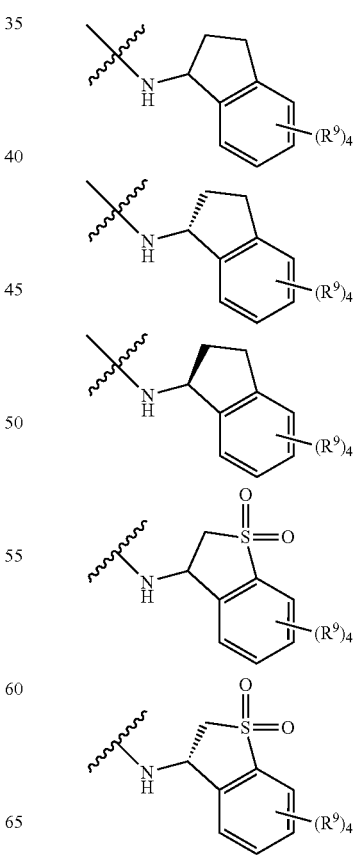

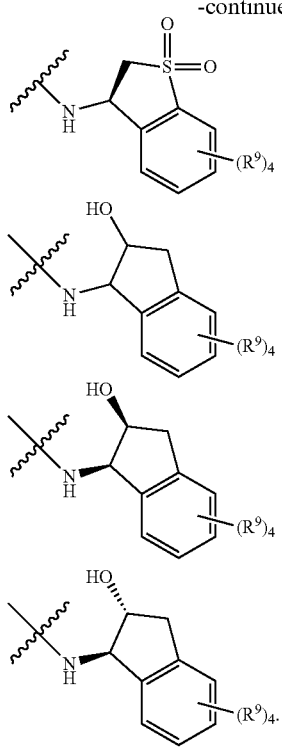
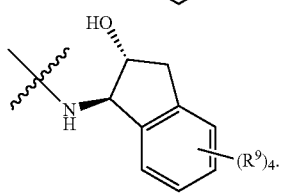
For example, in some embodiments, R³ of the structures of Groups IV(a) and (b) may be selected from Substituent Group 3 as defined hereinabove.
In still a further embodiment, R⁹ of Substituent Group 3 may be selected from:
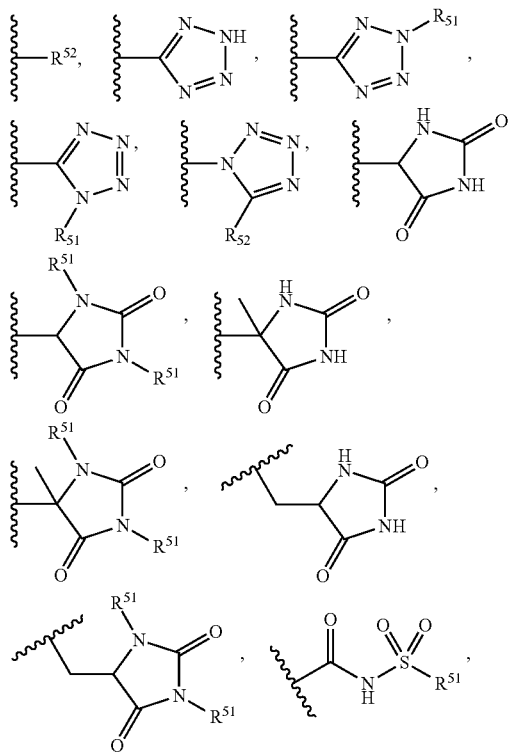
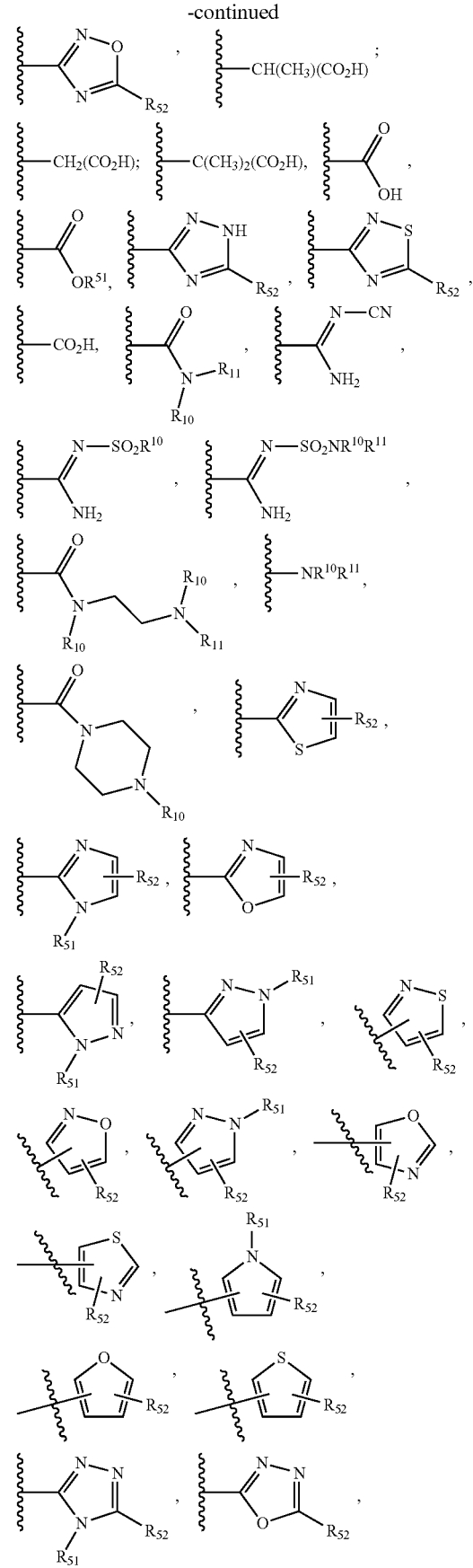

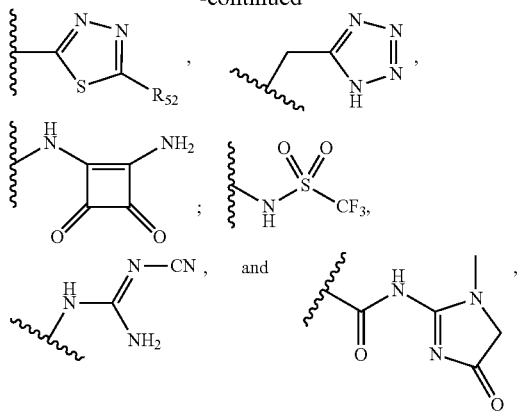

wherein all variables are as defined hereinabove.

In one embodiment, $R^3$ of Formula (IV) may be Substituent Group 16:

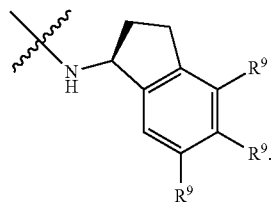

For example, in some embodiments, $R^3$ of the structures of Groups IV(a) and (b) may be Substituent Group 16 as defined hereinabove.

In another embodiment, $R^3$ of Formula (IV) may be selected from Substituent Group 5:

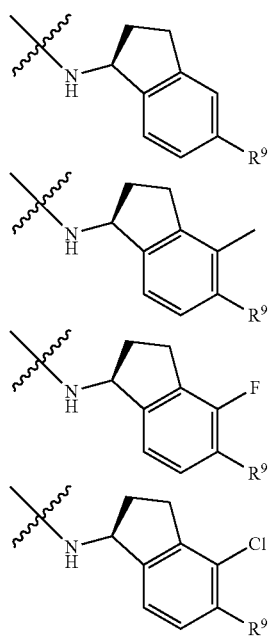

wherein $R^9$ is selected from hydrogen, fluoro, halo, CN, alkyl, $CO_2H$,

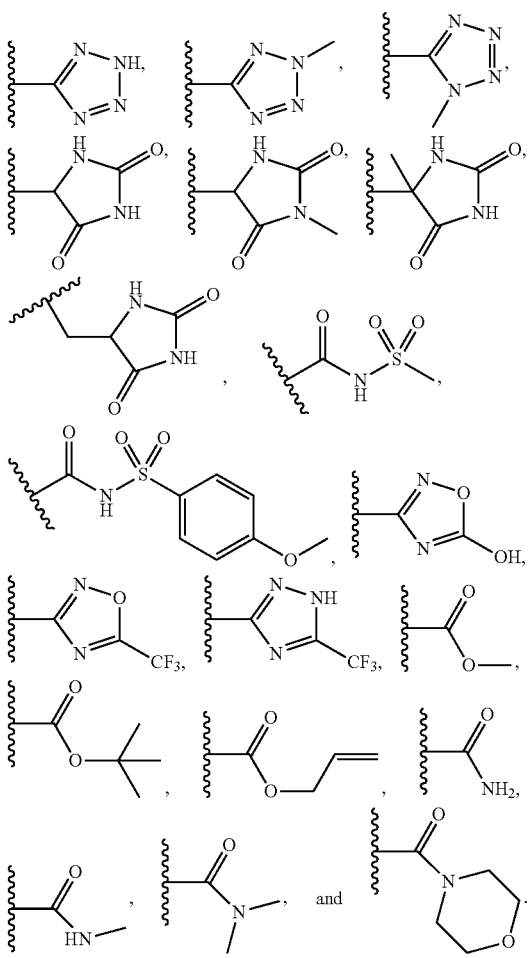

For example, in some embodiments, $R^3$ of the structures of Groups IV(a) and (b) may be selected from Substituent Group 5 as defined hereinabove.

In yet another embodiment, $R^1$ of Formula (IV) may be selected from Substituent Group 6:

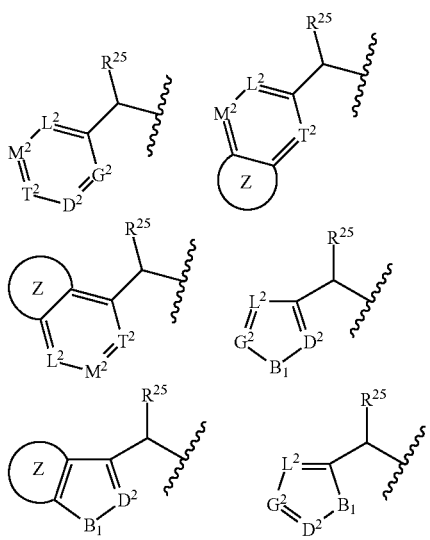

-continued
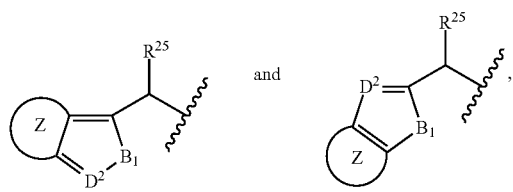
wherein all variables are as defined hereinabove.
For example, in some embodiments, $R^1$ of the structures of Groups IV(a) and (b) may be selected from Substituent Group 6 as defined hereinabove.
In still another embodiment, $R^1$ of Formula (IV) may be selected from Substituent Group 7:
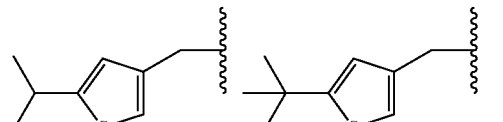
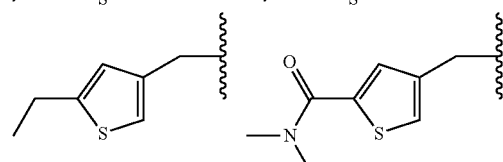
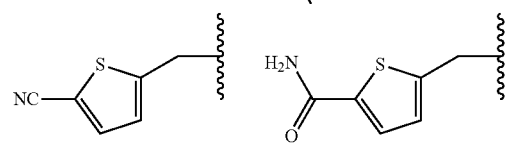
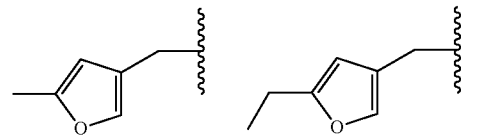
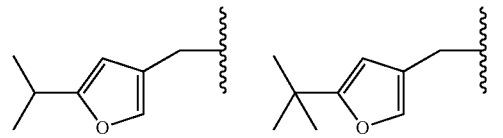
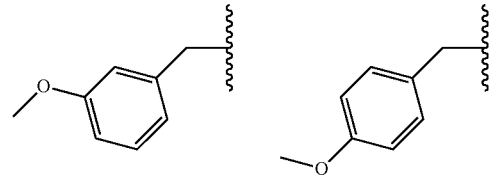

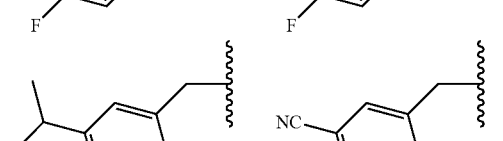
-continued
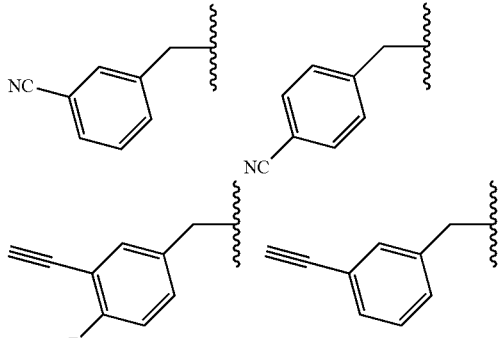
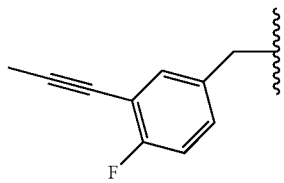
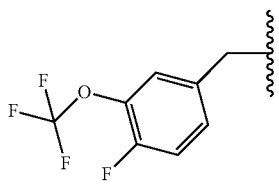
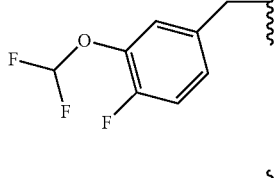
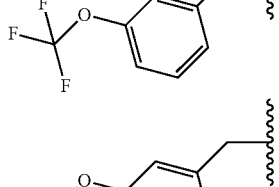
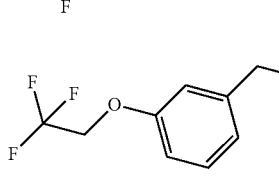
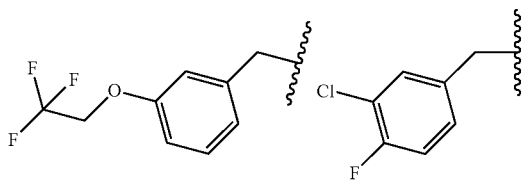

-continued
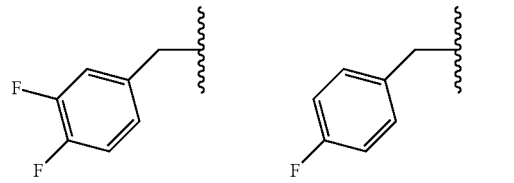
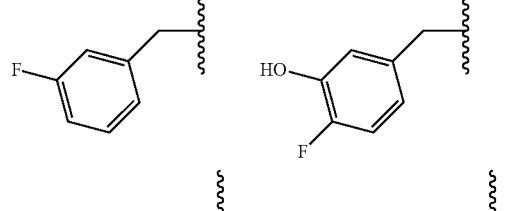
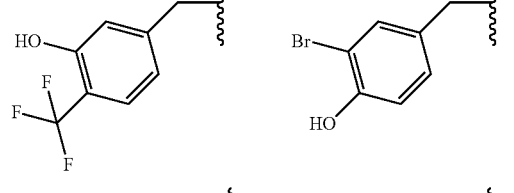
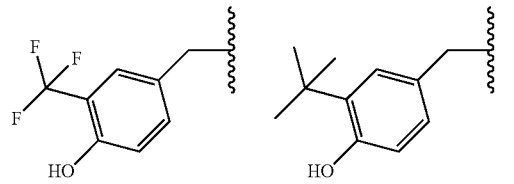
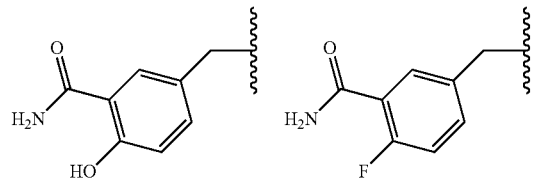
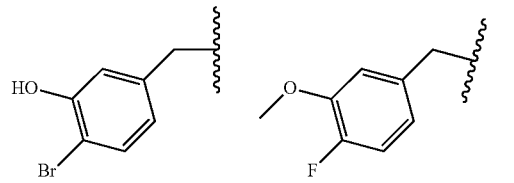
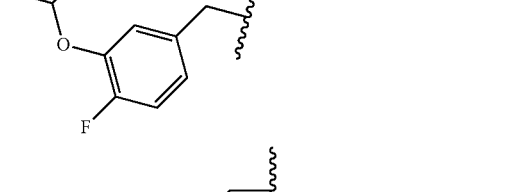
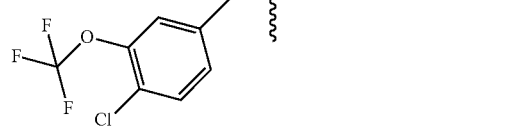
-continued
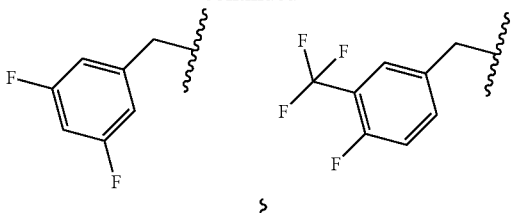
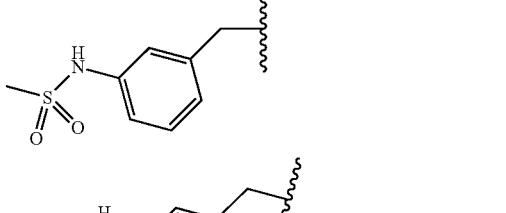
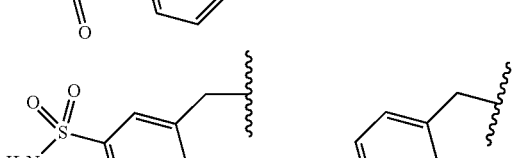
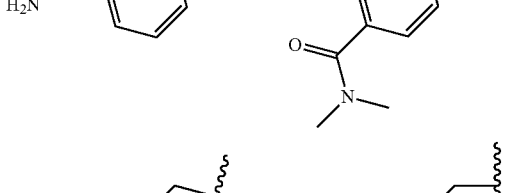
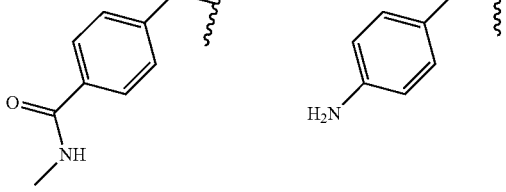
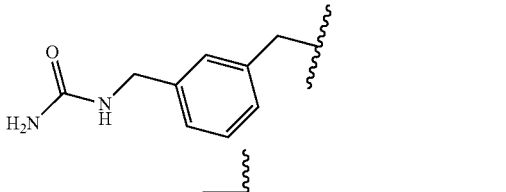
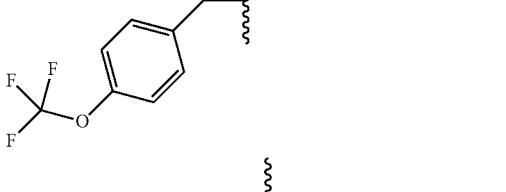
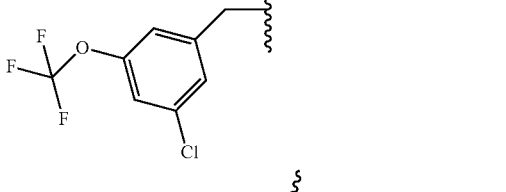
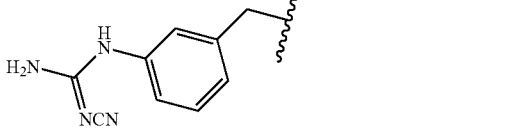

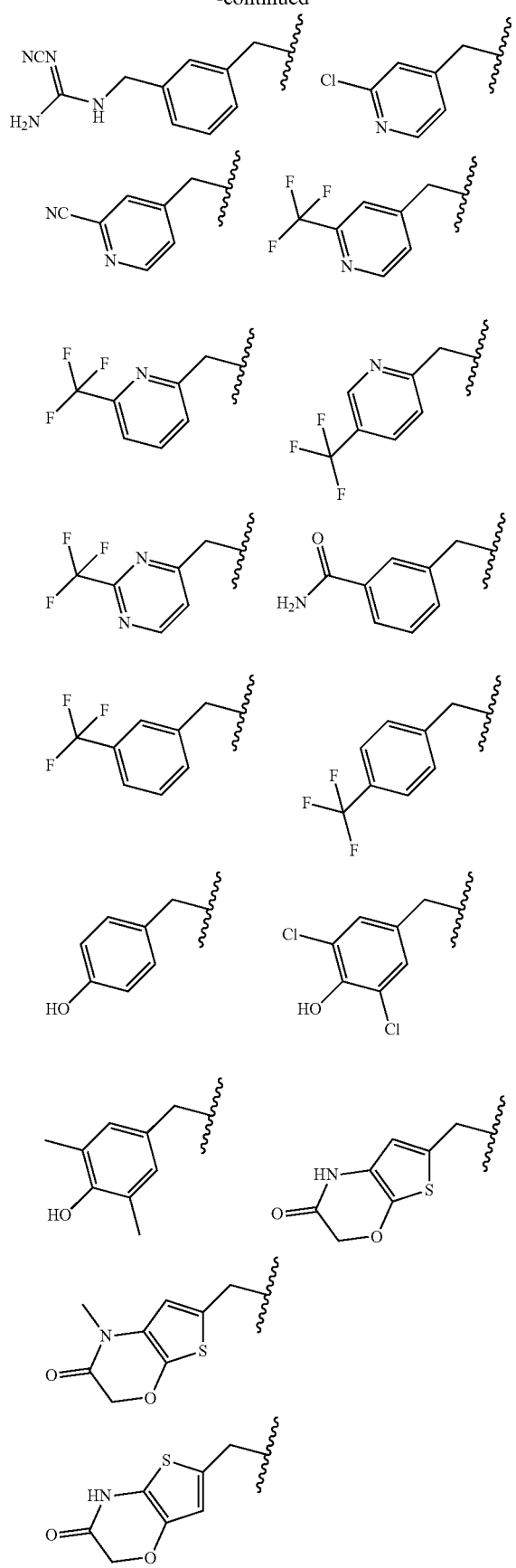
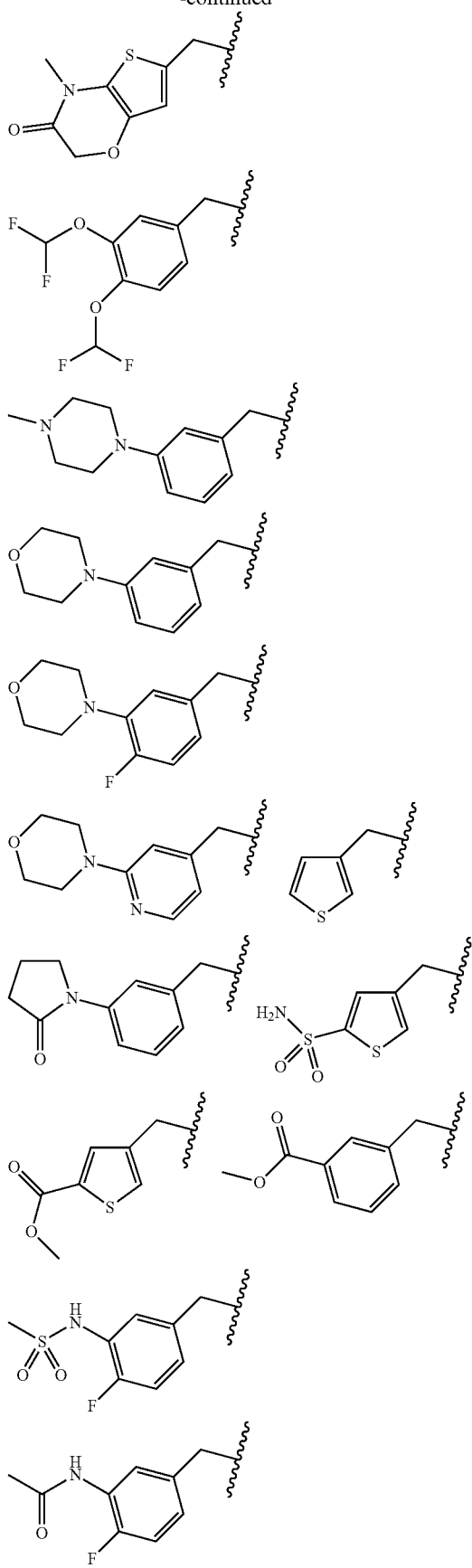

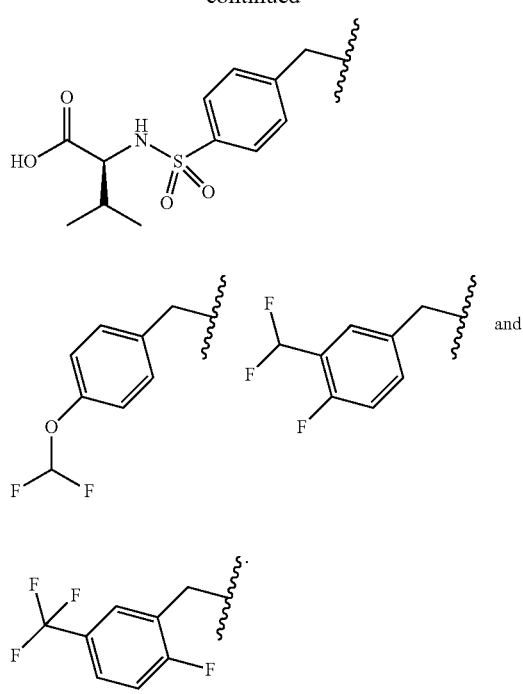

For example, in some embodiments, R¹ of the structures of Groups IV(a) and (b) may be selected from Substituent Group 7 as defined hereinabove.

In a further embodiment, R¹ of Formula (IV) may be selected from Substituent Group 8:

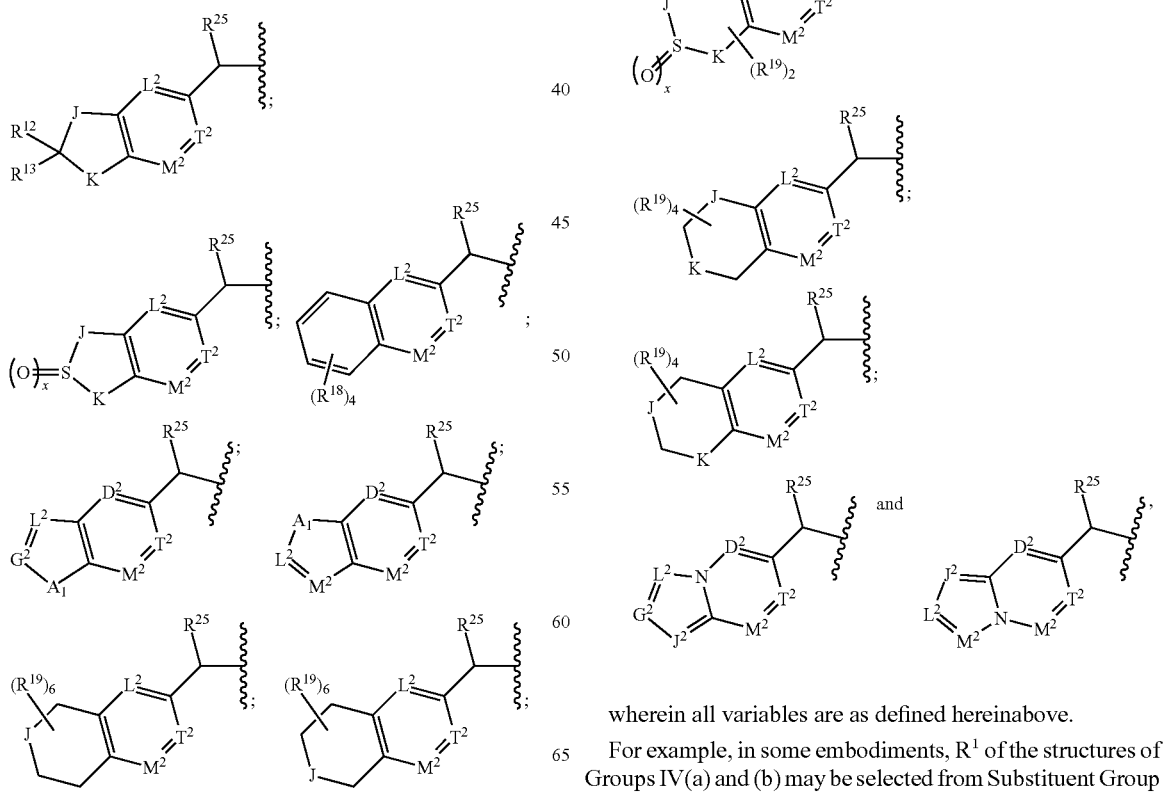

wherein all variables are as defined hereinabove.

For example, in some embodiments, R¹ of the structures of Groups IV(a) and (b) may be selected from Substituent Group 8 as defined hereinabove.

In yet a further embodiment, $R^1$ of Formula (IV) may be selected from Substituent Group 9:
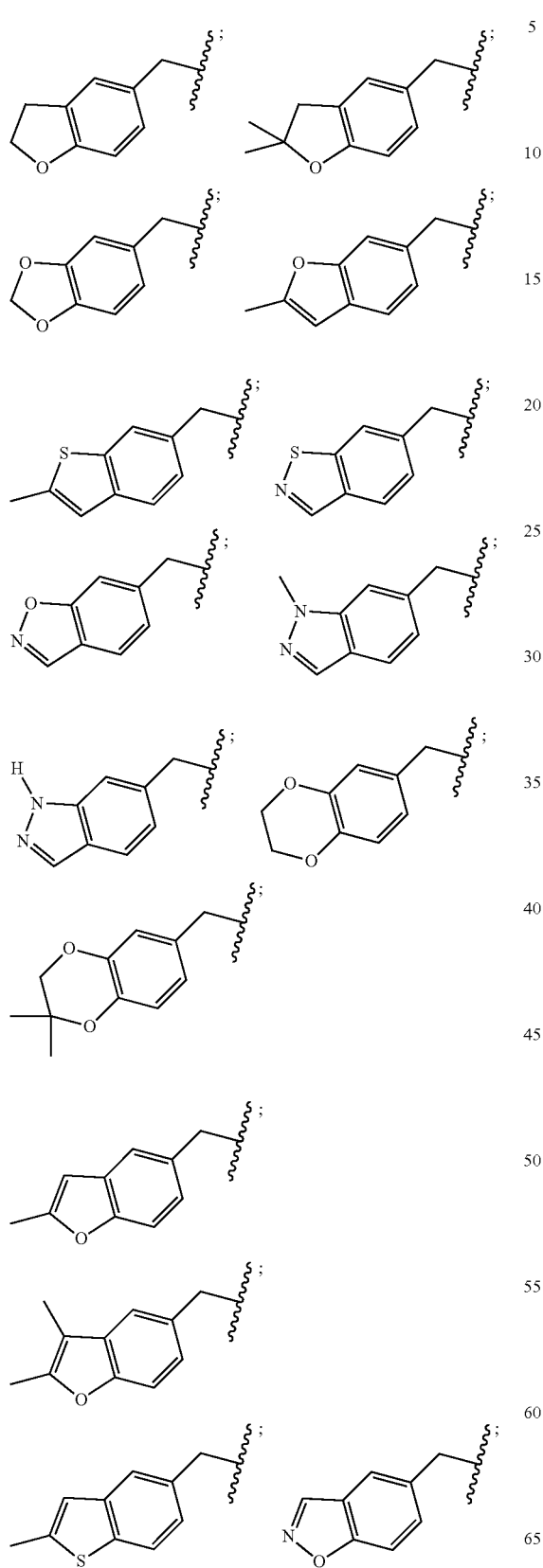
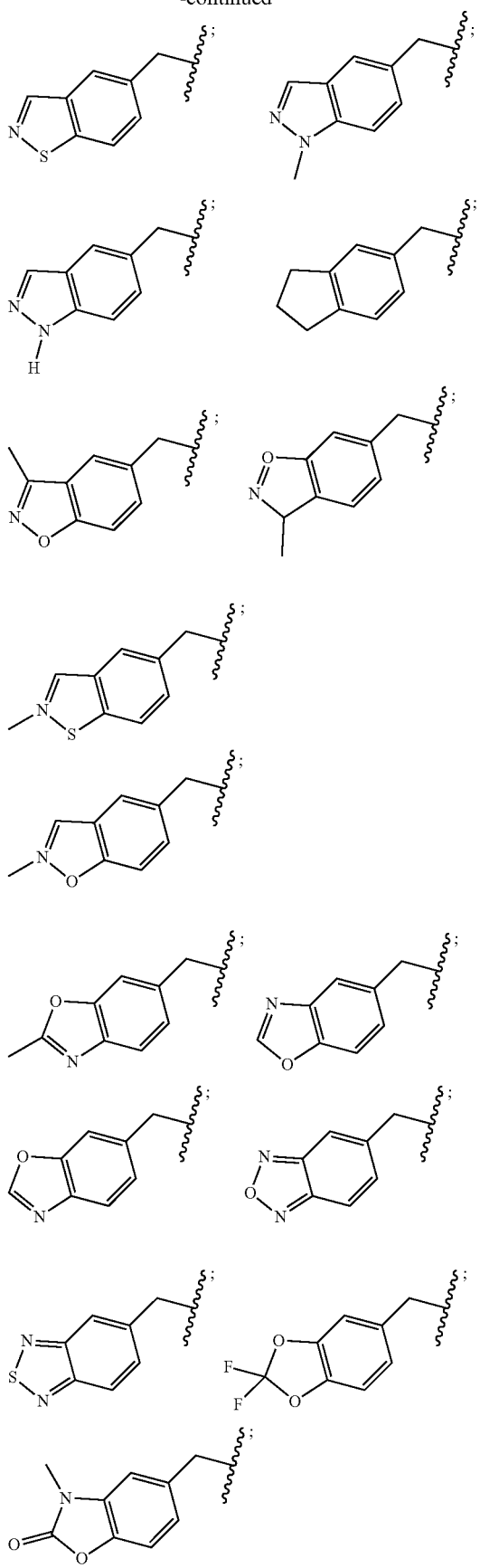

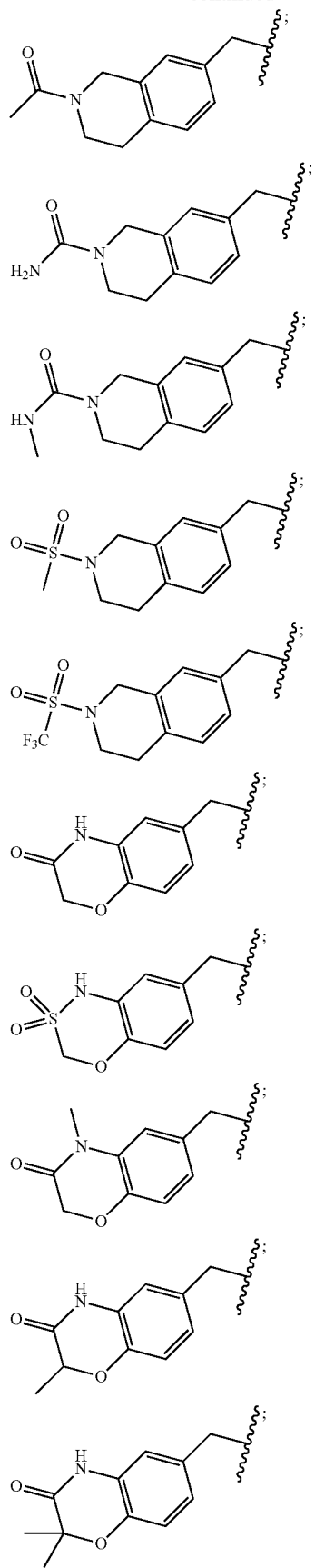
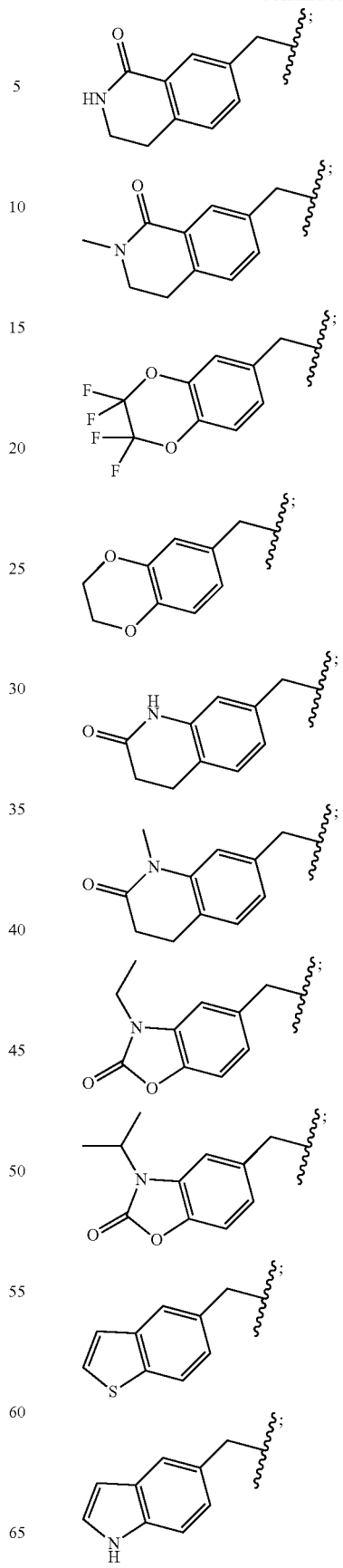

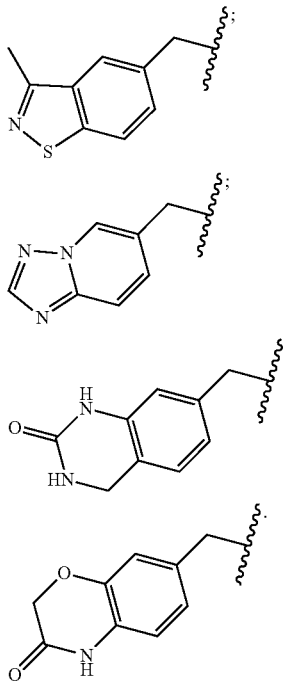
For example, in some embodiments, R¹ of the structures of Groups IV(a) and (b) may be selected from Substituent Group 9 as defined hereinabove.
In still a further embodiment, R¹ of Formula (IV) may be selected from Substituent Group 10:
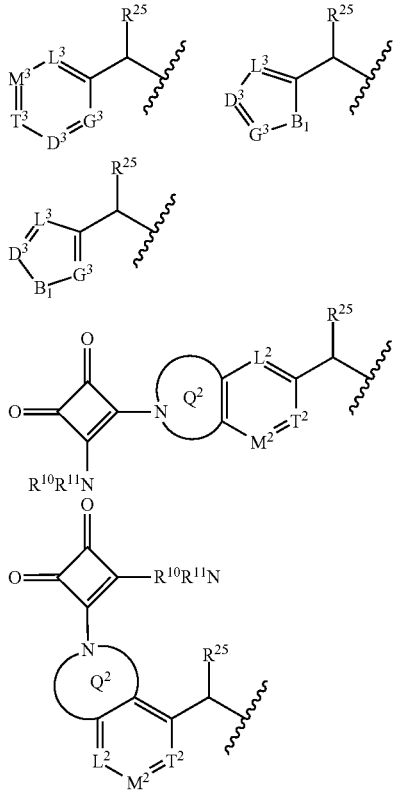
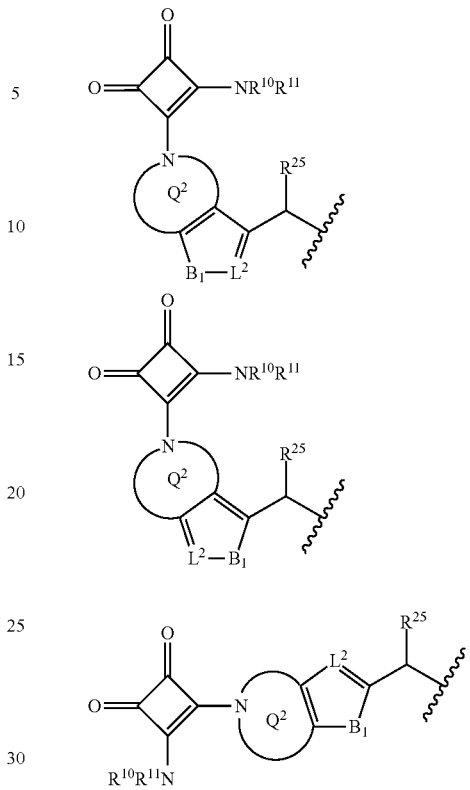

-continued
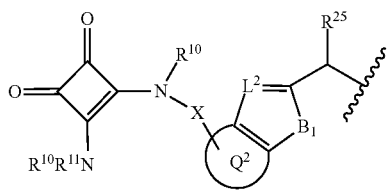
wherein all variables are as defined hereinabove.
For example, in some embodiments, $R^1$ of the structures of Groups IV(a) and (b) may be selected from Substituent Group 10 as defined hereinabove.
In one embodiment, $R^1$ of Formula (IV) may be selected from Substituent Group 11:
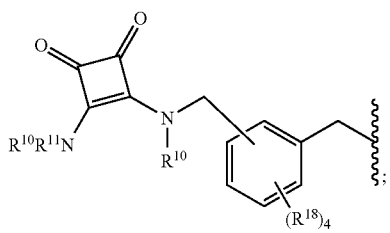
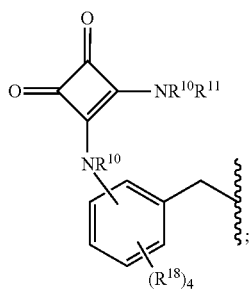
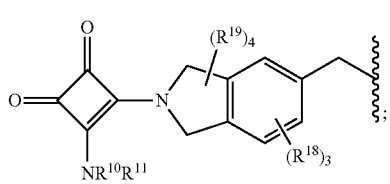
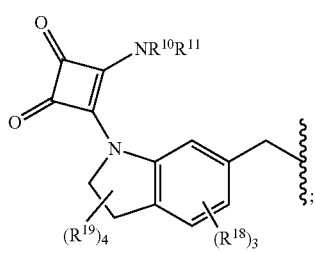
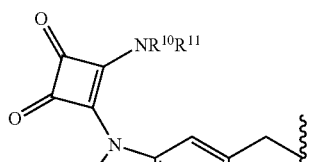
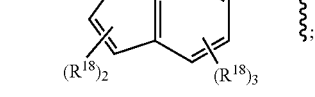
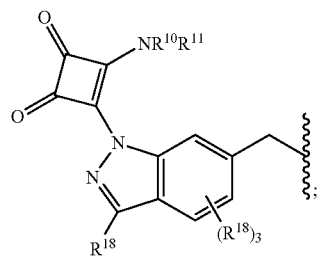
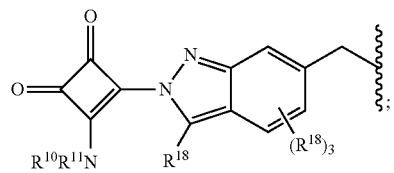
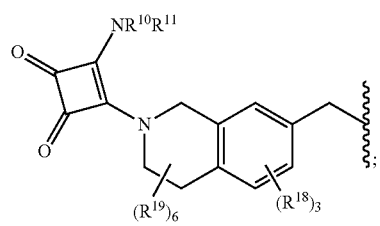
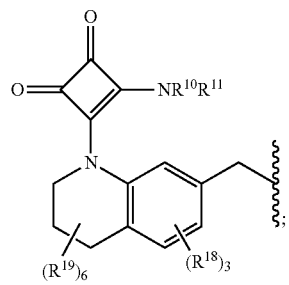
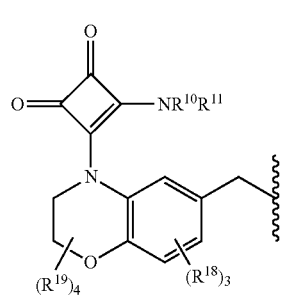
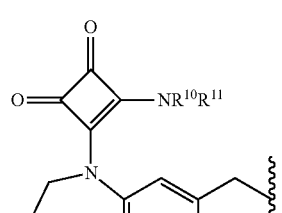
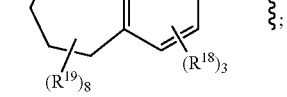

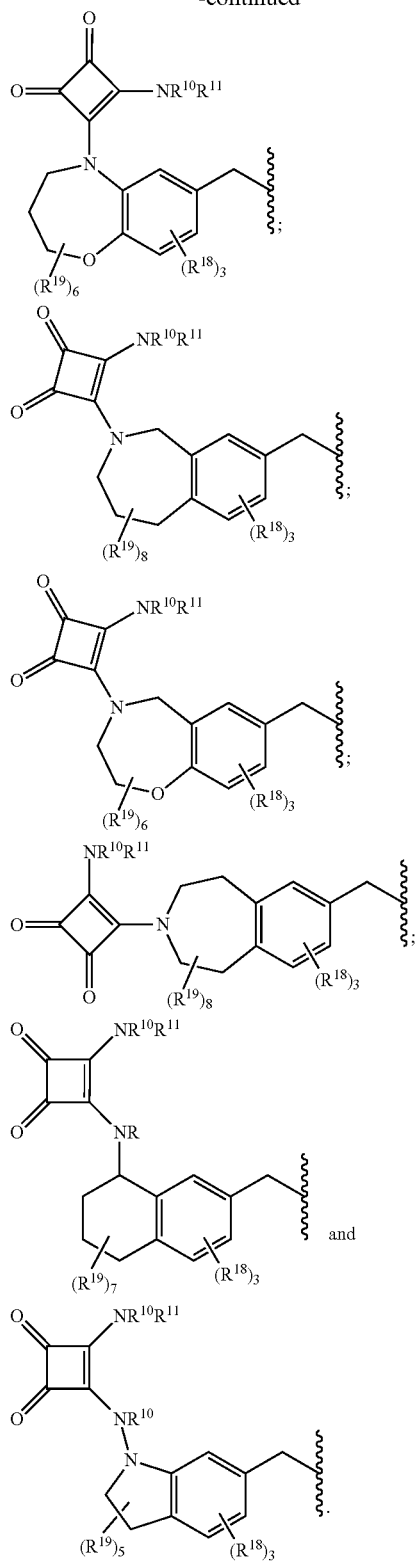
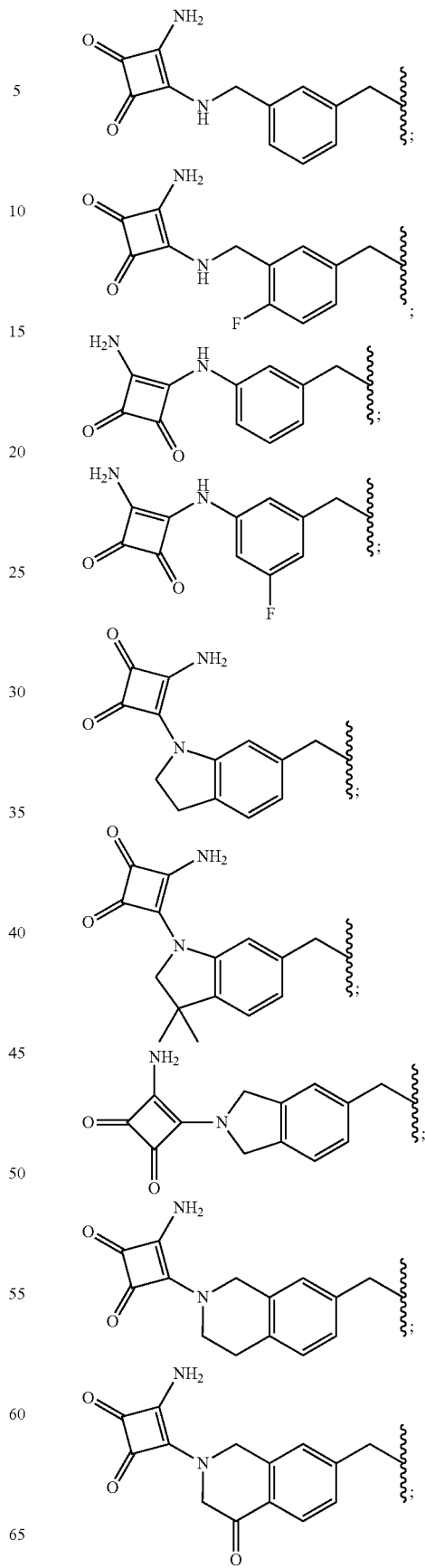
For example, in some embodiments, $R^1$ of the structures of Groups IV(a) and (b) may be selected from Substituent Group 11 as defined hereinabove.
In another embodiment, $R^1$ of Formula (IV) may be selected from Substituent Group 12:

145
-continued

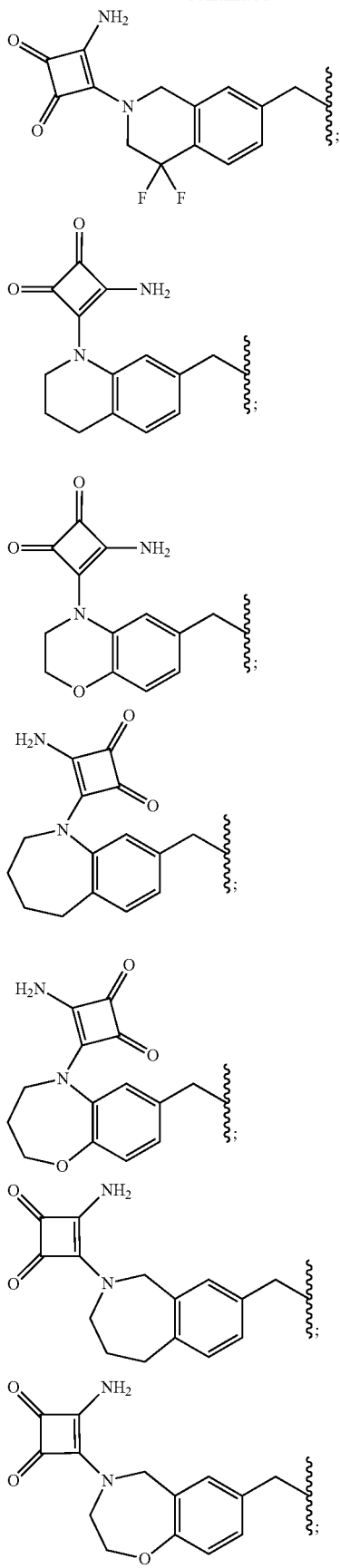

146
-continued

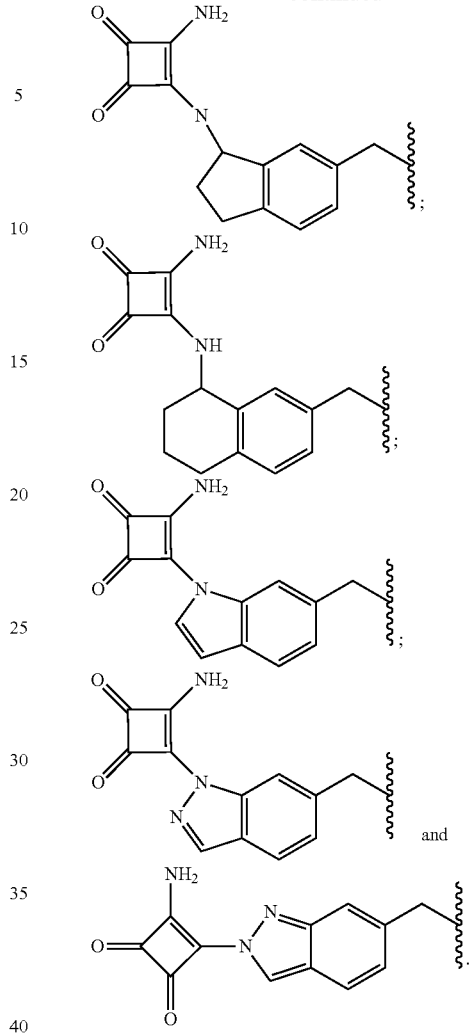

For example, in some embodiments, R¹ of the structures of Groups IV(a) and (b) may be selected from Substituent Group 12 as defined hereinabove.

In still another embodiment of the present invention, the amide containing heterobicyclic metalloprotease compounds may be represented by the general Formula (V):

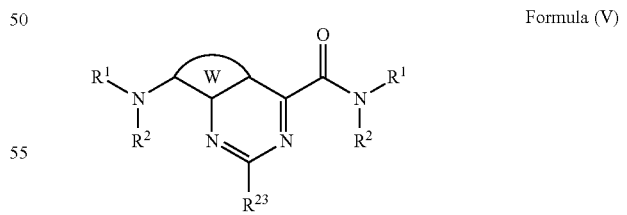

Formula (V)

and N-oxides, pharmaceutically acceptable salts, prodrugs, formulation, polymorphs, racemic mixtures and stereoisomers thereof,
wherein:
R¹ in each occurrence may be the same or different and is as defined hereinabove;
R² in each occurrence may be the same or different and is as defined hereinabove; and
all remaining variables are as defined hereinabove.

In a further embodiment, compounds of Formula (V) may be selected from Group V(a):
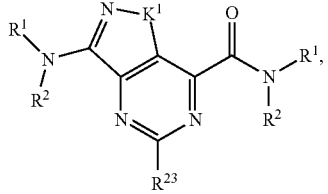
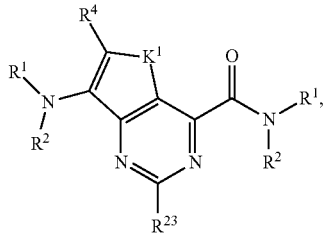
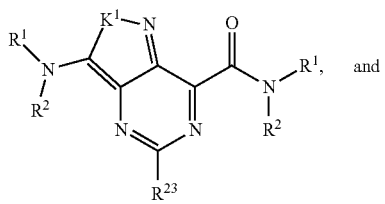
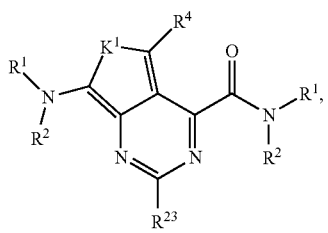
wherein all variables are as defined hereinabove.
In yet a further embodiment, the compounds of Formula (V) may be selected from Group V(b):
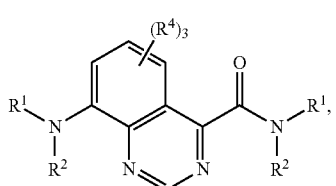
-continued
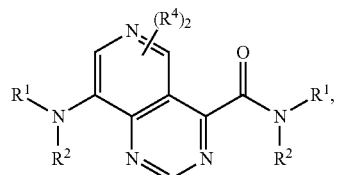
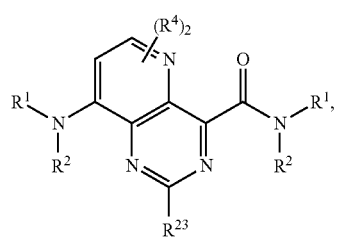
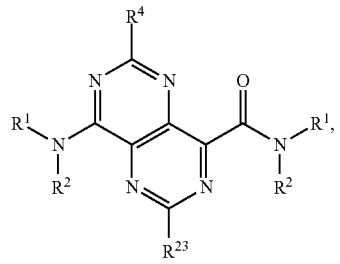
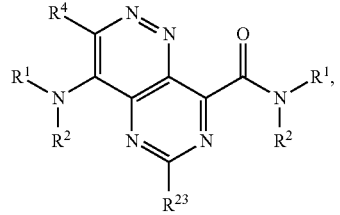
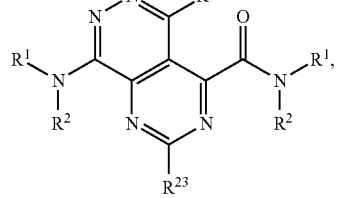
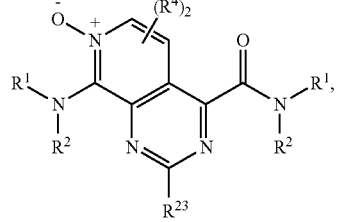
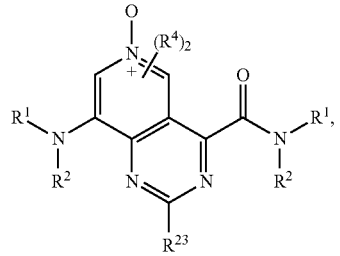

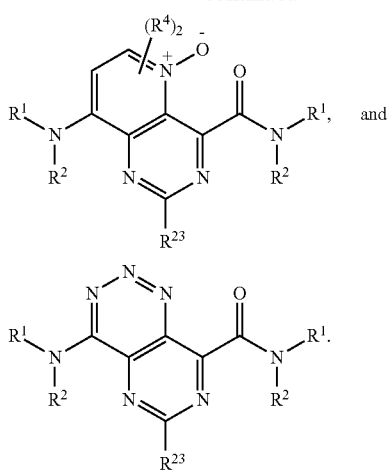
In still a further embodiment, at least one $R^1$ of Formula (V) may be selected from Substituent Group 13:
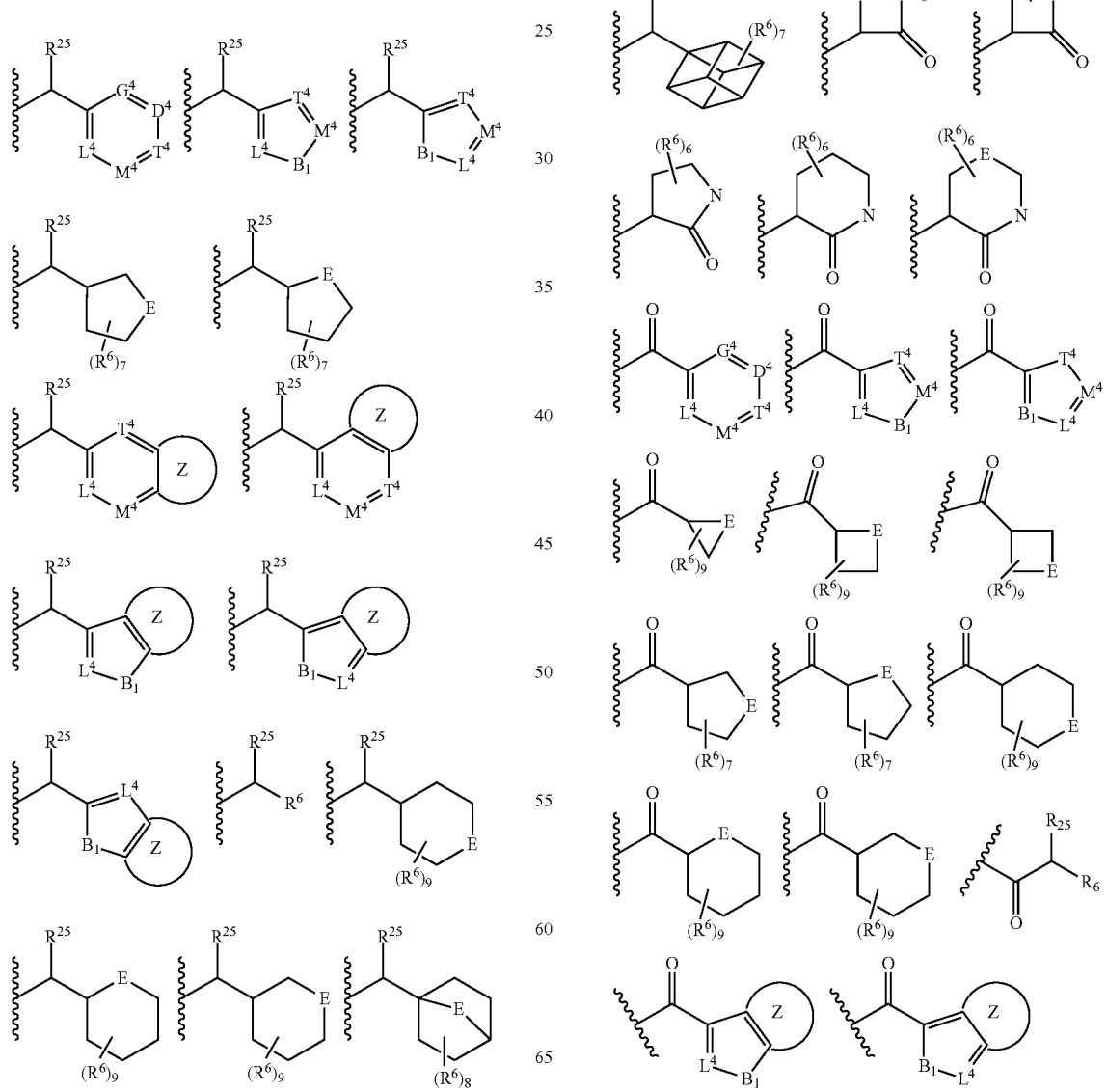

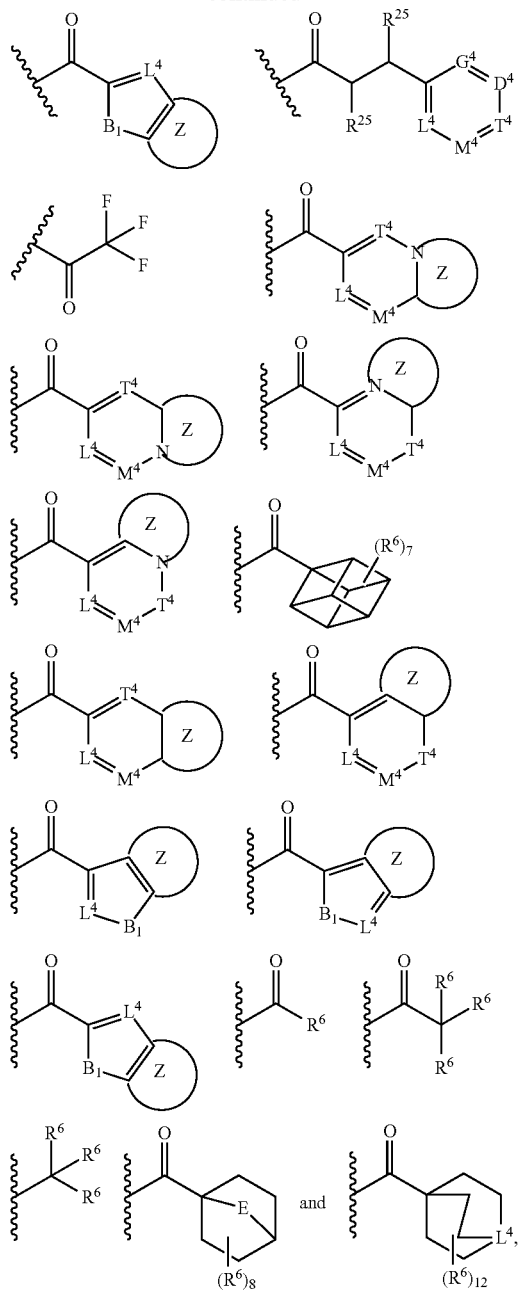
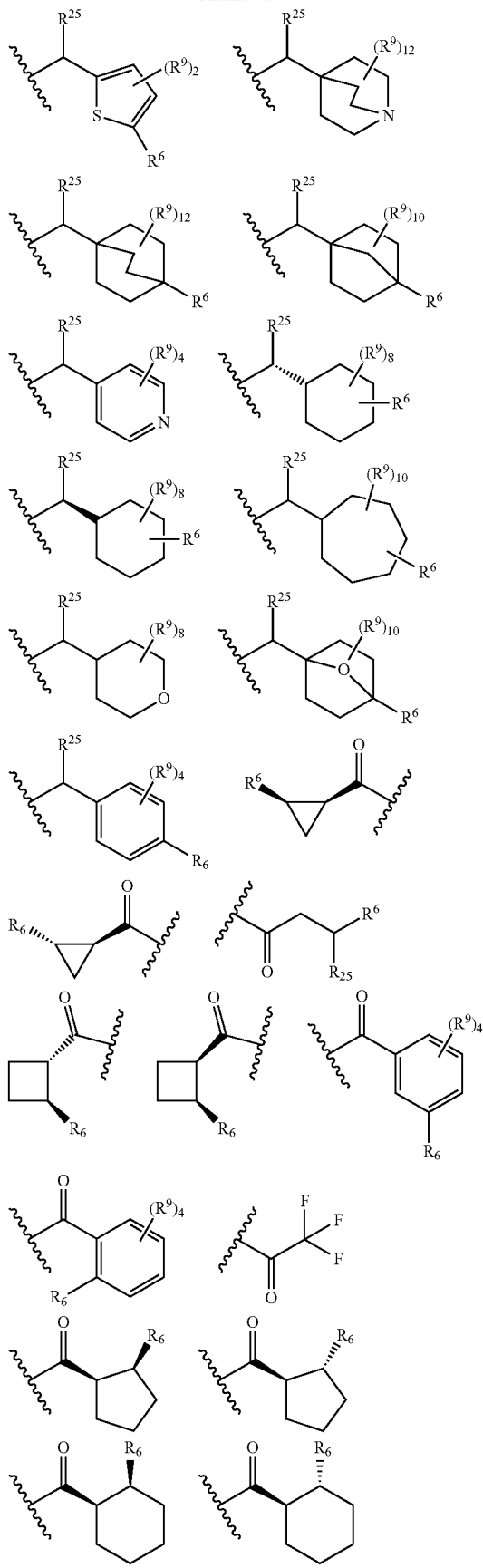
wherein all variables are as defined hereinabove.
For example, in some embodiments, at least one $R^1$ of the structures of Groups V(a) and (b) may be selected from Substituent Group 13 as defined hereinabove.
In one embodiment, at least one $R^1$ of the compounds of Formula (V) may be selected from Substituent Group 14:
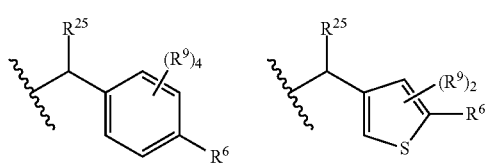

-continued

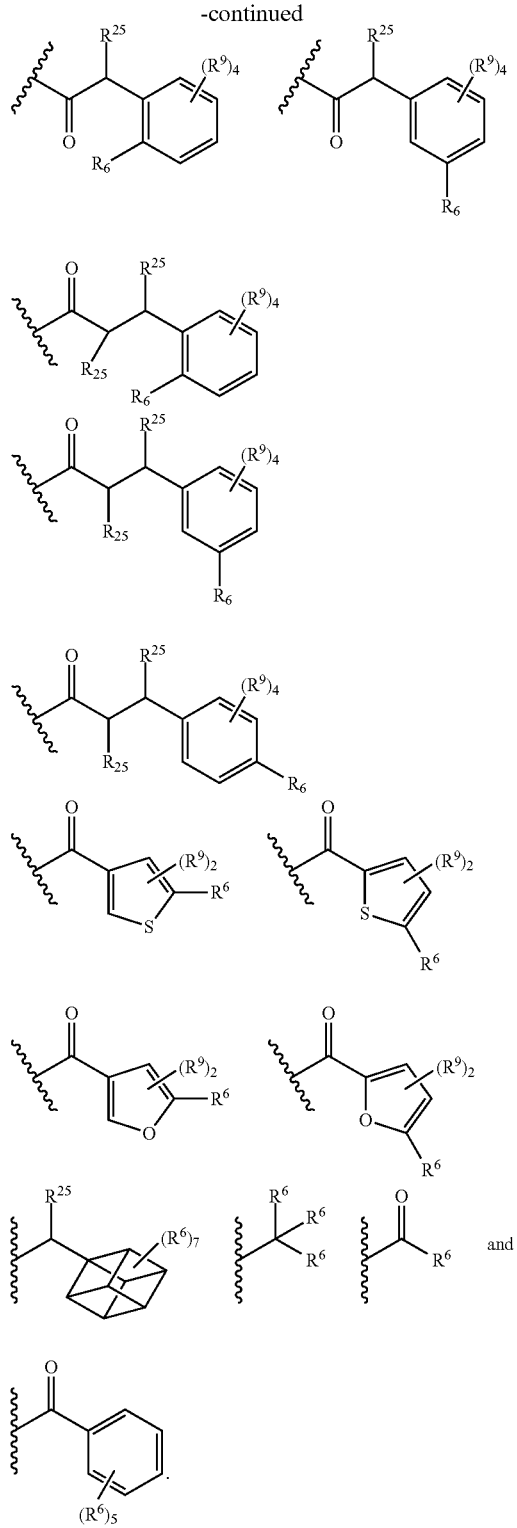

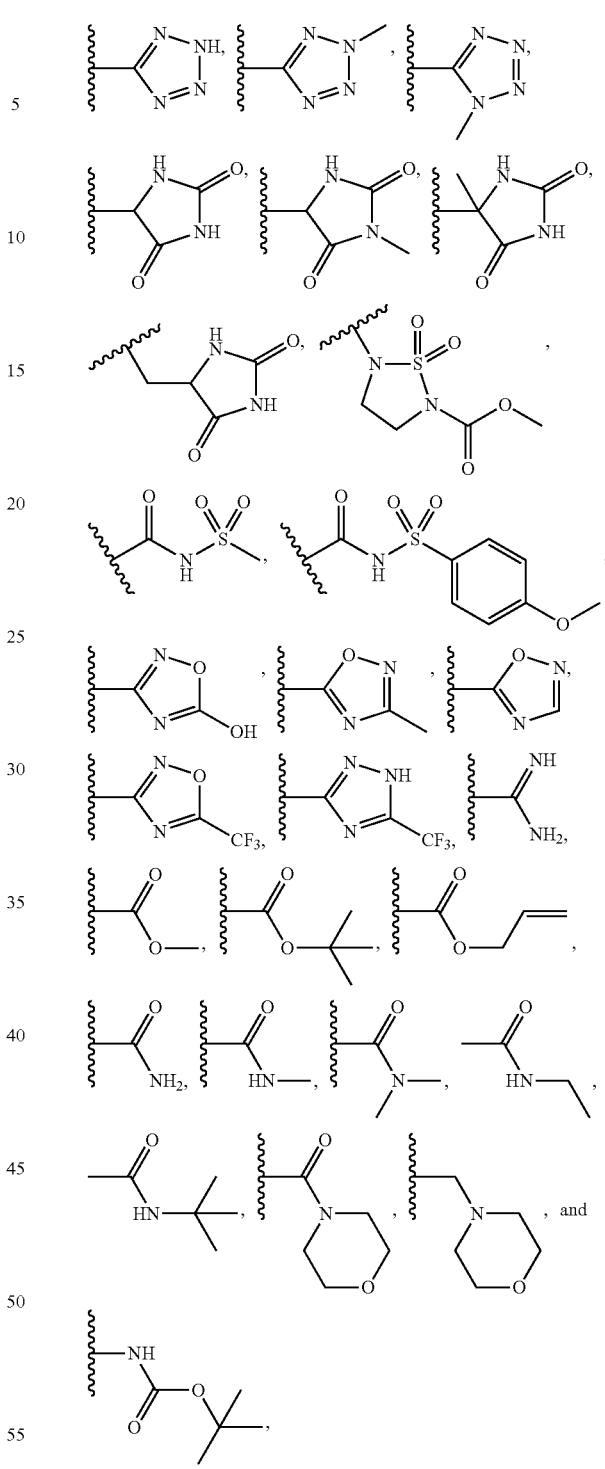

wherein

For example, in some embodiments, at least one $R^1$ of the structures of Groups V(a) and (b) may be selected from Substituent Group 14 as defined hereinabove.

In another embodiment, $R^6$ of Substituent Group 14 may be selected from hydrogen, halo, CN, OH, $CH_2OH$, $CF_3$, $CHF_2$, $OCF_3$, $OCHF_2$, $COCH_3$, $SO_2CH_3$, $SO_2CF_3$, $SO_2NH_2$, $SO_2NHCH_3$, $SO_2N(CH_3)_2$, $NH_2$, $NHCOCH_3$, $N(COCH_3)_2$, $NHCONH_2$, $NHSO_2CH_3$, alkoxy, alkyl, $CO_2H$, $R^9$ is independently selected from the group consisting of hydrogen, fluoro, chloro, $CH_3$, $CF_3$, $CHF_2$, $OCF_3$, and $OCHF_2$;

$R^{25}$ is selected from the group consisting of hydrogen, $CH_3$, $COOCH_3$, $COOH$, and $CONH_2$.

In yet another embodiment, at least one $R^1$ of Formula (V) may be selected from Substituent Group 15:

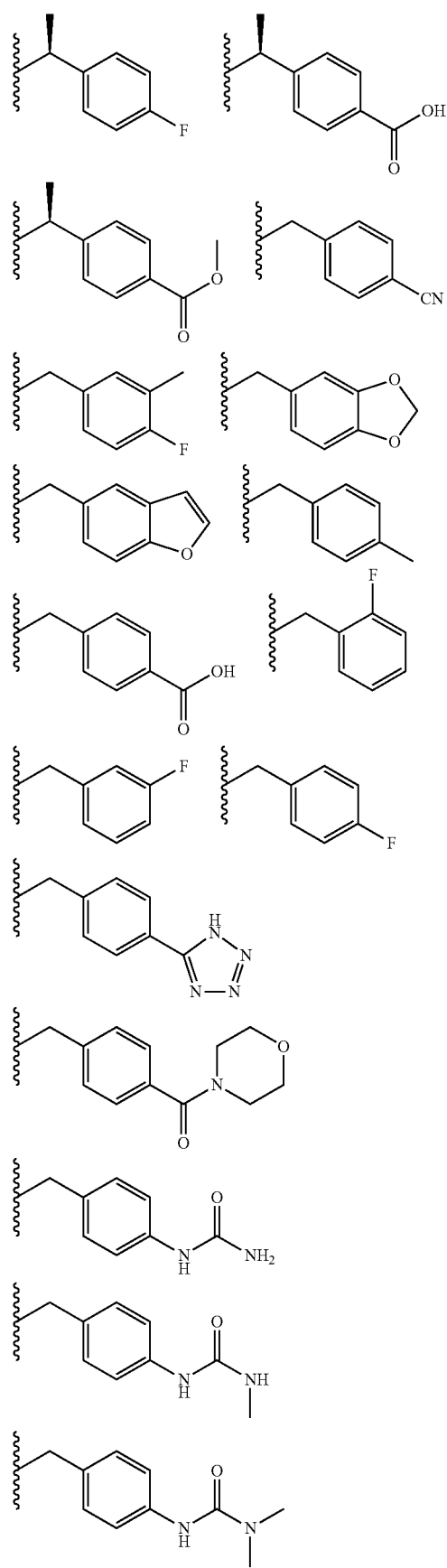
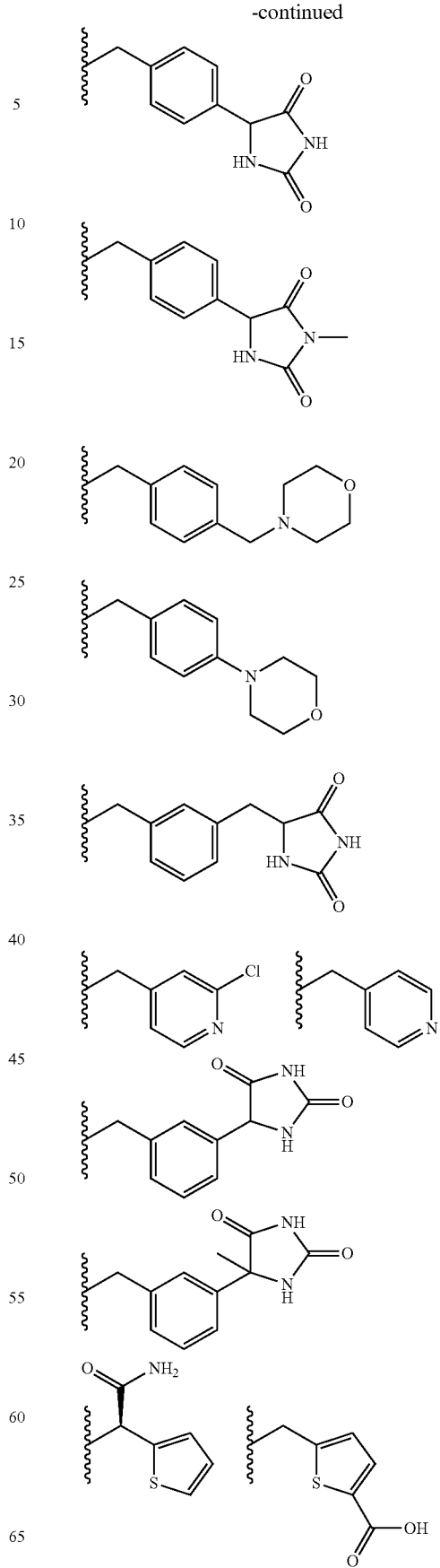

157
-continued
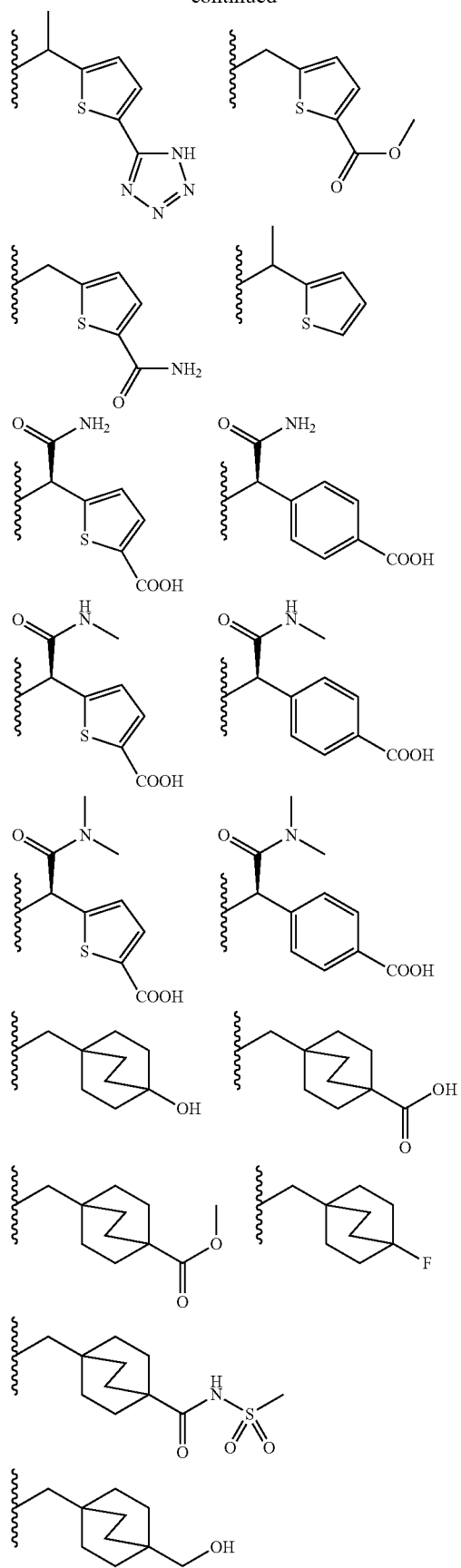
158
-continued
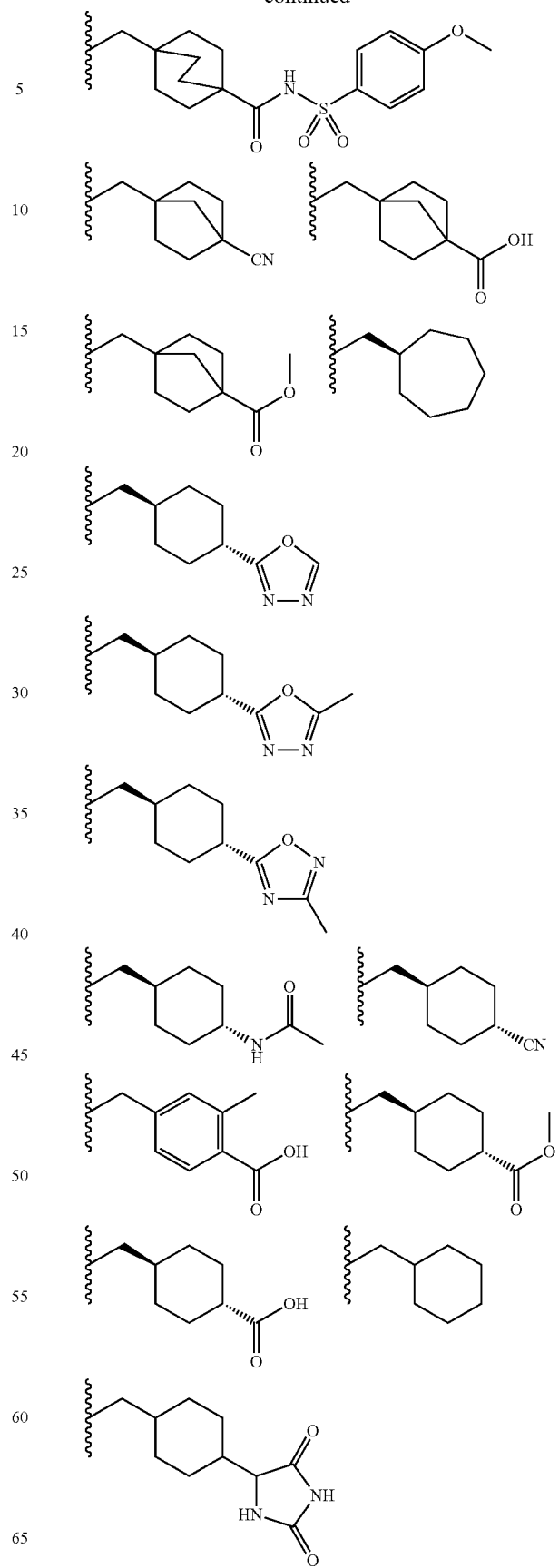

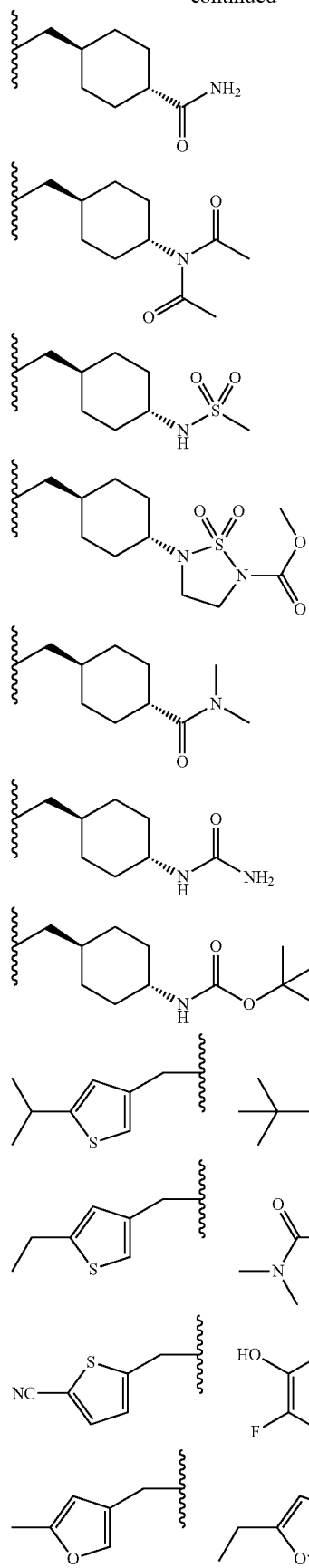
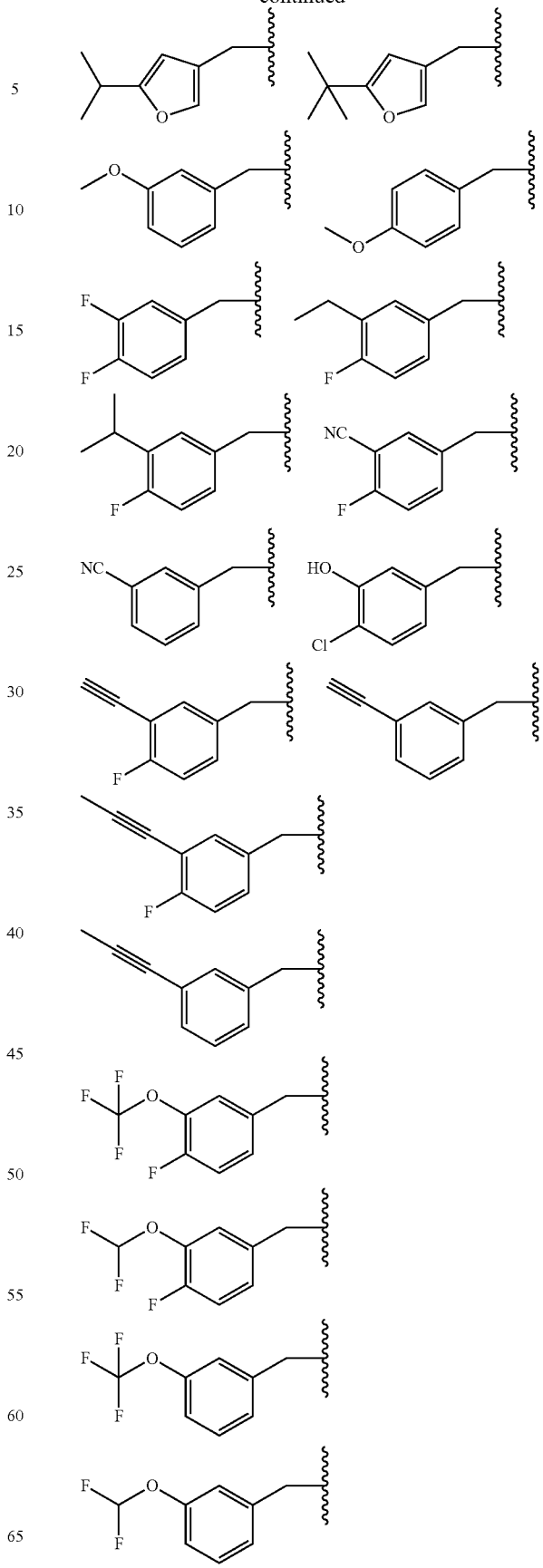

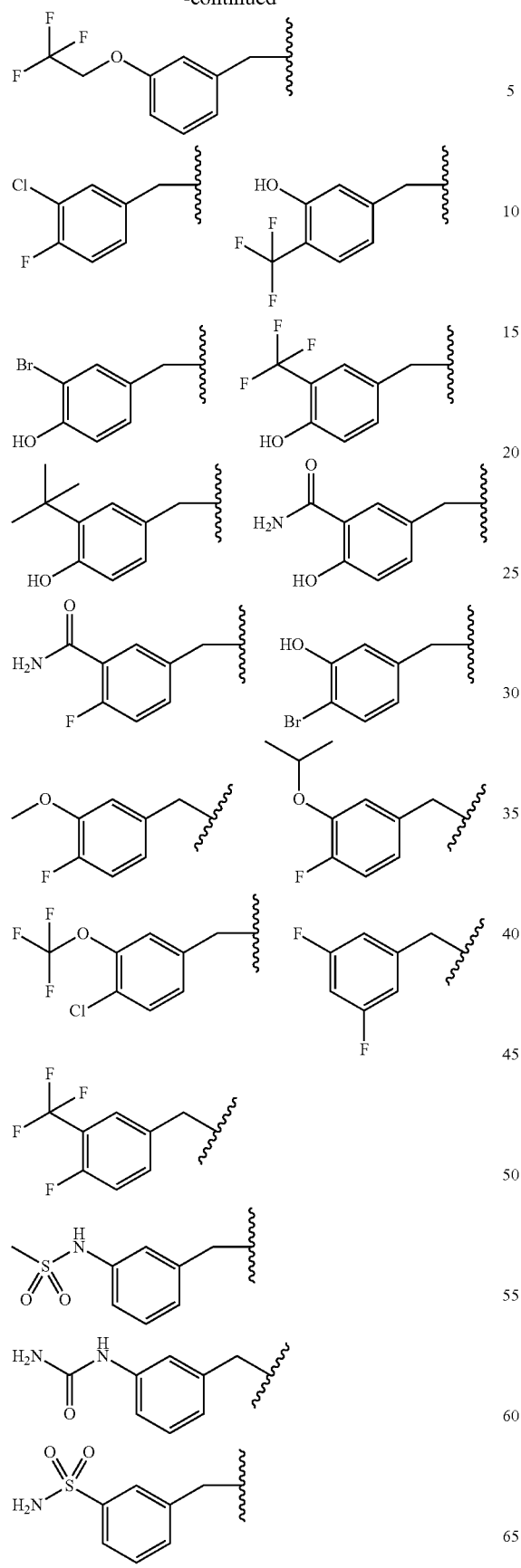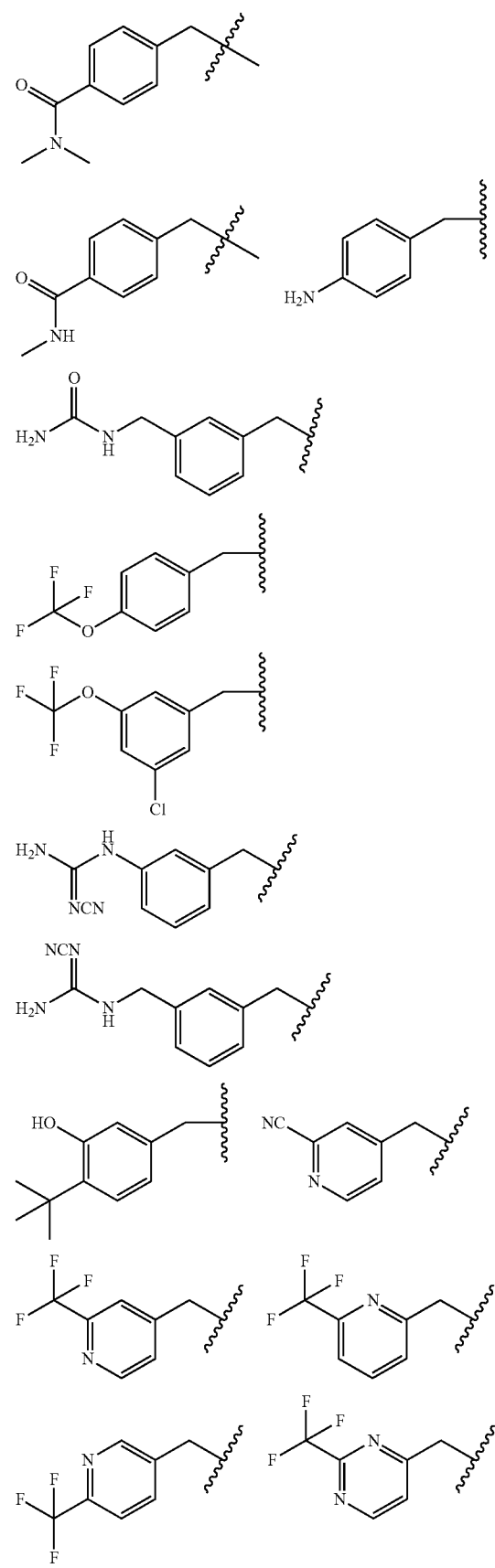

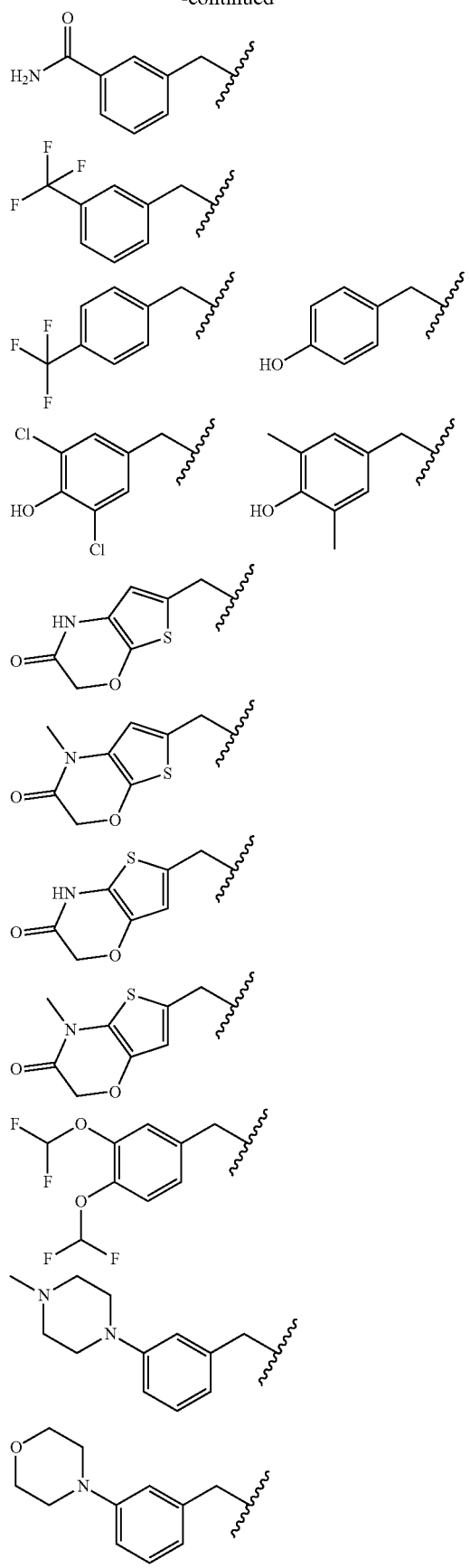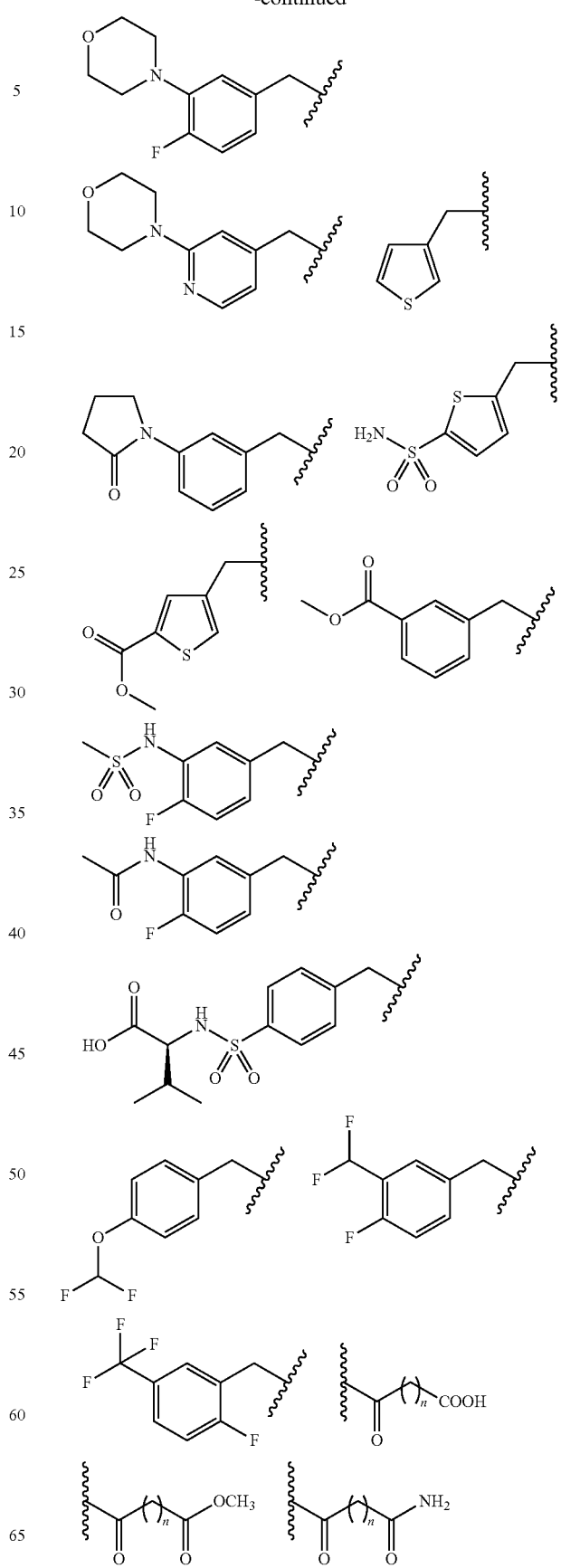

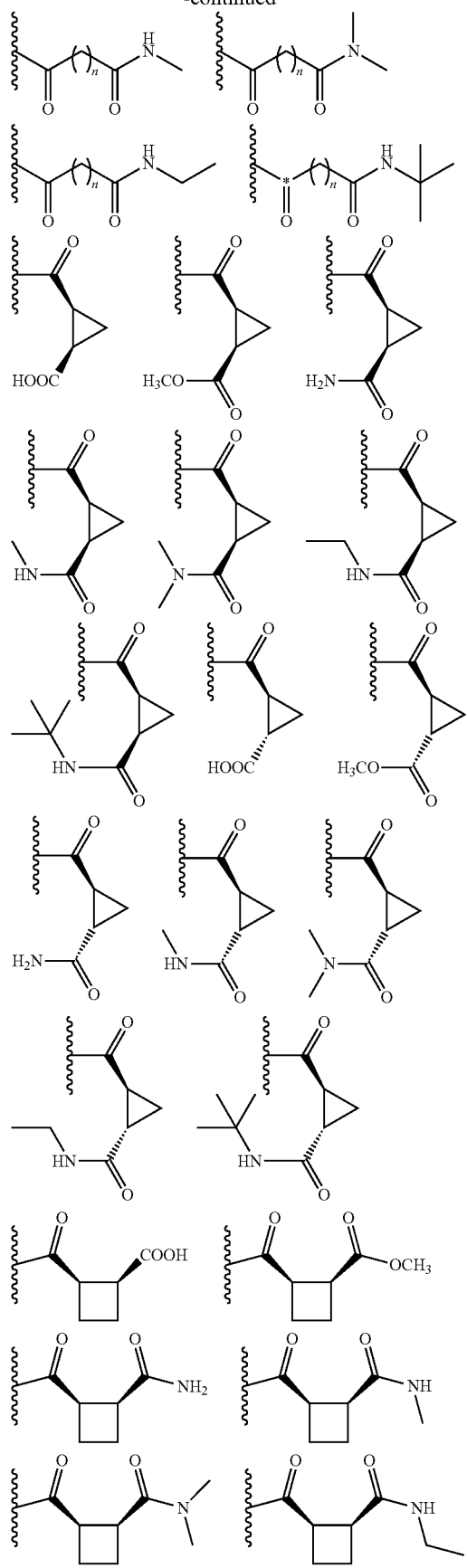
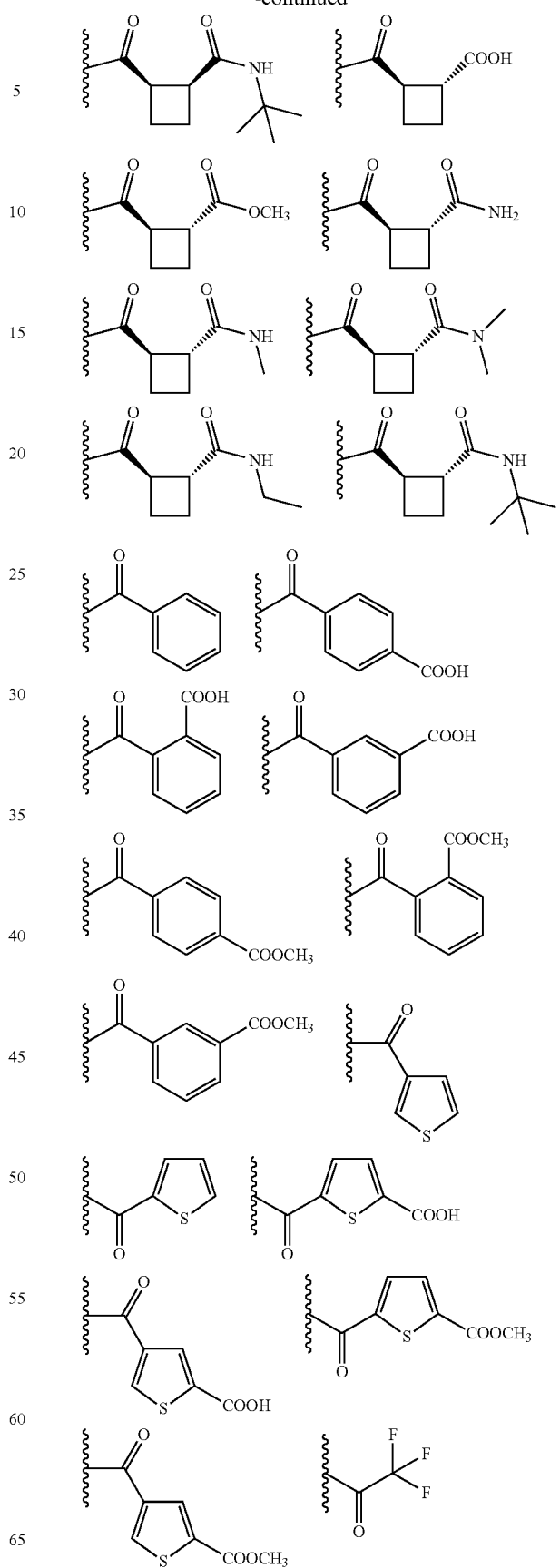

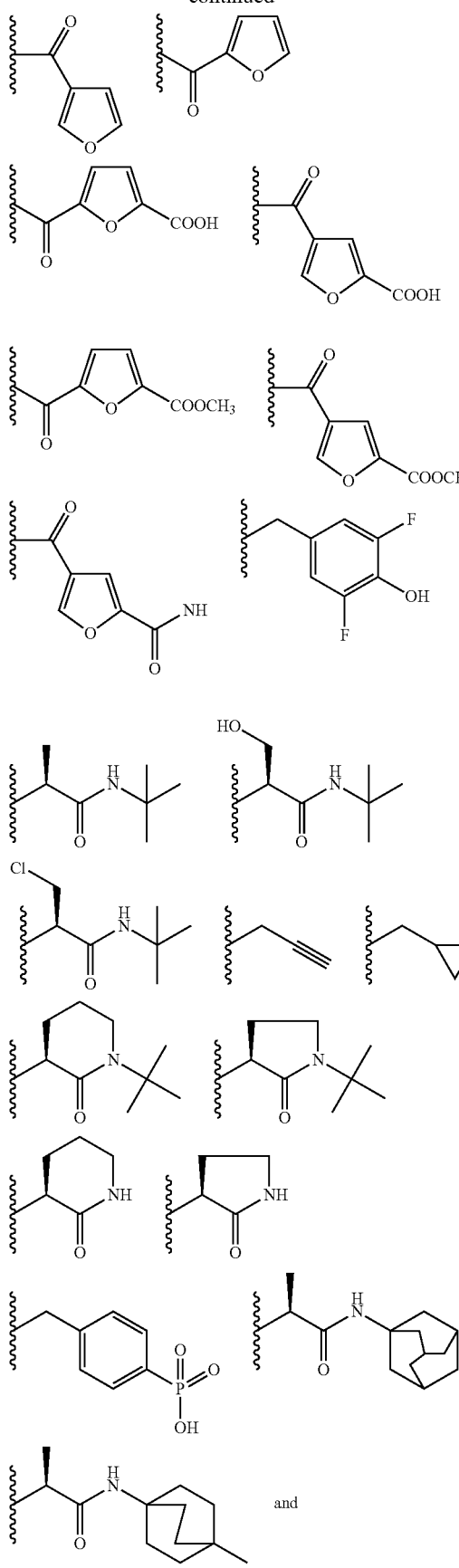
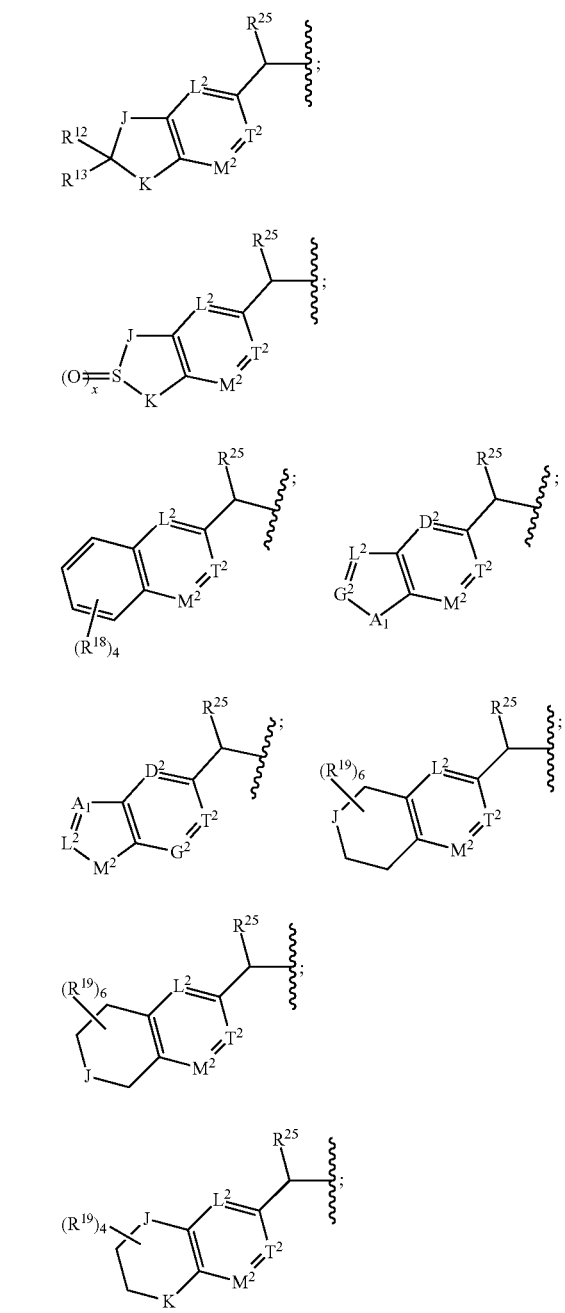
For example, in some embodiments, at least one $R^1$ of the structures of Groups V(a) and (b) may be selected from Substituent Group 15 as defined hereinabove.
In still another embodiment, at least one $R^1$ of Formula (V) may be selected from Substituent Group 8:

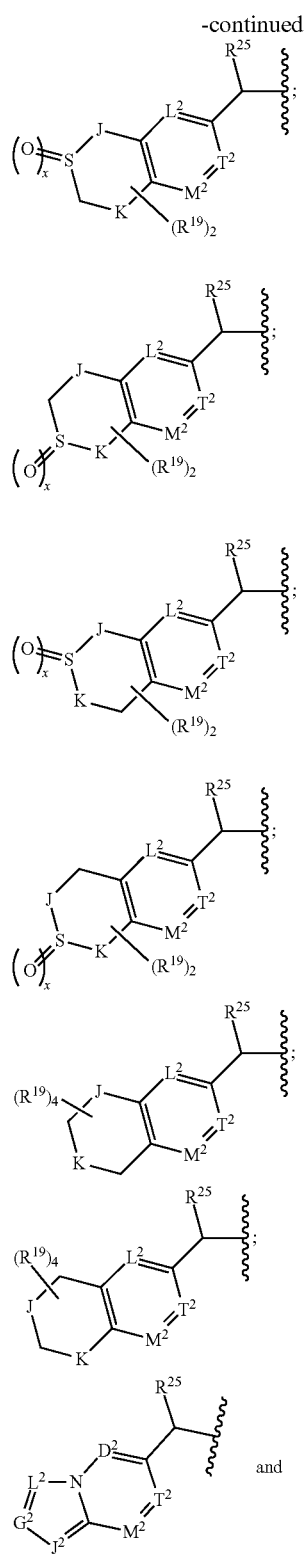
wherein all variables are as defined hereinabove.
For example, in some embodiments, at least one $R^1$ of the structures of Groups V(a) and (b) may be selected from Substituent Group 8 as defined hereinabove.
In a further embodiment, at least one $R^1$ of Formula (V) may be selected from Substituent Group 9:

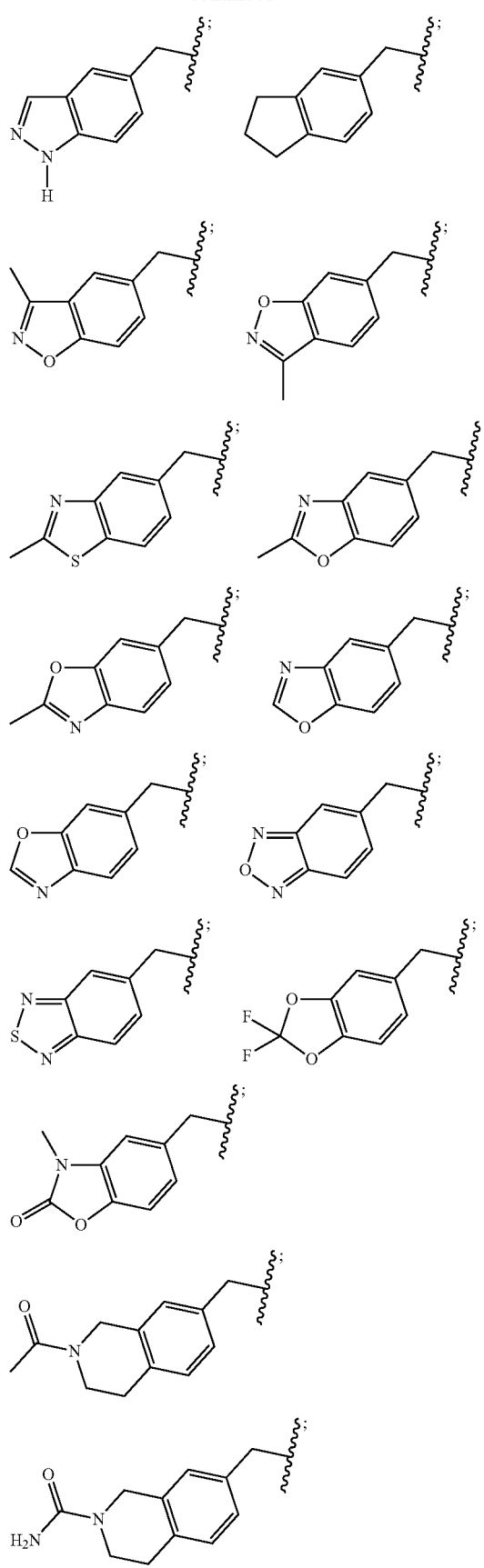
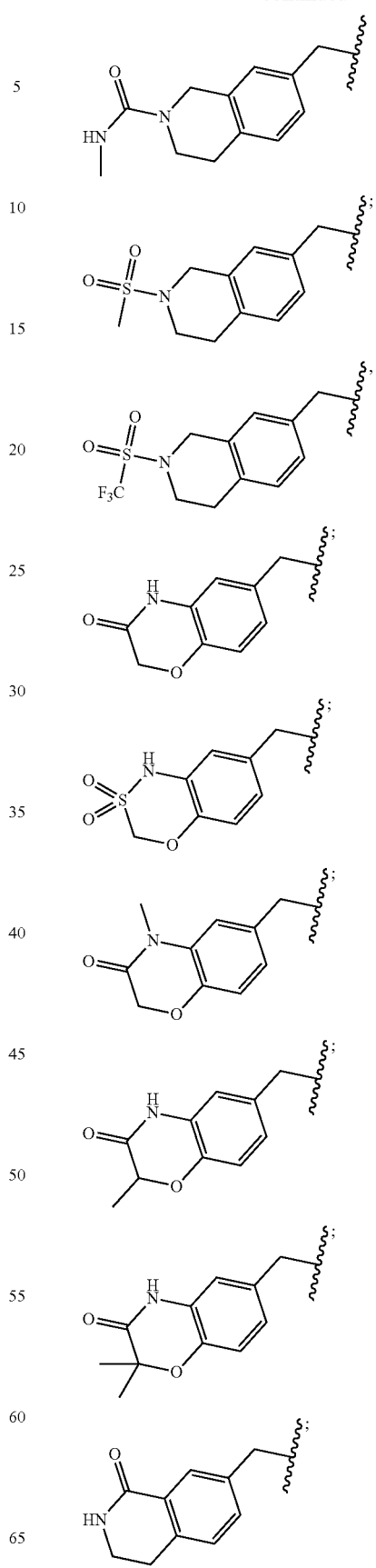

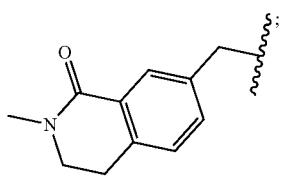
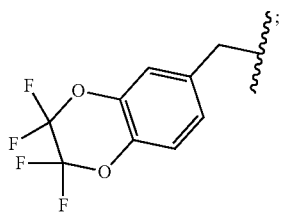
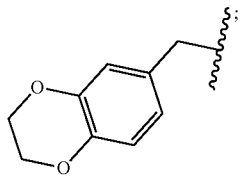
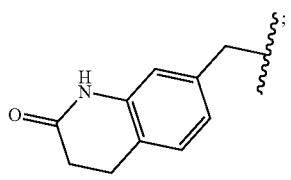
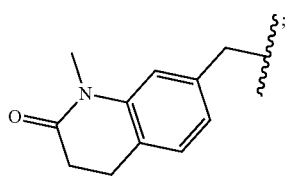
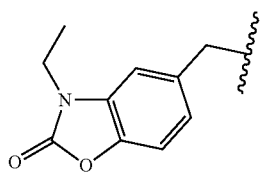
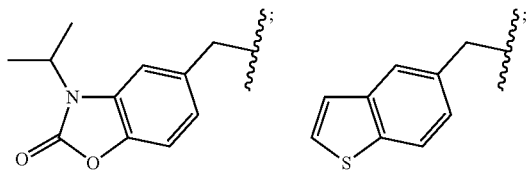
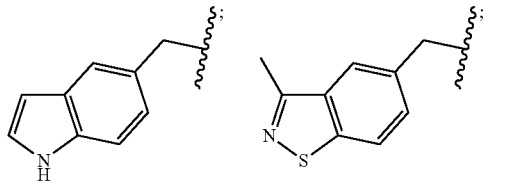
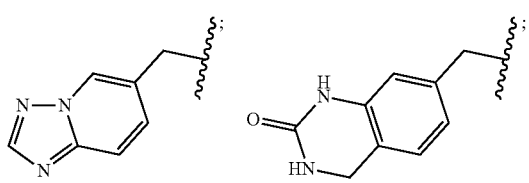
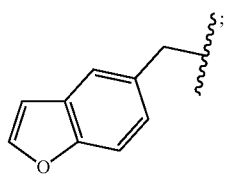
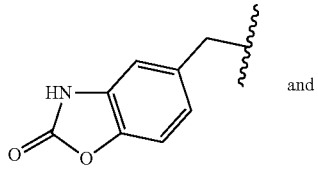 and
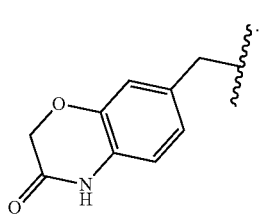
For example, in some embodiments, at least one $R^1$ of the structures of Groups V(a) and (b) may be selected from Substituent Group 9 as defined hereinabove.
In yet a further embodiment, one $R^1$ of Formula (V) may be selected from Substituent Group 10:
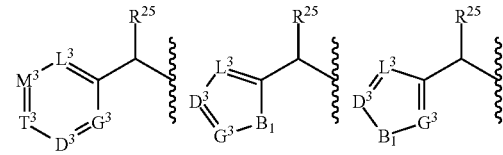
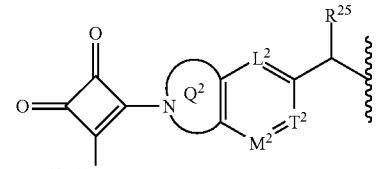
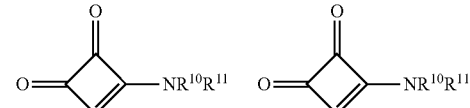
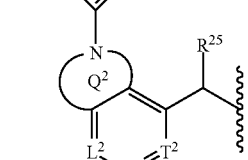
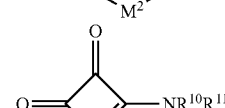
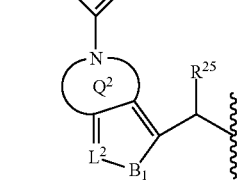

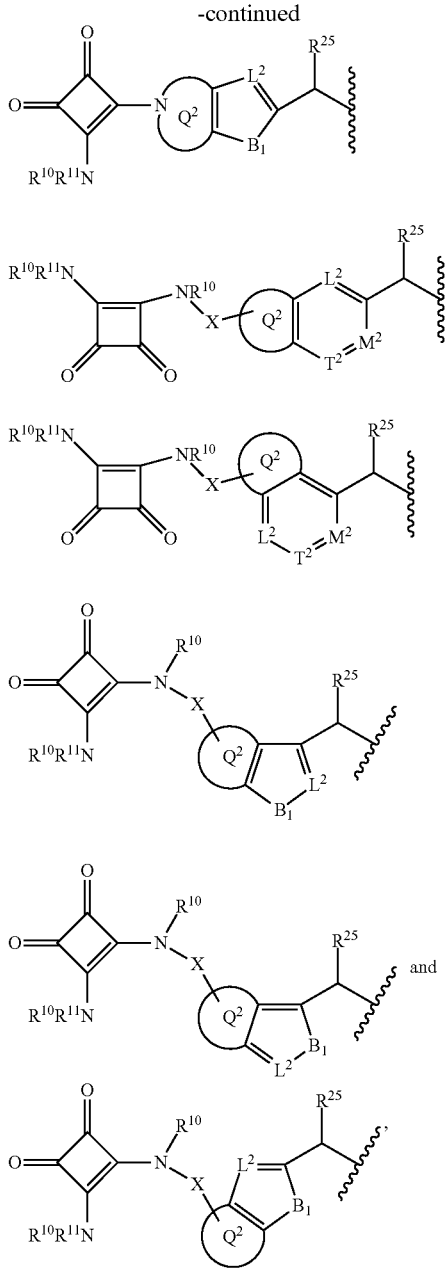
wherein all variables are as defined hereinabove.
For example, in some embodiments, one $R^1$ of the structures of Groups V(a) and (b) may be selected from Substituent Group 10 as defined hereinabove.
In still a further embodiment, each $R^1$ of Formula (V) may be independently selected from Substituent Group 11:
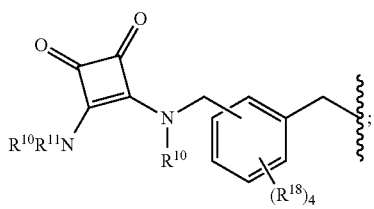
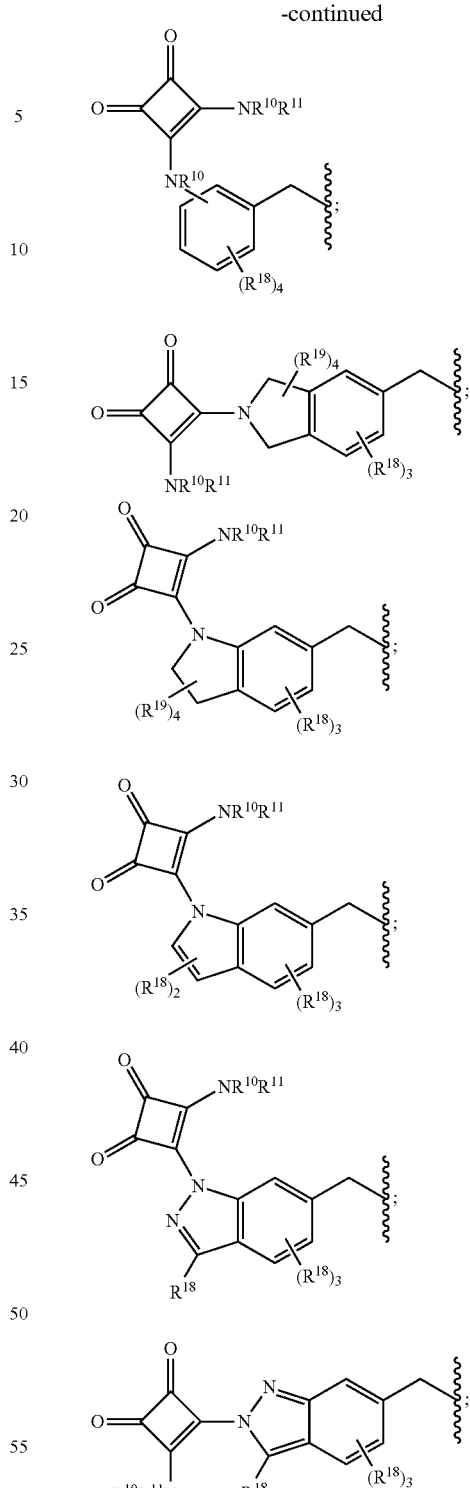
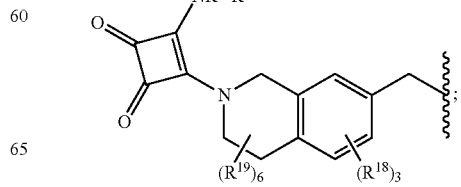

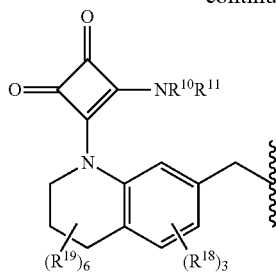
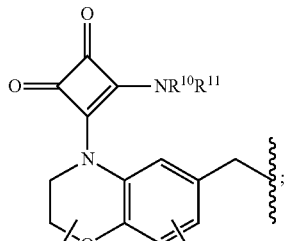
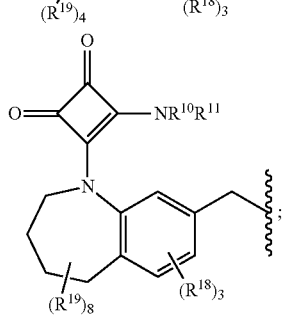
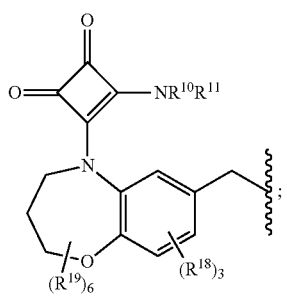
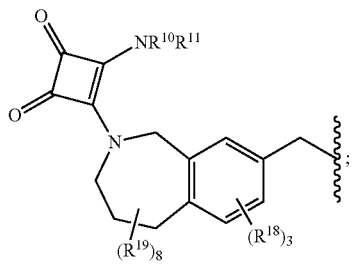
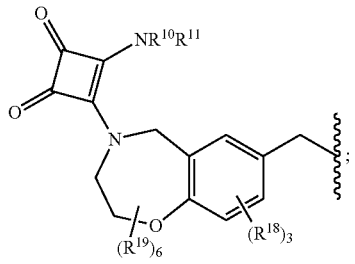
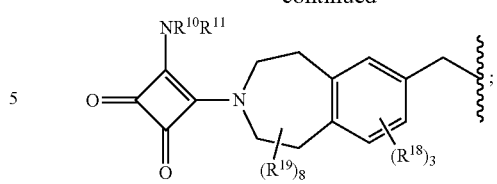
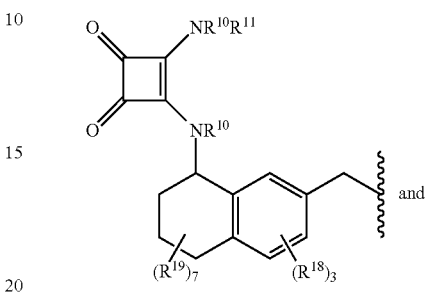
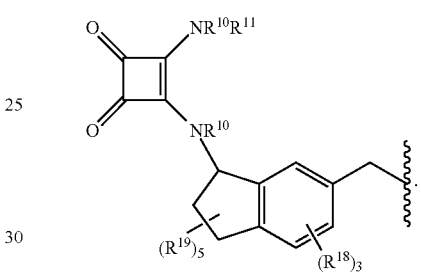
For example, in some embodiments, one $R^1$ of the structures of Groups V(a) and (b) may be selected from Substituent Group 11 as defined hereinabove.
In one embodiment, one $R^1$ of Formula (V) may be selected from Substituent Group 12:
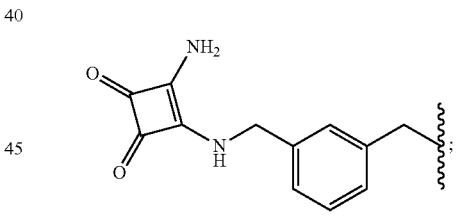
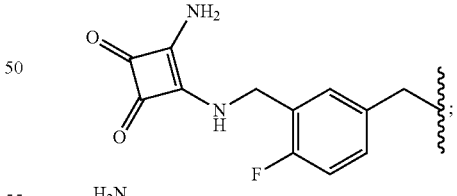
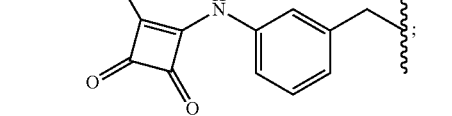
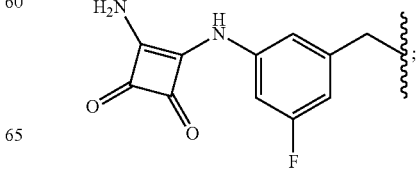

179
-continued
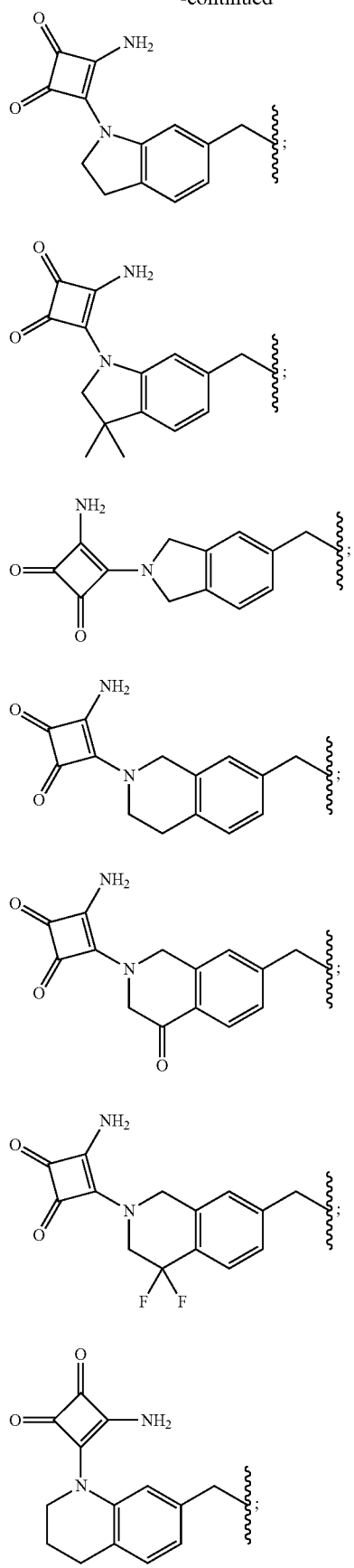
180
-continued
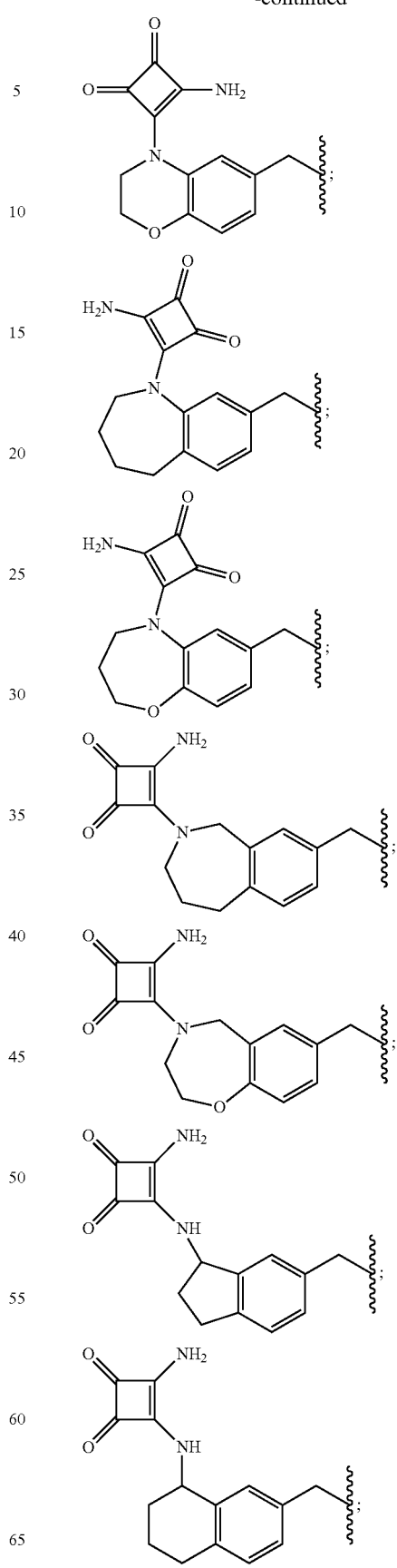

-continued
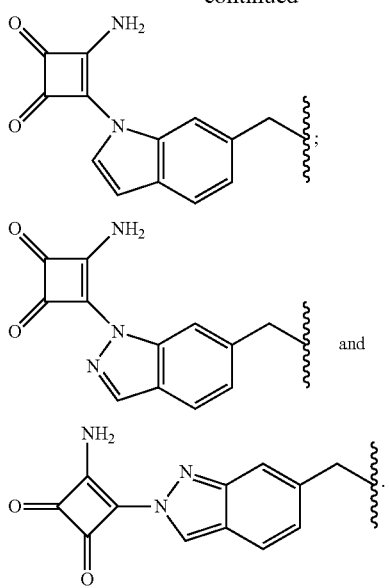
For example, in some embodiments, one R¹ of the structures of Groups V(a) and (b) may be selected from Substituent Group 12 as defined hereinabove.
In some embodiments:
A) the first occurrence of R¹ of Formula (V) is selected from Substituent Group 13:
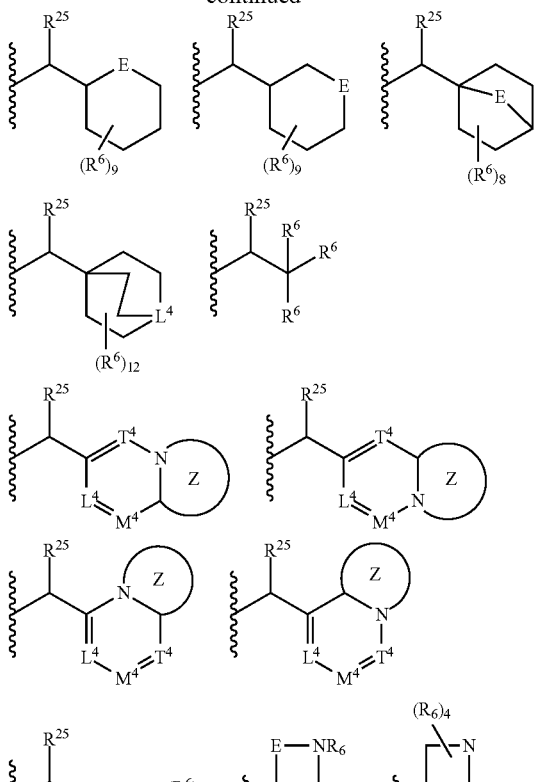
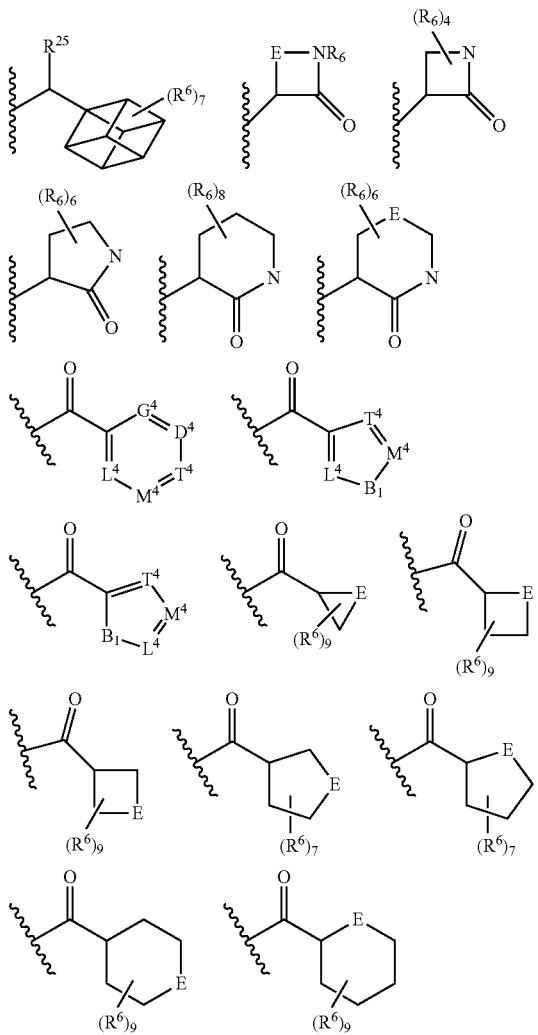
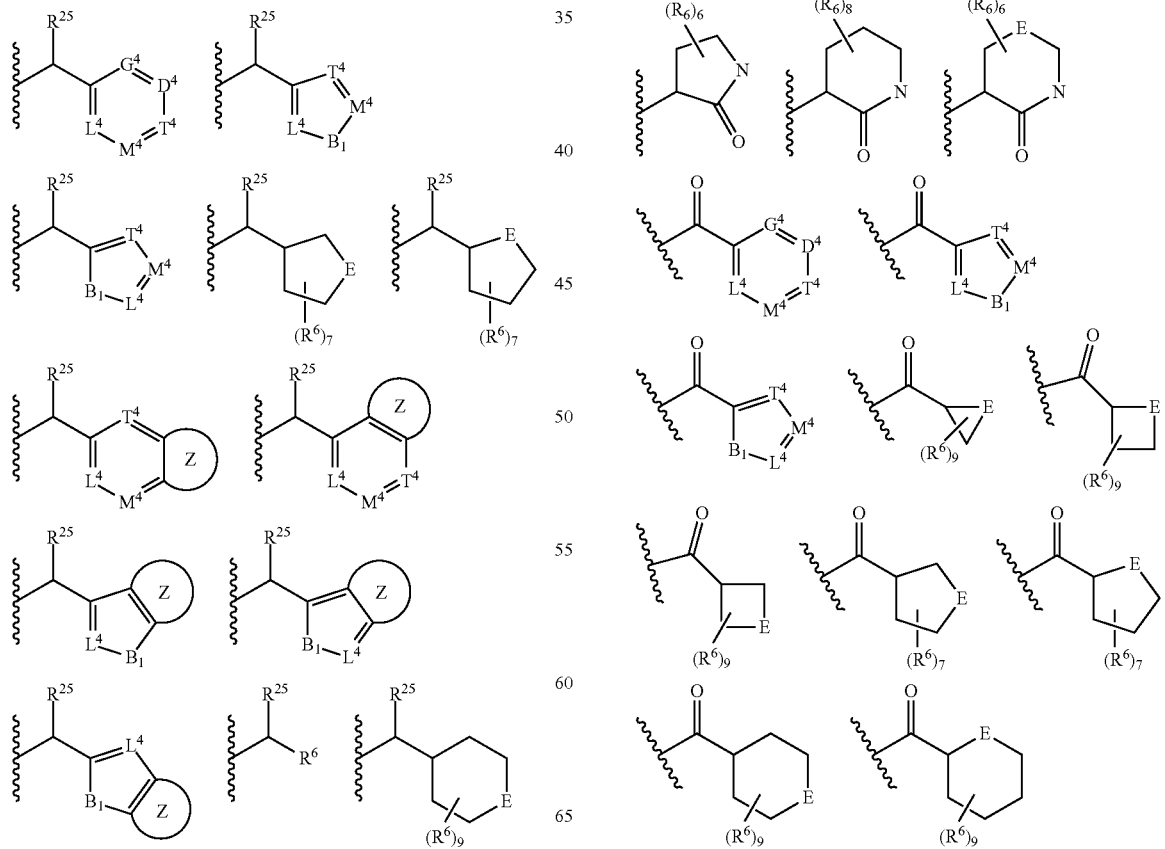

-continued
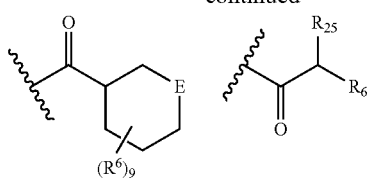
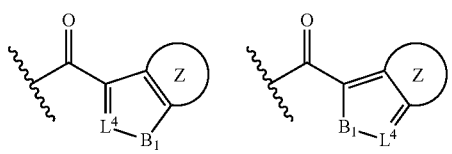
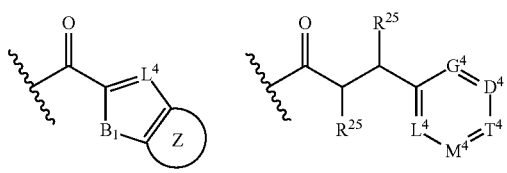
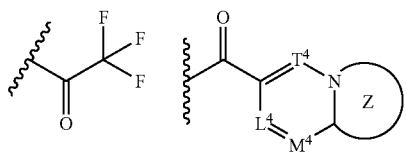
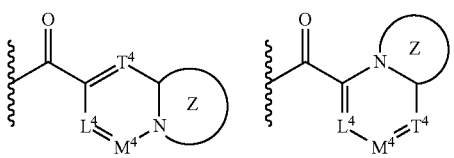
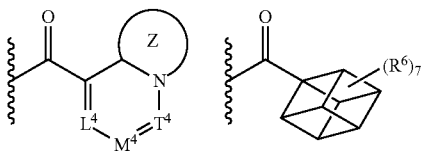
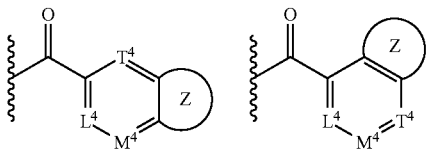
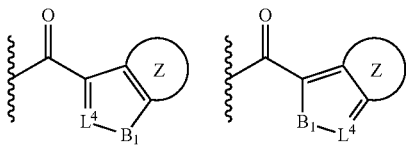
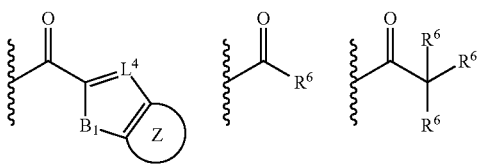
-continued
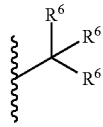
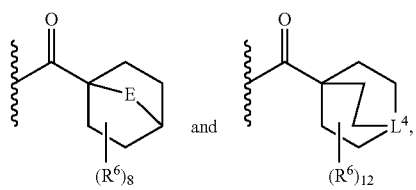
and
B) the second occurrence of $R^1$ of Formula (V) is selected from Substituent Group 10:
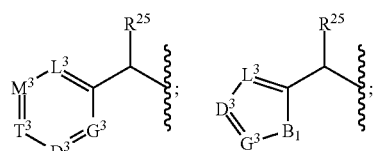
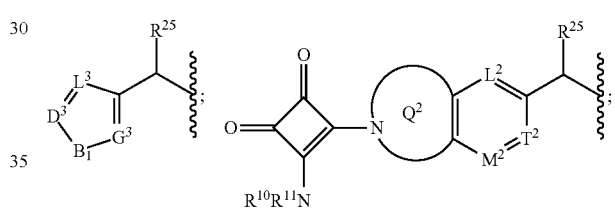
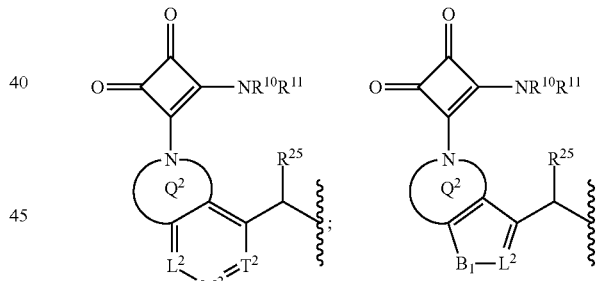
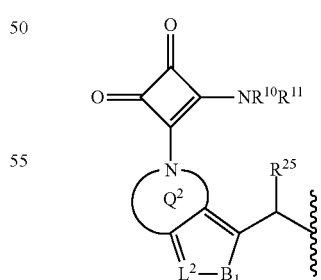
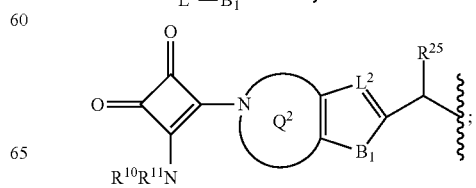

-continued
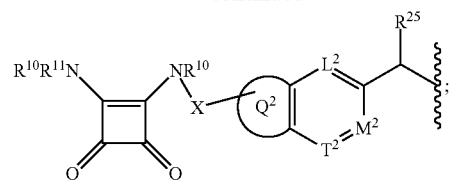
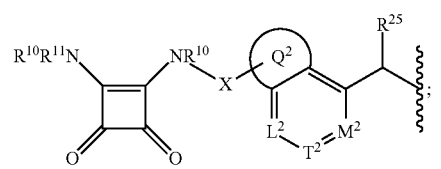
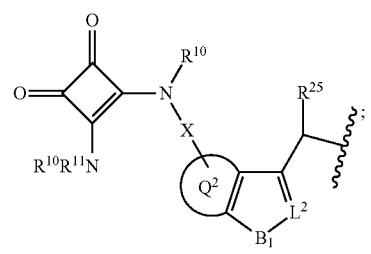
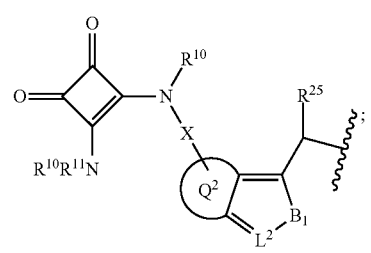
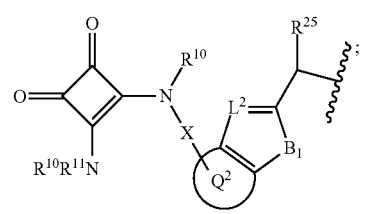
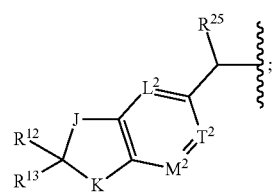
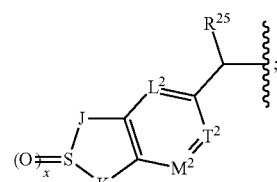
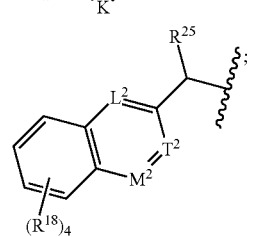 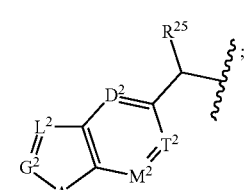
-continued
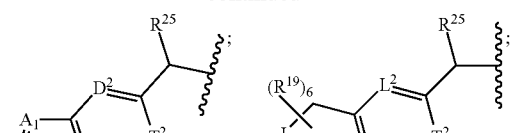

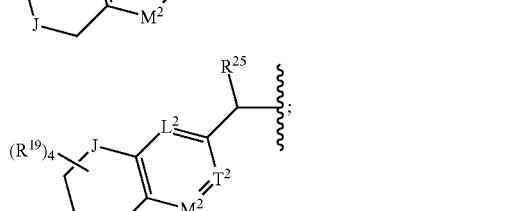
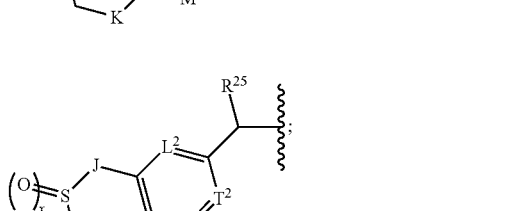
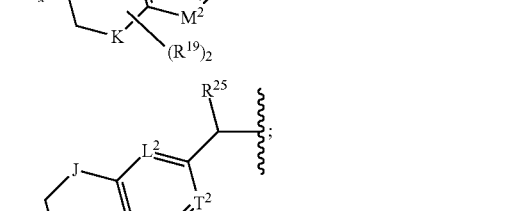
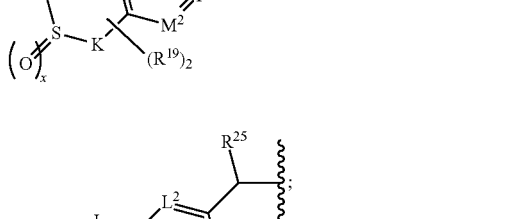
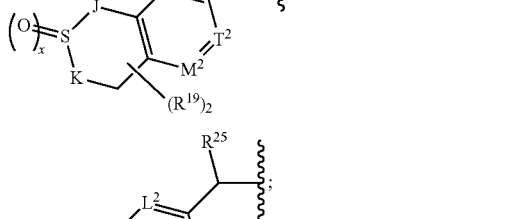
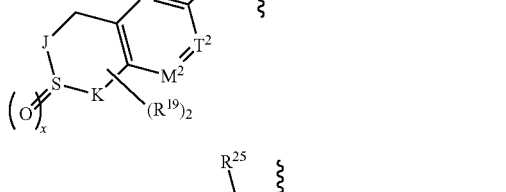
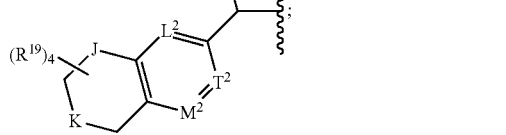

-continued

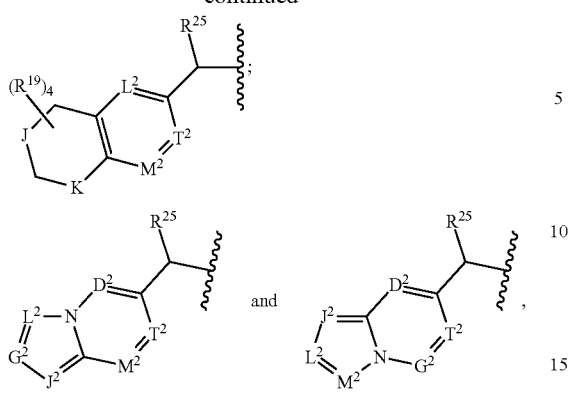

wherein all variables are as defined hereinabove.

For example in some embodiments, the first occurrence of $R^1$ of the structures of Groups V(a) and (b) may be selected from Substituent Group 13 as defined hereinabove, and the second occurrence of $R^1$ of the structures of Groups V(a) and (b) may be selected from Substituent Group 10 as defined hereinabove.

In another embodiment of the present invention, the amide containing heterobicyclic metalloprotease compounds may be represented by the general Formula (VI):

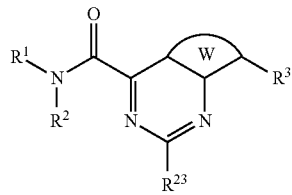

Formula (VI)

and N-oxides, pharmaceutically acceptable salts, prodrugs, formulation, polymorphs, racemic mixtures and stereoisomers thereof, wherein all variables are as defined hereinabove.

In yet another embodiment, the compounds of Formula (VI) may be selected from Group VI(a):

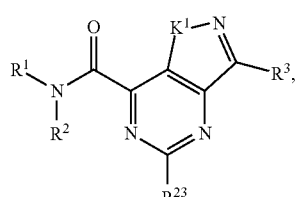

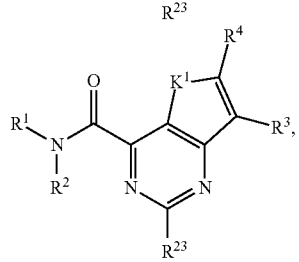

-continued

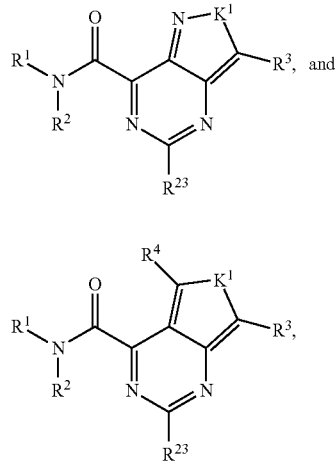

wherein all variables are as defined hereinabove.

In still another embodiment, the compounds of Formula (VI) may be selected from Group VI(b):

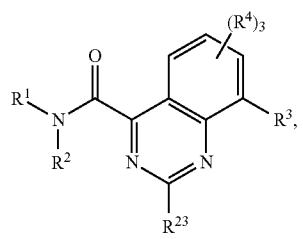

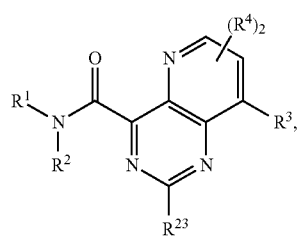

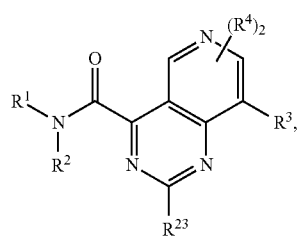

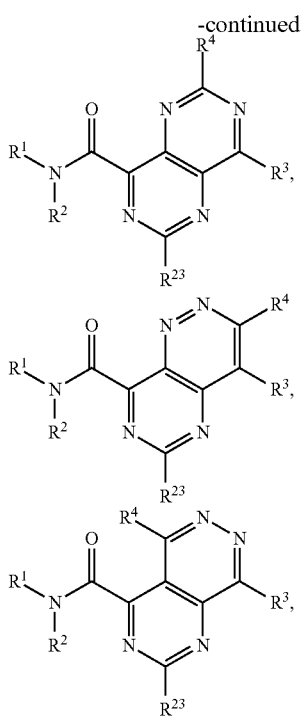
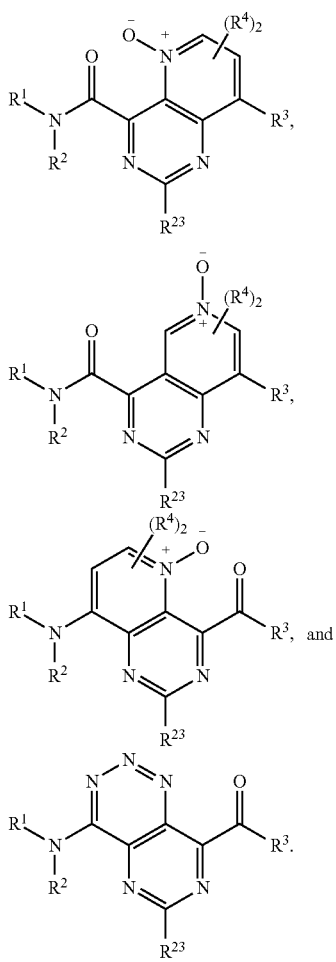
In a further embodiment, $R^3$ of Formula (VI) may be selected from Substituent Group 1:
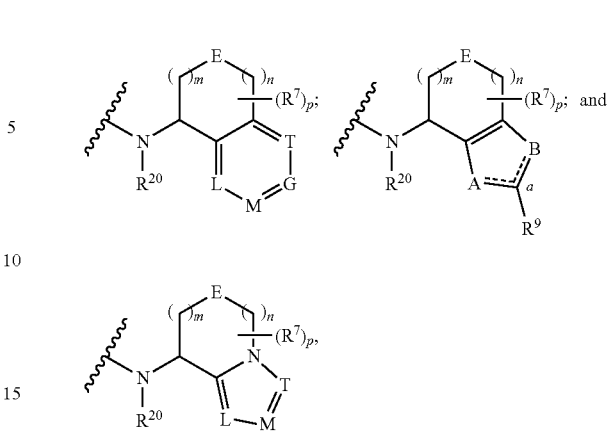
wherein all variables are as defined hereinabove.
For example, in some embodiments, $R^3$ of the structures of Groups VI(a) and (b) may be selected from Substituent Group 1 as defined hereinabove.
In yet a further embodiment, $R^3$ of Formula (VI) may be selected from Substituent Group 2:
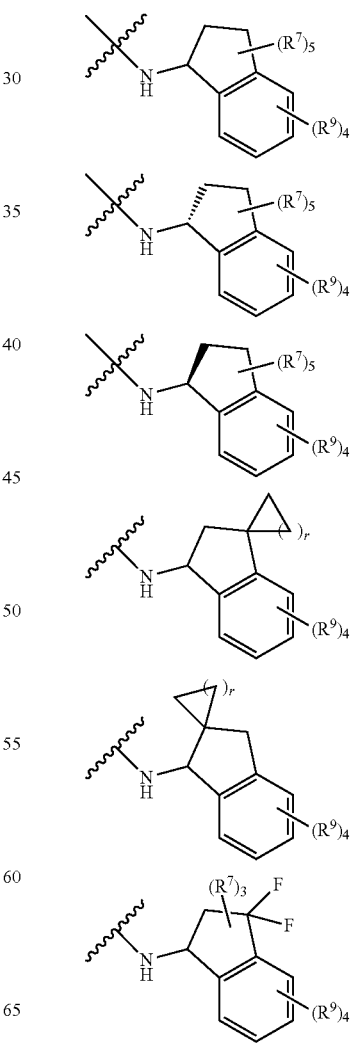

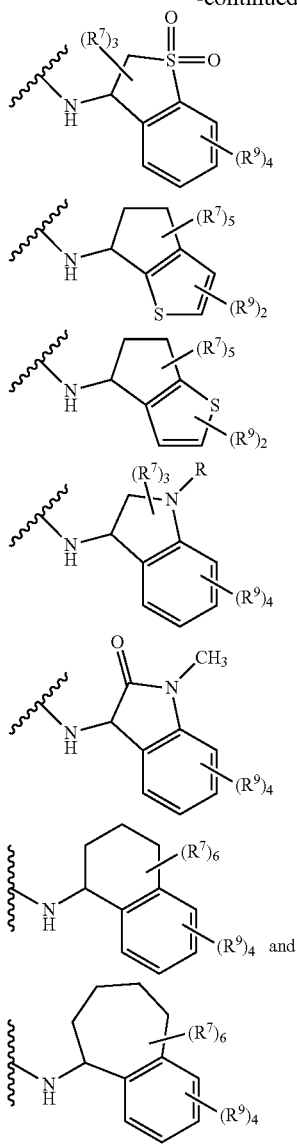

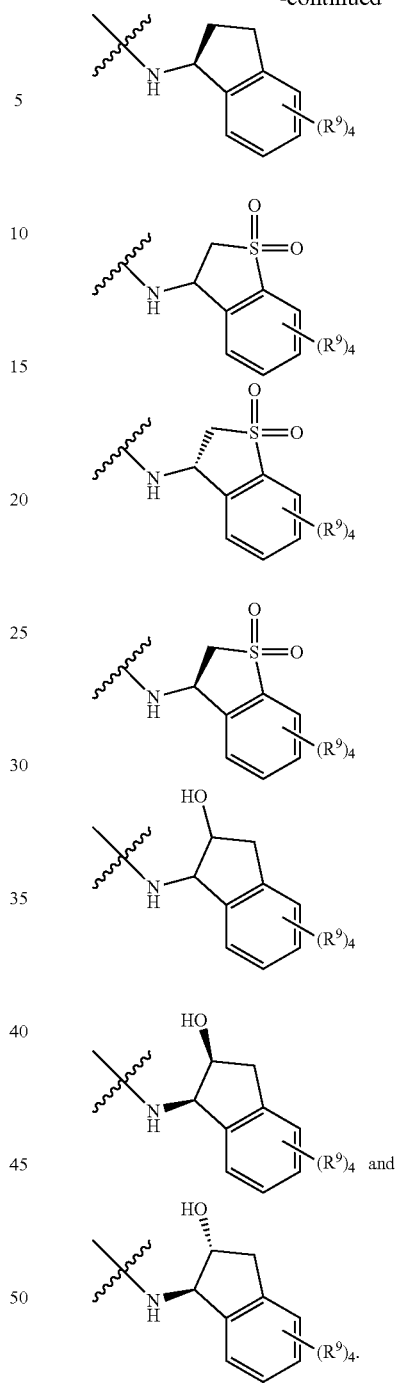

wherein all variables are as defined hereinabove.

For example, in some embodiments, in some embodiments, $R^3$ of the structures of Groups VI(a) and (b) may be selected from Substituent Group 2 as defined hereinabove.

In still a further embodiment, $R^3$ of Formula (VI) may be selected from Substituent Group 3:

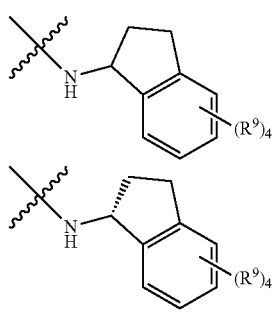

For example, in some embodiments, $R^3$ of the structures of Groups VI(a) and (b) may be selected from Substituent Group 3 as defined hereinabove.

In one embodiment, each $R^9$ of Substituent Group 3 may independently be selected from:

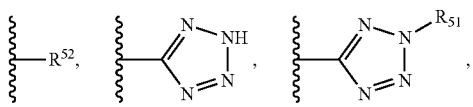

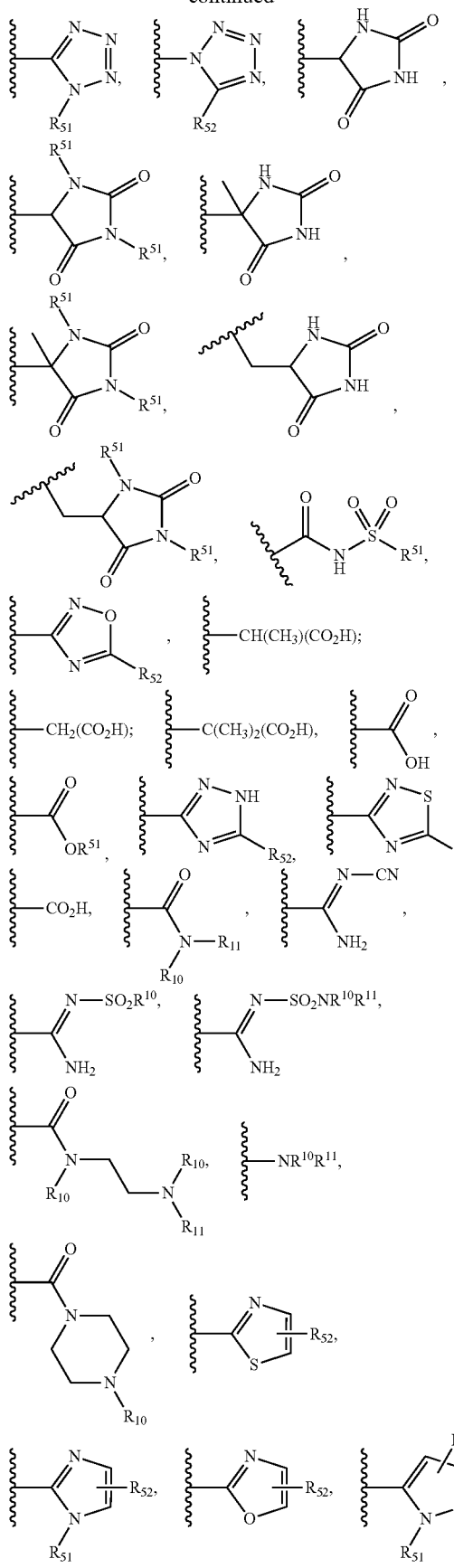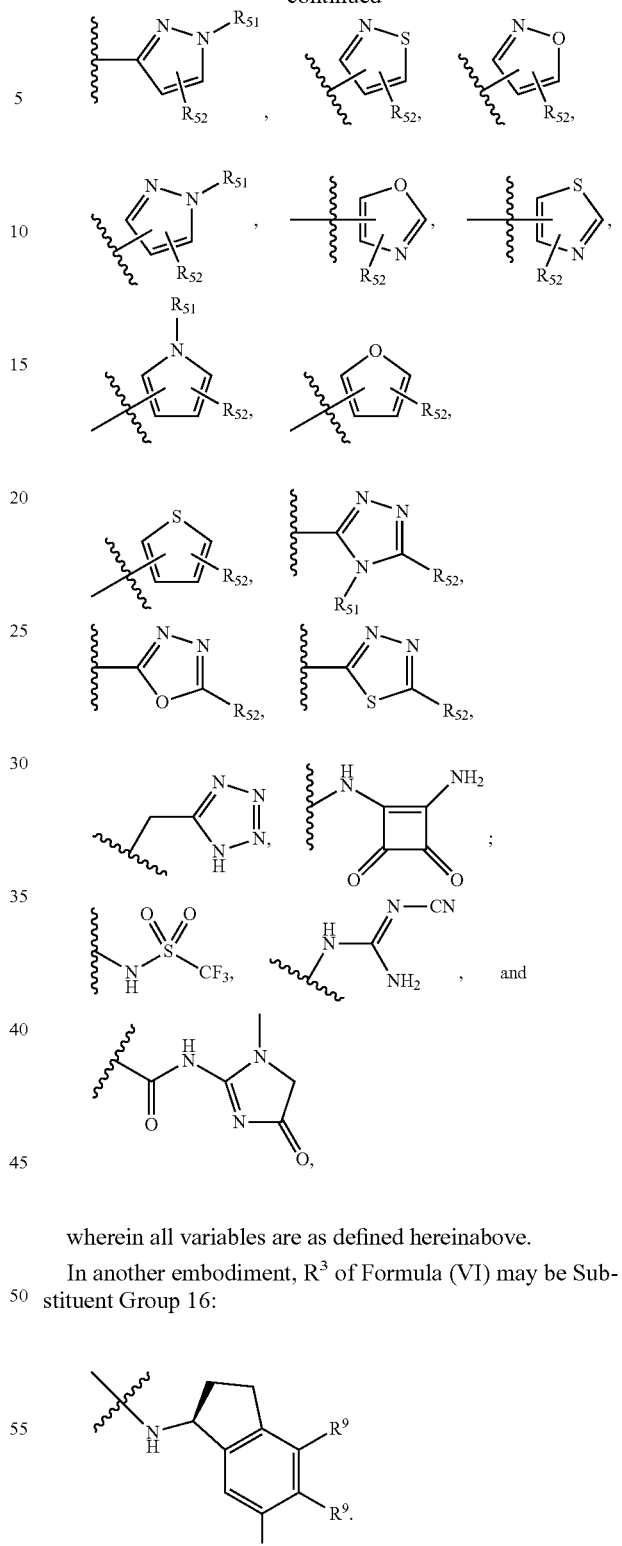
wherein all variables are as defined hereinabove.
In another embodiment, $R^3$ of Formula (VI) may be Substituent Group 16:
For example, in some embodiments, $R^3$ of the structures of Groups VI(a) and (b) may be selected from Substituent Group 16 as defined hereinabove.
In yet another embodiment, $R^3$ of Formula (VI) may be selected from Substituent Group 5:

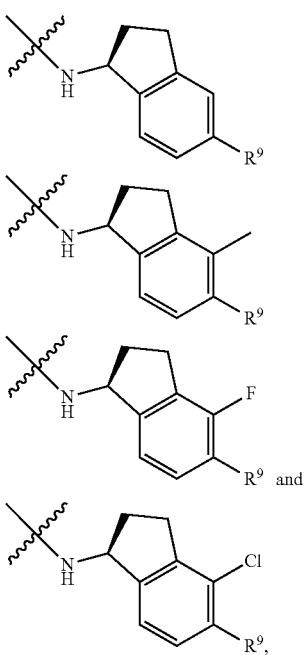

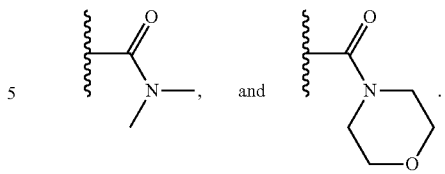

wherein:

R⁹ is selected from the group consisting of hydrogen, fluoro, halo, CN, alkyl, CO₂H,

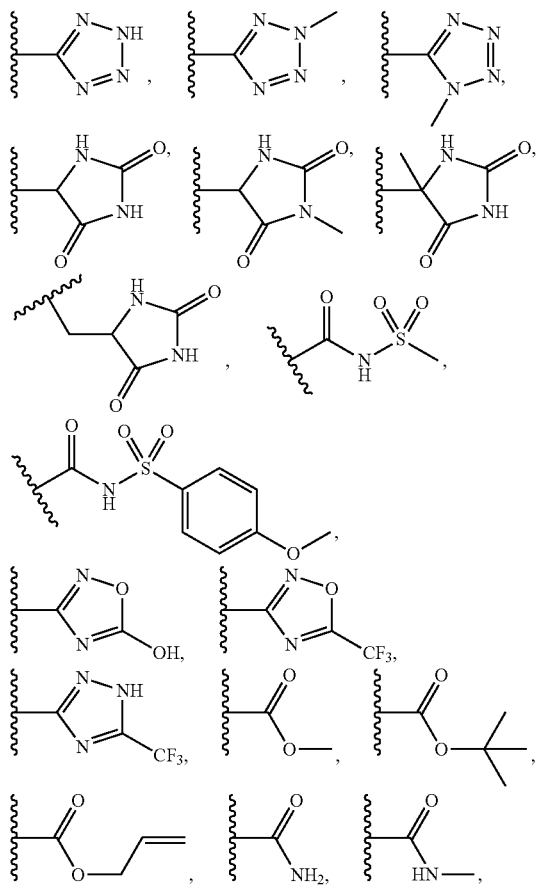

For example, in some embodiments, $R^3$ of the structures of Groups VI(a) and (b) may be selected from Substituent Group 5 as defined hereinabove.

In still another embodiment, $R^1$ of the compounds of Formula (VI) may be selected from Substituent Group 6:

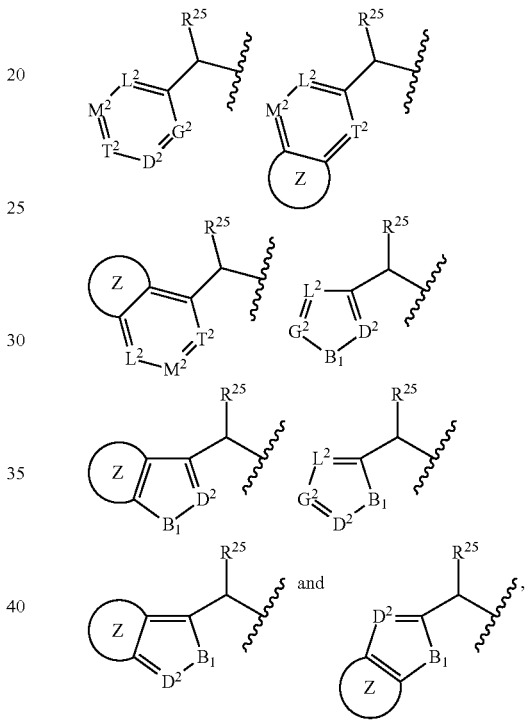

wherein all variables are as defined hereinabove.

For example, in some embodiments, $R^1$ of the structures of Groups VI(a) and (b) may be selected from Substituent Group 6 as defined hereinabove.

In a further embodiment, $R^1$ of Formula (VI) may be selected from Susbstituent Group 7:

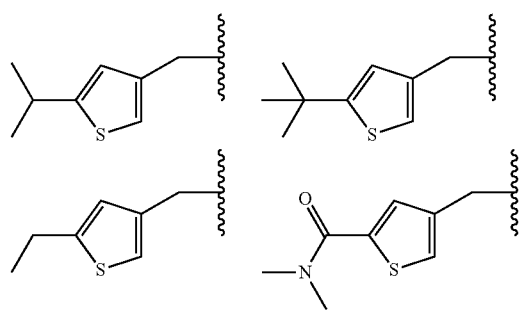

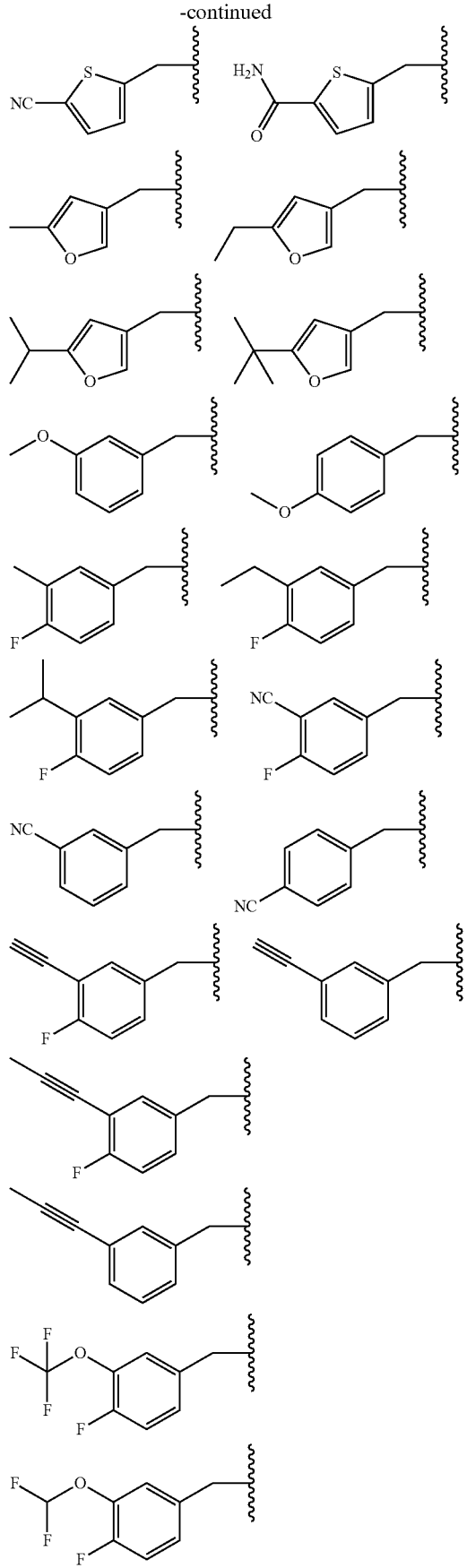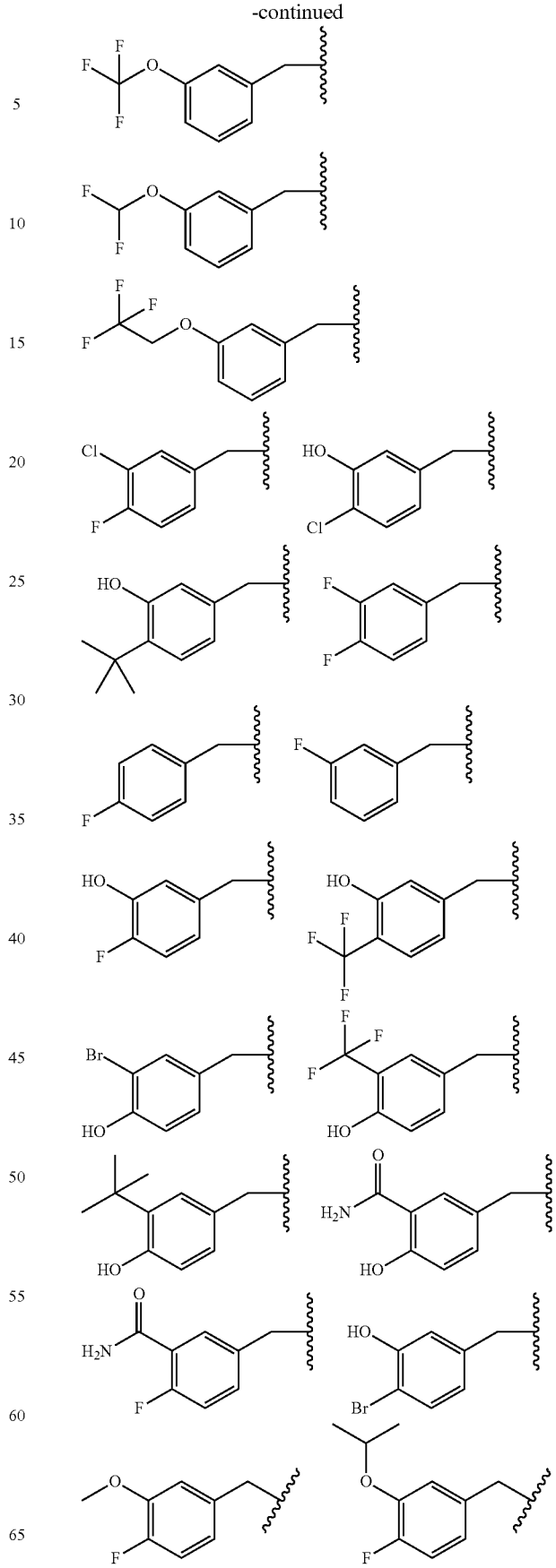

199
-continued
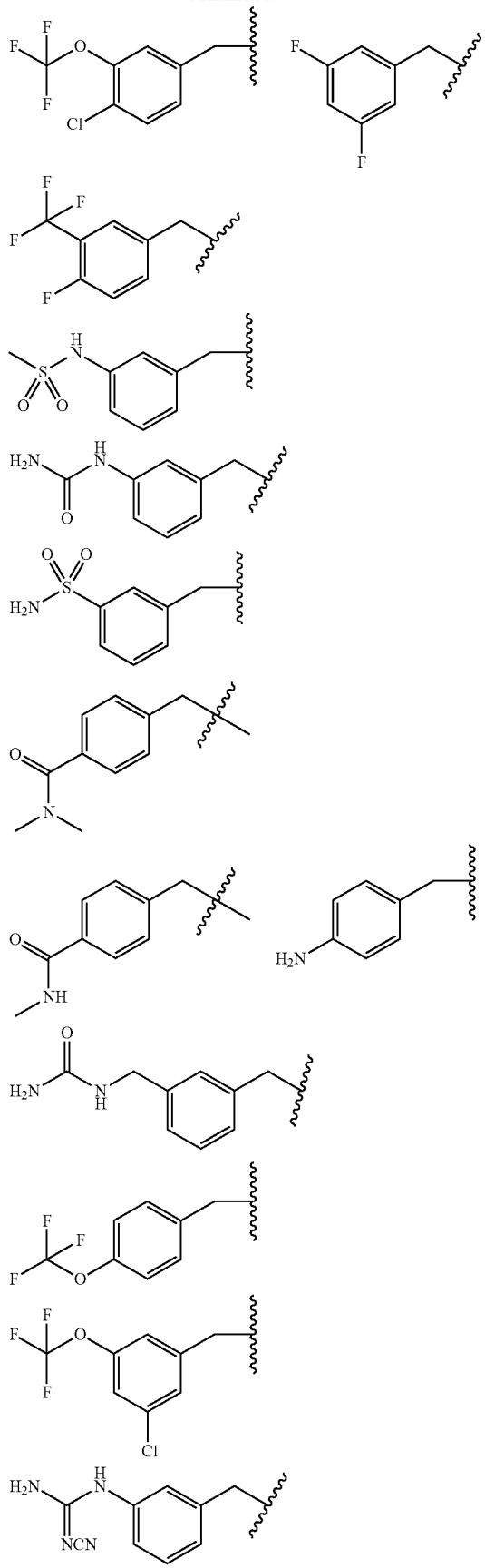
200
-continued
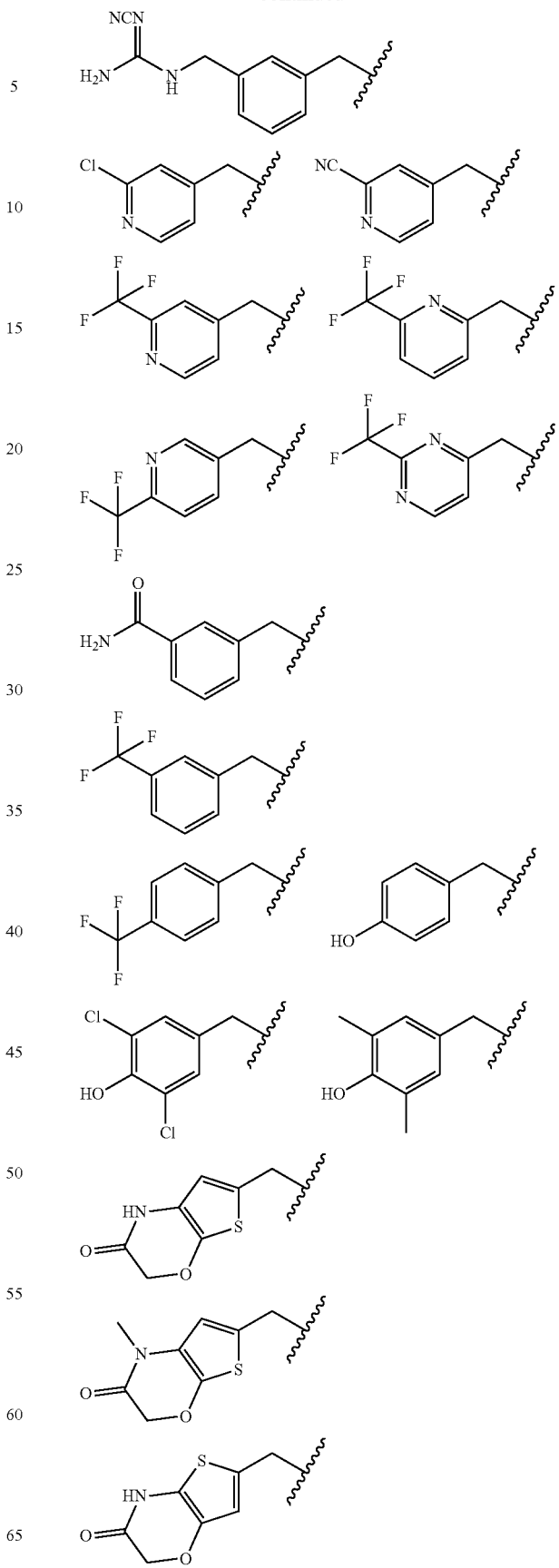

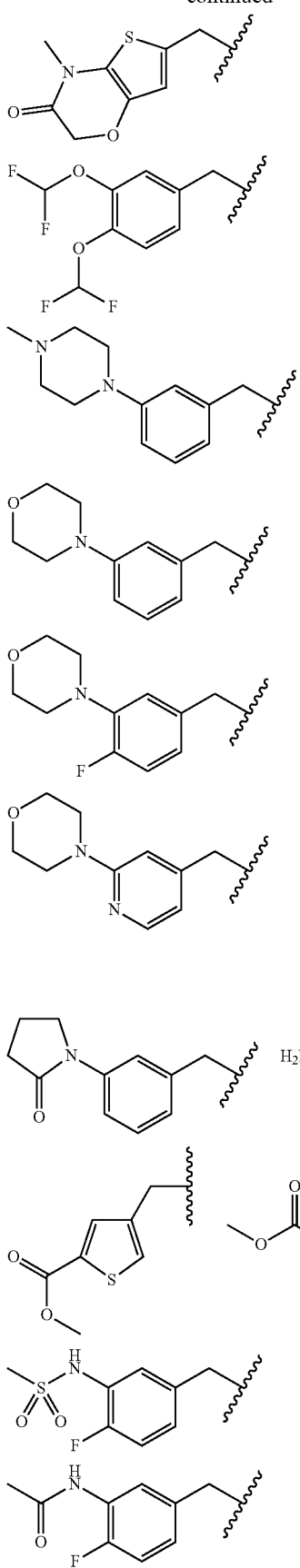
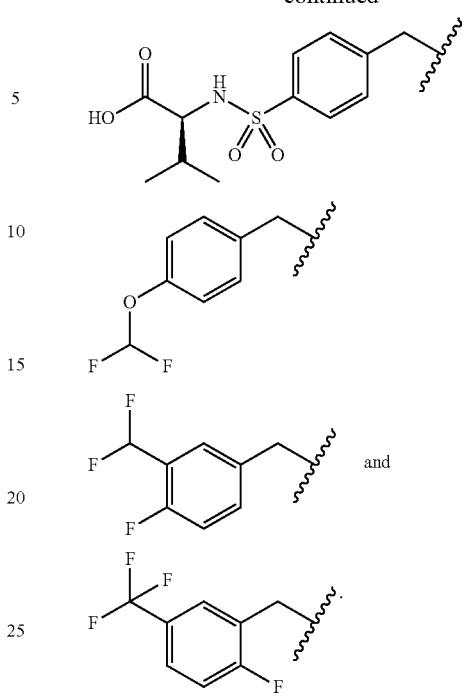
For example, in some embodiments, $R^1$ of the structures of Groups VI(a) and (b) may be selected from Substituent Group 7 as defined hereinabove.
In yet a further embodiment, $R^1$ of Formula (VI) may be selected from Substituent Group 8:
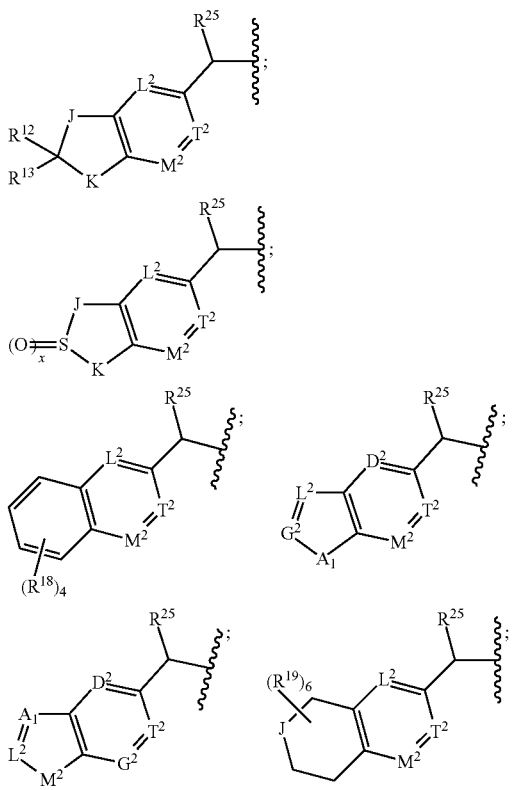

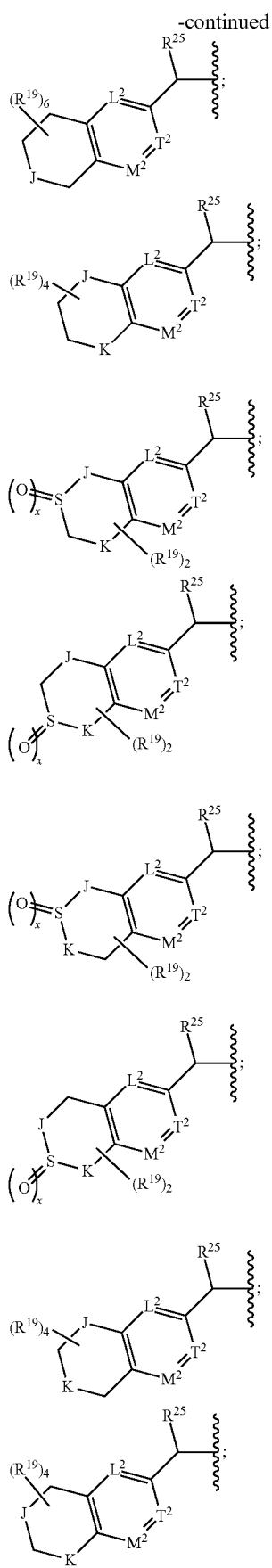
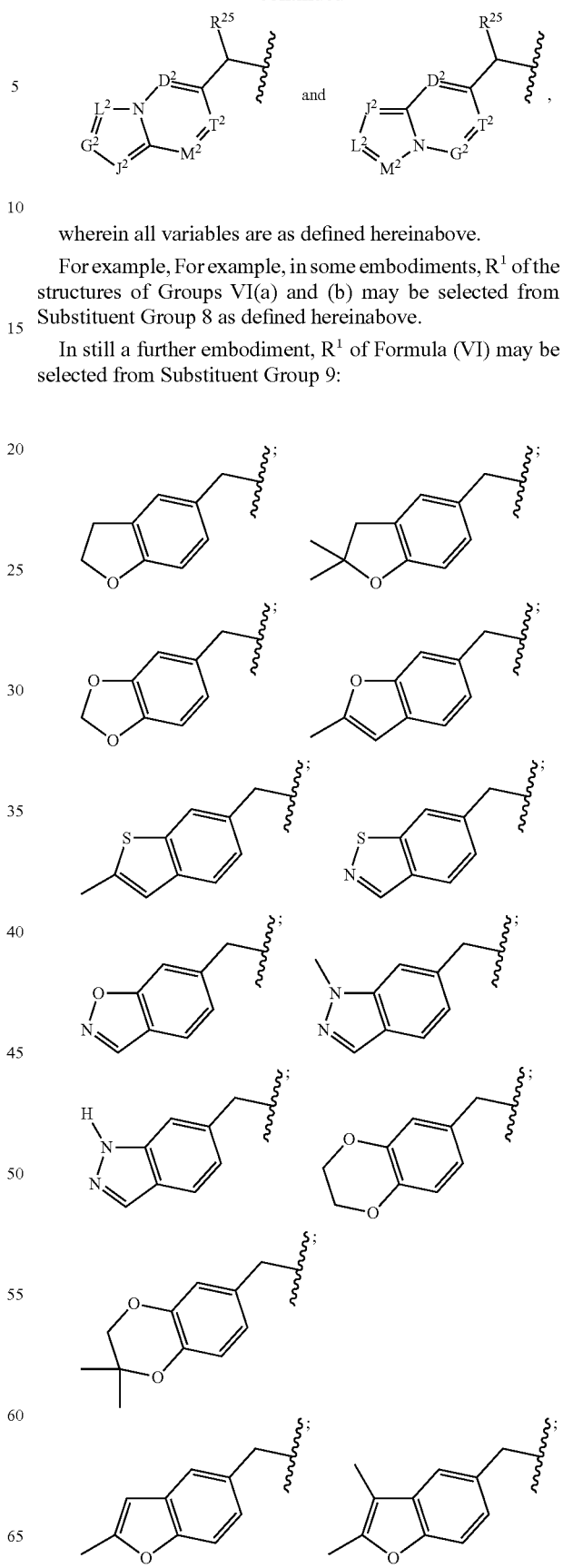
wherein all variables are as defined hereinabove.
For example, For example, in some embodiments, $R^1$ of the structures of Groups VI(a) and (b) may be selected from Substituent Group 8 as defined hereinabove.
In still a further embodiment, $R^1$ of Formula (VI) may be selected from Substituent Group 9:

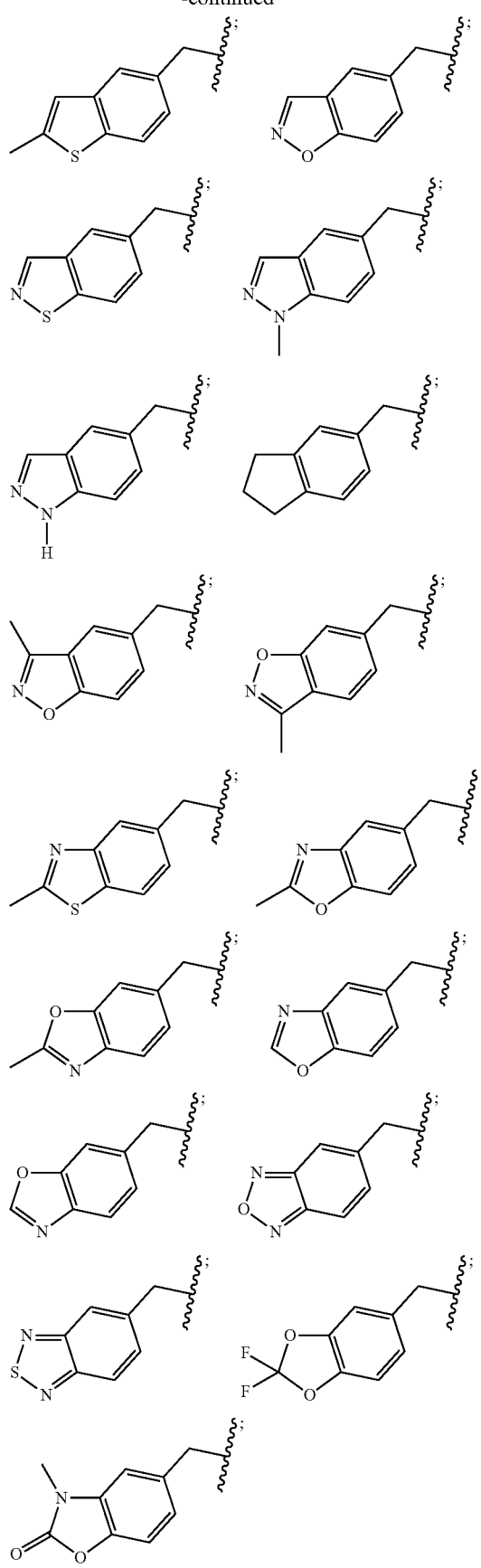
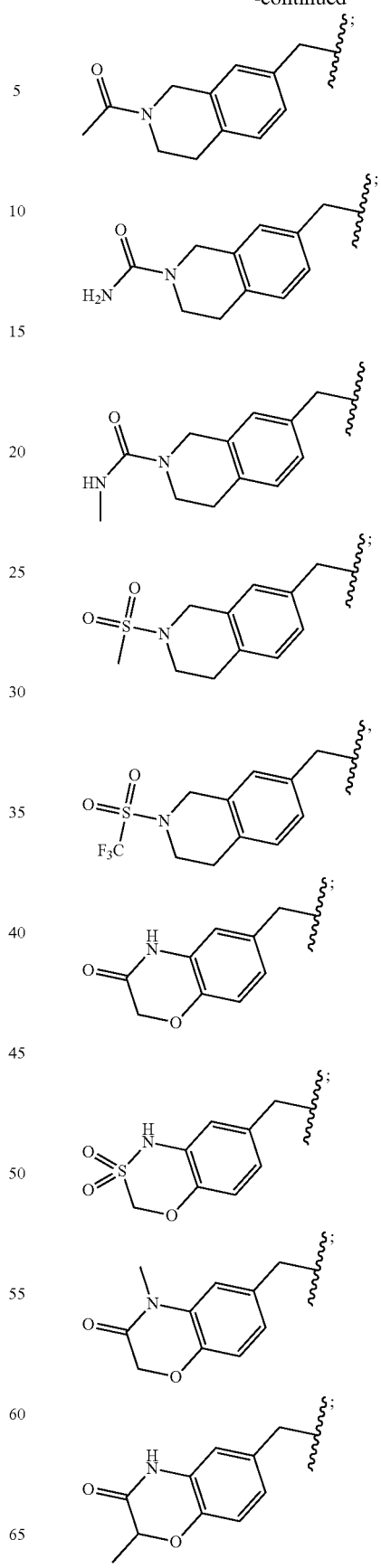

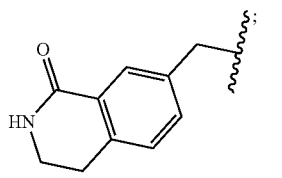
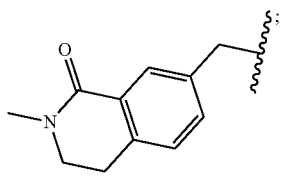
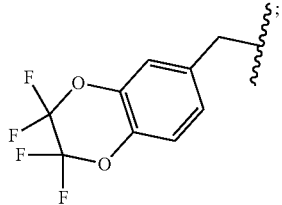
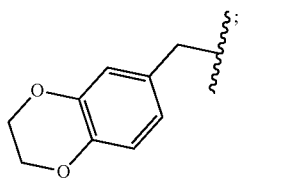
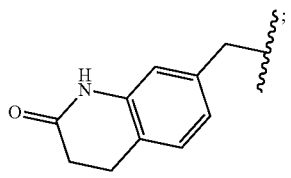
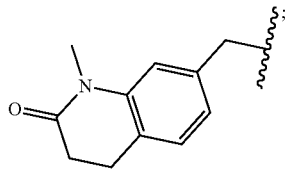
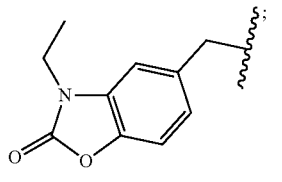
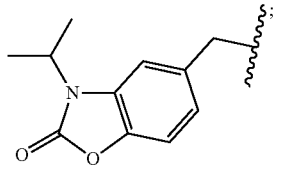
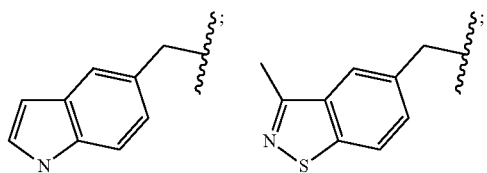
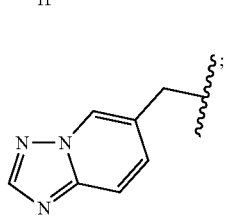
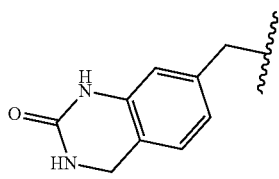
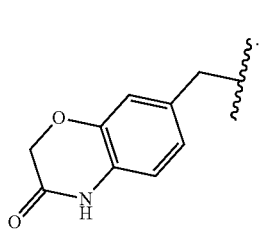
For example, in some embodiments, $R^1$ of the structures of Groups VI(a) and (b) may be selected from Substituent Group 9 as defined hereinabove.
In one embodiment, $R^1$ of Formula (VI) may be selected from Substituent Group 10:
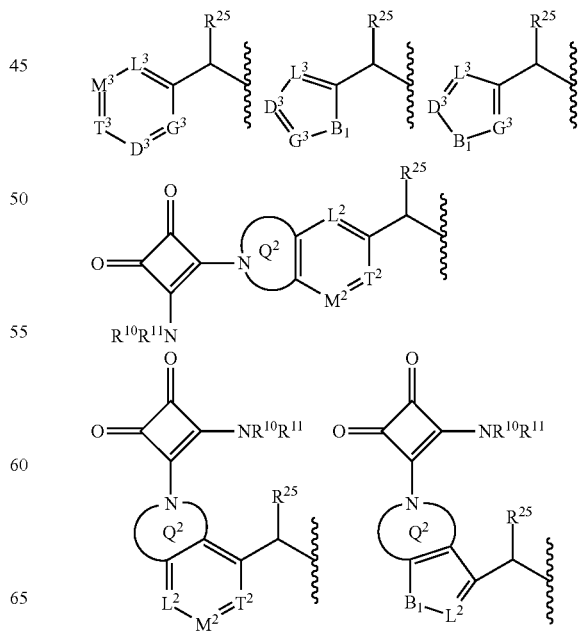

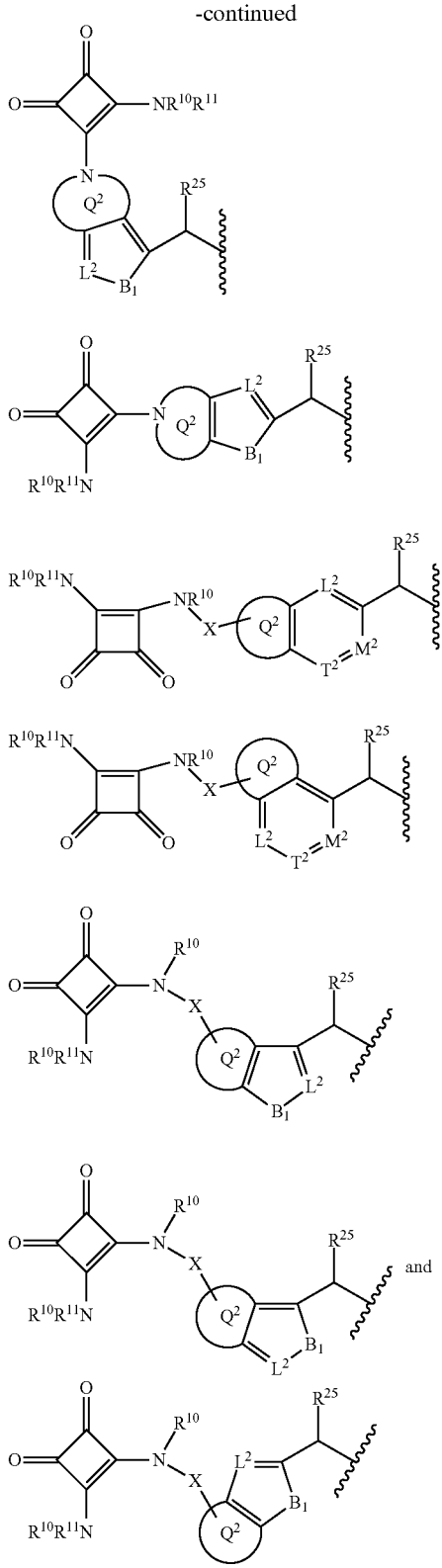
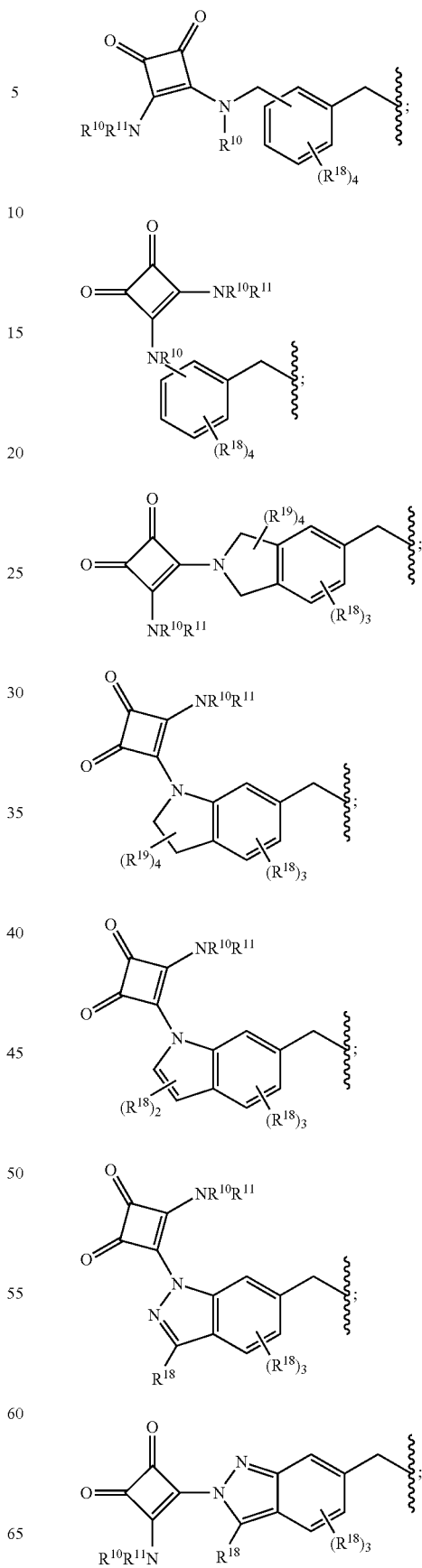
wherein all variables are as defined hereinabove.
For example, in some embodiments, $R^1$ of the structures of Groups VI(a) and (b) may be selected from Substituent Group 10 as defined hereinabove.
In another embodiment, $R^1$ of Formula (VI) may be selected from Substituent Group 11:

211
-continued
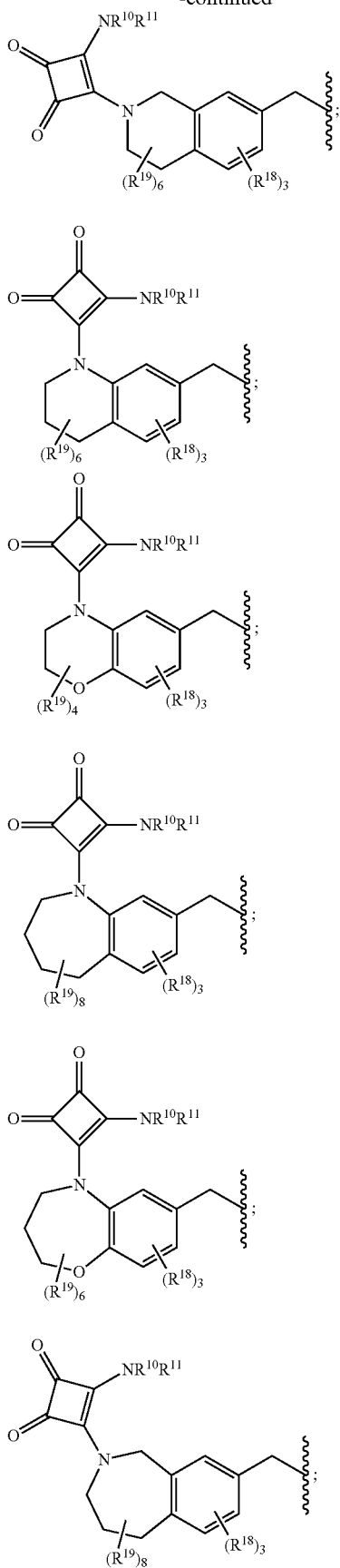
212
-continued
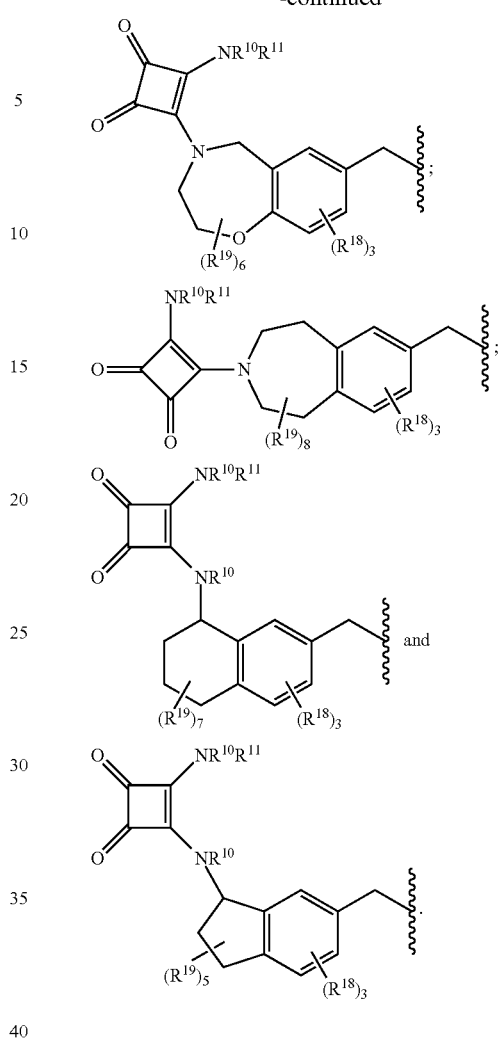
For example, in some embodiments, R¹ of the structures of Groups VI(a) and (b) may be selected from Substituent Group 11 as defined hereinabove.
In yet another embodiment, R¹ of Formula (VI) may be selected from Substituent Group 12:
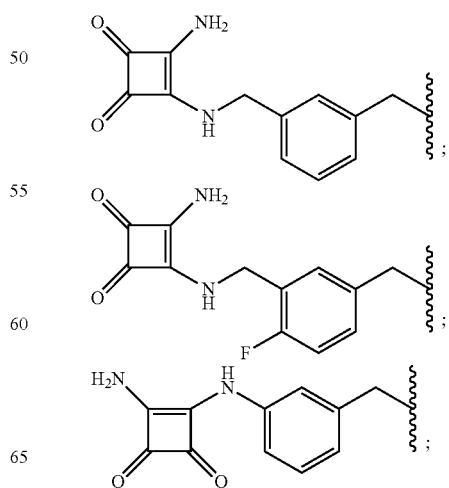

213
-continued
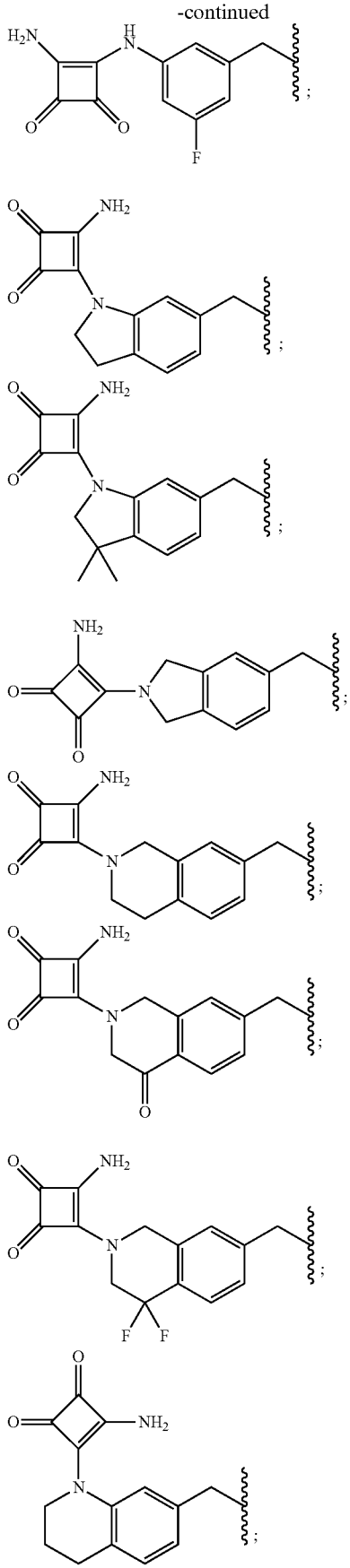
214
-continued
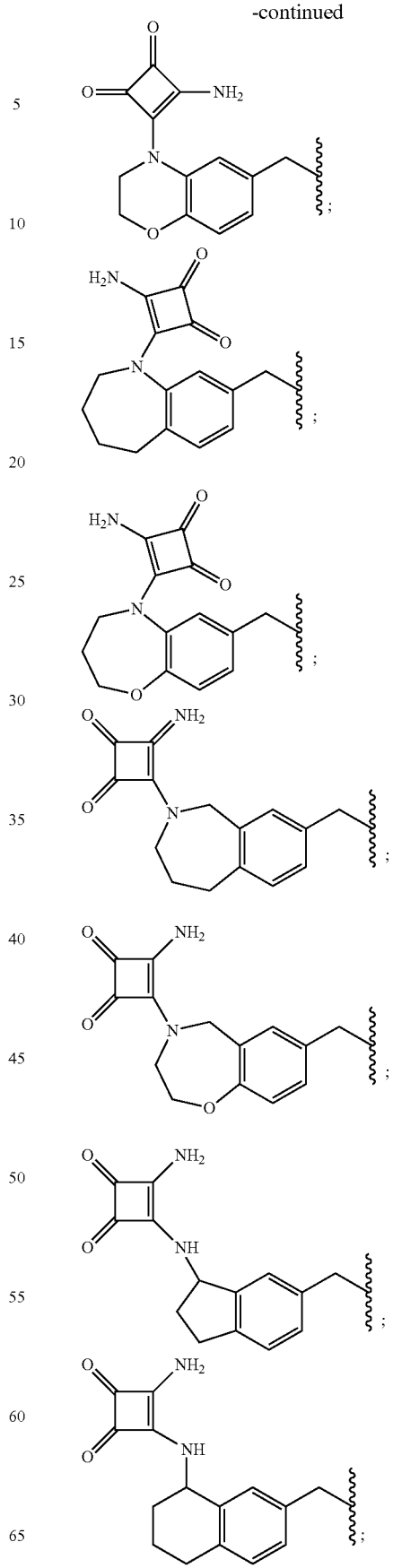

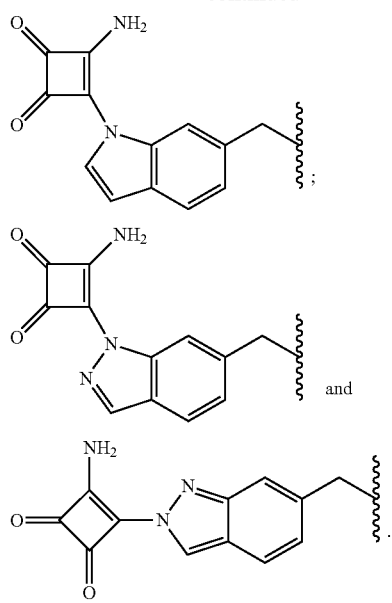
For example, in some embodiments, R¹ of the structures of Groups VI(a) and (b) may be selected from Substituent Group 12 as defined hereinabove.
In another embodiment, the present invention provides a compound selected from:
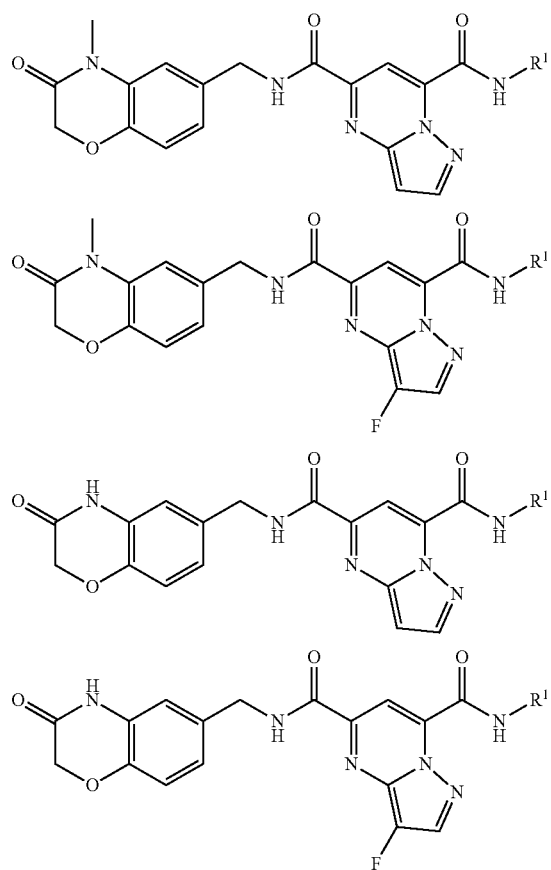
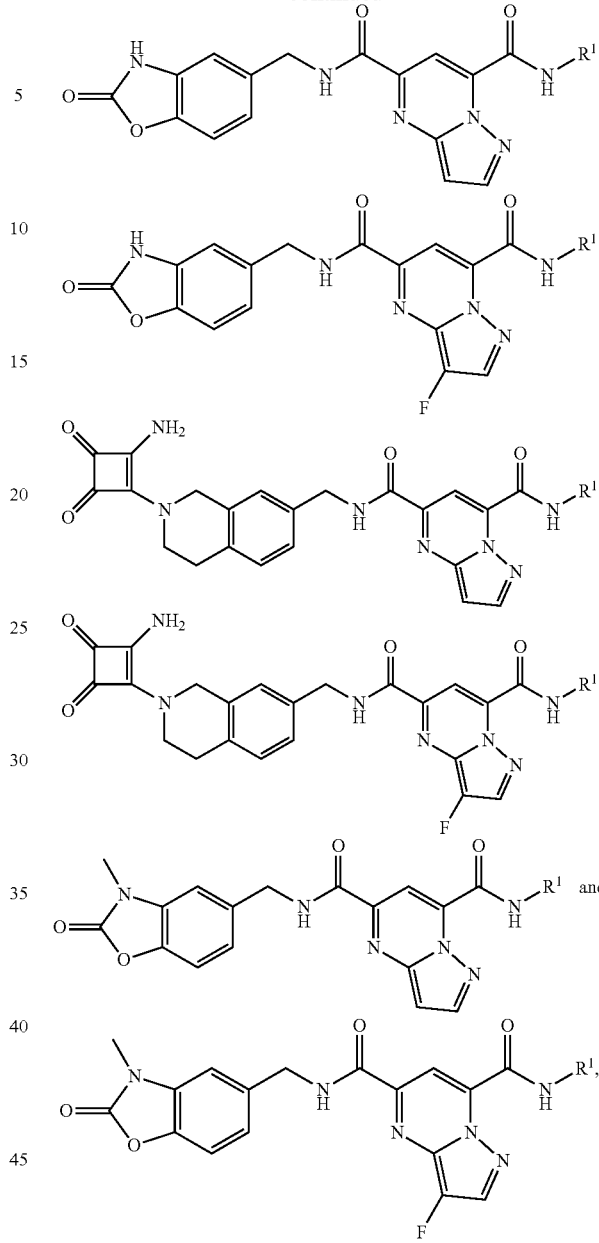
wherein all variables are as defined hereinabove.
In still another embodiment, the present invention provides a compound selected from:
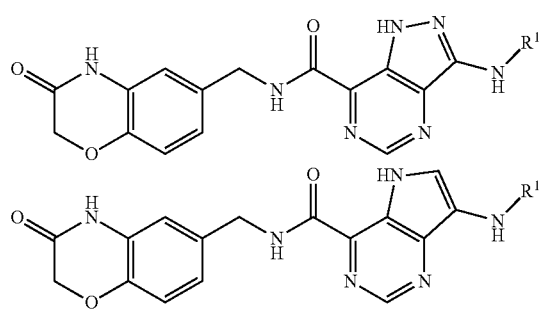

217
-continued
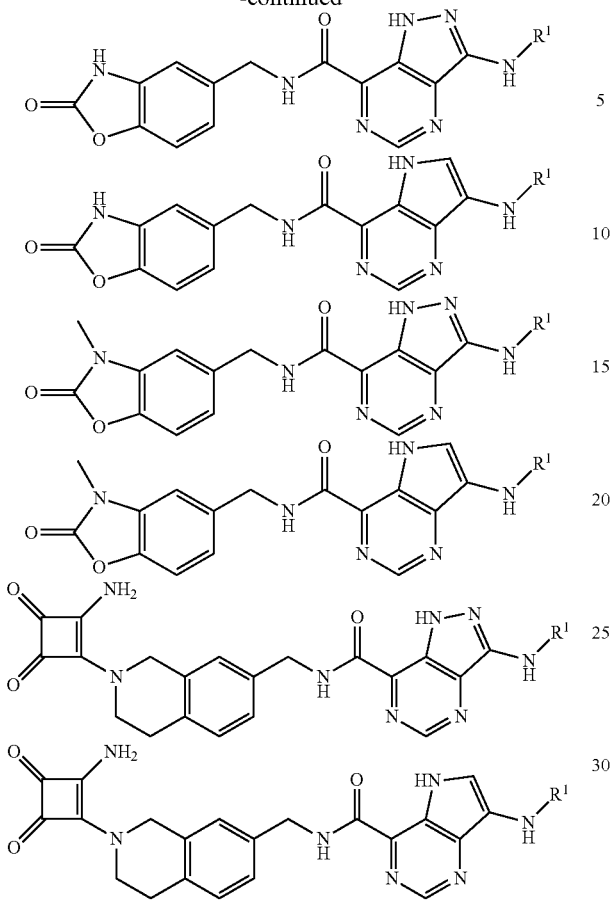
218
-continued
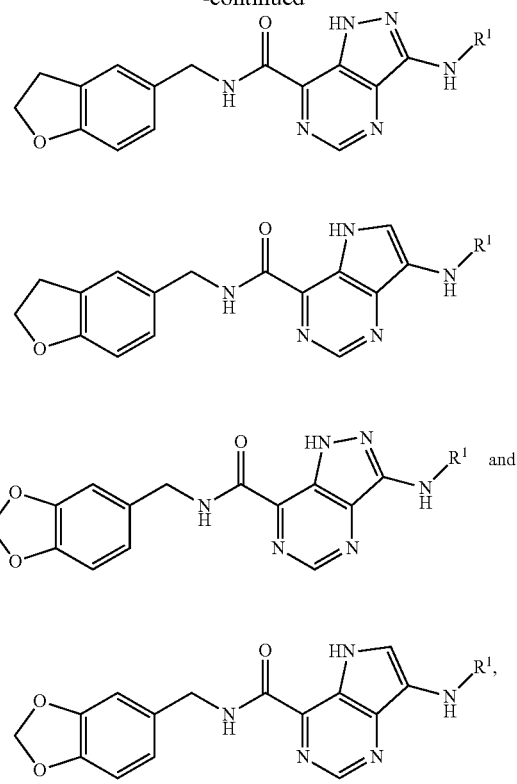
wherein all variables are as defined hereinabove.
In still another embodiment, the present invention provides a compound selected from:
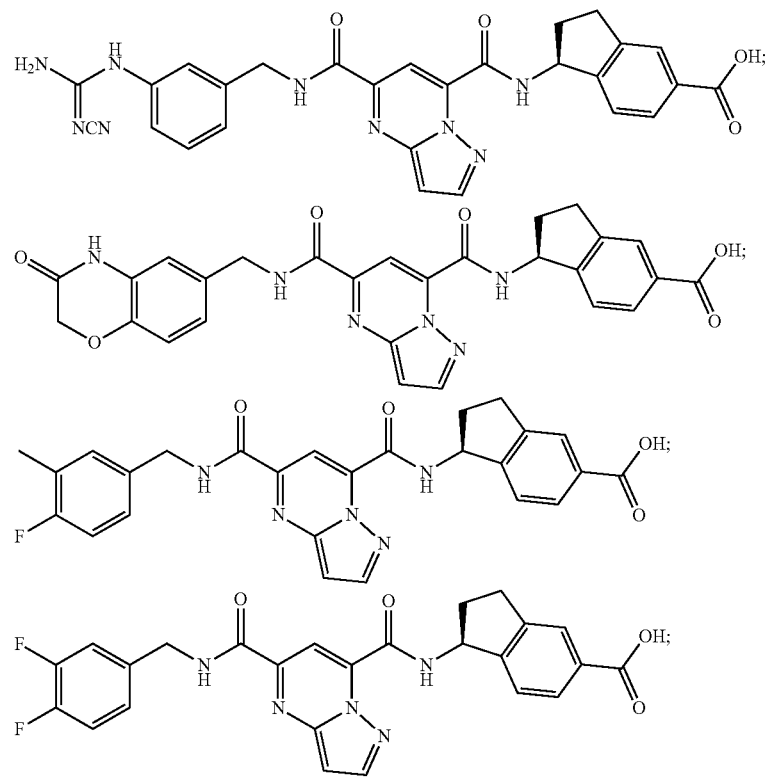

-continued
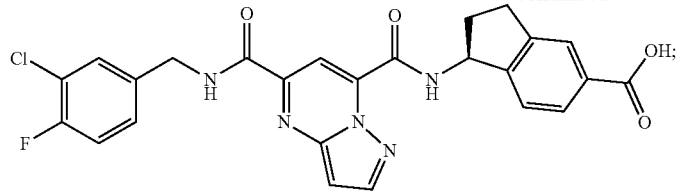
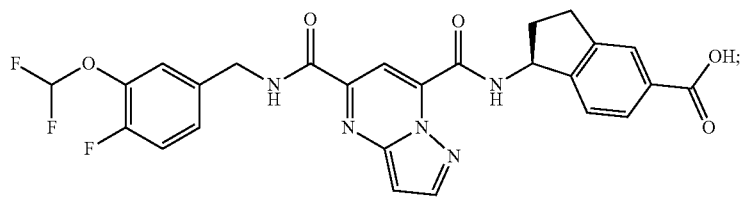
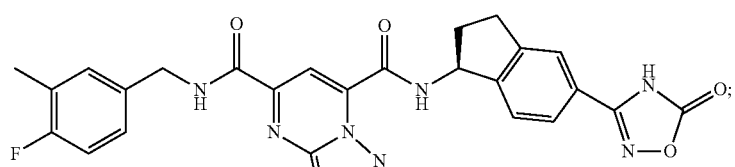
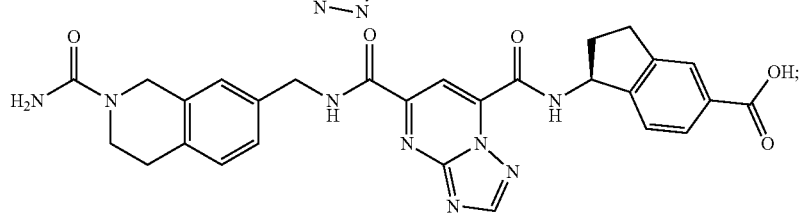
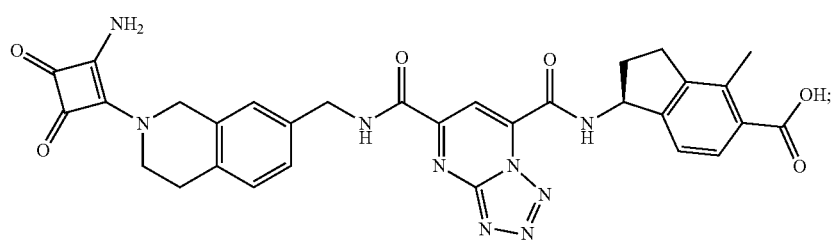
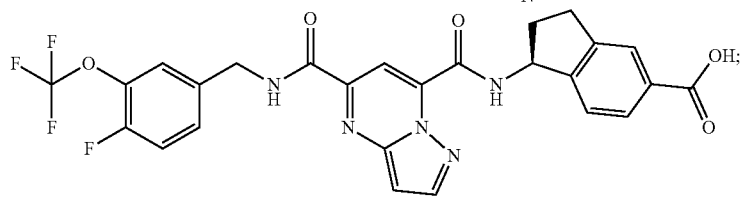
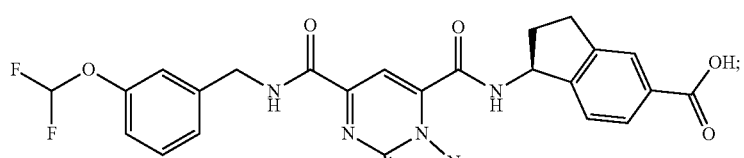
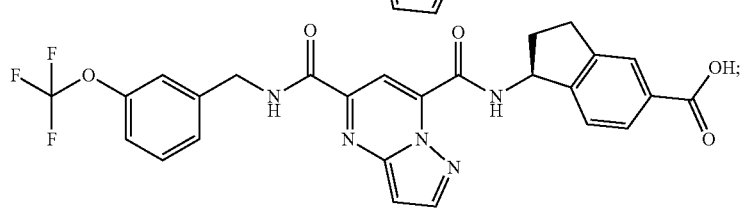

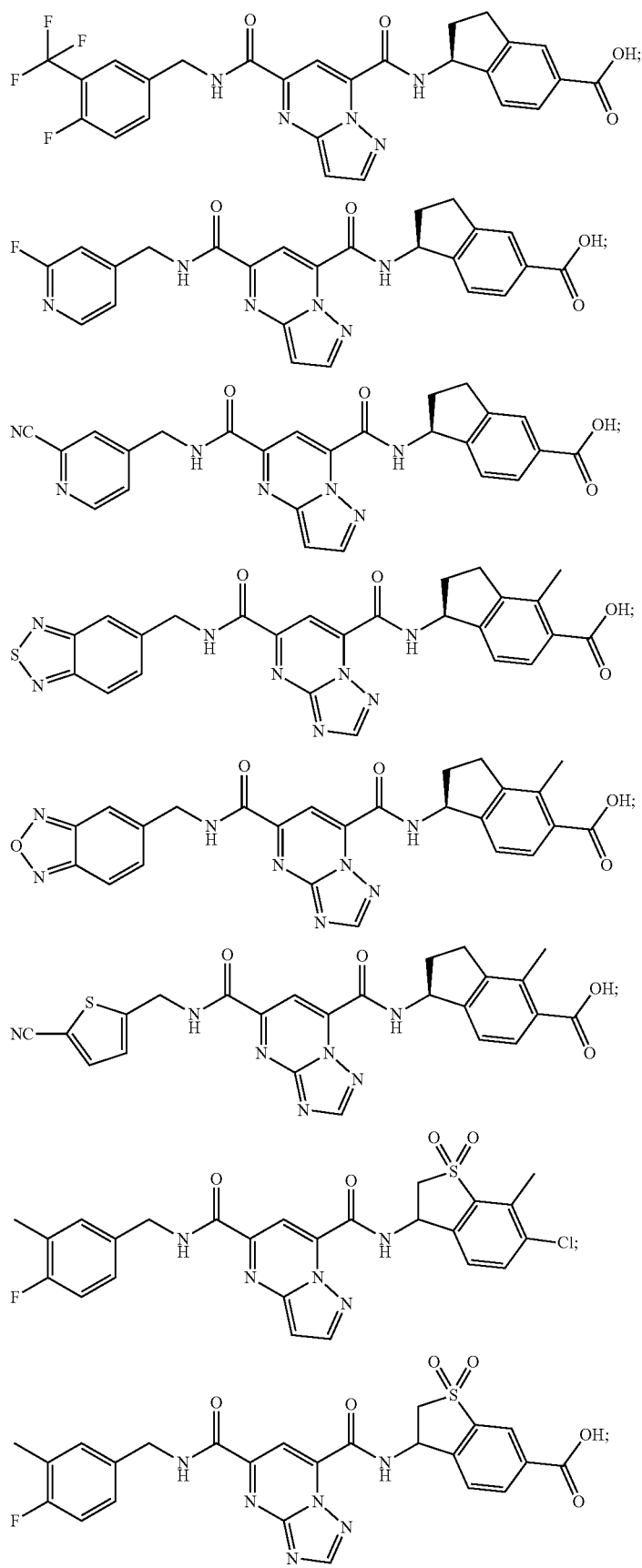

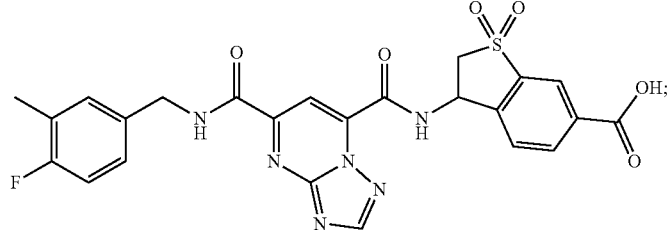
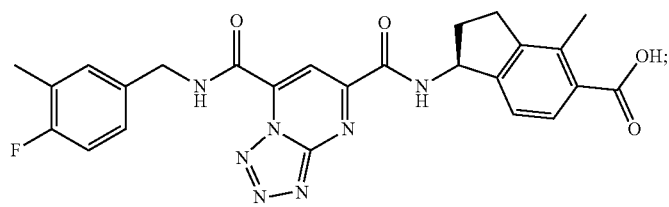
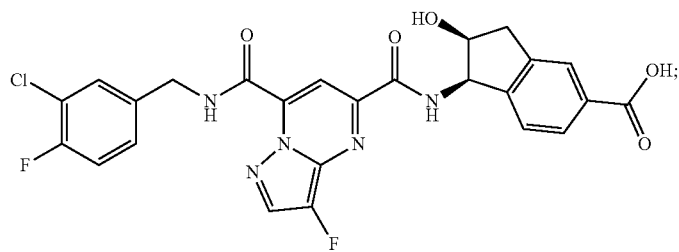
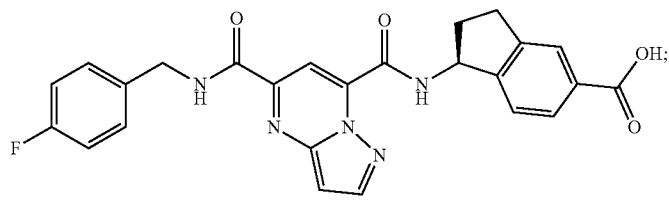
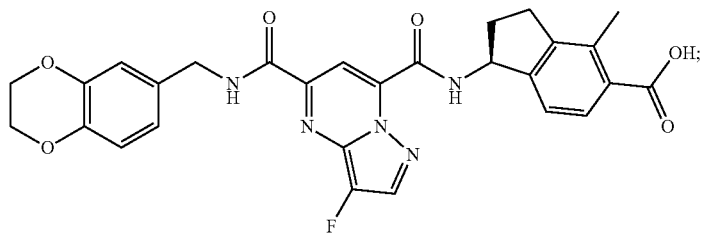
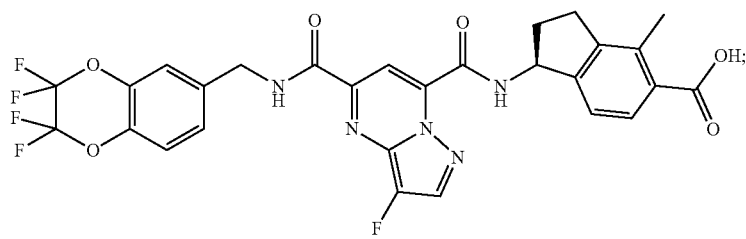
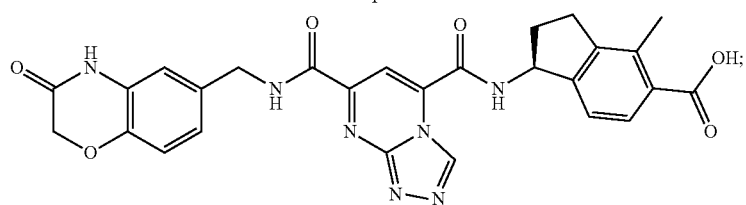

-continued
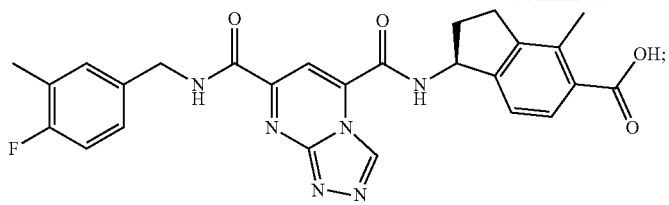
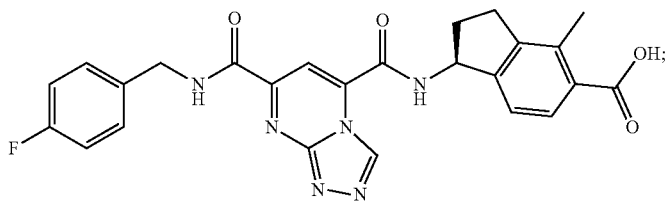
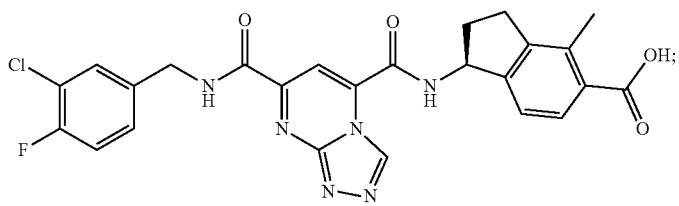
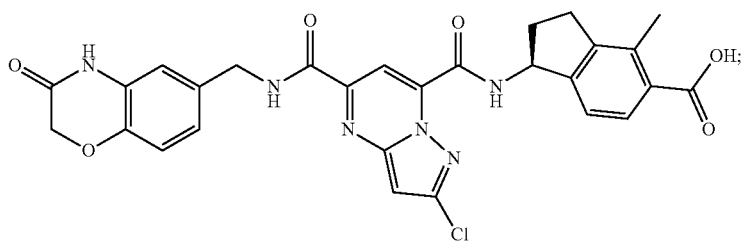
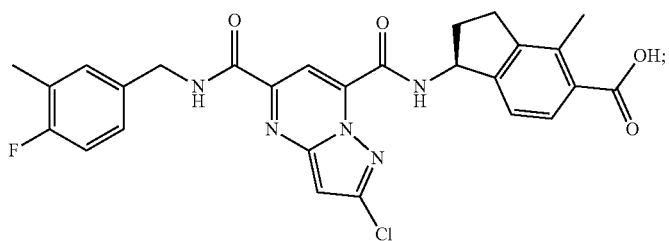
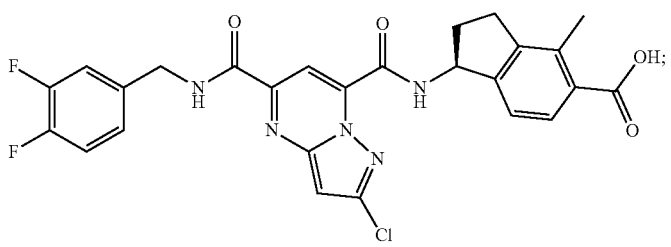
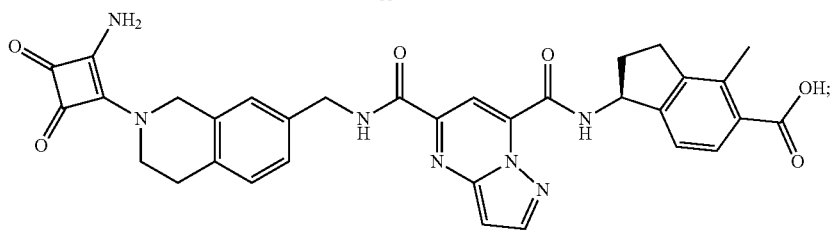

-continued
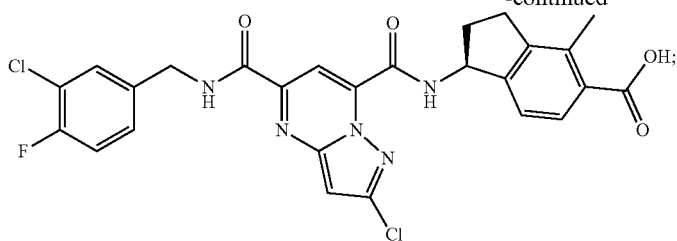
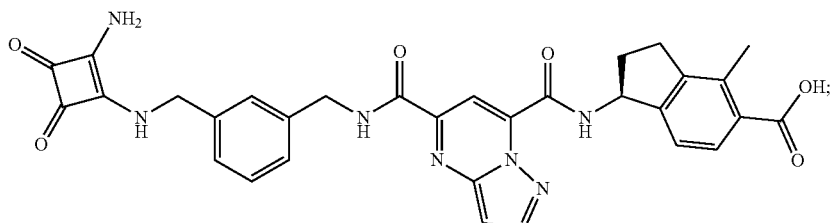
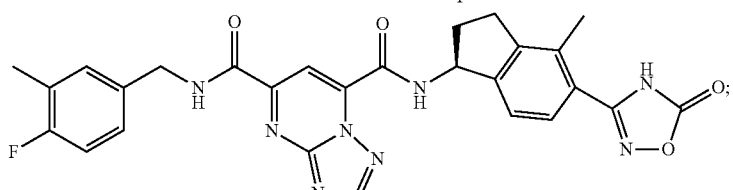
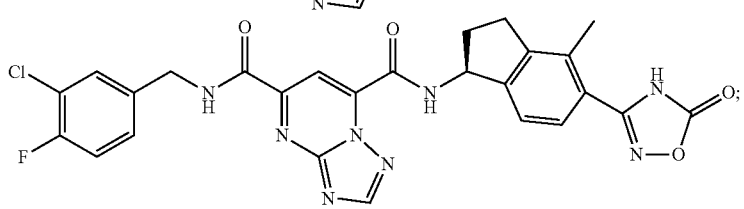
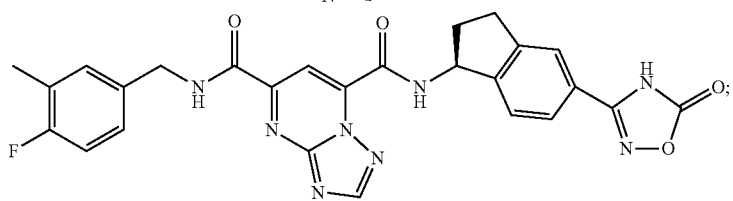
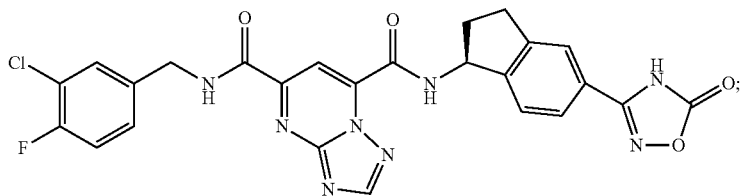
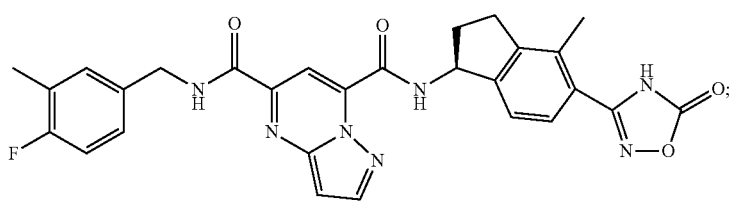
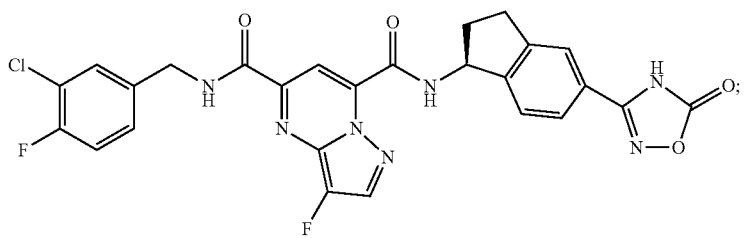

-continued
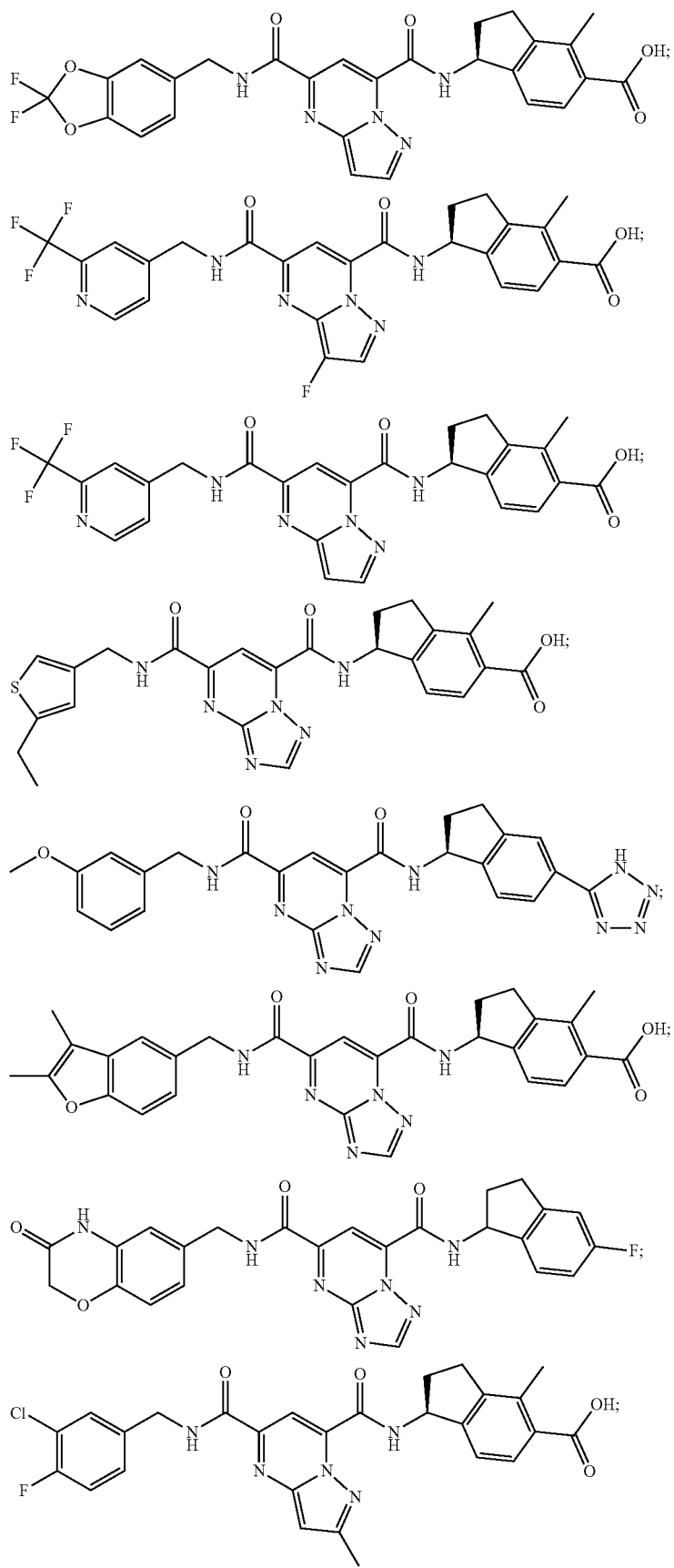

-continued
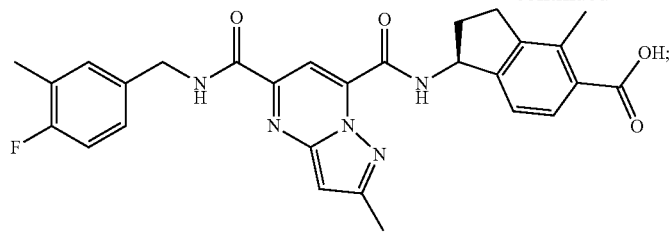
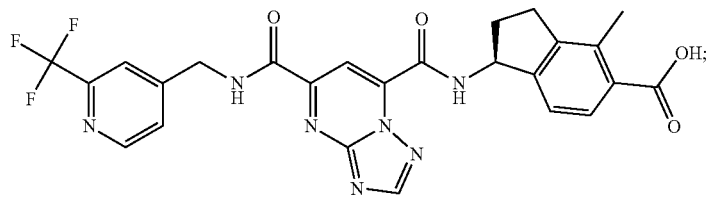
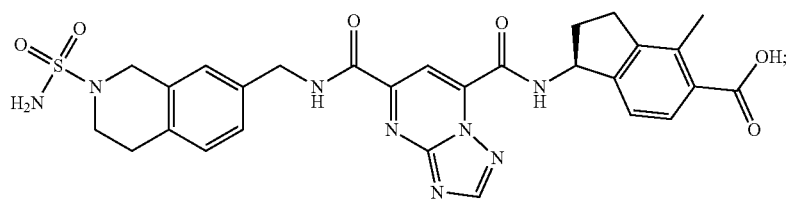
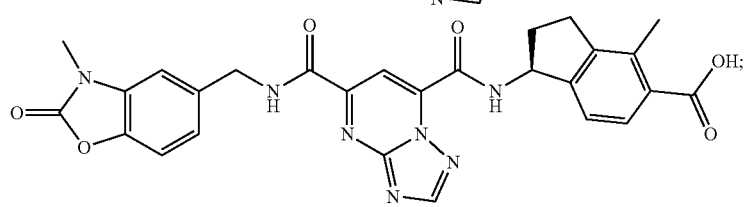
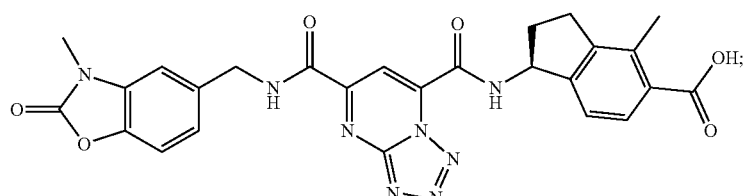
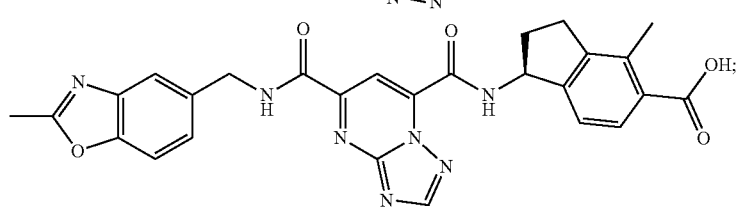
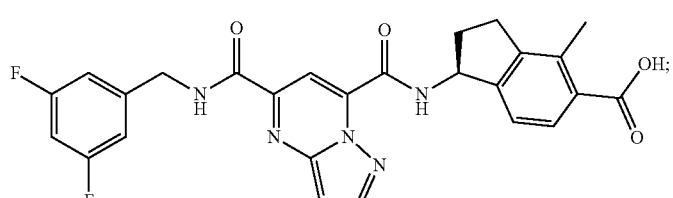
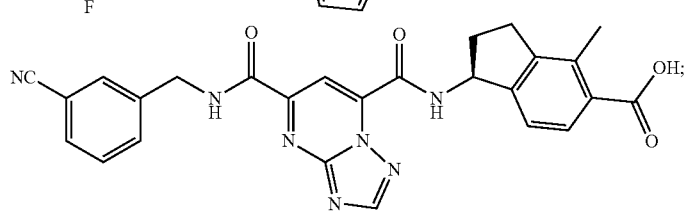

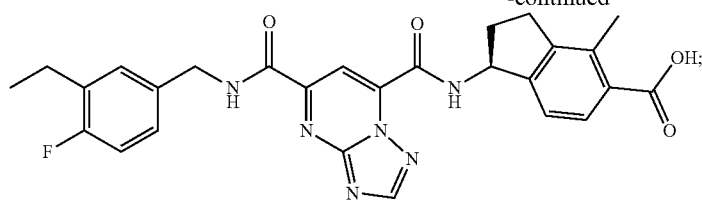
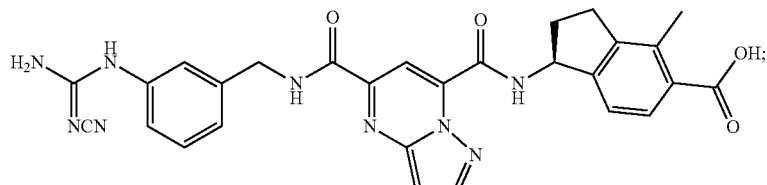
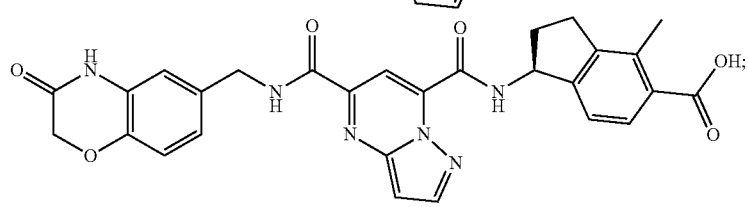
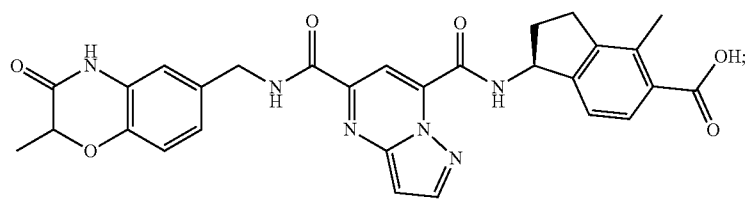
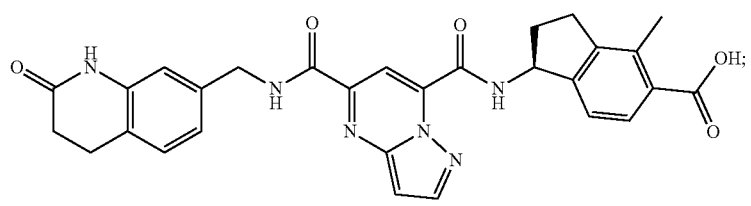
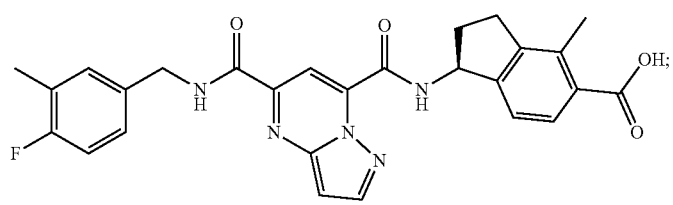
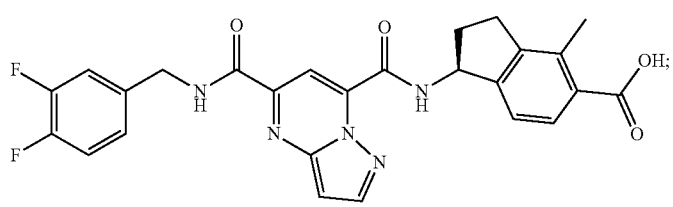
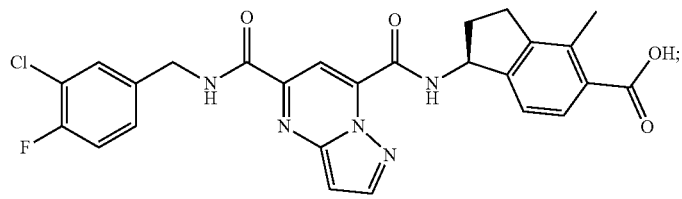

-continued
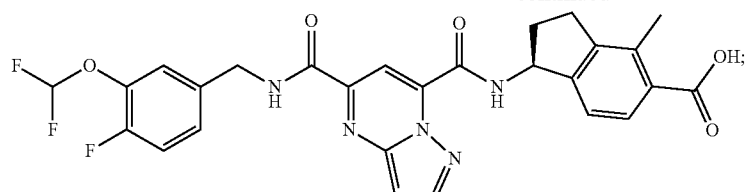
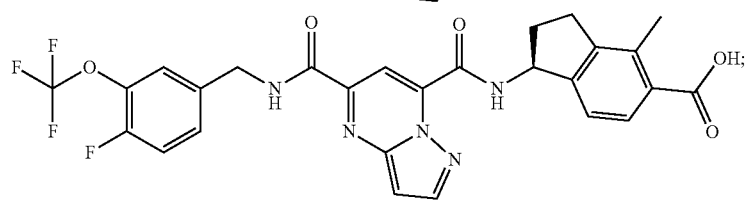
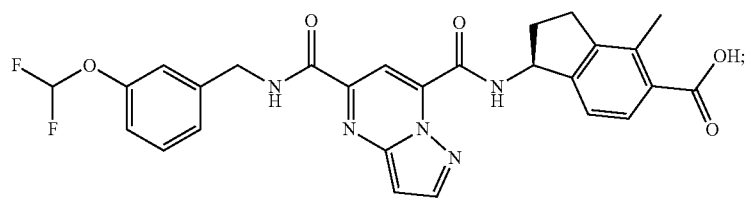
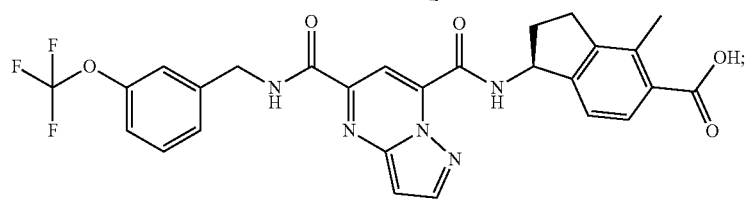
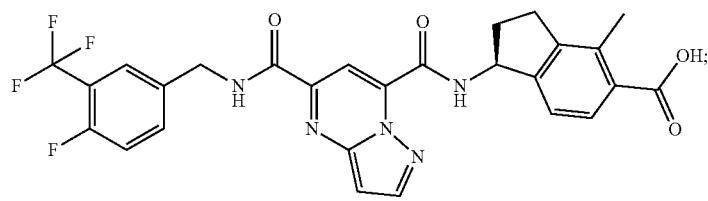
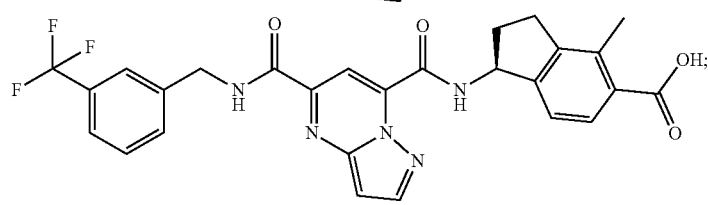
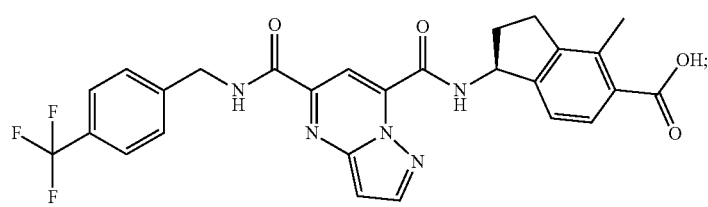
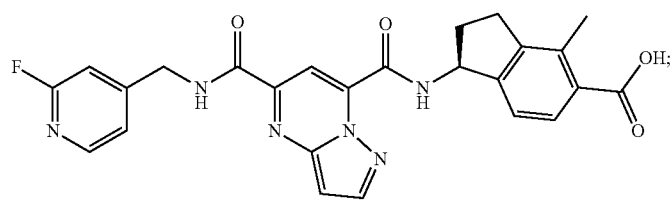

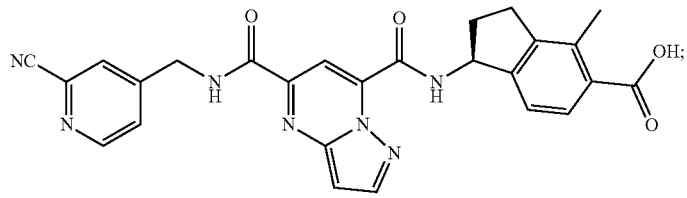
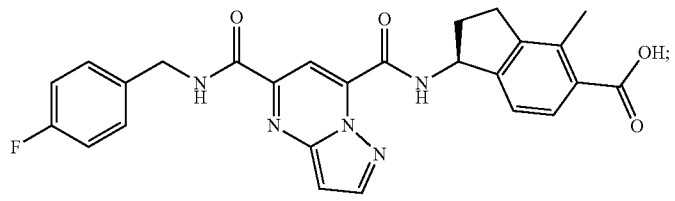
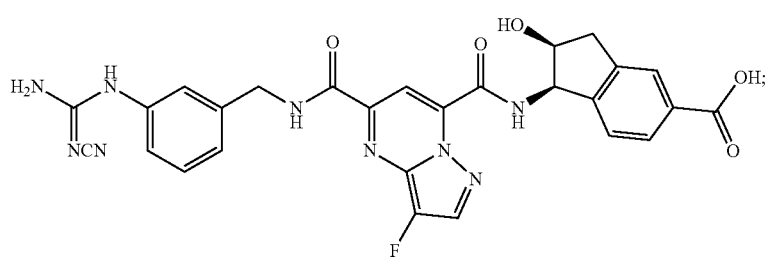
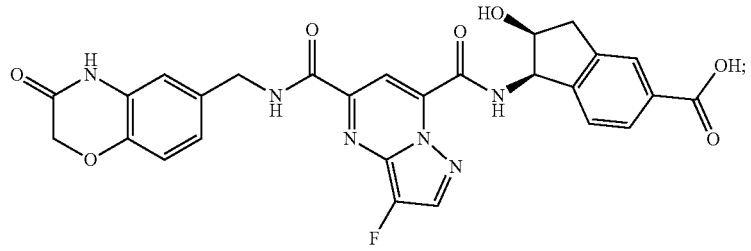
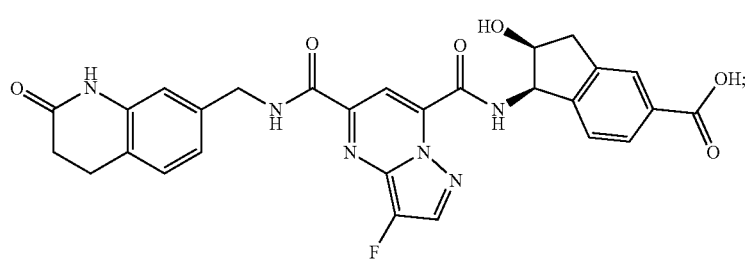

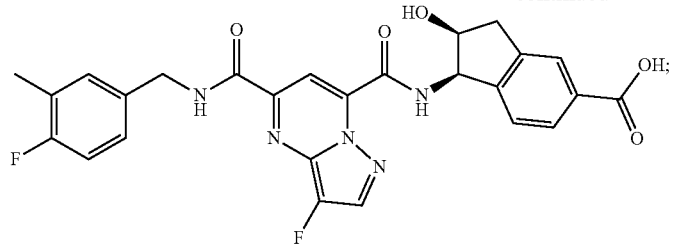
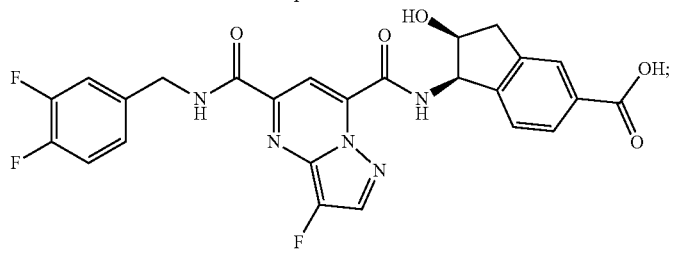
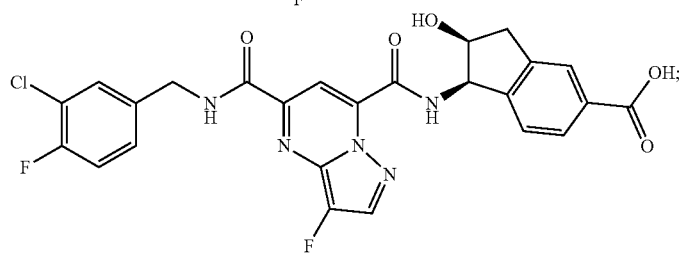
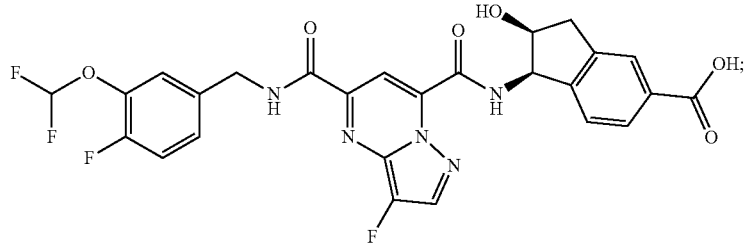
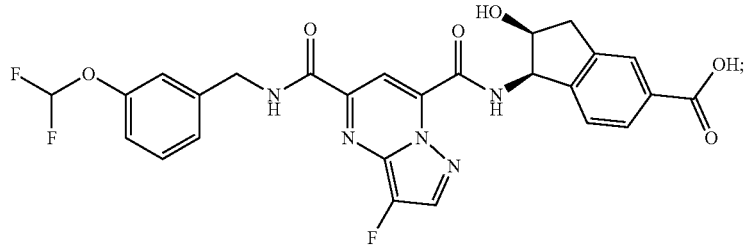
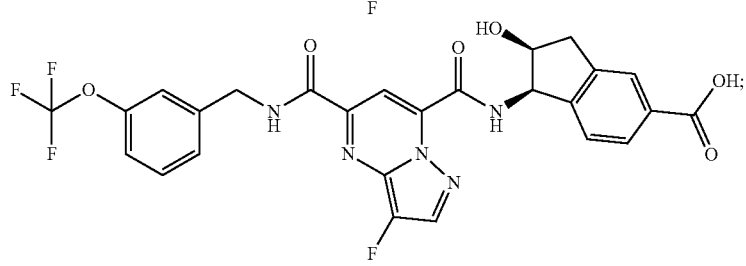

-continued
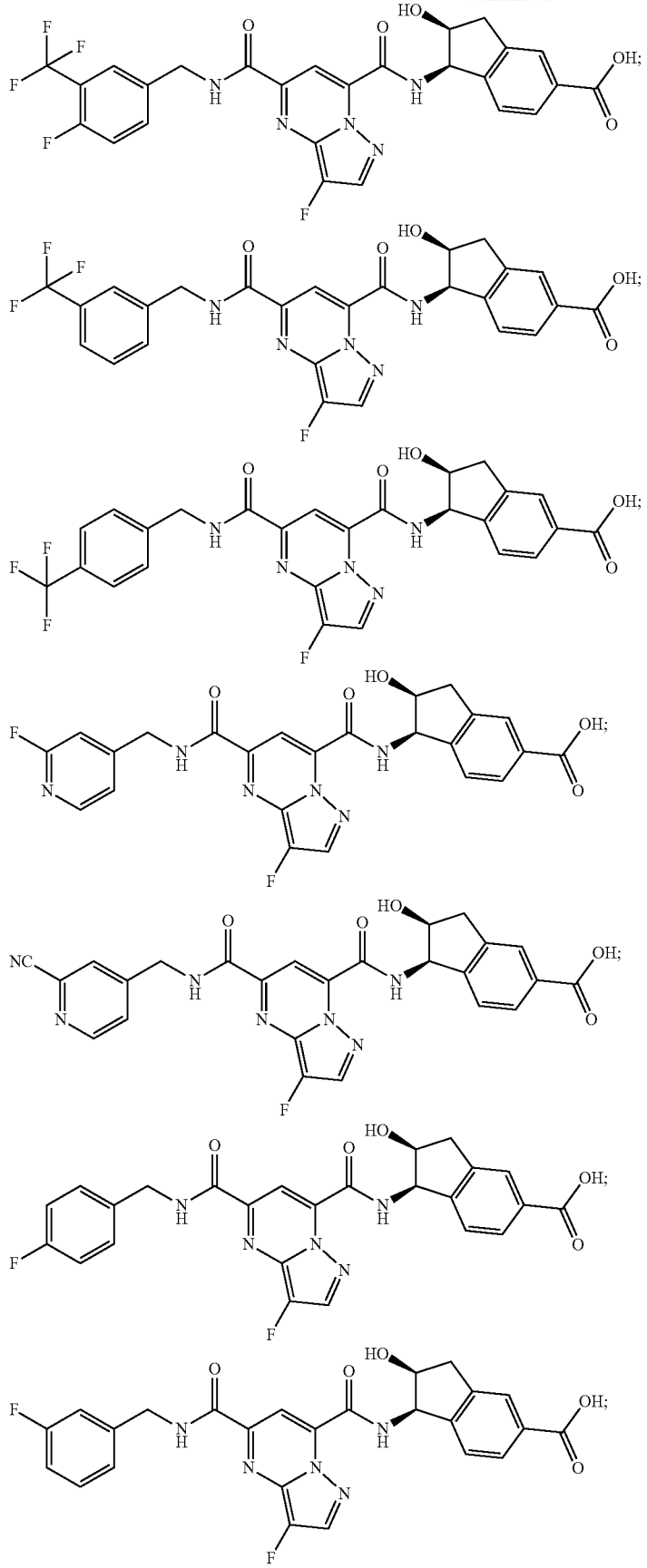

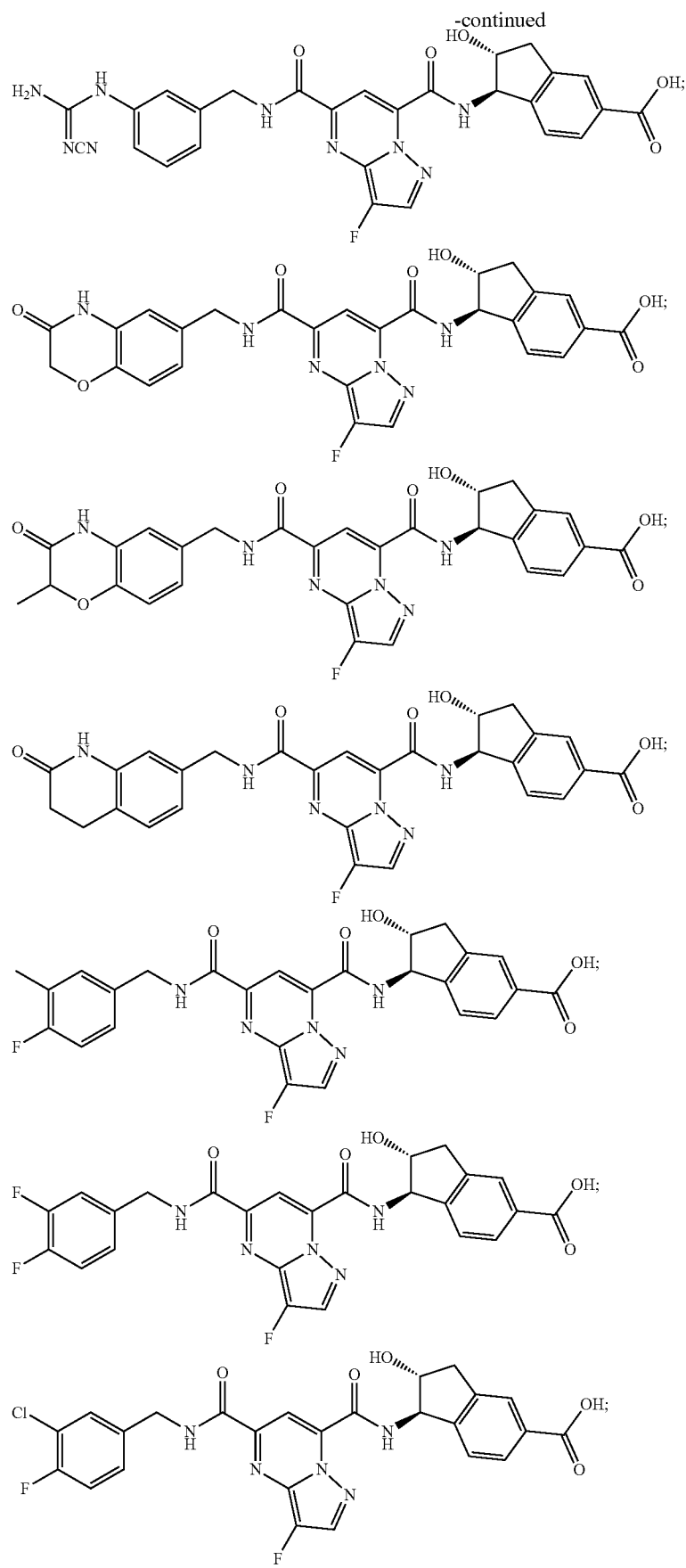

-continued
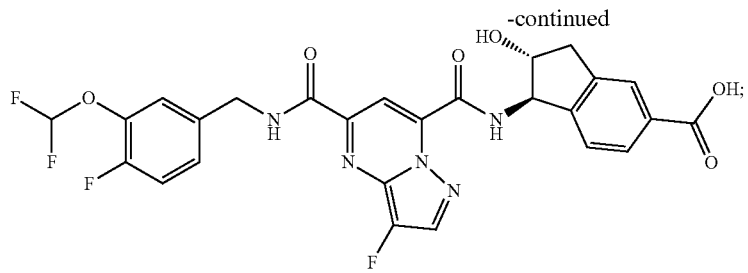
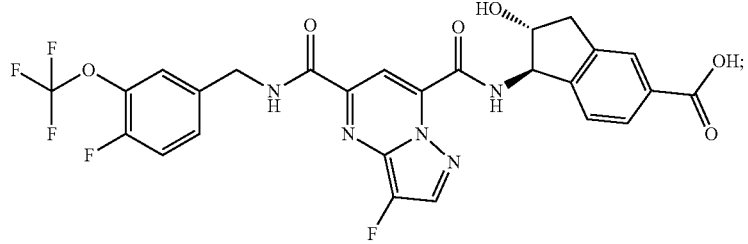
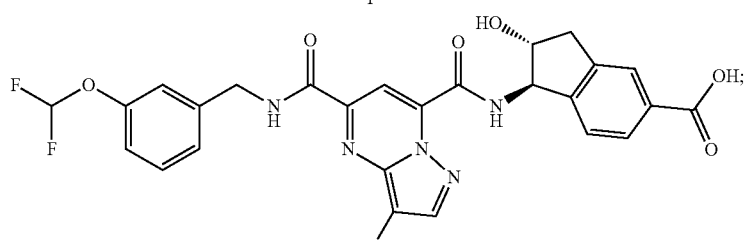
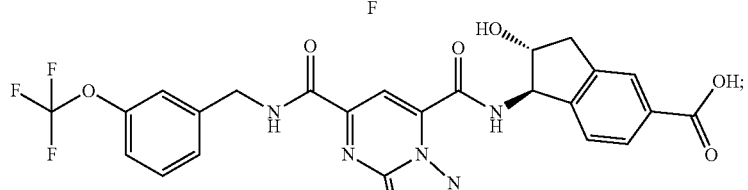
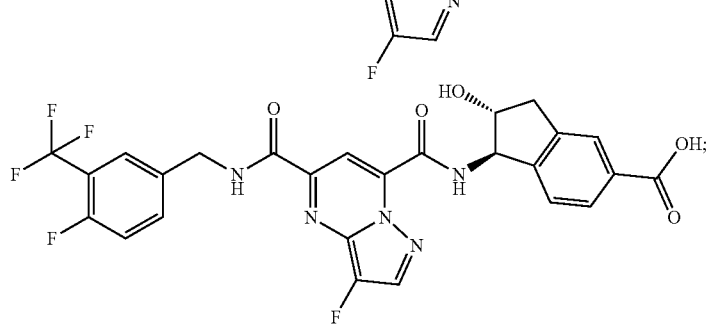
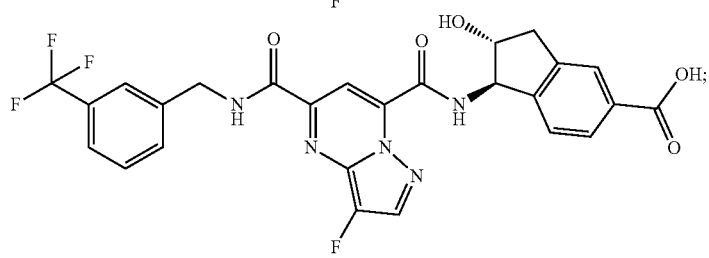
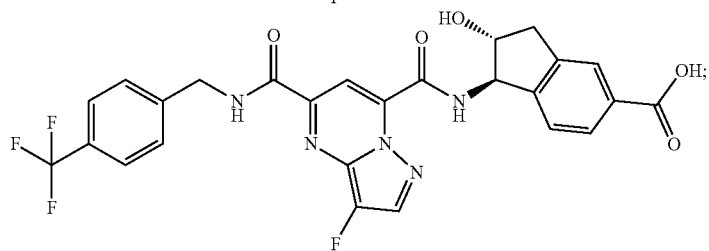

-continued
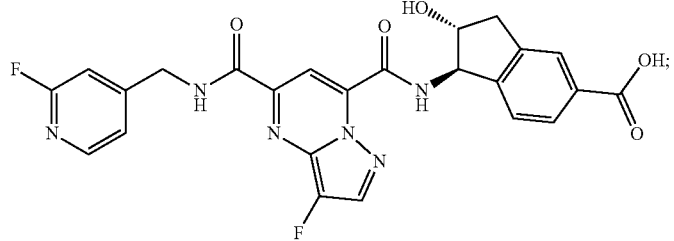
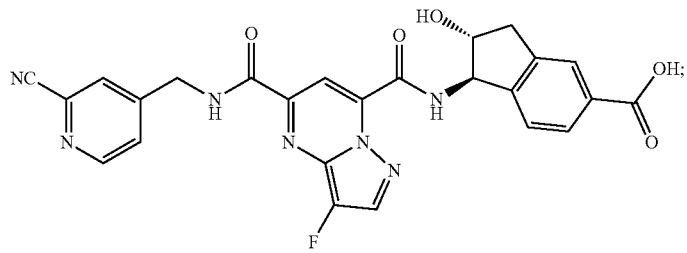
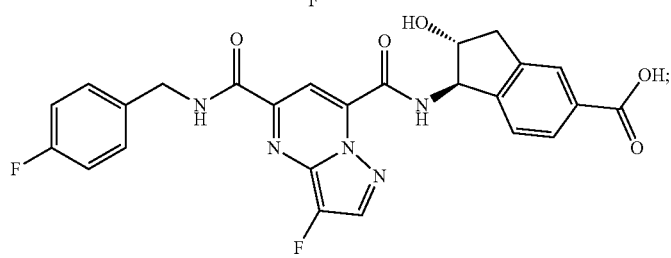
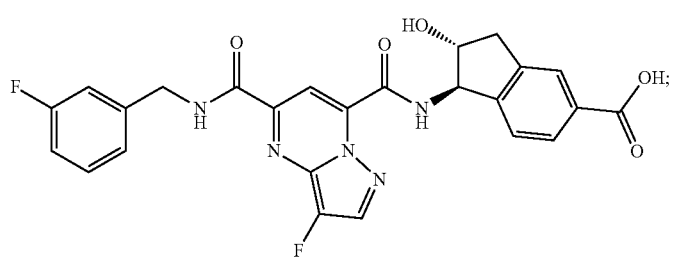
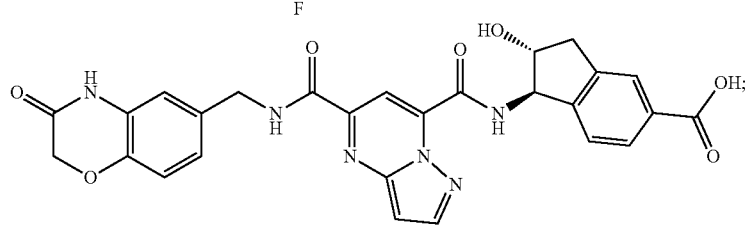
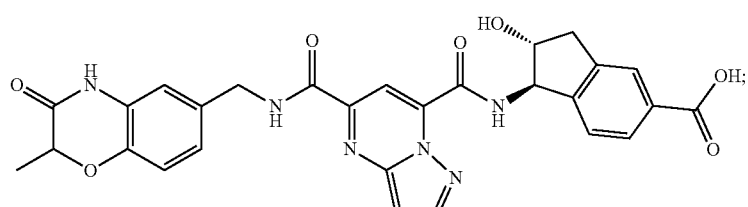
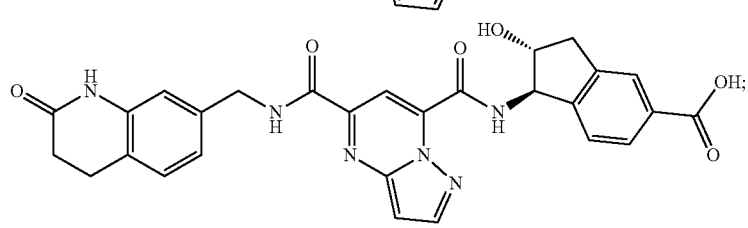

-continued
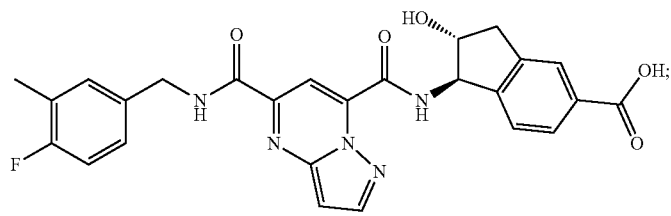
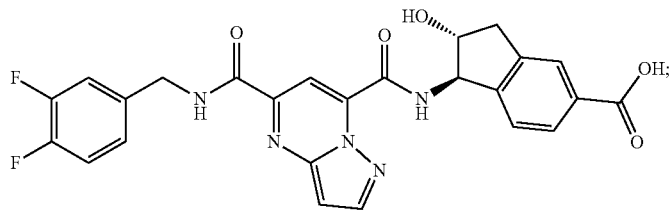
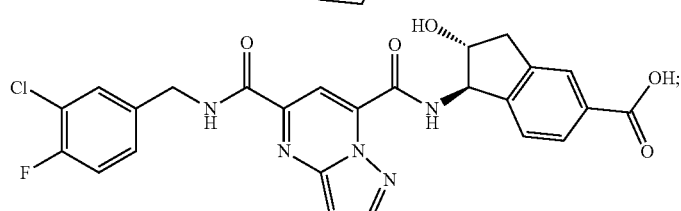
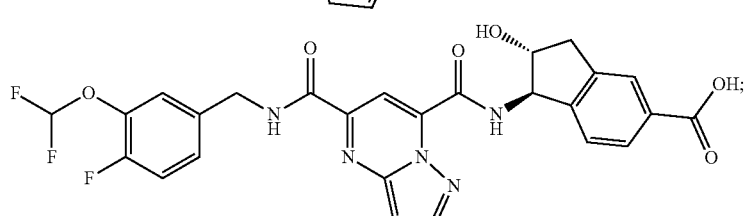
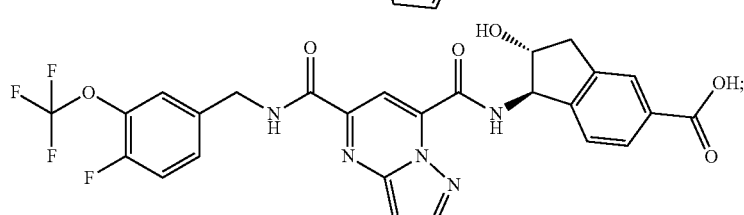
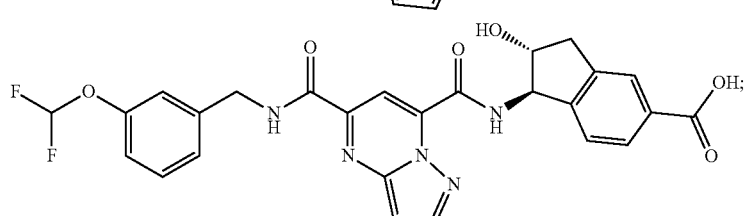
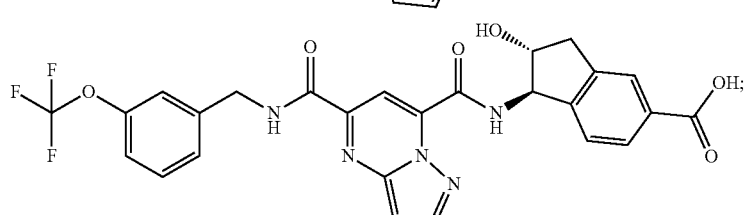
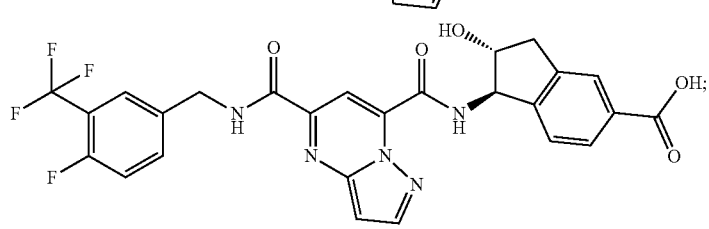

-continued
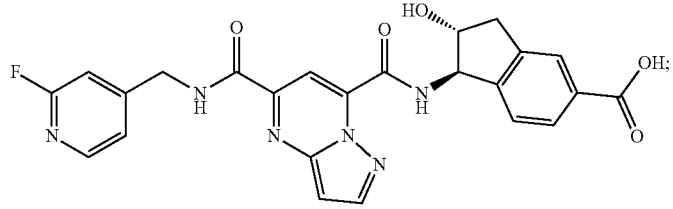
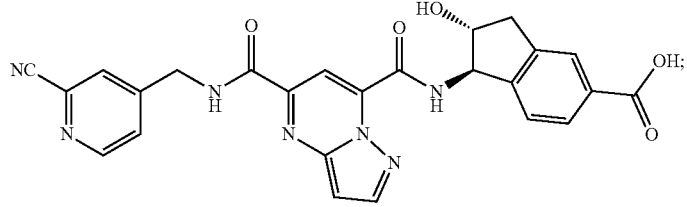
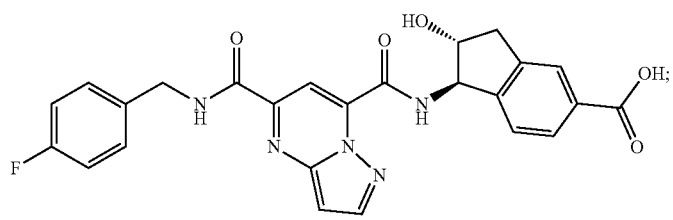
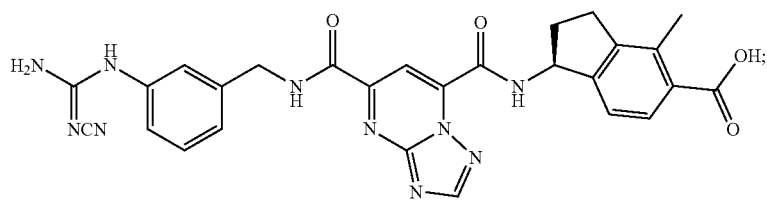
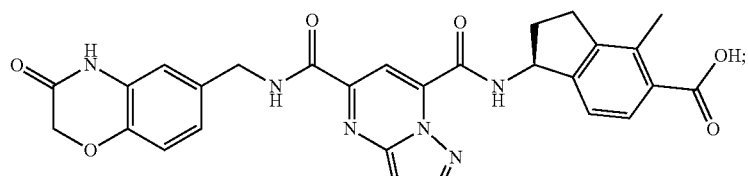
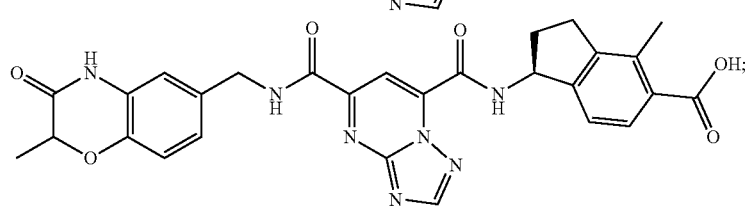
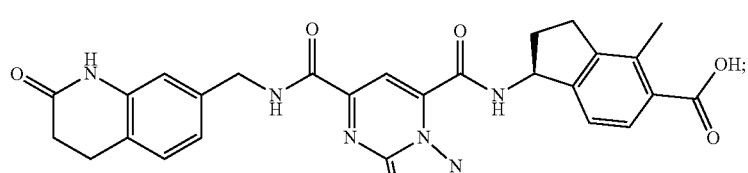
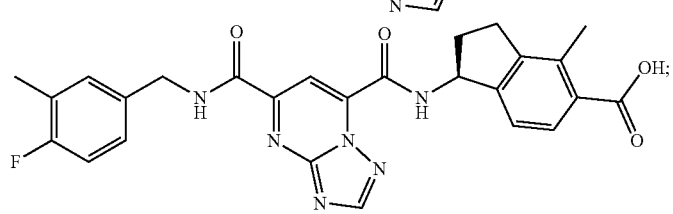

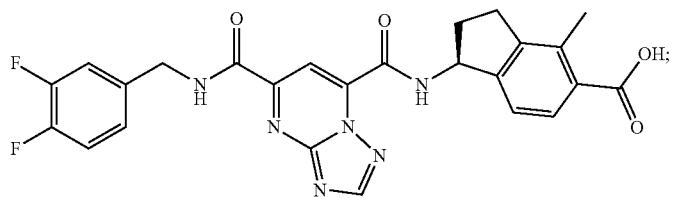
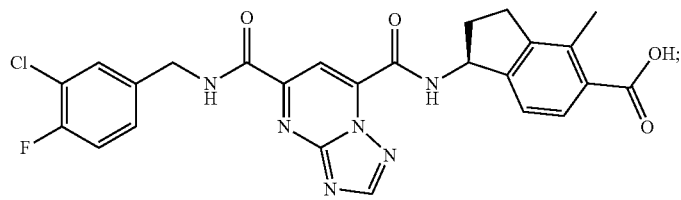

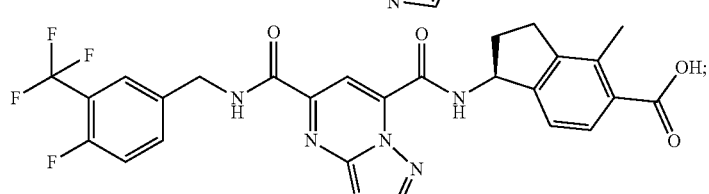
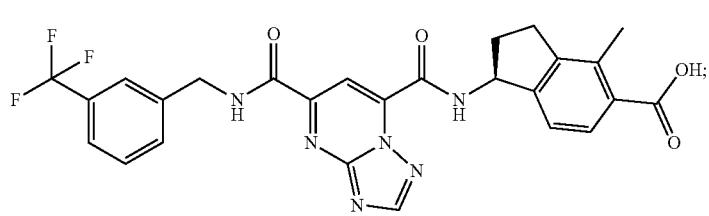

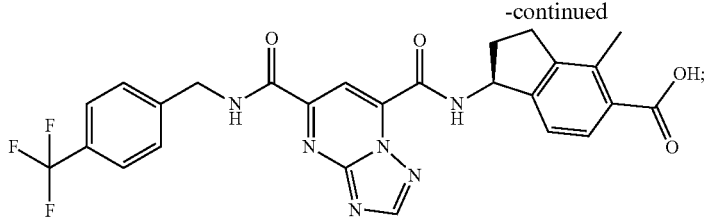
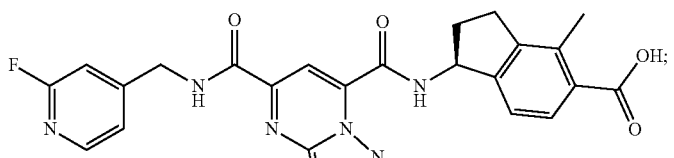
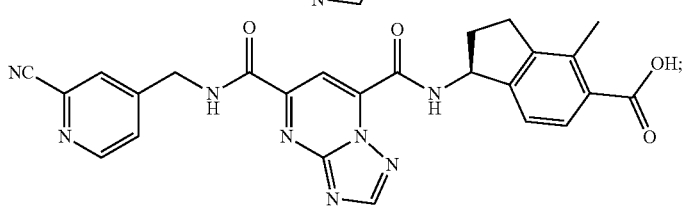
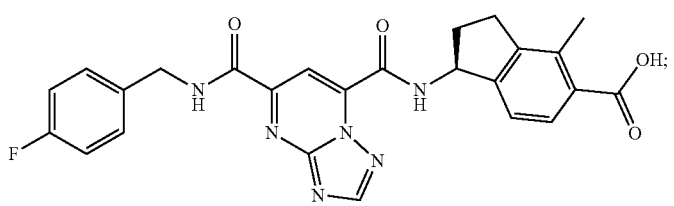
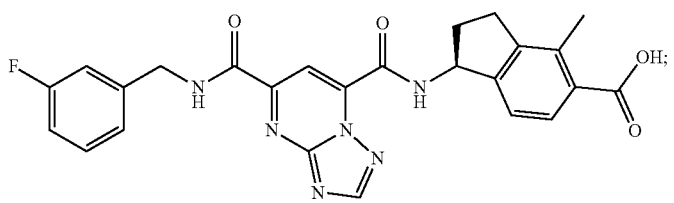
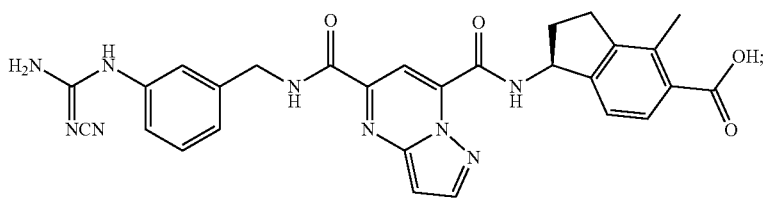
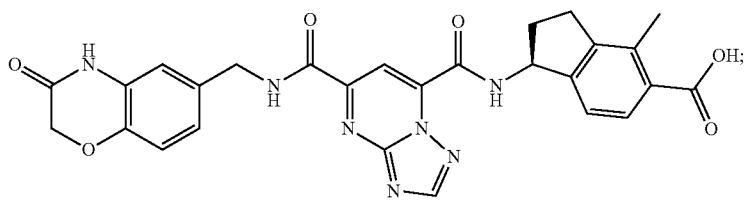
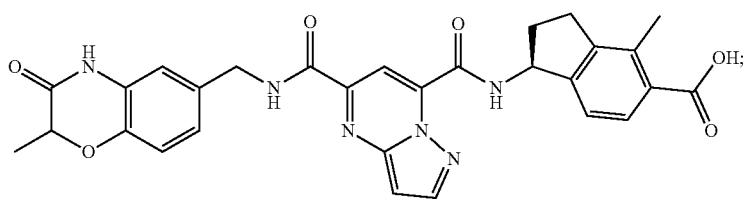

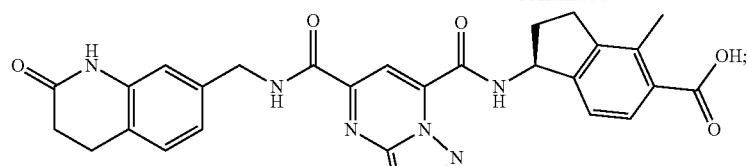
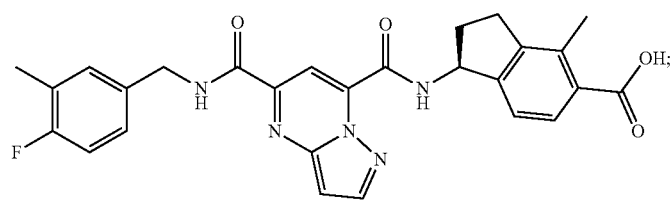
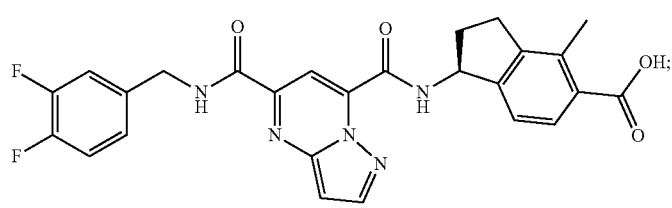
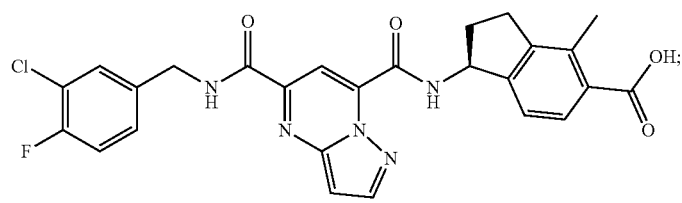
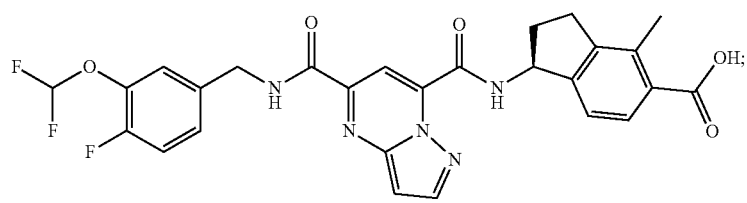
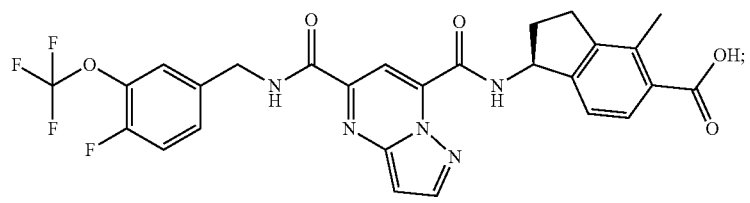
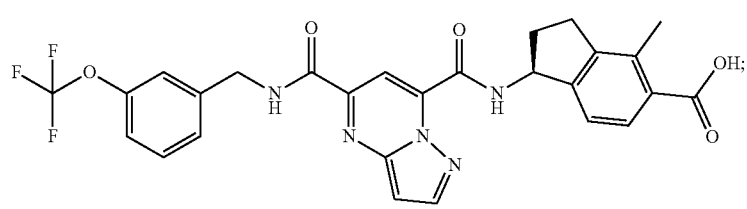

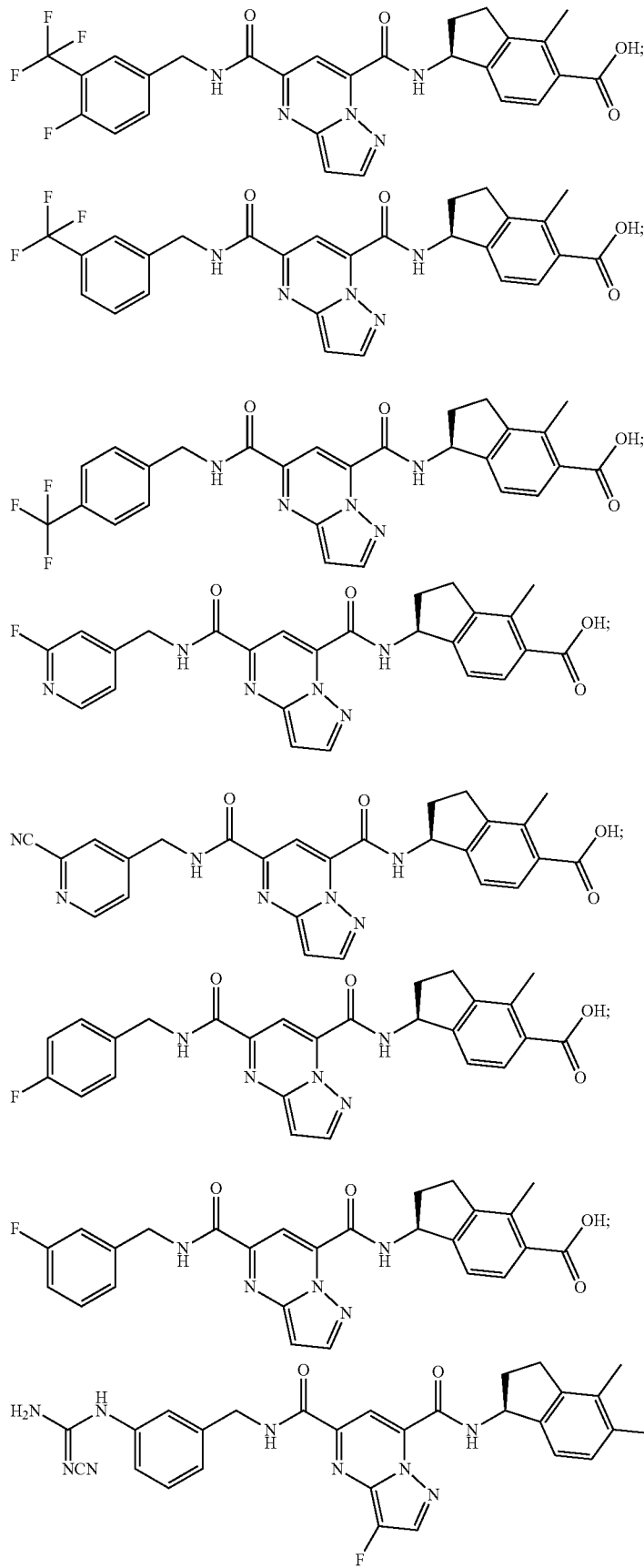

-continued
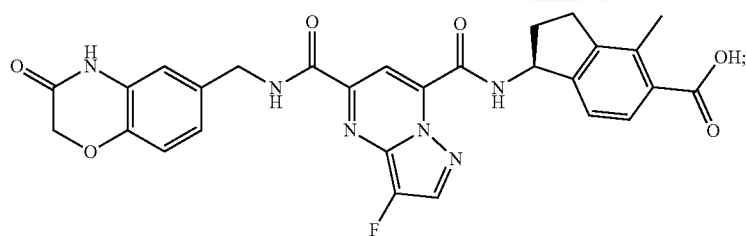
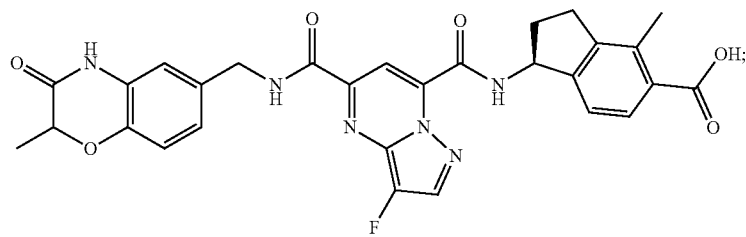
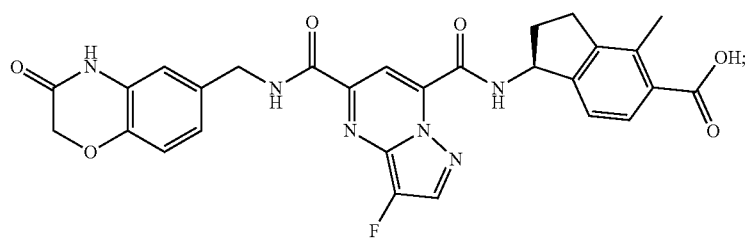
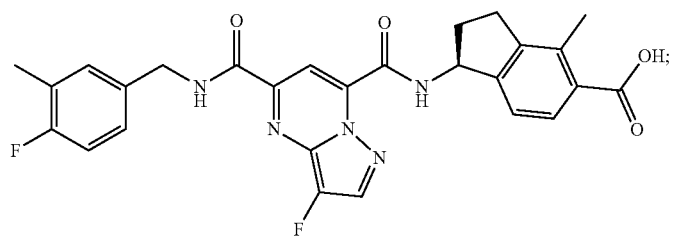
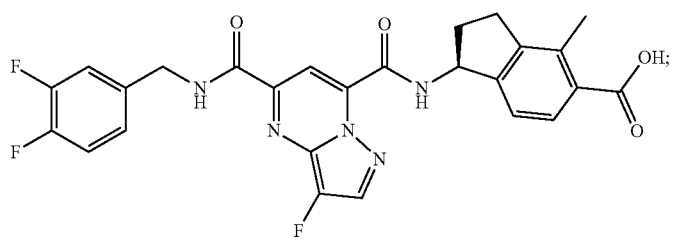
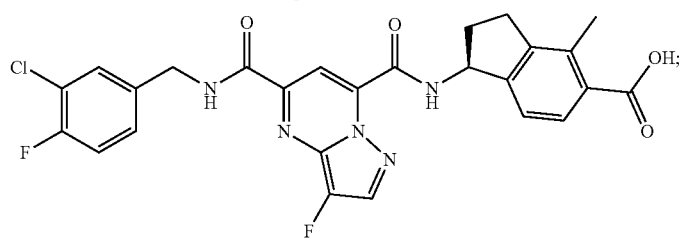
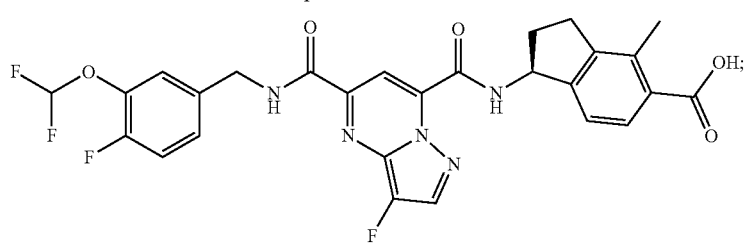

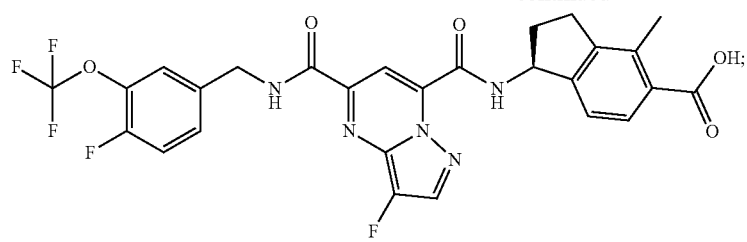
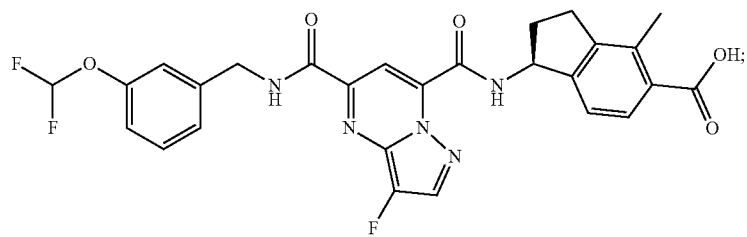
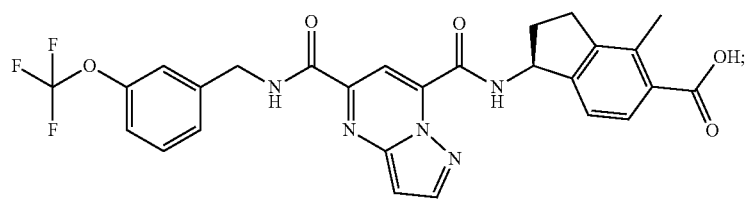
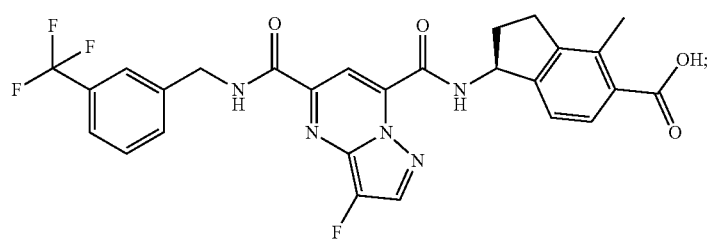
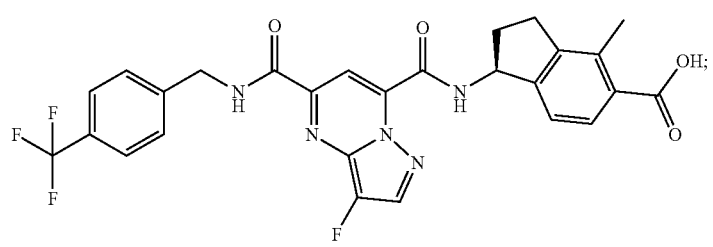
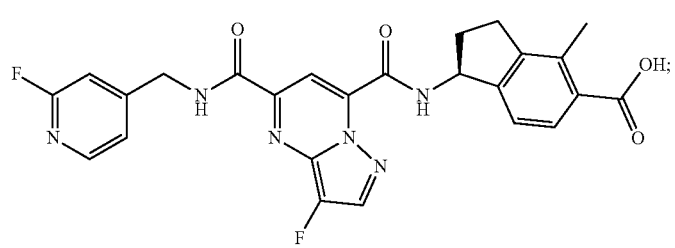

-continued
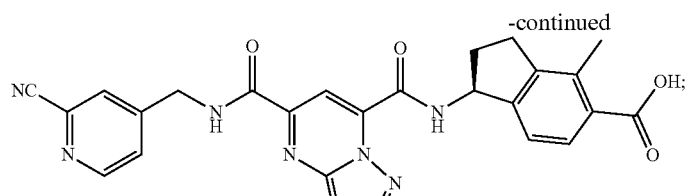
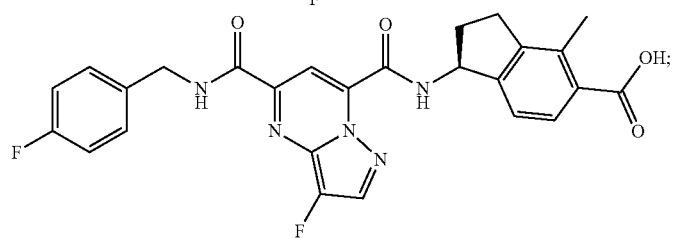
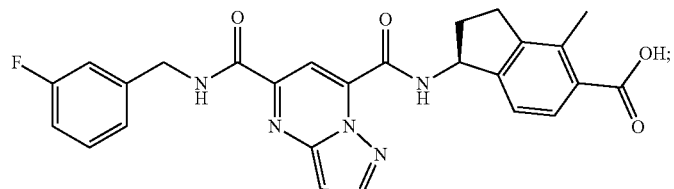
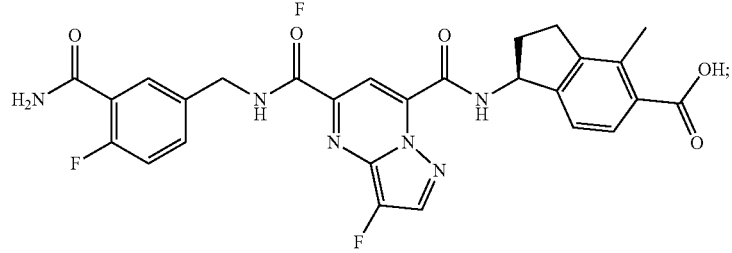
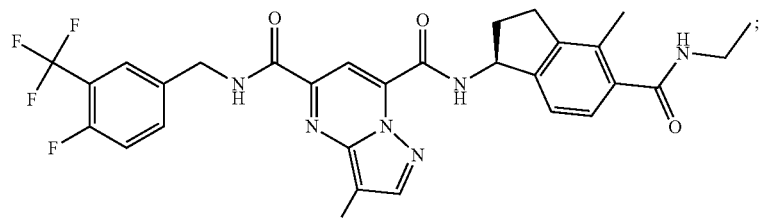
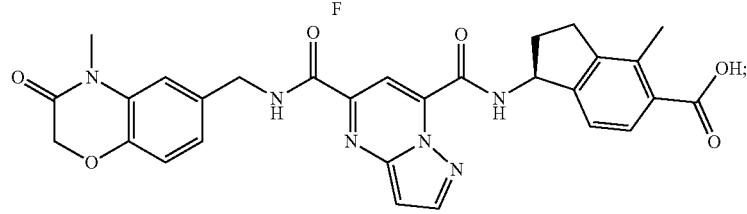
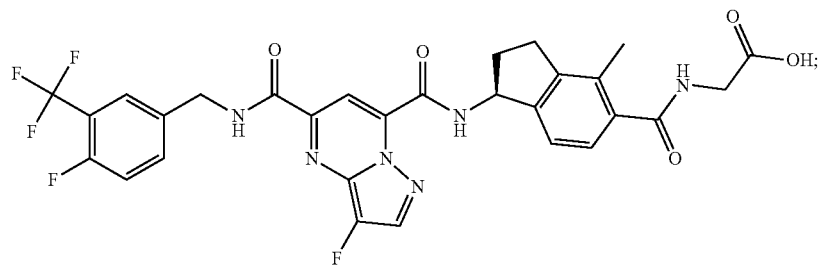

-continued
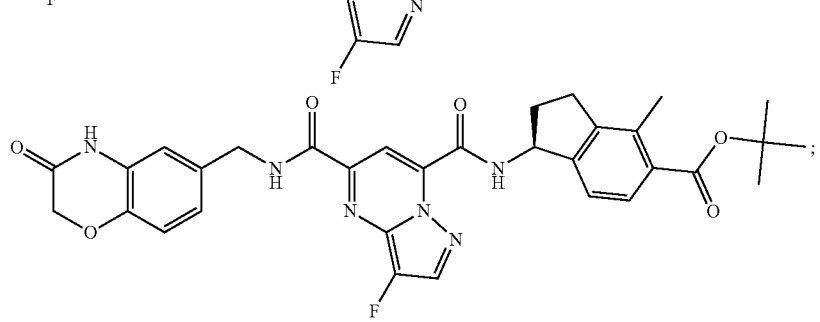
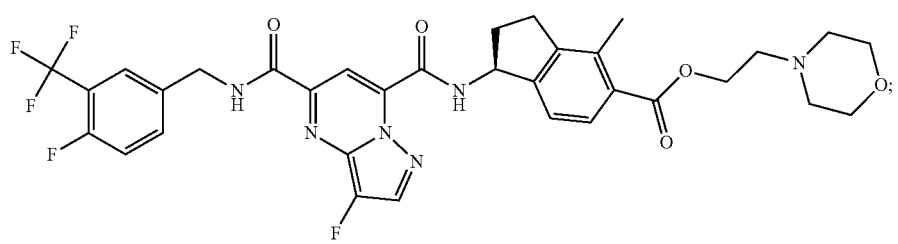
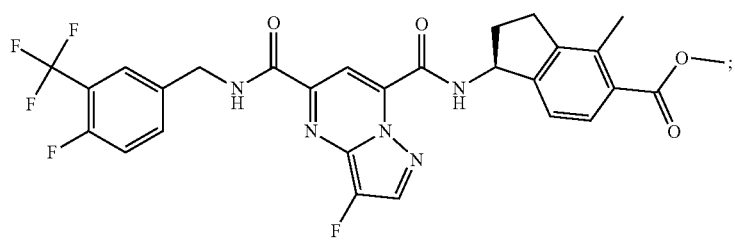
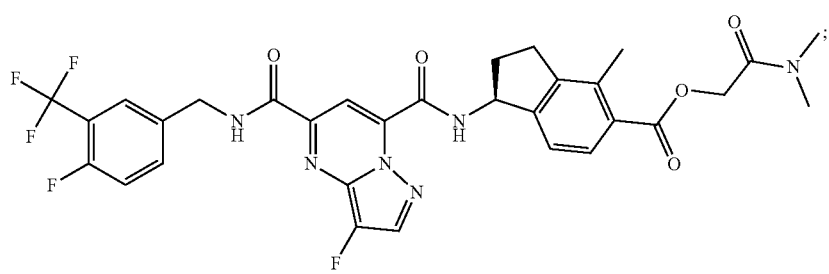
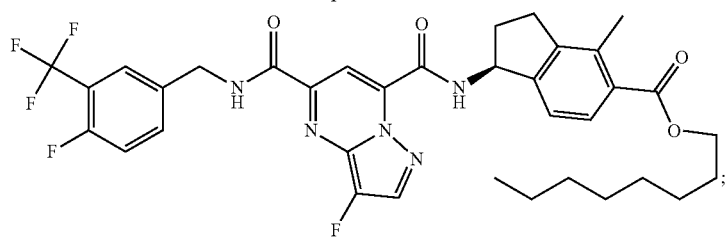
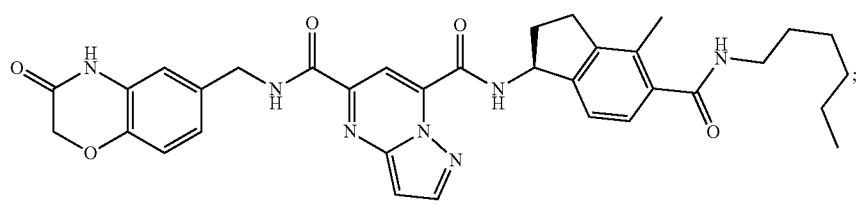

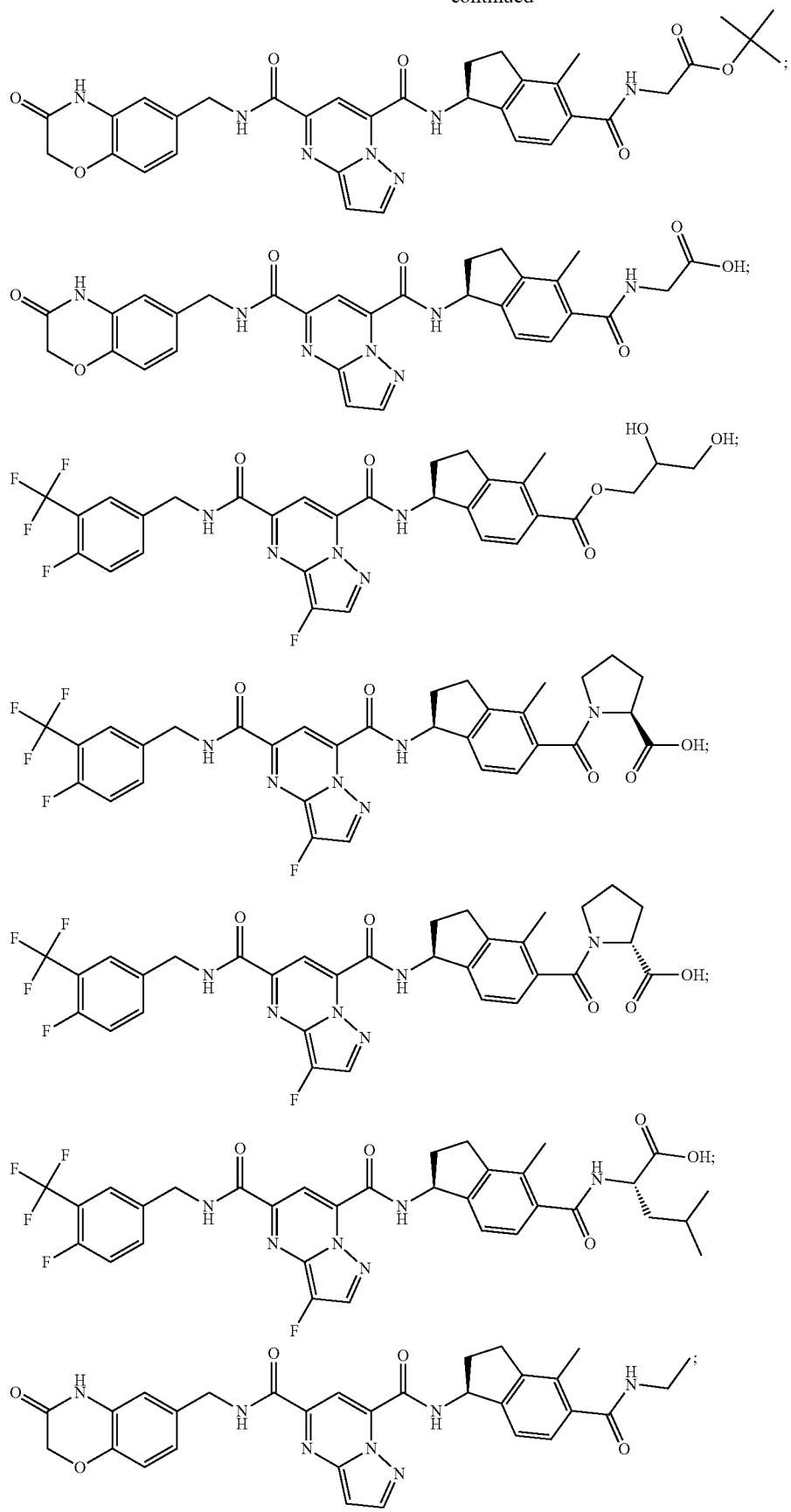

-continued
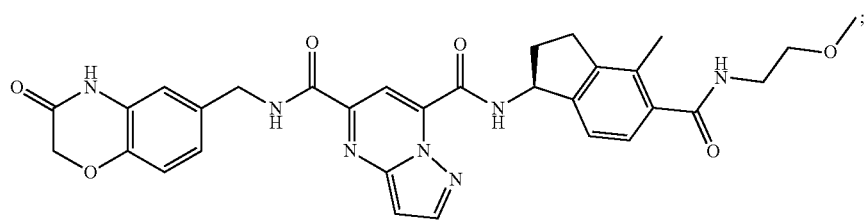
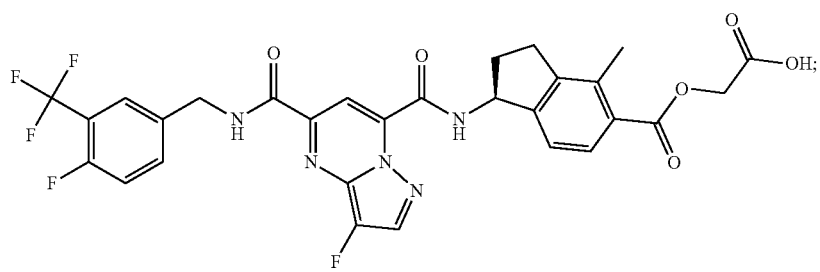
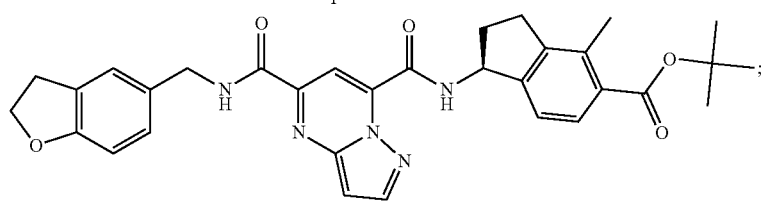
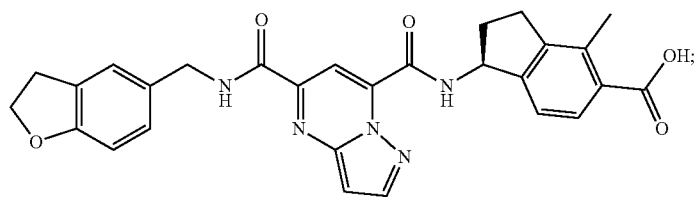
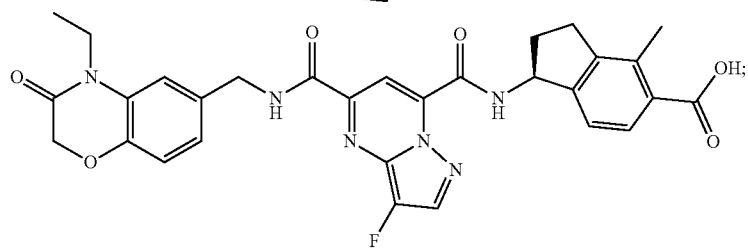
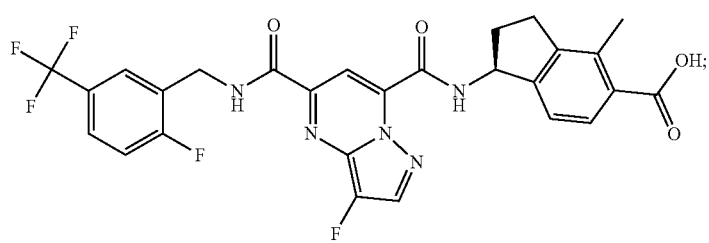
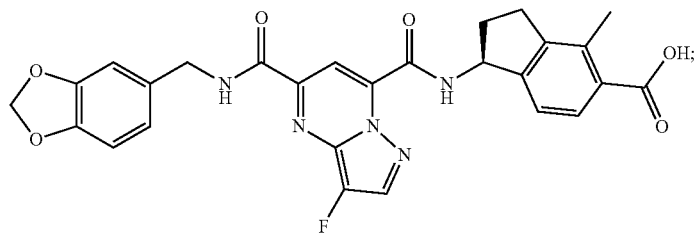

-continued
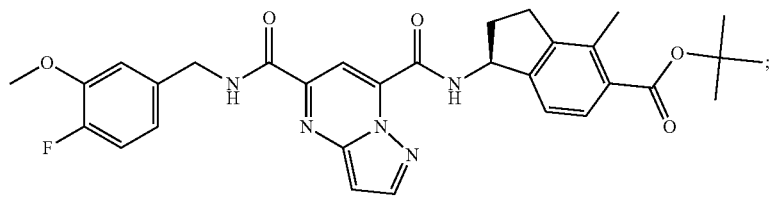
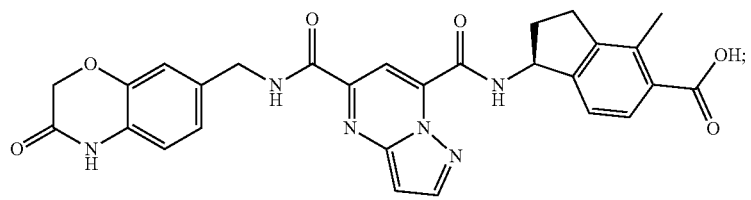
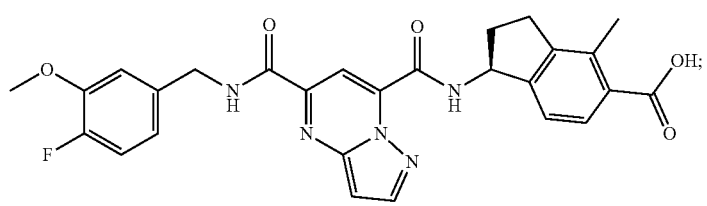
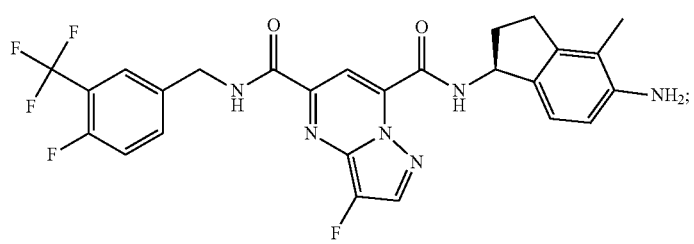
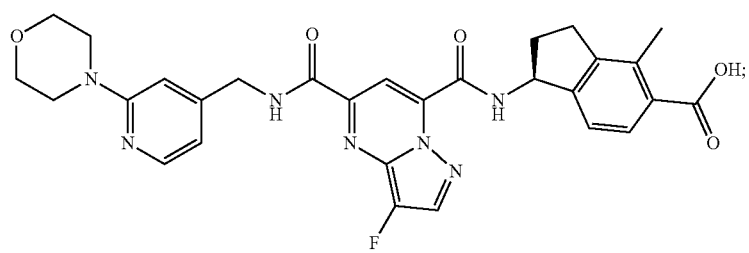
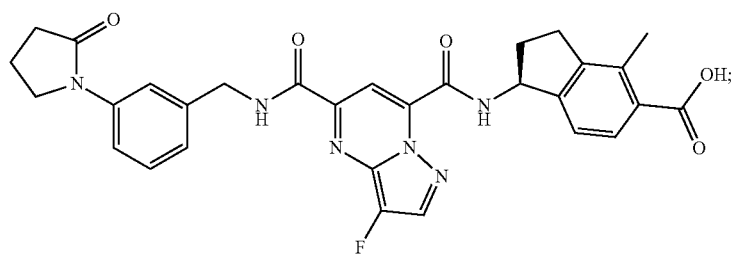
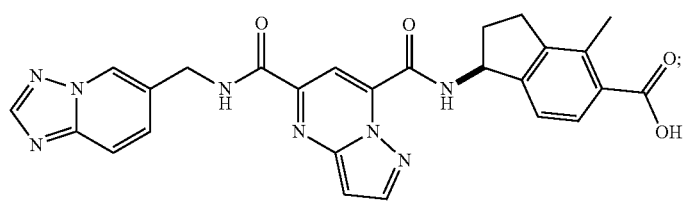

-continued
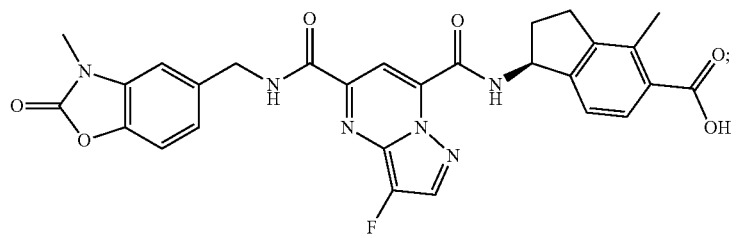
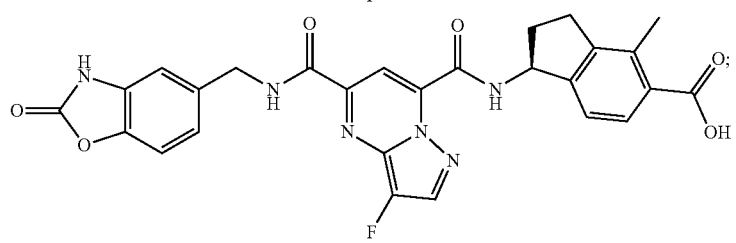
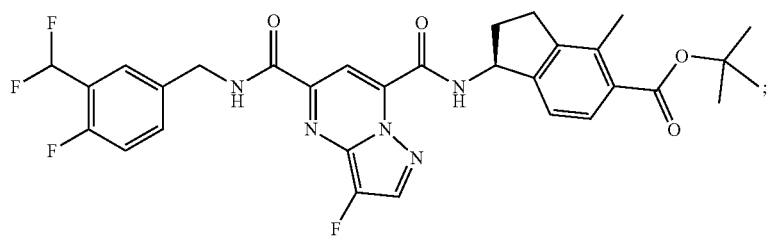
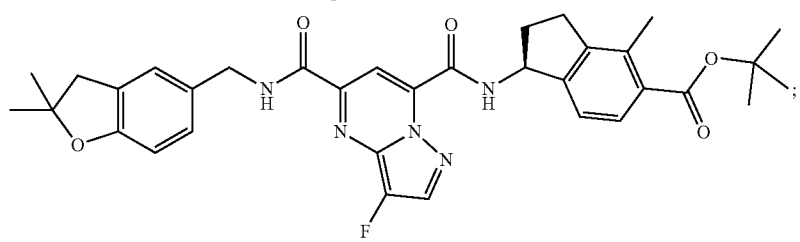
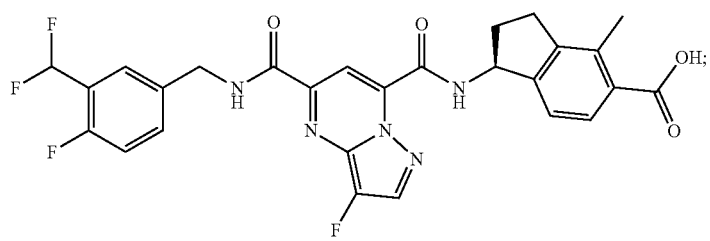
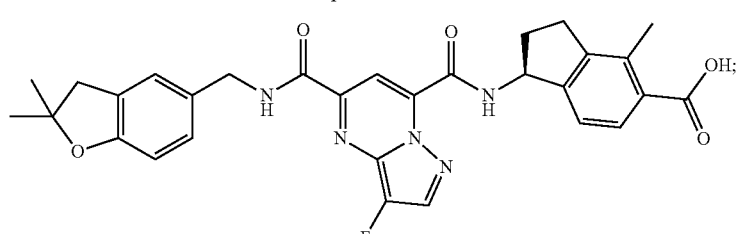
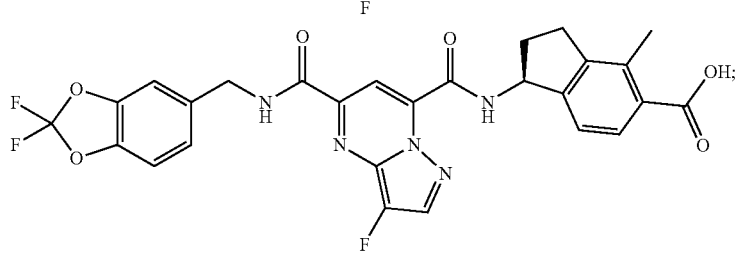

-continued
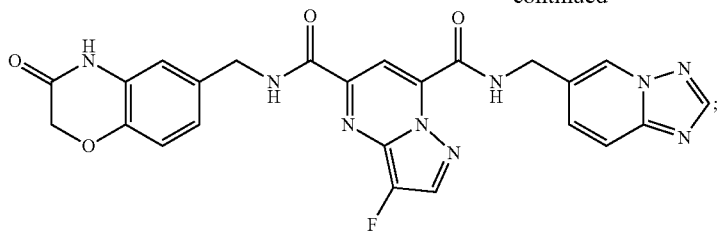
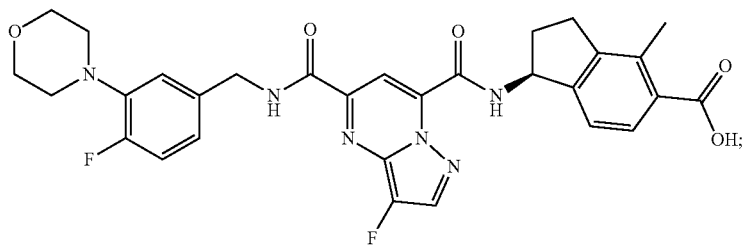
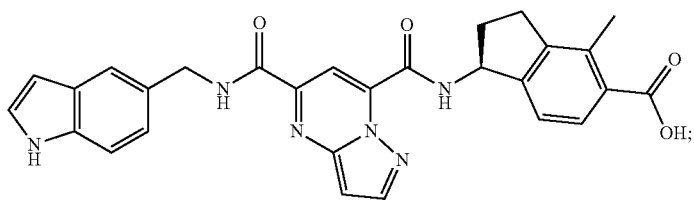
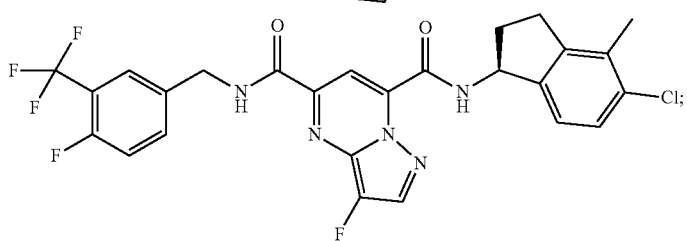
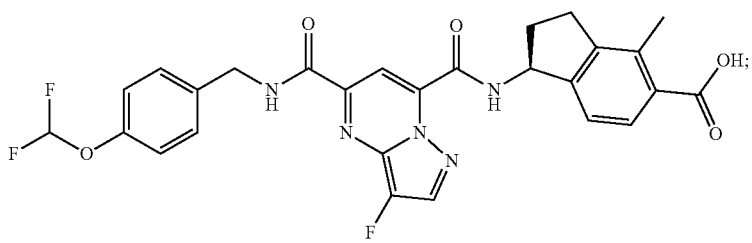
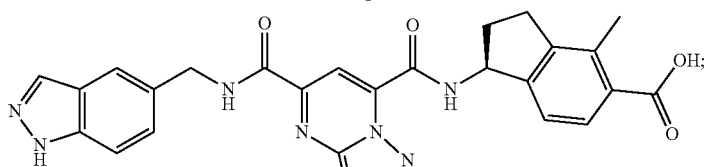
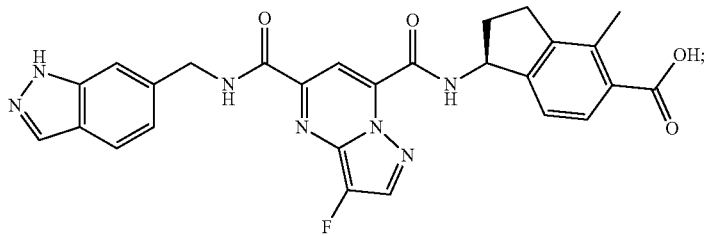

-continued
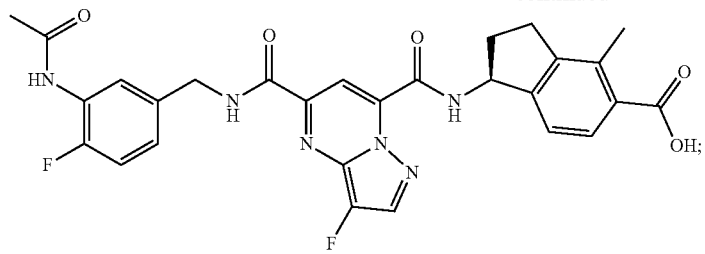
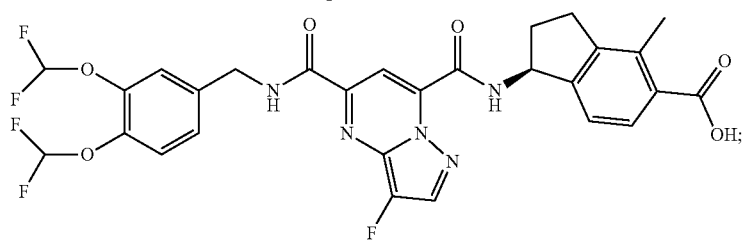
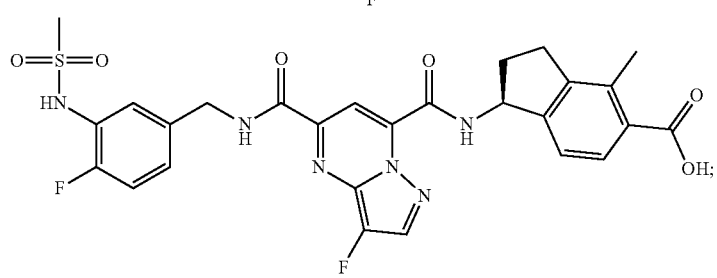
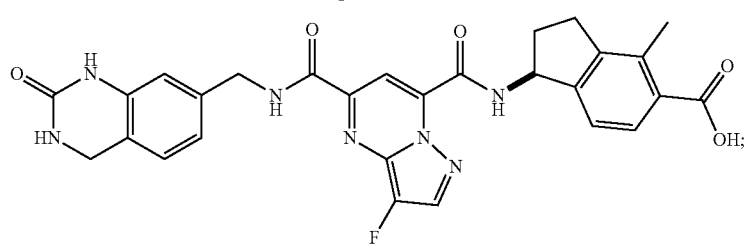
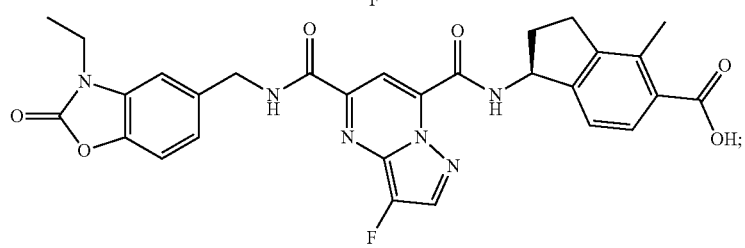
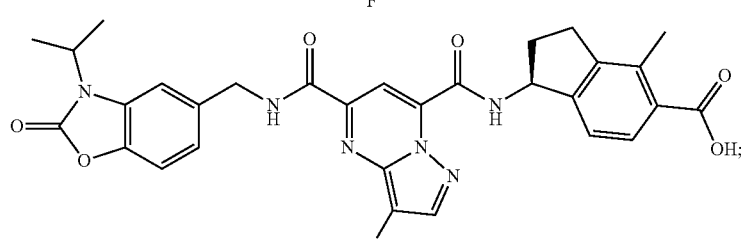
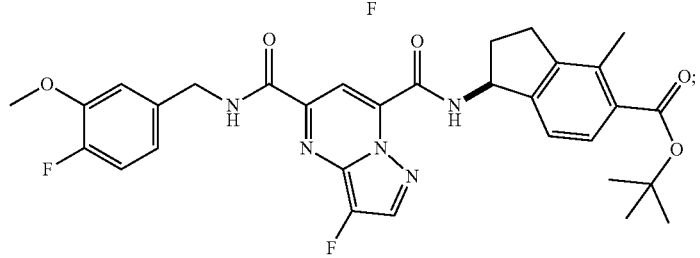

-continued
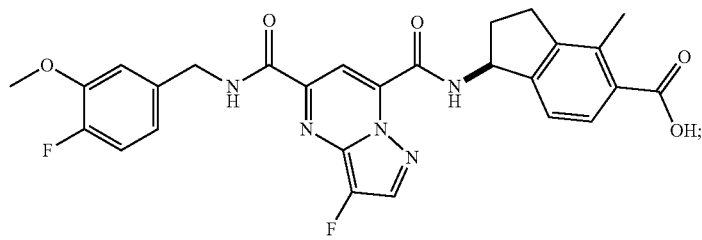
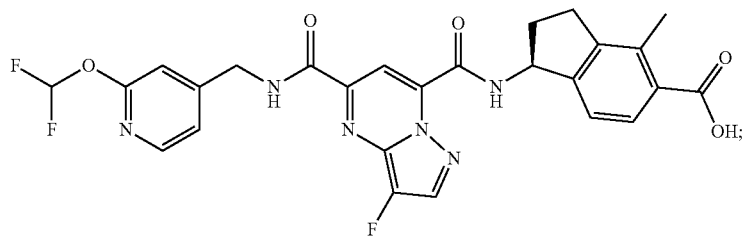
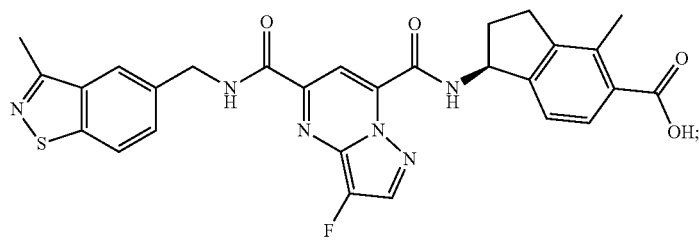
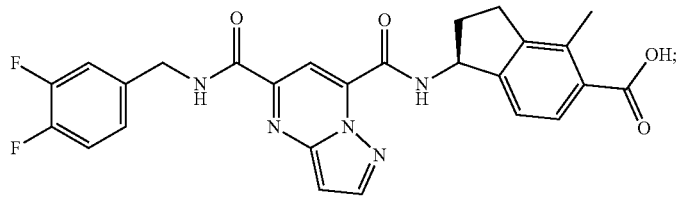
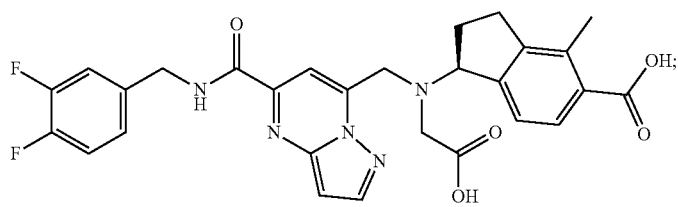
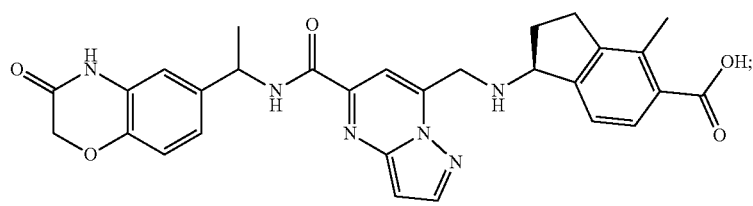
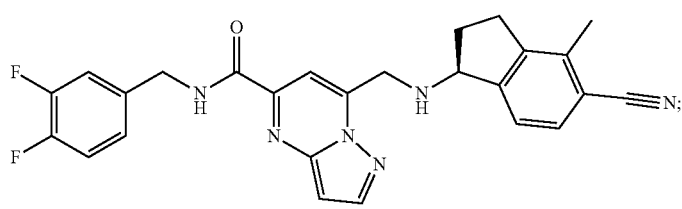

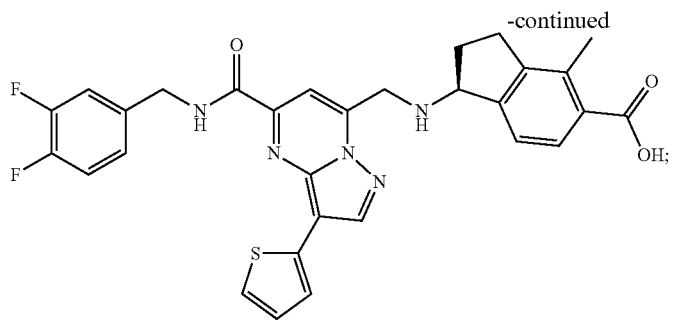
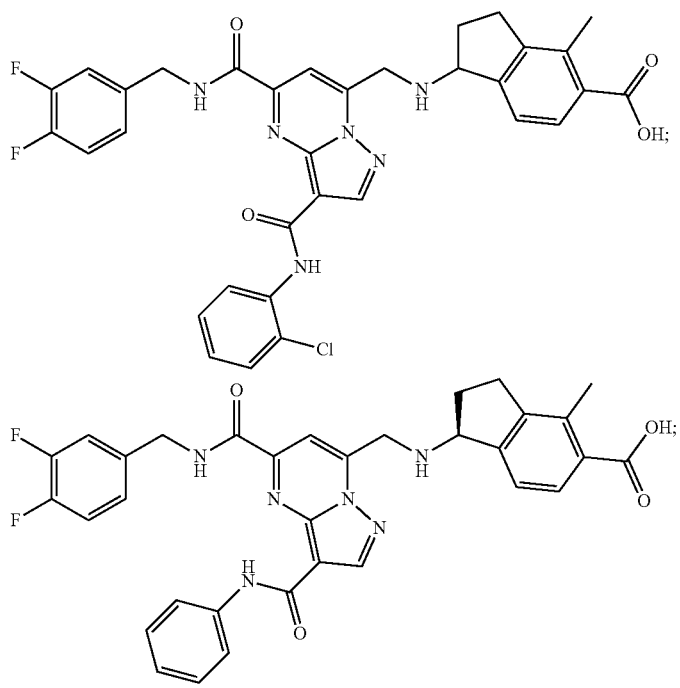
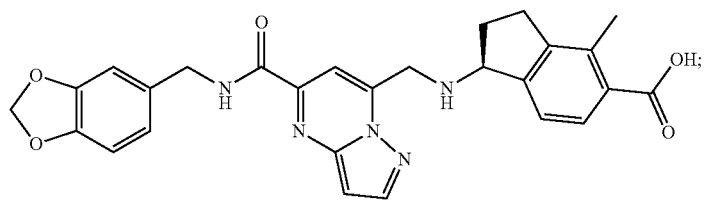
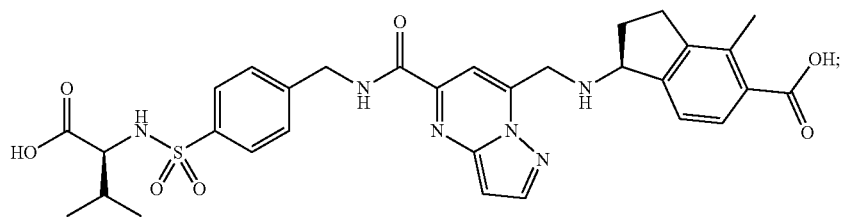
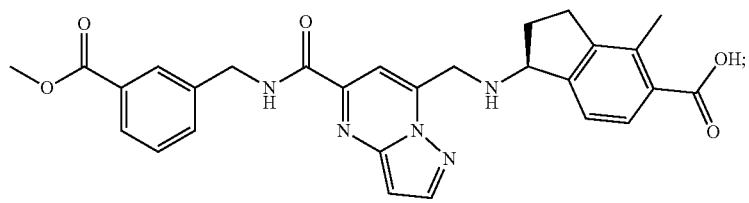

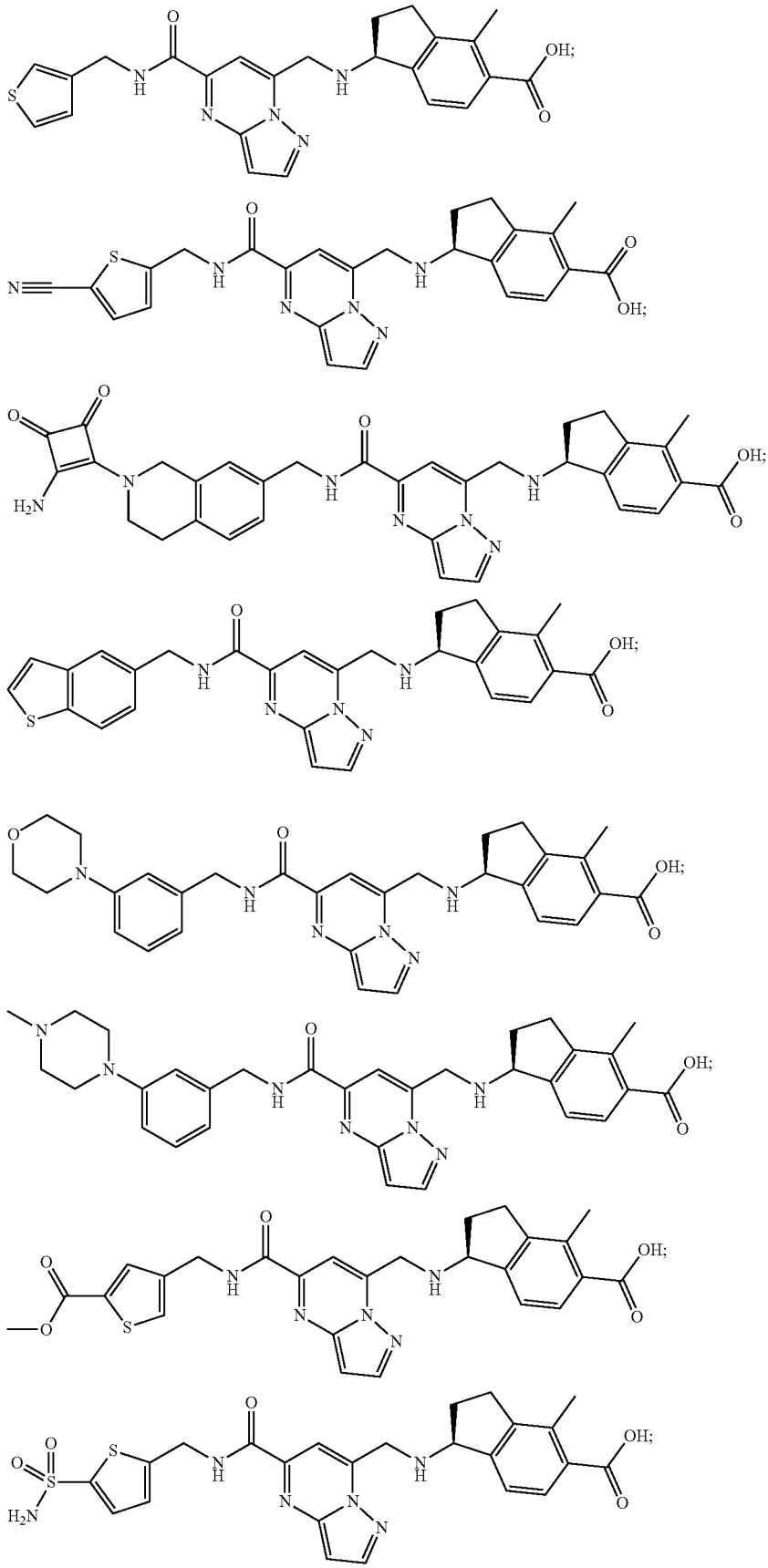

-continued
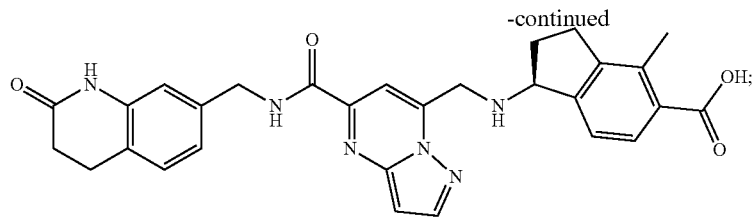
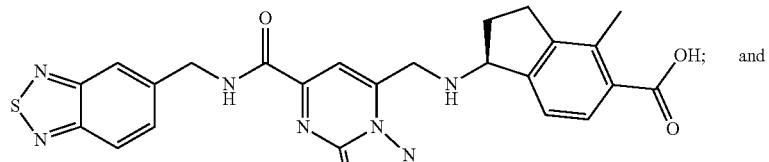
and
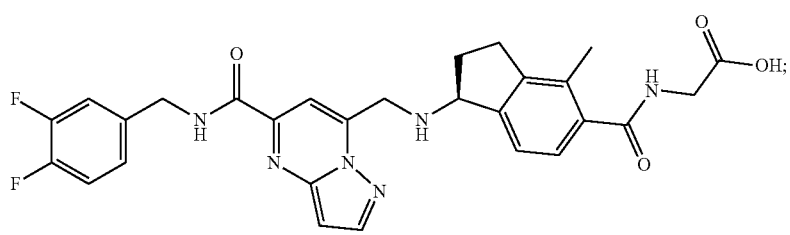
or a pharmaceutically acceptable salt thereof.
In a further embodiment, the present invention provides a compound selected from:
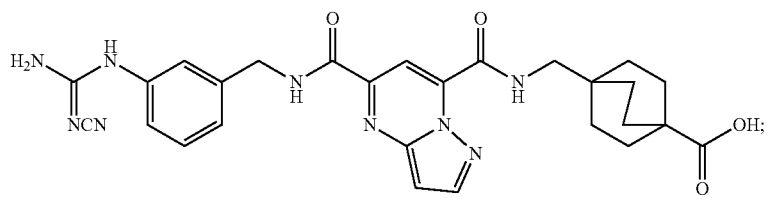
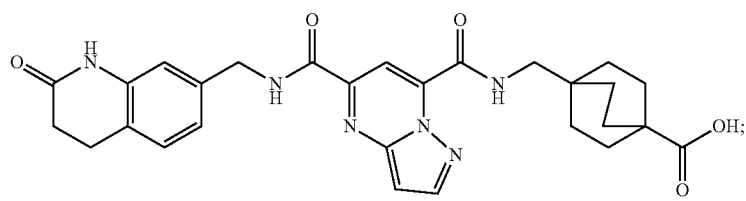
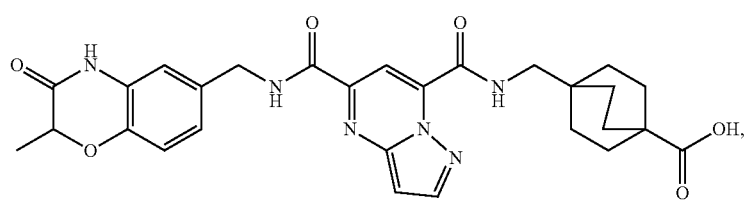
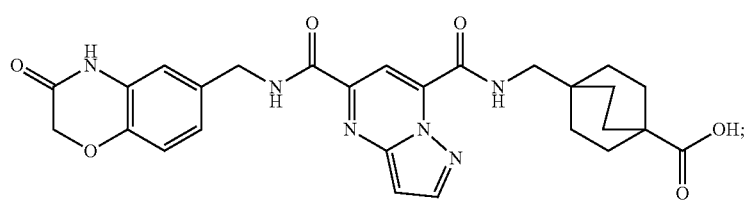

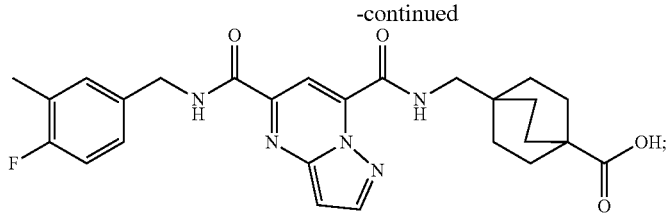
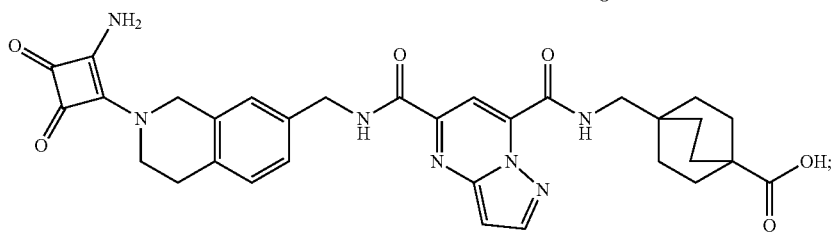
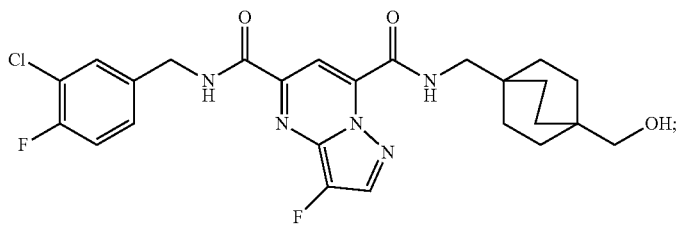
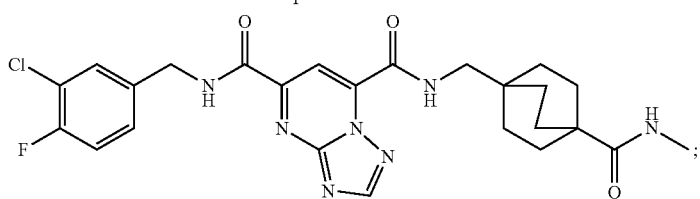
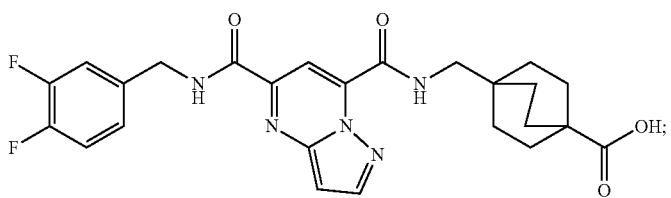
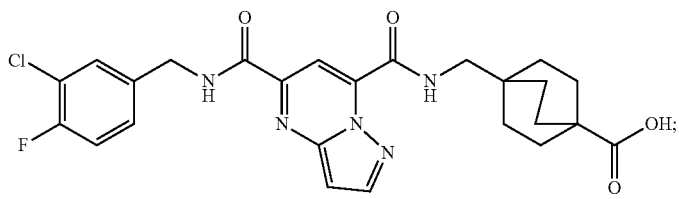
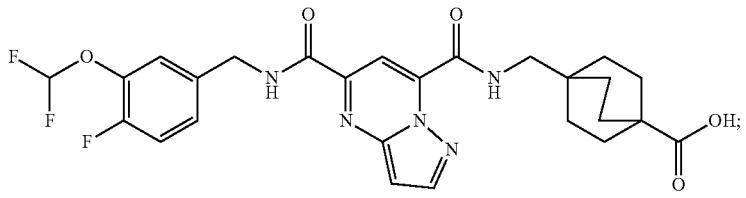
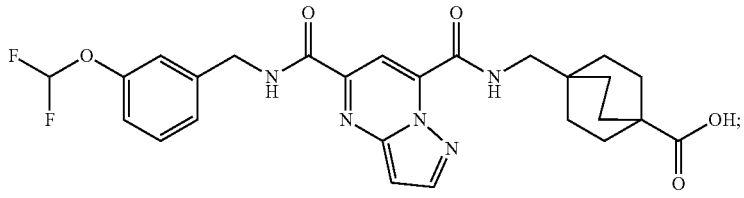

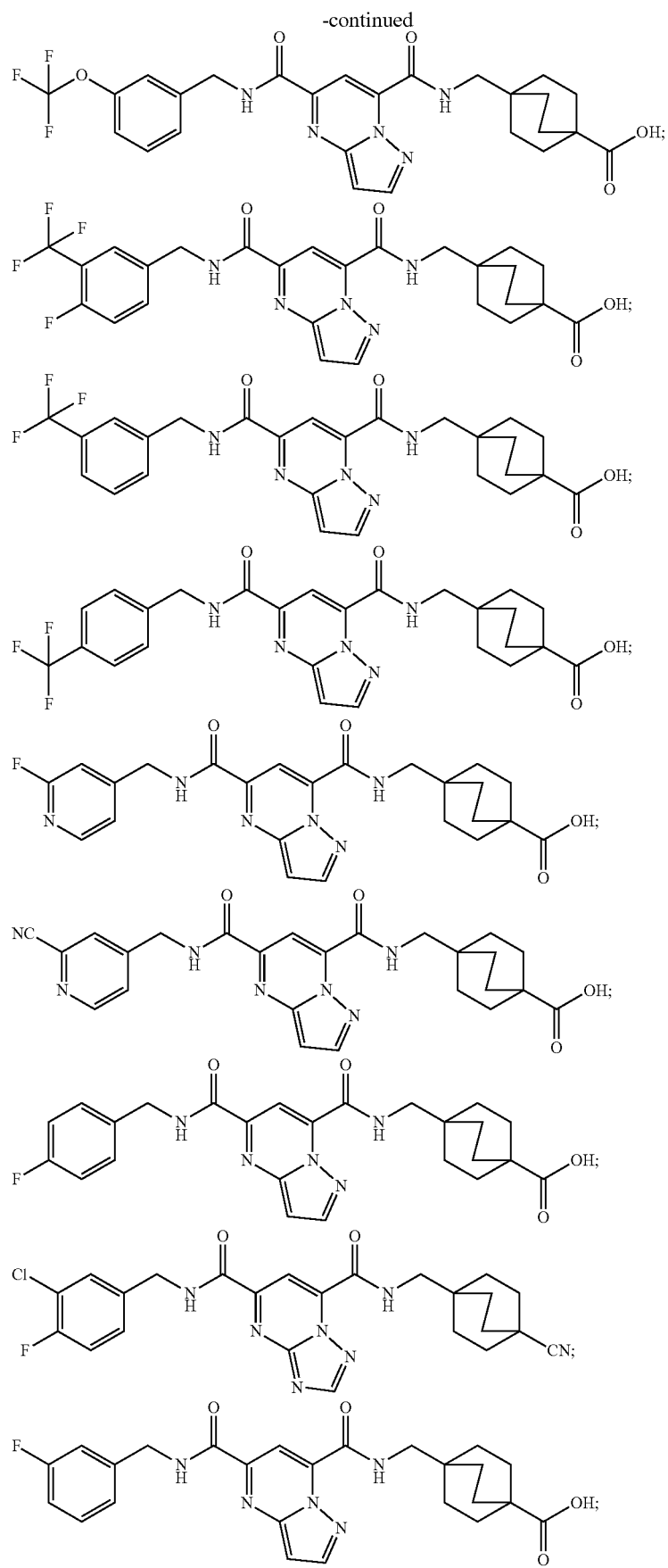

-continued
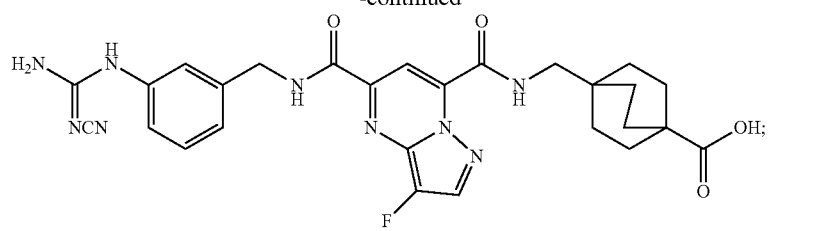
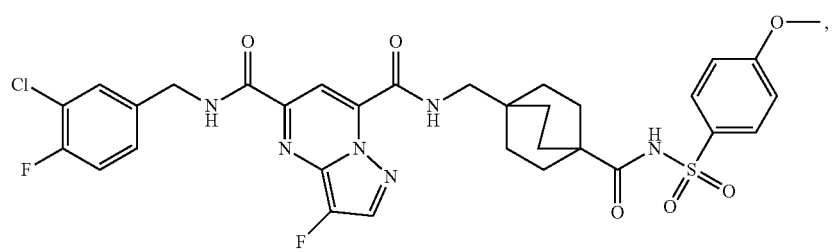
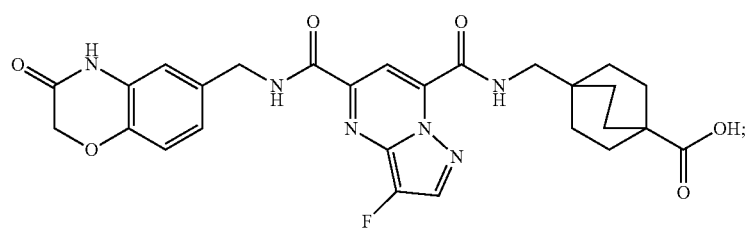
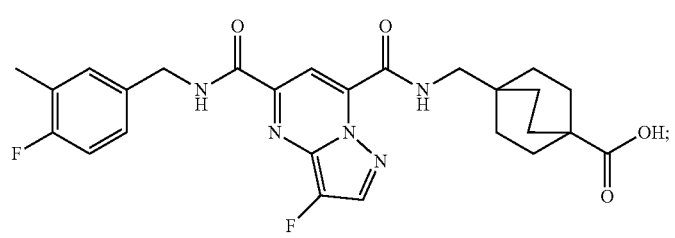
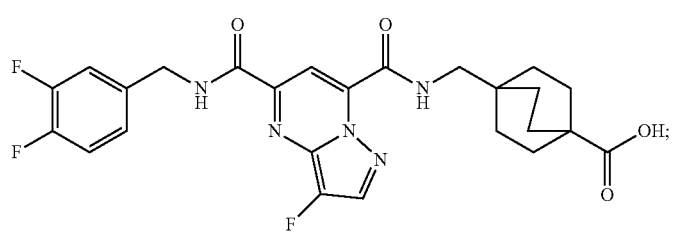
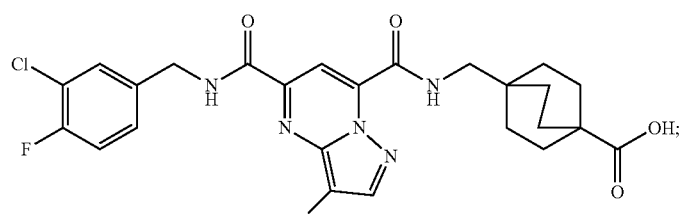
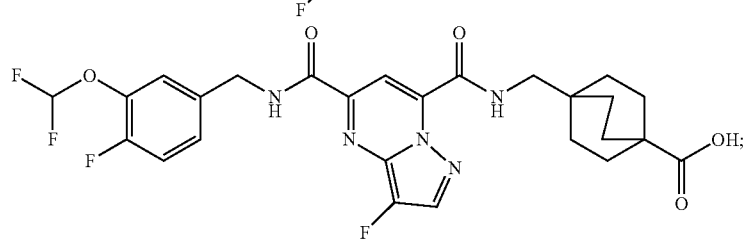

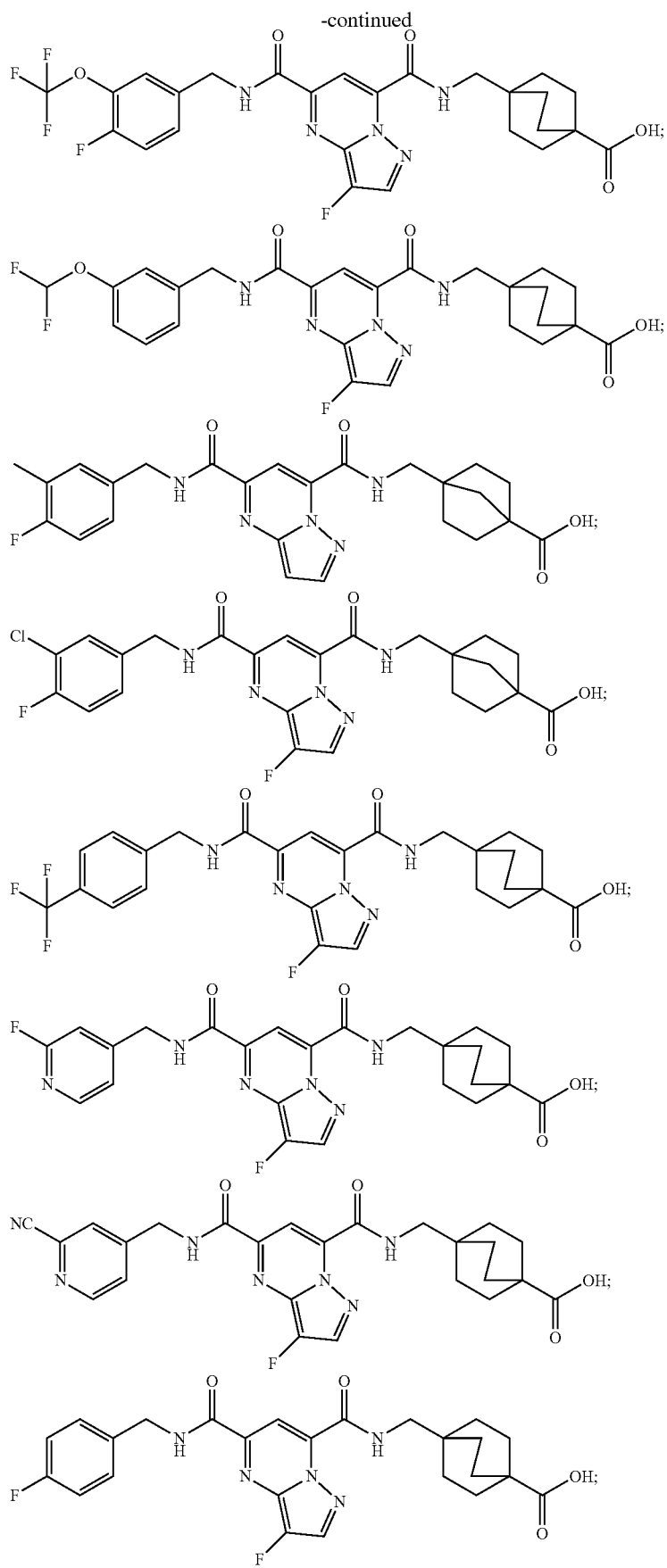

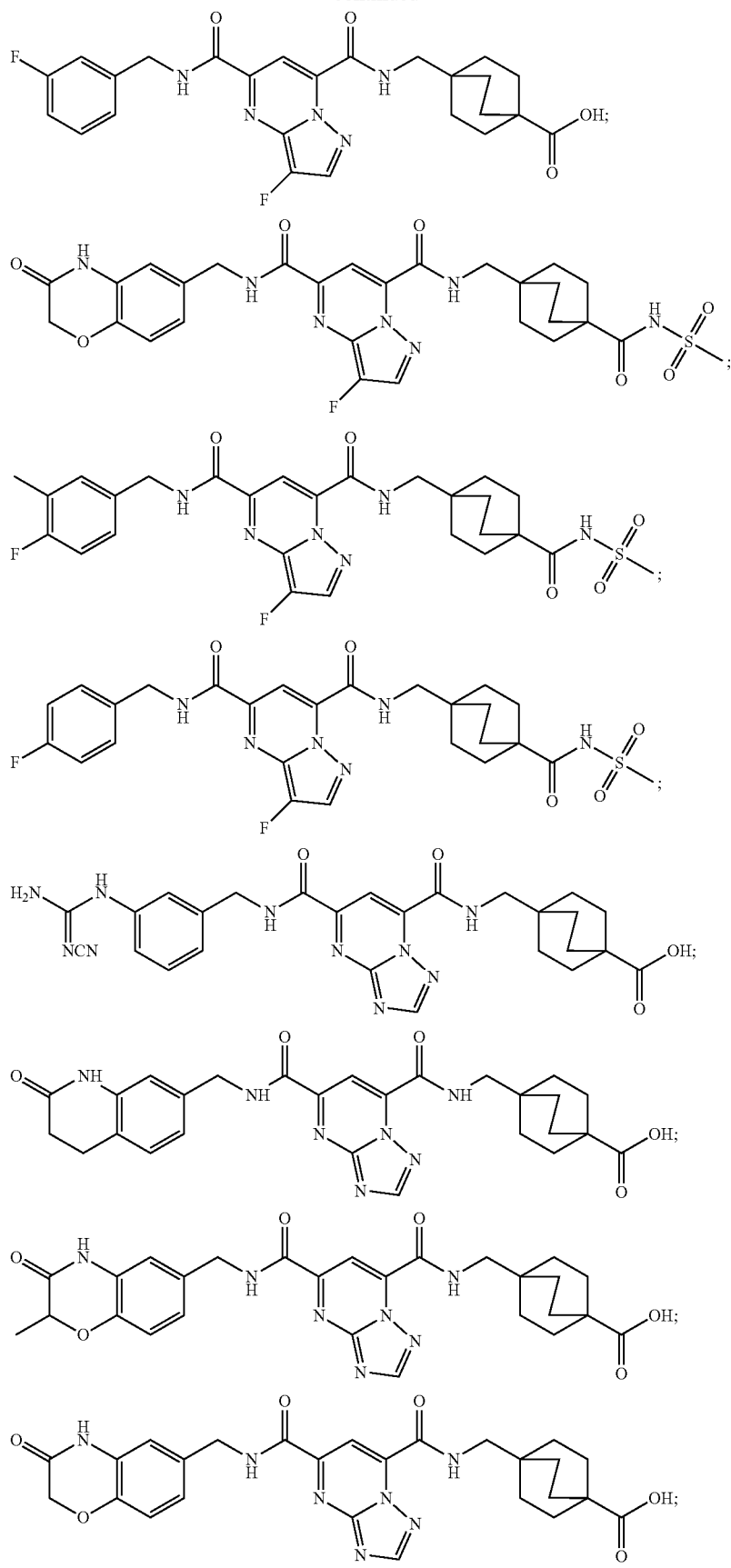

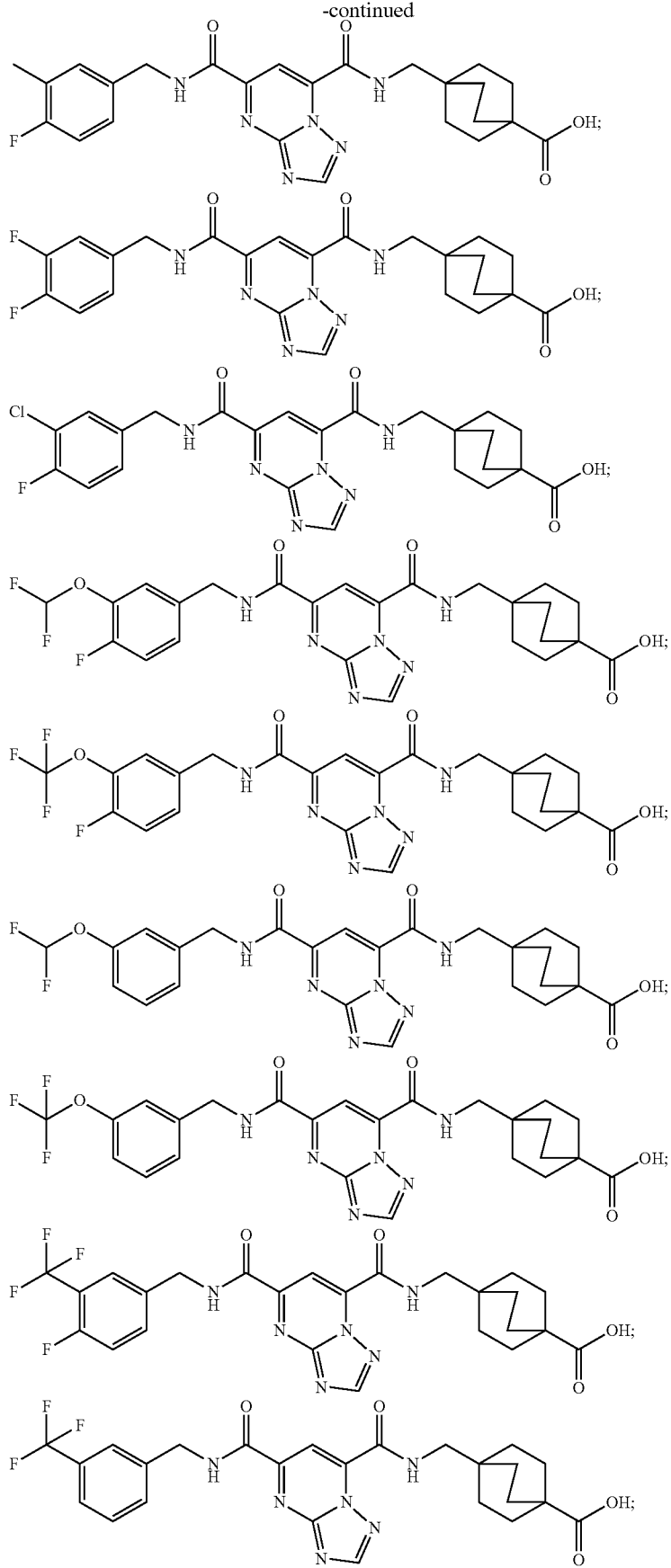

-continued
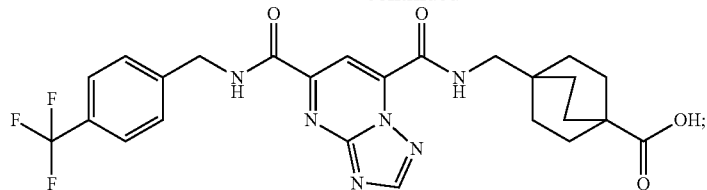
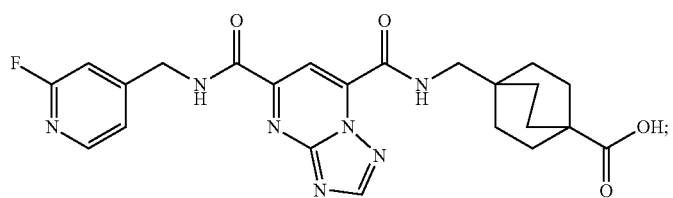
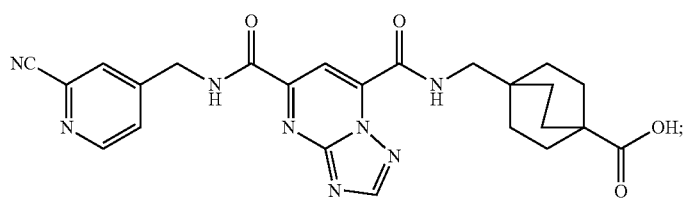
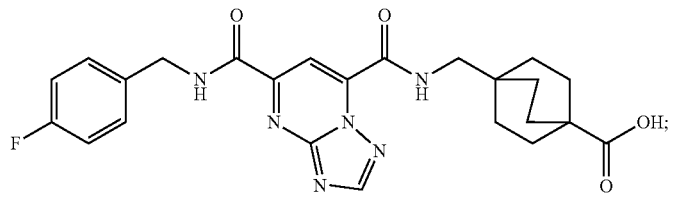
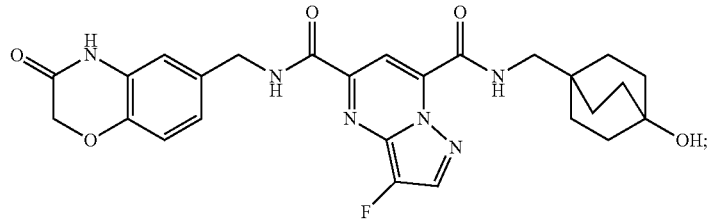
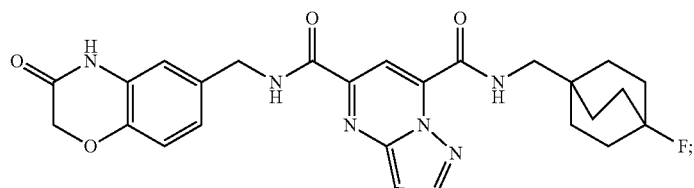
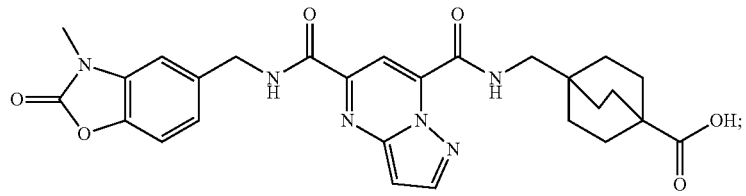

-continued
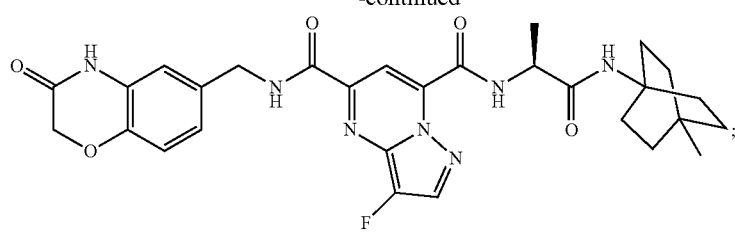
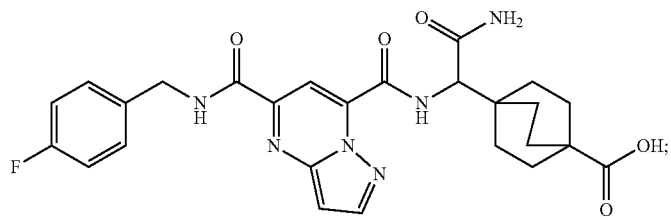
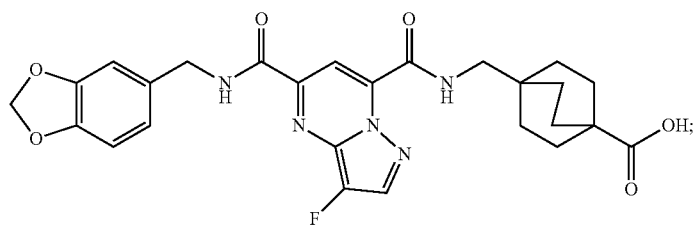
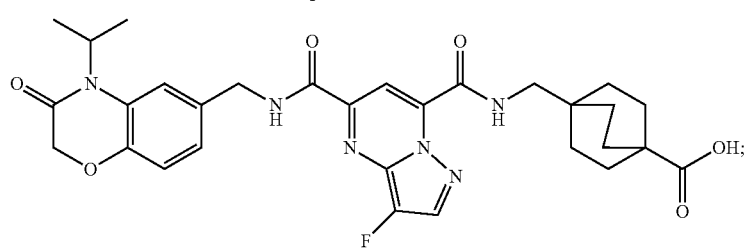
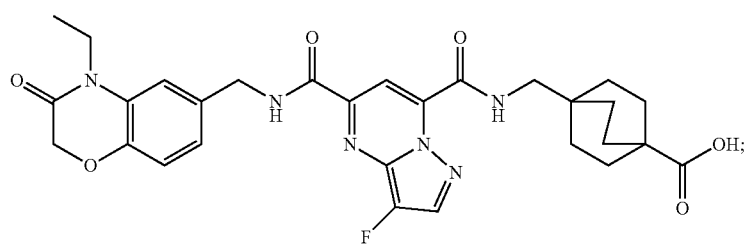
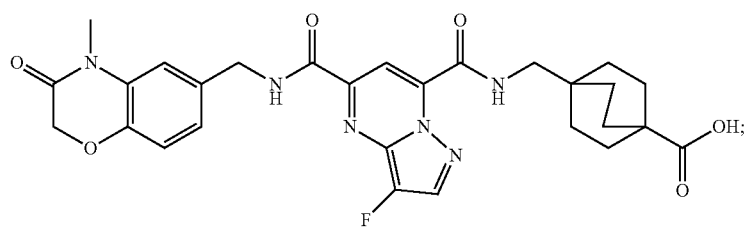
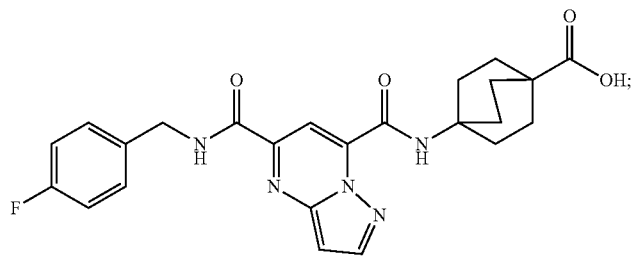

-continued
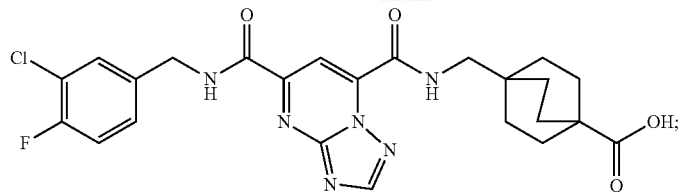
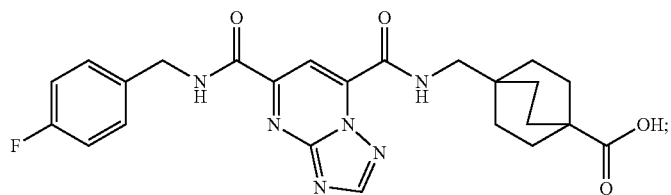
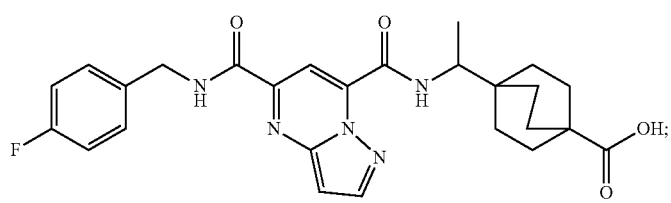
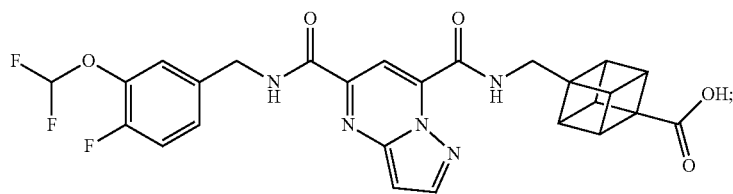
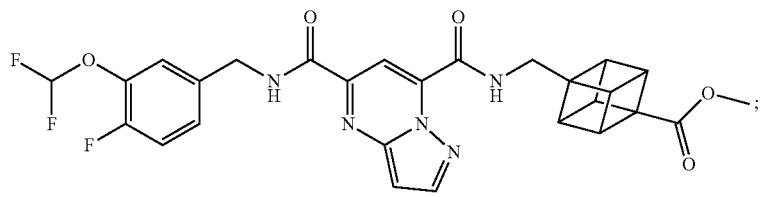
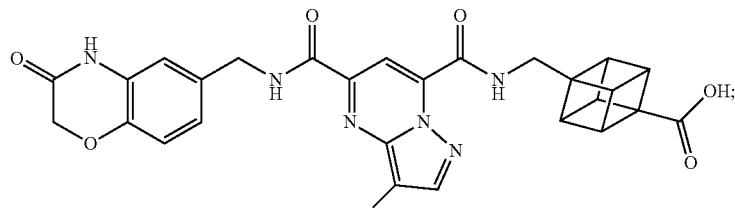
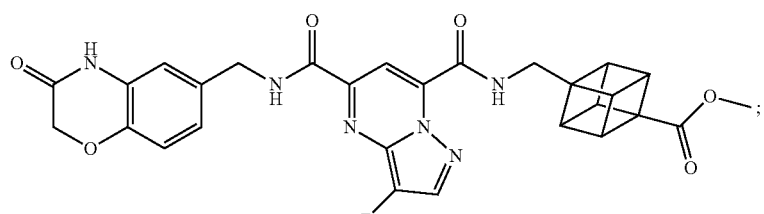
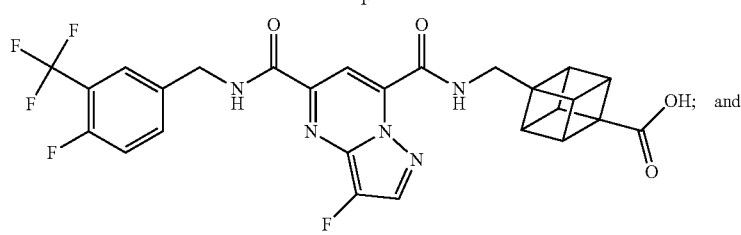

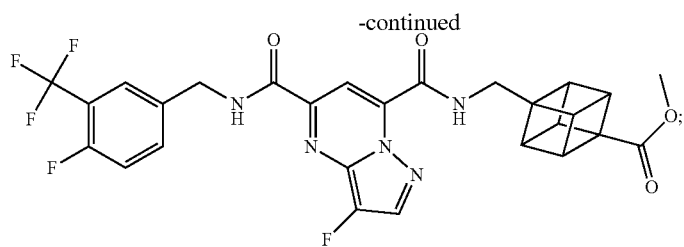
or a pharmaceutically acceptable salt thereof.
In yet a further embodiment, the present invention provides a compound selected from:
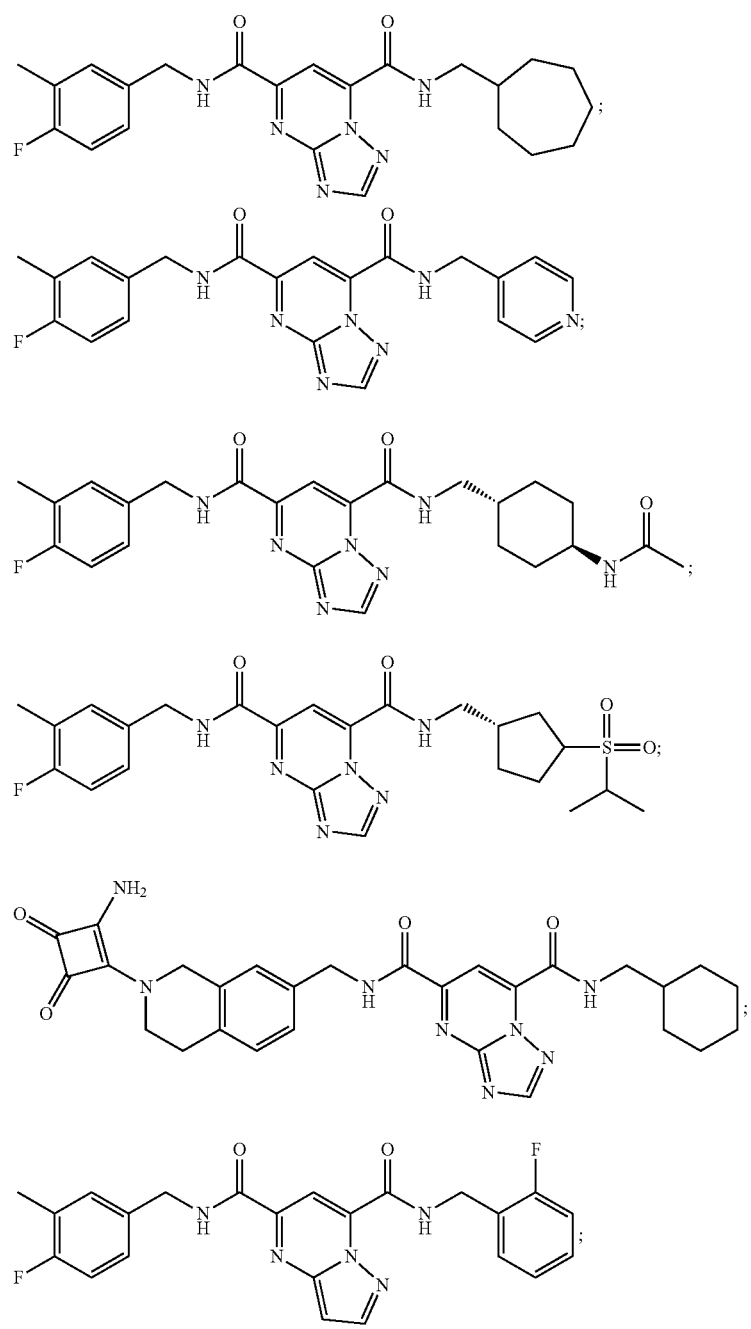

-continued
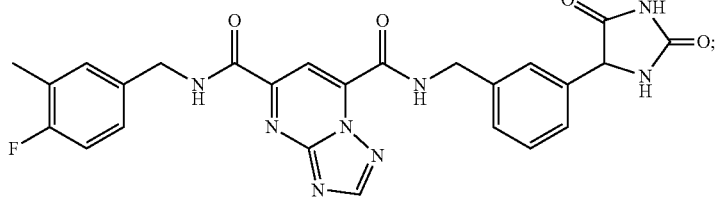
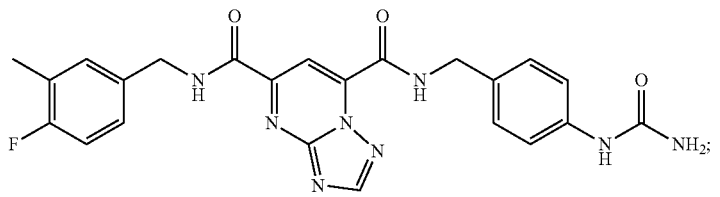
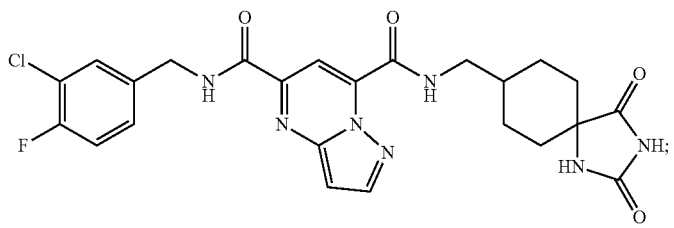
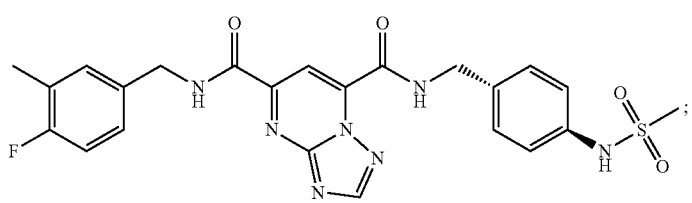
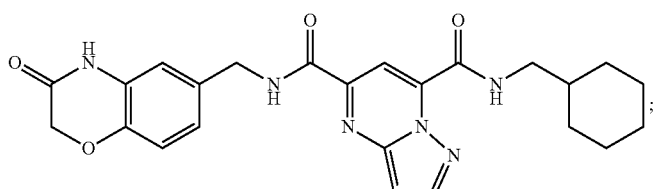
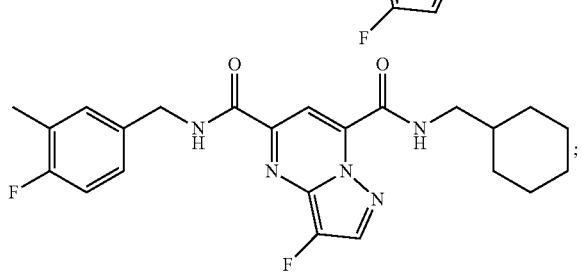
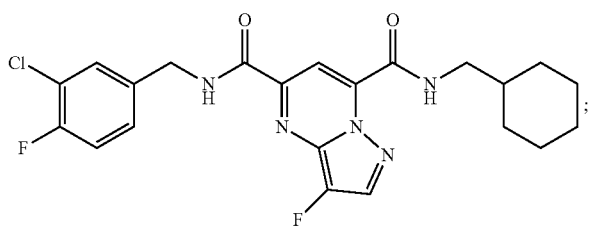
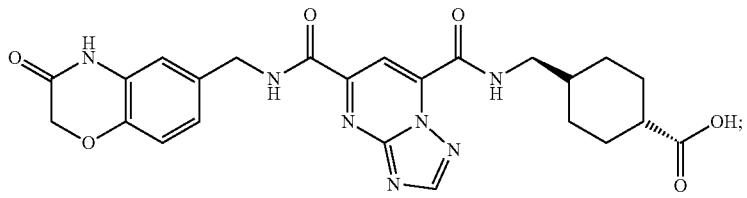

-continued
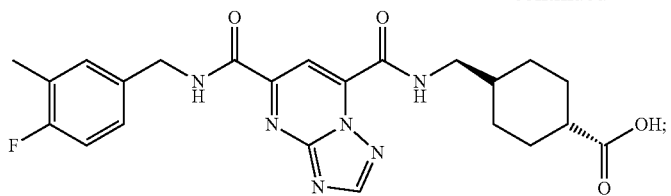
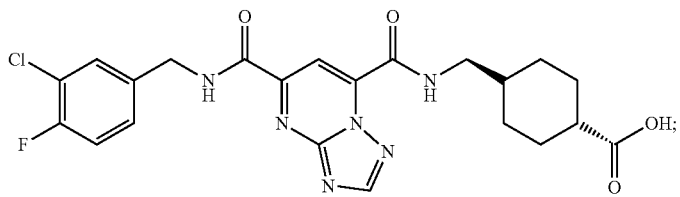
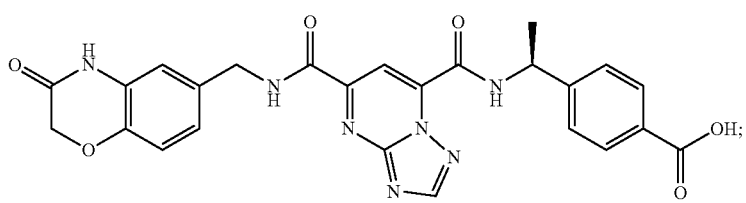
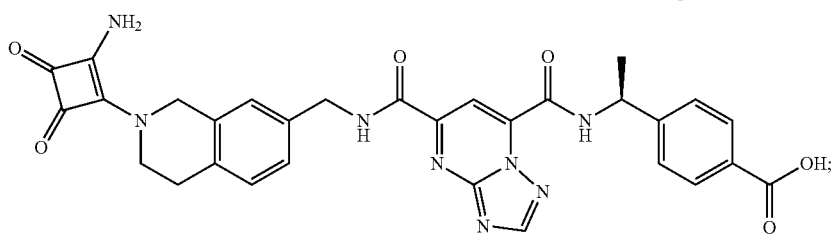
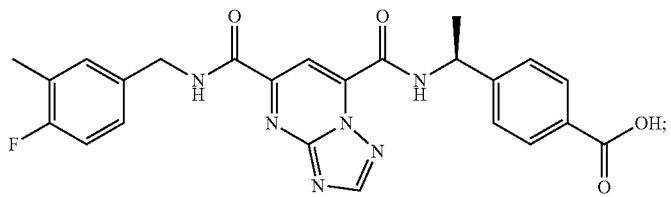
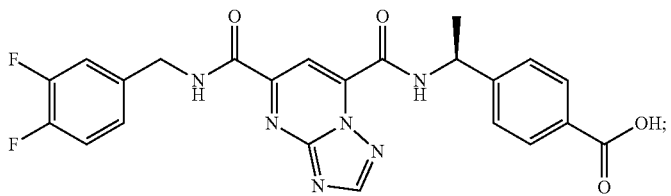
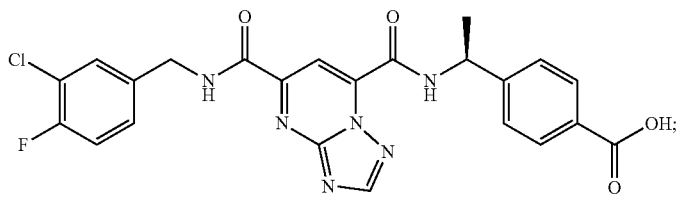
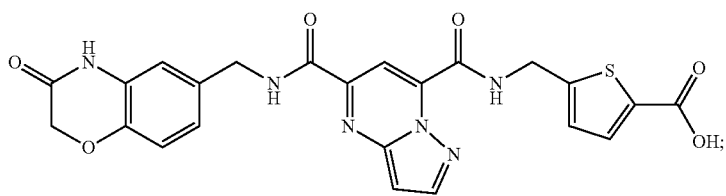

-continued
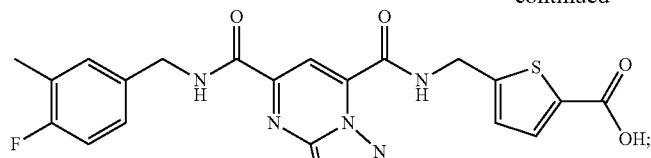
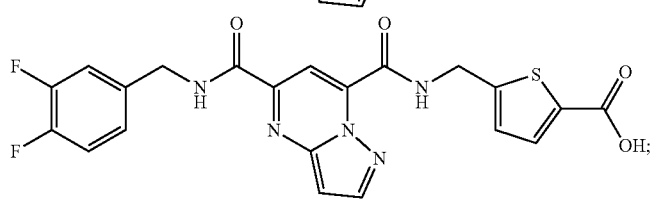
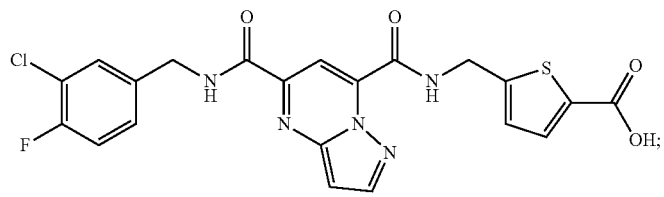
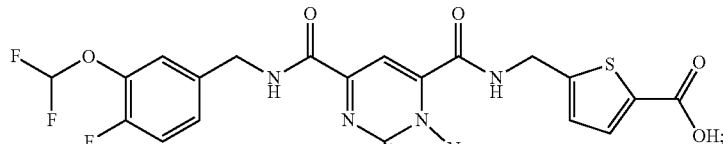
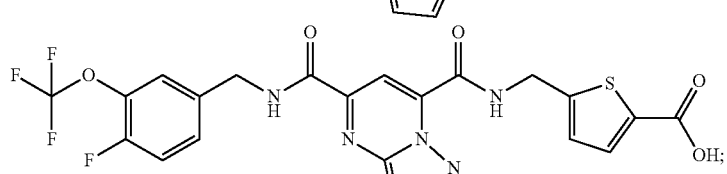
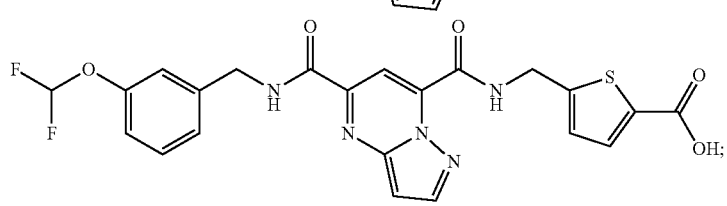
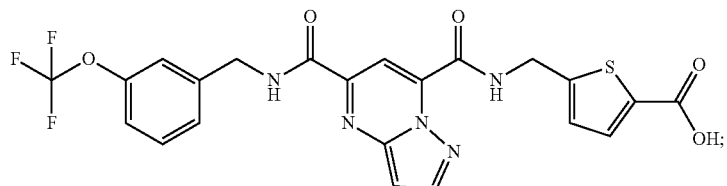
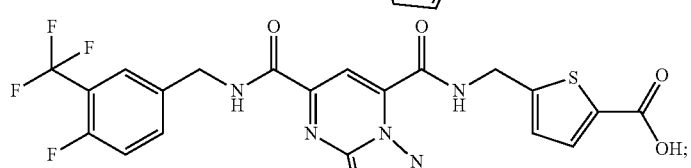
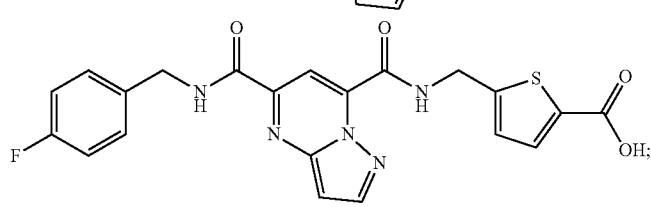

315
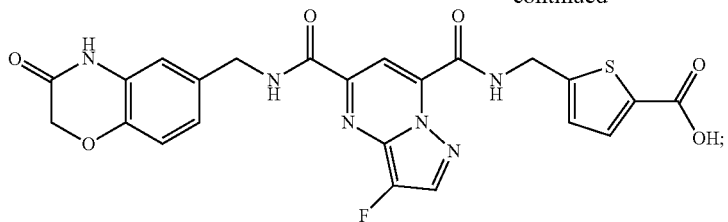
-continued
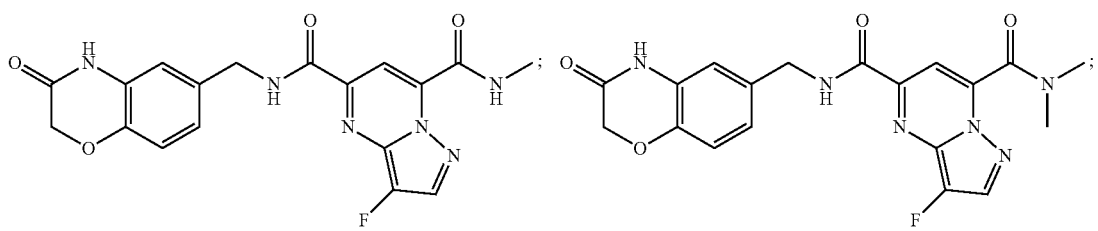
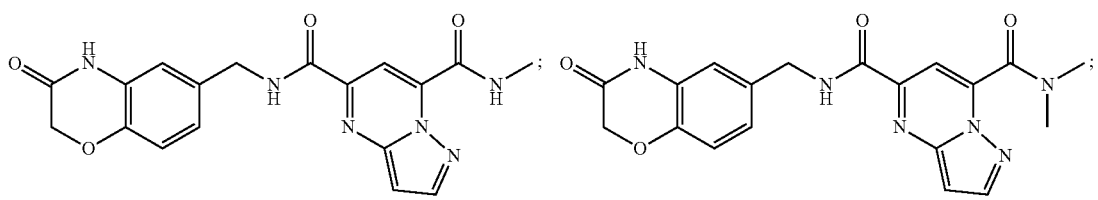
316
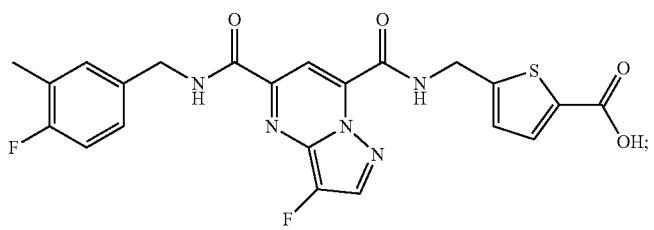
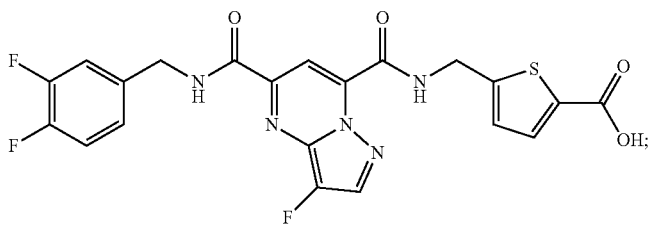
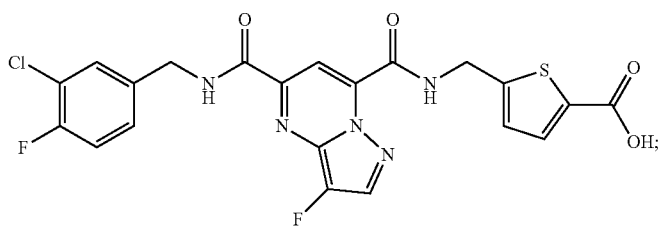
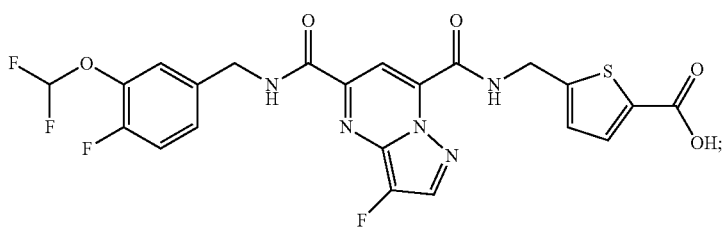

-continued
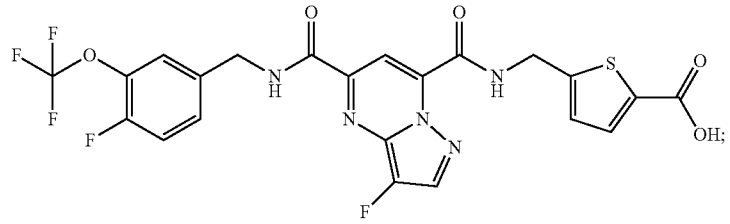
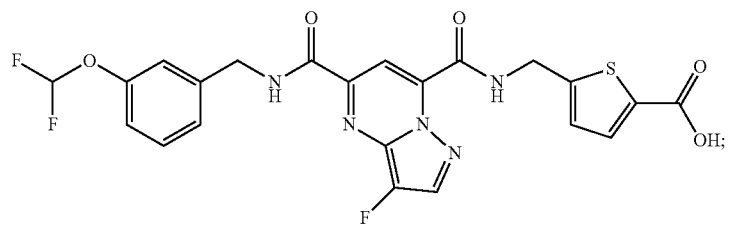
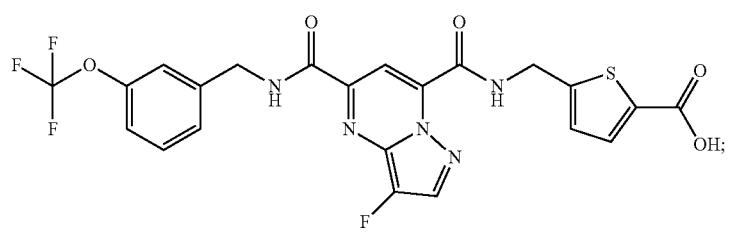
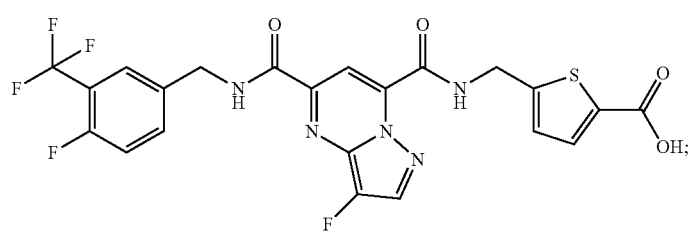
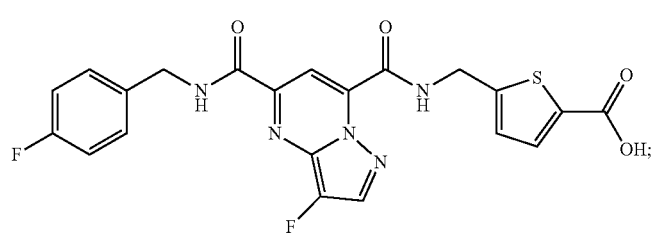
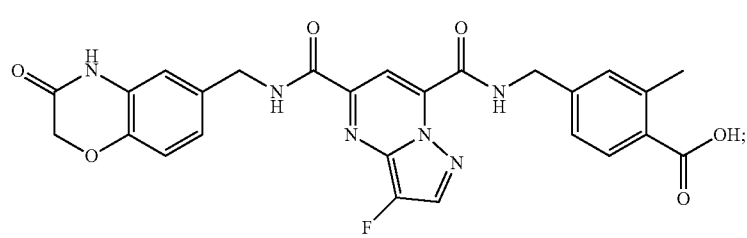
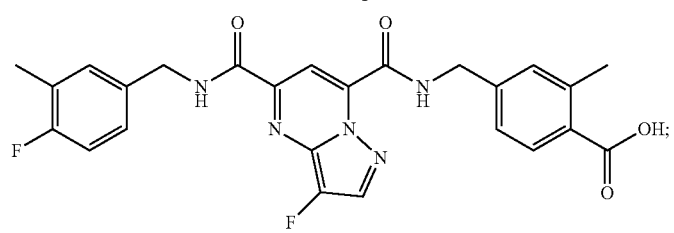

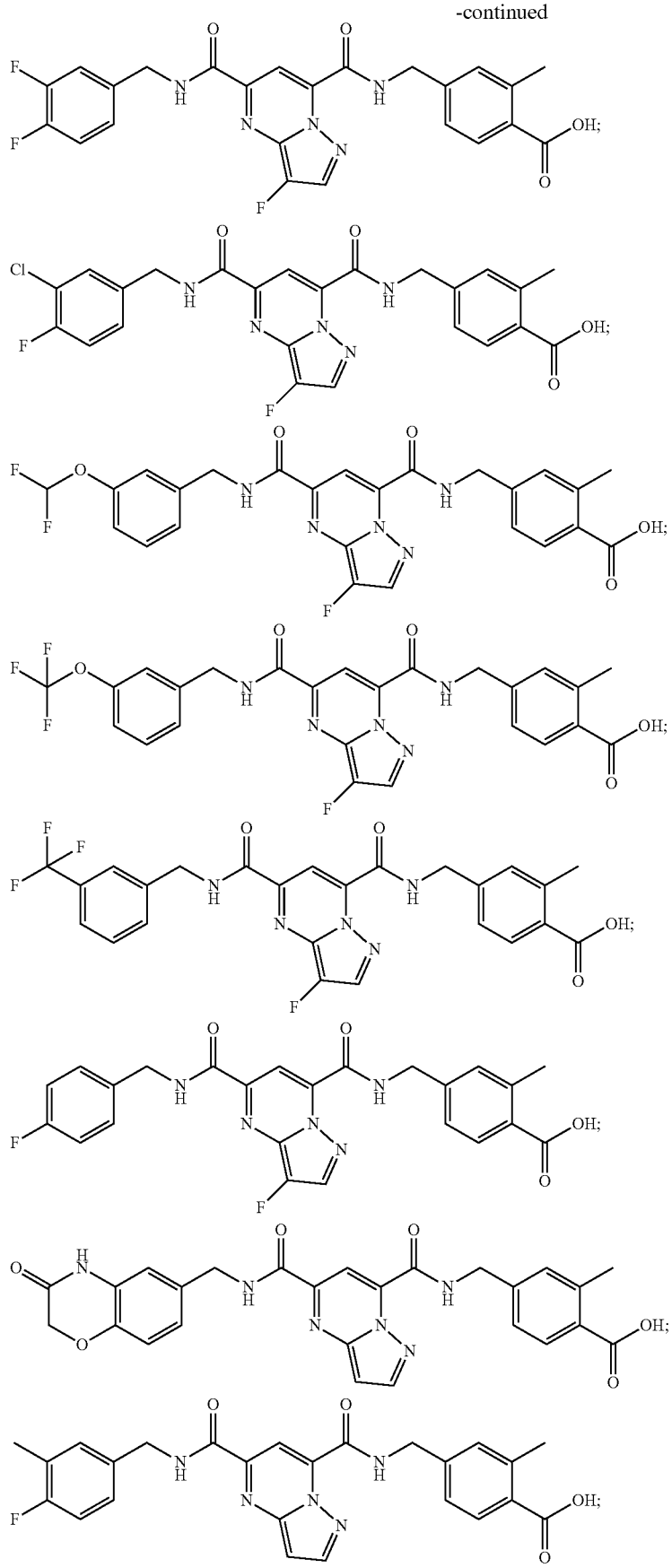

-continued
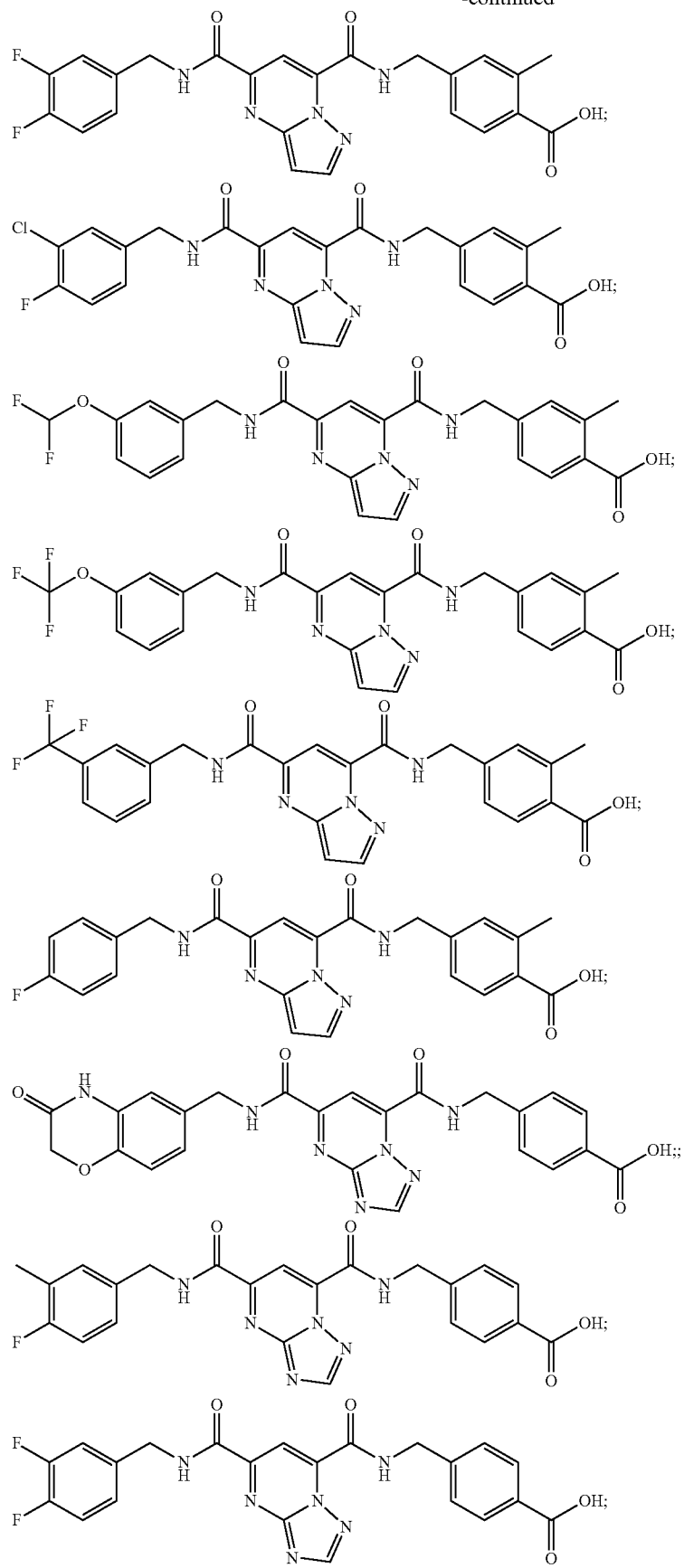

-continued
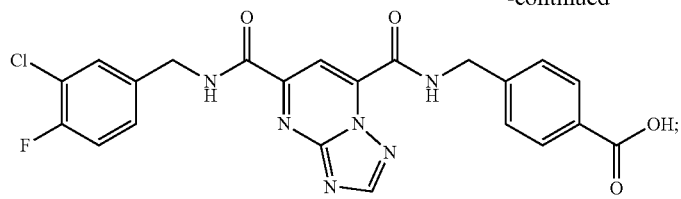
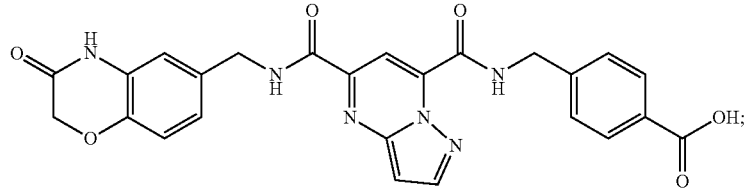
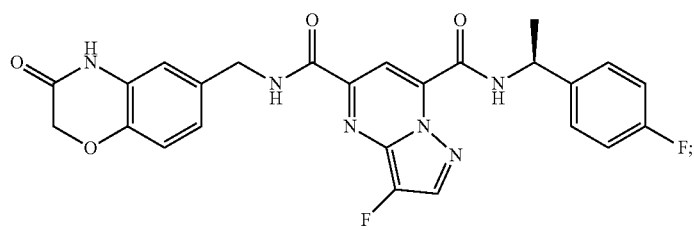
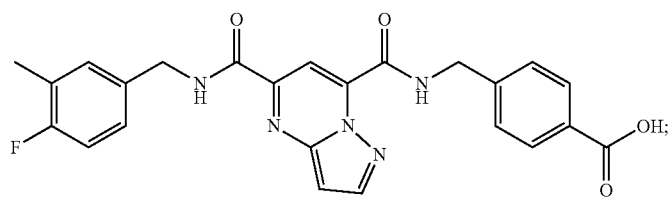
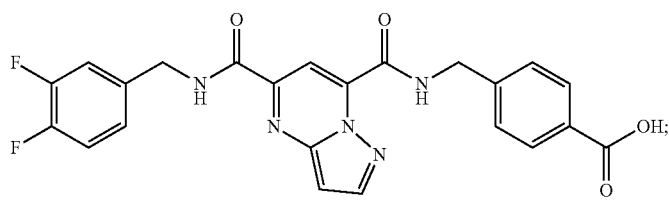
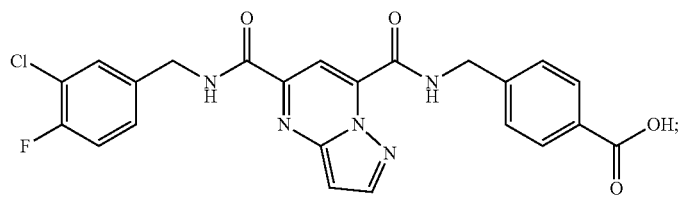
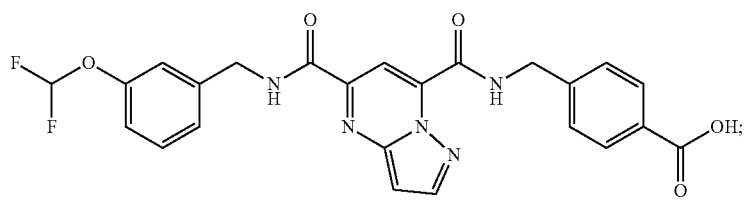
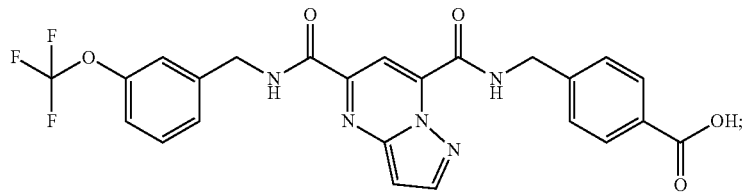

-continued
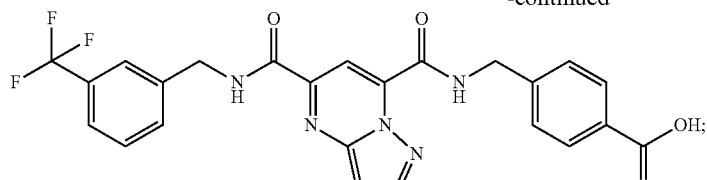
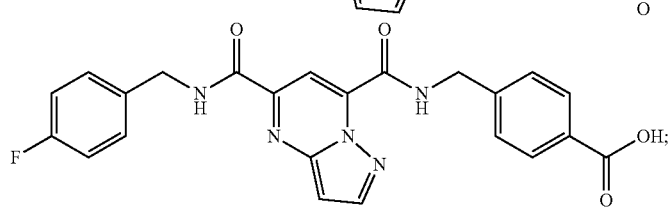
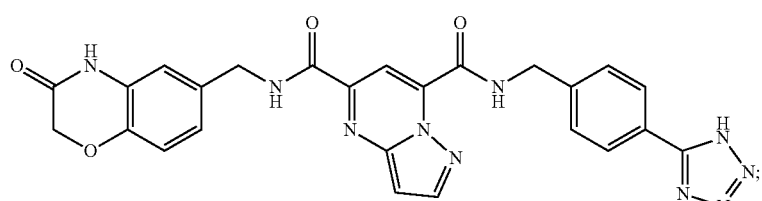
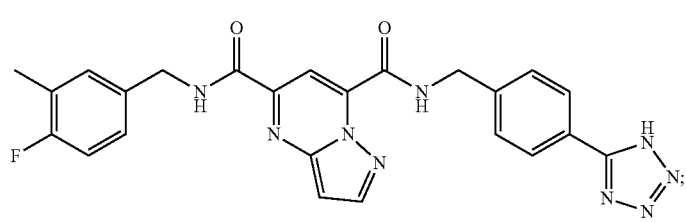
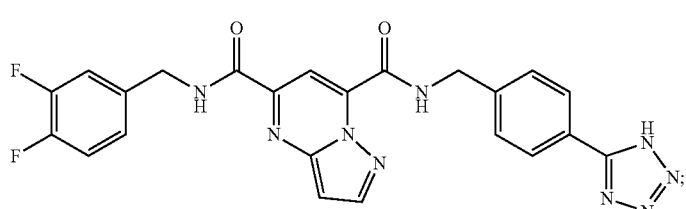
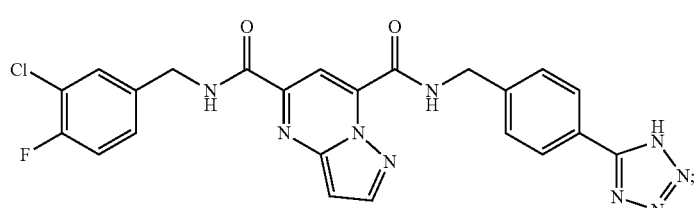
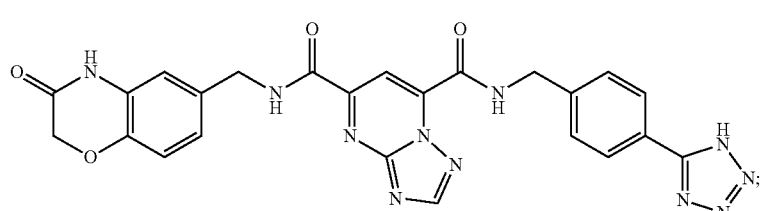
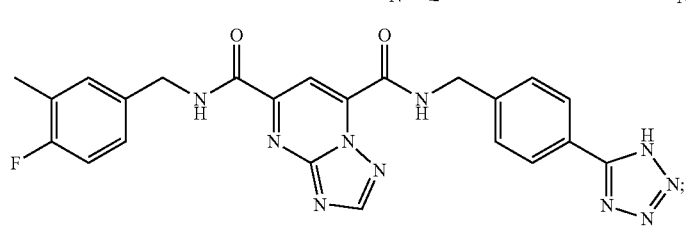

-continued
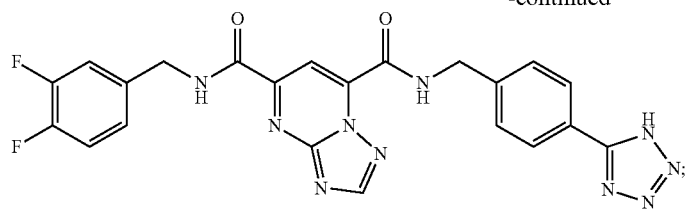
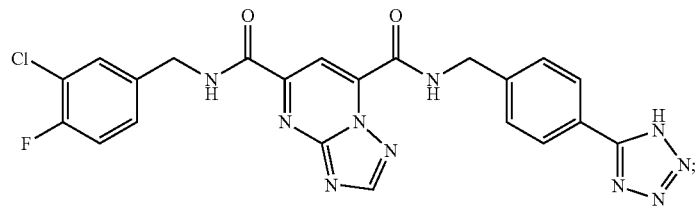
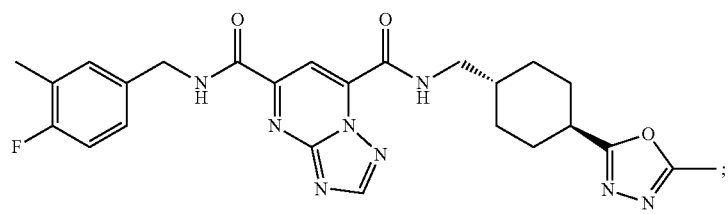
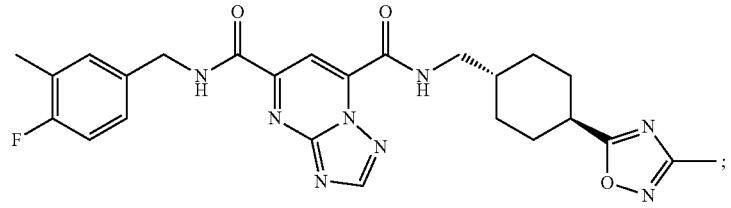
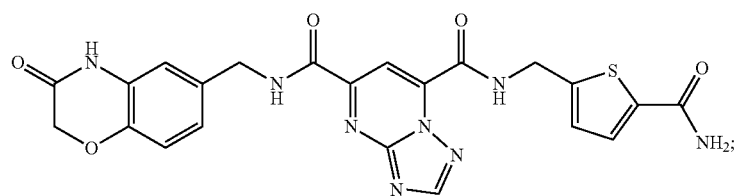
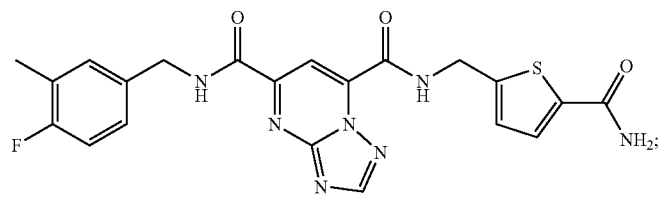
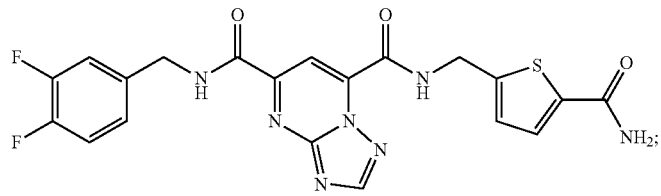
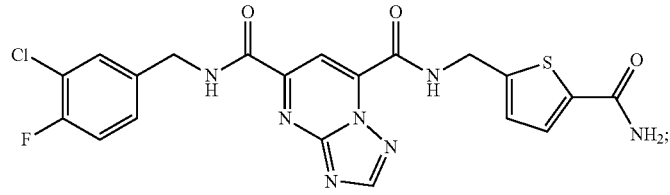

-continued
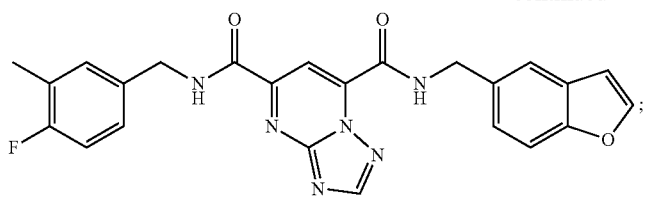
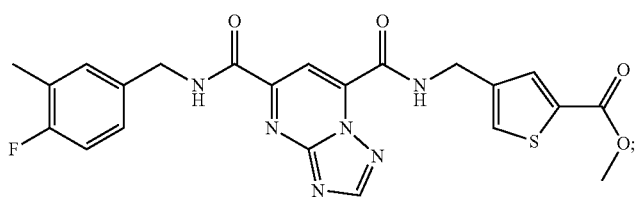
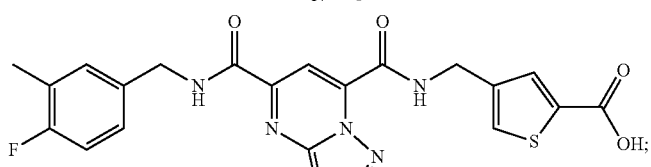
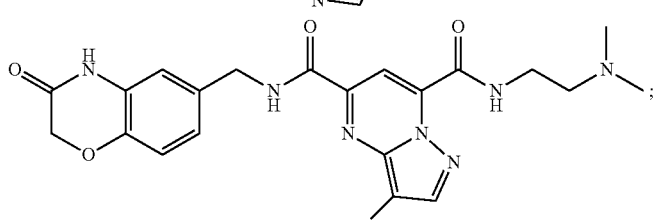
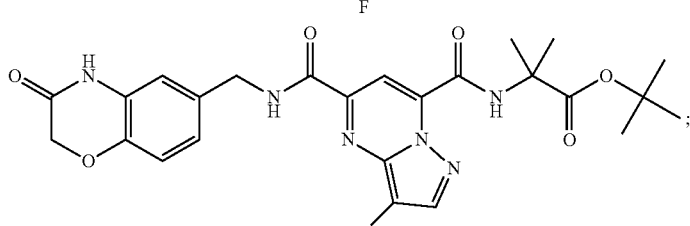
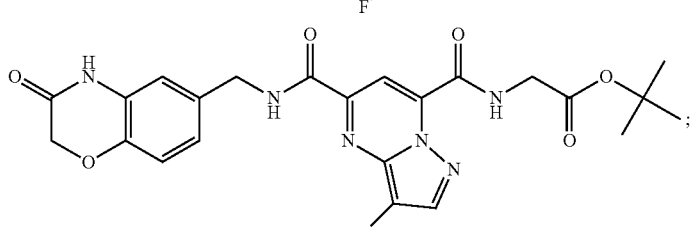
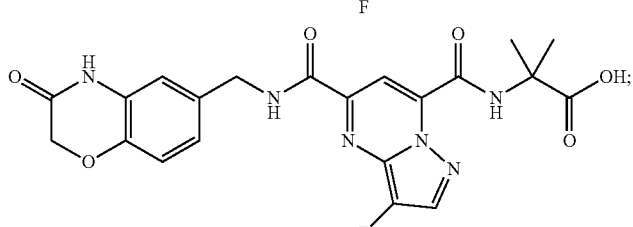
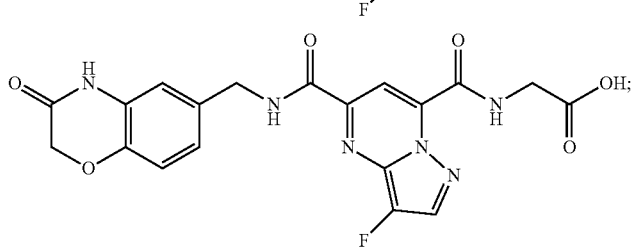

-continued
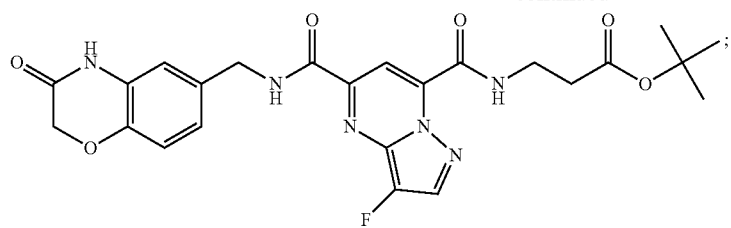
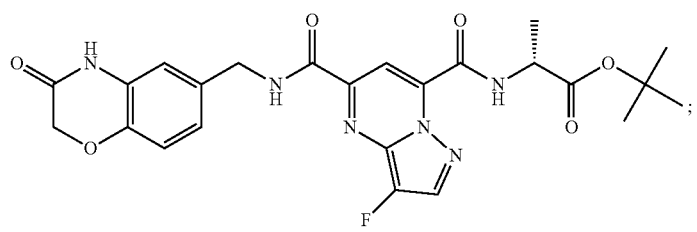
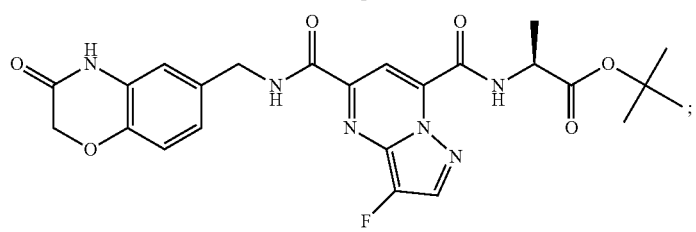
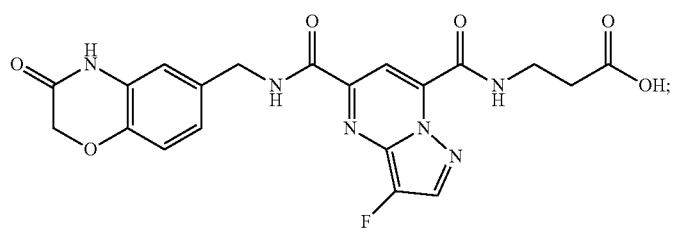
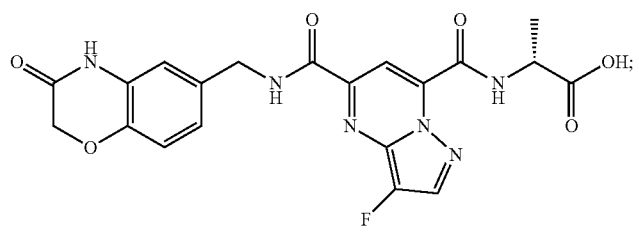
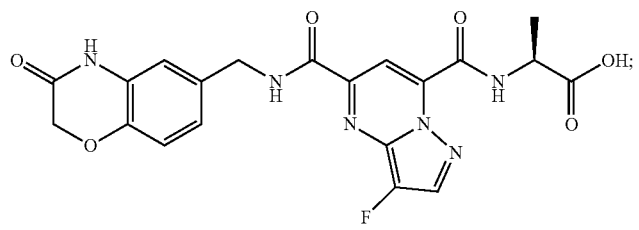
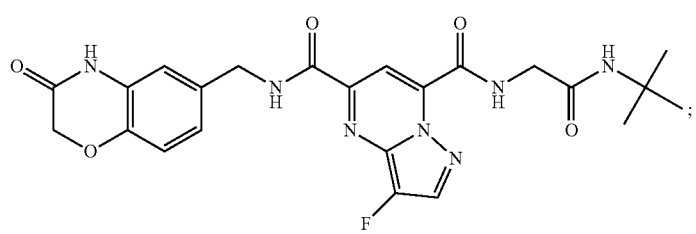

-continued
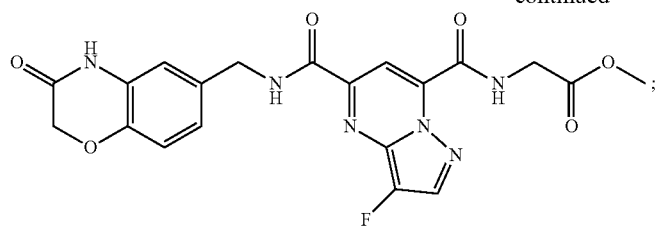
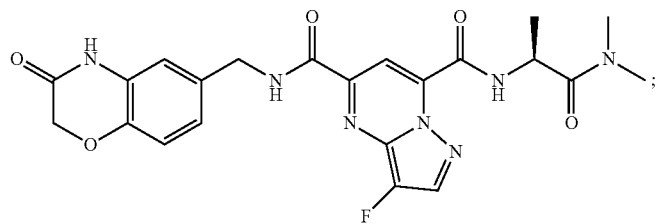
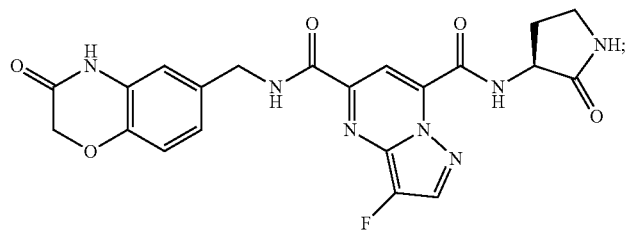
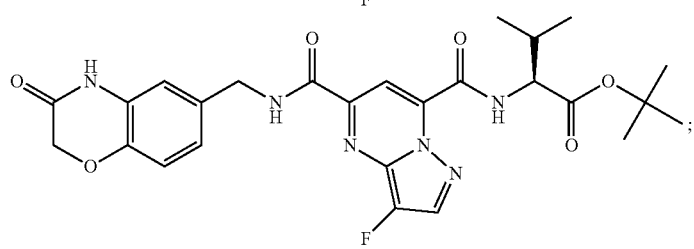
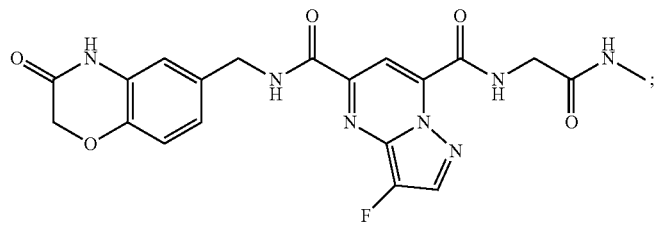
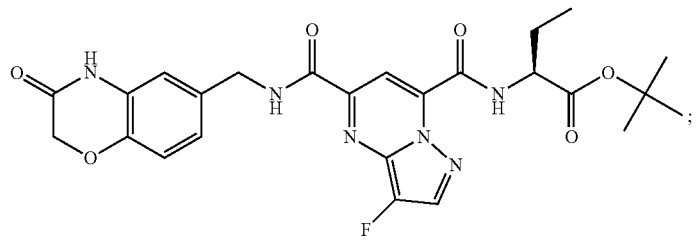
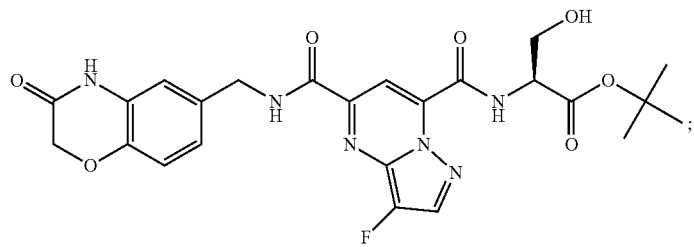

-continued
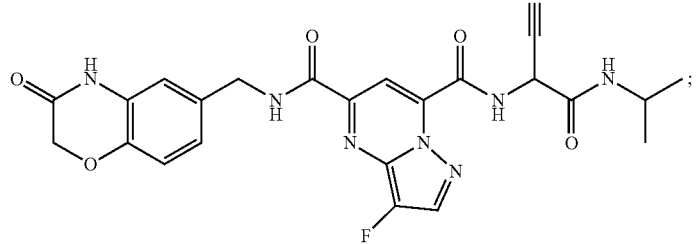
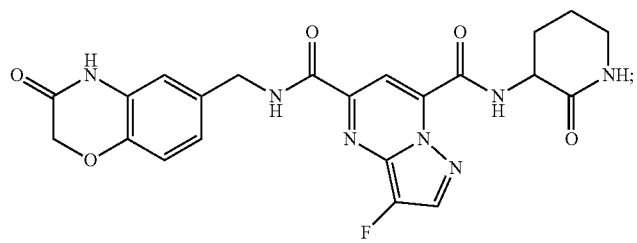
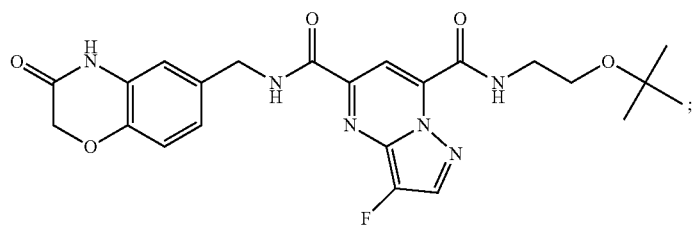
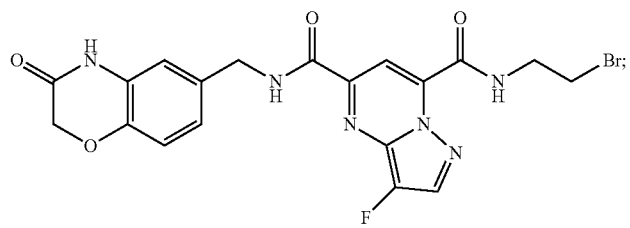
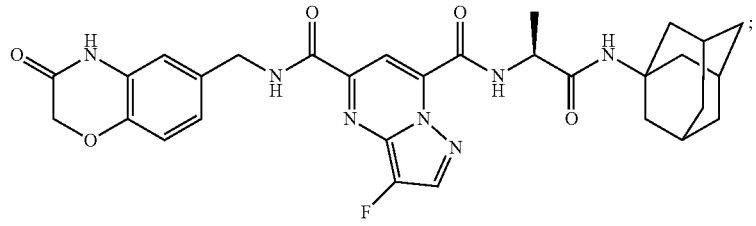
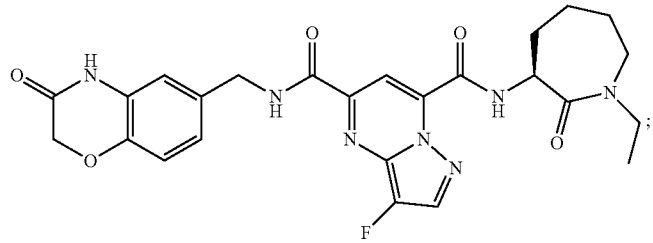
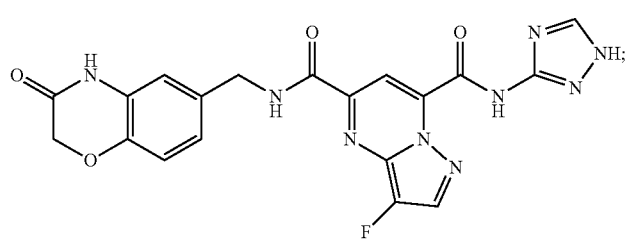

-continued
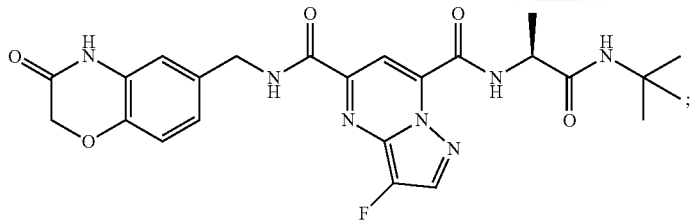
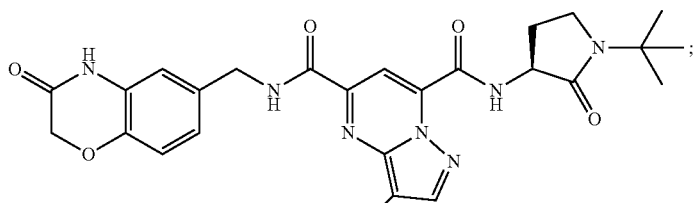
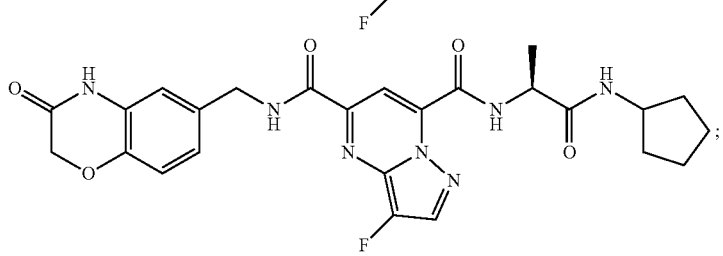
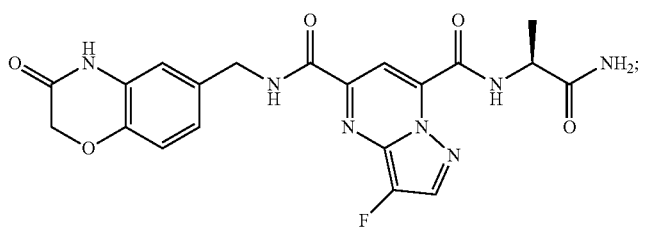
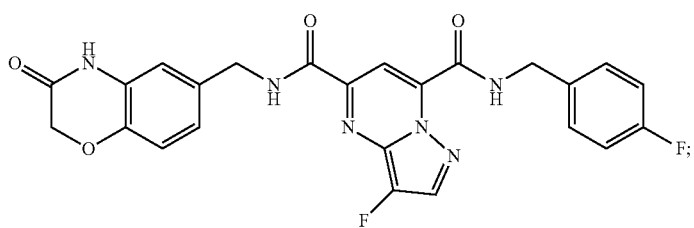
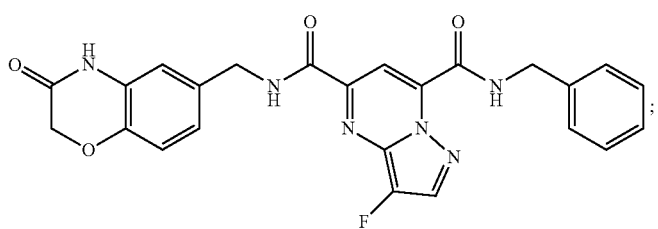
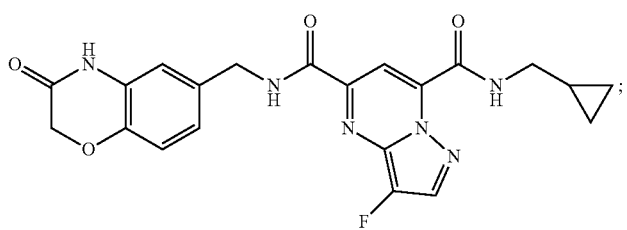

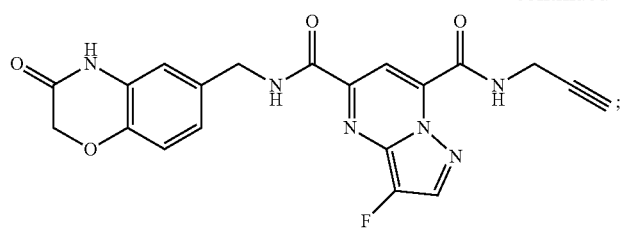
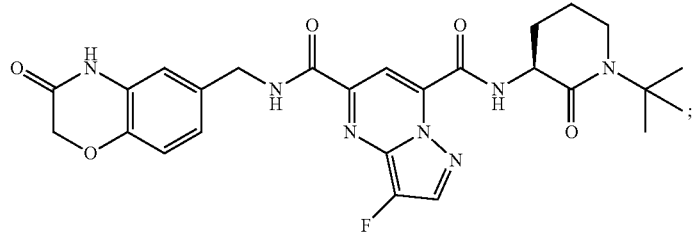
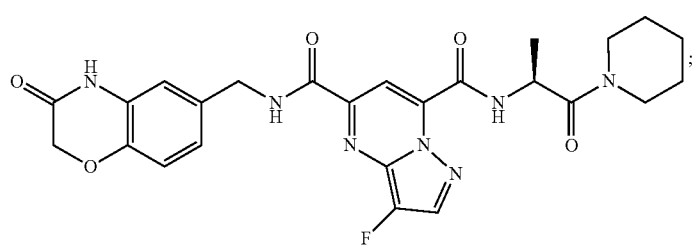
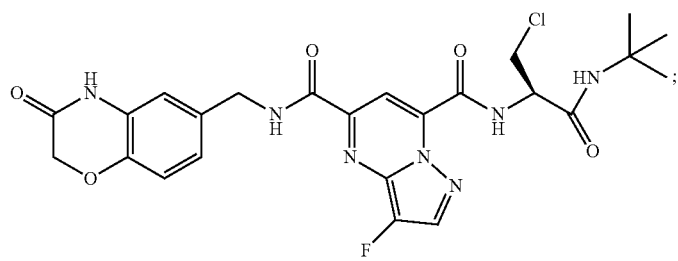
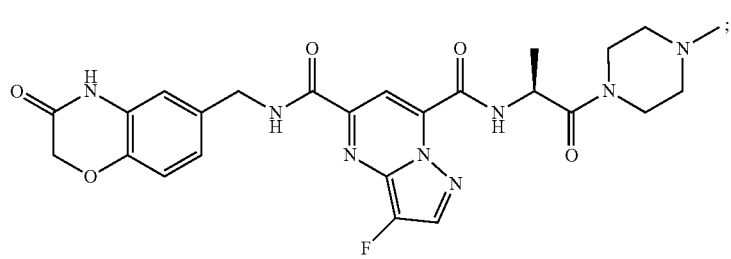
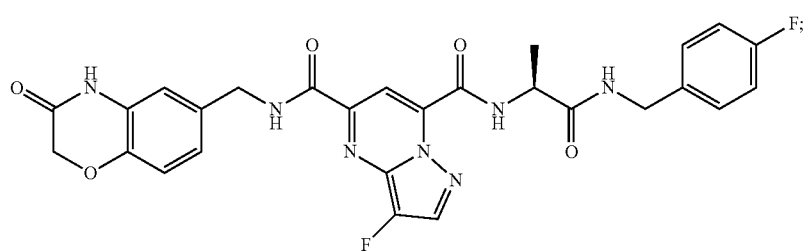
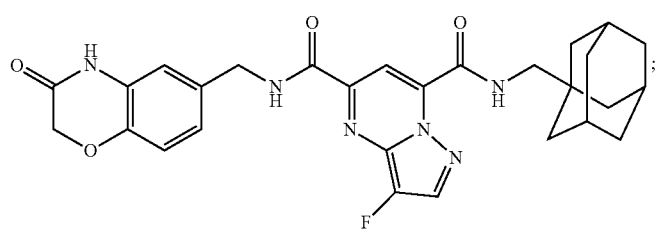

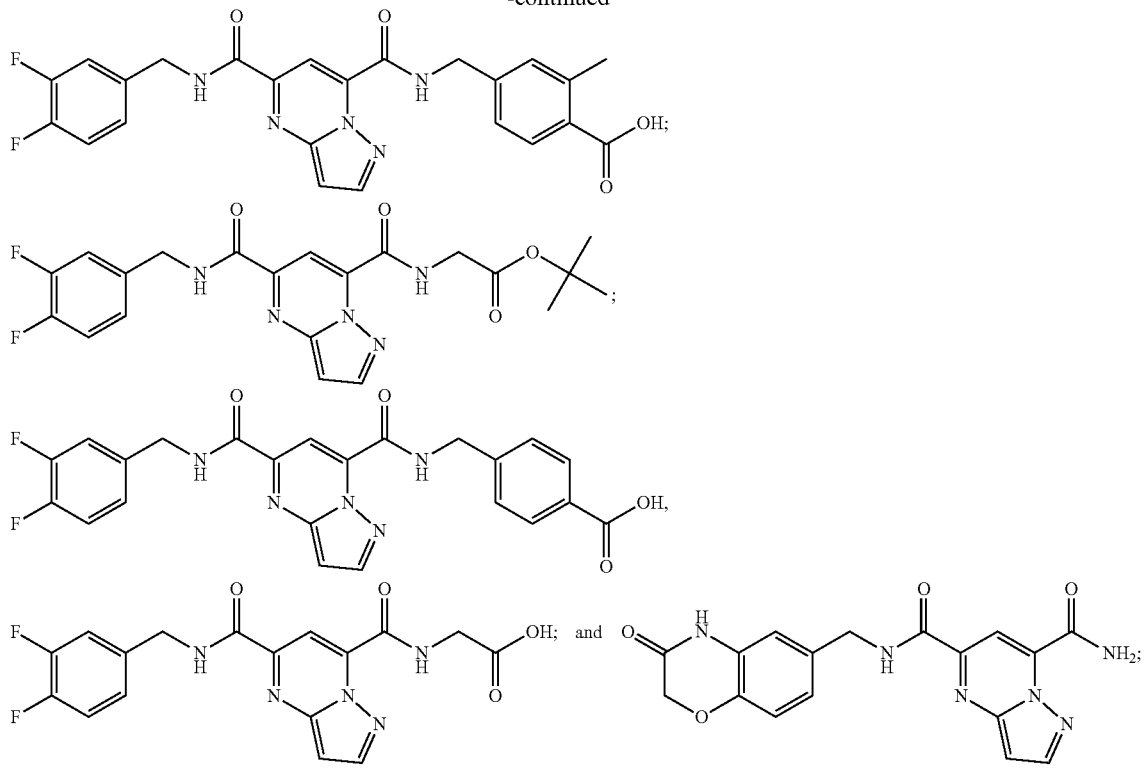
or a pharmaceutically acceptable salt thereof.
In still a further embodiment, the present invention provides a compound selected from:
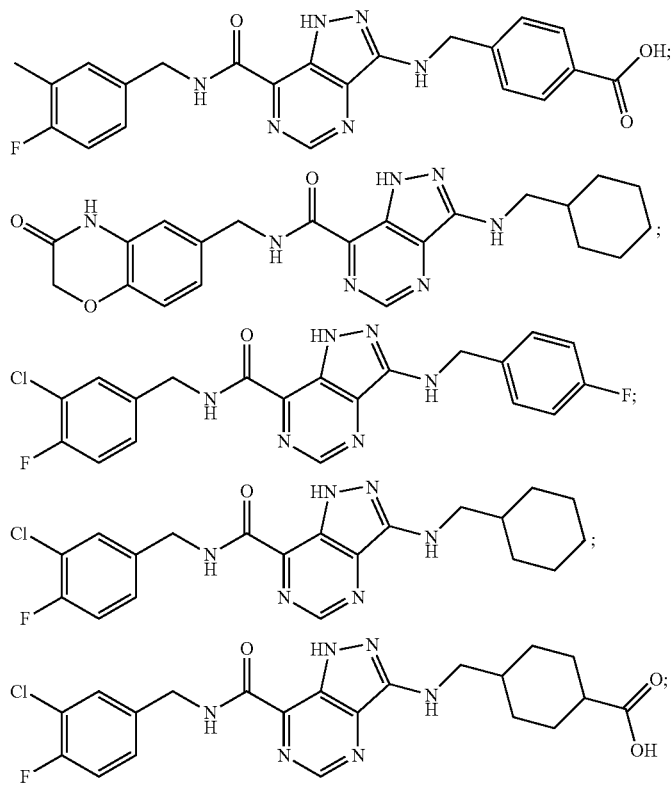

-continued
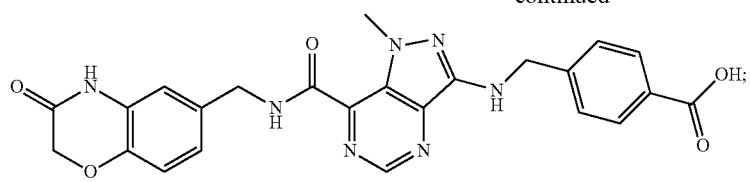
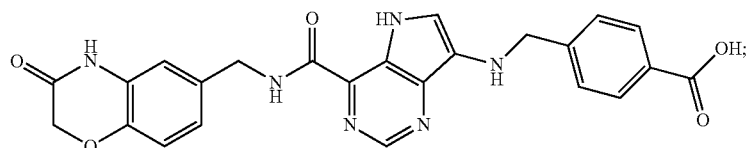
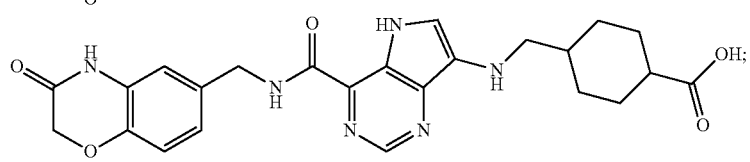
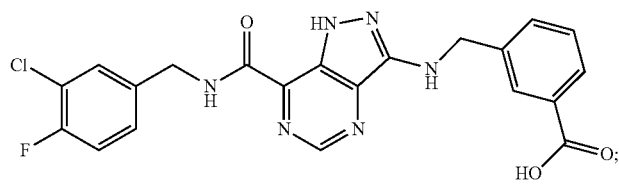
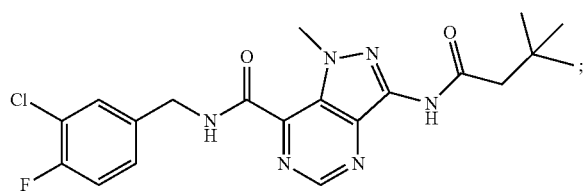
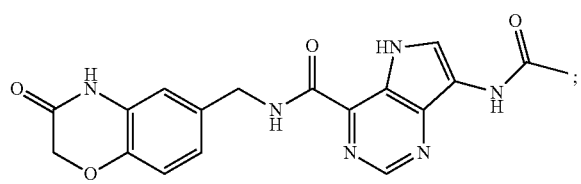
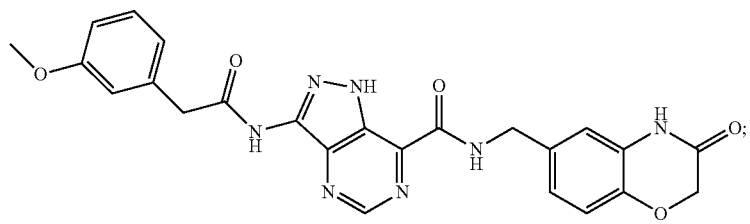
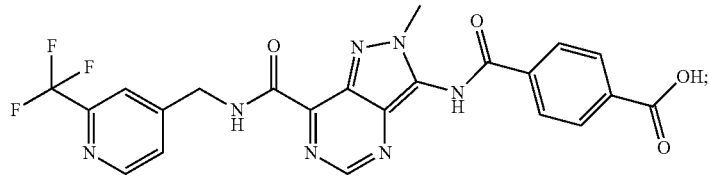
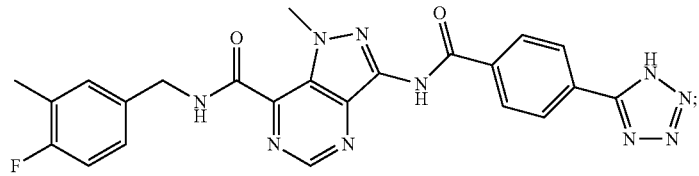

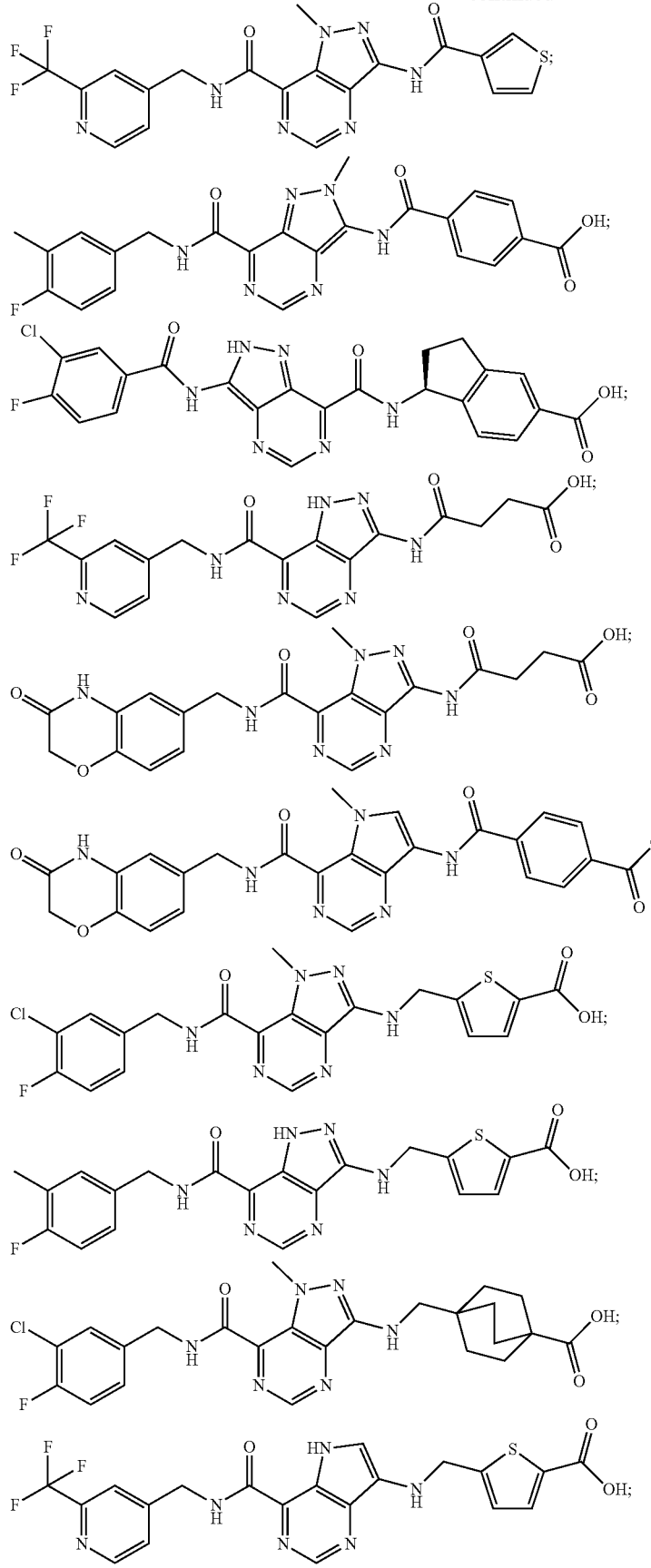

-continued
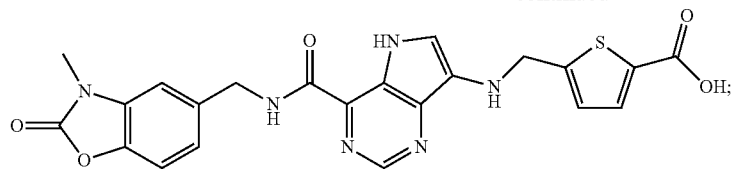
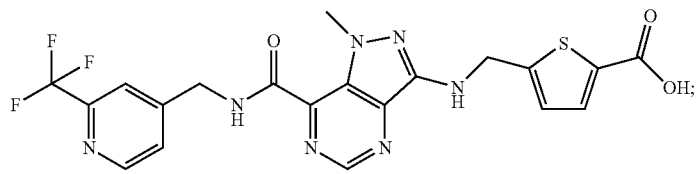
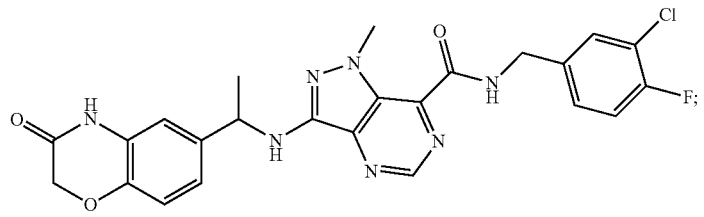
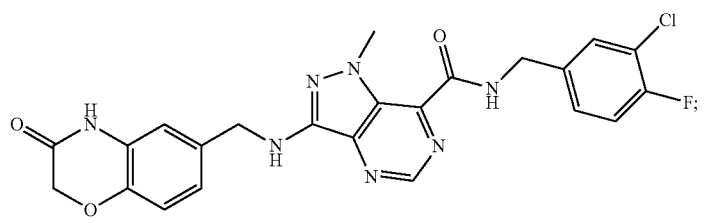
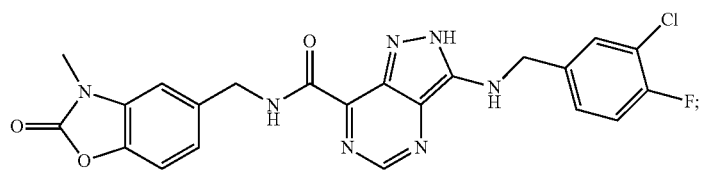
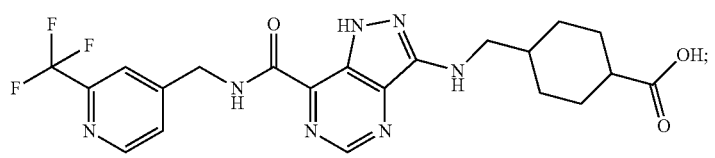
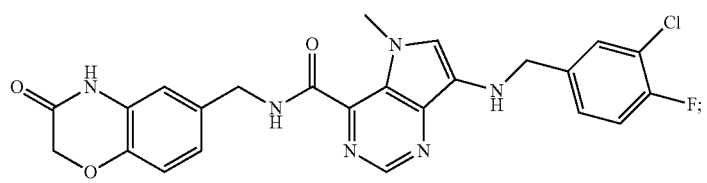
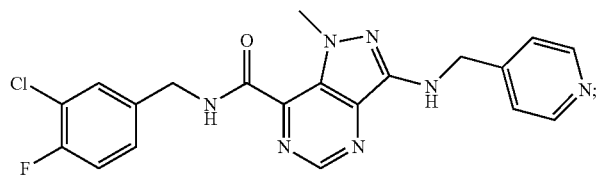

-continued
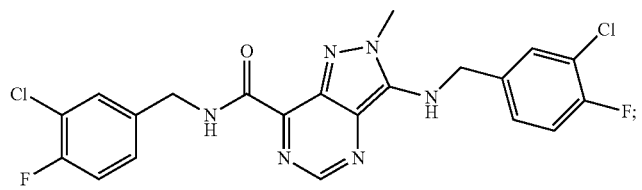
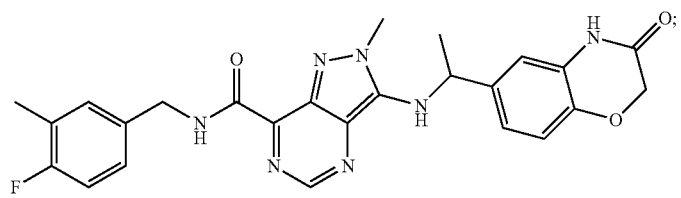
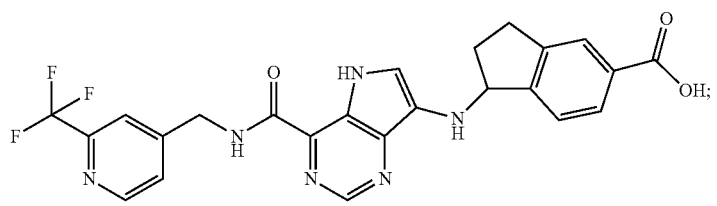
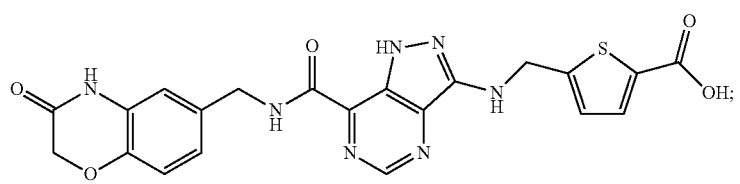
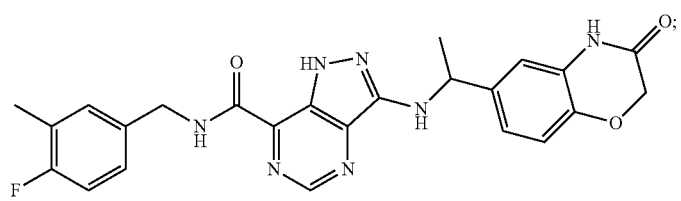
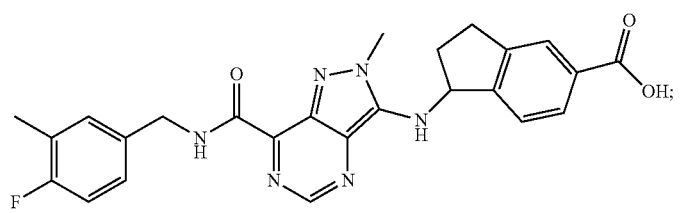
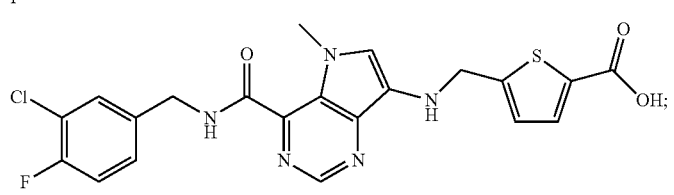
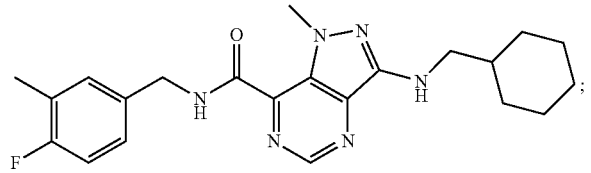

-continued
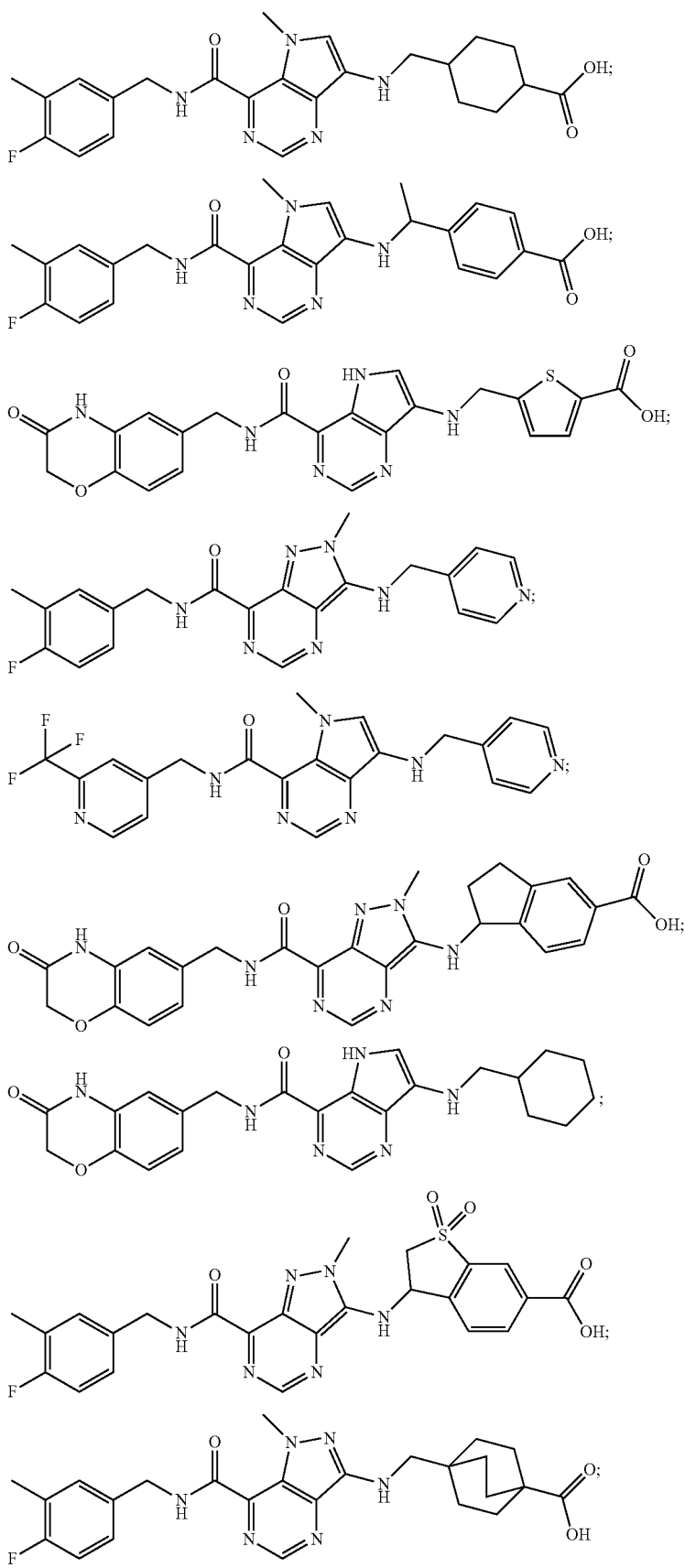

-continued
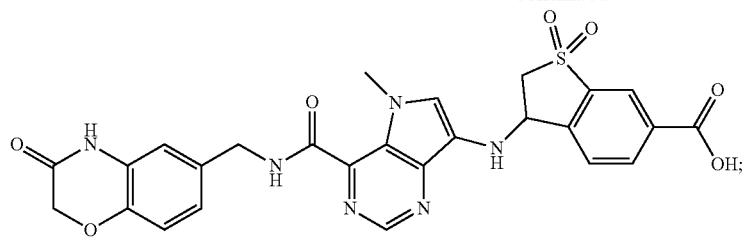
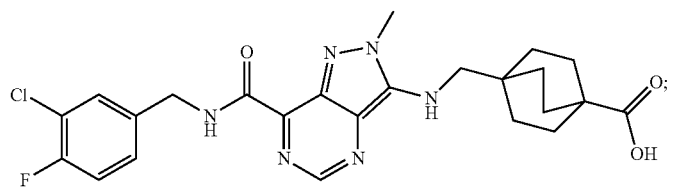
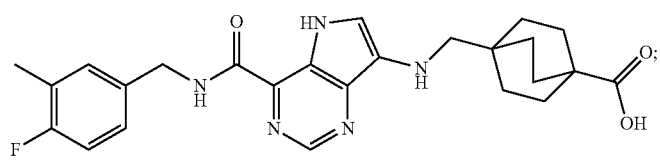
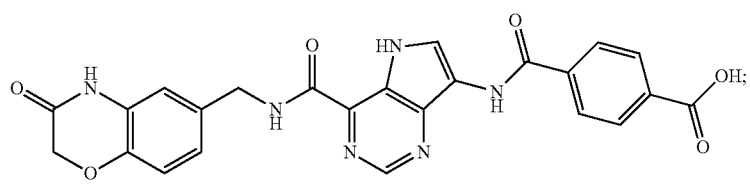
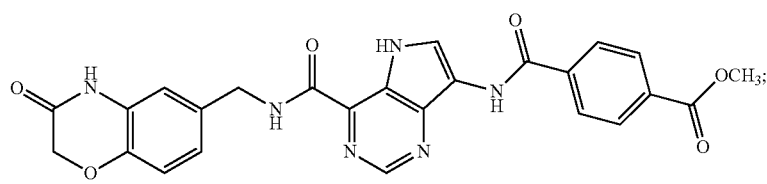
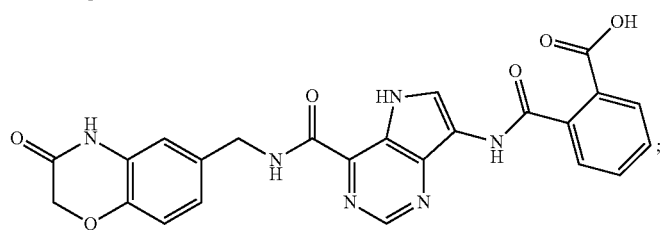
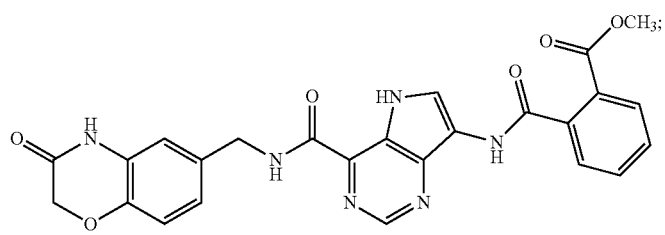
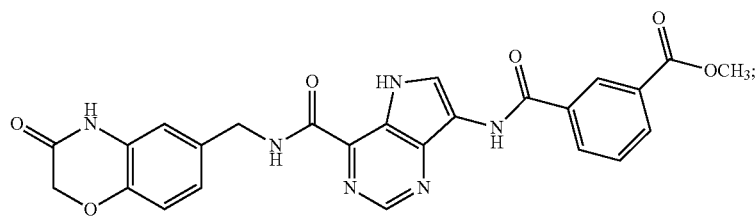

-continued
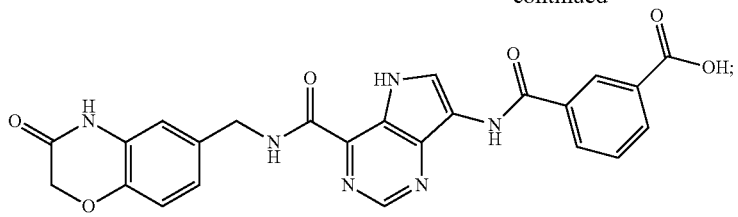
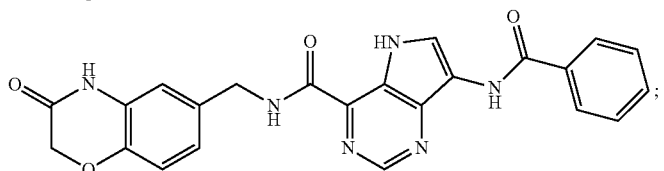
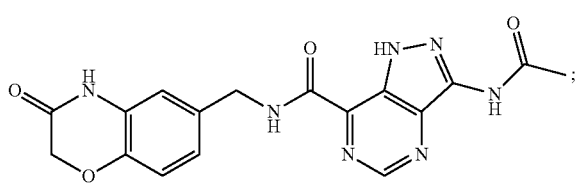
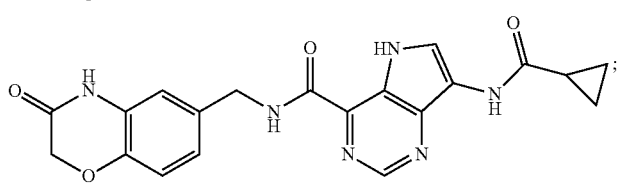
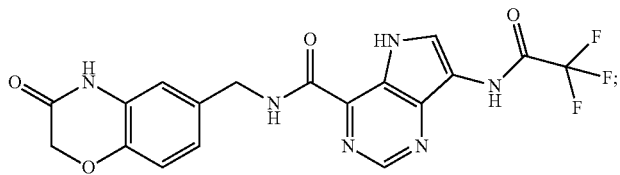
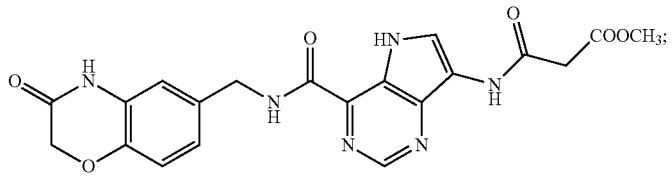
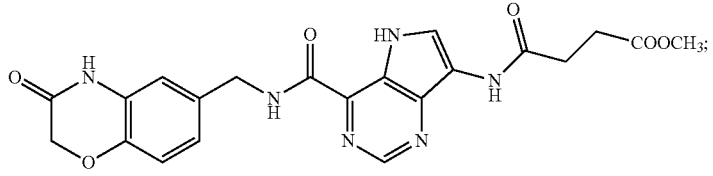
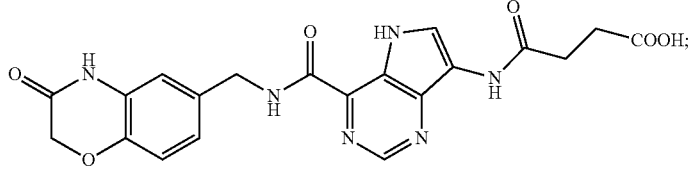
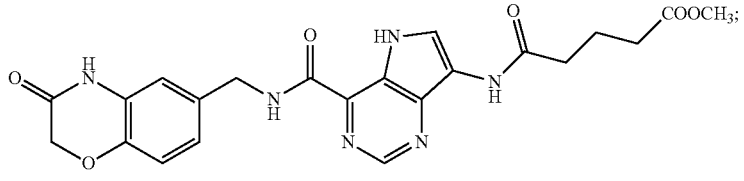

-continued
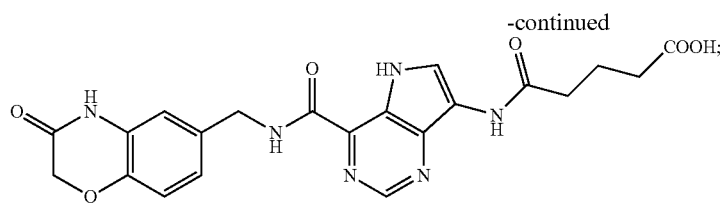
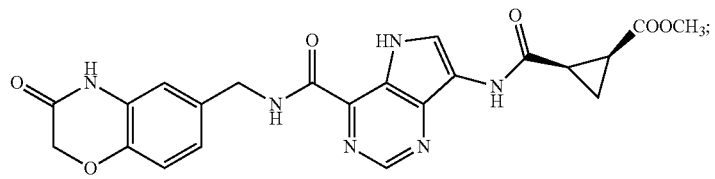
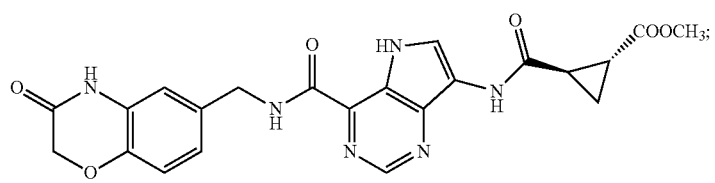
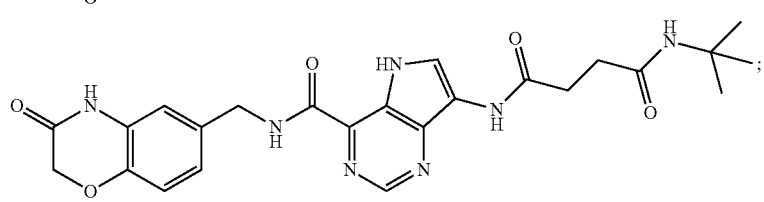
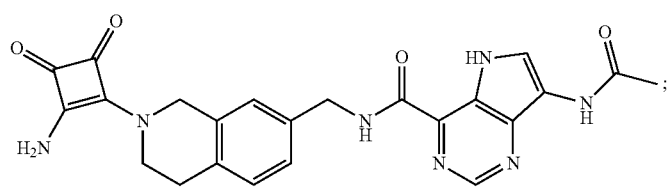
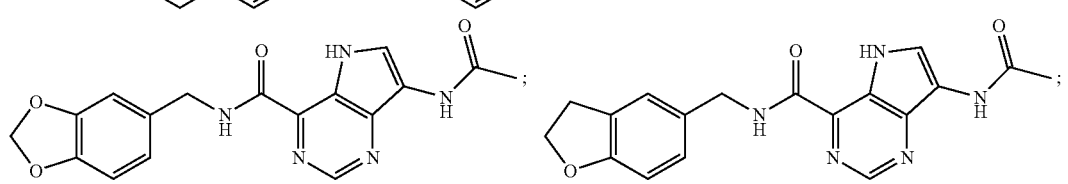
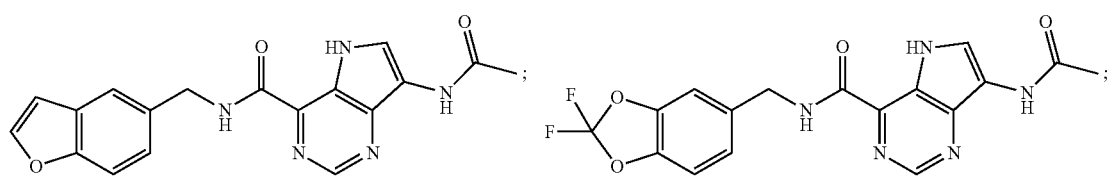
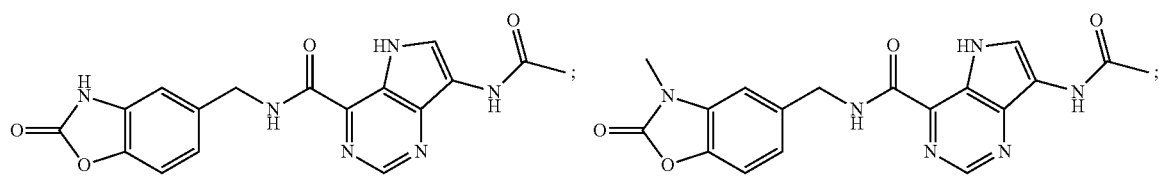
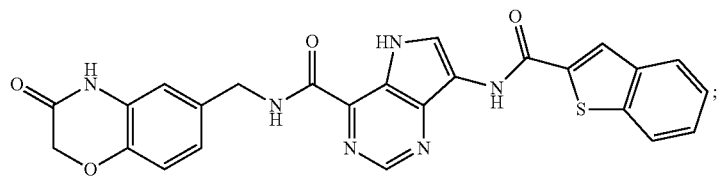

-continued
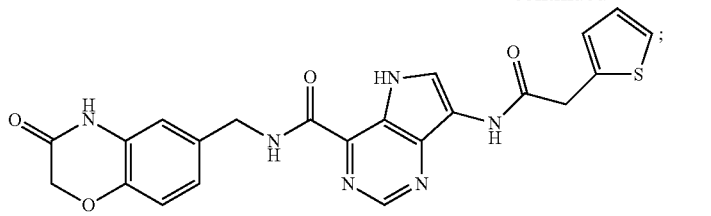
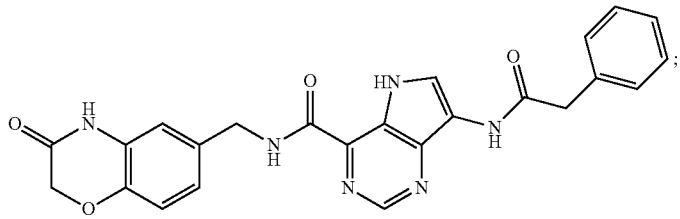
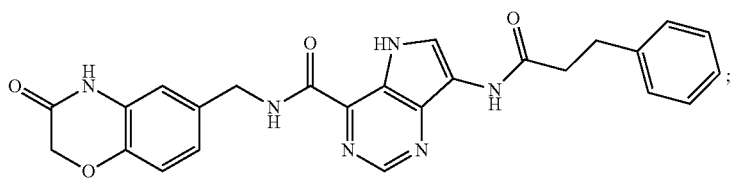
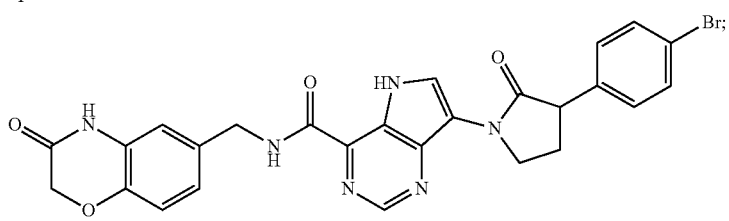
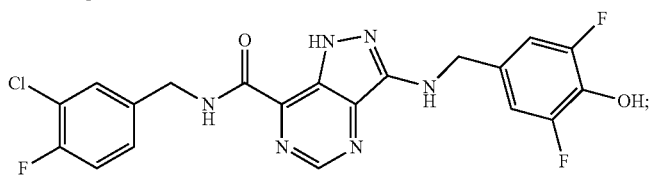
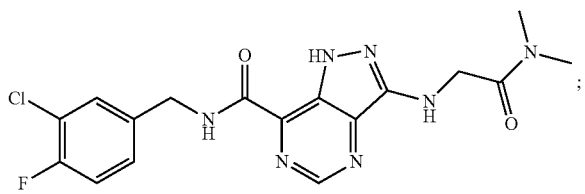
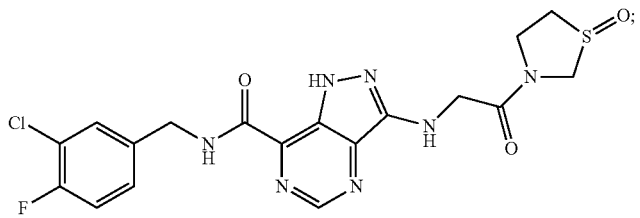

-continued
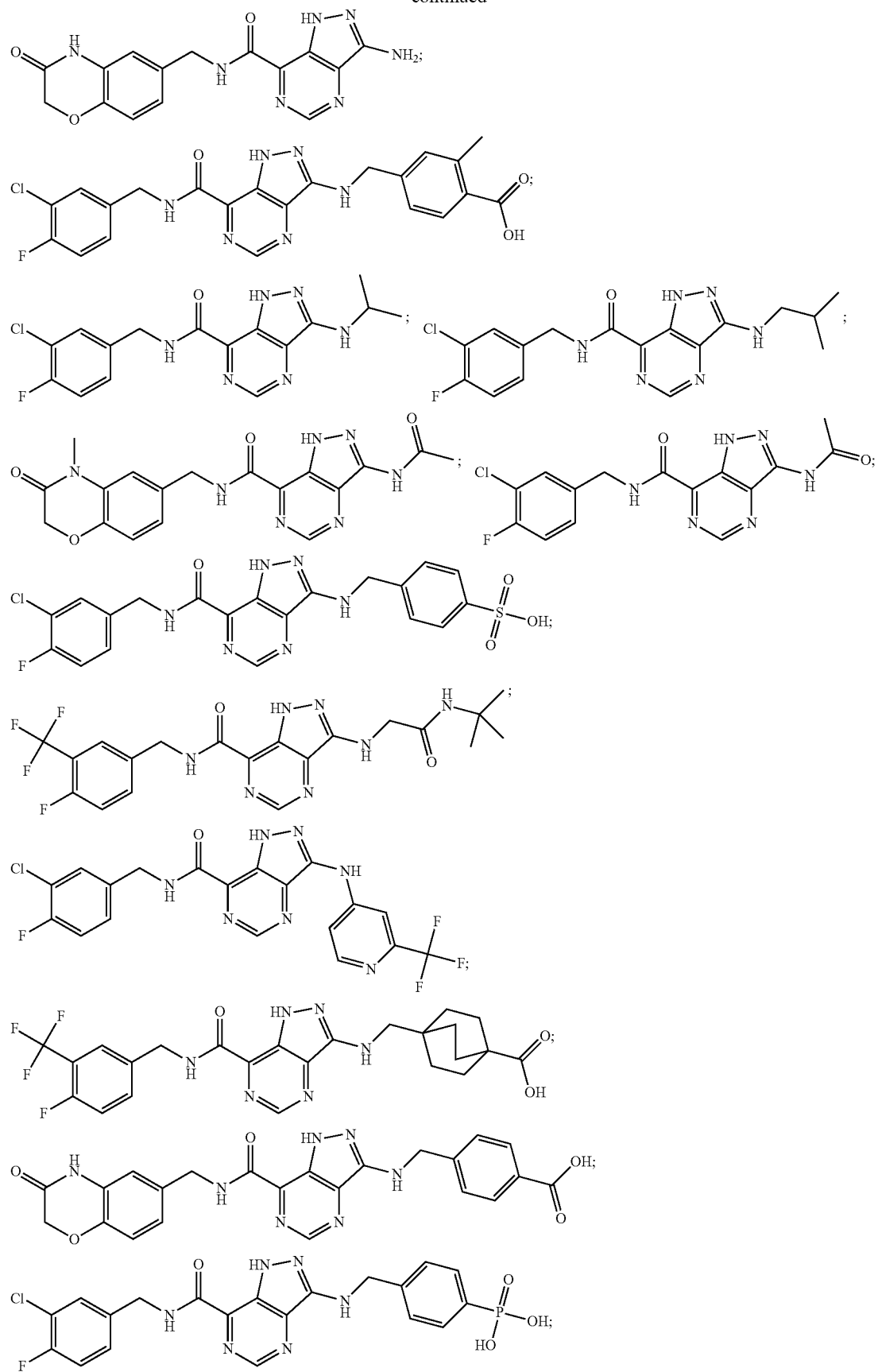

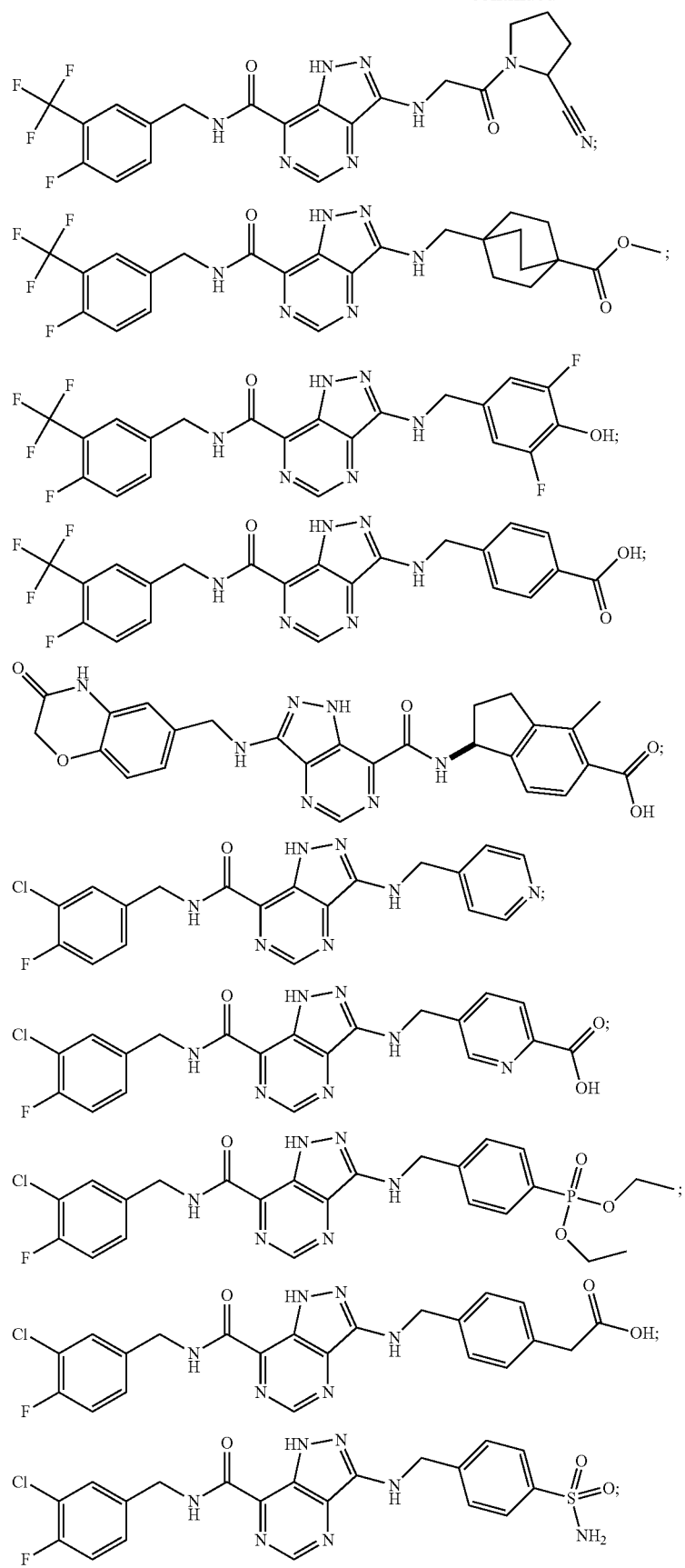

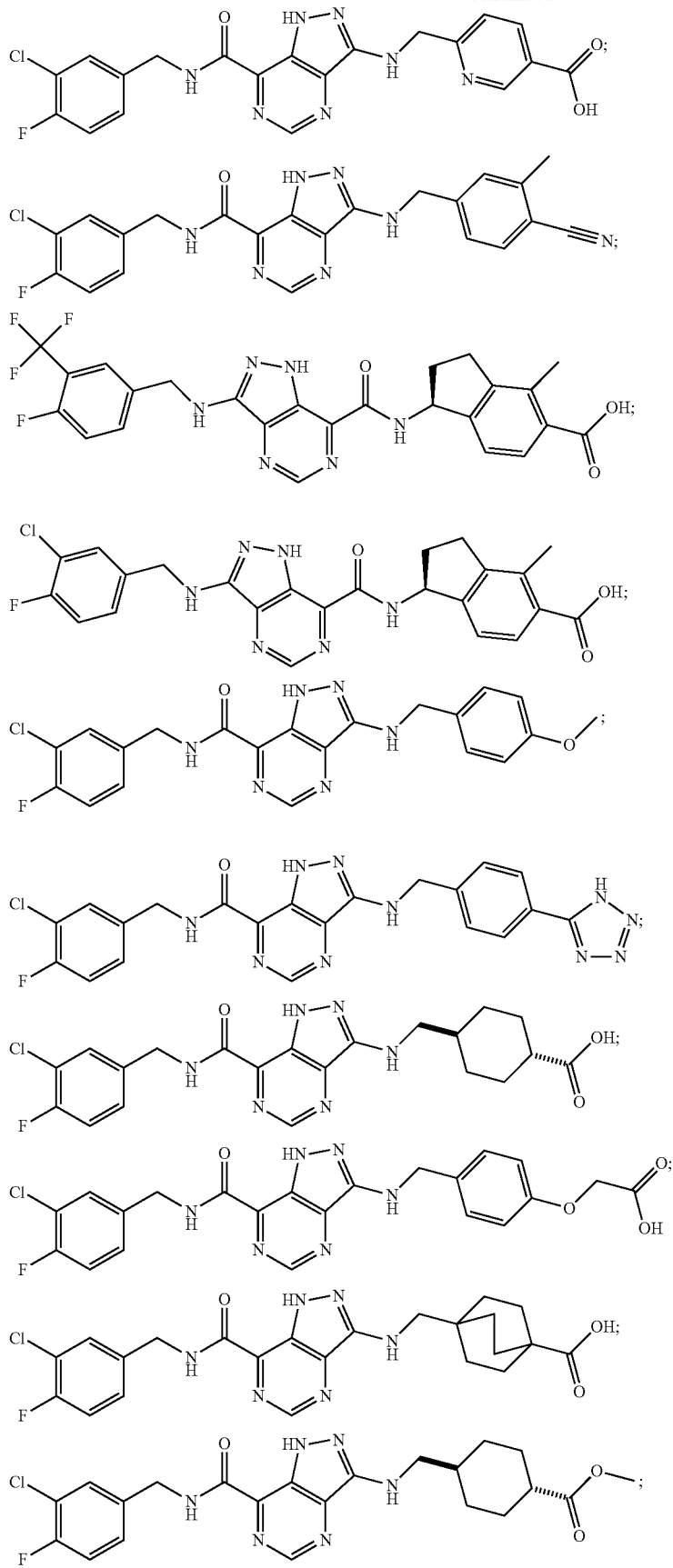

-continued
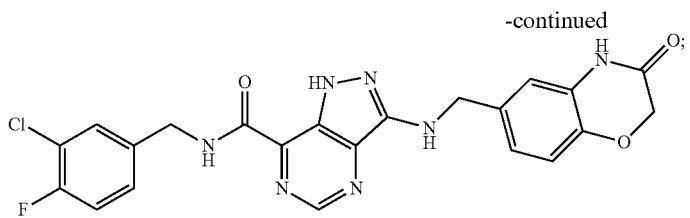
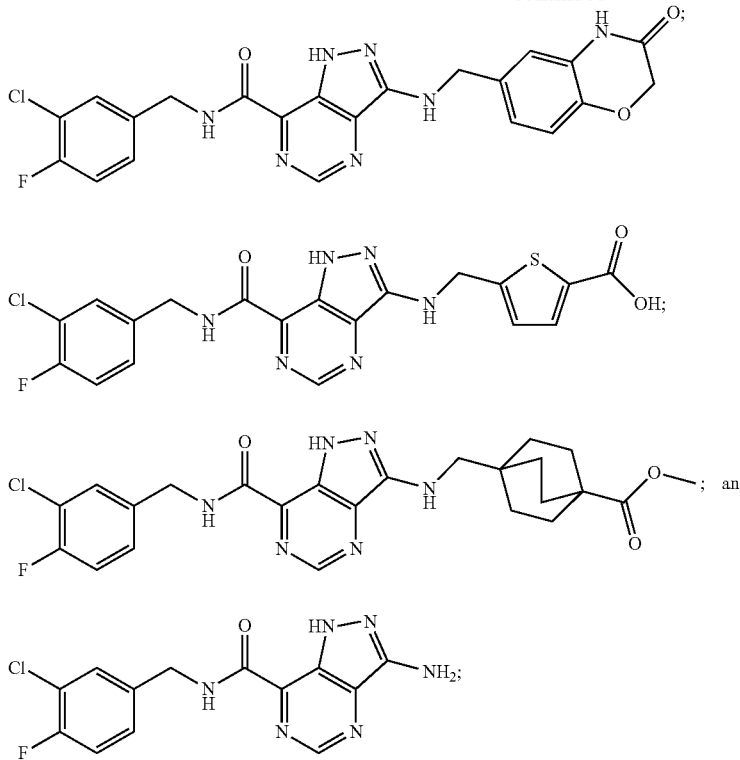 [SMILES: O=C1COc2ccc(CNc3n[nH]c4c(C(=O)NCc5ccc(F)c(Cl)c5)ncnc34)cc2N1 ; O=C(O)c1ccc(CNc2n[nH]c3c(C(=O)NCc4ccc(F)c(Cl)c4)ncnc23)s1 ; COC(=O)C12CCC(CNc3n[nH]c4c(C(=O)NCc5ccc(F)c(Cl)c5)ncnc34)(CC1)CC2 ; Nc1n[nH]c2c(C(=O)NCc3ccc(F)c(Cl)c3)ncnc12]
or a pharmaceutically acceptable salt thereof.
In a further embodiment, the present invention provides a compound selected from:
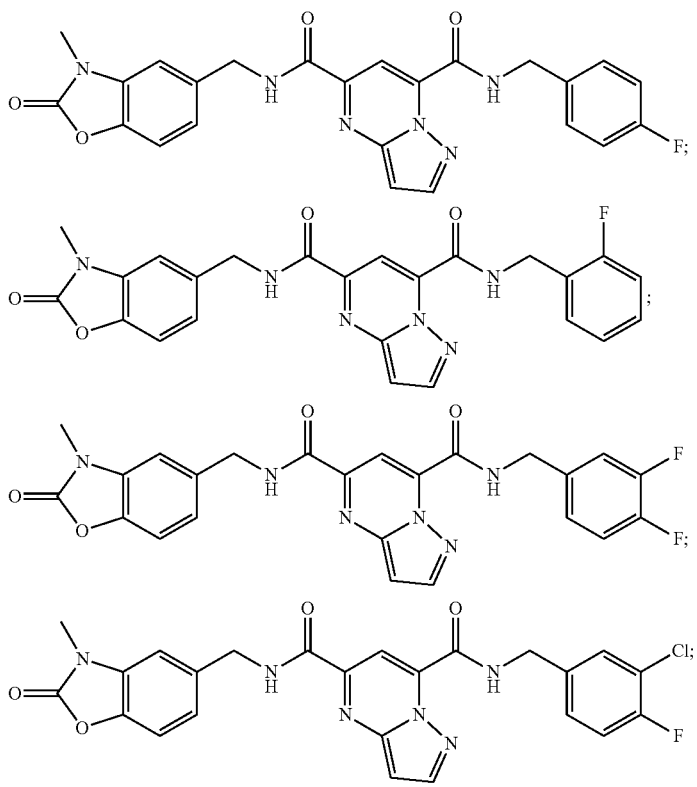

-continued
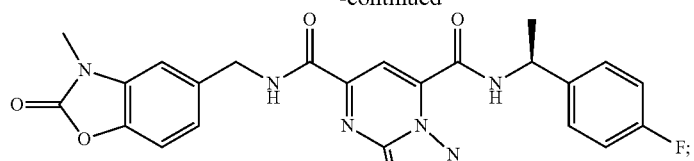
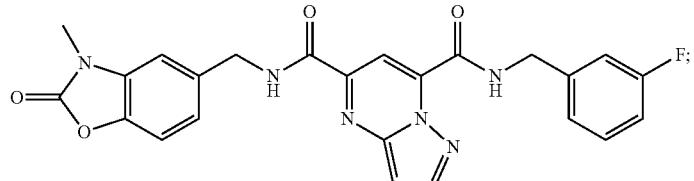
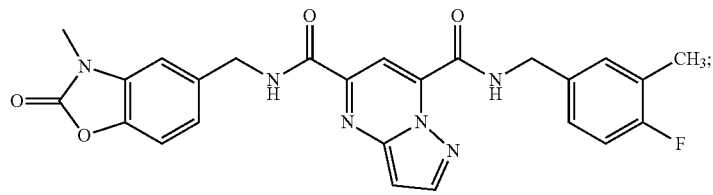
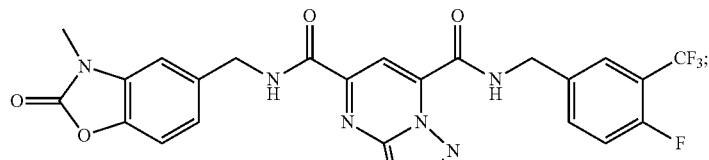
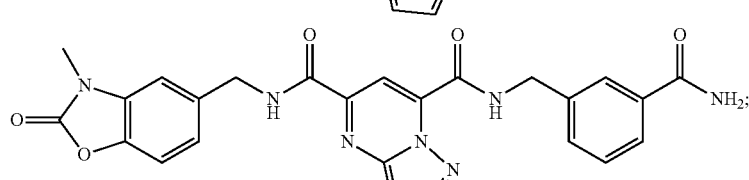
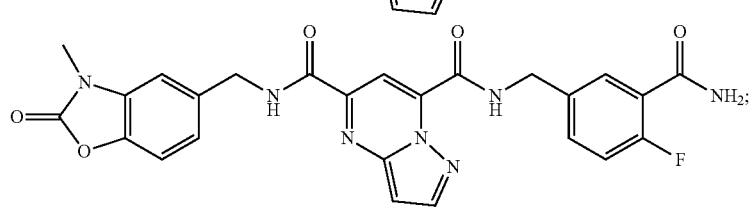
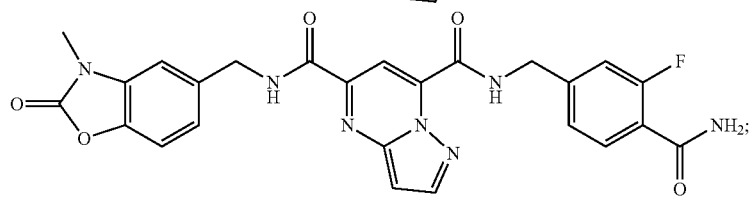
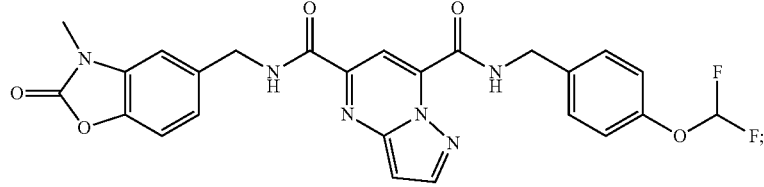
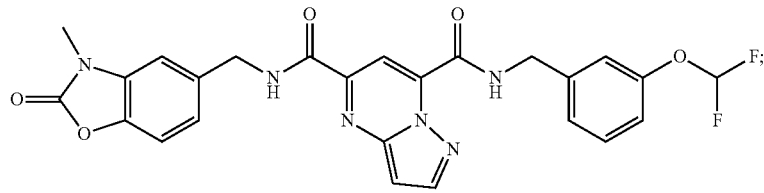

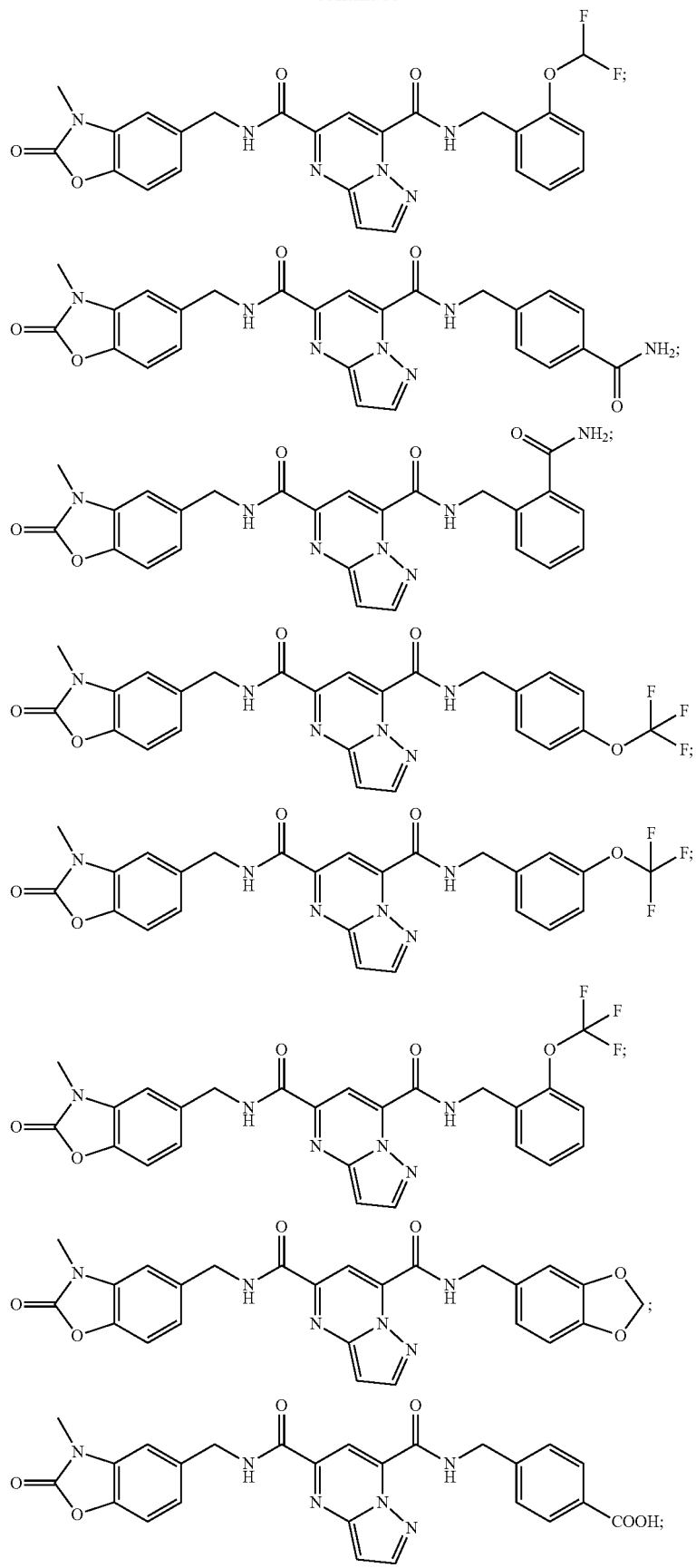

-continued
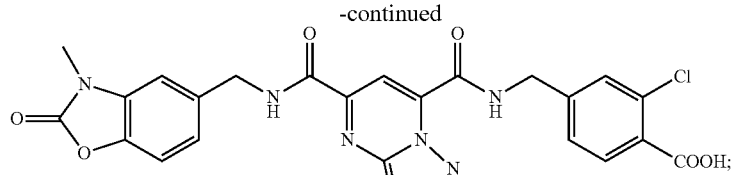
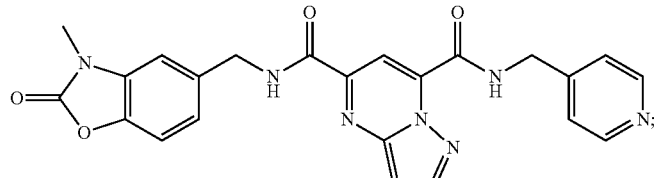
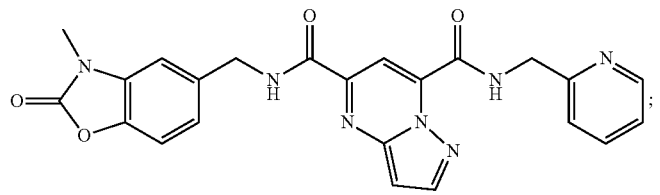
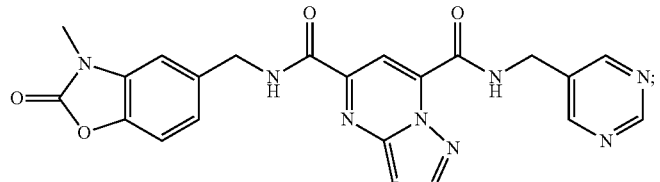
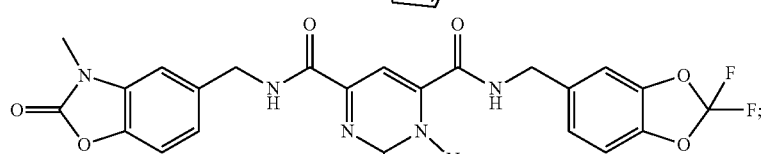
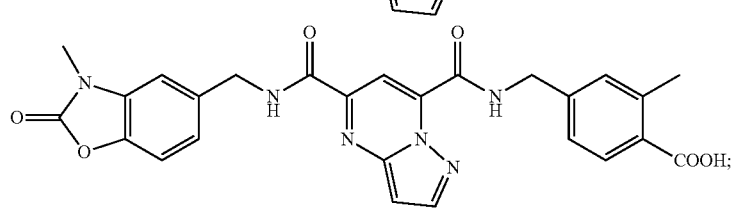
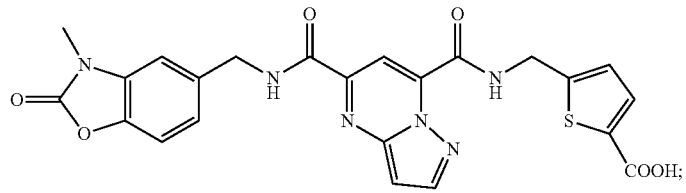
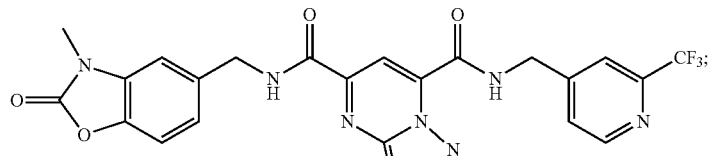
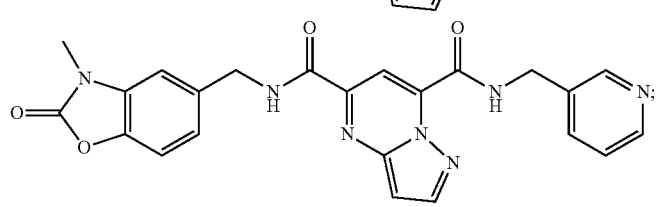

-continued
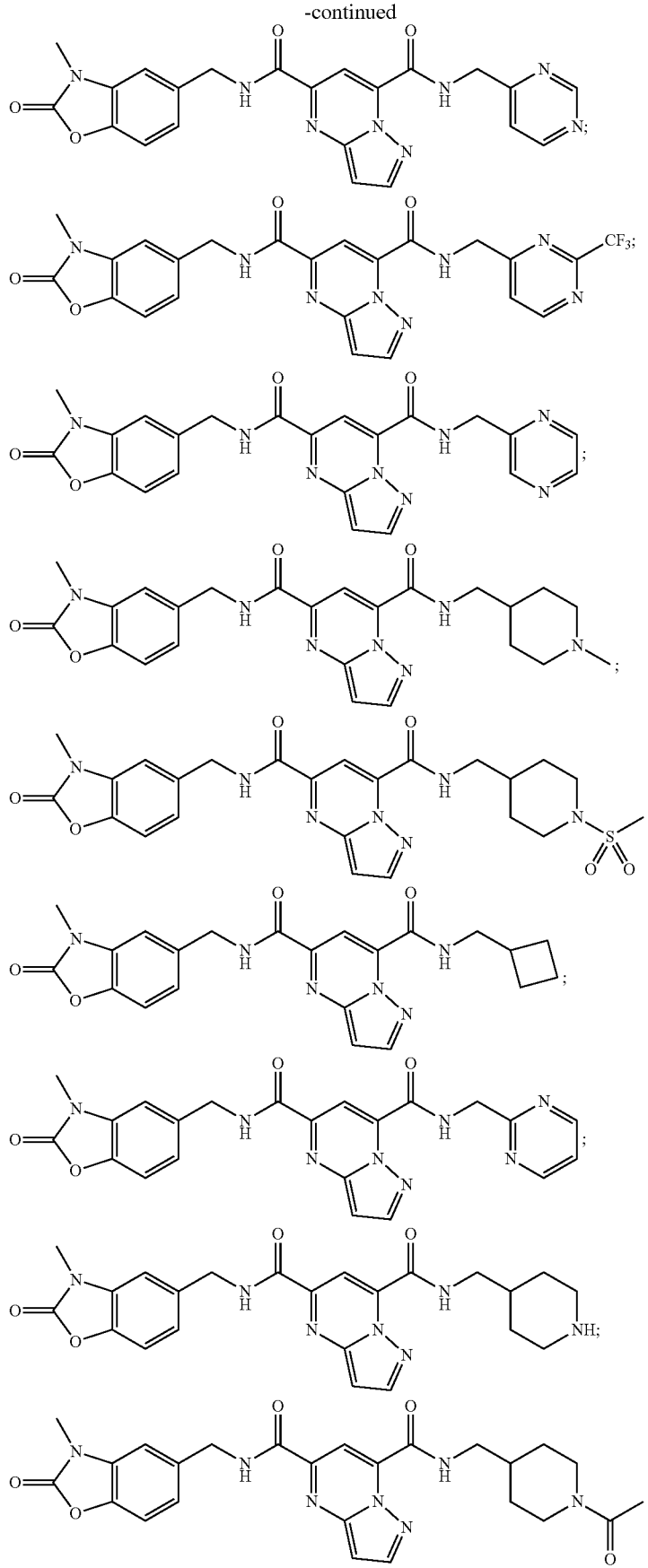

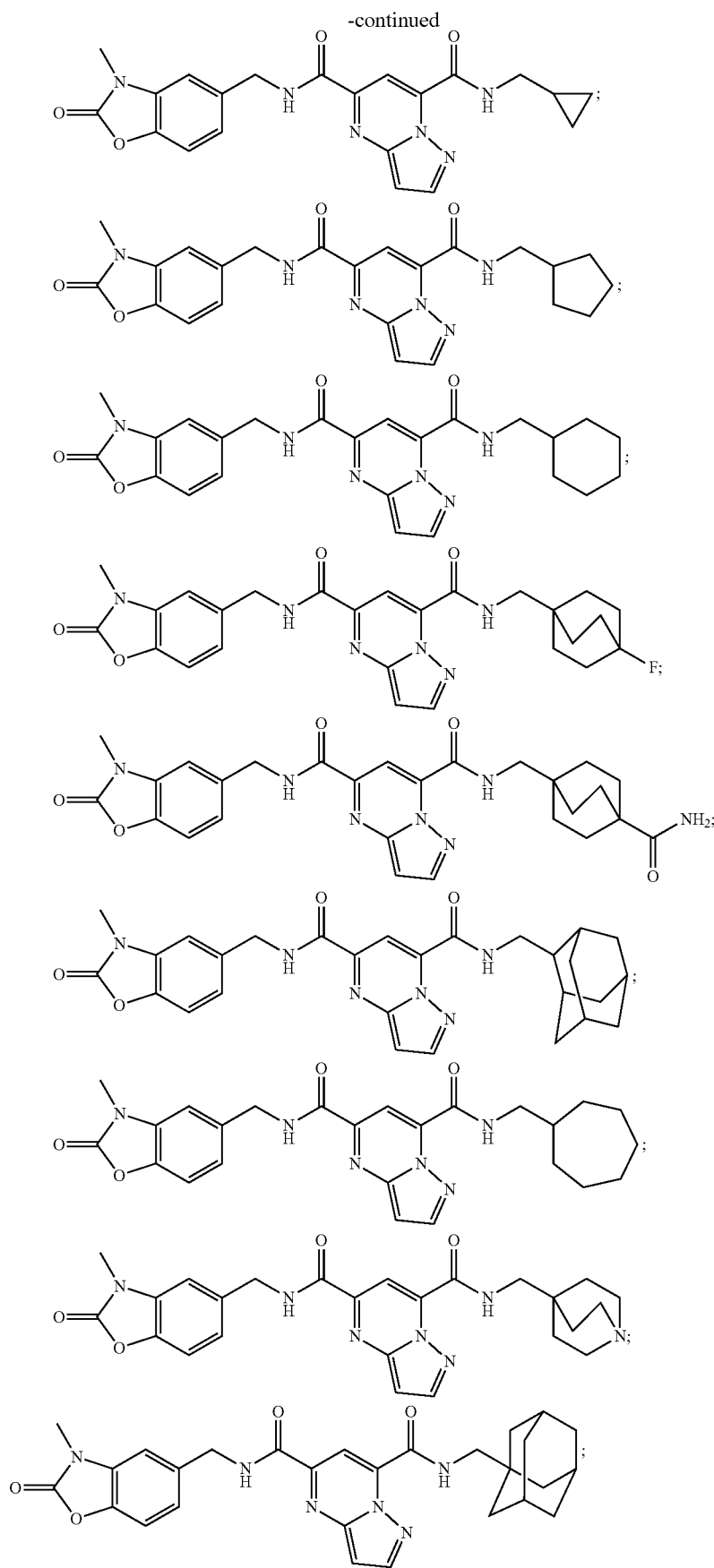

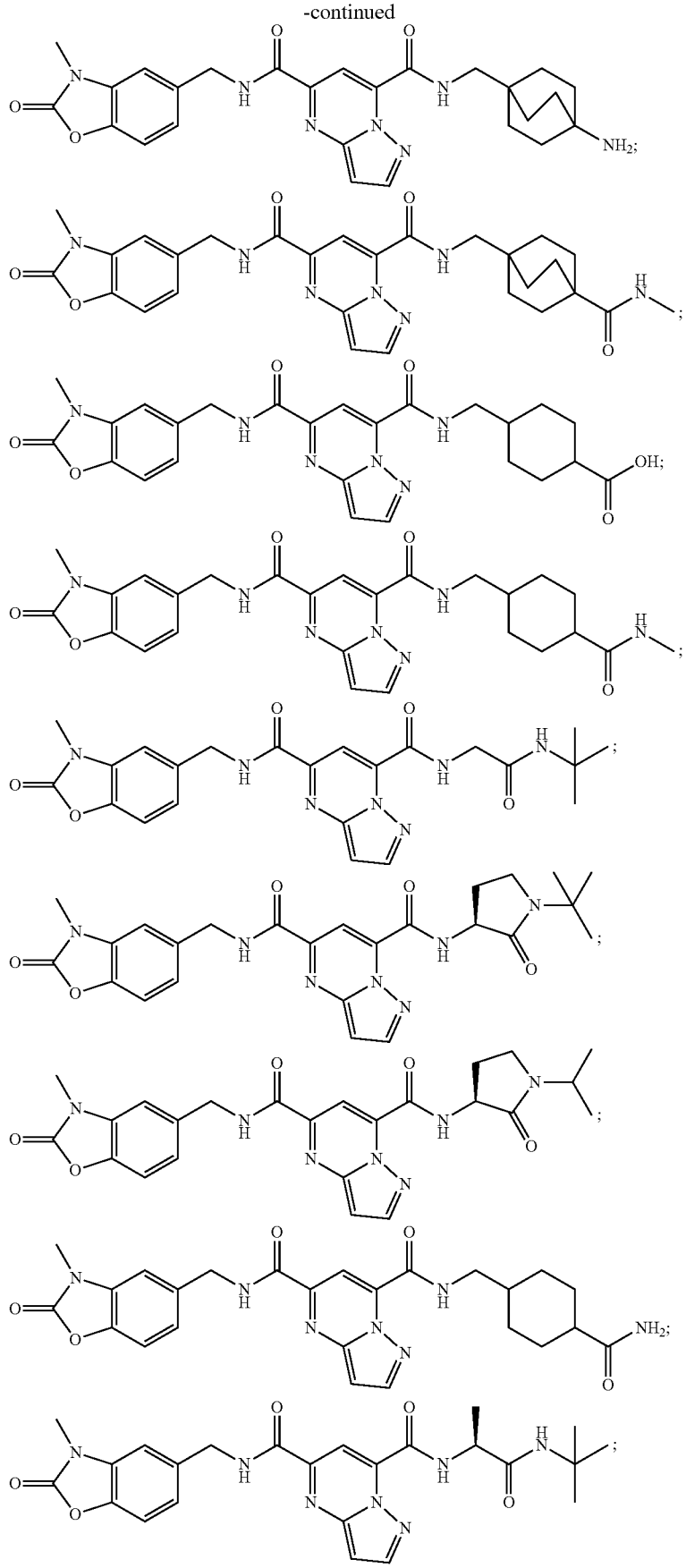

-continued
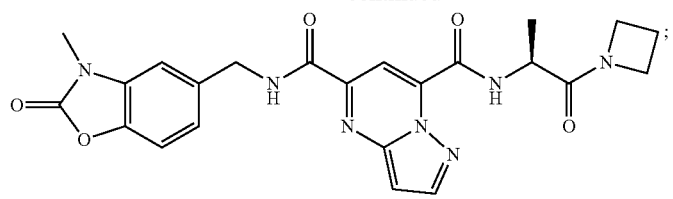
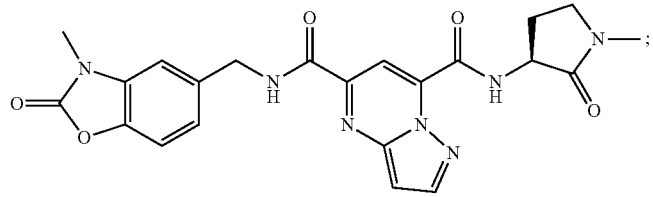
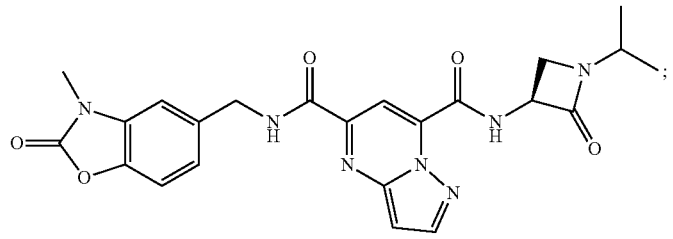
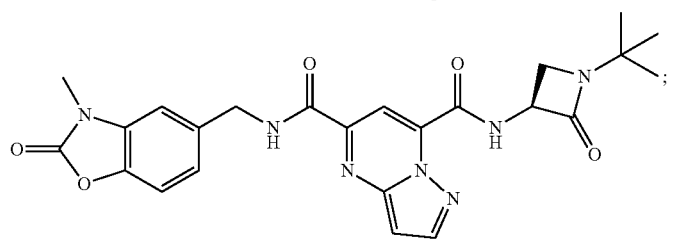
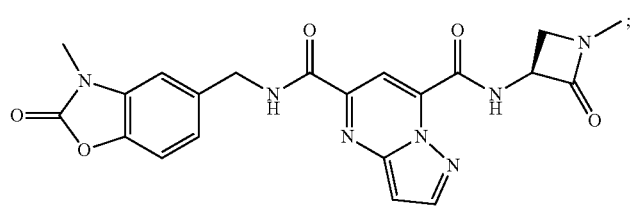
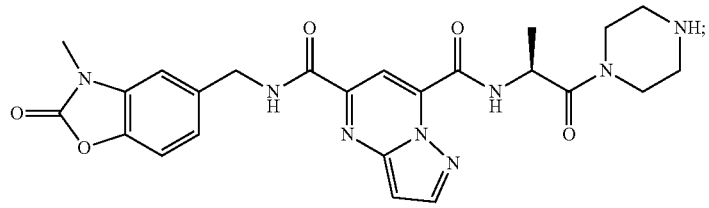
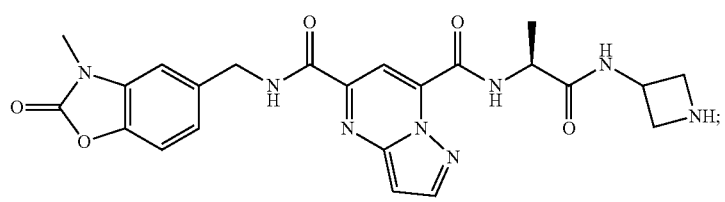
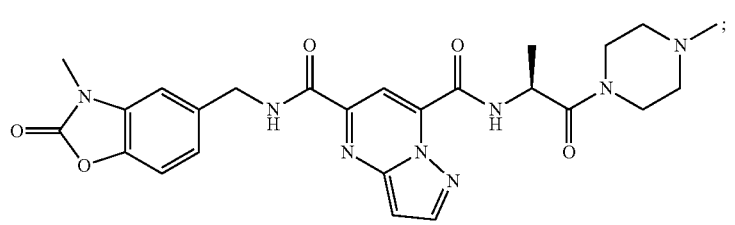

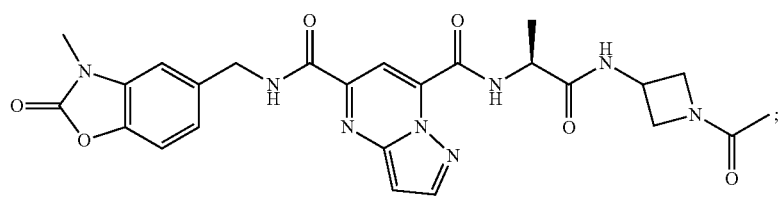
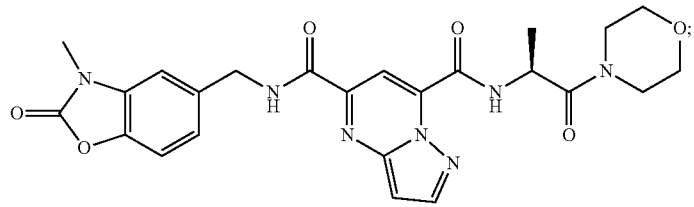
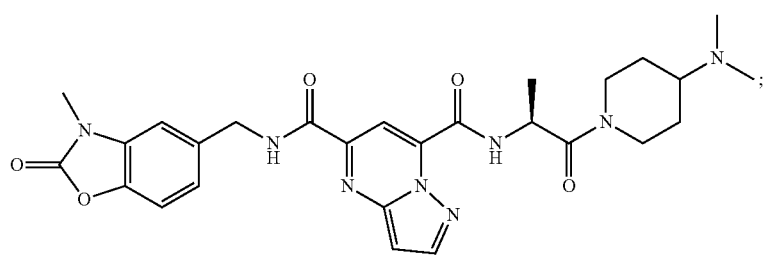
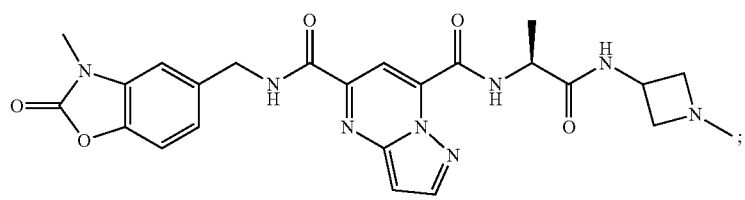
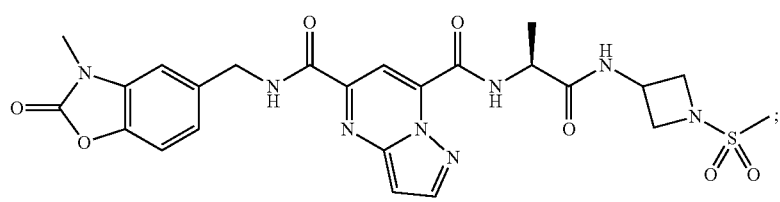
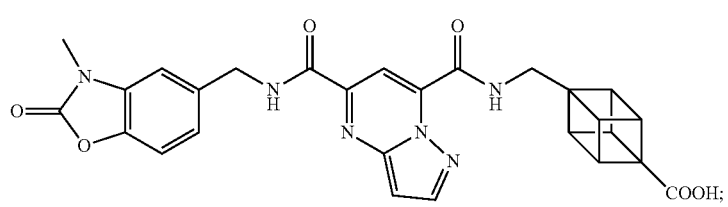
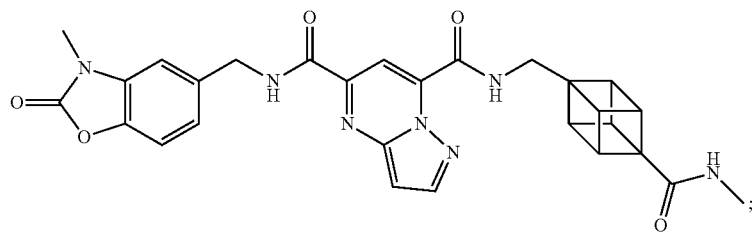
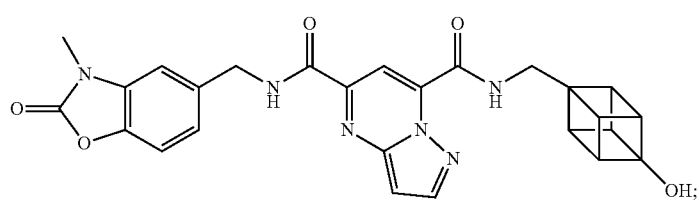

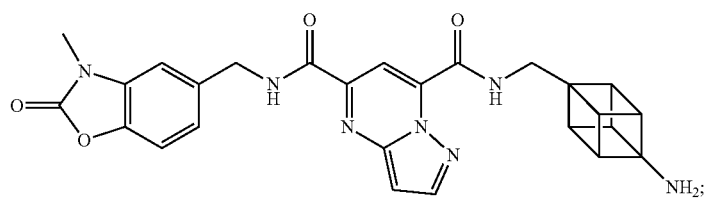
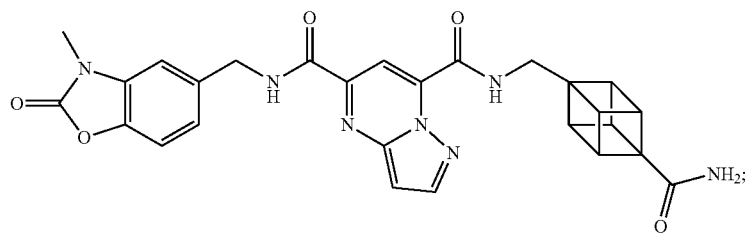
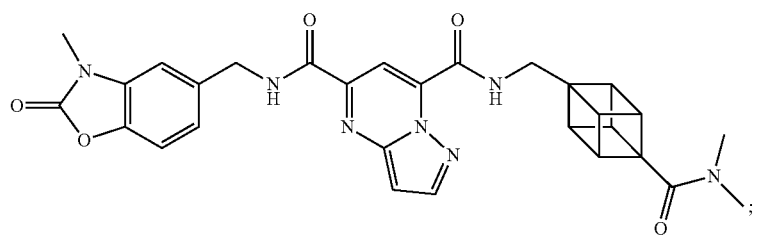
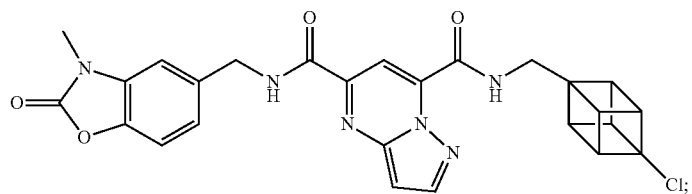
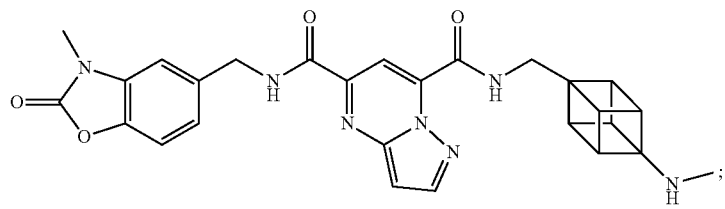
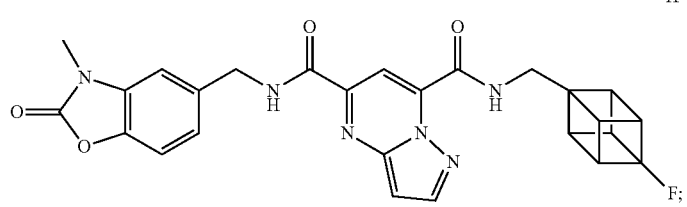
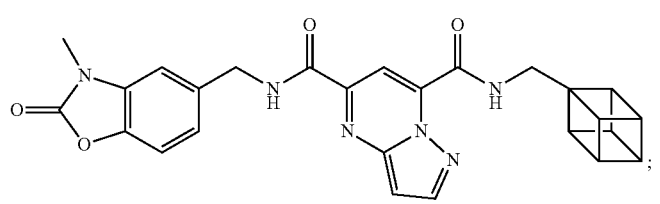
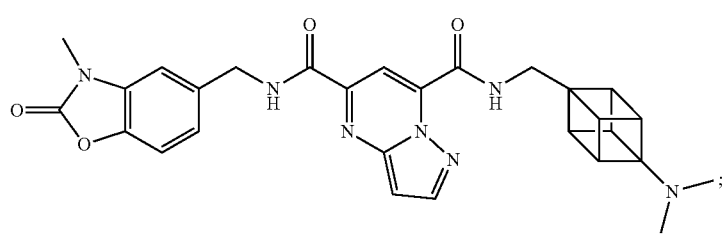

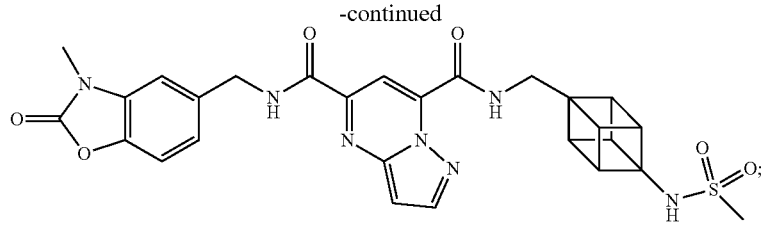
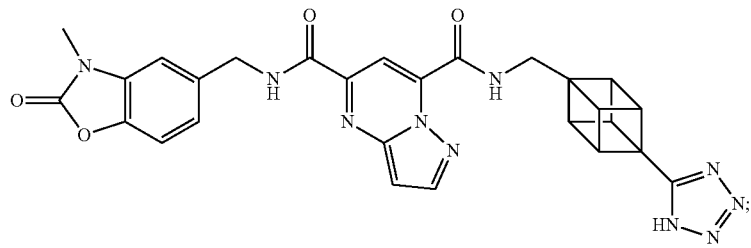
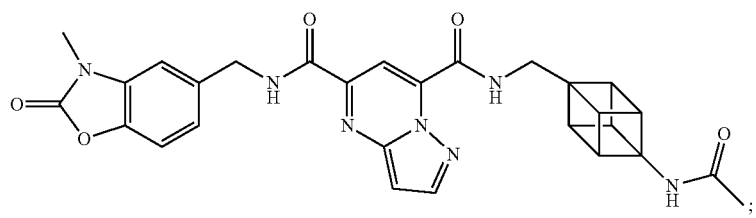
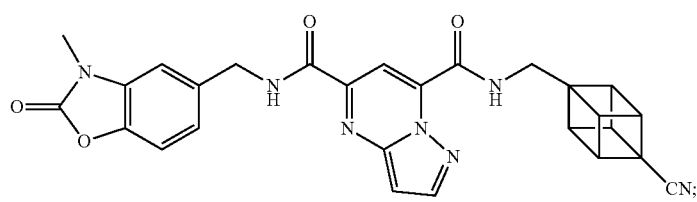
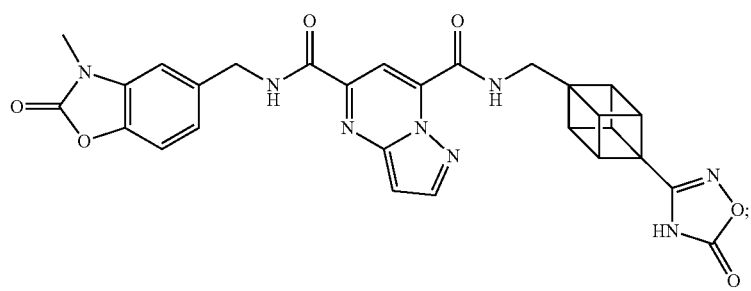
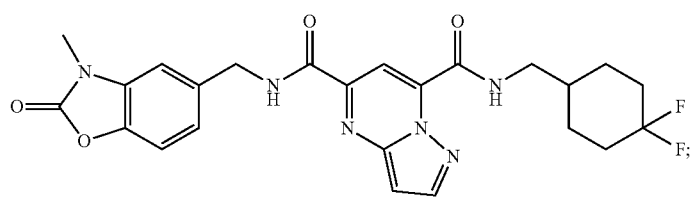
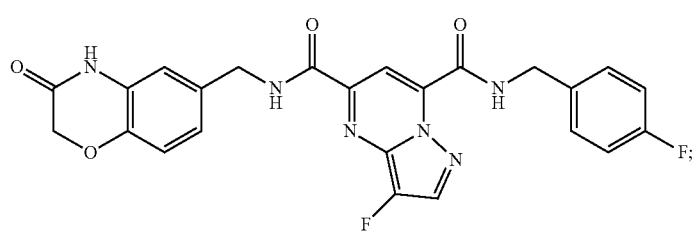

-continued
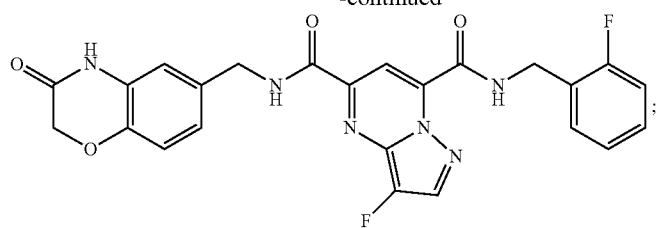
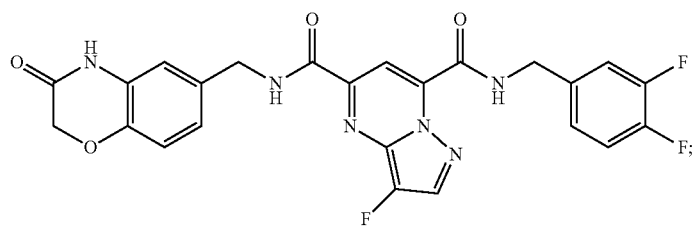
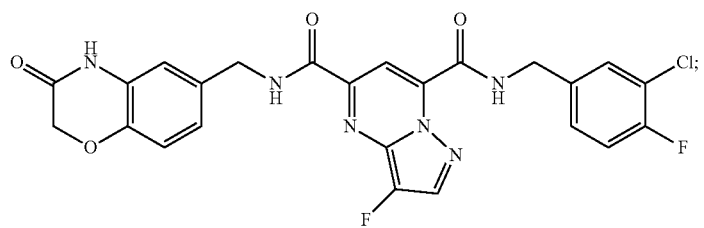
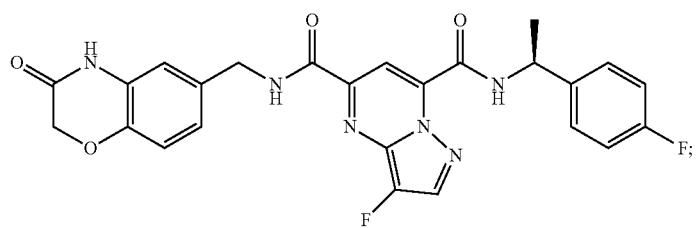
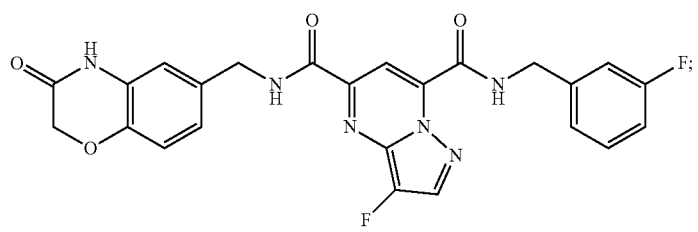
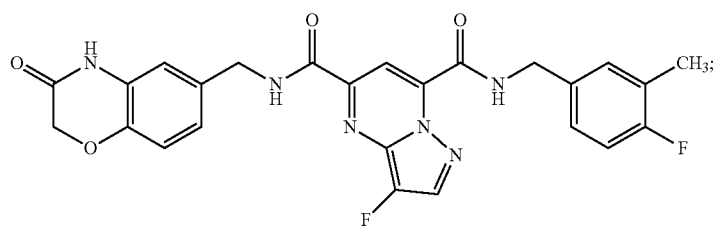
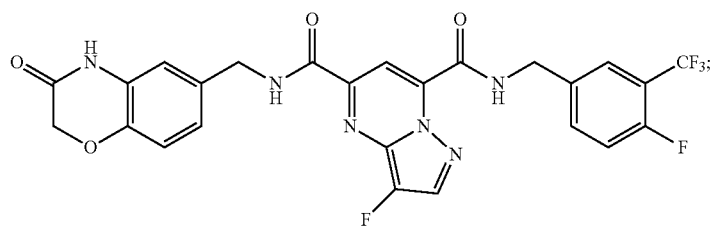

-continued
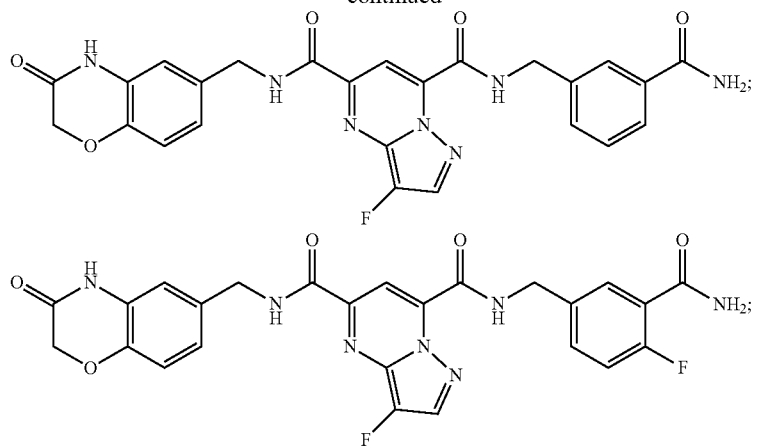
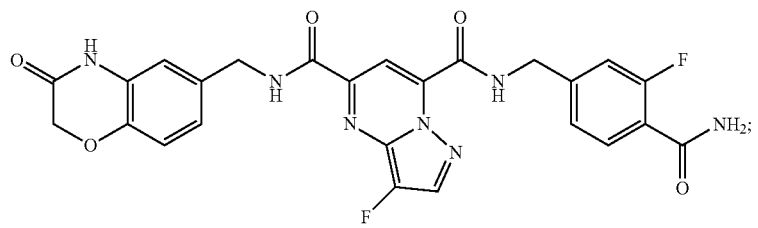
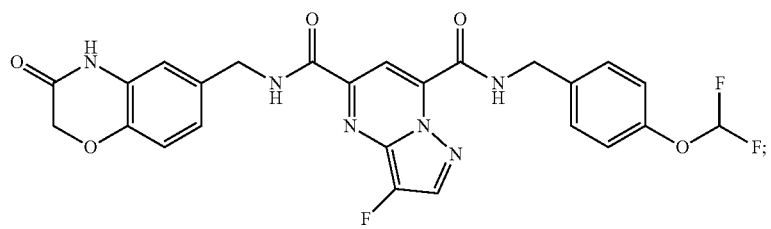
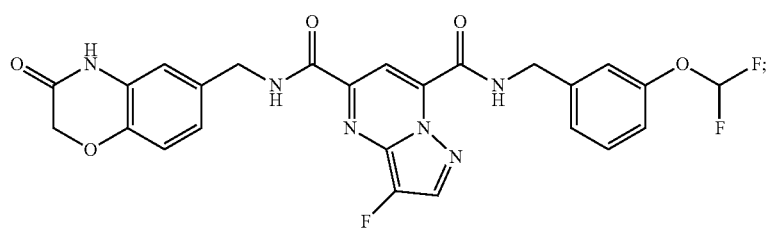
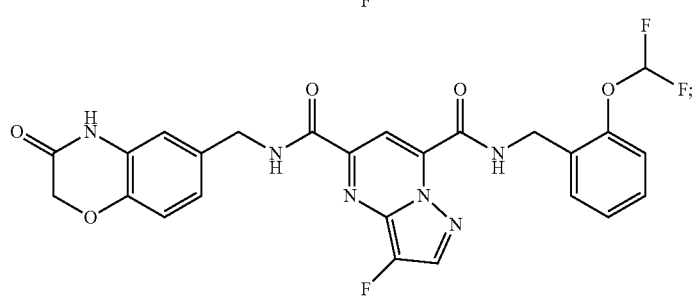
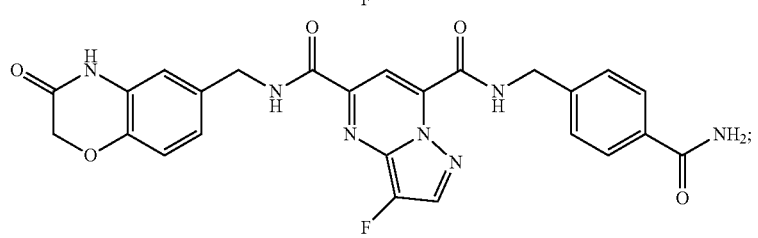

-continued
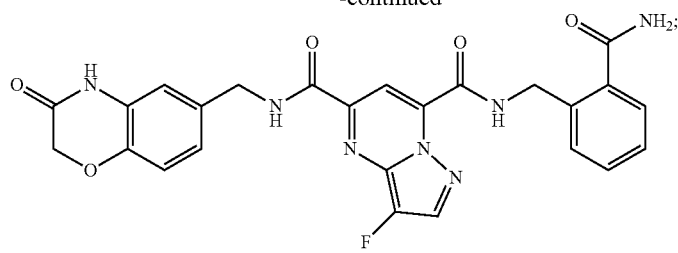
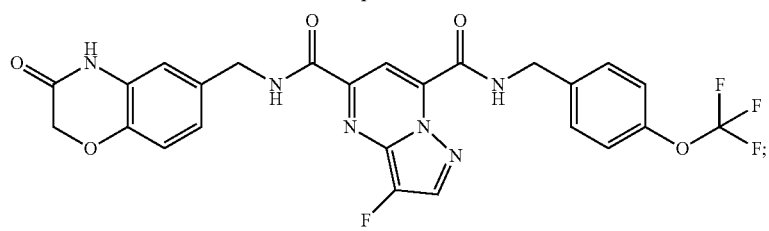
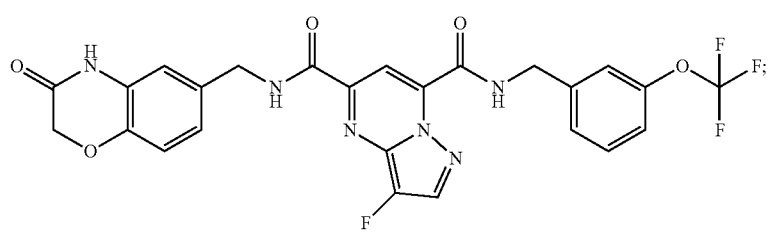
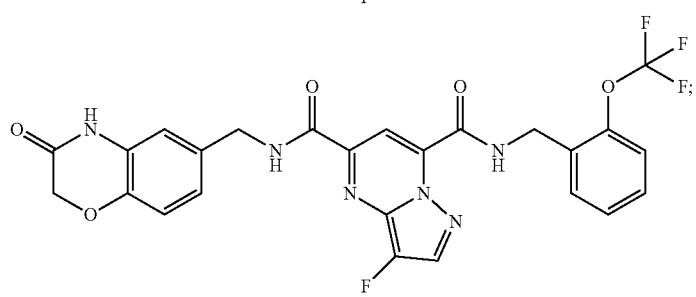
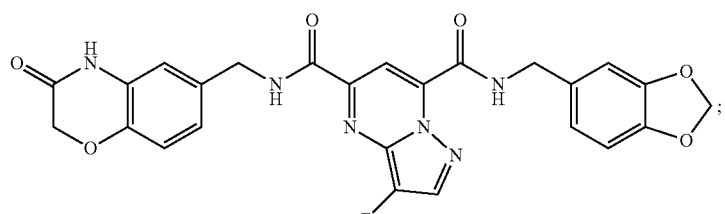
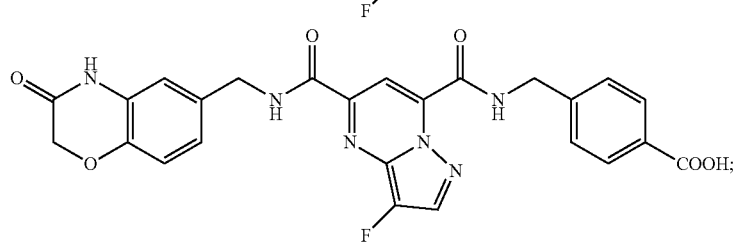
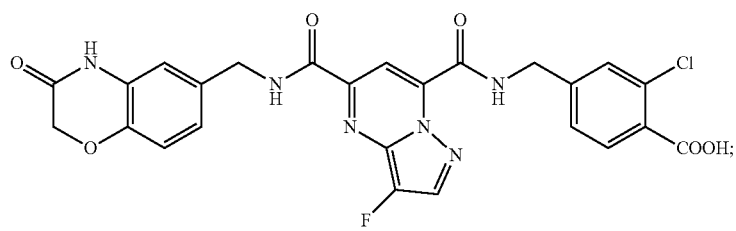

-continued
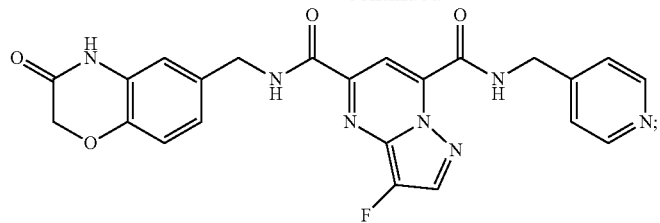
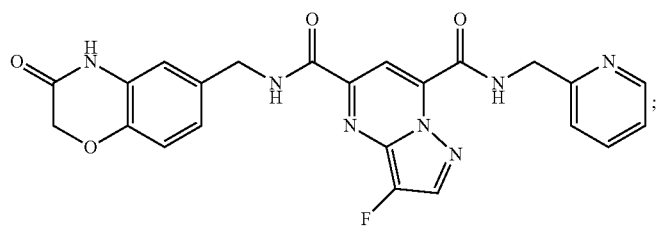
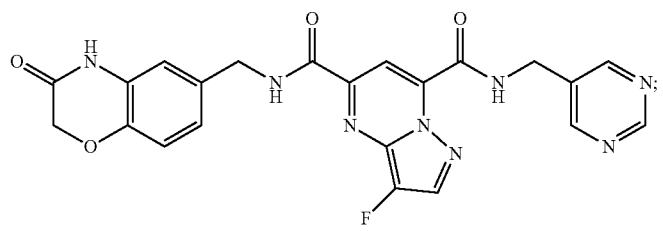
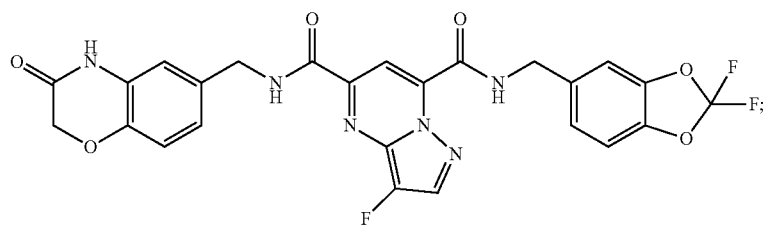
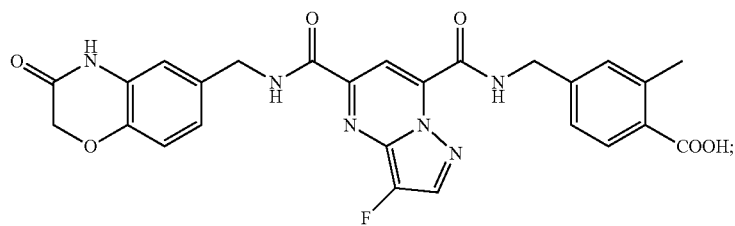
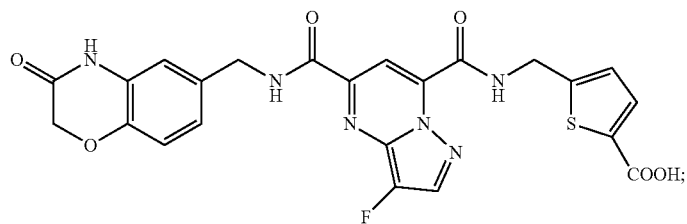
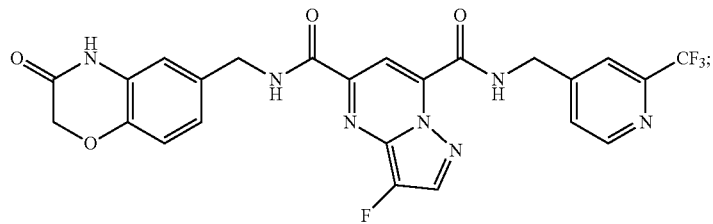

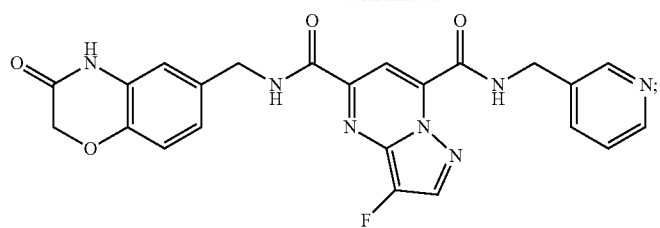
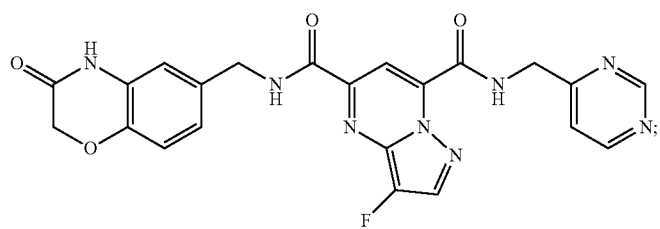
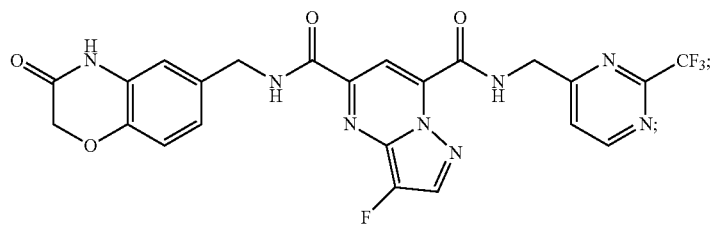
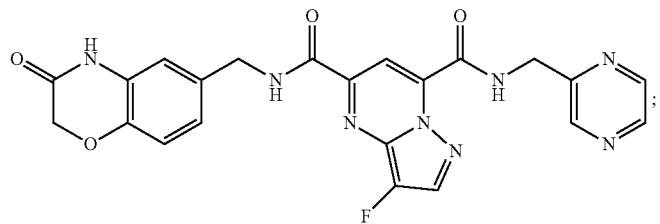
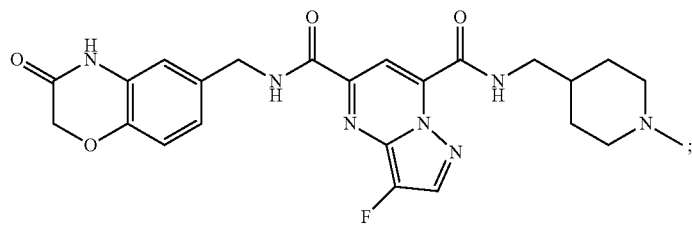
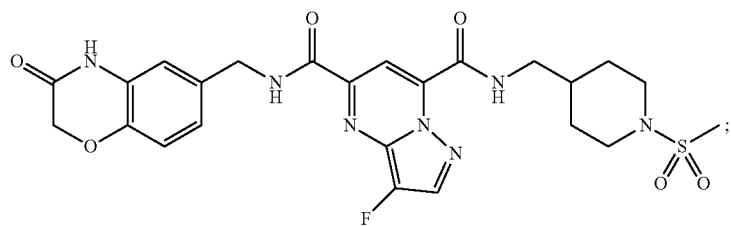
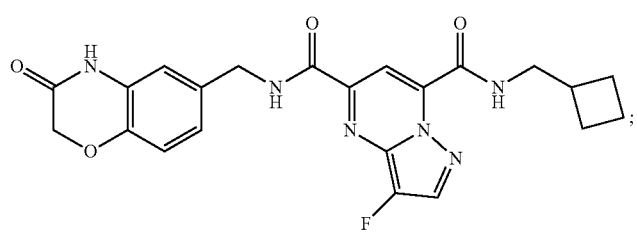

-continued
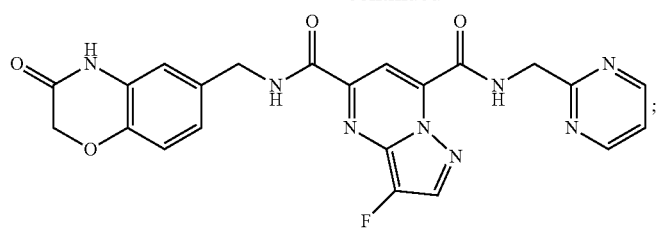
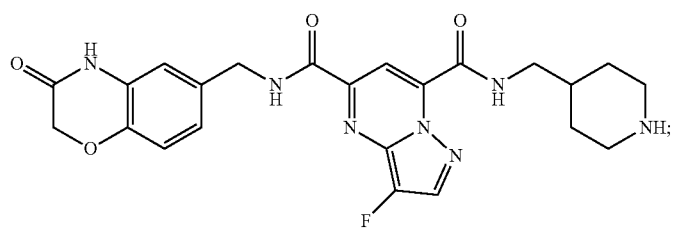
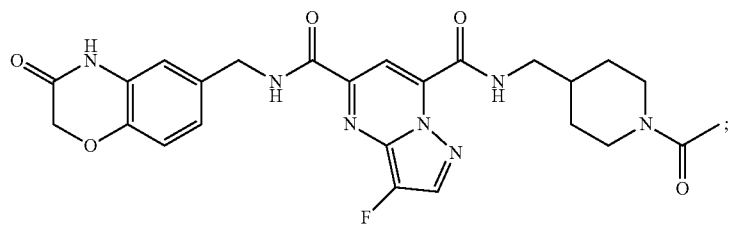
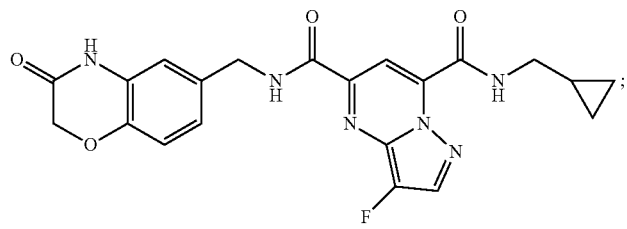
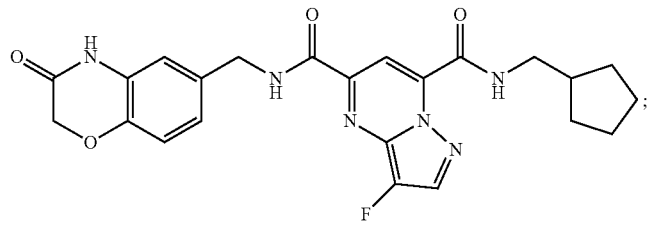
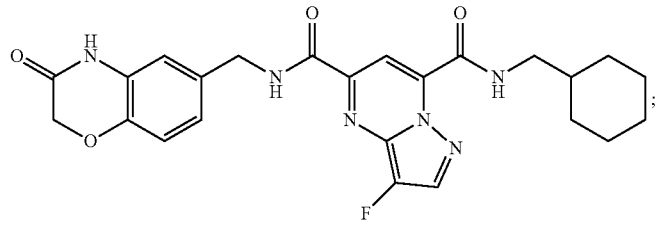
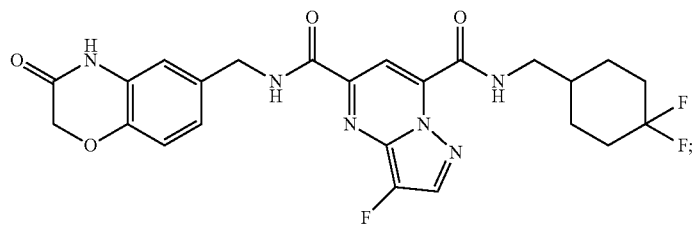

-continued
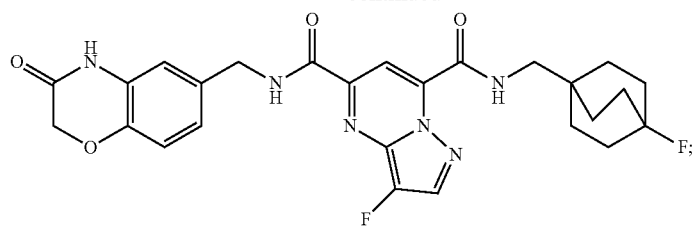
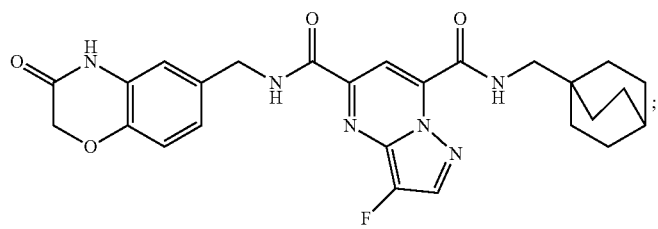
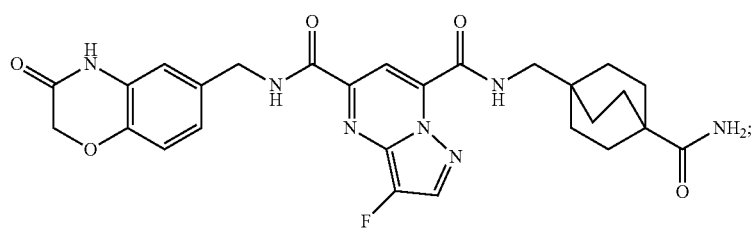
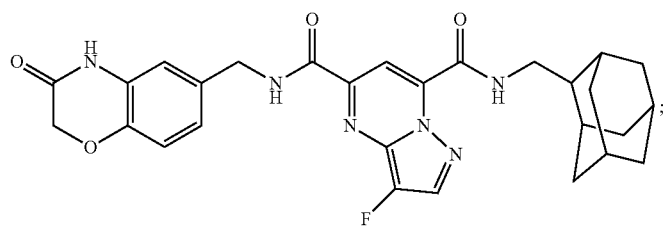
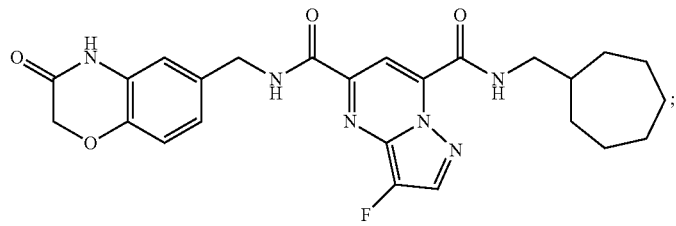
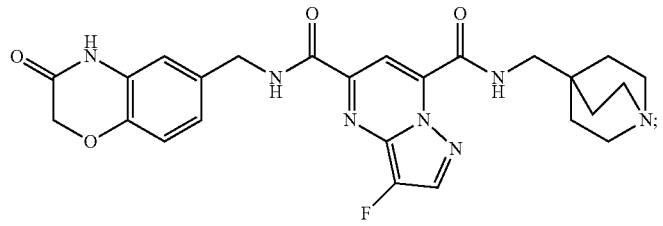
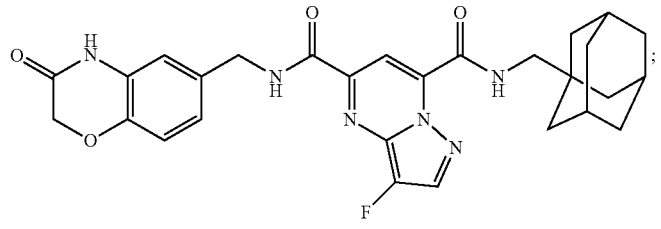

-continued
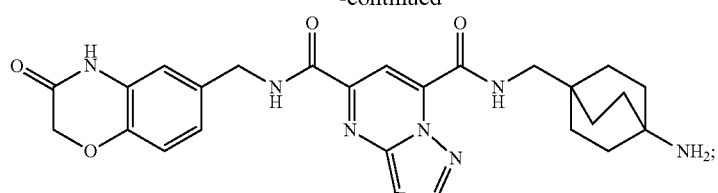
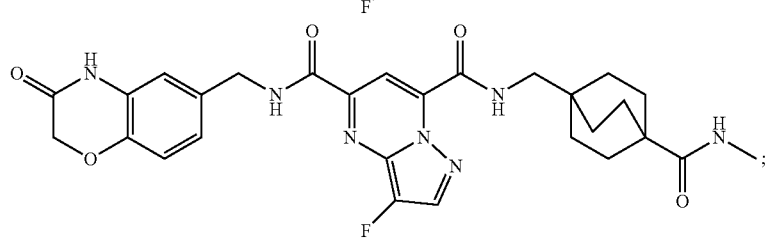
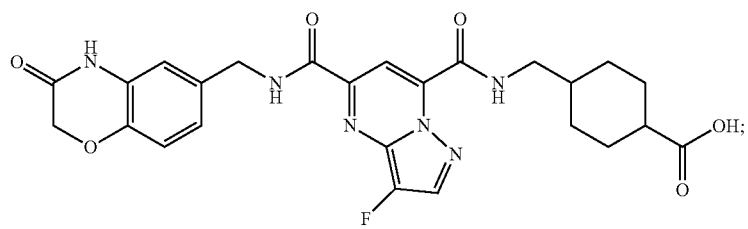
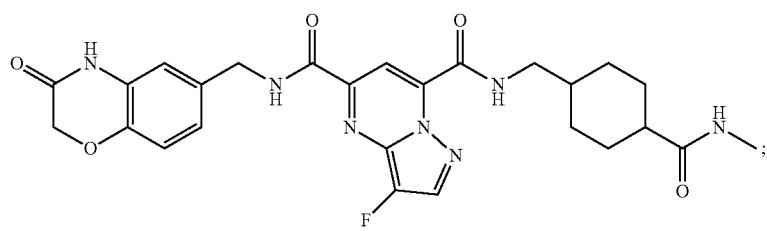
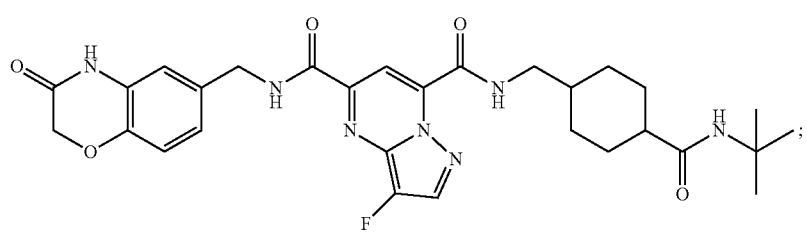
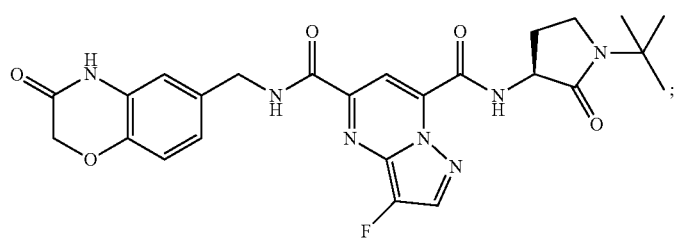
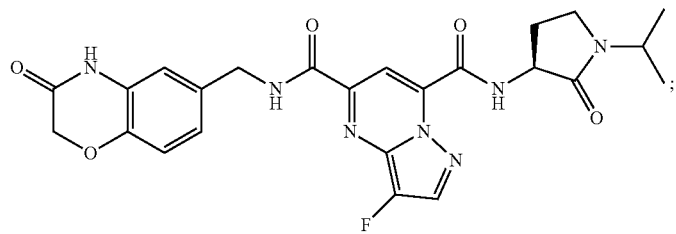

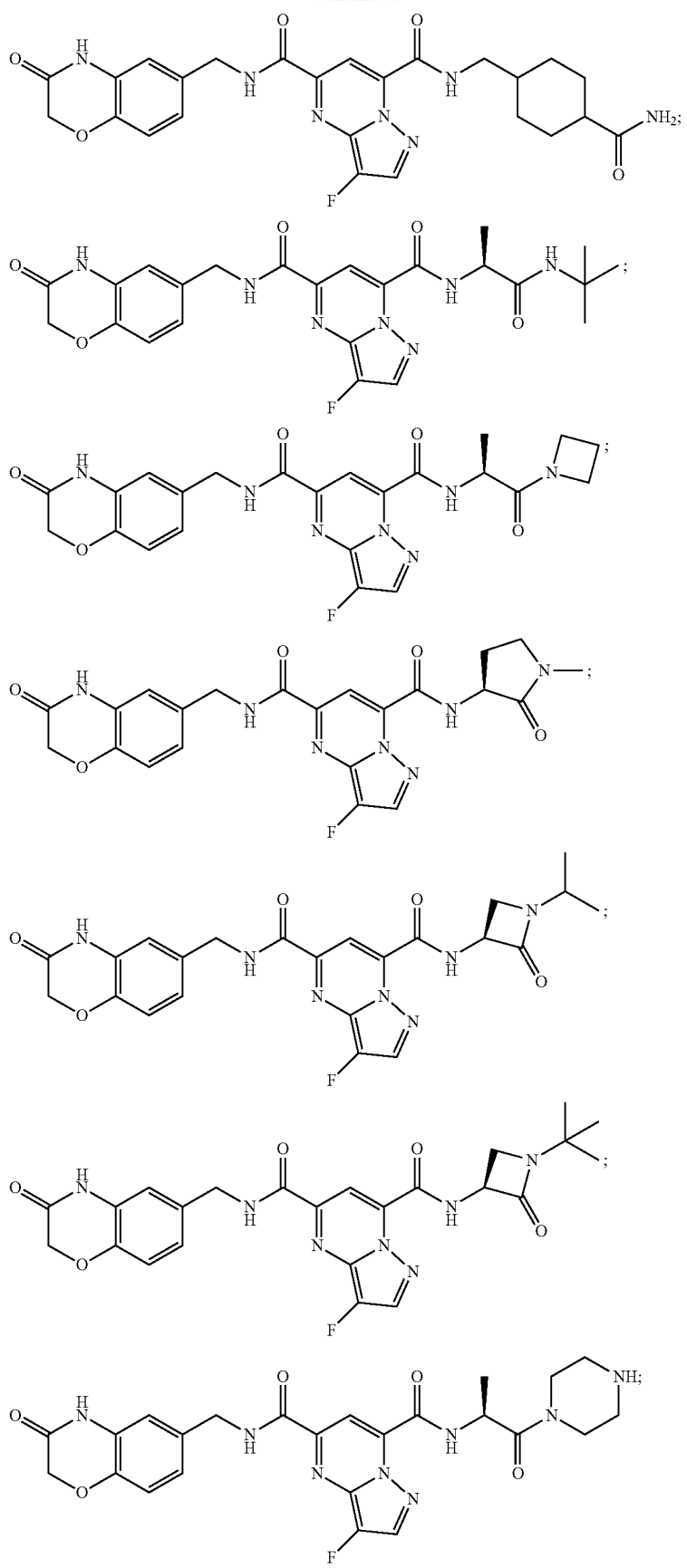

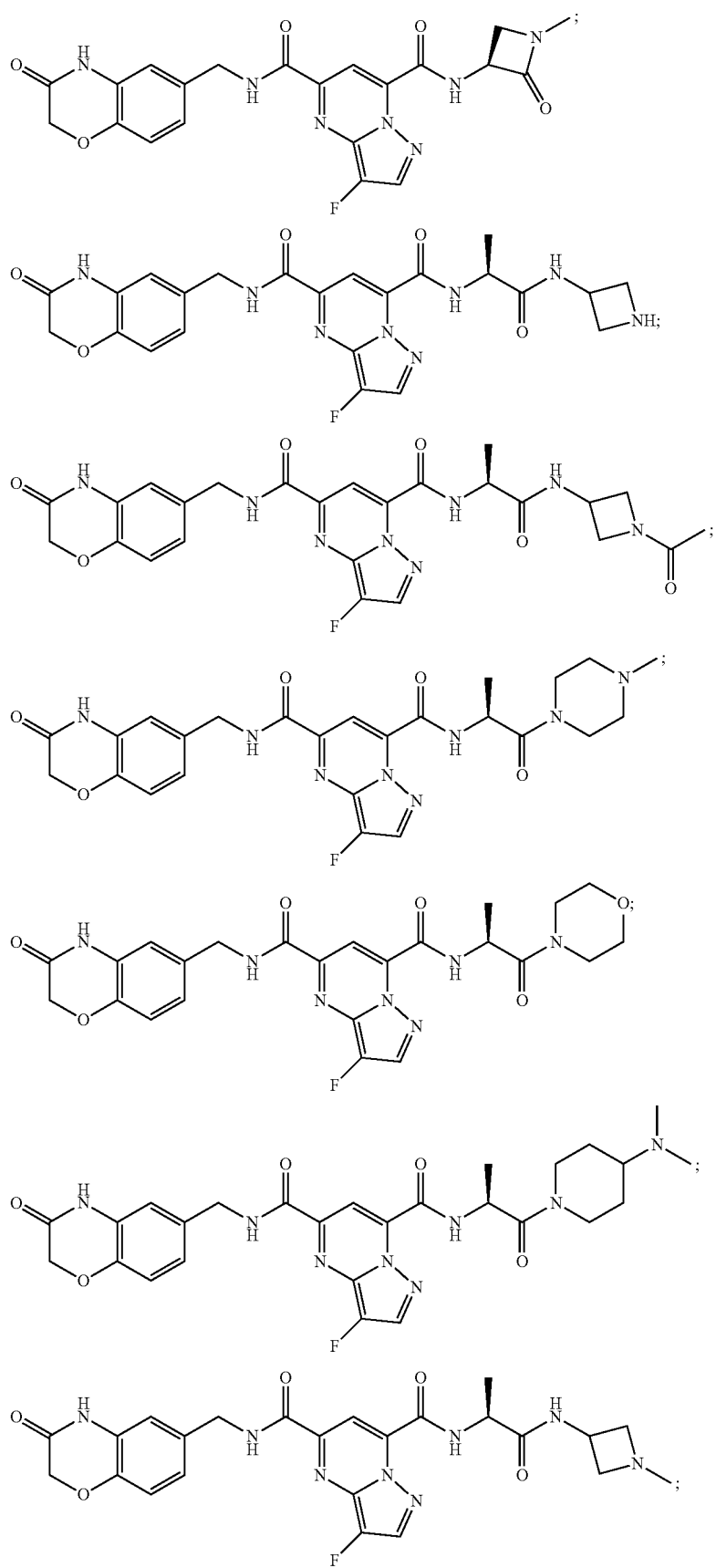

-continued
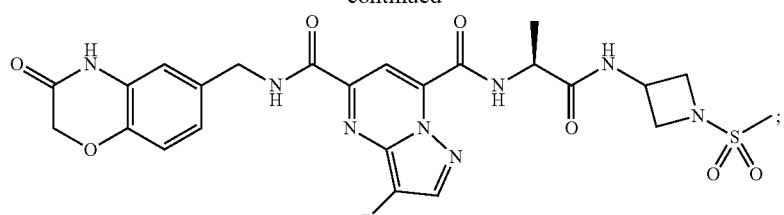
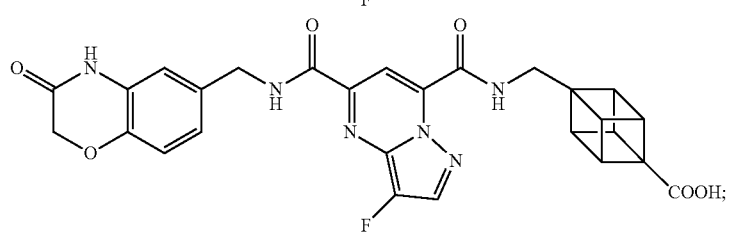
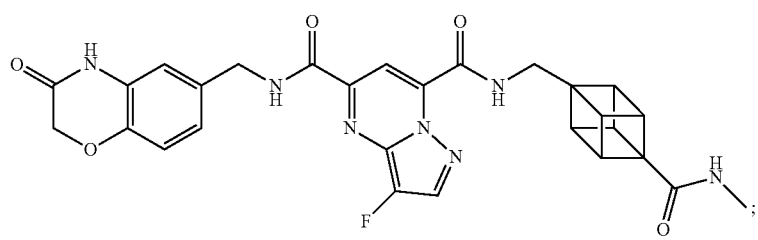
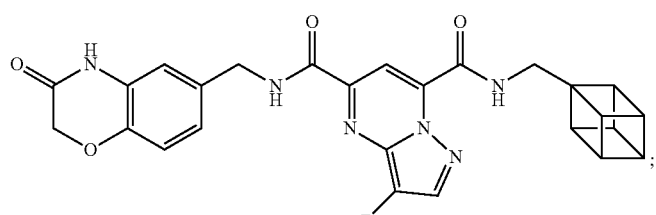
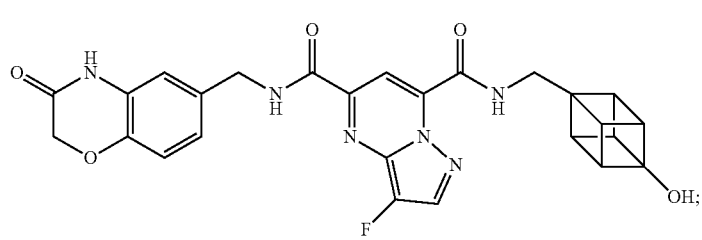
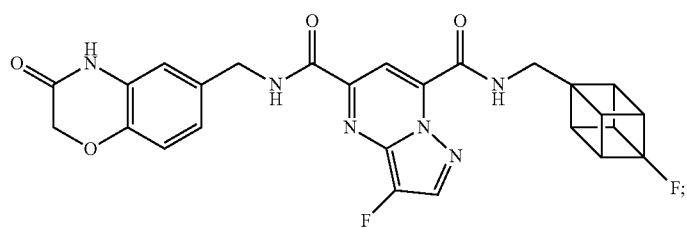
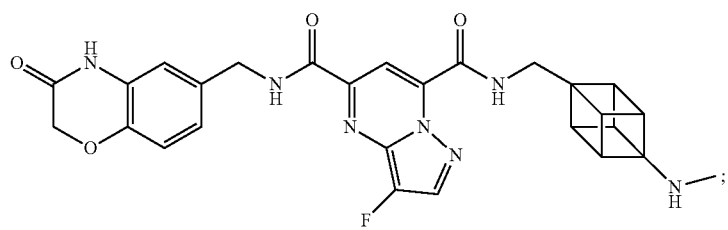

-continued
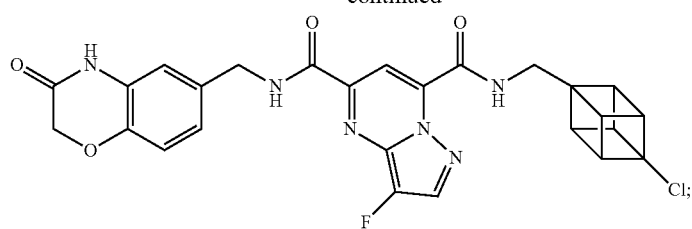
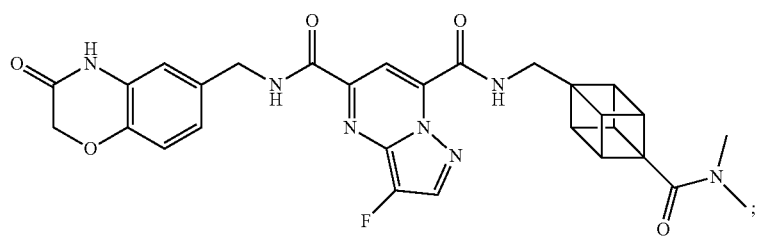
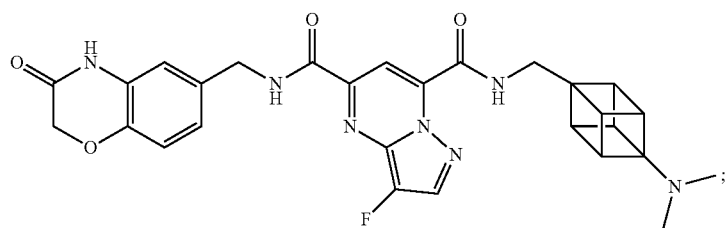
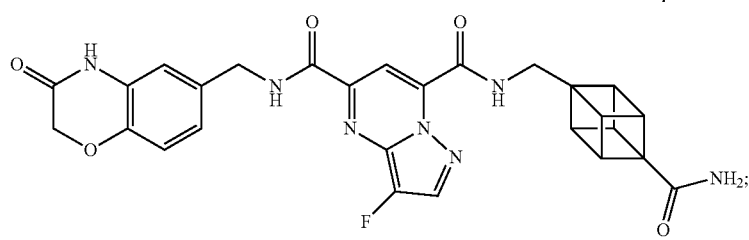
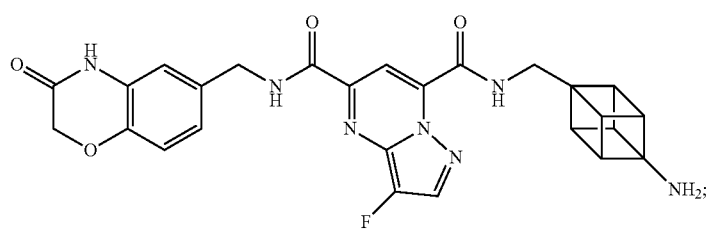
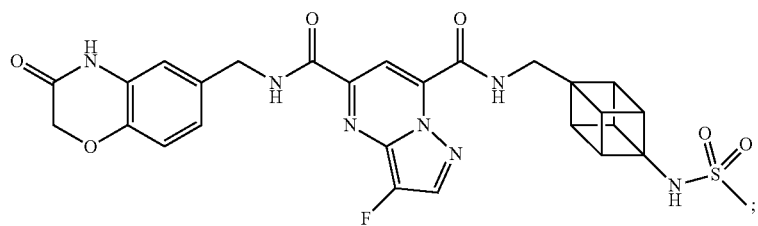
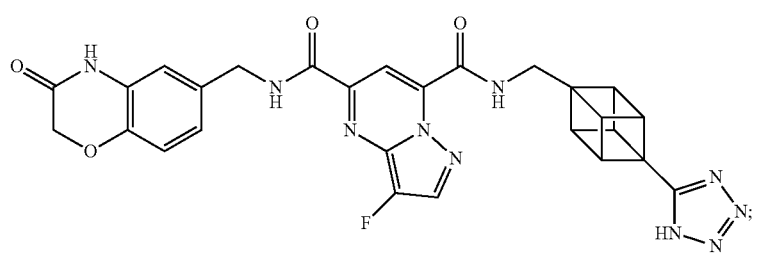

-continued
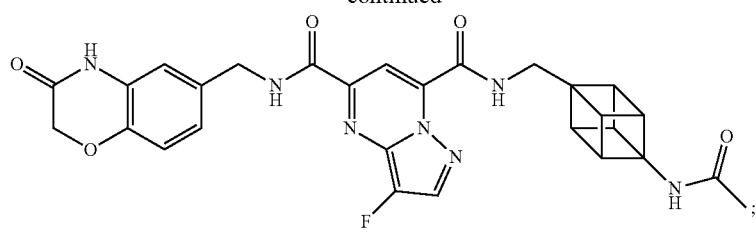
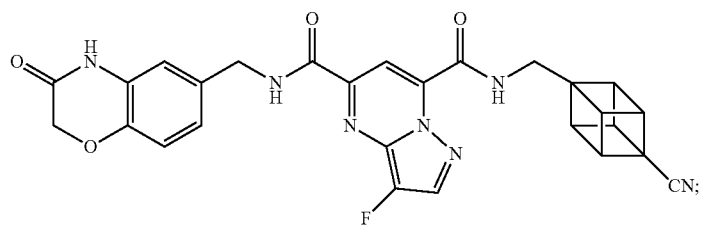
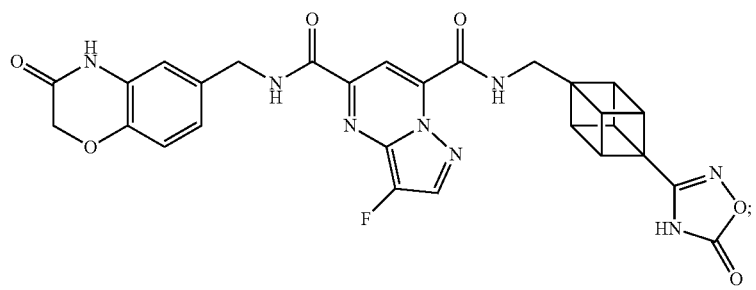
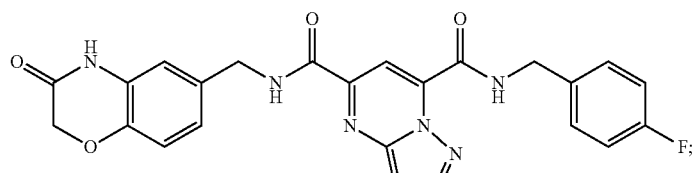
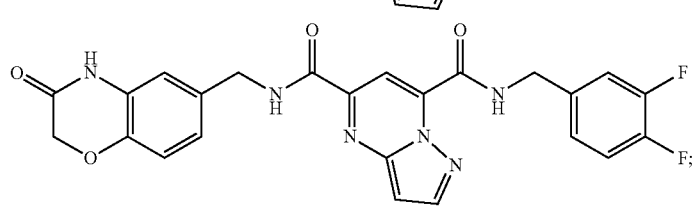
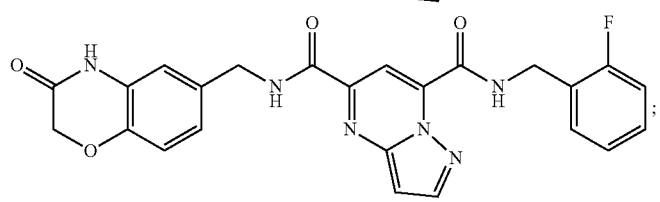
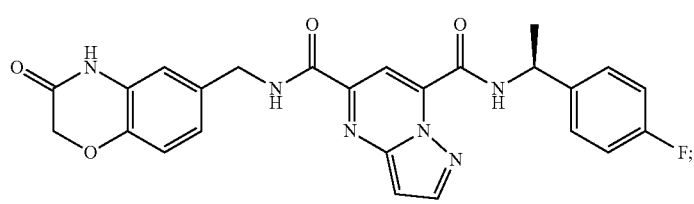
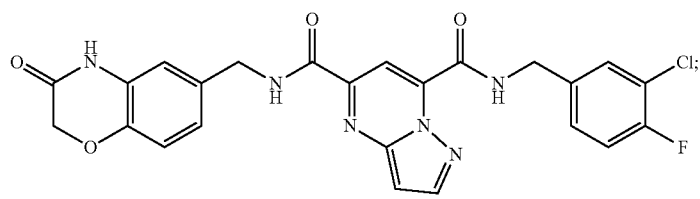

-continued
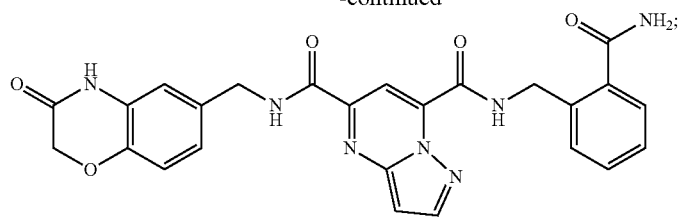
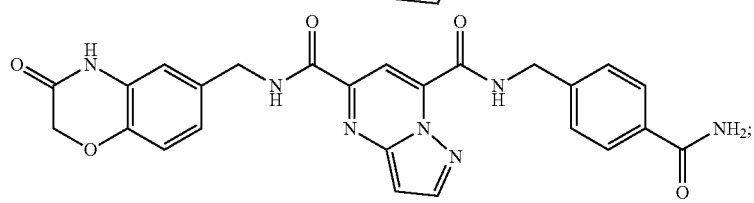
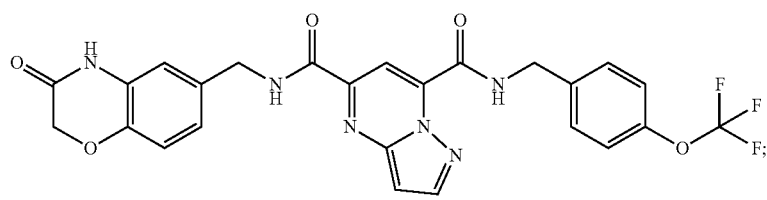
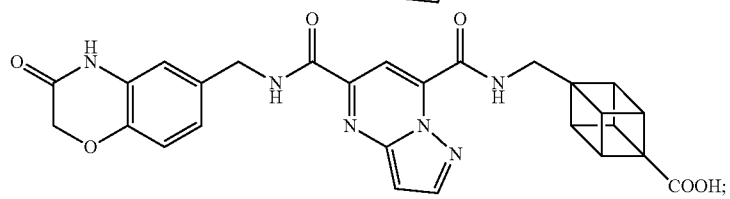
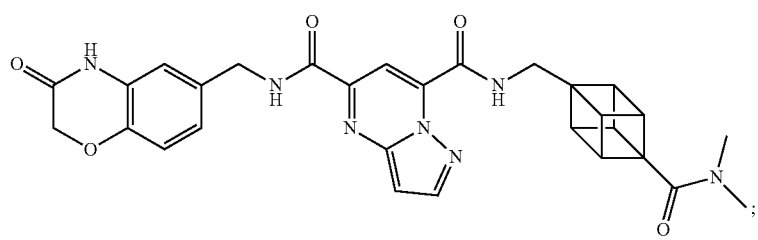
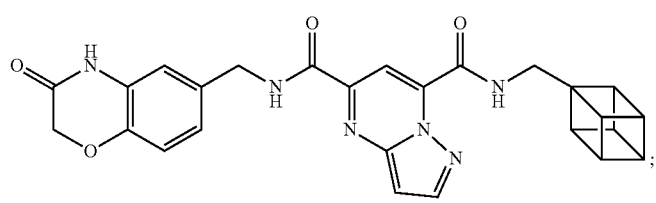
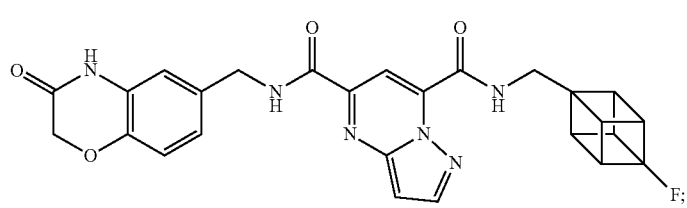
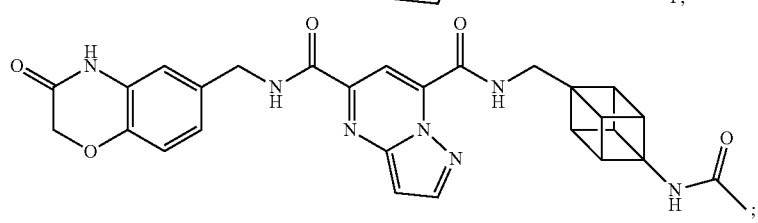

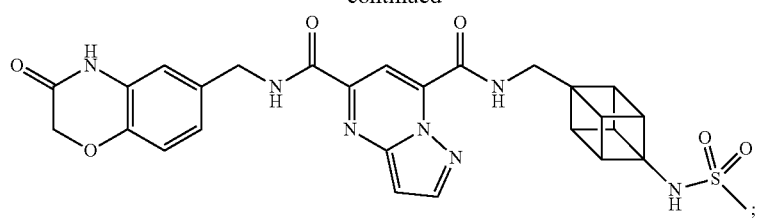
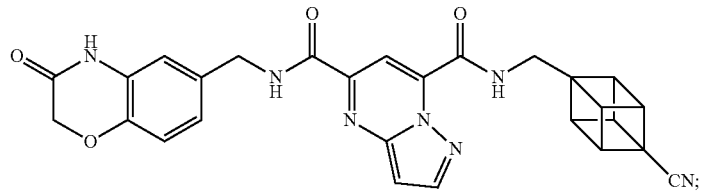
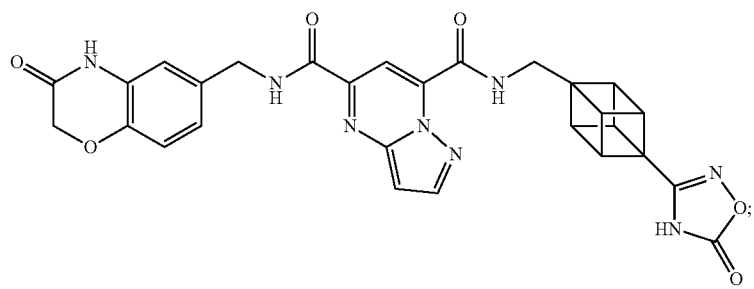
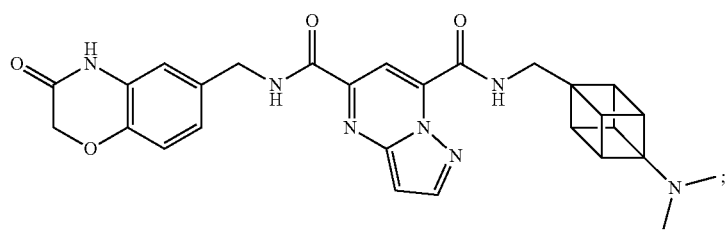
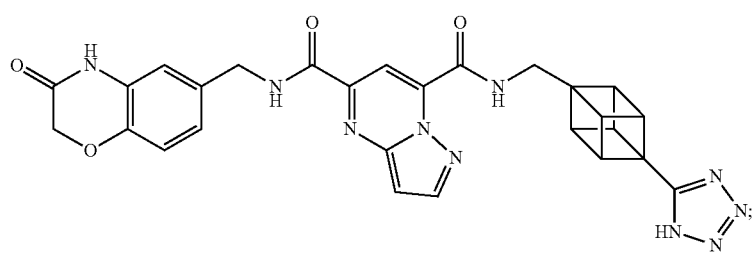
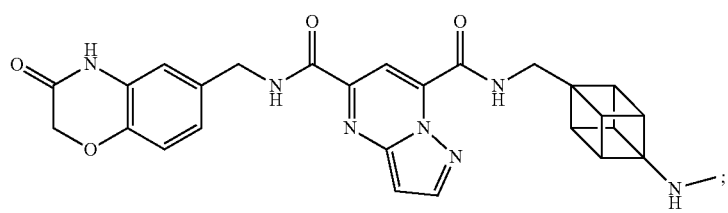
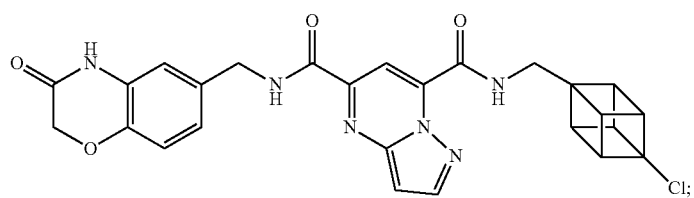

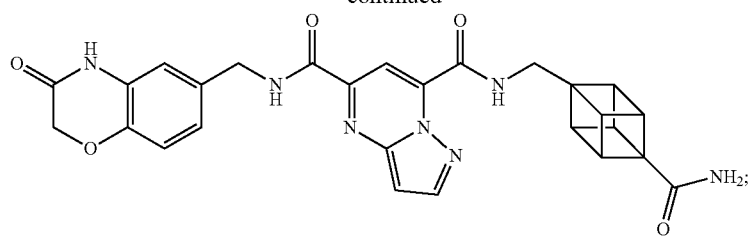
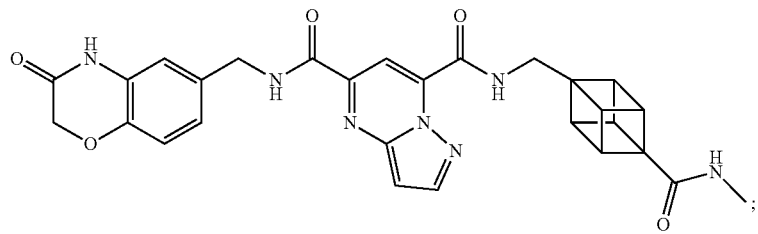
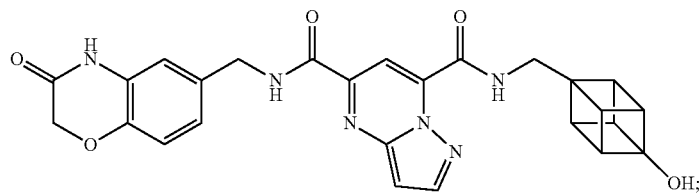
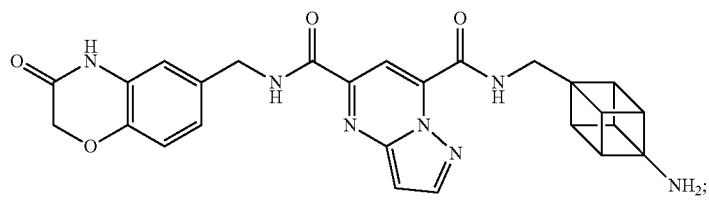
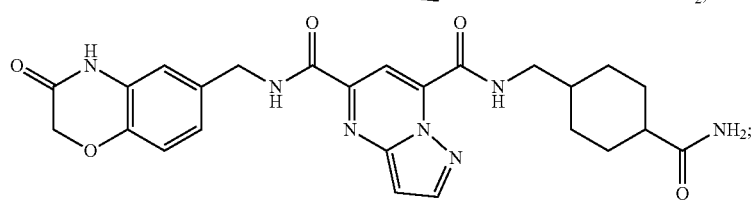
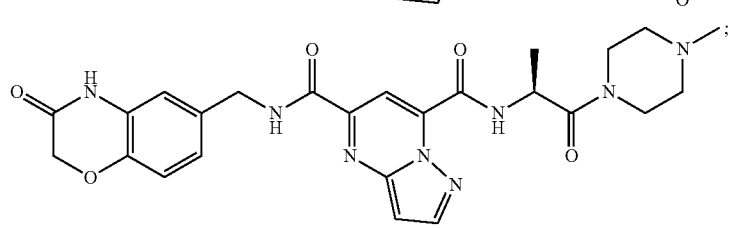
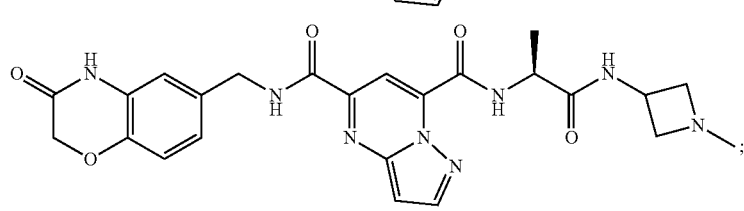
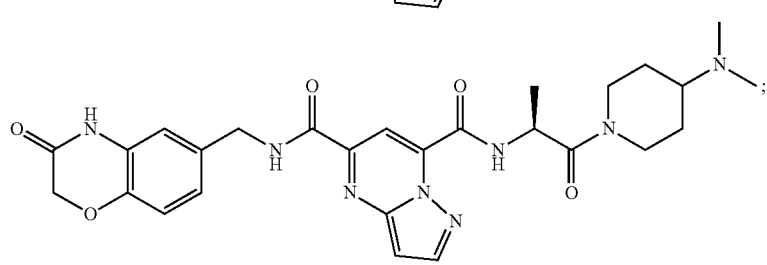

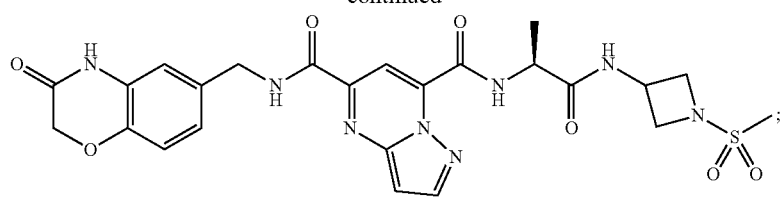
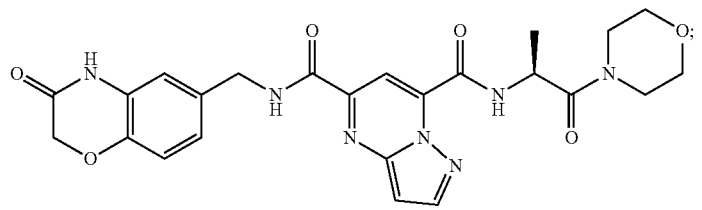
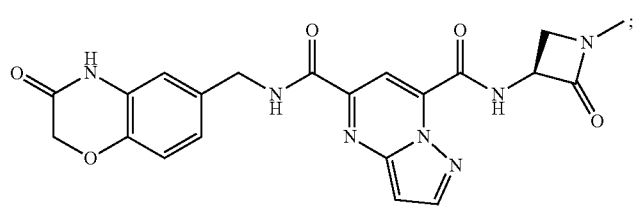
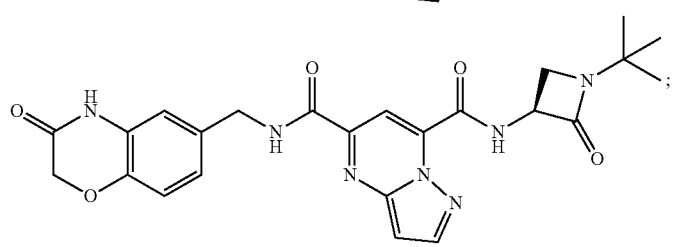
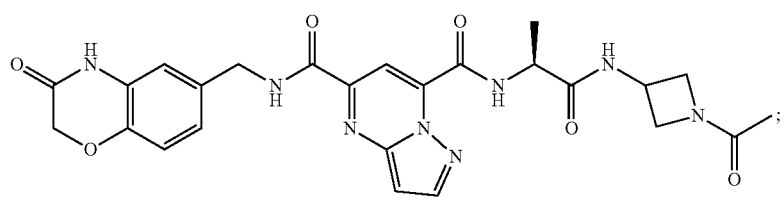
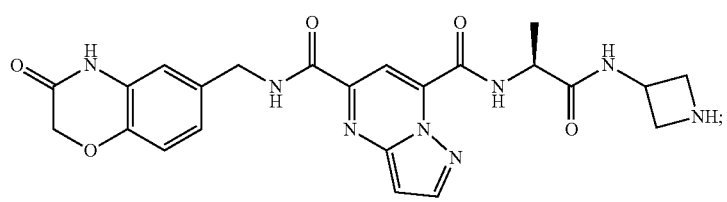
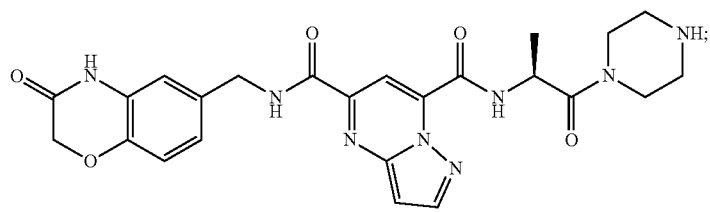
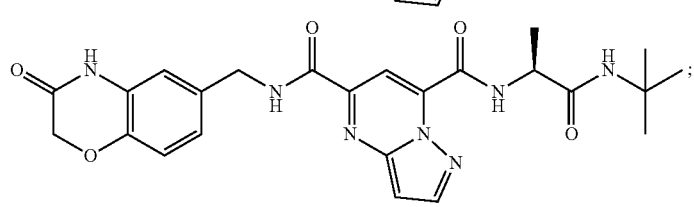

-continued
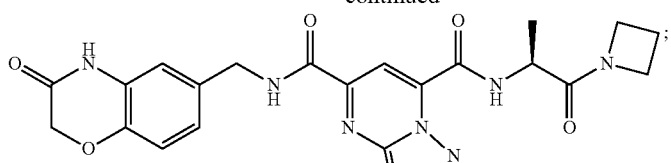
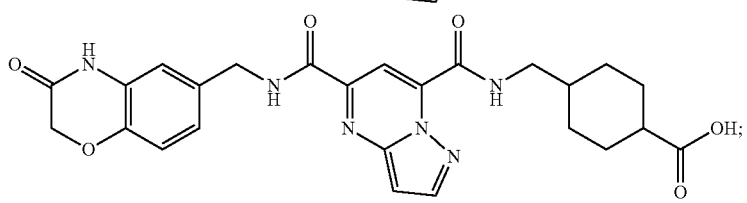
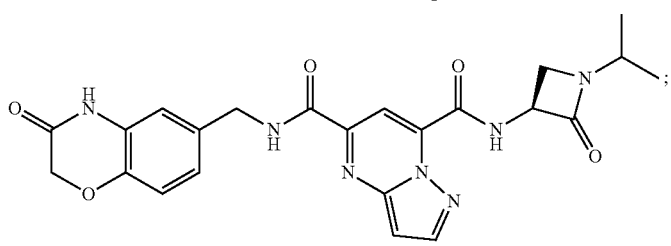
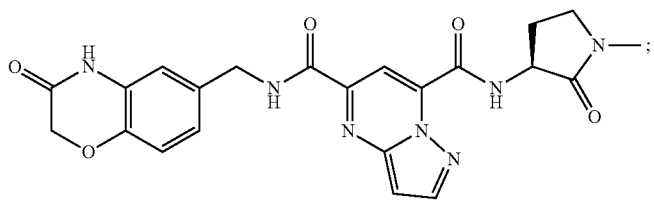
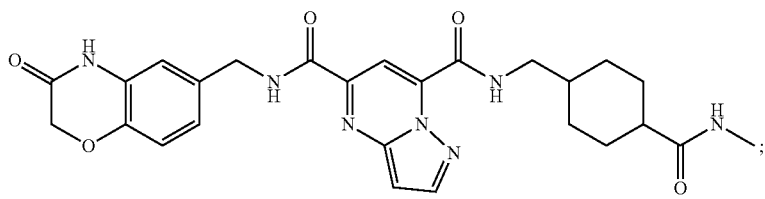
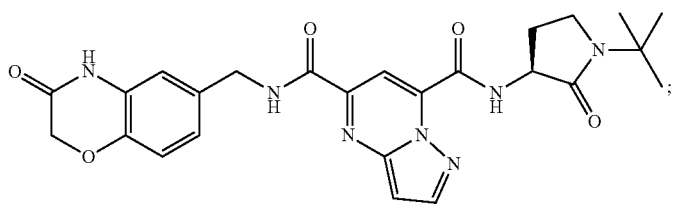
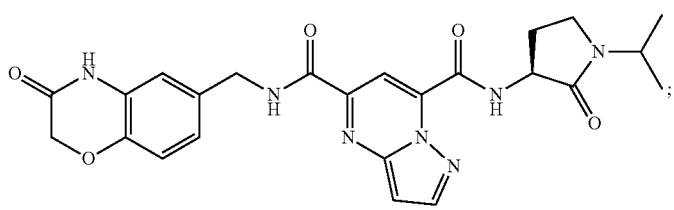
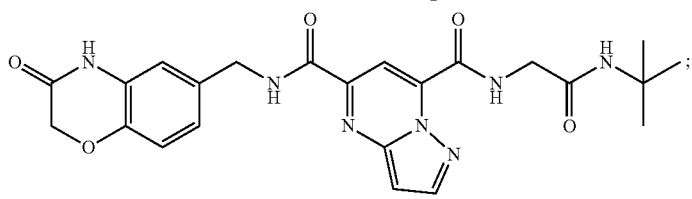

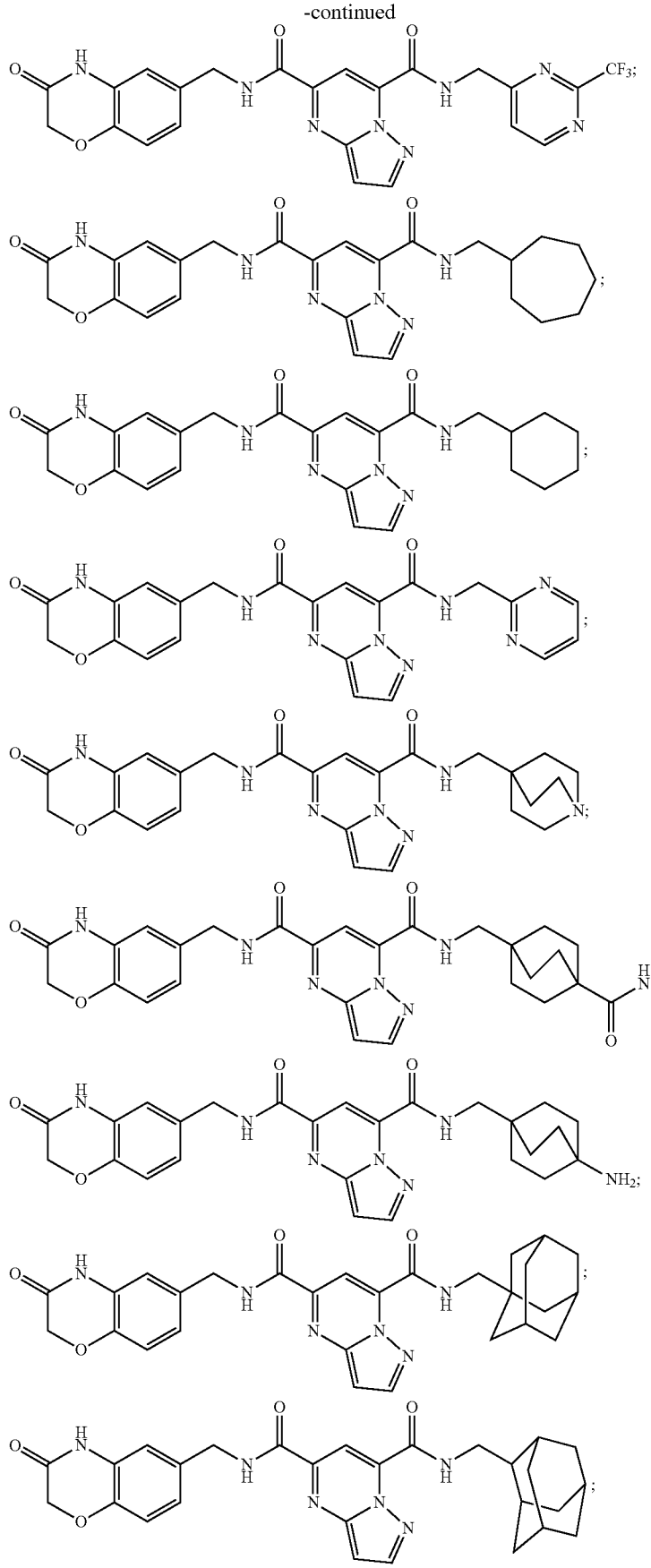

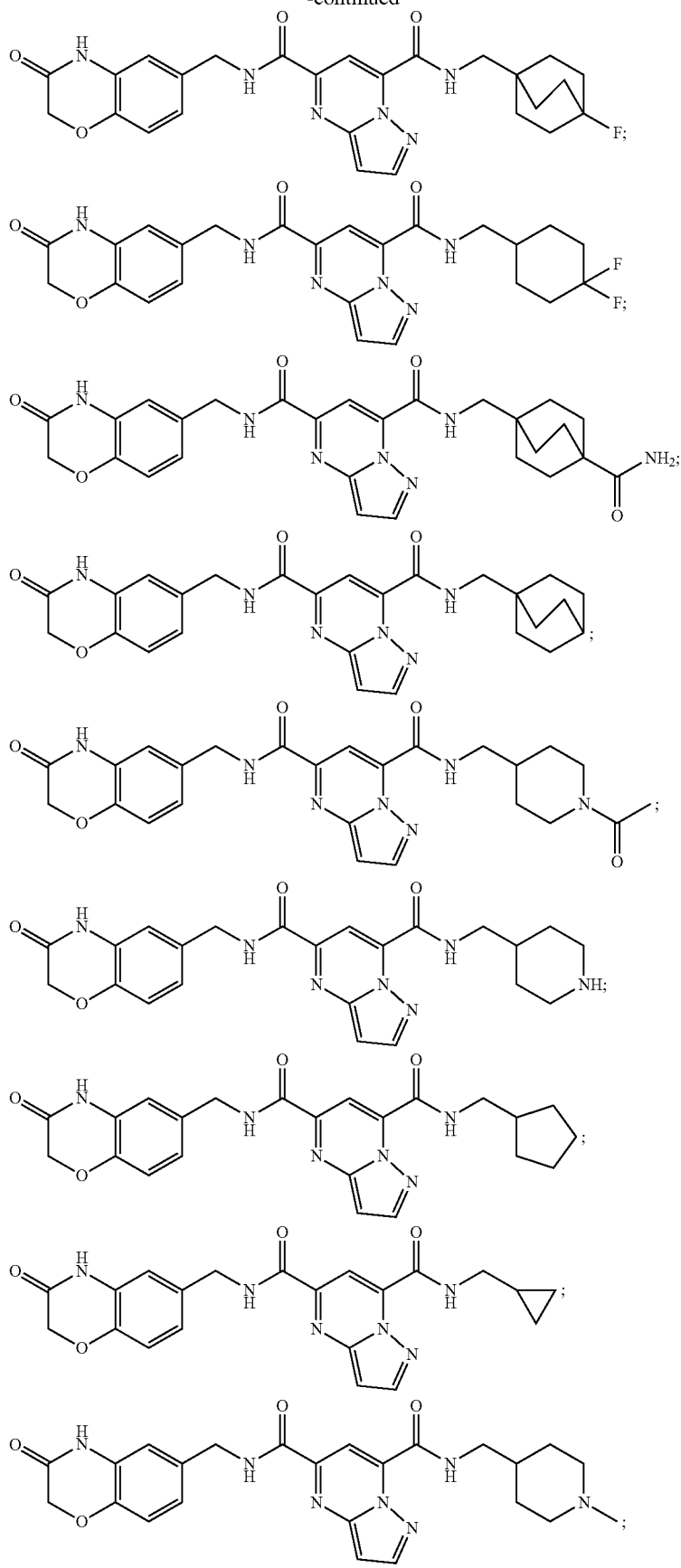

-continued
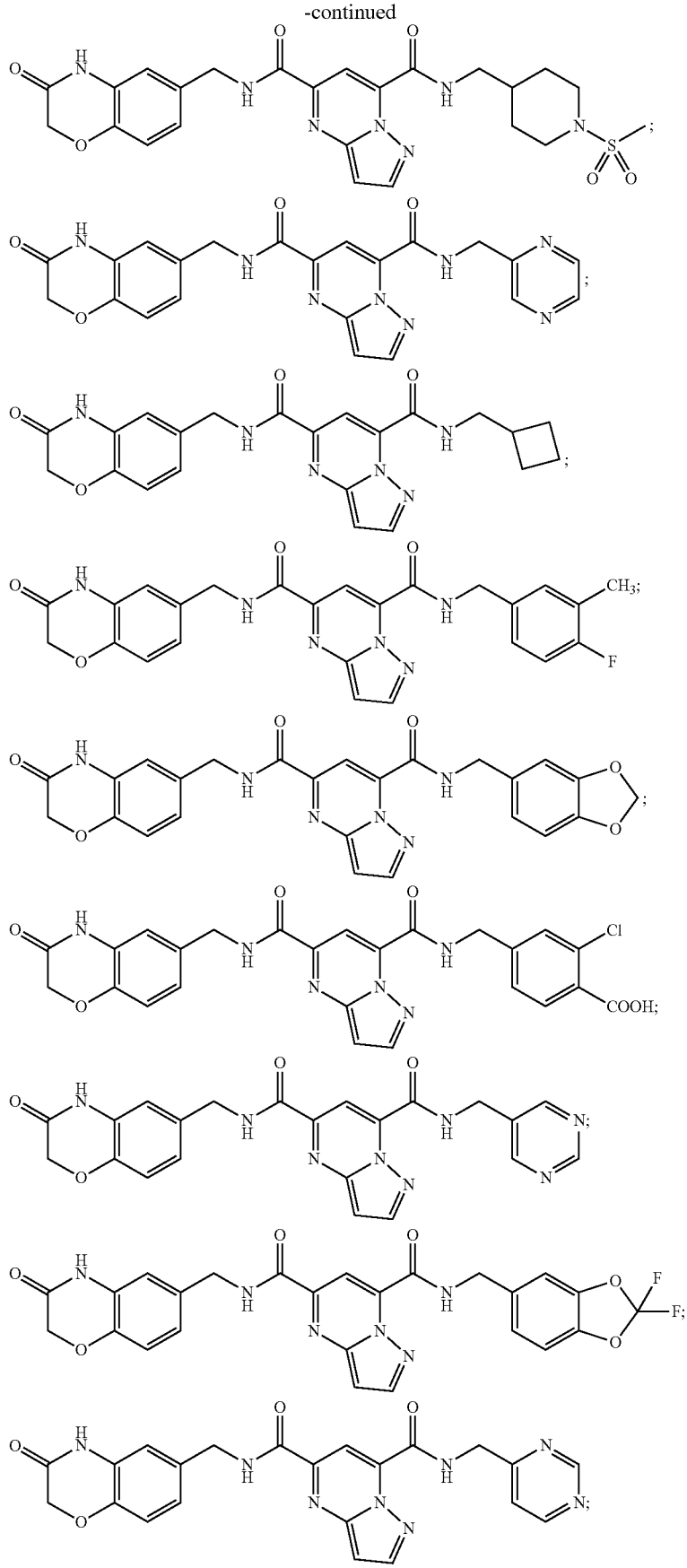

-continued
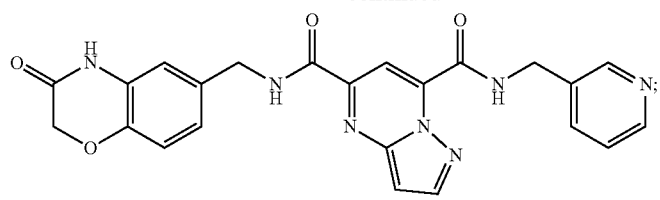
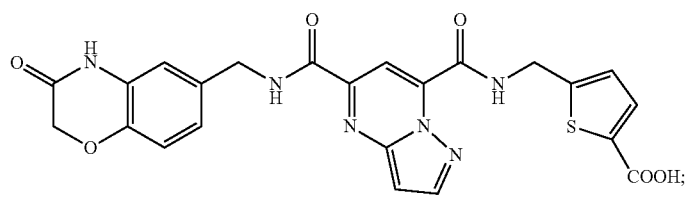
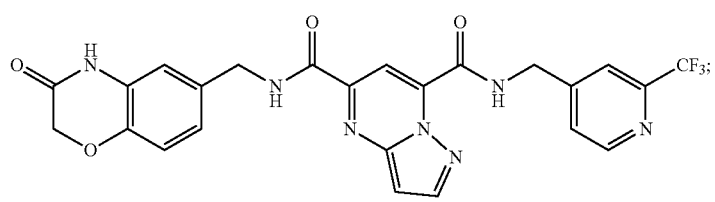
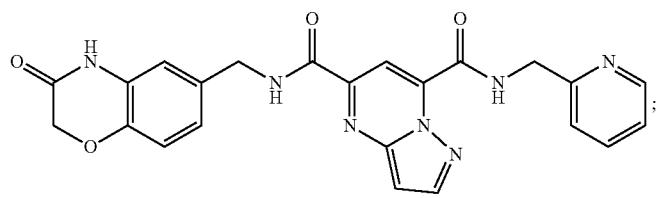
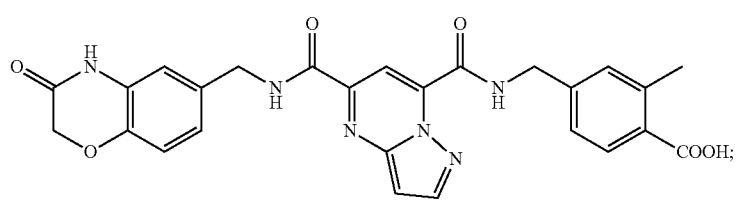
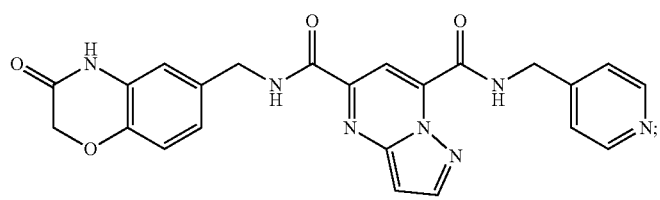
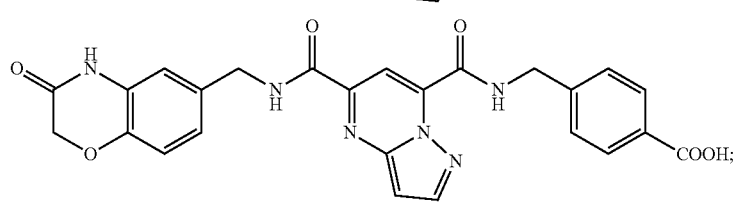
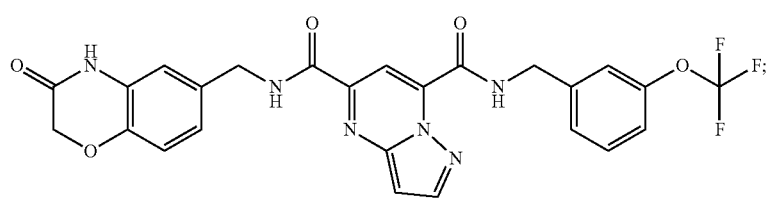

-continued
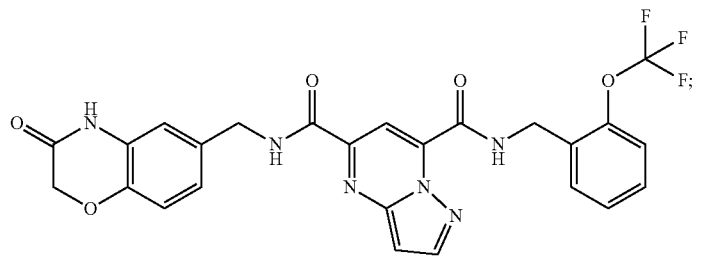
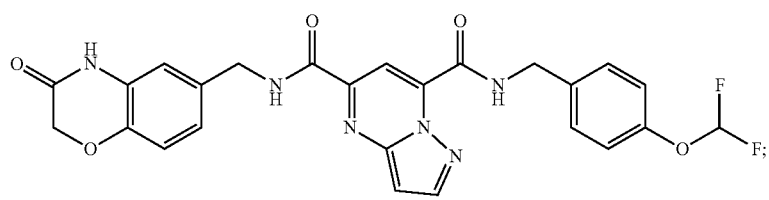
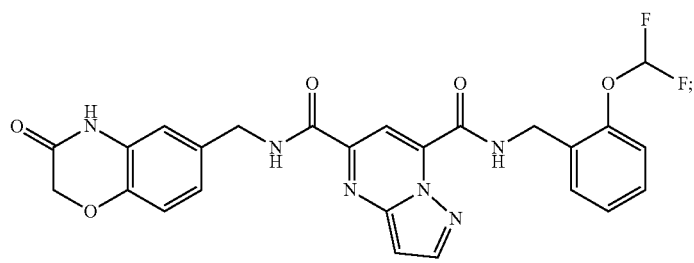
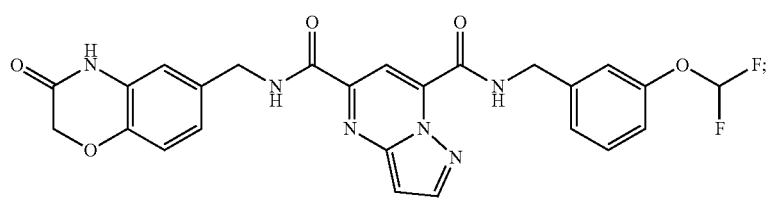
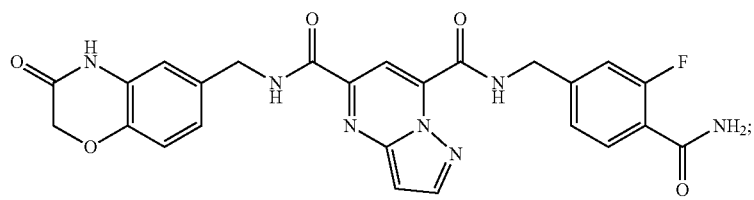
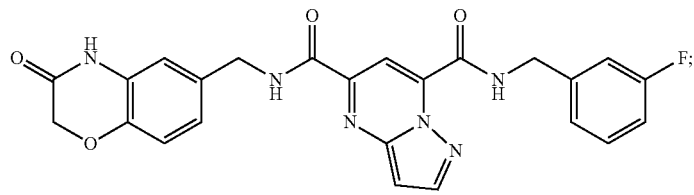
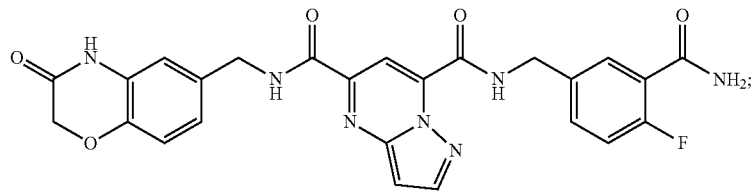
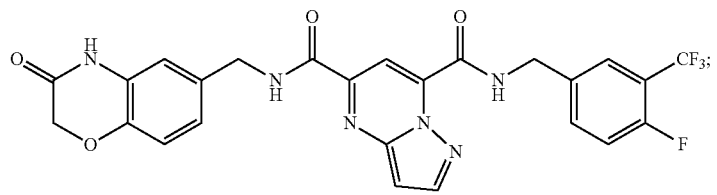

-continued
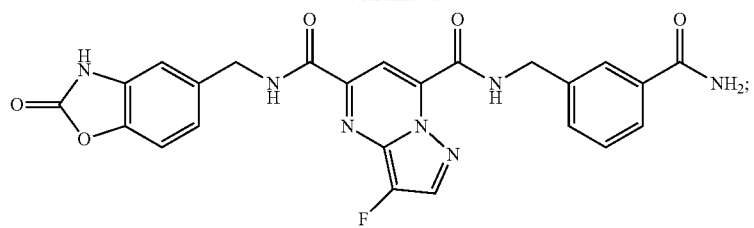
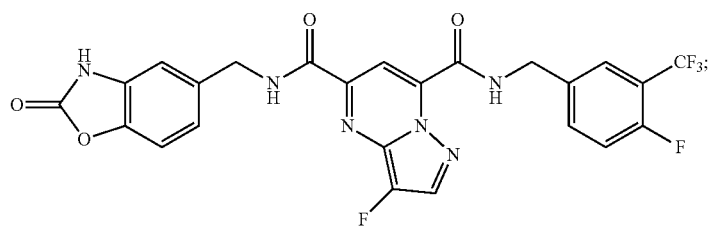
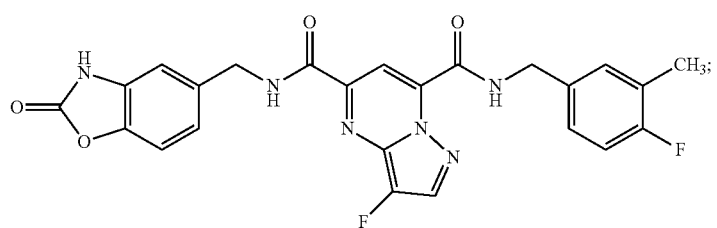
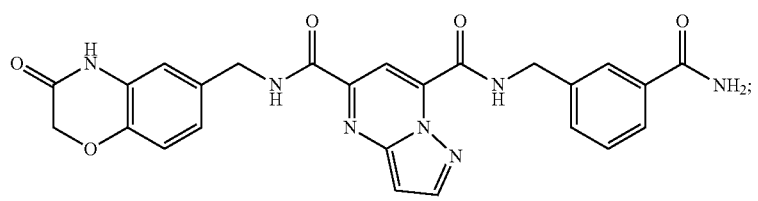
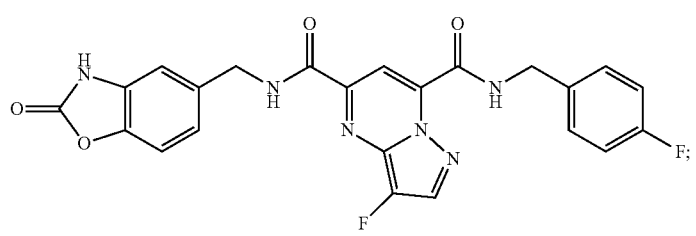
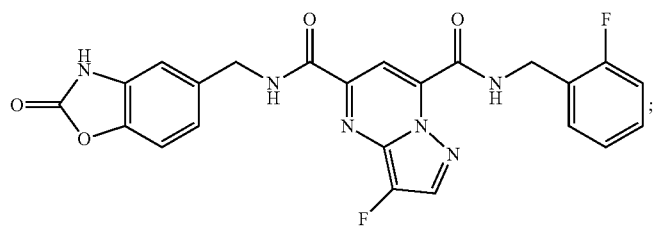

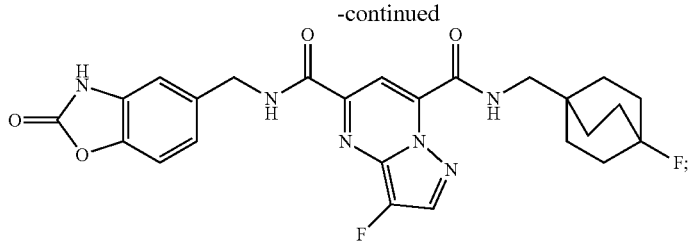
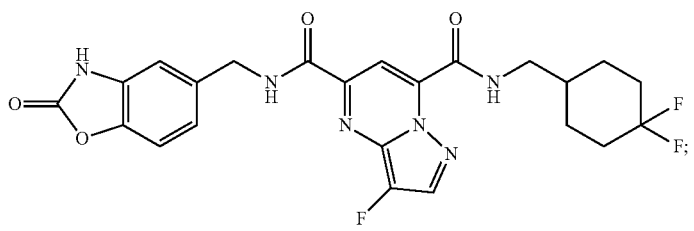
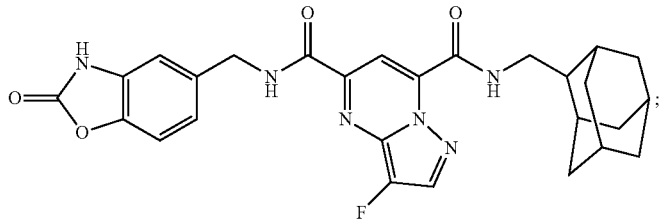
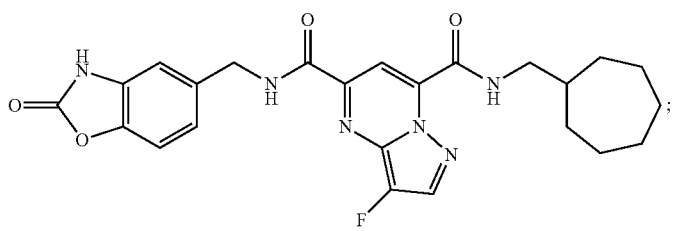
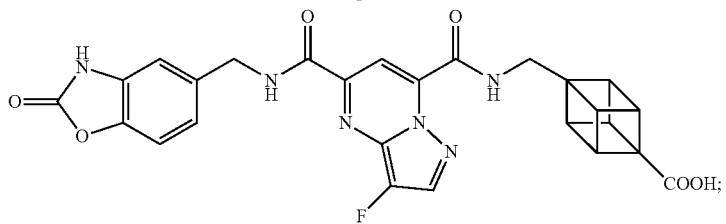
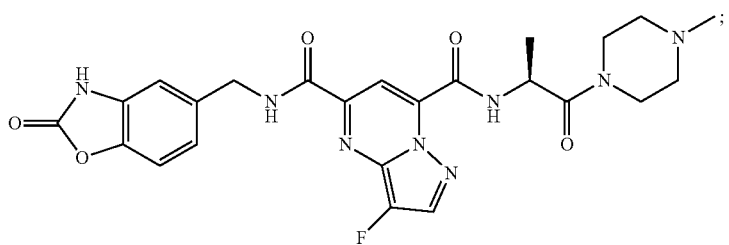
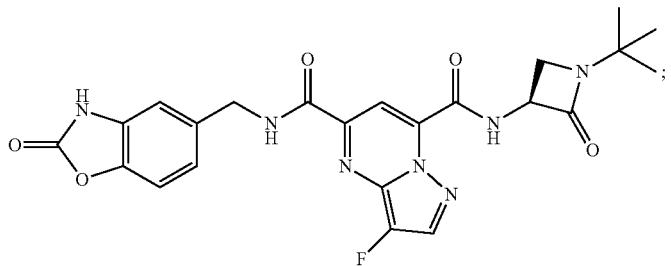

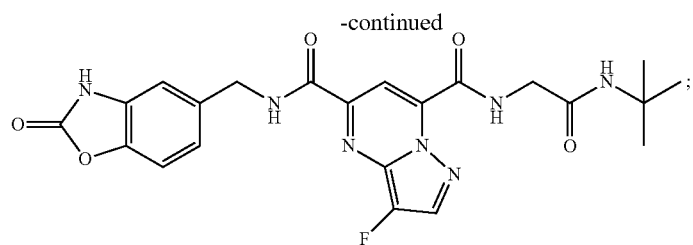
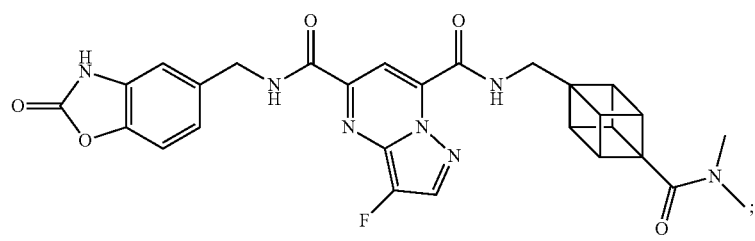
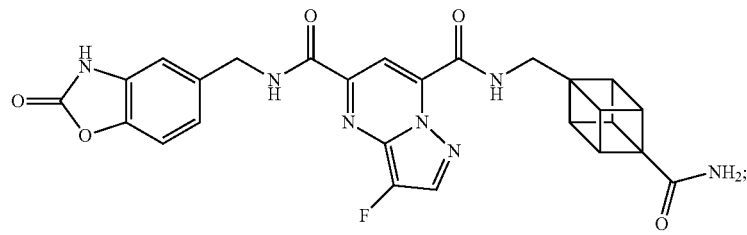
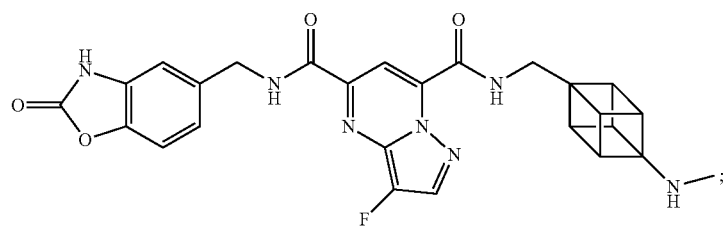
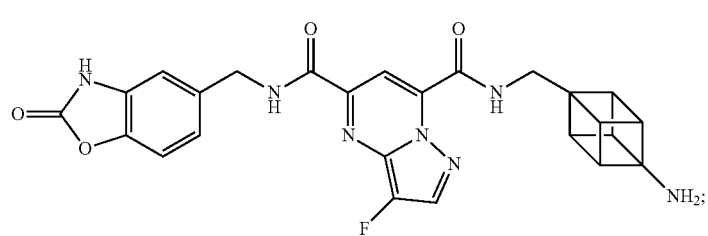
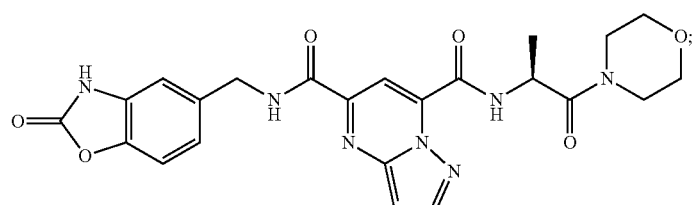
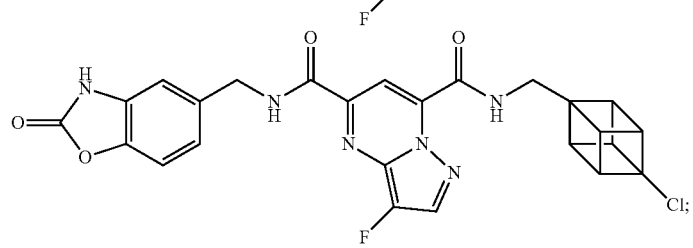

-continued
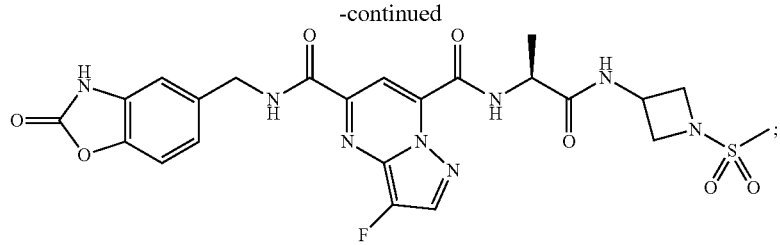
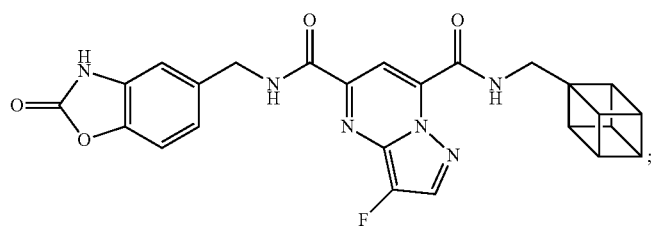
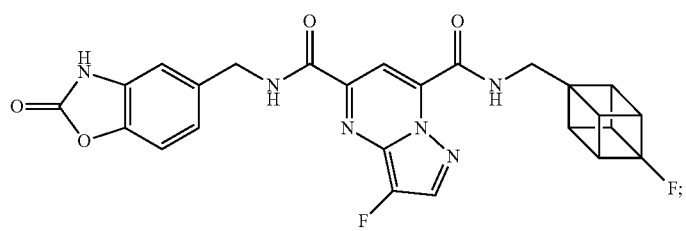
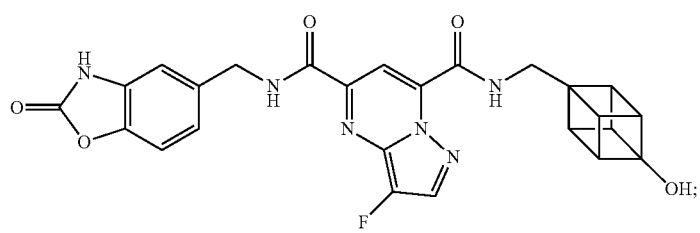
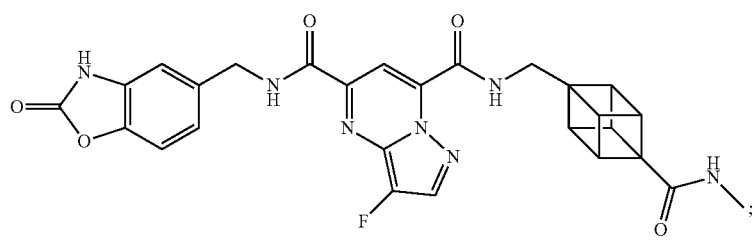
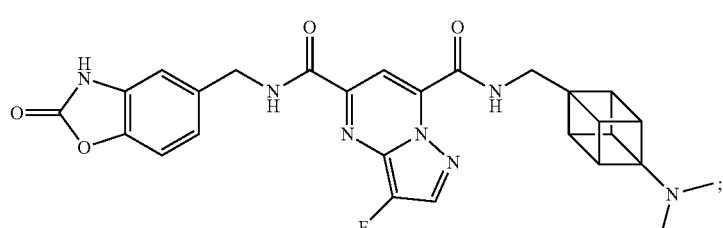
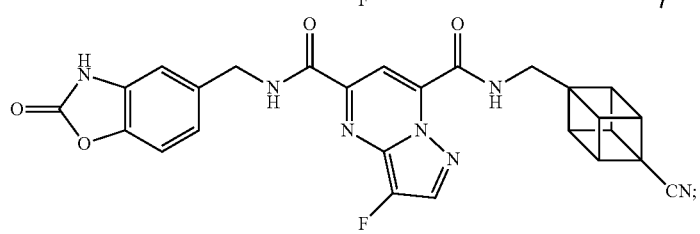

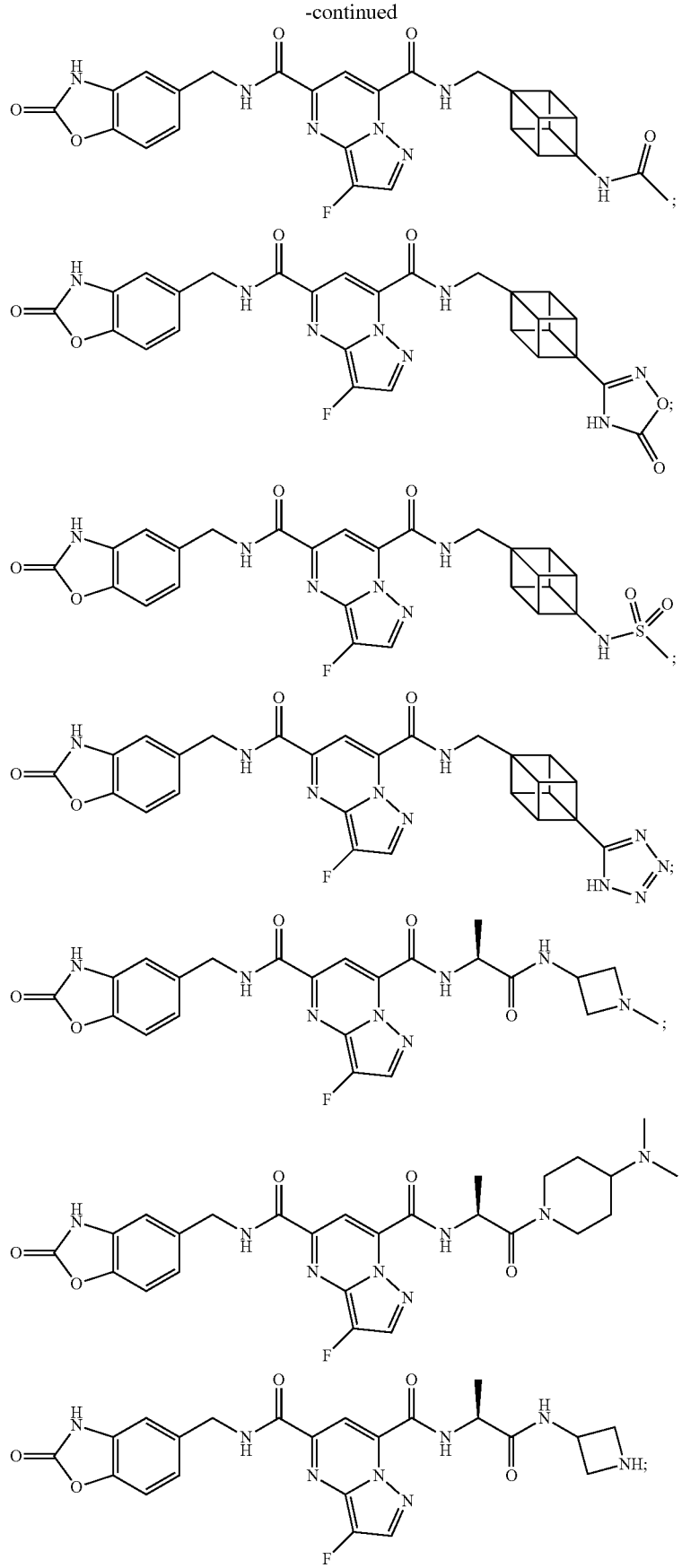

-continued
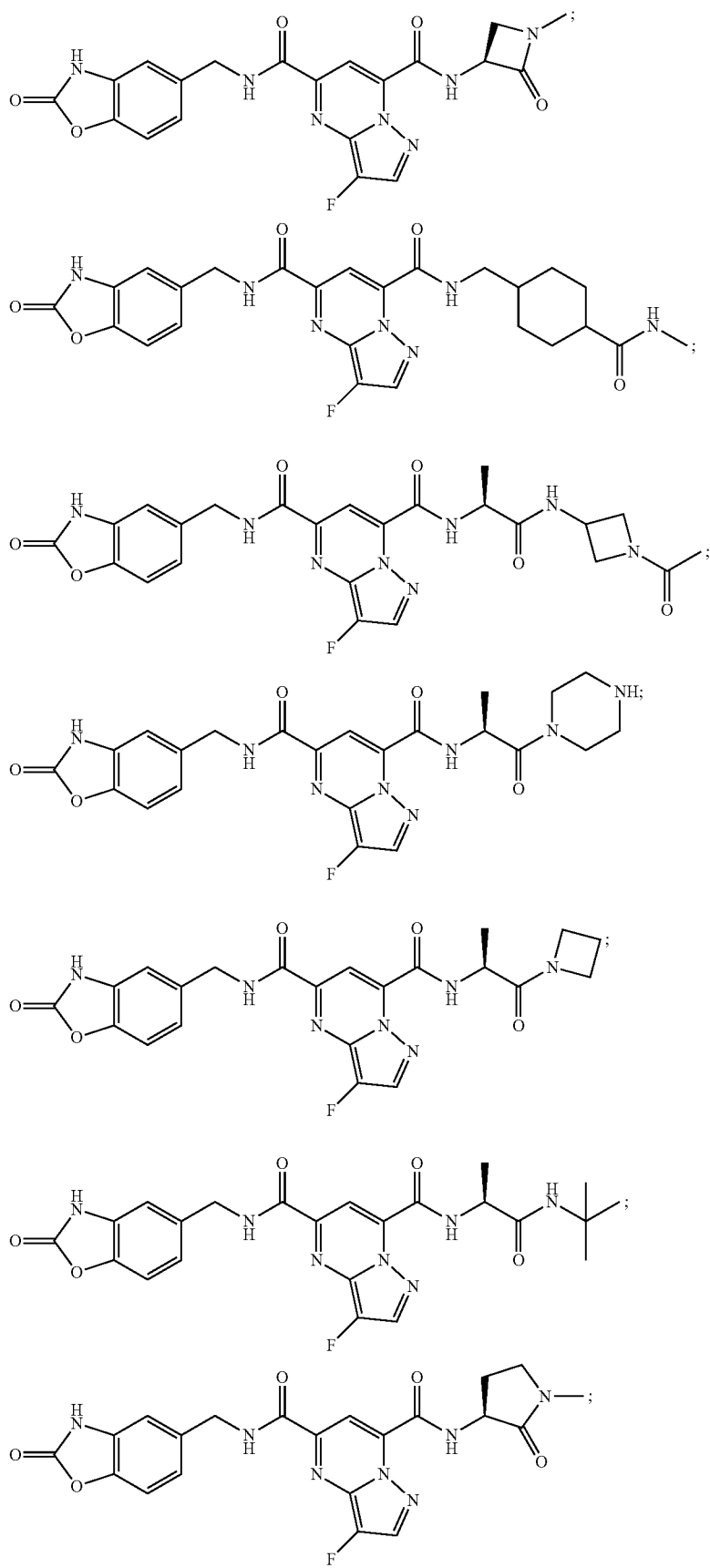

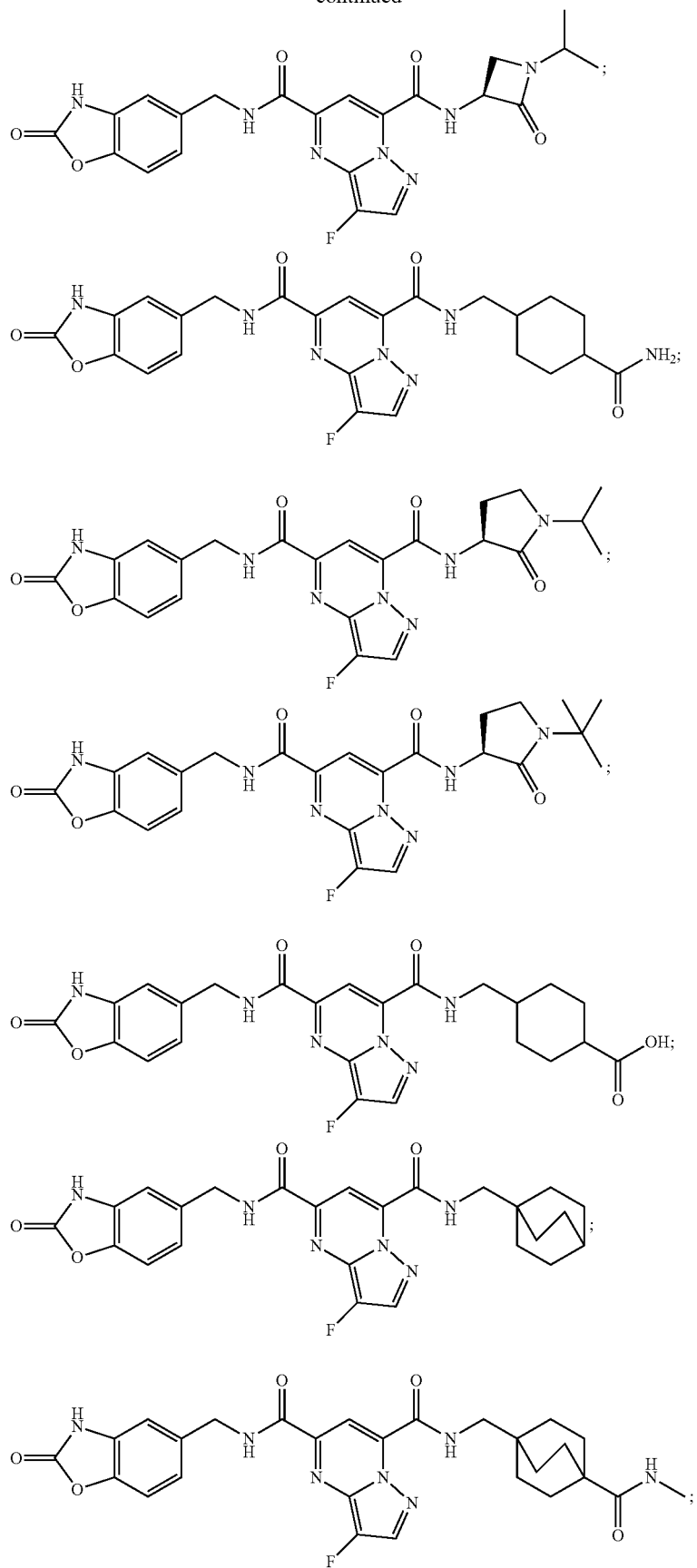

-continued
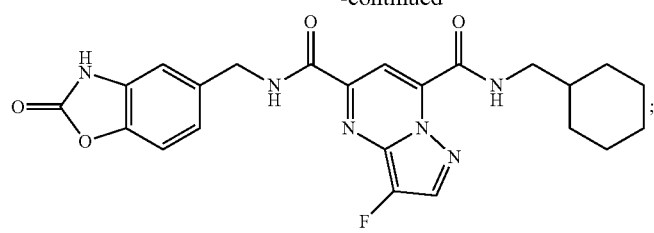
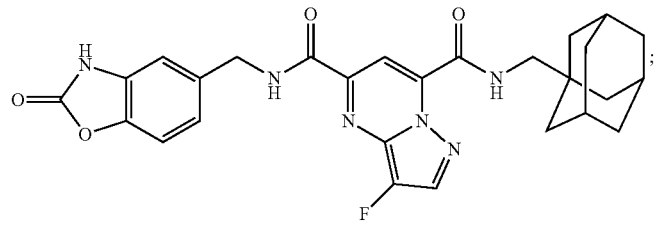
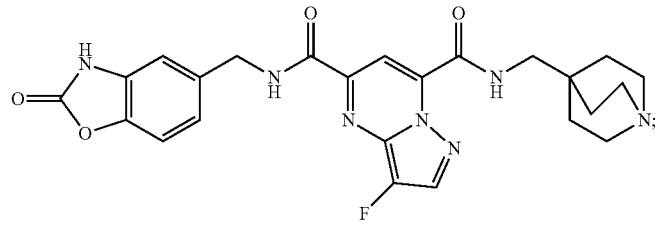
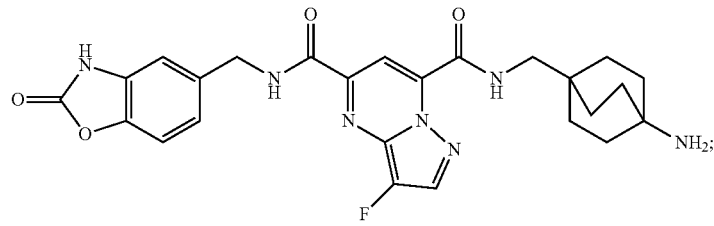
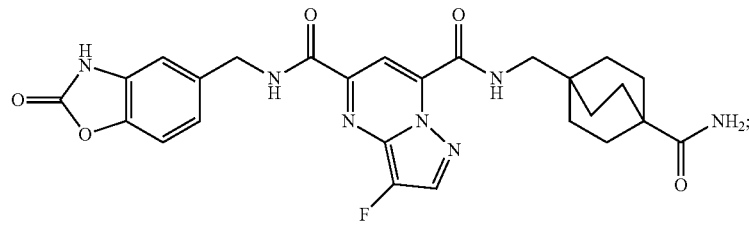
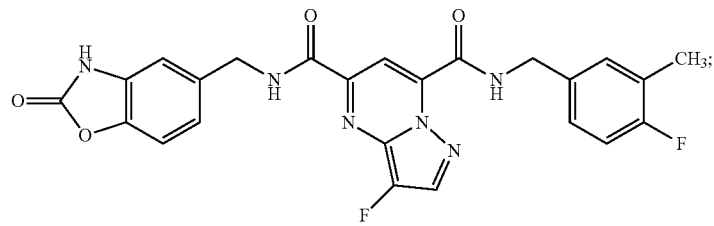
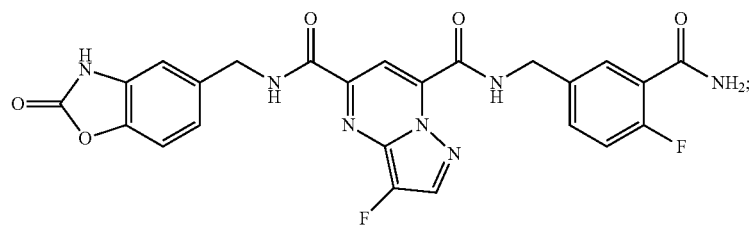

-continued
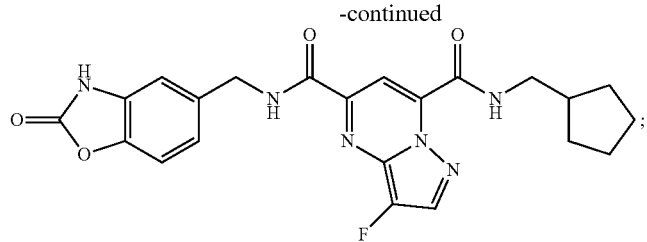
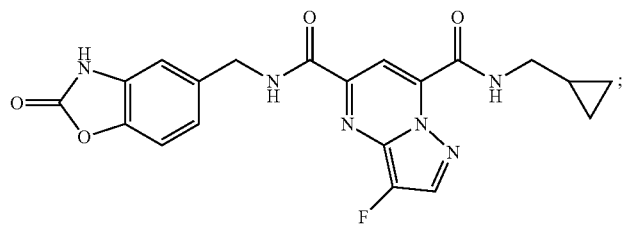
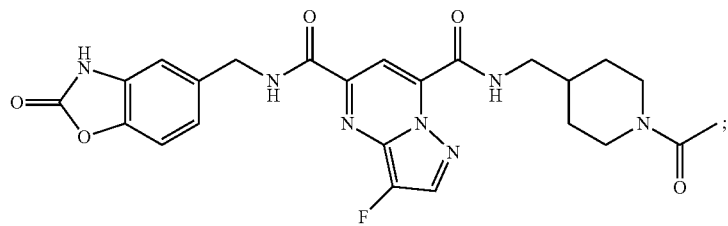
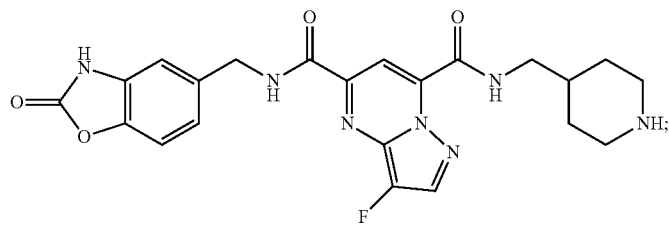
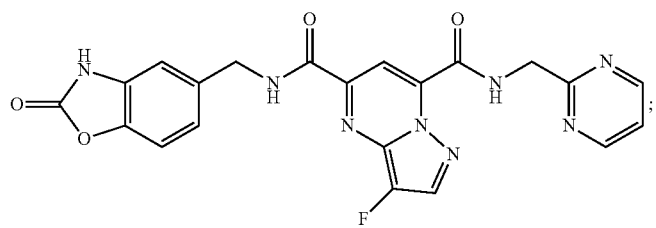
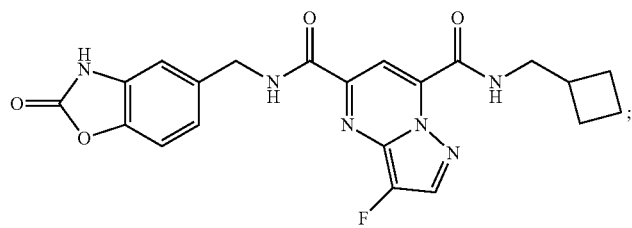
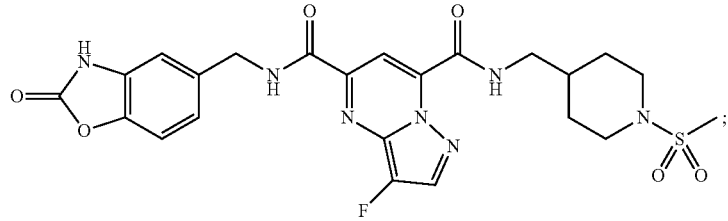

-continued
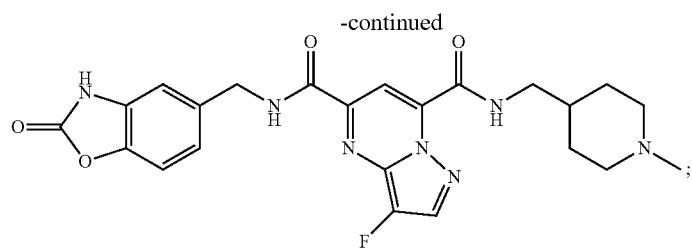
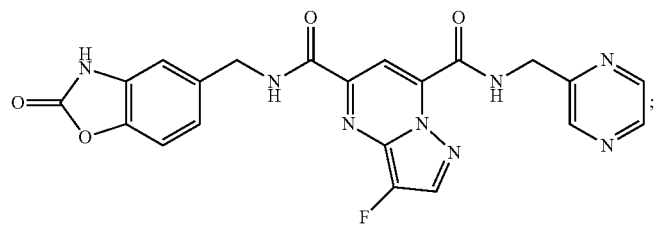
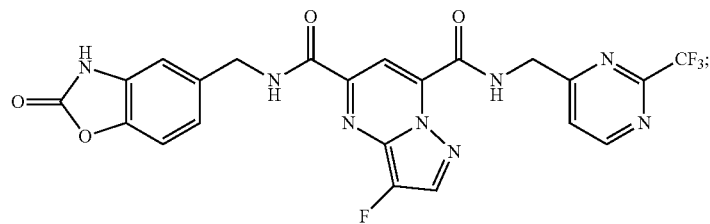
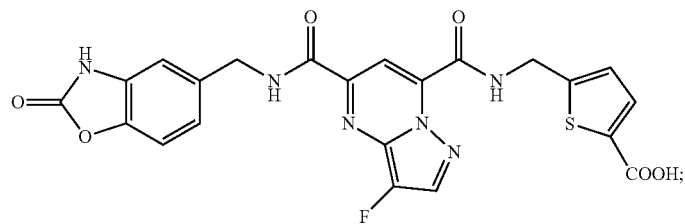
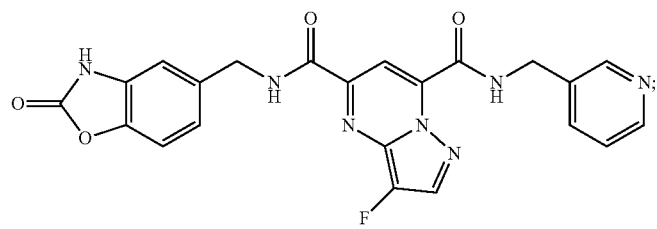
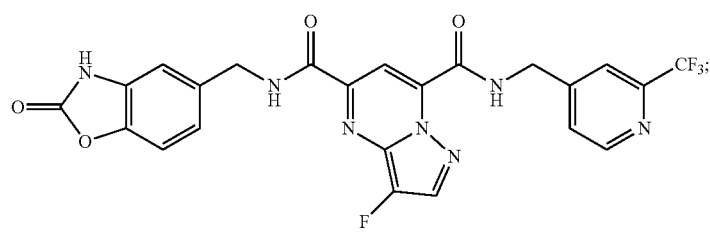
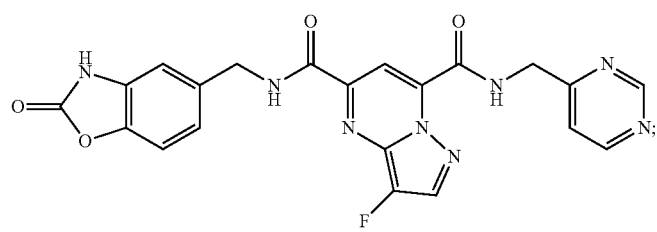

-continued
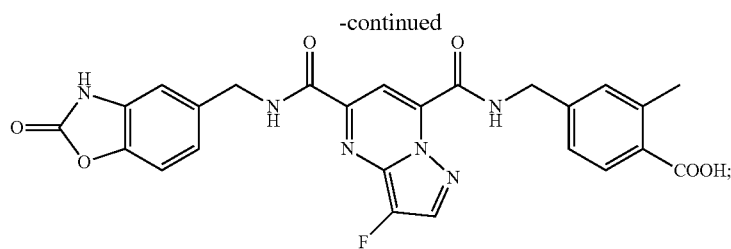
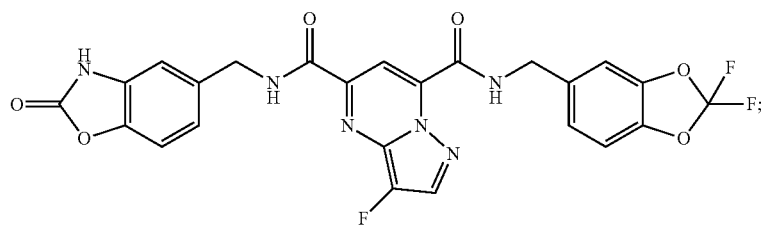
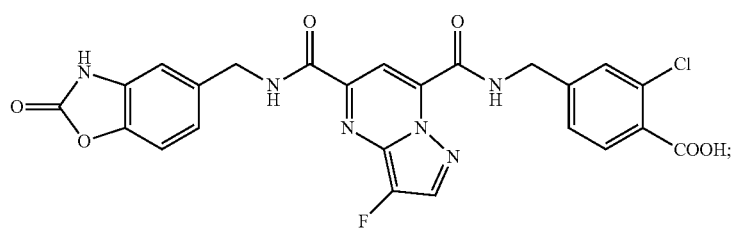
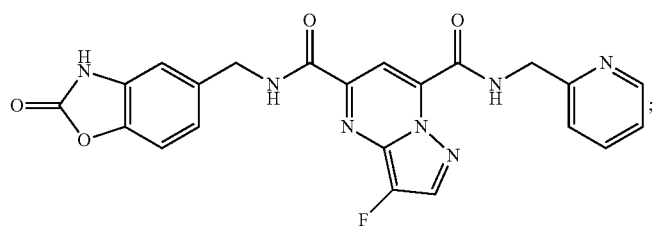
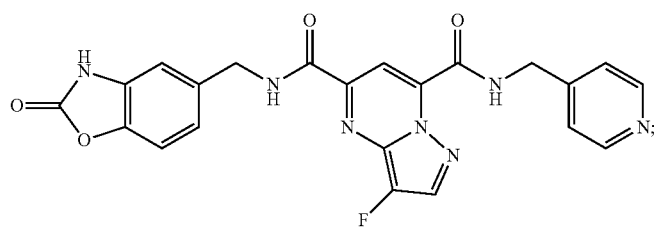
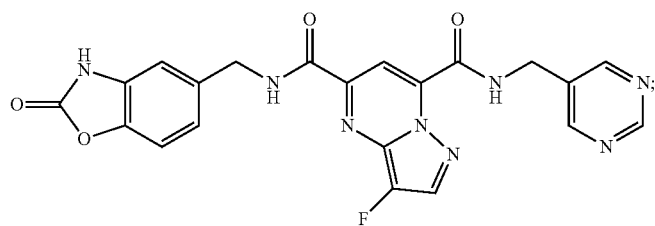
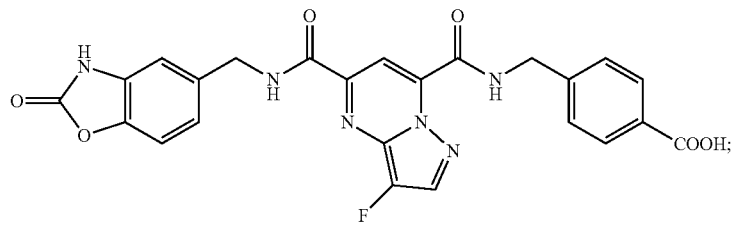

-continued
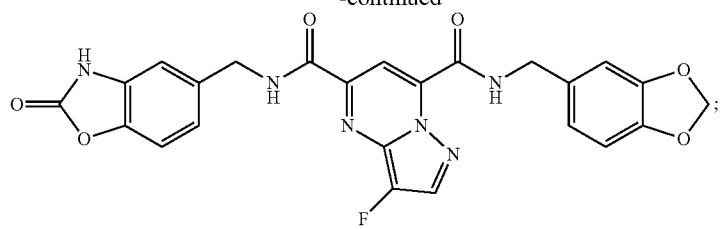
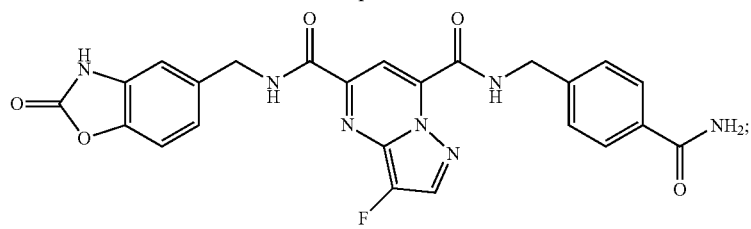
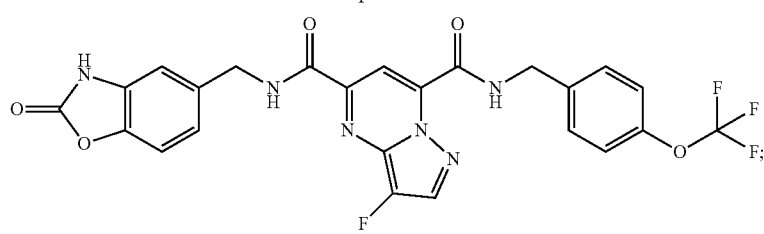
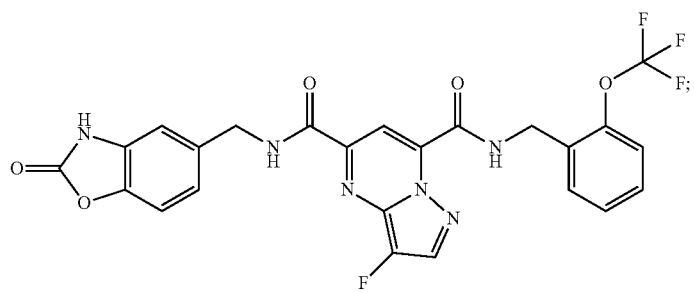
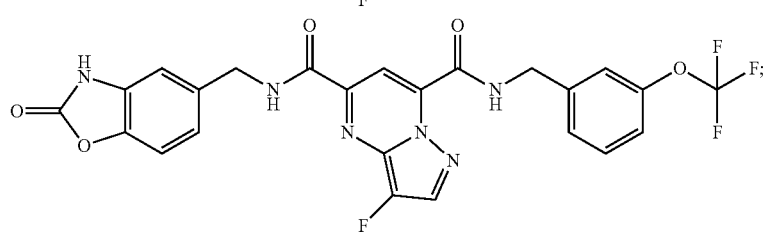
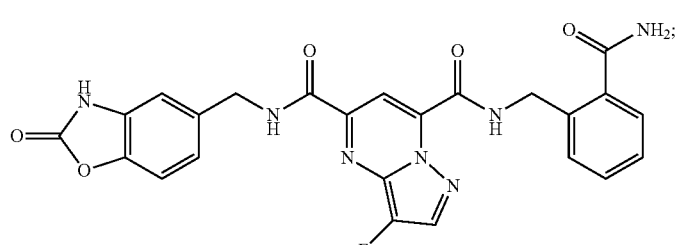
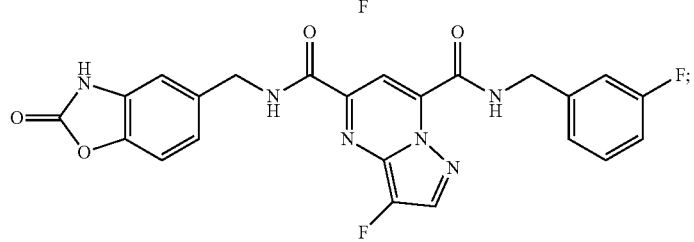

-continued
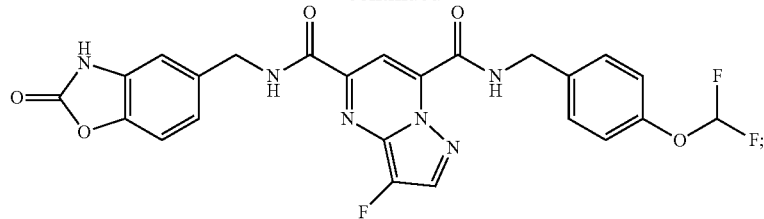
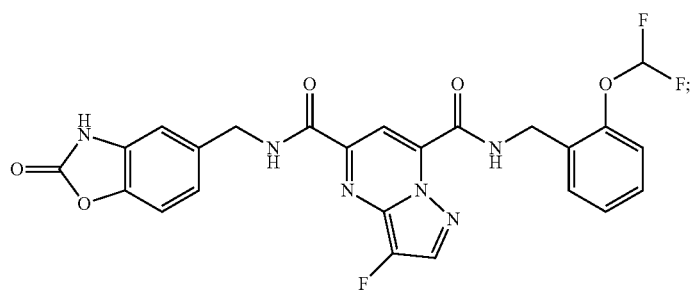
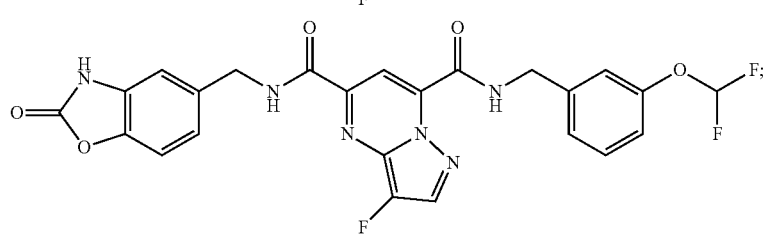
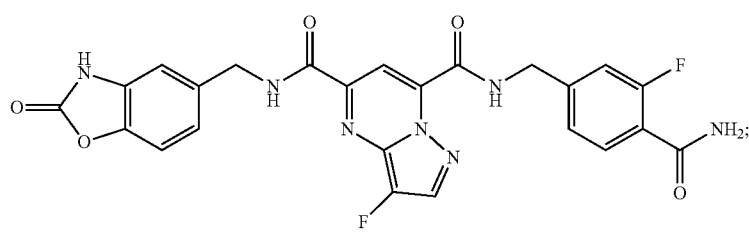
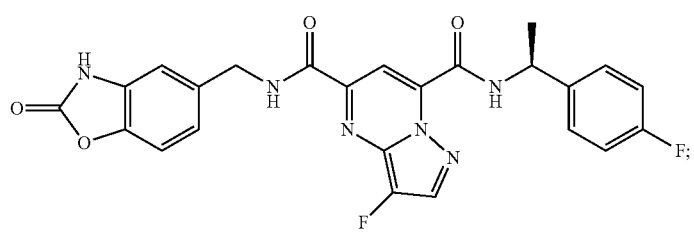
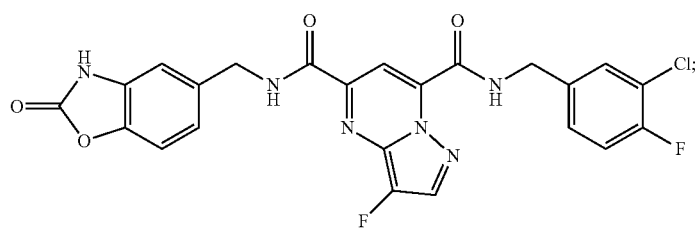
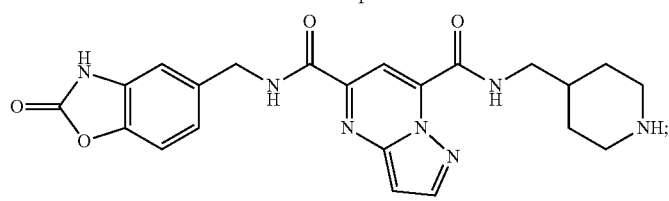

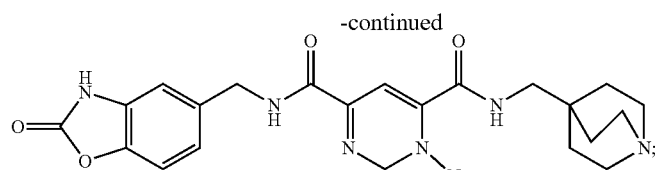
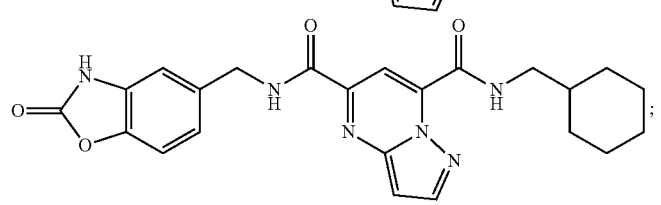
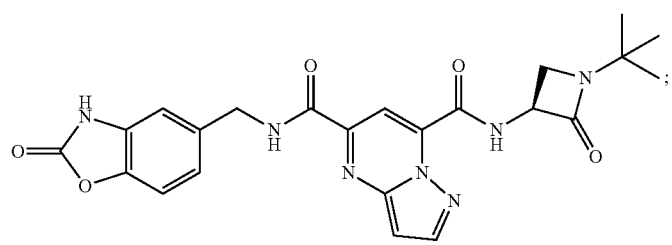
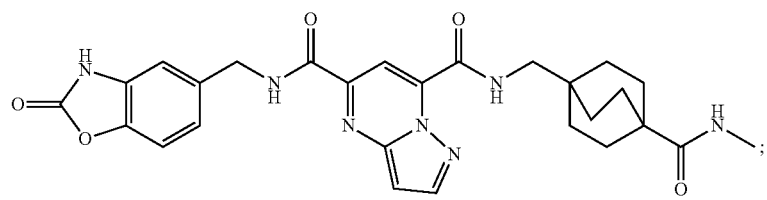
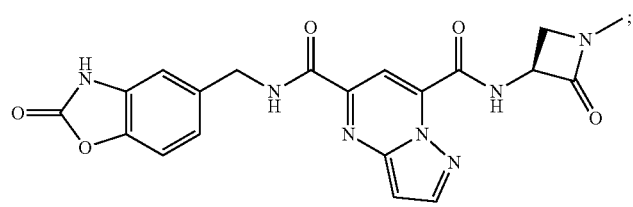
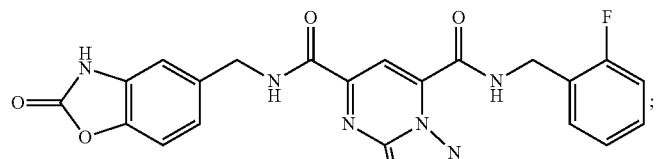
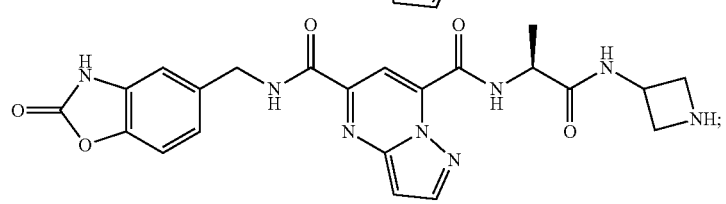
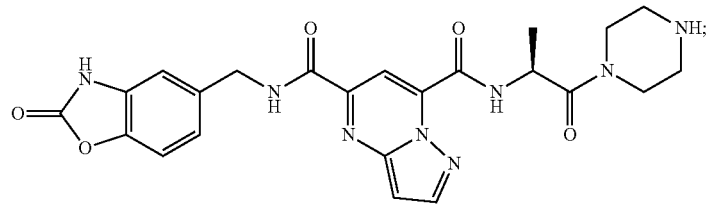

-continued
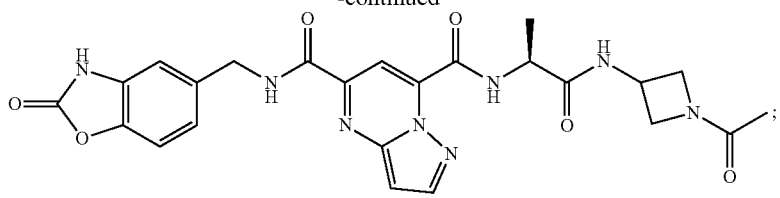
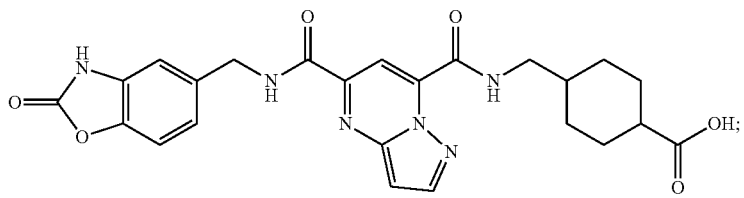
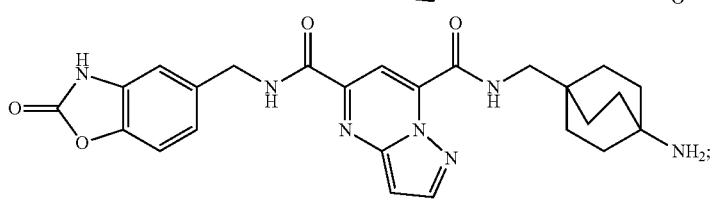
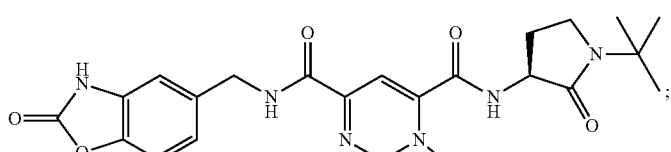
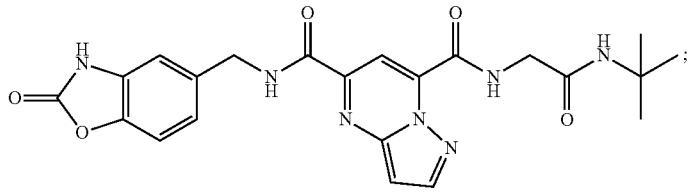
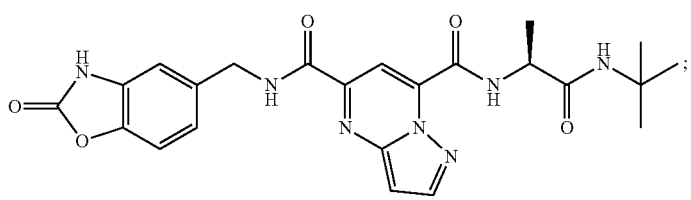
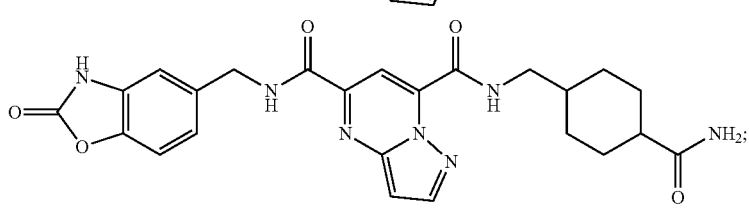
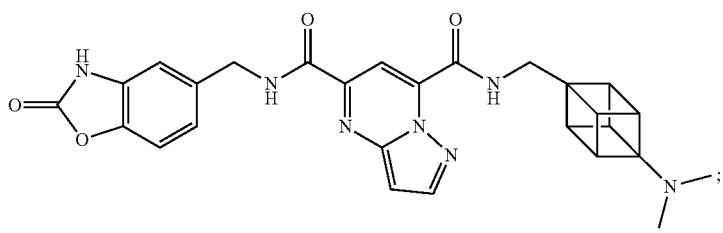

-continued
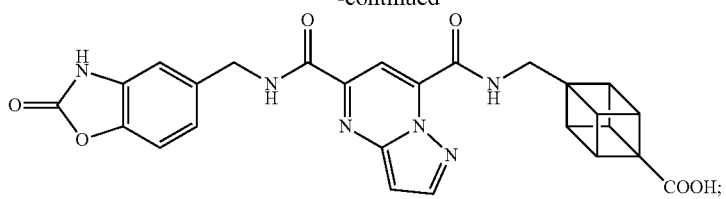
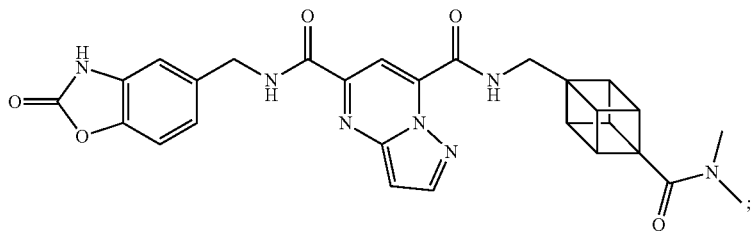
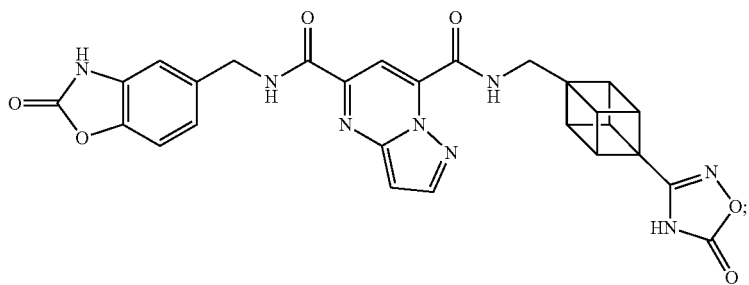
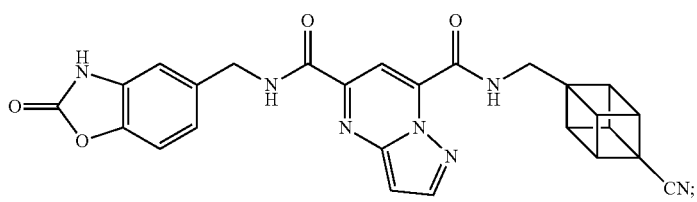
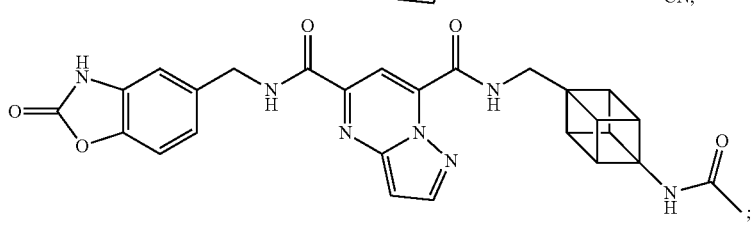
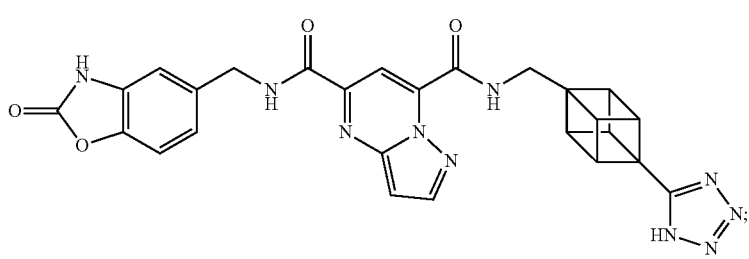
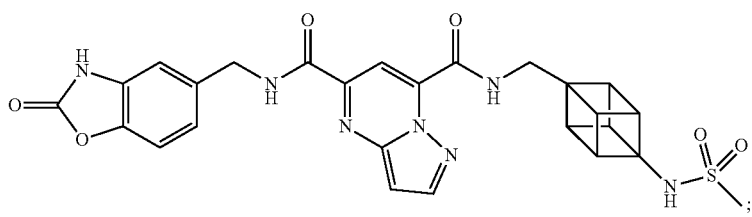

-continued
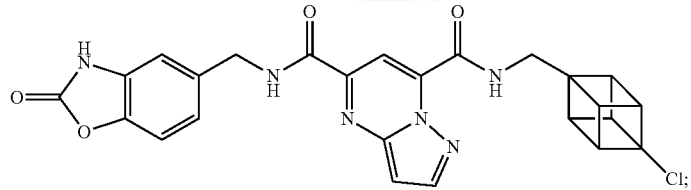
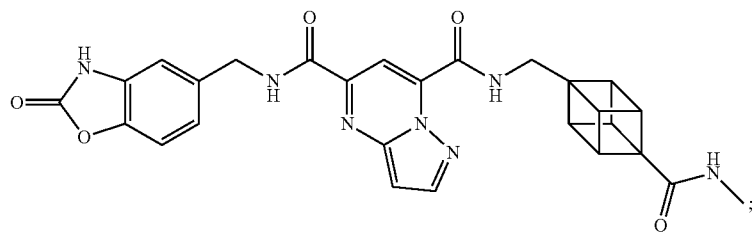
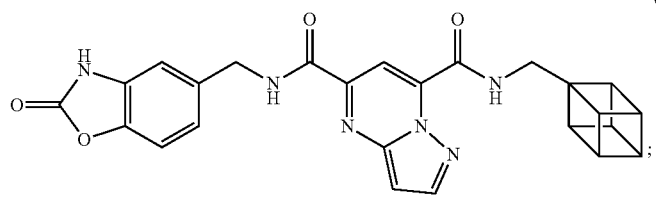
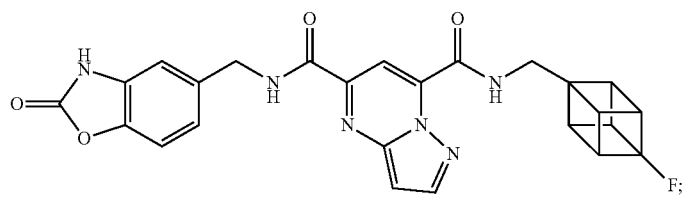
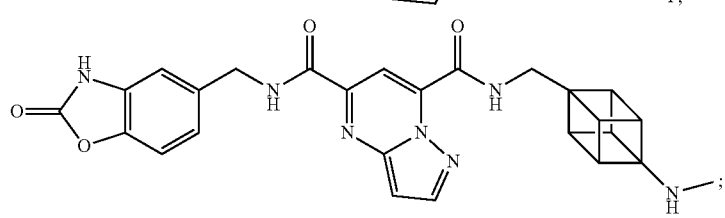
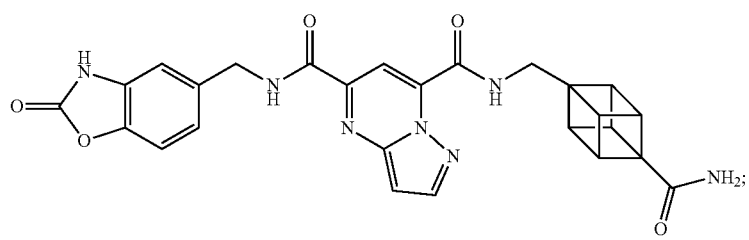
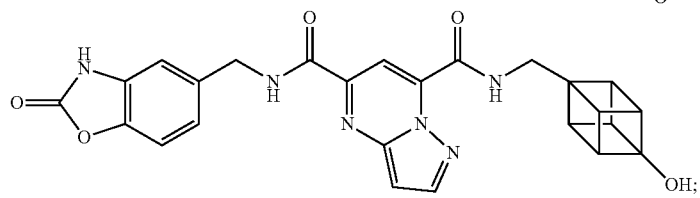
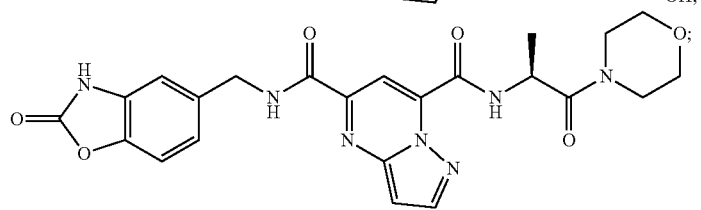

-continued
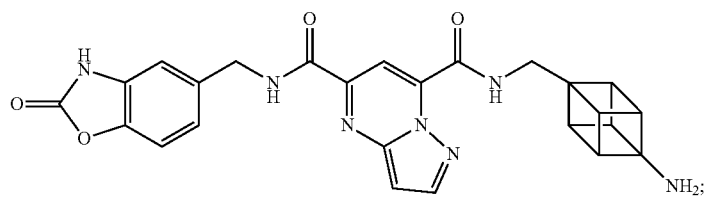
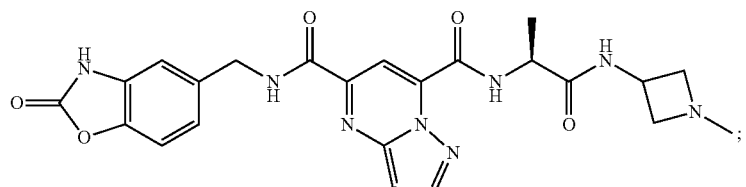
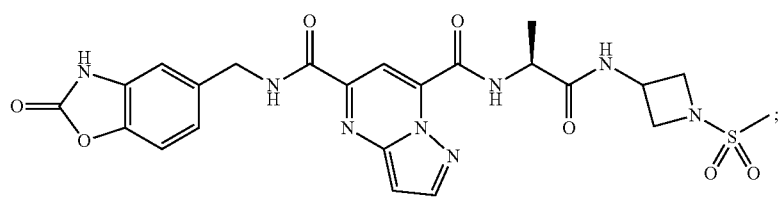
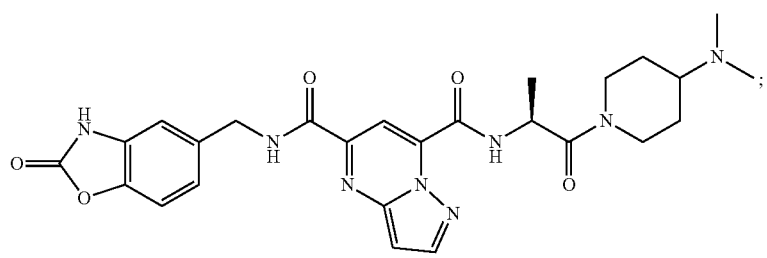
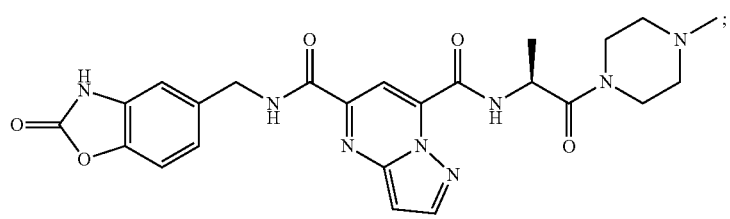
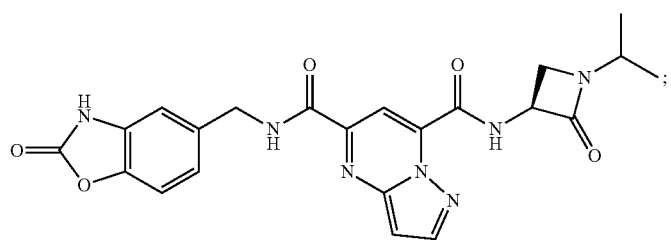
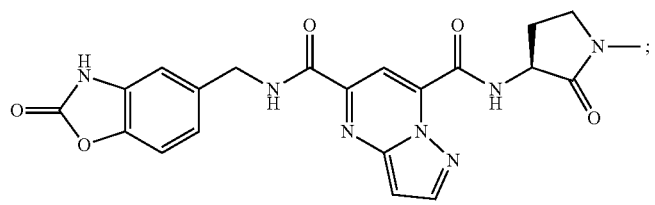
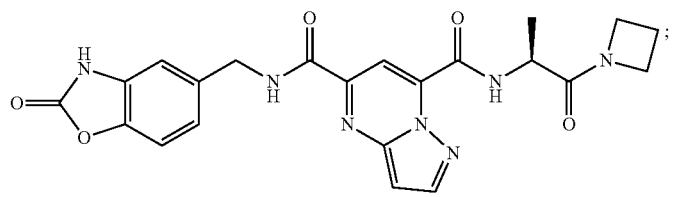

-continued
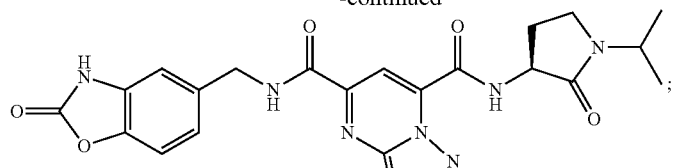
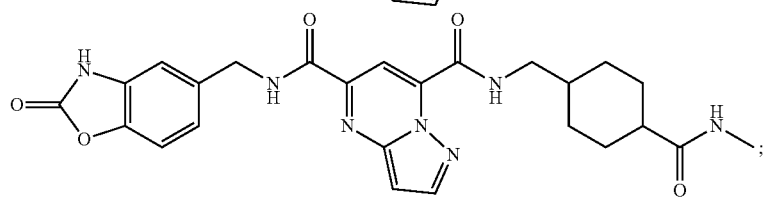
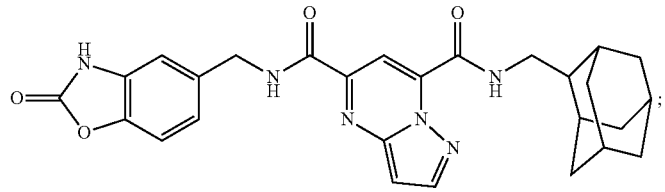
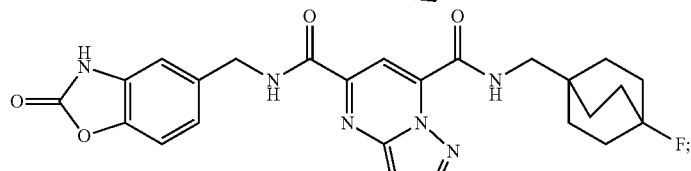
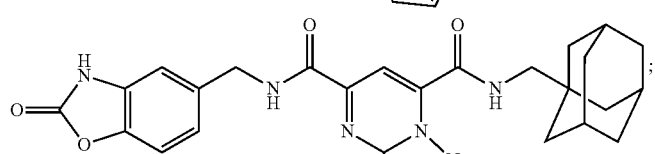
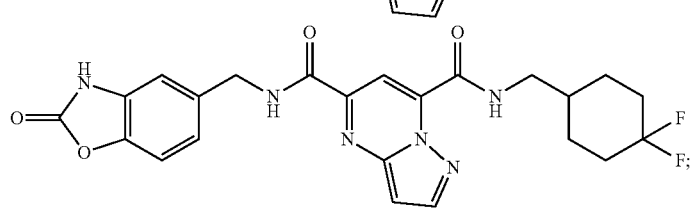
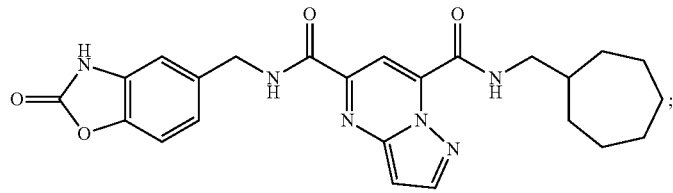
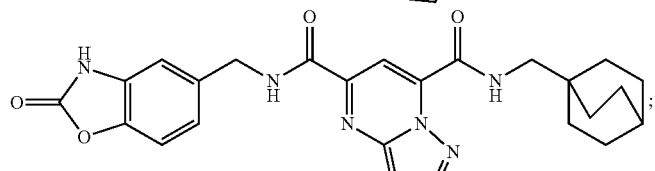
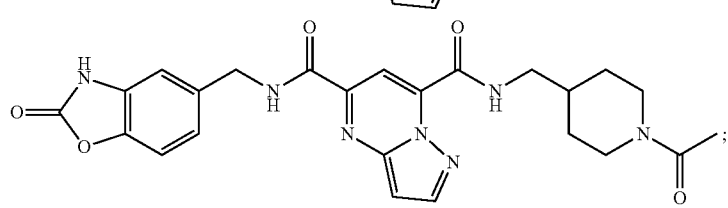

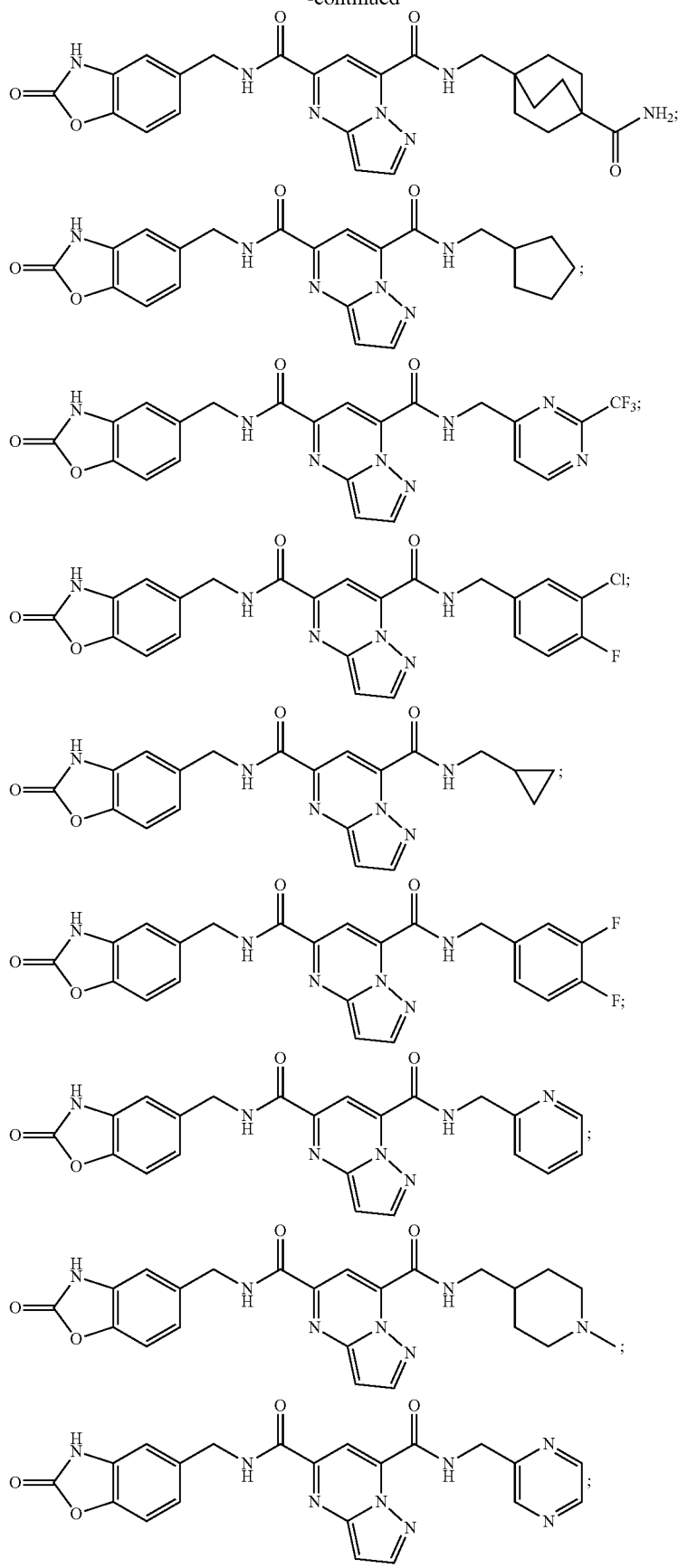

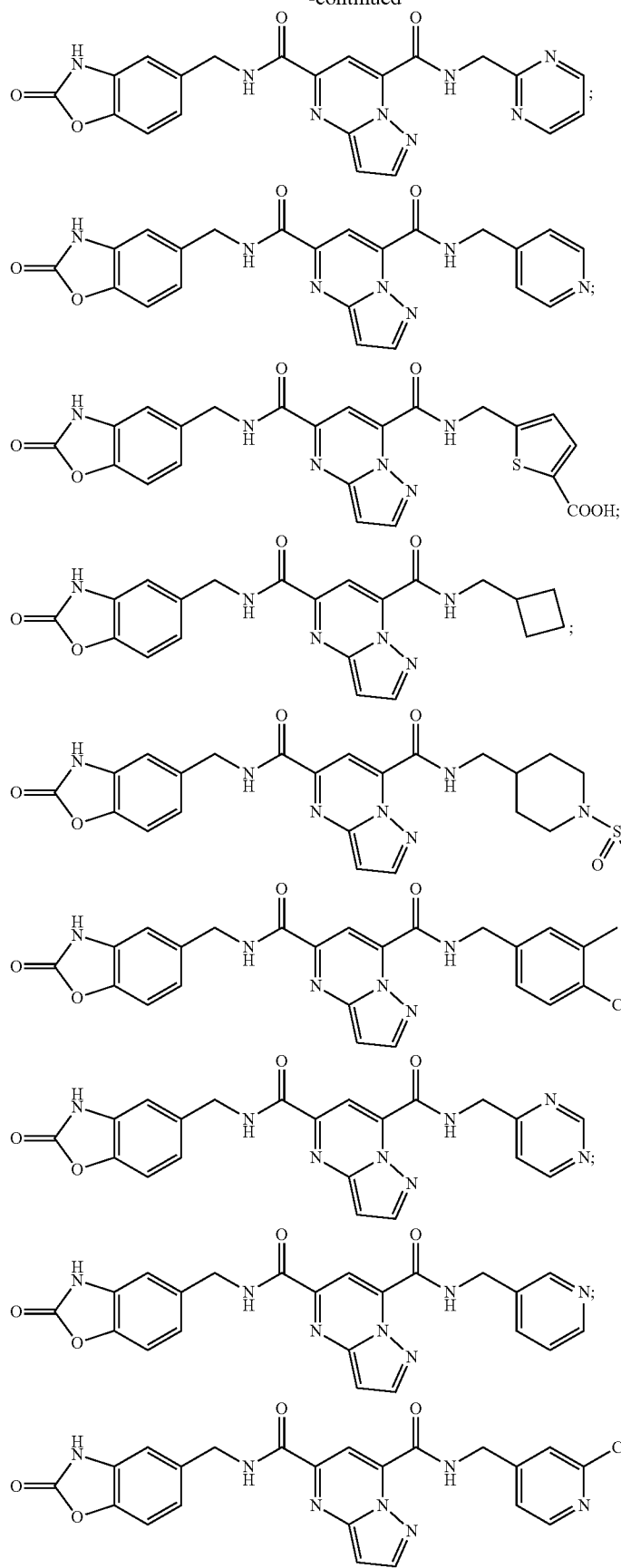

-continued
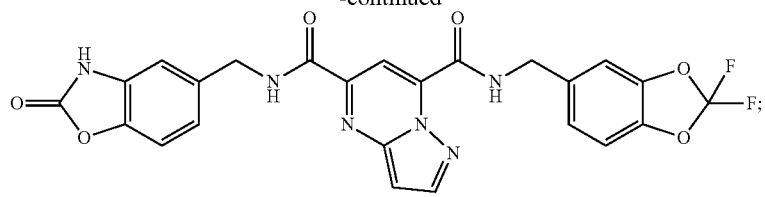
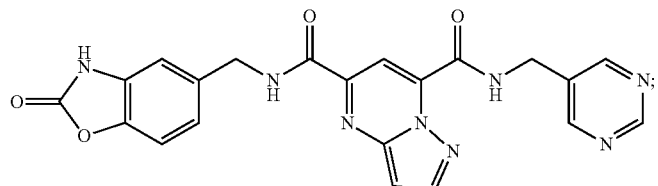
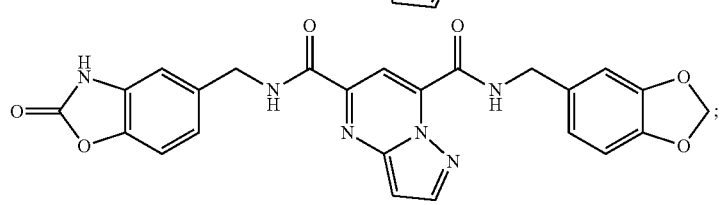
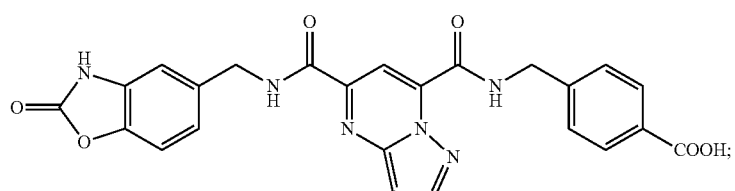
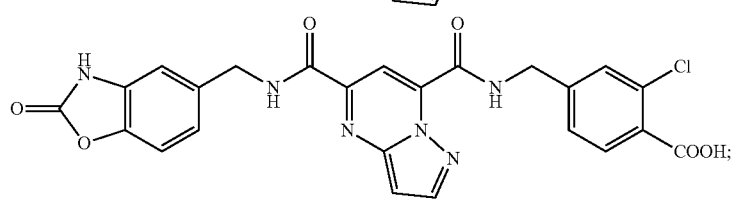
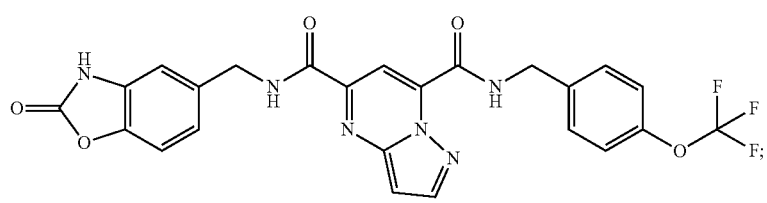
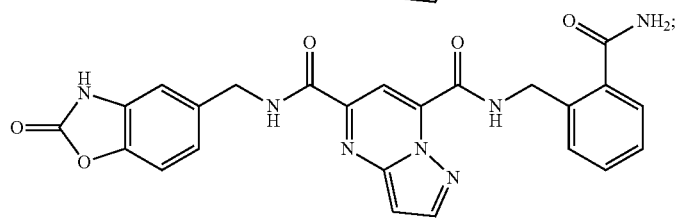
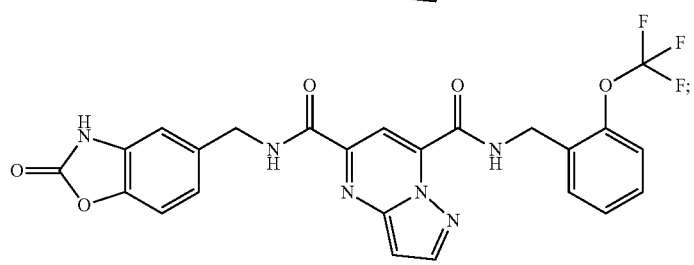

-continued
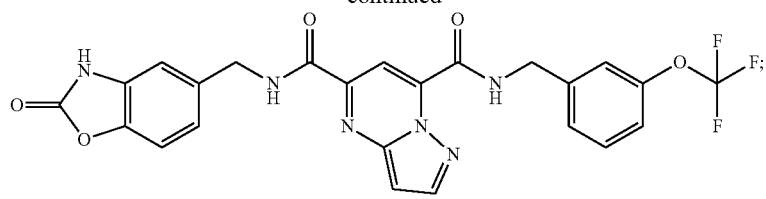
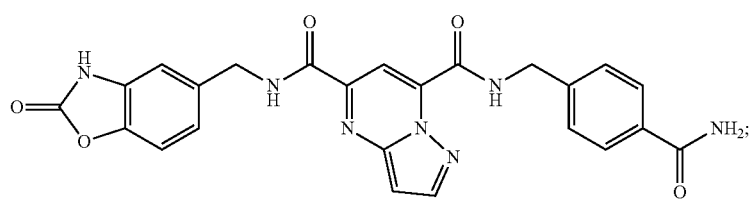
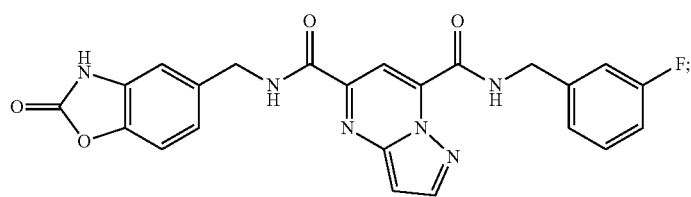
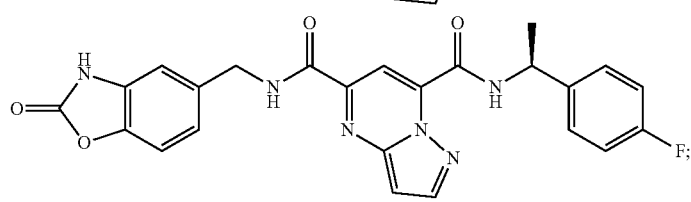
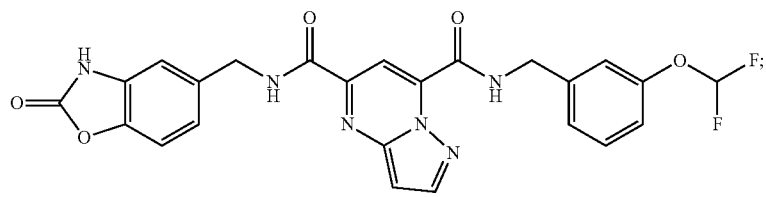
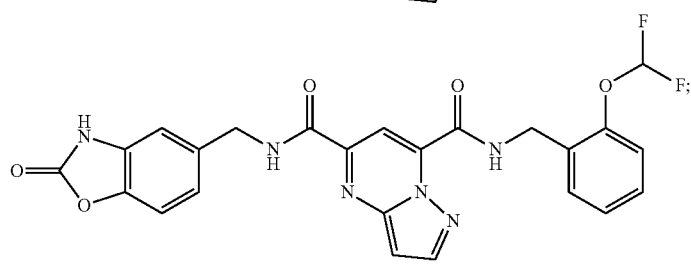
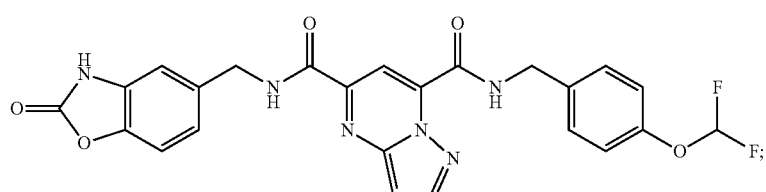
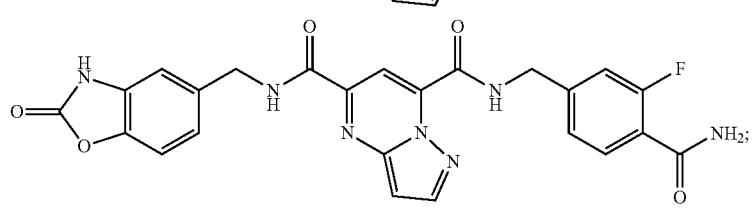

-continued
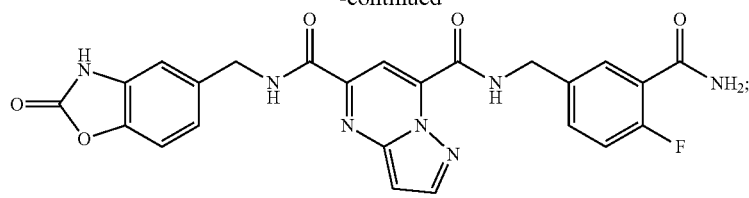
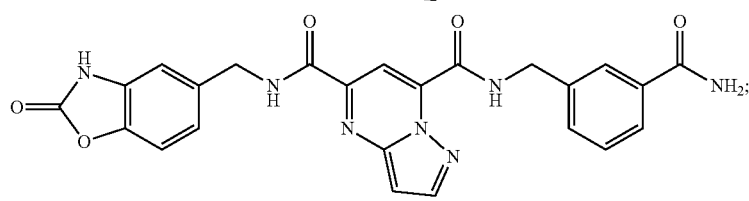
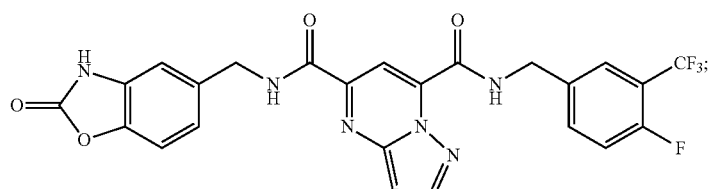
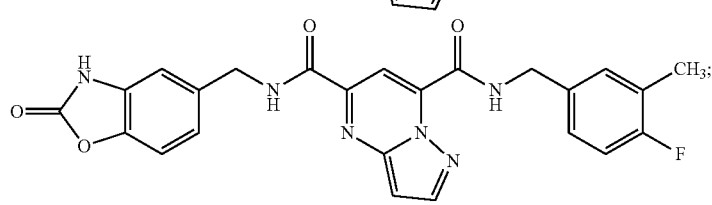
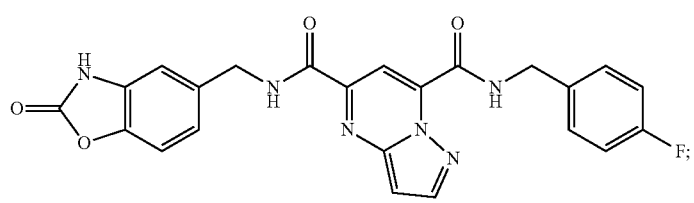
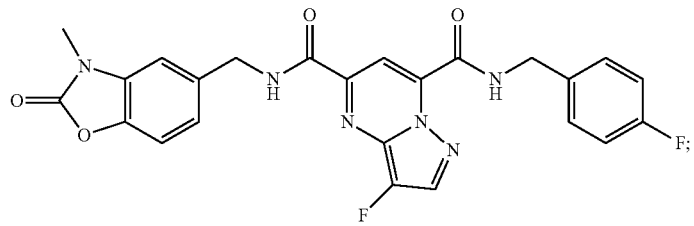
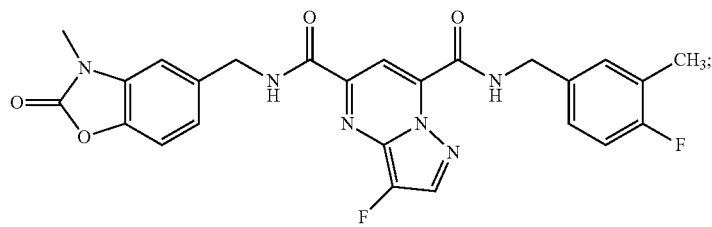
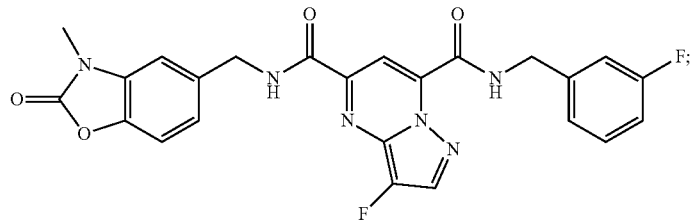

-continued
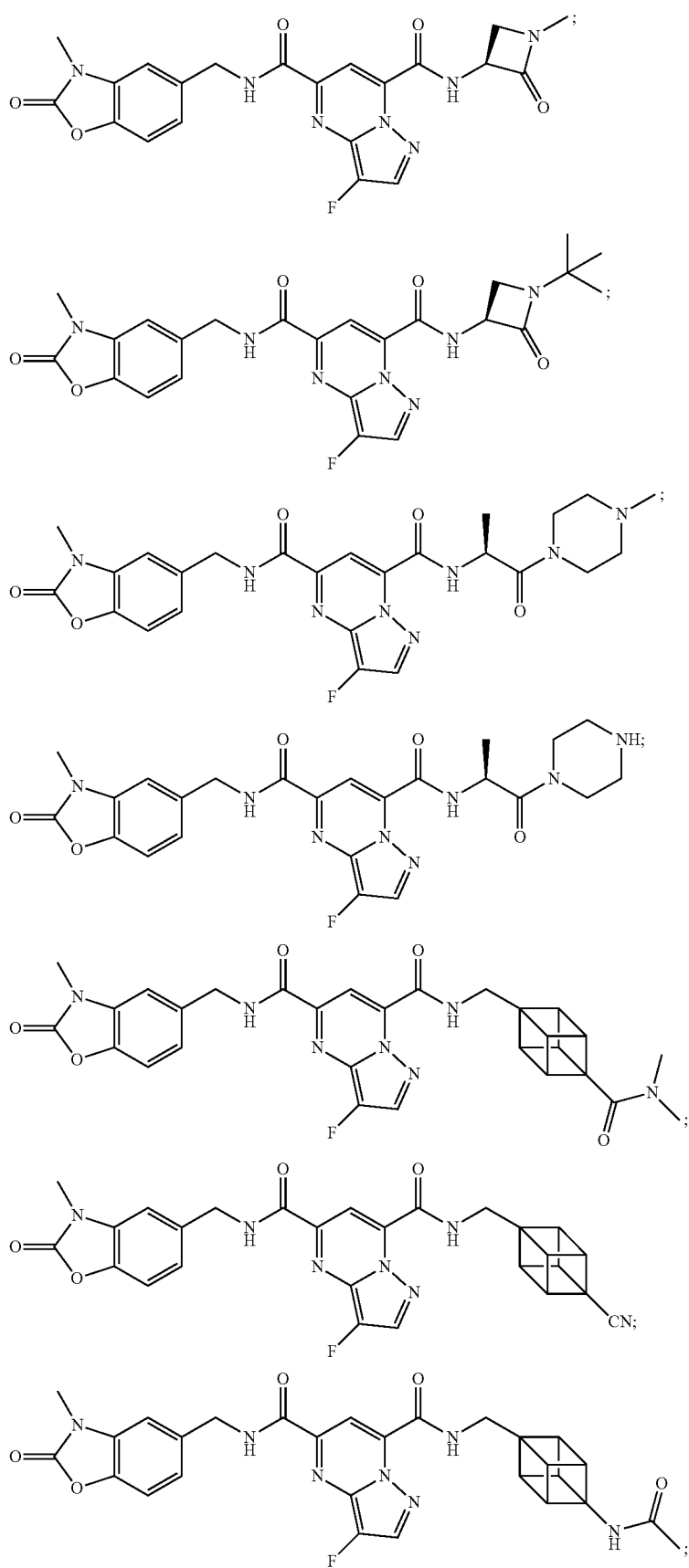

-continued
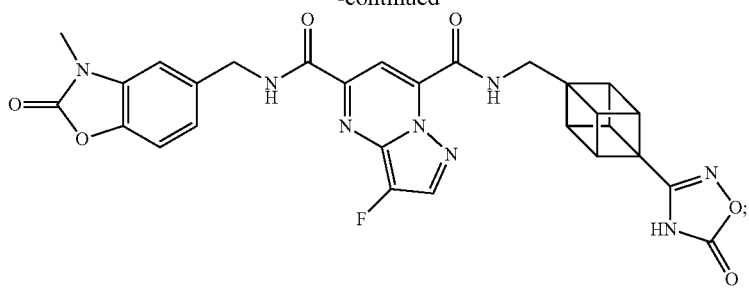
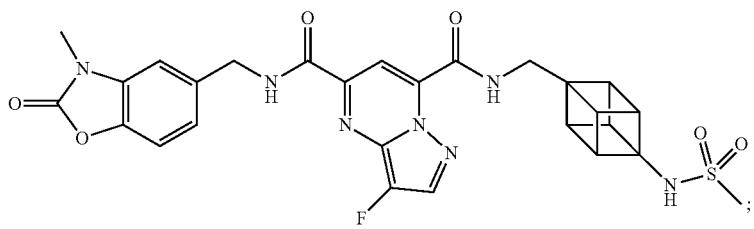
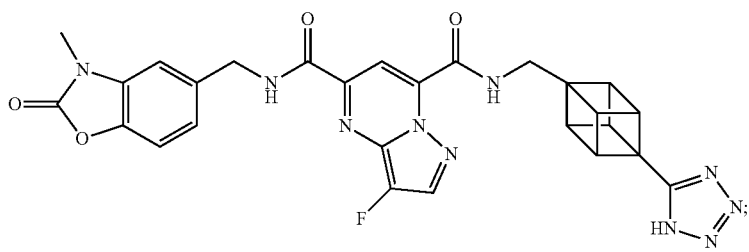
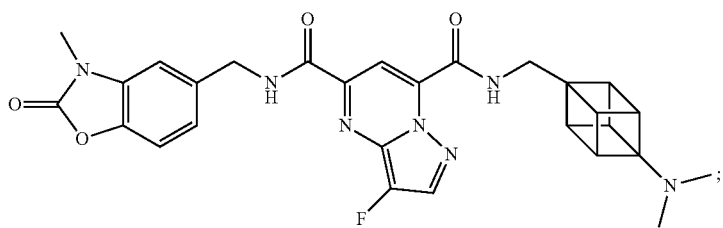
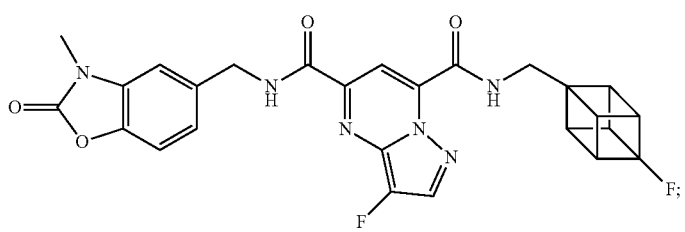
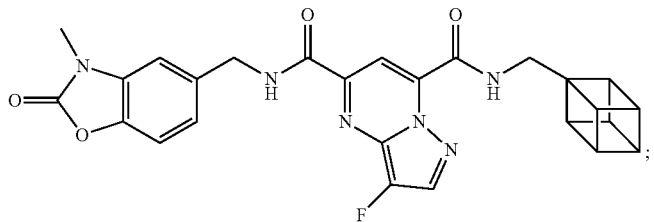
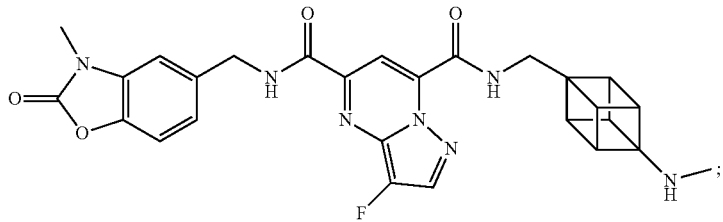

-continued
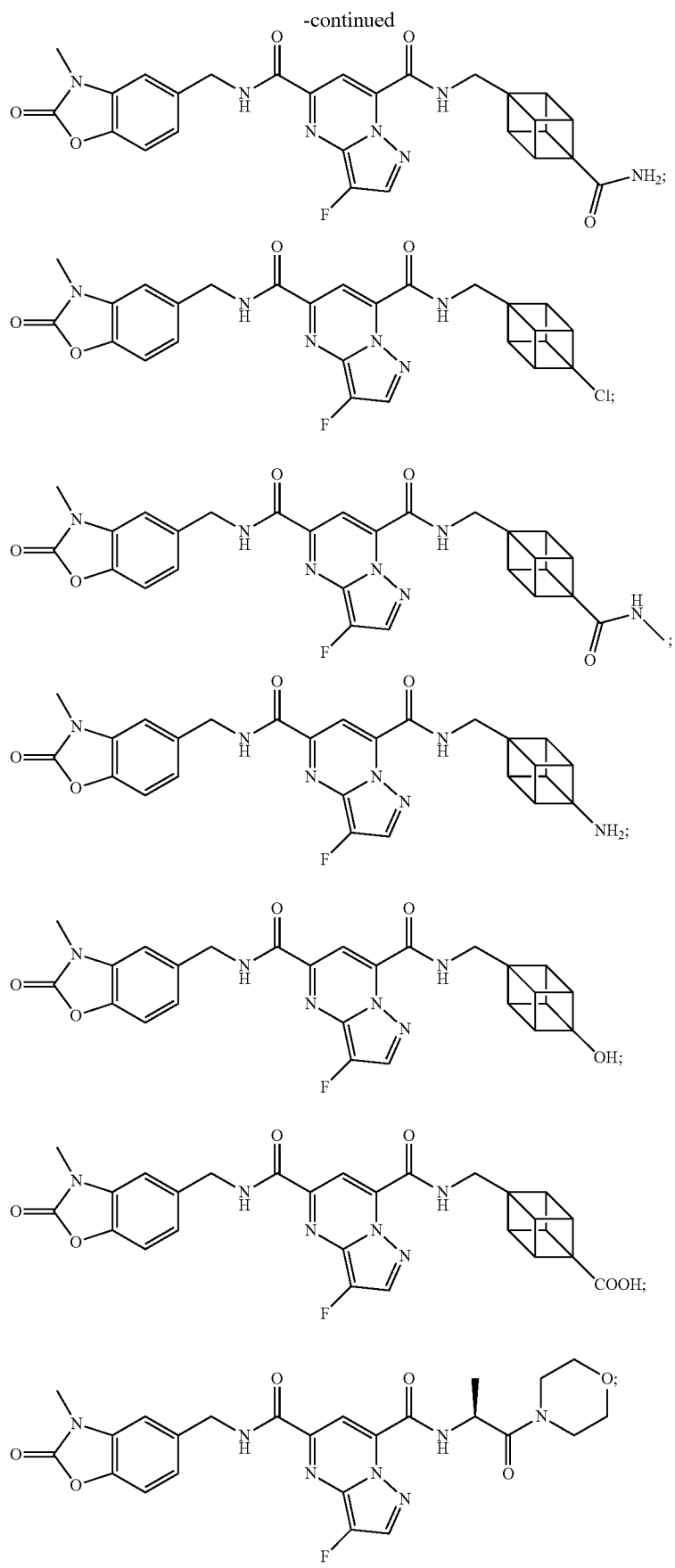

-continued
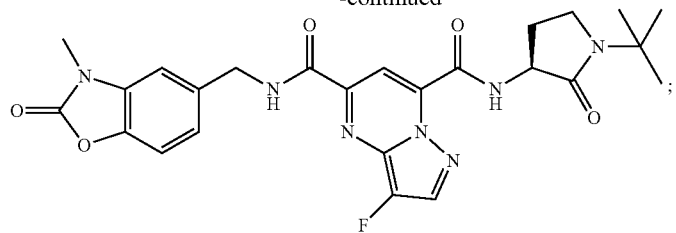
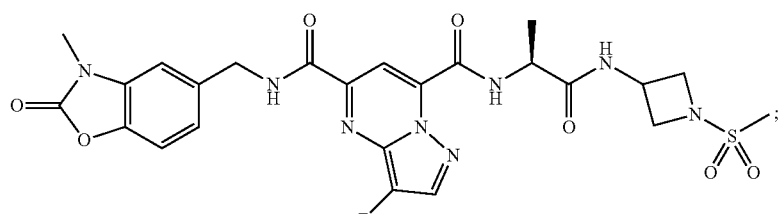
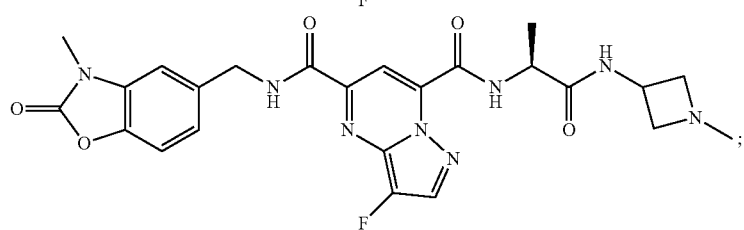
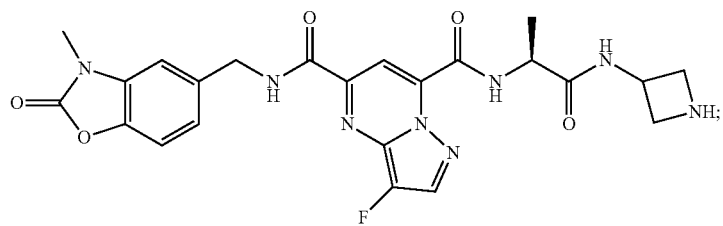
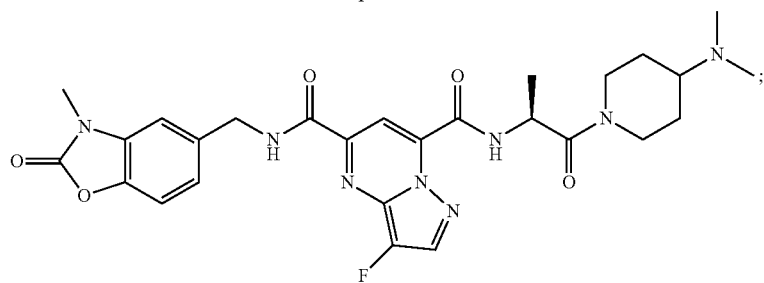
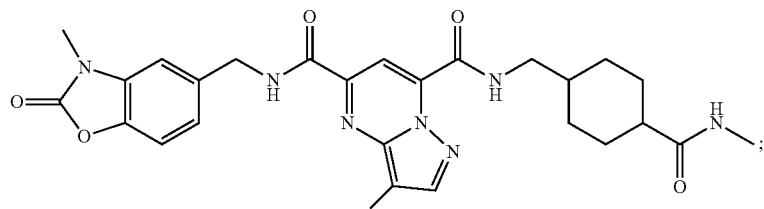
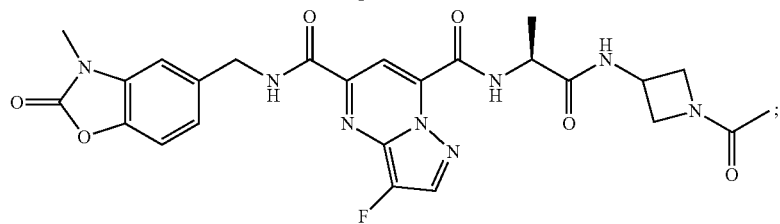

-continued
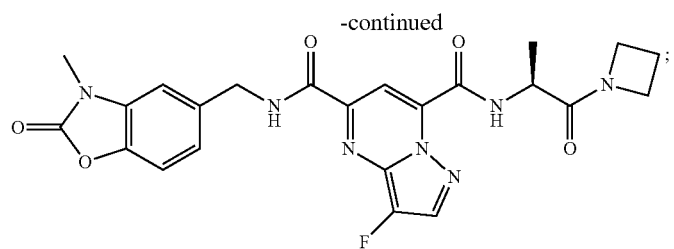
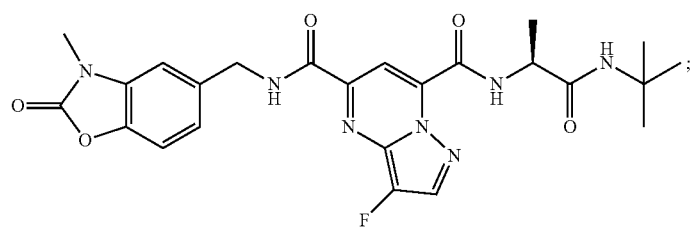
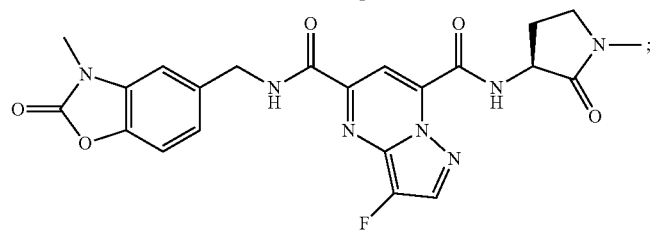
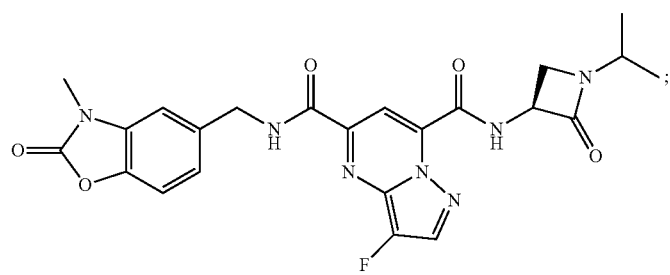
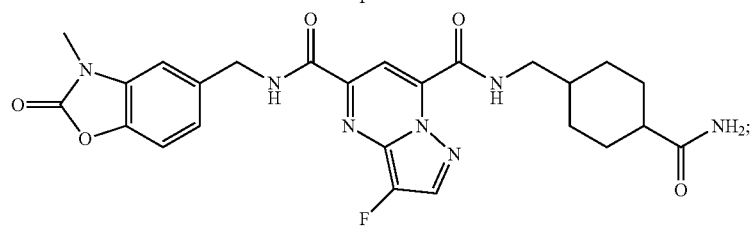
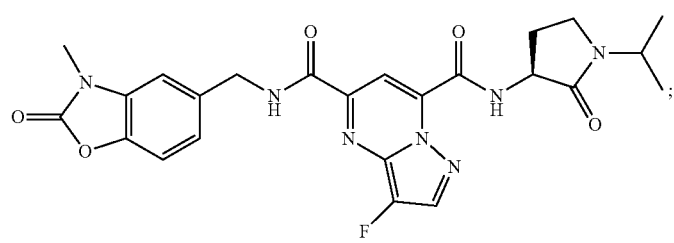
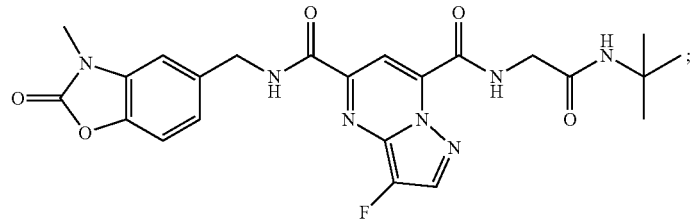

-continued
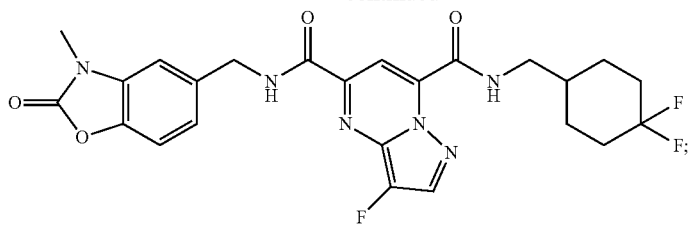
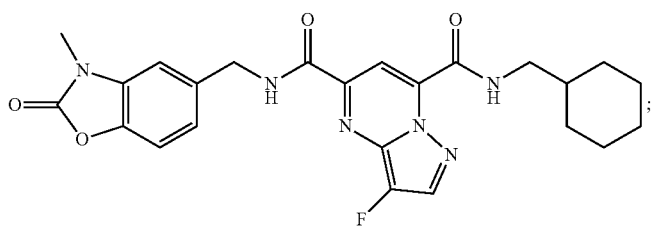
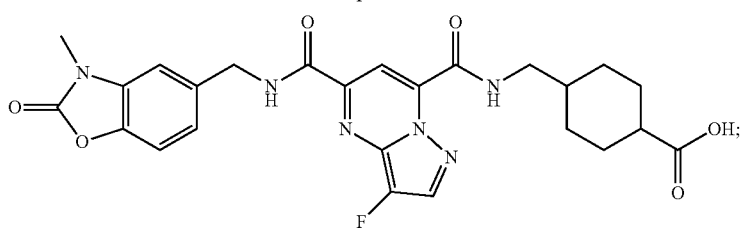
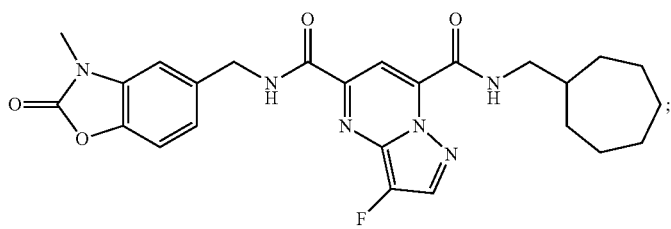
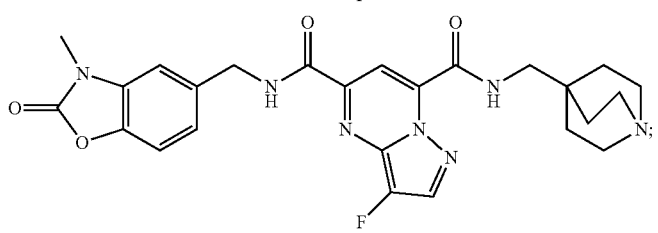
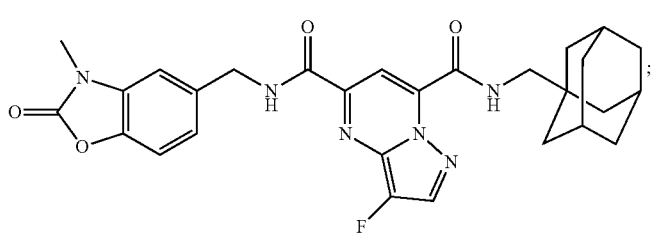
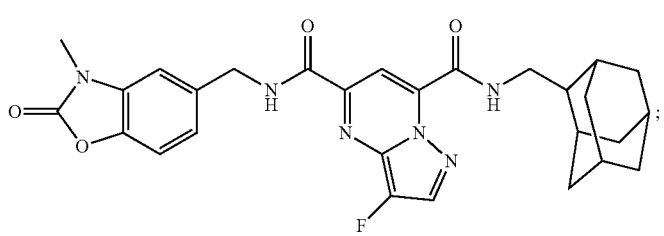

-continued
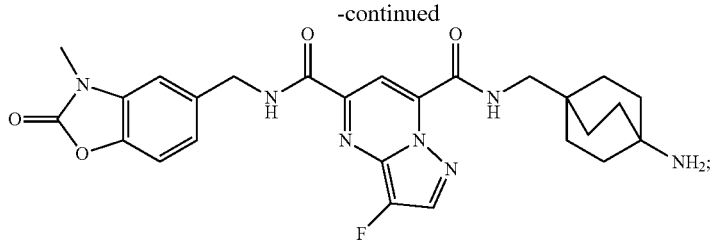
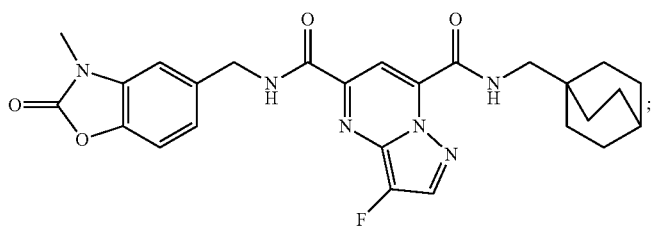
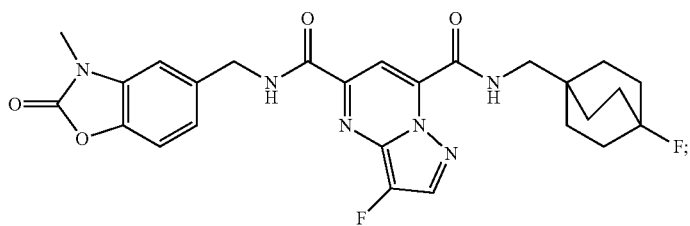
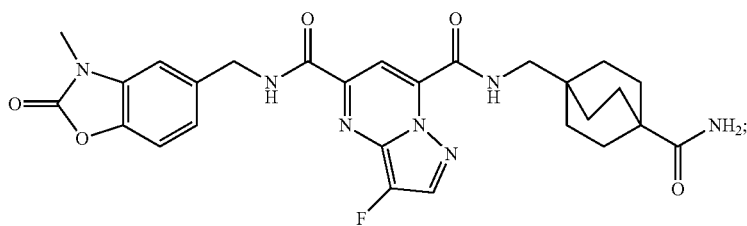
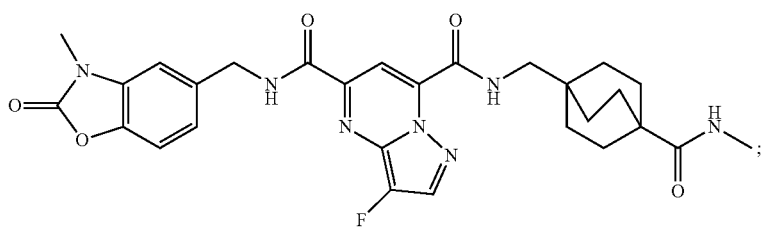
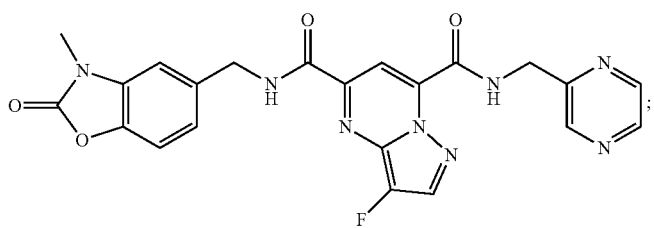
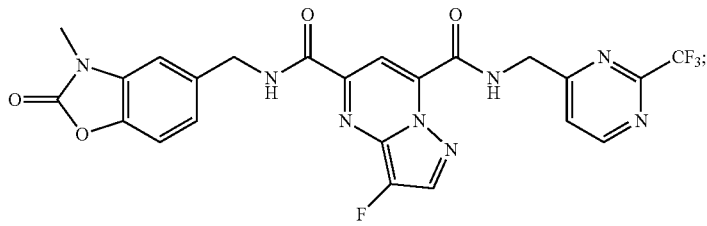

-continued
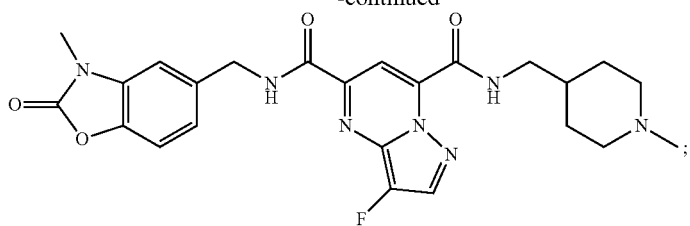
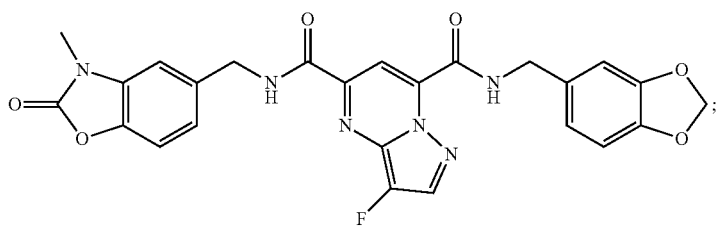
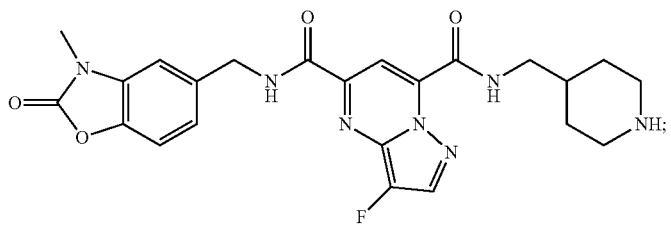
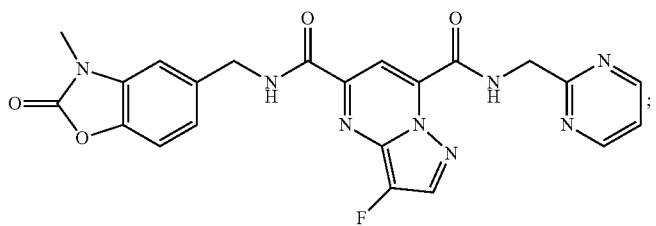
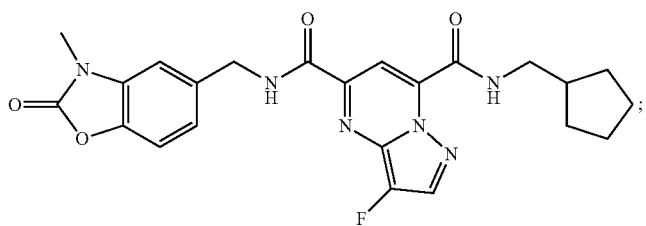
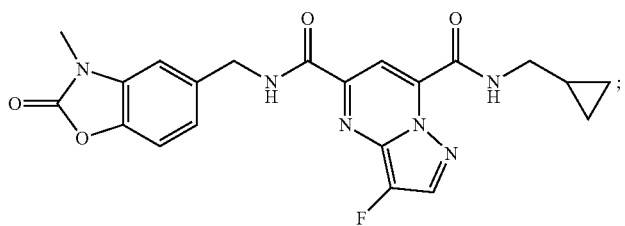
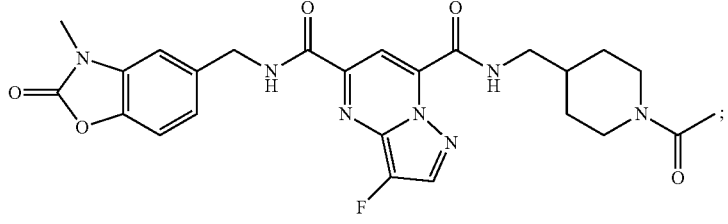

-continued
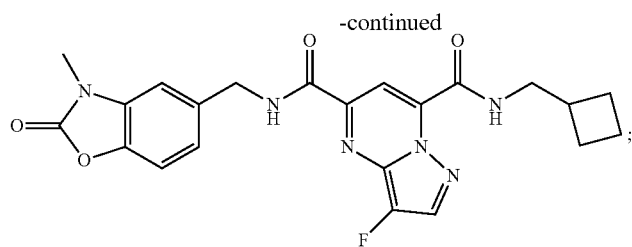
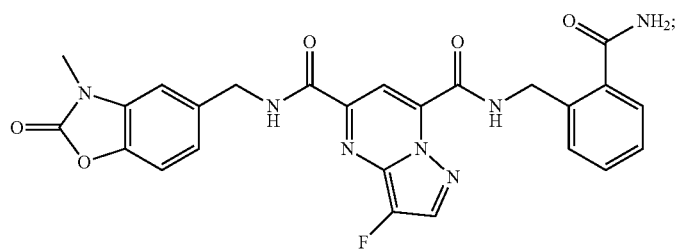
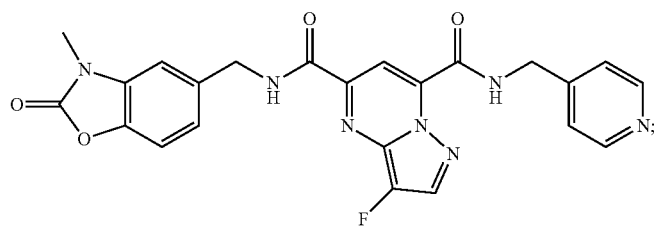
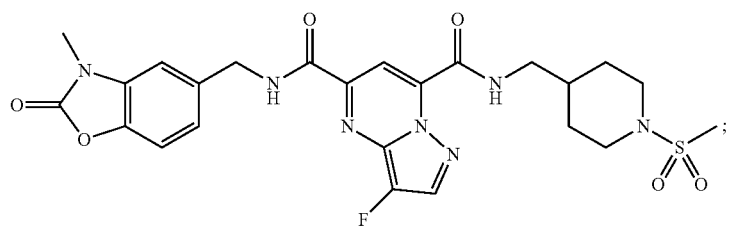
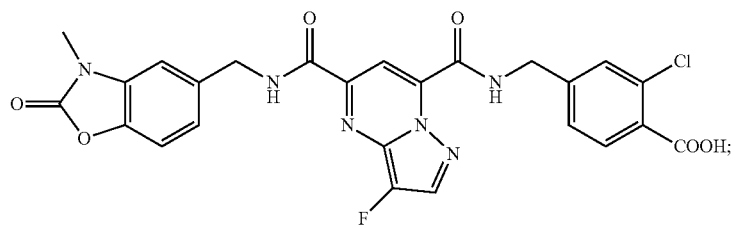
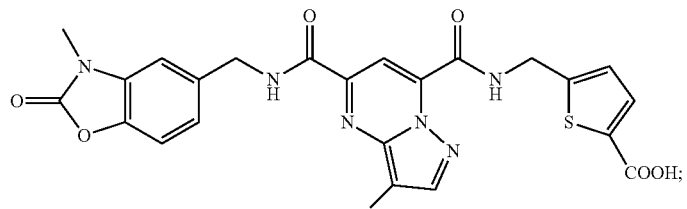
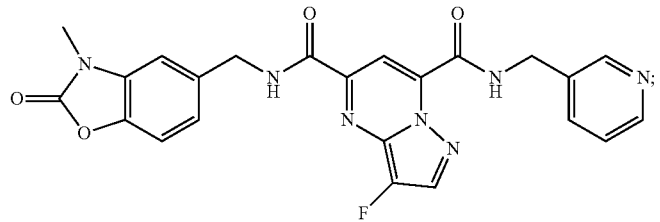

-continued
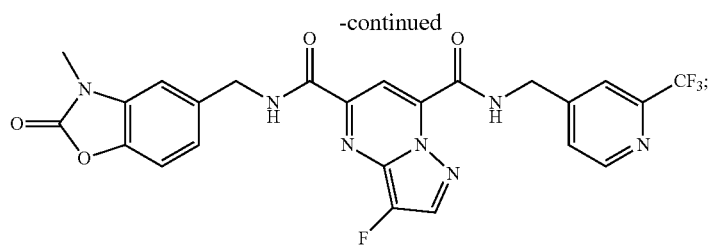
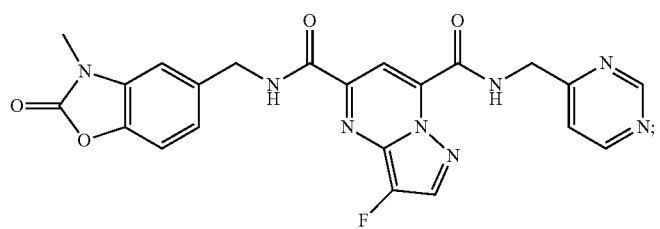
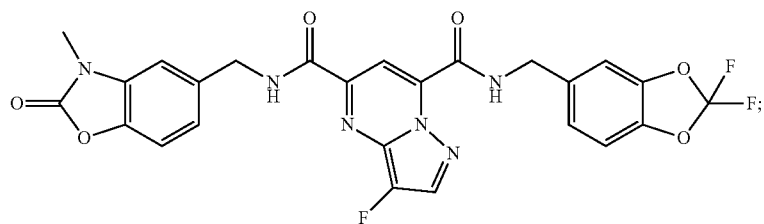
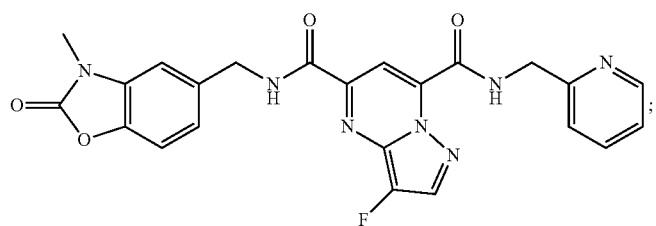
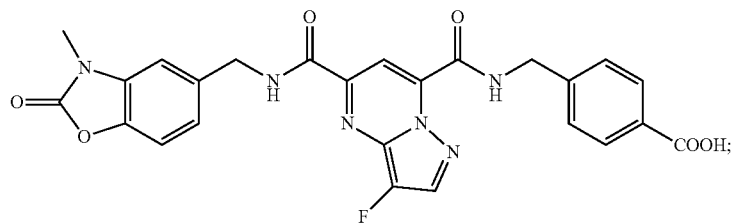
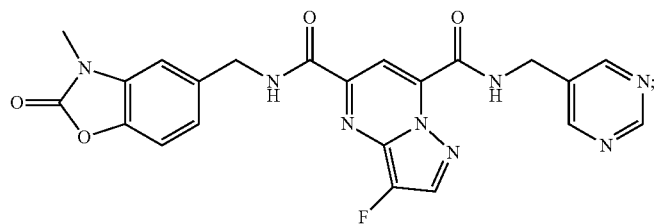
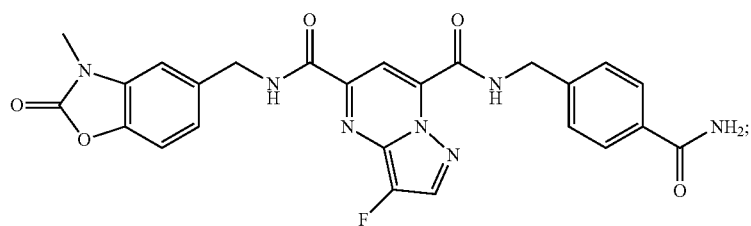

-continued
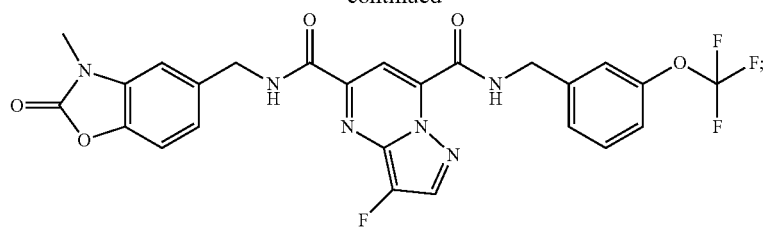
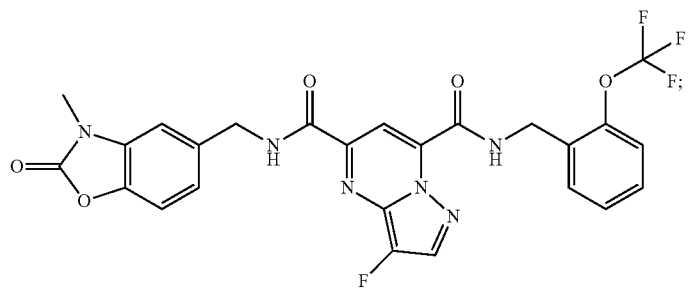
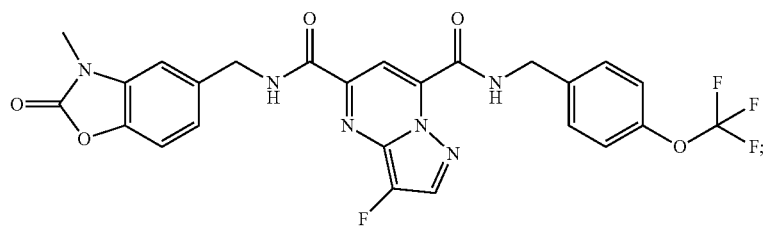
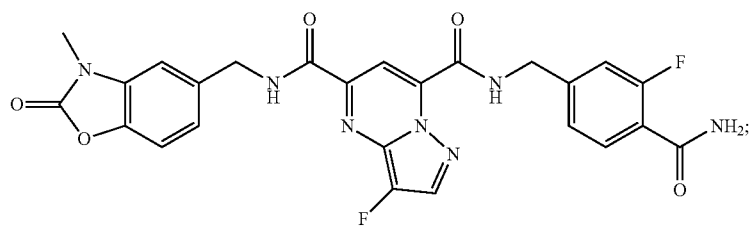
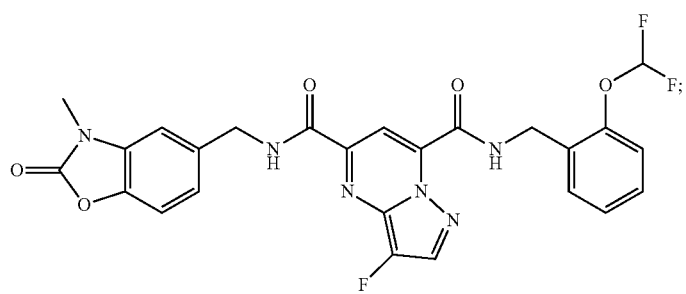
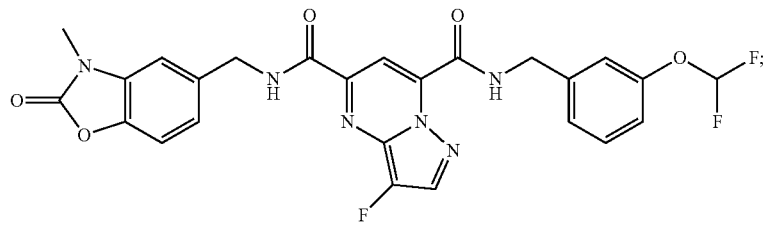
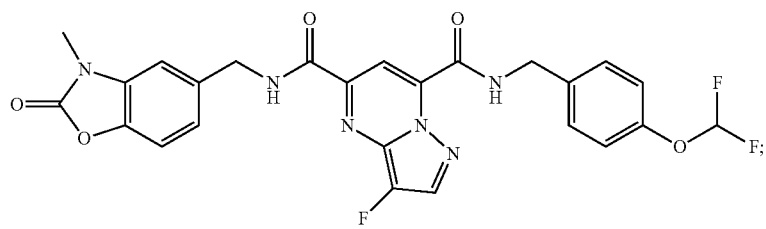

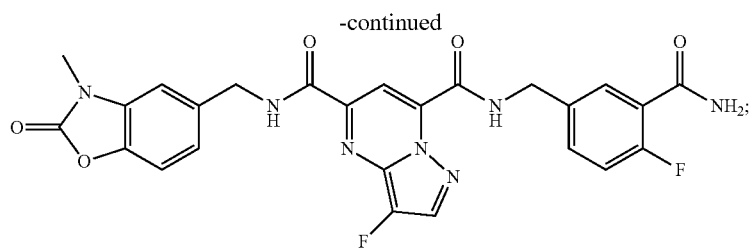
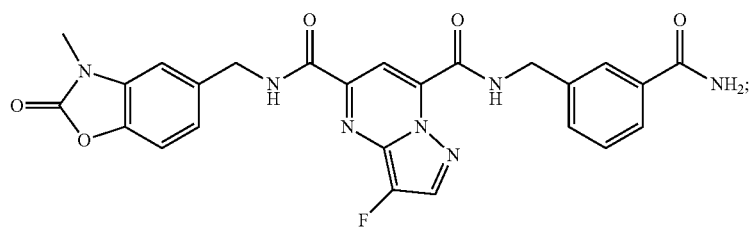
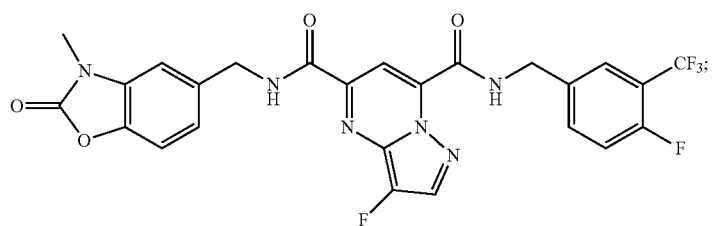
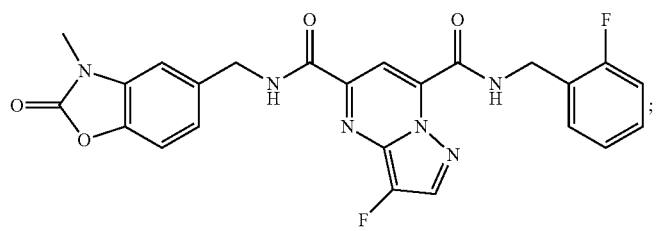
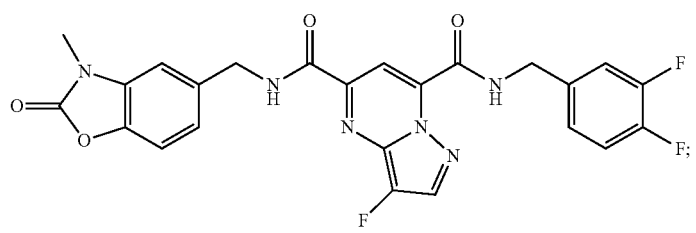
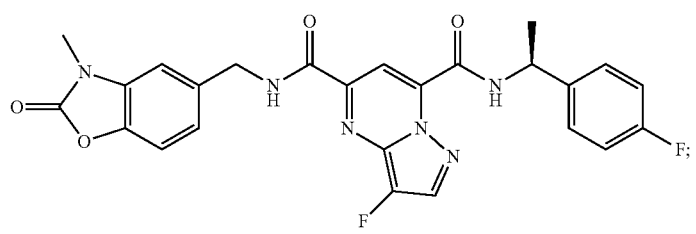
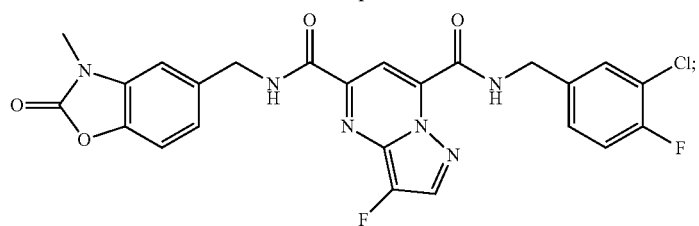

-continued
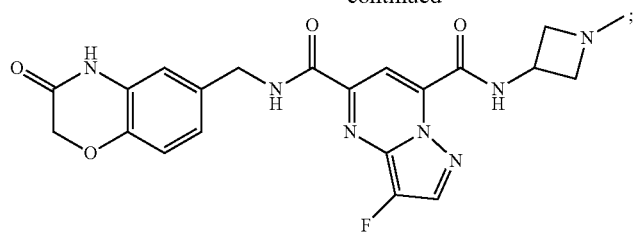
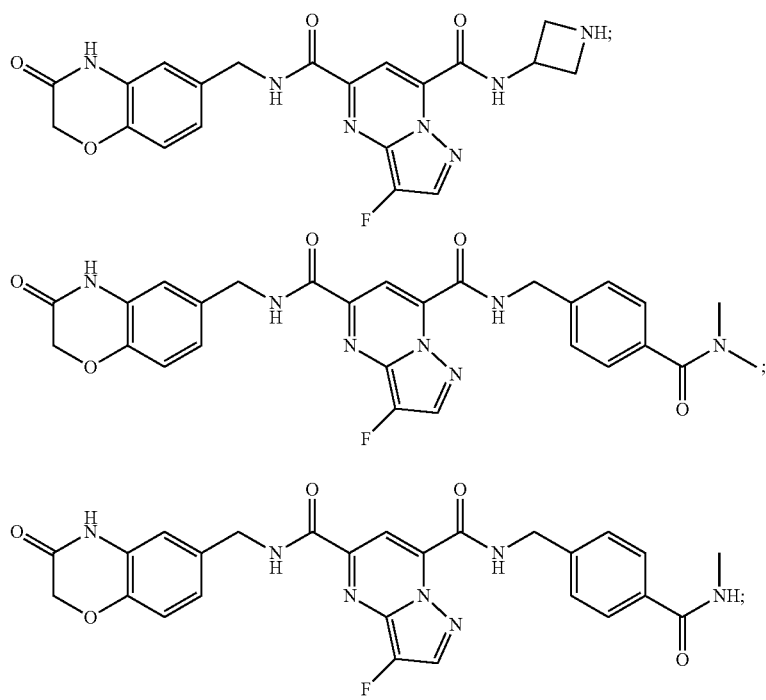
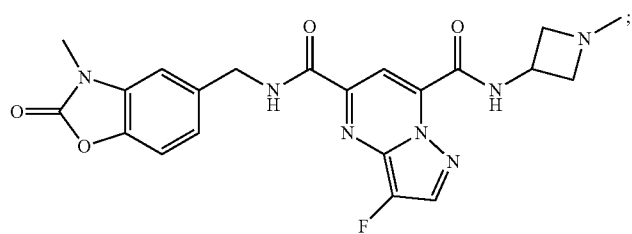
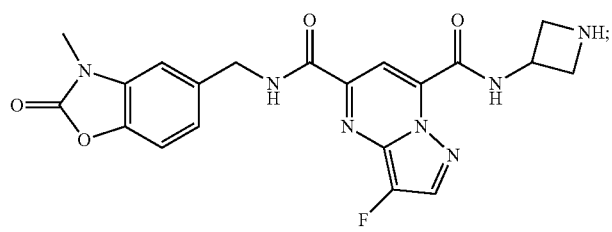
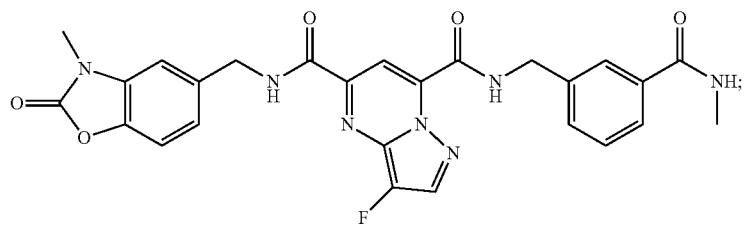

-continued
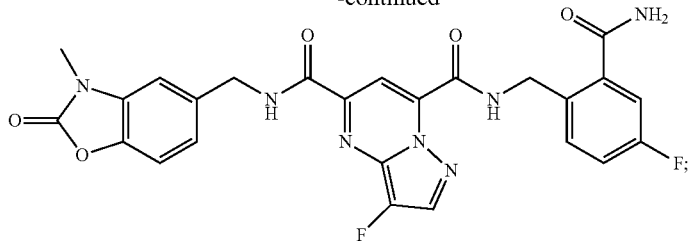
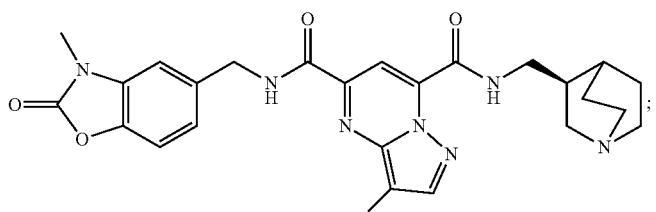
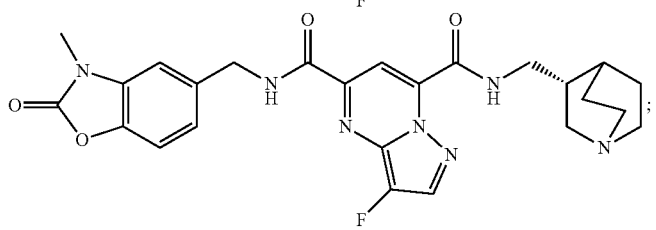
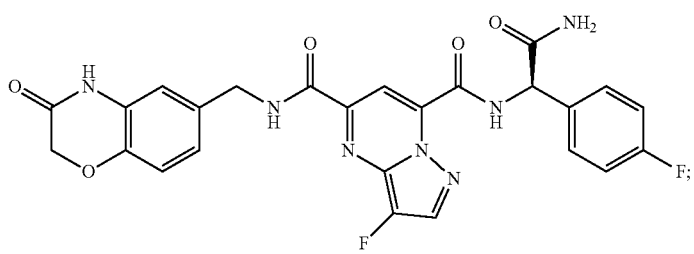
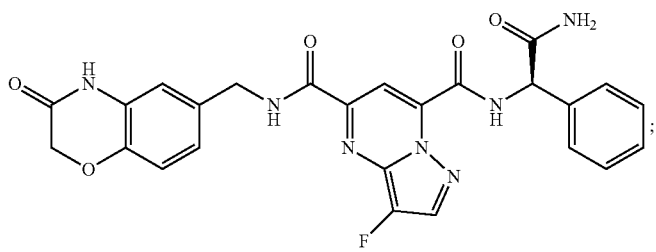
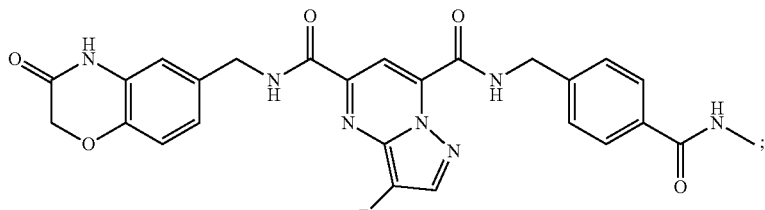
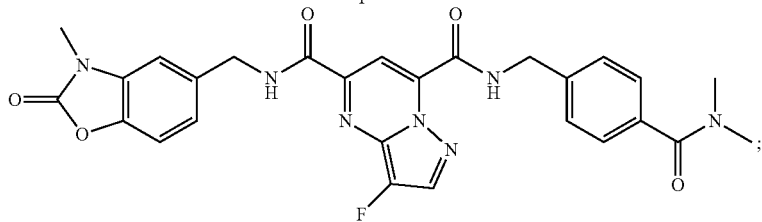

-continued
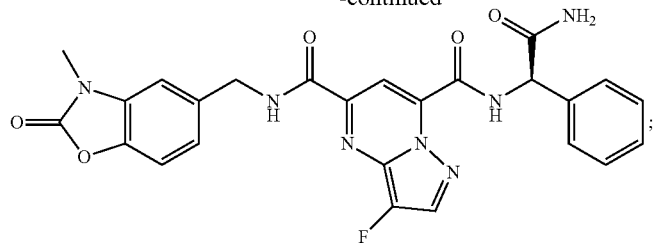
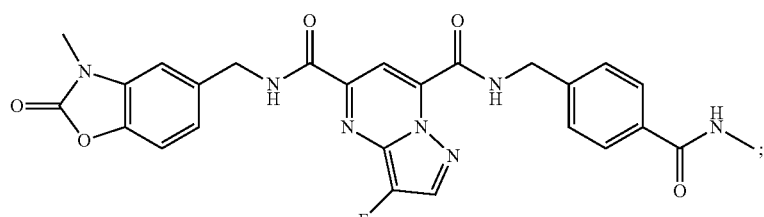
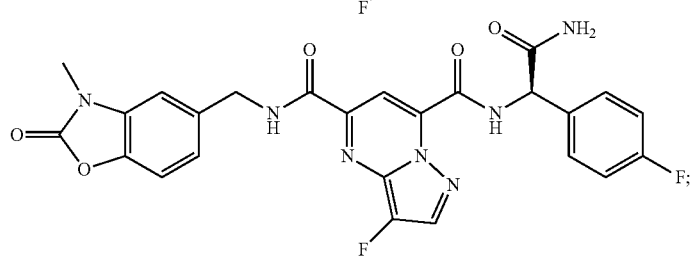
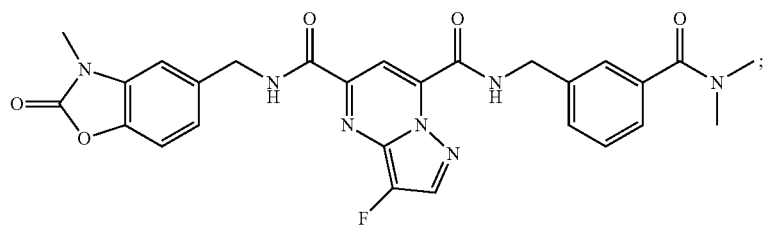
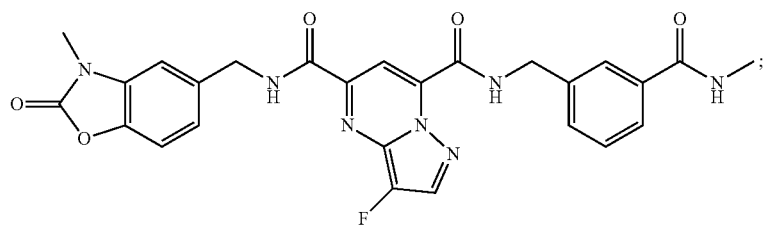
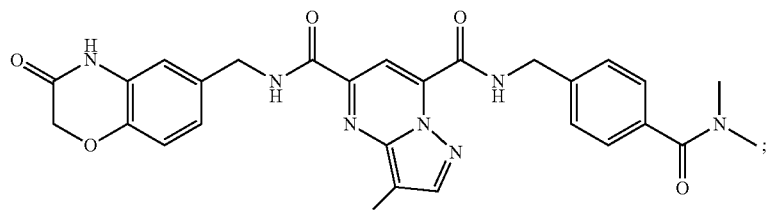
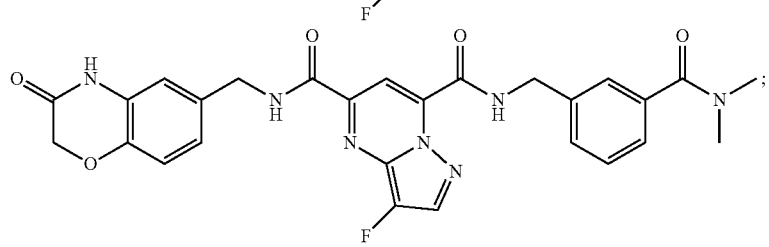

-continued
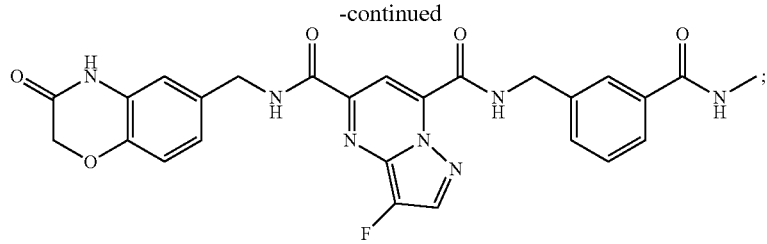
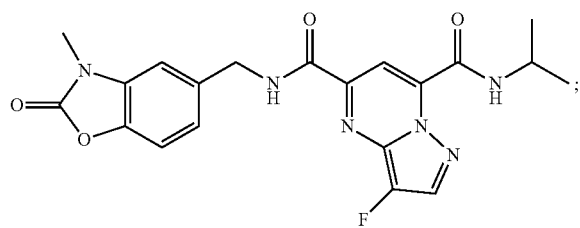
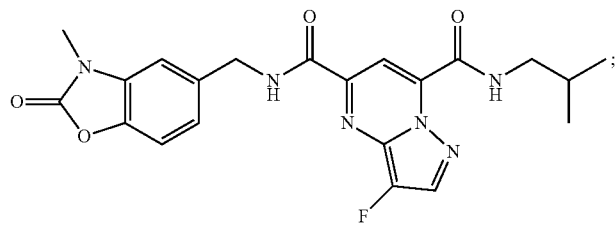
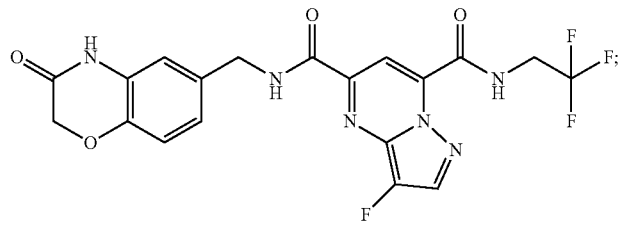
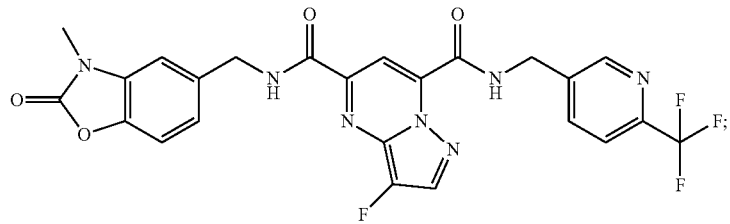
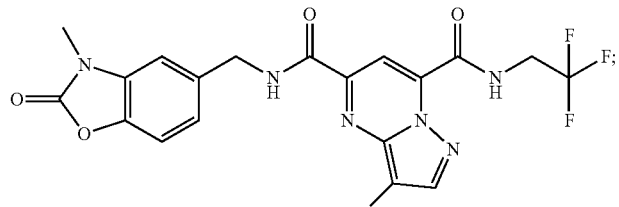
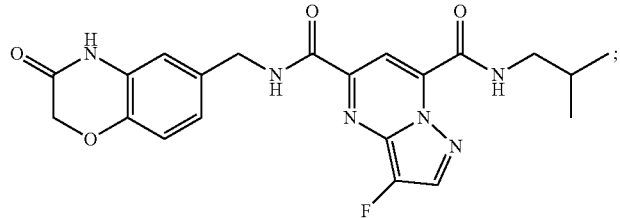

-continued
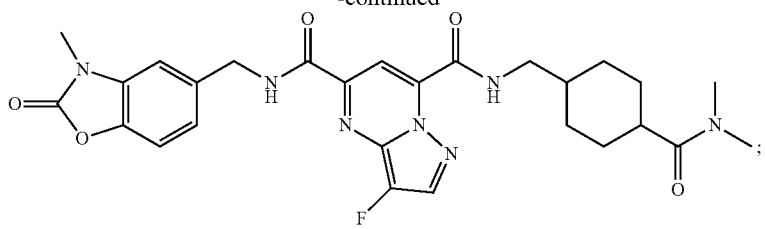
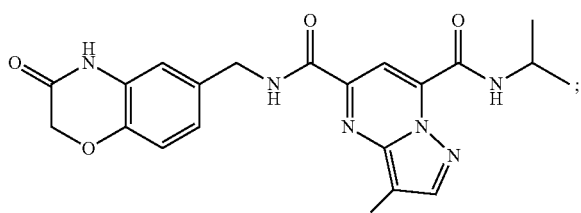
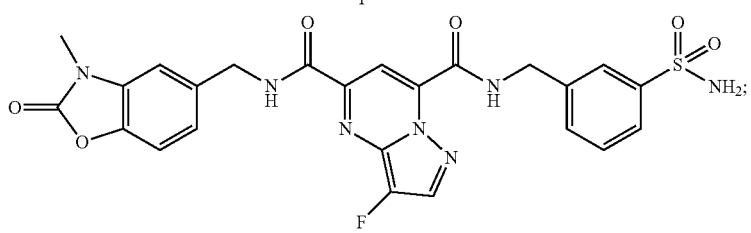
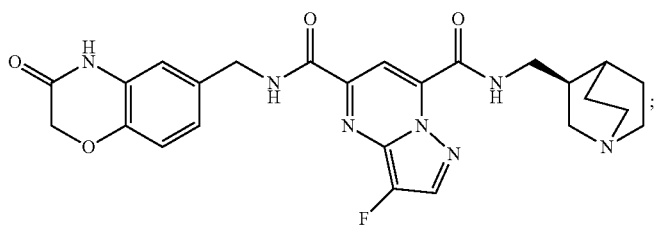
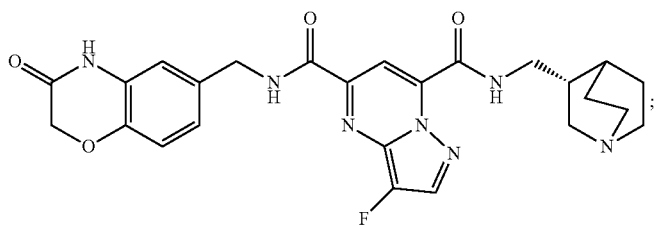
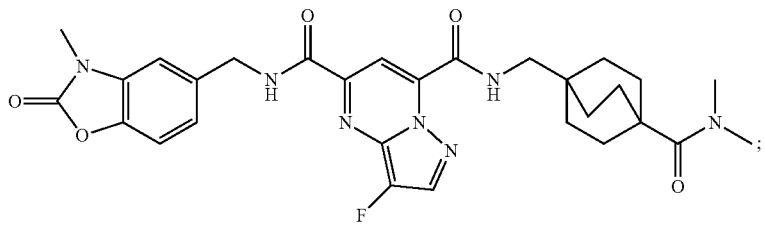
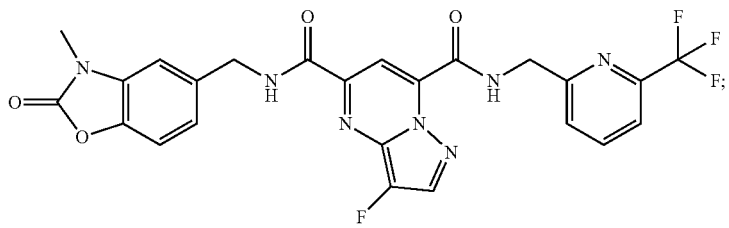

-continued
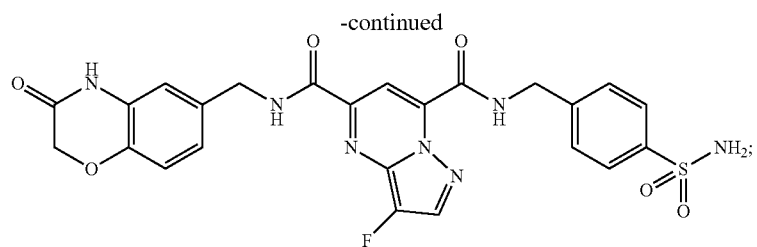
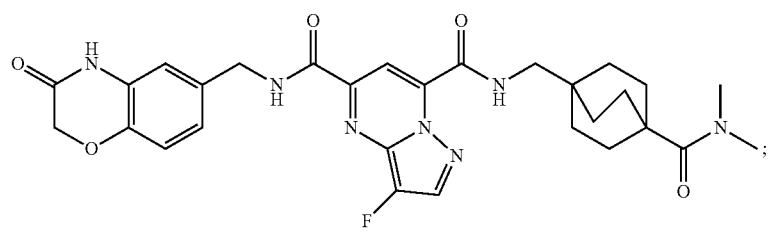
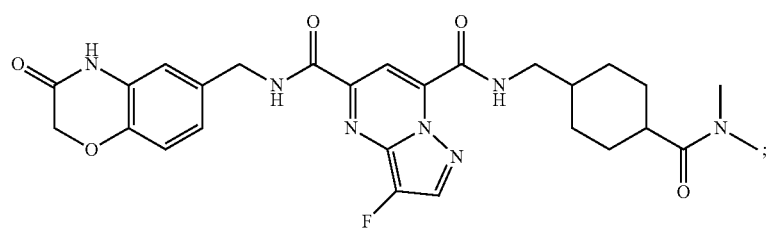
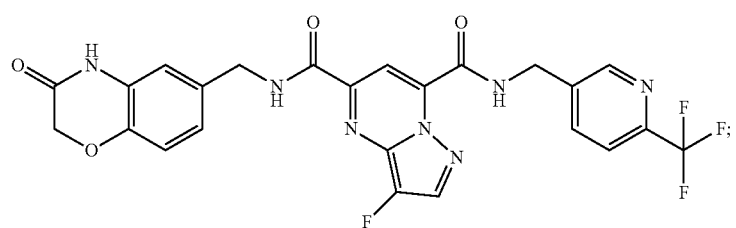
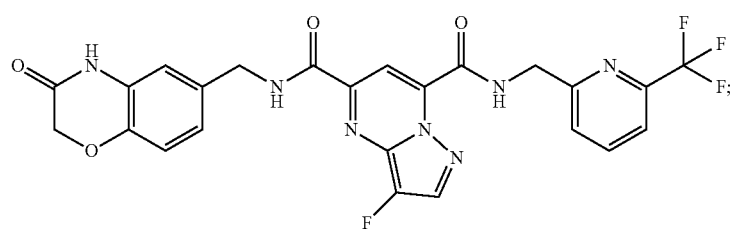
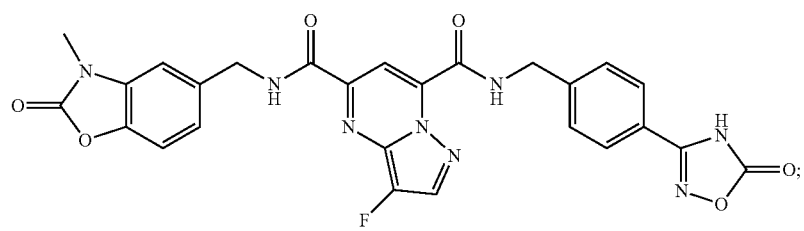
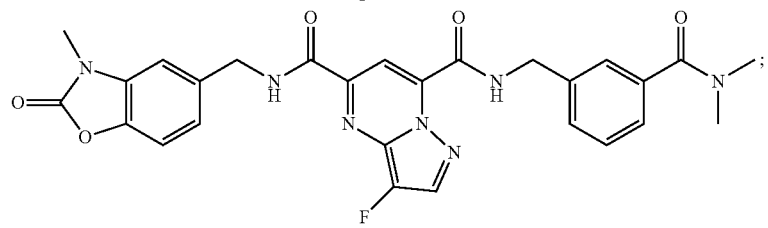

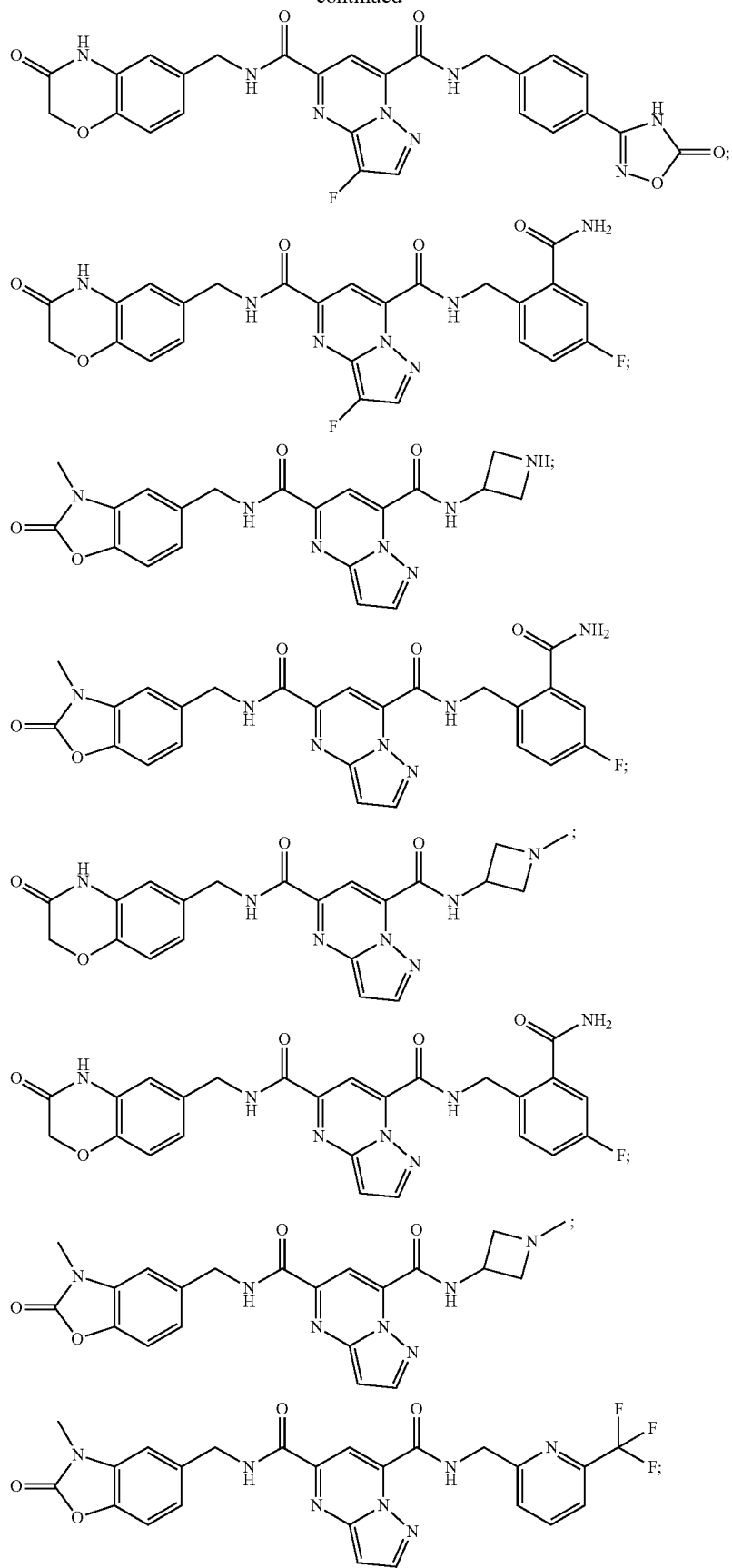

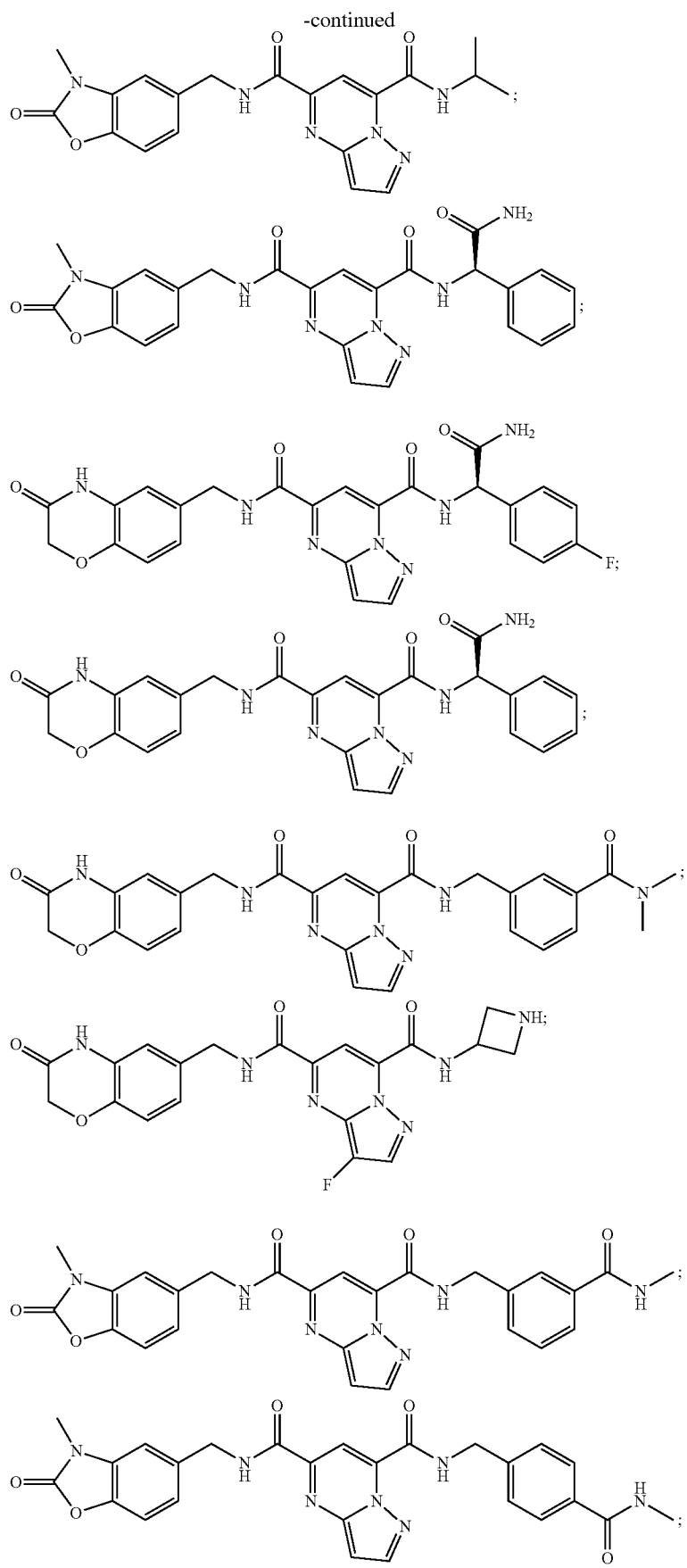

-continued
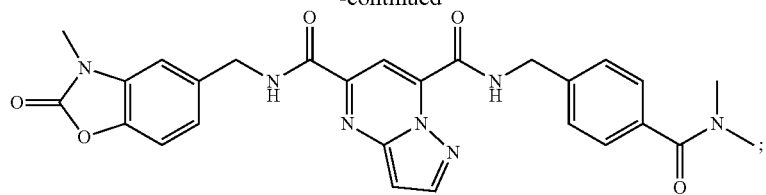
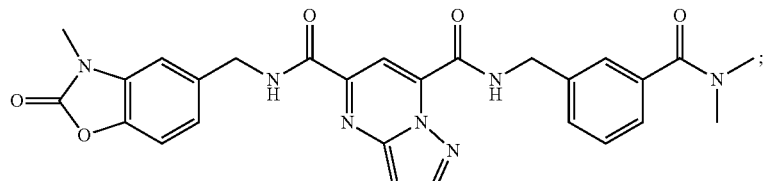
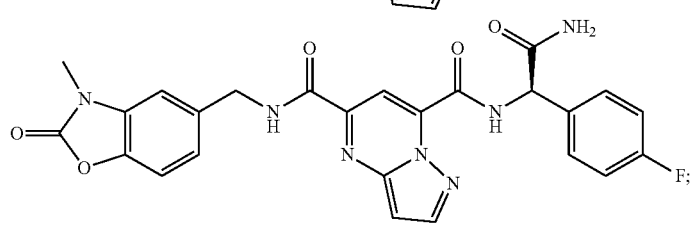
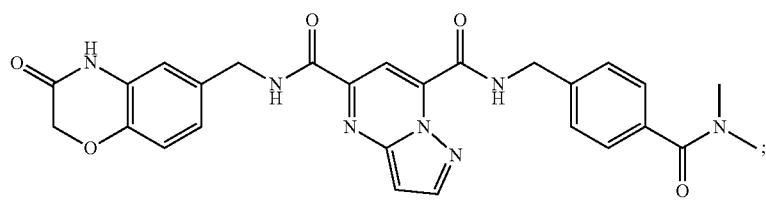
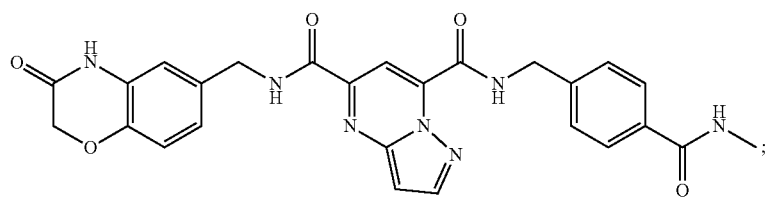
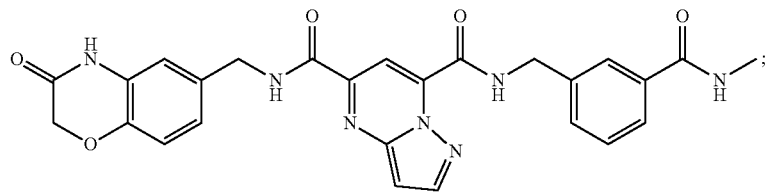
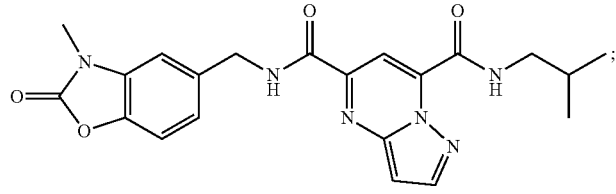
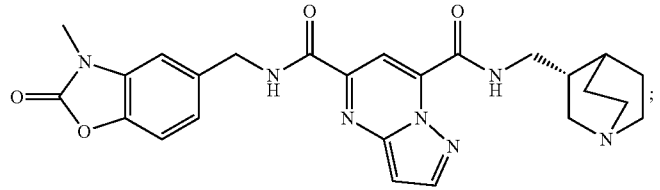

-continued
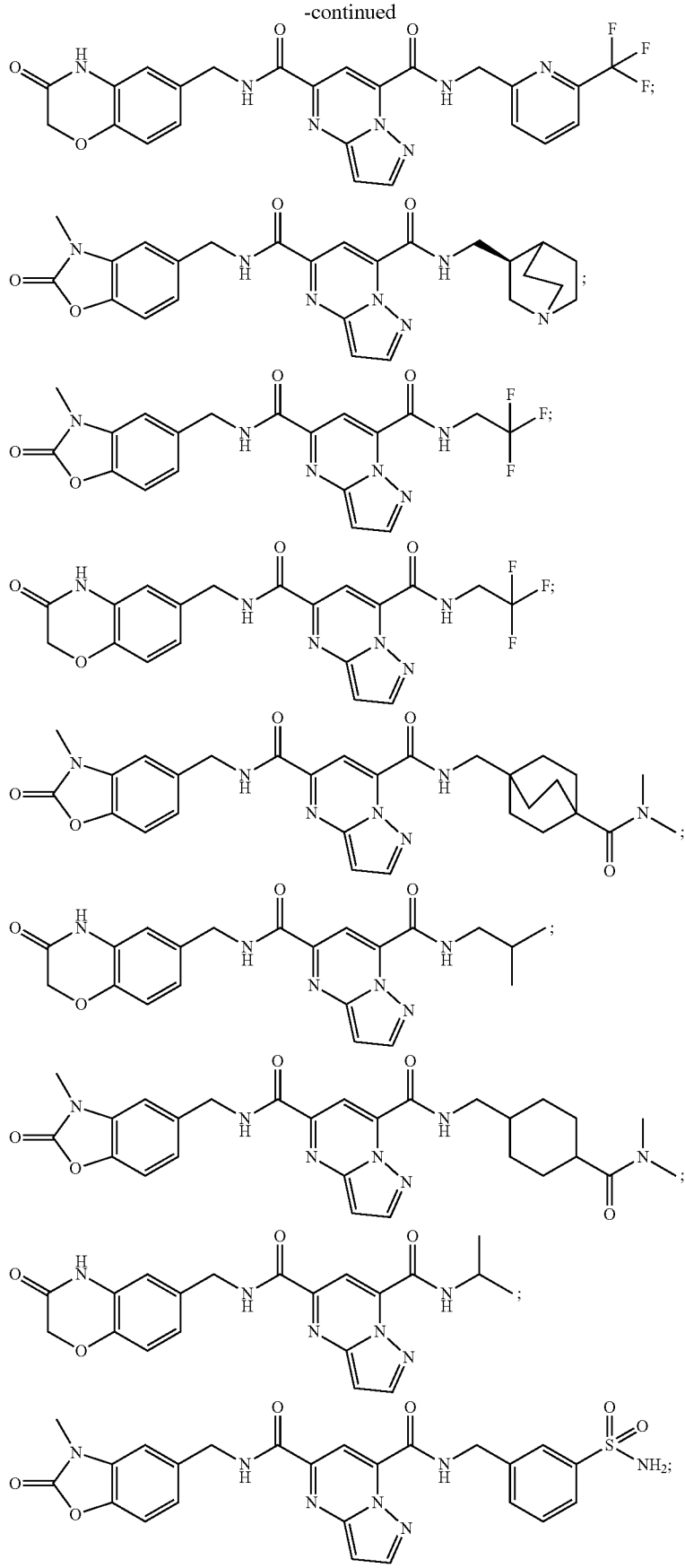

-continued
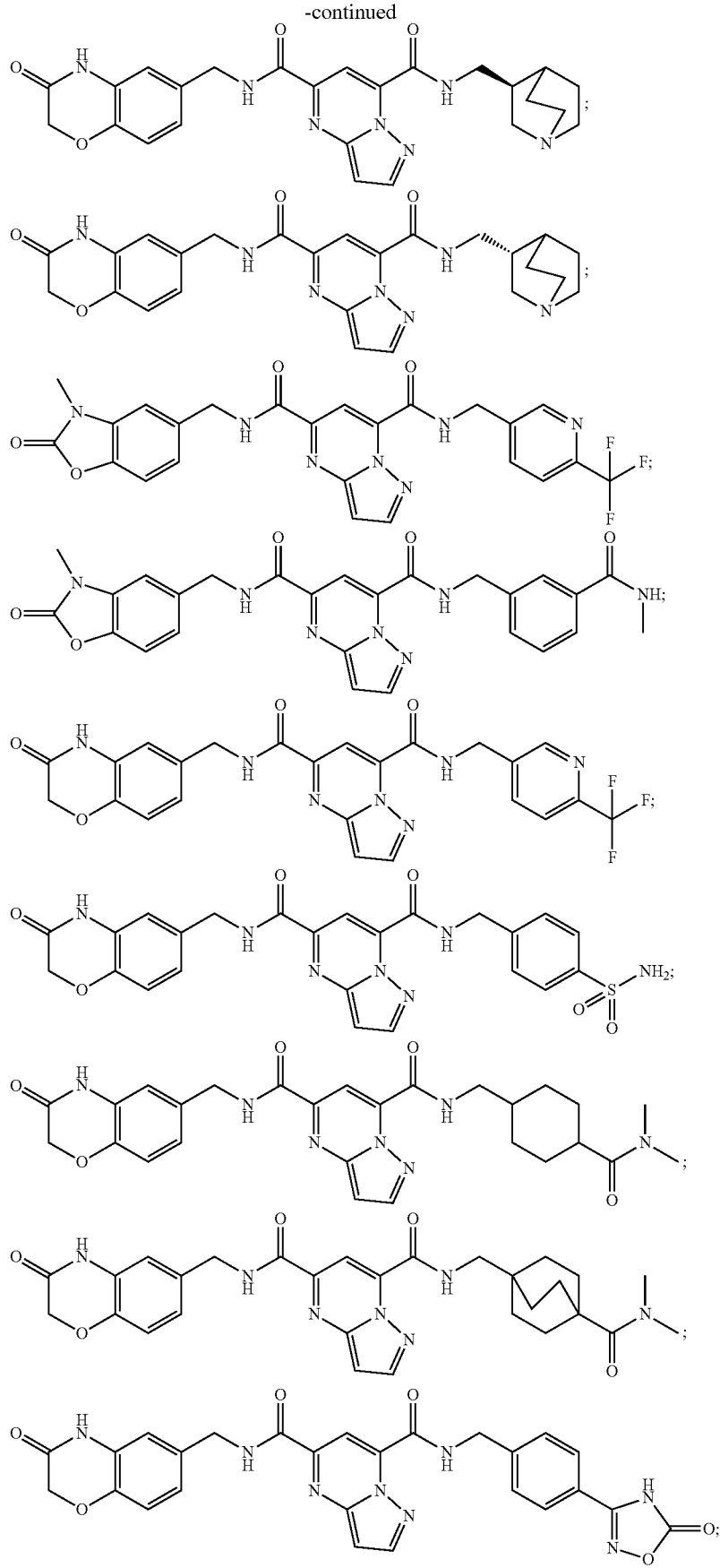

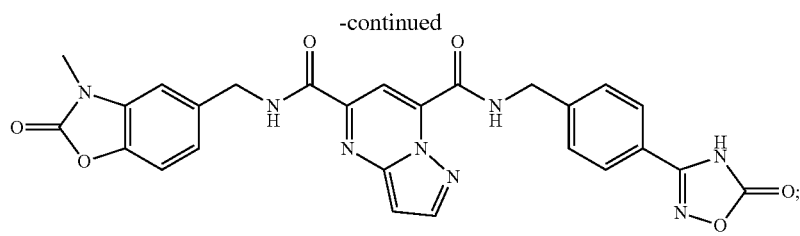

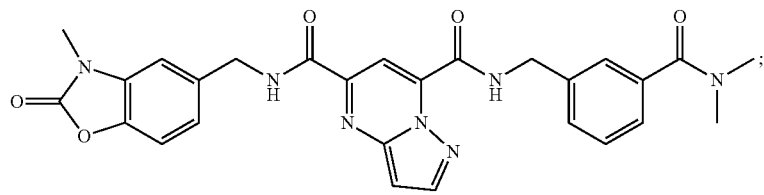

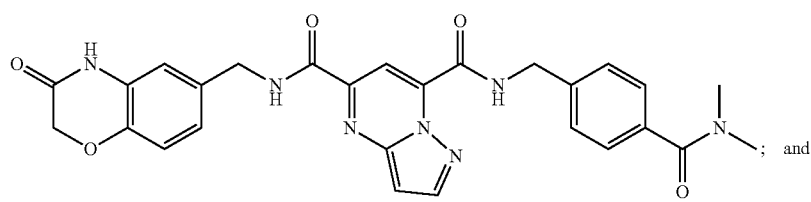

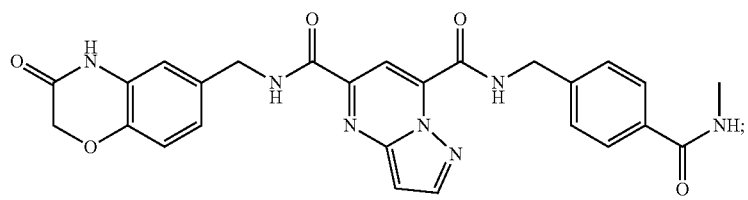

or a pharmaceutically acceptable salt thereof.

In one embodiment, the present invention provides a compound having the structure:

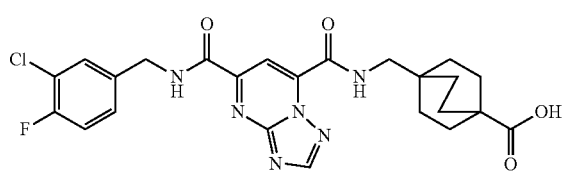 [SMILES: O=C(NCc1ccc(F)c(Cl)c1)c1cc(C(=O)NCC23CCC(C(=O)O)(CC2)CC3)n2ncnc2n1]

or a pharmaceutically acceptable salt thereof.

In another embodiment, the present invention provides a compound having the structure:

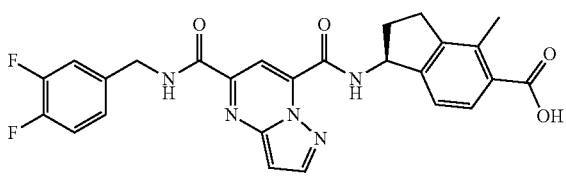 [SMILES: Cc1c(C(=O)O)ccc2c1CC[C@@H]2NC(=O)c1cc(C(=O)NCc2ccc(F)c(F)c2)nc2ccnn12]

or a pharmaceutically acceptable salt thereof.

In yet another embodiment, the present invention provides a compound having the structure:

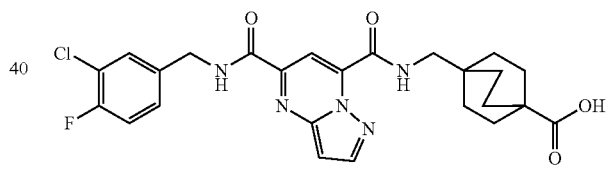

or a pharmaceutically acceptable salt thereof.

In still another embodiment, the present invention provides a compound having the structure:

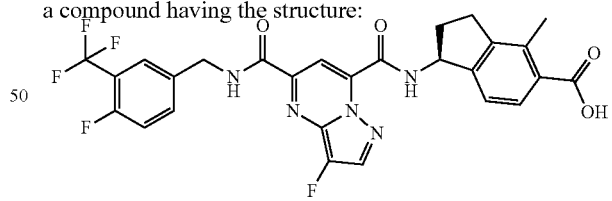

or a pharmaceutically acceptable salt thereof.

In a further embodiment, the present invention provides a compound having the structure:

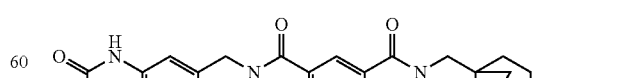

or a pharmaceutically acceptable salt thereof.

In yet a further embodiment, the present invention provides a compound having the structure:

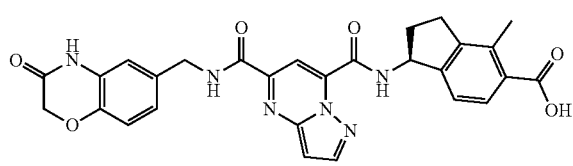 [SMILES: Cc1c(C(=O)O)ccc2c1CC[C@@H]2NC(=O)c1cc(C(=O)NCc2ccc3c(c2)NC(=O)CO3)nc2ccnn12]

or a pharmaceutically acceptable salt thereof.

In still a further embodiment, the present invention provides a compound having the structure:

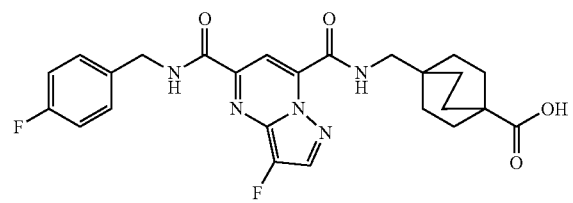 [SMILES: O=C(NCc1ccc(F)cc1)c1cc(C(=O)NCC23CCC(C(=O)O)(CC2)CC3)n2ncc(F)c2n1]

or a pharmaceutically acceptable salt thereof.

In another embodiment, the present invention provides a compound having the structure:

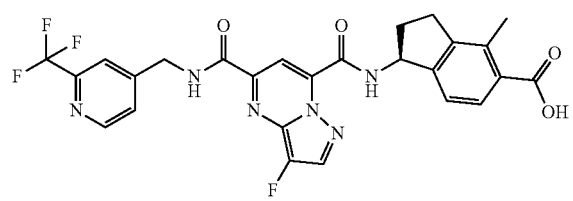 [SMILES: Cc1c(C(=O)O)ccc2c1CC[C@@H]2NC(=O)c1cc(C(=O)NCc2ccnc(C(F)(F)F)c2)nc2c(F)cnn12]

or a pharmaceutically acceptable salt thereof.

In yet another embodiment, the present invention provides a compound having the structure:

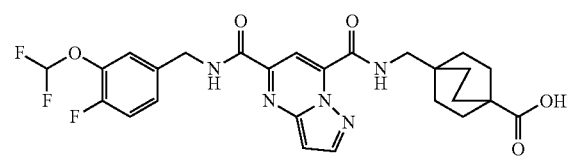 [SMILES: O=C(NCc1ccc(F)c(OC(F)F)c1)c1cc(C(=O)NCC23CCC(C(=O)O)(CC2)CC3)n2nccc2n1]

or a pharmaceutically acceptable salt thereof.

In still another embodiment, the present invention provides a compound having the structure:

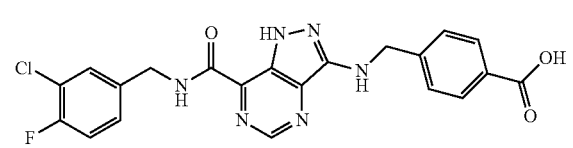

or a pharmaceutically acceptable salt thereof.

In one embodiment, the present invention provides a compound having the structure:

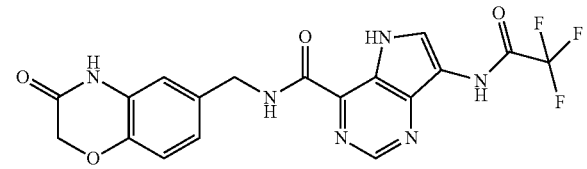 [SMILES: O=C1COc2ccc(CNC(=O)c3ncnc4c(NC(=O)C(F)(F)F)c[nH]c34)cc2N1]

or a pharmaceutically acceptable salt thereof.

In another embodiment, the present invention provides a compound having the structure:

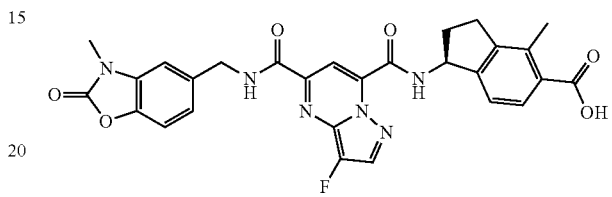

or a pharmaceutically acceptable salt thereof.

In yet another embodiment, the present invention provides a compound having the structure:

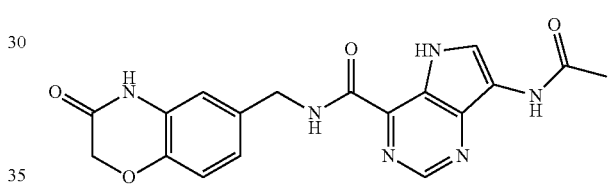

or a pharmaceutically acceptable salt thereof.

In still another embodiment, the present invention provides a compound having the structure:

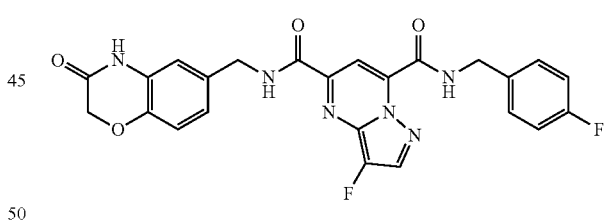

or a pharmaceutically acceptable salt thereof.

In a further embodiment, the present invention provides a compound having the structure:

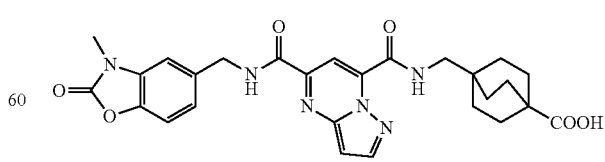

or a pharmaceutically acceptable salt thereof.

In yet a further embodiment, the present invention provides a compound having the structure:

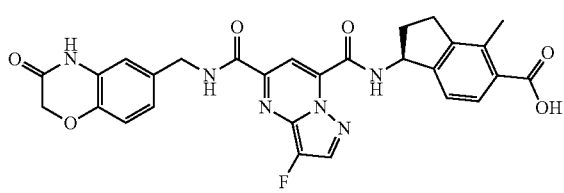 [SMILES: Cc1c(C(=O)O)ccc2c1CC[C@@H]2NC(=O)c1cc(C(=O)NCc2ccc3c(c2)NC(=O)CO3)nc2c(F)cnn12]

or a pharmaceutically acceptable salt thereof.

In still a further embodiment, the present invention provides a compound having the structure:

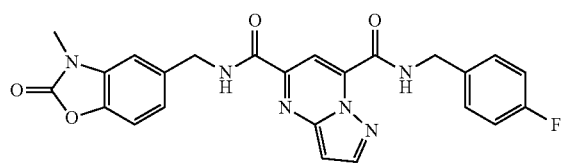 [SMILES: Cn1c(=O)oc2ccc(CNC(=O)c3cc(C(=O)NCc4ccc(F)cc4)n4nccc4n3)cc21]

or a pharmaceutically acceptable salt thereof.

In another embodiment, the present invention provides a compound having the structure:

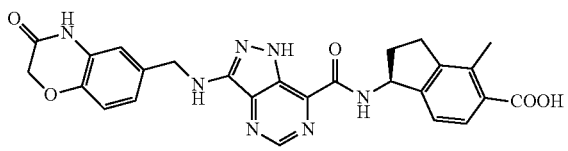 [SMILES: Cc1c(C(=O)O)ccc2c1CC[C@@H]2NC(=O)c1ncnc2c(NCc3ccc4c(c3)NC(=O)CO4)n[nH]c12]

or a pharmaceutically acceptable salt thereof.

In yet another embodiment, the present invention provides a compound having the structure:

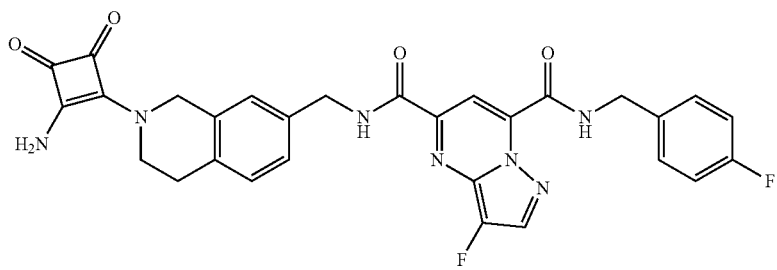 [SMILES: Nc1c(N2CCc3ccc(CNC(=O)c4cc(C(=O)NCc5ccc(F)cc5)n5ncc(F)c5n4)cc3C2)c(=O)c1=O]

or a pharmaceutically acceptable salt thereof.

In still another embodiment, the present invention provides a compound having the structure:

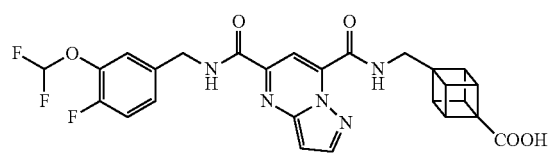 [SMILES: O=C(NCc1ccc(F)c(OC(F)F)c1)c1cc(C(=O)NCC23C4C5C2C2C3C4C52C(=O)O)n2nccc2n1]

or a pharmaceutically acceptable salt thereof.

The present invention is also directed to pharmaceutical compositions which include any of the amide containing heterobicyclic metalloproteases of the invention described hereinabove. In accordance therewith, some embodiments of the present invention provide a pharmaceutical composition which may include an effective amount of an amide containing heterobicyclic metalloprotease compound of the present invention and a pharmaceutically acceptable carrier.

In one embodiment, the present invention provides a pharmaceutical composition including an effective amount of the compound of Formula (I) and N-oxides, pharmaceutically acceptable salts, prodrugs, formulation, polymorphs, racemic mixtures and stereoisomers thereof, and a pharmaceutically acceptable carrier.

In yet another embodiment, the present invention provides a pharmaceutical composition including an effective amount of the compound of Formula (II) and N-oxides, pharmaceutically acceptable salts, prodrugs, formulation, polymorphs, racemic mixtures and stereoisomers thereof, and a pharmaceutically acceptable carrier.

In another embodiment, the present invention provides a pharmaceutical composition including an effective amount of the compound of Formula (III) and N-oxides, pharmaceutically acceptable salts, prodrugs, formulation, polymorphs, racemic mixtures and stereoisomers thereof, and a pharmaceutically acceptable carrier.

In still another embodiment, the present invention provides a pharmaceutical composition including an effective amount of the compound of Formula (IV) and N-oxides, pharmaceutically acceptable salts, prodrugs, formulation, polymorphs, racemic mixtures and stereoisomers thereof, and a pharmaceutically acceptable carrier.

In a further embodiment, the present invention provides a pharmaceutical composition including an effective amount of the compound of Formula (V) and N-oxides, pharmaceutically acceptable salts, prodrugs, formulation, polymorphs, racemic mixtures and stereoisomers thereof, and a pharmaceutically acceptable carrier.

In yet a further embodiment, the present invention provides a pharmaceutical composition including an effective amount of the compound of Formula (VI) and N-oxides, pharmaceutically acceptable salts, prodrugs, formulation, polymorphs, racemic mixtures and stereoisomers thereof, and a pharmaceutically acceptable carrier.

The present invention is also directed to methods of inhibiting metalloproteases and methods of treating diseases or symptoms mediated by an metalloprotease enzyme, particularly an MMP-13, MMP-8, MMP-3, MMP-12 and/or an ADAMTS-4 enzyme, and more particulary an MMP-13 enzyme and/or an MMP-3 enzyme. Such methods include administering a bicyclic metalloprotease inhibiting compound of the present invention, or a pharmaceutically acceptable salt thereof. Examples of diseases or symptoms mediated by an metalloprotease mediated enzyme include, but are not limited to, rheumatoid arthritis, osteoarthritis, abdominal aortic aneurysm, cancer (e.g. but not limited to melanoma, gastric carcinoma or non-small cell lung carcinoma), inflammation, atherosclerosis, multiple sclerosis, chronic obstructive pulmonary disease, ocular diseases (e.g. but not limited to ocular inflammation, retinopathy of prematurity, macular degeneration with the wet type preferred and corneal neovascularization), neurologic diseases, psychiatric diseases, thrombosis, bacterial infection, Parkinson's disease, fatigue, tremor, diabetic retinopathy, vascular diseases of the retina, aging, dementia, cardiomyopathy, renal tubular impairment, diabetes, psychosis, dyskinesia, pigmentary abnormalities, deafness, inflammatory and fibrotic syndromes, intestinal bowel syndrome, allergies, Alzheimers disease, arterial plaque formation, oncology, periodontal, viral infection, stroke, atherosclerosis, cardiovascular disease, reperfusion injury, trauma, chemical exposure or oxidative damage to tissues, wound healing, hemorroid, skin beautifying, pain, inflammatory pain, bone pain and joint pain, acne, acute alcoholic hepatitis, acute inflammation, acute pancreatitis, acute respiratory distress syndrome, adult respiratory disease, airflow obstruction, airway hyperresponsiveness, alcoholic liver disease, allograft rejections, angiogenesis, angiogenic ocular disease, arthritis, asthma, atopic dermatitis, bronchiectasis, bronchiolitis, bronchiolitis obliterans, burn therapy, cardiac and renal reperfusion injury, celiac disease, cerebral and cardiac ischemia, CNS tumors, CNS vasculitis, colds, contusions, cor pulmonae, cough, Crohn's disease, chronic bronchitis, chronic inflammation, chronic pancreatitis, chronic sinusitis, crystal induced arthritis, cystic fibrosis, delayted type hypersensitivity reaction, duodenal ulcers, dyspnea, early transplantation rejection, emphysema, encephalitis, endotoxic shock, esophagitis, gastric ulcers, gingivitis, glomerulonephritis, glossitis, gout, graft vs. host reaction, gram negative sepsis, granulocytic ehrlichiosis, hepatitis viruses, herpes, herpes viruses, HIV, hypercapnea, hyperinflation, hyperoxia-induced inflammation, hypoxia, hypersensitivity, hypoxemia, inflammatory bowel disease, interstitial pneumonitis, ischemia reperfusion injury, kaposi's sarcoma associated virus, lupus, malaria, meningitis, multi-organ dysfunction, necrotizing enterocolitis, osteoporosis, periodontitis, peritonitis associated with continous ambulatory peritoneal dialysis (CAPD), pre-term labor, polymyositis, post surgical trauma, pruritis, psoriasis, psoriatic arthritis, pulmatory fibrosis, pulmatory hypertension, renal reperfusion injury, respiratory viruses, restinosis, right ventricular hypertrophy, sarcoidosis, septic shock, small airway disease, sprains, strains, subarachnoid hemorrhage, surgical lung volume reduction, thrombosis, toxic shock syndrome, transplant reperfusion injury, traumatic brain injury, ulcerative colitis, vasculitis, ventilation-perfusion mismatching, wheeze In one embodiment, the present invention provides a method of inhibiting a metalloprotease, particularly MMP-13, MMP-8, MMP-3, MMP-12 and/or ADAMTS-4, and more particulary MMP-13, which includes administering to a subject in need of such treatment a compound of Formula (I) and N-oxides, pharmaceutically acceptable salts, prodrugs, formulation, polymorphs, racemic mixtures and stereoisomers thereof.

In one embodiment, the present invention provides a method of inhibiting a metalloprotease, particularly MMP-13, MMP-8, MMP-3, MMP-12 and/or ADAMTS-4, and more particulary MMP-13, which includes administering to a subject in need of such treatment a compound of Formula (II) and N-oxides, pharmaceutically acceptable salts, prodrugs, formulation, polymorphs, racemic mixtures and stereoisomers thereof.

In yet another embodiment, the present invention provides a method of inhibiting a metalloprotease, particularly MMP-13, MMP-8, MMP-3, MMP-12 and/or ADAMTS-4, and more particulary MMP-13, which includes administering to a subject in need of such treatment a compound of Formula (III) and N-oxides, pharmaceutically acceptable salts, prodrugs, formulation, polymorphs, racemic mixtures and stereoisomers thereof.

In still another embodiment, the present invention provides a method of inhibiting a metalloprotease, particularly MMP-13, MMP-8, MMP-3, MMP-12 and/or ADAMTS-4, and more particulary MMP-13 and/or MMP-3, which includes administering to a subject in need of such treatment a compound of Formula (IV) and N-oxides, pharmaceutically acceptable salts, prodrugs, formulation, polymorphs, racemic mixtures and stereoisomers thereof.

In a further embodiment, the present invention provides a method of inhibiting a metalloprotease, particularly MMP-13, MMP-8, MMP-3, MMP-12 and/or ADAMTS-4, and more particulary MMP-13 and/or MMP-3, which includes administering to a subject in need of such treatment a compound of Formula (V) and N-oxides, pharmaceutically acceptable salts, prodrugs, formulation, polymorphs, racemic mixtures and stereoisomers thereof.

In yet a further embodiment, the present invention provides a method of inhibiting a metalloprotease, particularly MMP-13, MMP-8, MMP-3, MMP-12 and/or ADAMTS-4, and more particularly MMP-13 and/or MMP-3, which includes administering to a subject in need of such treatment a compound of Formula (VI) and N-oxides, pharmaceutically acceptable salts, prodrugs, formulation, polymorphs, racemic mixtures and stereoisomers thereof.

In still a further embodiment, the present invention provides a method of treating an metalloprotease mediated disease, particulary a MMP-13 mediated disease, a MMP-8 mediated disease, a MMP-3 mediated disease, a MMP-12 mediated disease and/or an ADAMTS-4 mediated disease and more particulary a MMP-13 mediated disease, which includes administering to a subject in need of such treatment an effective amount of a compound of Formula (I) and N-oxides, pharmaceutically acceptable salts, prodrugs, formulation, polymorphs, racemic mixtures and stereoisomers thereof.

In one embodiment, the present invention provides a method of treating an metalloprotease mediated disease, particulary a MMP-13 mediated disease, a MMP-8 mediated disease, a MMP-3 mediated disease, a MMP-12 mediated disease and/or an ADAMTS-4 mediated disease and more particulary a MMP-13 mediated disease, which includes administering to a subject in need of such treatment an effective amount of a compound of Formula (II) and N-oxides, pharmaceutically acceptable salts, prodrugs, formulation, polymorphs, racemic mixtures and stereoisomers thereof.

In another embodiment, the present invention provides a method of treating an metalloprotease mediated disease, particulary a MMP-13 mediated disease, a MMP-8 mediated disease, a MMP-3 mediated disease, a MMP-12 mediated disease and/or an ADAMTS-4 mediated disease and more particulary a MMP-13 mediated disease, which includes administering to a subject in need of such treatment an effective amount of a compound of Formula (III) and N-oxides, pharmaceutically acceptable salts, prodrugs, formulation, polymorphs, racemic mixtures and stereoisomers thereof.

In another embodiment, the present invention provides a method of treating an metalloprotease mediated disease, particulary a MMP-13 mediated disease, a MMP-8 mediated disease, a MMP-3 mediated disease, a MMP-12 mediated disease and/or an ADAMTS-4 mediated disease and more particulary MMP-13 mediated disease and/or MMP-3 mediated disease, which includes administering to a subject in need of such treatment an effective amount of a compound of Formula (IV) and N-oxides, pharmaceutically acceptable salts, prodrugs, formulation, polymorphs, racemic mixtures and stereoisomers thereof.

In another embodiment, the present invention provides a method of treating an metalloprotease mediated disease, particulary a MMP-13 mediated disease, a MMP-8 mediated disease, a MMP-3 mediated disease, a MMP-12 mediated disease and/or an ADAMTS-4 mediated disease and more particulary a MMP-13 mediated disease and/or MMP-3 mediated disease, which includes administering to a subject in need of such treatment an effective amount of a compound of Formula (V) and N-oxides, pharmaceutically acceptable salts, prodrugs, formulation, polymorphs, racemic mixtures and stereoisomers thereof.

In another embodiment, the present invention provides a method of treating an metalloprotease mediated disease, particulary a MMP-13 mediated disease, a MMP-8 mediated disease, a MMP-3 mediated disease, a MMP-12 mediated disease and/or an ADAMTS-4 mediated disease and more particulary a MMP-13 mediated disease and/or MMP-3 mediated disease, which includes administering to a subject in need of such treatment an effective amount of a compound of Formula (VI) and N-oxides, pharmaceutically acceptable salts, prodrugs, formulation, polymorphs, racemic mixtures and stereoisomers thereof.

Illustrative of the diseases which may be treated with such methods are: rheumatoid arthritis, osteoarthritis, abdominal aortic aneurysm, cancer, inflammation, atherosclerosis, multiple sclerosis, chronic obstructive pulmonary disease, ocular diseases, neurological diseases, psychiatric diseases, thrombosis, bacterial infection, Parkinson's disease, fatigue, tremor, diabetic retinopathy, vascular diseases of the retina, aging, dementia, cardiomyopathy, renal tubular impairment, diabetes, psychosis, dyskinesia, pigmentary abnormalities, deafness, inflammatory and fibrotic syndromes, intestinal bowel syndrome, allergies, Alzheimer's disease, arterial plaque formation, oncology, periodontal, viral infection, stroke, atherosclerosis, cardiovascular disease, reperfusion injury, trauma, chemical exposure or oxidative damage to tissues, wound healing, hemorrhoids, skin beautifying, pain, inflammatory pain, bone pain and joint pain.

In some embodiments, of the present invention, the amide containing heterobicyclic metalloprotease compounds defined above are used in the manufacture of a medicament for the treatment of a disease or symptom mediated by an MMP enzyme, particularly an MMP-13, MMP-8, MMP-3, MMP-12 and/or an ADAMTS-4 enzyme, and more particulary an MMP-13 enzyme and/or an MMP-3 enzyme.

In some embodiments, the amide containing heterobicyclic metalloprotease compounds defined above may be used in combination with a drug, active, or therapeutic agent such as, but not limited to: (a) a disease modifying antirheumatic drug, such as, but not limited to, methotrexate, azathioptrineluflunomide, penicillamine, gold salts, mycophenolate, mofetil, and cyclophosphamide; (b) a nonsteroidal anti-inflammatory drug, such as, but not limited to, piroxicam, ketoprofen, naproxen, indomethacin, and ibuprofen; (c) a COX-2 selective inhibitor, such as, but not limited to, rofecoxib, celecoxib, and valdecoxib; (d) a COX-1 inhibitor, such as, but not limited to, piroxicam; (e) an immunosuppressive, such as, but not limited to, methotrexate, cyclosporin, leflunimide, tacrolimus, rapamycin, and sulfasalazine; (f) a steroid, such as, but not limited to, p-methasone, prednisone, cortisone, prednisolone, and dexamethasone; (g) a biological response modifier, such as, but not limited to, anti-TNF antibodies, TNF-α antagonists, IL-1 antagonists, anti-CD40, anti-CD28, IL-10, and anti-adhesion molecules; and (h) other anti-inflammatory agents or therapeutics useful for the treatment of chemokine mediated diseases, such as, but not limited to, p38 kinase inhibitors, PDE4 inhibitors, TACE inhibitors, chemokine receptor antagonists, thalidomide, leukotriene inhibitors, and other small molecule inhibitors of pro-inflammatory cytokine production.

In one embodiment, the present invention provides a pharmaceutical composition which includes:
A) an effective amount of a compound of Formula (I) and N-oxides, pharmaceutically acceptable salts, prodrugs, formulation, polymorphs, racemic mixtures and stereoisomers thereof;
B) a pharmaceutically acceptable carrier; and
C) a member selected from: (a) a disease modifying anti-rheumatic drug; (b) a nonsteroidal anti-inflammatory drug; (c) a COX-2 selective inhibitor; (d) a COX-1 inhibitor; (e) an immunosuppressive; (f) a steroid; (g) a biological response modifier; and (h) a small molecule inhibitor of pro-inflammatory cytokine production.

In another embodiment, the present invention provides a pharmaceutical composition which includes:
A) an effective amount of a compound of Formula (II) and N-oxides, pharmaceutically acceptable salts, prodrugs, formulation, polymorphs, racemic mixtures and stereoisomers thereof;
B) a pharmaceutically acceptable carrier; and
C) a member selected from: (a) a disease modifying anti-rheumatic drug; (b) a nonsteroidal anti-inflammatory drug; (c) a COX-2 selective inhibitor; (d) a COX-1 inhibitor; (e) an immunosuppressive; (f) a steroid; (g) a biological response modifier; and (h) a small molecule inhibitor of pro-inflammatory cytokine production.

In still another embodiment, the present invention provides a pharmaceutical composition which includes:
A) an effective amount of a compound of Formula (III) and N-oxides, pharmaceutically acceptable salts, prodrugs, formulation, polymorphs, racemic mixtures and stereoisomers thereof;
B) a pharmaceutically acceptable carrier; and
C) a member selected from: (a) a disease modifying anti-rheumatic drug; (b) a nonsteroidal anti-inflammatory drug; (c) a COX-2 selective inhibitor; (d) a COX-1 inhibitor; (e) an immunosuppressive; (f) a steroid; (g) a biological response modifier; and (h) a small molecule inhibitor of pro-inflammatory cytokine production.

In a further embodiment, the present invention provides a pharmaceutical composition which includes:
A) an effective amount of a compound of Formula (IV) and N-oxides, pharmaceutically acceptable salts, prodrugs, formulation, polymorphs, racemic mixtures and stereoisomers thereof;
B) a pharmaceutically acceptable carrier; and
C) a member selected from: (a) a disease modifying anti-rheumatic drug; (b) a nonsteroidal anti-inflammatory drug; (c) a COX-2 selective inhibitor; (d) a COX-1 inhibitor; (e) an immunosuppressive; (f) a steroid; (g) a biological response modifier; and (h) a small molecule inhibitor of pro-inflammatory cytokine production.

In yet a further embodiment, the present invention provides a pharmaceutical composition which includes:
A) an effective amount of a compound of Formula (V) and N-oxides, pharmaceutically acceptable salts, prodrugs, formulation, polymorphs, racemic mixtures and stereoisomers thereof;
B) a pharmaceutically acceptable carrier; and C) a member selected from: (a) a disease modifying antirheumatic drug; (b) a nonsteroidal anti-inflammatory drug; (c) a COX-2 selective inhibitor; (d) a COX-1 inhibitor; (e) an immunosuppressive; (f) a steroid; (g) a biological response modifier; and (h) a small molecule inhibitor of pro-inflammatory cytokine production.

In yet a further embodiment, the present invention provides a pharmaceutical composition which includes:

A) an effective amount of a compound of Formula (VI) and N-oxides, pharmaceutically acceptable salts, prodrugs, formulation, polymorphs, racemic mixtures and stereoisomers thereof;

B) a pharmaceutically acceptable carrier; and

C) a member selected from: (a) a disease modifying antirheumatic drug; (b) a nonsteroidal anti-inflammatory drug; (c) a COX-2 selective inhibitor; (d) a COX-1 inhibitor; (e) an immunosuppressive; (f) a steroid; (g) a biological response modifier; and (h) a small molecule inhibitor of pro-inflammatory cytokine production.

Biological Activity

The inhibiting activity towards different metalloproteases of the heterobicyclic metalloprotease inhibiting compounds of the present invention may be measured using any suitable assay known in the art. A standard in vitro assay for measuring the metalloprotease inhibiting activity is described in Examples 1700 to 1704. The heterobicyclic metalloprotease inhibiting compounds show activity towards MMP-3, MMP-8, MMP-12, MMP-13, ADAMTS-4 and/or ADAMTS-5.

The heterobicyclic metalloprotease inhibiting compounds of the invention have an MMP-13 inhibition activity ($IC_{50}$ MMP-13) ranging from below 0.1 nM to about 20 μM, and typically, from about 0.2 nM to about 2 μM. Heterobicyclic metalloprotease inhibiting compounds of the invention desirably have an MMP inhibition activity ranging from about 0.2 nM to about 20 nM. Table 1 lists typical examples of heterobicyclic metalloprotease inhibiting compounds of the invention that have an MMP-13 activity lower than 5 nM (Group A) and from 5 nM to 20 μM (Group B).

TABLE 1

Summary of MMP-13 Activity for Compounds

| Group | Ex. # |
|---|---|
| A | 32, 37, 49, 63, 66, 73, 115, 159, 235, 317, 318, 319, 322, 328, 332, 337, 339, 340, 341, 343, 346, 348, 349, 351, 358, 359, 365, 379, 395, 397, 398, 399, 402, 403, 418, 419, 423, 425, 428, 430, 440, 442, 443, 449, 453, 459, 469, 476, 480, 1748, 1749, 1751, 1758, 1759, 1768, 1778, 1782, 1820, 1861, 1864, 1865, 1875, 1876, 1878, 1880, 1887, 1890, 1894, 1912, 1920, 1922, 1948, 1949, 2065, 2081, 2093, 2095, 2100, 2182, 2188, 2206, 2207, 2212, 2221, 2244, 2328, 2341. |
| B | 3, 4, 36, 71, 86, 93, 113, 126, 156, 158, 161, 231, 244, 246, 280, 308, 323, 347, 355, 363, 367, 400, 411, 420, 432, 461, 464, 466, 467, 479, 483, 1767, 1779, 1780, 1787, 1805, 1821, 1829, 1872, 1884, 1881, 1891, 1893, 1895, 1911, 1913, 1917, 1921, 1923, 1943, 1951, 1952, 2146, 2163, 2165, 2183, 2222, 2225, 2227, 2253, 2256, 2258, 2261, 2263, 2267, 2268, 2269, 2283, 2284, 2285, 2288, 2291, 2294, 2295, 2297, 2299, 2321, 2324, 2332, 2333, 2336, 2338, 2339, 2343, 2346, 2389, 2390, 2392. |

Heterobicyclic metalloprotease inhibiting compounds, in particular compounds of Formula (V) of the invention have an MMP-3 inhibition activity ($IC_{50}$ MMP-3) ranging from below 5 nM to about 20 μM, and typically, from about 3 nM to about 2 μM. Heterobicyclic metalloprotease inhibiting compounds of the invention desirably have an MMP inhibition activity ranging from about 0.2 nM to about 20 nM. Table 2 lists typical examples of heterobicyclic metalloprotease inhibiting compounds of the invention that have an MMP-3 activity lower than 100 nM (Group A) and from 100 nM to 20 μM (Group B).

TABLE 2

Summary of MMP-3 Activity for Compounds

| Group | Ex. # |
|---|---|
| A | 2300, 2301, 2304, 2309, 2314, 2315, 2319, 2320, 2321, 2323, 2330, 2331, 2332, 2333, 2342, 2346. |
| B | 159, 318, 328, 346, 348, 349, 395, 397, 419, 459, 484, 2346, 2303, 2305, 2310, 2316. |

Some heterobicyclic metalloprotease inhibiting compounds of the invention have an MMP-8 inhibition activity ($IC_{50}$ MMP-8) ranging from about 2 μM to about 20 W. Examples of heterobicyclic metalloprotease inhibiting compounds of the invention that have an MMP-8 activity below 20 μM are Ex. #31, 318, 346, 395 and 397.

Some heterobicyclic metalloprotease inhibiting compounds of the invention have an MMP-12 inhibition activity ($IC_{50}$ MMP-12) ranging from below 1 μM to about 20 μM. Examples of heterobicyclic metalloprotease inhibiting compounds of the invention that have an MMP-12 activity below 20 μM are Ex. #318, 322, 346, 395, 397, 418, 430, 440 and 459.

Heterobicyclic metalloprotease inhibiting compounds, in particular compounds of Formula (V) of the invention, show an MMP-3 mediated proteoglycan degradation ranging from below 50 nM to about 20 μM. Typical examples of heterobicyclic metalloprotease inhibiting compounds of the invention that have an $IC_{50}$-range of 20 to 40 nM in the MMP-3 Mediated Proteoglycan Degradation Assay (Ex. #1705) are Ex. #483 and 2343.

Heterobicyclic metalloprotease inhibiting compounds, in particular compounds of Formula (V) of the invention, of the invention show an inhibition of MMP-3 mediated pro-collagenase 3 activation ranging from below 50 nM to about 20 μM. Typical examples of heterobicyclic metalloprotease inhibiting compounds of the invention that have an $IC_{50}$-range of 10 to 30 nM in the Assay for Determining Inhibition of MMP-3 mediated Pro-Collagenase 3 Activation (Ex. #1706) are Ex. #483 and 2343.

The synthesis of metalloprotease inhibiting compounds of the invention and their biological activity assay are described in the following examples which are not intended to be limiting in any way.

Schemes

Provided below are schemes according to which compounds of the present invention may be prepared. In schemes described herein, each of $R^A R^B$ and $R^C R^D$ may be the same or different, and each may independently be selected from $R^1 R^2$ and $R^{20} R^{21}$ as defined hereinabove. Each of $X^a$, $Y^a$, and $Z^a$ shown in the schemes below may be the same or different, and each may independently be selected from N and $CR^4$. $X^b$ shown in the schemes below in each occurrence may be the same or different and is independently selected from O, S, and $NR^{51}$. $Y^b$ shown in the schemes below in each occurrence may be the same and is independently selected from $CR^4$ and N.

In some embodiments the compounds of Formula (I)-(III) are synthesized by the general methods shown in Scheme 1 to Scheme 3.

Scheme 1

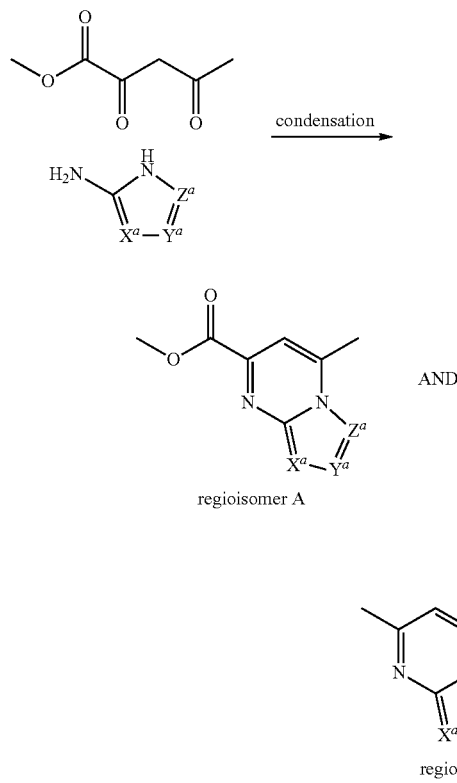

regioisomer A

AND regioisomer B

Methyl acetopyruvate is condensed (e.g. MeOH/reflux, aqueous HCl/100° C. or glacial AcOH/95° C.) with an amino substituted 5-membered heterocycle (e.g. 1H-pyrazol-5-amine) to afford a bicyclic ring system as a separable mixture of regioisomer A and regioisomer B (Scheme 1).

Scheme 2

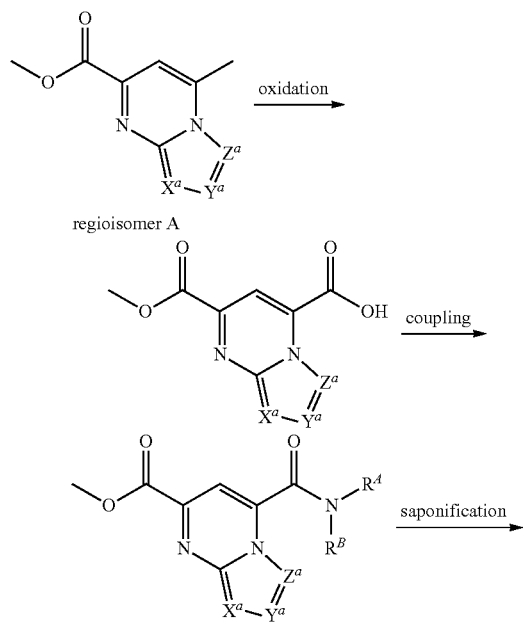

regioisomer A

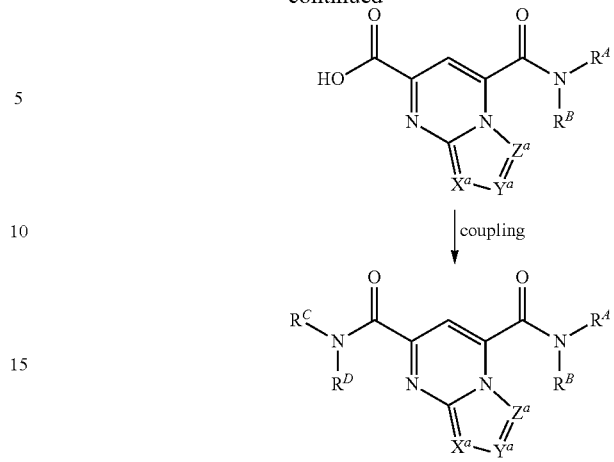

The regioisomer A of the bicyclic ring system from Scheme 1 (e.g. 7-methyl-pyrazolo[1,5-a]pyrimidine-5-carboxylic acid methyl ester) is oxidized (e.g. selenium dioxide/ 120-130° C. and then Oxone®/room temperature) to afford the corresponding carboxylic acid (Scheme 2). Activated acid coupling (e.g. oxalyl chloride, PyBOP, PyBrOP, EDCI/HOAt or HATU/HOAt) with $R^A R^B NH$ (e.g. 4-fluoro-3-methyl-benzylamine) in a suitable solvent gives the desired amide after purification. Saponification (e.g. aqueous LiOH/dioxane, NaOH/MeOH or TMSnOH/80° C.) and further activated acid coupling (e.g. oxalyl chloride, PyBOP, PyBrOP, EDCI/ HOAt, HATU/HOAt, N-cyclohexyl-carbodiimide-N'-methyl-polystyrene or polystyrene-IIDQ) with $R^C R^D NH$ gives the desired bicyclic bisamide inhibitor after purification. If necessary, the R group can be further manipulated (e.g. saponification of a COOMe group in R).

Scheme 3

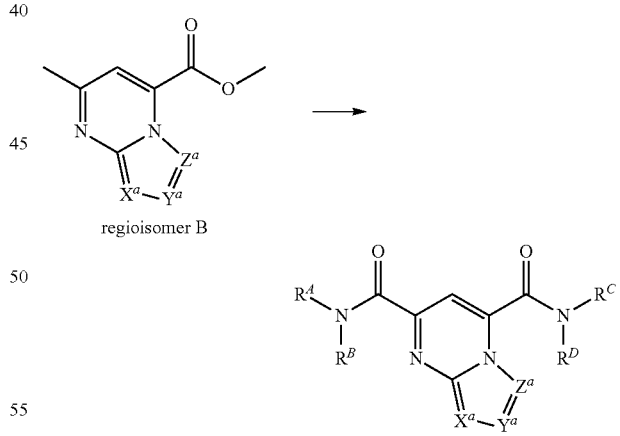

regioisomer B

The regioisomer B of the bicyclic ring system from Scheme 1 (e.g. 5-methyl-pyrazolo[1,5-a]pyrimidine-7-carboxylic acid methyl ester) is treated similarly as shown in Scheme 2 to give the desired bicyclic bisamide inhibitor after purification (Scheme 3). If necessary, the R group can be further manipulated (e.g. saponification of a COOMe group in R).

In some embodiments the compounds of Formula (I)-(III) are synthesized by the general methods shown in Scheme 4 to Scheme 8.

Scheme 4

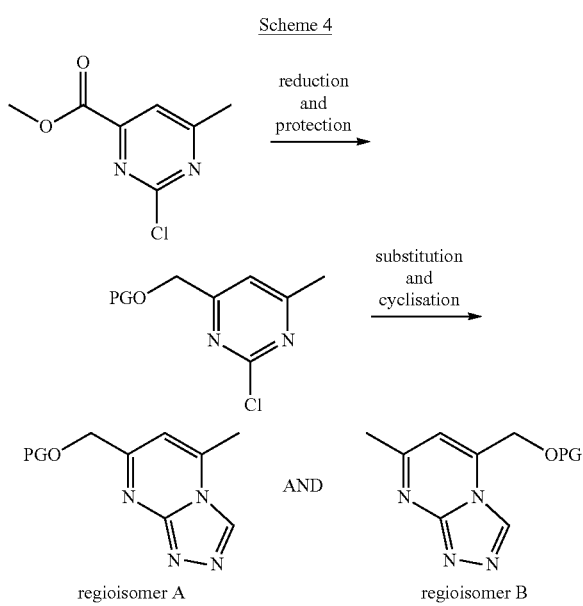

regioisomer A AND regioisomer B

2-Chloro-6-methyl-pyrimidine-4-carboxylic acid methyl ester is reduced (e.g. NaBH$_4$/MeOH) to the corresponding alcohol and protected with a suitable protecting group [PG, e.g. (2-methoxyethoxy)methyl] (Scheme 4). The obtained intermediate is stirred with hydrazine hydrate at 70° C. to afford the corresponding hydrazino pyrimidine after concentration. Cyclization with a suitable reagent (e.g. triethylortho formate) gives the protected hydroxymethyl substituted bicyclic ring system as a separable mixture of regioisomer A and regioisomer B.

The regioisomer A of the protected hydroxymethyl substituted bicyclic ring system from Scheme 4 (e.g. 7-(2-methoxy-ethoxymethoxymethyl)-5-methyl-[1,2,4]triazolo[4,3-a]pyrimidine) is deprotected (e.g. HCl/THF) and then oxidized (e.g. KMnO$_4$ in aqueous Na$_2$CO$_3$/50° C.) to afford the corresponding carboxy substituted bicyclic ring system (Scheme 5). Esterification (e.g. thionyl chloride/MeOH) and oxidation (e.g. selenium dioxide/70° C.) of this intermediate gives the corresponding carboxylic acid. Activated acid coupling (e.g. oxalyl chloride, PyBOP, PyBrOP, EDCI/HOAt or HATU/HOAt) with R$^A$R$^B$NH (e.g. 4-fluoro-3-methyl-benzylamine) in a suitable solvent gives the desired amide after purification. Saponification (e.g. aqueous LiOH/dioxane, NaOH/MeOH or TMSnOH/80° C.) and further activated acid coupling (e.g. oxalyl chloride, PyBOP, PyBrOP, EDCI/HOAt, HATU/HOAt) with R$^C$R$^D$NH gives the desired bicyclic bisamide inhibitor after purification. If necessary, the R group can be further manipulated (e.g. saponification of a COOMe group in R).

Scheme 6

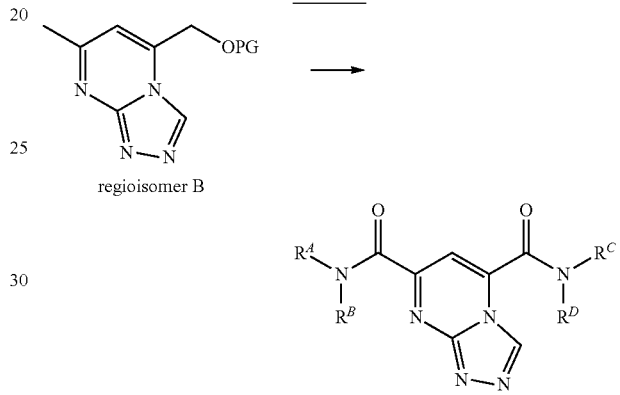

regioisomer B

Scheme 5

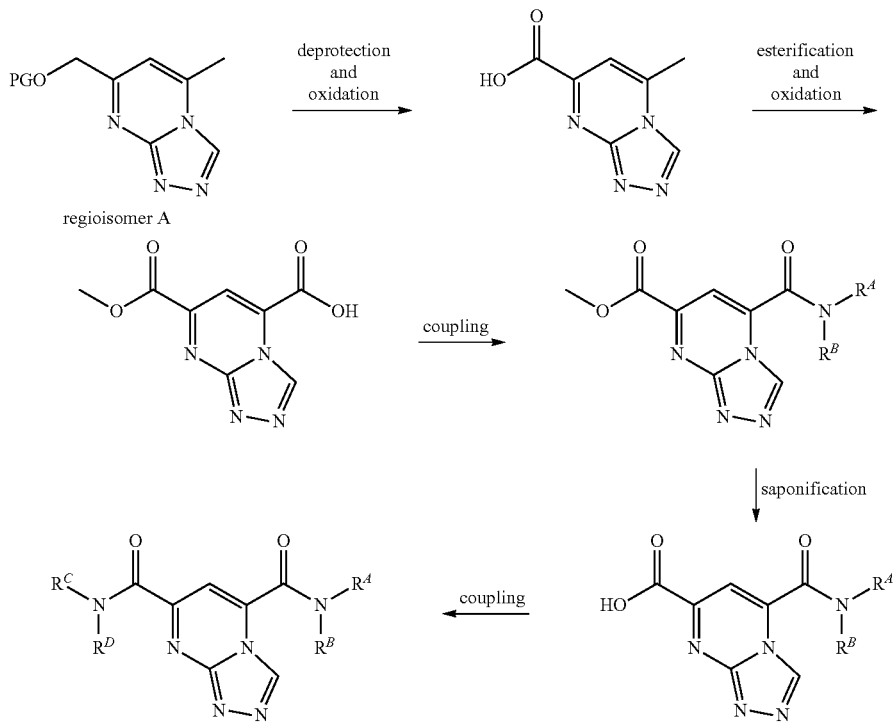

The regioisomer B of the protected hydroxymethyl substituted bicyclic ring system from Scheme 4 (e.g. 5-(2-methoxy-ethoxymethoxymethyl)-7-methyl-[1,2,4]triazolo[4,3-a]pyrimidine) is treated similarly as shown in Scheme 5 to give the desired bicyclic bisamide inhibitor after purification (Scheme 6). If necessary, the R group can be further manipulated (e.g. saponification of a COOMe group in R).

2-Chloro-6-methyl-pyrimidine-4-carboxylic acid methyl ester is oxidized (e.g. selenium dioxide/105° C.) to the corresponding carboxylic acid (Scheme 7). Activated acid coupling (e.g. oxalyl chloride) with $R^AR^BNH$ (e.g. 4-fluoro-3-methyl-benzylamine) in a suitable solvent gives the desired amide after purification. Saponification (e.g. aqueous LiOH/THF) and further activated acid coupling (e.g. PyBOP) with $R^CR^DNH$ (e.g. 4-aminomethyl-benzoic acid methyl ester) gives the corresponding benzotriazol-1-yloxy substituted pyrimidine bisamide.

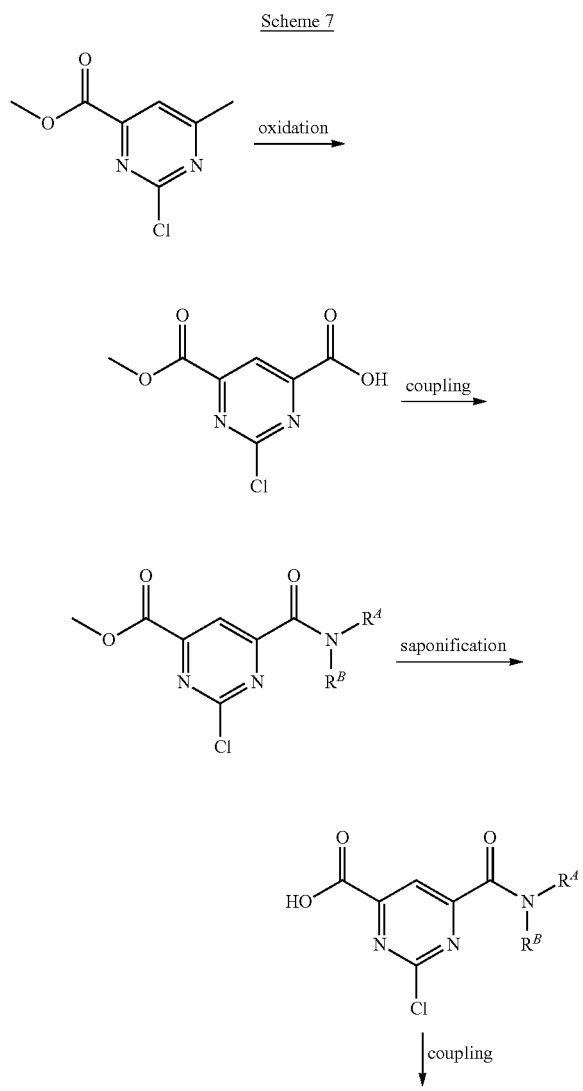

Scheme 7

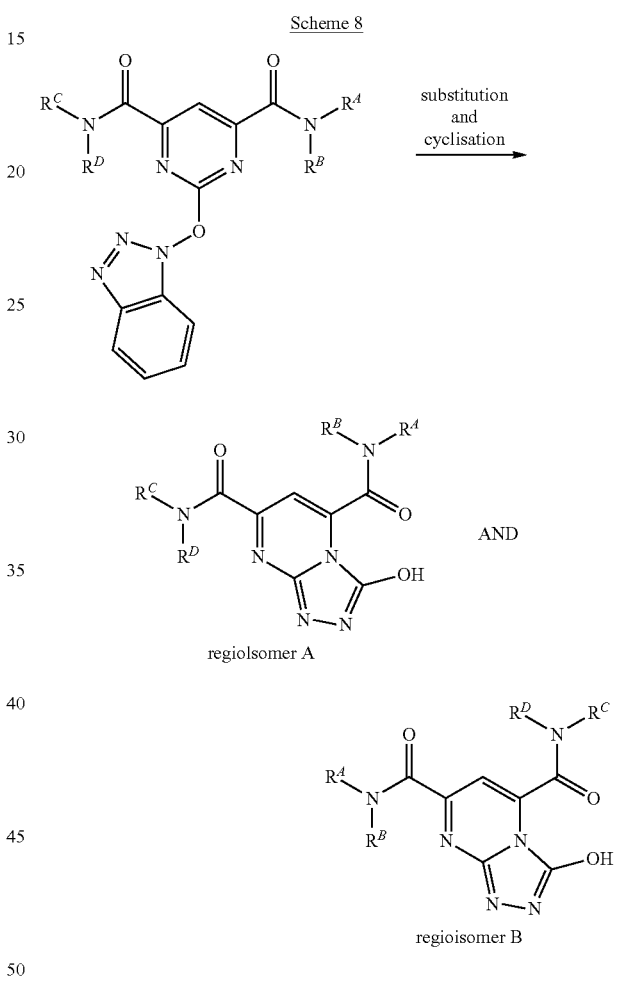

Scheme 8 regioisomer A regioisomer B

A benzotriazol-1-yloxy substituted pyrimidine bisamide from Scheme 7 (e.g. 4-({[2-(benzotriazol-1-yloxy)-6-(4-fluoro-3-methyl-benzylcarbamoyl)-pyrimidine-4-carbonyl]-amino}-methyl)-benzoic acid methyl ester) is stirred with hydrazine hydrate at room temperature to afford the corresponding hydrazino pyrimidine bisamide after concentration (Scheme 8). Cyclization with a suitable reagent (e.g. phosgene) gives the corresponding bicyclic bisamide inhibitor as a mixture of regioisomer A and regioisomer B. If necessary, the R group can be further manipulated (e.g. saponification of a COOMe group in R).

In some embodiments the compounds of Formula (IV)-(VI) are synthesized by the general methods shown in Scheme 9 to Scheme 12.

Scheme 9

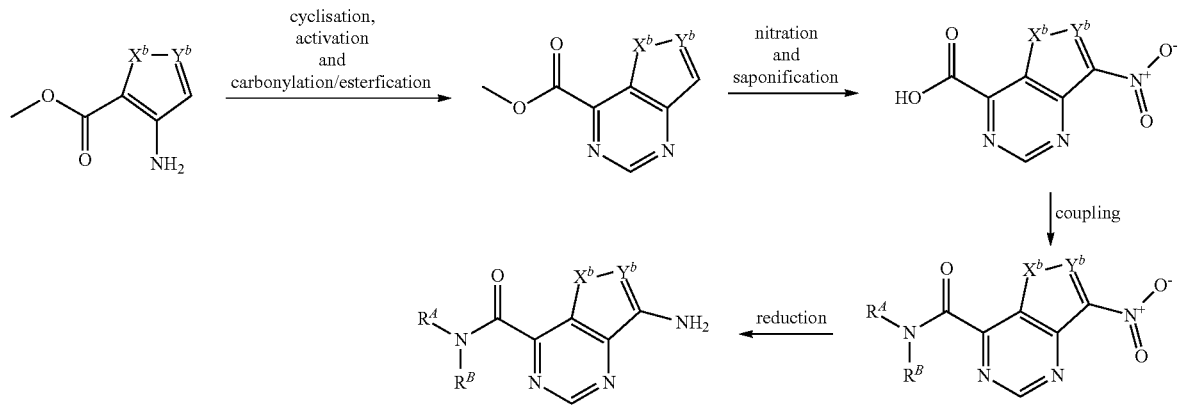

An ester and amino substituted heterocycle (e.g. 3-amino-1H-pyrrole-2-carboxylic acid ethyl ester) is condensed (e.g. EtOH/reflux) with formamidine to give a hydroxy substituted bicyclic ring system (Scheme 9). This intermediate is then converted into the corresponding bromo derivative using a suitable reagent (e.g. POBr$_3$/80° C.). The resulting bromide is heated to (e.g. 80° C.) with a suitable catalyst (e.g. Pd(OAc)$_2$, dppf) and base (e.g. Et$_3$N) under a carbon monoxide atmosphere in a suitable solvent (e.g. MeOH) to give the corresponding bicyclic methylester after purification. Nitration (e.g. concentrated HNO$_3$/0° C. to room temperature) and saponification (e.g. aqueous LiOH) gives the corresponding nitro substituted bicyclic carboxylic acid. Activated acid coupling (e.g. EDCI/HOAt) with R$^A$R$^B$NH (e.g. 6-aminomethyl-4H-benzo[1,4]oxazin-3-one) in a suitable solvent gives the desired amide. This intermediate is stirred with a suitable catalyst (e.g. Pd/C) and acid (e.g. AcOH) under a hydrogen atmosphere to afford corresponding amino substituted bicyclic amide after purification.

Commercially available 2-fluoro-3-oxo-butyric acid ethyl ester is condensed (e.g. MeOH/reflux) with thiourea to give the corresponding fluoro pyrimidinone derivative (Scheme 10). Removal of the sulphur with a catalyst (e.g. Raney-nickel) at elevated temperature (e.g. 100° C.) in a suitable solvent (e.g. H$_2$O) gives the corresponding fluoro pyrimidine derivative. This intermediate is converted into the corresponding bromo derivative by heating with base (e.g. K$_2$CO$_3$) and a suitable reagent (e.g. POBr$_3$) in a suitable solvent (e.g. CH$_3$CN). The resulting bromide is heated to (e.g. 80° C.) with a suitable catalyst (e.g. Pd(OAc)$_2$, dppf) and base (e.g. Et$_3$N) under a carbon monoxide atmosphere in a suitable solvent (e.g. MeOH) to give the corresponding fluoro pyrimidine carboxylic acid methyl ester after purification. Oxidation of the methyl group with a suitable reagent (e.g. selenium dioxide) in a suitable solvent (e.g. 1,4-dioxane) at elevated temperature (e.g. 120° C.) in a sealed vessel affords the corresponding fluoro pyrimidine monoacid monoester. Coupling of the acid derivative using an activated acid method (e.g.

Scheme 10

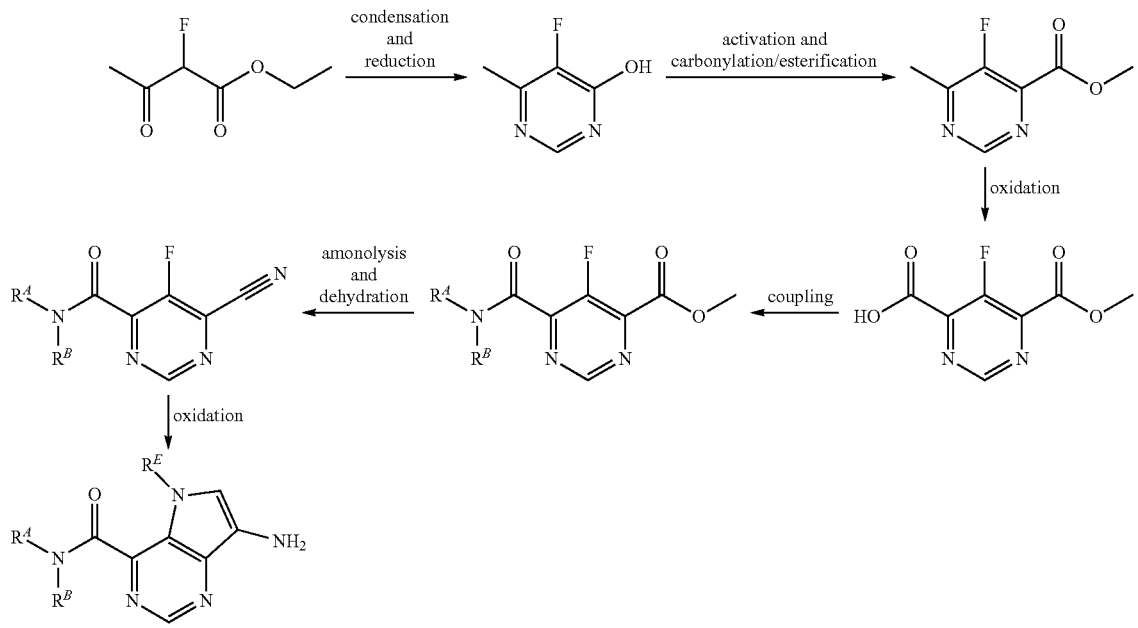

EDCI, HOAt, DMF, base) with R^A R^B NH (e.g. 3-chloro-4-fluoro benzylamine) affords the desired products after purification. Saponification of the remaining ester moiety with base (e.g. aqueous KOH) affords the corresponding free acid derivatives. This derivatives are converted to the corresponding amides via the formation of their acid chlorides using suitable conditions (e.g. oxalyl chloride, DMF, 0-5° C.), followed by treatment with anhydrous NH₃ (e.g. 0.5M in 1,4-dioxane) and subsequent purification. Dehydration under suitable conditions (e.g. oxalyl chloride, DMF, pyridine, 0-5° C.) affords the corresponding nitriles after workup. Cyclization of these derivatives with a suitable reagent (e.g. hydrazine) in a suitable solvent (e.g. 1,4-dioxane) affords the corresponding 3-hydroxy-1H-pyrazolo[4,3-d]pyrimidin derivatives. (Scheme 10).

Scheme 11

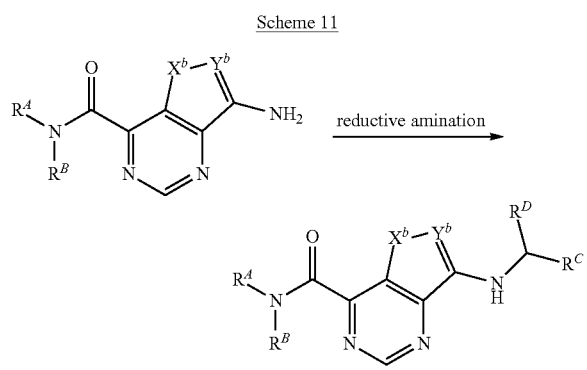

The amino substituted bicyclic amide from scheme 9 (e.g. 3-amino-1H-pyrazolo[4,3-d]pyrimidine-7-carboxylic acid 3-chloro-4-fluoro-benzylamide) and the carbonyl compound (CO)R^C R^D (e.g. 4-fluorobenzaldehyde) is stirred with a suitable reducing agent (e.g. NaCNBH₃) and a small amount of acid (e.g. AcOH) in a suitable solvent (e.g. MeOH) to give the corresponding bicyclic inhibitor after purification (Scheme 11). If necessary, the R group can be further manipulated (e.g. saponification of a COOMe group in R).

Scheme 12

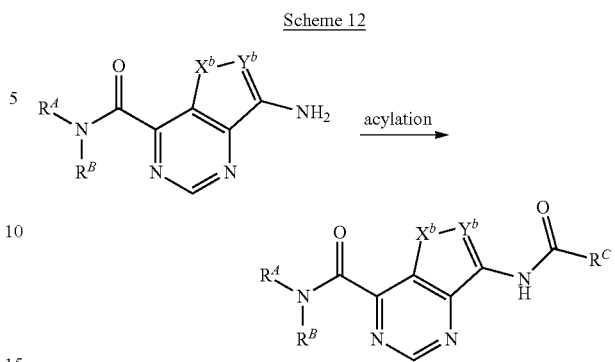

The amino substituted bicyclic amide from scheme 9 (e.g. 7-amino-5H-pyrrolo[3,2-d]pyrimidine-4-carboxylic acid (3-oxo-3,4-dihydro-2H-benzo[1,4]oxazin-6-ylmethyl)-amide is stirred with the acid chloride R^C COCl or with the acid anhydride (R^C CO)₂O (e.g. acetic anhydride) in a suitable solvent (e.g. pyridine) to give the corresponding bicyclic inhibitor after purification (Scheme 12). If necessary, the R group can be further manipulated (e.g. saponification of a COOMe group in R).

EXAMPLES AND METHODS

All reagents and solvents were obtained from commercial sources and used without further purification. Proton spectra (¹H-NMR) were recorded on a 400 MHz and a 250 MHz NMR spectrometer in deuterated solvents. Purification by column chromatography was performed using silica gel, grade 60, 0.06-0.2 mm (chromatography) or silica gel, grade 60, 0.04-0.063 mm (flash chromatography) and suitable organic solvents as indicated in specific examples. Preparative thin layer chromatography was carried out on silica gel plates with UV detection.

Preparative Examples 1-395, 805 and 836-1051 are directed to intermediate compounds useful in preparing the compounds of the present invention.

Preparative Example 1

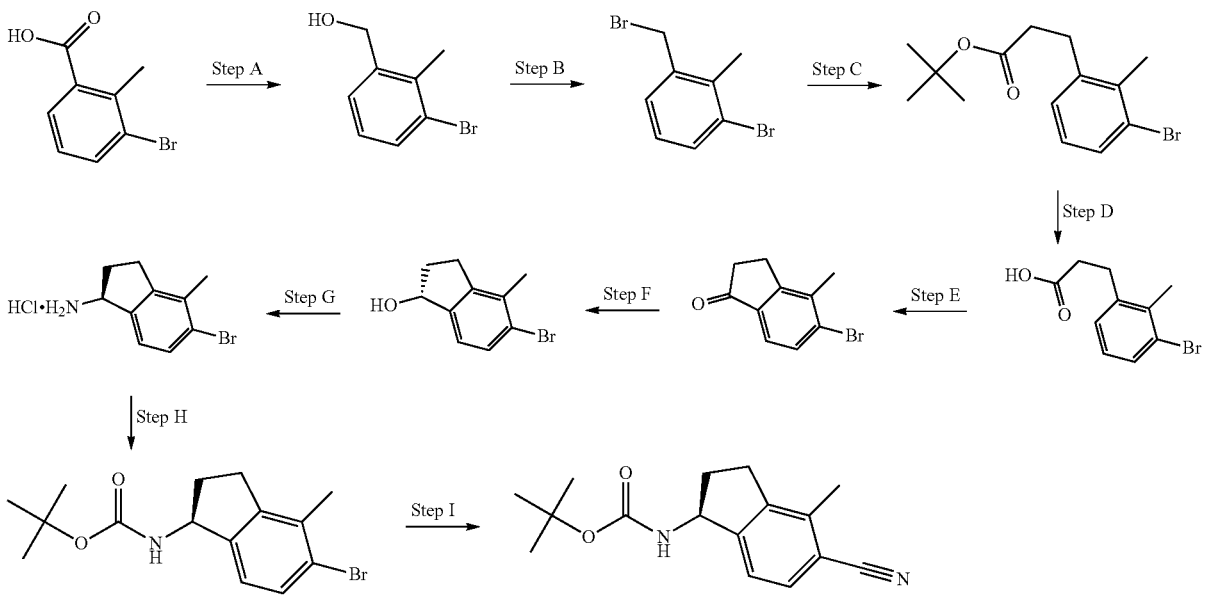

Step A

Under a nitrogen atmosphere a 1M solution of BH$_3$.THF complex in THF (140 mL) was added dropwise over a 3 h period to an ice cooled solution of commercially available 3-bromo-2-methyl-benzoic acid (20.0 g) in anhydrous THF (200 mL). Once gas evolution had subsided, the cooling bath was removed and mixture stirred at room temperature for 12 h. The mixture was then poured into a mixture of 1N aqueous HCl (500 mL) and ice and then extracted with Et$_2$O (3×150 mL). The combined organic phases were dried (MgSO$_4$), filtered and concentrated to afford the title compound as a colorless solid (18.1 g, 97%). $^1$H-NMR (CDCl$_3$) δ=7.50 (d, 1H), 7.30 (d, 1H), 7.10 (t, 1H), 4.70 (s, 2H), 2.40 (s, 3H).

Step B

Under a nitrogen atmosphere PBr$_3$ (5.52 mL) was added over a 10 min period to an ice cooled solution of the title compound from Step A above (18.1 g) in anhydrous CH$_2$Cl$_2$ (150 mL). The cooling bath was removed and mixture stirred at room temperature for 12 h. The mixture was cooled (0-5° C.), quenched by dropwise addition of MeOH (20 mL), washed with saturated aqueous NaHCO$_3$ (2×150 mL), dried (MgSO$_4$), filtered and concentrated to afford the title compound as a viscous oil (23.8 g, 97%). $^1$H-NMR (CDCl$_3$) δ=7.50 (d, 1H), 7.25 (d, 1H), 7.00 (t, 1H), 4.50 (s, 2H), 2.50 (s, 3H).

Step C

Under a nitrogen atmosphere a 1.5M solution of lithium diisopropylamide in cyclohexane (63 mL) was added dropwise to a cooled (−78° C., acetone/dry ice) solution of $^t$BuOAc in anhydrous THF (200 mL). The mixture was stirred at −78° C. for 1 h, then a solution of the title compound from Step B above (23.8 g) in THF (30 mL) was added and the mixture was stirred for 12 h while warming to room temperature. The mixture was concentrated, diluted with Et$_2$O (300 mL), washed with 0.5N aqueous HCl (2×100 mL), dried (MgSO$_4$), filtered and concentrated to afford the title compound as a pale-yellow viscous oil (21.5 g, 80%). $^1$H-NMR (CDCl$_3$) δ=7.50 (d, 1H), 7.25 (d, 1H), 7.00 (t, 1H), 3.00 (t, 2H), 2.50 (t, 2H), 2.40 (s, 3H), 1.50 (s, 9H).

Step D

A mixture of the title compound from Step C above (21.5 g) and polyphosphoric acid (250 g) was placed in a preheated oil bath (140° C.) for 10 min while mixing the thick slurry occasionally with a spatula. The oil bath was removed, ice and H$_2$O (1 L) was added and the mixture was stirred for 2 h. The precipitate was isolated by filtration, washed with H$_2$O (2×100 mL) and dried to afford the title compound (16.7 g, 96%). $^1$H-NMR (CDCl$_3$) δ=7.50 (d, 1H), 7.20 (d, 1H), 7.00 (t, 1H), 3.00 (t, 2H), 2.65 (t, 2H), 2.40 (s, 3H).

Step E

Under a nitrogen atmosphere oxalyl chloride (12.0 mL) was added dropwise to an ice cooled solution of the title compound from Step D above (11.6 g) in anhydrous CH$_2$Cl$_2$ (100 mL). The resulting mixture was stirred for 3 h and then concentrated. The remaining dark residue was dissolved in anhydrous CH$_2$Cl$_2$ (300 mL) and AlCl$_3$ (6.40 g) was added. The mixture was heated to reflux for 4 h, cooled and poured into ice water (500 mL). The aqueous phase was separated and extracted with CH$_2$Cl$_2$ (2×100 mL). The combined organic phases were dried (MgSO$_4$), filtered and concentrated to afford the title compound as a light brown solid (10.6 g, 98%). $^1$H-NMR (CDCl$_3$) δ=7.65 (d, 1H), 7.50 (d, 1H), 3.05 (t, 2H), 2.70 (t, 2H), 2.40 (s, 3H).

Step F

Using a syringe pump, a solution of the title compound from Step E above (9.66 g) in anhydrous CH$_2$Cl$_2$ (70 mL) was added over a 10 h period to a cooled (−20° C., internal temperature) mixture of a 1M solution of (S)-(−)-2-methyl-CBS-oxazaborolidine in toluene (8.6 mL) and a 1M solution of BH$_3$.Me$_2$S complex in CH$_2$Cl$_2$ (43.0 mL) in CH$_2$Cl$_2$ (200 mL). The mixture was then quenched at −20° C. by addition of MeOH (100 mL), warmed to room temperature, concentrated and purified by flash chromatography (silica, Et$_2$O/CH$_2$Cl$_2$) to afford the title compound as a colorless solid (8.7 g, 90%). (CDCl$_3$) δ=7.50 (d, 1H), 7.20 (d, 1H), 5.25 (m, 1H), 3.10 (m, 1H), 2.90 (m, 1H), 2.50 (m, 1H), 2.35 (s, 3H), 2.00 (m, 1H).

Step G

Under a nitrogen atmosphere NEt$_3$ (15.9 mL) and methanesulfonyl chloride (4.5 mL) were added subsequently to a cooled (−78° C., acetone/dry ice) solution of the title compound from Step F above (8.7 g) in anhydrous CH$_2$Cl$_2$ (200 mL). The mixture was stirred at −78° C. for 90 min, then NH$_3$ (−150 mL) was condensed into the mixture using a dry ice condenser at a rate of ~3 mL/min and stirring at −78° C. was continued for 2 h. Then the mixture was gradually warmed to room temperature allowing the NH$_3$ to evaporate. 1N aqueous NaOH (200 mL) was added, the organic phase was separated and the aqueous phase was extracted with CH$_2$Cl$_2$ (2×100 mL). The combined organic phases were dried (MgSO$_4$), filtered and concentrated. The remaining light brown oil was dissolved in Et$_2$O (200 mL) and a 4M solution of HCl in 1,4-dioxane (10 mL) was added. The formed precipitate was collected and dried to give the title compound (9.0 g, 90%). [M-NH$_3$Cl]$^+$=209/211.

Step H

To an ice cooled solution of the title compound from Step G above (5.2 g) in anhydrous CH$_2$Cl$_2$ (50 mL) were subsequently added di-tert-butyl dicarbonate (5.0 g) and NEt$_3$ (9.67 mL). The resulting mixture was stirred for 3 h, concentrated, diluted with Et$_2$O (250 mL), washed with saturated aqueous NaHCO$_3$ (100 mL) and saturated aqueous NaCl (100 mL), dried (MgSO$_4$), filtered and concentrated to afford the title compound as a colorless solid (7.28 g, 97%). $^1$H-NMR (CDCl$_3$, free base) δ=7.40 (m, H), 7.00 (d, 1H), 4.30 (t, 1H) 2.90 (m, 1H), 2.80 (m, 1H), 2.60 (m, 1H), 2.30 (s, 3H), 1.80 (m, 1H).

Step I

Under a nitrogen atmosphere a mixture of the title compound from Step H above (7.2 g), Zn(CN)$_2$ (5.2 g) and Pd(PPh$_3$)$_4$ (2.6 g) in anhydrous DMF (80 mL) was heated to 100° C. for 18 h, concentrated and purified by flash chromatography (silica, CH$_2$Cl$_2$/EtOAc) to afford the title compound as an off-white solid (4.5 g, 75%). $^1$H-NMR (CDCl$_3$) δ=7.50 (d, 1H), 7.20 (d, 1H), 5.15 (m, 1H), 4.75 (m, 1H), 2.95 (m, 1H), 2.80 (m, 1H), 2.70 (m, 1H), 2.40 (s, 3H), 1.90 (m, 1H), 1.50 (s, 9H).

Preparative Example 2

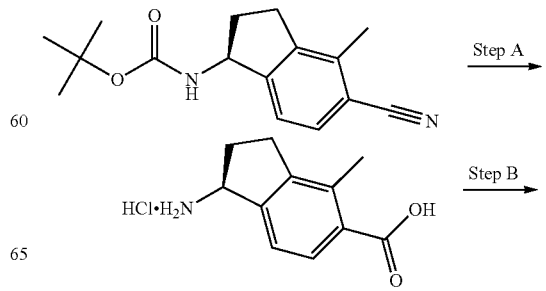

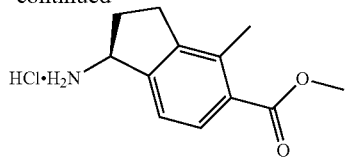

Step A

The title compound from the Preparative Example 1, Step I (1.0 g) was suspended in 6N aqueous HCl (20 mL), heated to 100° C. for 12 h and concentrated to give the title compound as a colorless solid. (834 mg, >99%). [M-NH$_3$Cl]$^+$=175.

Step B

Anhydrous HCl gas was bubbled through an ice cooled solution of the title compound from Step A above (1.0 g) in anhydrous MeOH (20 mL) for 2-3 min. The cooling bath was removed, the mixture was heated to reflux for 12 h, cooled to room temperature and concentrated to give the title compound as a colorless solid (880 mg, 83%). [M-NH$_3$Cl]$^+$=189.

Step C

To a boiling solution of the title compound from Step B above (1.13 g) in MeOH (2.3 mL) was added a hot solution of commercially available N-acetyl-L-leucine (924 mg) in MeOH (3 mL). The solution was allowed to cool to room temperature, which afforded a white precipitate. The precipitate was collected by filtration, washed with MeOH (2 mL) and recrystallized from MeOH (2×). The obtained solid was dissolved in a mixture of 10% aqueous NaOH (20 mL) and Et$_2$O (20 mL), the organic phase was separated and the aqueous phase was extracted with Et$_2$O. The combined organic phases were dried (MgSO$_4$), filtered and concentrated to give the title compound as a clear oil (99 mg, 18%). [MH]$^+$=212/214.

Step D

To a solution of the title compound from Step C above (300 mg) in THF (10 mL) were subsequently added di-tert-butyl dicarbonate (370 mg) and NEt$_3$ (237 µL). The resulting mixture was stirred at room temperature for 16 h, concentrated and purified by chromatography (silica, hexanes/EtOAc) to afford the title compound as a clear oil (460 mg, >99%). [MNa]$^+$=334/336.

Step E

Under an argon atmosphere a mixture of the title compound from Step D above (460 mg), Zn(CN)$_2$ (200 mg) and Preparative Example 3

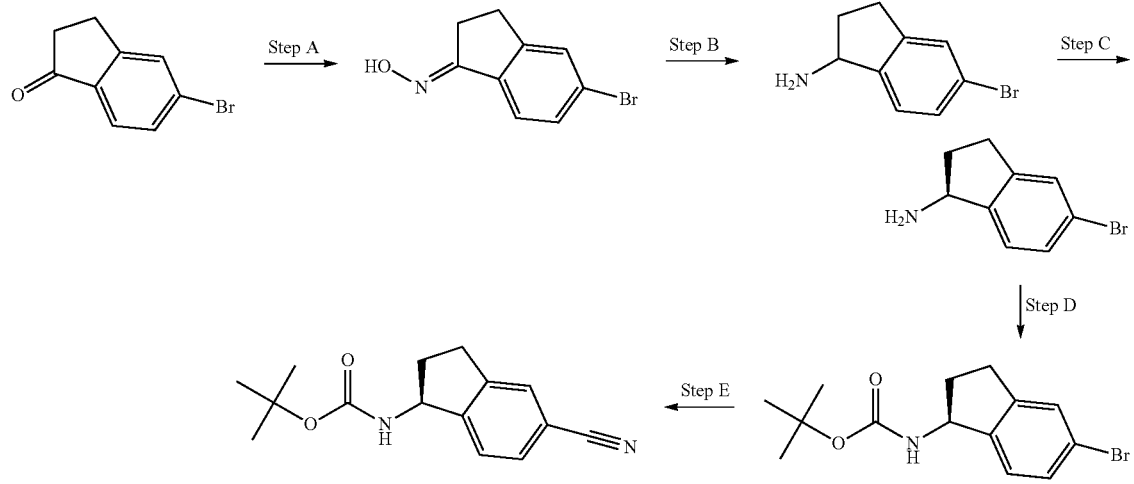

Step A

A mixture of commercially available 5-bromo-indan-1-one (1.76 g), hydroxylamine hydrochloride (636 mg) and NaOAc (751 mg) in MeOH (40 mL) was stirred at room temperature for 16 h and then diluted with H$_2$O (100 mL). The formed precipitate was collected by filtration, washed with H$_2$O (3×20 mL) and dried to afford the title compound as a colorless solid (1.88 g, >99%). [MH]$^+$=226/228.

Step B

Under an argon atmosphere a 1M solution of LiAlH$_4$ in Et$_2$O (42.4 mL) was slowly added to a cooled (−78° C., acetone/dry ice) solution of the title compound from Step A above (1.88 g) in Et$_2$O (20 mL). Then the cooling bath was removed and the mixture was heated to reflux for 5 h. The mixture was cooled (0-5° C.) and H$_2$O (1.6 mL), 15% aqueous NaOH (1.6 mL) and H$_2$O (4.8 mL) were carefully and sequentially added. The resulting mixture was filtered through a plug of Celite® and concentrated to give the title compound as a clear oil (1.65 g, 94%). [MH]$^+$=212/214.

Pd(PPh$_3$)$_4$ (89 mg) in anhydrous DMF (5 mL) was heated in a sealed vial to 110° C. for 18 h. The mixture was cooled to room temperature and diluted with Et$_2$O (20 mL) and H$_2$O (20 mL). The organic phase was separated and the aqueous phase was extracted with Et$_2$O (4×10 mL). The combined organic phases were washed with H$_2$O (3×10 mL) and saturated aqueous NaCl (10 mL), dried (MgSO$_4$), filtered, concentrated and purified by chromatography (silica, hexanes/EtOAc) to afford the title compound as a clear oil (170 mg, 47%). [MH]$^+$=259.

Preparative Example 4

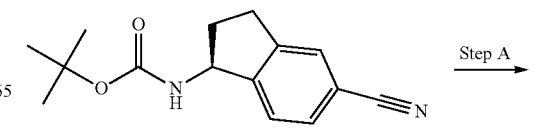

-continued

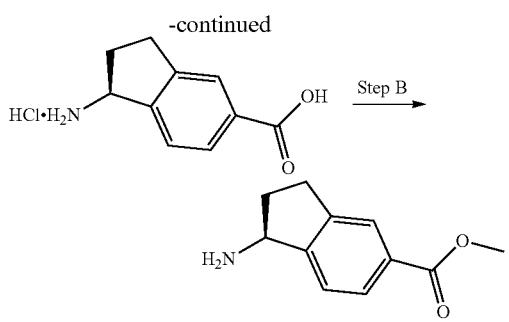

Step A

The title compound from the Preparative Example 3, Step E (1.0 g) was suspended in 6N aqueous HCl (50 mL), heated under closed atmosphere to 110-112° C. for 20 h and concentrated to give the title compound (827 mg, >99%). [M-Cl]⁺= 178.

Step B

The title compound from Step A above (827 mg) was dissolved in anhydrous MeOH (150 mL) and saturated with anhydrous HCl gas. The resulting mixture was heated to reflux for 20 h, cooled to room temperature and concentrated. The remaining oil was taken up in $CH_2Cl_2$ and washed with saturated aqueous $NaHCO_3$, dried ($MgSO_4$), filtered and concentrated to give the title compound as an oil which slowly crystallized into a light brown solid (660 mg, 89%). [MH]⁺= 192.

Preparative Example 5

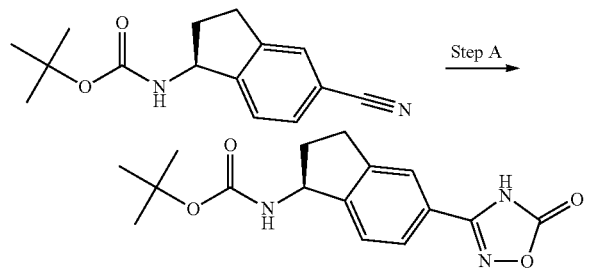

Step A

To a solution of hydroxylamine hydrochloride (2.78 g) in dry MeOH (100 mL) was added a 30 wt % solution of NaOMe in MeOH (7.27 mL). The resulting white suspension was stirred at room temperature for 15 min and a solution of the title compound from the Preparative Example 3, Step E (5.17 g) in dry MeOH (100 mL) was added. The mixture was heated to reflux for 20 h (complete conversion checked by HPLC/MS, [MH]⁺=292) and then cooled to room temperature. Diethyl carbonate (48.2 g) and a 30 wt % solution of NaOMe in MeOH (7.27 mL) were added successively and the resulting mixture was heated to reflux for 24 h. The mixture was concentrated, diluted with 1M aqueous $NH_4Cl$ (200 mL) and extracted with $CH_2Cl_2$/MeOH (60:40, 500 mL) and $CH_2Cl_2$ (3×200 mL). The combined organic layers were dried ($MgSO_4$), filtered, concentrated and purified by flash chromatography (silica, $CH_2Cl_2$/MeOH) to afford the title compound as a white solid (3.89 g, 61%) [MNa]⁺=340.

Preparative Example 6

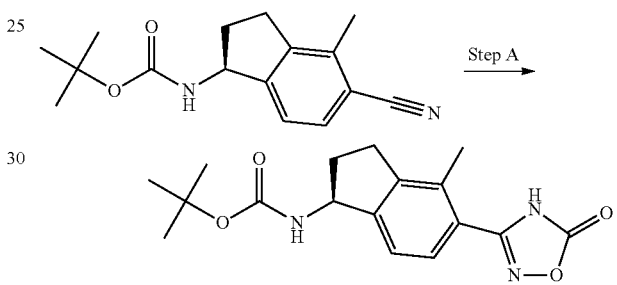

Step A

The title compound from the Preparative Example 1, Step I (1.37 mg) was treated similarly as described in the Preparative Example 5, Step A to afford the title compound as a white solid (845 mg, 51%). [MNa]⁺=354.

Preparative Example 7

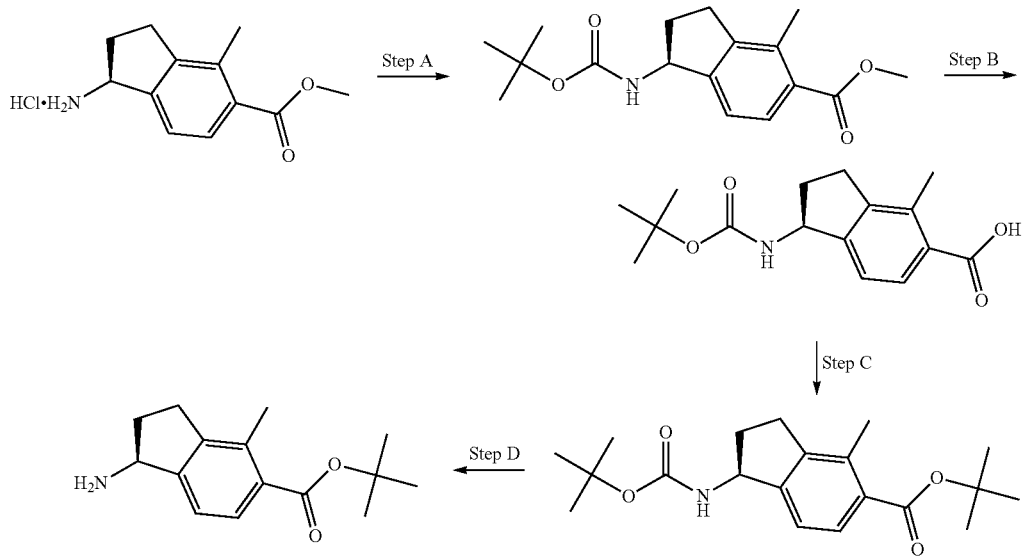

Step A

To an ice cooled solution of the title compound from the Preparative Example 2, Step B (5.94 g) in dry CH$_2$Cl$_2$ (50 mL) were subsequently added di-tert-butyl dicarbonate (1.6 g) and NEt$_3$ (1 mL). The mixture was stirred for 3 h, concentrated, diluted with Et$_2$O (250 mL), washed with saturated aqueous NaHCO$_3$ (100 mL) and saturated aqueous NaCl (100 mL), dried (MgSO$_4$), filtered and concentrated to afford the title compound as a colorless solid (7.28 g, 97%). [MNa]$^+$=328.

Step B

To a mixture of the title compound from Step A above (7.28 g) in THF (60 mL) was added 1M aqueous LiOH (60 mL). The mixture was stirred at 50° C. for 2 h, concentrated, diluted with H$_2$O, adjusted to pH 5 with HCl and extracted with EtOAc. The combined organic phases were dried (MgSO$_4$), filtered and concentrated to afford the title compound as colorless solid (1.87 g, 27%). [MNa]$^+$=314.

Step C

At 80° C. N,N-dimethylformamide di-tert-butyl acetal (6.2 mL) was added to a solution of the title compound from Step B above (1.87 g) in dry toluene (15 mL). The mixture was stirred at 80° C. for 3 h, cooled to room temperature, concentrated and purified by chromatography (silica, CH$_2$Cl$_2$) to afford the title compound as a colorless solid (820 mg, 38%). [MNa]$^+$=370.

Step D

To a solution of the title compound from Step C above (820 mg) in $^t$BuOAc (40 mL) was added concentrated H$_2$SO$_4$ (0.65 mL). The resulting mixture was stirred at room temperature for 5 h, concentrated, diluted with EtOAc, washed with saturated aqueous NaHCO$_3$ and saturated aqueous NaCl, dried (MgSO$_4$), filtered and concentrated to afford the title compound as a colorless solid (640 mg, 99%). [M-NH$_2$]$^+$=231.

Preparative Example 8

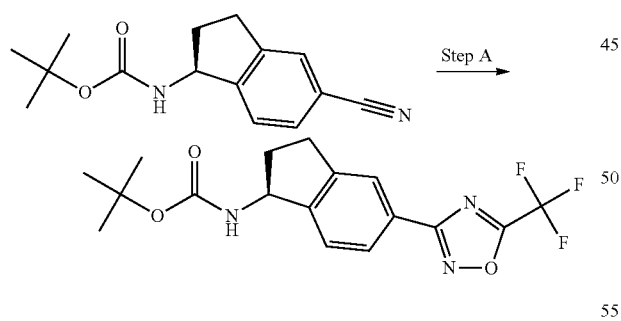

Step A

To a solution of the title compound from the Preparative Example 3, Step E (153 mg) in EtOH (10 mL) were added NEt$_3$ (0.16 mL) and hydroxylamine hydrochloride (81 mg). The mixture was heated to reflux for 4 h, then concentrated, dissolved in THF (5 mL) and pyridine (0.19 mL) and cooled to 0° C. Trifluoroacetic anhydride (0.25 mL) was added and the mixture was stirred for 16 h. Concentration and purification by chromatography (silica, hexanes/EtOAc) afforded the title compound as a white solid (217 mg, >99%). [MNa]$^+$=392.

Preparative Example 9

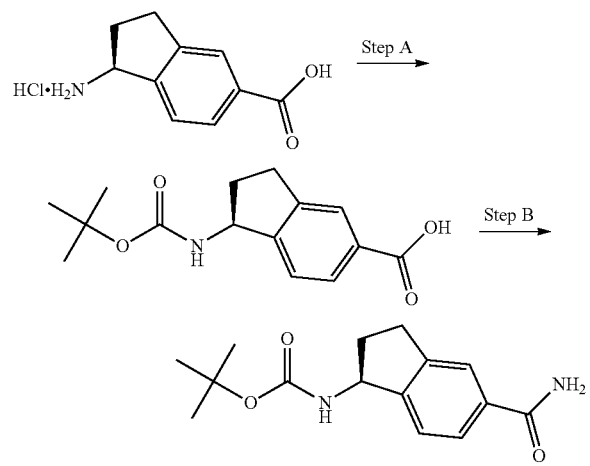

Step A

To a solution of the title compound from the Preparative Example 4, Step A (33.7 mg) in 1,4-dioxane/H$_2$O (1:1, 2 mL) were added NaOH (97.4 mg) and di-tert-butyl dicarbonate (68.7 mg). The resulting mixture was stirred at room temperature overnight, diluted with EtOAc, washed with 1N aqueous HCl and saturated aqueous NaCl, dried (MgSO$_4$), and concentrated to give a white solid (34.6 mg, 71%). [MNa]$^+$=300.

Step B

To a solution of the title compound from Step A above (34.6 mg) in CH$_2$Cl$_2$ (1 mL) were added oxalyl chloride (33 µL) and DMF (2 mL). The mixture was stirred at room temperature for 2 h and concentrated. The remaining residue was dissolved in CH$_2$Cl$_2$ (1 mL) and added to a cold (−78° C.) saturated solution of NH$_3$ in CH$_2$Cl$_2$ (1 mL). The mixture was stirred at −78° C. for 1 h, warmed to room temperature, concentrated, redissolved in CH$_2$Cl$_2$ (5 mL), filtered, and concentrated to give a white solid (25.9 mg, 75%). [MNa]$^+$=299.

Preparative Example 10

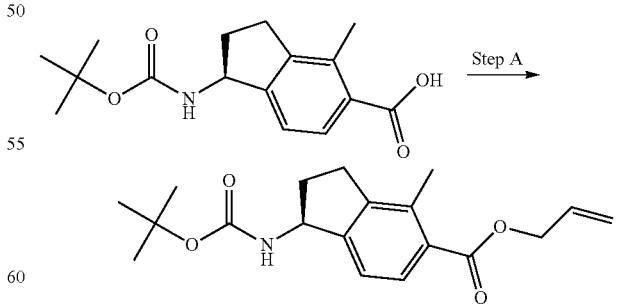

Step A

To mixture of the title compound from the Preparative Example 7, Step B (536 mg) and allyl bromide (1.6 mL) in CHCl$_3$/THF (1:1, 20 mL) were added Bu$_4$NHSO$_4$ (70 mg)

and a 1M solution of LiOH in H$_2$O (10 mL) and the resulting biphasic mixture was stirred at 40° C. overnight. The organic phase was separated, concentrated, diluted with CHCl$_3$, washed with H$_2$O, dried (MgSO$_4$), filtered, concentrated and purified by chromatography (silica, cyclohexane/EtOAc) to afford the title compound (610 mg, >99%). [MNa]$^+$=354.

Preparative Example 11

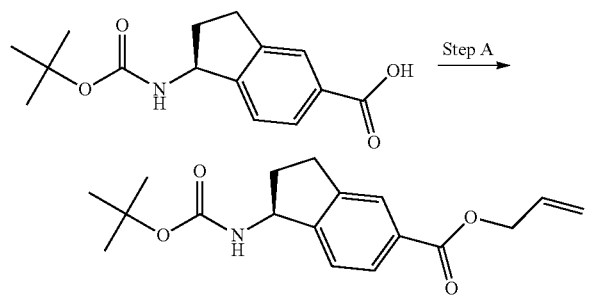

Step A

To a solution of the title compound from the Preparative Example 9, Step A (97 mg) in dry DMF (5 mL) were added K$_2$CO$_3$ (97 mg) and allyl bromide (22 µL). The mixture was stirred overnight, concentrated and purified by chromatography (silica, cyclohexane/EtOAc) to afford the title compound (81 mg, 68%). [MNa]$^+$=340.

Preparative Example 12

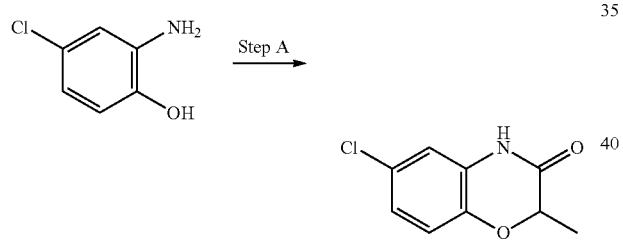

Step A

To a solution of commercially available 2-amino-4-chlorophenol (5.0 g) and NaHCO$_3$ (7.7 g) in acetone/H$_2$O was slowly added 2-bromopropionyl bromide (4 mL) at room temperature, before the mixture was heated to reflux for 3 h. The acetone was evaporated and the formed precipitate was isolated by filtration, washed with H$_2$O and dried to afford the title compound as brown crystals (6.38 g, 93%). [MH]$^+$=198.

Preparative Example 13

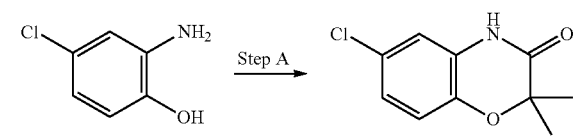

Step A

To a solution of commercially available 2-amino-4-chlorophenol (5.0 g) and NaHCO$_3$ (7.7 g) in acetone/H$_2$O (4:1, 200 mL) was slowly added 2-bromo-2-methylpropionyl bromide (8.3 mL) at room temperature, before the mixture was heated at ~90° C. overnight. The acetone was evaporated and the formed precipitate was filtered off, washed with H$_2$O (100 mL) and recrystallized from acetone/H$_2$O (1:1) to afford the title compound as a pale brown solid (4.8 g, 33%). [MH]$^+$=212.

Preparative Example 14

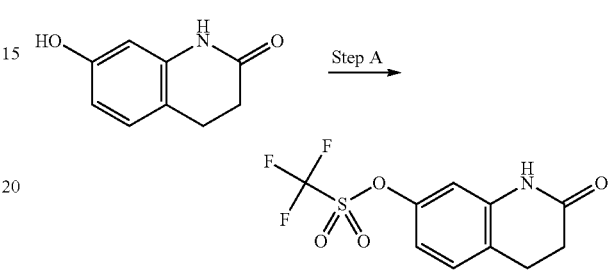

Step A

To a solution of commercially available 7-hydroxy-3,4-dihydro-1H-quinolin-2-one (1.63 g) in THF (20 mL) was added NaH (95%, 0.28 g). The mixture was stirred at room temperature for 5 min, N-phenyl-bis(trifluoromethanesulfonimide) (4.0 g) was added and stirring at room temperature was continued for 2 h. The mixture was cooled to 0° C., diluted with H$_2$O (40 mL) and extracted with EtOAc (3×30 mL). The combined organic layers were washed with saturated aqueous NaCl, dried (MgSO$_4$), filtered, concentrated and purified by chromatography (silica, CH$_2$Cl$_2$/MeOH) to afford the title compound (2.29 g, 78%). [MH]$^+$=296.

Preparative Example 15

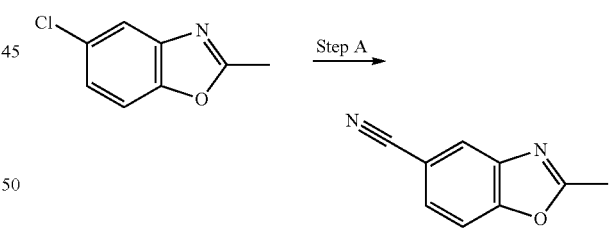

Step A

Commercially available 5-chloro-2-methylbenzoxazole (1.5 g), KCN (612 mg), dipiperidinomethane (720 µL), Pd(OAc)$_2$ (80 mg) and 1,5-bis-(diphenylphosphino)pentane (315 mg) were dissolved in dry toluene (20 mL), degassed and heated at 160° C. in a sealed pressure tube under an argon atmosphere for 24 h. The mixture was diluted with EtOAc, washed subsequently with saturated aqueous NH$_4$Cl and saturated aqueous NaCl, dried (MgSO$_4$), filtered, concentrated and purified by chromatography (silica, cyclohexane/EtOAc) to afford the title compound as a colorless solid (372 mg, 26%). $^1$H-NMR (CDCl$_3$) δ=7.90 (s, 1H), 7.48-7.58 (s, 2H), 2.63 (s, 3H).

Preparative Example 16

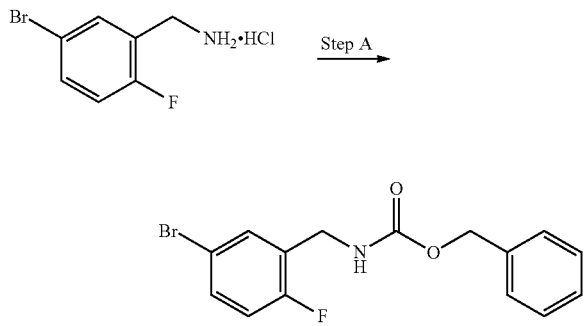

Step A
A solution of 5-bromo-2-fluorobenzylamine hydrochloride (5.39 g), $K_2CO_3$ (7.74 g) and benzyl chloroformate (3.8 mL) in THF/$H_2O$ was stirred at room temperature for 90 min. The resulting mixture was concentrated, diluted with EtOAc, washed with 10% aqueous citric acid, saturated aqueous $NaHCO_3$ and saturated aqueous NaCl, dried ($MgSO_4$), filtered, concentrated and slurried in pentane. The formed precipitate was collected by filtration to give the title compound as colorless needles (7.74 g, >99%). $[MH]^+=338/340$.

Preparative Example 17

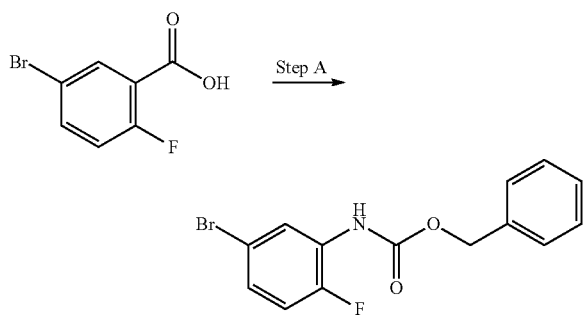

Step A
To a suspension of commercially available 5-bromo-2-fluoro-benzoic acid (4.52 g) in dry toluene (200 mL) were added $NEt_3$ (3.37 mL) and diphenylphosphoryl azide (5.28 mL). The resulting clear solution was heated to reflux for 16 1/2 h, then benzyl alcohol (2.51 mL) was added and heating to reflux was continued for 3 h. The mixture was concentrated and purified by flash chromatography (silica, cyclohexane/EtOAc) to afford the title compound (2.96 g, 46%). $[MH]^+=324/326$.

Preparative Example 18

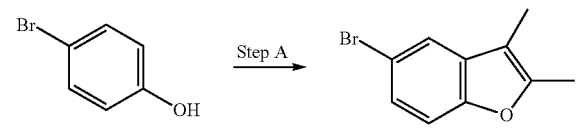

Step A
A solution of commercially available 4-bromophenol (3.36 g), 3-chloro-butan-2-one (2.2 mL) and $K_2CO_3$ (4 g) in acetone (40 mL) was heated to reflux for 3 h. Then an additional amount of 3-chloro-butan-2-one and $K_2CO_3$ was added and heating to reflux was continued overnight. The mixture was concentrated, dissolved in EtOAc, washed with $H_2O$, 10% aqueous citric acid and saturated aqueous NaCl, dried ($MgSO_4$), filtered and concentrated. The obtained colorless oil was added dropwise at 100° C. to phosphorous oxychloride (4.7 mL). The resulting mixture was stirred at 100° C. for 1 h, cooled to room temperature and ice, followed by EtOAc was added. The organic layer was separated, washed subsequently with saturated aqueous NaCl and saturated aqueous $NaHCO_3$, concentrated and purified by chromatography (silica, cyclohexane) to afford the title compound as a bright yellow solid (2.55 g, 58%). $^1$H-NMR ($CDCl_3$) δ=7.50 (s, 1H), 7.20-7.30 (m, 2H), 2.33 (s, 3H), 2.10 (s, 3H).

Preparative Example 19

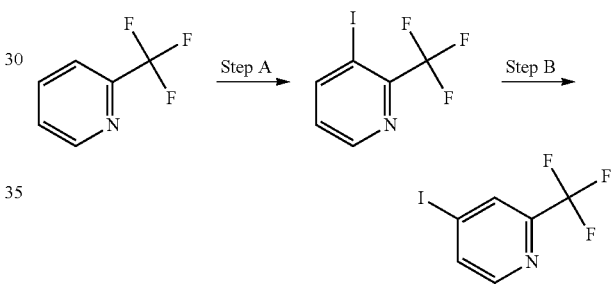

Step A
A 2.5M solution of BuLi in hexane (13.6 mL) was diluted in THF (50 mL) and cooled to −78° C. (dry ice/acetone). To this solution were subsequently added 2,2,6,6-tetramethylpiperidine (4.8 g) and commercially available 2-(trifluoromethyl)pyridine (5 g). The mixture was stirred at −78° C. for 2 h and then a solution of iodine (17.3 g) in THF (50 mL) was added. The cooling bath was removed and the mixture was stirred at room temperature overnight. Then the mixture was quenched with 1M aqueous $Na_2S_2O_3$ (50 mL), the organic phase was separated and the aqueous phase was extracted with EtOAc. The combined organic phases were dried ($MgSO_4$), filtered, concentrated and purified by chromatography (silica, $CH_2Cl_2$) to afford the title compound as a pale yellow solid (6.3 g, 68%). $^1$H-NMR ($CDCl_3$) δ=8.63 (dd, 1H), 8.36 (d, 1H), 7.20 (dd, 1H).

Step B
A 2.5M solution of BuLi in hexane (7.2 mL) was diluted in THF (30 mL) and cooled to −78° C. (dry ice/acetone). To this solution were subsequently and dropwise added $^i$Pr$_2$NH (2.5 mL) and the title compound from Step A above (4.9 g). The mixture was stirred at −78° C. for 2 h, quenched at −78° C. with MeOH (2 mL), concentrated and purified by chromatography (silica, cyclohexane/EtOAc) to afford the title compound as yellow needles (1.6 g, 32%). $^1$H-NMR (CDCl$_3$) δ=8.40 (d, 1H), 8.06 (s, 1H), 7.90 (d, 1H).

Preparative Example 20

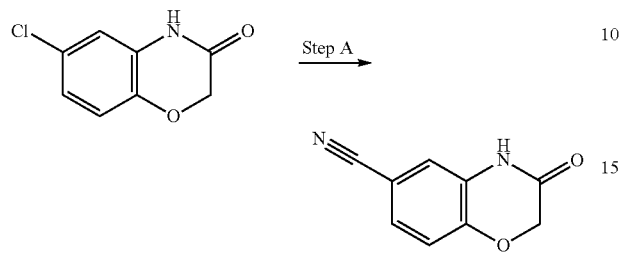

Step A

A suspension of commercially available 6-chloro-4H-benzo[1,4]oxazin-3-one (3.2 g) and CuCN (2.9 g) in dry N-methyl-pyrrolidin-2-one (15 mL) was placed in a preheated oil bath (~250° C.). After stirring at this temperature overnight, the mixture was concentrated, diluted with H$_2$O (200 mL) and extracted with EtOAc (3×200 mL). The combined organic layers were washed with H$_2$O (2×200 mL) and saturated aqueous NaCl (200 mL), dried (MgSO$_4$), filtered and concentrated. The remaining residue crystallized from EtOAc/toluene to afford the title compound as a tan solid (720 mg, 24%). [MH]$^+$=175.

Preparative Examples 21-24

Following a similar procedure as described in the Preparative Example 20, except using the intermediates indicated in Table I-1 below, the following compounds were prepared.

Preparative Example 25

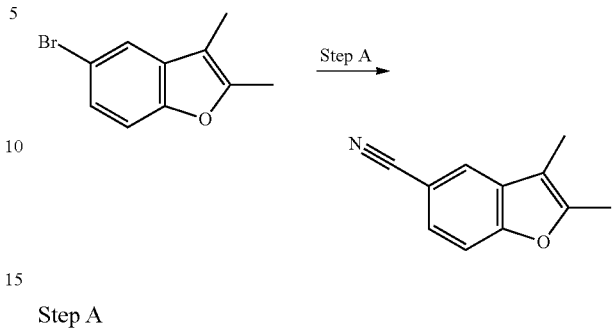

Step A

A mixture of the title compound from the Preparative Example 18, Step A (2.55 g), Zn(CN)$_2$ (1.0 g) and Pd(PPh$_3$)$_4$ (653 mg) in dry DMF (10 mL) was degassed and heated at 85° C. under an argon atmosphere for 40 h. The mixture was concentrated, diluted with EtOAc, washed subsequently with 10% aqueous citric acid and saturated aqueous NaCl, dried (MgSO$_4$), concentrated and purified by chromatography (silica, cyclohexane/EtOAc) to afford the title compound as colorless crystals (1.05 g, 54%). $^1$H-NMR (CDCl$_3$) δ=7.72 (s, 1H), 7.35-7.50 (m, 2H), 2.40 (s, 3H), 2.18 (s, 3H).

Preparative Examples 26-30

Following a similar procedure as described in the Preparative Example 25, except using the intermediates indicated in Table I-2 below, the following compounds were prepared.

TABLE I-1

| Prep. Ex. # | intermediate | product | yield |
|---|---|---|---|
| 21 | | | 39% [MH]$^+$ = 189 |
| 22 | | | 45% [MH]$^+$ = 203 |
| 23 | | | 74% $^1$H-NMR (CDCl$_3$) δ = 7.30 (d, 1 H), 7.06 (s, 1 H), 7.03 (d, 1 H). |
| 24 | | | 64% [MH]$^+$ = 173 |

TABLE I-2

| Prep. Ex. # | intermediate | product | yield |
| --- | --- | --- | --- |
| 26 | | | >99%<br>[MNa]⁺ = 261 |
| 27 | | | 94%<br>[MH]⁺ = 173 |
| 28 | | | 86%<br>[MH]⁺ = 173 |
| 29 | | | 98%<br>¹H-NMR (CDCl₃)<br>δ = 7.10-7.75 (m,<br>8 H), 5.22 (br s, 1 H),<br>5.13 (s, 2 H), 4.42 (d,<br>2 H). |
| 30 | | | 56%<br>[MH]⁺ = 271 |

Preparative Example 31

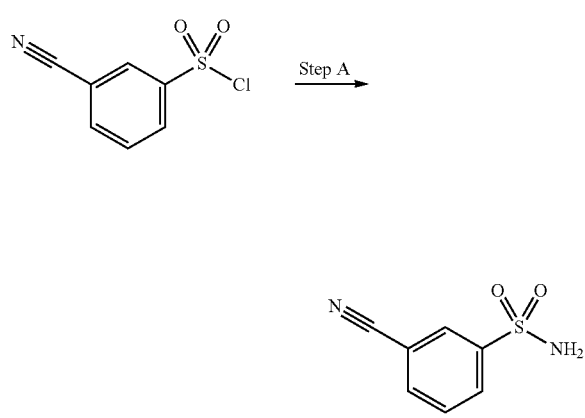 [SMILES: N#Cc1cccc(S(=O)(=O)Cl)c1 ; N#Cc1cccc(S(N)(=O)=O)c1]

Preparative Example 32

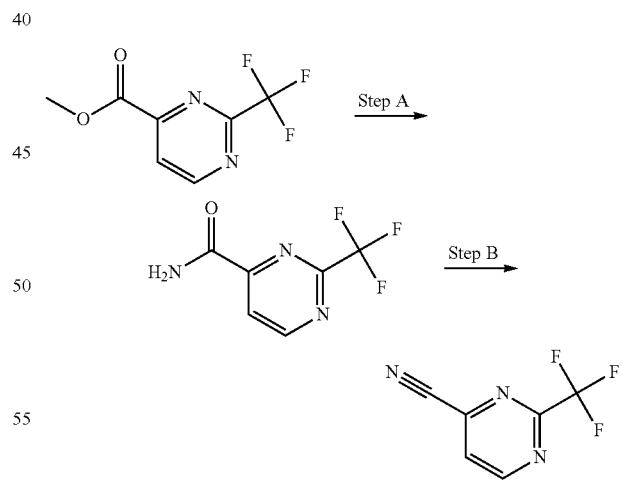

Step A

A solution of commercially available 3-cyano-benzene-sulfonyl chloride (1.07 g) in a 33% solution of NH₃ in H₂O (40 mL) was stirred at room temperature for 1 h, then concentrated to ~20 mL and placed in an ice bath. The formed precipitate was separated by filtration, washed with H₂O and dried in vacuo to afford the title compound as a colorless solid (722 mg, 75%). [MH]⁺=183.

Step A

Commercially available 2-trifluoromethyl-pyrimidine-4-carboxylic acid methyl ester (1.0 g) was dissolved in a 7M solution of NH₃ in MeOH and heated in a sealed pressure tube to 50° C. for 16 h. Cooling to room temperature and concentration afforded the title compound (941 mg, >99%). [MH]⁺= 192.

Step B

A 2M solution of oxalyl chloride in CH$_2$Cl$_2$ (520 µL) was diluted in DMF (3 mL) and then cooled to 0° C. Pyridine (1684) and a solution of the title compound from Step A above (100 mg) in DMF (1 mL) were added and the mixture was stirred at 0° C. for 3 h and then at room temperature overnight. The mixture was concentrated, diluted with EtOAc, washed with saturated aqueous NaHCO$_3$, dried (MgSO$_4$), filtered and concentrated to afford the title compound (60 mg, 65%). $^1$H-NMR (CDCl$_3$) δ=9.20 (d, 1H), 7.85 (d, 1H).

Preparative Example 33

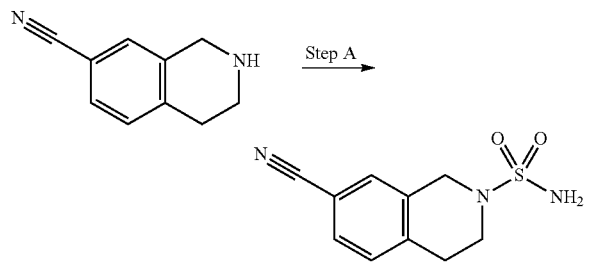

Step A

A solution of commercially available 7-cyano-1,2,3,4-tetrahydroisoquinoline (103 mg) and sulfamide (69 mg) in dry 1,2-dimethoxyethane (10 mL) was heated to reflux overnight, concentrated, diluted with EtOAc, washed subsequently with 10% aqueous citric acid and saturated aqueous NaCl, dried (MgSO$_4$), filtered and concentrated to give the title compound as a colorless solid (165 mg, >99%). [MH]$^+$=238.

Preparative Example 34

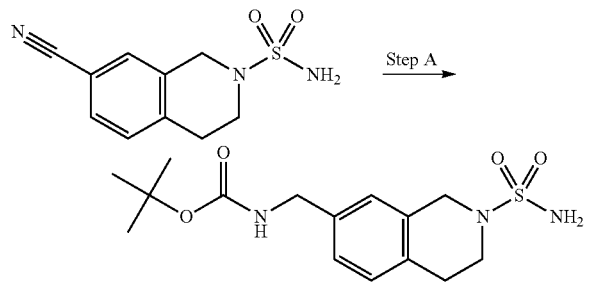

Step A

To an ice cooled solution of the title compound from the Preparative Example 33, Step A (165 mg) in dry MeOH (20 mL) were added di-tert-butyl dicarbonate (300 mg) and NiCl$_2$.6H$_2$O (20 mg), followed by the careful portionwise addition of NaBH$_4$ (220 mg). The resulting black mixture was stirred for 20 min at 0-5° C. (ice bath), then the ice bath was removed and stirring at room temperature was continued overnight. Then diethylenetriamine was added and the mixture was concentrated to dryness. The remaining residue was suspended in EtOAc washed subsequently with 10% aqueous citric acid, saturated aqueous NaHCO$_3$ and saturated aqueous NaCl, dried (MgSO$_4$), filtered, concentrated and purified by chromatography (silica, cyclohexane/EtOAc) to afford the title compound as a colorless solid (109 mg, 46%). [MNa]$^+$= 364.

Preparative Example 35

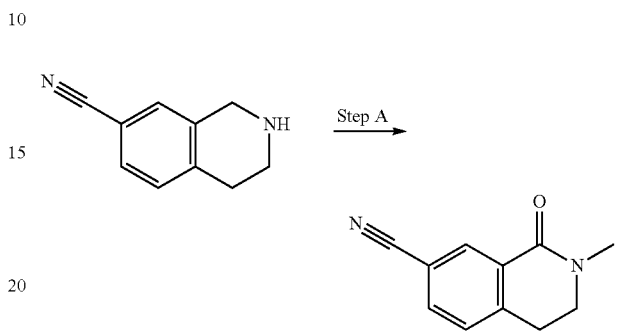

Step A

A solution of commercially available 7-cyano-1,2,3,4-tetrahydroisoquinoline (407 mg) in dry CH$_2$Cl$_2$ (10 mL) was added iodosobenzene (1.13 g). The reaction mixture was stirred at room temperature overnight, diluted with CH$_2$Cl$_2$, washed subsequently with 10% aqueous citric acid and saturated aqueous NaCl, dried (MgSO$_4$), filtered, absorbed on silica and purified by chromatography (silica, CH$_2$Cl$_2$/MeOH). The obtained intermediate (240 mg) was dissolved in dry DMF (7 mL) and cooled to 0° C. An excess of NaH and methyl iodide were added subsequently and the mixture was stirred for 2 h while warming to room temperature. The mixture was diluted with EtOAc, washed subsequently with 1N aqueous HCl and saturated aqueous NaCl, dried (MgSO$_4$), filtered, concentrated and purified by chromatography (silica, cyclohexane/EtOAc) to give the title compound as a slowly crystallizing oil (104 mg, 22%). [MH]$^+$=187.

Preparative Example 36

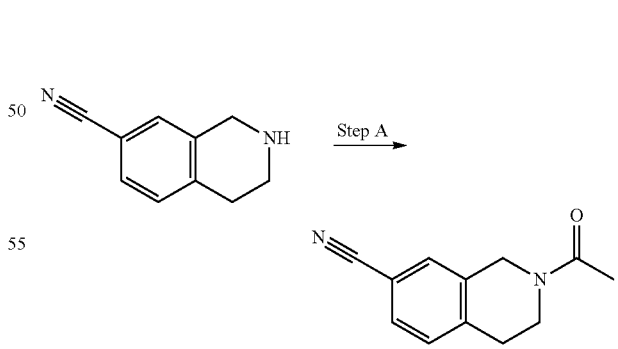

Step A

To a solution of commercially available 7-Cyano-1,2,3,4-tetrahydroisoquinoline (158 mg) in acetic anhydride (5 mL) was added pyridine (0.2 mL). The mixture was stirred overnight and then concentrated to afford the crude title compound. [MNa]$^+$=223.

Preparative Example 37

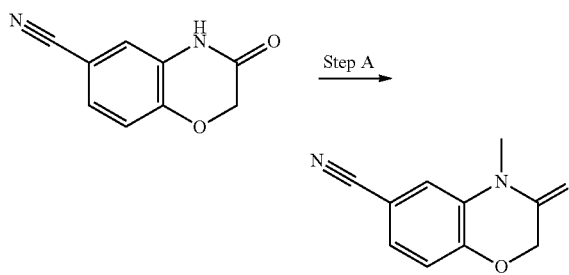

Step A

The title compound from the Preparative Example 20, Step A (549 mg) was dissolved in dry DMF (7 mL) and cooled to 0° C. An excess of NaH and methyl iodide were added subsequently and the mixture was stirred for 2 h while warming to room temperature. The mixture was diluted with EtOAc, washed subsequently with 1N aqueous HCl and saturated aqueous NaCl, dried (MgSO$_4$), filtered, absorbed on silica and purified by chromatography (silica, cyclohexane/EtOAc) to afford the title compound as colorless needles (311 mg, 52%). [MH]$^+$=189.

Preparative Example 38

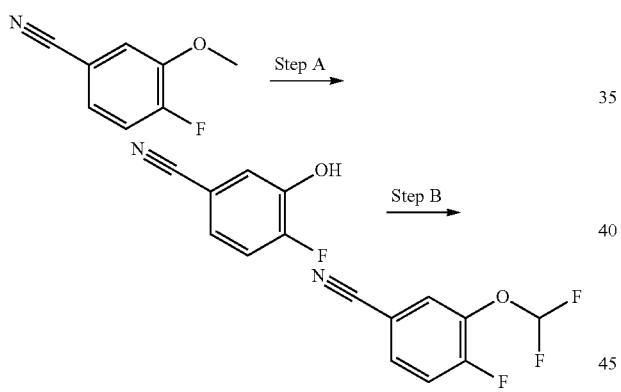

Step A

Under an argon atmosphere a mixture of commercially available 4-fluoro-3-methoxybenzonitrile (5.0 g), AlCl$_3$ (8.8 g) and NaCl (1.94 g) was heated (melted) to 190° C. for 45 min, cooled, poured on ice (200 mL) and extracted with CHCl$_3$ (3×). The combined organic phases were washed with H$_2$O, dried (MgSO$_4$), filtered, concentrated and purified by chromatography (silica, cyclohexanefEtOAc) to afford the title compound as colorless needles (3.45 g, 76%). [MH]$^+$= 138.

Step B

A suspension of the title compound from Step A above (883 mg) and K$_2$CO$_3$ (980 mg) in dry DMF (15 mL) was heated to 50° C. for 10 min and then cooled to −40° C. Chlorodifluoromethane (50 g) was condensed into the mixture and the resulting slurry was stirred at 80° C. with a dry ice condenser for 6 h and then at room temperature overnight without condenser. The mixture was concentrated, diluted with EtOAc, washed subsequently with 1N aqueous HCl and saturated aqueous NaCl, dried (MgSO$_4$), filtered and concentrated. Purification by chromatography (silica, cyclohexandEtOAc) afforded the crude title compound as a colorless oil (1.31 g). [MH]$^+$=188.

Preparative Example 39

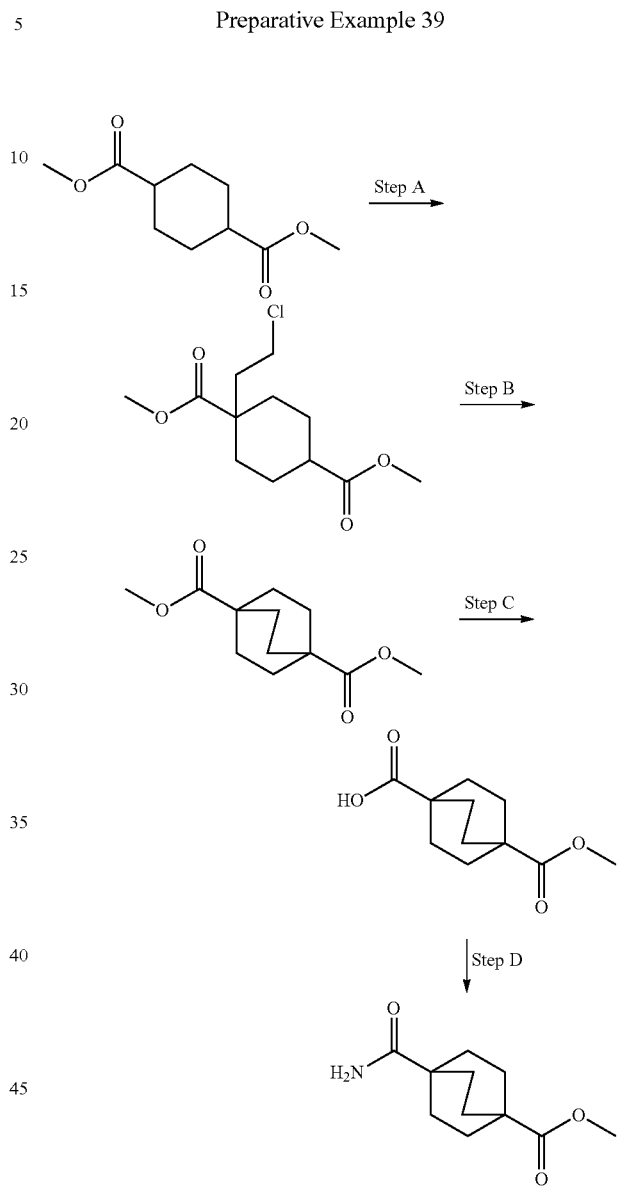

Step A

To a cooled (−30° C.) solution of $^i$Pr$_2$NH (16.9 mL) in THF (140 mL) was dropwise added a 2.5M solution of BuLi in hexane (43.2 mL). The mixture was stirred between −20° C. and −30° C. for 20 min and then cooled to −78° C. To this solution dry HMPA (72 mL) was added dropwise not allowing the temperature of the mixture to exceed −70° C. The resultant mixture was cooled again to −78° C. and a solution of commercially available dimethylcyclohexane-1,4-dicarboxylate (20 g) in THF (20 mL) was added dropwise over a period of ~10 min. Stirring at −78° C. was continued for 40 min, then 1-bromo-2-chloroethane (10 mL) was added over a period of 5 min, the cooling bath was removed and the mixture was allowed to warm to room temperature. The mixture was then quenched with saturated aqueous NH$_4$Cl, the volatiles were removed by evaporation and the mixture was diluted with cyclohexane and H$_2$O. The aqueous phase was separated and extracted with cyclohexane (2×). The combined organic phases were washed with H₂O and saturated aqueous NaCl, dried (MgSO₄), filtered and concentrated. The remaining residue was distilled (10⁻² mbar, 100° C.) to give the title compound as a pale yellow oil (17 g, 65%). [MH]⁺=263.

Step B

To a cooled (−30° C.) solution of ⁱPr₂NH (18.7 mL) in THF (180 mL) was dropwise added a 2.5M solution of BuLi in hexane (53.6 mL). The mixture was stirred between −20° C. and −30° C. for 20 min and then cooled to −78° C. This solution was canulated over a period of 30 min into a cooled (−78° C.) mixture of the title compound from Step A above (32 g) and HMPA (90 mL) in THF (440 mL) not allowing the temperature of the mixture to exceed −70° C. Stirring at −78° C. was continued for 25 min and then the mixture was allowed to warm to room temperature over a period of 1½ h. The mixture was kept at room temperature for 1 h and then quenched with saturated aqueous NH₄Cl. The volatiles were removed by evaporation and the mixture was diluted with cyclohexane and H₂O. The aqueous phase was separated and extracted with cyclohexane (3×). The combined organic phases were washed with H₂O and saturated aqueous NaCl, dried (MgSO₄), filtered and concentrated. The remaining residue was recrystallized from cyclohexane to give the title compound (13.8 g, 50%). [MH]⁺=227.

Step C

A mixture of the title compound from Step B above (20 g) and KOH (5.5 g) in MeOH/H₂O (10:1, 106 mL) was heated to reflux overnight, cooled to room temperature and concentrated. The residue was diluted with EtOAc and extracted with 1N aqueous NaOH (2×100 mL). The organic phase was dried (MgSO₄), filtered and concentrated to give the starting material as a white solid. The combined aqueous phases were adjusted with 2N aqueous HCl to pH 1-2 and extracted with EtOAc (4×250 mL). The combined turbid organic phases were filtered through a fluted filter, washed with saturated aqueous NaCl, dried (MgSO₄), filtered and concentrated to give the title compound as a colorless solid (13.1 g, 70%). [MH]⁺=213.

Step D

To a cooled (−40° C.) solution of the title compound from Step C above (500 mg) and NEt₃ (1.23 mL) in THF (50 mL) was slowly added ethyl chloroformate (0.67 mL). The mixture was allowed to warm to −25° C. and stirred at this temperature for 1 h. A 7N solution of NH₃ in MeOH (10 mL) was added and the mixture was stirred at −20° C. for 30 min. The cooling bath was removed and the mixture was stirred at room temperature for 15 min before it was concentrated. To the remaining residue were added H₂O (10 mL) and CH₂Cl₂ (20 mL), the organic phase was separated and the aqueous phase was extracted with CH₂Cl₂ (2×10 mL). The combined organic phases were washed with 1N aqueous KOH (10 mL), dried (MgSO₄), filtered and concentrated to afford the title compound (458 mg, 92%). [MH]⁺=212.

Preparative Example 40

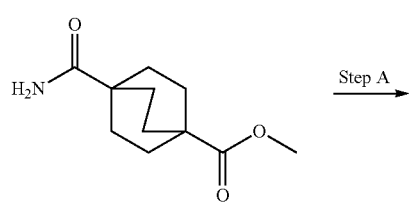

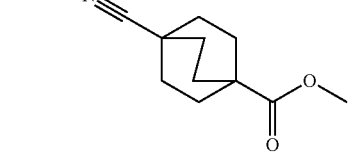

Step A

To a cooled (0° C.) mixture of the title compound from the Preparative Example 39, Step A (228 mg) and imidazole (147 mg) in pyridine (10 mL) was slowly added POCl₃ (0.40 mL). The mixture was stirred at 0° C. for 1 h and then added to a mixture of ice, NaCl and EtOAc. The organic phase was separated and washed with 1N aqueous HCl until the aqueous phase remained acidic. Drying (MgSO₄), filtration and concentration afforded the title compound (137 mg, 72%). [MH]⁺=194.

Preparative Example 41

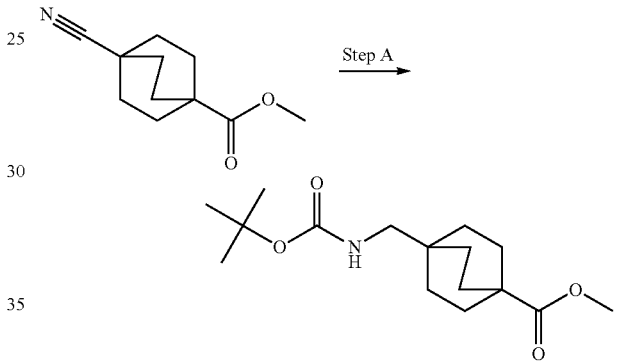

Step A

The title compound from the Preparative Example 40, Step A (137 mg) was treated similarly as described in the Preparative Example 34, Step A to afford the title compound (163 mg, 77%). [MNa]⁺=320.

Preparative Example 42

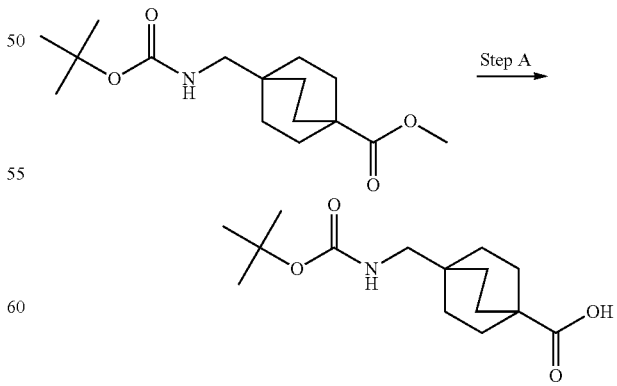

Step A

To a solution of the title compound from the Preparative Example 41, Step A (2.0 g) in MeOH (10 mL) was added a solution of KOH (753 mg) in H$_2$O (2 mL). The mixture was heated to reflux for 15 h, concentrated to approximately half of its volume and diluted with H$_2$O (50 mL). EtOAc (100 mL) was added and the organic phase was separated. The aqueous phase was acidified to pH 4.5 and extracted with EtOAc (3×40 mL). The combined organic phases were washed with saturated aqueous NaCl (50 mL), dried (MgSO$_4$), filtered and concentrated to afford the title compound (1.1 g, 56%). [MNa]$^+$=306.

Preparative Example 43

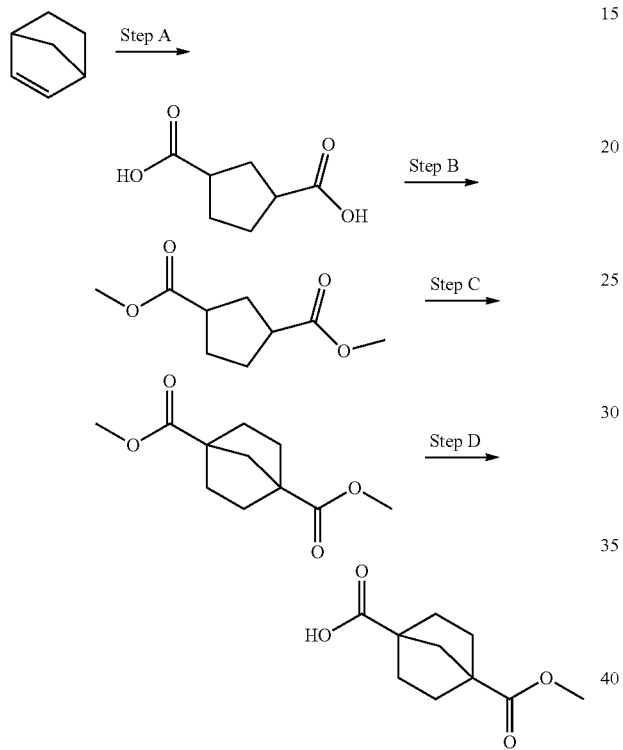

Step A

A mixture of commercially available norbonene (15 g) and RuCl$_3$ (0.3 g) in CHCl$_3$ (100 mL) was stirred at room temperature for 5 min. Then a solution of NaIO$_4$ (163 g) in H$_2$O (1200 mL) was added and the mixture was stirred at room temperature for 2 d. The mixture was filtered through a pad of Celite® and the organic phase was separated. The aqueous phase was saturated with NaCl and extracted with EtOAc (3×500 mL). The combined organic phases were treated with MgSO$_4$ and charcoal, filtered and concentrated to afford the crude title compound as thick slightly purple liquid (13.5 g, 53%). [MH]$^+$=159.

Step B

To a solution of the title compound from Step A above (11.2 g) in MeOH (250 mL) was added concentrated H$_2$SO$_4$ (0.5 mL) at room temperature. The mixture was heated to reflux for 15 h, cooled to room temperature, filtrated and concentrated. The remaining residue was diluted with EtOAc (100 mL), washed with saturated aqueous NaHCO$_3$ (3×50 mL) and saturated aqueous NaCl (50 mL), dried (MgSO$_4$), filtered, concentrated and purified by chromatography (silica, cyclohexane/EtOAc) to afford the title compound as a colorless solid (8.43 g, 64%). [MH]$^+$=187.

Step C

To a cooled (−20° C.) solution of $^i$Pr$_2$NH (17.3 mL) in THF (230 mL) was dropwise added a 2.5M solution of BuLi in hexane (45.3 mL). The mixture was stirred between −20° C. and −30° C. for 20 min and then cooled to −78° C. To this solution dry HMPA (63.2 mL) was added dropwise not allowing the temperature of the mixture to exceed −70° C. The resultant mixture was cooled again to −78° C. and a solution of the title compound from Step B above (8.43 g) in THF (40 mL) was added dropwise over a period of 20 min. Then the mixture was stirred at 0° C. for 20 min and cooled again to −78° C. 1-Bromo-2-chloroethane (6.32 mL) was added over a period of 40 min, the cooling bath was removed and the mixture was allowed to warm to room temperature over a period of 2 h. The mixture was then quenched with saturated aqueous NH$_4$Cl (60 mL), concentrated to ⅕ volume and diluted with H$_2$O (120 mL). The aqueous phase was separated and extracted with cyclohexane (3×100 mL). The combined organic phases were washed with H$_2$O (100 mL) and saturated aqueous NaCl (100 mL), dried (MgSO$_4$), filtered, concentrated and purified by chromatography (silica, cyclohexane/EtOAc) to afford the title compound as a colorless solid (7.86 g, 82%). [MH]$^+$=213.

Step D

To a solution of the title compound from Step C above (3.5 g) in MeOH (15 mL) was added a solution of KOH (1.6 g) in H$_2$O (1.75 mL). Using a microwave, the mixture was heated to 140° C. for 25 min before H$_2$O (30 mL) was added. The aqueous mixture was washed with cyclohexane (2×30 mL), adjusted to pH 1 with 1N aqueous HCl and extracted with CH$_2$Cl$_2$ (2×30 mL). The combined organic phases were washed with saturated aqueous NaCl (15 mL), dried (MgSO$_4$), filtered, concentrated and purified by flash chromatography (silica, CH$_2$Cl$_2$/MeOH) to afford the title compound (2.3 g, 70%). [MH]$^+$=199.

Preparative Example 44

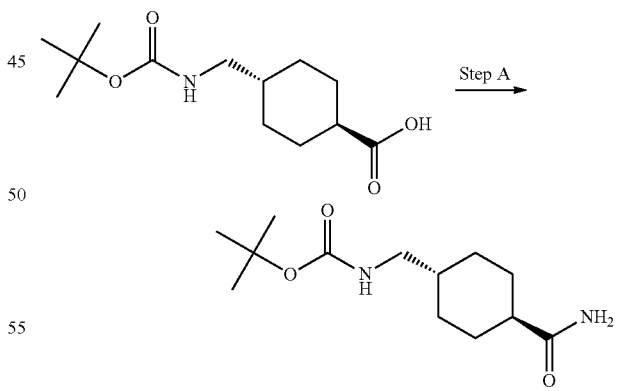

Step A

To a solution of commercially available trans-4-(tert-butoxycarbonylamino-methyl)-cyclohexanecarboxylic acid (262 mg) in dry THF (5 mL) was added 1,1'-carbonyldiimidazole (243 mg). The resulting clear colorless solution was stirred at room temperature for 1 h, then a 0.5M solution of NH$_3$ in 1,4-dioxane (20 mL) was added and stirring at room temperature was continued for 5 h. The mixture was concentrated and purified by flash chromatography (silica, CH₂Cl₂/MeOH) to afford the title compound (250 mg, 97%). [MNa]⁺=279.

Preparative Example 45

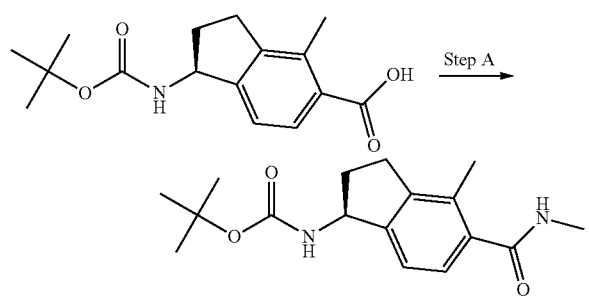

Step A

To a solution of title compound from the Preparative Example 7, Step B (35 mg) in DMF (3 mL) were added HATU (60 mg), HOAt (20 mg) and a 2M solution of MeNH₂ in THF (150 µL). The mixture was stirred for 16 h, concentrated, diluted with EtOAc, washed with saturated aqueous NaHCO₃ and saturated aqueous NaCl, dried (MgSO₄), filtered, concentrated and purified by chromatography (silica, CH₂Cl₂/acetone) to afford the title compound (35 mg, 95%). [MH]⁺=291.

Preparative Examples 46-53

Following similar procedures as described in the Preparative Examples 39 (method A), 44 (method B) or 45 (method C), except using the acids and amines indicated in Table I-3 below, the following compounds were prepared.

TABLE I-3

| Prep. Ex. # | acid, amine | product | method, yield |
|---|---|---|---|
| 46 | <br>2M MeNH₂ in THF | | A, 79%<br>[MH]⁺ = 297 |
| 47 | <br>2M Me₂NH in THF | | B, 90%<br>[MH]⁺ = 311 |
| 48 | <br>HN-morpholine | | B, 44%<br>[MH]⁺ = 353 |
| 49 | <br>7N NH₃ in MeOH | | A, 51%<br>[MH]⁺ = 283 |

TABLE I-3-continued

| Prep. Ex. # | acid, amine | product | method, yield |
|---|---|---|---|
| 50 | 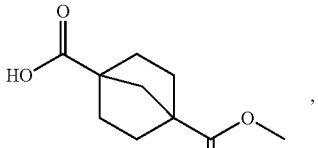<br>7N NH3 in MeOH | 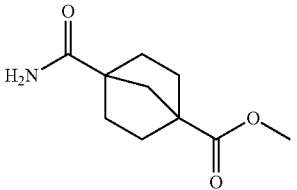 | A, 37%<br>[MH]+ = 198 |
| 51 | 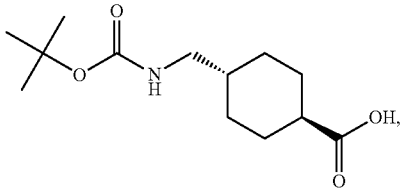<br>2M MeNH2 in THF | 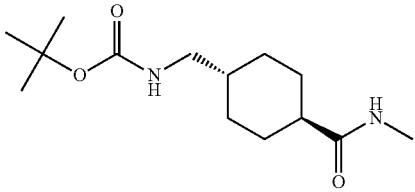 [SMILES: CNC(=O)[C@H]1CC[C@H](CNC(=O)OC(C)(C)C)CC1] | B, 99%<br>[MNa]+ = 293 |
| 52 | 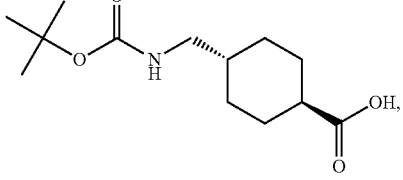<br>2M Me2NH in THF | 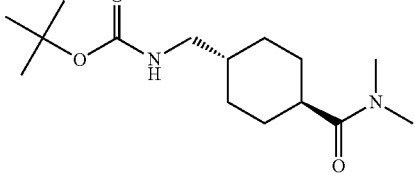 | B, 98%<br>[MNa]+ = 307 |
| 53 | 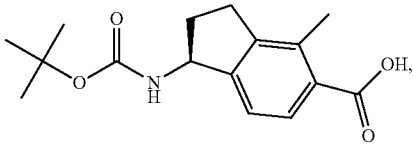<br>2M Me2NH in THF | 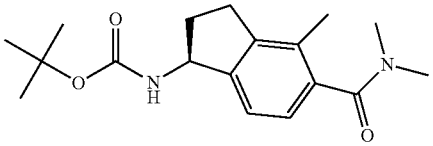 [SMILES: Cc1c(C(=O)N(C)C)ccc2c1CC[C@@H]2NC(=O)OC(C)(C)C] | C, 60%<br>[MH]+ = 305 |

Preparative Example 54

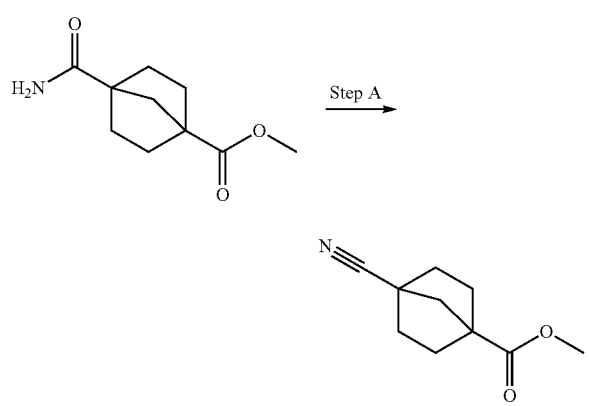

Step A

The title compound from the Preparative Example 50 (300 mg) was treated similarly as described in the Preparative Example 40, Step A to afford the title compound (250 mg, 92%). [MH]+=180.

Preparative Example 55

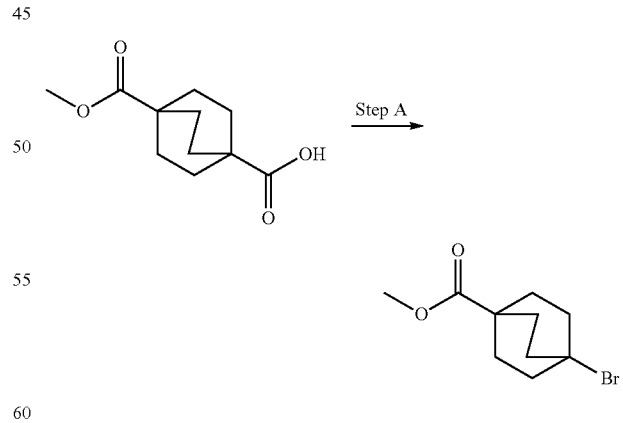

Step A

To a suspension of the title compound from the Preparative Example 39, Step C (1.0 g) in acetone (7.5 mL) was added phenolphthaleine (1 crystal). To this mixture was added 1M aqueous NaOH until the color of the solution changed to red (pH ~8.5). Then a solution of AgNO3 (850 mg) in H2O (1.25 mL) was added. The formed precipitate (Ag-salt) was collected by filtration, washed with H₂O, acetone and Et₂O and dried in vacuo at room temperature for 6 h and at 100° C. for 18 h. The obtained solid (1.28 g) was suspended in hexane (15 mL), bromine (643 mg) was added dropwise and the mixture was stirred at room temperature for 30 min. Then the mixture was placed in a preheated oil bath (80° C.) and stirred at the temperature for another 30 min. The mixture was filtered and the filter cake was washed with Et₂O (2×30 mL). The combined filtrates were washed with saturated aqueous NaHCO₃ (2×25 mL), dried (MgSO₄), filtered and concentrated to afford the title compound (817 mg, 70%). [MH]⁺=247/249.

Preparative Example 56

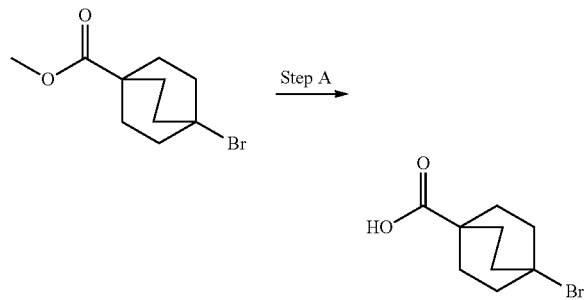

Step A

To the title compound from the Preparative Example 55, Step A (600 mg) was added 1% aqueous NaOH (65 mL). The mixture was stirred at 100° C. (temperature of the oil bath) for 18 h, concentrated to 15 mL and diluted with 1N aqueous HCl (20 mL). The resulting mixture was acidified to pH 1 with 12N aqueous HCl and extracted with EtOAc (2×75 mL). The combined organic phases were dried (MgSO₄), filtered and concentrated to afford the crude title compound, which was not further purified (340 mg, 82%). [M-CO₂]⁺=188/190.

Preparative Example 57

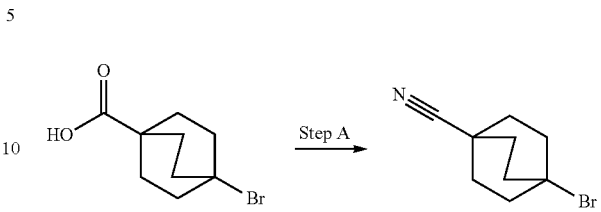

Step A

To a cooled (−30° C.) solution of the title compound from the Preparative Example 56, Step A (540 mg) and NEt₃ (375 mL) in THF (25 mL) was added ethyl chloroformate (200 μL). The mixture was stirred at −30° C. for 1 h and then filtered. The precipitated salts were washed with THF (15 mL). The combined filtrates were cooled to −20° C. and a 33% solution of NH₃ in H₂O (7 mL) was added. The mixture was stirred at −20° C. for 20 min, then the cooling bath was removed and the mixture was stirred at room temperature for 40 min. Then the mixture was concentrated and dissolved in THF (12 mL). Pyridine (6904) was added and the mixture was cooled to 0° C. Trifluoroacetic anhydride (600 μL) was added and the mixture was stirred at 0° C. for 2 h. Then the mixture was concentrated to 5 mL, diluted with MeOH (10 mL) and 10% aqueous K₂CO₃ (5 mL) and stirred at room temperature for 2½ h. The MeOH was evaporated and Et₂O/EtOAc (9:1, 80 mL), H₂O (10 mL), saturated aqueous NaCl (10 mL) and saturated aqueous NH₄Cl (15 mL) were added. The organic phase was separated, washed with 0.1N aqueous HCl (30 mL), dried (MgSO₄), filtered and concentrated to afford the crude title compound, which was not further purified (222 mg, 86%). [MH]⁺=214/216.

Preparative Examples 58-80

Following a similar procedure as described in the Preparative Example 34, except using the nitriles indicated in Table I-4 below, the following compounds were prepared.

TABLE I-4

| Prep. Ex. # | nitrile | product | yield |
| --- | --- | --- | --- |
| 58 |  |  | 68% [MNa]⁺ = 310 |
| 59 |  |  | 73% [MNa]⁺ = 285 |
| 60 |  |  | 68% [MNa]⁺ = 298 |

TABLE I-4-continued

| Prep. Ex. # | nitrile | product | yield |
|---|---|---|---|
| 61 | | | 69% [MNa]⁺ = 313 |
| 62 | | | 41% [MNa]⁺ = 301 |
| 63 | | | 51% [MNa]⁺ = 315 |
| 64 | | | 62% [MNa]⁺ = 315 |
| 65 | | | n.d. [MNa]⁺ = 314 |
| 66 | | | 98% [MH]⁺ = 307 |
| 67 | | | 67% [MH]⁺ = 277 |
| 68 | | | 18% ¹H-NMR (CDCl₃) δ = 8.80 (d, 1 H), 7.50 (d, 1 H), 5.40 (br s, 1 H), 4.50 (br d, 2 H), 1.40 (s, 9 H) |

TABLE I-4-continued

| Prep. Ex. # | nitrile | product | yield |
|---|---|---|---|
| 69 | 3-cyanobenzenesulfonamide | tert-butyl 3-sulfamoylbenzylcarbamate | n.d. [MNa]⁺ = 309 |
| 70 | 4-hydroxy-3-(trifluoromethyl)benzonitrile | tert-butyl 4-hydroxy-3-(trifluoromethyl)benzylcarbamate | 67% [MH]⁺ = 292 |
| 71 | 2-chloro-4-cyanopyridine | tert-butyl (2-chloropyridin-4-yl)methylcarbamate | 74% [MH]⁺ = 243 |
| 72 | 2,2,3,3-tetrafluoro-2,3-dihydrobenzo[b][1,4]dioxine-6-carbonitrile | tert-butyl (2,2,3,3-tetrafluoro-2,3-dihydrobenzo[b][1,4]dioxin-6-yl)methylcarbamate | 38% [M-isobutene]⁺ = 282 |
| 73 | 4-bromobicyclo[2.2.2]octane-1-carbonitrile | tert-butyl (4-bromobicyclo[2.2.2]octan-1-yl)methylcarbamate | 24% [M-isobutene]⁺ = 262 |
| 74 | methyl 4-cyanobicyclo[2.2.2]octane-1-carboxylate | methyl 4-((tert-butoxycarbonylamino)methyl)bicyclo[2.2.2]octane-1-carboxylate | 57% [MH]⁺ = 284 |
| 75 | bicyclo[2.2.1]heptane-2-carbonitrile | tert-butyl (bicyclo[2.2.1]heptan-2-yl)methylcarbamate | 61% [MH]⁺ = 226 |
| 76 | 2-acetyl-1,2,3,4-tetrahydroisoquinoline-7-carbonitrile | tert-butyl (2-acetyl-1,2,3,4-tetrahydroisoquinolin-7-yl)methylcarbamate | n.d. [MNa]⁺ = 305 |
| 77 | 6-(trifluoromethyl)picolinonitrile | tert-butyl (6-(trifluoromethyl)pyridin-2-yl)methylcarbamate | 75% [MNa]⁺ = 299 |

TABLE I-4-continued

| Prep. Ex. # | nitrile | product | yield |
|---|---|---|---|
| 78 | 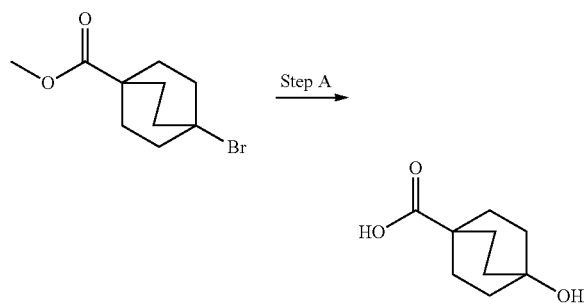 | | 79% [MH]⁺ = 277 |
| 79 | | | >99% [MNa]⁺ = 411 |
| 80 | | | 89% [MNa]⁺ = 397 |

Preparative Example 81

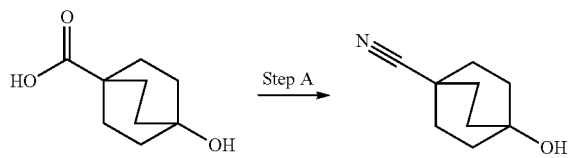 [SMILES: O=C(O)C12CCC(O)(CC1)CC2 ; N#CC12CCC(O)(CC1)CC2]

Step A

To the title compound from the Preparative Example 55, Step A (677 mg) was added 10% aqueous NaOH (65 mL). The mixture was stirred at 100° C. (temperature of the oil bath) for 42 h, concentrated to 15 mL and diluted with 1N aqueous HCl (30 mL). The resulting mixture was acidified to pH 1 with 12N aqueous HCl and extracted with EtOAc (5×70 mL). The combined organic phases were dried (MgSO$_4$), filtered and concentrated to afford the title compound (540 mg, 89%). [MH]⁺=171.

Preparative Example 82

Step A

To a cooled (−30° C.) solution of the title compound from the Preparative Example 81, Step A (540 mg) and NEt$_3$ (590 μL) in THF (35 mL) was added ethyl chloroformate (320 μL). The mixture was stirred at −30° C. for 1 h and then filtered. The precipitated salts were washed with THF (20 mL). The combined filtrates were cooled to −20° C. and a 33% solution of NH$_3$ in H$_2$O (10 mL) was added. The mixture was stirred at −20° C. for 20 min, then the cooling bath was removed and the mixture was stirred at room temperature for 40 min. The mixture was concentrated and dissolved in THF/CH$_3$CN (4:1, 25 mL). Pyridine (1.26 mL) was added and the mixture was cooled to 0° C. Trifluoroacetic anhydride (1.10 mL) was added and the mixture was stirred at 0° C. for 2 h. Then the mixture was concentrated to 5 mL, diluted with MeOH (18 mL) and 10% aqueous K$_2$CO$_3$ (9 mL), stirred at room temperature overnight, concentrated to 10 mL, acidified to pH 1 with 1N aqueous HCl and extracted with CH$_2$Cl$_2$ (4×75 mL). The combined organic phases were dried (MgSO$_4$), filtered, concentrated and purified by chromatography (silica, CH$_2$Cl$_2$/MeOH) to afford the title compound (433 mg, 90%). [MH]⁺=152.

Preparative Example 83

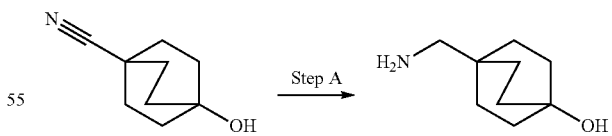

Step A

To a suspension of LiAlH$_4$ (219 mg) in THF (12 mL) was added a solution of the title compound from the Preparative Example 82, Step A (433 mg) in THF (35 mL) over a period of 20 min. The mixture was heated to reflux for 36 h and then cooled to 0° C. 1N aqueous NaOH (1 mL) was added and the mixture was stirred overnight while warming to room temperature. The mixture was filtered through a pad of Celite® and the filter cake was washed with Et$_2$O (250 mL). The combined filtrates were concentrated to afford the title compound (410 mg, 92%). [MH]$^+$=156.

Preparative Example 84

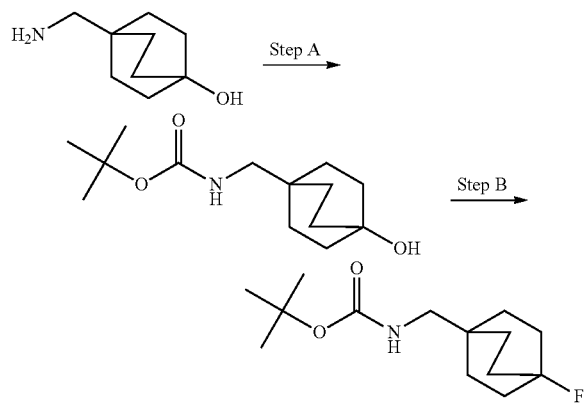

Step A

To a solution of the title compound from the Preparative Example 83, Step A (390 mg) in THF (80 mL) were successively added $^i$Pr$_2$NEt (0.66 mL) and di-tert-butyl dicarbonate (740 mg). The mixture was stirred at room temperature for 3 d, concentrated, diluted with EtOAc (100 mL), washed subsequently with H$_2$O (15 mL), 0.1N aqueous HCl and saturated aqueous NaCl, dried (MgSO$_4$), concentrated and purified by chromatography (silica, CH$_2$Cl$_2$/MeOH) to afford the title compound (196 mg, 30%). [MNa]$^+$=278.

Step B

To a cooled (−78° C.) solution of the title compound from Step A above (85 mg) in CH$_2$Cl$_2$ (4 mL) was added a solution of diethylaminosulfur trifluoride (73 μL) in CH$_2$Cl$_2$ (4 mL). The mixture was stirred at −78° C. for 15 min and then poured on saturated aqueous NaHCO$_3$ (40 mL). The organic phase was separated and the aqueous phase was extracted with CH$_2$Cl$_2$ (3×40 mL). The combined organic phases were washed with saturated aqueous NaCl (30 mL), dried over MgSO$_4$, filtered, concentrated and purified by chromatography (silica, cyclohexane/EtOAc) to afford the title compound (28 mg, 32%). [MNa]$^+$=280.

Preparative Example 85

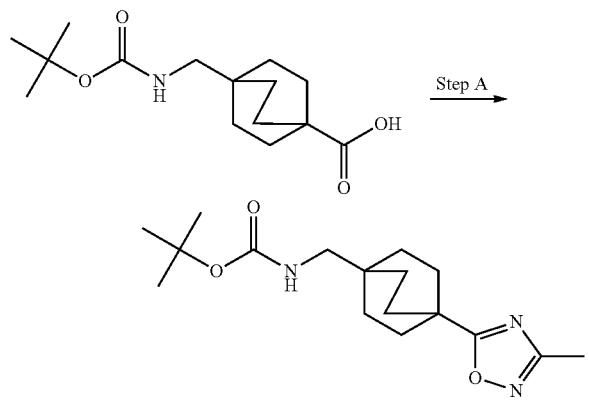

Step A

To a solution of the title compound from the Preparative Example 42, Step A (50 mg) in DMF (1.6 mL) were added HATU (67 mg), $^i$Pr$_2$NEt (68 μL) and N-hydroxyacetamidine (~60%, 22 mg). Using a microwave, the mixture was heated in a sealed tube to 130° C. for 30 min. Additional HATU (130 mg) and N-hydroxyacetamidine (50 mg) were added and the mixture was again heated to 130° C. (microwave) for 30 min. Additional HATU (130 mg) and N-hydroxyacetamidine (59 mg) were added and the mixture was heated to 140° C. (microwave) for 30 min. The mixture was concentrated and purified by flash chromatography (silica, cyclohexane/EtOAc) to afford the title compound (18 mg, 32%). [MNa]$^+$=322.

Preparative Example 86

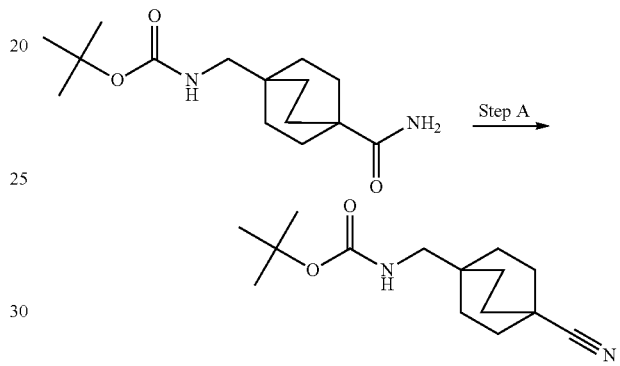

Step A

To a solution of the title compound from the Preparative Example 49 (150 mg) in THF (6 mL) was added methyl N-(triethylammoniosulfonyl) carbamate ["Burgess reagent"] (316 mg). The mixture was stirred at room temperature for 15 h, diluted with EtOAc (15 mL), filtered, concentrated and purified by flash chromatography (silica, CH$_2$Cl$_2$/MeOH) to afford the title compound (77 mg, 55%). [MH]$^+$=265.

Preparative Example 87

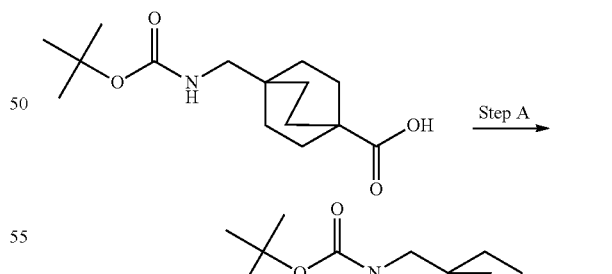

Step A

To a cooled (−40° C.) solution of the title compound from the Preparative Example 42, Step A (60 mg) and NEt$_3$ (40 μL) in THF (5 mL) was added ethyl chloroformate (24 μL). The mixture was stirred at −40° C. for 1 h and then filtered. The precipitated salts were washed with THF (30 mL). The combined filtrates were cooled to 0° C. and a solution of NaBH$_4$ (24 mg) in H$_2$O (430 μL) was added. The mixture was stirred at 0° C. for 1 h, then the cooling bath was removed and the mixture was stirred at room temperature for 1 h. The mixture was diluted with saturated aqueous NaHCO$_3$ (5 mL) and saturated aqueous NaCl (5 mL) and extracted with EtOAc (3×20 mL). The combined organic phases were washed with saturated aqueous NaCl, dried (MgSO$_4$), filtered, concentrated and purified by chromatography (silica, CH$_2$Cl$_2$/MeOH) to afford the title compound (22 mg, 39%). [MH]$^+$=292.

Preparative Example 88

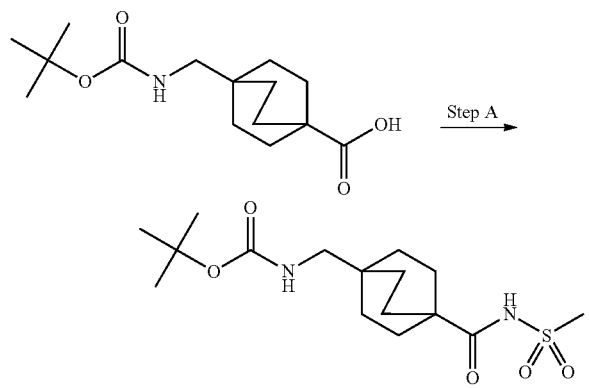

Step A

To a ice cooled solution of the title compound from the Preparative Example 42, Step A (95 mg) in CH$_2$Cl$_2$ (5 mL) were successively added DMAP (61 mg), EDCI (96 mg) and methane sulfonamide (32 mg). The cooling bath was removed and the mixture was stirred at room temperature for 24 h. The mixture was diluted with CH$_2$Cl$_2$ (20 mL), washed with 1M aqueous citric acid (15 mL) and saturated aqueous NaCl (15 mL), dried (MgSO$_4$), filtered, concentrated and purified by flash chromatography (silica, CH$_2$Cl$_2$/MeOH) to afford the title compound (63 mg, 51%). [MNa]$^+$=383.

Preparative Example 89

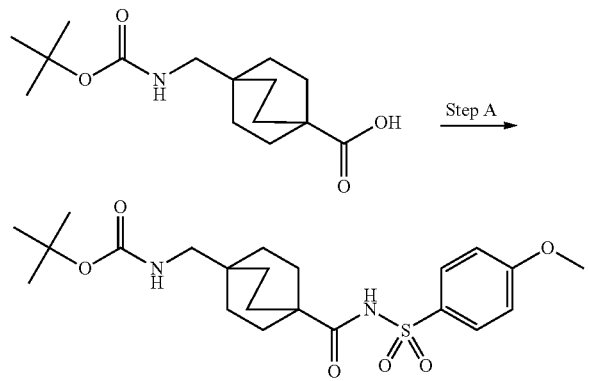

Step A

The title compound from the Preparative Example 42, Step A (95 mg) was treated similarly as described in the Preparative Example 88, Step A, except using 4-methoxy-phenyl sulfonamide (64 mg) to afford the title compound (58 mg, 38%). [MH]$^+$=453.

Preparative Example 90

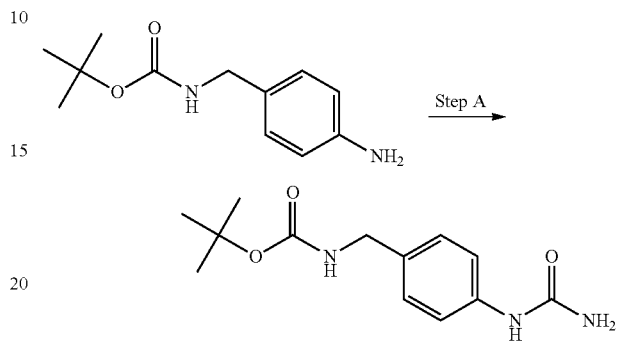

Step A

To a solution of commercially available (4-amino-benzyl)-carbamic acid tert-butyl ester (229 mg) in dry CH$_2$Cl$_2$ (1 mL) were successively added $^i$PrOH (100 μL) and trimethylsilyl isocyanate (154 mL). The resulting reaction mixture was stirred at room temperature for 17½ h. Additional trimethylsilyl isocyanate (154 μL) was added and stirring at room temperature was continued for 75 h. The resulting reaction mixture was diluted with MeOH (5 mL), concentrated and purified by flash chromatography (silica, CH$_2$Cl$_2$/MeOH) to afford the title compound (263 mg, 99%). [MH]$^+$=266.

Preparative Example 91

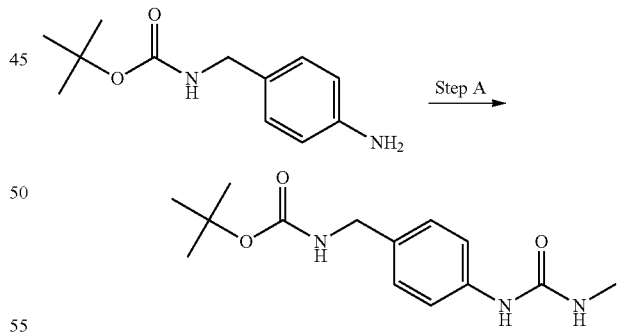

Step A

To a solution of commercially available (4-amino-benzyl)-carbamic acid tert-butyl ester (229 mg) in dry CH$_2$Cl$_2$ (1 mL) were successively added $^i$Pr$_2$NEt (349 μL) and N-succinimidyl N-methylcarbamate (355 mg). The resulting reaction mixture was stirred at room temperature for 72 h, diluted with EtOAc (20 mL), washed with 0.1M aqueous NaOH (3×10 mL), dried (MgSO$_4$), filtered and concentrated to afford the title compound (269 mg, 96%). [MH]$^+$=280.

Preparative Example 92

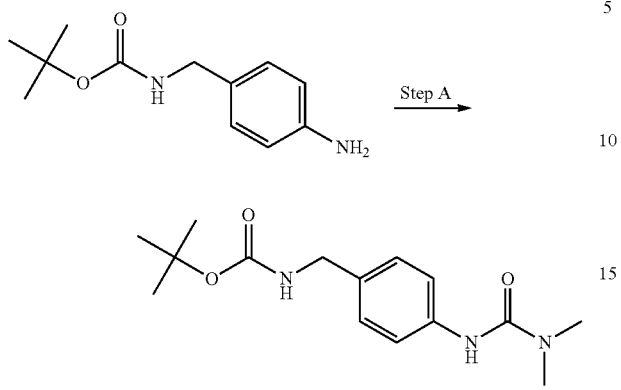

Step A

To a solution of commercially available (4-amino-benzyl)-carbamic acid tert-butyl ester (222 mg) in dry pyridine (1 mL) was added N,N-dimethylcarbamoyl chloride (103 µL). The resulting dark red reaction mixture was stirred at room temperature for 17½ h and then diluted with H$_2$O (10 mL) and EtOAc (20 mL). The organic phase was separated and washed with 1M aqueous NH$_4$Cl (2×10 mL). The aqueous phases were combined and extracted with EtOAc (2×10 mL). The combined organic phases were dried (MgSO$_4$), filtered and concentrated to afford the title compound (284 mg, 97%). [MH]$^+$=294.

Preparative Example 93

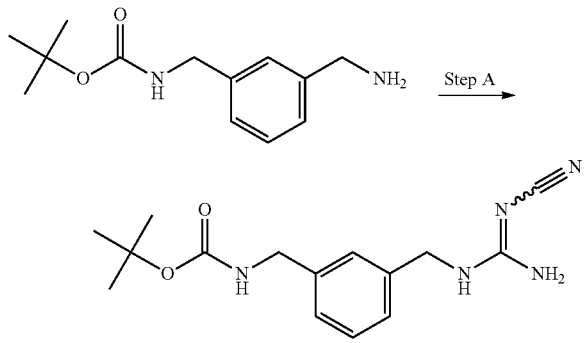

Step A

To a solution of commercially available (3-aminomethyl-benzyl)-carbamic acid tert-butyl ester (236 mg) in DMF (3 mL) was added dimethyl-N-cyano-dithioiminocarbonate (146 mg). The mixture was stirred at room temperature overnight, a 7M solution of NH$_3$ in MeOH (5 mL) and HgCl$_2$ (300 mg) were added and stirring at room temperature was continued for 2 d. Concentration and purification by chromatography (silica, CHCl$_3$/MeOH) afforded the title compound as a white solid (260 mg, 85%). [MH]$^+$=304.

Preparative Example 94

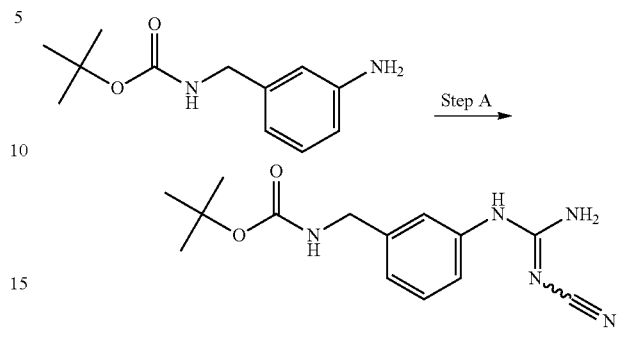

Step A

To a solution of commercially available (3-amino-benzyl)-carbamic acid tert-butyl ester (97 mg) in DMF (5 mL) were added N-cyano-methylthioiminocarbonate (50 mg) and HgCl$_2$ (120 mg). The reaction mixture was stirred at room temperature overnight, concentrated and purified by chromatography (silica, CHCl$_3$/MeOH) to afford the title compound as a pale yellow solid (53 mg, 43%). [MH]$^+$=290.

Preparative Example 95

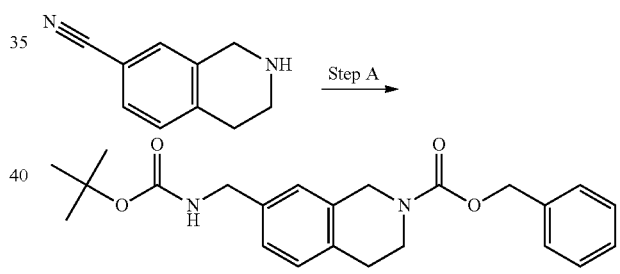

Step A

A solution of commercially available 7-cyano-1,2,3,4-tetrahydroisoquinoline (2.75 g), K$_2$CO$_3$ (3.60 g) and benzylchloroformate (2.7 mL) in THF/H$_2$O was stirred overnight and then concentrated. The residue was diluted with EtOAc, washed with 10% aqueous citric acid, saturated aqueous NaHCO$_3$ and saturated aqueous NaCl, dried (MgSO$_4$) and concentrated. The residue was dissolved in MeOH (100 mL) and di-tert-butyl dicarbonate (7.60 g) and NiCl$_2$.6H$_2$O (400 mg) was added. The solution was cooled to 0° C. and NaBH$_4$ (2.60 g) was added in portions. The mixture was allowed to reach room temperature and then vigorously stirred overnight. After the addition of diethylenetriamine (2 mL) the mixture was concentrated, diluted with EtOAc, washed subsequently with 10% aqueous citric acid, saturated aqueous NaHCO$_3$ and saturated aqueous NaCl, dried (MgSO$_4$), concentrated and purified by chromatography (silica, CH$_2$Cl$_2$/MeOH) to afford the title compound as a colorless oil (1.81 g, 26%). [MH]$^+$=397.

Preparative Example 96

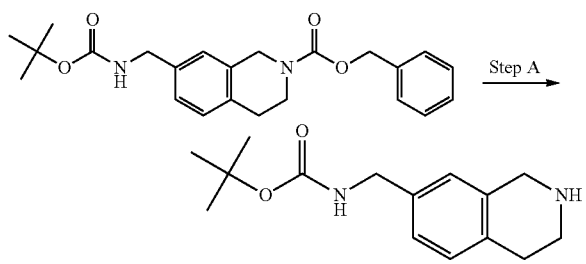

Step A
A mixture of the title compound from the Preparative Example 95, Step A (1.4 g) and Pd/C (10 wt %, 200 mg) in MeOH (40 mL) was hydrogenated at atmospheric pressure overnight, filtered and concentrated to afford the title compound as an off-white solid (960 mg, >99%.) [MH]$^+$=263.

Preparative Example 97

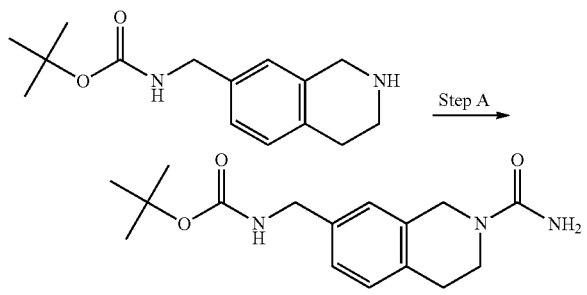

Step A
To a solution of the title compound from the Preparative Example 96, Step A (100 mg) in dry CH$_2$Cl$_2$ (5 mL) were successively added $^i$PrOH (500 μL) and trimethylsilyl isocyanate (100 μL). The resulting mixture was stirred at room temperature for 70 h, diluted with MeOH (5 mL), concentrated and purified by chromatography (silica, CH$_2$Cl$_2$/MeOH) to afford the title compound as a colorless solid (80 mg, 69%). [MNa]$^+$=328.

Preparative Example 98

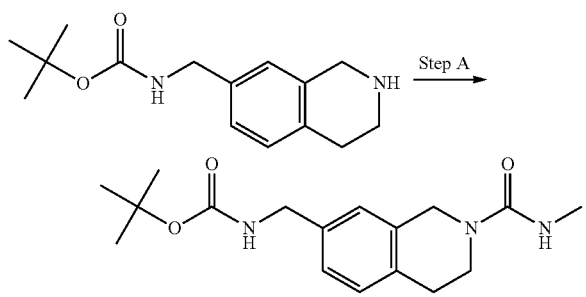

Step A
To a solution of the title compound from the Preparative Example 96, Step A (100 mg) in dry CH$_2$Cl$_2$ (5 mL) were successively added $^i$Pr$_2$NEt (132 μL) and N-succinimidyl N-methylcarbamate (131 mg). The resulting mixture was stirred at room temperature for 72 h, diluted with EtOAc (5 mL), washed with 0.1M aqueous NaOH (3×10 mL), dried (MgSO$_4$), filtered, concentrated and purified by chromatography (silica, CH$_2$Cl$_2$/MeOH) to afford the title compound (92 mg, 76%). [MNa]$^+$=342.

Preparative Example 99

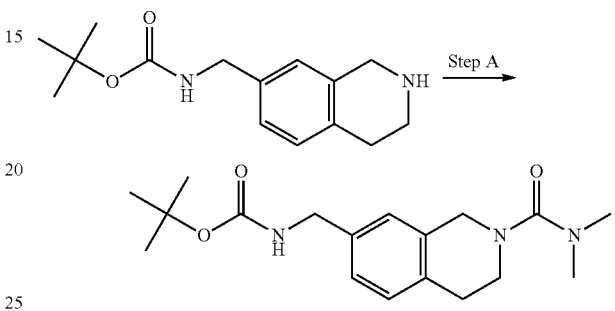

Step A
To a solution of the title compound from the Preparative Example 96, Step A (100 mg) in dry pyridine (2 mL) was added N,N-dimethylcarbamoyl chloride (38 μL). The resulting mixture was stirred at room temperature for 70 h, diluted with MeOH (5 mL), concentrated and purified by chromatography (silica, CH$_2$Cl$_2$/MeOH) to afford the title compound as a white solid (40 mg, 32%). [MNa]$^+$=356.

Preparative Example 100

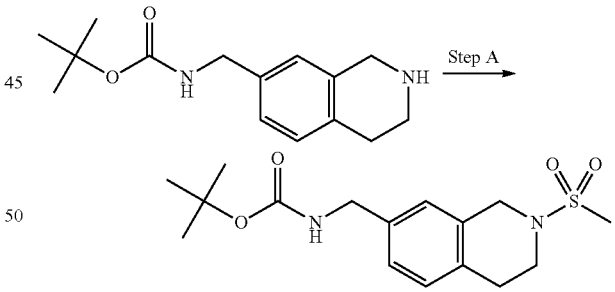

Step A
To a suspension of the title compound from the Preparative Example 96, Step A (100 mg) and N-methylmorpholine (145 μL) in dry CH$_2$Cl$_2$/THF (5:1, 12 mL) was added methanesulfonyl chloride (88 μL). The mixture was stirred for 2 h, diluted with CH$_2$Cl$_2$, washed subsequently with 10% aqueous citric acid, saturated aqueous NaHCO$_3$ and saturated aqueous NaCl, dried (MgSO$_4$), filtered, concentrated and purified by chromatography (silica, cyclohexane/EtOAc) to afford the title compound as a colorless solid (96.3 mg, 74%). [MNa]$^+$=363.

Preparative Example 101

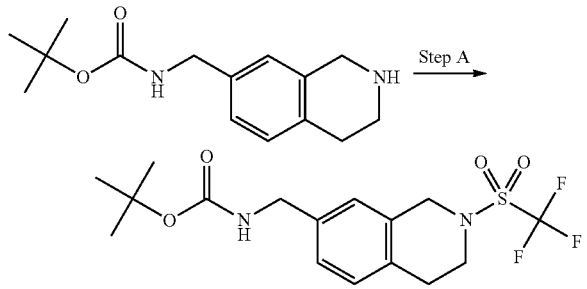

Step A

To a suspension of the title compound from the Preparative Example 96, Step A (84 mg) and $^i$Pr$_2$NEt (70 µL) in dry THF (10 mL) was added trifluoromethanesulfonyl chloride (50 µL) at −20° C. under an argon atmosphere. The cooling bath was removed and the mixture was stirred for 4 h, diluted with EtOAc, washed subsequently with 10% aqueous citric acid, saturated aqueous NaHCO$_3$ and saturated aqueous NaCl, dried (MgSO$_4$), filtered, concentrated and purified by chromatography (silica, cyclohexane/EtOAc) to afford the title compound as colorless crystals (47 mg, 37%). [MNa]$^+$=417.

Preparative Example 102

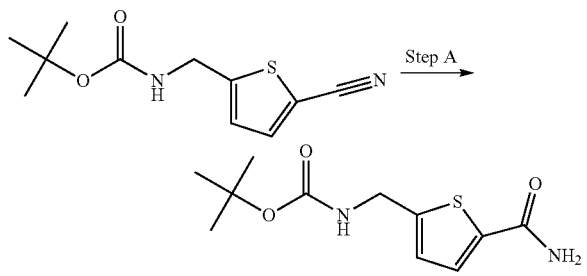

Step A

To a solution of the title compound from the Preparative Example 26 (242 mg) in MeOH/H$_2$O (2:1, 30 mL) was added sodium perborate tetrahydrate (470 mg). The mixture was heated to 50° C. overnight, concentrated, diluted with EtOAc, washed subsequently with 10% aqueous citric acid and saturated aqueous NaCl, dried (MgSO$_4$), filtered and concentrated to give the title compound as colorless crystals (220 mg, 85%). [MNa]$^+$=279.

Preparative Example 103

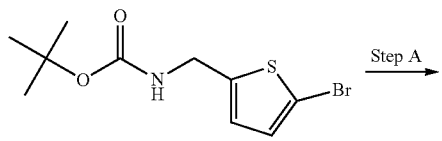

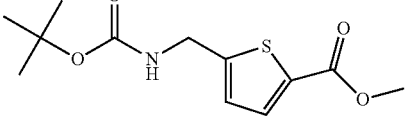

Step A

Commercially available tert-butyl-N-[(5-bromo-2-thienyl)methyl]carbamate (2.0 g), Pd(OAc)$_2$ (76 mg), dppp (282 mg) and NEt$_3$ (2.9 mL) were dissolved in dry DMSO/MeOH (3:1, 60 mL) and stirred at 80° C. under a carbon monoxide atmosphere at 7 bar over the weekend. The mixture was concentrated, diluted with EtOAc, washed subsequently with 1N aqueous HCl, H$_2$O and saturated aqueous NaCl, dried (MgSO$_4$), filtered and concentrated. Purification by chromatography (silica, cyclohexane/EtOAc) afforded the title compound as colorless crystals (1.73 g, 94%). [MNa]$^+$=294.

Preparative Example 104

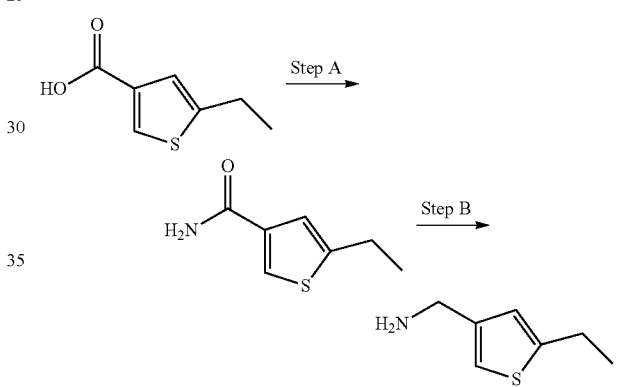

Step A

To an ice cooled solution of commercially available 5-ethyl-thiophene-3-carboxylic acid (3.0 g) in CH$_2$Cl$_2$ (50 mL) were subsequently added oxalyl chloride (2.3 mL) and DMF (0.4 mL). The mixture was stirred at 0° C. for 1 h and then at room temperature for 3 h. The mixture was concentrated, diluted with CH$_2$Cl$_2$ (3 mL) and then slowly added to condensed NH$_3$ (~30 mL) at ~−40° C. The resulting mixture was stirred at ~−30° C. for 1 h, slowly warmed to room temperature over a period of ~10 h and then concentrated to give the title compound as a tan solid (2.0 g, 68%). [MH]$^+$=156.

Step B

A vigorously stirred mixture of the title compound from Step A above (1.0 g) and Bu$_4$NBH4 (4.9 g) in dry CH$_2$Cl$_2$ (30 mL) was heated at 55-62° C. for 24 h and then concentrated. The remaining oil was cooled to 0° C. and 1N aqueous HCl (15 mL) was slowly added over a period of 1 h. Then the mixture was heated to 100° C. for 1 h, cooled to room temperature, washed with Et$_2$O (100 mL), adjusted to pH ~10 with concentrated aqueous KOH and extracted with Et$_2$O (100 mL). The organic extract was dried (MgSO$_4$), filtered and concentrated to give the title compound as an oil (0.25 g, 27%). [MH]$^+$=142.

Preparative Example 105

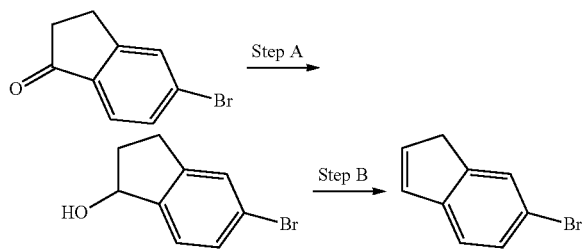

Step A

To an ice cooled mixture of commercially available 5-bromo-1-indanone (29.84 g) in MeOH (300 mL) was added NaBH$_4$ (2.67 g). After 10 min the mixture was allowed to warm to room temperature. The mixture was stirred for 1½ h and then concentrated. The resulting oil was brought up in EtOAc (300 mL), washed with 1N aqueous NaOH (200 mL) and saturated aqueous NaCl (200 mL), dried (MgSO$_4$), filtered and concentrated to give a white solid (30.11 g, >99%). [M-OH]$^+$=195.

Step B

A solution of the title compound from Step A above (9.03 g) and 4-toluenesulfonic acid monohydrate (150 mg) in benzene (300 mL) was heated to reflux for 1 h using a Dean Starks trap. Once cooled the reaction solution was washed with H$_2$O, dried (MgSO$_4$), filtered and concentrated to give a clear oil (7.86 g, 95%). $^1$H-NMR (CDCl$_3$) δ=7.60 (s, 1H), 7.40 (dd, J=8.0, 1.7 Hz, 1H), 7.26 (d, J=8.0 Hz, 1H), 6.83 (dtd, J=5.7, 2.1, 1.1 Hz, 1H), 6.55 (dt, J=5.5, 2.1 Hz, 1H), 3.39 (br s, 2H).

Preparative Example 106

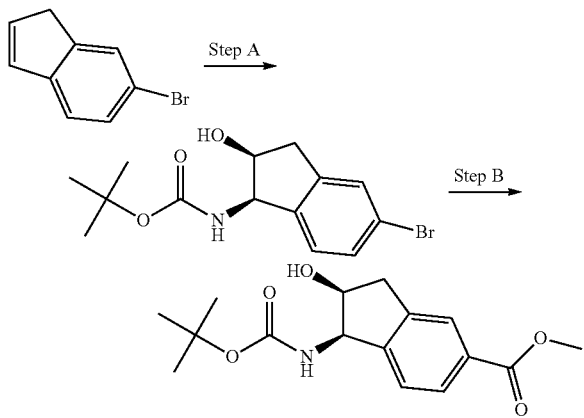

Step A

To an ice cooled vigorously stirred mixture of the title compound from the Preparative Example 105, Step B (9.99 g), (S,S)-(+)-N,N'-bis(3,5-di-tert-butyl-salicylindene)-1,2-cyclohexane-diaminomanganese(III) chloride (390 mg) and 4-phenylpyridine N-oxide (526 mg) in CH$_2$Cl$_2$ (6.2 mL) was added a solution of NaOH (425 mg) in 1.25M aqueous NaClO (53.2 mL) by an addition funnel over 2½ h. After the addition was complete, stirring at 0° C. was continued for another 3 h. Hexanes (30 mL) was added, the resulting biphasic mixture was filtered through Celite® and the filter cake was washed with CH$_2$Cl$_2$ (3×20 mL). The supernatant was placed in a separatory funnel, the aqueous layer was removed and the organic layer was washed with saturated aqueous NaCl, dried (MgSO$_4$), filtered and concentrated. The resulting solid was dissolved in EtOH (100 mL) and a 28% solution of NH$_3$ in H$_2$O (200 mL) was added. The solution was stirred at 110° C. for 30 min, cooled to room temperature and washed with CH$_2$Cl$_2$ (4×200 mL). The combined organic layers were dried (MgSO$_4$), filtered and concentrated to give a dark brown solid (7.50 g). [M-NH$_2$]$^+$=211. This solid was dissolved in CH$_2$Cl$_2$ (150 mL) and NEt$_3$ (5.5 mL) and di-tert-butyl-dicarbonate (7.87 g) were added subsequently. The resulting solution was stirred for 4 h at room temperature, then absorbed on silica and purified by chromatography (silica, hexanes/EtOAc) to give an off-white solid (6.87 g, 41%), [MNa]$^+$=350.

Step B

A solution of the title compound from Step A above (6.87 g), Pd(PPh$_3$)$_4$ (1.20 g) in MeOH (100 mL), DMSO (100 mL) and NEt$_3$ (14 mL) was stirred at 80° C. under an atmosphere of carbon monoxide (1 atm) for 18 h. Once the mixture was cooled to room temperature, it was placed in a separatory funnel and EtOAc (200 mL) and 1N aqueous HCl (200 mL) were added. The layers were separated and the aqueous layer was washed with EtOAc (200 mL). The organic layers were combined, washed with 1N aqueous HCl (200 mL), saturated aqueous NaHCO$_3$ (200 mL) and saturated aqueous NaCl (200 mL), dried (MgSO$_4$), filtered and absorbed on silica. Purification by chromatography (silica, hexanes/EtOAc) afforded an off-white solid (1.45 g, 23%). [MNa]$^+$=330.

Preparative Example 107

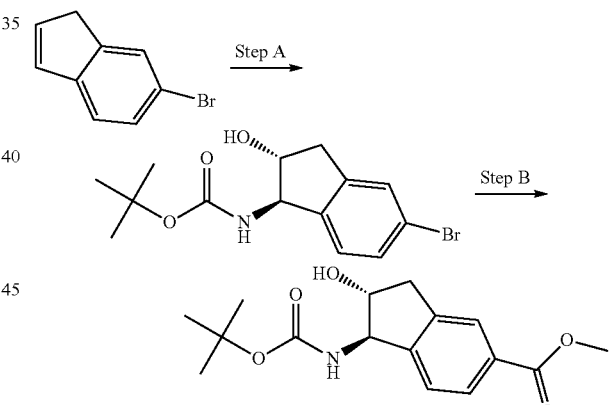

Step A

To an ice cooled vigorously stirred mixture of the title compound from the Preparative Example 105, Step B (3.92 g), (R,R)—(−)—N,N'-bis(3,5-di-tert-butyl-salicylindene)-1,2-cyclohexane-diaminomanganese(III) chloride (76.2 mg) and 4-phenylpyridine N-oxide (103 mg) in CH$_2$Cl$_2$ (2.4 mL) was added a solution of NaOH (122 mg) in 1.25M aqueous NaClO (15.3 mL) by an addition funnel over 2½ h. After the addition was complete, stirring at 0° C. was continued for another 3 h. Hexanes (20 mL) was added, the resulting biphasic mixture was filtered through Celite® and the filter cake was washed with CH$_2$Cl$_2$ (3×20 mL). The supernatant was placed in a separatory funnel, the aqueous layer was removed and the organic layer was washed with saturated aqueous NaCl, dried (MgSO$_4$), filtered and concentrated. The remaining brown solid was suspended in CH$_3$CN (10 mL) at −40° C., trifluoromethane sulfonic acid (1.2 mL) was added and the resulting mixture was stirred at −40° C. for 1½ h. H₂O (20 mL) was added and the mixture was stirred at 110° C. for 5 h, while distilling off the CH₃CN. Once the reaction mixture was cooled to room temperature, the aqueous layer was washed with CH₂Cl₂ (2×50 mL). The organic layers were discarded and the aqueous layer was basified with 3N aqueous NaOH and washed with EtOAc (3×50 mL). The EtOAc phases were combined, dried (MgSO₄), filtered and concentrated. [M-NH₂]⁺=211. The remaining solid residue was dissolved in CH₂Cl₂ (30 mL) and NEt₃ (515 µL) and di-tert-butyl-dicarbonate (707 g) were added subsequently. The resulting solution was stirred for 6 h at room temperature, then absorbed on silica and purified by chromatography (silica, hexanes/EtOAc) to give an off-white solid (774 mg, 12%). [MNa]⁺=350.

Step B

A solution of the title compound from Step A above (774 mg), Pd(PPh₃)₄ (136 mg) in MeOH (10 mL), DMSO (10 mL) and NEt₃ (1.6 mL) was stirred at 80° C. under an atmosphere of carbon monoxide (1 atm) for 18 h. Once the mixture was cooled to room temperature, it was placed in a separatory funnel and EtOAc (30 mL) and 1N aqueous HCl (30 mL) were added. The layers were separated and the aqueous layer was washed with EtOAc (30 mL). The organic layers were combined, washed with 1N aqueous HCl (30 mL), saturated aqueous NaHCO₃ (30 mL) and saturated aqueous NaCl (30 mL), dried (MgSO₄), filtered and absorbed on silica. Purification by chromatography (silica, hexanes/EtOAc) afforded an off-white solid (333 mg, 46%). [MNa]⁺=330.

Preparative Example 108

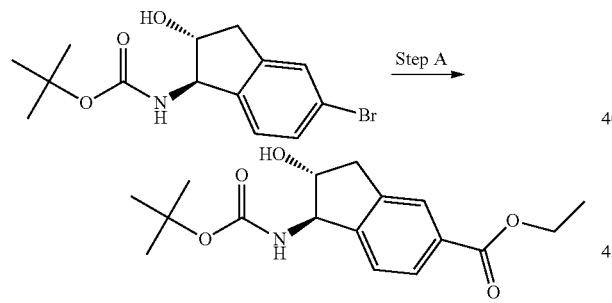

Step A

The title compound from the Preparative Example 107, Step A above (406 mg) was treated similarly as described in the Preparative Example 107, Step B, except using EtOH (10 mL) as the solvent to afford the title compound (353 mg, 89%). [MNa]⁺=344.

Preparative Example 109

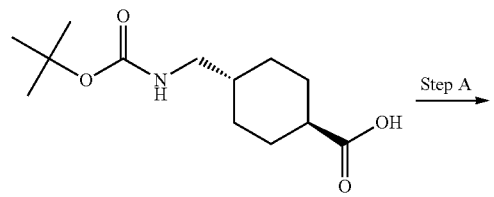

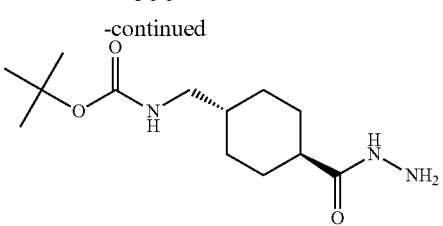

Step A

To a solution of commercially available trans-4-(tert-butoxycarbonylamino-methyl)-cyclohexanecarboxylic acid (262 mg) in dry THF (5 mL) was added 1,1′-carbonyldiimidazole (243 mg). The resulting clear colorless solution was stirred at room temperature for 1 h, then hydrazine monohydrate (219 µL) was added and stirring at room temperature was continued for 17 h. The mixture was concentrated and purified by flash chromatography (silica, CH₂Cl₂/MeOH). The isolated white solid was dissolved in EtOAc (50 mL) and washed with 0.01 M aqueous HCl (2×50 mL) and saturated aqueous NaCl (50 mL). The combined HCl layers were saturated with NaCl and extracted with EtOAc (2×100 mL). The combined EtOAc layers were dried (MgSO₄), filtered and concentrated to afford the title compound (264 mg, 97%). [MNa]⁺=294.

Preparative Example 110

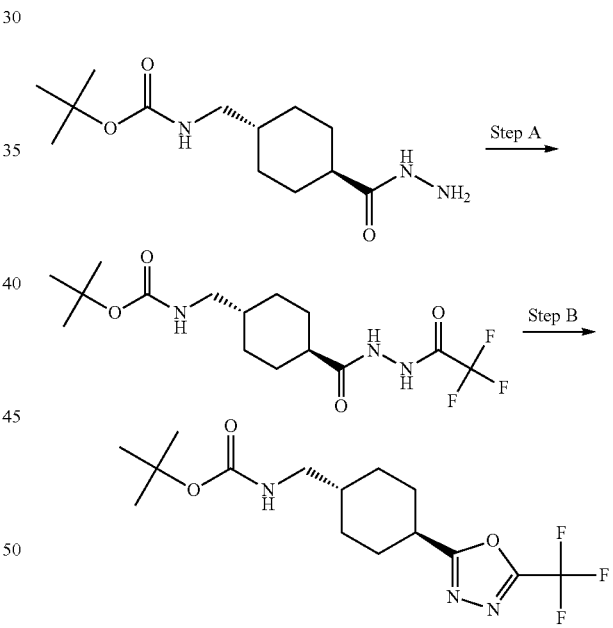

Step A

To a solution of the title compound from the Preparative Example 109, Step A (136 mg) in dry MeOH (12.5 mL) were successively added trifluoroacetic anhydride (104 µL) and ⁱPr₂NEt (130 µL). The resulting reaction mixture was stirred at room temperature for 23 h, concentrated and purified by flash chromatography (silica, CH₂Cl₂/MeOH) to afford the title compound (66 mg, 43%). [MNa]⁺=390.

Step B

To a solution of the title compound from Step A above (66 mg) in dry THF (3.6 mL) was added methyl N-(triethylammoniosulfonyl) carbamate ["Burgess reagent"] (88 mg). The resulting reaction mixture was heated in a sealed tube to 150°

C. (microwave) for 15 min, concentrated and purified by flash chromatography (silica, CH$_2$Cl$_2$/MeOH) to afford the title compound (52 mg, 83%). [MNa]$^+$=372.

Preparative Example 111

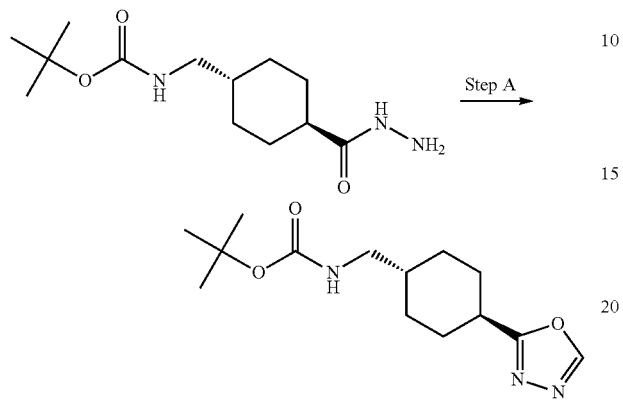

Step A

To a suspension of the title compound from the Preparative Example 109, Step A (54.3 mg) in trimethyl orthoformate (2 mL) was added dry MeOH (200 µL). The resulting clear solution was heated in a sealed tube to 150° C. (microwave) for 24 h, concentrated and purified by flash chromatography (silica, CH$_2$Cl$_2$/MeOH) to afford the title compound (45.6 mg, 81%). [MNa]$^+$=304.

Preparative Example 112

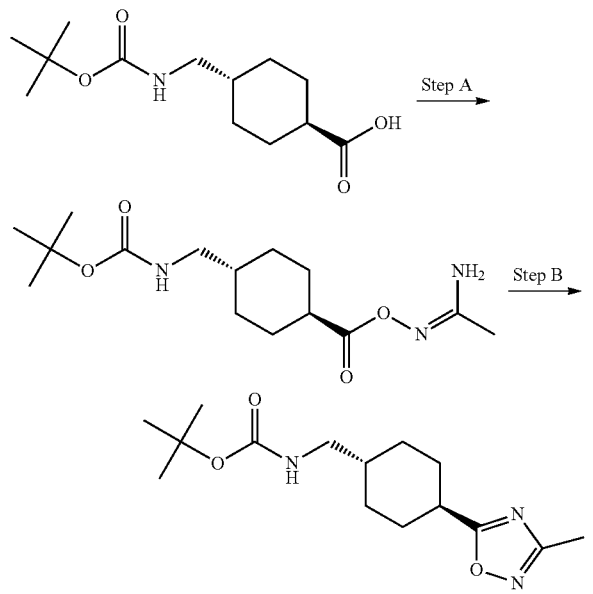

Step A

To a solution of commercially available trans-4-(tert-butoxycarbonylamino-methyl)-cyclohexanecarboxylic acid (262 mg) and N-hydroxyacetamidine (19 mg) in DMF/ CH$_2$Cl$_2$ (9:1, 2 mL) were added N,N'-diisopropylcarbodiimide (33 mg) and HOBt (36 mg). The resulting mixture was stirred at room temperature for 2 h, concentrated, dissolved in EtOAc, washed subsequently with saturated aqueous NaHCO$_3$, 0.5N aqueous HCl and saturated aqueous NaCl, dried (MgSO$_4$), filtered and concentrated to afford the title compound (255 mg, 80%). [MH]$^+$=314.

Step B

To a solution of the title compound from Step A above (55 mg) in EtOH (3 mL) was added a solution of NaOAc (12 mg) in H$_2$O (270 µL). Using a microwave, the mixture was heated in a sealed vial at 120° C. for 50 min. Concentration and purification by chromatography (silica, cyclohexane/EtOAc) afforded the title compound as a colorless oil (24 mg, 46%). [MH]$^+$=296.

Preparative Example 113

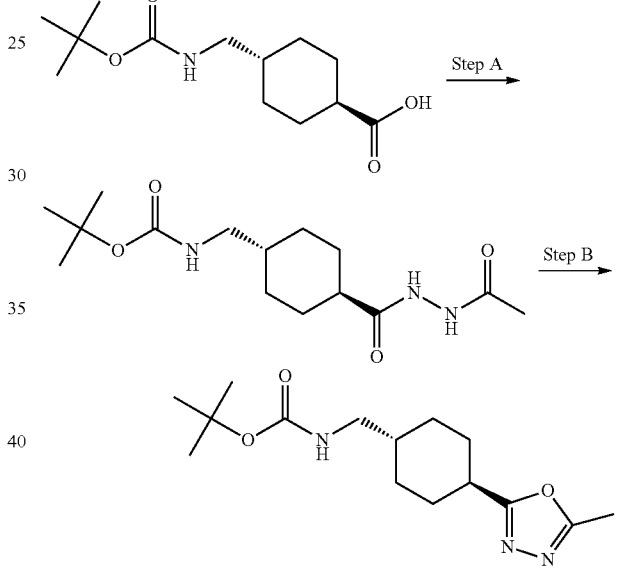

Step A

To a solution of commercially available trans-4-(tert-butoxycarbonylamino-methyl)-cyclohexanecarboxylic acid (520 mg) and acetic acid hydrazide (178 mg) in DMF (10 mL) were added N,N'-diisopropylcarbodiimide (303 mg) and HOBt (326 mg). The resulting mixture was stirred at room temperature for 2 h, concentrated, dissolved in EtOAc, washed with saturated aqueous NaHCO$_3$ and saturated aqueous NaCl, dried (MgSO$_4$), filtered, concentrated and purified by chromatography (silica, CH$_2$Cl$_2$/MeOH) to afford the title compound (400 mg, 64%). [MH]$^+$=314.

Step B

To a solution of the title compound from Step A above (216 mg) in dry THF (10 mL) was added methyl N-(triethylammoniosulfonyl) carbamate ["Burgess reagent"] (300 mg). Using a microwave, the mixture was heated in a sealed vial at 150° C. for 15 min. Concentration and purification by chromatography (silica, CH$_2$Cl$_2$/MeOH) afforded the title compound as a colorless oil (143 mg, 70%). [MH]$^+$=296.

Preparative Example 114

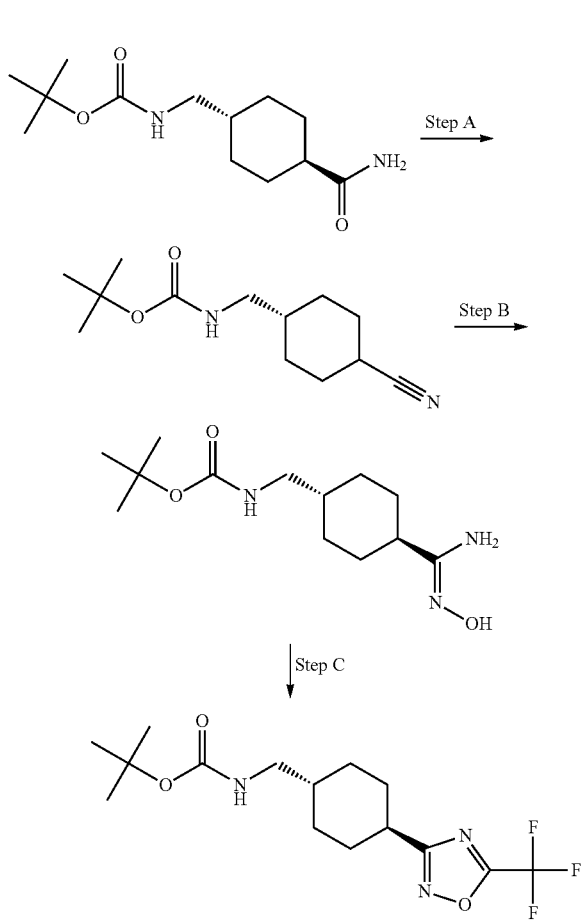

Step A

To a suspension of the title compound from the Preparative Example 44, Step A (552 mg) in dry THF (11 mL) was added methyl N-(triethylammoniosulfonyl) carbamate ["Burgess reagent"] (375 mg). The mixture was stirred at room temperature for 30 min, concentrated and purified by chromatography (silica, CH$_2$Cl$_2$/MeOH) to afford the title compound as a colorless solid (160 mg, 31%). [MH]$^+$=239.

Step B

To a solution of hydroxyl amine hydrochloride in dry MeOH (1 mL) were successively added a 30 wt % solution of NaOMe in MeOH (250 µL) and a solution of the title compound from Step A above (160 mg) in dry MeOH (3 mL). The mixture was heated to reflux for 24 h and then concentrated to afford the crude title compound, which was used without further purification (170 mg, 93%). [MH]$^+$=272.

Step C

To a solution of the title compound from Step B above (170 mg) in toluene (5 mL) were successively added $^i$Pr$_2$NEt (132 µL) and trifluoroacetic anhydride (280 µL). The mixture was heated to reflux for 2½ h, concentrated, dissolved in EtOAc, washed with saturated aqueous NaHCO$_3$ and saturated aqueous NaCl, dried (MgSO$_4$), filtered, concentrated and purified by chromatography (silica, cyclohexane/EtOAc) to afford the title compound (46 mg, 20%). [MH]$^+$=350.

Preparative Example 115

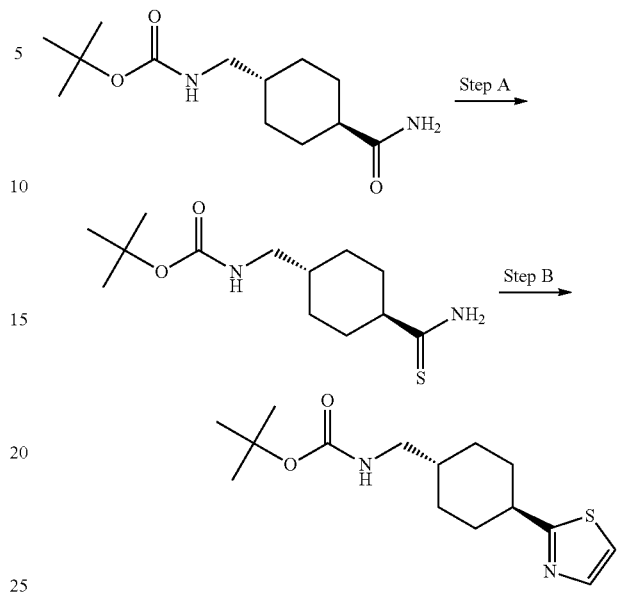

Step A

To a suspension of the title compound from the Preparative Example 44, Step A (266 mg) in THF (5 mL) was added 2,4-bis-(4-methoxyphenyl)-1,3-dithia-2,4-diphosphetane 2,4-disulfide ["Lawesson reagent"] (311 mg). The mixture was stirred at room temperature for 1 h, concentrated and purified by chromatography (silica, CH$_2$Cl$_2$/MeOH) to afford the title compound as a pale yellow solid (190 mg, 67%). [MH]$^+$=273.

Step B

To a solution of the title compound from Step A above (190 mg) in DMF (5 mL) were added a 4M solution of HCl in 1,4-dioxane (6 µL) and 2-bromo-1,1-diethoxy-ethane (323 µL). Using a microwave, the mixture was heated in a sealed vial at 100° C. for 25 min. The mixture was concentrated, dissolved in EtOAc, washed with saturated aqueous NaHCO$_3$ and saturated aqueous NaCl, dried (MgSO$_4$), filtered, concentrated and purified by chromatography (silica, cyclohexane/EtOAc) to afford the title compound (50 mg, 24%). [MH]$^+$=297.

Preparative Example 116

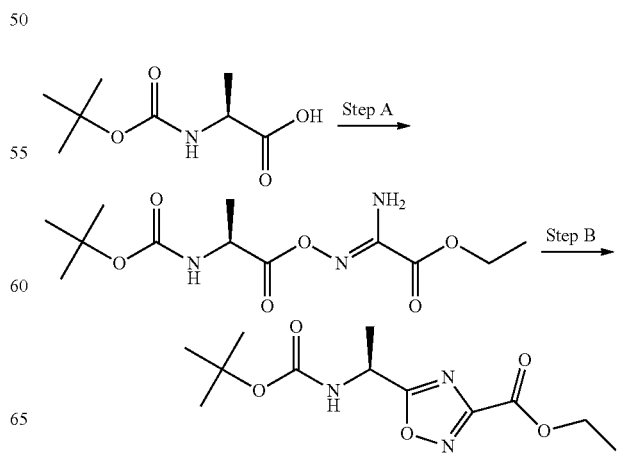

Step A

To a solution of commercially available N-(tert-butoxycarbonyl) alanine (227 mg) in DMF (3 mL) were successively added ethyl 2-oximinooxamate (158 mg) and HATU (684 mg). The mixture was stirred at room temperature for 2 h, concentrated, dissolved in EtOAc, washed with saturated aqueous NaHCO$_3$, 1N aqueous HCl and saturated aqueous NaCl, dried (MgSO$_4$), filtered and concentrated to afford the title compound as a colorless solid (163 mg, 45%). [MH]$^+$= 304.

Step B

To a solution of the title compound from Step A above (163 mg) in EtOH (15 mL) was added a solution of NaOAc (78 mg) in H$_2$O (1 mL). Using a microwave, the mixture was heated in a sealed vial at 120° C. for 50 min. Concentration and purification by chromatography (silica, cyclohexane/EtOAc) afforded the title compound as a colorless oil (46 mg, 30%). NM$^+$=286.

Preparative Example 117

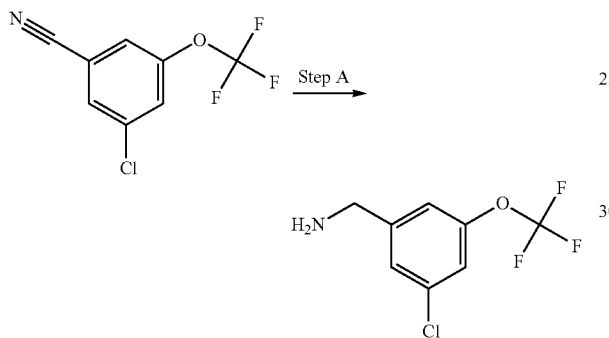

Step A

A mixture of commercially available 3-chloro-5-trifluoromethoxy-benzonitrile (263 mg) and Bu$_4$NBH$_4$ in CH$_2$Cl$_2$ (2 mL) was heated to reflux for 12 h. The reaction was quenched with 1M aqueous NaOH, extracted with CH$_2$Cl$_2$, dried (MgSO$_4$), filtered and concentrated to afford the title compound. [MH]$^+$=226.

Preparative Example 118

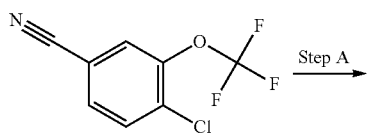

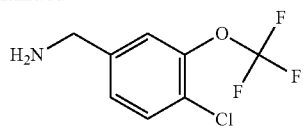

Step A

Commercially available 4-chloro-3-trifluoromethoxy-benzonitrile (227 mg) was treated similarly as described in the Preparative Example 117, Step A to afford the title compound. [MH]$^+$=226.

Preparative Example 119

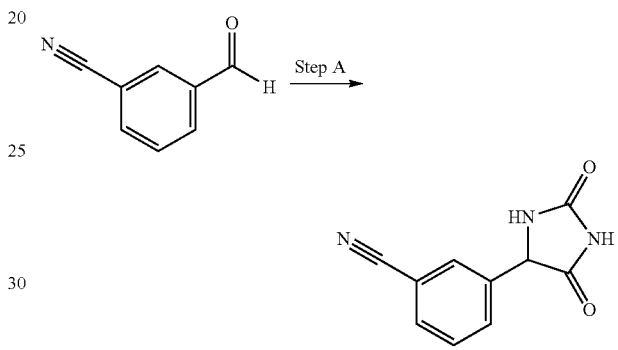

Step A

A mixture of commercially available 3-cyanobenzaldehyde (263 mg), KCN (130 mg) and (NH$_4$)$_2$CO$_3$ (769 mg) in EtOH/H$_2$O (1:1, 12 mL) was heated to 55° C. overnight, cooled, filtered and concentrated. The remaining aqueous mixture was extracted with Et$_2$O (3×10 mL). The combined organic phases were washed with saturated aqueous NaCl, dried (MgSO$_4$), filtered, concentrated and purified by chromatography (silica, hexanes/EtOAc) to give the title compound as a colorless solid (347 mg, 86%). [MH]$^+$=202.

Preparative Examples 120-121

Following a similar procedure as described in the Preparative Example 119, except using the nitriles indicated in Table I-5 below, the following compounds were prepared.

TABLE I-5

| Prep. Ex. # | protected amine | product | yield |
|---|---|---|---|
| 120 | 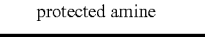 | 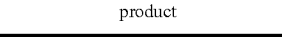 | 90% [MH]$^+$ = 202 |

TABLE I-5-continued

| Prep. Ex. # | protected amine | product | yield |
|---|---|---|---|
| 121 | 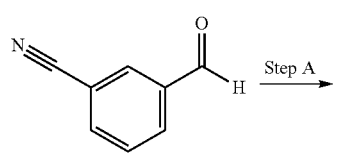 | 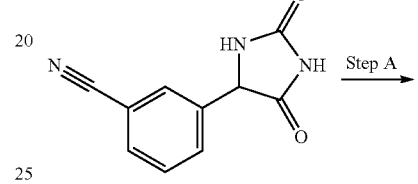 | n.d. [MH]$^+$ = 216 |

Preparative Example 122

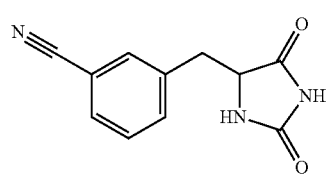 [SMILES: N#Cc1cccc(CC2NC(=O)NC2=O)c1]

Step A
A mixture of commercially available 3-cyanobenzaldehyde (262 mg), hydantoin (220 mg) and KOAc (380 mg) in AcOH (2 mL) was heated to reflux for 3 h and then poured on ice (20 g). The colorless precipitate was collected by filtration, washed with ice water and dried to give the title compound as a yellow solid. [MH]$^+$=216.

Preparative Example 123

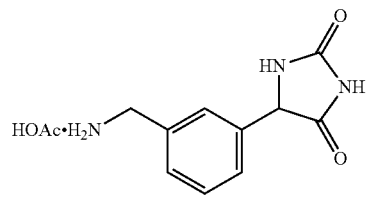

Step A
A mixture of the title compound from the Preparative Example 119, Step A above (347 mg), 50% aqueous AcOH (2 mL) and Pd/C (10 wt %, 200 mg) in EtOH was hydrogenated at 50 psi overnight, filtered and concentrated to give the title compound as colorless solid (458 mg, >99%). [M-OAc]$^+$= 206.

Preparative Examples 124-126

Following a similar procedure as described in the Preparative Example 123, except using the nitriles indicated in Table I-6 below, the following compounds were prepared.

TABLE I-6

| Prep. Ex. # | protected amine | product | yield |
|---|---|---|---|
| 124 | | | 50% (over 2 steps) [M-OAc]$^+$ = 220 |
| 125 | | | n.d. [M-OAc]$^+$ = 220 |

TABLE I-6-continued

| Prep. Ex. # | protected amine | product | yield |
|---|---|---|---|
| 126 | | | 76%<br>[M-OAc]⁺ = 206 |

(See original for structures in table)

Preparative Example 127

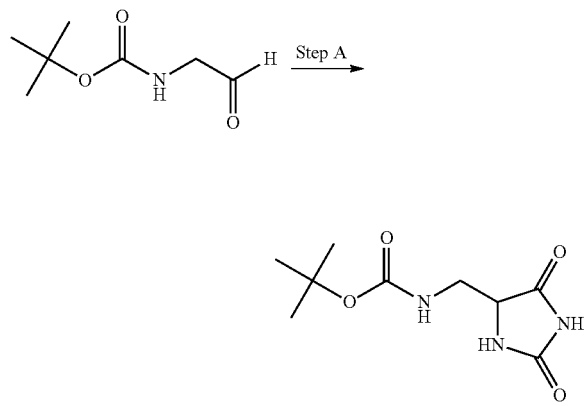

Step A

To the solution of commercially available 2-N-(tert-butoxycarbonylamino)acetaldehyde (250 mg) in MeOH/H₂O (1:1, 10 mL) were added KCN (130 mg) and (NH₄)₂CO₃ (650 mg). The mixture was stirred at 55° C. overnight, then cooled to room temperature, acidified (pH 2) with 3N aqueous HCl and extracted with EtOAc (2×10 mL). The combined organic layers were washed with saturated aqueous NaCl, dried (MgSO₄) and concentrated to give a white solid (75 mg, 21%). [MH]⁺=230.

Preparative Example 128

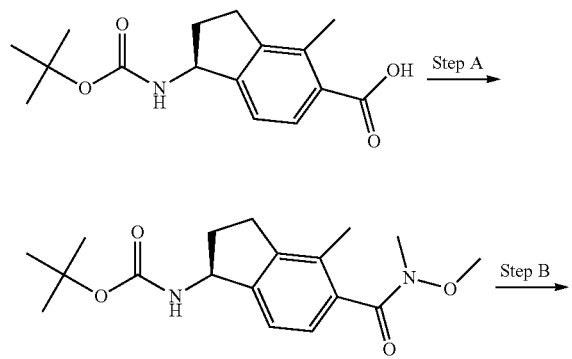

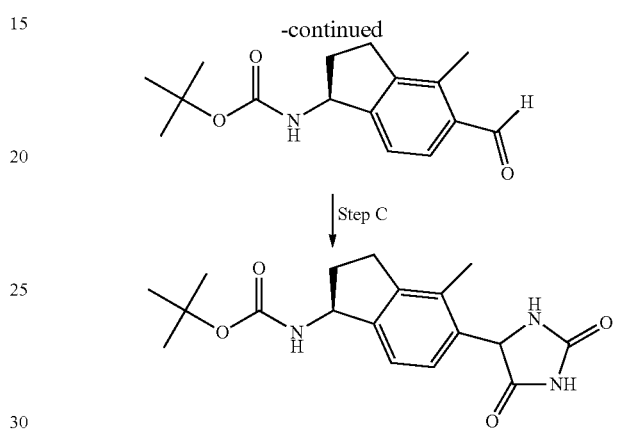

Step A

To a solution of the title compound from the Preparative Example 7, Step B (100 mg), N-methyl-N-methoxyamine hydrochloride (42.2 mg) in CH₂Cl₂ (3 mL) and DMF (1 mL) were added EDCI (84.3 mg), HOBt (58 mg) and NaHCO₃ (121 mg). The mixture was stirred at room temperature overnight, washed with saturated aqueous Na₂CO₃ (5 mL) and 1N aqueous HCl (5 mL) and concentrated to give the desired product, which was used without further purification (97 mg, 84%). [MH]⁺=321.

Step B

To the title compound from Step A above (256 mg) in anhydrous Et₂O (10 mL) was added a 1M solution of LiAlH₄ in Et₂O (4 mL). The mixture was stirred for 20 min and then cooled to 0° C. 1M aqueous NaOH (5 mL) was added dropwise, followed by the addition of Et₂O (10 mL). The organic phase was separated and the aqueous phase was extracted with Et₂O (2×5 mL). The combined organic layers were washed with saturated aqueous NaCl (5 mL), dried (MgSO₄), concentrated and purified by chromatography (silica, hexanes/EtOAc) to give a white solid (178 mg, 85%). [MH]⁺= 262.

Step C

To the title compound from Step B above (178 mg) in MeOH/H₂O (1:1, 10 mL) were added KCN (67 mg) and (NH₄)₂CO₃ (262 mg). The mixture was stirred at 55° C. overnight, then cooled to room temperature, acidified (pH 2) with 3N aqueous HCl and extracted with EtOAc (2×10 mL). The combined organic layers were washed with saturated aqueous NaCl, dried (MgSO₄) and concentrated to give a white solid (170 mg, 73%). [MH]⁺=346.

Preparative Example 129

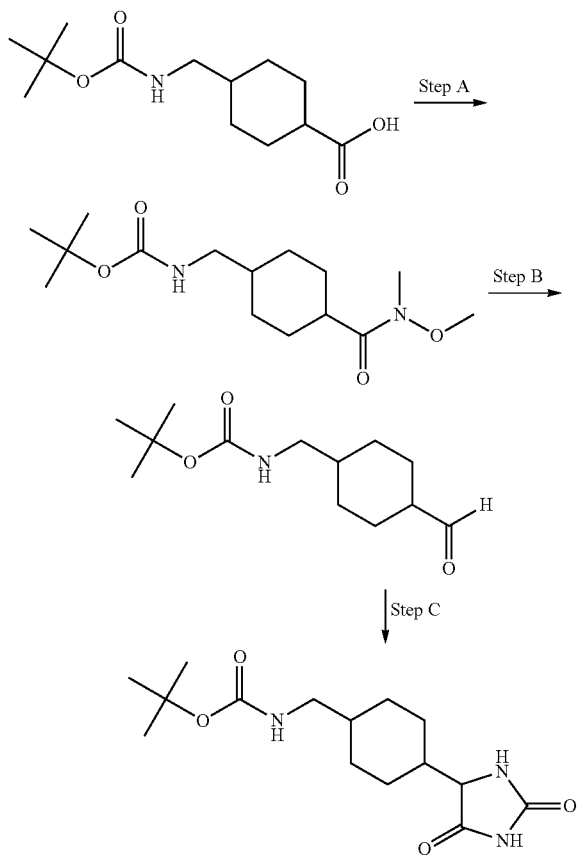

Step A

To the solution of commercially available 4-(tert-butoxycarbonylamino-methyl)-cyclohexanecarboxylic acid (515 mg), N-methyl-N-methoxyamine hydrochloride (390 mg) in CH$_2$Cl$_2$ (20 mL) were added PyBOP (1.04 g) and NEt$_3$ (0.84 mL). The mixture was stirred for 2 h at room temperature, washed with saturated aqueous Na$_2$CO$_3$ (5 mL) and 1N aqueous HCl (5 mL), concentrated and purified by chromatography (silica, hexanes/EtOAc) to give a white solid (544 mg, 91%). [MH]$^+$=323.

Step B

To the title compound from Step A above (544 mg) in anhydrous Et$_2$O (10 mL) was added a 1M solution of LiAlH$_4$ in Et$_2$O (1.8 mL). The mixture was stirred for 20 min and then cooled to 0° C. 1M aqueous NaOH (5 mL) was added dropwise, followed by the addition of Et$_2$O (10 mL). The organic phase was separated and the aqueous phase was extracted with Et$_2$O (2×5 mL). The combined organic layers were washed with saturated aqueous NaCl (5 mL), dried (MgSO$_4$), concentrated and purified by chromatography (silica, hexanes/EtOAc) to give a white solid (440 mg, >99%). [MH]$^+$= 242.

Step C

To the title compound from Step B above (440 mg) in MeOH/H$_2$O (1:1, 12 mL) was added were added KCN (178 mg) and (NH$_4$)$_2$CO$_3$ (670 mg). The mixture was stirred at 55° C. overnight, then cooled to room temperature, acidified (pH 2) with 3N aqueous HCl and extracted with EtOAc (2×10 mL). The combined organic layers were washed with saturated aqueous NaCl, dried (MgSO$_4$) and concentrated to give a white solid (454 mg, 81%). [MH]$^+$=312.

Preparative Example 130

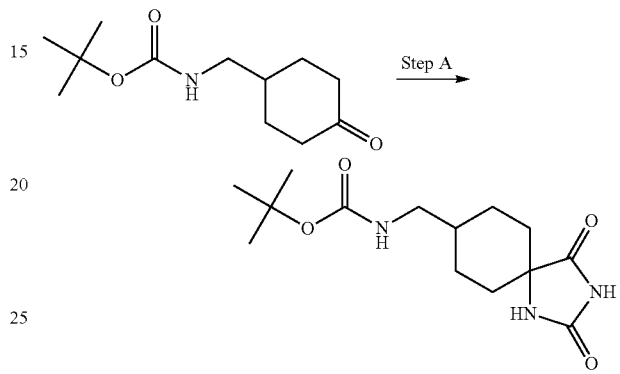

Step A

To a solution of commercially available 4-N-(tert-butoxycarbonylamino-methyl)-cyclohexanone (0.26 g) in EtOH/H$_2$O (1:1, 20 mL) were added NaCN (0.10 g) and (NH$_4$)$_2$CO$_3$ (0.56 g). The resulting mixture was heated to reflux overnight, partially concentrated, diluted with H$_2$O and filtered to give a white solid (0.19 g, 56%). [MNa]$^+$=320.

Preparative Example 131

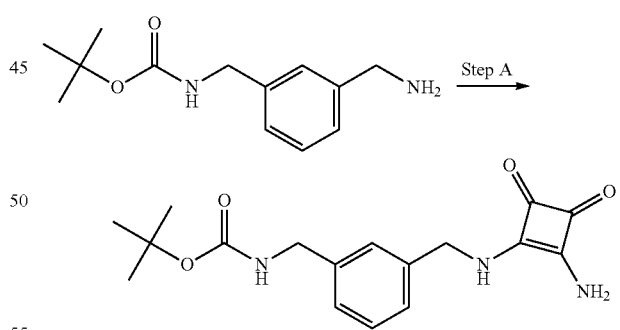

Step A

To a solution of 3,4-diethoxy-3-cyclobutene-1,2-dione (1.3 mL) in EtOH (40 mL) was added commercially available (3-aminomethyl-benzyl)-carbamic acid tert-butyl ester (1.39 g). The mixture was stirred for 2 h, a 28% solution of NH$_3$ in H$_2$O (40 mL) was added and stirring was continued for 2 h. Then the mixture was concentrated and slurried in MeOH (20 mL). The formed precipitate was collected by filtration to give the title compound (1.6 g, 82%). [MNa]$^+$=354.

Preparative Example 132

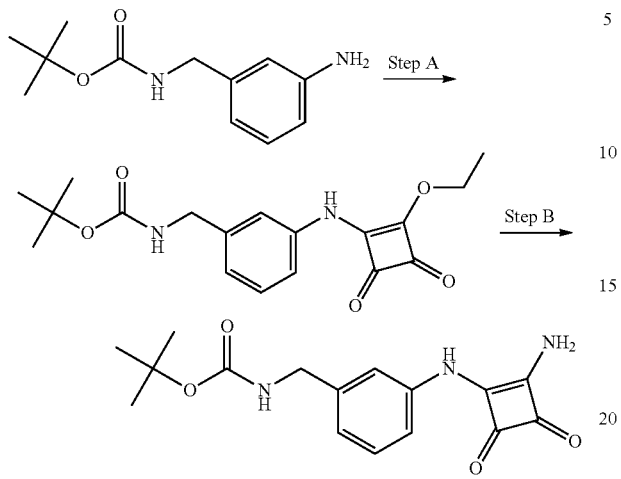

Step A

To a solution of commercially available (3-amino-benzyl)-carbamic acid tert-butyl ester (1.11 g) in EtOH (20 mL) was added 3,4-diethoxy-3-cyclobutene-1,2-dione (1.30 g). The mixture was heated to reflux for 2½ h, cooled to room temperature filtered and concentrated. The remaining solid residue was crystallized from refluxing EtOH to afford the title compound (687 mg, 40%). [MNa]$^+$=369.

Step B

The title compound from Step A above (346 mg) was dissolved in a ~7N solution of NH$_3$ in MeOH (14.3 mL). The reaction mixture was stirred at room temperature for 3 h and then concentrated to afford the title compound (316 mg, >99%). [MNa]$^+$=340.

Preparative Example 133

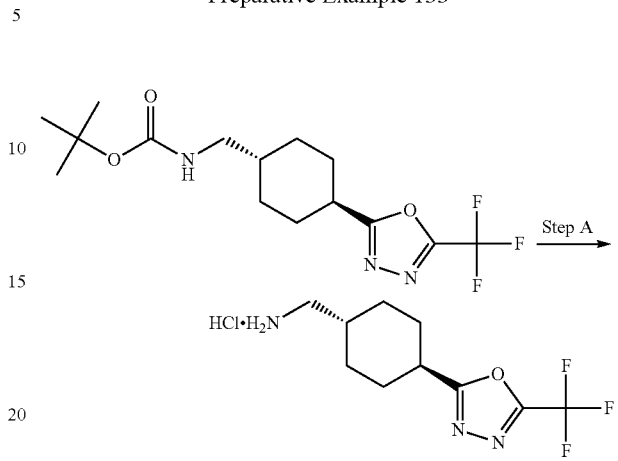

Step A

To a suspension of the title compound from the Preparative Example 110, Step B (52 mg) in EtOAc (600 μL) was added a 4M solution of HCl in 1,4-dioxane (600 μL). The reaction mixture was stirred at room temperature for 1½ h and concentrated to afford the title compound (43 mg, 99%). [M-Cl]$^+$=250.

Preparative Examples 134-207

Following a similar procedure as described in the Preparative Example 133, except using the protected amines indicated in Table I-7 below, the following compounds were prepared.

TABLE I-7

| Prep. Ex. # | protected amine | product | yield |
|---|---|---|---|
| 134 | ![structure] | ![structure] | >99% [M-NH$_3$Cl]$^+$ = 156 |
| 135 | ![structure] | ![structure] | >99% [M-Cl]$^+$ = 159 |
| 136 | ![structure] | ![structure] | 99% [M-Cl]$^+$ = 218 |
| 137 | ![structure] | ![structure] | >99% [M-Cl]$^+$ = 232 |

TABLE I-7-continued

| Prep. Ex. # | protected amine | product | yield |
|---|---|---|---|
| 138 | | | >99% [M-NH₃Cl]⁺ = 215 |
| 139 | | | >99% [M-NH₃Cl]⁺ = 201 |
| 140 | | | >99% [M-Cl]⁺ = 198 |
| 141 | | | 99% [M-Cl]⁺ = 207 |
| 142 | | | 64% [M-Cl]⁺ = 177 |
| 143 | | | >99% [M-Cl]⁺ = 178 |
| 144 | | | >99% [M-NH₃Cl]⁺ = 195/197 |
| 145 | | | 67% (over 2 steps) [M-Cl]⁺ = 187 |
| 146 | | | >99% [M-Cl]⁺ = 192 |

TABLE I-7-continued

| Prep. Ex. # | protected amine | product | yield |
|---|---|---|---|
| 147 | | | n.d. [M-NH₃]⁺ = 210/212 |
| 148 | | | 81% [M-Cl]⁺ = 222 |
| 149 | | | 77% [M-NH₃]⁺ = 253 |
| 150 | | | >99% [M-Cl]⁺ = 143 |
| 151 | | | >99% [M-Cl]⁺ = 238 |
| 152 | | | >99% [M-Cl]⁺ = 191 |
| 153 | | | >99% [M-Cl]⁺ = 205 |
| 154 | | | >99% [M-NH₃]⁺ = 188 |
| 155 | | | >99% [M-Cl]⁺ = 163 |

TABLE I-7-continued

| Prep. Ex. # | protected amine | product | yield |
|---|---|---|---|
| 156 | | | >99% [M-NH₃Cl]⁺ = 159 |
| 157 | | | >99% [M-Cl]⁺ = 241 |
| 158 | | | >99% [M-Cl]⁺ = 295 |
| 159 | | | >99% [M-Cl]⁺ = 242 |
| 160 | | | >99% [M-Cl]⁺ = 191 |
| 161 | | | >99% [M-NH₃Cl]⁺ = 162 |
| 162 | | | >99% [M-NH₃Cl]⁺ = 176 |
| 163 | | | >99% [M-Cl]⁺ = 193 |
| 164 | | | 96% [M-Cl]⁺ = 139 |
| 165 | | | >99% [M-Cl]⁺ = 157 |

TABLE I-7-continued
| Prep. Ex. # | protected amine | product | yield |
|---|---|---|---|
| 166 | 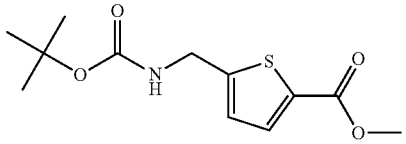 [SMILES: COC(=O)c1ccc(CNC(=O)OC(C)(C)C)s1] | 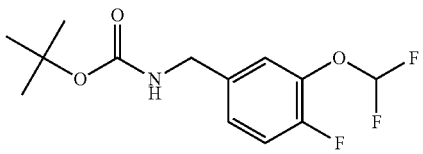 [SMILES: CC(C)(C)OC(=O)NCc1ccc(F)c(OC(F)F)c1] | >99% [M-NH₃Cl]⁺ = 155 |
| 167 | 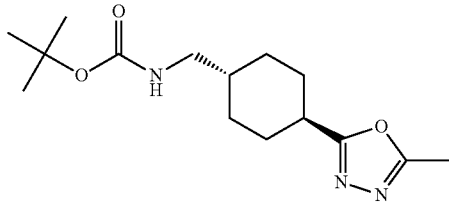 [SMILES: Cc1nnc([C@H]2CC[C@H](CNC(=O)OC(C)(C)C)CC2)o1] | 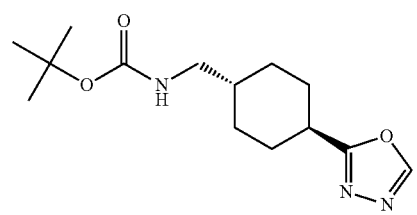 [SMILES: CC(C)(C)OC(=O)NC[C@H]1CC[C@H](c2nnco2)CC1] | >99% [M-Cl]⁺ = 192 |
| 168 | 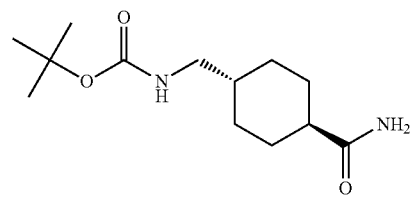 [SMILES: CC(C)(C)OC(=O)NC[C@H]1CC[C@H](C(N)=O)CC1] | 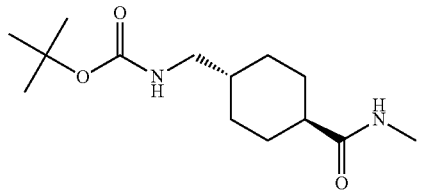 [SMILES: CNC(=O)[C@H]1CC[C@H](CNC(=O)OC(C)(C)C)CC1] | 95% [M-Cl]⁺ = 196 |
| 169 | 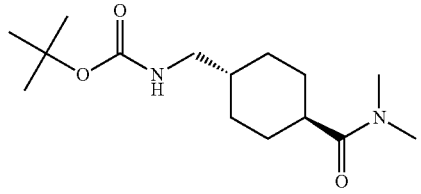 [SMILES: CN(C)C(=O)[C@H]1CC[C@H](CNC(=O)OC(C)(C)C)CC1] | 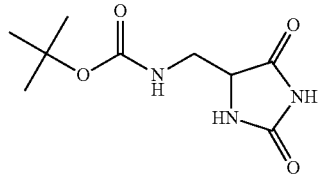 [SMILES: CC(C)(C)OC(=O)NCC1NC(=O)NC1=O] | >99% [M-Cl]⁺ = 182 |
| 170 | | | 99% [M-Cl]⁺ = 157 |
| 171 | | | 99% [M-Cl]⁺ = 171 |
| 172 | | | 98% [M-Cl]⁺ = 185 |
| 173 | | | 93% [M-Cl]⁺ = 130 |

TABLE I-7-continued

| Prep. Ex. # | protected amine | product | yield |
|---|---|---|---|
| 174 | | | >99% [M-Cl]+ = 246 |
| 175 | | | >99% [M-Cl]+ = 212 |
| 176 | | | >99% [M-NH₃Cl]+ = 191 |
| 177 | | | >99% [M-NH₃Cl]+ = 191 |
| 178 | | | >99% [M-Cl]+ = 198 |
| 179 | | | >99% [M-Cl]+ = 197 |
| 180 | | | >99% [M-Cl]+ = 211 |
| 181 | | | >99% [M-Cl]+ = 253 |

TABLE I-7-continued

| Prep. Ex. # | protected amine | product | yield |
|---|---|---|---|
| 182 | | | >99% [M-Cl]⁺ = 223 |
| 183 | | | >99% [M-Cl]⁺ = 183 |
| 184 | | | >99% [M-Cl]⁺ = 165 |
| 185 | | | >99% [M-Cl]⁺ = 170 |
| 186 | | | >99% [M-Cl]⁺ = 261 |
| 187 | | | >99% [M-Cl]⁺ = 353 |
| 188 | | | >99% [M-Cl]⁺ = 184 |
| 189 | | | n.d. [M-Cl]⁺ = 196 |

TABLE I-7-continued

| Prep. Ex. # | protected amine | product | yield |
|---|---|---|---|
| 190 | | | n.d. [M-Cl]⁺ = 250 |
| 191 | | | n.d. [M-Cl]⁺ = 197 |
| 192 | | | n.d. [M-Cl]⁺ = 139 |
| 193 | | | n.d. [M-Cl]⁺ = 286 |
| 194 | | | n.d. [M-Cl]⁺ = 286 |
| 195 | | | >99% [M-HCl₂]⁺ = 204 |
| 196 | | | 94% [M-HCl₂]⁺ = 190 |
| 197 | | | 99% [M-Cl]⁺ = 206 |

TABLE I-7-continued

| Prep. Ex. # | protected amine | product | yield |
|---|---|---|---|
| 198 | | | 99% [M-Cl]⁺ = 220 |
| 199 | | | 99% [M-Cl]⁺ = 134 |
| 200 | | | 99% [M-Cl]⁺ = 205 |
| 201 | | | 92% [M-HCl₂]⁺ = 177 |
| 202 | | | >99% [M-HCl₂]⁺ = 177 |
| 203 | | | 99% [M-Cl]⁺ = 166 |
| 204 | | | 99% [M-Cl]⁺ = 180 |
| 205 | | | 99% [M-Cl]⁺ = 194 |
| 206 | | | 98% [M-Cl]⁺ = 232 |

TABLE I-7-continued

| Prep. Ex. # | protected amine | product | yield |
|---|---|---|---|
| 207 | (structure) | (structure) | >99% [M-NH₃Cl]⁺ = 218 |

Preparative Example 208

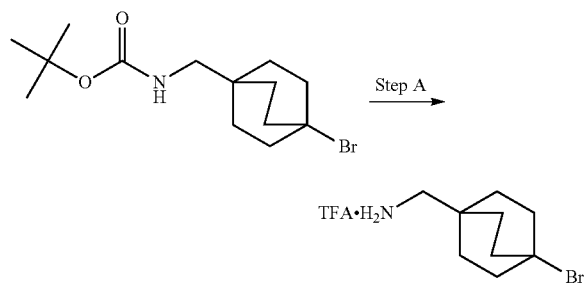

Preparative Example 211

Step A

To a ice cooled solution of the title compound from the Preparative Example 73 (89 mg) in CHCl₃ (3 mL) was added a solution of trifluoroacetic acid (1.5 mL) in CHCl₃ (1.5 mL). The mixture was stirred at 0° C. for 5 min, then the cooling bath was removed and the mixture was stirred at room temperature for 1½ h. The mixture was concentrated, dissolved in CH₃CN (5 mL), again concentrated and dried in vacuo to afford the title compound (93 mg, >99%). [M-TFA]⁺=218/220.

Preparative Examples 209-210

Following a similar procedure as described in the Preparative Example 208, except using the protected amines indicated in Table I-8 below, the following compounds were prepared.

Step A

Commercially available 3-aminomethyl-benzoic acid methyl ester hydrochloride (500 mg) was dissolved in a 33% solution of NH₃ in H₂O (50 mL) and heated in a sealed pressure tube to 90° C. for 20 h. Cooling to room temperature and concentration afforded the title compound (469 mg, >99%). [M-Cl]⁺=151.

Preparative Example 212

TABLE I-8

| Prep. Ex. # | protected amine | product | yield |
|---|---|---|---|
| 209 | (structure) | (structure) | >99% [M-TFA]⁺ = 158 |
| 210 | (structure) | (structure) | 93% [M-(NH₂•TFA)]⁺ = 160 |

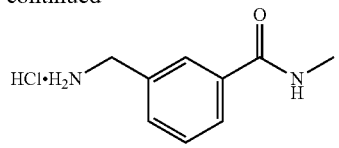

Step A

Commercially available 3-aminomethyl-benzoic acid methyl ester hydrochloride (100 mg) was dissolved in a 40% solution of MeNH$_2$ in H$_2$O (20 mL) and heated in a sealed pressure tube to 90° C. for 20 h. Cooling to room temperature and concentration afforded the title compound (107 mg, >99%). [M-Cl]$^+$=165.

Preparative Example 213

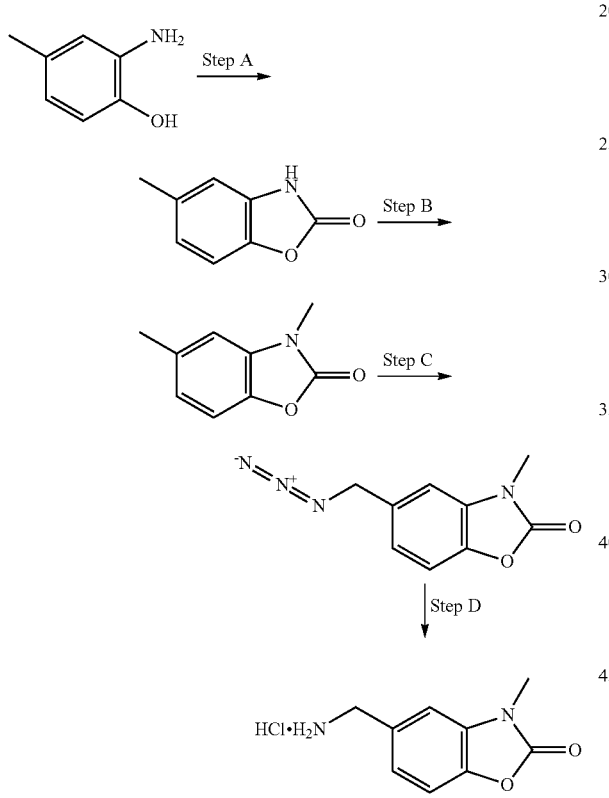

Step A

A mixture of commercially available 2-hydroxy-5-methylaniline (5.2 g) and N,N'-carbonyldiimidazole (6.85 g) in dry THF (60 mL) was heated to reflux for 6 h, cooled to room temperature, poured on ice and adjusted to pH 4 with 6N aqueous HCl. The formed precipitate was isolated by filtration, dried and recrystallized from toluene to afford the title compound as a grey solid (4.09 g, 65%).

Step B

The title compound from Step A above (1.5 g), K$_2$CO$_3$ (1.7 g) and methyl iodide (6 mL) were dissolved in dry DMF (15 mL). The mixture was stirred at 50° C. for 2 h, concentrated and acidified to pH 4 with 1N HCl. The precipitate was isolated by filtration and dried to afford the title compound as an off-white solid (1.48 g, 90%). $^1$H-NMR (CDCl$_3$) δ=7.05 (s, 1H), 6.90 (d, 1H), 6.77 (s, 1H), 3.38 (s, 3H), 2.40 (s, 3H).

Step C

The title compound from Step B above (1.1 g), N-bromosuccinimide (1.45 g) and α,α'-azoisobutyronitrile (150 mg) were suspended in CCl$_4$ (50 mL), degassed with argon and heated to reflux for 1 h. The mixture was cooled, filtered, concentrated and dissolved in dry DMF (20 mL). Then NaN$_3$ (1 g) was added and the mixture was vigorously stirred for 3 h, diluted with EtOAc, washed subsequently with H$_2$O and saturated aqueous NaCl, dried (MgSO$_4$), filtered, concentrated and purified by chromatography (silica, cyclohexane/EtOAc) to afford the title compound as colorless needles (963 mg, 70%). $^1$H-NMR (CDCl$_3$) δ=7.07 (s, 1H), 6.98 (d, 1H), 6.88 (s, 1H), 4.25 (s, 2H), 3.36 (s, 3H).

Step D

A mixture of he title compound from Step C above (963 mg) and PPh$_3$ (1.36 g) in THF (30 mL) were stirred for 14 h, then H$_2$O was added and stirring was continued for 2 h. The mixture was concentrated and coevaporated twice with toluene. The remaining residue was diluted with dry dioxane and a 4M solution of HCl in 1,4-dioxane (1.5 mL) was added. The formed precipitate was isolated by filtration and dried to afford the title compound as a colorless solid (529 mg, 52%). [M-Cl]$^+$=179.

Preparative Example 214

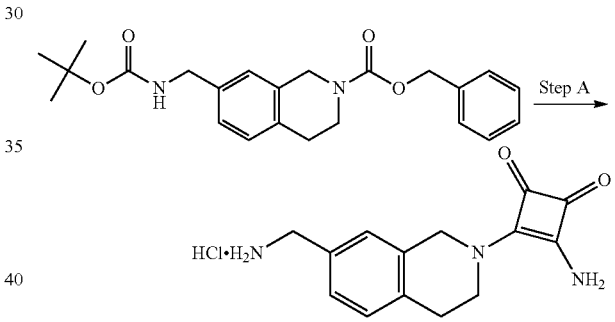

Step A

A mixture of the title compound from the Preparative Example 95, Step A (1.81 g) and Pd/C (10 wt %, 200 mg) in EtOH (50 mL) was hydrogenated at atmospheric pressure overnight, filtered and concentrated to a volume of ~20 mL. 3,4-Diethoxy-3-cyclobutene-1,2-dione (0.68 mL) and NEt$_3$ (0.5 mL) were added and the mixture was heated to reflux for 4 h. Concentration and purification by chromatography (silica, cyclohexane/EtOAc) afforded a slowly crystallizing colorless oil. This oil was dissolved in EtOH (20 mL) and a 28% solution of NH$_3$ in H$_2$O (100 mL) was added. The mixture was stirred for 3 h, concentrated, slurried in H$_2$O, filtered and dried under reduced pressure. The remaining residue was dissolved in a 4M solution of HCl in 1,4-dioxane (20 mL), stirred for 14 h, concentrated, suspended in Et$_2$O, filtered and dried to afford the title compound as an off-white solid (1.08 g, 92%). [M-Cl]$^+$=258.

Preparative Examples 215-216

Following a similar procedure as described in the Preparative Example 214, except using the intermediates indicated in Table I-9 below, the following compounds were prepared.

TABLE I-9

| Ex. # | intermediate | product | yield |
|---|---|---|---|
| 215 | | | n.d. [M-Cl]⁺ = 250 |
| 216 | | | 67% [M-NH₃Cl]⁺ = 236 |

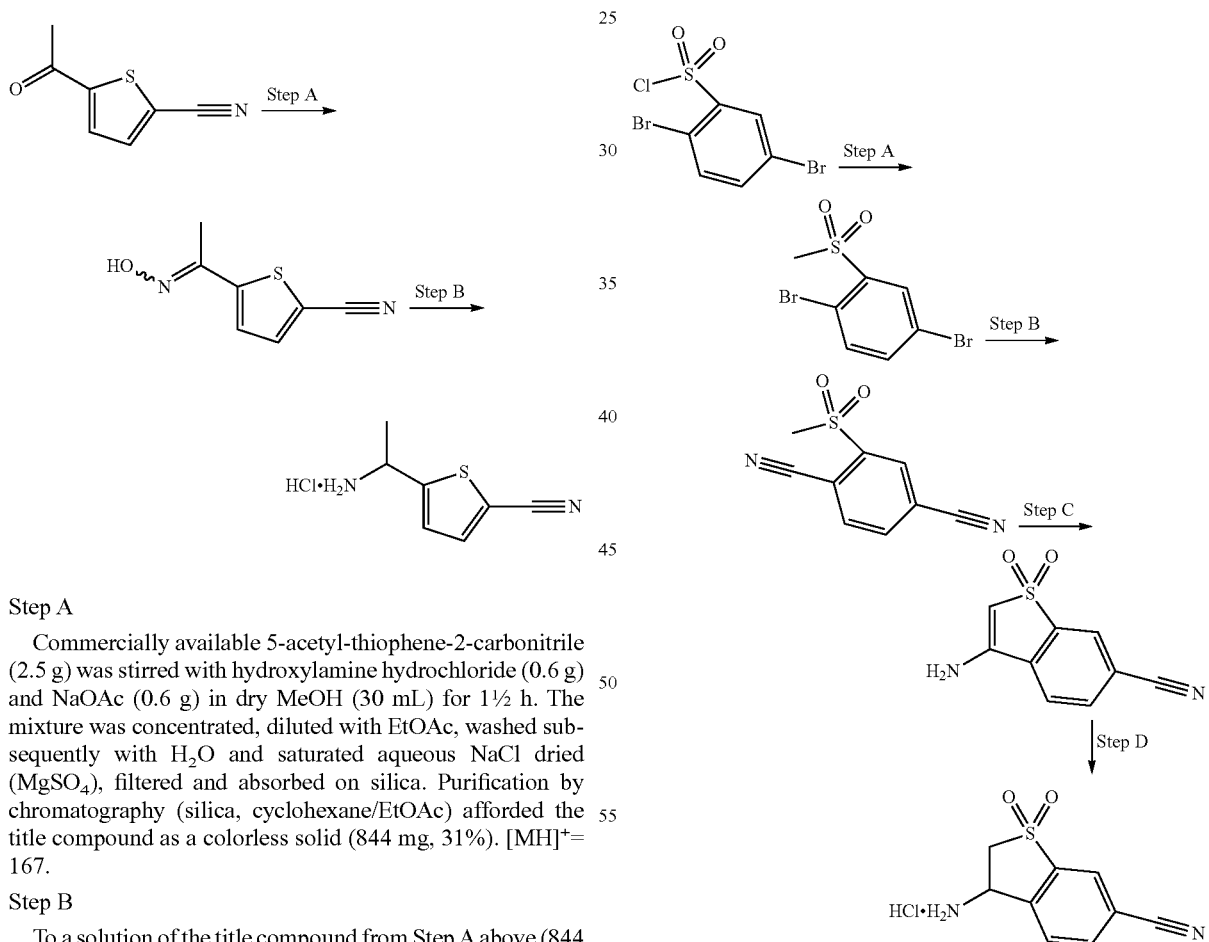

Preparative Example 217

Preparative Example 218

Step A

Commercially available 5-acetyl-thiophene-2-carbonitrile (2.5 g) was stirred with hydroxylamine hydrochloride (0.6 g) and NaOAc (0.6 g) in dry MeOH (30 mL) for 1½ h. The mixture was concentrated, diluted with EtOAc, washed subsequently with $H_2O$ and saturated aqueous NaCl dried ($MgSO_4$), filtered and absorbed on silica. Purification by chromatography (silica, cyclohexane/EtOAc) afforded the title compound as a colorless solid (844 mg, 31%). [MH]⁺= 167.

Step B

To a solution of the title compound from Step A above (844 mg) in AcOH (30 mL) was added zinc dust (1.7 g). The mixture was stirred for 5 h, filtered, concentrated, diluted with $CHCl_3$, washed with saturated aqueous $NaHCO_3$, dried ($MgSO_4$) and filtered. Treatment with a 4M solution of HCl in 1,4-dioxane (2 mL) and concentration afforded the title compound as an off-white solid (617 mg, 64%). [M-NH₃Cl]⁺= 136.

Step A

A suspension of commercially available 2,5-dibromobenzenesulfonyl chloride (1.0 g), $Na_2SO_3$ (0.46 g) and NaOH (0.27 g) in $H_2O$ (10 mL) was heated to 70° C. for 5 h. To the cooled solution was added methyl iodide (4 mL) and MeOH.

The biphasic system was stirred vigorously at 50° C. overnight, concentrated and suspended in H₂O. Filtration afforded the title compound as colorless needles (933 mg, 99%). [MH]⁺=313/315/317.

Step B

Under an argon atmosphere in a sealed tube was heated a mixture of the title compound from Step A above (8.36 g) and CuCN (7.7 g) in degassed N-methylpyrrolidone (30 mL) to 160° C. overnight. Concentration, absorbtion on silica and purification by chromatography (silica, cyclohexane/EtOAc) afforded the title compound as beige crystals (1.08 g, 20%).

Step C

A mixture of the title compound from Step B above (980 mg) and 1,8-diazabicyclo-[5.4.0]undec-7-ene (0.72 mL) in degassed DMSO was heated to 50° C. for 45 min under an argon atmosphere. The solution was diluted with EtOAc, washed subsequently with 10% aqueous citric acid and saturated aqueous NaCl, dried (MgSO₄), concentrated and purified by chromatography (silica, cyclohexane/EtOAc) to afford the title compound as a bright yellow solid (694 mg, 71%). ¹H-NMR (CD₃CN) δ=8.00-8.10 (m, 2H), 7.72 (d, 1H), 5.75 (br s, 2H), 5.70 (s, 1H).

Step D

A mixture of the title compound from Step C above (892 mg) and Pd/C (10 wt %, 140 mg) in DMF (10 mL) was hydrogenated at atmospheric pressure for 2 h and then filtered. Di-tert-butyl dicarbonate (440 mg) was added and the mixture was stirred overnight. The mixture was concentrated, diluted with EtOAc, washed subsequently with 10% aqueous citric acid and saturated aqueous NaCl, dried (MgSO₄), and concentrated. Purification by chromatography (silica, cyclohexane/EtOAc) afforded a colorless solid, which was stirred in a 4M solution of HCl in 1,4-dioxane (20 mL) overnight and then concentrated to give the title compound as colorless crystals (69 mg, 8%). [M-Cl]⁺=209.

Preparative Example 219

Step A

A solution of commercially available 4-bromobenzoic acid (24 g) in chlorosulfonic acid (50 mL) was stirred at room temperature for 2 h and then heated to 150° C. for 3 h. The mixture was cooled to room temperature and poured on ice (600 mL). The formed precipitate was collected by filtration and washed with H₂O. To the obtained solid material were added H₂O (300 mL), Na₂SO₃ (20 g) and NaOH (17 g) and the resulting mixture was stirred at 80° C. for 5 h. Then the mixture was cooled to room temperature and diluted with MeOH (250 mL). Iodomethane (100 mL) was slowly added and the mixture was heated to reflux overnight. Concentration, acidification, cooling and filtration afforded the title compound as a white powder (28.0 g, 84%). [MH]⁺=279/281.

Step B

To a solution of the title compound from Step A above (5.0 g) in dry MeOH (120 mL) was slowly added SOCl₂ (4 mL). The resulting mixture was heated to reflux for 4 h, concentrated and diluted with NMP (20 mL). CuCN (1.78 g) was added and the resulting mixture was heated in a sealed tube under an argon atmosphere to 160° C. overnight. The mixture was concentrated, absorbed on silica and purified by chromatography (silica, cyclohexane/EtOAc) to afford the title compound as colorless needles (976 mg, 23%). [MH]⁺=240.

Step C

To a solution of the title compound from Step B above (1.89 g) in MeOH (40 mL) and was added NaOMe (1.3 g). The mixture was heated to reflux for 90 min, cooled to room temperature, diluted with concentrated HCl (2 mL) and H₂O (10 mL) and heated again to reflux for 30 min. The mixture was concentrated, diluted with EtOAc, washed with saturated aqueous NaCl, concentrated and purified by chromatography (silica, cyclohexane/EtOAc) to afford the title compound as colorless crystals (682 mg, 36%). [MH]⁺=241.

Step D

A solution the title compound from Step C above (286 mg), NaOAc (490 mg) and hydroxylamine hydrochloride (490 mg) in dry MeOH (20 mL) was heated to reflux for 2% h. The

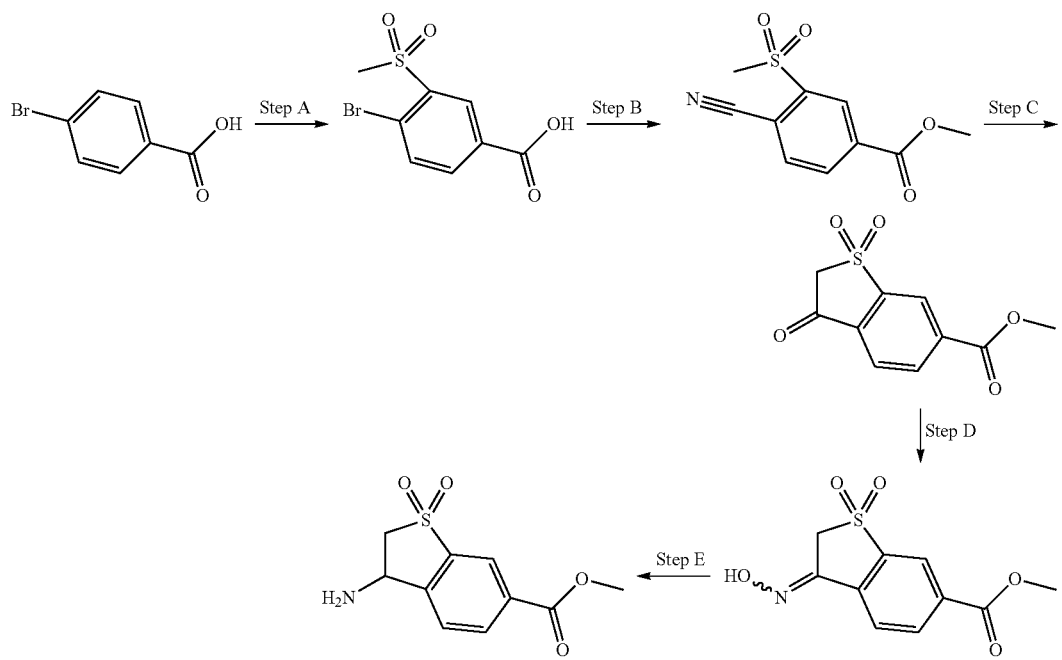

mixture was concentrated, dissolved in EtOAc, washed with saturated aqueous NaCl and concentrated to afford the title compound as an off-white solid (302 mg, 99%). $^1$H-NMR (DMSO): δ=12.62 (s, 1H), 8.25-8.28 (m, 2H), 8.04 (d, 1H), 4.57 (s, 2H), 3.90 (s, 3H).

Step E

The title compound from Step D above (170 mg) was dissolved in MeOH (50 mL) and heated to 60° C. Then zinc dust (500 mg) and 6N aqueous HCl (5 mL) were added in portions over a period of 30 min. The mixture was cooled, filtered, concentrated, diluted with EtOAc, washed subsequently with a saturated aqueous NaHCO$_3$ and saturated aqueous NaCl, dried (MgSO$_4$), filtered and concentrated to afford the title compound as a yellow oil (128 mg, 80%). [MH]$^+$=242.

Preparative Example 220

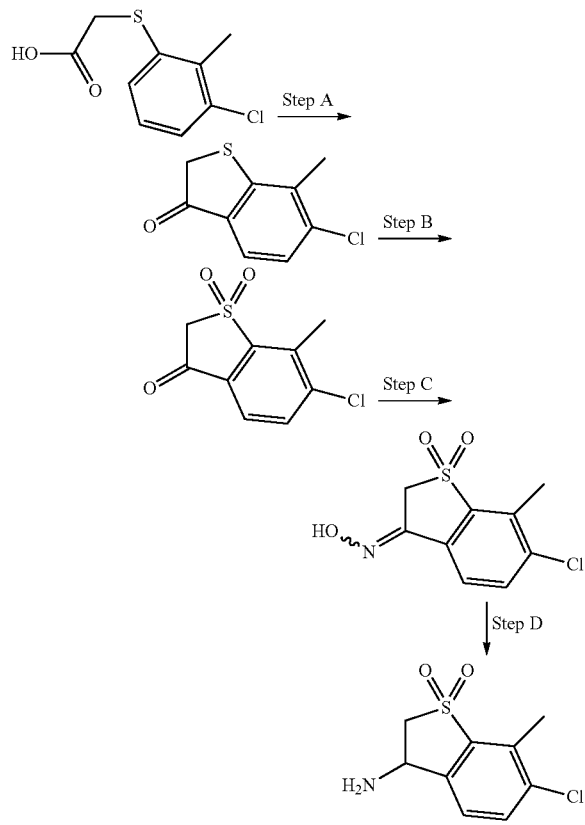

Step A

To a solution of commercially available 2-[(3-chloro-2-methylphenyl)thio]acetic acid (2.1 g) in DMF (3 drops) was added dropwise oxalyl chloride (5 mL). After 1.5 h the mixture was concentrated, redissolved in 1,2-dichloroethane (20 mL) and cooled to −10° C. AlCl$_3$ (1.6 g) was added and the cooling bath was removed. The mixture was stirred for 1 h, poured on ice and extracted with CH$_2$Cl$_2$ to afford the crude title compound as a brown solid (2.01 g). [MH]$^+$=199.

Step B

To a solution of the title compound from Step A above (1.01 g) in CH$_2$Cl$_2$ (40 mL) was added mCPBA (70-75%, 1.14 g) at room temperature. The mixture was stirred for 1 h, diluted with CH$_2$Cl$_2$, washed subsequently with 1N aqueous HCl, saturated aqueous NaHCO$_3$ and saturated aqueous NaCl, dried (MgSO$_4$), filtered and concentrated. Purification by chromatography (silica, cyclohexane/EtOAc) afforded the title compound as a colorless solid (668 mg). [MH]$^+$=231.

Step C

A mixture of the title compound from Step B above (430 mg), NaOAc (800 mg) and hydroxylamine hydrochloride (800 mg) in dry MeOH (20 mL) was heated to reflux for 2 h. The mixture was concentrated, dissolved in EtOAc, washed with saturated aqueous NaCl and concentrated to afford the title compound as colorless crystals (426 mg, 93%). [MH]$^+$=246.

Step D

The title compound from Step C above (426 mg) was dissolved in MeOH (50 mL) and heated to 60° C. Then zinc dust (1.3 g) and 6N aqueous HCl (20 mL) were added in portions over a period of 30 min. The mixture was cooled, filtered, concentrated, diluted with CHCl$_3$, washed subsequently with a saturated aqueous NaHCO$_3$ and saturated aqueous NaCl, dried (MgSO$_4$), filtered and concentrated to afford the title compound as an off-white solid (313 mg, 78%). [MH]$^+$=232.

Preparative Example 221

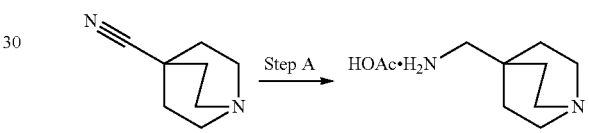

Step A

A mixture of commercially available 1-aza-bicyclo[2.2.2]octane-4-carbonitrile (0.5 g), AcOH (1 mL) and Pd/C (10 wt %, 200 mg) in THF (20 mL) was hydrogenated at atmospheric pressure overnight, filtered and concentrated to afford the crude title compound as a brown solid. [M-OAc]$^+$=141.

Preparative Example 222

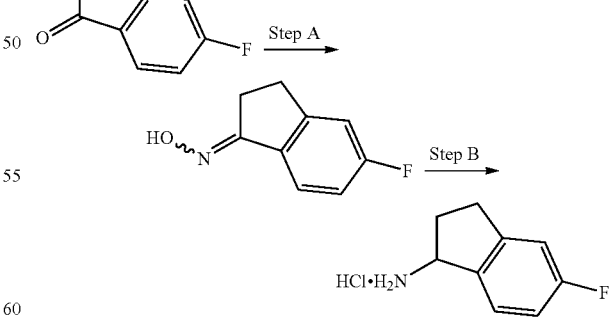

Step A

Commercially available 5-fluoroindanone (1.0 g) was treated similarly as described in the Preparative Example 220, Step C to afford the title compound as a colorless solid (1.3 g, >99%). [MH]$^+$=166.

Step B

The title compound from Step A above (1.35 g) was treated similarly as described in the Preparative Example 217, Step B to afford the title compound as a colorless solid (36.5 mg). [M-NH$_3$Cl]$^+$=135.

Preparative Example 223

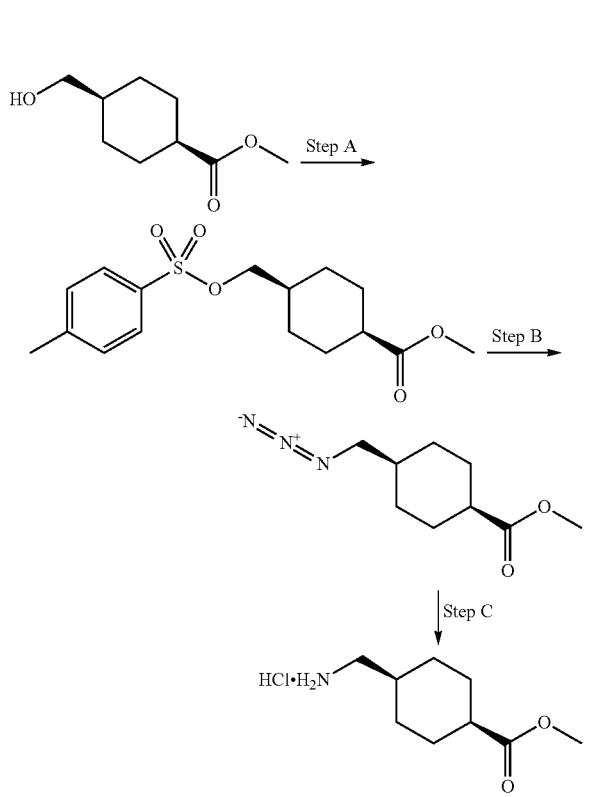

Step A

To an ice cooled solution of commercially available cis-4-hydroxymethyl-cyclohexanecarboxylic acid methyl ester (330 mg) in CH$_2$Cl$_2$/pyridine (3:1, 4 mL) was added 4-toluenesulfonic acid chloride (0.49 g). The mixture was stirred at room temperature overnight, cooled to 0° C., quenched with 2N aqueous HCl (35 mL) and extracted with CH$_2$Cl$_2$ (3×40 mL). The combined organic phases were dried (MgSO$_4$), filtered and concentrated to afford the title compound (643 mg, >99%). [MH]$^+$=327.

Step B

A mixture of the title compound from Step A above (643 mg) and NaN$_3$ (636 mg) in DMA (5 mL) was stirred at 70° C. overnight. The mixture was concentrated and diluted with EtOAc (25 mL), H$_2$O (5 mL) and saturated aqueous NaCl (5 mL). The organic phase was separated, dried (MgSO$_4$), filtered, concentrated and purified by chromatography (silica, cyclohexane/EtOAc) to afford the title compound (299 mg, 77%). [MNa]$^+$=220.

Step C

A mixture of the title compound from Step B above (299 mg) and Pd/C (10 wt %, 50 mg) in MeOH (10 mL) was hydrogenated at atmospheric pressure for 4 h, filtered and concentrated. The remaining residue was taken up in MeOH (7 mL), treated with 1N HCl in Et$_2$O (6 mL) and concentrated to afford the crude title compound (248 mg, 95%). [MH]$^+$=172.

Preparative Example 224

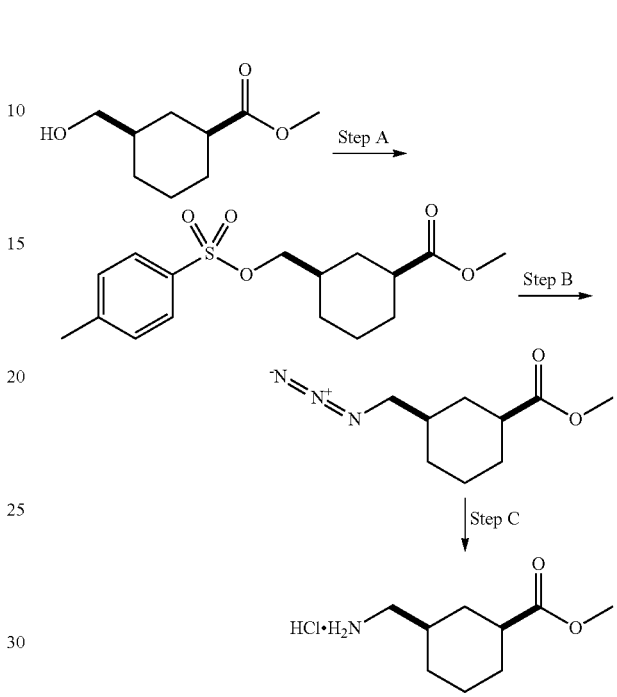

Step A

Commercially available cis-3-hydroxymethyl-cyclohexanecarboxylic acid methyl ester (330 mg) was treated similarly as described in the Preparative Example 223, Step A to afford the title compound (606 mg, 97%). [MH]$^+$=327.

Step B

The title compound from Step A above (606 mg) was treated similarly as described in the Preparative Example 223, Step B to afford the title compound (318 mg, 87%). [MNa]$^+$=220.

Step C

The title compound from Step B above (318 mg) was treated similarly as described in the Preparative Example 223, Step C to afford the crude title compound (345 mg, >99%). [MH]$^+$=172.

Preparative Example 225

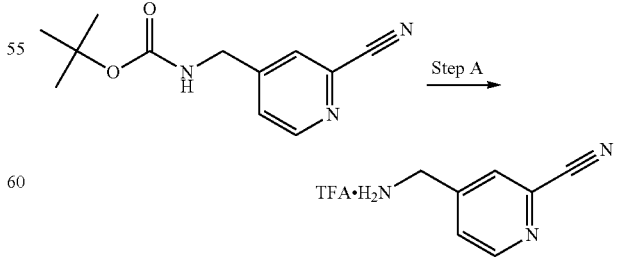

Step A

To a suspension of commercially available (3-cyano-benzyl)-carbamic acid tert-butyl ester (50 mg) in CHCl$_3$ (2 mL)

Preparative Example 226

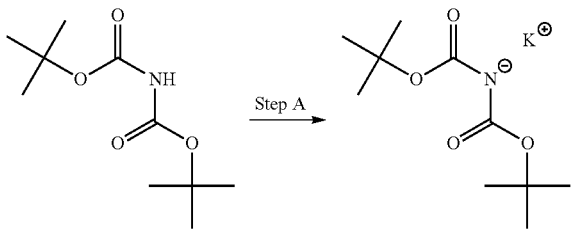

Step A

To a stirred solution of KOH (1.2 g) in EtOH (10 mL) was added commercially available bis(tert-butyldicarbonyl)amine (4.5 g). The mixture was stirred at room temperature for 1 h and then diluted with Et$_2$O. The formed precipitate was collected by filtration and washed with Et$_2$O (3×10 mL) to afford the title compound (3.4 g, 64%).

Preparative Example 227

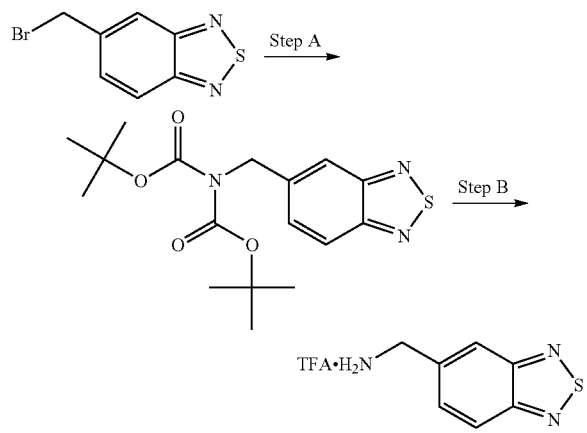

Step A

To a stirred solution of the title compound from the Preparative Example 226, Step A (160 mg) in DMF (2 mL) was added a solution of commercially available 5-bromomethyl-benzo[1,2,5]thiadiazole (115 mg) in DMF (1 mL). The mixture was stirred at 50° C. for 2 h, concentrated, diluted with EtOAc, washed with saturated aqueous NaHCO$_3$, dried (MgSO$_4$), filtered and concentrated to afford the crude title compound (180 mg, 71%). [MH]$^+$=366.

Step B

A solution of the title compound from Step A above (180 mg) in trifluoroacetic acid (2 mL) was stirred at room temperature for 1 h at room temperature and then concentrated to afford the title compound (140 mg, >99%). [M-TFA]$^+$=166.

Preparative Example 228

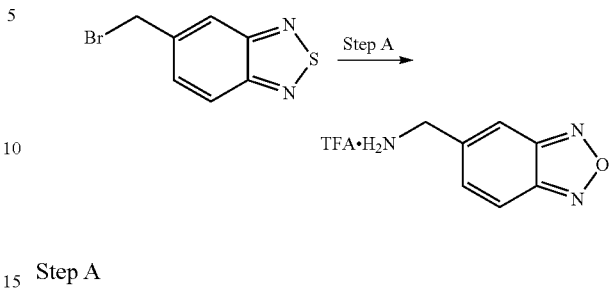

Step A

Commercially available 5-bromomethyl-benzo[1,2,5]oxadiazole was treated similarly as described in the Preparative Example 227 to afford the title compound. [M-TFA]$^+$=150.

Preparative Example 229

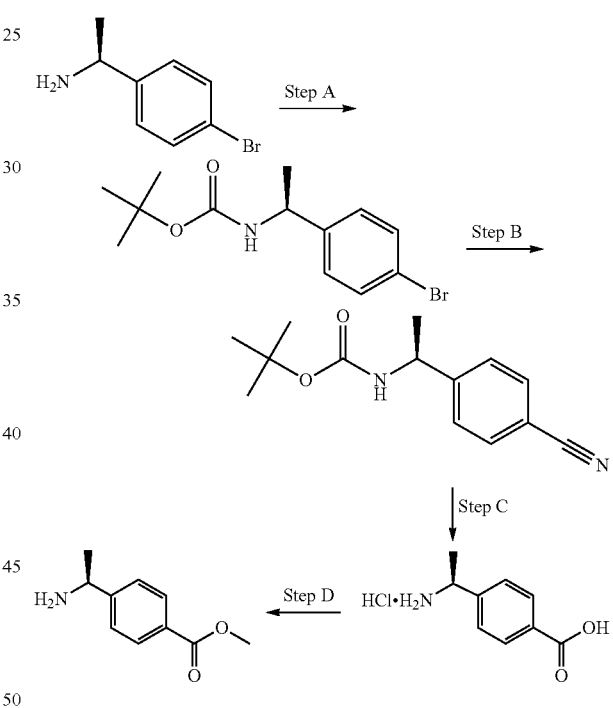

Step A

Commercially available (S)-(−)-1-(4-bromophenyl)ethylamine (2.0 g) was treated similarly as described in the Preparative Example 3, Step D to afford the title compound as a white solid (2.5 g, 92%). $^1$H-NMR (CDCl$_3$) δ=7.43 (d, 2H), 7.17 (d, 2H), 4.72 (br s, 2H), 1.35 (br s, 12H).

Step B

The title compound from Step A above (4.0 g) was treated similarly as described in the Preparative Example 3, Step E to afford the title compound (2.0 g, 60%). [MH]$^+$=247.

Step C

The title compound from Step B above (2.0 g) was treated similarly as described in the Preparative Example 2, Step A to afford the title compound (1.8 g, >99%). [M-Cl]$^+$=166.

Step D

The title compound from Step C above (1.0 g) was treated similarly as described in the Preparative Example 2, Step B to afford the title compound (310 mg, 35%). [MH]$^+$=180.

Preparative Example 230

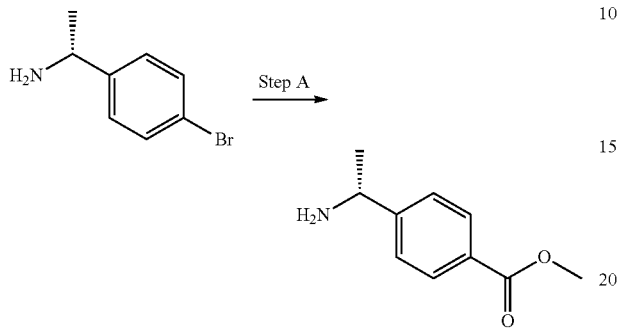

Step A

If one were to follow a similar procedure as described in the Preparative Example 229, except using commercially available (R)-(+)-1-(4-bromophenyl)ethylamine instead of (S)-(−)-1-(4-bromophenyl)ethyl amine, one would obtain the title compound.

Preparative Example 231

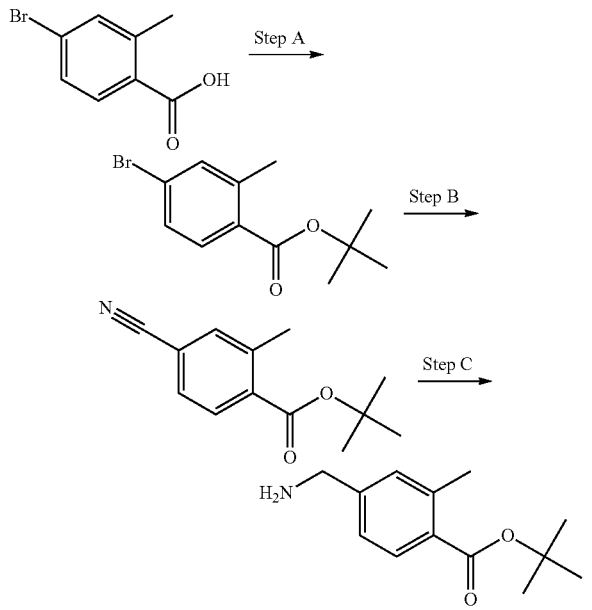

Step A

To a solution of commercially available 4-bromo-2-methyl-benzoic acid (1.5 g) in anhydrous CH$_2$Cl$_2$ (10 mL) was added tert-butyl 2,2,2-trichloroacetimidate (3.0 mL). The resulting mixture was heated to reflux for 24 h, cooled to room temperature, concentrated and purified by chromatography (silica, CH$_2$Cl$_2$) to give the desired title compound (1.0 g, 52%). [MH]$^+$=271.

Step B

A mixture of the title compound from Step A above (1.0 g), Zn(CN)$_2$ (1.0 g) and Pd(PPh$_3$)$_4$ (1.0 g) in anhydrous DMF (15 mL) was heated at 110° C. under a nitrogen atmosphere for 18 h, concentrated and purified by chromatography (silica, hexane/CH$_2$Cl$_2$) to give the desired title compound (0.6 g, 75%). [MH]$^+$=218.

Step C

To a solution of the title compound from Step B above (0.55 g), in anhydrous CH$_2$Cl$_2$ (30 mL) was added Bu$_4$NBH$_4$ (1.30 g). The mixture was heated to reflux under a nitrogen atmosphere for 12 h and then cooled to room temperature. 1N aqueous NaOH (5 mL) was added and the mixture was stirred for 20 min before it was concentrated. The remaining residue was then taken up in Et$_2$O (150 mL), washed with 1N aqueous NaOH (25 mL) and saturated aqueous NaCl, dried (MgSO$_4$), filtered and concentrated to give the title compound (0.50 g, 89%). [MH]$^+$=222.

Preparative Example 232

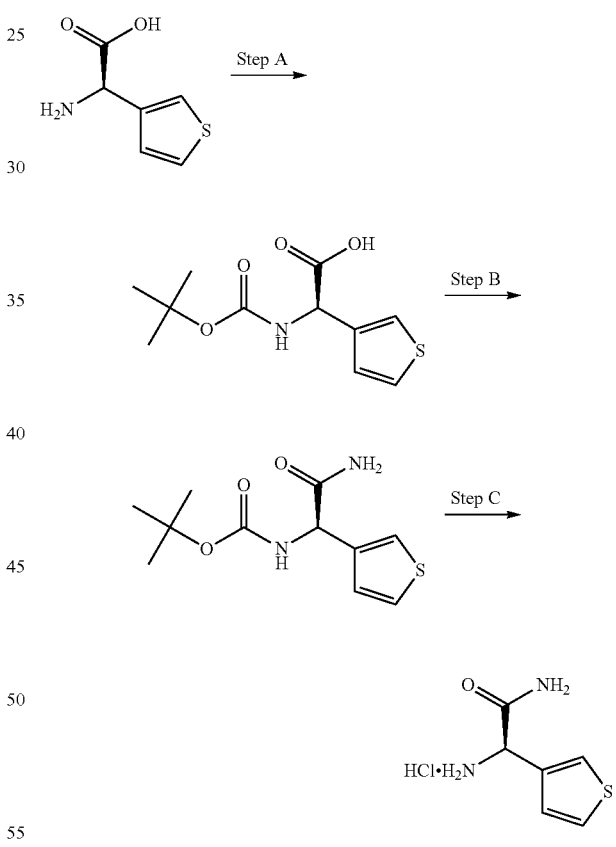

Step A

A solution of commercially available (R)-amino-thiophen-3-yl-acetic acid (0.50 g), 2-(tert-butoxycarbonyloxyimino)-2-phenylacetonitrile (0.86 g) and NEt$_3$ (0.65 mL) in 1,4-dioxane/H$_2$O (3:2, 7 mL) was stirred for 24 h, concentrated to ⅓ volume and diluted with H$_2$O (100 mL). The resulting aqueous mixture was extracted with Et$_2$O (100 mL), acidified with 1N aqueous HCl and extracted with Et$_2$O (2×80 mL). The combined organic layers were dried (MgSO$_4$), filtered and concentrated to give the desired title compound (0.7 g, 86%). [MH]$^+$=258.

Step B

To a stirred mixture of the title compound from Step A above (0.43 g) and (NH$_4$)$_2$CO$_3$ (0.48 g) in 1,4-dioxane/DMF (6:1, 3.5 mL) were added pyridine (0.4 mL) and di-tert-butyl dicarbonate (0.50 g). The mixture was stirred for 48 h, diluted with EtOAc (40 mL), washed with 1N aqueous HCl and saturated aqueous NaCl, dried (MgSO$_4$), filtered and concentrated to give the desired title compound, which was not further purified (0.35 g, 86%). [MH]$^+$=257.

Step C

The title compound from Step B above (0.35 g) was taken up in a 4M solution of HCl in 1,4-dioxane (10 mL). The mixture was stirred overnight and concentrated to give the title compound (0.15 g, n.d.). [MH]$^+$=157.

Preparative Examples 233-235

Following a similar procedure as described in the Preparative Example 232, except using the amino acids indicated in Table I-10 below, the following compounds were prepared.

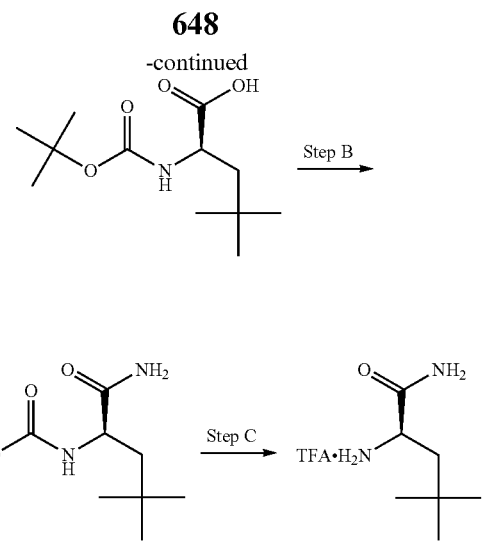

TABLE I-10

| Prep. Ex. # | amino acid | product | yield |
|---|---|---|---|
| 233 | (structure) | (structure) | n.d. [M-Cl]$^+$ = 194 |
| 234 | (structure) | (structure) | n.d. [M-Cl]$^+$ = 157 |
| 235 | (structure) | (structure) | n.d. [M-Cl]$^+$ = 113 |

Preparative Example 236

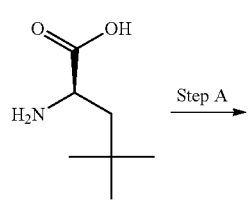

Step A

Commercially available (R)-2-amino-4,4-dimethyl-pentanoic acid (250 mg) was treated similarly as described in the Preparative Example 232, Step A to afford the title compound (370 mg, 87%). [MNa]$^+$=268.

Step B

The title compound from Step A above (370 mg) was treated similarly as described in the Preparative Example 232, Step B to afford the title compound. [MNa]$^+$=267.

Step C

The title compound from Step B above was treated similarly as described in the Preparative Example 208, Step A to afford the title compound (30 mg, 14% over 2 steps). [M-TFA]⁺=145.

Preparative Example 237

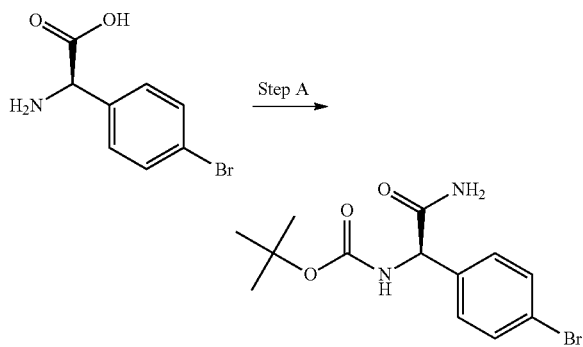

Step A

If one were to follow a similar procedure as described in the Preparative Example 232, Step A and Step B, except using commercially available (R)-amino-(4-bromo-phenyl)-acetic acid instead of (R)-amino-thiophen-3-yl-acetic acid in Step A, one would obtain the title compound.

Preparative Example 238

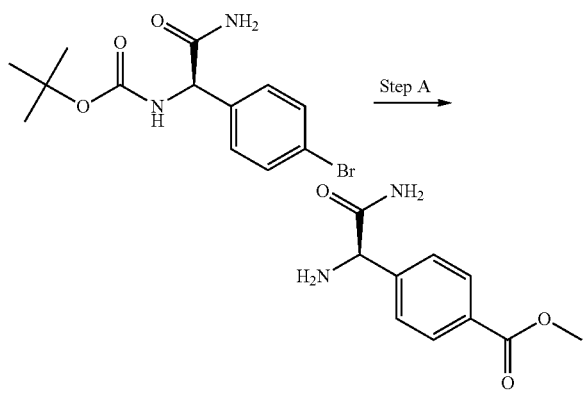

Step A

If one were to follow a similar procedure as described in the Preparative Example 229, Step B to Step D, except using the title compound from the Preparative Example 237, Step A instead of (R)-amino-thiophen-3-yl-acetic acid, one would obtain the title compound.

Preparative Example 239

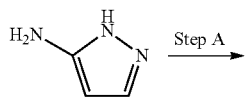

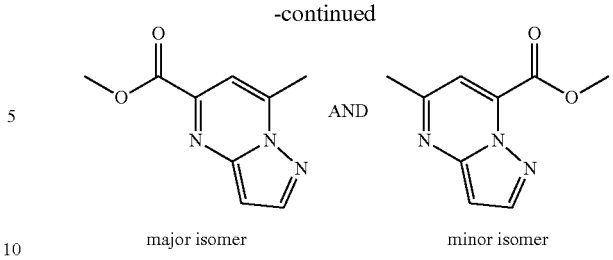

major isomer  AND  minor isomer

Step A

To a solution of commercially available 1H-pyrazol-5-amine (86.4 g) in MeOH (1.80 L) was added commercially available methyl acetopyruvate (50.0 g). The mixture was heated to reflux for 5 h and then cooled to room temperature overnight. The precipitated yellow needles were collected by filtration and the supernatant was concentrated at 40° C. under reduced pressure to ~⅔ volume until more precipitate began to form. The mixture was cooled to room temperature and the precipitate was collected by filtration. This concentration/precipitation/filtration procedure was repeated to give 3 batches. This material was combined and recrystallized from MeOH to give the major isomer of the title compound (81.7 g, 72%). [MH]⁺=192.

The remaining supernatants were combined, concentrated and purified by chromatography (silica, cyclohexane/EtOAc) to afford the minor isomer of title compound (6.8 g, 6%). [MH]⁺=192.

Preparative Example 240

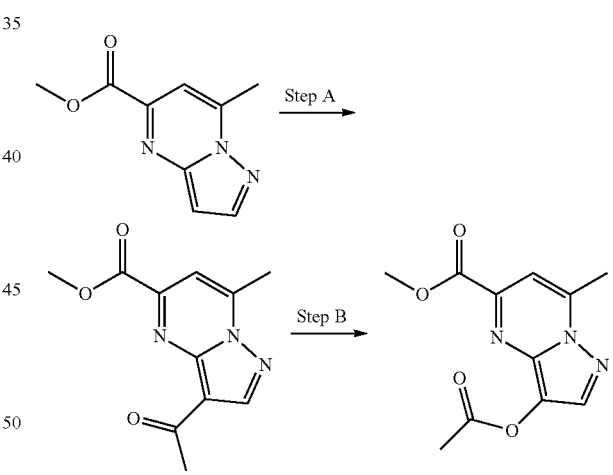

Step A

To a solution of the major isomer of the title compound from the Preparative Example 239, Step A (2.0 g) in CH₂Cl₂ (20 mL) were added acetyl chloride (3.0 mL) and SnCl₄ (10.9 g). The resulting mixture was heated to reflux overnight, cooled and quenched with H₂O (10 mL). The aqueous phase was separated and extracted with CH₂Cl₂ (2×). The combined organic phases were concentrated and purified by chromatography (silica, cyclohexane/EtOAc) to afford the title compound (1.2 g, 49%). [MH]⁺=234.

Step B

Trifluoroacetic anhydride (4.6 mL) was added dropwise to an ice cooled suspension of urea hydrogen peroxide (5.8 g) in CH₂Cl₂ (40 mL). The mixture was stirred for 30 min, then a solution of the title compound from Step A above (1.8 g) in CH₂Cl₂ (20 mL) was added and the mixture was stirred at room temperature overnight. NaHSO₃ (1.0 g) was added and the resulting mixture was diluted with saturated aqueous NaHCO₃ (40 mL). The aqueous phase was separated and extracted with CH₂Cl₂. The combined organic phases were concentrated and purified by chromatography (silica, cyclohexane/EtOAc) to afford the title compound (500 mg, 26%). ¹H-NMR (CDCl₃) δ=8.40 (s, 1H), 7.47 (d, 1H), 4.03 (s, 3H), 2.84 (d, 3H), 2.42 (s, 3H).

Preparative Example 241

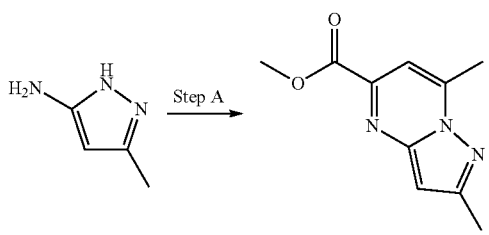

Step A

A mixture of commercially available 5-amino-3-methylpyrazole (1.44 g) and methyl acetopyruvate (0.97 g) in MeOH (20 mL) was heated to reflux for 2 h and then cooled to 0° C. The formed precipitate was collected by filtration to give the desired ester (1.78 g, 87%). [MH]⁺=206.

Preparative Example 242

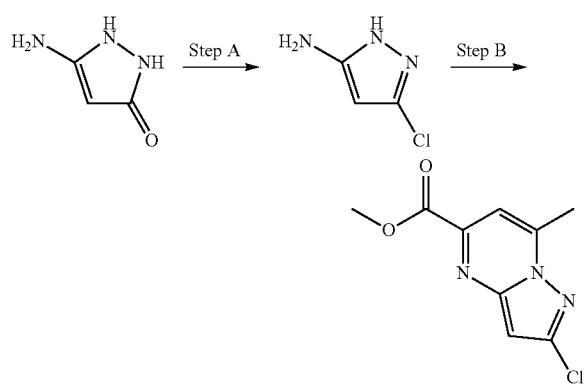

Step A

A mixture of commercially available 5-aminopyrazolone (5 g) and POCl₃ (50 mL) was heated to 210° C. for 5 h, concentrated and quenched with MeOH (10 mL) at 0° C. Purification by chromatography (silica, hexanes/EtOAc) afforded the desired product (293 mg, 5%). [MH]⁺=118.

Step B

A mixture of the title compound from Step A above (117 mg) and methyl acetopyruvate (144 mg) in MeOH (5 mL) was heated to reflux for 2 h and then cooled to 0° C. The formed precipitate was collected by filtration to give the desired ester (200 mg, 89%). [MH]⁺=226.

Preparative Example 243

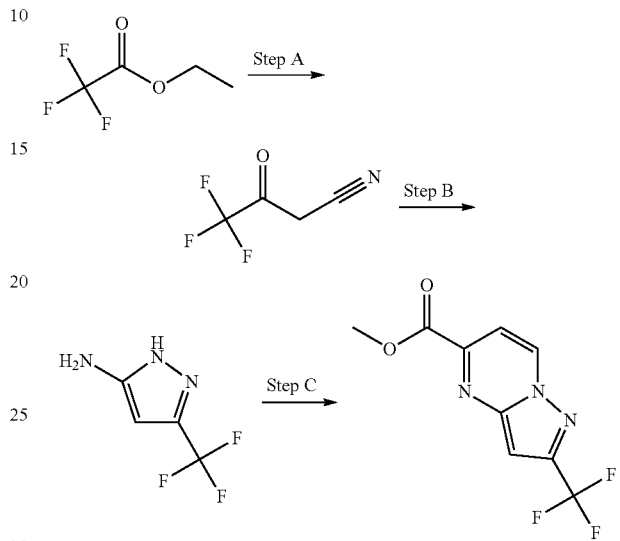

Step A

Under a nitrogen atmosphere at 0° C. was slowly added 1,4-dioxane (350 mL) to NaH (60% in mineral oil, 9.6 g) followed by the slow addition of CH₃CN (12.6 mL). The mixture was allowed to warm to room temperature before ethyl trifluoroacetate (23.8 mL) was added. The mixture was stirred at room temperature for 30 min, heated at 100° C. for 5 h, cooled to room temperature and concentrated. The remaining solid was taken up in H₂O (400 mL), washed with Et₂O (300 mL), adjusted to pH ~2 with concentrated HCl and extracted with CH₂Cl₂ (300 mL). The CH₂Cl₂ extract was dried (MgSO₄), filtered and concentrated to give a brown liquid, which was not further purified (12.5 g, 74%). [M-H]'= 136.

Step B

A mixture of the title compound from Step A above (12.5 g) and hydrazine monohydrate (6.0 g) in absolute EtOH (300 mL) was heated to reflux under a nitrogen atmosphere for 8 h, cooled to room temperature and concentrated. The remaining oil was taken up in CH₂Cl₂ (150 mL), washed with saturated aqueous NaCl, dried (MgSO₄), filtered, concentrated and purified by chromatography (silica, CH₂Cl₂/MeOH) to give the title compound (0.25 g, 2%). [MH]⁺=152.

Step C

Using a microwave, a mixture of the title compound from Step B above (150 mg) and commercially available methyl acetopyruvate (150 mg) in MeOH (1 mL) in a sealed vial was heated at 120° C. for 12 min, concentrated and purified by chromatography (silica, CH₂Cl₂) to give the title compound (0.15 g, 58%). [MH]⁺=260.

Preparative Example 244

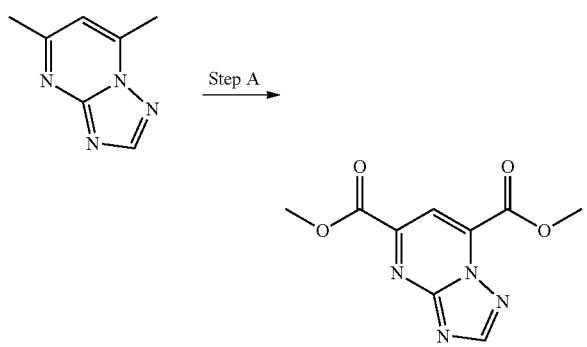

Step A

To a suspension of selenium dioxide (9 g) in 1,4-dioxane (35 mL) was added commercially available 5,7-dimethyl-[1,2,4]triazolo[1,5-a]pyrimidine (3 g). The mixture was heated to reflux for 24 h, cooled to room temperature, filtered through a plug of Celite® and concentrated. The remaining solid residue was taken up in MeOH (50 mL), ozone (7 g) was added and the mixture was heated to reflux for 24 h, cooled to room temperature, diluted with $CH_2Cl_2$ (50 mL), filtered through a plug of Celite® and concentrated. The remaining residue was dissolved in a saturated solution of HCl in MeOH (150 mL), heated to reflux under a nitrogen atmosphere for 24 h, filtered through a medium porosity fritted glass funnel, concentrated and partially purified by chromatography (silica, $CH_2Cl_2$/MeOH) to give the title compound, which was not further purified (0.2 g, 4%). $[MH]^+=238$.

Preparative Example 245

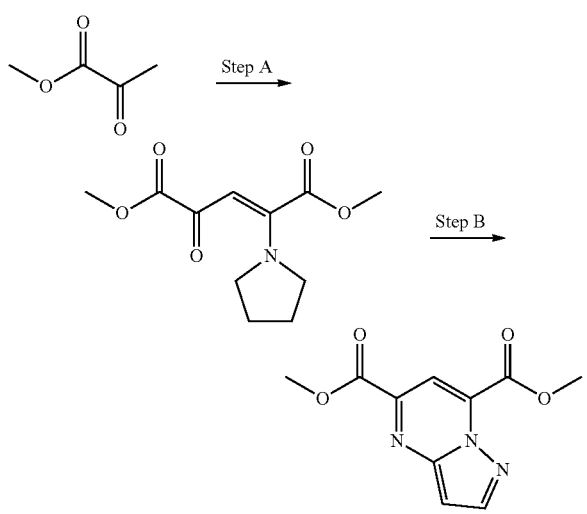

Step A

A solution of methyl pyruvate (13.6 mL) in $^tBuOMe$ (100 mL) was added dropwise to a cooled (−10° C.) solution of pyrrolidine (12.6 mL) in $^tBuOMe$ (100 mL) over a period of 30 min. The mixture was stirred at −10° C. for 15 min, then trimethylborate (8.0 mL) was added dropwise over a period of 2 min and stirring at −10° C. was continued for 2 h. $NEt_3$ (55 mL) was added, followed by the dropwise addition of a solution of methyl oxalylchloride (24.6 mL) in $^tBuOMe$ (100 mL) over a period of 30 min. The resulting thick slurry was stirred for 30 min and then diluted with saturated aqueous $NaHCO_3$ (250 mL) and $CH_2Cl_2$ (200 mL). The aqueous phase was separated and extracted with $CH_2Cl_2$ (2×100 mL). The combined organic phases were concentrated to give an oil, which was triturated with $^tBuOMe$ to afford the title compound as a yellowish solid (15.75 g, 45%). $[MH]^+=242$.

Step B

To mixture of the title compound from Step A above (6 g) and commercially available 2-aminopyrazole (2.1 g) in MeOH (10 mL) was added 3N aqueous HCl (3 mL). The mixture was heated to reflux overnight and cooled. The precipitated title compound was collected by filtration. The supernatant was concentrated and purified by chromatography (silica, hexane/EtOAc) to afford additional solid material, which was combined with the collected precipitate to give title compound (3.7 g, 60%). $[MH]^+=250$.

Preparative Example 246

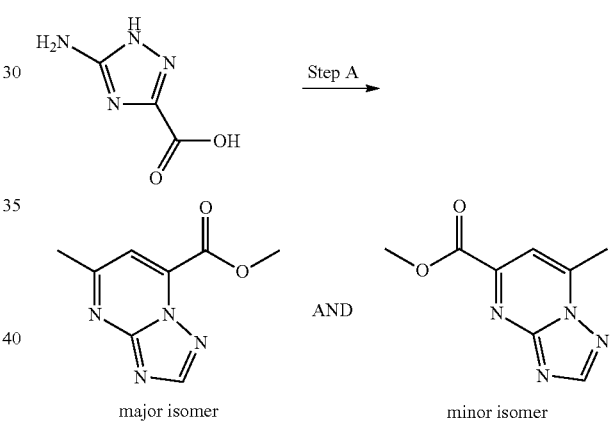

major isomer     AND     minor isomer

Step A

A mixture of commercially available 5-amino-1H-[1,2,4]triazole-3-carboxylic acid (20.3 g) and methyl acetopyruvate (20.0 g) in glacial AcOH (250 mL) was heated to 95° C. for 3 h. The mixture was concentrated and diluted with saturated aqueous $NaHCO_3$ (200 mL) and $CH_2Cl_2$ (500 mL). The organic phase was separated, dried ($MgSO_4$), filtered and concentrated to give a pale orange mixture of regioisomers (80:20, 21.3 g, 80%). Recrystallization of the crude material from hot THF (110 mL) afforded the major isomer of the title compound (13.0 g, 49%). $[MH]^+=193$.

The supernatant was concentrated and purified by chromatography (silica, hexanes/EtOAc) to afford the minor isomer of title compound. $[MH]^+=193$.

Preparative Examples 247-248

Following a similar procedure as described in the Preparative Example 246, except using the amines indicated in Table I-11 below, the following compounds were prepared.

TABLE I-11

| Prep. Ex. # | amine | product | yield |
|---|---|---|---|
| 247 | | | 96% [MH]⁺ = 208 |
| 248 | | | 92% [MH]⁺ = 236 |

Preparative Example 249

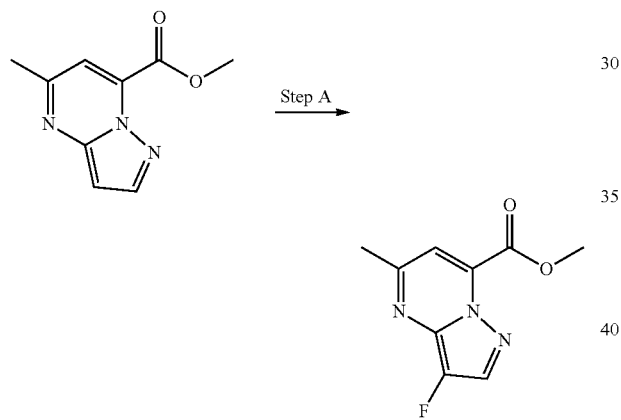

Step A

To a solution of the minor isomer of the title compound from the Preparative Example 239, Step A (500 mg) in CH₃CN (10 mL) were added AcOH (2 mL) and 1-chloromethyl-4-fluoro-1,4-diazoniabicyclo[2.2.2]octane bis(tetrafluoroborate) [Selectfluor®] (551 mg). The resulting mixture was stirred at 70° C. for 7 h, cooled to room temperature, concentrated and purified by chromatography (silica, cyclohexane/EtOAc) to afford the title compound (149 mg, 27%). [MH]⁺=210.

Preparative Example 250

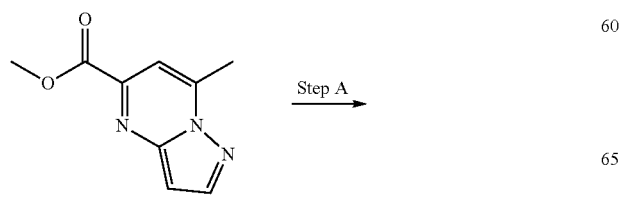

-continued

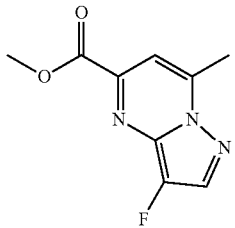

Step A

To a suspension of the major isomer of the title compound from the Preparative Example 239, Step A (10.0 g) in H₂O (1.0 L) was added 1-chloromethyl-4-fluoro-1,4-diazoniabicyclo[2.2.2]octane bis(tetrafluoroborate) [Selectfluor®] (18.6 g). The resulting mixture was stirred at 50° C. for 18 h, cooled to room temperature and extracted with CH₂Cl₂ (3×350 mL). The combined organic phases were dried (MgSO₄), filtered, concentrated and purified by chromatography (silica, CH₂Cl₂/acetone) to afford the title compound (4.25 g, 39%). [MH]⁺=210.

Preparative Example 251

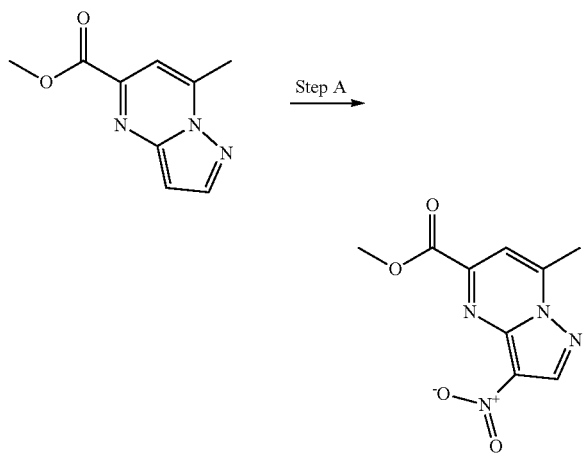

Step A

To a stirred solution of Bu₄N(NO₃) (1.39 g) in CH₂Cl₂ (10 mL) was added trifluoroacetic acid (579 µL). The resulting mixture was cooled to 0° C. and added to an ice cooled solution of the major isomer of the title compound from the Preparative Example 239, Step A (796 mg) in CH₂Cl₂ (10 mL). The mixture was allowed to reach room temperature overnight, diluted with CHCl₃, washed with saturated aqueous NaHCO₃, dried (MgSO₄), filtered, concentrated and purified by chromatography (silica, cyclohexane/EtOAc) to afford the title compound (200 mg, 20%). [MH]⁺=237.

Preparative Example 252

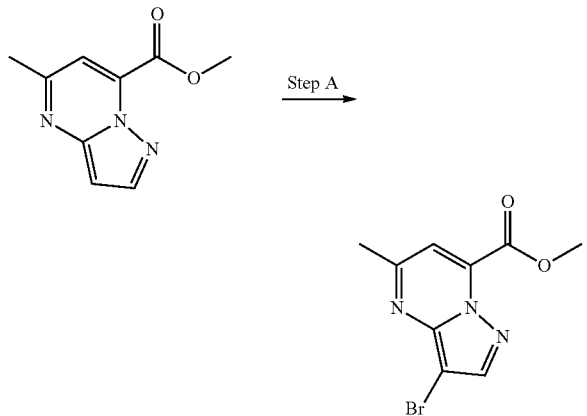

Step A

To a suspension of the minor isomer of the title compound from the Preparative Example 239, Step A (500 mg) in CHCl₃ (10 mL) was added N-bromosuccinimide (465 mg). The resulting mixture was heated to reflux for 1 h, cooled to room temperature, concentrated and purified by chromatography (silica, cyclohexane/EtOAc) to afford the title compound (599 mg, 85%). [MI-1]⁺=270/272.

Preparative Example 253

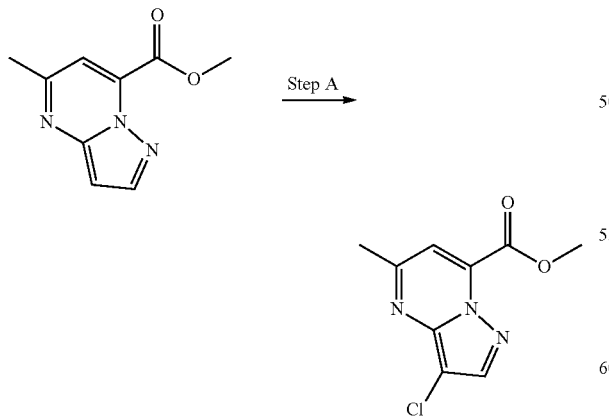

Step A

A mixture of the minor isomer of title compound from the Preparative Example 239, Step A (100 mg) and N-chlorosuccinimide (77 mg) in CCl₄ (5 mL) was heated to reflux for 24 h, cooled, concentrated and purified by chromatography (silica, cyclohexane/EtOAc) to afford the title compound (98 mg, 83%). [MH]⁺=226.

Preparative Example 254

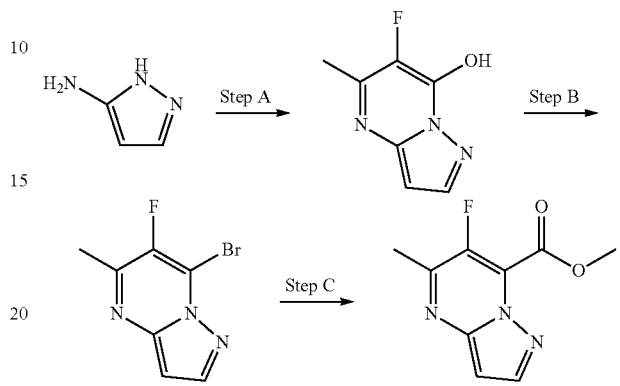

Step A

A mixture of commercially available 2H-pyrazol-3-ylamine (2.0 g) and 2-fluoro-3-oxo-butyric acid methyl ester (4.4 g) in MeOH (15 mL) was heated at 80° C. for 16 h and then cooled to room temperature. The formed precipitate was isolated by filtration and dried to afford the title compound (4.2 g, 84%). [MH]⁺=168.

Step B

To a mixture of the title compound from Step A above (1.67 g) in CH₃CN (150 mL) were added K₂CO₃ (4.15 g) and POBr₃ (8.58 g). The mixture was heated to reflux for 16 h, concentrated, diluted with CHCl₃, washed with saturated aqueous NaHCO₃, dried (MgSO₄), filtered, concentrated and purified by chromatography (silica, CH₂Cl₂/MeOH) to afford the title compound as a colorless solid (690 mg, 30%). [MH]⁺=230/232.

Step C

The title compound from Step B above (28 mg) was treated similarly as described in the Preparative Example 103, Step A to afford the title compound (295 mg, 70%). [MH]⁺=210.

Preparative Example 255

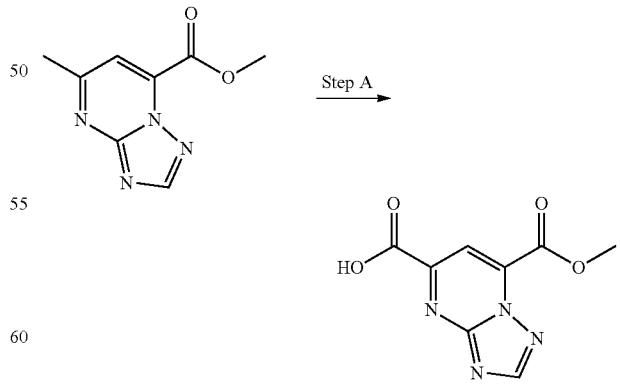

Step A

A mixture of the major isomer of title compound from the Preparative Example 246, Step A (1.34 g) and selenium dioxide (1.78 g) in 1,4-dioxane (20 mL) was heated to 120° C. under closed atmosphere for 12 h, cooled and filtered through Celite®. To the filtrate were added ozone (1.70 g) and H₂O (400 μL) and the resulting suspension was stirred at room temperature overnight. Concentration and purification by chromatography (silica, CH$_2$Cl$_2$/MeOH) afforded the title compound (1 g, 64%). [MH]$^+$=223.

Preparative Examples 256-270

Following a similar procedure as described in the Preparative Example 255, except using the intermediates indicated in Table I-12 below, the following compounds were prepared.

TABLE I-12

| Prep. Ex. # | intermediate | product | yield |
| --- | --- | --- | --- |
| 256 | | | 69% [MH]$^+$ = 223 |
| 257 | | | 70% [MH]$^+$ = 238 |
| 258 | | | 77% [MH]$^+$ = 266 |
| 259 | | | 34% [MH]$^+$ = 222 |
| 260 | | | 24% [MH]$^+$ = 222 |
| 261 | | | 60% [MH]$^+$ = 240 |

TABLE I-12-continued

| Prep. Ex. # | intermediate | product | yield |
|---|---|---|---|
| 262 | | | 71% [MH]⁺ = 240 |
| 263 | | | 87% [MH]⁺ = 280 |
| 264 | | | 46% [MH]⁺ = 267 |
| 265 | | | n.d. [MH]⁺ = 300/302 |
| 266 | | | 80% [MH]⁺ = 256 |
| 267 | | | 55% [MH]⁺ = 236 |

TABLE I-12-continued

| Prep. Ex. # | intermediate | product | yield |
|---|---|---|---|
| 268 | methyl 7-methyl-3-chloropyrazolo[1,5-a]pyrimidine-5-carboxylate | 5-(methoxycarbonyl)-3-chloropyrazolo[1,5-a]pyrimidine-7-carboxylic acid | 82% [MH]⁺ = 256 |
| 269 | methyl 7-methyl-2-(trifluoromethyl)pyrazolo[1,5-a]pyrimidine-5-carboxylate | 5-(methoxycarbonyl)-2-(trifluoromethyl)pyrazolo[1,5-a]pyrimidine-7-carboxylic acid | 68% [MH]⁺ = 290 |
| 270 | methyl 6-fluoro-5-methylpyrazolo[1,5-a]pyrimidine-7-carboxylate | 7-(methoxycarbonyl)-6-fluoropyrazolo[1,5-a]pyrimidine-5-carboxylic acid | 80% [MH]⁺ = 240 |

Preparative Example 271

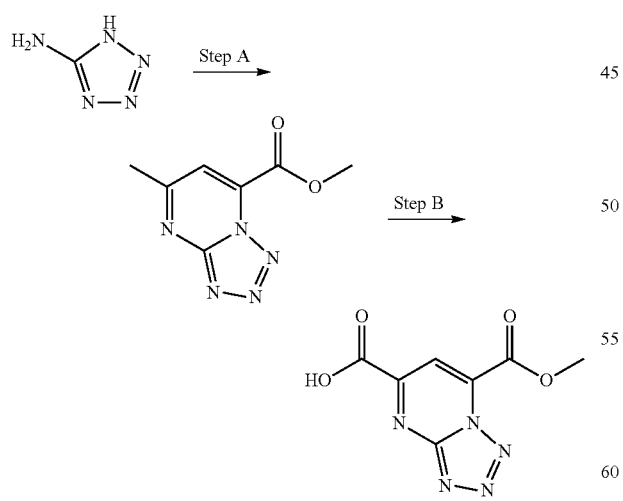

Step A

A suspension of commercially available methyl acetopyruvate (3.60 g) in H$_2$O (10 mL) was heated to 40° C., then a mixture of commercially available 1H-tetrazol-5-amine (2.10 g) and concentrated HCl (2 mL) in H$_2$O (4 mL) was added and the mixture was heated to reflux for 1 h, before it was cooled to 0° C. The formed precipitate was filtered off, washed with H$_2$O, dried in vacuo and purified by flash chromatography (silica, CH$_2$Cl$_2$/acetone) to afford the title compound as a mixture of regioisomers (~91:9, 2.15 g, 45%). [MH]⁺=194.

Step B

To a mixture of selenium dioxide (780 mg) in 1,4-dioxane (10 mL) was added dropwise a 5.5M solution of tert-butyl hydroperoxide in hexanes (5 mL). The mixture was stirred at room temperature for 30 min, then the title compound from Step A above (600 mg) was added and the mixture was heated to reflux for 24 h. The mixture was filtered through a plug of Celite®, concentrated, diluted with H$_2$O (10 mL) and extracted with CHCl$_3$. The combined organic phases were dried (MgSO$_4$), filtered and concentrated to afford the crude title compound, which was used without further purification. [MH]⁺=224.

Preparative Example 272

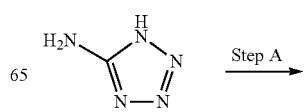

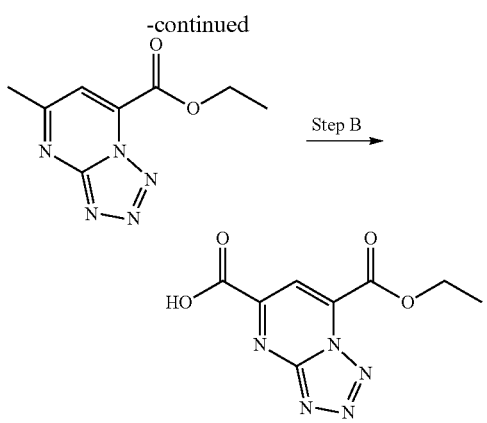

Step A

Commercially available 1H-tetrazol-5-amine (2.15 g) was treated similarly as described in the Preparative Example 271, Step A, except using ethyl acetopyruvate (4.00 g) to afford the title compound as a pale orange mixture of regioisomers (~75:25, 4.20 g, 80%). [MH]⁺=208.

Step B

The title compound from Step B above (4.00 g) was treated similarly as described in the Preparative Example 271, Step B to afford the title compound as a orange red solid (1.30 g, 28%). [MH]⁺=238

Preparative Example 273

Step A

To an ice cooled solution of commercially available 2-chloro-6-methyl-pyrimidine-4-carboxylic acid methyl ester (20.05 g) in MeOH (500 mL) was added NaBH₄ (8.10 g) in small portions over a period of 3 h. The cooling bath was removed and the mixture was stirred at room temperature for 10 h. The mixture was poured into saturated aqueous NH₄Cl and extracted with EtOAc (3×100 mL). The combined organic layers were dried (MgSO₄), filtered and concentrated to afford the title compound as an off-white solid (17.26 g, >99%). [MH]⁺=159.

Step B

To an ice cooled suspension of the title compound from Step A above (17.08 g) in CH₂Cl2 (300 mL) were subsequently added ⁱPr₂NEt (30 mL) and (2-methoxyethoxy)methyl chloride (13.5 mL). The mixture was stirred at room temperature for 12 h, additional ⁱPr₂NEt (11 mL) and (2-methoxyethoxy)methyl chloride (6.1 mL) were added and stirring at room temperature was continued for 6 h. Then the mixture was concentrated and purified by chromatography (silica, hexane/EtOAc) to afford the title compound as a yellow oil (10.75 g, 42%). [MH]⁺=247.

Step C

Under a nitrogen atmosphere a solution of the title compound from Step B above (10.75 g) in MeOH (60 mL) was added dropwise to a stirred solution of hydrazine hydrate (10.60 mL) in MeOH (300 mL) at 70° C. The mixture was stirred at 70° C. for 14 h, cooled and concentrated. The remaining residue was diluted with CH₂Cl₂ (200 mL), filtered and concentrated to afford the title compound as a yellow oil (10.00 g, 95%). [MH]⁺=243.

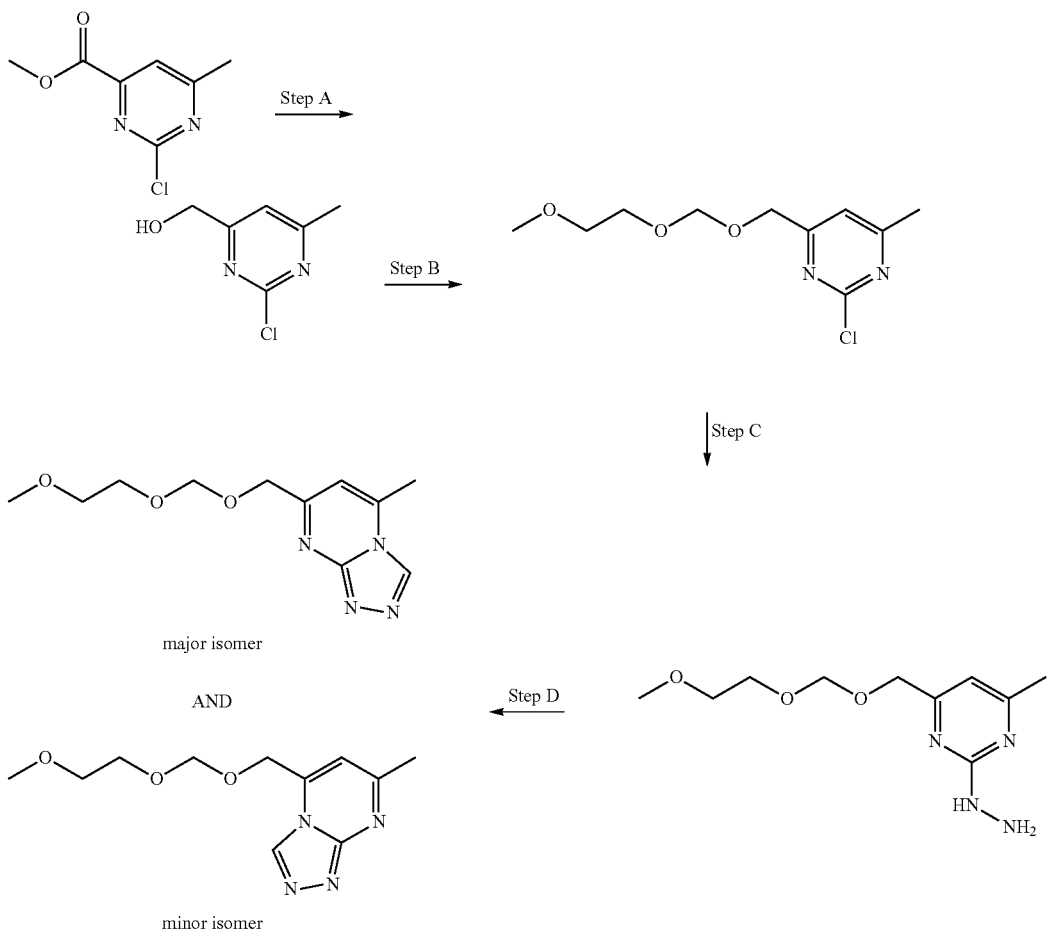

Step D

A suspension of the title compound from Step C above (9.50 g) in (EtO)₃CH (200 mL) was heated to reflux for 6 h. Then AcOH (5 mL) was added at heating to reflux was continued for 6 h. The mixture was cooled, concentrated and purified by chromatography (silica) to afford major isomer (7.05 g, 71%) and the minor isomer (2.35 g, 24%) of the title compound. [MH]⁺=253.

Preparative Example 274

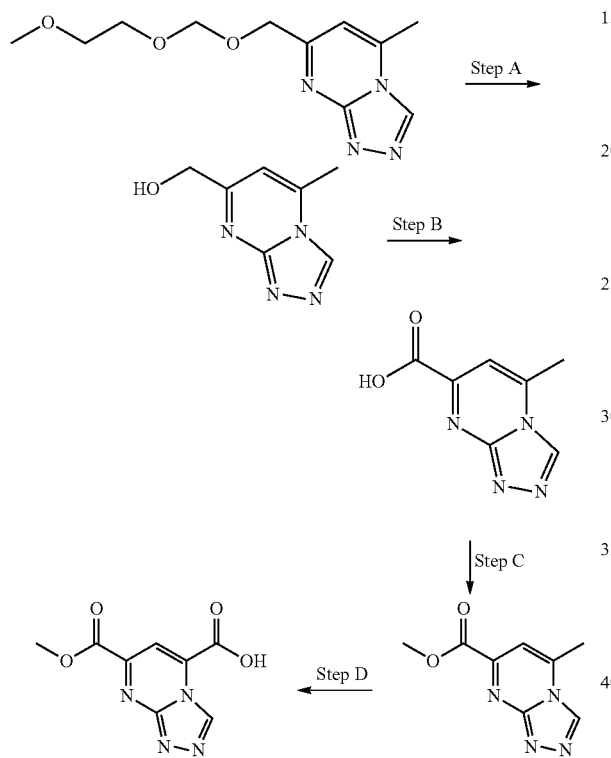

Step A

To a solution of the major isomer of title compound from the Preparative Example 273, Step D (9.40 g) in THF (200 mL) was added a 4M solution of HCl in 1,4-dioxane (37 mL). The mixture was stirred at room temperature for 2 h and then concentrated to afford the title compound (8.53 g, >99%). [MH]⁺=165.

Step B

The title compound from Step A above (8.53 g) and Na₂CO₃ (4.26 g) were dissolved in H₂O (250 mL). The suspension was heated to 50° C. and KMnO₄ (8.13 g) was added in small portions over a period of 30 min. The mixture was stirred at 50° C. for 2 h, cooled to room temperature, filtered through a pad of Celite® and concentrated to afford the crude title compound, which was used without further purification (13.42 g). [MH]⁺=179.

Step C

SOCl₂ (10.9 mL) was added dropwise to an ice cooled suspension of the title compound from Step B above (13.4 g) in MeOH (400 mL). The cooling bath was removed and the mixture was stirred at room temperature for 12 h. Concentration and purification by chromatography (silica, CH₂Cl₂/MeOH) afforded the title compound as an orange solid (2.23 g, 16%). [MH]⁺=193.

Step D

A mixture of the title compound from Step C above (1.21 g) and selenium dioxide (1.40 g) in 1,4-dioxane (20 mL) was heated to 70° C. for 4 h. Cooling to room temperature, filtration through a pad of Celite® and concentration afforded the crude title compound as a red solid, which was used without further purification (1.4 g). [MH]⁺=223.

Preparative Example 275

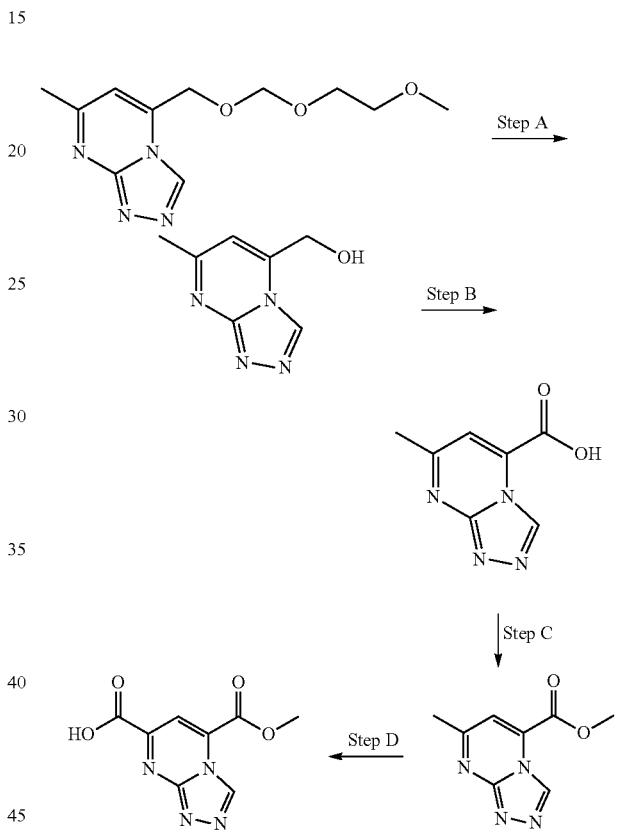

Step A

The minor isomer of title compound from the Preparative Example 273, Step D (2.35 g) was treated similarly as described in the Preparative Example 274, Step A to afford the title compound (1.53 g, >99%). [MH]⁺=165.

Step B

The title compound from Step A above (1.53 g) was treated similarly as described in the Preparative Example 274, Step B to afford the title compound. [MH]⁺=179.

Step C

The title compound from Step B above was treated similarly as described in the Preparative Example 274, Step C to afford the title compound. [MH]⁺=193.

Step D

The title compound from Step C above was treated similarly as described in the Preparative Example 274, Step D to afford the title compound. [MH]⁺=223.

Preparative Example 276

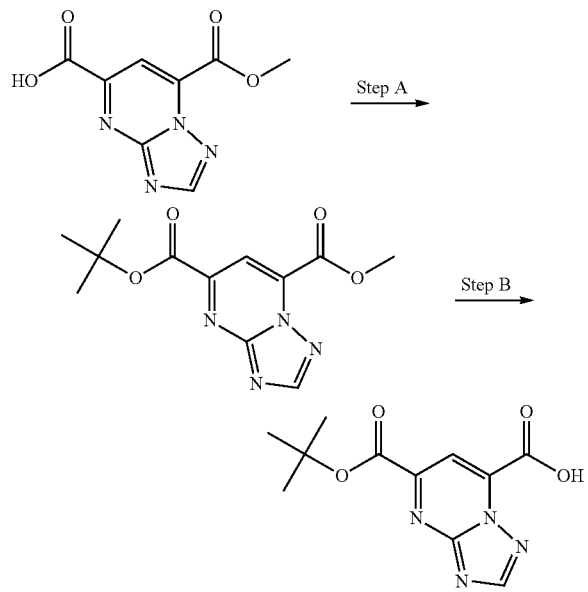

Step A

A suspension of the title compound from the Preparative Example 255, Step A (2.22 g) in dry toluene (15 mL) was placed in a preheated oil bath (~80° C.). Then N,N-dimethylformamide di-tert-butyl acetal (9.60 mL) was added carefully over a period of ~10 min and the resulting black/brown mixture was stirred at ~80° C. for 1 h. The mixture was cooled to room temperature, diluted with EtOAc (150 mL), washed with H$_2$O (2×150 mL) and saturated aqueous NaCl (150 mL), dried (MgSO$_4$), filtered, concentrated and purified by flash chromatography (silica, cyclohexane/EtOAc) to afford the title compound (1.39 g, 50%). [MH]$^+$=279.

Step B

To a solution of the title compound from Step A above (1.39 g) in dry 1,2-dichloroethane (50 mL) was added trimethyltin hydroxide (1.01 g). The resulting yellow suspension was placed in a preheated oil bath (~80° C.) and stirred at this temperature for 2 h. The mixture was cooled to room temperature, diluted with EtOAc (250 mL), washed with 5% aqueous HCl (2×250 mL) and saturated aqueous NaCl (250 mL), dried (MgSO$_4$), filtered, concentrated and vacuum dried for ~15 h to afford a beige solid, which was used without further purification (756 mg, 57%). [MH]$^+$=265.

Preparative Example 277

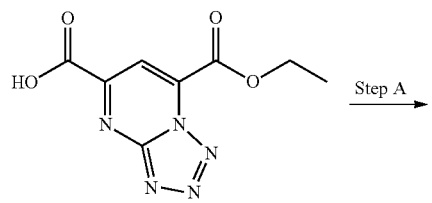

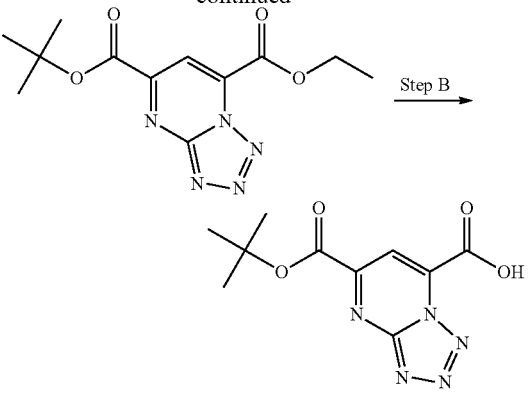

Step A

The title compound from the Preparative Example 272, Step B (2.37 g) was treated similarly as described in the Preparative Example 276, Step A to afford the title compound (1.68 g, 57%). [MH]$^+$=294.

Step B

The title compound from Step A above (1.36 g) was treated similarly as described in the Preparative Example 276, Step B to afford the title compound as a beige solid (1.20 g, 97%). [MH]$^+$=266.

Preparative Example 278

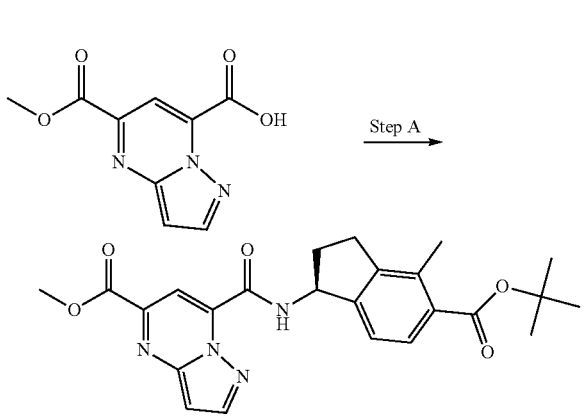

Step A

To a solution of the title compound from the Preparative Example 259 (94 mg) in DMF (3 mL) were added the title compound from the Preparative Example 7, Step D (94 mg), PyBrOP (216 mg) and $^i$Pr$_2$NEt (123 mL). The mixture was stirred at room temperature for 2 h, concentrated and purified by chromatography (silica, CH$_2$Cl$_2$/acetone) to afford the title compound (60 mg, 37%). [MH]$^+$=451.

Preparative Example 279

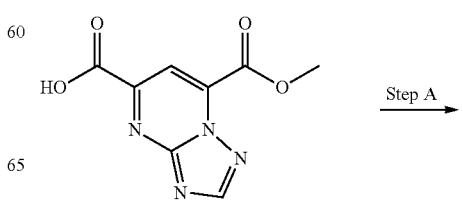

-continued

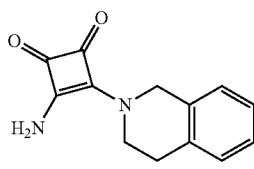

Step A

To an ice cooled solution of the title compound from the Preparative Example 255, Step A (250 mg) and the title compound from the Preparative Example 214, Step A (329 mg) in DMF (10 mL) were added N-methylmorpholine (170 μL), HATU (570 mg) and HOAt (204 mg). The mixture was stirred overnight while warming to room temperature and then concentrated. The remaining residue was dissolved in CHCl$_3$, washed with saturated aqueous NaHCO$_3$, 1N aqueous HCl and saturated aqueous NaCl, dried (MgSO$_4$), filtered, absorbed on silica and purified by chromatography (silica, CH$_2$Cl$_2$/MeOH) to afford the title compound as a yellow/brown gummy solid (177 mg, 35%). [MH]$^+$=462.

Preparative Example 280

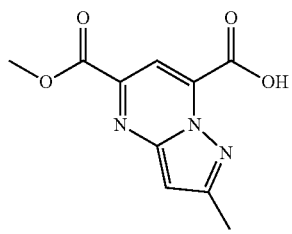

Step A

To a solution of the title compound from the Preparative Example 267 (236 mg) in anhydrous CH$_2$Cl$_2$ (5 mL) was added oxalyl chloride (0.32 mL) at 0° C., followed by the addition of anhydrous DMF (0.1 mL). The mixture was allowed to warm to room temperature, stirred for 1 h and concentrated. To the remaining reddish solid residue was added anhydrous CH$_2$Cl$_2$ (5 mL) at 0° C., followed by the addition of a solution of the title compound from the Preparative Example 138 (231 mg) and NEt$_3$ (0.42 mL) in anhydrous CH$_2$Cl$_2$ (5 mL). The mixture was allowed to warm to room temperature, stirred overnight, concentrated and purified by chromatography (silica, CH$_2$Cl$_2$/MeOH) to give the desired product (150 mg, 34%). [MH]$^+$=449.

Preparative Example 281

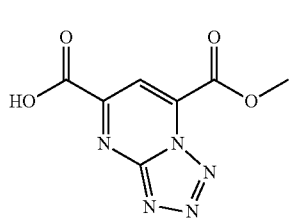

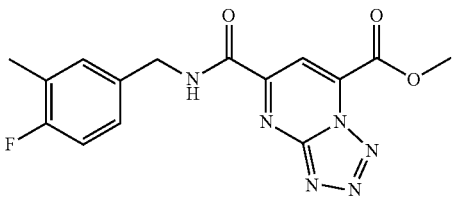

Step A

A solution of the title compound from the Preparative Example 271, Step B (~670 mg), PyBOP (2.35 g) and $^i$Pr$_2$NEt (780 μL) in DMF (5 mL) was stirred at room temperature for 1 h. Commercially available 4-fluoro-3-methyl benzylamine (500 mg) and $^i$Pr$_2$NEt (780 μL) were added and stirring at room temperature was continued overnight. The mixture was concentrated, diluted with EtOAc, washed with H$_2$O and saturated aqueous NaCl, dried (MgSO$_4$), filtered, concentrated and purified by chromatography (silica, CH$_2$Cl$_2$/acetone) to afford the title compound as a single regioisomer (200 mg, 19% over two steps). [MH]$^+$=345.

Preparative Example 282

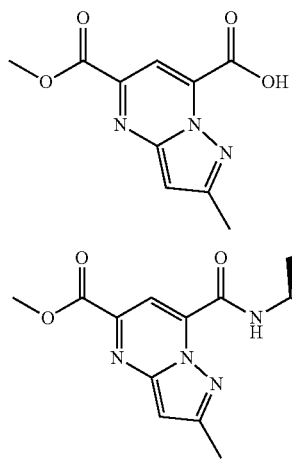

Step A

To a solution of the title compound from the Preparative Example 260 (506 mg) and the title compound from the Preparative Example 161 (555 mg) in DMF (15 mL) were added N-methylmorpholine (250 μL), EDCI (530 mg) and HOAt (327 mg). The mixture was stirred overnight and then concentrated. The remaining residue was dissolved in CHCl$_3$, washed with 10% aqueous citric acid and saturated aqueous NaCl, dried (MgSO$_4$), filtered, absorbed on silica and purified by chromatography (silica, CH$_2$Cl$_2$/MeOH) to afford the title compound as an orange solid (208 mg, 24%). [MH]$^+$=382.

Preparative Examples 283-320
Following similar procedures as described in the Preparative Examples 279 (method A), 280 (method B), 281 (method C), 278 (method D) or 282 (method E), except using the acids and amines indicated in Table I-13 below, the following compounds were prepared.
TABLE I-13
| Prep. Ex. # | acid, amine | product | method, yield |
|---|---|---|---|
| 283 | 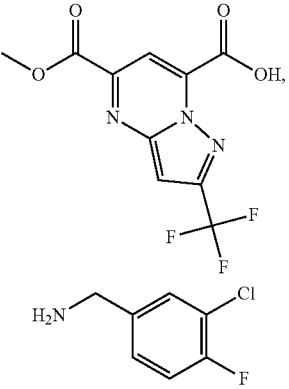 | 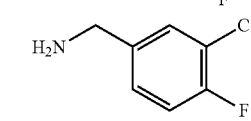 | B, 36% [MH]+ = 431 |
| 284 | 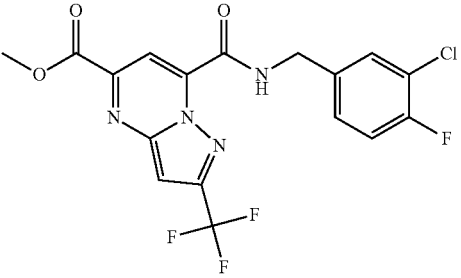 [SMILES: COC(=O)c1cc(C(=O)NCc2ccc(F)c(Cl)c2)n2nc(C(F)(F)F)cc2n1] | 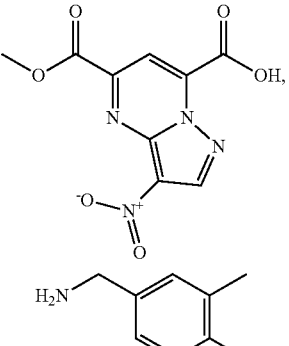 | C, 47% [MH]+ = 388 |
| 285 | 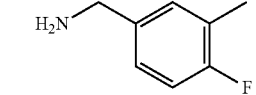 | 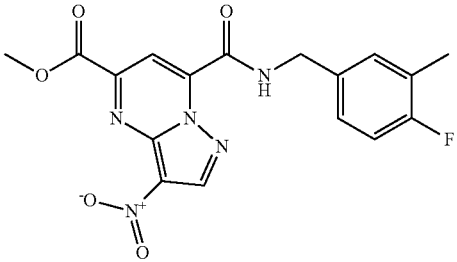 | C, n.d. [MH]+ = 421/423 |

| Prep. Ex. # | acid, amine | product | method, yield |
|---|---|---|---|
| 286 | 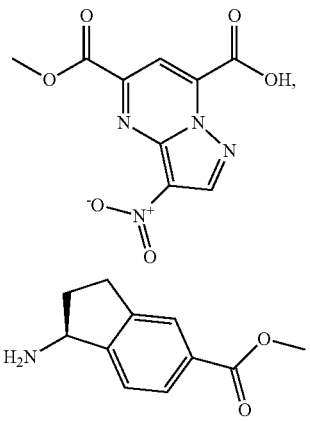 | 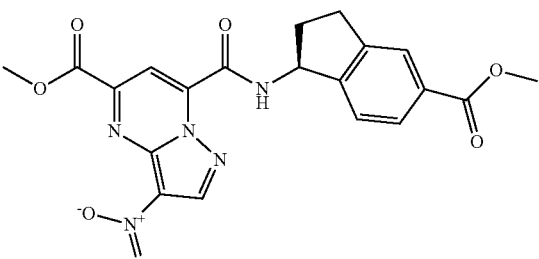 | C, 33% [MH]+ = 440 |
| 287 | 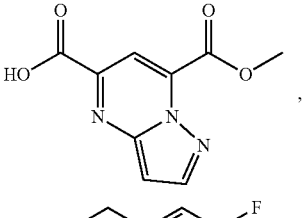 | 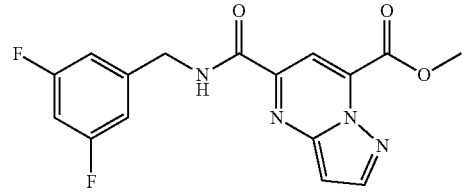 [SMILES: COC(=O)c1cc(C(=O)NCc2cc(F)cc(F)c2)nc2ccnn12] | A, 41% [MH]+ = 347 |
| 288 | 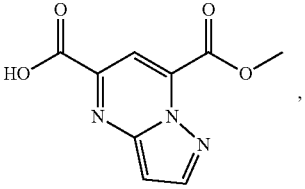 | 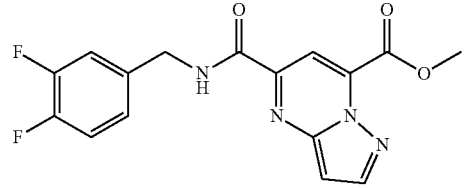 | A, 44% [MH]+ = 347 |
| 289 | 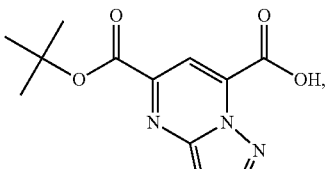 | 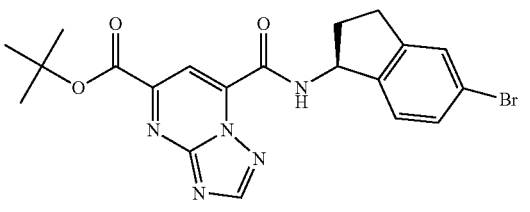 [SMILES: CC(C)(C)OC(=O)c1cc(C(=O)N[C@H]2CCc3cc(Br)ccc32)n2ncnc2n1] | A, 76% [MH]+ = 458/460 |

TABLE I-13-continued
| Prep. Ex. # | acid, amine | product | method, yield |
|---|---|---|---|
| 290 | 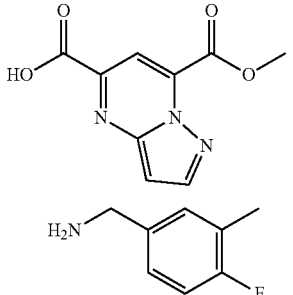 | 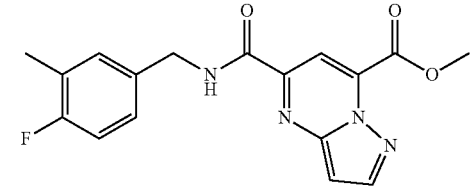 | D, 11% [MH]⁺ = 343 |
| 291 | 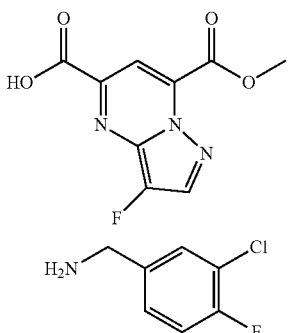 | 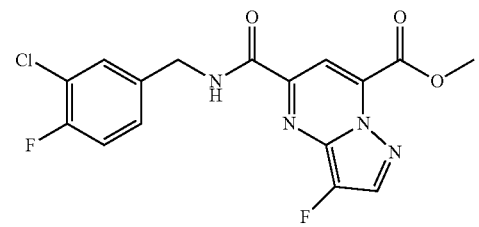 [SMILES: COC(=O)c1cc(C(=O)NCc2ccc(F)c(Cl)c2)nc2c(F)cnn12] | A, 83% [MH]⁺ = 381 |
| 292 | 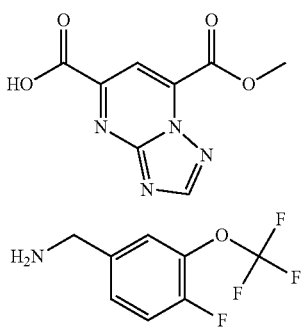 | 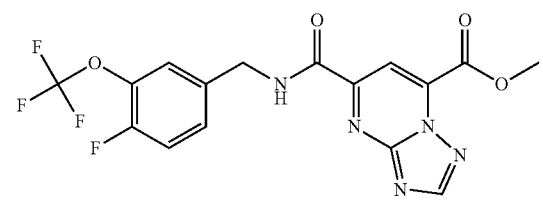 [SMILES: COC(=O)c1cc(C(=O)NCc2ccc(F)c(OC(F)(F)F)c2)nc2ncnn12] | A, 73% [MH]⁺ = 414 |
| 293 | 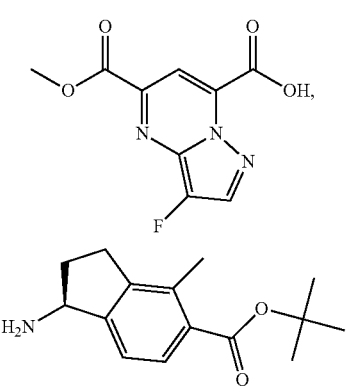 | 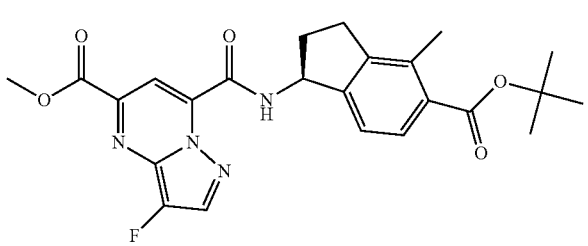 [SMILES: COC(=O)c1cc(C(=O)N[C@H]2CCc3c2ccc(C(=O)OC(C)(C)C)c3C)n2ncc(F)c2n1] | A, 32% [MH]⁺ = 491 |

TABLE I-13-continued
| Prep. Ex. # | acid, amine | product | method, yield |
|---|---|---|---|
| 294 | 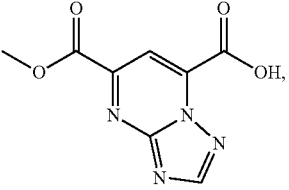 | 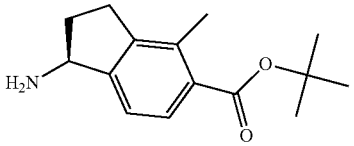 | B, 76% [MH]+ = 452 |
| 295 |  |  | A, 7% (over 2 steps), [MH]+ = 410 |
| 296 | 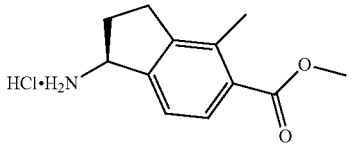 | 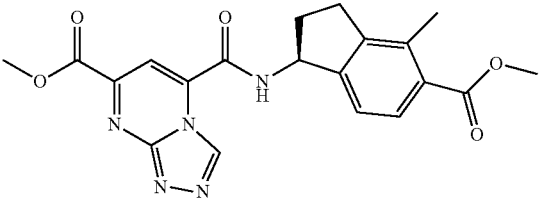 | A, n.d. [MH]+ = 344 |
| 297 | 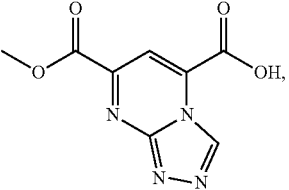 | 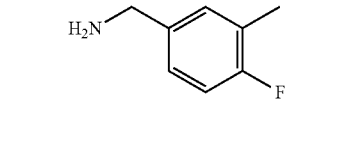 | B, 34% [MH]+ = 364 |

TABLE I-13-continued
| Prep. Ex. # | acid, amine | product | method, yield |
|---|---|---|---|
| 298 | 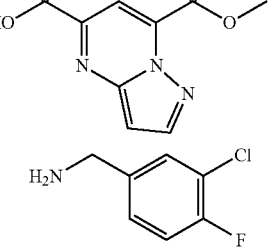 | 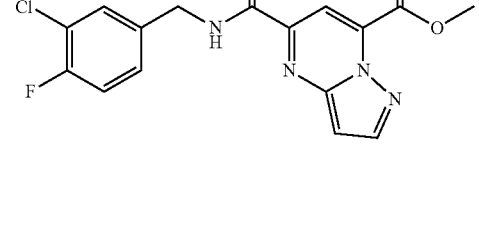 | B, 72% [MH]⁺ = 363 |
| 299 | 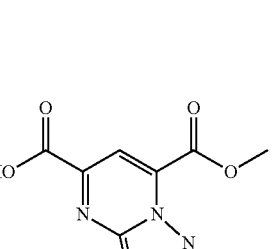 | 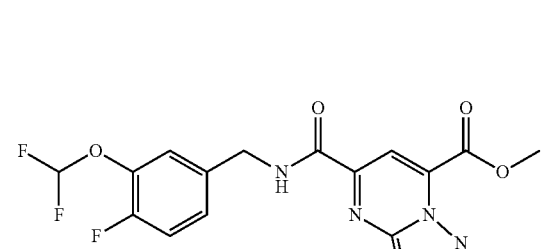 | A, 37% [MH]⁺ = 395 |
| 300 | 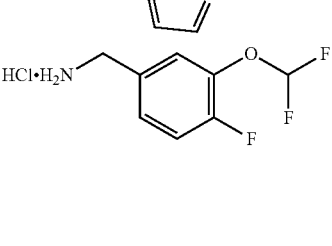 |  | A, 79% [MH]⁺ = 381 |
| 301 | 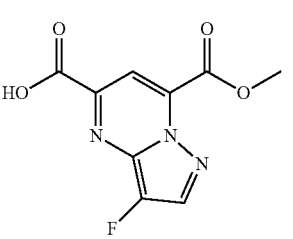 | 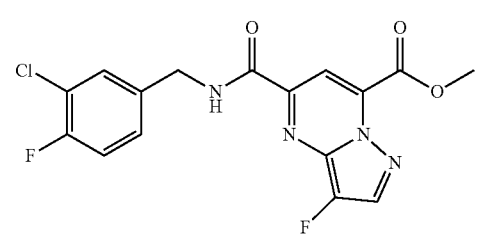 | A, 71% [MH]⁺ = 364 |

TABLE I-13-continued

| Prep. Ex. # | acid, amine | product | method, yield |
|---|---|---|---|
| 302 | (structures) | (structure) | A, 43% [MH]+ = 435 |
| 303 | (structures) | (structure) | E, 82% [MH]+ = 400 |
| 304 | (structures) | (structure) | A, 67% [MH]+ = 500 |
| 305 | (structures) | (structure) | A, 73% [MNa]+ = 475 |

TABLE I-13-continued
| Prep. Ex. # | acid, amine | product | method, yield |
|---|---|---|---|
| 306 | 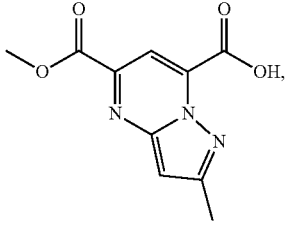 | 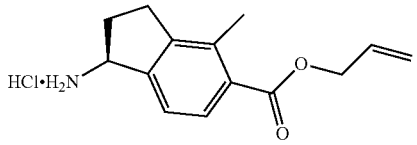 | B, 34% [MH]⁺ = 449 |
| 307 | 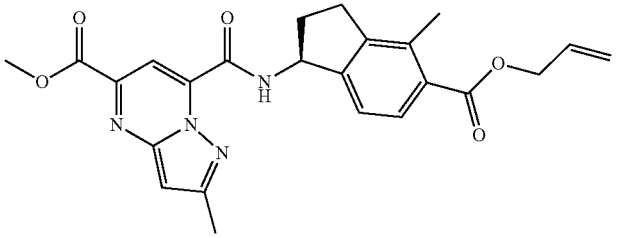 [SMILES: C=CCOC(=O)c1ccc2c(c1C)CC[C@@H]2NC(=O)c1cc(C(=O)OC)nc2cc(C)nn12] | 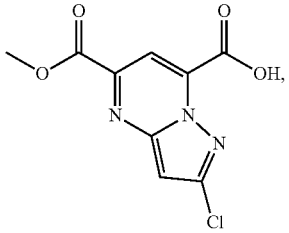 | B, 34% [MNa]⁺ = 491 |
| 308 | 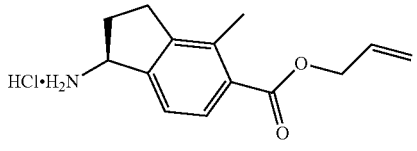 | 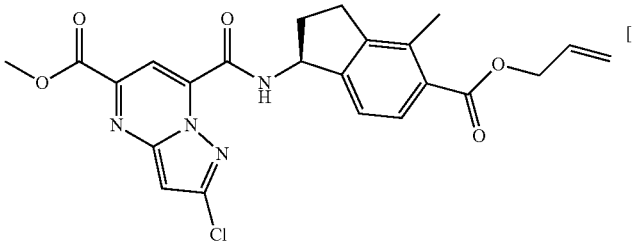 | B, 73% [M-H]⁻ = 501 |
| 309 | 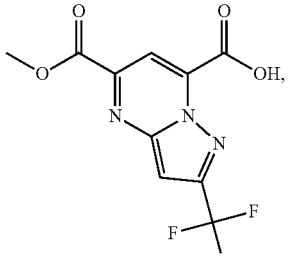 | 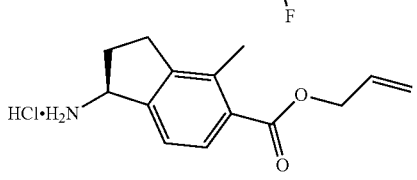 | A, 20% [MH]⁺ = 342 |

TABLE I-13-continued
| Prep. Ex. # | acid, amine | product | method, yield |
|---|---|---|---|
| 310 | 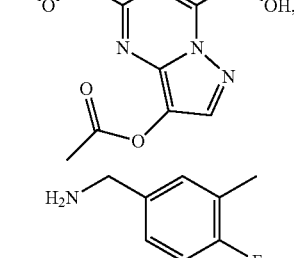 |  | A, 21% [MH]+ = 401 |
| 311 | 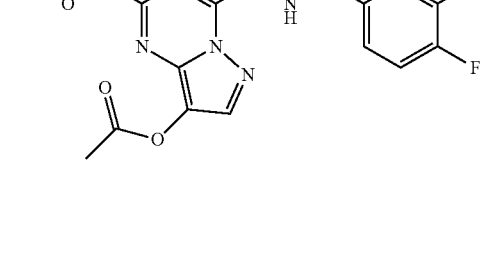 | 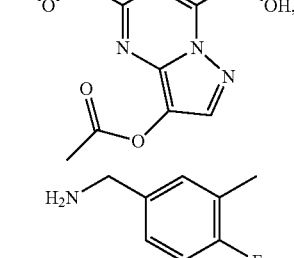 | A, 10% [MH]+ = 453 |
| 312 | 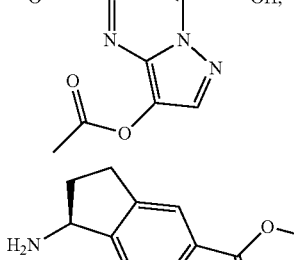 |  | A, 73% [MH]+ = 414 |
| 313 | 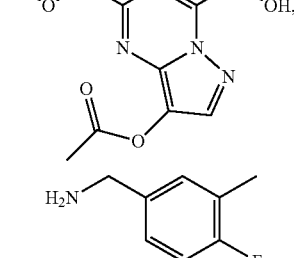 | 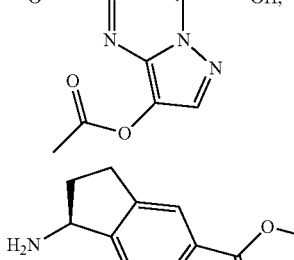 | A, 71% [MH]+ = 453 |

TABLE I-13-continued
| Prep. Ex. # | acid, amine | product | method, yield |
|---|---|---|---|
| 314 | 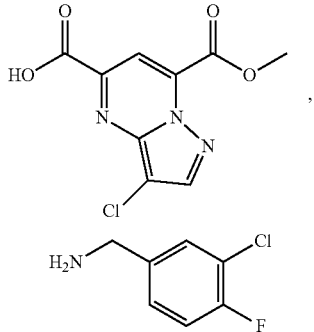 | 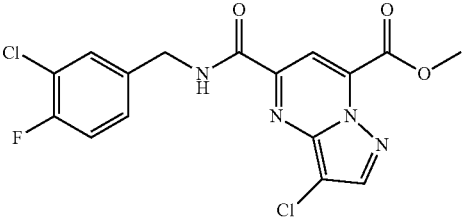 | A, >99% [MH]+ = 397 |
| 315 | 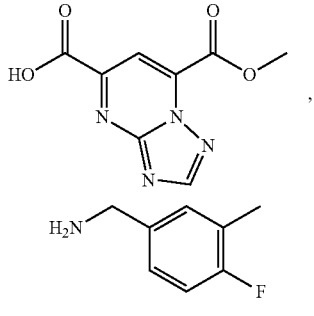 | 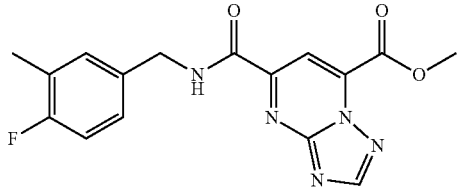 | A, 70% [MH]+ = 344 |
| 316 |  |  | A, 33% [MH]+ = 359 |
| 317 | 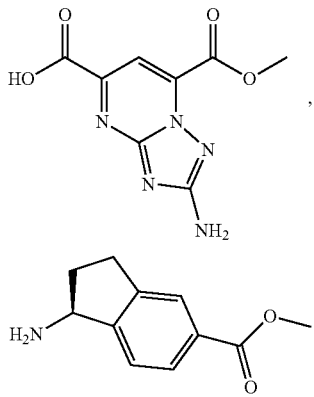 [SMILES: COC(=O)c1cc(C(=O)O)nc2nc(N)nn12 ; COC(=O)c1ccc2c(c1)CC[C@@H]2N] | 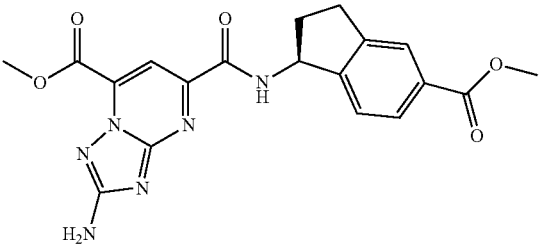 | A, 54% [MH]+ = 411 |

TABLE I-13-continued
| Prep. Ex. # | acid, amine | product | method, yield |
|---|---|---|---|
| 318 | 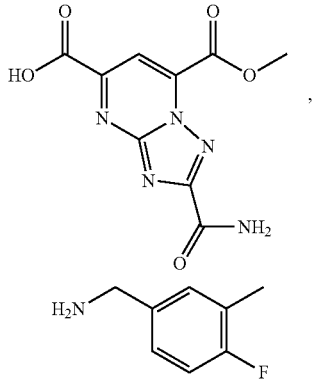 | 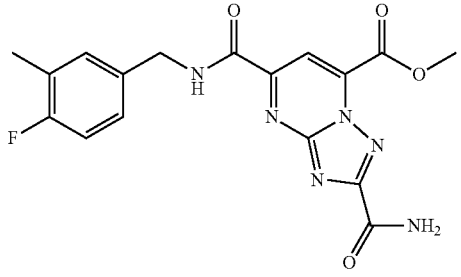 | A, 60% [MH]⁺ = 387 |
| 319 | 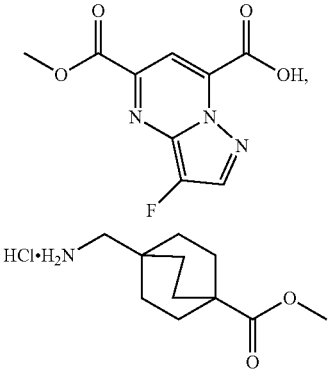 | 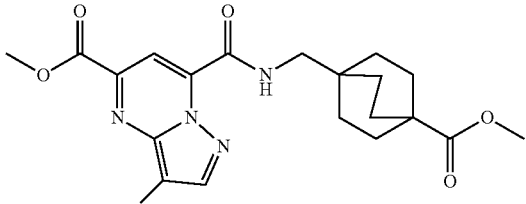 | A, 47% [MH]⁺ = 419 |
| 320 | 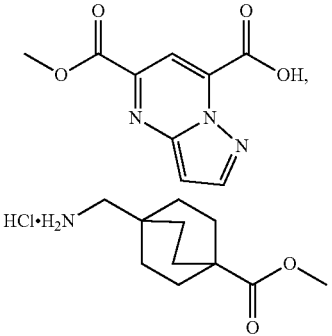 | 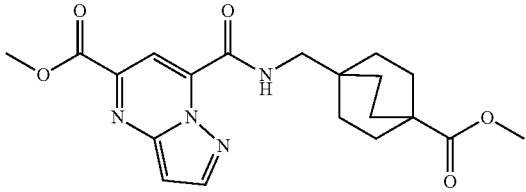 | A, 29% [MH]⁺ = 401 |

Preparative Example 321

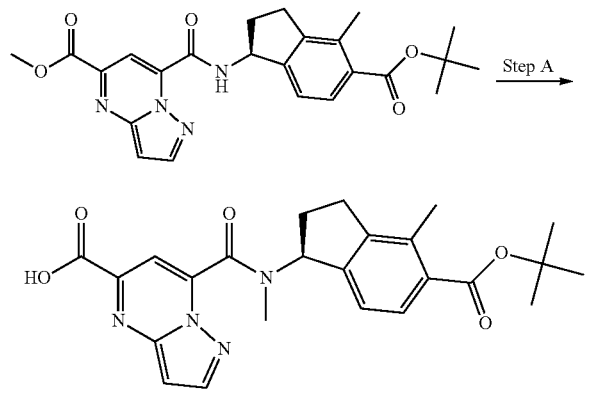

Step A

To an ice cooled solution of the title compound from the Preparative Example 278, Step A (75 mg) in dry THF (10 mL) were successively added NaH (95%, 10 mg) and methyl iodide (250 μL). The cooling bath was removed and the resulting mixture was stirred at room temperature for 2 h. Concentration and purification by chromatography (silica, CHCl$_3$/MeOH) afforded the title compound as a colorless solid (52 mg, 69%). [MNa]$^+$=473.

Preparative Example 322

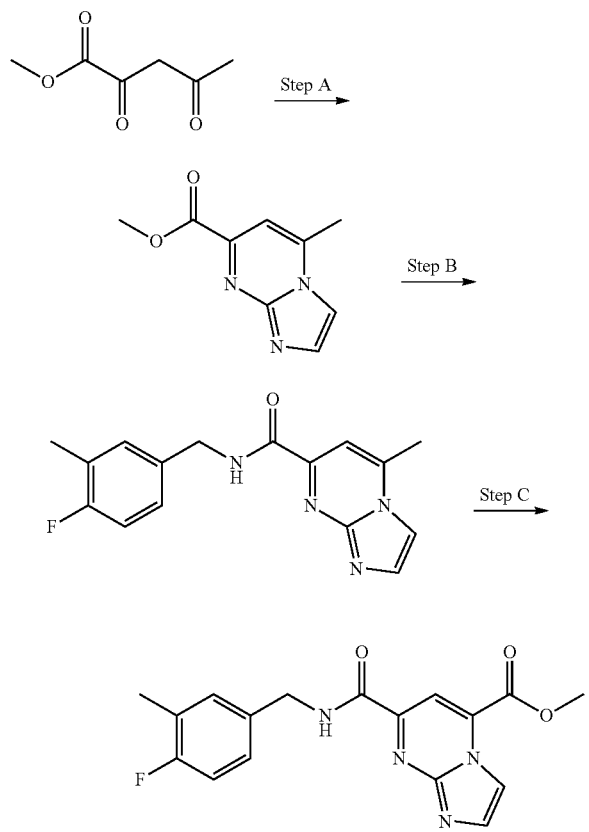

Step A

A mixture of commercially available 2-aminoimidazole sulfate (1.0 g), NH$_4$OAc (1.2 g) and methyl acetopyruvate (1.1 g) in AcOH (10 mL) was stirred at 120° C. for 3 h, then absorbed on silica and purified by chromatography (silica, EtOAc/MeOH) to give an off-white solid (396 mg, 14%). [MH]$^+$=192.

Step B

A solution of the title compound from Step A above (14 mg) in THF (100 μL), MeOH (100 μL), and 1N aqueous LiOH (80 μL) was stirred at 0° C. for 2 h and then concentrated to give a yellow residue. [MH]$^+$=178. A mixture of this residue, PyBOP (42 mg), 4-fluoro-3-methyl-benzylamine (11 mg), and NEt$_3$ (20 μL) in DMF (200 μL) and THF (400 μL) was stirred for 4 h, then absorbed on silica and purified by chromatography (silica, EtOAc/MeOH) to give an off-white solid (12 mg, 55%). [MH]$^+$=299.

Step C

A mixture of the title compound from Step B above (100 mg) and selenium dioxide (93 mg) in dioxane (1.5 mL) was stirred at 80° C. for 2 h. The mixture was cooled to room temperature and filtered through Celite®. The filter cake was washed with dioxane (3×1 mL). To the supernatant were added oxone (206 mg) and H$_2$O (100 μL) and the resulting mixture was stirred for 4 h and then filtered. The supernatant was concentrated and then stirred in a premixed solution of acetyl chloride (100 μL) in MeOH (2 mL) in a sealed vial for 3 h at 65° C. The solution was absorbed on silica and purified by chromatography (silica, hexanes/EtOAc) to give a yellow solid (40 mg, 35%). [MH]$^+$=343.

Preparative Example 323

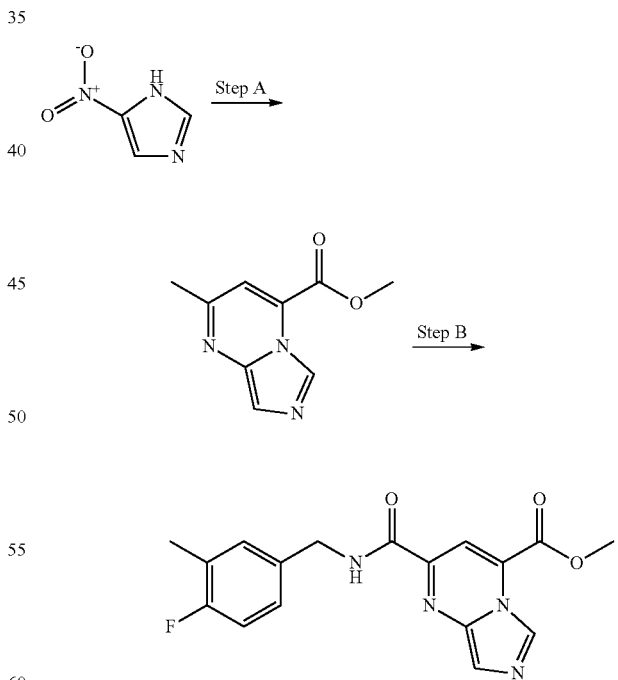

Step A

A mixture of commercially available 4-nitroimidazole (5 g) and Pd/C (10 wt %, 500 mg) in a premixed solution of acetyl chloride (4 mL) in MeOH (100 mL) was hydrogenated in a Parr shaker at 35 psi for 5 h. The mixture was filtered through Celite® and concentrated to give a black oil. [MH]$^+$=

115. This oil and methyl acetylpyruvate (6.4 g) were stirred in AcOH (70 mL) and MeOH (70 mL) at 65° C. for 18 h. The resulting mixture was absorbed on silica and purified by chromatography (silica, CH₂Cl₂/MeOH). Further purification of the resulting residue by chromatography (silica, EtOAc) afforded an orange solid (120 mg, 1.4%). [MH]⁺=192.

Step B

A mixture of the title compound from Step A above (50 mg) and selenium dioxide (116 mg) in dioxane (1 mL) was heated to 130° C. in a sealed tube for 6 h, cooled and filtered through Celite®. The supernatant was concentrated to give a orange residue. [MH]⁺=222. This residue was stirred with 4-fluoro-3-methyl-benzylamine (27 μL), PyBOP (150 mg), and NEt₃ (73 μL) in THF (2 mL) for 3 h, absorbed on silica and purified by chromatography (silica, hexanes/EtOAc) to give a yellow solid (22 mg, 24%). [MH]⁺=343.

Preparative Example 324

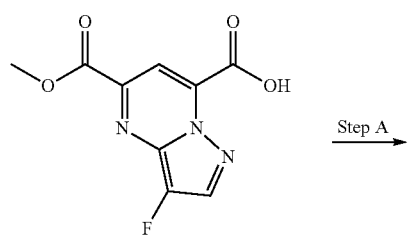

Step A

A solution of the title compound from the Preparative Example 262 (0.5 g) and 4-fluoro-3-trifluoromethylbenzyl amine (1.6 g) in DMF (2.5 mL) was stirred at 48° C. for 10 h and then concentrated to an oil. The oil was taken up in EtOAc (120 mL), washed with 1N aqueous HCl (2×70 mL) and saturated aqueous NaCl (70 mL), dried (MgSO₄), filtered and concentrated. The remaining solid was washed with hexanes/Et₂O (1:1) and MeOH to give a yellow solid (0.31 g, 35%). [MH]⁺=401.

Preparative Examples 325-327

Following a similar procedure as described in the Preparative Example 324, except using the acids and amines indicated in Table I-14 below, the following compounds were prepared.

TABLE I-14

| Prep. Ex. # | acid, amine | product | yield |
|---|---|---|---|
| 325 | | | n.d. [MNa]⁺ = 355 |
| 326 | | | 33% [MH]⁺ = 344 |

TABLE I-14-continued

| Prep. Ex. # | acid, amine | product | yield |
|---|---|---|---|
| 327 | 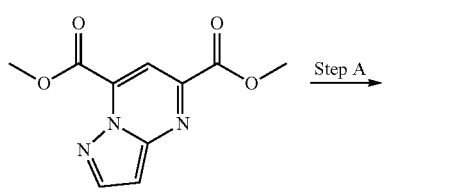 | 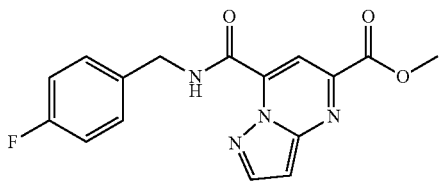 | 65% [MH]⁺ = 381 |

Preparative Example 328

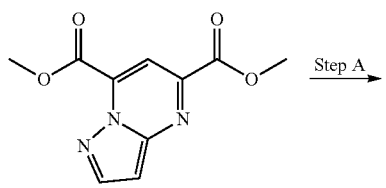

Step A

A mixture of the title compound from the Preparative Example 245, Step B (10 mg), commercially available 4-fluorobenzylamine (5.3 mg) and scandium triflate (1 mg) in anhydrous DMF (1 mL) was heated to 60° C. for 12 h, concentrated and purified by chromatography (silica) to afford the title compound as a yellow solid (11.5 mg, 83%). $[\alpha]^+=329$.

Preparative Example 329

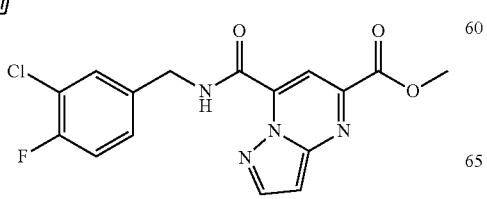

Step A

The title compound from the Preparative Example 245, Step B (10 mg) was treated similarly as described in the Preparative Example 328, Step A, except using commercially available 3-chloro-4-fluorobenzylamine instead of 4-fluorobenzylamine to afford the title compound as a yellow solid (11.5 mg, 79%). $[MH]^+=363$.

Preparative Example 330

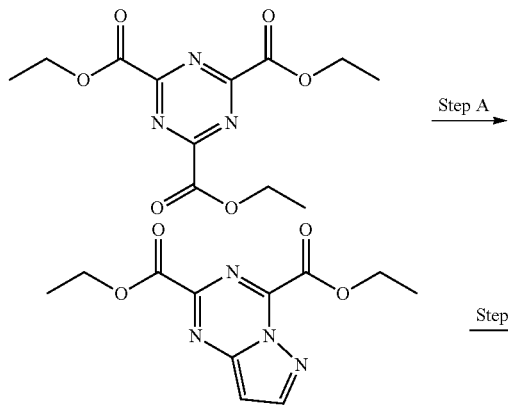

AND

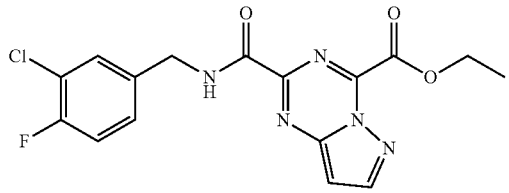

Step A

Under an argon atmosphere a solution of commercially available [1,3,5]triazine-2,4,6-tricarboxylic acid triethyl ester (818 mg) and 3-aminopyrazole (460 mg) in dry DMF (8 mL) was heated to 100° C. overnight and then concentrated. The remaining residue was dissolved in CHCl$_3$, washed with 10% aqueous citric acid and saturated aqueous NaCl, dried (MgSO$_4$), filtered, concentrated and purified by chromatography (silica, CH$_2$Cl$_2$/MeOH) to afford the title compound as a colorless solid (409 mg, 56%). [MH]$^+$=265.

Step B

A mixture of the title compound from Step A above (203 mg) and commercially available 3-chloro-4-fluorobenzylamine (160 mg) in dry DMF (3 mL) was heated to 70° C. overnight and concentrated. The remaining residue was dissolved in CHCl$_3$, washed with 10% aqueous citric acid and saturated aqueous NaCl, dried (MgSO$_4$), filtered, concentrated and purified by preparative thin layer chromatography (silica, CH$_2$Cl$_2$/MeOH) to afford the title compound from the Example 286 and the separated regioisomers of the title compound. [MH]$^+$=378.

Preparative Example 331

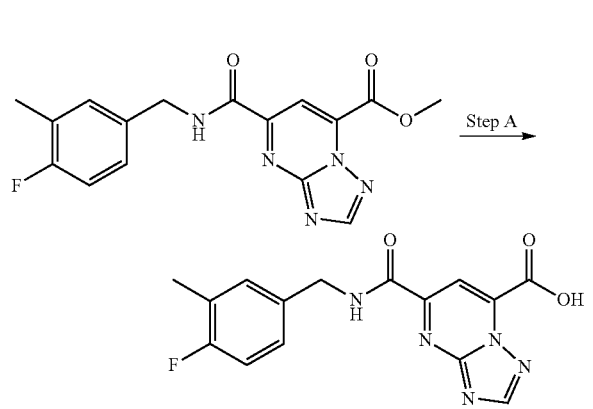

Step A

To a solution of NaOH (24 mg) in dry MeOH (3.2 mL) was added the title compound from the Preparative Example 315 (170 mg). The resulting suspension was stirred at room temperature for 1 h, acidified with 1N aqueous HCl and concentrated. The remaining residue was dissolved in EtOAc, washed with 1N aqueous HCl, dried (MgSO$_4$), filtered and concentrated to afford the title compound (130 mg, 80%). [MH]$^+$=330.

Preparative Example 332

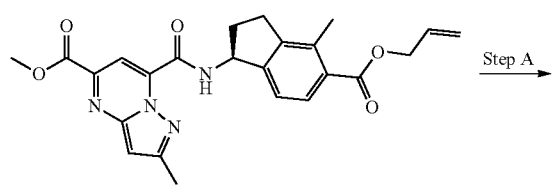

Step A

To a solution of the title compound from the Preparative Example 280, Step A (45 mg) in dioxane (3 mL) was added 1M aqueous LiOH (0.12 mL). The resulting mixture was stirred at room temperature for 2 h, adjusted to pH 2 and concentrated to give a red solid, which was used without further purification (43 mg, 99%). [MH]$^+$=435.

Preparative Example 333

Step A

A mixture of the title compound from the Preparative Example 281, Step A (23 mg) and trimethyltin hydroxide (30 mg) in 1,2-dichloroethane (2 mL) was heated at 80° C. for 3 h, concentrated, diluted with EtOAc (5 mL), washed with 10% aqueous KHSO$_4$ (5 mL) and saturated aqueous NaCl (5 mL), dried (MgSO$_4$), filtered and concentrated to afford the crude title compound (22 mg, 95%). [MH]$^+$=331.

Preparative Examples 334-372

Following similar procedures as described in the Preparative Examples 331 (method A), 332 (method B) or 333 (method C), except using the esters indicated in Table I-15 below, the following compounds were prepared.

TABLE I-15
| Prep. Ex. # | ester | product | method, yield |
|---|---|---|---|
| 334 | 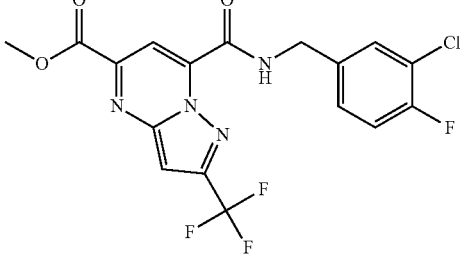 | 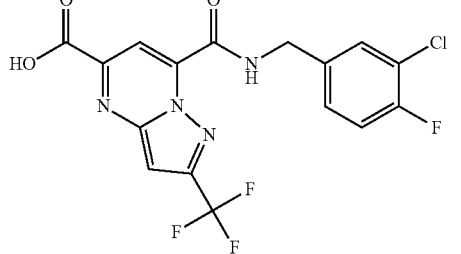 | B, >99% [MH]⁺ = 415 |
| 335 | 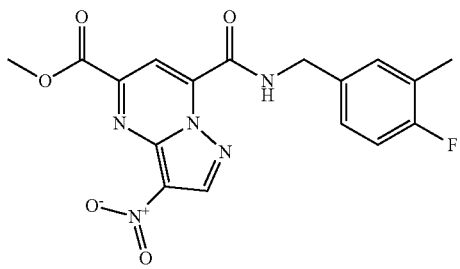 [SMILES: COC(=O)c1cc(C(=O)NCc2ccc(F)c(C)c2)n2ncc([N+](=O)[O-])c2n1] | 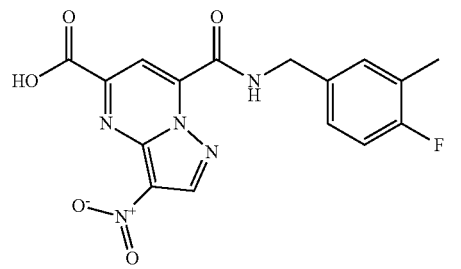 [SMILES: Cc1cc(CNC(=O)c2cc(C(=O)O)nc3c([N+](=O)[O-])cnn23)ccc1F] | C, 97% [MH]⁺ = 374 |
| 336 | 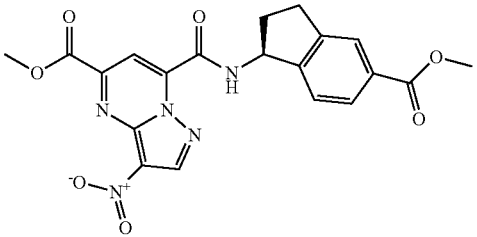 | 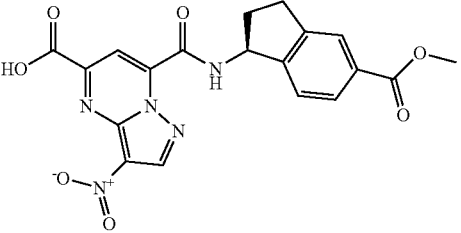 | C, 95% [MNa]⁺ = 462 |
| 337 | 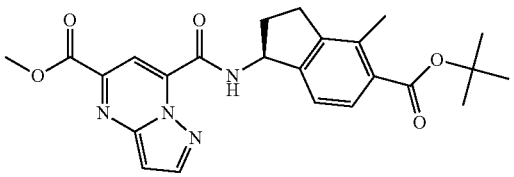 [SMILES: COC(=O)c1cc(C(=O)N[C@H]2CCc3c2ccc(C(=O)OC(C)(C)C)c3C)n2nccc2n1] | 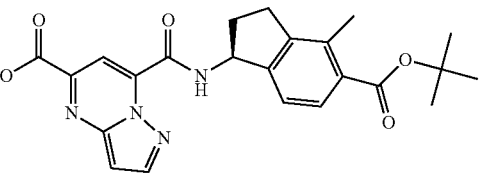 | A, 98% [MH]⁺ = 437 |
| 338 | 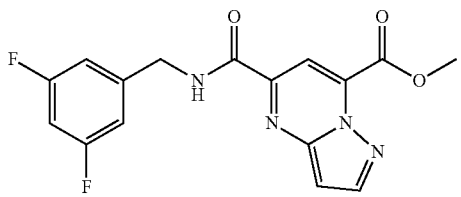 [SMILES: COC(=O)c1cc(C(=O)NCc2cc(F)cc(F)c2)nc2ccnn12] | 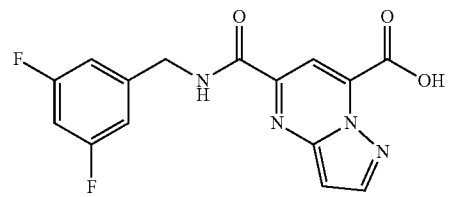 [SMILES: O=C(NCc1cc(F)cc(F)c1)c1cc(C(=O)O)n2nccc2n1] | A, 78% [MH]⁺ = 333 |
| 339 | 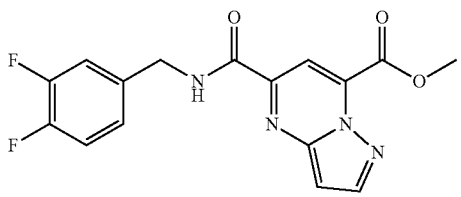 [SMILES: COC(=O)c1cc(C(=O)NCc2ccc(F)c(F)c2)nc2ccnn12] | 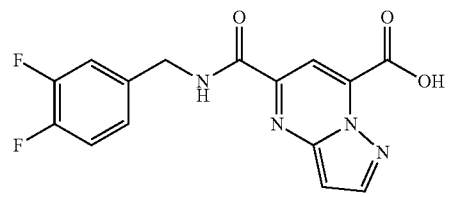 [SMILES: O=C(NCc1ccc(F)c(F)c1)c1cc(C(=O)O)n2nccc2n1] | A, 93% [MH]⁺ = 333 |

TABLE I-15-continued

| Prep. Ex. # | ester | product | method, yield |
|---|---|---|---|
| 340 | | | A, n.d. [MH]+ = 407/409 |
| 341 | | | A, 98% [MH]+ = 329 |
| 342 | | | A, 96% [MH]+ = 367 |
| 343 | | | B, 61% [MH]+ = 400 |
| 344 | | | A, 96% [MNa]+ = 477 |
| 345 | | | C, n.d. [MH]+ = 396 |
| 346 | | | B, 83% [MH]+ = 350 |

TABLE I-15-continued

| Prep. Ex. # | ester | product | method, yield |
|---|---|---|---|
| 347 | | | B, 97% [MH]⁺ = 349 |
| 348 | | | B, n.d. [MH]⁺ = 330 |
| 349 | | | A, 67% [MH]⁺ = 448 |
| 350 | | | A, 91% [MH]⁺ = 381 |
| 351 | | | A, >99% [MH]⁺ = 367 |
| 352 | | | B, 85% [MH]⁺ = 350 |
| 353 | | | A, 93% [MH]⁺ = 421 |
| 354 | | | B, 96% [MH]⁺ = 368 |

TABLE I-15-continued

| Prep. Ex. # | ester | product | method, yield |
|---|---|---|---|
| 355 | | | B, 82% [MH]+ = 386 |
| 356 | | | B, 98% [MH]+ = 455 |
| 357 | | | B, >99% [MH]+ = 330 |
| 358 | | | B, >99% [MH]+ = 489 |
| 359 | | | A, n.d. [MH]+ = 315 |
| 360 | | | A, 18% [MH]+ = 349 |
| 361 | | | B, n.d. [MH]+ = 345 |

TABLE I-15-continued

| Prep. Ex. # | ester | product | method, yield |
|---|---|---|---|
| 362 | | | C, n.d. [MH]+ = 397 |
| 363 | | | B, 61% [MH]+ = 414 |
| 364 | | | B, >99% [MH]+ = 439 |
| 365 | | | B, n.d. [MH]+ = 329 |
| 366 | | | B, n.d. [MH]+ = 329 |
| 367 | | | A, >99% [MH]+ = 383 |
| 368 | | | A, n.d. [MH]+ = 345 |

TABLE I-15-continued

| Prep. Ex. # | ester | product | method, yield |
|---|---|---|---|
| 369 | | | A, n.d. [MH]+ = 397 |
| 370 | | | A, n.d. [MH]+ = 373 |
| 371 | | | A, 95% [MH]+ = 405 |
| 372 | | | A, 95% [MH]+ = 387 |

Preparative Example 373

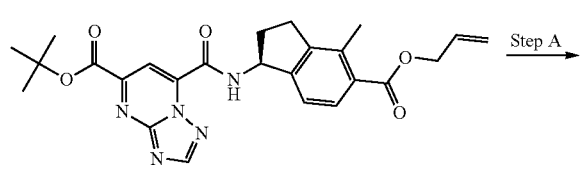 Step A

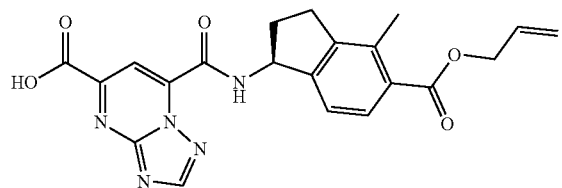

Step A

The title compound from the Preparative Example 304 (142 mg) was dissolved in trifluoroacetic acid/H$_2$O (9:1, 1.5 mL), stirred at room temperature for 1 h and concentrated by co-evaporation with toluene (3×10 mL) to yield a citreous/white solid, which was used without further purification (114 mg, 91%). [MNa]+=445.

Preparative Examples 374-375

Following a similar procedure as described in the Preparative Example 373, except using the esters indicated in Table I-16 below, the following compounds were prepared.

TABLE I-16

| Prep. Ex. # | ester | product | yield |
|---|---|---|---|
| 374 | | | >99% [MH]⁺ = 402/404 |
| 375 | | | 97% [MH]⁺ = 419 |

Preparative Example 376

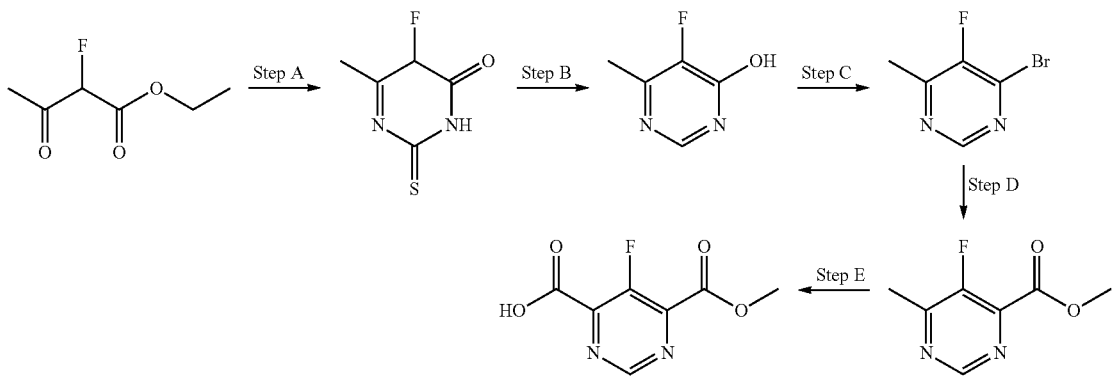

Step A

A mixture of NaOMe (5.40 g), thiourea (5.35 g) and commercially available 2-fluoro-3-oxo-butyric acid ethyl ester (6.27 mL) in anhydrous MeOH (50 mL) was stirred at 100° C. (temperature of the oil bath) for 5½ h and then allowed to cool to room temperature. The obtained beige suspension was concentrated and diluted with $H_2O$ (50 mL). To the resulting aqueous solution was added concentrated HCl (9 mL). The formed precipitate was collected by filtration and washed with $H_2O$ (100 mL) to afford the title compound as a pale beige solid (5.6 g, 70%). [MH]⁺=161.

Step B

A suspension of the title compound from Step A above (5.6 g) and Raney®-nickel (50% slurry in $H_2O$, 8 mL) in $H_2O$ (84 mL) was heated to reflux for 16 h. The mixture was allowed to cool to room temperature and then filtered. The filter cake was washed successively with MeOH and EtOAc and the combined filtrates were concentrated. The obtained viscous oily residue was diluted with EtOAc and concentrated to afford the title compound as a reddish solid (3.6 g, 80%). [MH]⁺=129.

Step C

A mixture of the title compound from Step B above (3.6 g), $K_2CO_3$ (11.6 g) and POBr₃ (24.0 g) in anhydrous $CH_3CN$ (200 mL) was heated to reflux for 19 h, cooled to room temperature and concentrated. A mixture of ice (180 g) and $H_2O$ (30 mL) was added and the mixture was stirred for 30 min. The aqueous mixture was extracted with $CHCl_3$ (2×150 mL) and EtOAc (2×150 mL) and the combined organic extracts were washed with saturated aqueous NaCl, dried ($MgSO_4$), filtered and concentrated to afford the title compound as a yellow liquid (3.15 g, 58%). [α]⁺=191/193.

Step D

Under a carbon monoxide atmosphere (7 bar) a mixture of the title compound from Step C above (2.91 g), Pd(OAc)₂ (142 mg), 1,1'-bis-(diphenylphosphino)ferrocene (284 mg) and Et₃N (4.2 mL) in anhydrous DMA/MeOH (1:1, 150 mL) was heated at 80° C. for 17 h. The mixture was cooled to room temperature, concentrated, absorbed on silica (500 mg) and purified by chromatography (silica, cyclohexane/EtOAc) to afford the title compound as a beige solid (1.53 g, 59%). [MH]⁺=171.

Step E

The title compound from Step D above (473 mg) was treated similarly as described in the Preparative Example 255, Step A to afford the title compound (514 mg, 92%). [MH]⁺=201.

Preparative Example 377

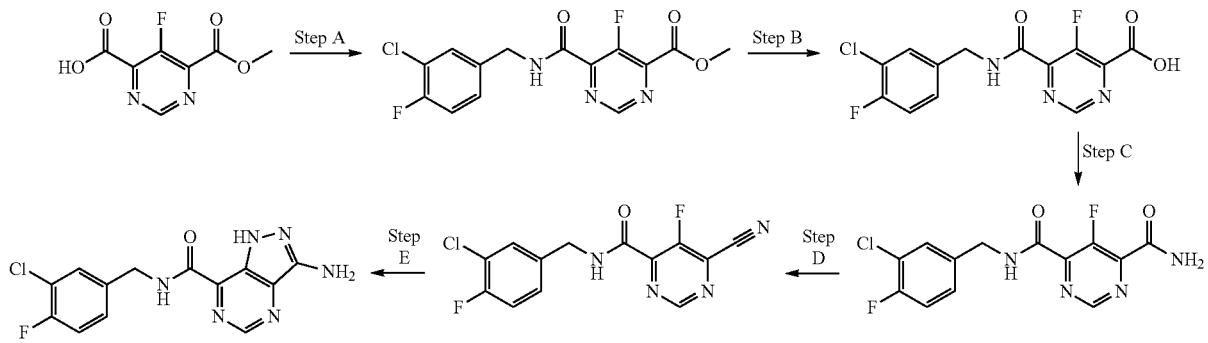 [SMILES: COC(=O)c1ncnc(C(=O)O)c1F ; COC(=O)c1ncnc(C(=O)NCc2ccc(F)c(Cl)c2)c1F ; O=C(O)c1ncnc(C(=O)NCc2ccc(F)c(Cl)c2)c1F ; Nc1n[nH]c2c(C(=O)NCc3ccc(F)c(Cl)c3)ncnc12 ; N#Cc1ncnc(C(=O)NCc2ccc(F)c(Cl)c2)c1F ; NC(=O)c1ncnc(C(=O)NCc2ccc(F)c(Cl)c2)c1F]

Step A

The title compound from the Preparative Example 376, Step E (360 mg) was treated similarly as described in the Preparative Example 279, Step A, except using commercially available 3-chloro-4-fluoro-benzylamine instead of the title compound from the Preparative Example 214, Step A to afford the title compound (195 mg, 32%). [MH]$^+$=342.

Step B

The title compound from Step A above (195 mg) was treated similarly as described in the Preparative Example 331, Step A to afford the title compound (175 mg, 93%). [MH]$^+$=328.

Step C

The title compound from Step B above (175 mg) was treated similarly as described in the Preparative Example 280, Step A, except using a commercially available 0.5M solution of NH$_3$ in 1,4-dioxane instead of the title compound from the Preparative Example 138 to afford the title compound (160 mg, 92%). [W]$^+$=327.

Step D

A 2M solution of oxalyl chloride in CH$_2$Cl$_2$ (450 µL) was diluted in DMF (8 mL) and then cooled to 0° C. Pyridine (144 µL) and a solution of the title compound from Step C above (146 mg) in DMF (2 mL) were added and the mixture was stirred at 0° C. for 3 h and then at room temperature overnight. The mixture was concentrated, diluted with EtOAc, washed with saturated aqueous NaHCO$_3$, dried (MgSO$_4$), filtered and concentrated to afford the title compound (57 mg, 41%). [MH]$^+$=309.

Step E

To a stirring solution of the title compound from Step D above (9 mg) in 1,4-dioxane (3 mL) was added a 1M solution of hydrazine hydrate in 1,4-dioxane (45 µL). The mixture was stirred at room temperature for 3 h and then concentrated to afford the title compound (10 mg, >99%). [MH]$^+$=321.

Preparative Example 378

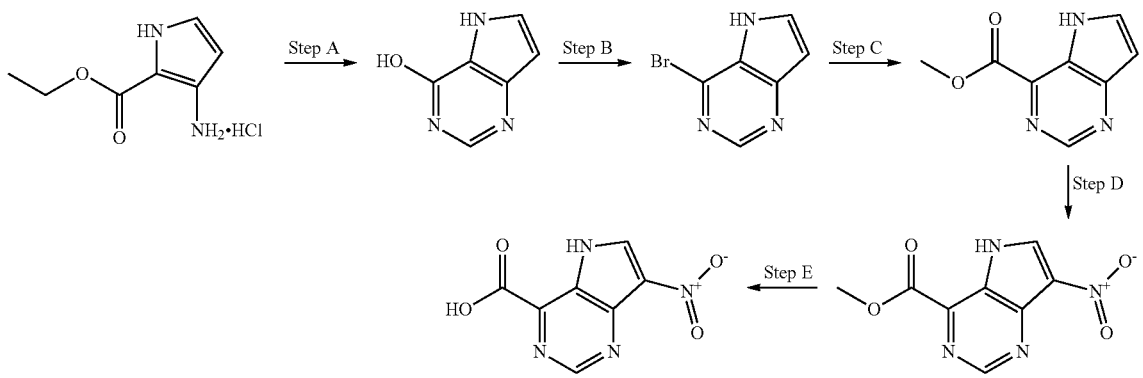

Step A

A suspension of commercially available 3-amino-1H-pyrrole-2-carboxylic acid ethyl ester hydrochloride (5.06 g) and formamidine acetate (4.20 g) in EtOH (35 mL) was heated to reflux overnight and cooled to room temperature. The formed precipitate was collected by filtration, washed with EtOH and dried to afford the title compound as colorless needles (3.65 g, >99%). [MH]$^+$=136.

Step B

A mixture of the title compound from Step A above (491 mg) and POBr$_3$ (4 g) was heated to 80° C. for 2 h. The mixture was cooled to room temperature, poured into saturated aqueous NaHCO$_3$ and extracted with CHCl$_3$. The organic extracts were concentrated and purified by chromatography (silica, CH$_2$Cl$_2$/MeOH) to afford the title compound as an off-white solid (276 mg, 38%). [MH]$^+$=198/200.

Step C

Under a carbon monoxide atmosphere (7 bar) a mixture of the title compound from Step B above (276 mg), Pd(OAc)$_2$ (13 mg), 1,1'-bis-(diphenylphosphino)ferrocene (31 mg) and Et$_3$N (370 µL) in anhydrous DMA/MeOH (1:2, 15 mL) was heated at 80° C. for 3 d. The mixture was cooled to room temperature, concentrated, absorbed on silica and purified by chromatography (silica, CH$_2$Cl$_2$/MeOH) to afford the title compound as a brown solid (260 mg, >99%). [MH]$^+$=178.

Step D

To the ice cooled title compound from Step C above (120 mg) was added concentrated HNO$_3$ (ρ=1.5, 1 mL). The mixture was stirred at 0° C. (ice bath) for 30 min, the cooling bath was removed and stirring was continued for 30 min. Ice was added and the formed precipitate was collected by filtration and dried to afford the title compound as a brown solid (87 mg, 58%). [MH]$^+$=223.

Step E

To the title compound from Step D above (87 mg) was added a solution of LiOH (47 mg) in H$_2$O. The resulting mixture was stirred for 2 h and then acidified with 1N aqueous HCl. The formed precipitate was collected by filtration and dried to afford the title compound as a brown solid (93 mg, >99%). [MH]$^+$=209.

Preparative Example 379

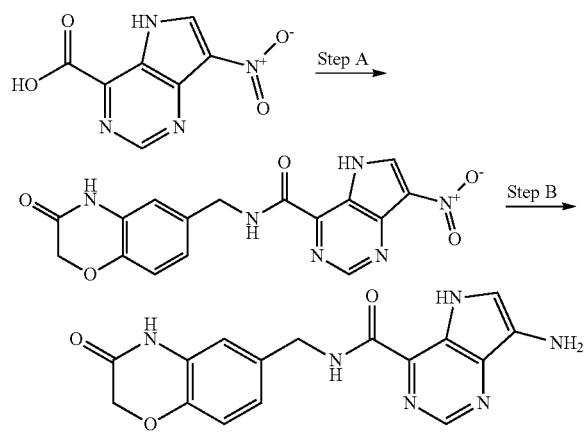

Step A

To a solution of the title compound from the Preparative 378, Step E above (93 mg) and the title compound from the Preparative Example 161 (110 mg) in DMF (5 mL) were added N-methylmorpholine (40 μL), EDCI (120 mg) and HOAt (60 mg). The mixture was stirred overnight and then concentrated. 10% aqueous citric acid was added and the formed precipitate was collected by filtration and dried to afford the title compound as a brown solid (91.5 mg, 63%). [MH]$^+$=369.

Step B

A mixture of the title compound from Step A above (91 mg), AcOH (200 μL) and Pd/C (10 wt %, 55 mg) in THF/MeOH was hydrogenated at atmospheric pressure overnight, filtered, concentrated and diluted with saturated aqueous NaHCO$_3$. The formed precipitate was collected by filtration and purified by preparative thin layer chromatography (silica, CH$_2$Cl$_2$/MeOH) to afford the title compound as a brown solid (12 mg, 9%). [MH]$^+$=339.

Preparative Example 380

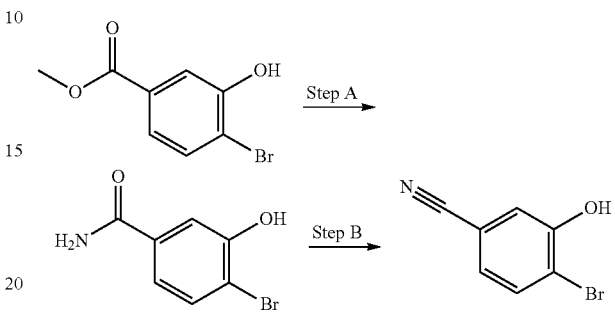

Step A

Commercially available 4-bromo-3-hydroxy-benzoic acid methyl ester (500 mg) was treated similarly as described in the Preparative Example 32, Step A to afford the title compound (475 mg, >99%). [MH]$^+$=216.

Step B

The title compound from Step A above (475 mg) was treated similarly as described in the Preparative Example 32, Step B to afford the title compound as a colorless solid (316 mg, 73%). [MH]$^+$=298.

Preparative Example 381

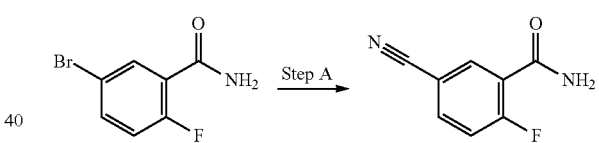

Step A

Commercially available 5-bromo-2-fluoro-benzamide (500 mg) was treated similarly as described in the Preparative Example 25, Step A to afford the title compound as colorless needles (196 mg, 52%). [MH]$^+$=165.

Preparative Example 382

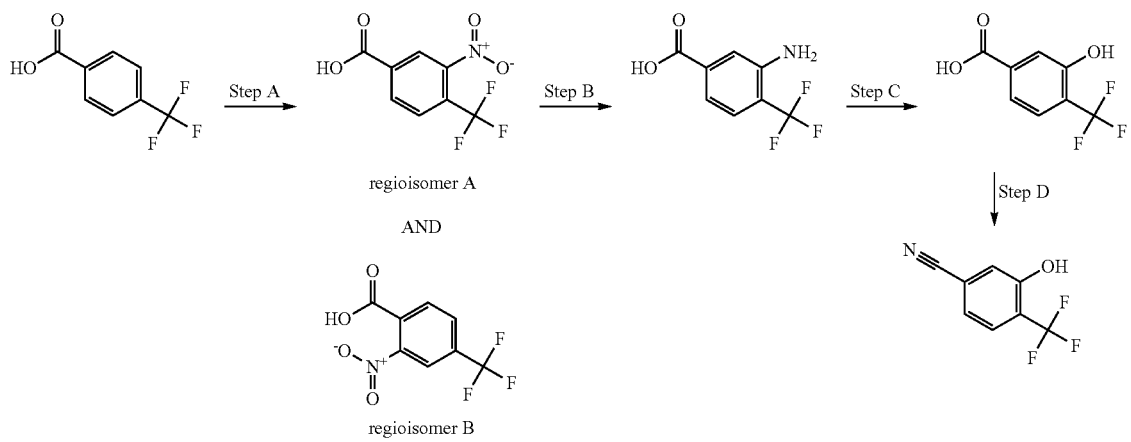

regioisomer A

AND regioisomer B

Step A

At room temperature commercially available 4-trifluoromethyl benzoic acid (4.90 g) was slowly added to a 90% solution of HNO$_3$ (10 mL). H$_2$SO$_4$ (12 mL) was added and the mixture was stirred at room temperature for 20 h. The mixture was poured on a mixture of ice (250 g) and H$_2$O (50 mL). After 30 min the precipitate was collected by filtration, washed with H$_2$O and air dried. Purification by chromatography (CH$_2$Cl$_2$/cyclohexane/AcOH) afforded the title compound as regioisomer A (2.30 g, 38%) and regioisomer B (1.44 g, 23%). $^1$H-NMR (acetone-d$_6$) regioisomer A: S=8.36 (s, 1H), 8.13-8.25 (m, 2H), regioisomer B: S=8.58 (s, 1H), 8.50 (m, 1H), 8.20 (d, 1H).

Step B

A mixture of the regioisomer A from Step A above (1.44 g) and Pd/C (10 wt %, 400 mg) in MeOH (150 mL) was hydrogenated at atmospheric pressure for 1 h and filtered. The filter cake was washed with MeOH (50 mL) and the combined filtrates were concentrated to afford the title compound (1.20 g, 95%). [MH]$^+$=206.

Step C

To a cooled to (0-5° C.) mixture of the title compound from Step B above (1.2 g) and concentrated H$_2$SO$_4$ (6 mL) in H$_2$O (34 mL) was slowly added a solution of NaNO$_3$ (420 mg) in H$_2$O (6 mL). The mixture was stirred at 0-5° C. for 45 min and then added to a mixture of H$_2$O (48 mL) and concentrated H$_2$SO$_4$ (6 mL), which was kept at 135° C. (temperature of the oil bath). The resulting mixture was stirred at 135° C. (temperature of the oil bath) for 2½ h, cooled to room temperature, diluted with ice water (50 mL) and extracted with EtOAc (2×100 mL). The combined organic phases were washed with saturated aqueous NaCl (50 mL), dried (MgSO$_4$), filtered, concentrated and purified by chromatography (silica, CH$_2$Cl$_2$/cyclohexane/AcOH) to afford the title compound (797 mg, 66%). [MH]$^+$=207.

Step D

To a cooled (−30° C.) solution of the title compound from Step C above (790 mg) and NEt$_3$ (1.4 mL) in THF (45 mL) was added ethyl chloroformate (790 µL). The mixture was stirred at −30° C. to −20° C. for 1 h and then filtered. The precipitated salts were washed with THF (20 mL). The combined filtrates were cooled to −20° C. and a 33% solution of NH$_3$ in H$_2$O (20 mL) was added. The mixture was stirred at −20° C. for 20 min, then the cooling bath was removed and the mixture was stirred at room temperature for 40 min. Then the mixture was concentrated and dissolved in THF (25 mL) and CH$_3$CN (6 mL). Pyridine (3.15 mL) was added and the mixture was cooled to 0° C. Trifluoroacetic anhydride (2.73 mL) was added and the mixture was stirred at 0° C. for 3 h. Then the mixture was concentrated in vacuo, diluted with MeOH (22 mL) and 10% aqueous K$_2$CO$_3$ (22 mL) and stirred at room temperature for 48 h. The mixture was concentrated to −20 mL, acidified (pH ~1) with 1N aqueous HCl and extracted with EtOAc (2×100 mL). The combined organic phases were dried (MgSO$_4$), filtered, concentrated and purified by chromatography (silica, CH$_2$Cl$_2$/MeOH) to afford the title compound (490 mg, 67%). [MH]$^+$=188.

Preparative Examples 383-386

Following a similar procedure as described in the Preparative Example 34, except using the nitriles indicated in Table I-17 below, the following compounds were prepared.

TABLE I-17

| Prep. Ex. # | nitrile | product | yield |
|---|---|---|---|
| 383 | | | 51% $^1$H-NMR (DMSO-d$_6$) δ = 7.78 (d, 1 H), 7.58 (t, 1 H), 7.38 (d, 1 H), 7.32 (s, 1 H), 4.25 (d, 2 H), 1.52 (s, 9 H), 1.40 (s, 9 H) |
| 384 | | | 53% [MNa]$^+$ = 324/326 |
| 385 | | | n.d. [MNa]$^+$ = 291 |
| 386 | | | n.d. [MH]$^+$ = 292 |

Preparative Examples 387-389

Following a similar procedure as described in the Preparative Example 133, except using the protected amines indicated in Table I-18 below, the following compounds were prepared.

TABLE I-18

| Prep. Ex. # | protected amine | product | yield |
|---|---|---|---|
| 387 | 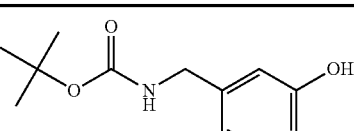 | 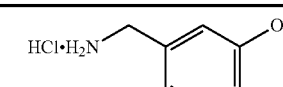 | >99% [M − Cl]⁺ = 201/203 |
| 388 | 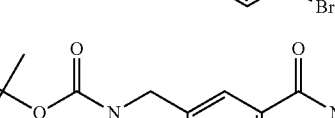 | 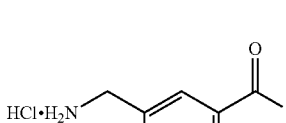 | n.d. [M − Cl]⁺ = 169 |
| 389 | 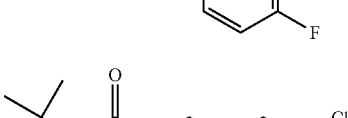 | 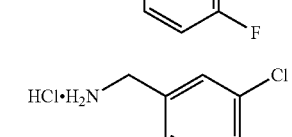 | >99% [M − Cl]⁺ = 192 |

Preparative Example 390

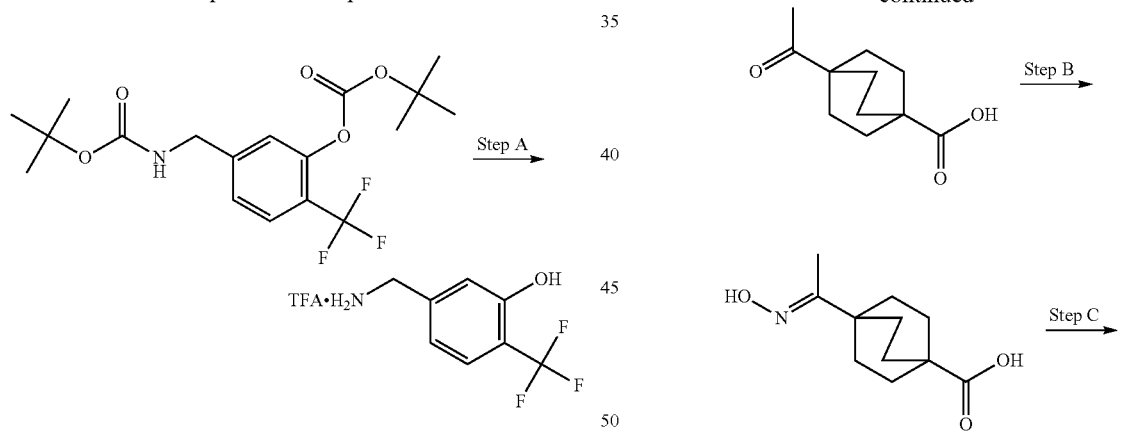

Step A

The title compound from the Preparative Example 383 (42 mg) was treated similarly as described in the Preparative Example 208, Step A to afford the title compound (32 mg, 98%). [M-TFA]⁺=165.

Preparative Example 391

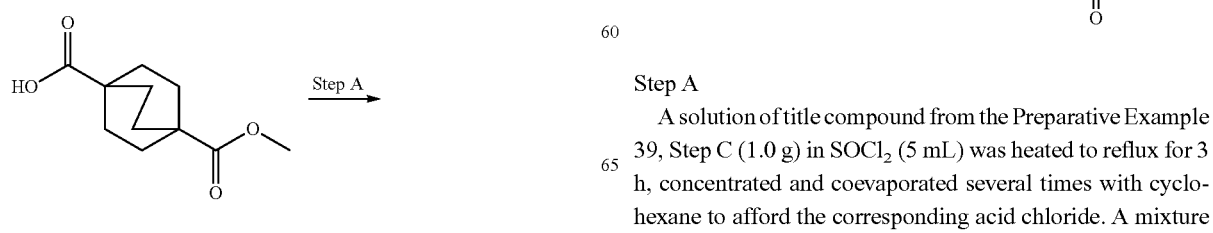

Step A

A solution of title compound from the Preparative Example 39, Step C (1.0 g) in $SOCl_2$ (5 mL) was heated to reflux for 3 h, concentrated and coevaporated several times with cyclohexane to afford the corresponding acid chloride. A mixture of magnesium turnings (127 mg) and EtOH (100 μL) in dry benzene (2 mL) was heated to reflux until the dissolution of the magnesium started. A mixture of diethyl malonate (810 μl) and EtOH (700 μL) in benzene (3 mL) was added over a period of 30 min and heating to reflux was continued for 3 h (complete dissolution of the magnesium). The EtOH was then removed by azeotropic distillation with fresh portions of benzene and the volume was brought to ~5 mL by addition of benzene. The mixture was heated to reflux, a solution of the acid chloride in benzene (5 mL) was added over a period of 30 min and heating to reflux was continued for 3½ h. The resulting viscous mixture was poured on a mixture of ice and 6N aqueous HCl. The organic phase was separated and the aqueous phase was extracted was benzene (2×10 mL). The combined organic phases were washed with $H_2O$, dried ($MgSO_4$), filtered and concentrated. The remaining residue was diluted with AcOH (25 mL) and concentrated HCl (25 mL), heated to reflux for 16 h, concentrated and purified by chromatography (silica, cyclohexane/EtOAc) to afford the title compound (665 mg, 76%). $[MH]^+$=197.

Step B

A mixture of hydroxylamine hydrochloride (807 mg) and pyridine (4.5 mL) in EtOH (4.5 mL) was heated to reflux for 5 min, the title compound from Step A above (759 mg) was added and heating to reflux was continued for 3 h. The mixture was cooled, concentrated and diluted with cold 3N aqueous HCl (30 mL). The formed precipitate was collected by filtration, washed with $H_2O$ and air dried to afford the title compound (590 mg, 72%). $[MH]^+$=212.

Step C

A mixture of the title compound from Step B above (440 mg), 6N aqueous HCl (5 mL) and $PtO_2$ (95 mg) in 90% aqueous EtOH (40 mL) was hydrogenated at atmospheric pressure for 36 h, filtered and concentrated to afford the crude title compound as a colorless solid (436 mg, 80%). $[M-Cl]^+$=226.

Preparative Examples 392-393

Following similar procedures as described in the Preparative Examples 280, except using the acids and amines indicated in Table I-19 below, the following compounds were prepared.

TABLE I-19

| Prep. Ex. # | acid, amine | product | yield |
|---|---|---|---|
| 392 | | | 69% $[MH]^+$ = 330 |
| 393 | | | 41% $[MH]^+$ = 429 |

Preparative Examples 394-395

Following similar procedures as described in the Preparative Examples 331, except using the esters indicated in Table I-20 below, the following compounds were prepared.

TABLE I-20

| Prep. Ex. # | ester | product | yield |
|---|---|---|---|
| 394 | | | 95% [MH]⁺ = 316 |
| 395 | | | 95% [MH]⁺ = 415 |

The Preparative Example numbers 396 to 804 were intentionally excluded.

Preparative Example 805

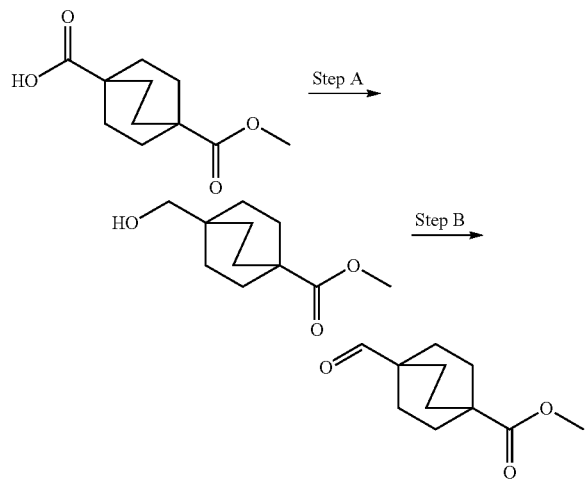

Step A

To a cooled (−40° C.) solution of the title compound from the Preparative Example 39, Step C (1.0 g) and NEt₃ (890 µL) in THF (50 mL) was slowly added ethyl chloroformate (490 µL). The mixture was stirred at −25° C. for 1 h and then filtered. The precipitated salts were washed with THF (40 mL). The combined filtrates were cooled to 0° C. and a solution of NaBH₄ (528 mg) in H₂O (9.4 mL) was added carefully. The mixture was stirred at 0° C. for 45 min, the cooling bath was removed and stirring was continued at room temperature for 45 min. Then the mixture was diluted with saturated aqueous NaHCO₃ (40 mL) and saturated aqueous NaCl (40 mL). The organic phase was separated, dried (MgSO₄), filtered, concentrated and purified by chromatography (silica, CH₂Cl₂/acetone) to afford the title compound (910 mg, 97%). [MH]⁺=199.

Step B

To a mixture of the title compound from Step A above (20 mg) in CH₂Cl₂ (2 ml) was added IBX-polystyrene (500 mg) and the mixture was stirred at room temperature for 5 h, filtered and concentrated to afford the title compound (19 mg, 97%). [MH]⁺=197.

The Preparative Example numbers 806 to 835 and the Table numbers 1-21 to 11-30 were intentionally excluded.

Preparative Example 836

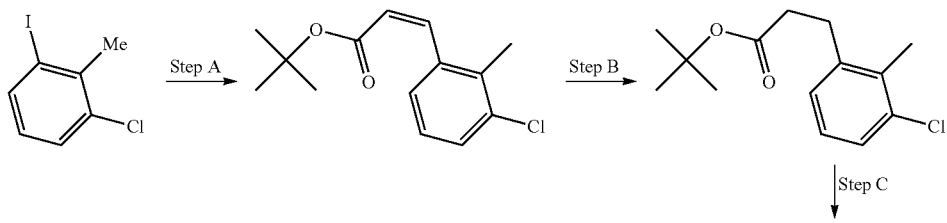

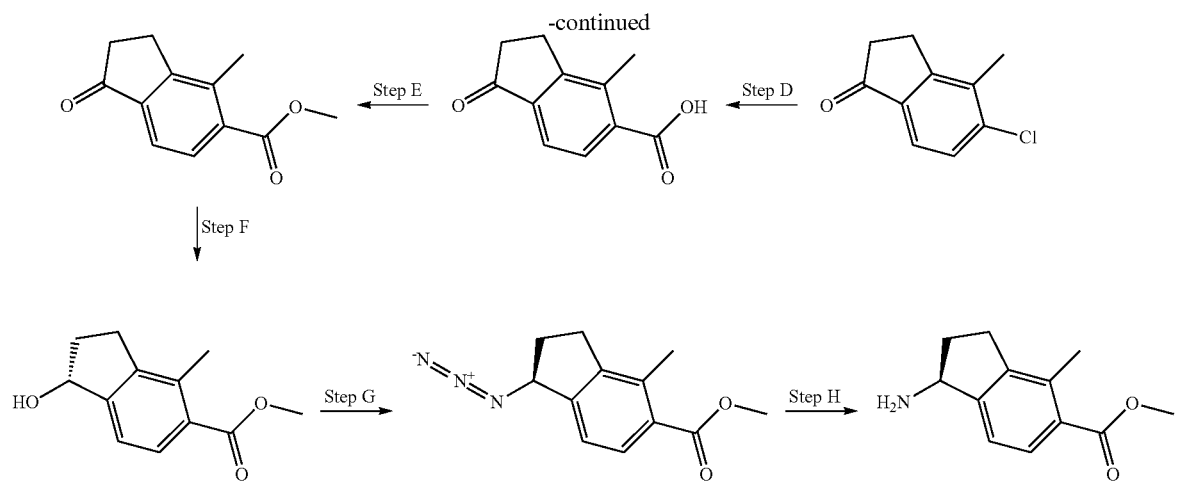

Step A

To a mixture of the commercial available 1-chloro-3-iodo-2-methylbenzene (2 52 g), tert.-butyl acrylate (4.35 mL) and NaOAc (1.65 g) in DMF (10 mL) was added Ru/Al$_2$O$_3$ (5 wt %, 1.00 g). The reaction mixture was stirred at 150° C. for 12 h, extracted with EtOAc and Et$_2$O, washed with H$_2$O, dried (MgSO$_4$), filtered and concentrated. The remaining residue was purified by short pad filtration (silica, cyclohexane/EtOAc) to afford the title compound as a liquid (2.40 g, 95%). [MH]$^+$=253.

Step B

A mixture of the title compound from Step A above (2.4 g) and Pt/C (10 wt %, 200 mg) in MeOH (10 mL) was hydrogenated at 1.5 bar overnight, filtered and concentrated. The remaining residue was purified by short pad filtration (silica, CH$_2$Cl$_2$/MeOH) to afford the title compound as a liquid (2.39 g, 95%). [MH]$^+$=255.

Step C

To a solution of the title compound from Step B above (2.1 g) in CH$_2$Cl$_2$ (300 mL) was added dropwise pure CSA (2.5 mL) The resulting mixture was stirred at room temperature for 3 h, concentrated, diluted with EtOAc and Et$_2$O and carefully added to ice water. The organic phase was separated, washed with saturated aqueous NaHCO$_3$ and saturated aqueous NaCl, dried (MgSO$_4$), filtered and concentrated to afford the title compound as a white solid (1.26 g, 85%). [NH]$^+$=181.

Step D

Under an argon atmosphere a pressure reactor was charged with the title compound from Step C above (1.0 g), Na$_2$CO$_3$ (1.1 g), Pd(OAc)$_2$ (120 mg), H$_2$O (2 mL), dppp (410 mg) and DMA (20 mL). The reactor was purged with carbon monoxide, the reactor pressure was adjusted to 1 bar and placed in a preheated oil bath (135° C.). The reactor vessel was pressurized with carbon monoxide (6 bar) and heating to 135° C. was continued overnight. The resulting mixture was cooled to room temperature, purged with argon, diluted with H$_2$O (15 mL) and hexane (15 mL) and stirred at room temperature for 15 min. Activated carbon was added and stirring at room temperature was continued for 20 min. The mixture was filtered through a pad Celite®, adjusted to pH=1-2 and extracted with EtOAc. The combined organic phases were dried (MgSO$_4$), filtered, concentrated and slurried in Et$_2$O. Filtration and drying in vacuo afforded the title compound (840 mg, 80%). [MH]$^+$=191.

Step E

A mixture of the title compound from Step D above (100 g) and Na$_2$CO$_3$ (55.7 g) in DMF (500 mL) was stirred at room temperature for 18 h and then quenched at 0-5° C. (ice bath) with H$_2$O (600 mL). The formed precipitate was collected by filtration, washed with H$_2$O (2×200 mL), dissolved in CH$_2$Cl$_2$, washed with H$_2$O, dried (MgSO$_4$), filtered and concentrated to afford the title compound (91 mg, 85%). [MH]$^+$=205.

Step F

A solution of the title compound from Step E above (21.7 g) in CH$_2$Cl$_2$ (50 mL) was added over a 10 h period to a cooled (−20° C.) mixture of a 1M solution of (S)-(−)-2-methyl-CBS-oxazaborolidine in toluene (21.2 mL) and a 1M solution of BH$_3$.Me$_2$S complex in CH$_2$Cl$_2$ (107 mL) in CH$_2$Cl$_2$ (150 mL). The mixture was then quenched at −20° C. by addition of MeOH (210 mL), warmed to room temperature and concentrated. The obtained solid residue was dissolved in CH$_2$Cl$_2$ (210 mL), washed with 1M aqueous H$_3$PO$_4$ (2×100 mL), saturated aqueous NaHCO$_3$ (100 mL) and saturated aqueous NaCl (100 mL), dried (MgSO$_4$), filtered and concentrated to afford the title compound (21 g, 96%, ~99% ee). [MH]$^+$=207.

Step G

To an cooled (0° C.) mixture of the title compound from Step F above (50 g) and diphenylphosphoryl azide (70 mL) in toluene was added DBU (55 mL). The resulting mixture was stirred at 0° C. for 2 h and then at 20° C. for 16 h. The resulting biphasic mixture was washed with H$_2$O (750 mL), 1M aqueous H$_3$PO$_4$ (650 mL), saturated aqueous NaHCO$_3$ (650 mL) and saturated aqueous NaCl (650 mL), dried (MgSO$_4$) and filtered. The obtained filtrate was agitated with charcoal (25 g), filtered and concentrated to afford the crude title compound. [MH]$^+$=232.

Step H

A mixture of the title compound from Step G above (2.5 g) and Pt/C (10 wt %, 250 mg) in toluene (78 mL) was hydrogenated at 200 psi for 21 h, filtered through Celite® and extracted with 1M aqueous HCl. The aqueous phase was washed with EtOAc, basified with 1M aqueous K$_3$PO$_4$ (400 ml), extracted with CH$_2$Cl$_2$ (2×50 mL), dried (MgSO$_4$), filtered and concentrated to afford the title compound (1.8 g, 81%, 98.8% ee). [MH]$^+$=206.

Preparative Example 837

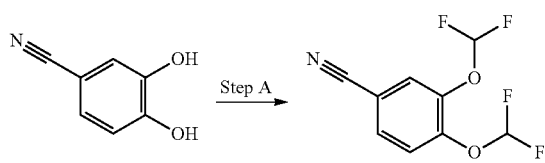 [SMILES: N#Cc1ccc(O)c(O)c1 ; N#Cc1ccc(OC(F)F)c(OC(F)F)c1]

Step A

A suspension of commercially available 3,4-dihydroxybenzonitrile (2.00 g) and Na$_2$CO$_3$ (4.91 g) in dry DMF (50 mL) was stirred at room temperature for 16 h. Into this mixture was condensed commercially available chlorodifluoromethane (~50 g) using a dry ice condenser. The resulting slurry was stirred at 160° C. (temperature of the oil bath) for 5 h, cooled and stirred at room temperature overnight without condenser. The mixture was concentrated, diluted with EtOAc, washed with 5% aqueous NaOH, dried (MgSO$_4$), filtered, concentrated and purified by chromatography (silica, cyclohexane/EtOAc) to afford the title compound as an oil (49 mg, 1%). [MH]$^+$=236.

Preparative Example 838

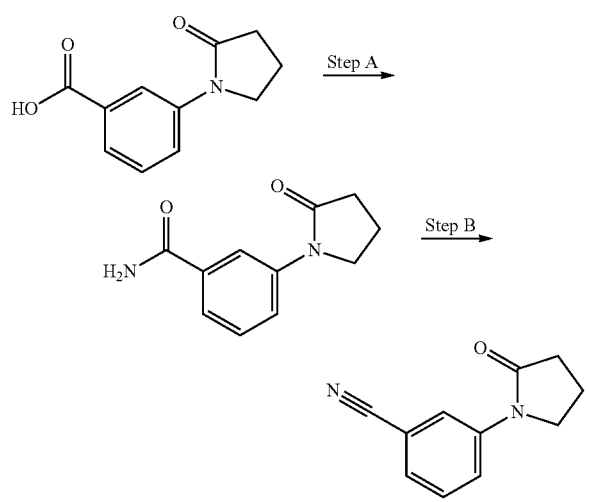

Step A

To a suspension of commercially available 3-(2-oxopyrrolidin-1-yl)benzoic acid (500 mg) in CH$_2$Cl$_2$ (10 mL) was added a 2M solution of oxalyl chloride in CH$_2$Cl$_2$ (1.83 mL). The resulting mixture was stirred at room temperature for 4 h and then concentrated to dryness. A 0.5M solution of NH$_3$ in 1,4-dioxane (20 mL) was added and stirring at room temperature was continued for 16 h. The resulting mixture was diluted with 1,4-dioxane (20 mL), filtered and concentrated to afford the title compound (374 mg, 75%). [MH]$^+$=205.

Step B

To a suspension of the title compound from Step A above (376 mg) in CH$_2$Cl$_2$ (8 mL) was added trifluoroacetic anhydride (566 µL). The resulting mixture was stirred at room temperature for 2 d, an additional portion of trifluoroacetic anhydride (566 µL) was added and stirring at room temperature was continued for 1 d. The mixture was concentrated and purified by chromatography (silica, CH$_2$Cl$_2$/MeOH) to afford the title compound (63.1 mg, 18%). [MH]$^+$=187.

Preparative Example 839

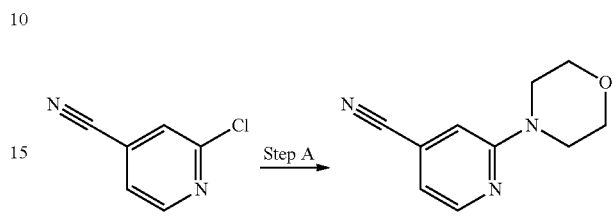

Step A

In a sealed pressure tube a mixture of commercially available 2-chloropyridine-4-carbonitrile (1.00 g) in morpholine (30 mL) was heated to 130° C. for 13 h. The resulting mixture was concentrated and purified by chromatography (silica, CHCl$_3$/MeOH) to afford the title compound (256 mg, 19%). [MH]$^+$=190.

Preparative Example 840

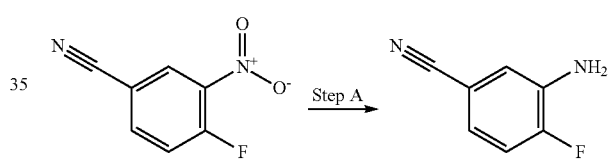

Step A

A mixture of commercially available 4-fluoro-3-nitro-benzonitrile (1.5 g) and Pd/C (10 wt %, 400 mg) in EtOH (10 mL) was hydrogenated at atmospheric pressure overnight, filtered and concentrated to afford the title compound (1.2 g, >99%.) [MH]$^+$=137.

Preparative Example 841

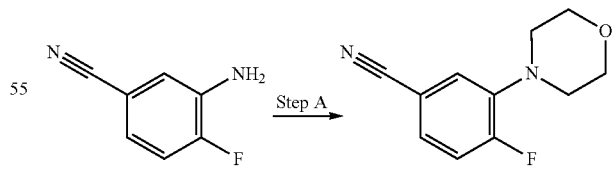

Step A

A mixture of the title compound from the Preparative Example 840, Step A (566 mg), $^i$Pr$_2$NEt (2.15 mL) and commercially available 1-(2-bromoethoxy)-2-bromoethane (627 µL) was stirred at 100° C. for 16 h and at 140° C. for 6 h. An additional portion of 1-(2-bromoethoxy)-2-bromoethane (627 µL) was added and stirring was continued at 160° C. for 6 h. The resulting mixture was concentrated and purified by chromatography (silica, CHCl$_3$/MeOH) to afford the title compound. [MH]$^+$=207.

Preparative Example 842

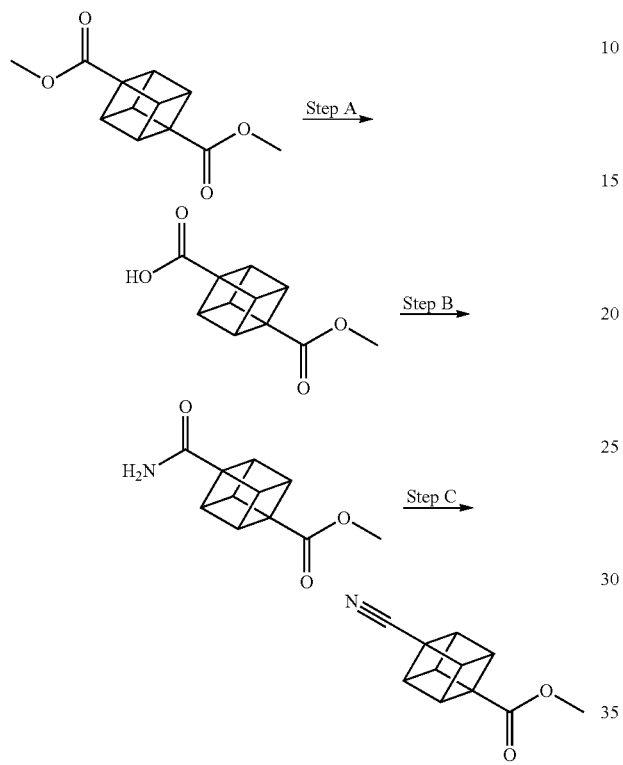

Step A

A mixture of the commercially available cubane-1,4-dicarboxylic acid dimethyl ester (1.65 g) and KOH (300 mg) in MeOH/H$_2$O (10:1, 11 mL) was heated to reflux overnight, cooled to room temperature, concentrated, diluted with EtOAc and extracted with 1N aqueous NaOH (2×10 mL). The combined aqueous phases were adjusted to pH 1-2 with 2N aqueous HCl and extracted with EtOAc (4×25 mL). The combined turbid organic phases were filtered through a fluted filter, washed with saturated aqueous NaCl, dried (MgSO$_4$), filtered and concentrated to give the title compound as a colorless solid (500 mg, 32%). [MH]$^+$=207.

Step B

To a cooled (−40° C.) solution of the title compound from Step A above (490 mg) and NEt$_3$ (400 μL) in THF (20 mL) was slowly added ethyl chloroformate (240 μL). The mixture was allowed to warm to −25° C. and stirred at this temperature for h. A 0.5N solution of NH$_3$ in 1,4-dioxane (5.5 mL) was added and the mixture was stirred at −20° C. for 30 min. The cooling bath was removed and stirring was continued for 15 min. The mixture was concentrated diluted H$_2$O (10 mL) and extracted with CH$_2$Cl$_2$ (1×20 mL, 2×10 mL). The combined organic phases were washed with saturated aqueous NaCl (10 mL), dried (MgSO$_4$), filtered and concentrated to afford the title compound (208 mg, 42%). [MH]$^+$=206.

Step C

DMF (10 mL) was cooled to 0-5° C. (ice bath) and a 2M solution of oxalyl chloride in CH$_2$Cl$_2$ (650 μL) was added followed by a solution of the title compound from Step B above (208 mg) in DMF (10 mL). The resulting mixture was stirred at 0-5° C. (ice bath) for 5 h, diluted with EtOAc, washed with saturated aqueous NaHCO$_3$, dried (MgSO$_4$), filtered and concentrated to afford the title compound (140 mg, 75%). [MH]$^+$=188.

Preparative Example 843

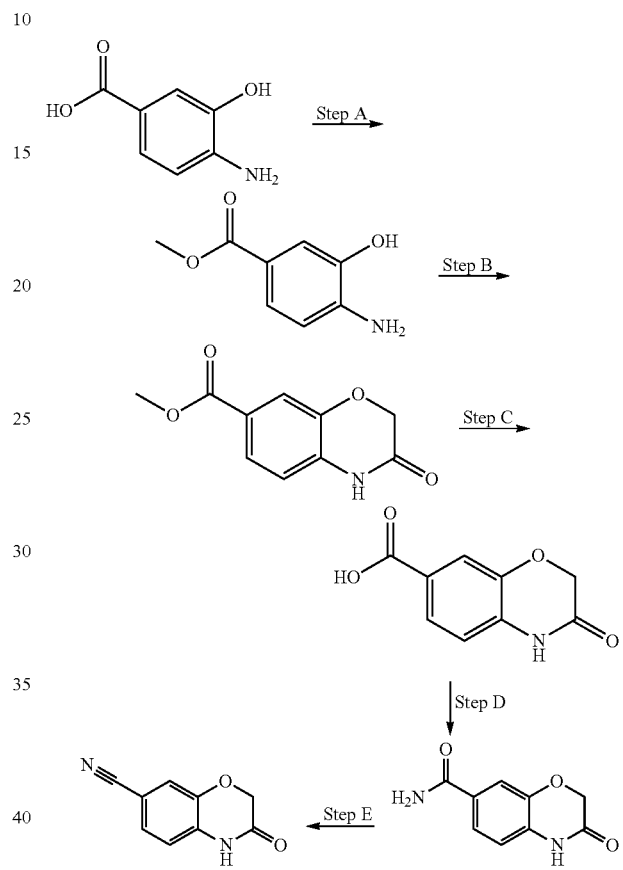

Step A

To an ice cooled (0-5° C.) suspension of commercially available 4-amino-3-hydroxybenzoic acid (5 g) in MeOH (50 mL) was dropwise added thionyl chloride (10.9 mL). The ice bath was removed and the mixture was stirred at room temperature for 12 h, before it was concentrated to afford the title compound as a solid (5.34 g, >99%). [MH]$^+$=168.

Step B

To a mixture of the title compound from Step A above (5.34 g) and NaHCO$_3$ (10 g) in acetone/H$_2$O (1:1, 120 mL) was slowly added 2-bromopropionyl bromide (3 mL). The resulting mixture was heated to reflux for 2 h, cooled and stirred at 25° C. overnight. The formed precipitate was collected by filtration and washed several times with H$_2$O to afford the title compound (3.6 g, 50%). [MH]$^+$=208.

Step C

To a solution of the title compound from Step B above (3.55 g) in THF/MeOH (2:1, 120 mL) was added 1M aqueous LiOH (50 mL). The resulting mixture was stirred at room temperature for 24 h, adjusted to pH 2 with 1M aqueous HCl and concentrated. The formed precipitate was collected by filtration and washed with H$_2$O to afford the crude title compound, which used without further purification (3.0 g, 90%). [MH]$^+$=194.

Step D

To an ice cooled (0-5° C.) solution of the title compound from Step C above (1.00 g) in DMF (10 mL) was added 1,1'-carbonyldiimidazole (1.44 g). The resulting solution was stirred at 0-5° C. (ice bath) for 50 min, then a 0.5M solution of NH$_3$ in 1,4-dioxane (20 mL) was added, the ice bath was removed and the mixture was stirred at room temperature overnight. The formed precipitate was collected by filtration and washed with H$_2$O and dried in vacuo to afford the title compound (795 mg, 80%). [MH]$^+$=193.

Step E

DMF (10 mL) was cooled to 0-5° C. (ice bath) and a 2M solution of oxalyl chloride in CH$_2$Cl$_2$ (2.5 mL) was added followed by a solution of the title compound from Step D above (795 mg) in DMF (10 mL). The resulting mixture was stirred at 0-5° C. (ice bath) for 5 h, diluted with EtOAc, washed with saturated aqueous NaHCO$_3$, dried (MgSO$_4$), filtered and concentrated to afford the title compound (140 mg, 90%). [MH]$^+$=175.

Preparative Example 844

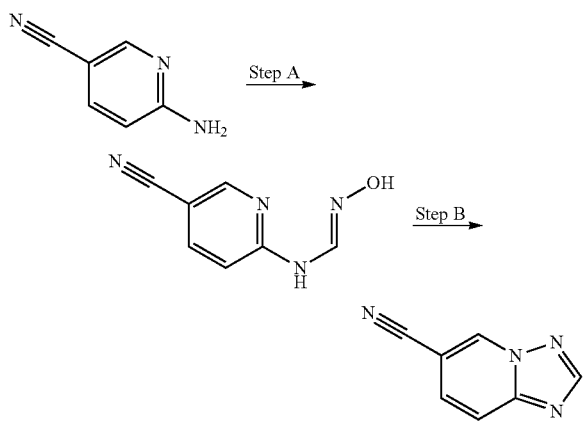

Step A

At room temperature dimethylformamide dimethyl acetal (3 5 mL) was added to a solution of the commercially available 2-amino-5-cyanopyridine (2.4 g) in $^i$PrOH (10 mL). The resulting mixture was heated to reflux for 3 h and then cooled to 50° C. Hydroxylamine hydrochloride (1.8 g) was added and the mixture was aged under sonication at 50° C. for 6 h. All volatile components were evaporated and the remaining residue was purified by chromatography (silica, EtOAc/MeOH) to afford the title compound (2.6 g, 80%). [MH]$^+$=163.

Step B

To an ice cooled (0-5° C.) solution of the title compound from Step A above (2.6 g) in 1,4-dioxane/DMF (1:1, 60 mL) trifluoroacetic anhydride (2.5 mL) was slowly added over a period of 10 min, keeping the internal temperature below 20° C. After the complete addition the ice bath was removed and the mixture was heated to 90° C. for 48 h. The mixture was cooled, concentrated and purified by chromatography (silica, EtOAc/MeOH) to afford the title compound (322 mg, 11%). [MH]$^+$=145.

Preparative Example 845

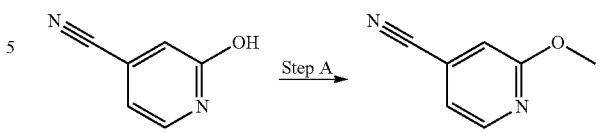

Step A

To a cooled (−78° C.) solution of the commercial available 2-hydroxy-isonicotinonitrile (1.08 g) in THF/DMF (1:1, 40 mL) was added NaH (260 mg) in portions. The mixture was stirred at −25° C. for 2 h and then cooled to −78° C. again. Iodomethane (680 µL) was added, the cooling bath was removed and the mixture was stirred at room temperature overnight. The mixture was diluted with EtOAc, washed with 10% aqueous KHSO$_4$ (10 mL) and saturated aqueous NaCl (20 mL), dried (MgSO$_4$), filtered, concentrated and purified by chromatography (silica, CH$_2$Cl$_2$/acetone) to afford the title compound (600 mg, 49%). [MH]$^+$=135.

Preparative Example 846

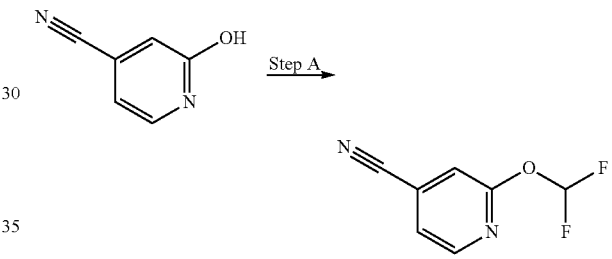

Step A

Commercially available chlorodifluoromethane was passed through a cooled (−78° C.) suspension of the commercial available 2-hydroxy-isonicotinonitrile (230 mg) and Cs$_2$CO$_3$ (650 mg) in 1,2-dichloroethane/DMA (10:1, 11 mL) for 30 min. The reaction vessel was sealed and—using a microwave—the chlorodifluoromethane saturated mixture was heated at 150° C. for 5 h. Then the mixture was cooled to room temperature, diluted with CHCl$_3$ (20 mL), washed with H$_2$O (10 mL) and saturated aqueous NaCl (20 mL), dried (MgSO$_4$), filtered and concentrated to afford the crude title compound (200 mg, 55%). [MH]$^+$=171.

Preparative Example 847

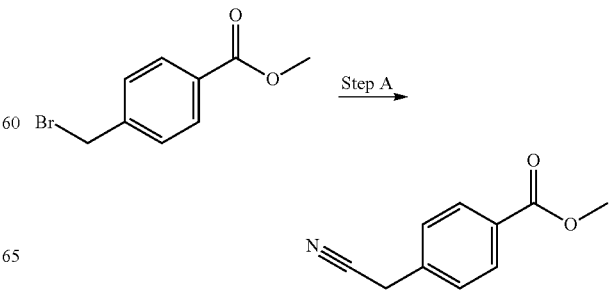

Step A

A mixture of commercially available 4-bromomethyl-benzoic acid methyl ester (500 mg) and KCN (354 mg) in DMA (9 mL) was stirred at 60-70° C. (temperature of the oil bath) overnight, concentrated and diluted with Et$_2$O (200 mL) and H$_2$O (80 mL). The organic phase was separated, washed with H$_2$O (2×80 mL), dried (MgSO$_4$), filtered, concentrated and purified by chromatography (silica, cyclohexane/EtOAc) to afford the title compound (273 mg, 71%). [MH]$^+$=176.

Preparative Examples 848-854

Following a similar procedure as described in the Preparative Example 25, except using the intermediates indicated in Table I-31 below, the following compounds were prepared.

TABLE I-31

| Prep. Ex. # | intermediate | product | yield |
|---|---|---|---|
| 848 | | | n.d. [MH]$^+$ = 144 |
| 849 | | | [MH]$^+$ = 144 |
| 850 | | | 67% [MH]$^+$ = 175 |
| 851 | | | n.d. |
| 852 | | | 61% [MH]$^+$ = 161 |
| 853 | | | n.d. |
| 854 | | | 93% [MH]$^+$ = 175 |

Preparative Examples 855-859

Following a similar procedure as described in the Preparative Example 37, except using the intermediates and reagents indicated in Table I-32 below, the following compounds were prepared.

TABLE I-32

| Prep. Ex. # | intermediate, reagent | product | yield |
|---|---|---|---|
| 855 | | | 99% [MH]+ = 175 |
| 856 | | | 73% [MH]+ = 189 |
| 857 | | | 22% [MH]+ = 203 |
| 858 | | | 80% [MH]+ = 203 |
| 859 | | | n.d. [MH]+ = 217 |

Preparative Example 860

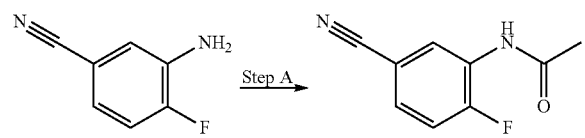

Step A

A solution of the title compound from the Preparative Example 840, Step A (100 mg) in acetic anhydride (3 mL) was stirred at room temperature for 2 h, concentrated and purified by chromatography (silica, cyclohexane/EtOAc) to afford the title compound as a white solid (77.6 mg, 60%). [MH]+=179.

Preparative Example 861

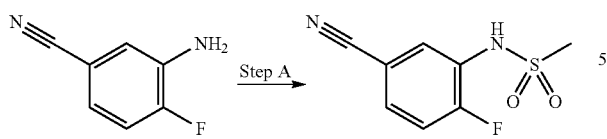

Step A

To an ice cooled (0-5° C.) solution of the title compound from the Preparative Example 840, Step A (100 mg) in pyridine (2 mL) was added methanesulfonyl chloride (67.8 μL). The resulting mixture was stirred overnight while warming to room temperature, cooled to 0-5° C. (ice bath) again, neutralized with 1M aqueous HCl, diluted with $H_2O$ and extracted with EtOAc. The combined organic phases were dried ($MgSO_4$), filtered, concentrated and purified by chromatography (silica, cyclohexane/EtOAc) to afford the title compound as a colorless solid (47.4 mg, 30%). $[MH]^+=215$.

Preparative Example 862

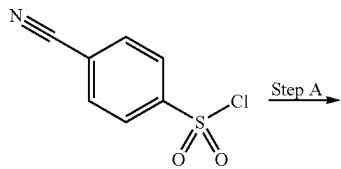

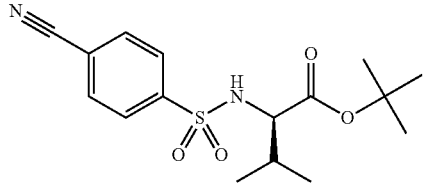 [SMILES: CC(C)[C@@H](NS(=O)(=O)c1ccc(C#N)cc1)C(=O)OC(C)(C)C]

Step A

To a mixture of morpholinomethyl polystyrene (295 mg) in 1,2-dichlorethane (1 mL) were added commercially available 4-cyanobenzene-1-sulfonylchloride (50 mg) and commercially available 2-amino-3-methyl-butyric acid tert.-butyl ester hydrochloride (52 mg). The mixture was agitated at room temperature overnight, filtered and concentrated to afford the title compound as pale yellow solid, which was used without further purification. (75 mg, 90%). $[MH]^+=339$.

Preparative Examples 863-867

Following a similar procedure as described in the Preparative Example 862, except using the acids and acid chlorides indicated in Table I-33 below, the following compounds were prepared.

TABLE I-33

| Prep. Ex. # | amine, acid chloride | product | yield |
|---|---|---|---|
| 863 | | | 92% $[MH]^+ = 339$ |
| 864 | | | 88% $[MH]^+ = 339$ |

TABLE I-33-continued

| Prep. Ex. # | amine, acid chloride | product | yield |
|---|---|---|---|
| 865 | 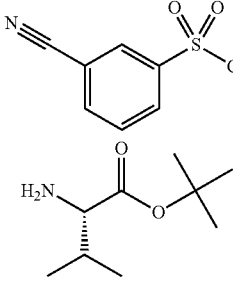 | 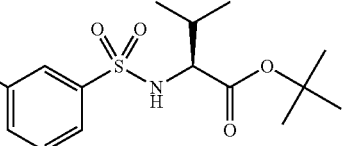 | 88% [MH]$^+$ = 339 |
| 866 | 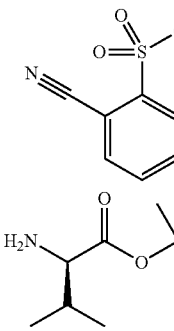 | 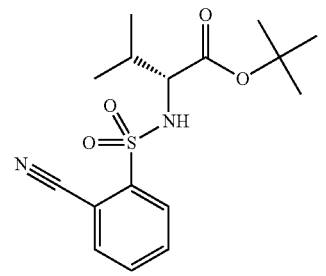 [SMILES: CC(C)[C@@H](NS(=O)(=O)c1ccccc1C#N)C(=O)OC(C)(C)C] | 88% [MH]$^+$ = 339 |
| 867 | 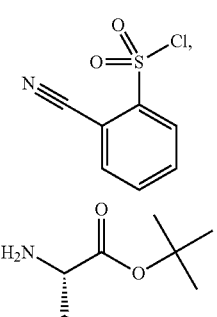 | 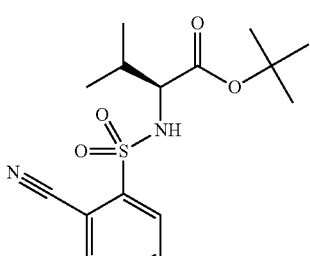 | 87% [MH]$^+$ = 339 |

Preparative Example 868

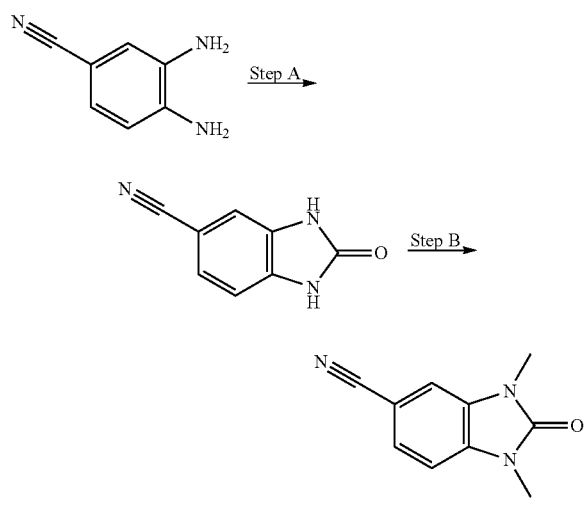

Step A

Commercially available 3,4-diamino-benzonitrile (1.02 g) was treated similarly as described in the Preparative Example 213, Step A to afford the title compound as a brown solid (1.18 g, 97%). [MH]$^+$=160.

Step B

Title compound from Step A above (1.18 g) was treated similarly as described in the Preparative Example 213, Step B to afford the title compound as an off-white solid (1.14 g, 80%). [MH]$^+$=188.

Step C

The title compound from Step A above (1.32 g) was treated similarly as described in the Preparative Example 213, Step C to afford the title compound as a white solid (496 mg, 38%). [MH]$^+$=191.

Step D

The title compound from Step C above (1.32 g) was treated similarly as described in the Preparative Example 213, Step D to afford the title compound as white crystals (264 mg, >99%). [M-Cl]$^+$=165.

Preparative Example 869

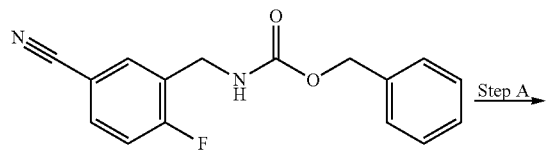

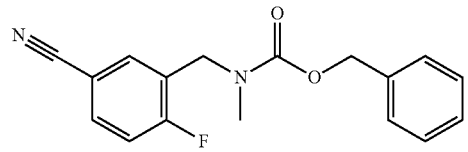 [SMILES: N#Cc1ccc(F)c(CNC(=O)OCc2ccccc2)c1]

Step A

To an ice cooled (0-5° C.) solution of the title compound from the Preparative Example 29 (1.10 g) in DMF (8 mL) were added NaH (102 mg) and iodomethane (500 μL). The ice bath was removed and the resulting mixture was stirred at room temperature overnight, concentrated and diluted with H$_2$O and extracted with EtOAc. The organic phase was separated, dried (MgSO$_4$), filtered and concentrated to afford the title compound (1.02 g, 88%). [MH]$^+$=299

Preparative Examples 870-901

Following a similar procedure as described in the Preparative Example 34, except using the nitriles indicated in Table I-34 below, the following compounds were prepared.

TABLE I-34

| Prep. Ex. # | nitrile | product | yield |
|---|---|---|---|
| 870 | | | 69% (over 2 steps) [MH]$^+$ = 248 |
| 871 | | | n.d. [MH]$^+$ = 248 |
| 872 | | | 25% [MNa]$^+$ = 362 |
| 873 | | | 66% [MNa]$^+$ = 313 |
| 874 | | | n.d. [MH]$^+$ = 294 |
| 875 | | | 53% [MH]$^+$ = 311 |

TABLE I-34-continued

| Prep. Ex. # | nitrile | product | yield |
|---|---|---|---|
| 876 | | | 42% [MH]+ = 279 |
| 877 | | | 50% [MH]+ = 292 |
| 878 | | | 35% [MH]+ = 301 |
| 879 | | | 50% [MH]+ = 271 |
| 880 | | | 70% [MH]+ = 278 |
| 881 | | | n.d. [MNa]+ = 261 |
| 882 | | | n.d. [MNa]+ = 297 |
| 883 | | | 50% (over 2 steps) [MNa]+ = 298 |

TABLE I-34-continued

| Prep. Ex. # | nitrile | product | yield |
|---|---|---|---|
| 884 | | | 40% ¹H-NMR (CDCl₃) δ = 7.96 (d, 2 H), 7.24 (d, 2 H), 4.98 (br s, 1 H), 3.90 (s, 3 H), 3.30-3.40 (m, 2 H), 2.82 (t, 2 H), 1.40 (s, 9 H). |
| 885 | | | 99% [MNa]⁺ = 274 |
| 886 | | | 45% [MH]⁺ = 443 |
| 887 | | | 62% [MH]⁺ = 443 |
| 888 | | | 49% [MH]⁺ = 443 |
| 889 | | | 68% [MH]⁺ = 443 |
| 890 | | | 62% [MH]⁺ = 443 |

TABLE I-34-continued

| Prep. Ex. # | nitrile | product | yield |
|---|---|---|---|
| 891 | | | 64% [MH]⁺ = 443 |
| 892 | | | 89% [MH]⁺ = 279 |
| 893 | | | 52% [MH]⁺ = 293 |
| 894 | | | >99% [MH]⁺ = 307 |
| 895 | | | 53% [MNa]⁺ = 329 |
| 896 | | | 81% [MNa]⁺ = 343 |
| 897 | | | n.d. [MNa]⁺ = 300 |
| 898 | | | n.d. [MNa]⁺ = 301 |
| 899 | | | n.d. [MNa]⁺ = 425 |

TABLE I-34-continued

| Prep. Ex. # | nitrile | product | yield |
|---|---|---|---|
| 900 | 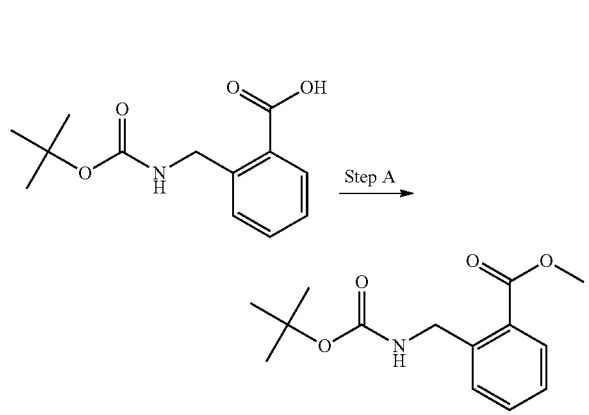 | | 8% [MNa]⁺ = 286 |
| 901 | | | 80% [MNa]⁺ = 314 |

Preparative Example 902

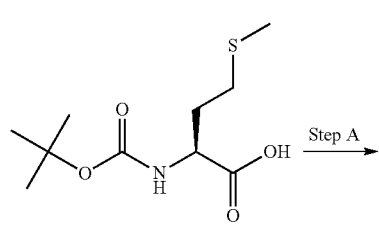

Step A

A mixture of The title compound from the Preparative Example 885 (507 mg), $^i$Pr$_2$NEt (6.5 mL) and iodomethane (700 μL) in DMF (8 mL) was stirred at room temperature over the weekend, concentrated and diluted with EtOAc (60 mL) and H$_2$O (20 mL). The organic phase was separated, washed with 0.1M aqueous HCl (15 mL) and saturated aqueous NaCl (15 mL), dried (MgSO$_4$), filtered and concentrated to afford the title compound (430 mg, 80%). $^1$H-NMR (CDCl$_3$) δ=7.95 (d, 1H), 7.45-7.49 (m, 2H) 7.29-7.37 (m, 1H), 5.55 (br s, 1H), 4.49 (d, 2H), 3.90 (s, 3H), 1.40 (s, 9H).

Preparative Example 903

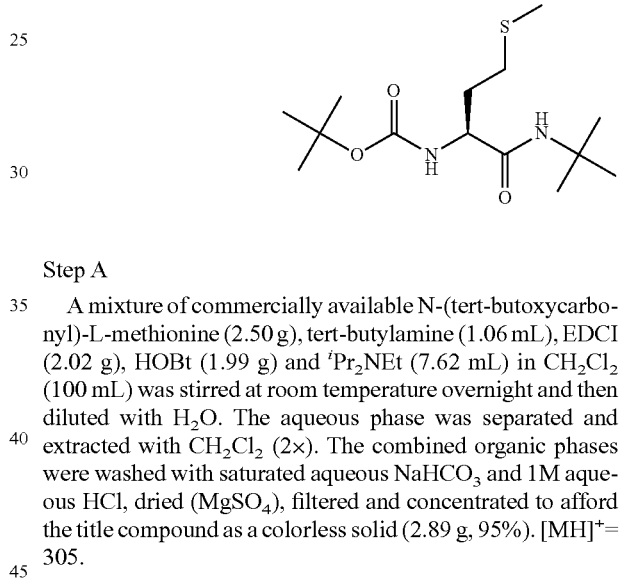

Step A

A mixture of commercially available N-(tert-butoxycarbonyl)-L-methionine (2.50 g), tert-butylamine (1.06 mL), EDCI (2.02 g), HOBt (1.99 g) and $^i$Pr$_2$NEt (7.62 mL) in CH$_2$Cl$_2$ (100 mL) was stirred at room temperature overnight and then diluted with H$_2$O. The aqueous phase was separated and extracted with CH$_2$Cl$_2$ (2×). The combined organic phases were washed with saturated aqueous NaHCO$_3$ and 1M aqueous HCl, dried (MgSO$_4$), filtered and concentrated to afford the title compound as a colorless solid (2.89 g, 95%). [MH]⁺= 305.

Preparative Example 904

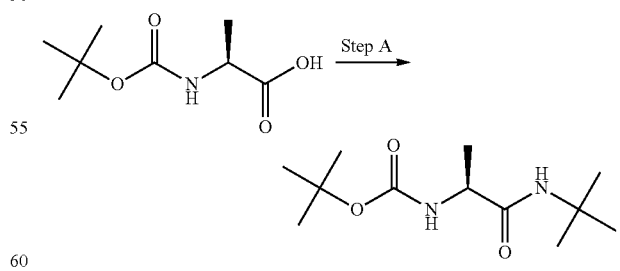

Step A

Commercially available N-(tert-butoxycarbonyl)-L-alanine (1.00 g) was treated similarly as described in the Preparative Example 903, Step A to afford the title compound as a white solid (1.38 g, >99%). [MNa]⁺=267.

Preparative Example 905

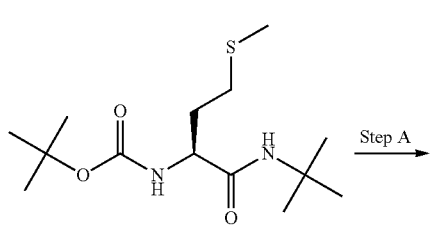

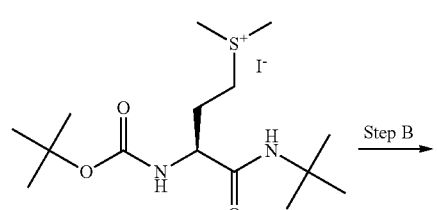

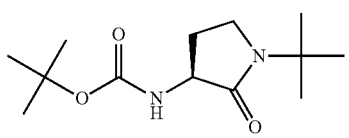

Step A

A solution of the title compound from the Preparative Example 903, Step A (1.89 g) in iodomethane (10 mL) was stirred at room temperature overnight and then concentrated to afford the title compound as a yellow solid (2.67 g, 97%). $[M-S(CH_3)_2I]^+=257$.

Step B

Under an argon atmosphere NaH (166 mg, 60% in mineral oil) was added at once to an ice cooled (0-5° C.) solution of the title compound from Step A above (1.85 g) in DMF (25 mL). The resulting mixture was stirred at 0-5° C. (ice bath) for 15 min and at room temperature for 2 h, diluted with $H_2O$ and saturated aqueous $NH_4Cl$ and extracted with EtOAc (3×). The combined organic phases were washed with $H_2O$ and saturated aqueous NaCl, dried ($MgSO_4$), filtered, concentrated and purified by chromatography (silica, cyclohexane/EtOAc) to afford the title compound as a colorless oil (800 mg, 75%). $[MNa]^+=279$.

Preparative Example 906

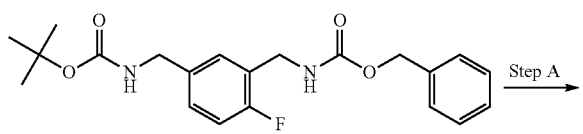

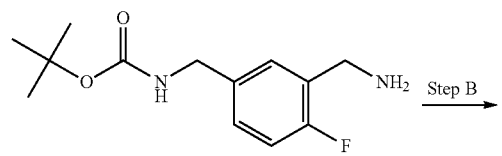

Step A

The title compound from the Preparative Example 79 (2.50 g) was treated similarly as described in the Preparative Example 96, Step A to afford the title compound as an oil (1.63 g, >99%). $[MNa]^+=277$.

Step B

The title compound from Step A above (1.63 g) was treated similarly as described in the Preparative Example 97, Step A to afford the title compound as a white solid (1.43 g, 68%). $[MNa]^+=320$.

Preparative Example 907

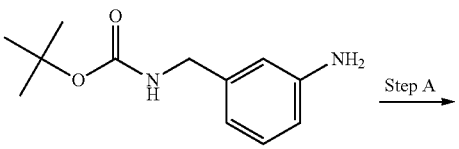

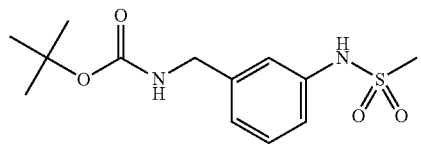 [SMILES: CC(C)(C)OC(=O)NCc1cccc(NS(C)(=O)=O)c1]

Step A

To an ice cooled (0-5° C.) solution of commercially available (3-amino-benzyl)-carbamic acid tert-butyl ester (400 mg) in pyridine (5 mL) was added methanesulfonyl chloride (1704) before the stirring mixture was allowed to warm to room temperature overnight. The resulting mixture was cooled to 0-5° C. (ice bath), carefully neutralized with 1M aqueous HCl, diluted with $H_2O$ and extracted with $CH_2Cl_2$. The organic phase was washed $H_2O$ and saturated aqueous NaCl, dried ($MgSO_4$), filtered, concentrated and purified by chromatography (silica, cyclohexane/EtOAc) to afford the title compound as colorless crystals (407 mg, 75%). [MNa]⁺=323.

Preparative Example 908

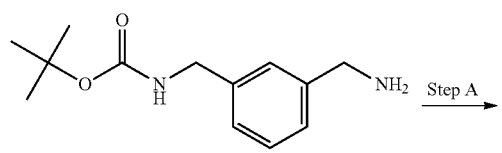

Step A

To a solution of 3,4-diethoxy-3-cyclobutene-1,2-dione (790 µL) in MeOH (20 mL) was added commercially available (3-aminomethyl-benzyl)-carbamic acid tert-butyl ester (840 mg). The mixture was stirred for 2 h, 30% aqueous solution of methylamine (30 mL) was added and stirring was continued for 2 h. The formed precipitate was collected by filtration to afford the title compound as a white solid (1.17 g, 95%). [MNa]⁺=368.

Preparative Example 909

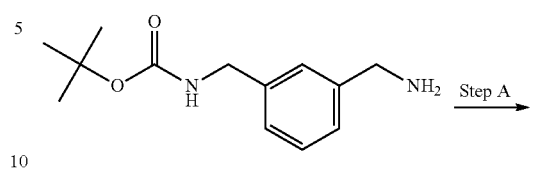

Step A

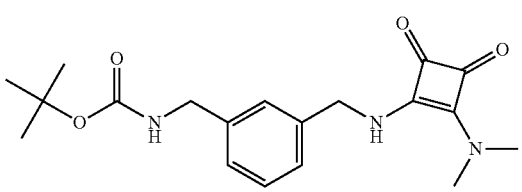 [SMILES: CN(C)c1c(NCc2cccc(CNC(=O)OC(C)(C)C)c2)c(=O)c1=O]

Step A

Commercially available (3-aminomethyl-benzyl)-carbamic acid tert-butyl ester (1.39 g) was treated similarly as described in the Preparative Example 907, Step A, except using a 2M solution of dimethylamine in THF instead of 30% aqueous methylamine to afford the title compound as black needles (632 mg, 88%). [MNa]⁺=382.

Preparative Examples 910-911

Following a similar procedure as described in the Preparative Example 7, Step C, except using the acids indicated in Table I-35 below, the following compounds were prepared.

TABLE I-35

| Prep. Ex. # | acid | product | yield |
|---|---|---|---|
| 910 | ![acid] | ![product] | >99% [MH]⁺ = 308 |
| 911 | ![acid] | ![product] | 35% [MNa]⁺ = 356 |

Preparative Example 912

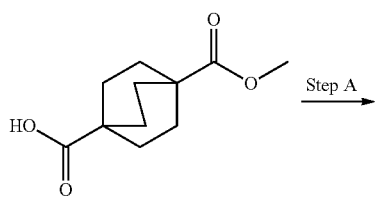

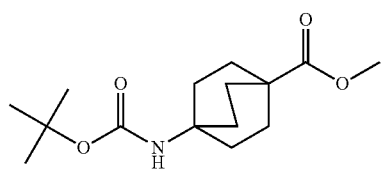

Step A

The title compound from the Preparative Example 39, Step C (500 mg) was treated similarly as described in the Preparative Example 17, Step A to afford the title compound (460 mg, 60%). [MNa]⁺=306.

Preparative Example 913

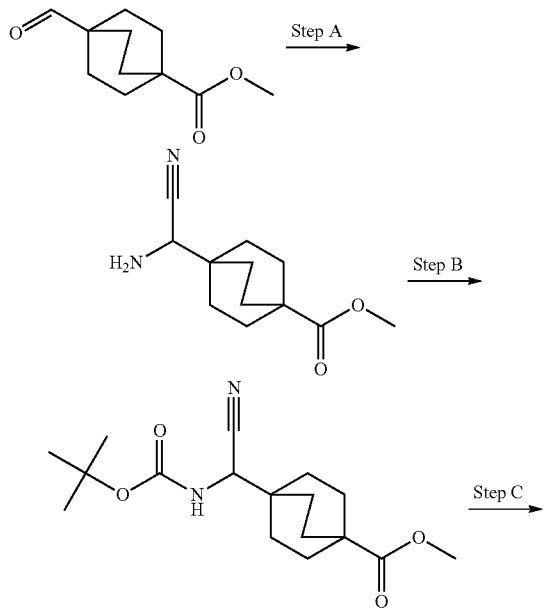

Step A

To a solution of the title compound from the Preparative Example 805, Step B (339 mg), 30% aqueous NH₄OH (240 µL) and KCN (124 mg) in MeOH/H₂O (2:1, 15 mL) was added NH₄Cl (104 mg). The resulting mixture was stirred at 70° C. overnight, diluted with H₂O and extracted with EtOAc (2×). The combined organic phases were washed with saturated aqueous NaHCO₃ and saturated aqueous NaCl, dried (MgSO₄), filtered and concentrated to afford the crude title compound (330 mg, 86%). [MH]⁺=223.

Step B

To a solution of the title compound from Step A above (330 mg) in THF (10 mL) were subsequently added di-tert-butyl dicarbonate (487 mg) and NaHCO₃ (249 mg). The resulting mixture was stirred at room temperature overnight, concentrated, diluted with EtOAc, washed with saturated aqueous NH₄Cl and saturated aqueous NaCl, dried (MgSO₄), filtered and concentrated to afford the title compound (385 mg, 85%). [MNa]⁺=345.

Step C

To a solution of the title compound from Step B above (385 mg) in MeOH/H₂O (2:1, 15 mL) was added sodium perborate tetrahydrate (552 mg). The resulting mixture was stirred at 50° C. overnight, concentrated and diluted with EtOAc and saturated aqueous NH₄Cl. The organic phase was separated, washed with H₂O and saturated aqueous NaCl, dried (MgSO₄), filtered and concentrated to afford the title compound (393 mg, 97%). [MNa]⁺=363.

Preparative Examples 914-946

Following a similar procedure as described in the Preparative Example 133, except using the protected amines indicated in Table I-36 below, the following compounds were prepared.

TABLE I-36

| Prep. Ex. # | protected amine | product | yield |
|---|---|---|---|
| 914 | | | >99% [M − Cl]⁺ = 148 |

| Prep. Ex. # | protected amine | product | yield |
|---|---|---|---|
| 915 | tert-butyl ((1H-indazol-6-yl)methyl)carbamate | HCl·H₂N-CH₂-(1H-indazol-6-yl) | >99% (over 3 steps) [M − Cl]⁺ = 148 |
| 916 | tert-butyl (3,4-bis(difluoromethoxy)benzyl)carbamate | HCl·H₂N-CH₂-(3,4-bis(difluoromethoxy)phenyl) | >99% [M − Cl]⁺ = 240 |
| 917 | tert-butyl (3-(2-oxopyrrolidin-1-yl)benzyl)carbamate | HCl·H₂N-CH₂-(3-(2-oxopyrrolidin-1-yl)phenyl) | >99% [M − Cl]⁺ = 191 |
| 918 | tert-butyl ((2-morpholinopyridin-4-yl)methyl)carbamate | HCl·H₂N-CH₂-(2-morpholinopyridin-4-yl) | >99% [M − HCl₂]⁺ = 194 |
| 919 | tert-butyl (4-fluoro-3-morpholinobenzyl)carbamate | HCl·H₂N-CH₂-(4-fluoro-3-morpholinophenyl) | >99% [M − Cl]⁺ = 211 |
| 920 | tert-butyl ((3-methylbenzo[d]isothiazol-5-yl)methyl)carbamate | HCl·H₂N-CH₂-(3-methylbenzo[d]isothiazol-5-yl) | >99% [M − NH₃Cl]⁺ = 162 |
| 921 | tert-butyl ((4-fluorobicyclo[2.2.2]octan-1-yl)methyl)carbamate | HCl·H₂N-CH₂-(4-fluorobicyclo[2.2.2]octan-1-yl) | >99% [M − Cl]⁺ = 158 |
| 922 | tert-butyl ((4-hydroxybicyclo[2.2.2]octan-1-yl)methyl)carbamate | HCl·H₂N-CH₂-(4-hydroxybicyclo[2.2.2]octan-1-yl) | >99% [M − Cl]⁺ = 156 |
| 923 | methyl 4-(((tert-butoxycarbonyl)amino)methyl)cubane-1-carboxylate | HCl·H₂N-CH₂-(methyl cubane-1-carboxylate) | 99% [M − Cl]⁺ = 192 |

TABLE I-36-continued

| Prep. Ex. # | protected amine | product | yield |
|---|---|---|---|
| 924 | | | 99% [M − Cl]⁺ = 179 |
| 925 | | | 99% [M − Cl]⁺ = 149 |
| 926 | | | >99% [M − Cl]⁺ = 156 |
| 927 | | | n.d. [M − Cl]⁺ = 139 |
| 928 | | | n.d. [M − Cl]⁺ = 175 |
| 929 | | | 95% [M − Cl]⁺ = 176 |
| 930 | | | >99% [M − NH₃Cl]⁺ = 162 |
| 931 | | | >99% [M − NH₃Cl]⁺ = 176 |
| 932 | | | >99% [M − NH₃Cl]⁺ = 190 |
| 933 | | | >99% [M − Cl]⁺ = 157 |

TABLE I-36-continued

| Prep. Ex. # | protected amine | product | yield |
|---|---|---|---|
| 934 | | | >99%<br>[M − Cl]⁺ = 145 |
| 935 | | | >99%<br>[M − Cl]⁺ = 207 |
| 936 | | | >99%<br>[M − Cl]⁺ = 221 |
| 937 | | | >99%<br>[M − Cl]⁺ = 184 |
| 938 | | | >99%<br>[M − Cl]⁺ = 241 |
| 939 | | | 57%<br>(over 3 steps)<br>[M − NH₃Cl]⁺ = 161 |
| 940 | | | 37%<br>(over 2 steps)<br>[M − NH₃Cl]⁺ = 162 |
| 941 | | | >99%<br>[M − Cl]⁺ = 198 |
| 942 | | | >99%<br>[M − NH₃Cl]⁺ = 184 |

TABLE I-36-continued

| Prep. Ex. # | protected amine | product | yield |
|---|---|---|---|
| 943 | | | >99% [M − Cl]⁺ = 164 |
| 944 | | | >99% [M − Cl]⁺ = 192 |
| 945 | | | >99% [M − Cl]⁺ = 246 |
| 946 | | | 88% [M − Cl]⁺ = 260 |

Preparative Example 947

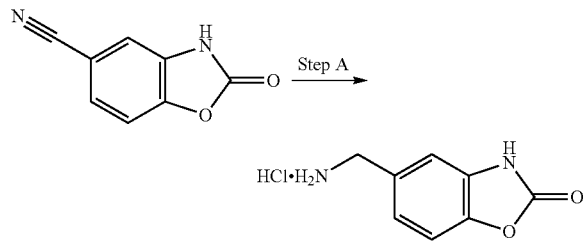

Step A

A mixture of the title compound from the Preparative Example 852 (127 mg), Pd/C (10 wt %, 93 mg) and 50% aqueous AcOH (1 mL) in EtOH (5 mL) was hydrogenated at atmospheric pressure overnight, filtered and concentrated. The remaining residue was diluted with a 4M solution of HCl in 1,4-dioxane (3 mL), stirred at room temperature for 1 h and concentrated to afford the title compound as a white solid (148 mg, 93%). [M-NH₃Cl]⁺=148.

Preparative Examples 948-949

Following a similar procedure as described in the Preparative Example 947, except using the nitriles indicated in Table I-37 below, the following compounds were prepared.

TABLE I-37

| Prep. Ex. # | nitrile | product | yield |
|---|---|---|---|
| 948 | | | >99% [M − NH₃Cl]⁺ = 156 |
| 949 | | | 27% [M − NH₃Cl]⁺ = 202 |

Preparative Examples 950-951

Following a similar procedure as described in the Preparative Example 214, except using the intermediates and amines indicated in Table I-38 below instead of the title compound from the Preparative Example 95, Step A and NH₃, the following compounds were prepared.

TABLE I-38

| Prep. Ex. # | intermediate, amine | product | yield |
|---|---|---|---|
| 950 | 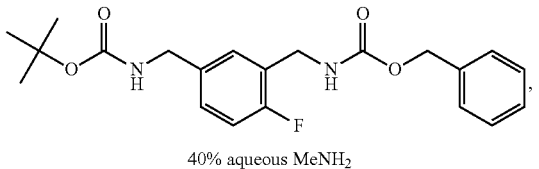 [SMILES: CC(C)(C)OC(=O)NCc1ccc(F)c(CNC(=O)OCc2ccccc2)c1] 40% aqueous MeNH₂ | 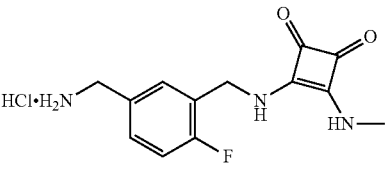 | n.d. [M − Cl]⁺ = 264 |
| 951 | 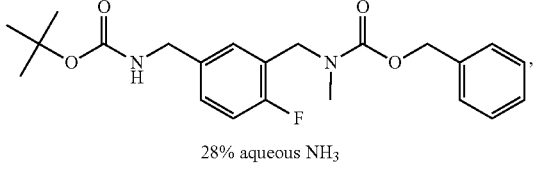 [SMILES: CN(Cc1cc(CNC(=O)OC(C)(C)C)ccc1F)C(=O)OCc1ccccc1] 28% aqueous NH₃ | 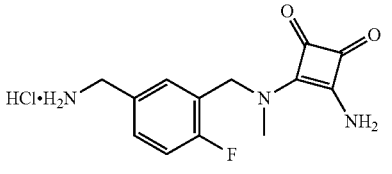 | 50% (over 3 steps) [M − Cl]⁺ = 264 |

Preparative Example 952

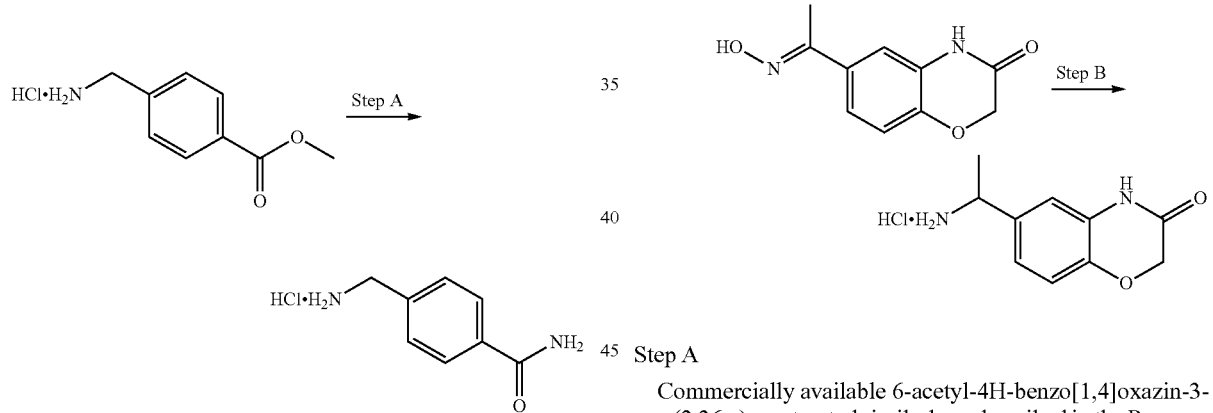

Step A

Commercially available 4-aminomethyl-benzoic acid methyl ester hydrochloride (500 mg) was dissolved in a 33% solution of NH₃ in H₂O (50 mL) and heated in a sealed pressure tube to 90° C. for 20 h. Cooling to room temperature and concentration afforded the title compound. [M-Cl]⁺=151.

Step A

Commercially available 6-acetyl-4H-benzo[1,4]oxazin-3-one (2.36 g) was treated similarly as described in the Preparative Example 217, Step A to afford the title compound as a colorless fluffy needles (2.19 g, 86%). [MH]⁺=207.

Step B

The title compound from Step B above (888 mg) was treated similarly as described in the Preparative Example 217, Step B to afford the title compound as a colorless solid (163 mg, 32%). [MH]⁺=193.

Preparative Example 953

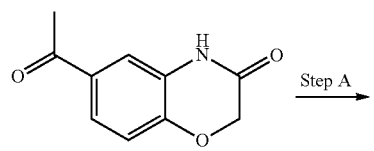

Preparative Example 954

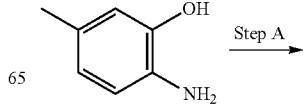

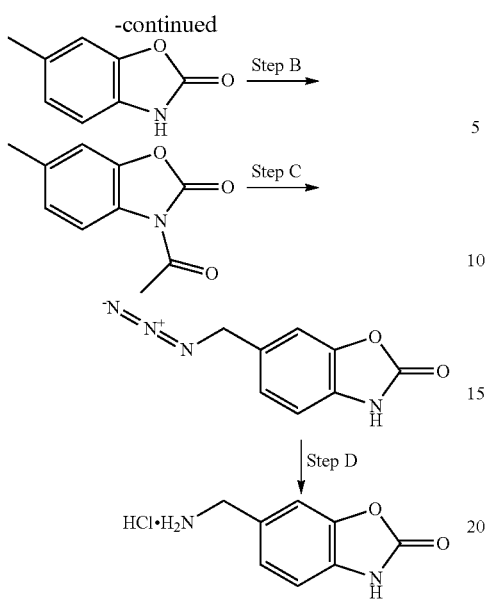

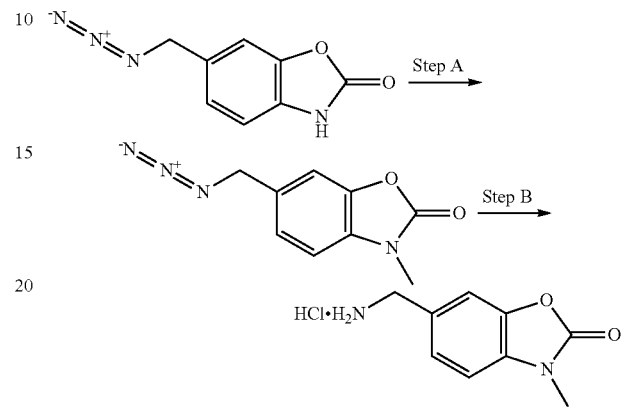

Step D

The title compound from Step C above (1.32 g) was treated similarly as described in the Preparative Example 213, Step D to afford the title compound as white crystals (264 mg, >99%). [M-Cl]$^+$=165.

Preparative Example 955

Step A

The title compound from Preparative Example 954, Step C (240 mg) was treated similarly as described in the Preparative Example 213, Step B to afford the title compound as a white solid (243 mg, 94%). [MI-1]$^+$=205.

Step B

The title compound from Step A above (243 mg) was treated similarly as described in the Preparative Example 213, Step D to afford the title compound as a white solid (118 mg, 44%). [M-Cl]$^+$=179.

Preparative Examples 956-957

Following a similar procedure as described in the Preparative Example 208, except using the protected amines indicated in Table I-39 below, the following compounds were prepared.

Step A

Commercially available 2-hydroxy-4-methylaniline (4.64 g) was treated similarly as described in the Preparative Example 213, Step A to afford the title compound as black needles (5.00 g, 89%).

Step B

A mixture of the title compound from Step A above (1.03 g) in acetic anhydride (20 mL) was heated to 80° C. for 2 h, concentrated, diluted with toluene (2×), concentrated (2×) and dried in vacuo to afford the title compound as brown crystals (1.32 g, >99%).

Step C

The title compound from Step A above (1.32 g) was treated similarly as described in the Preparative Example 213, Step C to afford the title compound as a white solid (496 mg, 38%). [MH]$^+$=191.

TABLE I-39

| Prep. Ex. # | protected amine | product | yield |
|---|---|---|---|
| 956 | ![structure] | ![structure] | >99%<br>[M − TFA]$^+$ = 180 |
| 957 | ![structure] | ![structure] | >99%<br>[M − TFA]$^+$ = 164 |

Preparative Examples 958-965

Following a similar procedure as described in the Preparative Example 7, Step D, except using the protected amines indicated in Table I-40 below, the following compounds were prepared.

TABLE I-40

| Prep. Ex. # | protected amine | product | yield |
|---|---|---|---|
| 958 | | | 58% [MH]⁺ = 208 |
| 959 | | | 20% [M − NH₂]⁺ = 217 |
| 960 | | | 84% [MH]⁺ = 343 |
| 961 | | | 63% [MH]⁺ = 343 |
| 962 | | | 55% [MH]⁺ = 343 |
| 963 | | | 51% [MH]⁺ = 343 |
| 964 | | | 50% [MH]⁺ = 343 |

TABLE I-40-continued

| Prep. Ex. # | protected amine | product | yield |
|---|---|---|---|
| 965 | | | 50%<br>[MH]+ = 343 |

Preparative Example 966

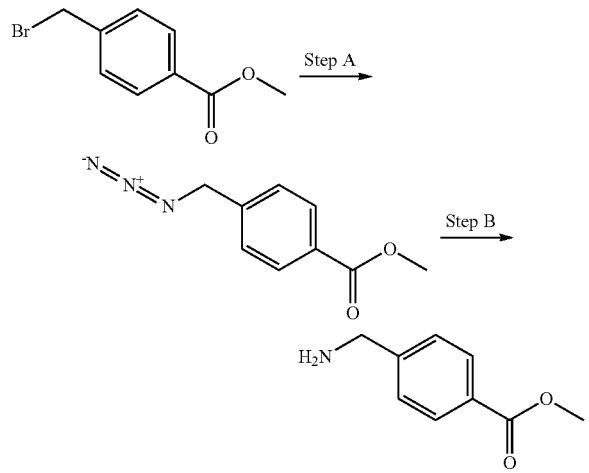

Step A

A mixture of commercially available 4-bromomethyl-benzoic acid methyl ester (500 mg) and NaN$_3$ (666 mg) in DMA (9 mL) was stirred at 60-70° C. (temperature of the oil bath) overnight, concentrated and diluted with Et$_2$O (200 mL) and H$_2$O (80 mL). The organic phase was separated, washed with H$_2$O (2×80 mL), dried (MgSO$_4$), filtered and concentrated to afford the title compound (375 mg, 90%). $^1$H-NMR (CDCl$_3$) δ=8.03 (d, 2H), 7.39 (d, 2H), 4.40 (s, 2H), 3.90 (s, 3H).

Step B

A mixture of the title compound from Step A above (375 mg) and Pd/C (10 wt %, 150 mg) in MeOH (100 mL) was hydrogenated at atmospheric pressure for 1 h, filtered and concentrated to afford the title compound (291 mg, 90%). [MH]+=166.

Preparative Examples 967-968

Following a similar procedure as described in the Preparative Example 245, Step B, except using the aminopyrazoles indicated in Table I-41 below instead of 2-aminopyrazole, the following compounds were prepared.

TABLE I-41

| Prep. Ex. # | aminopyrazole | product | yield |
|---|---|---|---|
| 967 | | | 6%<br>[MH]+ = 312 |
| 968 | | | 13%<br>[MH]+ = 318 |

Preparative Example 969

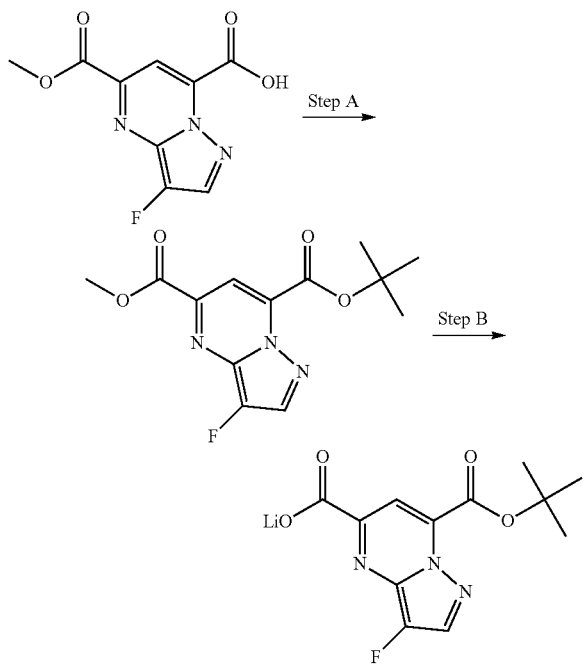

Step A
A mixture of title compound from the Preparative Example 262 (100 mg), di-tert.-butyl dicarbonate (182 mg) and DMAP (15 mg) in THF (2 mL) was stirred at room temperature for 3 h, concentrated and purified by chromatography (silica, hexanes/EtOAc) to afford title compound as yellow solid (84 mg, 68%). [MNa]$^+$=318.

Step B
To a solution of the title compound from Step A (77 mg) in THF/MeOH (1:1, 2 mL) was added 1M aqueous LiOH (340 µL). The resulting mixture was stirred at room temperature for 2 h and then concentrated to afford the crude title compound, which was used without further purification (85 mg). [(M-Li)HNa]$^+$=304.

Preparative Example 970

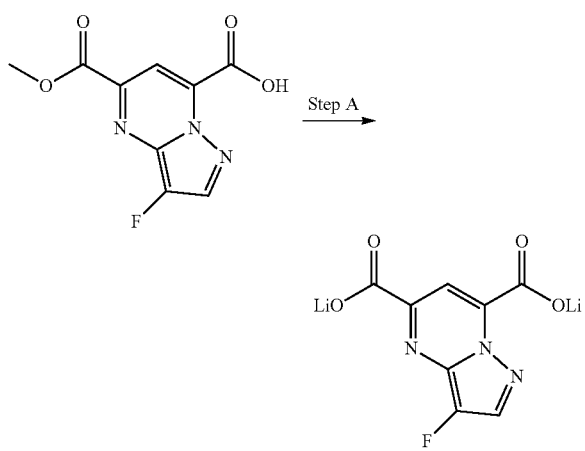

Step A
The title compound from the Preparative Example 262 (50 mg) was treated similarly as described in the Preparative Example 969, Step B to afford the title compound. [(M-]$^-$=224.

Preparative Example 971

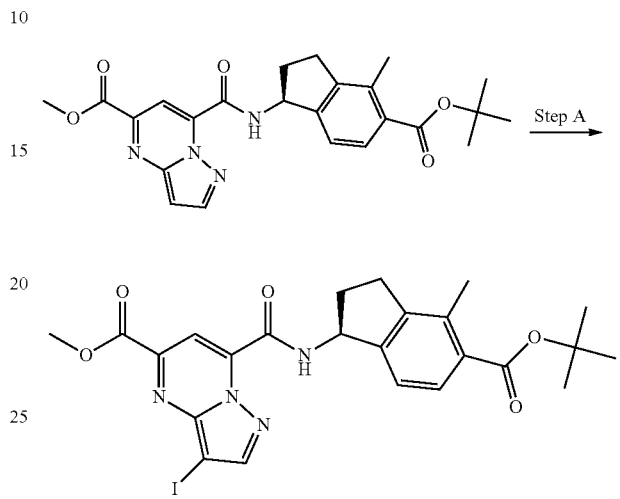

Step A
To the title compound from the Preparative Example 278, Step A (462 mg) in CHCl$_3$ (5 mL) was added N-iodosuccinimide (277 mg). The resulting mixture was heated to reflux for 16 h, concentrated and purified by chromatography (silica, hexanes/EtOAc) to afford the title compound (587 mg, >99%). [MNa]$^+$=599.

Preparative Example 972

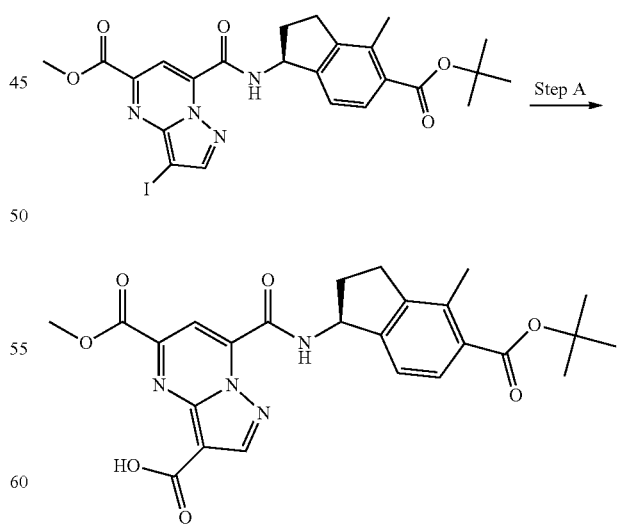

Step A
The title compound from the Preparative Example 971, Step A (520 mg), Pd(OAc)$_2$ (20 mg), dppf (200 mg) and KOAc (354 mg) were dissolved in dry DMSO (5.4 mL) and Preparative Example 973

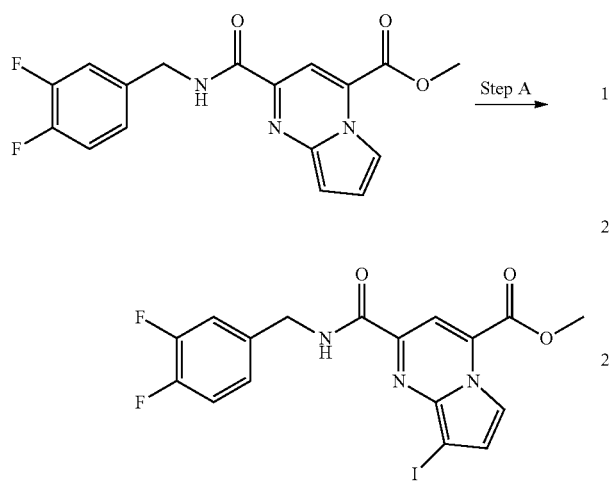

Step A

The title compound from the Preparative Example 288 (210 mg) in CHCl₃ (5 mL) was added N-iodosuccinimide (167 mg). The resulting mixture was stirred at 70° C. for 1 h, absorbed onto silica and purified by chromatography (silica, hexanes/EtOAc) to afford the title compound (365 mg, 97%). [MH]⁺=473.

Preparative Example 974

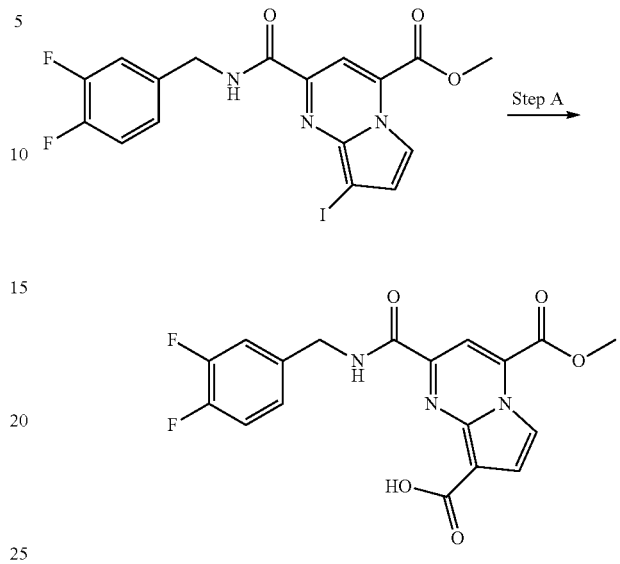

Step A

The title compound from the Preparative Example 973, Step A (95 mg), Pd(OAc)₂ (4.5 mg), dppf (45 mg) and KOAc (79 mg) were dissolved in dry DMSO (1.5 mL) and stirred at 60° C. under a carbon monoxide atmosphere at 1 atm for 4 h. The mixture was diluted with EtOAc, washed subsequently with 1N aqueous HCl (2×) and saturated aqueous NaCl, dried (MgSO₄), filtered and concentrated to afford the crude title compound, which was use with out further purification (92 mg). [MH]⁺=391.

Preparative Example 975

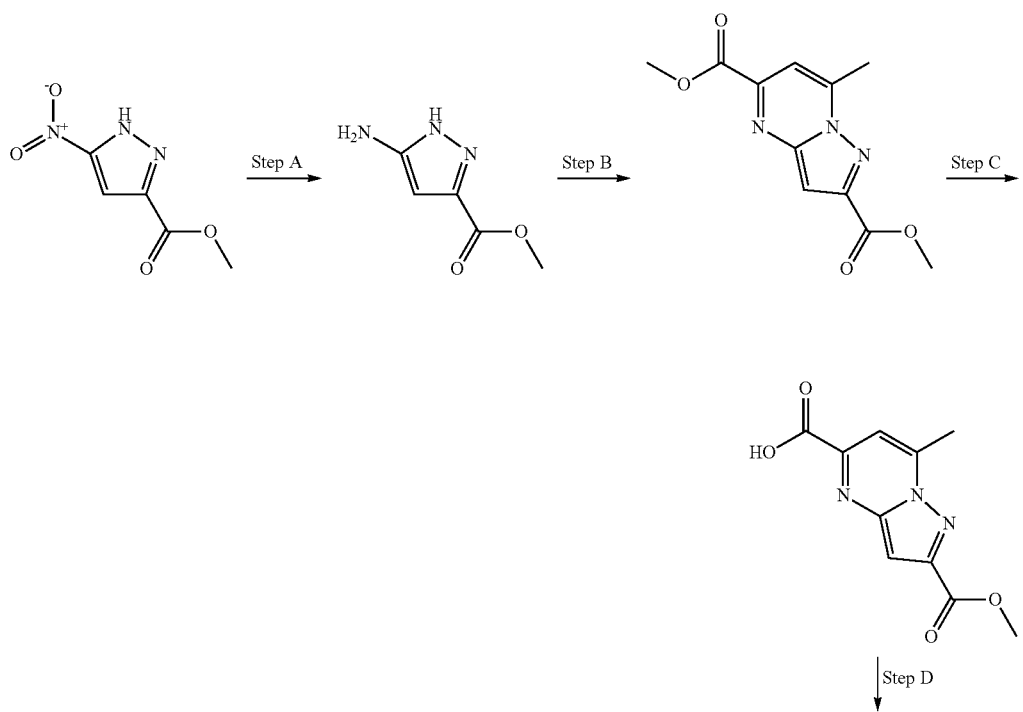

stirred at 60° C. under a carbon monoxide atmosphere at 1 atm for 16 h. The mixture was diluted with EtOAc, washed subsequently with 1N aqueous HCl and saturated aqueous NaCl, dried (MgSO₄), filtered and concentrated. Purification by chromatography (silica, CH₂Cl₂/MeOH) afforded the title compound as a yellow solid (391 mg, 88%). [M-H]⁻=588.

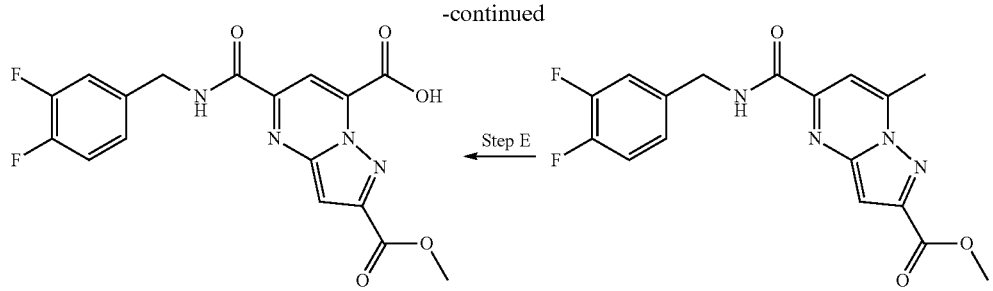

Step E

Step A

A mixture of commercially available 5-nitro-1H-pyrazole-3-carboxylic acid methyl ester (1.45 g) and Pd/C (10 wt %, 106 mg) in MeOH (25 mL) was hydrogenated at 25 psi for 2 h, filtered through Celite® and concentrated to afford the title compound (1.25 g, 88%). [MH]$^+$=142.

Step B

A mixture of the title compound from Step A above (325 mg) and methyl acetopyruvate (330 mg) in MeOH (10 mL) was heated to reflux for 2 h and then cooled to room temperature. The formed precipitate was collected by filtration and dried to afford the title compound as a white solid (356 mg, 62%). [MH]$^+$=250.

Step C

To a solution of the title compound from Step B above (229 mg) in 1,4-dioxane/MeOH (5:1, 12 mL) was added 1M aqueous NaOH (1 mL). The resulting mixture was stirred at room temperature overnight and then acidified. The formed precipitate was collected by filtration to afford the crude title compound as a white solid. (177 mg, 38%). [MH]$^+$=236.

Step D

The title compound from Step C above (172 mg) was treated similarly as described in the Preparative Example 280, Step A to afford the title compound (171 mg, 65%). [MH]$^+$=361.

Step E

The title compound from Step D above (151 mg) was treated similarly as described in the Preparative Example 274, Step D to afford the title compound. [MH]$^+$=391.

Preparative Examples 976-982

Following similar procedures as described in the Preparative Examples 279 (method A), 280 (method B), 281 (method C), 278 (method D) or 282 (method E), except using the acids and amines indicated in Table I-42 below, the following compounds were prepared.

TABLE I-42

| Prep. Ex. # | acid, amine | product | method, yield |
|---|---|---|---|
| 976 | | | E, 68% [MNa]$^+$ = 435 |
| 977 | | | E, 67% [M − H]$^-$ = 602 |

TABLE I-42-continued
| Prep. Ex. # | acid, amine | product | method, yield |
|---|---|---|---|
| 978 | 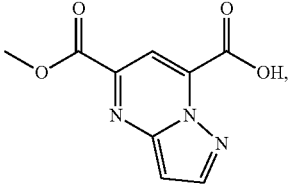 | 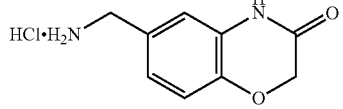 | E, 95% [MH]⁺ = 382 |
| 979 | 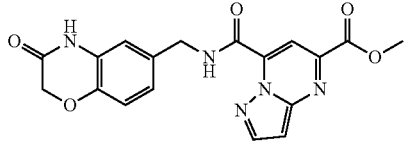 [SMILES: COC(=O)c1cc(C(=O)NCc2ccc3c(c2)NC(=O)CO3)n2nccc2n1] |  | E, 84% [MH]⁺ = 221 |
| 980 | 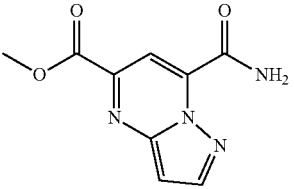 [SMILES: COC(=O)c1cc(C(N)=O)n2nccc2n1] 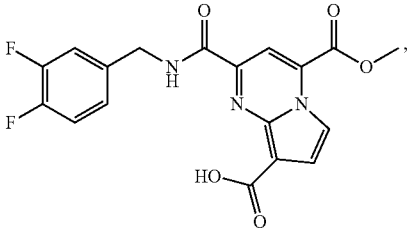 | 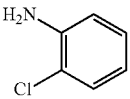 | B, 42% (over 2 steps) [M − H]⁻ = 500 |
| 981 | 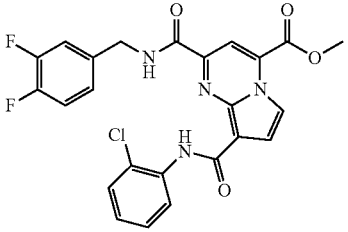 [SMILES: COC(=O)c1cc(C(=O)NCc2ccc(F)c(F)c2)nc2c(C(=O)Nc3ccccc3Cl)ccn12] 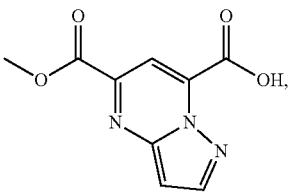 | 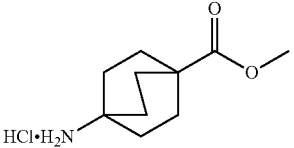 | A, n.d. [MH]⁺ = 387 |

TABLE I-42-continued
| Prep. Ex. # | acid, amine | product | method, yield |
|---|---|---|---|
| 982 | 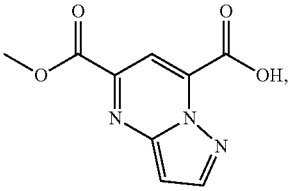 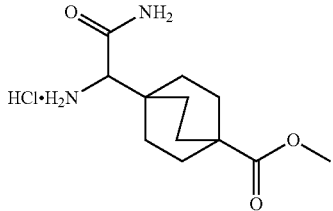 | 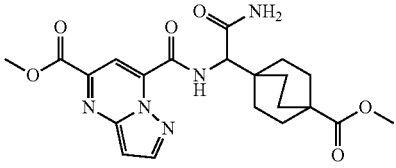 | A, n.d. [MH]+ = 444 |
Preparative Examples 983-986
Following a similar procedure as described in the Preparative Example 328, Step A, except using the esters and nucleophiles indicated in Table I-43 below, the following compounds were prepared.
TABLE I-43
| Prep. Ex. # | ester, nucleophile | product | yield |
|---|---|---|---|
| 983 | 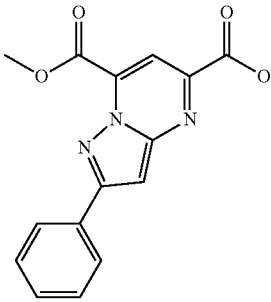 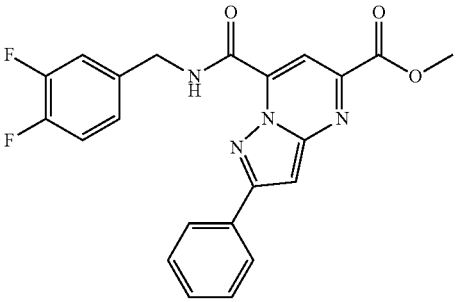 [SMILES: COC(=O)c1cc(C(=O)NCc2ccc(F)c(F)c2)n2nc(-c3ccccc3)cc2n1] | 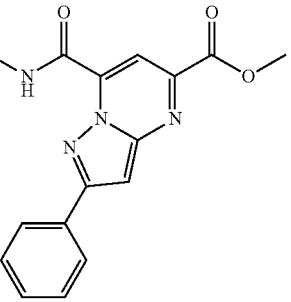 | 39% [MH]+ = 423 |
| 984 | 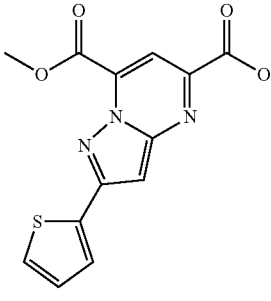 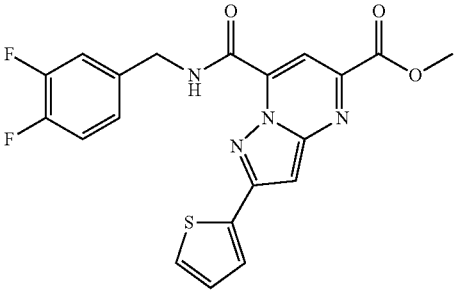 [SMILES: COC(=O)c1cc(C(=O)NCc2ccc(F)c(F)c2)n2nc(-c3cccs3)cc2n1] | 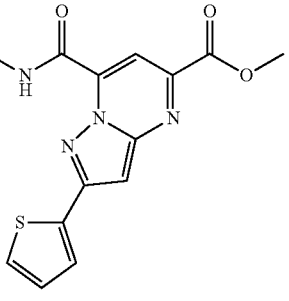 | 32% [MH]+ = 429 |

TABLE I-43-continued

| Prep. Ex. # | ester, nucleophile | product | yield |
|---|---|---|---|
| 985 | (dimethyl 2-phenylpyrazolo[1,5-a]pyrimidine-5,7-dicarboxylate), NaOH | 5-methyl ester, 7-carboxylic acid of 2-phenylpyrazolo[1,5-a]pyrimidine | 80%<br>[MH]⁺ = 298 |
| 986 | (dimethyl 2-(thiophen-2-yl)pyrazolo[1,5-a]pyrimidine-5,7-dicarboxylate), NaOH | 5-methyl ester, 7-carboxylic acid of 2-(thiophen-2-yl)pyrazolo[1,5-a]pyrimidine | 94%<br>[MH]⁺ = 304 |

Preparative Examples 987-993

Following similar procedures as described in the Preparative Examples 331 (method A), 332 (method B) or 333 (method C), except using the esters indicated in Table I-44 below, the following compounds were prepared.

TABLE I-44

| Prep. Ex. # | ester | product | method, yield |
|---|---|---|---|
| 987 | methyl 7-carbamoylpyrazolo[1,5-a]pyrimidine-5-carboxylate | 7-carbamoylpyrazolo[1,5-a]pyrimidine-5-carboxylic acid | A, >99%<br>[MH]⁺ = 207 |
| 988 | methyl ester with (3,4-difluorobenzyl)carbamoyl and carboxylic acid substituents on pyrrolo-pyrimidine | corresponding carboxylic acid product | B, n.d.<br>[MH]⁺ = 376 |

TABLE I-44-continued

| Prep. Ex. # | ester | product | method, yield |
|---|---|---|---|
| 989 | | | B, 99% [MH]⁺ = 486 |
| 990 | | | C, 70% [MH]⁺ = 409 |
| 991 | | | C, 67% [MH]⁺ = 415 |
| 992 | | | A, n.d. [MH]⁺ = 373 |
| 993 | | | A, n.d. [MH]⁺ = 430 |

Preparative Example 994

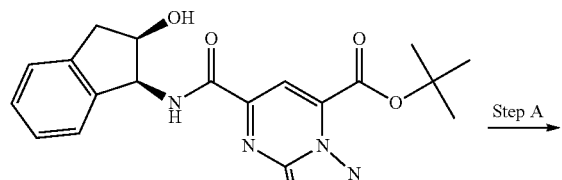

Step A

The title compound from the Preparative Example 976 was treated similarly as described in the Preparative Example 373 to afford the title compound (>99%). [MH]$^+$=357

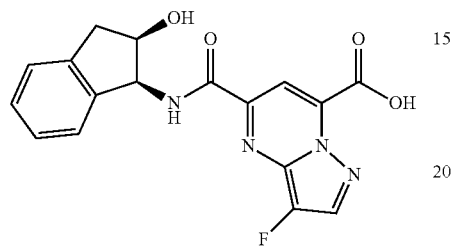

Preparative Examples 995-996

Following a similar procedures as described in the Preparative Example 324, Step A, except using the esters and amines indicated in Table I-45 below, the following compounds were prepared.

TABLE I-45

| Prep. Ex. # | ester, amine | product | yield |
|---|---|---|---|
| 995 | ![structure], ![amine with 3,4-F] | ![product structure] | 74%<br>[MH]$^+$ = 409 |
| 996 | ![structure], ![amine with 3,4-F] | ![product structure] | 87%<br>[MH]$^+$ = 415 |

Preparative Example 997

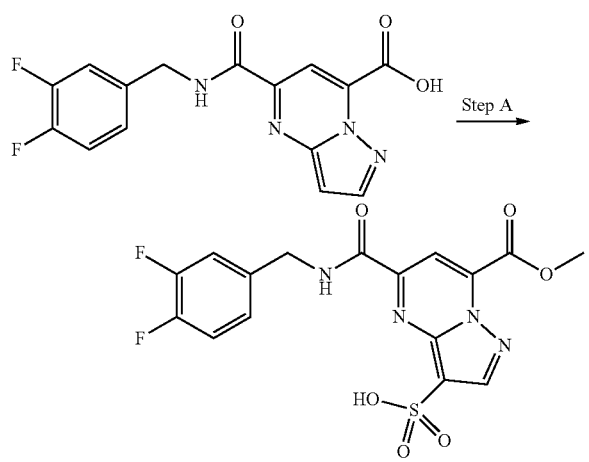

Step A

A mixture of the title compound from the Preparative Example 339 (50 mg) and HSO₃Cl (500 μL) was stirred at 90° C. for 1 h, cooled and the cautiously poured onto ice (5 g). The formed precipitate was collected by filtration, dried in vacuo and then added to a premixed solution of acetyl chloride (100 μL) in MeOH (1 mL). The resulting mixture was stirred at 40° C. for 1 h and concentrated to afford the title compound (42 mg, 65%). [M-H]⁻=425.

Preparative Example 998

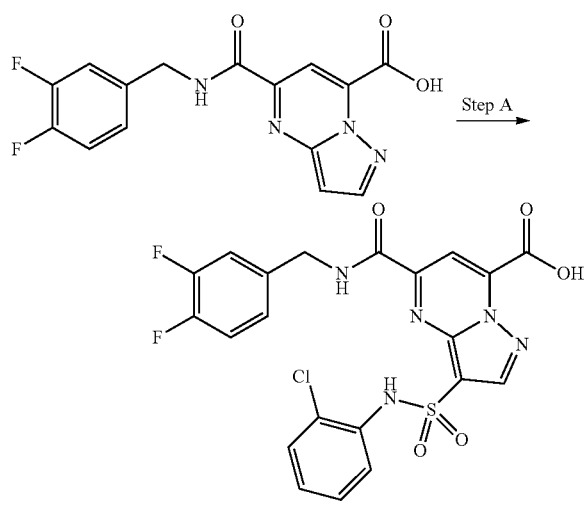

Step A

A mixture of the title compound from the Preparative Example 339 (168 mg) and HSO₃Cl (2 mL) was stirred at 90° C. for 2 h, cooled and the cautiously poured onto ice (15 g). The formed precipitate was collected by filtration, dried in vacuo and then added to solution of commercially available 2-chloroaniline (100 μL) in CHCl₃ (5 mL). The resulting mixture was stirred at 70° C. for 18 h, concentrated and purified by chromatography (silica) to afford a residue containing the title compound (9 mg). [M-H]⁻=519.

Preparative Example 999

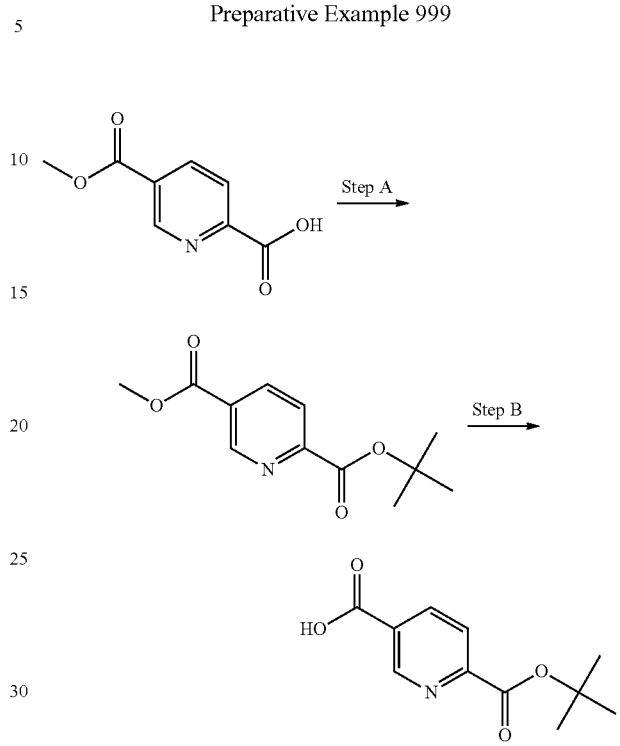

Step A

At 100° C. N,N-dimethylformamide di-tert-butyl acetal (3.6 mL) was added to a solution of commercial available pyridine-2,5-dicarboxylic acid 5-methyl ester (1.36 g) in dry toluene (10 mL). The mixture was stirred at 100° C. for 3 h, cooled to room temperature, concentrated, diluted with EtOAc (20 mL), washed with water (20 mL) and saturated aqueous NaCl (10 mL), dried (MgSO₄), filtered and concentrated to afford the crude title compound (726 mg, 40%). [MH]⁺=238.

Step B

Using a microwave, a mixture of the title compound from Step A above (600 mg) and trimethyltin hydroxide (1.35 mg) in 1,2-dichloroethane (20 mL) was heated at 100° C. for 1 h. The mixture was cooled to room temperature, diluted with CHCl₃ (30 mL), washed with 10% aqueous KHSO₄ (20 mL) and saturated aqueous NaCl (20 mL), dried (MgSO₄), filtered and concentrated to afford the crude title compound (307 mg, 55%). [MH]⁺=224.

Preparative Example 1000

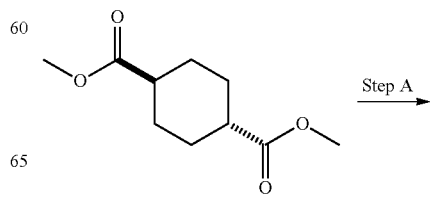

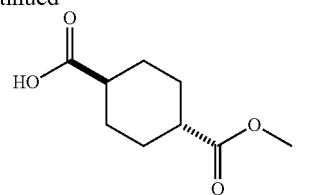

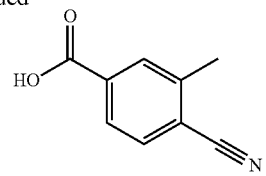

Step A

A mixture of the commercial available trans-dimethylcyclohexane-1,4-dicarboxylate (1 g) and KOH (300 mg) in THF/H$_2$O (10:1, 30 mL) was stirred at 100° C. overnight, cooled to room temperature and concentrated. The residue was diluted with EtOAc and adjusted to pH 1-2 with 1N aqueous HCl and extracted with EtOAc (3×50 mL). The combined organic phases were washed with saturated aqueous NaCl, dried (MgSO$_4$), filtered, concentrated and purified by chromatography (silica, CH$_2$Cl$_2$/MeOH) to afford the title compound (820 mg, 88%). [MH]$^+$=187.

Preparative Example 1001

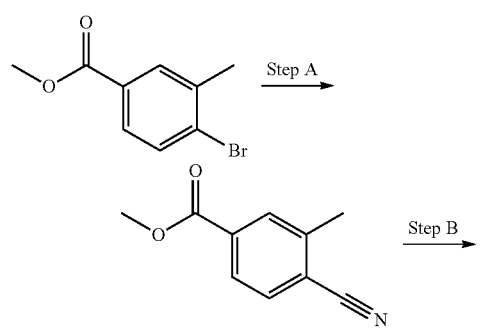

Step A

Using a microwave, a suspension of commercially available 4-bromo-3-methyl-benzoic acid methyl ester (1.5 g) and CuCN (490 mg) in dry N-methyl-pyrrolidin-2-one (10 mL) was heated at 230° C. for 10 h. The mixture was cooled to room temperature, diluted with 35% aqueous NH$_3$ (20 mL) and extracted with EtOAc (3×20 mL). The combined organic layers were washed with saturated aqueous NaCl (200 mL), dried (MgSO$_4$), filtered and concentrated to afford the title compound as a solid (590 mg, 67%). [MH]$^+$=176.

Step B

To a solution of the title compound from Step A above (590 mg) in THF/MeOH (2:1, 60 mL) was added 1M aqueous LiOH (10 mL). The resulting mixture was stirred at room temperature for 2 h, adjusted to pH 2 and concentrated to afford the crude title compound as a solid, which was used without further purification (540 mg, 99%). [MH]$^+$=162.

Preparative Examples 1002-1007

Following a similar procedure as described in the Preparative Example 805, Step A, except using the intermediates indicated in Table I-46 below, the following compounds were prepared.

TABLE 1-46

| Prep. Ex. # | intermediate | product | yield |
|---|---|---|---|
| 1002 | ![] | ![] | 52% [MH]$^+$ = 210 |
| 1003 | ![] | ![] | 57% [MH]$^+$ = 168 |
| 1004 | ![] | ![] | 51% [MH]$^+$ = 199 |

TABLE 1-46-continued

| Prep. Ex. # | intermediate | product | yield |
|---|---|---|---|
| 1005 | | | 52%<br>[MH]⁺ = 173 |
| 1006 | | | 61%<br>[MH]⁺ = 148 |
| 1007 | | | 18%<br>[MH]⁺ = 188 |

Preparative Examples 1008-1013

Following a similar procedure as described in the Preparative Example 805, Step B, except using the intermediates indicated in Table I-47 below, the following compounds were prepared.

TABLE I-47

| Prep. Ex. # | intermediate | product | yield |
|---|---|---|---|
| 1008 | | | 99%<br>[MH]⁺ = 208 |
| 1009 | | | 99%<br>[MH]⁺ = 166 |
| 1010 | | | 92%<br>[MH]⁺ = 197 |
| 1011 | | | 95%<br>[MH]⁺ = 171 |

TABLE I-47-continued

| Prep. Ex. # | intermediate | product | yield |
|---|---|---|---|
| 1012 | HO-[3-methyl-4-cyanophenyl]-CH2OH | O=CH-[3-methyl-4-cyanophenyl] | 95% [MH]+ = 146 |
| 1013 | HO-[4-sulfamoylphenyl]-CH2OH | O=CH-[4-sulfamoylphenyl] | 87% [MH]+ = 186 |

Preparative Example 1014

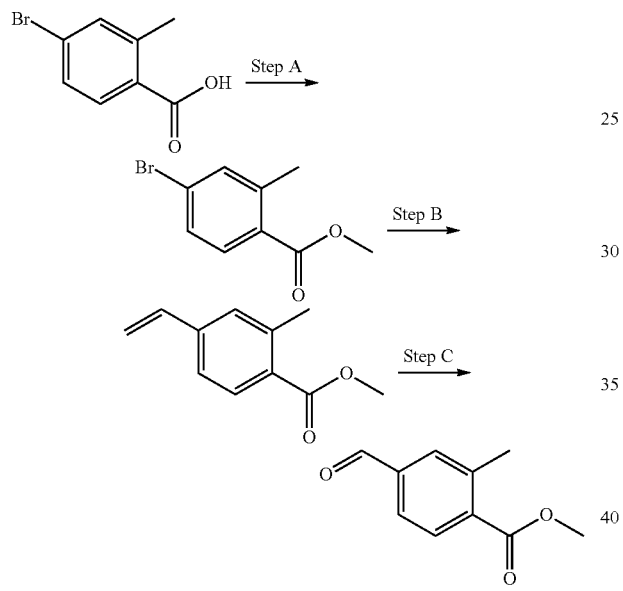

Step A

To an ice cooled (0-5° C.) suspension of commercially available 4-bromo-2-methylbenzoic acid (3.22 g) in MeOH (60 mL) was dropwise added thionyl chloride (3.2 mL). The ice bath was removed and the mixture was stirred at room temperature for 12 h. The mixture was concentrated, diluted with EtOAc (20 mL), washed with H$_2$O (20 mL) and saturated aqueous NaCl (10 mL), dried (MgSO$_4$), filtered and concentrated to afford the title compound as a solid (2.94 g, 86%). [MH]+=230.

Step B

Using a microwave, a mixture of the title compound from Step A above (1.37 g), Pd(PPh$_3$)$_4$ (135 mg) and tributyl(vinyl) tin (2.1 mL) in 1,4-dioxane (15 mL) was heated at 120° C. for 5 h. The mixture was cooled to room temperature and Florisil® was added. The resulting mixture was allowed to stand for 2 h and then filtered. The filter cake was washed with H$_2$O and EtOAc. The combined filtrates were washed with H$_2$O (20 mL) and saturated aqueous NaCl (20 mL), dried (MgSO$_4$), filtered, concentrated and purified by chromatography (silica, CH$_2$Cl$_2$/acetone) to afford the title compound (800 mg, 75%). [MH]+=177.

Step C

A slow flow of ozone was passed through a cooled (-78° C.) solution of the title compound from Step B above (627 mg) in CHCl$_3$ (50 mL) over a period of 20 min. The mixture was purged with nitrogen and dimethylsulfide (1 mL) was added. The resulting mixture was stirred at -78° C. for 1 h, allowed to warm to room temperature, concentrated and purified by chromatography (silica, CH$_2$Cl$_2$/acetone) to afford the title compound (570 mg, 90%). [MH]+=179.

Preparative Example 1015

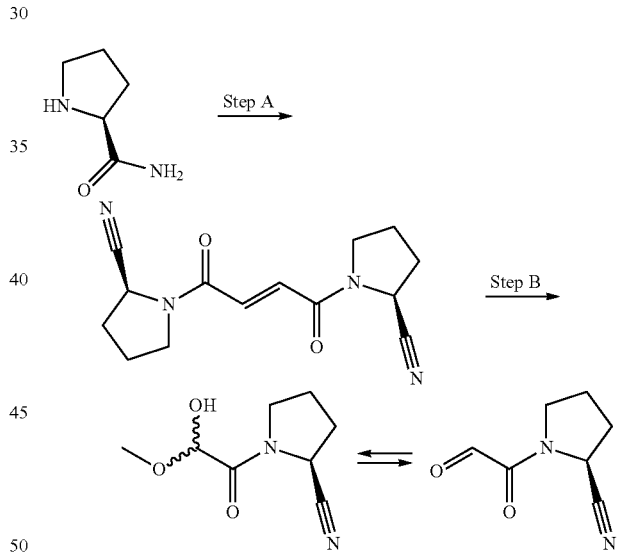

Step A

To an ice cooled (0-5° C.) mixture of commercially available L-prolinamide (25 g), NEt$_3$ (30 mL) and DMAP (1.9 g) in CH$_2$Cl$_2$ (1.2 L) was added fumaryl chloride (11.7 ml). The ice bath was removed and the resulting dark mixture was stirred at room temperature for 16 h. The mixture was cooled again to 0-5° C. (ice bath), trifluoroacetic anhydride (77 mL) was dropwise added and the resulting mixture was stirred for 2 d while warming to room temperature. Ice (500 g) was added followed by cautious addition of saturated aqueous NaHCO$_3$ (600 mL). After the evolution of gas had ceased, the organic phase was separated and washed with saturated aqueous NaHCO$_3$ (350 mL), H$_2$O (350 mL) and saturated aqueous NaCl (200 mL), dried (MgSO$_4$), filtered and concentrated to afford the title compound (28.6 g, 98%). $^1$H-NMR (CDCl$_3$)

δ=7.26 (s, 2H), 4.72-4.83 (m, 2H), 3.73-3.89 (m, 2H), 3.58-3.69 (m, 2H), 2.12-2.30 (m, 8H).

Step B

A slow flow of ozone was passed through a cooled (−78° C.) solution of the title compound from Step A above (9.6 g) in CHCl$_3$/MeOH (1:1, 180 mL) over a period of 3 h. The mixture was purged with nitrogen and dimethylsulfide (6 mL) was added. The resulting mixture was stirred at −78° C. for 1 h, allowed to warm to room temperature, concentrated and purified by chromatography (silica, CH$_2$Cl$_2$/MeOH) to afford the title compound as a ~9:1 mixture of the corresponding methoxy hemiacetal and the free aldehyde (8.9 g, 69%). $^1$H-NMR (D$_2$O) δ=7.90 (s, $^1$/$_{10}$H), 5.50 (s, $^9$/$_{10}$H), 4.72-4.81 (m, 1H), 3.60-3.84 (m, 2H), 3.32 (s, 3H), 2.10-2.38 (m, 4H).

Preparative Example 1016

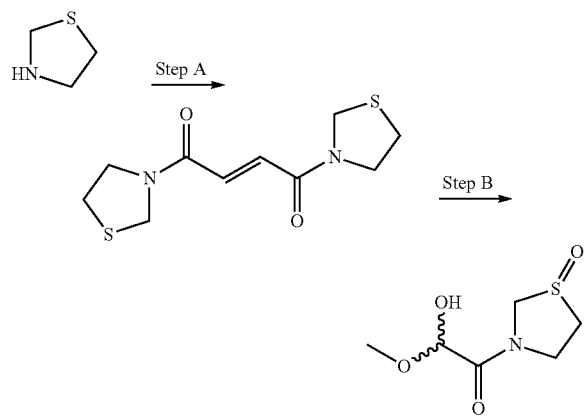

Step A

To an ice cooled (0-5° C.) mixture of commercially available thiazolidine (1 g), NEt$_3$ (780 μL) and DMAP (136 mg) in CH$_2$Cl$_2$ (56 mL) was added fumaryl chloride (604 μl). The ice bath was removed and the resulting dark mixture was stirred at room temperature overnight, filtered and concentrated to afford the crude title compound (2.69 g, 98%). [MH]$^+$=259.

Step B

A slow flow of ozone was passed through a cooled (−78° C.) solution of the title compound from Step A above (833 mg) in CH$_2$Cl$_2$/MeOH (1:1, 16 mL) over a period of 45 min. The mixture was purged with nitrogen and dimethylsulfide (1.2 mL) was added. The resulting mixture was stirred at −78° C. for 1 h, allowed to warm to room temperature, concentrated and purified by chromatography (silica, EtOAc/MeOH) to afford the title compound (293 mg, 23%).

Preparative Example 1017

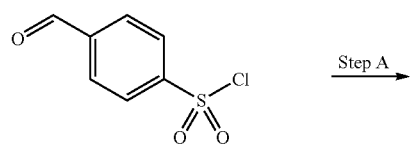

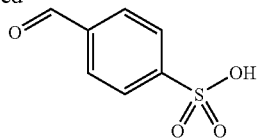

Step A

Commercially available 4-formyl-benzenesulfonyl chloride (70 mg) was suspended in 1M aqueous HCl (3 mL) and stirred at room temperature for 2 h and then concentrated to afford the title compound, which was used without further purification.

Preparative Example 1018

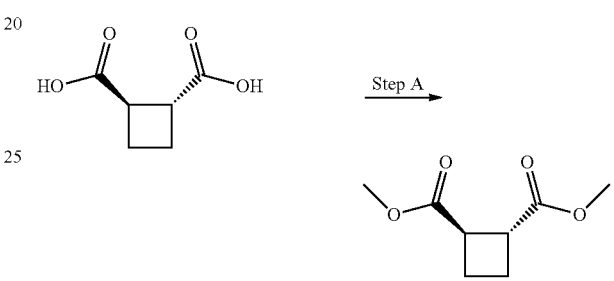

Step A

To a solution of commercially available trans-cyclobutane-1,2-dicarboxylic acid (1.5 g) in MeOH (50 mL) was added thionyl chloride (2.3 mL). The resulting mixture was heated to reflux for 2 h and then concentrated to afford the title compound as a yellow liquid (1.79 g, >99%). $^1$H-NMR (CDCl$_3$) δ=3.67 (s, 6H), 3.33-3.43 (m, 2H), 2.11-2.19 (m, 4H).

Preparative Example 1019

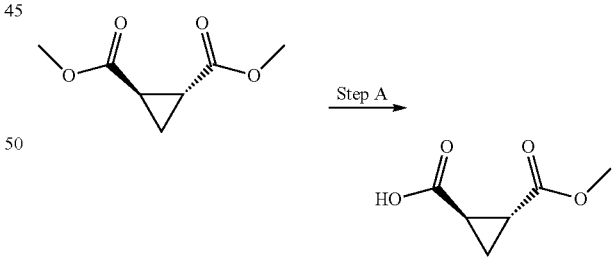

Step A

To a solution of commercially available trans-cyclopropane-1,2-dicarboxylic acid (1.0 g) in MeOH/H$_2$O (10:1, 7.7 mL) was added KOH (354 mg). The resulting mixture was stirred at room temperature for 6 h, diluted with H$_2$O (40 mL), washed with cyclohexane (2×30 mL), acidified to pH~1 with a 1M aqueous HCl and extracted with EtOAc (3×40 mL). The combined organic phases were dried (MgSO$_4$), filtered and concentrated to afford the title compound as a colorless oil (685 mg, 75%). $^1$H-NMR (CDCl$_3$) δ=3.70 (s, 3H), 2.11-2.27 (m, 2H), 1.43-1.52 (m, 2H).

Preparative Examples 1020-1021

Following a similar procedure as described in the Preparative Example 1019, except using the bisesters indicated in Table I-48 below, the following compounds were prepared.

TABLE I-48

| Prep. Ex. # | bisester | product | yield |
|---|---|---|---|
| 1020 | | | 80%<br>¹H-NMR (CDCl₃)<br>δ = 3.70 (s, 3 H),<br>2.06-2.15 (m, 2 H),<br>1.63-1.73 (m, 1 H),<br>1.30-1.40 (m, 1 H). |
| 1021 | | | 69%<br>¹H-NMR (CDCl₃)<br>δ = 3.70 (s, 3 H),<br>3.38-3.48 (m, 2 H),<br>2.15-2.23 (m, 4 H). |

Preparative Example 1022

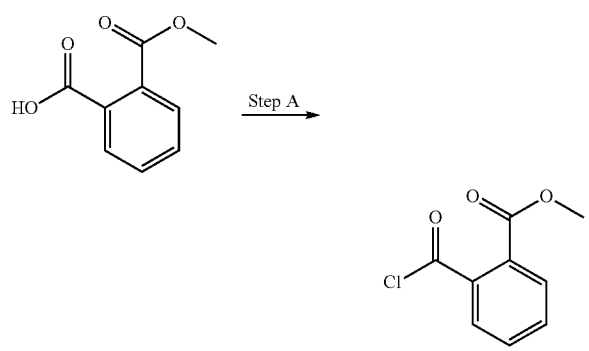

Step A

To a suspension of commercially available phthalic acid monomethyl ester (900 mg) in toluene (6 mL) were added DMF (1 drop) and thionyl chloride (2.3 mL). The resulting mixture was heated at 95° C. (temperature of the oil bath) for 1½ h, concentrated and dried in vacuo to afford the title compound as a pale yellow oil (964 mg, 97%). ¹H-NMR (CDCl₃) δ=7.81-7.87 (m, 1H), 7.72-7.76 (m, 1H), 7.58-7.64 (m, 2H), 3.91 (s, 3H).

Preparative Examples 1023-1026

Following a similar procedure as described in the Preparative Example 1022, except using the acids indicated in Table I-49 below, the following compounds were prepared.

TABLE I-49

| Prep. Ex. # | acid | product | yield |
|---|---|---|---|
| 1023 | | | 92%<br>¹H-NMR (CDCl₃)<br>δ = 8.73 (t, 1 H), 8.32 (dt, 1 H), 8.27 (dt, 1 H),<br>7.60 (t, 1 H), 3.92 (s, 3 H). |
| 1024 | | | 87%<br>¹H-NMR (CDCl₃)<br>δ = 3.74 (s, 3 H),<br>2.58-2.68 (m, 1 H),<br>2.38-2.48 (m, 1 H),<br>1.54-1.70 (m, 2 H). |
| 1025 | | | 91%<br>¹H-NMR (CDCl₃)<br>δ = 3.75 (s, 3 H),<br>2.58-2.68 (m, 1 H),<br>2.27-2.37 (m, 1 H),<br>1.85-1.95 (m, 1 H),<br>1.40-1.50 (m, 1 H). |

TABLE I-49-continued

| Prep. Ex. # | acid | product | yield |
|---|---|---|---|
| 1026 | 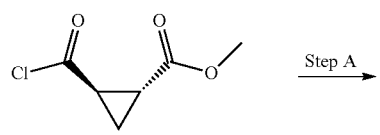 | | 91%<br>¹H-NMR (CDCl₃)<br>δ = 3.84 (q, 1 H), 3.72<br>(s, 3 H), 3.84 (q, 1 H),<br>2.10-2.38 (m, 4 H). |

Preparative Example 1027

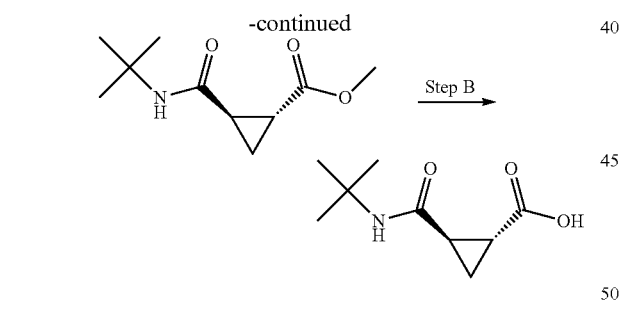

Step A

To a solution of commercially available tert-butylamine (66 µL) in pyridine (3 mL) was added the title compound from the Preparative Example 1024 (100 mg). The resulting mixture was stirred at room temperature overnight, concentrated and diluted with EtOAc (40 mL) and H₂O (15 mL). The organic phase was separated, washed with 1M aqueous HCl (15 mL) and H₂O (15 mL), dried (MgSO₄), filtered and concentrated to afford the title compound as a yellow oil (67.6 mg, 55%). [MH]⁺=200.

Step B

The title compound from Step A above (67.6 mg) in THF/H₂O (1:1, 6 mL) was added a 1M aqueous KOH (680 µL). The mixture was stirred at room temperature overnight. Additional 1M aqueous KOH (680 µL) was added and stirring at room temperature was continued for 4 h. The mixture was concentrated, acidified to pH~1 with a 1M aqueous HCl and extracted with EtOAc (3×20 mL). The combined organic phases were dried (MgSO₄), filtered and concentrated to afford the title compound as a white solid (60 mg, 95%). [α]⁺=186.

Preparative Examples 1028-1029

Following a similar procedure as described in the Preparative Example 1027, except using the acids indicated in Table I-50 below, the following compounds were prepared.

TABLE I-50

| Prep. Ex. # | acid | product | yield |
|---|---|---|---|
| 1028 | | | 59%<br>[MH]⁺ = 174 |
| 1029 | | | 37%<br>[MH]⁺ = 186 |

Preparative Example 1030

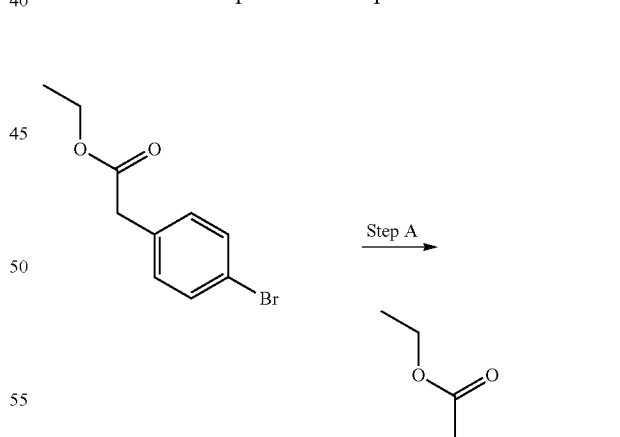

Step A

To a solution of potassium 1,1,1,3,3,3-hexamethyl-disilazane (3.29 g) in DMF (40 mL) was added a solution of commercially available (4-bromo-phenyl)-acetic acid ethyl ester (3.6 g) in DMF (10 mL). The resulting mixture was stirred at room temperature for 10 min, before bromoacetaldehyde diethylacetal (3.25 g) was added dropwise. After complete addition the mixture was heated at 45° C. for 1 h, cooled (ice bath), diluted with saturated aqueous NH₄Cl (5 mL) and ice water (45 mL) and extracted with cyclohexane (3×50 mL). The combined organic phases were concentrated, suspended in H₂O (7.5 mL) and cooled to 0-5° C. (ice bath). A 1:1 mixture of trifluoroacetic acid and CHCl₃ (45 mL) was added and the mixture was stirred for 2 h. The mixture was poured into a mixture of 1M aqueous K₂CO₃ (115 mL) and CH₂Cl₂ (200 mL) and the pH was adjusted to pH~7.5 by addition of solid K₂CO₃. The organic phase was separated and the aqueous phase was extracted with CH₂Cl₂ (120 mL). The combined organic phases were washed with H₂O (200 mL) and saturated aqueous NaCl (200 mL), dried (MgSO₄), filtered, concentrated and purified by chromatography (silica, petroleum ether/EtOAc) to afford the title compound (3.35 g, 79%). ¹H-NMR (CDCl₃) δ=9.77 (s, 1H), 7.43-7.51 (m, 2H), 7.13-7.22 (m, 2H), 4.02-4.25 (m, 3H), 3.36 (dd, 1H), 2.78 (dd, 1H), 1.20 (t, 3H).

Preparative Example 1031

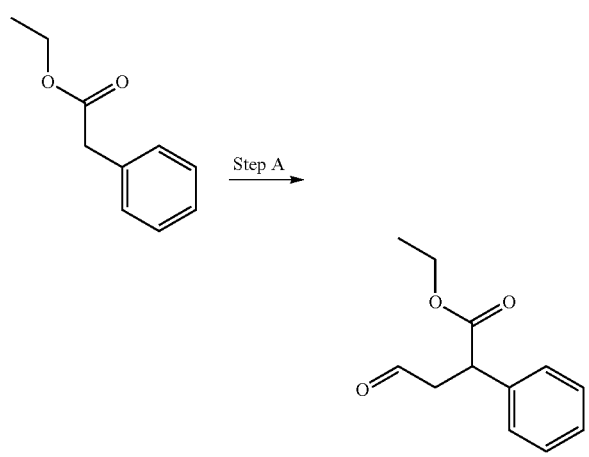

Step A

Commercially available phenyl-acetic acid ethyl ester was treated similarly as described in the Preparative Example 1030, Step A to afford the title compound (88%). ¹H-NMR (CDCl₃)=9.78 (s, 1H), 7.21-7.38 (m, 5H), 4.02-4.25 (m, 3H), 3.39 (dd, 1H), 2.80 (dd, 1H), 1.20 (t, 3H).

Preparative Example 1032

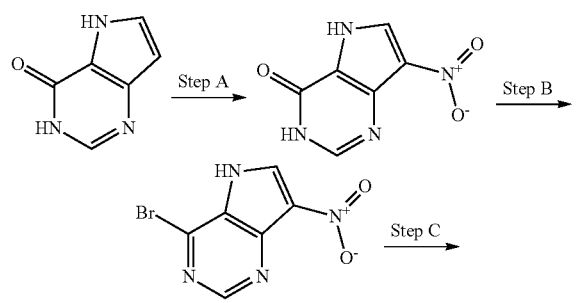

-continued

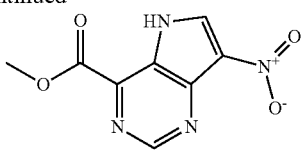

Step A

The title compound from the Preparative Example 378, Step A (4 g) was added in portions to an ice cooled mixture of 90% HNO₃ (8 mL) and 65% HNO₃ (4 mL). After complete addition, conc. H₂SO₄ (13.6 mL) was added slowly keeping the reaction temperature below 12° C. After the complete addition, the mixture was stirred at 0-5° C. (ice bath) for 2 h. The obtained clear yellow solution was then poured onto a mixture of ice (30 g) and H₂O (60 mL). The formed precipitate was collected by filtration, washed with H₂O (160 mL) and dried in vacuo to afford the title compound as a yellow solid (4.78 g, 89%). ¹H-NMR (DMSO-d₆) δ=13.50 (s, 1H), 12.58 (s, 1H), 8.52 (d, 1H), 8.10 (s, 1H).

Step B

The title compound from Step A above (4.78 g) was grinded in a mortar and added at 110-115° C. in portions to neat POBr₃ (40 g). The obtained mixture was stirred at 110-115° C. overnight, cooled to 0-5° C. (ice bath) and hydrolyzed by careful addition with ice water (450 mL). The mixture was adjusted to pH-8 by careful addition of solid NaHCO₃ and then extracted with EtOAc (6×400 mL). The combined organic phase was dried (MgSO₄), filtered and concentrated to afford the title compound (1.30 g, 20%). [MH]⁺=243/245. The remaining aqueous phase was acidified (pH ~1) by addition of 37% HCl. The formed precipitate was collected by filtration, washed with H₂O and dried in vacuo to afford a solid residue (2.7 g) containing a mixture of the title compound (70%) and the unreacted title compound from Step A (30%).

Step C

To a slurry of a mixture (2.7 g) of the title compound from Step B above (70%) and the title compound from Step A (30%) in MeOH/DMA (60:40, 125 mL) and MeOH (75 ml) was added NEt₃ (3.5 mL). The resulting mixture was sonicated for 25 min while a stream of N₂ was passed through the mixture. Pd(OAc)₂ (130 mg) and dppf (252 mg) were added and the mixture was stirred at 80° C. under a carbon monoxide atmosphere at 6.5 bar until the bromo starting material was consumed. The mixture was filtered and the filter cake was washed with MeOH. The combined filtrate concentrated in vacuo, coated on silica and purified by chromatography (silica, CH₂Cl₂/MeOH) to afford the title compound as an orange solid (1 g, 41%). [MH]⁺=223.

Preparative Example 1033

-continued

Step A

A mixture of the title compound from the Preparative Example 1032, Step C (832 mg) and Pd/C (10 wt %, 300 mg) in MeOH (80 mL) was hydrogenated at atmospheric pressure for 30 min, filtered and concentrated to afford the title compound as a red solid residue (719 mg, >99%). [MH]⁺=193.

Preparative Example 1034

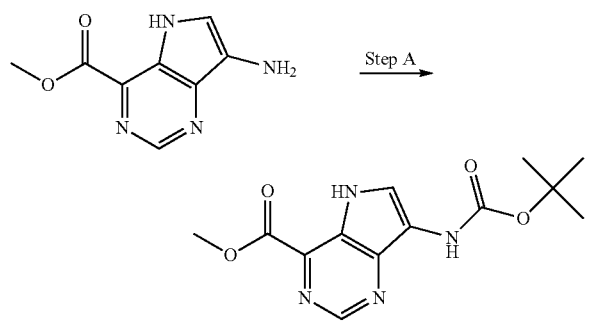

Step A

A mixture of the title compound from the Preparative Example 1033, Step A (540 mg), di-tert-butyl dicarbonate (590 mg) and NEt₃ (400 µL) in THF/ACN (1:1, 24 mL) was stirred at room temperature overnight, concentrated, coated on silica and purified by chromatography (silica, CH₂Cl₂/MeOH) to afford the title compound as a yellow solid (300 mg, 32%). [MH]⁺=293.

Preparative Example 1035

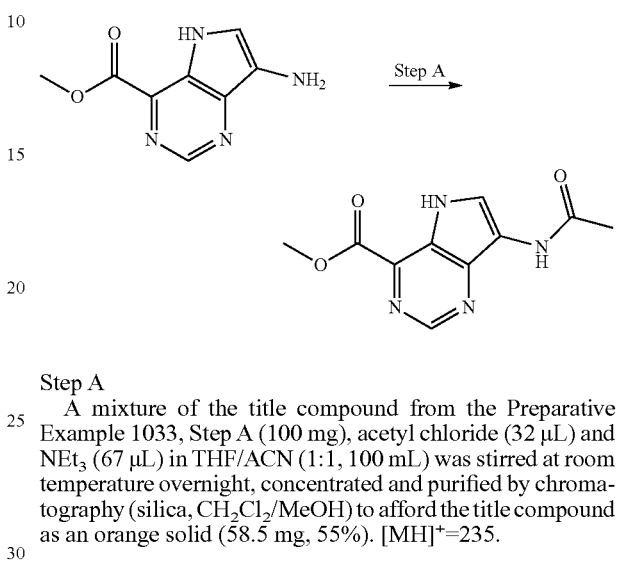

Step A

A mixture of the title compound from the Preparative Example 1033, Step A (100 mg), acetyl chloride (32 µL) and NEt₃ (67 µL) in THF/ACN (1:1, 100 mL) was stirred at room temperature overnight, concentrated and purified by chromatography (silica, CH₂Cl₂/MeOH) to afford the title compound as an orange solid (58.5 mg, 55%). [MH]⁺=235.

Preparative Examples 1036-1039

Following a similar procedure as described in the Preparative Example 1035, except using the acid chlorides indicated in Table I-51 below, the following compounds were prepared.

TABLE I-51

| Prep. Ex. # | acid chloride | product | yield |
|---|---|---|---|
| 1036 | | | n.d. [MH]⁺ = 297 |
| 1037 | | | n.d. [MH]⁺ = 355 |
| 1038 | | | n.d. [MH]⁺ = 355 |

TABLE I-51-continued

| Prep. Ex. # | acid chloride | product | yield |
|---|---|---|---|
| 1039 | | | n.d. [MH]$^+$ = 355 |

Preparative Example 1040

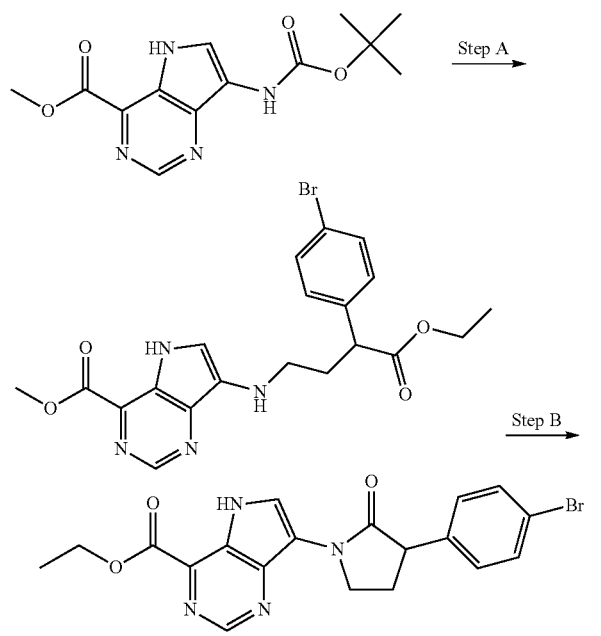

Step A

A mixture of the title compound from the Preparative Example 1034, Step A (50 mg) in a 4M solution of HCl in 1,4-dioxane (1 mL) was stirred at room temperature for 1 h and then concentrated. The remaining residue was added to solution of NaBH$_3$CN (25 mg) in THF/MeOH (1:1, 1 mL). To the resulting solution was slowly added a solution of the title compound from the Preparative Example 1030, Step A (50 mg) in THF/MeOH (1:1, 1 mL) over a period of 2 h. Then the mixture was concentrated, diluted with saturated aqueous NaHCO$_3$ and extracted with EtOAc (3×). The combined organic phases were dried (MgSO$_4$), filtered, absorbed onto silica and purified by chromatography (silica) to afford the title compound (23 mg, 28%). [MH]$^+$=461/463.

Step B

To an ice cooled (0-5° C.) solution of the title compound from Step A above (13 mg) in THF (1 mL) was added a 1M solution of tert.-butyl magnesium chloride (60 μL). The resulting mixture was stirred at 0-5° C. (ice bath) for 1½ h, diluted with saturated aqueous NaHCO$_3$ and extracted with EtOAc (3×). The combined organic phases were dried (MgSO$_4$), filtered, concentrated and purified by preparative thin layer chromatography (silica, EtOAc) to afford the title compound as a brown solid (7 mg, 60%). [MH]$^+$=429/431.

Preparative Example 1041

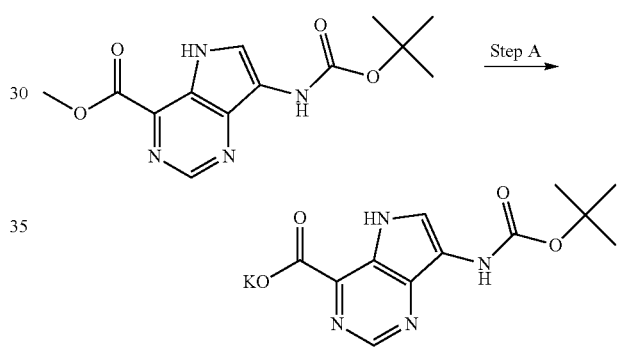

Step A

To a solution of the title compound from the Preparative Example 1034, Step A (150 mg) in THF/ACN/H$_2$O (1:1:1, 12.9 mL) was added a 1M aqueous KOH (770 μL). The mixture was stirred at room temperature for 1 h, concentrated and dried in vacuo to afford the title compound (162 mg, >99%). [(M-K)H$_2$]$^+$=279.

Preparative Examples 1042-1046

Following a similar procedure as described in the Preparative Example 1041, except using the esters indicated in Table I-52 below, the following compounds were prepared.

TABLE I-52

| Prep. Ex. # | ester | product | yield |
|---|---|---|---|
| 1042 | | | n.d. [(M − K)H$_2$]$^+$ = 221. |

TABLE I-52-continued

| Prep. Ex. # | ester | product | yield |
|---|---|---|---|
| 1043 | | | n.d. [(M − K)H₂]⁺ = 283 |
| 1044 | | | n.d. [(M − K)H₂]⁺ = 341 |
| 1045 | | | n.d. [(M − K)H₂]⁺ = 341 |
| 1046 | | | n.d. [(M − K)H₂]⁺ = 401/403 |

Preparative Example 1047

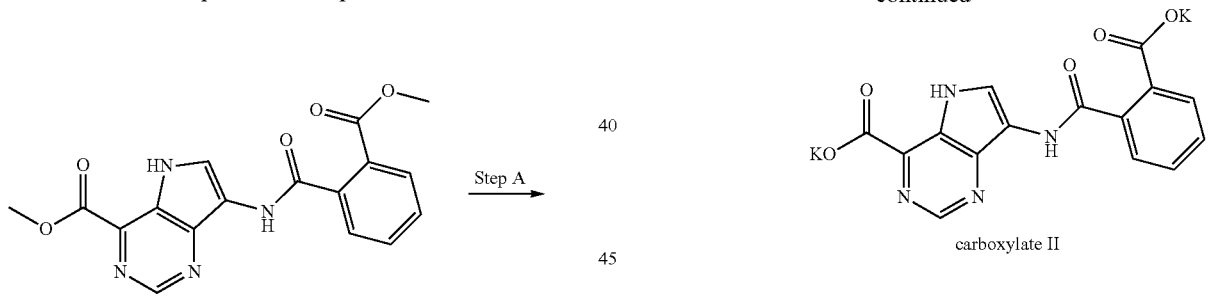

Step A

To a solution of the title compound from the Preparative Example 1038 (24.6 mg) in THF/ACN/H₂O (1:1:1, 1.8 mL) was added a 1M aqueous KOH (69 µL). The mixture was stirred at room temperature for 1 h, concentrated and dried in vacuo to afford a ~1:1 mixture of the carboxylate I ([(M-K)H₂]⁺=341) and the carboxylate II ([(M-K2)H₃]⁺=327).

Preparative Example 1048

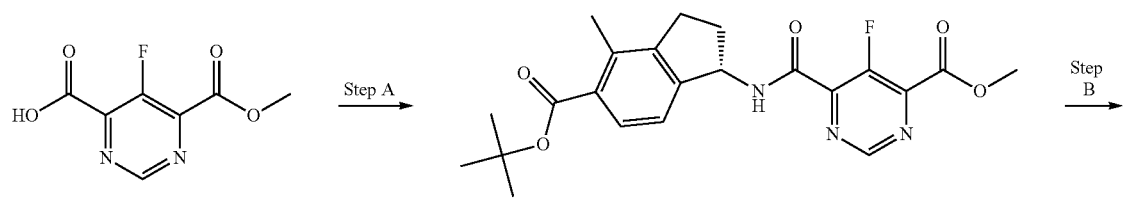

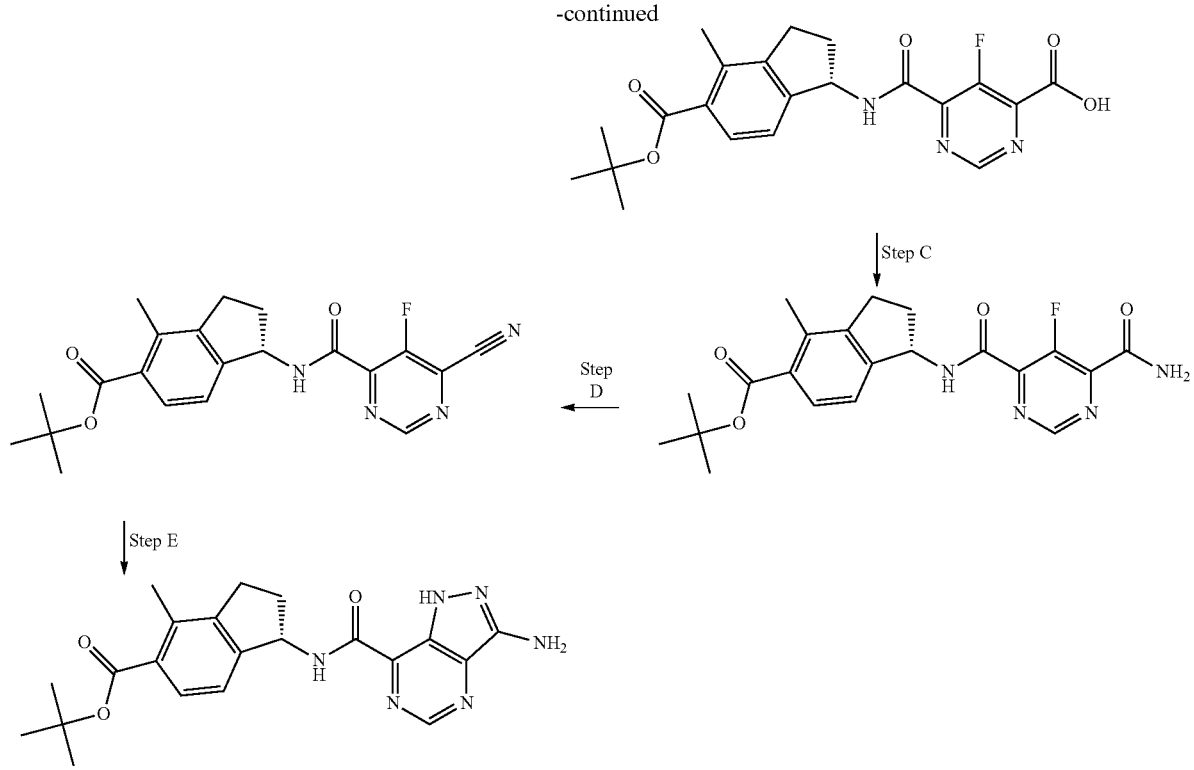

Step A

The title compound from the Preparative Example 376, Step E (400 mg) was treated similarly as described in the Preparative Example 279, Step A, except using the title compound from the Preparative Example 7, Step D (500 mg) instead of the title compound from the Preparative Example 214, Step A to afford the title compound (287 mg, 33%). [MH]$^+$=430.

Step B

The title compound from Step A above (287 mg) was treated similarly as described in the Preparative Example 331, Step A to afford the title compound (260 mg, 94%). [α]$^+$=416.

Step C

The title compound from Step B above (260 mg) was treated similarly as described in the Preparative Example 280, Step A, except using a commercially available 0.5M solution of NH$_3$ in 1,4-dioxane instead of the title compound from the Preparative Example 138 to afford the title compound (196 mg, 76%). [MH]$^+$=415.

Step D

The title compound from Step C above (196 mg) was treated similarly as described in the Preparative Example 377, Step D to afford the title compound (113 mg, 61%). [MH]$^+$=397.

Step E

The title compound from Step D above (113 mg) was treated similarly as described in the Preparative Example 377, Step E to afford the title compound (110 mg, 98%). [MH]$^+$=409.

Preparative Example 1049

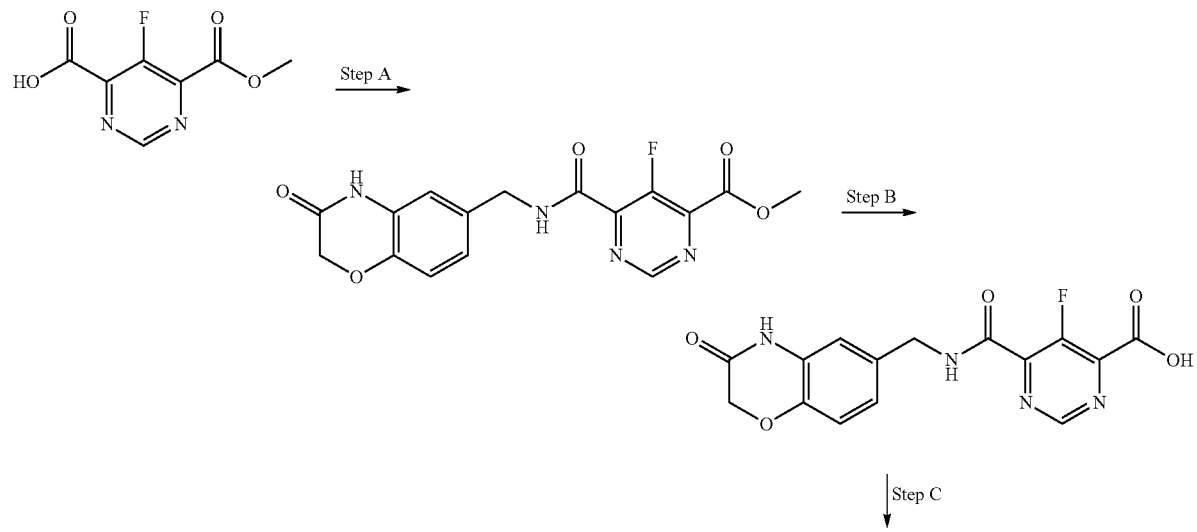

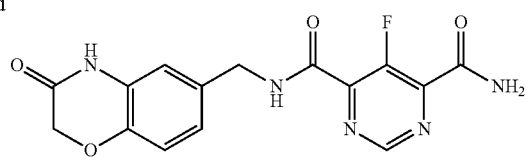

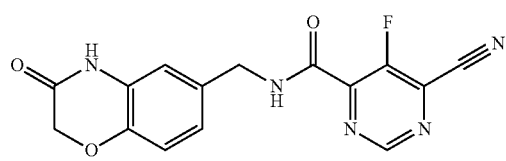

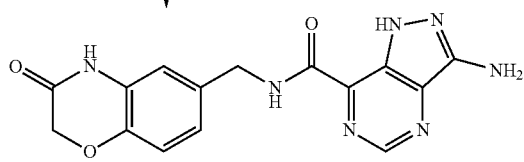

Step A

The title compound from the Preparative Example 376, Step E (2.93 g) was treated similarly as described in the Preparative Example 279, Step A, except using the title compound from the Preparative Example 161 (3.35 g) instead of the title compound from the Preparative Example 214, Step A to afford the title compound (1.89 g, 36%). (MH)$^+$=361.

Step B

The title compound from Step A above (1.89 g) was treated similarly as described in the Preparative Example 331, Step A to afford the crude title compound (2.0 g). [MH]$^+$=347.

Step C

The crude title compound from Step B above (2.0 g) was treated similarly as described in the Preparative Example 280, Step A, except using a commercially available 0.5M solution of NH$_3$ in 1,4-dioxane instead of the title compound from the Preparative Example 138 to afford the crude title compound (5.0 g). [MH]$^+$=346.

Step D

The crude title compound from Step C above (4.6 g) was treated similarly as described in the Preparative Example 377, Step D to afford the title compound (233 mg, 5% over 3 steps). [MH]$^+$=328.

Step E

The title compound from Step D above (233 mg) was treated similarly as described in the Preparative Example 377, Step E to afford the title compound (245 mg, 96%). [MH]$^+$= 340.

Preparative Example 1050

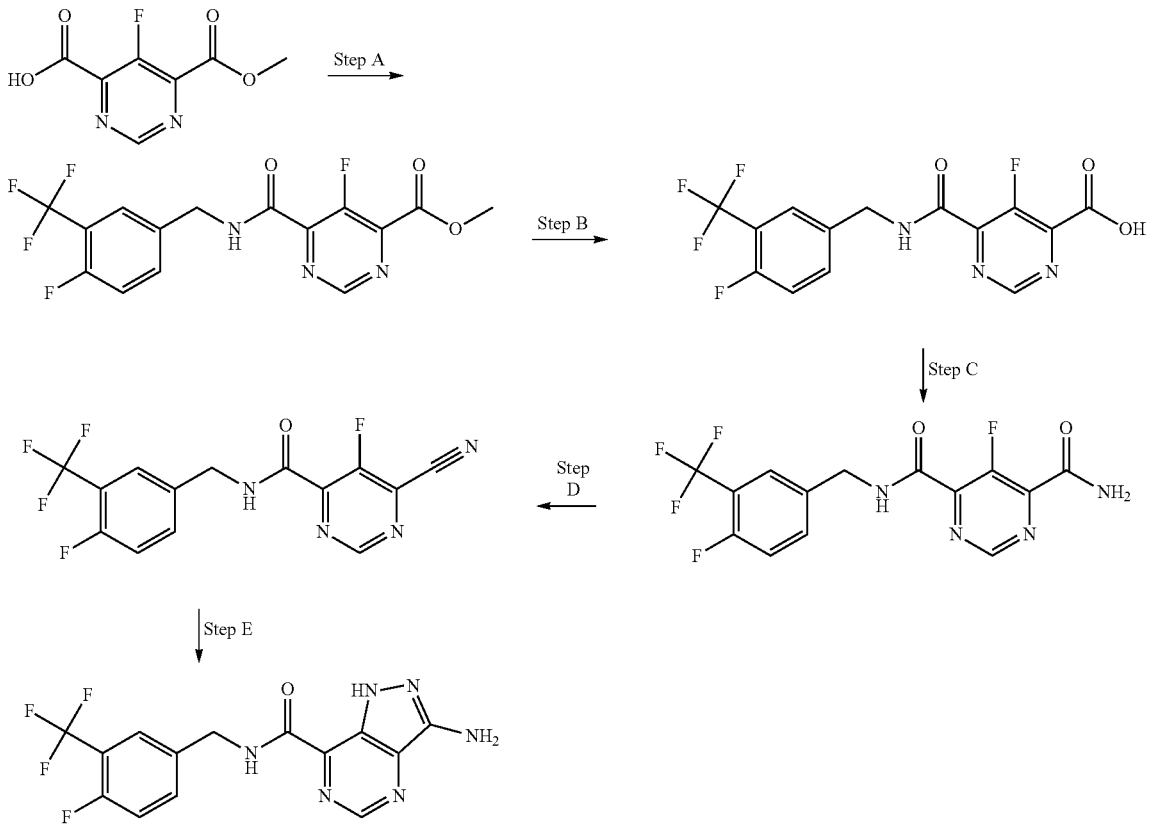

Step A

The title compound from the Preparative Example 376, Step E (1.19 g) was treated similarly as described in the Preparative Example 279, Step A, except using commercially available 4-fluoro-3-trifluoromethyl-benzylamine instead of the title compound from the Preparative Example 214, Step A to afford the title compound (1.42 g, 64%). [MH]+=376.

Step B

The title compound from Step A above (1.42 g) was treated similarly as described in the Preparative Example 331, Step A to afford the crude title compound (1.36 g, 99%). [MH]+=347.

Step C

The title compound from Step B above (1.36 g) was treated similarly as described in the Preparative Example 280, Step A, except using a commercially available 0.5M solution of NH$_3$ in 1,4-dioxane instead of the title compound from the Preparative Example 138 to afford the crude title compound (969 mg, >99%). [MH]+=361.

Step D

The crude title compound from Step C above (969 mg) was treated similarly as described in the Preparative Example 377, Step D to afford the title compound (152 mg, 24%). [MH]+=343.

Step E

The title compound from Step D above (110 mg) was treated similarly as described in the Preparative Example 377, Step E to afford the title compound (123 mg, >99%). [MH]+=355.

Preparative Example 1051

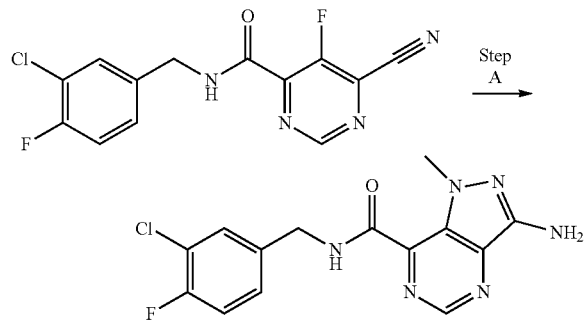

Step A

The title compound from Preparative Example 377, Step D (22 mg) was treated similarly as described in the Preparative Example 377, Step E, except using commercially available methylhydrazine instead of hydrazine to afford the title compound (26 mg, >99%). [MH]+=335.

Example 1

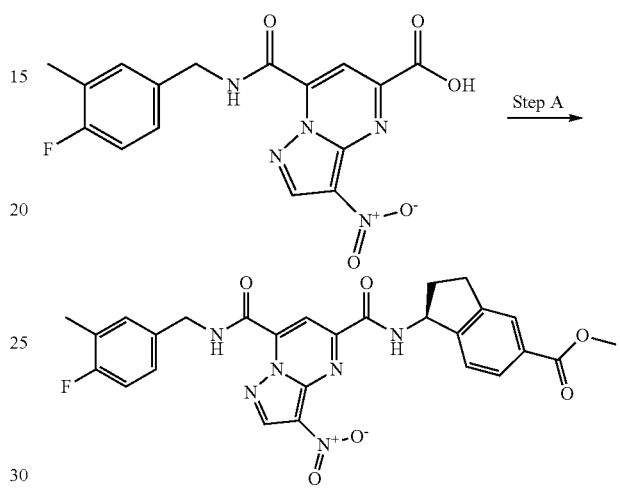

Step A

To a solution of the title compound from the Preparative Example 335 (40 mg) in DMF (2 mL) were added the title compound from the Preparative Example 4, Step B (34 mg), PyBOP (84 mg) and $^i$Pr$_2$NEt (46 µL). The mixture was stirred overnight, concentrated and purified by chromatography (silica, cyclohexane/EtOAc) to afford the title compound (23 mg, 40%). $^1$H-NMR (CDCl$_3$) δ=10.50 (br d, 1H), 9.00 (s, 1H), 8.85 (s, 1H), 8.30 (br t, 1H), 7.95 (s, 1H), 7.90 (d, 2H), 7.40 (d, 2H), 7.25-7.10 (m, 2H), 6.95 (m, 1H), 5.80 (m, 1H), 4.65 (d, 2H), 3.90 (s, 3H), 3.20-2.70 (m, 3H), 2.25 (s, 3H), 2.20-2.00 (m, 1H).

Example 2

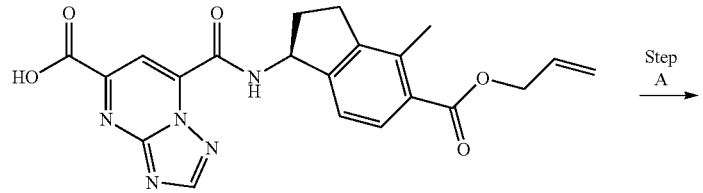

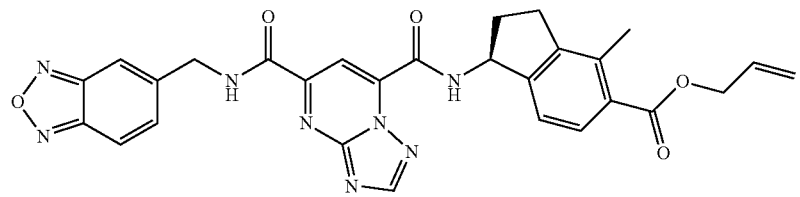

Step A

To a solution of the title compound from the Preparative Example 373, Step A (30 mg) and the title compound from the Preparative Example 228, Step A (30 mg) in DMF (3 mL) were added N-methylmorpholine (40 μL), EDCI (25 mg) and HOAt (13 mg). The mixture was stirred overnight and then concentrated. The remaining residue was dissolved in EtOAc, washed with saturated NaHCO₃, 1N aqueous HCl and saturated aqueous NaCl, dried (MgSO₄), filtered, concentrated and purified by chromatography (silica, CH₂Cl₂/MeOH) to afford the title compound as a colorless solid (35 mg, 90%). [MH]⁺=553.

Example 3

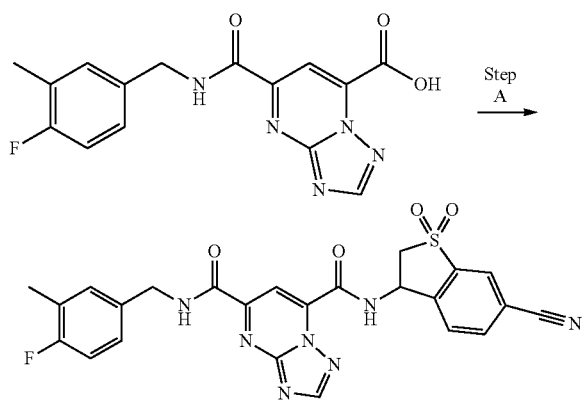

Step A

To a solution of the title compound from the Preparative Example 331, Step A (31 mg) and the title compound from the Preparative Example 218, Step D (27 mg) in DMF (5 mL) were added N-methylmorpholine (13 μL), HATU (57 mg) and HOAt (16 mg). The mixture was stirred overnight and then concentrated. The remaining residue was dissolved in EtOAc, washed with saturated aqueous NaHCO₃, 1N aqueous HCl and saturated aqueous NaCl, dried (MgSO₄), filtered, concentrated and purified by chromatography (silica, CH₂Cl₂/MeOH) to afford the title compound as a colorless solid (57 mg, >99%). [MH]⁺=520.

Example 4

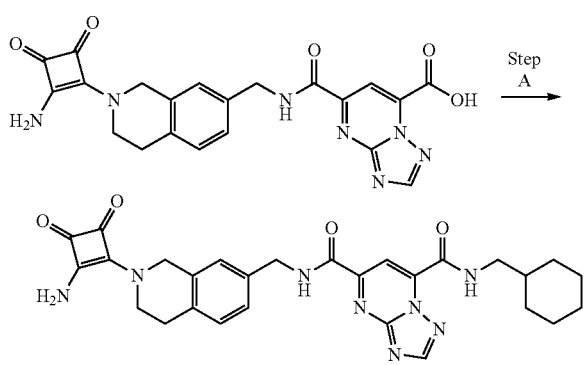

Step A

To a solution of the title compound from the Preparative Example 349 (21.5 mg) in DMF (3 mL) were added cyclo-hexanemethylamine (30 μL), PyBrOP (29 mg) and HOAt (8 mg). The mixture was stirred over the weekend and then concentrated. The remaining residue was dissolved in CHCl₃, washed with saturated aqueous NaI-1CO₃, 1N aqueous HCl and saturated aqueous NaCl, dried (MgSO₄), filtered, concentrated and purified by preparative thin layer chromatography (silica, CH₂Cl₂/MeOH) to afford the title compound as an off-white solid (11.9 mg, 46%). [MH]⁺=543.

Example 5

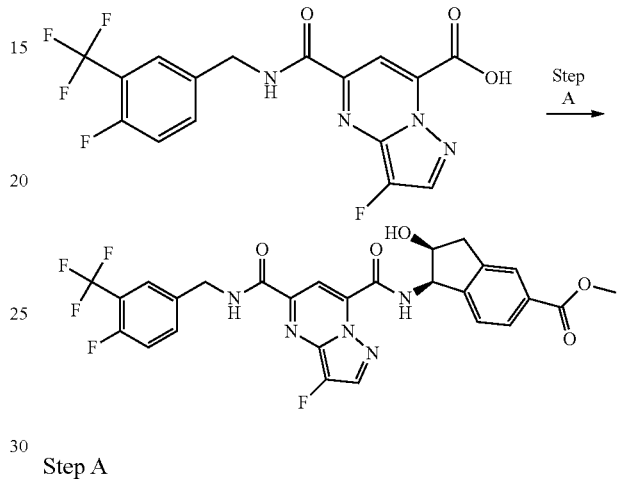

Step A

To a mixture of the title compound from the Preparative Example 324, Step A (106 mg), DMF (20 mL) and CH₂Cl₂ (2.5 mL) at 0° C. was added oxalyl chloride (116 μL). The ice bath was removed and the mixture was stirred for 45 min and concentrated. The resulting residue was brought up in CH₂Cl₂ (1.5 mL) and cannulated into a mixture of the title compound from the Preparative Example 176, Step A (75 mg) and NEt₃ (122 μL) in CH₂Cl₂ (1 mL). The resulting mixture was stirred for 16 h and concentrated. The remaining solid was washed with MeOH (10 mL). The supernatant was concentrated and the resulting solid was washed with MeOH (10 mL). The yellow solids were combined to give the title compound (51 mg, 33%). [M-H]⁻=588.

Example 6

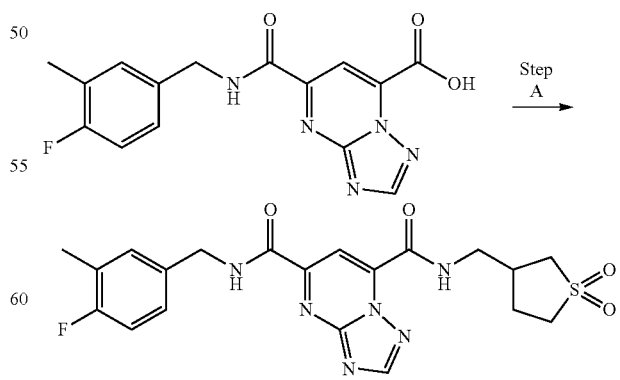

Step A

To a mixture of N-cyclohexyl-carbodiimide-N'-methyl-polystyrene (43 mg) in DMF (100 μL) were added a 0.2M solution of the title compound from the Preparative Example 331, Step A in DMF (150 μL) and a 0.5M solution of HOBt in DMF (60 μL). The mixture was agitated for 30 min, then a 0.5M solution of (1,1-dioxidotetrahydrothien-3-yl)-methylamine in DMF (54 μL) was added and agitation at room temperature was continued for 12 h. The mixture was filtered, concentrated and dissolved in 1,2-dichloroethane (200 μL). (Polystyrylmethyl)-trimethylammonium bicarbonate (16 mg) was added and the mixture was agitated at room temperature for 2 h. Filtration and concentration afforded the title compound (13.1 mg, 95%). [MH]⁺=461.

Example 7

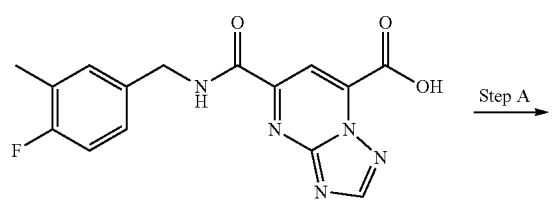

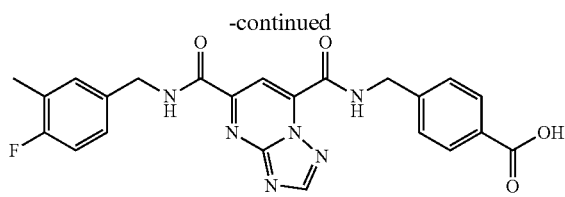

Step A

To a mixture of polystyrene-IIDQ (131 mg) in DMF (800 μL) were added the title compound from the Preparative Example 331, Step A (39 mg) and a 0.5M solution of commercially available 4-aminomethyl-benzoic acid (40 mg). The mixture was agitated for 24 h, filtered and concentrated to afford the title compound (40 mg, 73%). [MH]⁺=463.

Examples 8-277

Following similar procedures as described in the Examples 1 (method A), 2 (method B), 3 (method C), 4 (method D), 5 (method E), 6 (method F) or 7 (method G), except using the acids and amines indicated in Table II-1 below, the following compounds were prepared.

TABLE II-1

| Ex. # | acid, amine | product | method, yield |
|---|---|---|---|
| 8 | | | B, 90% [MH]+ = 579 |
| 9 | | | B, 80% [MH]+ = 644 |

TABLE II-1-continued

| Ex. # | acid, amine | product | method, yield |
|---|---|---|---|
| 10 | | | B, 86% [MH]⁺ = 698 |
| 11 | | | B, >99% [MH]⁺ = 645 |
| 12 | | | B, 98% [MH]⁺ = 542 |

TABLE II-1-continued

| Ex. # | acid, amine | product | method, yield |
|---|---|---|---|
| 13 | | | B, >99% [MH]+ = 594 |
| 14 | | | B, 95% [MH]+ = 582 |
| 15 | | | B, >99% [MH]+ = 596 |

TABLE II-1-continued

| Ex. # | acid, amine | product | method, yield |
|---|---|---|---|
| 16 | | | B, n.d. [MH]⁺ = 577 |
| 17 | | | B, n.d. [MH]⁺ = 560 |
| 18 | | | B, n.d. [MH]⁺ = 566 |

TABLE II-1-continued
| Ex. # | acid, amine | product | method, yield |
|---|---|---|---|
| 19 | 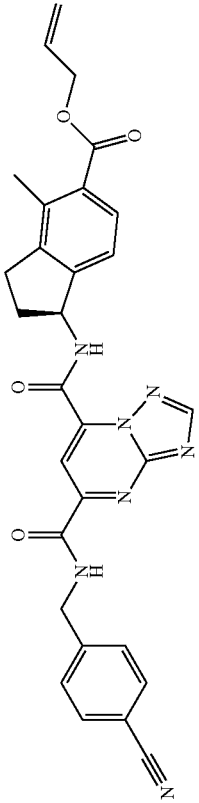 | 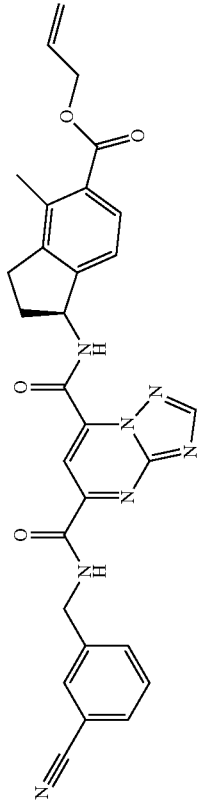 | B, n.d. [MH]⁺ = 536 |
| 20 | 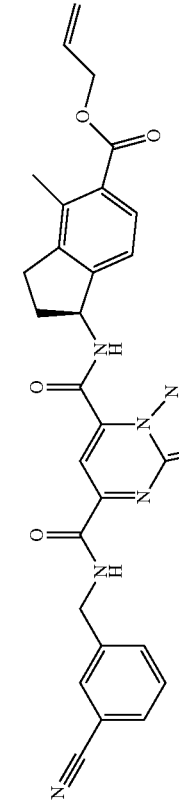 | 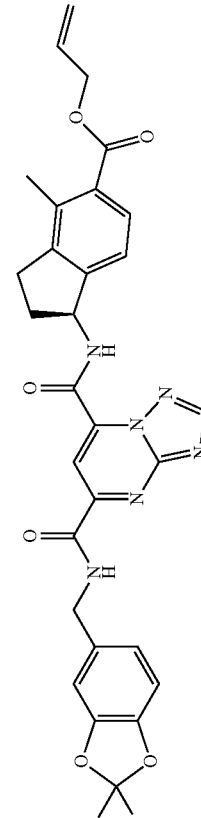 | B, n.d. [MH]⁺ = 536 |
| 21 | 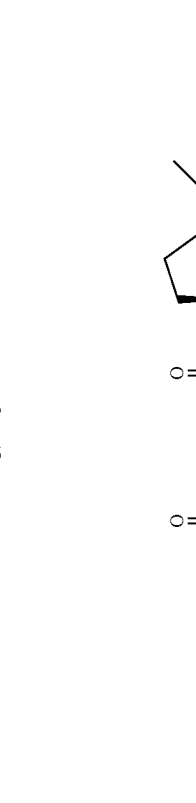 | 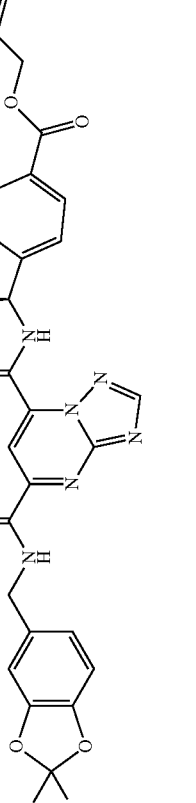 | B, n.d. [MH]⁺ = 591 |

TABLE II-1-continued

| Ex. # | acid, amine | product | method, yield |
|---|---|---|---|
| 22 | (imidazo[1,2-a]pyrimidine dicarboxylic acid with indane amide; 5-(1-aminoethyl)thiophene-2-carbonitrile·HCl) | (corresponding bis-amide product with allyl ester) | B, n.d. [MH]+ = 556 |
| 23 | (imidazo[1,2-a]pyrimidine dicarboxylic acid with indane amide allyl ester; 6-(aminomethyl)-2-methyl-2H-benzo[b][1,4]oxazin-3(4H)-one·HCl) | (corresponding bis-amide product) | B, n.d. [MH]+ = 596 |
| 24 | (pyrazolo[1,5-a]pyrimidine dicarboxylic acid mono-(3-chloro-4-fluorobenzyl)amide; 5-(1-aminoethyl)thiophene-2-carbonitrile·HCl) | (corresponding bis-amide product) | B, 92% [MH]+ = 483 |

TABLE II-1-continued

| Ex. # | acid, amine | product | method, yield |
|---|---|---|---|
| 25 | (3-chloro-4-fluorobenzyl amide pyrazolo[1,5-a]pyrimidine carboxylic acid; methyl 5-(aminomethyl)thiophene-2-carboxylate·HCl) | corresponding bis-amide product | B, 85% [MH]⁺ = 502 |
| 26 | (tert-butyl 4-methyl-indane-amino pyrazolo[1,5-a]pyrimidine carboxylic acid; 2,2-difluoro-benzo[1,3]dioxol-5-ylmethylamine·HCl) | corresponding bis-amide product | B, 79% [MH]⁺ = 606 |
| 27 | (tert-butyl 4-methyl-indane-amino pyrazolo[1,5-a]pyrimidine carboxylic acid; 3-(difluoromethoxy)benzylamine) | corresponding bis-amide product | B, 88% [MH]⁺ = 592 |

TABLE II-1-continued

| Ex. # | acid, amine | product | method, yield |
|---|---|---|---|
| 28 | | | B, 95% [MH]⁺ = 599 |
| 29 | | | B, 18% [MH]⁺ = 489 |
| 30 | | | B, 95% [MH]⁺ = 595 |

TABLE II-1-continued

| Ex. # | acid, amine | product | method, yield |
|---|---|---|---|
| 31 | [pyrazolo[1,5-a]pyrimidine-F carboxylic acid with benzoxazinone-methylamine amide]; 0.5M NH₃ in 1,4-dioxane | [corresponding primary amide product] | B, 41% [MH]⁺ = 385 |
| 32 | [pyrazolo[1,5-a]pyrimidine-F carboxylic acid with benzoxazinone-methylamine amide]; HCl·H₂N-CH₂-(methyl thiophene-2-carboxylate) | [corresponding thiophene methyl ester amide] | B, 87% [MH]⁺ = 539 |
| 33 | [pyrazolo[1,5-a]pyrimidine-F carboxylic acid with benzoxazinone-methylamine amide]; (S)-1-(4-fluorophenyl)ethylamine | [corresponding (S)-1-(4-fluorophenyl)ethyl amide] | B, 45% [MH]⁺ = 507 |

TABLE II-1-continued

| Ex. # | acid, amine | product | method, yield |
|---|---|---|---|
| 34 | (acid shown); H2N-CH2-cyclohexyl | (product shown) | B, 77% [MH]+ = 481 |
| 35 | (acid shown); HCl·H2N-CH3 | (product shown) | B, 65% [MH]+ = 399 |
| 36 | (acid shown); 2M Me2NH in THF | (product shown) | B, 35% [MH]+ = 413 |

TABLE II-1-continued

| Ex. # | acid, amine | product | method, yield |
|---|---|---|---|
| 37 | | | B, 97% [MH]⁺ = 547 |
| 38 | | | B, 84% [MH]⁺ = 581 |
| 39 | | | B, 81% [MH]⁺ = 612 |

TABLE II-1-continued

| Ex. # | acid, amine | product | method, yield |
|---|---|---|---|
| 40 | | | B, 85% [MH]+ = 578 |
| 41 | | | B, n.d. % [MH]+ = 554 |
| 42 | | | B, 68% [MH]+ = 560 |

TABLE II-1-continued
| Ex. # | acid, amine | product | method, yield |
|---|---|---|---|
| 43 | 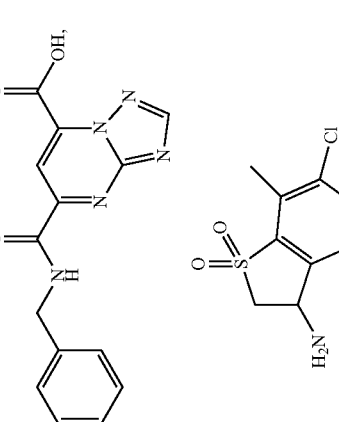 | 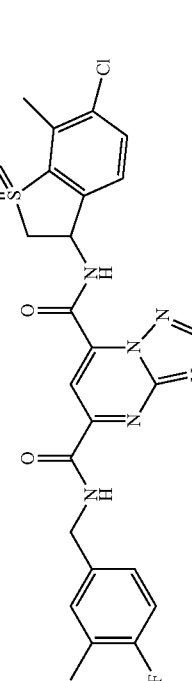 | C, 95% [MH]⁺ = 543 |
| 44 | 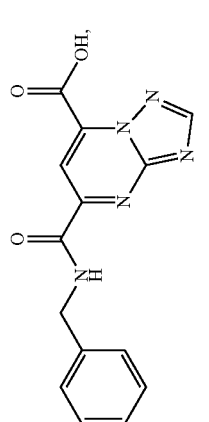 | 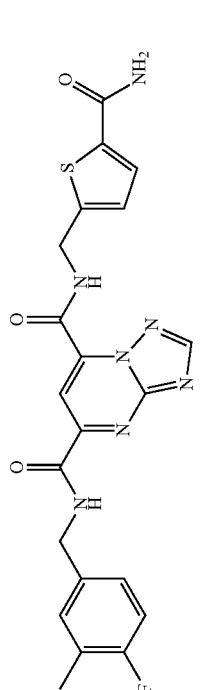 | C, 56% [MH]⁺ = 468 |

TABLE II-1-continued
| Ex. # | acid, amine | product | method, yield |
|---|---|---|---|
| 45 |  | 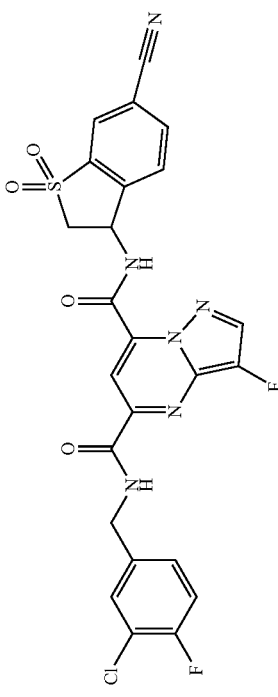 | D, >99%<br>[MH]+ = 557 |
| 46 | 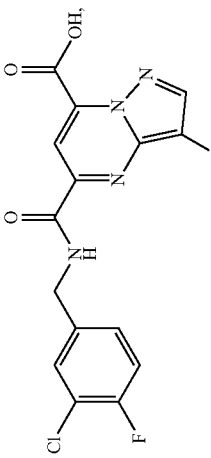 | 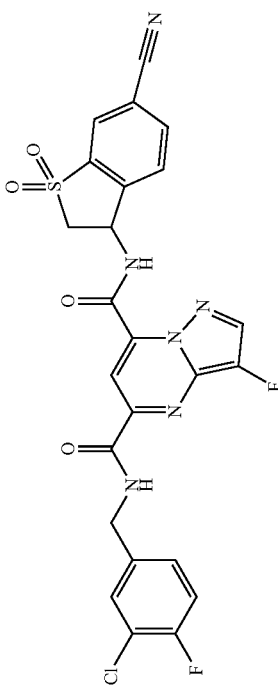 | D, 47%<br>[MH]+ = 590 |

TABLE II-1-continued

| Ex. # | acid, amine | product | method, yield |
|---|---|---|---|
| 47 | (structures) | (structure) | D, >99% [MH]$^+$ = 521 |
| 48 | (structures) | (structure) | D, >99% [MH]$^+$ = 507 |

TABLE II-1-continued

| Ex. # | acid, amine | product | method, yield |
|---|---|---|---|
| 49 | | | D, 76% [MH]+ = 501 |
| 50 | | | D, >99% [MH]+ = 519 |

TABLE II-1-continued

| Ex. # | acid, amine | product | method, yield |
|---|---|---|---|
| 51 | | | D, 30% [MH]+ = 501 |
| 52 | | | D, 77% [MH]+ = 594 |
| 53 | | | C, 62% [MNa]+ = 661 |

TABLE II-1-continued
| Ex. # | acid, amine | product | method, yield |
|---|---|---|---|
| 54 | 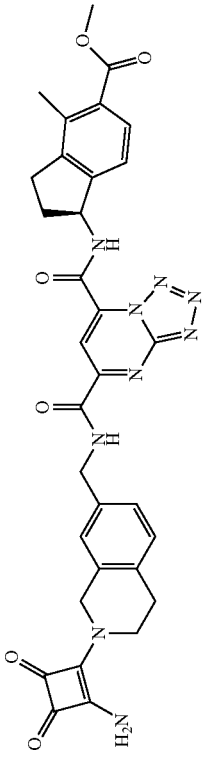 | 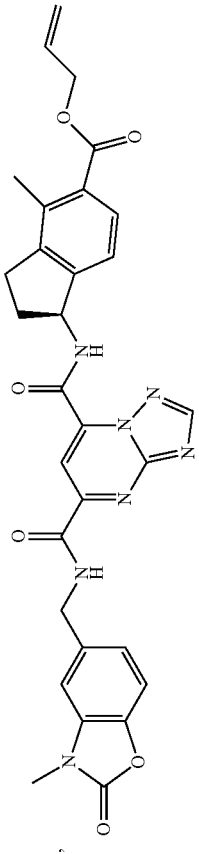 | C, 76% [MH]+ = 636 |
| 55 | 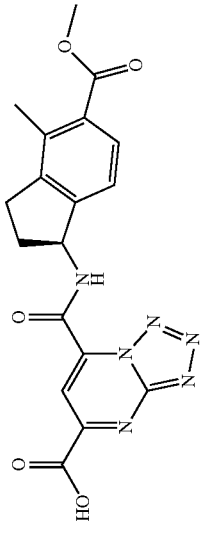 | 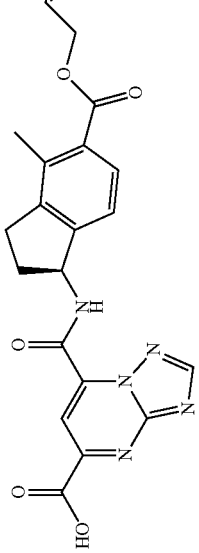 | C, 85% [MH]+ = 582 |

TABLE II-1-continued

| Ex. # | acid, amine | product | method, yield |
|---|---|---|---|
| 56 | | | C, 77% [MH]+ = 557 |
| 57 | | | C, 91% [MNa]+ = 562 |
| 58 | | | C, 85% [M − Boc]+ = 412 |

TABLE II-1-continued

| Ex. # | acid, amine | product | method, yield |
|---|---|---|---|
| 59 | | | C, 98% [M − Boc]+ = 412 |
| 60 | | | C, 92% [MH]+ = 468 |
| 61 | | | C, 71% [MH]+ = 482 |

TABLE II-1-continued

| Ex. # | acid, amine | product | method, yield |
|---|---|---|---|
| 62 | | | C, 86% [MH]+ = 496 |
| 63 | | | C, 75% [MH]+ = 483 |

TABLE II-1-continued
| Ex. # | acid, amine | product | method, yield |
|---|---|---|---|
| 64 | 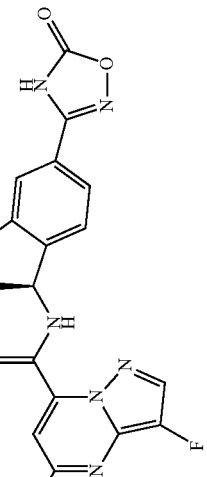 | 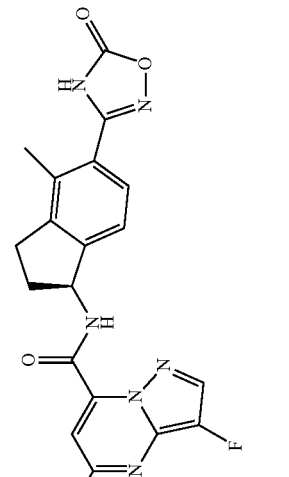 | C, 81% [MH]⁺ = 566 |
| 65 | 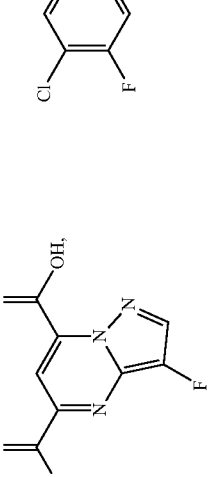 | 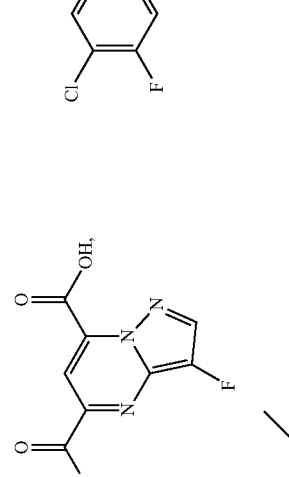 | C, 97% [MH]⁺ = 580 |

TABLE II-1-continued
| Ex. # | acid, amine | product | method, yield |
|---|---|---|---|
| 66 | 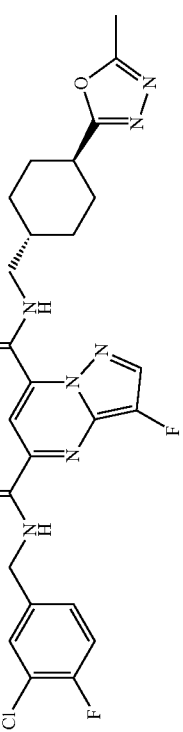 | 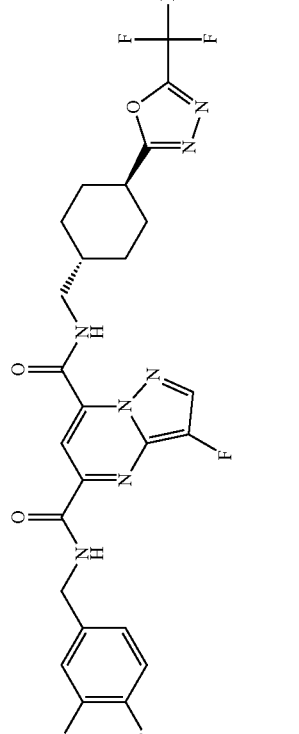 | C, 87% [MH]⁺ = 544 |
| 67 | 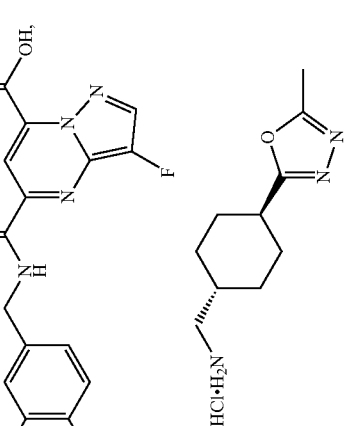 | 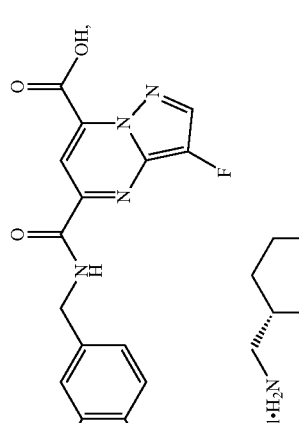 | C, 88% [MH]⁺ = 598 |

| Ex. # | acid, amine | product | method, yield |
|---|---|---|---|
| 68 | | | C, 71%<br>[MH]+ = 530 |
| 69 | | | E, 23%<br>[MH]+ = 517 |

TABLE II-1-continued
| Ex. # | acid, amine | product | method, yield |
|---|---|---|---|
| 70 | 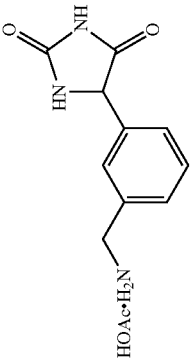 | 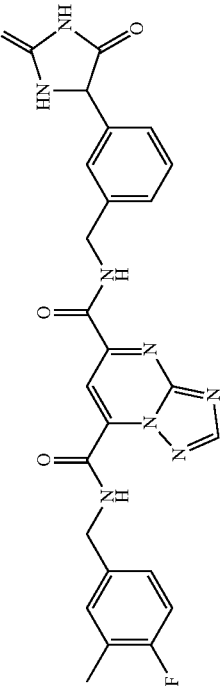 | E, 39% [MH]+ = 517 |
| 71 | 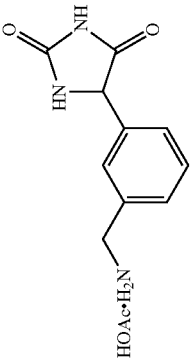 | 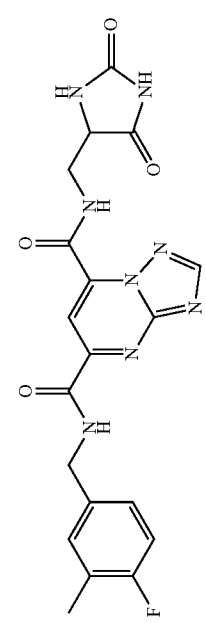 | E, 82% [MH]+ = 441 |

TABLE II-1-continued
| Ex. # | acid, amine | product | method, yield |
|---|---|---|---|
| 72 | 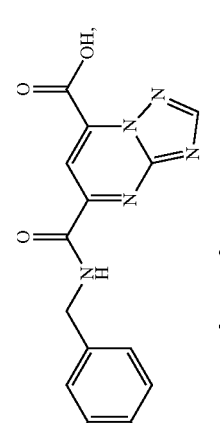 | 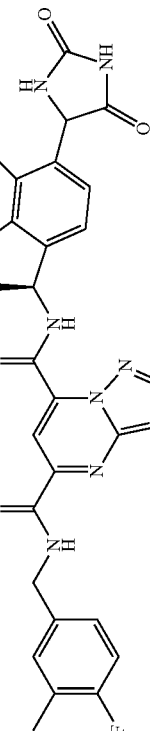 | E, 59% [MH]⁺ = 557 |
| 73 | 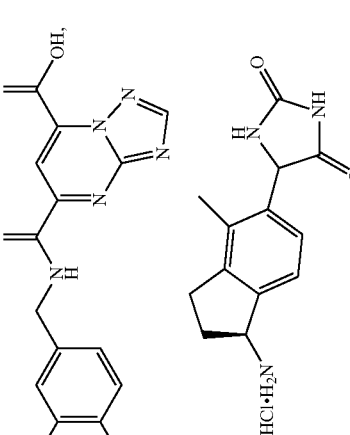 | 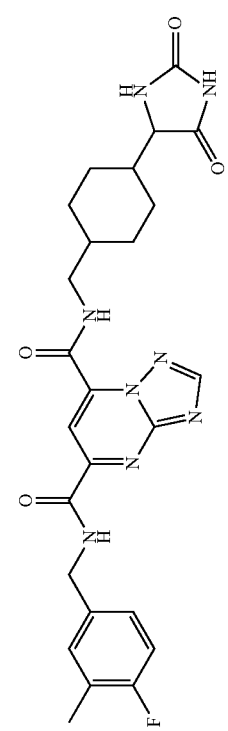 | E, 21% [MH]⁺ = 523 |

TABLE II-1-continued

| Ex. # | acid, amine | product | method, yield |
|---|---|---|---|
| 74 | | | E, 73% [MH]⁺ = 576 |
| 75 | | | E, 73% [MH]⁺ = 576 |

TABLE II-1-continued
| Ex. # | acid, amine | product | method, yield |
|---|---|---|---|
| 76 | 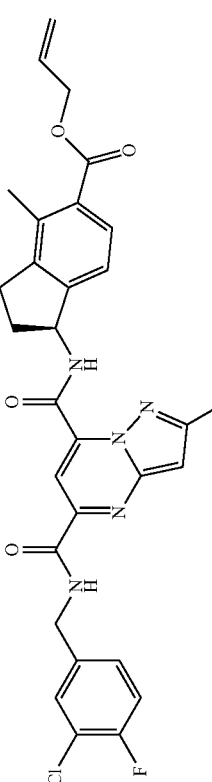 | 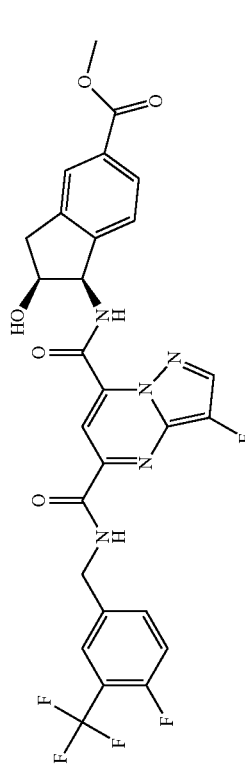 | E, 38% [MH]⁺ = 596 |
| 77 | 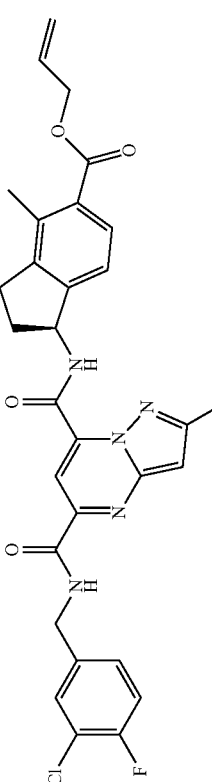 | 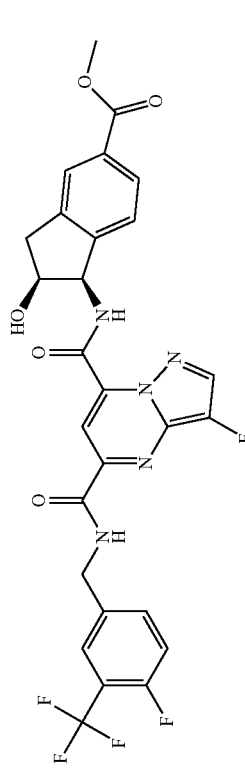 | E, 33% [M − H]⁻ = 588 |

TABLE II-1-continued
| Ex. # | acid, amine | product | method, yield |
|---|---|---|---|
| 78 | 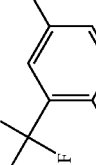 | 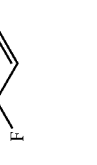 | E, 40% [M − H]⁻ = 588 |
| 79 |  |  | E, 30% [M − H]⁻ = 568 |

TABLE II-1-continued
| Ex. # | acid, amine | product | method, yield |
|---|---|---|---|
| 80 | 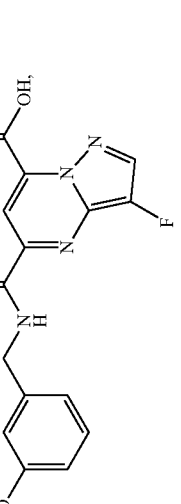 | 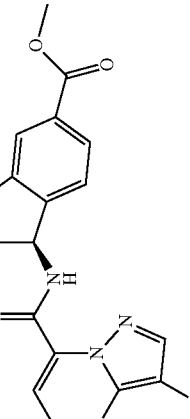 | E, 42% [M − H]⁻ = 568 |
| 81 | 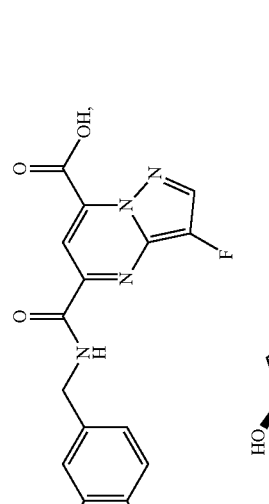 | 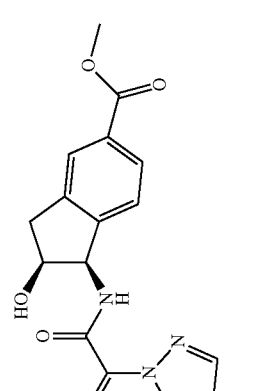 | E, 42% [M − H]⁻ = 588 |

TABLE II-1-continued
| Ex. # | acid, amine | product | method, yield |
|---|---|---|---|
| 82 | 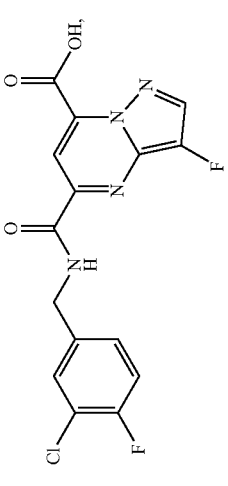 | 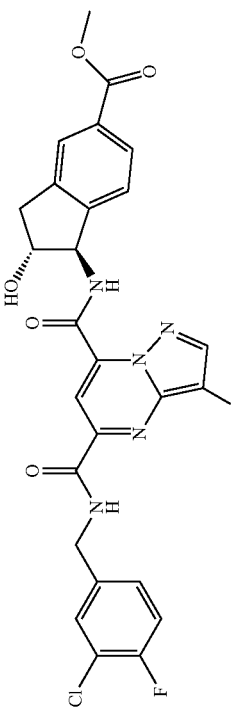 | E, 26% [M − H]⁻ = 554 |
| 83 | 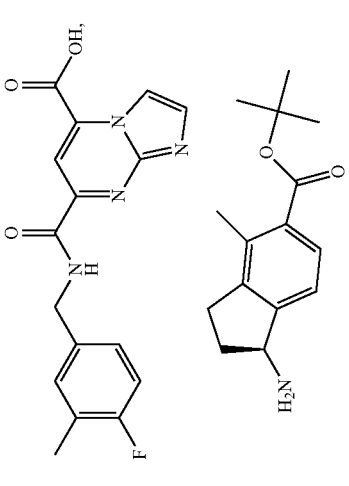 | 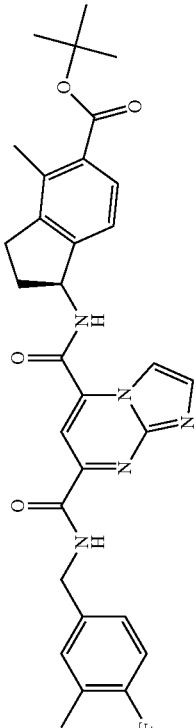 | E, 60% (over 2 steps), [M − H]⁻ = 556 |

TABLE II-1-continued

| Ex. # | acid, amine | product | method, yield |
|---|---|---|---|
| 84 | | | E, 11% (over 2 steps), [M − H]⁻ = 556 |
| 85 | | | C, 77% [MH]⁺ = 483 |
| 86 | | | C, 66% [MH]⁺ = 483 |

TABLE II-1-continued
| Ex. # | acid, amine | product | method, yield |
|---|---|---|---|
| 87 | 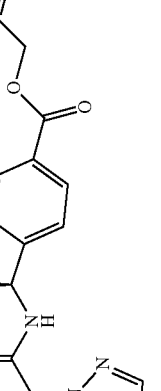 |  | C, >99% [MH]⁺ = 614 |
| 88 | 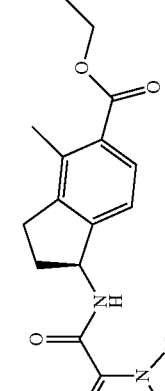 | 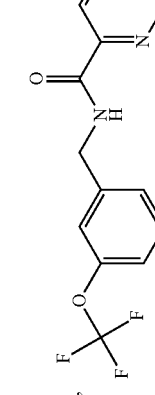 | C, >99% [MH]⁺ = 612 |

TABLE II-1-continued

| Ex. # | acid, amine | product | method, yield |
|---|---|---|---|
| 89 | | | C, 48% [MNa]⁺ = 634 |
| 90 | | | C, 54% [MH]⁺ = 410 |
| 91 | | | F, 87% [MH]⁺ = 397 |

TABLE II-1-continued

| Ex. # | acid, amine | product | method, yield |
|---|---|---|---|
| 92 | (imidazo[1,2-a]pyrazine dicarboxylic acid with 3-methyl-4-fluorobenzylamide; isoamylamine) | (bis-amide product) | F, >99%; [MH]⁺ = 399 |
| 93 | (imidazo[1,2-a]pyrazine dicarboxylic acid with 3-methyl-4-fluorobenzylamide; (1-hydroxycyclohexyl)methylamine) | (bis-amide product) | F, 61%; [MH]⁺ = 441 |
| 94 | (imidazo[1,2-a]pyrazine dicarboxylic acid with 3-methyl-4-fluorobenzylamide; 2-azabicyclo[2.2.1]heptane) | (bis-amide product) | F, 67%; [MH]⁺ = 409 |

TABLE II-1-continued

| Ex. # | acid, amine | product | method, yield |
|---|---|---|---|
| 95 | | | F, 40% [MH]+ = 437 |
| 96 | | | F, 36% [MH]+ = 433 |
| 97 | | | F, 54% [MH]+ = 463 |

TABLE II-1-continued

| Ex. # | acid, amine | product | method, yield |
|---|---|---|---|
| 98 | (imidazo[1,2-a]pyrazine-5,7-dicarboxylic acid mono-(3-fluoro-4-methylbenzyl)amide; 4-fluorobenzylamine) | N-(4-fluorobenzyl)-N'-(3-fluoro-4-methylbenzyl) imidazo[1,2-a]pyrazine-5,7-dicarboxamide | F, 52%, [MH]⁺ = 437 |
| 99 | (imidazo[1,2-a]pyrazine-5,7-dicarboxylic acid mono-(3-fluoro-4-methylbenzyl)amide; 2-fluorobenzylamine) | N-(2-fluorobenzyl)-N'-(3-fluoro-4-methylbenzyl) imidazo[1,2-a]pyrazine-5,7-dicarboxamide | F, 48%, [MH]⁺ = 437 |
| 100 | (imidazo[1,2-a]pyrazine-5,7-dicarboxylic acid mono-(3-fluoro-4-methylbenzyl)amide; 4-(aminomethyl)pyridine) | N-(pyridin-4-ylmethyl)-N'-(3-fluoro-4-methylbenzyl) imidazo[1,2-a]pyrazine-5,7-dicarboxamide | F, 51%, [MH]⁺ = 420 |

TABLE II-1-continued

| Ex. # | acid, amine | product | method, yield |
|---|---|---|---|
| 101 | | | F, 56% [MH]⁺ = 459 |
| 102 | | | F, 56% [MH]⁺ = 518 |
| 103 | | | F, 23% [MH]⁺ = 504 |

TABLE II-1-continued

| Ex. # | acid, amine | product | method, yield |
|---|---|---|---|
| 104 | | | F, 68% [MH]⁺ = 439 |
| 105 | | | F, 56% [MH]⁺ = 439 |
| 106 | | | F, 95% [MH]⁺ = 465 |

TABLE II-1-continued

| Ex. # | acid, amine | product | method, yield |
|---|---|---|---|
| 107 | | | F, 93% [MH]⁺ = 447 |
| 108 | | | G, 87% [MH]⁺ = 451 |
| 109 | | | G, >99% [MH]⁺ = 462 |

TABLE II-1-continued

| Ex. # | acid, amine | product | method, yield |
|---|---|---|---|
| 110 | (imidazo[1,2-a]pyrazine-dicarboxylic acid with 3-fluoro-4-methylbenzylamide) + cyclohexylmethylamine | bis-amide product | G, 99% [MH]⁺ = 425 |
| 111 | same acid + prolinamide | bis-amide product | G, 85% [MH]⁺ = 426 |
| 112 | same acid + cycloheptylmethylamine | bis-amide product | F, 64% [MH]⁺ = 439 |

TABLE II-1-continued

| Ex. # | acid, amine | product | method, yield |
|---|---|---|---|
| 113 | | | F, 97% [MH]⁺ = 447 |
| 114 | | | G, 94% [MH]⁺ = 427 |
| 115 | | | G, 26% [MH]⁺ = 491 |

TABLE II-1-continued

| Ex. # | acid, amine | product | method, yield |
|---|---|---|---|
| 116 | (imidazopyridine dicarboxylic acid with 4-fluoro-3-methylbenzylamide) + HCl·H₂N-CH₂-C₆H₄-NHC(O)N(CH₃)₂ | bis-amide product | G, 40% [MH]⁺ = 505 |
| 117 | (imidazopyridine dicarboxylic acid with 4-fluoro-3-methylbenzylamide) + H₂N-CH₂-cyclopentyl | bis-amide product | C, 54% [MH]⁺ = 411 |
| 118 | (imidazopyridine dicarboxylic acid with 4-fluoro-3-methylbenzylamide) + HCl·H₂N-CH₂-norbornyl | bis-amide product | C, 86% [MH]⁺ = 437 |

TABLE II-1-continued

| Ex. # | acid, amine | product | method, yield |
|---|---|---|---|
| 119 | | | C, 21% [MH]+ = 477 |
| 120 | | | C, 57% [MH]+ = 454 |
| 121 | | | C, 31% [MH]+ = 544 |

TABLE II-1-continued
| Ex. # | acid, amine | product | method, yield |
|---|---|---|---|
| 122 | 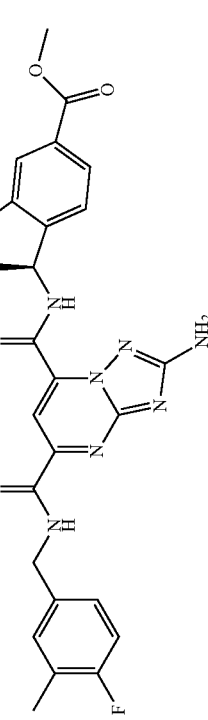 | 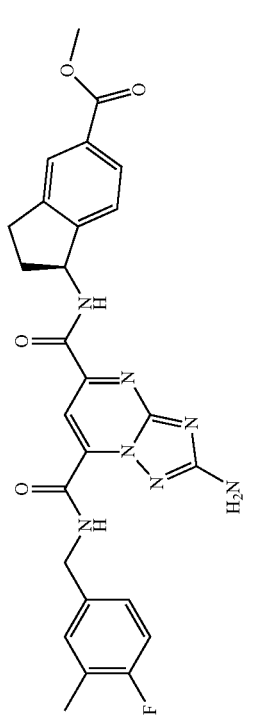 | C, 66% [MH]+ = 544 |
| 123 | 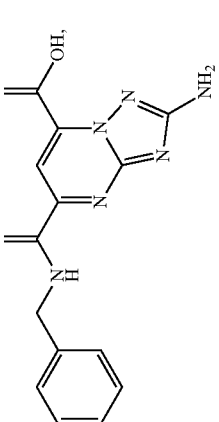 | 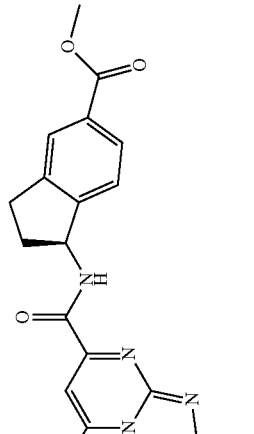 | C, 26% [MH]+ = 518 |

TABLE II-1-continued

| Ex. # | acid, amine | product | method, yield |
|---|---|---|---|
| 124 | | | C, 14%<br>[MH]+ = 494 |
| 125 | | | C, 41%<br>[MH]+ = 483 |
| 126 | | | C, 75%<br>[MH]+ = 450 |

TABLE II-1-continued

| Ex. # | acid, amine | product | method, yield |
|---|---|---|---|
| 127 | (structures) | (structure) | C, 78% [MH]⁺ = 507 |
| 128 | (structures) | (structure) | C, 61% [MH]⁺ = 507 |
| 129 | (structures) | (structure) | C, 75% [MH]⁺ = 483 |

TABLE II-1-continued
| Ex. # | acid, amine | product | method, yield |
|---|---|---|---|
| 130 |  | 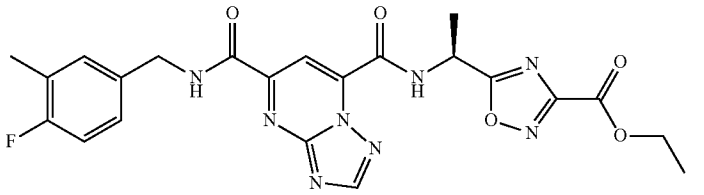 [SMILES: CCOC(=O)c1noc([C@H](C)NC(=O)c2cc(C(=O)NCc3ccc(F)c(C)c3)nc3ncnn23)n1] | C, 59% [MH]+ = 497 |
| 131 | 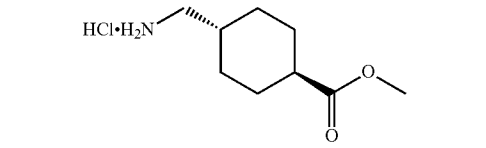 | 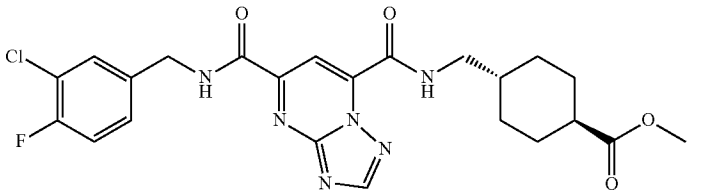 [SMILES: COC(=O)[C@H]1CC[C@H](CNC(=O)c2cc(C(=O)NCc3ccc(F)c(Cl)c3)nc3ncnn23)CC1] | C, 52% [MH]+ = 503 |

TABLE II-1-continued
| Ex. # | acid, amine | product | method, yield |
|---|---|---|---|
| 132 |  |  | C, 31% [MH]⁺ = 527 |
| 133 |  |  | C, 77% [MH]⁺ = 527 |

TABLE II-1-continued
| Ex. # | acid, amine | product | method, yield |
|---|---|---|---|
| 134 | 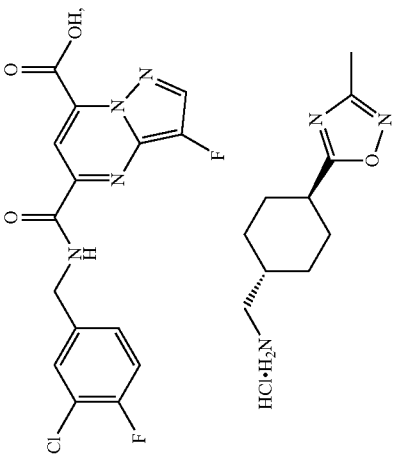 | 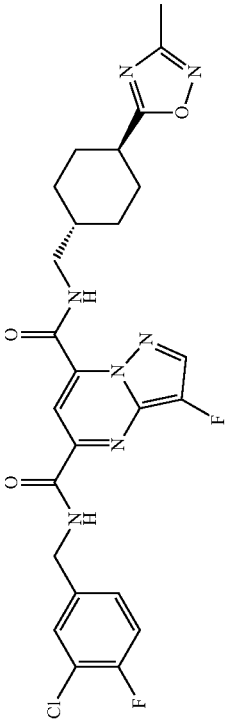 | C, 26% [MH]⁺ = 544 |
| 135 | 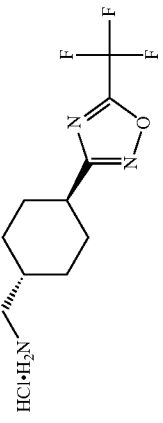 | 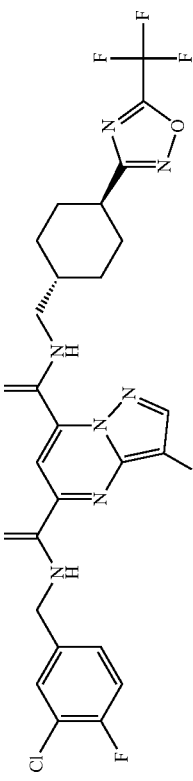 | C, 51% [MH]⁺ = 598 |

TABLE II-1-continued

| Ex. # | acid, amine | product | method, yield |
|---|---|---|---|
| 136 | | | C, 33% [MH]⁺ = 546 |
| 137 | | | C, 80% [MH]⁺ = 483 |

TABLE II-1-continued

| Ex. # | acid, amine | product | method, yield |
|---|---|---|---|
| 138 | | | C, 72% [MH]+ = 483 |
| 139 | | | C, 48% [MH]+ = 532 |
| 140 | | | C, 83% [MH]+ = 608 |

TABLE II-1-continued
| Ex. # | acid, amine | product | method, yield |
|---|---|---|---|
| 141 |  |  | C, 94% [MH]⁺ = 609 |
| 142 | 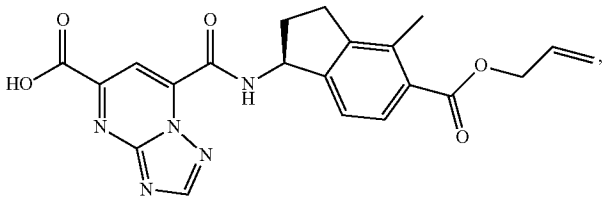 |  | C, 80% [MH]⁺ = 623 |

TABLE II-1-continued
| Ex. # | acid, amine | product | method, yield |
|---|---|---|---|
| 143 | 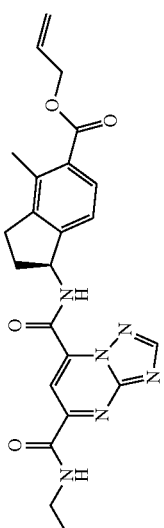 | 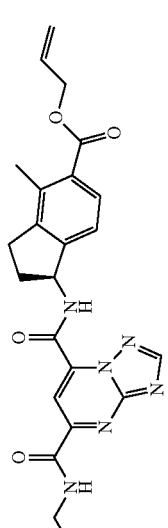 | C, 78%<br>[MH]+ = 637 |
| 144 | 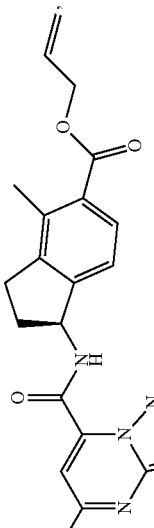 | 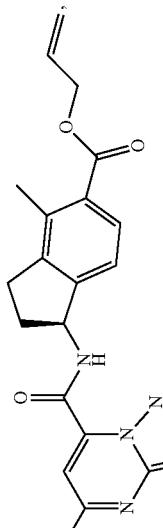 | C, 90%<br>[MH]+ = 593 |

TABLE II-1-continued

| Ex. # | acid, amine | product | method, yield |
|---|---|---|---|
| 145 | | | C, 59% [MH]+ = 607 |
| 146 | | | C, 30% [MH]+ = 564 |

TABLE II-1-continued
| Ex. # | acid, amine | product | method, yield |
|---|---|---|---|
| 147 | 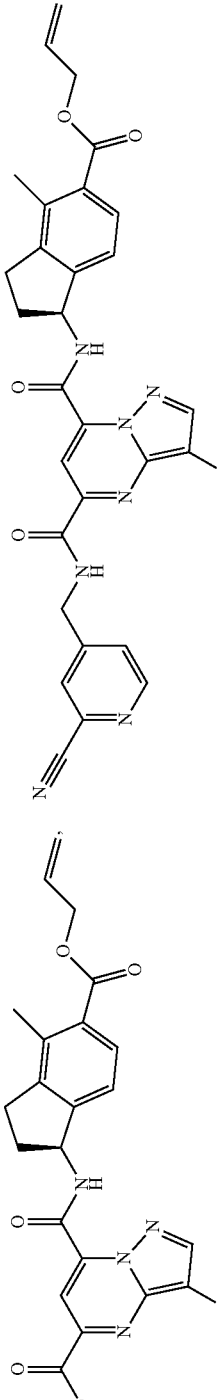 | 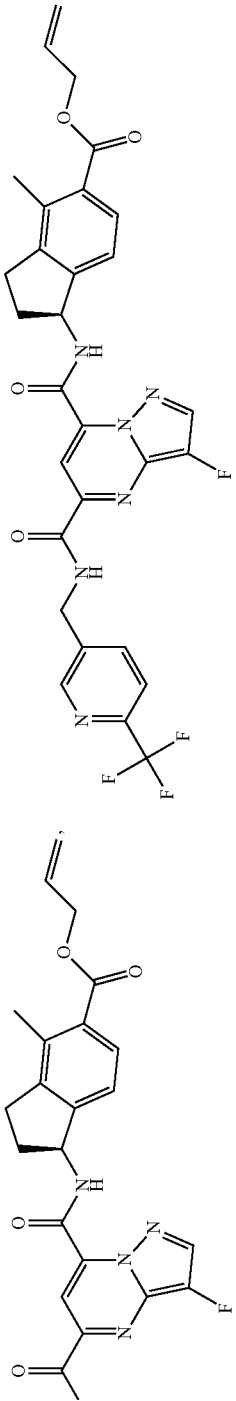 | C, 76% [MH]+ = 554 |
| 148 | 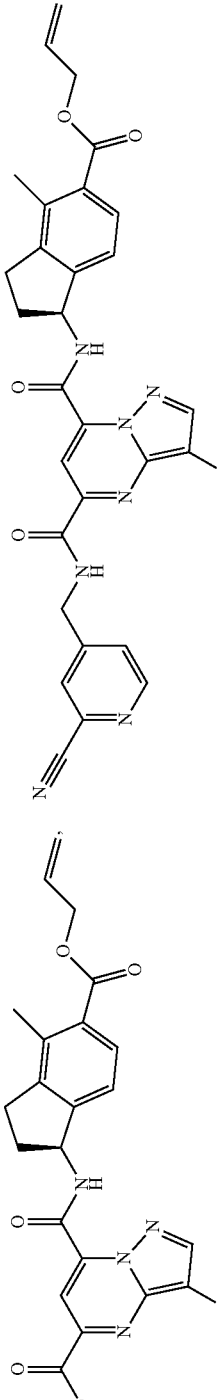 | 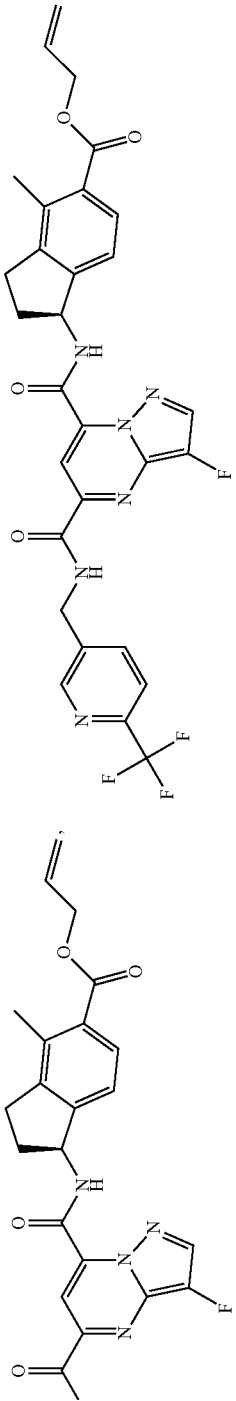 | C, 64% [MH]+ = 597 |

TABLE II-1-continued
| Ex. # | acid, amine | product | method, yield |
|---|---|---|---|
| 149 |  |  | C, 84% [MH]+ = 597 |
| 150 |  |  | C, 78% [MH]+ = 597 |

TABLE II-1-continued

| Ex. # | acid, amine | product | method, yield |
|---|---|---|---|
| 151 | | | C, 49% [MH]⁺ = 566 |
| 152 | | | C, 75% [M−"indene"]⁺ = 362 |
| 153 | | | C, 82% [MH]⁺ = 495 |

TABLE II-1-continued

| Ex. # | acid, amine | product | method, yield |
|---|---|---|---|
| 154 | (structures) | (structure) | C, 29%<br>[MH]⁺ = 553 |
| 155 | (structures) | (structure) | C, 26%<br>[MH]⁺ = 496 |
| 156 | (structures) | (structure) | C, 56%<br>[MH]⁺ = 518 |

TABLE II-1-continued

| Ex. # | acid, amine | product | method, yield |
|---|---|---|---|
| 157 | (structures) | (structures) | C, 5% [MH]+ = 514 |
| 158 | (structures) | (structures) | C, 52% [MH]+ = 506 |

TABLE II-1-continued

| Ex. # | acid, amine | product | method, yield |
|---|---|---|---|
| 159 | | | C, 38% [MH]+ = 610 |
| 160 | | | C, 19% [MH]+ = 702 |

TABLE II-1-continued

| Ex. # | acid, amine | product | method, yield |
|---|---|---|---|
| 161 | | | C, 25% [MH]+ = 549/551 |
| 162 | | | C, 48% [MH]+ = 504 |
| 163 | | | C, 41% [MH]+ = 546 |

TABLE II-1-continued

| Ex. # | acid, amine | product | method, yield |
|---|---|---|---|
| 164 | | | C, 48% [MH]+ = 509 |
| 165 | | | C, 55% [MH]+ = 528 |
| 166 | | | C, 20% [MH]+ = 528 |

| Ex. # | acid, amine | product | method, yield |
|---|---|---|---|
| 167 | | | C, 71%  [MH]+ = 508 |
| 168 | | | C, 72%  [MH]+ = 526 |
| 169 | | | C, 41%  [MH]+ = 565 |

TABLE II-1-continued

TABLE II-1-continued

| Ex. # | acid, amine | product | method, yield |
|---|---|---|---|
| 170 | | | C, 68% [MH]⁺ = 512 |
| 171 | | | C, 72% [MH]⁺ = 530 |
| 172 | | | C, 78% [MH]⁺ = 580 |

TABLE II-1-continued

| Ex. # | acid, amine | product | method, yield |
|---|---|---|---|
| 173 | | | C, 79% [MH]+ = 512 |
| 174 | | | C, 75% [MH]+ = 596 |

TABLE II-1-continued

| Ex. # | acid, amine | product | method, yield |
|---|---|---|---|
| 175 | | | C, 83% [MH]⁺ = 560 |
| 176 | | | C, 82% [MH]⁺ = 578 |
| 177 | | | C, 21% [MH]⁺ = 546 |

TABLE II-1-continued
| Ex. # | acid, amine | product | method, yield |
|---|---|---|---|
| 178 | 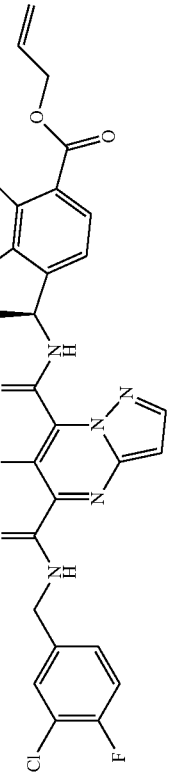 | 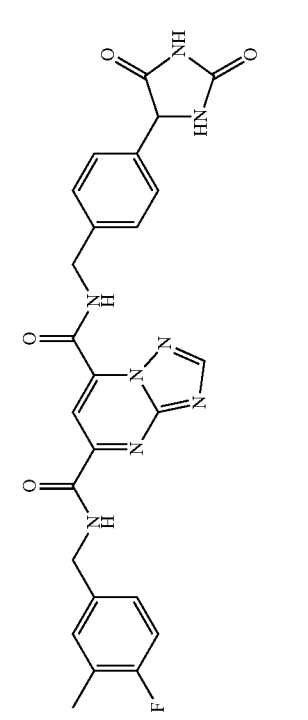 | C, 15% [MH]⁺ = 580 |
| 179 | 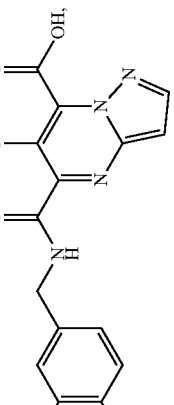 | 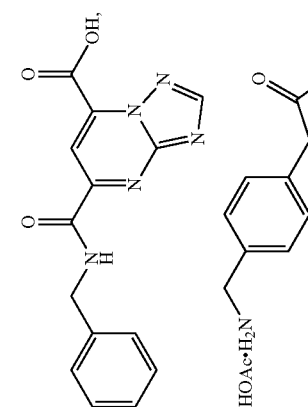 | E, 21% [M − H]⁻ = 515 |

| Ex. # | acid, amine | product | method, yield |
|---|---|---|---|
| 180 | | | E, 23% [M − H]⁻ = 529 |
| 181 | | | E, 24% [M − H]⁻ = 529 |

TABLE II-1-continued
| Ex. # | acid, amine | product | method, yield |
|---|---|---|---|
| 182 | 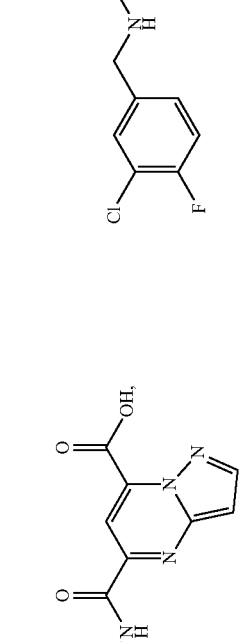 | 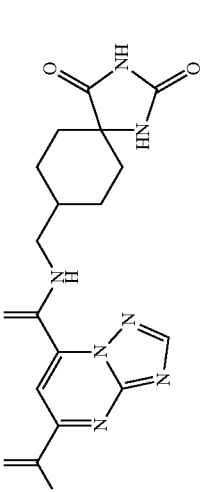 | E, 11% [M − H]− = 526 |
| 183 |  | 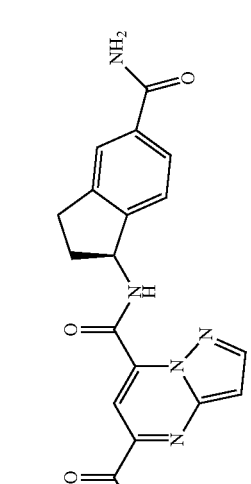 | E, 34% [MH]+ = 507 |

TABLE II-1-continued

| Ex. # | acid, amine | product | method, yield |
|---|---|---|---|
| 184 | | | E, 52% [MH]⁺ = 563 |
| 185 | | | E, n.d. [MH]⁺ = 644 |
| 186 | | | E, n.d. [MH]⁺ = 644 |

TABLE II-1-continued
| Ex. # | acid, amine | product | method, yield |
|---|---|---|---|
| 187 |  |  | E, 57% [M − H]⁻ = 628 |
| 188 |  |  | B, n.d. [MH]⁺ = 627 |

TABLE II-1-continued

| Ex. # | acid, amine | product | method, yield |
|---|---|---|---|
| 189 | | | B, n.d. [MH]⁺ = 597 |
| 190 | | | D, 72% [MH]⁺ = 628 |
| 191 | | | A, 54% [MH]⁺ = 612 |

TABLE II-1-continued
| Ex. # | acid, amine | product | method, yield |
|---|---|---|---|
| 192 | 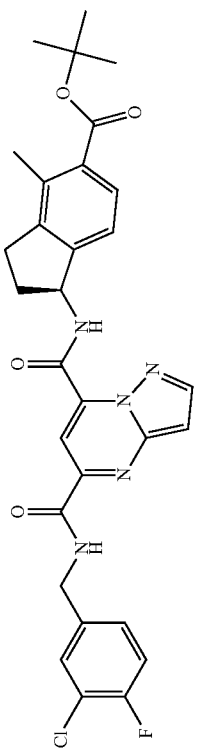 | 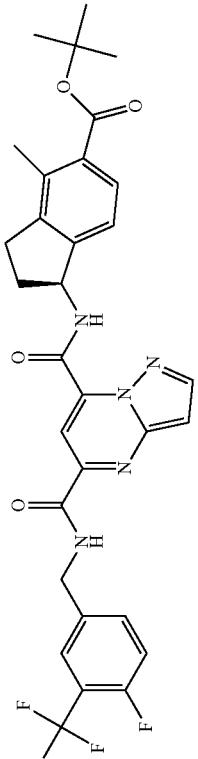 | A, 27% [MH]⁺ = 578 |
| 193 | 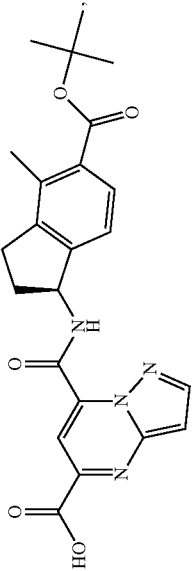 | 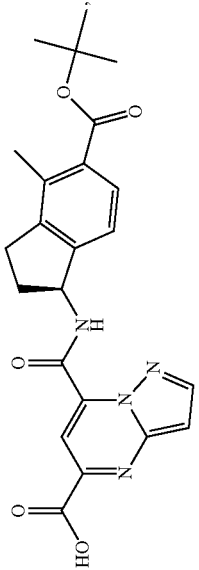 | A, 28% [MH]⁺ = 612 |

TABLE II-1-continued

| Ex. # | acid, amine | product | method, yield |
|---|---|---|---|
| 194 | | | A, 33% $^1$H-NMR (CDCl$_3$) δ = 10.50 (br d, 1 H), 9.00 (s, 1 H), 8.85 (s, 1 H), 8.35 (br t, 1 H), 8.00 (s, 1 H), 7.95 (d, 1 H), 7.40 (d, 1 H), 7.25-7.00 (m, 2 H), 7.00-6.90 (m, 1 H), 5.80 (m, 1 H), 4.65 (br d, 2 H), 3.90 (s, 3 H), 3.20-2.70 (m, 3 H), 2.25 (s, 3 H), 2.20-2.00 (m, 1 H). |
| 195 | | | A, n.d. [MH]$^+$ = 594/596 |

TABLE II-1-continued

| Ex. # | acid, amine | product | method, yield |
|---|---|---|---|
| 196 | | | A, n.d. [MH]⁺ = 528/530 |
| 197 | | | A, 43% [MH]⁺ = 558 |
| 198 | | | C, 66% [MH]⁺ = 562 |

TABLE II-1-continued

| Ex. # | acid, amine | product | method, yield |
|---|---|---|---|
| 199 | (pyrazolo[1,5-a]pyrimidine carboxylic acid with 3,4-difluorobenzylamide; tert-butyl 4-methyl-1-amino-indane-6-carboxylate) | (coupled product) | C, 44% [MH]⁺ = 562 |
| 200 | (allyl 4-methyl-1-(imidazo[1,2-a]pyrimidine-carboxamido)indane-6-carboxylate; 4-fluoro-3-(trifluoromethoxy)benzylamine) | (coupled product) | C, 48% [MH]⁺ = 613 |
| 201 | (allyl 4-methyl-1-(imidazo[1,2-a]pyrimidine-carboxamido)indane-6-carboxylate; 3-(aminomethyl)benzenesulfonamide·HCl) | (coupled product) | C, n.d. [MH]⁺ = 550 |

| Ex. # | acid, amine | product | method, yield |
|---|---|---|---|
| 202 | | | C, 65% [MH]⁺ = 523/525 |
| 203 | | | C, 52% [MH]⁺ = 543/545 |
| 204 | | | C, 54% ¹H-NMR (CDCl₃) δ = 10.25 (br d, 1 H), 8.60 (s, 1 H), 8.10 (m, 1 H), 8.00 (d, 1 H), 7.60 (d, 1 H), 7.30 (d, 1 H), 7.20-7.10 (m, 2 H), 7.10-7.00 (m, 1 H), 5.70 (m, 1 H), 4.55 (d, 2 H), 3.10-2.60 (m, 3 H), 2.40 (s, 9 H), 2.00-1.90 (m, 1 H). |

TABLE II-1-continued

| Ex. # | acid, amine | product | method, yield |
|---|---|---|---|
| 205 | (structures) | (structure) | C, 70% [MH]+ = 595 |
| 206 | (structures) | (structure) | C, 79% [MH]+ = 599 |
| 207 | (structures) | (structure) | C, 55% [MH]+ = 522 |

TABLE II-1-continued

| Ex. # | acid, amine | product | method, yield |
|---|---|---|---|
| 208 | | | C, 59% [MH]⁺ = 536 |
| 209 | | | C, 63% [MH]⁺ = 598 |

TABLE II-1-continued

| Ex. # | acid, amine | product | method, yield |
|---|---|---|---|
| 210 | (acid structure), (amine: 4-hydroxy-3-(trifluoromethyl)benzylamine·HCl) | (product structure) | C, 32% [M – "indene"]+ = 398 |
| 211 | (acid structure), (amine: 3-bromo-4-hydroxybenzylamine) | (product structure) | C, 66% [MH]+ = 623 |

TABLE II-1-continued

| Ex. # | acid, amine | product | method, yield |
|---|---|---|---|
| 212 | (acid + amine structures); HCl·H₂N-benzyl-C(O)NH₂ | (product structure) | C, 61% [MH]⁺ = 571 |
| 213 | (acid + amine structures); HCl·H₂N-benzyl-C(O)NHMe | (product structure) | C, 86% [MH]⁺ = 585 |

| Ex. # | acid, amine | product | method, yield |
|---|---|---|---|
| 214 | | | E, 60% [M − H]⁻ = 520 |
| 215 | | | E, 65% [M − H]⁻ = 520 |

TABLE II-1-continued

TABLE II-1-continued

| Ex. # | acid, amine | product | method, yield |
|---|---|---|---|
| 216 | | | E, 49% [MH]⁺ = 539/541 |
| 217 | | | E, 90% [MH]⁺ = 533 |
| 218 | | | E, 80% [MH]⁺ = 550 |

TABLE II-1-continued

| Ex. # | acid, amine | product | method, yield |
|---|---|---|---|
| 219 | | | C, 45% [MH]+ = 452 |
| 220 | | | C, 43% [MH]+ = 461 |
| 221 | | | C, 46% [MH]+ = 572 |

TABLE II-1-continued

| Ex. # | acid, amine | product | method, yield |
|---|---|---|---|
| 222 | (structures) | (structure) | C, 47% [MH]+ = 586 |
| 223 | (structures) | (structure) | C, n.d. [MH]+ = 569 |
| 224 | (structures) | (structure) | C, n.d. [MH]+ = 517 |

TABLE II-1-continued

| Ex. # | acid, amine | product | method, yield |
|---|---|---|---|
| 225 | | | C, n.d. [MH]⁺ = 459 |
| 226 | | | C, n.d. [MH]⁺ = 546 |
| 227 | | | C, n.d. [MNa]⁺ = 584 |

TABLE II-1-continued

| Ex. # | acid, amine | product | method, yield |
|---|---|---|---|
| 228 | (structures) | (structure) | C, n.d. [MNa]⁺ = 669 |
| 229 | (structures) | (structure) | C, n.d. [MNa]⁺ = 696 |

| Ex. # | acid, amine | product | method, yield |
|---|---|---|---|
| 230 | | | C, n.d. [MNa]+ = 624 |
| 231 | | | C, 60% (over 2 steps), [MH]+ = 517 |
| 232 | | | A, 51% [MH]+ = 530 |

TABLE II-1-continued

| Ex. # | acid, amine | product | method, yield |
|---|---|---|---|
| 233 | | | A, 7% (over 2 steps), [MH]⁺ = 451 |
| 234 | | | A, 20% (over 2 steps), [MH]⁺ = 451 |
| 235 | | | E, 35% [M − H]⁻ = 502 |

TABLE II-1-continued
| Ex. # | acid, amine | product | method, yield |
|---|---|---|---|
| 236 |  |  | E, 29% [M – H]⁻ = 488 |
| 237 | 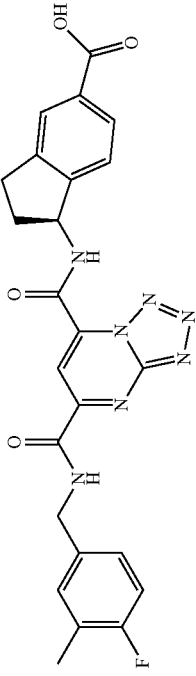 |  | A, 98% [MH]⁺ = 471 |
| 238 | 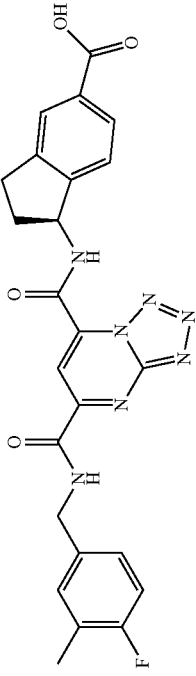 |  | A, 16% [MH]⁺ = 517 |

TABLE II-1-continued

| Ex. # | acid, amine | product | method, yield |
|---|---|---|---|
| 239 | | | E, 52% [MNa]⁺ = 566 |
| 240 | | | E, 31% [M − H]⁻ = 576 |
| 241 | | | A, n.d. [MH]⁺ = 599 |

TABLE II-1-continued

| Ex. # | acid, amine | product | method, yield |
|---|---|---|---|
| 242 | (structures) | (structure) | E, 51% [MH]⁺ = 533 |
| 243 | (structures) | (structure) | E, 50% [MH]⁺ = 462 |
| 244 | (structures) | (structure) | E, 40% [MH]⁺ = 428 |

TABLE II-1-continued

| Ex. # | acid, amine | product | method, yield |
|---|---|---|---|
| 245 | | | E, 30% [MH]+ = 469 |
| 246 | | | E, 10% [MH]+ = 426 |

TABLE II-1-continued
| Ex. # | acid, amine | product | method, yield |
|---|---|---|---|
| 247 | 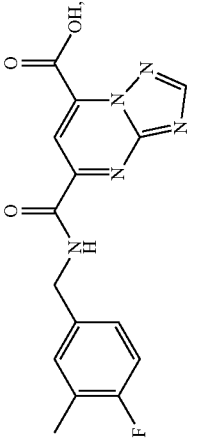 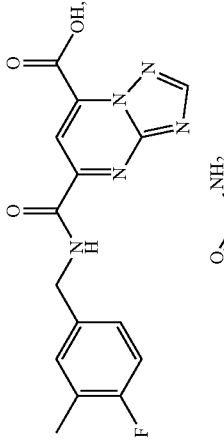 | 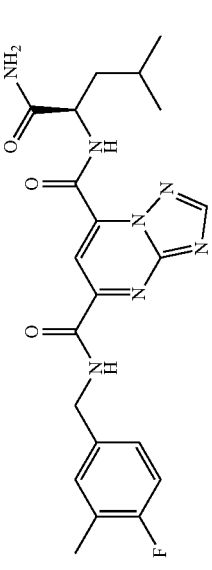 | E, 34% [MH]⁺ = 442 |
| 248 | 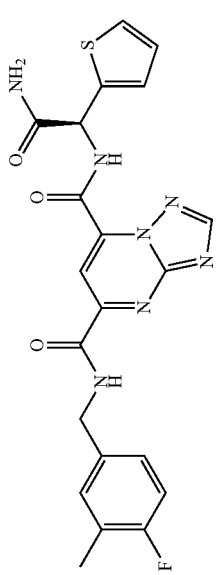 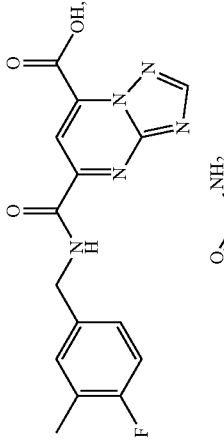 | 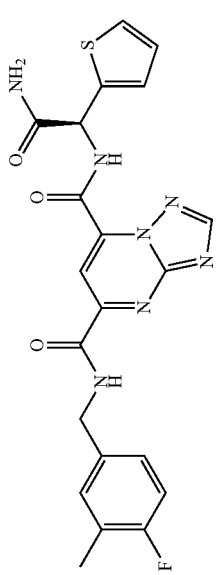 | E, 20% [MH]⁺ = 468 |

TABLE II-1-continued

| Ex. # | acid, amine | product | method, yield |
|---|---|---|---|
| 249 | | | E, 30% [MH]⁺ = 456 |
| 250 | | | E, 25% [MH]⁺ = 424 |

TABLE II-1-continued
| Ex. # | acid, amine | product | method, yield |
|---|---|---|---|
| 251 | 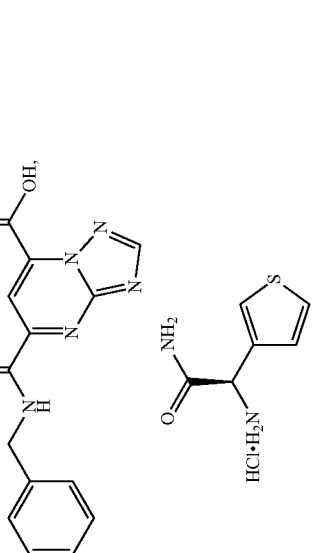 | 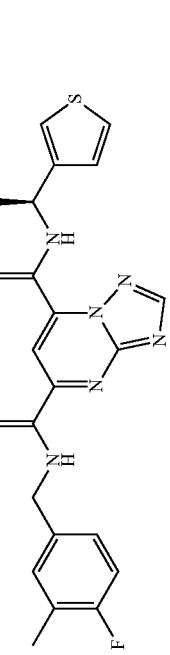 | E, 30% [MH]$^+$ = 468 |
| 252 | 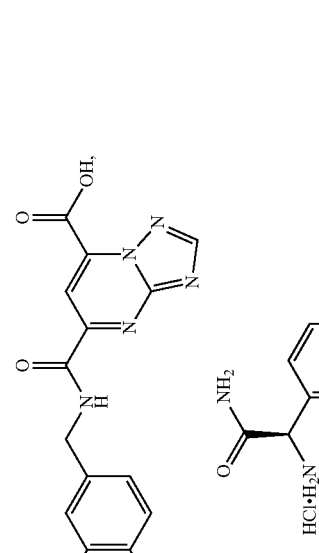 | 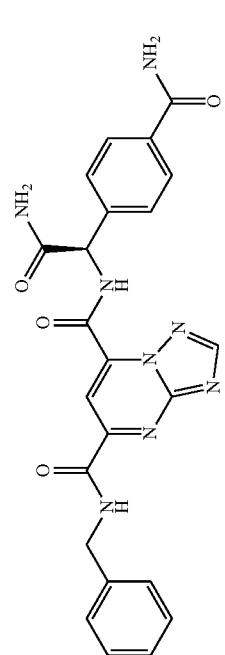 | E, 34% [MH]$^+$ = 525 |

TABLE II-1-continued
| Ex. # | acid, amine | product | method, yield |
|---|---|---|---|
| 253 | 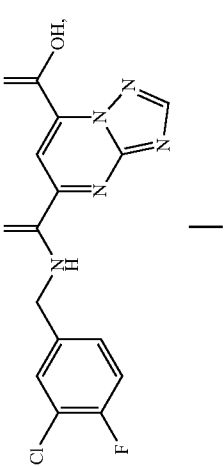 | 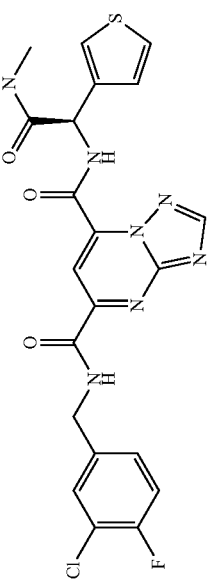 | E, 18% [MH]⁺ = 516 |
| 254 | 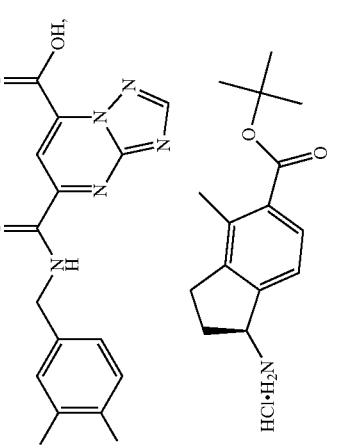 | 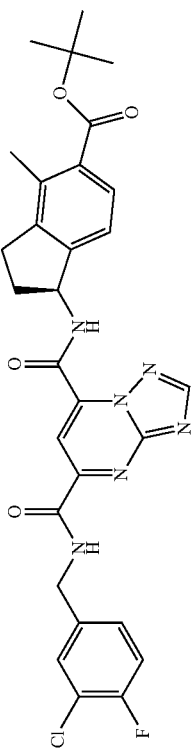 | E, n.d. [MH]⁺ = 579 |

TABLE II-1-continued

| Ex. # | acid, amine | product | method, yield |
|---|---|---|---|
| 255 | (imidazo[1,2-a]pyrimidine dicarboxylic acid with 3-methyl-4-fluorobenzylamide; 4-cyanobenzylamine) | (bis-amide product) | E, 42%<br>[MH]⁺ = 444 |
| 256 | (allyl ester indane pyrazolo[1,5-a]pyrimidine carboxylic acid; 3-chloro-4-fluorobenzylamine) | (amide product) | E, 70%<br>[MH]⁺ = 630 |

TABLE II-1-continued

| Ex. # | acid, amine | product | method, yield |
|---|---|---|---|
| 257 | | | C, 10% [MH]$^+$ = 518 |
| 258 | | | C, 29% [MH]$^+$ = 518 |
| 259 | | | C, 96% [MH]$^+$ = 564 |

TABLE II-1-continued

| Ex. # | acid, amine | product | method, yield |
|---|---|---|---|
| 260 | (structures) | (structure) | C, 91% [MH]⁺ = 547 |
| 261 | (structures) | (structure) | C, n.d. [MH]⁺ = 597 |
| 262 | (structures) | (structure) | C, 93% [MH]⁺ = 547 |

TABLE II-1-continued

| Ex. # | acid, amine | product | method, yield |
|---|---|---|---|
| 263 | | | C, 81% [MH]$^+$ = 529 |
| 264 | | | C, 86% [MH]$^+$ = 529 |
| 265 | | | C, 76% [MH]$^+$ = 545 |

TABLE II-1-continued

| Ex. # | acid, amine | product | method, yield |
|---|---|---|---|
| 266 | | | C, n.d.<br>[MH]+ = 543 |
| 267 | | | C, n.d.<br>[MH]+ = 543 |
| 268 | | | C, n.d.<br>[MH]+ = 537 |

TABLE II-1-continued

| Ex. # | acid, amine | product | method, yield |
|---|---|---|---|
| 269 | [structure: imidazopyrimidine dicarboxylic acid with indanyl-methyl-allyl ester amide; and 1-aminoindane] | [structure: corresponding bis-amide product] | C, n.d. [MH]⁺ = 537 |
| 270 | [structure: imidazopyrimidine dicarboxylic acid with indanyl-methyl-allyl ester amide; and 3-ethyl-4-fluorobenzylamine] | [structure: corresponding bis-amide product] | C, n.d. [MH]⁺ = 557 |
| 271 | [structure: imidazopyrimidine dicarboxylic acid with indanyl-methyl-allyl ester amide; and 3-(trifluoromethoxy)benzylamine] | [structure: corresponding bis-amide product] | C, n.d. [MH]⁺ = 595 |

TABLE II-1-continued

| Ex. # | acid, amine | product | method, yield |
|---|---|---|---|
| 272 | (structures) | (structure) | C, 38%<br>[MH]⁺ = 540 |
| 273 | (structures) | (structure) | C, n.d.<br>[MH]⁺ = 537 |
| 274 | (structures) | (structure) | C, n.d.<br>[MNa]⁺ = 584 |

TABLE II-1-continued
| Ex. # | acid, amine | product | method, yield |
|---|---|---|---|
| 275 | 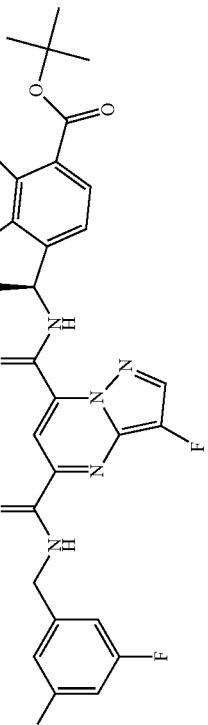 | 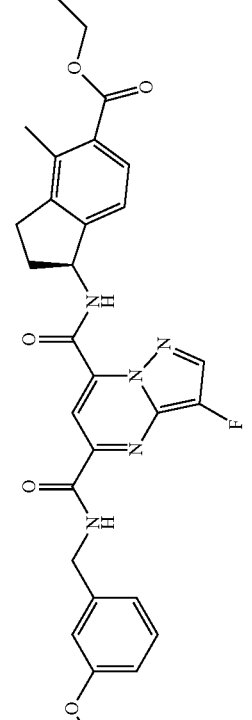 | C, n.d.<br>[MNa]⁺ = 602 |
| 276 | 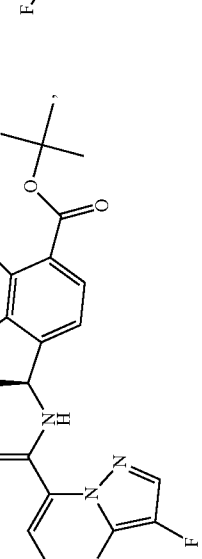 | 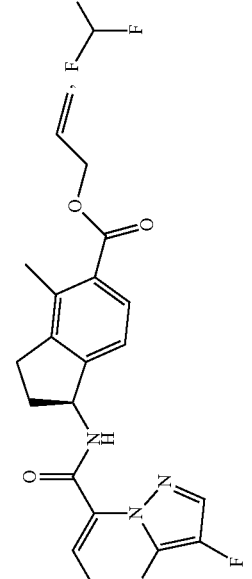 | C, n.d.<br>[MH]⁺ = 594 |

TABLE II-1-continued
| Ex. # | acid, amine | product | method, yield |
|---|---|---|---|
| 277 | 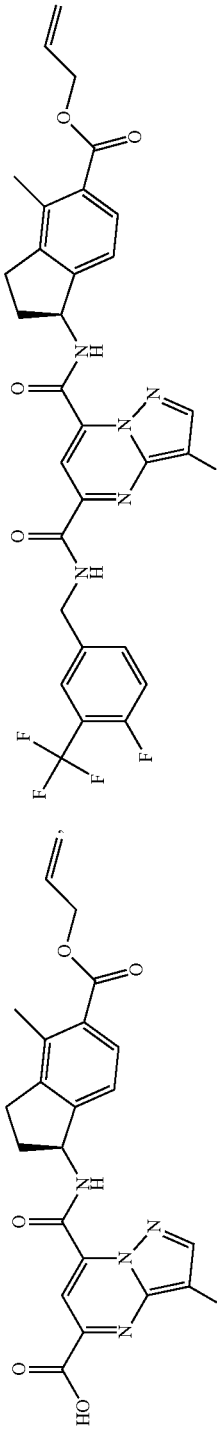 |  | C, n.d. [MH]⁺ = 614 |

Example 278

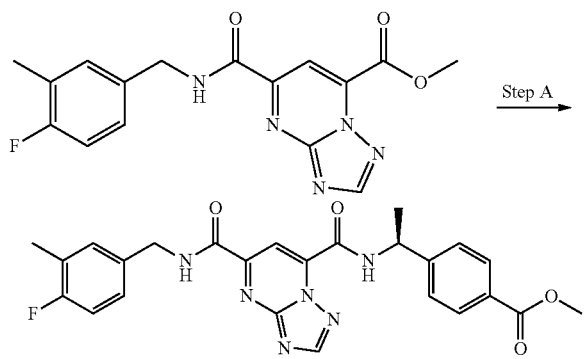

Step A

To a solution of the title compound from the Preparative Example 315 (67 mg) in anhydrous DMF (500 µL) was added a solution of the title compound from the Preparative Example 229, Step D (75 mg). The resulting mixture was heated at 60° C. for 15 h, concentrated and purified by preparative thin layer chromatography (silica, CH$_2$Cl$_2$/MeOH) to give the desired title compound (39 mg, 41%). [MH]$^+$=491.

Examples 279-284

Following a similar procedure as described in the Example 278, except using the esters and amines indicated in Table II-2 below, the following compounds were prepared.

TABLE II-2

| Ex. # | ester, amine | product | yield |
|---|---|---|---|
| 279 | 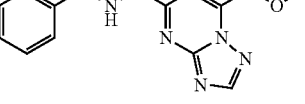 | 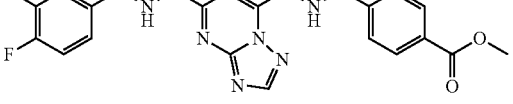 | 47% [MH]$^+$ = 477 |
| 280 | 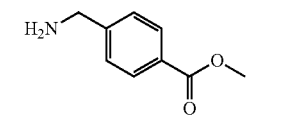 | 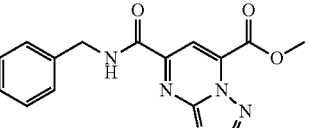 | 48% [MH]$^+$ = 462 |
| 281 | 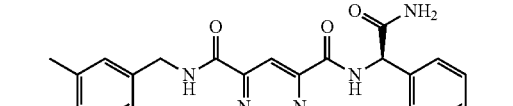 | 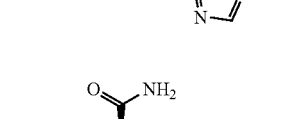 | 43% [MH]$^+$ = 439 |
| 282 | 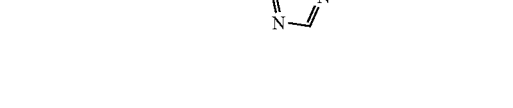 | 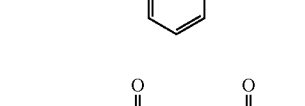 | 60% [MH]$^+$ = 552 |

TABLE II-2-continued

| Ex. # | ester, amine | product | yield |
|---|---|---|---|
| 283 | 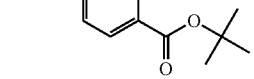 | 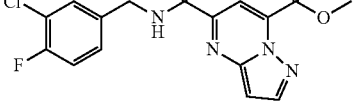 | 50% [MH]⁺ = 458 |
| 284 | 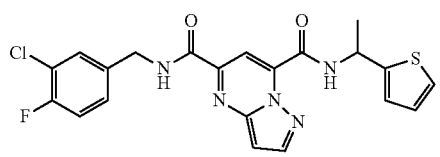 [SMILES: CC(NC(=O)c1cc(C(=O)NCc2ccc(F)c(Cl)c2)nc2ccnn12)c1cccs1] | 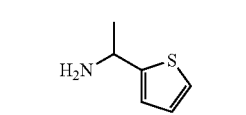 | 53% [MH]⁺ = 442 |

Example 285

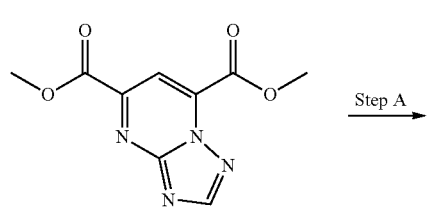

Step A

Step A

To a solution of the title compound from the Preparative Example 244, Step A (200 mg) in anhydrous DMF (2 mL) was added commercially available 4-fluoro-3-methyl-benzylamine (120 mg). The resulting mixture was heated at 60° C. for 24 h, concentrated and purified by preparative thin layer chromatography (silica, CH₂Cl₂/MeOH) to give the title compound (30 mg, 8%). [MH]⁺=452.

Example 286

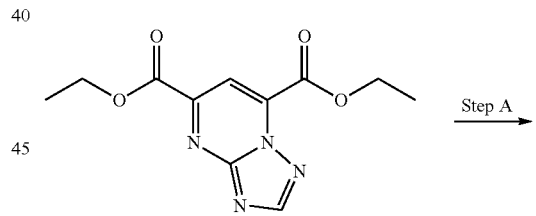

Step A

Step A

A mixture of the title compound Preparative Example 330, Step A (203 mg) and commercially available 3-chloro-4-fluorobenzylamine (160 mg) in dry DMF (3 mL) was heated to 70° C. overnight and concentrated. The remaining residue was dissolved in CHCl₃, washed with 10% aqueous citric acid and saturated aqueous NaCl, dried (MgSO₄), filtered, concentrated and purified by preparative thin layer chromatography (silica, CH₂Cl₂/MeOH) to afford the title compound as a colorless solid (111 mg, 29%). [MH]⁺=492.

Example 287

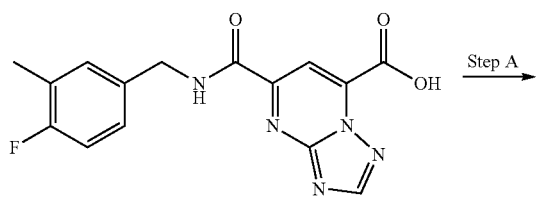

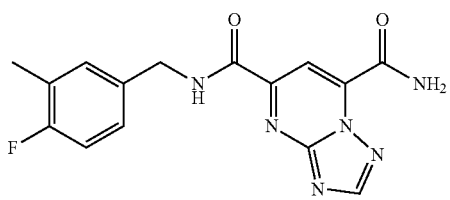

Step A
A solution of the title compound from the Preparative Example 331, Step A (26 mg) in a 7M solution of NH$_3$ in MeOH (1 mL) was heated at 90° C. for 2 h. The formed precipitate was isolated by filtration to afford the title compound as a colorless solid (8.6 mg, 34%). [MH]$^+$=329.

Example 288

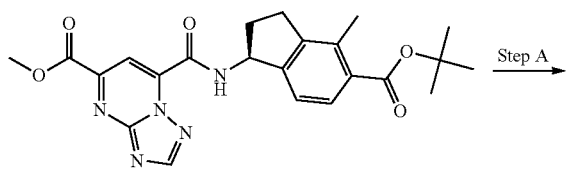

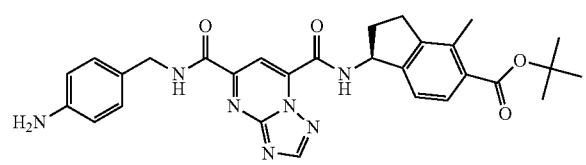

Step A
The title compound from the Preparative Example 294 (9.7 mg) and commercially available 4-aminomethyl-phenylamine (10 mg) were dissolved in N-methylpyrrolidin-2-one (0.5 mL). The mixture was heated in a sealed tube at 160° C. (microwave) for 15 min, diluted with EtOAc, washed with aqueous LiCl, concentrated and purified by chromatography (silica, CH$_2$Cl$_2$/MeOH) to afford the title compound (9.6 mg, 84%). [M-H]'=540.

Example 289

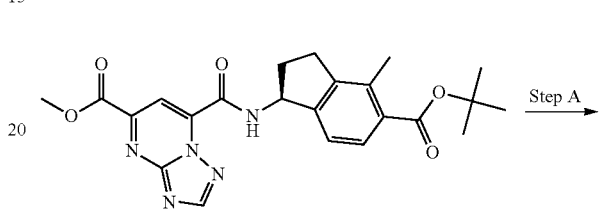

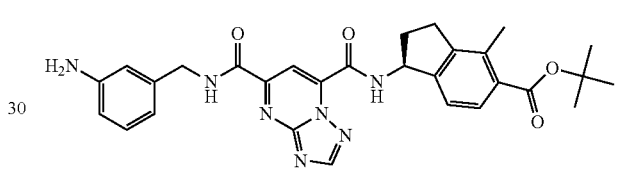

Step A
The title compound from the Preparative Example 294 (154 mg) and commercially available 3-aminomethyl-phenylamine (57 mg) were dissolved in N-methylpyrrolidin-2-one (3 mL). The mixture was heated in a sealed tube at 160° C. (microwave) for 55 min, diluted with EtOAc, washed with aqueous LiCl, concentrated and purified by chromatography (silica, CH$_2$Cl$_2$/MeOH) to afford the title compound (110 mg, 84%). [M-H]$^-$=540.

Example 290

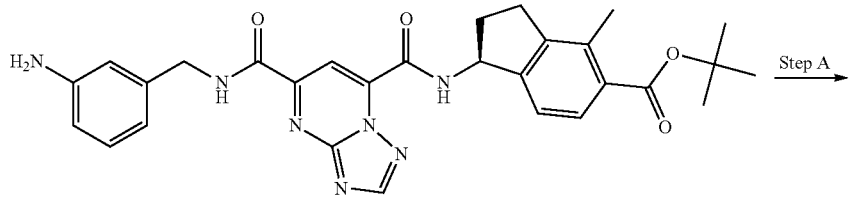

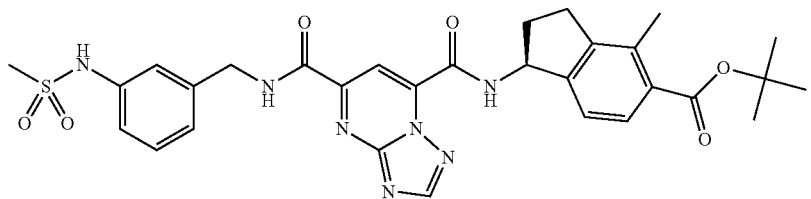

Step A

To a solution of the title compound from the Example 289, Step A (19.1 mg) in $CH_2Cl_2$ (1 mL) were successively added pyridine (0.1 mL) and methanesulfonyl chloride (8.1 mg). The mixture was stirred for 1d, concentrated and purified by chromatography (silica, $CH_2Cl_2$/MeOH) to afford the title compound (13.1 mg, 60%). [M-H]'=618.

Example 291

Step A

To a solution of the title compound from the Preparative Example 342 (51 mg) in THF (5 mL) were added the title compound from the Preparative Example 149, EDCI (53 mg), HOBt (38 mg) and $K_2CO_3$ (44 mg). The mixture was stirred for 16 h, absorbed on silica (500 mg) and purified by chromatography (silica, hexanes/EtOAc) to afford the title compound as a solid (79.3 mg, 92%). [M-H]'=616.

Example 292

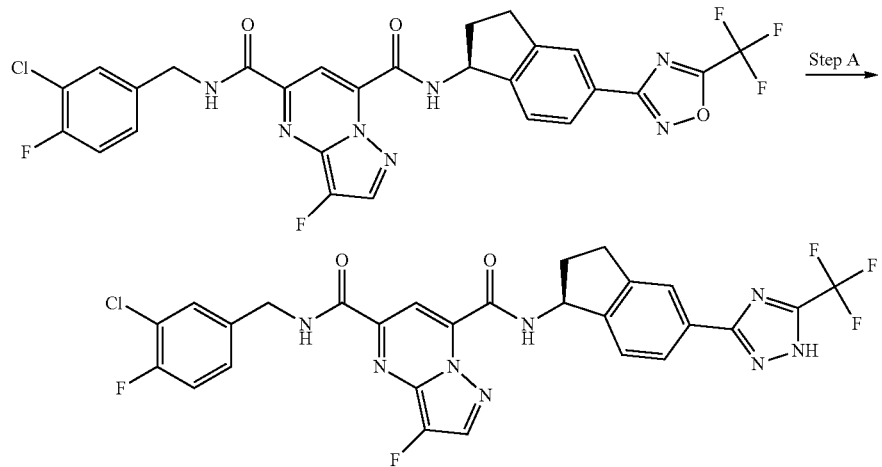 [SMILES: O=C(NCc1ccc(F)c(Cl)c1)c1cc(C(=O)N[C@H]2CCc3cc(-c4noc(C(F)(F)F)n4)ccc32)n2ncc(F)c2n1 ; O=C(NCc1ccc(F)c(Cl)c1)c1cc(C(=O)N[C@H]2CCc3cc(-c4n[nH]c(C(F)(F)F)n4)ccc32)n2ncc(F)c2n1]

Step A

To a solution of the title compound from the Example 291, Step A (50 mg) in MeOH/CH$_2$Cl$_2$ (1:1, 2 mL) was added hydrazine (26 mg). The resulting mixture was stirred for 1 d, concentrated and purified by chromatography (silica, CH$_2$Cl$_2$/MeOH) to afford the title compound as a yellow solid. (37.1 mg, 74%). [M-H]'=615.

Example 293

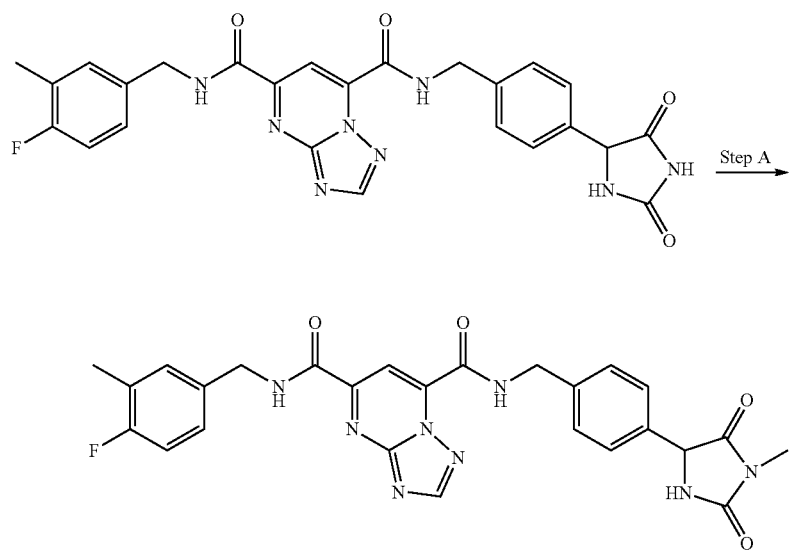

Step A

To a solution of the title compound from the Example 179 (2.5 mg) in toluene/MeOH (3:1, 2 mL) was added a 2M solution of (trimethylsilyl)diazomethane in Et$_2$O (portions à 10 μL) until complete consumption of the starting material. The mixture was concentrated and then triturated with Et$_2$O (4×) to give the title compound as a yellow solid (1.0 mg, 40%). [M-H]'=529.

Example 294

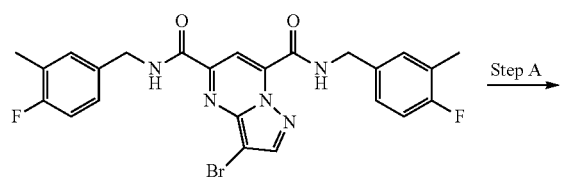

-continued

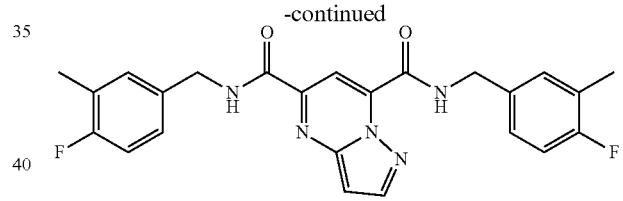

Step A

A mixture of the title compound from the Example 196 (52 mg) and Pd/C (10 wt %, 20 mg) in MeOH/EtOAc (1:1, 4 mL) was hydrogenated at atmospheric pressure for 18 h, filtered, concentrated and purified by chromatography (silica, CH$_2$Cl$_2$/acetone) to afford the title compound (19 mg, 43%). [MH]$^+$=450.

Example 295

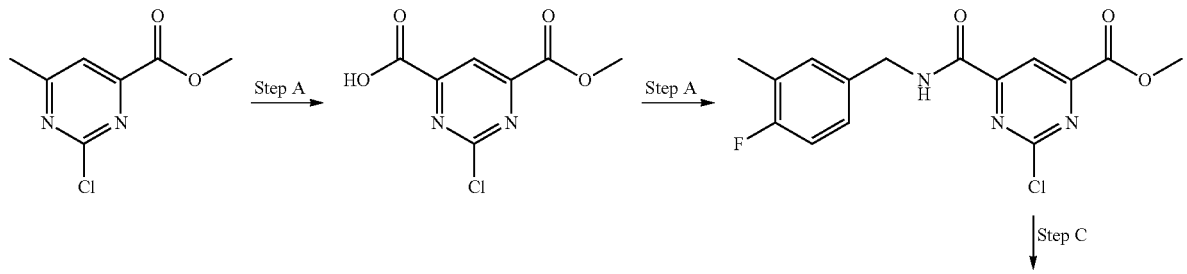

-continued

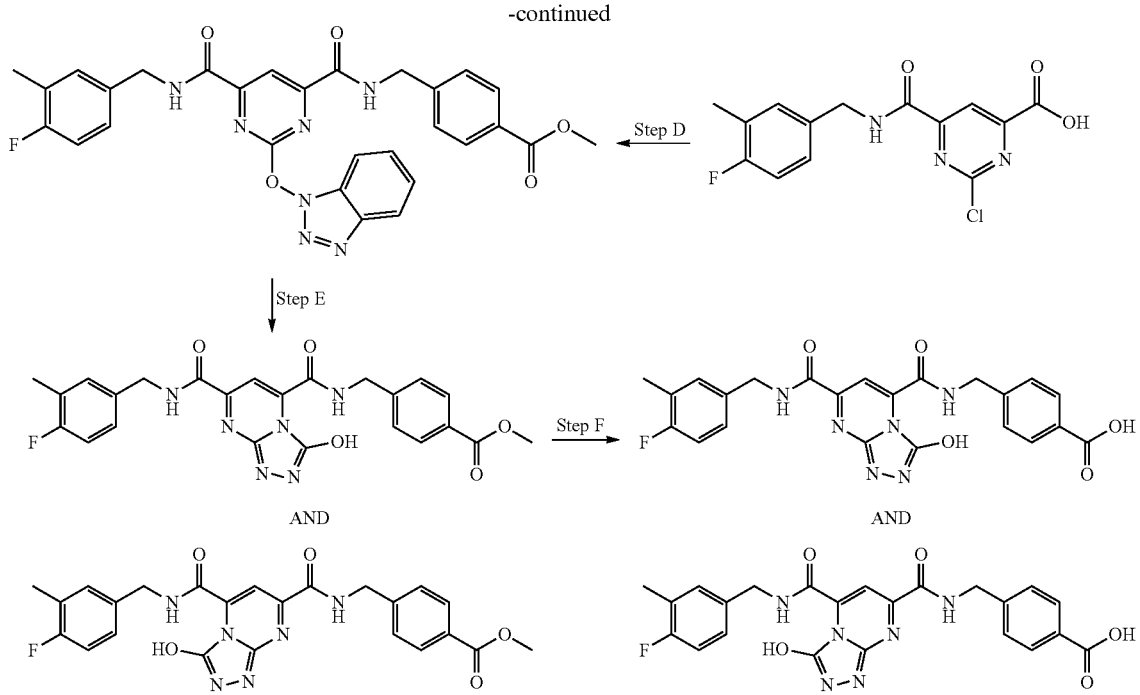

Step A

Under an argon atmosphere a mixture of commercially available 2-chloro-6-methyl-pyrimidine-4-carboxylic acid methyl ester (9.38 g) and selenium dioxide (8.93 g) in 1,4-dioxane (50 mL) was stirred at 105° C. for 12 h. The mixture was filtered twice through Celite®, the filter cake was rinsed with 1,4-dioxane (2×100 mL) and the combined filtrates were concentrated to afford the title compound as viscous orange oil (8.0 g, 74%). [MH]$^+$=217.

Step B

To an ice cooled solution of the title compound from Step A above (900 mg) in anhydrous CH$_2$Cl$_2$ (20 mL) were subsequently and slowly added oxalyl chloride (870 µL) and DMF (3 drops). The cooling bath was removed and the mixture was stirred at room temperature until gas evolution ceased. The mixture was then concentrated and diluted with CH$_2$Cl$_2$. Pyridine (340 µL) and commercially available 4-fluoro-3-methylbenzylamine (530 µL) were added subsequently and the mixture was stirred at room temperature for 30 min. Filtration, absorption onto silica and purification by chromatography (silica, hexane/EtOAc) afforded the title compound as a yellow solid (670 mg, 48%). [MH]$^+$=338.

Step C

To an ice cooled solution of the title compound from Step B above (670 mg) in THF (20 mL) was slowly added 1M aqueous LiOH (3.98 mL). The mixture was stirred at 0° C. for 2 h, quenched with 1M aqueous HCl (4.0 mL), warmed to room temperature and concentrated. The remaining residue was triturated with THF, filtered and concentrated to afford the title compound as an orange solid. [MH]$^+$=324.

Step D

The title compound from Step C above (256 mg), commercially available 4-aminomethyl-benzoic acid methyl ester hydrochloride (160 mg), PyBOP (800 mg) and NEt$_3$ (202 µL) were dissolved in THF/DMF (2:1, 15 mL). The mixture was stirred at room temperature for 2 h, concentrated, diluted with EtOAc, washed with saturated aqueous NaHCO$_3$ and saturated aqueous NaCl, dried (MgSO$_4$), filtered, concentrated and purified by chromatography (silica, CH$_2$Cl$_2$/acetone) to afford the title compound (196 mg, 44%). [MH]$^+$=570.

Step E

To a stirred solution of the title compound from Step D above (50 mg) in anhydrous THF (5 mL) was added hydrazine hydrate (40 µL). The mixture was stirred at room temperature for 2 h and then concentrated. The residue was dissolved in anhydrous 1,2-dichloroethane (2 mL) and cooled to 0° C. A 20% solution of phosgene in toluene (500 µL) was added, the cooling bath was removed and the mixture was stirred at room temperature for 2 h. Concentration afforded the crude title compound as a mixture of two isomers, which was used without further purification. [MH]$^+$=493.

Step F

To a solution of the title compound from Step E above (30 mg) in THF/MeOH (2:1, 1.5 mL) was added 1N aqueous LiOH (0.2 mL). The mixture was stirred at room temperature overnight, adjusted to pH 4.5 with 2N aqueous HCl and extracted with EtOAc. The organic phase was washed with saturated aqueous NaCl, dried (MgSO$_4$), filtered, concentrated and purified by preparative thin layer chromatography (silica, CH$_2$Cl$_2$/MeOH) to afford the title compound as a mixture of two isomers (3 mg, 8% over 2 steps). [MH]$^+$=479.

Example 296

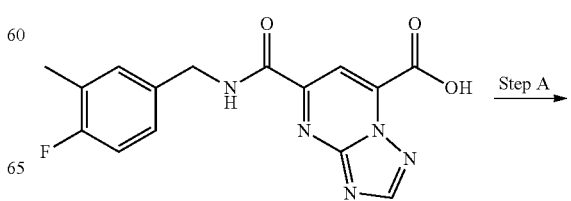

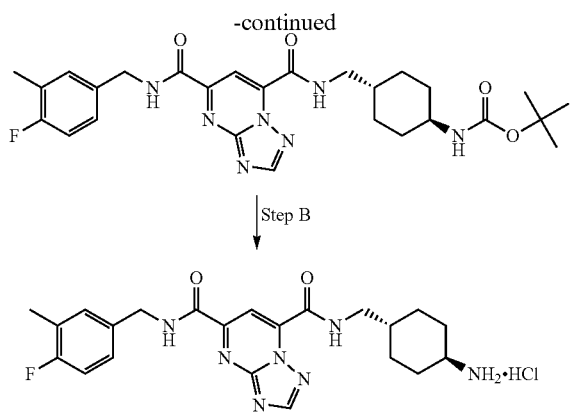

Step A

To a solution of the title compound from the Preparative Example 331, Step A (329 mg) in DMF (10 mL) were successively added HATU (427 mg), HOAt (153 mg), commercially available trans-(4-aminomethyl-cyclohexyl)-carbamic acid tert-butyl ester (291 mg) and $^i$Pr$_2$NEt (191 µL) and the mixture was stirred at room temperature for 5 h. Additional HATU (427 mg), trans-(4-aminomethyl-cyclohexyl)-carbamic acid tert-butyl ester (291 mg) and $^i$Pr$_2$NEt (191 µL) were successively added and stirring at room temperature was continued for 2 h. The mixture was diluted with EtOAc (100 mL), washed with 0.01N aqueous HCl (3×100 mL) and saturated aqueous NaCl (100 mL), dried (MgSO$_4$) and filtered. The filter cake was rinsed with CH$_2$Cl$_2$/MeOH (95:5, 500 mL) and the combined filtrates were concentrated and purified by chromatography (silica, CH$_2$Cl$_2$/MeOH) to afford the title compound as a colorless solid (493 mg, 91%). [MNa]$^+$= 562.

Step B

To a suspension of the title compound from Step A above (436 mg) in EtOAc (3.22 mL) was added a 4M solution of HCl in 1,4-dioxane (3.22 mL). The reaction mixture was stirred at room temperature for 2½ h, diluted with MeOH (10 mL), concentrated, suspended in CH$_3$CN/MeOH (4:1, 20 mL) and concentrated again to afford the title compound (384 mg, 99%). [M-Cl]$^+$=440.

Examples 297-299

Following a similar procedure as described in the Example 296, Step B, except using the protected amines indicated in Table II-3 below, the following compounds were prepared.

TABLE II-3

| Ex. # | protected amine | product | yield |
|---|---|---|---|
| 297 | | | >99% [M − Cl]$^+$ = 426 |
| 298 | | | 98% [M − Cl]$^+$ = 412 |
| 298 | | | 98% [M − Cl]$^+$ = 412 |

Example 299

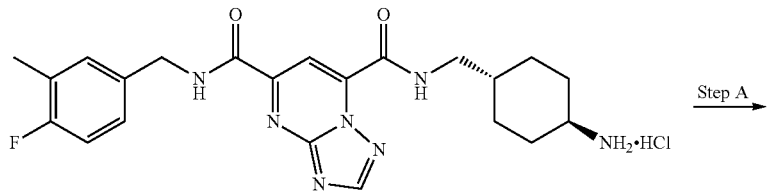

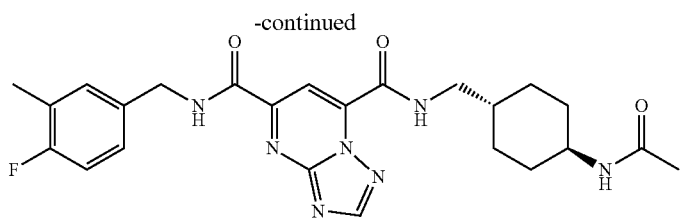

Step A

To a suspension of the title compound from the Example 296, Step B (23.8 mg) in dry CH$_2$Cl$_2$ (1 mL) were added a 1M solution of acetyl chloride in dry CH$_2$Cl$_2$ (50 μL) and $^i$Pr$_2$NEt (26.1 μL). The reaction mixture was stirred at room temperature for 1 h, concentrated and purified by flash chromatography (silica, CH$_2$Cl$_2$/MeOH) to afford the title compound as a beige/white solid (24.1 mg, >99%). [MH]$^+$=482.

Examples 300-309

Following a similar procedure as described in the Example 299, except using the amines and the acid chlorides indicated in Table II-4 below, the following compounds were prepared.

TABLE II-4

| Ex. # | amine, acid chloride | product | yield |
|---|---|---|---|
| 300 | | | 92% [MH]$^+$ = 524 |
| 301 | | | 99% [MH]$^+$ = 518 |
| 302 | | | 73% [MH]$^+$ = 468 |
| 303 | | | 75% [MH]$^+$ = 504 |

TABLE II-4-continued
| Ex. # | amine, acid chloride | product | yield |
|---|---|---|---|
| 304 | 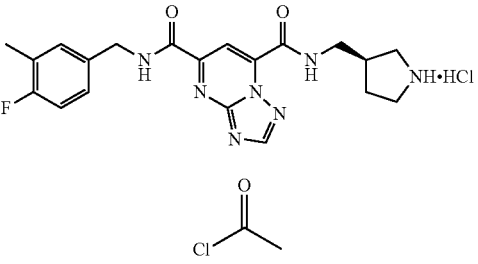 | 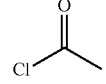 | 97%<br>[MH]⁺ = 454 |
| 305 | 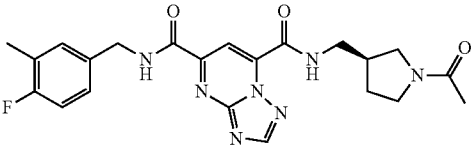 [SMILES: CC(=O)N1CC[C@@H](CNC(=O)c2cc(C(=O)NCc3ccc(F)c(C)c3)nc3ncnn23)C1] |  | 94%<br>[MH]⁺ = 490 |
| 306 | 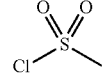 | 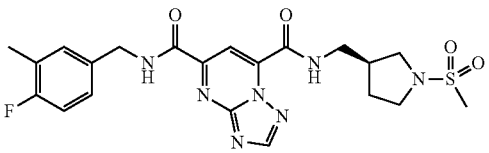 [SMILES: Cc1cc(CNC(=O)c2cc(C(=O)NC[C@@H]3CCN(S(C)(=O)=O)C3)n3ncnc3n2)ccc1F] | 89%<br>[MH]⁺ = 454 |
| 307 | 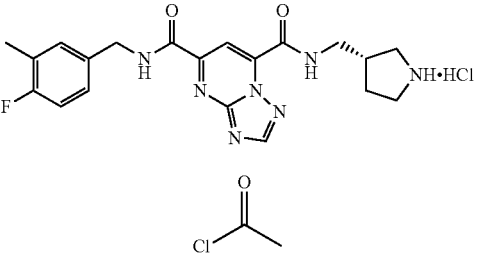 | 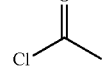 | 95%<br>[MH]⁺ = 490 |
| 308 | 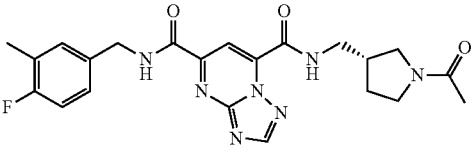 [SMILES: CC(=O)N1CC[C@H](CNC(=O)c2cc(C(=O)NCc3ccc(F)c(C)c3)nc3ncnn23)C1] | 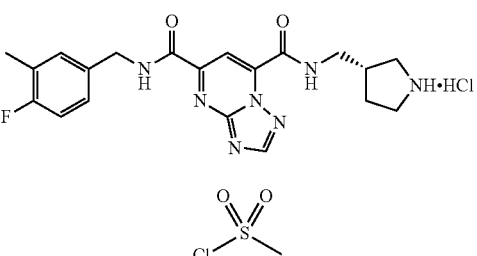 | 71%<br>[MH]⁺ = 544 |

TABLE II-4-continued

| Ex. # | amine, acid chloride | product | yield |
|---|---|---|---|
| 309 | 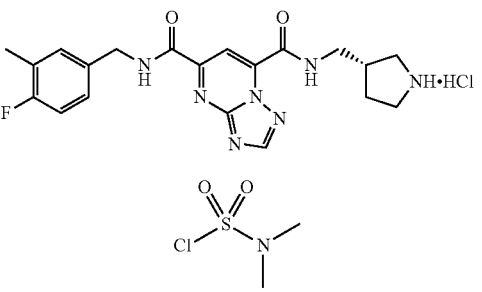 | 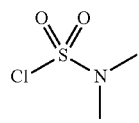 | 83% [MH]⁺ = 519 |

Example 310

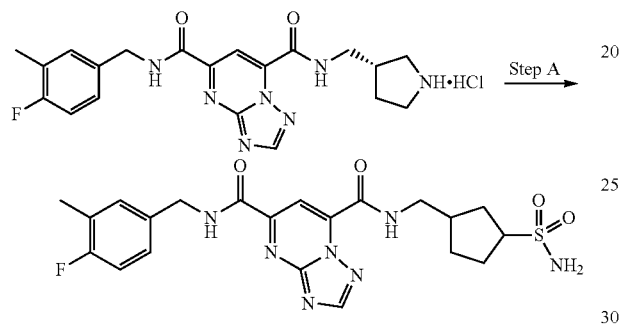

Step A

To a solution of the title compound from the Example 298 (22.4 mg) in dry $CH_2Cl_2$ (500 μL) were added $^iPr_2NEt$ (17.4 μL) and sulfamide (10.8 mg). The resulting reaction mixture was heated in a sealed tube to 140° C. (microwave) for 2 h, concentrated and purified by flash chromatography (silica, $CH_2Cl_2$/MeOH) to afford the title compound (11.7 mg, 48%). $[MH]^+=491$.

Example 311

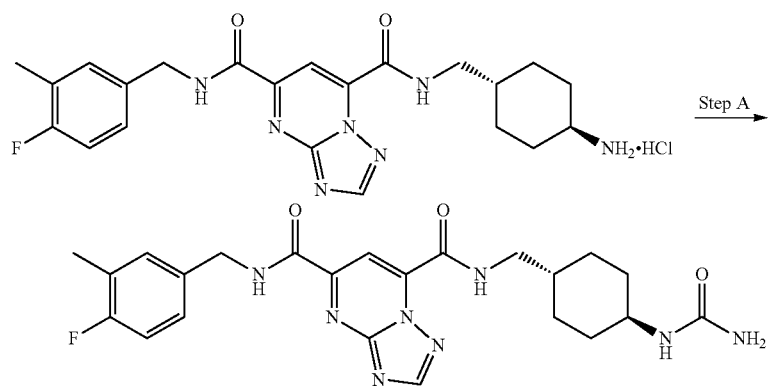

Step A

To a suspension of the title compound from the Example 296, Step B (23.8 mg) in dry $CH_2Cl_2$ (500 μL) was added $KO^tBu$ (6.4 mg). The resulting reaction mixture was stirred at room temperature for 5 min, then $^iPrOH$ (50 μL) and trimethylsilyl isocyanate (13.9 μL) were added and stirring at room temperature was continued for 19 h. The mixture was diluted with MeOH (5 mL), concentrated and purified by flash chromatography (silica, $CH_2Cl_2$/MeOH) to afford the title compound (15 mg, 62%). $[MH]^+=483$.

Example 312

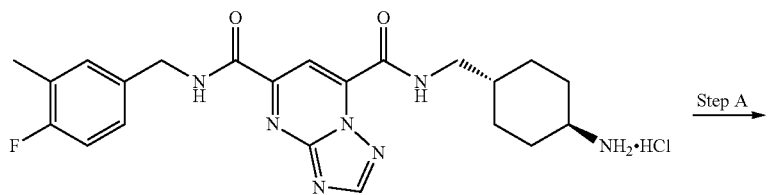

Step A

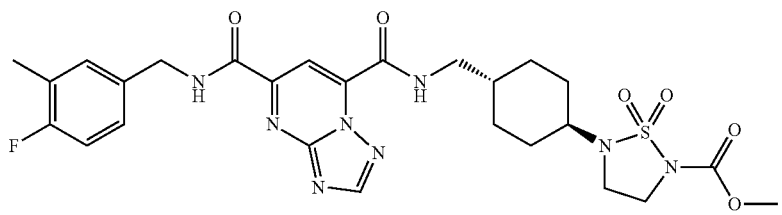

Step A

To a solution of the title compound from the Example 296, Step B (20 mg) in DMF (2.5 mL) were successively added $^i$Pr$_2$NEt (15 µL) and 2-iodoethanol (3.5 µL). Using a microwave, the mixture was heated in a sealed vial at 100° C. for 10 min. The mixture was concentrated and dissolved in dry THF (1 mL). Methyl N-(triethylammoniosulfonyl) carbamate ["Burgess reagent"] (27 mg) was added and using a microwave, the mixture was heated in a sealed vial at 130° C. for 7 min. Concentration and purification by chromatography (silica, CH$_2$Cl$_2$/MeOH) afforded the title compound as a colorless solid (1.7 mg, 6%). [MH]$^+$=603.

Example 313

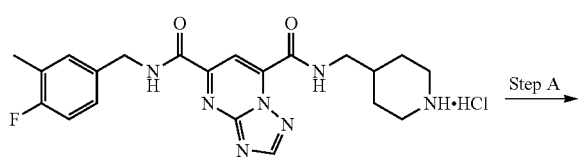 Step A

-continued

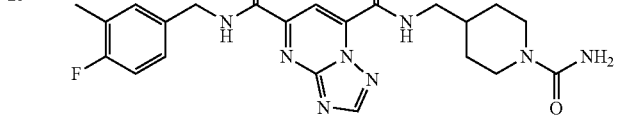

Step A

To a suspension of the title compound from the Example 297 (23.1 mg) in dry CH$_2$Cl$_2$ (500 µL) was added KO$^t$Bu (6.4 mg). The resulting reaction mixture was stirred at room temperature for 5 min, then $^i$PrOH (50 µL) and trimethylsilyl isocyanate (13.9 µL) were added and stirring at room temperature was continued for 16 h. The mixture was diluted with MeOH (5 mL), concentrated and purified by flash chromatography (silica, CH$_2$Cl$_2$/MeOH) to afford the title compound (10 mg, 43%). [α]$^+$=469.

Example 314

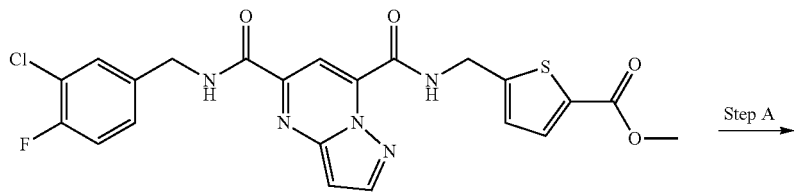 Step A

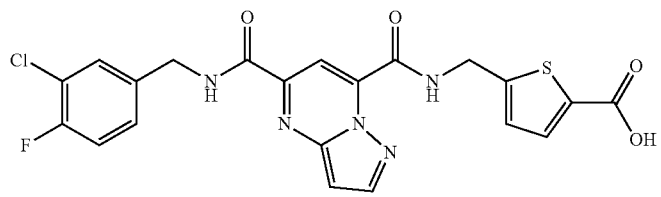

Step A

To a solution of the title compound from the Example 25 (43.9 mg) in THF (10 mL) was added a solution of LiOH (18 mg) in H$_2$O (10 mL). The solution was stirred for 5 h, acidified, concentrated and purified by preparative thin layer chromatography (silica, CH$_2$Cl$_2$/MeOH) to afford the title compound as a bright yellow solid (16.4 mg, 38%). [MH]$^+$=488.

Example 315

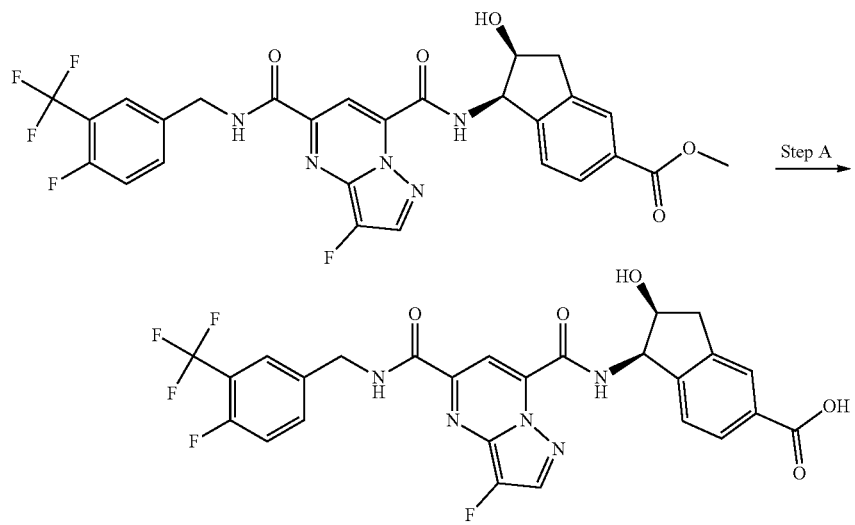

Step A

Using a microwave, a mixture of the title compound from the Example 5 (51 mg) and trimethyltin hydroxide (236 mg) in 1,2-dichloroethane (2 mL) in a sealed vial was stirred at 160° C. for 1 h. The contents were loaded onto a silica and purified by chromatography (silica, CH$_2$Cl$_2$/MeOH) to give a yellow solid (18 mg, 35%). [MH]'=574.

Examples 316-361

Following similar procedures as described in the Examples 314 (method A) or 315 (method B), except using the esters indicated in Table II-5 below, the following compounds were prepared.

TABLE II-5

| Ex. # | ester | product | method, yield |
|---|---|---|---|
| 316 | | | A, 60% [MH]+ = 576 |
| 317 | | | A, 8% [MH]+ = 525 |
| 318 | | | B, 40% [MH]+ = 533 |
| 319 | | | B, 54% [MH]+ = 564 |
| 320 | | | B, 40% [MH]+ = 546 |

TABLE II-5-continued

| Ex. # | ester | product | method, yield |
|---|---|---|---|
| 321 | | | A, 40%<br>¹H-NMR (CDCl₃)<br>δ = 10.50 (br d, 1 H), 9.00 (s, 1 H), 8.90 (s, 1 H), 8.25 (d, 1 H), 7.95 (s, 1 H), 7.90 (d, 1 H), 7.35 (d, 1 H), 7.25-7.10 (m, 2 H), 7.00 (m, 1 H), 5.75 (m, 1 H), 4.70 (d, 2 H), 3.20-2.80 (m, 3 H), 2.25 (s, 3 H), 2.25-2.00 (m, 1 H). |
| 322 | | | A, 31%<br>[MH]⁺ = 488 |
| 323 | | | A, 37%<br>[MH]⁺ = 533 |
| 324 | | | B, 66%<br>[M − H]⁻ = 506 |
| 325 | | | B, 71%<br>[M − H]⁻ = 506 |

TABLE II-5-continued

| Ex. # | ester | product | method, yield |
|---|---|---|---|
| 326 | | | B, 70% [M − H]⁻ = 531 |
| 327 | | | B, 82% [M − H]⁻ = 522 |
| 328 | | | B, 45% [MH]⁺ = 503 |
| 329 | | | B, 18% [MH]⁺ = 622 |
| 330 | | | B, 15% [MH]⁺ = 543 |
| 331 | | | B, 14% [M − H]⁻ = 501 |

TABLE II-5-continued

| Ex. # | ester | product | method, yield |
|---|---|---|---|
| 332 | | | B, 50% [MH]⁺ = 477 |
| 333 | | | B, 32% [MH]⁺ = 463 |
| 334 | | | A, 86% [MH]⁺ = 504 |
| 335 | | | A, 51% [MH]⁺ = 504 |
| 336 | | | B, 34% [M − H]⁻ = 574 |

TABLE II-5-continued

| Ex. # | ester | product | method, yield |
|---|---|---|---|
| 337 | | | B, 46% [M − H]⁻ = 554 |
| 338 | | | B, 29% [M − H]⁻ = 554 |
| 339 | | | B, 45% [M − H]⁻ = 540 |
| 340 | | | B, 44% [M − H]⁻ = 540 |
| 341 | | | B, 52% [MH]⁺ = 532 |

TABLE II-5-continued

| Ex. # | ester | product | method, yield |
|---|---|---|---|
| 342 | | | B, 42% [MH]+ = 495 |
| 343 | | | B, 40% [MH]+ = 514 |
| 344 | | | B, 35% [MH]+ = 494 |
| 345 | | | B, 43% [MH]+ = 512 |
| 346 | | | B, 39% [MH]+ = 551 |
| 347 | | | B, 21% [MH]+ = 481 |

TABLE II-5-continued

| Ex. # | ester | product | method, yield |
|---|---|---|---|
| 348 | | | B, 41% [MH]+ = 498 |
| 349 | | | B, 39% [MH]+ = 516 |
| 350 | | | B, 32% [MH]+ = 566 |
| 351 | | | B, 37% [MH]+ = 498 |
| 352 | | | B, 44% [MH]+ = 582 |

TABLE II-5-continued

| Ex. # | ester | product | method, yield |
|---|---|---|---|
| 353 | | | B, 42% [MH]⁺ = 546 |
| 354 | | | B, 46% [MH]⁺ = 564 |
| 355 | | | B, 15% [MH]⁺ = 532 |
| 356 | | | A, 11% [MH]⁺ = 504 |
| 357 | | | B, 10% [MH]⁺ = 504 |

TABLE II-5-continued

| Ex. # | ester | product | method, yield |
|---|---|---|---|
| 358 | (ester structure) | (product structure) | B, 68% [MH]⁺ = 489 |
| 359 | (ester structure) | (product structure) | B, 66% [MH]⁺ = 469 |
| 360 | (ester structure) | (product structure) | B, 94% [MH]⁺ = 469 |
| 361 | (ester structure) | (product structure) | B, 95% [MH]⁺ = 469 |

Example 362

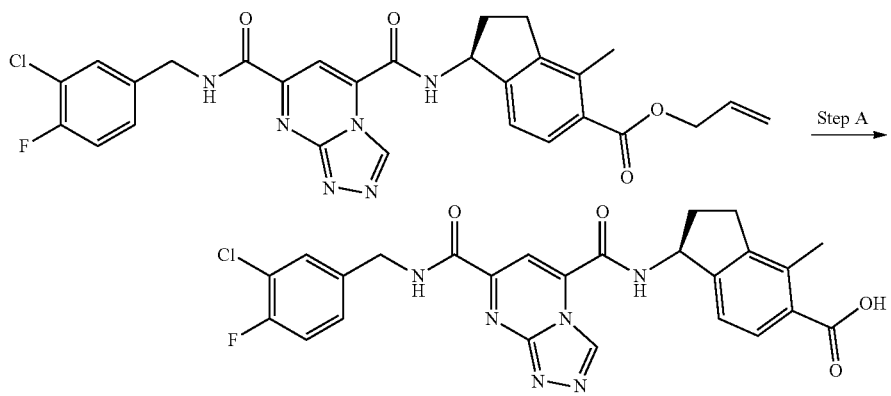

Step A

To a solution of the title compound from the Example 184 (109 mg) in THF (4 mL) were added morpholine (0.17 mL) and Pd(PPh$_3$)$_4$ (23.8 mg). The mixture was stirred at room temperature for 3½ h, diluted with a 4M solution of HCl in 1,4-dioxane (490 µL) and concentrated. The remaining residue was purified by chromatography (silica, CH$_2$Cl$_2$/MeOH) and preparative thin layer chromatography (silica, CH$_2$Cl$_2$/MeOH) to give the title compound as a yellow solid (39.4 mg, 39%). [M-H]$^-$=521.

Examples 363-435

Following a similar procedure as described in the Example 362, except using the esters indicated in Table II-6 below, the following compounds were prepared.

TABLE II-6

| Ex. # | ester | product | yield |
|---|---|---|---|
| 363 | | | 53% [M − H]⁻ = 588 |
| 364 | | | n.d. [MH]⁺ = 609 |
| 365 | | | n.d. [MH]⁺ = 557 |
| 366 | | | 42% [MH]⁺ = 573 |

TABLE II-6-continued

| Ex. # | ester | product | yield |
|---|---|---|---|
| 367 | | | 42% (over 2 steps) [MH]⁺ = 550 |
| 368 | | | 37% [MH]⁺ = 555 |
| 369 | | | 48% [MH]⁺ = 558 |
| 370 | | | 90% [MH]⁺ = 572 |

TABLE II-6-continued

| Ex. # | ester | product | yield |
|---|---|---|---|
| 371 | | | 49% [MH]+ = 583 |
| 372 | | | 59% [MNa]+ = 553 |
| 373 | | | 40% [MNa]+ = 567 |
| 374 | | | 37% (over 2 steps) [MH]+ = 529 |

TABLE II-6-continued

| Ex. # | ester | product | yield |
|---|---|---|---|
| 375 | | | 20% (over 2 steps) [MH]⁺ = 477 |
| 376 | | | 34% (over 2 steps) [MH]⁺ = 419 |
| 377 | | | 29% (over 2 steps) [MH]⁺ = 506 |
| 378 | | | 90% [MH]⁺ = 579 |
| 379 | | | 90% [MH]⁺ = 579 |

TABLE II-6-continued

| Ex. # | ester | product | yield |
|---|---|---|---|
| 380 | | | 41% [MH]+ = 604 |
| 381 | | | 77% [MH]+ = 658 |
| 382 | | | 71% [MH]+ = 605 |
| 383 | | | 67% [MH]+ = 502 |
| 384 | | | 75% [MH]+ = 554 |

TABLE II-6-continued

| Ex. # | ester | product | yield |
|---|---|---|---|
| 385 | | | 18% [MH]+ = 542 |
| 386 | | | 62% [MH]+ = 556 |
| 387 | | | 33% [MH]+ = 537 |
| 388 | | | 69% [MH]+ = 520 |
| 389 | | | 22% [MH]+ = 526 |

TABLE II-6-continued

| Ex. # | ester | product | yield |
|---|---|---|---|
| 390 | | | 8% [MH]⁺ = 496 |
| 391 | | | 77% [MH]⁺ = 496 |
| 392 | | | 71% [MH]⁺ = 551 |
| 393 | | | 65% [MH]⁺ = 516 |
| 394 | | | 46% [MH]⁺ = 556 |

TABLE II-6-continued

| Ex. # | ester | product | yield |
|---|---|---|---|
| 395 | | | 98% [MH]⁺ = 559 |
| 396 | | | 80% [MH]⁺ = 554 |
| 397 | | | 58% [MH]⁺ = 541 |
| 398 | | | 90% [MH]⁺ = 572 |

TABLE II-6-continued

| Ex. # | ester | product | yield |
|---|---|---|---|
| 399 | | | 95% [MH]+ = 554 |
| 400 | | | 77% [MH]+ = 621 |
| 401 | | | 68% [MH]+ = 542 |
| 402 | | | 86% [MH]+ = 536 |

TABLE II-6-continued

| Ex. # | ester | product | yield |
|---|---|---|---|
| 403 | | | 87% [MH]⁺ = 556 |
| 404 | | | 50% [MH]⁺ = 524 |
| 405 | | | 45% [MH]⁺ = 507 |
| 406 | | | 30% (over 2 steps) [MH]⁺ = 557 |
| 407 | | | n.d. [MH]⁺ = 507 |

TABLE II-6-continued

| Ex. # | ester | product | yield |
|---|---|---|---|
| 408 | | | 90% [MH]⁺ = 489 |
| 409 | | | 78% [MH]⁺ = 489 |
| 410 | | | 86% [MH]⁺ = 505 |
| 411 | | | 57% (over 2 steps) [MH]⁺ = 503 |
| 412 | | | 57% (over 2 steps) [MH]⁺ = 503 |

TABLE II-6-continued

| Ex. # | ester | product | yield |
|---|---|---|---|
| 413 | | | 20% (over 2 steps) [MH]+ = 497 |
| 414 | | | 29% (over 2 steps) [MH]+ = 497 |
| 415 | | | 36% (over 2 steps) [MH]+ = 517 |
| 416 | | | 19% [MH]+ = 555 |
| 417 | | | 7% (over 2 steps) [MH]+ = 497 |

TABLE II-6-continued

| Ex. # | ester | product | yield |
|---|---|---|---|
| 418 | | | 82% (over 2 steps) [MH]⁺ = 554 |
| 419 | | | 82% (over 2 steps) [MH]⁺ = 614 |
| 420 | | | 40% [M − H]⁻ = 588 |
| 421 | | | 60% [MH]⁺ = 540 |

TABLE II-6-continued

| Ex. # | ester | product | yield |
|---|---|---|---|
| 422 | | | 94% [MH]⁺ = 574 |
| 423 | | | 98% [MH]⁺ = 572 |
| 424 | | | 45% [MH]⁺ = 568 |
| 425 | | | 20% [MH]⁺ = 569 |
| 426 | | | 51% [MH]⁺ = 583 |

TABLE II-6-continued

| Ex. # | ester | product | yield |
|---|---|---|---|
| 427 | | | 15% [MH]+ = 597 |
| 428 | | | 24% [MH]+ = 553 |
| 429 | | | 31% [MH]+ = 567 |
| 430 | | | >99% [MH]+ = 524 |
| 431 | | | 46% [MH]+ = 514 |

TABLE II-6-continued
| Ex. # | ester | product | yield |
|---|---|---|---|
| 432 | 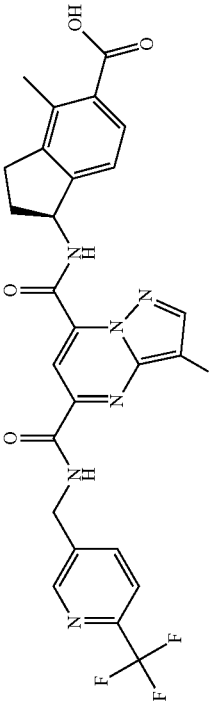 | 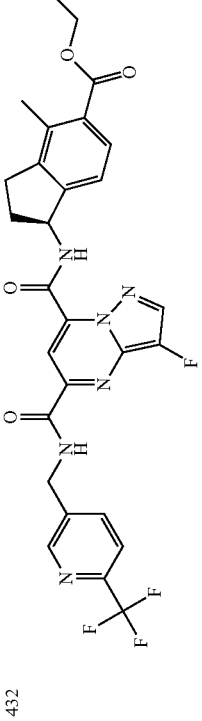 | 64% [MH]+ = 557 |
| 433 | 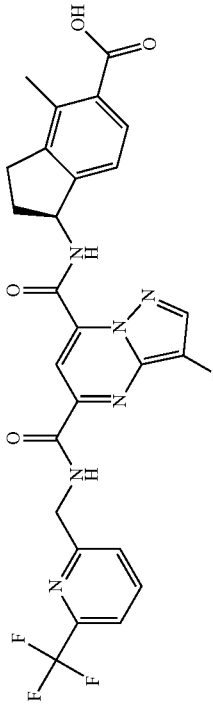 | 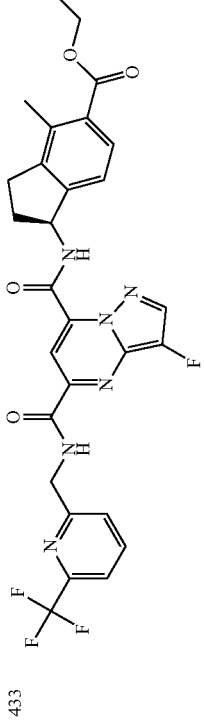 | 78% [MH]+ = 557 |
| 434 | 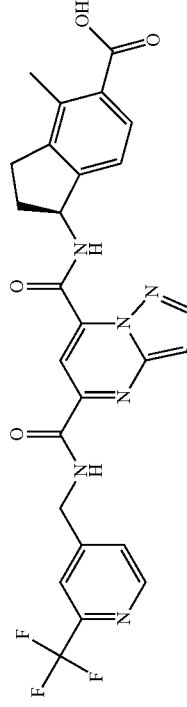 | 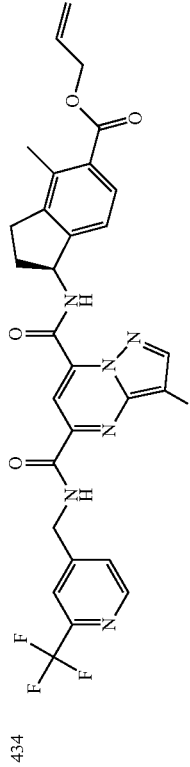 | 65% [MH]+ = 557 |
| 435 | 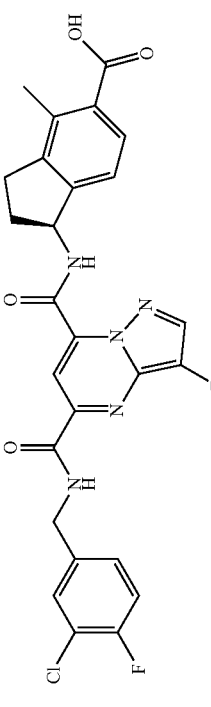 | 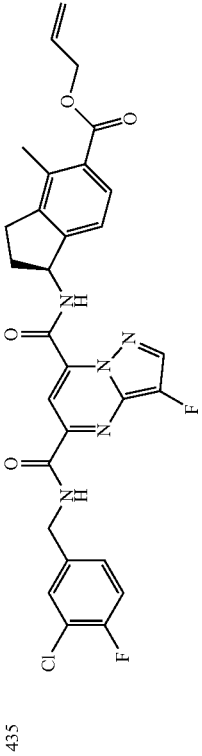 | 71% [MH]+ = 526 |

Example 436

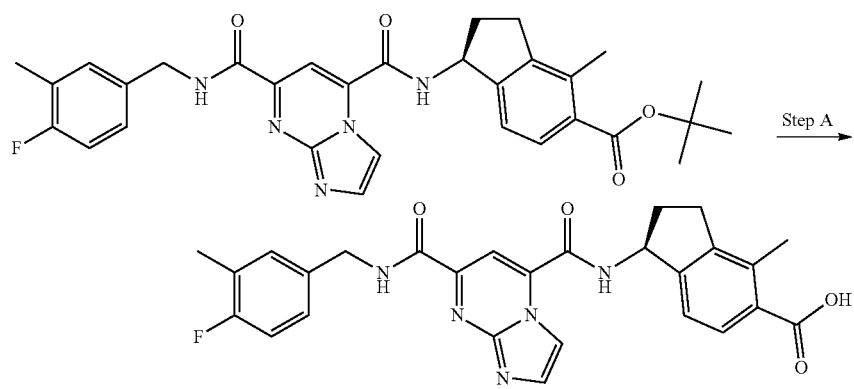

Step A

A solution of the title compound from the Example 83 (20 mg) in a mixture of trifluoroacetic acid (100 µL) and CH$_2$Cl$_2$ (100 µL) was stirred for 30 min and then concentrated. The remaining residue was washed with Et$_2$O (200 µL) to give a yellow solid (17 mg, 92%). [MH]$^+$=502.

Examples 437-464

Following a similar procedure as described in the Example 436, except using the esters as indicated in Table II-7 below, the following compounds were prepared.

TABLE II-7

| Ex. # | ester | product | yield |
|---|---|---|---|
| 437 | | | n.d. [M − H]⁻ = 586 |
| 438 | | | n.d. [M − H]⁻ = 586 |
| 439 | | | 95% [MH]⁺ = 572 |
| 440 | | | 89% [MH]⁺ = 522 |

TABLE II-7-continued

| Ex. # | ester | product | yield |
|---|---|---|---|
| 441 | | | 98% [MH]+ = 556 |
| 442 | | | 35% [MH]+ = 506 |
| 443 | | | 98% [MH]+ = 506 |
| 444 | | | 96% [MH]+ = 540 |

TABLE II-7-continued

| Ex. # | ester | product | yield |
|---|---|---|---|
| 445 | | | 74% [MH]⁺ = 502 |
| 446 | | | 96% [MH]⁺ = 486 |
| 447 | | | 79% [M − H]⁻ = 562 |
| 448 | | | 56% (over 2 steps) [MH]⁺ = 506 |

TABLE II-7-continued

| Ex. # | ester | product | yield |
|---|---|---|---|
| 449 | | | 63% (over 2 steps) [MH]⁺ = 590 |
| 450 | | | 32% (over 2 steps) [MH]⁺ = 618 |
| 451 | | | 10% (over 2 steps) [MH]⁺ = 546 |
| 452 | | | 90% [MH]⁺ = 550 |

TABLE II-7-continued

| Ex. # | ester | product | yield |
|---|---|---|---|
| 453 | | | 90% [MH]⁺ = 536 |
| 454 | | | 73% [M − H]⁻ = 488 |
| 455 | | | 53% [M − H]⁻ = 501 |
| 456 | | | 36% [MH]⁺ = 477 |

TABLE II-7-continued

| Ex. # | ester | product | yield |
|---|---|---|---|
| 457 | | | 50% [MH]⁺ = 523 |
| 458 | | | 50% [MH]⁺ = 496 |
| 459 | | | 67% (over 2 steps) [MH]⁺ = 506 |
| 460 | | | 65% [MH]⁺ = 524 |

TABLE II-7-continued

| Ex. # | ester | product | yield |
|---|---|---|---|
| 461 | | | 56% [MH]+ = 502 |
| 462 | | | 83% [M − H]− = 520 |
| 463 | | | >99% [MH]+ = 556 |
| 464 | | | >99% [M − "indene"]+ = 362 |

Example 465

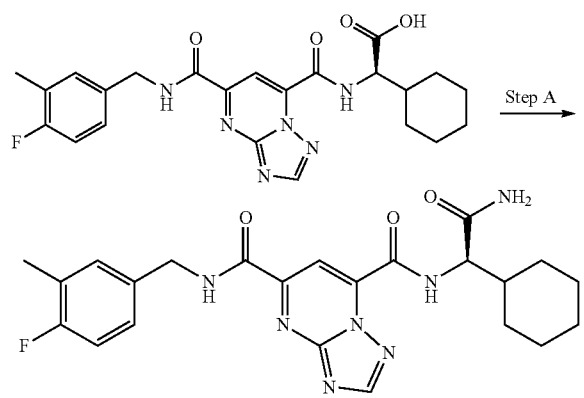

Step A

To a solution of the title compound from the Example 360 (50 mg) in THF (1.5 mL) was added N,N'-carbonyldiimidazole (26 mg). The mixture was stirred at room temperature for 2 h, then a 0.5M solution of NH₃ in 1,4-dioxane (5 mL) was added and stirring at room temperature was continued for 2 h. Concentration and purification by chromatography (silica, CH₂Cl₂/MeOH) afforded the title compound as a colorless solid (29 mg, 60%). [MH]⁺=468.

Example 466

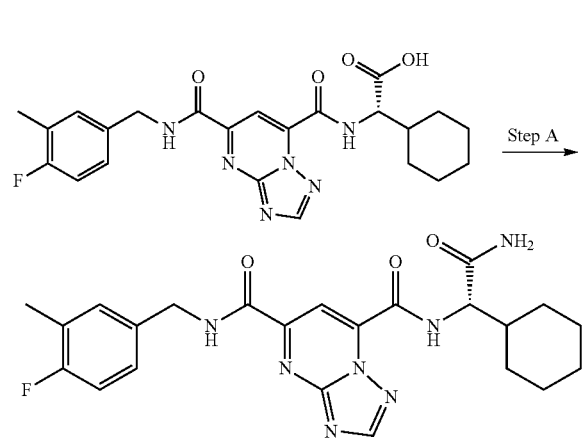

Step A

The title compound from the Example 361 (45 mg) was treated similarly as described in the Example 465, Step A to afford the title compound (21 mg, 48%). [MH]⁺=468.

Example 467

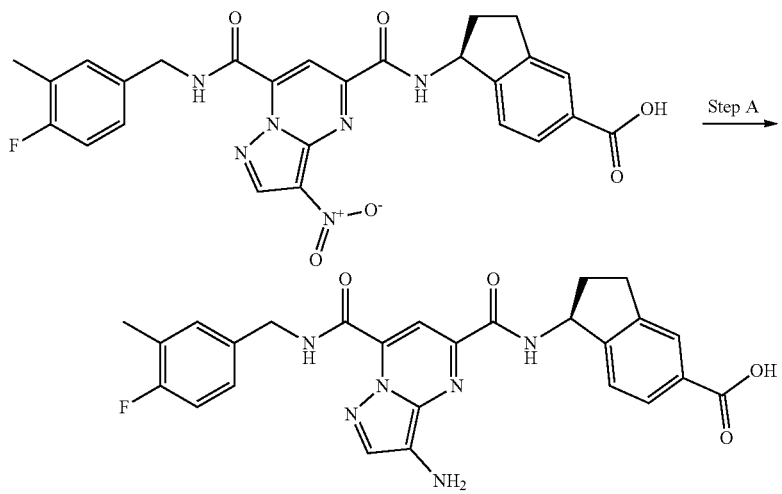

Step A

A mixture of the title compound from the Example 321 (10 mg) and Pd/C (10 wt %, 5 mg) in EtOH was hydrogenated at atmospheric pressure for 5 h, filtered, concentrated and purified by preparative thin layer chromatography (silica, CHCl₃/MeOH) to afford the title compound (1 mg, 10%). [MH]⁺= 503.

Example 468

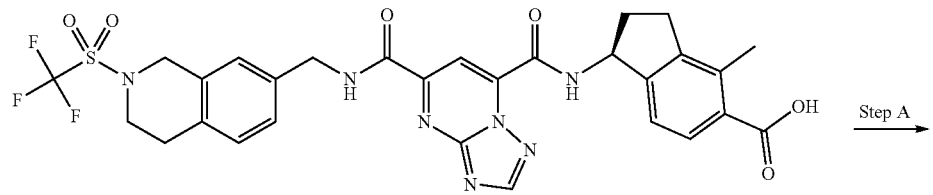

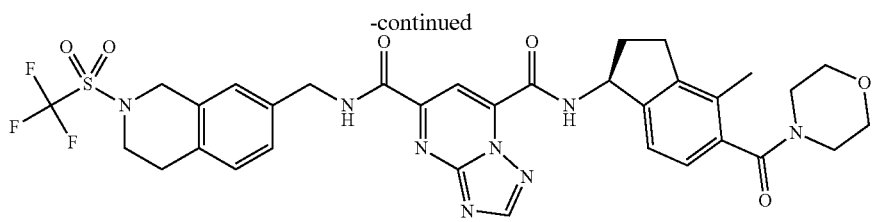

Step A

To a solution of the title compound from the Example 381 (26 mg) in DMF (3 mL) was added morpholine (80 μL), EDCI (10 mg) and HOAt (5 mg). The mixture was stirred overnight and then concentrated. The remaining residue was dissolved in EtOAc, washed with saturated aqueous $NaHCO_3$, 1N aqueous HCl and saturated aqueous NaCl, dried ($MgSO_4$), filtered, concentrated and purified by chromatography (silica, $CH_2Cl_2$/MeOH) to afford the title compound as a colorless solid (9.9 mg, 34%). $[MH]^+=727$.

Example 469

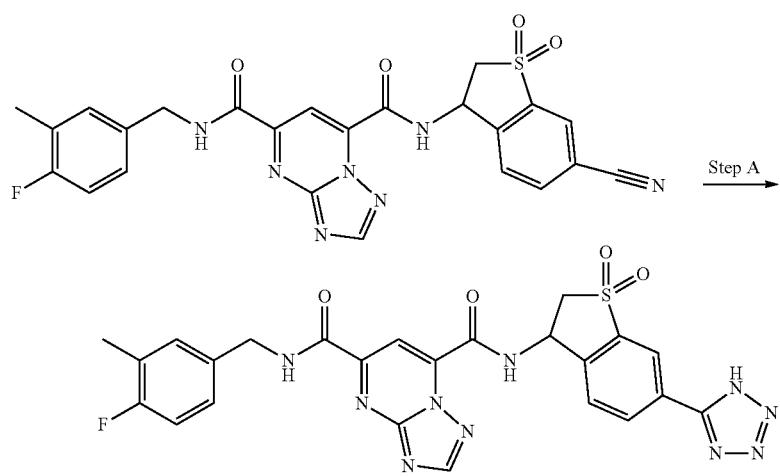

Step A

In a sealed vial was a mixture of the title compound from the Example 3, Step A (54 mg), dibutyltin oxide (15 mg) and azidotrimethylsilane (400 μL) in toluene (10 mL) under an argon atmosphere heated at 110° C. for 18 h. The reaction mixture was then diluted with MeOH, concentrated and purified by chromatography (silica, $CH_2Cl_2$/MeOH) to give the title compound as an off-white solid (8.6 mg, 15%). $[Mi]^+=563$.

Examples 470-477

Following a similar procedure as described in the Example 469, except using the nitriles indicated in Table II-8 below, the following compounds were prepared.

TABLE II-8

| Ex. # | nitrile | product | yield |
|---|---|---|---|
| 470 | (structure) | (structure) | 74% [MH]+ = 526 |
| 471 | (structure) | (structure) | 34% [MH]+ = 600 |
| 472 | (structure) | (structure) | 38% [MH]+ = 564 |
| 473 | (structure) | (structure) | 40% [MH]+ = 550 |

TABLE II-8-continued

| Ex. # | nitrile | product | yield |
|---|---|---|---|
| 474 | | | 55% [MH]⁺ = 514 |
| 475 | | | 27% [MH]⁺ = 487 |
| 476 | | | 46% [MH]⁺ = 485 |
| 477 | | | 53% [MH]⁺ = 583 |

Example 478

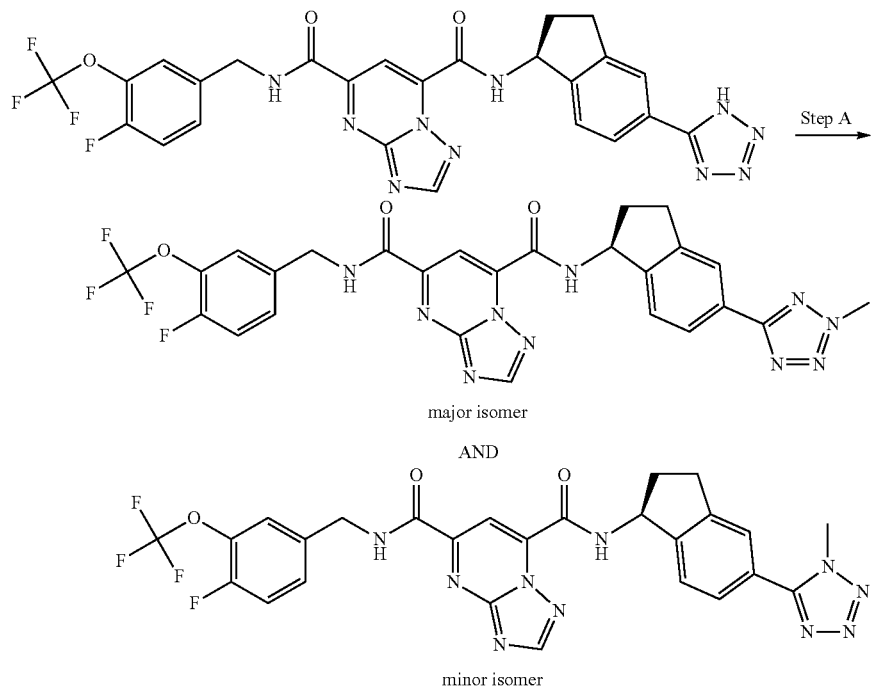

Step A

To a solution of the title compound from the Example 477 (80 mg) in DMF (3 mL) were added iodomethane (9 μL) and K₂CO₃ (19 mg) and the mixture was stirred at room temperature overnight. Additional iodomethane (8 μL) was added and stirring at room temperature was continued for 2 h. The mixture was concentrated and purified by preparative thin layer chromatography (silica, EtOAc) to afford the major isomer (30 mg, 37%) and the minor isomer (15 mg, 18%) of the title compound. [MH]⁺=597.

Example 479

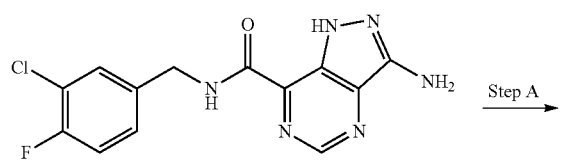

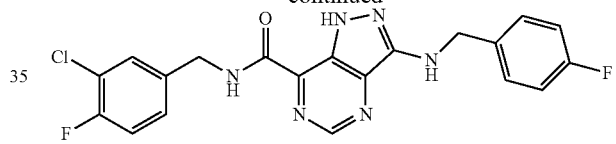

Step A

To a stirring solution of the title compound from the Preparative Example 377, Step E (9 mg) in MeOH (3 mL) were added AcOH (a few drops), a 1M solution of commercially available 4-fluorobenzaldehyde in MeOH (30 μL) and NaBH(OAc)₃ (5 mg). The mixture was stirred at room temperature overnight, concentrated, diluted with EtOAc, washed with saturated aqueous NaHCO₃ and saturated aqueous NaCl, dried (MgSO₄), filtered, concentrated and purified by preparative thin layer chromatography (silica, cyclohexane/EtOAc) to afford the title compound as an off-white solid (5 mg, 42%). [MH]⁺=429.

Example 480-482

Following similar procedures as described in the Example 479, except using the aldehydes indicated in Table II-9 below, the following compounds were prepared.

TABLE II-9

| Ex. # | aldehyde | product | yield |
|---|---|---|---|
| 480 | ![aldehyde] | ![product] | >99%<br>[MH]⁺ = 455 |

… TABLE II-9-continued

| Ex. # | aldehyde | product | yield |
|---|---|---|---|
| 481 | | | 63% [MH]+ = 455 |
| 482 | | | n.d. [MH]+ = 417 |

Example 483

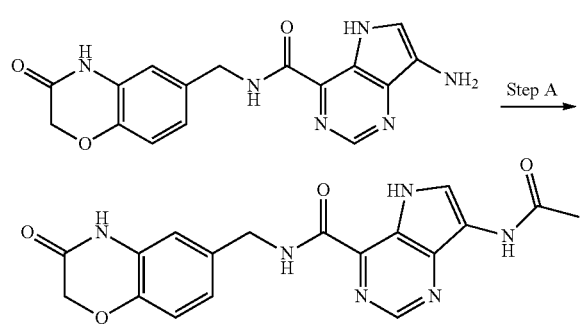

Step A
To a solution of the title compound from the Preparative Example 379, Step G (7 mg) in anhydrous pyridine (1 mL) was added Ac$_2$O (1 mL). The mixture was stirred at room temperature for 5 h, concentrated and slurried in MeOH. The formed precipitate was collected by filtration and dried to afford the title compound as a brown solid (5.1 mg, 64%). NM+=381.

Example 484

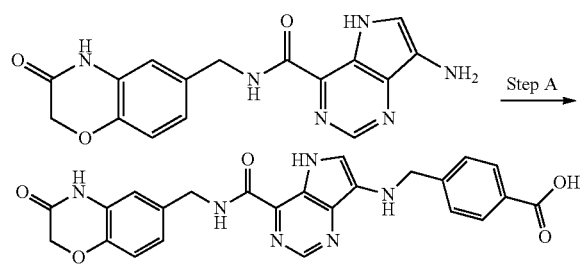

Step A
A stirring solution of the title compound from the Preparative Example 377, Step G (9 mg) in MeOH/H$_2$O/THF (3:2:1, 6 mL) was adjusted to pH 6 with 3M aqueous NaOAc. 4-Formylbenzoic acid (6 mg) was added and the mixture was stirred at room temperature for 30 min. NaBH$_3$CN (5 mg) was added and stirring at room temperature was continued overnight. The mixture was concentrated and diluted with 0.1N aqueous HCl (5 mL). The formed precipitate was collected by filtration, washed with 0.1N aqueous HCl (8 mL) and dried to afford the title compound as an orange solid (7.8 mg, 61%). [MH]+=473.

Example 485

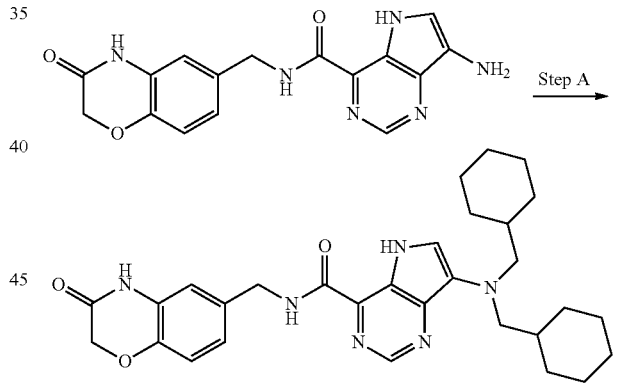

Step A
The title compound from the Preparative Example 377, Step G (9 mg) was treated similarly as described in the Preparative Example 484, except using cyclohexanecarbaldehyde (0.04 mL) instead of 4-formylbenzoic acid to afford the title compound as a reddish glass (6.5 mg, 45%). [MH]+=531.

Examples 486-504

Following similar procedures as described in the Examples 1 (method A), 2 (method B), 3 (method C), 4 (method D), 5 (method E), 6 (method F) or 7 (method G), except using the acids and amines indicated in Table II-10 below, the following compounds were prepared.

TABLE II-10
| Ex. # | acid, amine | product | method, yield |
|---|---|---|---|
| 486 | 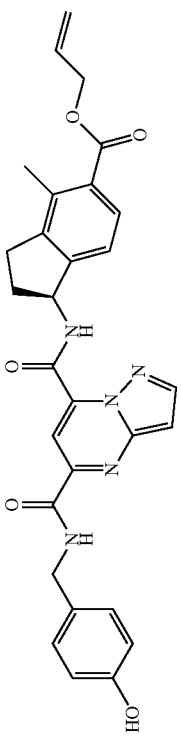 |  | B, n.d. [MH]⁺ = 526 |
| 487 |  |  | B, 34% [MH]⁺ = 739 |
| 488 |  | 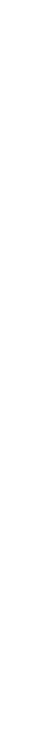 | B, 75% [MH]⁺ = 738 |

TABLE II-10-continued

| Ex. # | acid, amine | product | method, yield |
|---|---|---|---|
| 489 | (structures) | (structure) | B, n.d. [MH]$^+$ = 1015 |
| 490 | (structures) | (structure) | B, 31% [MH]$^+$ = 491 |
| 491 | (structures) | (structure) | C, 77% [MH]$^+$ = 562 |

| Ex. # | acid, amine | product | method, yield |
|---|---|---|---|
| 492 | | | C, 69% [MH]$^+$ = 494 |
| 493 | | | C, 71% [MH]$^+$ = 542 |
| 494 | | | C, 69% [MH]$^+$ = 560 |

TABLE II-10-continued

TABLE II-10-continued
| Ex. # | acid, amine | product | method, yield |
|---|---|---|---|
| 495 | 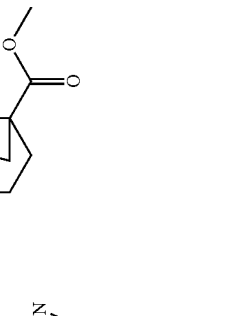 | 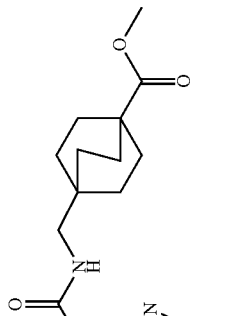 | C, 54%<br>[MH]⁺ = 545 |
| 496 | 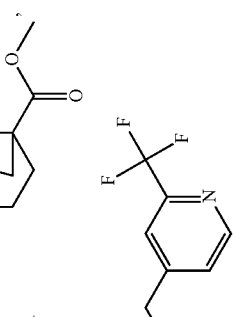 | 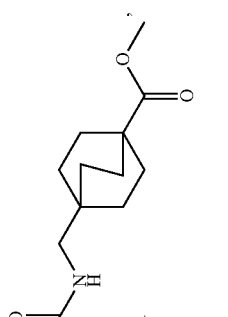 | C, 55%<br>[MH]⁺ = 563 |

TABLE II-10-continued

| Ex. # | acid, amine | product | method, yield |
|---|---|---|---|
| 497 | | | C, 90% [MH]⁺ = 529 |
| 498 | | | C, 90% [MH]⁺ = 495 |
| 499 | | | C, n.d. [MH]⁺ = 522 |

TABLE II-10-continued
| Ex. # | acid, amine | product | method, yield |
|---|---|---|---|
| 500 | 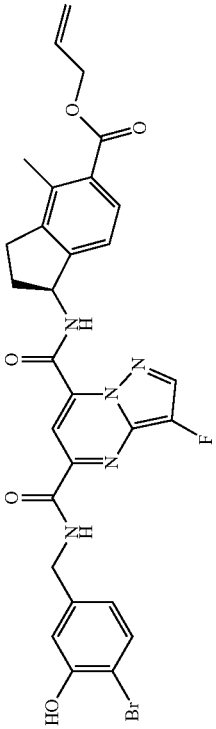 | 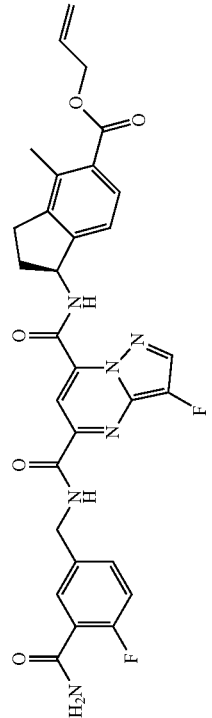 | C, 33% [M − "indene"]+ = 408 |
| 501 | 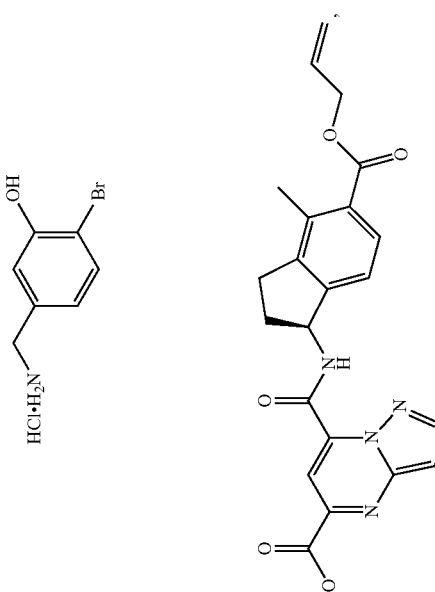 | 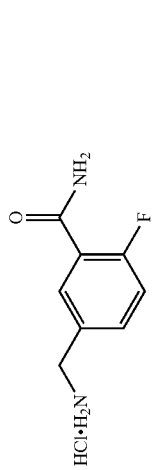 | C, n.d. [MH]+ = 571 |

TABLE II-10-continued
| Ex. # | acid, amine | product | method, yield |
|---|---|---|---|
| 502 | 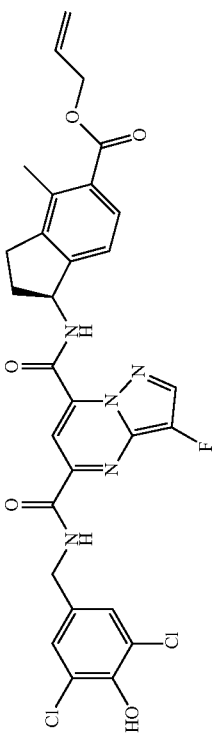 | 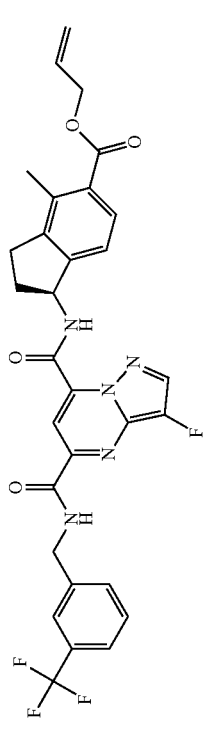 | C, n.d. [MH]+ = 612 |
| 503 | 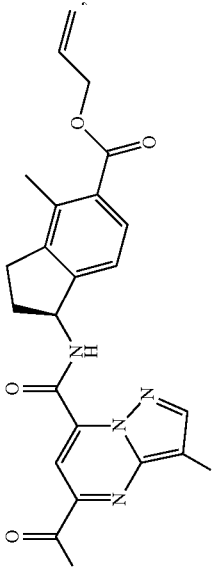 | 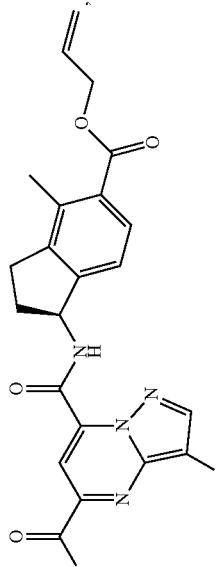 | C, 40% [MNa]+ = 618 |

TABLE II-10-continued

| Ex. # | acid, amine | product | method, yield |
|---|---|---|---|
| 504 | [structure of acid and amine with TFA·H₂N] | [structure of product] | C, 40%<br>¹H-NMR (CDCl₃)<br>δ = 10.34 (d, 1 H), 8.69 (s, 1 H), 8.08 (t, 1 H), 8.06 (d, 1 H), 7.78 (d, 1 H), 7.47 (d, 1 H), 7.20-7.24 (m, 1 H), 6.95-7.02 (m, 2 H), 5.93-6.08 (m, 2 H), 5.72-5.82 (m, 1 H), 5.37 (dd, 1 H), 5.25 (dd, 1 H), 4.78 (d, 2 H), 4.67 (d, 2 H), 3.00-3.16 (m, 1 H), 2.71-2.95 (m, 2 H), 2.50 (s, 3 H), 1.96-2.10 (m, 1 H) |

Examples 505-513

Following similar procedures as described in the Examples 314 (method A) or 315 (method B), except using the esters indicated in Table H-11 below, the following compounds were prepared.

TABLE II-11

| Ex. # | ester | product | method, yield |
|---|---|---|---|
| 505 | | | A, 41% [MH]+ = 548 |
| 506 | | | A, 49% [MH]+ = 480 |
| 507 | | | A, 39% [MH]+ = 528 |

TABLE II-11-continued

| Ex. # | ester | product | method, yield |
|---|---|---|---|
| 508 | | | A, 49% [MH]+ = 546 |
| 509 | | | A, n.d. [MH]+ = 531 |
| 510 | | | A, n.d. [MH]+ = 549 |

TABLE II-11-continued

| Ex. # | ester | product | method, yield |
|---|---|---|---|
| 511 | methyl 4-({[(3-{[(3-chloro-4-fluorobenzyl)amino]carbonyl}pyrazolo[1,5-a]pyrimidin-7-yl)carbonyl]amino}methyl)bicyclo[2.2.2]octane-1-carboxylate | 4-({[(3-{[(3-chloro-4-fluorobenzyl)amino]carbonyl}pyrazolo[1,5-a]pyrimidin-7-yl)carbonyl]amino}methyl)bicyclo[2.2.2]octane-1-carboxylic acid | B, n.d. [MH]+ = 515 |
| 512 | methyl 4-({[(3-{[(4-fluorobenzyl)amino]carbonyl}pyrazolo[1,5-a]pyrimidin-7-yl)carbonyl]amino}methyl)bicyclo[2.2.2]octane-1-carboxylate | 4-({[(3-{[(4-fluorobenzyl)amino]carbonyl}pyrazolo[1,5-a]pyrimidin-7-yl)carbonyl]amino}methyl)bicyclo[2.2.2]octane-1-carboxylic acid | B, n.d. [MH]+ = 481 |
| 513 | ethyl 4-(1-{[(3-{[(4-fluorobenzyl)amino]carbonyl}pyrazolo[1,5-a]pyrimidin-7-yl)carbonyl]amino}ethyl)bicyclo[2.2.2]octane-1-carboxylate | 4-(1-{[(3-{[(4-fluorobenzyl)amino]carbonyl}pyrazolo[1,5-a]pyrimidin-7-yl)carbonyl]amino}ethyl)bicyclo[2.2.2]octane-1-carboxylic acid | A, n.d. [MH]+ = 508 |

Examples 514-518

Following a similar procedure as described in the Example 362, except using the esters indicated in Table II-12 below, the following compounds were prepared.

TABLE II-12

| Ex. # | ester | product | yield |
|---|---|---|---|
| 514 | | | n.d. % [MH]⁺ = 486 |
| 515 | | | 17% [M − "indene"]⁺ = 408 |
| 516 | | | n.d. [MH]⁺ = 549 |
| 517 | | | n.d. [MH]⁺ = 572 |

TABLE II-12-continued

| Ex. # | ester | product | yield |
|---|---|---|---|
| 517 | (structure) | (structure) | >99% [MH]⁺ = 556 |
| 518 | (structure) | (structure) | 69% ¹H-NMR (CDCl₃) δ = 12.20-13.20 (br s, 1 H), 10.40-10.70 (br s, 1 H), 10.06 (d, 1 H), 9.73 (t, 1 H), 8.68 (d, 1 H), 8.07 (s, 1 H), 7.72 (d, 1 H), 7.49 (d, 1 H), 7.32 (d, 1 H), 7.04 (s, 1 H), 6.93 (d, 1 H), 5.61-5.71 (m, 1 H), 4.52 (d, 2 H), 2.80-3.11 (m, 2 H), 2.61-2.72 (m, 1 H), 2.50 (s, 3 H), 1.96-2.10 (m, 1 H) |

Example 519

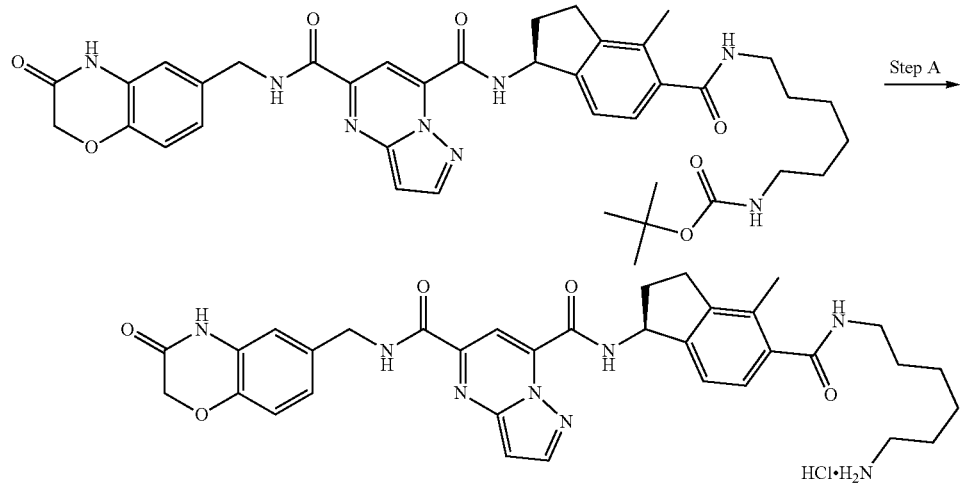

Step A

The title compound from the Example 487 (42 mg) was treated similarly as described in the Example 296, Step B to afford the title compound (44 mg, >99%). [M-Cl]$^+$=639.
The Example numbers 520 to 1699 and the Table numbers 11-13 to 11-38 were intentionally excluded.

Example 1700

Assay for Determining MMP-13 Inhibition

The typical assay for MMP-13 activity is carried out in assay buffer comprised of 50 mM Tris, pH 7.5, 150 mM NaCl, 5 mM CaCl$_2$ and 0.05% Brij-35. Different concentrations of tested compounds are prepared in assay buffer in 50 μL aliquots. 10 μL of a 50 nM stock solution of catalytic domain of MMP-13 enzyme (produced by Alantos) is added to the compound solution. The mixture of enzyme and compound in assay buffer is thoroughly mixed and incubated for 10 min at room temperature. Upon the completion of incubation, the assay is started by addition of 40 μL of a 12.5 μM stock solution of MMP-13 fluorescent substrate (Calbiochem, Cat. No. 444235). The time-dependent increase in fluorescence is measured at the 320 nm excitation and 390 nm emission by automatic plate multireader. The IC$_{50}$ values are calculated from the initial reaction rates.

Example 1701

Assay for Determining MMP-3 Inhibition

The typical assay for MMP-3 activity is carried out in assay buffer comprised of 50 mM MES, pH 6.0, 10 mM CaCl$_2$ and 0.05% Brij-35. Different concentrations of tested compounds are prepared in assay buffer in 50 μL aliquots. 10 μL of a 100 nM stock solution of the catalytic domain of MMP-3 enzyme (Biomol, Cat. No. SE-109) is added to the compound solution. The mixture of enzyme and compound in assay buffer is thoroughly mixed and incubated for 10 min at room temperature. Upon the completion of incubation, the assay is started by addition of 40 μL of a 12.5 μM stock solution of NFF-3 fluorescent substrate (Calbiochem, Cat. No. 480455). The time-dependent increase in fluorescence is measured at the 330 nm excitation and 390 nm emission by an automatic plate multireader. The IC$_{50}$ values are calculated from the initial reaction rates.

Example 1702

Assay for Determining MMP-8 Inhibition

The typical assay for MMP-8 activity is carried out in assay buffer comprised of 50 mM Tris, pH 7.5, 150 mM NaCl, 5 mM CaCl$_2$ and 0.05% Brij-35. Different concentrations of tested compounds are prepared in assay buffer in 50 μL aliquots. 10 μL of a 50 nM stock solution of activated MMP-8 enzyme (Calbiochem, Cat. No. 444229) is added to the compound solution. The mixture of enzyme and compound in assay buffer is thoroughly mixed and incubated for 10 min at 37° C. Upon the completion of incubation, the assay is started by addition of 40 μL of a 10 μM stock solution of OmniMMP fluorescent substrate (Biomol, Cat. No. P-126). The time-dependent increase in fluorescence is measured at the 320 nm excitation and 390 nm emission by an automatic plate multireader at 37° C. The IC$_{50}$ values are calculated from the initial reaction rates.

Example 1703

Assay for Determining MMP-12 Inhibition

The typical assay for MMP-12 activity is carried out in assay buffer comprised of 50 mM Tris, pH 7.5, 150 mM NaCl, 5 mM CaCl$_2$ and 0.05% Brij-35. Different concentrations of tested compounds are prepared in assay buffer in 50 μL aliquots. 10 μL of a 50 nM stock solution of the catalytic domain of MMP-12 enzyme (Biomol, Cat. No. SE-138) is added to the compound solution. The mixture of enzyme and compound in assay buffer is thoroughly mixed and incubated for 10 min at room temperature. Upon the completion of incubation, the assay is started by addition of 40 μL of a 12.5 μM stock solution of OmniMMP fluorescent substrate (Biomol, Cat. No. P-126). The time-dependent increase in fluorescence is measured at the 320 nm excitation and 390 nm emission by automatic plate multireader at 37° C. The IC$_{50}$ values are calculated from the initial reaction rates.

Example 1704

Assay for Determining Aggrecanase-1 Inhibition

The typical assay for aggrecanase-1 activity is carried out in assay buffer comprised of 50 mM Tris, pH 7.5, 150 mM NaCl, 5 mM CaCl$_2$ and 0.05% Brij-35. Different concentrations of tested compounds are prepared in assay buffer in 50 µL aliquots. 10 µL of a 75 nM stock solution of aggrecanase-1 (Invitek) is added to the compound solution. The mixture of enzyme and compound in assay buffer is thoroughly mixed. The reaction is started by addition of 40 µL of a 250 nM stock solution of aggrecan-IGD substrate (Invitek) and incubation at 37° C. for exact 15 min. The reaction is stopped by addition of EDTA and the samples are analysed by using aggrecanase ELISA (Invitek, InviLISA, Cat. No. 30510111) according to the protocol of the supplier. Shortly: 100 µL of each proteolytic reaction are incubated in a pre-coated micro plate for 90 min at room temperature. After 3 times washing, antibody-peroxidase conjugate is added for 90 min at room temperature. After 5 times washing, the plate is incubated with TMB solution for 3 min at room temperature. The peroxidase reaction is stopped with sulfurous acid and the absorbance is red at 450 nm. The IC$_{50}$ values are calculated from the absorbance signal corresponding to residual aggrecanase activity.

Example 1705

Assay for Determining Inhibition of MMP-3 Mediated Proteoglycan Degradation

The assay for MMP-3 activity is carried out in assay buffer comprised of 50 mM MES, pH 6.0, 10 mM CaCl$_2$ and 0.05% Brij-35. Articular cartilage is isolated fresh from the first phalanges of adult cows and cut into pieces (~3 mg). Bovine cartilage is incubated with 50 nM human MMP-3 (Chemikon, cat.#25020461) in presence or absence of inhibitor for 24 h at 37° C. Sulfated glycosaminoglycan (aggrecan) degradation products (sGAG) are detected in supernatant, using a modification of the colorimetric DMMB (1,9-dimethylmethylene blue dye) assay (Billinghurst et al., 2000, Arthritis & Rheumatism, 43 (3), 664). 10 µL of the samples or standard are added to 190 µL of the dye reagent in microtiter plate wells, and the absorbance is measured at 525 nm immediately. All data points are performed in triplicates.

Example 1706

Assay for Determining Inhibition of MMP-3 mediated Pro-Collagenase 3 Activation The assay for MMP-3 mediated activation of pro-collagenase 3 (pro-MMP-13) is carried out in assay buffer comprised of 50 mM MES, pH 6.0, 10 mM CaCl$_2$ and 0.05% Brij-35 (Nagase; *J. Biol. Chem.*1994 Aug. 19; 269(33):20952-7).

Different concentrations of tested compounds are prepared in assay buffer in 5 µL aliquots. 10 µL of a 100 nM stock solution of trypsin-activated (Knauper V., et al., 1996 *J. Biol. Chem.* 271 1544-1550) human pro-MMP-3 (Chemicon; CC1035) is added to the compound solution. To this mixture, 35 µL of a 286 nM stock solution of pro-collagenase 3 (Invitek; 30100803) is added to the mixture of enzyme and compound. The mixture is thoroughly mixed and incubated for 5 h at 37° C. Upon the completion of incubation, 10 µL of the incubation mixture is added to 50 µL assay buffer comprised of 50 mM Tris, pH 7.5, 150 mM NaCl, 5 mM CaCl$_2$ and 0.05% Brij-35 and the mixture is thoroughly mixed.

The assay to determine the MMP-13 activity is started by addition of 40 µL of a 10 µM stock solution of MMP-13 fluorogenic substrate (Calbiochem, Cat. No. 444235) in assay buffer comprised of 50 mM Tris, pH 7.5, 150 mM NaCl, 5 mM CaCl$_2$ and 0.05% Brij-35 (Knauper, V., et al., 1996. *J. Biol. Chem.* 271, 1544-1550). The time-dependent increase in fluorescence is measured at 320 nm excitation and 390 nm emission by an automatic plate multireader at room temperature. The IC$_{50}$ values are calculated from the initial reaction rates.

Example 1707

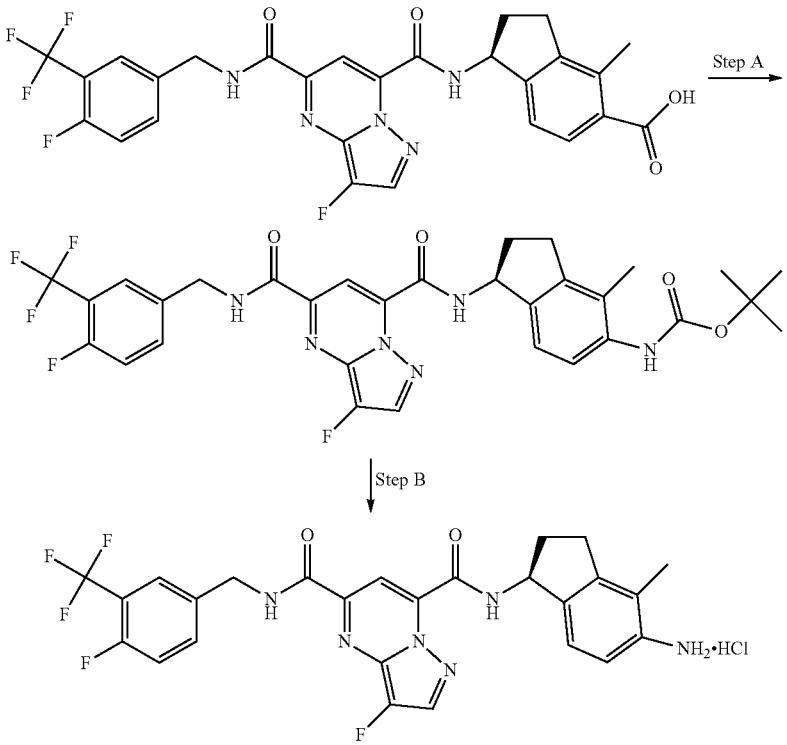

Step A

A mixture of the title compound from the Example 418 (130 mg), NEt₃ (71 µL) and diphenylphosphoryl azide (104 µL) in tBuOH (4 mL) was heated to 70° C. overnight, concentrated and purified by chromatography (silica, cyclohexane/EtOAc) to afford the title compound (43 mg, 30%). [MH]⁺=645.

Step B

A solution of the title compound from Step A above (43 mg) in a mixture of trifluoroacetic acid (1 mL) and CH₂Cl₂ (6 mL) was stirred at room temperature for 2 h, diluted with CH₃CN (3 mL) and then concentrated. The remaining residue was diluted with 0.1M aqueous HCl, concentrated, again diluted with 0.1M aqueous HCl and concentrated to afford the title compound (39 mg, >99%). [M-Cl]⁺=581.

Example 1708

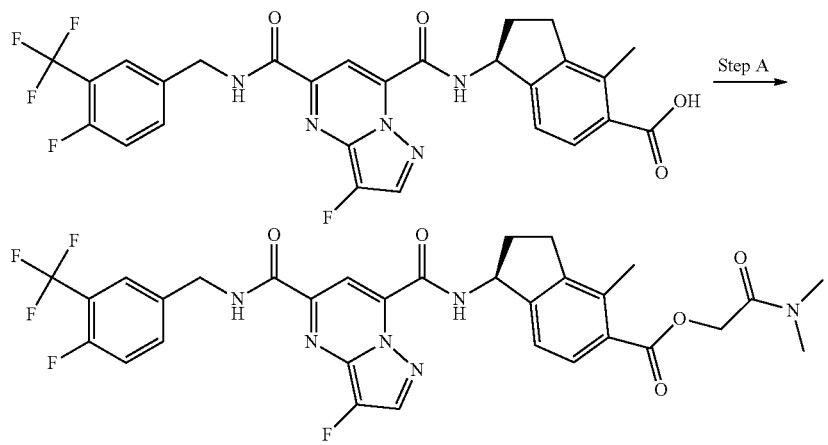

Step A

A mixture of the title compound from the Example 418 (40 mg), 2-chloro-N,N-dimethylacetamide (7.9 mL), NaI (11 mg) and NEt₃ (10.5 µL) in EtOAc (3 mL) was heated to reflux for 3 h, cooled, filtered, washed with saturated aqueous NaS₂O₃, half saturated aqueous NaHCO₃ and saturated aqueous NaCl (200 mL), dried (MgSO₄), filtered, concentrated and purified by preparative thin layer chromatography (silica, CH₂Cl₂/acetone) to afford the title compound (25 mg, 72%). [MH]⁺=659.

Example 1709

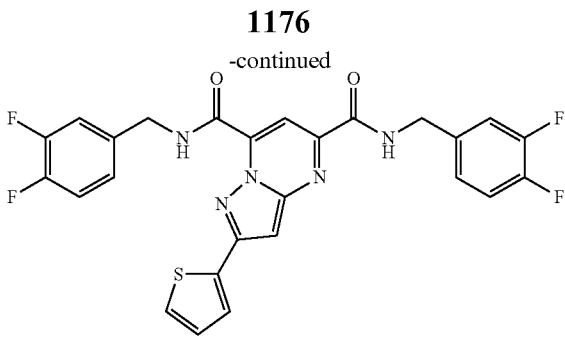

Step A

The title compound from the Preparative Example 968 (109 mg) was treated similarly as described in the Preparative Example 328, Step A, except using commercially available 3,4-difluorobenzylamine instead of 4-fluorobenzylamine to afford title compound from the Preparative Example 984 (47 mg, 32%, [MH]⁺=429) and the title compound (4.1 mg, 3%). [M-H]′=538.

Example 1710

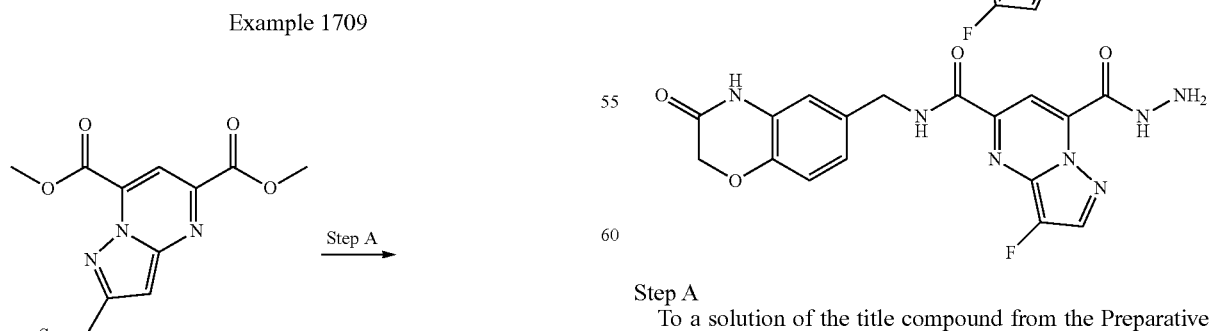

Step A

To a solution of the title compound from the Preparative Example 355 (50 mg) in MeOH (5 mL) was added thionyl chloride (150 µL). The resulting mixture was heated to reflux for 2 h and then concentrated. The remaining residue was dissolved in EtOH (10 mL), hydrazine monohydrate (100 µL)

was added and the resulting mixture was heated to reflux for 2 h and then cooled to room temperature. The formed precipitate was collected by filtration to afford the title compound (69 mg, >99%). [MH]⁺=400.

Example 1711

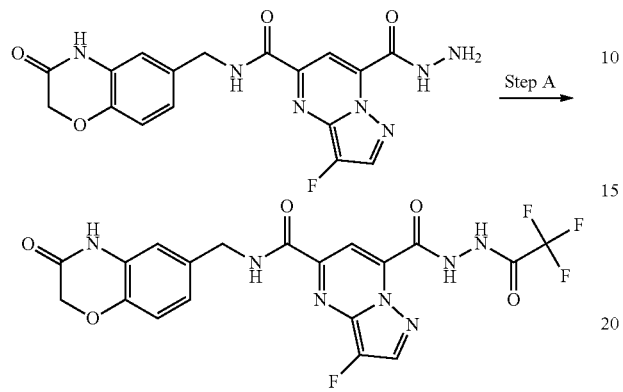

Step A

To a solution of the title compound from the Example 1710, Step A (35 mg) in CHCl₃ (2 mL) was added trifluoroacetic anhydride (1 mL). The resulting mixture was heated to 50° C. for 3 h, concentrated and dried in vacuo to afford the title compound (47 mg, ≥99%). [MH]⁺=496.

Examples 1712-1829

Following similar procedures as described in the Examples 1 (method A), 2 (method B), 3 (method C), 4 (method D), 5 (method E), 6 (method F) or 7 (method G), except using the acids and amines indicated in Table II-39 below, the following compounds were prepared.

TABLE II-39

| Ex. # | acid, amine | product | method, yield |
|---|---|---|---|
| 1712 | | | C, 53% [MH]+ = 482 |
| 1713 | | | B, 83% [MH]+ = 630 |

TABLE II-39-continued

| Ex. # | acid, amine | product | method, yield |
|---|---|---|---|
| 1714 | | | E, 29% [MH]⁺ = 506 |
| 1715 | | | E, 45% [MH]⁺ = 448 |
| 1716 | | | E, 30% [MH]⁺ = 448 |

TABLE II-39-continued

| Ex. # | acid, amine | product | method, yield |
|---|---|---|---|
| 1717 | [structure] | [structure] | E, 35% [MH]+ = 448 |
| 1718 | [structure] | [structure] | E, 55% [MH]+ = 436 |
| 1719 | [structure] | [structure] | E, 55% [MH]+ = 436 |

TABLE II-39-continued

| Ex. # | acid, amine | product | method, yield |
|---|---|---|---|
| 1720 | | | E, 40% [MH]⁺ = 462 |
| 1721 | | | E, 26% [MH]⁺ = 536 |
| 1722 | | | E, 25% [MH]⁺ = 487 |

TABLE II-39-continued

| Ex. # | acid, amine | product | method, yield |
|---|---|---|---|
| 1723 | | | E, 55% [MH]⁺ = 446 |
| 1724 | | | E, 40% [MH]⁺ = 456 |
| 1725 | | | E, n.d. [MH]⁺ = 522 |

| Ex. # | acid, amine | product | method, yield |
|---|---|---|---|
| 1726 | | | E, 25% [MH]+ = 506 |
| 1727 | | | C, 76% [MNa]+ = 632 |
| 1728 | | | C, 76% [MH]+ = 584 |

TABLE II-39-continued

| Ex. # | acid, amine | product | method, yield |
|---|---|---|---|
| 1729 | | | C, 67% [MH]+ = 584 |
| 1730 | | | C, 47% [MNa]+ = 698 |

TABLE II-39-continued

| Ex. # | acid, amine | product | method, yield |
|---|---|---|---|
| 1731 | | | B, 91% [M − tBu]+ = 555 |
| 1732 | | | C, 48% [MNa]+ = 594 |

TABLE II-39-continued
| Ex. # | acid, amine | product | method, yield |
|---|---|---|---|
| 1733 | 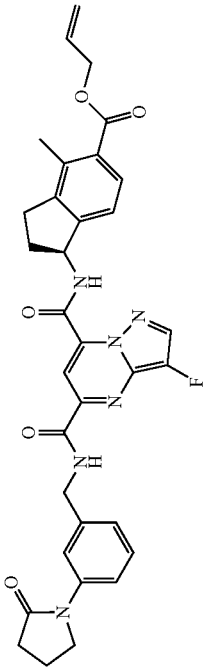 | 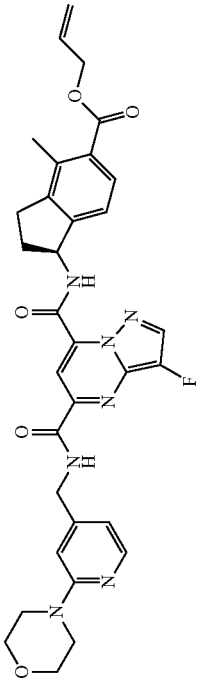 | C, 90%<br>[MNa]+ = 611 |
| 1734 | 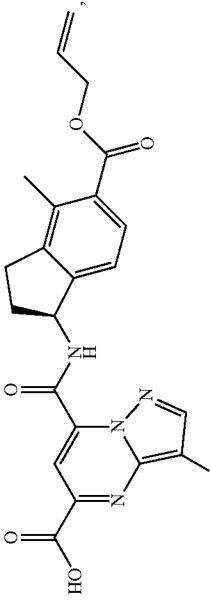 | 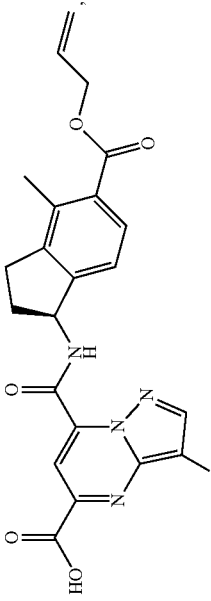 | C, 77%<br>[MNa]+ = 614 |

TABLE II-39-continued

| Ex. # | acid, amine | product | method, yield |
|---|---|---|---|
| 1735 | | | C, 53% [MNa]+ = 631 |
| 1736 | | | C, n.d. [MH]+ = 565 |

TABLE II-39-continued

| Ex. # | acid, amine | product | method, yield |
|---|---|---|---|
| 1737 | | | C, 20%<br>[MH]+ = 615 |
| 1738 | | | C, n.d.<br>[MH]+ = 467 |

TABLE II-39-continued
| Ex. # | acid, amine | product | method, yield |
|---|---|---|---|
| 1739 | 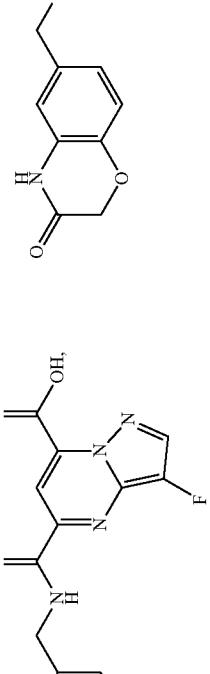 | 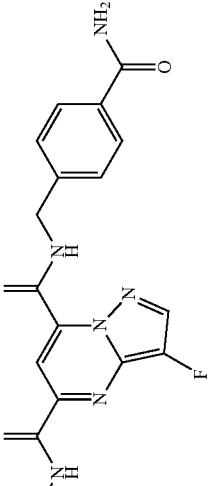 | C, n.d. [MH]+ = 518 |
| 1740 | 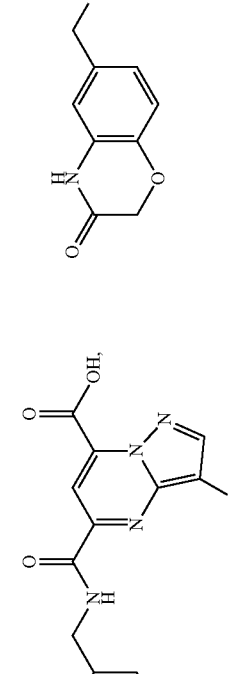 | 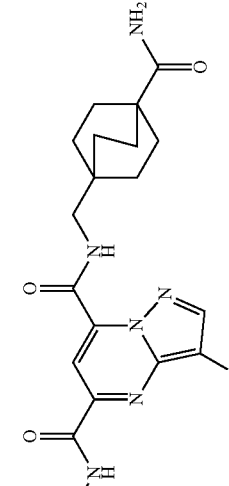 | C, 58% [MH]+ = 550 |

TABLE II-39-continued
| Ex. # | acid, amine | product | method, yield |
|---|---|---|---|
| 1741 | 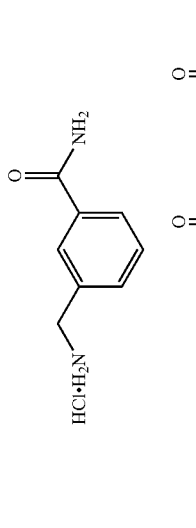 | 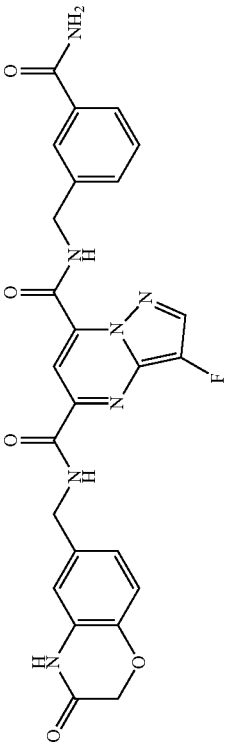 | C, 36% [MH]$^+$ = 518 |
| 1742 |  | 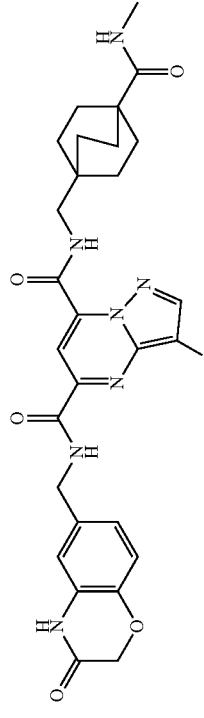 | C, 19% [MH]$^+$ = 564 |

TABLE II-39-continued
| Ex. # | acid, amine | product | method, yield |
|---|---|---|---|
| 1743 | 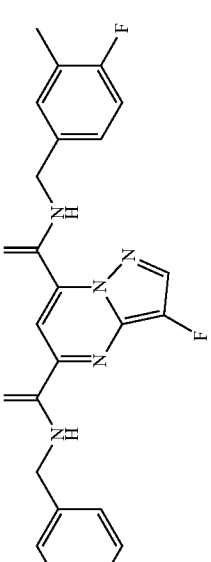 | 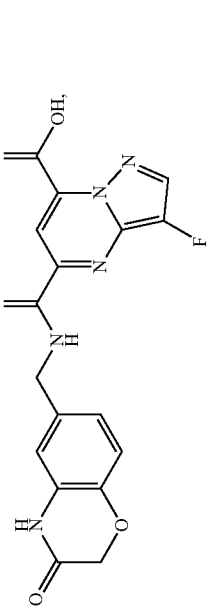 | C, 86% [MH]+ = 507 |
| 1744 | 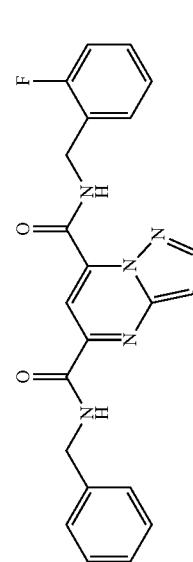 | 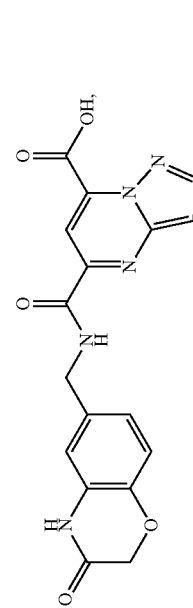 | C, 89% [MH]+ = 493 |

TABLE II-39-continued
| Ex. # | acid, amine | product | method, yield |
|---|---|---|---|
| 1745 | 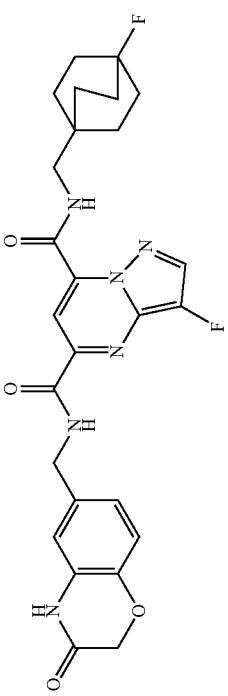 | 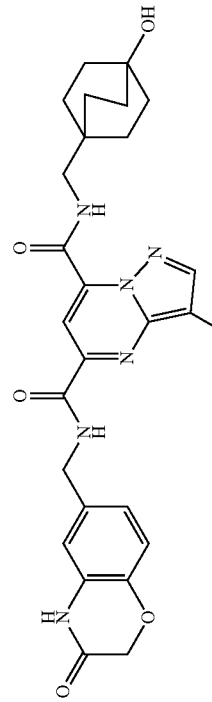 | C, >99% [MH]+ = 525 |
| 1746 | 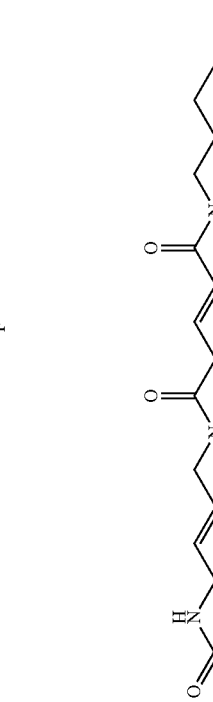 | 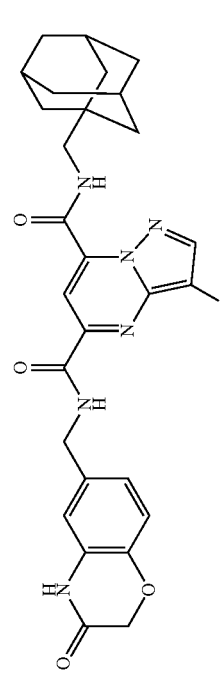 | C, 95% [MH]+ = 523 |
| 1747 | 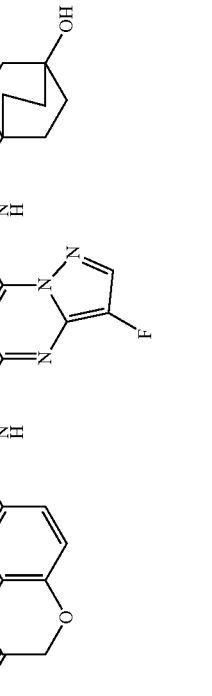 | 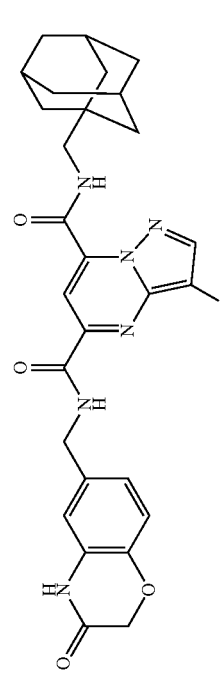 | C, 72% [MH]+ = 533 |

TABLE II-39-continued

| Ex. # | acid, amine | product | method, yield |
|---|---|---|---|
| 1748 | | | C, 26% [MH]⁺ = 423 |
| 1749 | | | C, 32% [MH]⁺ = 439 |
| 1750 | | | C, 25% [MH]⁺ = 475 |

TABLE II-39-continued

| Ex. # | acid, amine | product | method, yield |
|---|---|---|---|
| 1751 | | | C, 51% [MH]$^+$ = 493 |
| 1752 | | | C, n.d. [MH]$^+$ = 547 |
| 1753 | | | B, 70% [MH]$^+$ = 462 |

TABLE II-39-continued
| Ex. # | acid, amine | product | method, yield |
|---|---|---|---|
| 1754 | 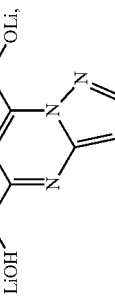 | 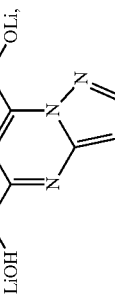 | E, n.d. [MH]+ = 488 |
| 1755 | 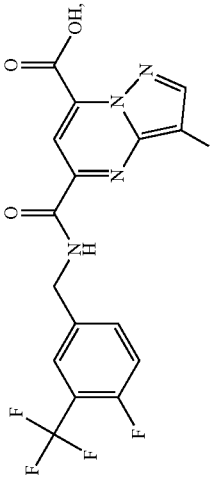 | 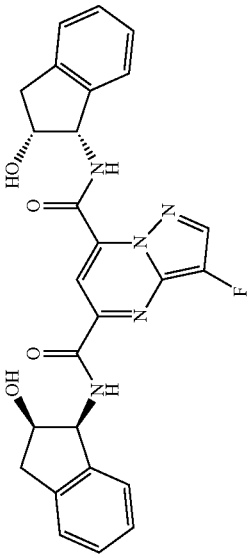 | G, 70% [MH]+ = 561 |

TABLE II-39-continued
| Ex. # | acid, amine | product | method, yield |
|---|---|---|---|
| 1756 | 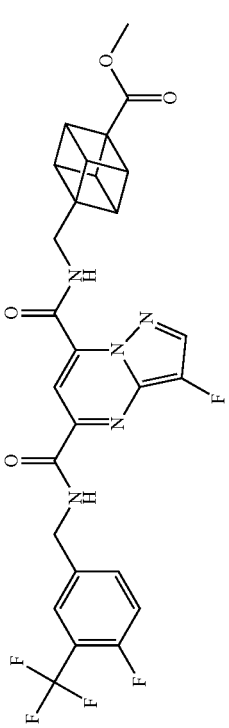 | 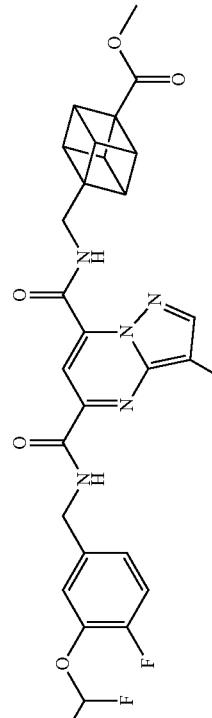 | G, 83% [MH]⁺ = 574 |
| 1757 | 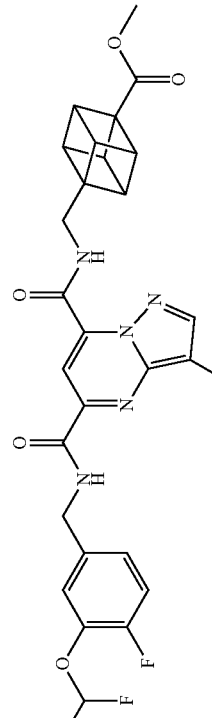 | 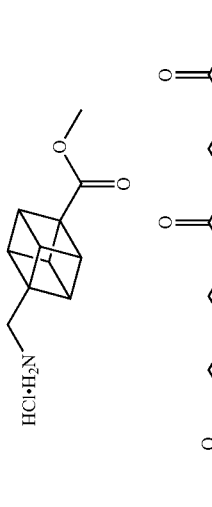 | G, 66% [MH]⁺ = 554 |

| Ex. # | acid, amine | product | method, yield |
|---|---|---|---|
| 1758 | | | G, 97% [MH]+ = 559 |
| 1759 | | | G, 79% [MH]+ = 516 |
| 1760 | | | G, 90% [MNa]+ = 619 |

TABLE II-39-continued

| Ex. # | acid, amine | product | method, yield |
|---|---|---|---|
| 1761 | | | G, 87% [MNa]+ = 596 |
| 1762 | | | G, 89% [MH]+ = 567 |
| 1763 | | | G, n.d. [MNa]+ = 614 |

TABLE II-39-continued

| Ex. # | acid, amine | product | method, yield |
|---|---|---|---|
| 1764 | (structures) | (structure) | G, n.d. [MNa]+ = 633 |
| 1765 | (structures) | (structure) | B, 91% [MH]+ = 637 |
| 1766 | (structures) | (structure) | B, 50% [MH]+ = 456 |

TABLE II-39-continued

| Ex. # | acid, amine | product | method, yield |
|---|---|---|---|
| 1767 | | | B, >99% [MNa]⁺ = 549 |
| 1768 | | | B, 83% [MNa]⁺ = 521 |
| 1769 | | | B, 82% [MNa]⁺ = 535 |

TABLE II-39-continued

| Ex. # | acid, amine | product | method, yield |
|---|---|---|---|
| 1770 | | | B, 86% [MNa]⁺ = 535 |
| 1771 | | | B, 87% [MNa]⁺ = 535 |
| 1772 | | | B, 55% [MH]⁺ = 457 |

TABLE II-39-continued

| Ex. # | acid, amine | product | method, yield |
|---|---|---|---|
| 1773 | | | B, 87% [MH]+ = 568 |
| 1774 | | | B, 84% [MH]+ = 468 |
| 1775 | | | B, 94% [MNa]+ = 563 |

TABLE II-39-continued

| Ex. # | acid, amine | product | method, yield |
|---|---|---|---|
| 1776 | (pyrazolopyrimidine dicarboxylic acid with benzoxazinone methylamine amide; HCl·H2N-CH2-C(O)-NHMe) | (corresponding bis-amide product) | B, 91% [MH]+ = 456 |
| 1777 | (pyrazolopyrimidine dicarboxylic acid with benzoxazinone methylamine amide; HCl·H2N-CH(Et)-C(O)-O-tBu) | (corresponding bis-amide product) | B, 98% [M − Boc]+ = 471 |

TABLE II-39-continued

| Ex. # | acid, amine | product | method, yield |
|---|---|---|---|
| 1778 | | | B, 93% [M − Boc]+ = 473 |
| 1779 | | | B, 78% [MH]+ = 509 |

TABLE II-39-continued

| Ex. # | acid, amine | product | method, yield |
|---|---|---|---|
| 1780 | | | B, 77% [MH]+ = 482 |
| 1781 | | | B, n.d. [MNa]+ = 652 |

TABLE II-39-continued

| Ex. # | acid, amine | product | method, yield |
|---|---|---|---|
| 1782 | | | B, 82% [MH]⁺ = 485 |
| 1783 | | | B, 68% [MH]⁺ = 491/493 |
| 1784 | | | B, n.d. [MNa]⁺ = 634 |

TABLE II-39-continued

| Ex. # | acid, amine | product | method, yield |
|---|---|---|---|
| 1785 | | | B, n.d. [MNa]+ = 636 |
| 1786 | | | B, n.d. [MNa]+ = 646 |
| 1787 | | | B, 88% [MH]+ = 524 |

TABLE II-39-continued

| Ex. # | acid, amine | product | method, yield |
|---|---|---|---|
| 1788 | (structures) | (structure) | B, 72% [MH]+ = 581 |
| 1789 | (structures) | (structure) | B, n.d. [MH]+ = 595 |
| 1790 | (structures) | (structure) | B, 88% [MH]+ = 367 |

TABLE II-39-continued

| Ex. # | acid, amine | product | method, yield |
|---|---|---|---|
| 1791 | | | E, 23% [MNa]+ = 642 |
| 1792 | | | C, 59% [MH]+ = 533 |

TABLE II-39-continued
| Ex. # | acid, amine | product | method, yield |
|---|---|---|---|
| 1793 | 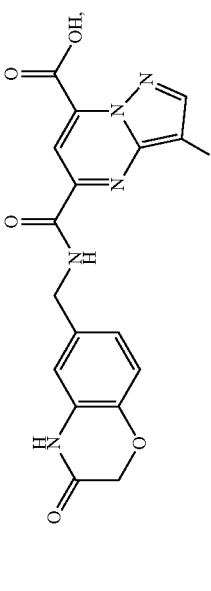 | 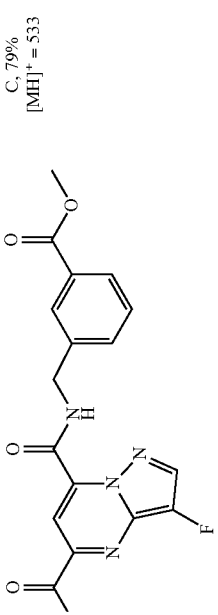 | C, 79% [MH]⁺ = 533 |
| 1794 | 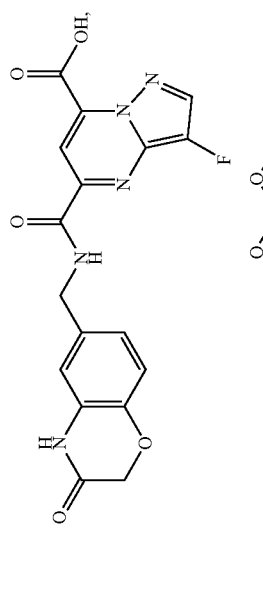 | 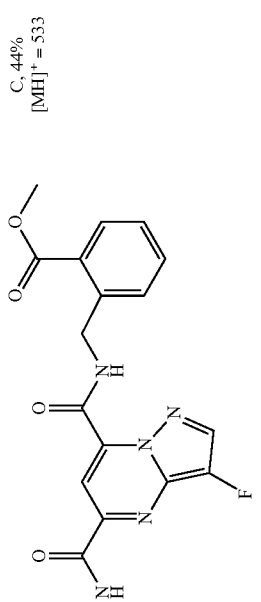 | C, 44% [MH]⁺ = 533 |

TABLE II-39-continued
| Ex. # | acid, amine | product | method, yield |
|---|---|---|---|
| 1795 | 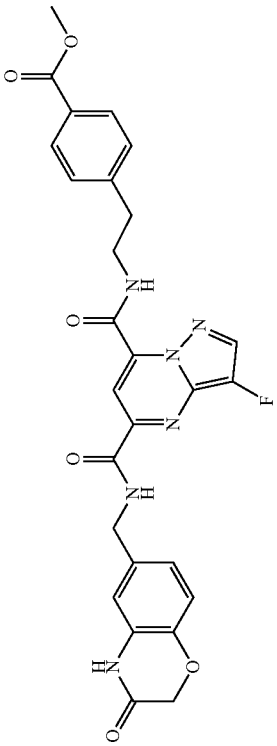 | 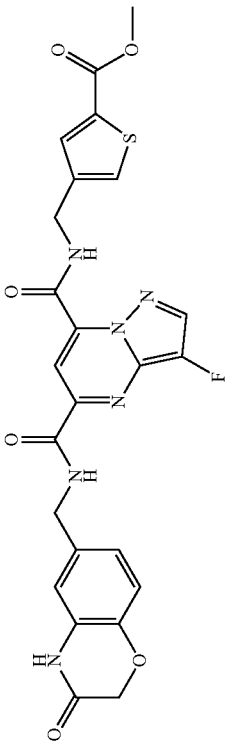 | C, 59% [MH]+ = 547 |
| 1796 | 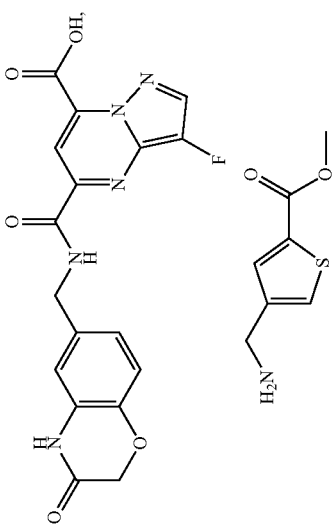 | | C, 75% [MH]+ = 539 |

TABLE II-39-continued

| Ex. # | acid, amine | product | method, yield |
|---|---|---|---|
| 1797 | | | E, 67% [M − H]⁻ = 636 |
| 1798 | | | E, 85% [M − H]⁻ = 642 |

TABLE II-39-continued
| Ex. # | acid, amine | product | method, yield |
|---|---|---|---|
| 1799 |  | 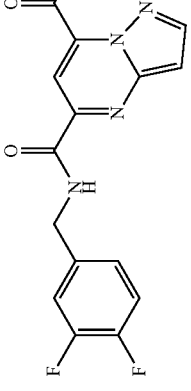 | E, 55% [M − H]⁻ = 520 |
| 1800 | 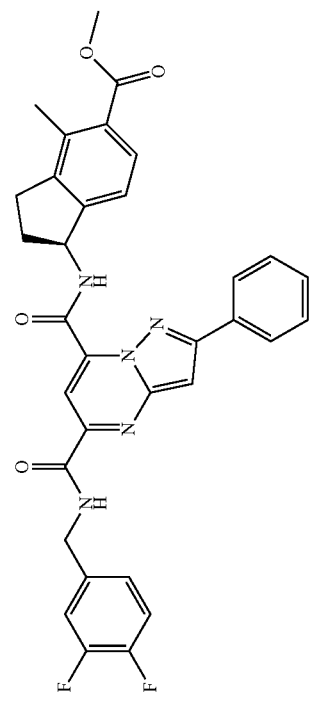 | 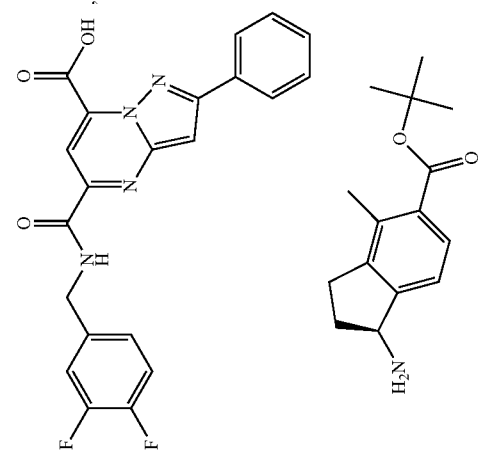 | E, 65% [M − H]⁻ = 636 |

TABLE II-39-continued
| Ex. # | acid, amine | product | method, yield |
|---|---|---|---|
| 1801 | 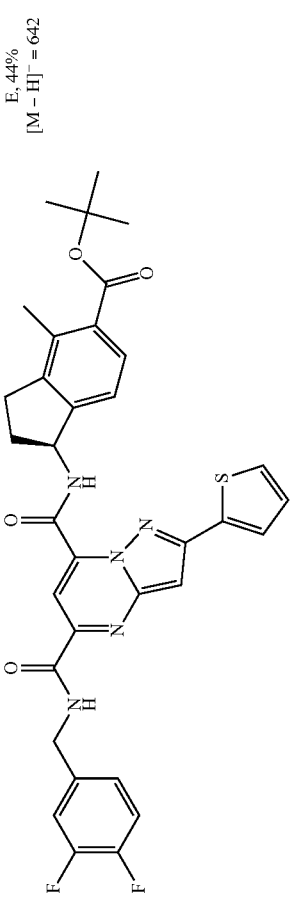 | 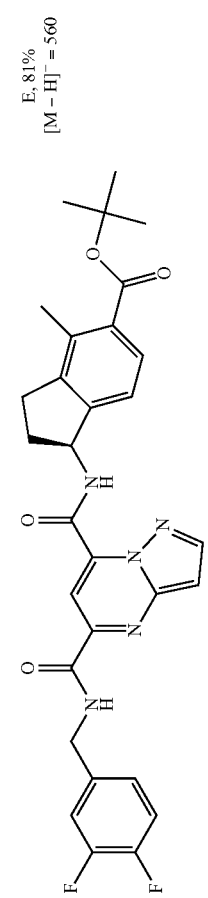 | E, 44% [M − H]⁻ = 642 |
| 1802 | 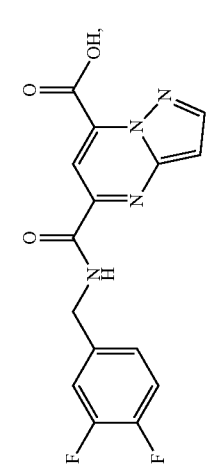 |  | E, 81% [M − H]⁻ = 560 |

TABLE II-39-continued
| Ex. # | acid, amine | product | method, yield |
|---|---|---|---|
| 1803 | 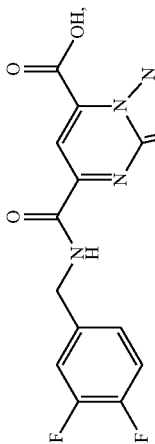 | 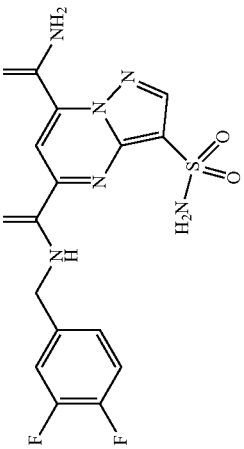 | E, 31% [MH]⁺ = 411 |
| 1804 |  | 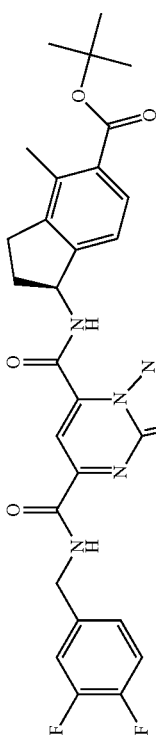 | E, n.d. [M − H]⁻ = 749 |

TABLE II-39-continued

| Ex. # | acid, amine | product | method, yield |
|---|---|---|---|
| 1805 | | | C, 17% [MH]⁺ = 452 |
| 1806 | | | C, 7% [(M − ⁱPr₂NEt)H]⁺ = 453 |
| 1807 | | | F, 74% [MH]⁺ = 761 |

TABLE II-39-continued
| Ex. # | acid, amine | product | method, yield |
|---|---|---|---|
| 1808 | 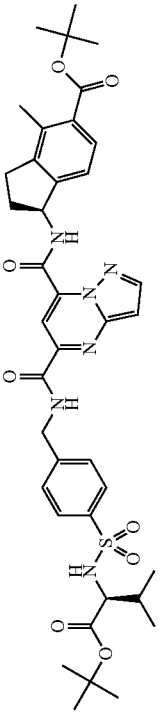 | 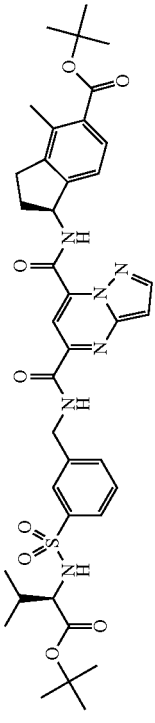 | F, 73% [MH]+ = 761 |
| 1809 | 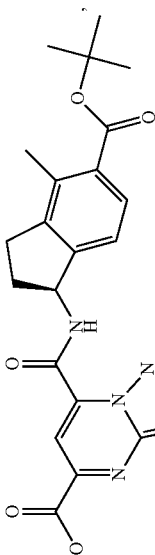 | 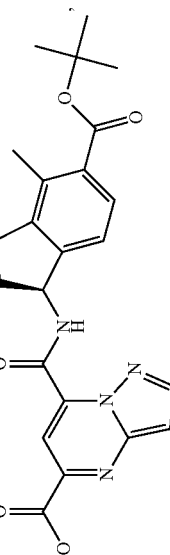 | F, 74% [MH]+ = 761 |

TABLE II-39-continued
| Ex. # | acid, amine | product | method, yield |
|---|---|---|---|
| 1810 | 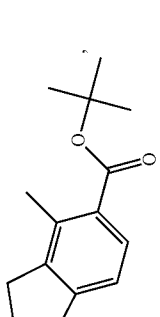 | 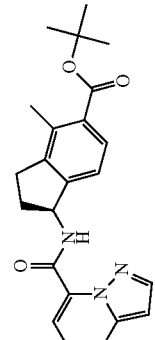 | F, 58% [MH]+ = 761 |
| 1811 | 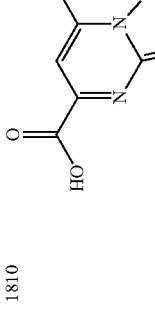 | 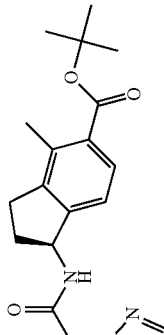 | F, 58% [MH]+ = 761 |

TABLE II-39-continued

| Ex. # | acid, amine | product | method, yield |
|---|---|---|---|
| 1812 | | | F, 68% [MH]+ = 761 |
| 1813 | | | C, 43% [MNa]+ = 623 |

TABLE II-39-continued

| Ex. # | acid, amine | product | method, yield |
|---|---|---|---|
| 1814 | | | C, 50% [MNa]+ = 637 |
| 1815 | | | C, 99% [MNa]+ = 651 |

TABLE II-39-continued
| Ex. # | acid, amine | product | method, yield |
|---|---|---|---|
| 1816 | 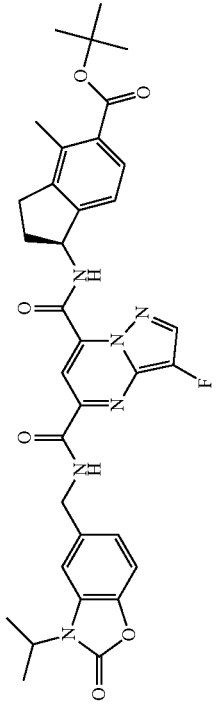 | 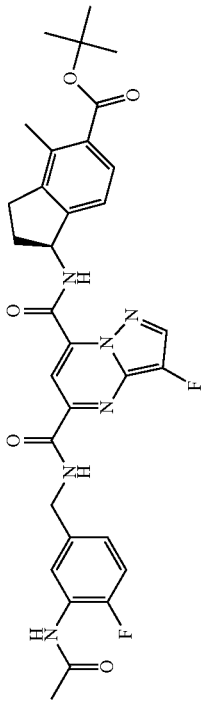 | C, 85% [MH]+ = 665 |
| 1817 | 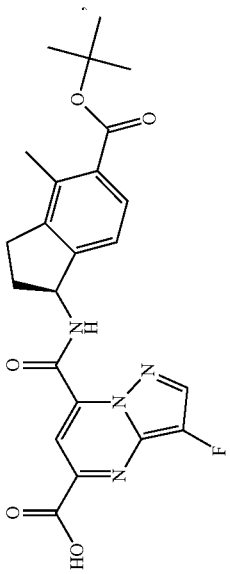 | 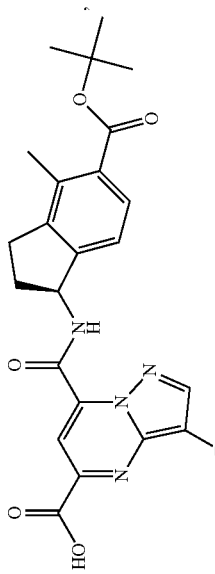 | C, 50% [MNa]+ = 641 |

TABLE II-39-continued

| Ex. # | acid, amine | product | method, yield |
|---|---|---|---|
| 1818 | | | C, 47% [MNa]+ = 677 |
| 1819 | | | B, 19% [MH]+ = 456 |

TABLE II-39-continued

| Ex. # | acid, amine | product | method, yield |
|---|---|---|---|
| 1820 | | | B, 64% [MH]⁺ = 512 |
| 1821 | | | B, 74% [MH]⁺ = 524 |

TABLE II-39-continued

| Ex. # | acid, amine | product | method, yield |
|---|---|---|---|
| 1822 | | | C, n.d. [MH]+ = 529 |
| 1823 | | | C, 70% [MH]+ = 480 |

TABLE II-39-continued

| Ex. # | acid, amine | product | method, yield |
|---|---|---|---|
| 1824 | | | C, >99% [MH]⁺ = 579 |
| 1825 | | | C, 63% [MH]⁺ = 593 |

TABLE II-39-continued

| Ex. # | acid, amine | product | method, yield |
|---|---|---|---|
| 1826 | (acid + amine structures) | (product structure) | C, n.d. [MNa]⁺ = 607 |
| 1827 | (acid + amine structures) | (product structure) | C, n.d. [MH]⁺ = 538 |

TABLE II-39-continued

| Ex. # | acid, amine | product | method, yield |
|---|---|---|---|
| 1828 | | | C, 42% [MH]⁺ = 538 |
| 1829 | | | C, 17% [MH]⁺ = 537 |

Example 1830

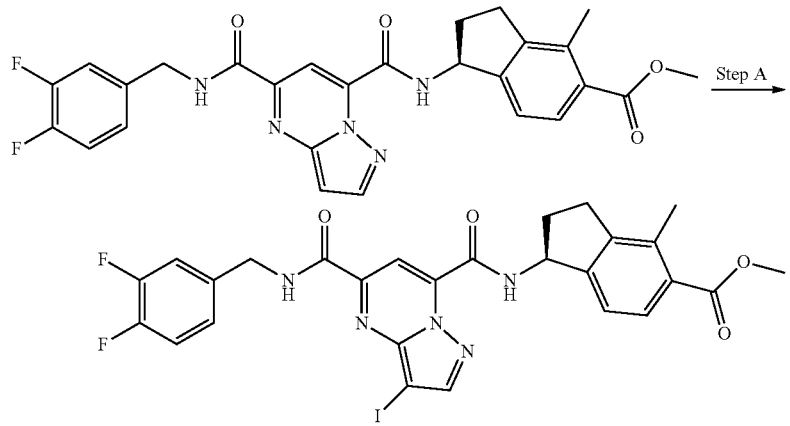

Step A

To the title compound from the Example 1799 (500 mg) in CHCl$_3$ (10 mL) was added N-iodosuccinimide (259 mg). The resulting mixture was stirred at 70° C. for 1 h, absorbed onto silica and purified by chromatography (silica) to afford the title compound (485 mg, 78%). [M-H]'=644.

Example 1831

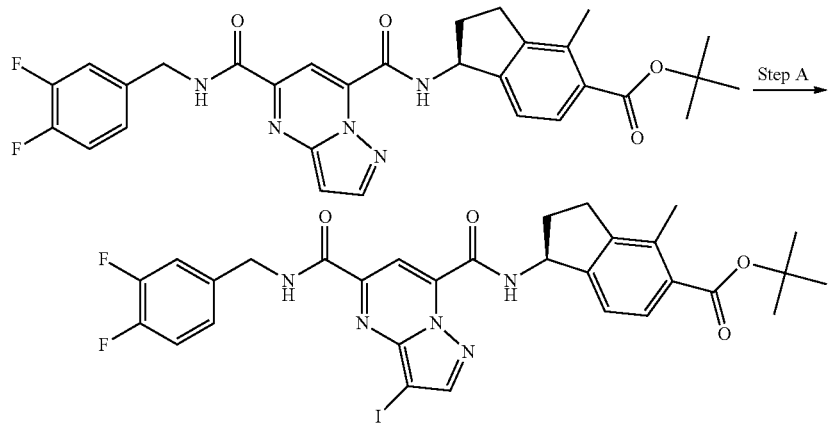

Step A

The title compound from the Example 1802 (309 mg) was treated similarly as described in the Example 1830, Step A to afford the title compound (365 mg, 97%). [M-H]⁻=686.

Example 1832

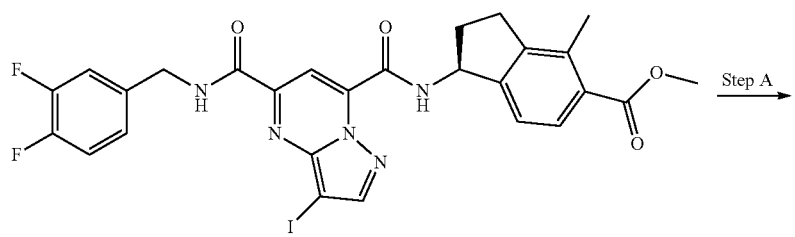

-continued

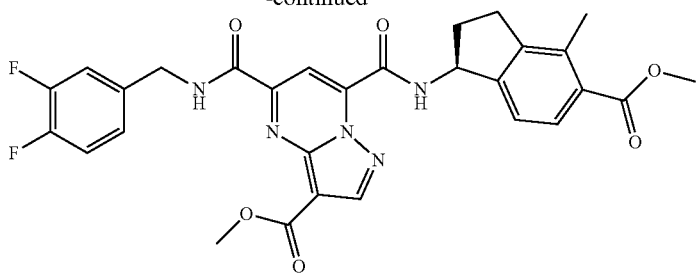

Step A

A mixture of the title compound from the Example 1830, Step A (30 mg), Pd(PPh$_3$)$_4$ (5 mg) and NEt$_3$ (50 μL) in DMSO/MeOH (1:1, 400 μL) was stirred at 80° C. under a carbon monoxide atmosphere at 1 atm for 18 h, diluted with 1N aqueous HCl and extracted with EtOAc (3×). The combined organic phases were washed with 1N aqueous HCl (2×) and saturated aqueous NaCl, dried (MgSO$_4$), filtered, absorbed onto silica and purified by chromatography (silica) to afford the title compound (27 mg, 99%). [M-H]$^-$=576.

Example 1833

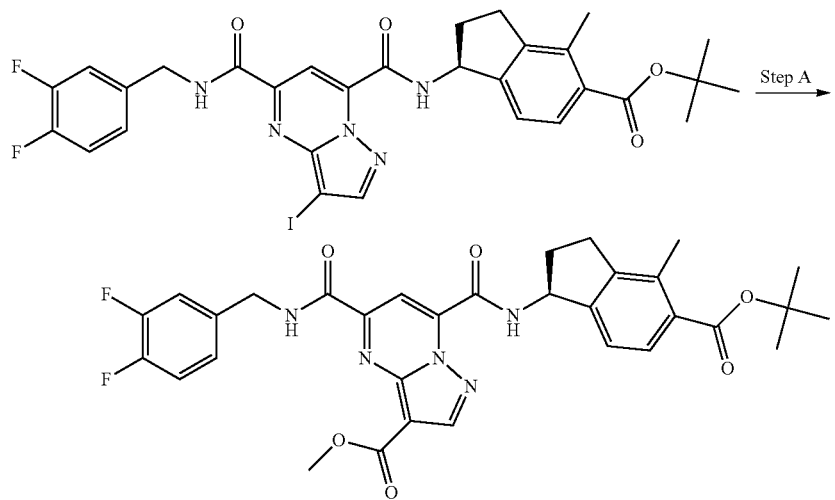

Step A

The title compound from the Example 1831, Step A (393 mg) was treated similarly as described in the Example 1832, Step A to afford the title compound (195 mg, 55%). [M-H]$^-$=618.

Example 1834

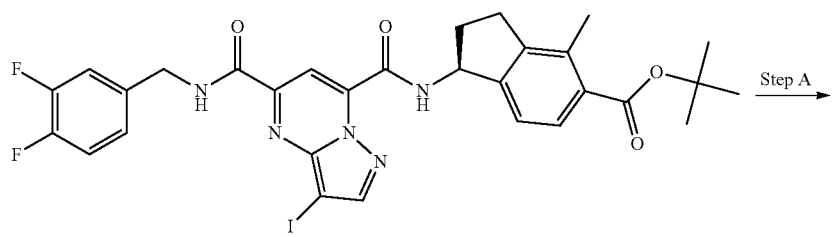

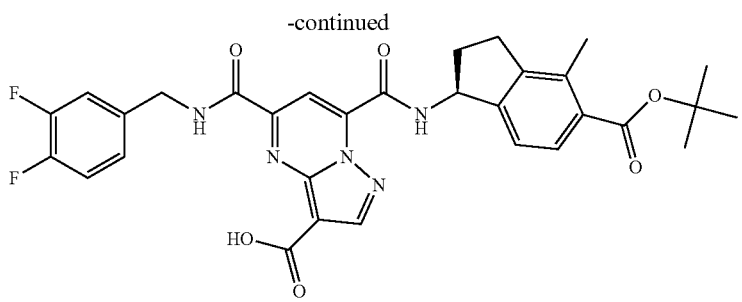

Step A

The title compound from the Example 1831, Step A (188 mg), Pd(OAc)$_2$ (4.6 mg), dppf (32.2 mg) and KOAc (110 mg) were dissolved in dry DMSO (1.5 mL) and stirred at 60° C. under a carbon monoxide atmosphere at 1 atm for 18 h. The mixture was diluted with EtOAc, washed subsequently with 1N aqueous HCl (2×) and saturated aqueous NaCl, dried (MgSO$_4$), filtered, absorbed onto silica and purified by chromatography (silica) to afford the title compound (150 mg, 85%). [M-H]$^-$=604.

Example 1835

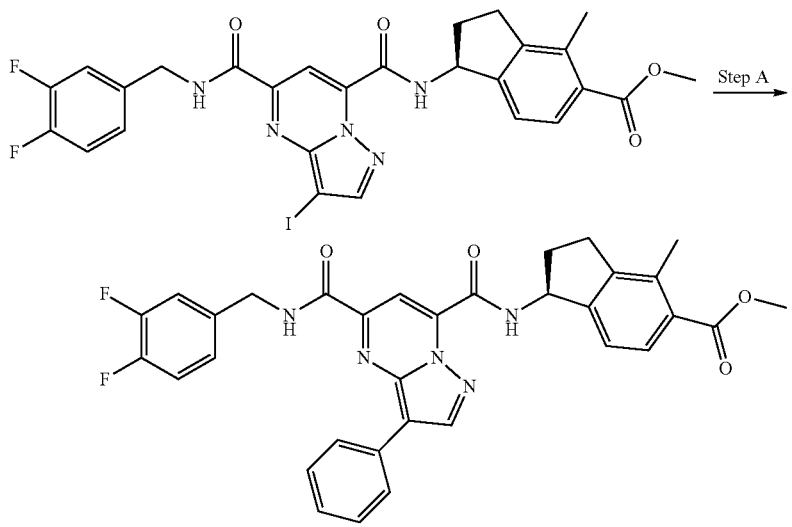

Step A

A mixture of the title compound from the Example 1830, Step A (30 mg), Pd(PPh$_3$)$_4$ (3 mg) and commercially available trimethyl(phenyl)tin (5 µL) in THF (250 µL) was stirred at 80° C. under an argon atmosphere for 2 d, absorbed onto silica and purified by chromatography (silica) to afford the title compound (9 mg, 66%). [M-H]'=594.

Example 1836

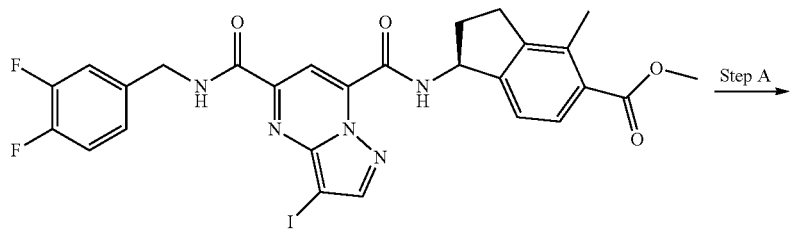

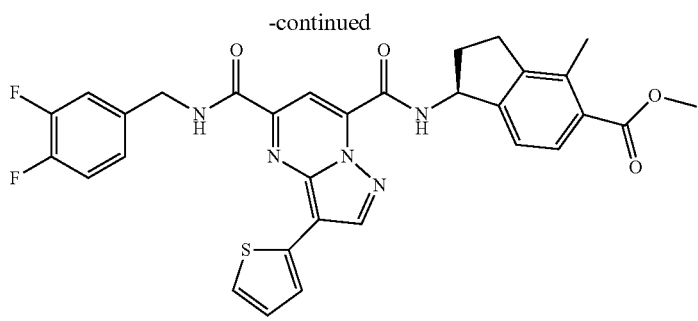

Step A

The title compound from the Example 1830, Step A (15 mg) was treated similarly as described in the Example 1835, Step A, except using commercially available (tributylstannyl) thiophene instead of trimethyl(phenyl)tin to afford the title compound (14 mg, 99%). [M-H]'=600.

Example 1837

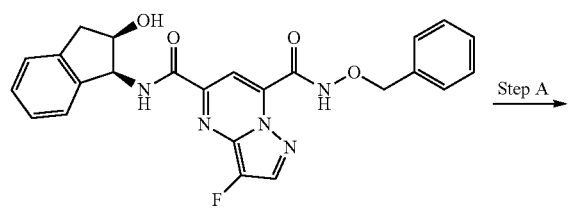

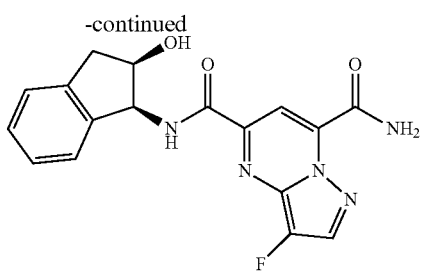

Step A

A mixture of the title compound from the Example 1753 (7.8 mg) and Pd/C (10 wt %, 10 mg) in MeOH (5 mL) was hydrogenated at 30 psi for 12 h, filtered through Celite® and concentrated to afford the title compound (6.0 mg, 95%). [MH]$^+$=356.

Examples 1838-1853

Following a similar procedure as described in the Examples 288, except using the esters and amines indicated in Table II-40 below, the following compounds were prepared.

TABLE II-40

| Ex. # | ester, amine |
|---|---|
| 1838 | |
| 1839 | |

TABLE II-40-continued
1840
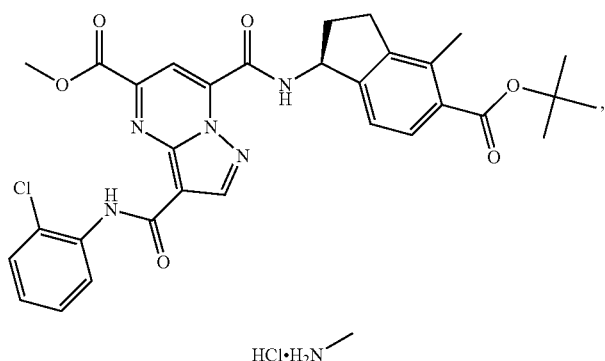
HCl·H2N—
1841
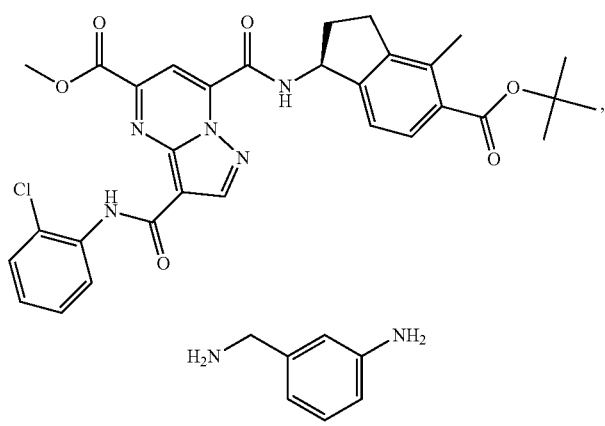 [SMILES: COC(=O)c1cc(C(=O)N[C@H]2CCc3c2ccc(C(=O)OC(C)(C)C)c3C)n2ncc(C(=O)Nc3ccccc3Cl)c2n1 ; NCc1cccc(N)c1]
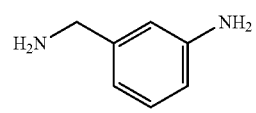
1842
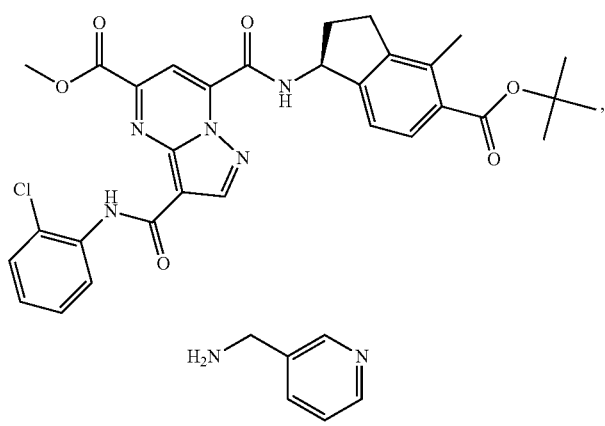 [SMILES: COC(=O)c1cc(C(=O)N[C@H]2CCc3c2ccc(C(=O)OC(C)(C)C)c3C)n2ncc(C(=O)Nc3ccccc3Cl)c2n1 ; NCc1cccnc1]
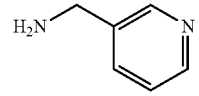
1843
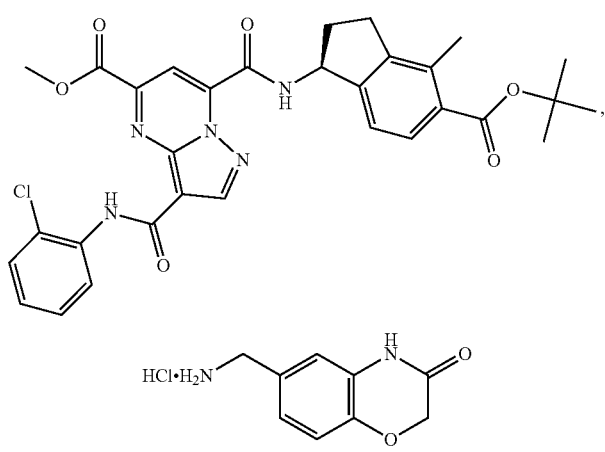
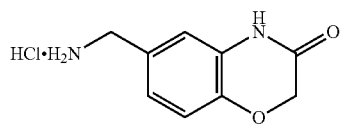

TABLE II-40-continued
| 1844 | 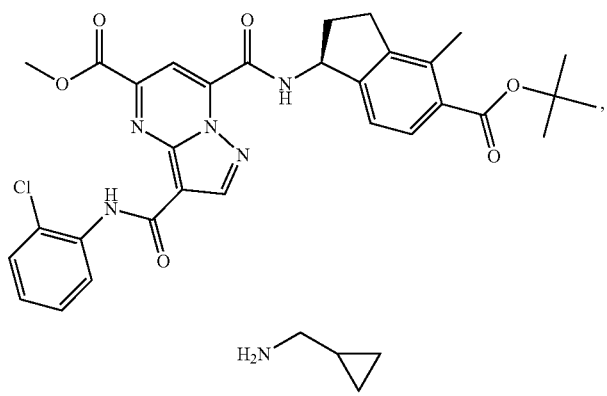 [SMILES: COC(=O)c1cc(C(=O)N[C@H]2CCc3c2ccc(C(=O)OC(C)(C)C)c3C)n2ncc(C(=O)Nc3ccccc3Cl)c2n1 ; NCC1CC1] |
| 1845 | 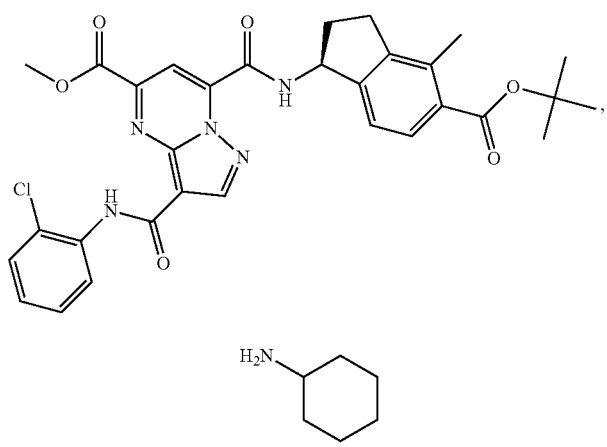 [SMILES: COC(=O)c1cc(C(=O)N[C@H]2CCc3c2ccc(C(=O)OC(C)(C)C)c3C)n2ncc(C(=O)Nc3ccccc3Cl)c2n1 ; NC1CCCCC1] |
| 1846 | 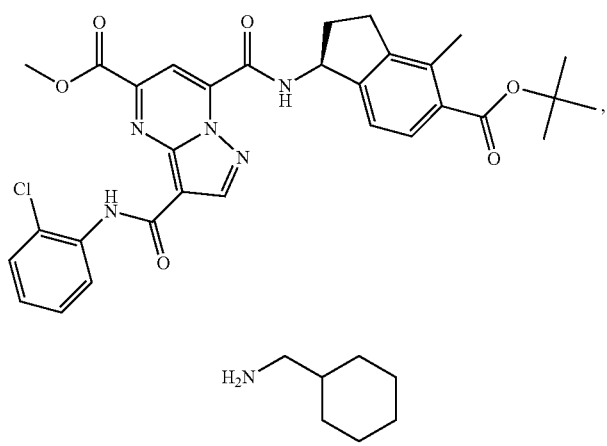 [SMILES: COC(=O)c1cc(C(=O)N[C@H]2CCc3c2ccc(C(=O)OC(C)(C)C)c3C)n2ncc(C(=O)Nc3ccccc3Cl)c2n1 ; NCC1CCCCC1] |

TABLE II-40-continued
1847
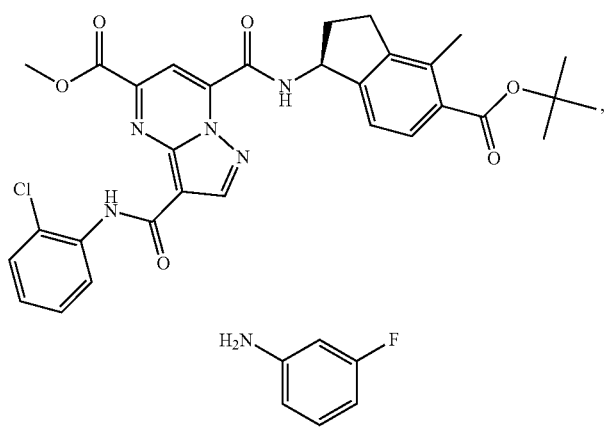 [SMILES: COC(=O)c1cc(C(=O)N[C@H]2CCc3c2ccc(C(=O)OC(C)(C)C)c3C)n2ncc(C(=O)Nc3ccccc3Cl)c2n1 ; Nc1cccc(F)c1]
1848
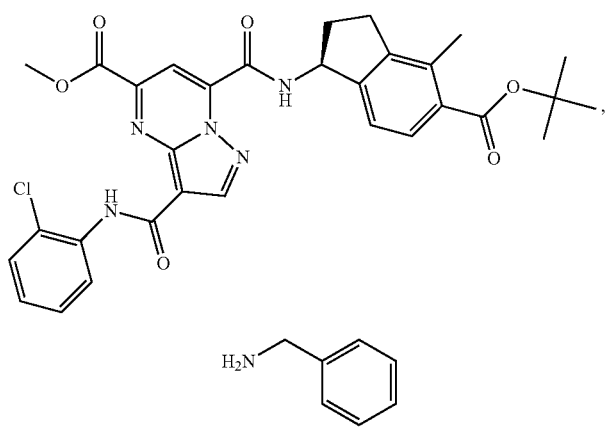 [SMILES: COC(=O)c1cc(C(=O)N[C@H]2CCc3c2ccc(C(=O)OC(C)(C)C)c3C)n2ncc(C(=O)Nc3ccccc3Cl)c2n1 ; NCc1ccccc1]
1849
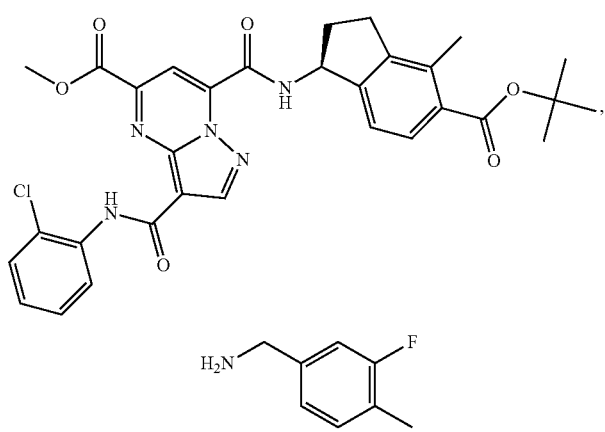

TABLE II-40-continued
1850
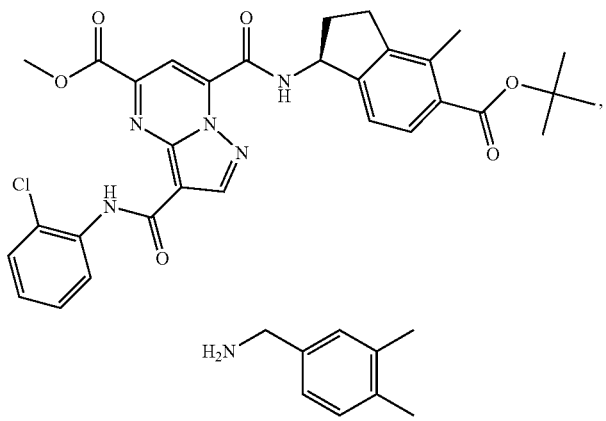
1851
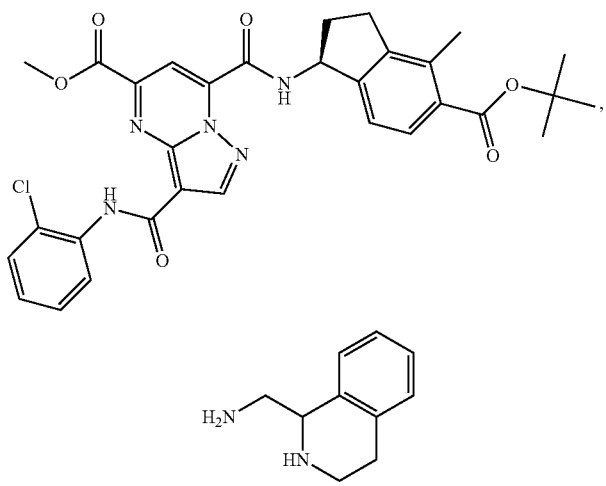 [SMILES: COC(=O)c1cc(C(=O)N[C@H]2CCc3c2ccc(C(=O)OC(C)(C)C)c3C)n2ncc(C(=O)Nc3ccccc3Cl)c2n1 ; NCC1NCCc2ccccc21]
1852
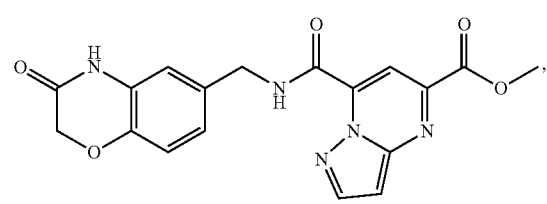 [SMILES: COC(=O)c1cc(C(=O)NCc2ccc3c(c2)NC(=O)CO3)n2nccc2n1]
7M NH₃ in MeOH TABLE II-40-continued
| 1853 | 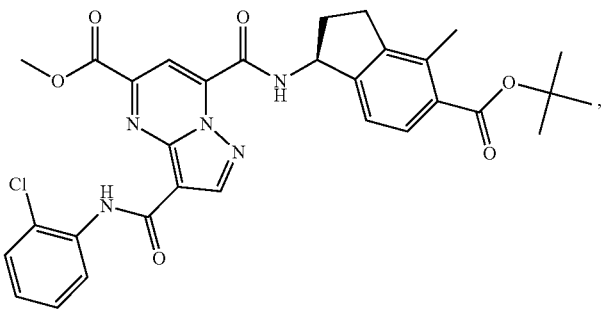 |
| --- | --- |
| | 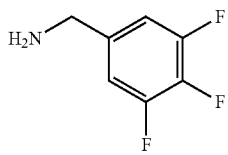 |
| Ex. # | product | yield |
| --- | --- | --- |
| 1838 | 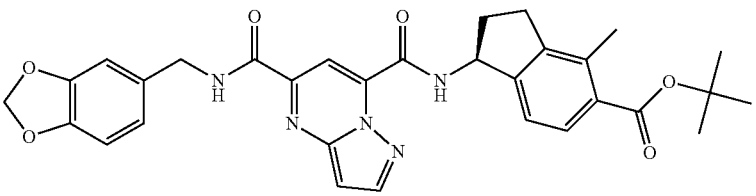 [SMILES: Cc1c(C(=O)OC(C)(C)C)ccc2c1CC[C@@H]2NC(=O)c1cc(C(=O)NCc2ccc3c(c2)OCO3)nc2ccnn12] | 18%<br>[MH]⁺ = 570 |
| 1839 | 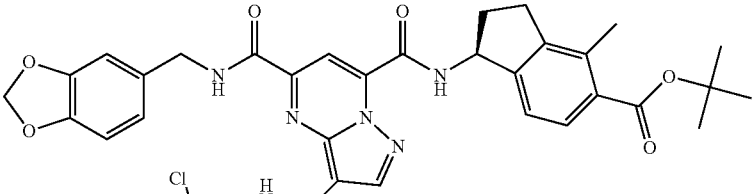 | 65%<br>[M − H]⁻ = 721 |
| 1840 | 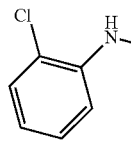 | >99%<br>[M − H]⁻ = 601 |
| 1841 | 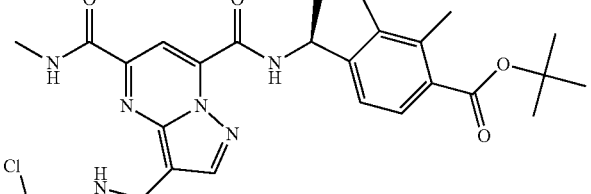 | 48%<br>[M − H]⁻ = 601 |

TABLE II-40-continued

| # | Structure | Yield / MS |
|---|---|---|
| 1842 | 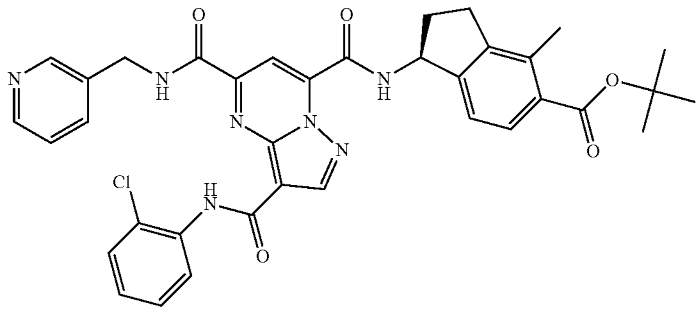 [SMILES: Cc1c(C(=O)OC(C)(C)C)ccc2c1CC[C@@H]2NC(=O)c1cc(C(=O)NCc2cccnc2)nc2c(C(=O)Nc3ccccc3Cl)cnn12] | 37% [M − H]⁻ = 678 |
| 1843 | 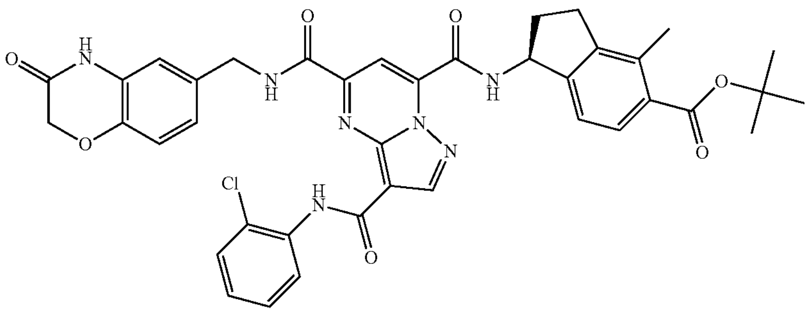 [SMILES: Cc1c(C(=O)OC(C)(C)C)ccc2c1CC[C@@H]2NC(=O)c1cc(C(=O)NCc2ccc3c(c2)NC(=O)CO3)nc2c(C(=O)Nc3ccccc3Cl)cnn12] | 40% [M − H]⁻ = 748 |
| 1844 | 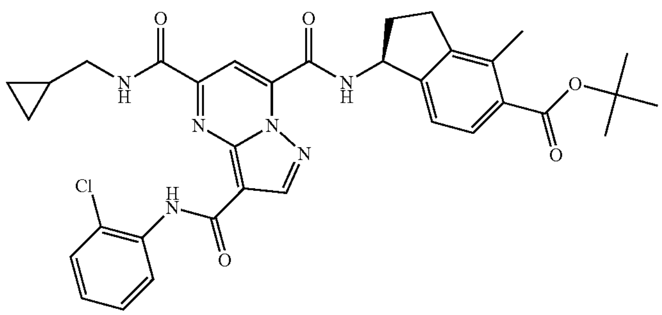 [SMILES: Cc1c(C(=O)OC(C)(C)C)ccc2c1CC[C@@H]2NC(=O)c1cc(C(=O)NCC2CC2)nc2c(C(=O)Nc3ccccc3Cl)cnn12] | 67% [M − H]⁻ = 641 |
| 1845 | 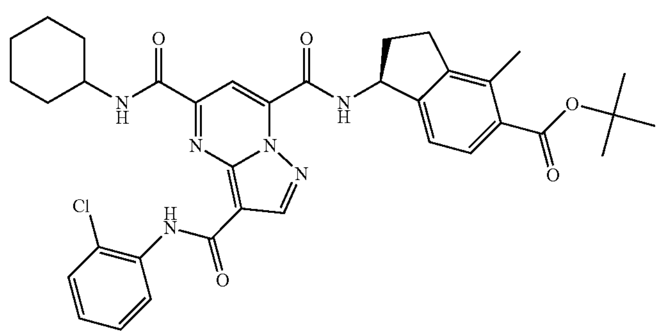 [SMILES: Cc1c(C(=O)OC(C)(C)C)ccc2c1CC[C@@H]2NC(=O)c1cc(C(=O)NC2CCCCC2)nc2c(C(=O)Nc3ccccc3Cl)cnn12] | 73% [M − H]⁻ = 669 |
| 1846 | 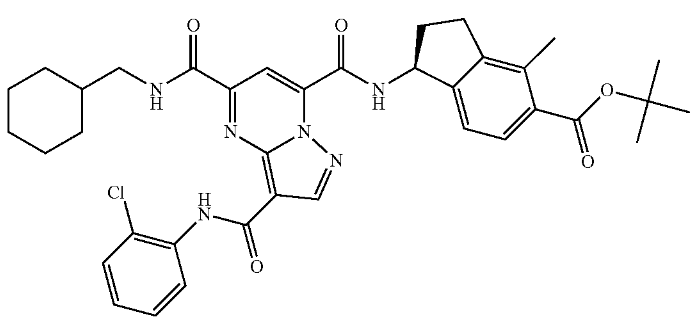 [SMILES: Cc1c(C(=O)OC(C)(C)C)ccc2c1CC[C@@H]2NC(=O)c1cc(C(=O)NCC2CCCCC2)nc2c(C(=O)Nc3ccccc3Cl)cnn12] | 63% [M − H]⁻ = 683 |

TABLE II-40-continued

| 1847 | (structure) | 68% [M − H]⁻ = 681 |
| 1848 | (structure) | 62% [M − H]⁻ = 677 |
| 1849 | (structure) | 70% [M − H]⁻ = 677 |
| 1850 | (structure) | 47% [M − H]⁻ = 705 |
| 1851 | (structure) | 42% [M − H]⁻ = 732 |

TABLE II-40-continued

| 1852 | 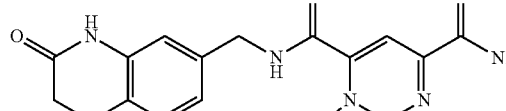 | 50% [MH]+ = 367 |
| 1853 | 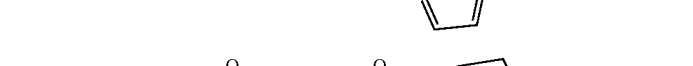 | n.d. [MNa]+ = 755 |

Example 1854

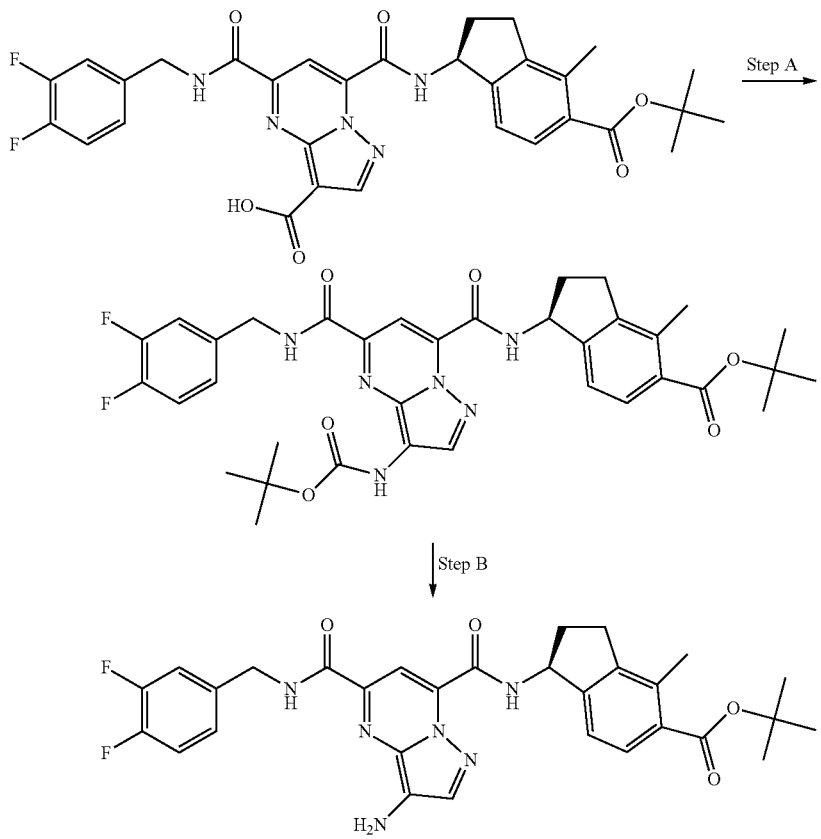

Step A

To an ice cooled (0-5° C.) mixture of the title compound from the Example 1834, Step A (150 mg) and DMF (2 μL) in CH$_2$Cl$_2$ (2.5 mL) was added oxalyl chloride (108 μL). The ice bath was removed and the mixture was stirred for 2 h and then concentrated. The resulting residue was brought up in acetone (1.5 mL) and cooled to 0-5° C. (ice bath). A solution of NaN$_3$ (100 mg) in H$_2$O (500 μL) was added and the ice bath was removed. The mixture was stirred at room temperature for 1 h, diluted with H$_2$O (5 mL) and extracted with toluene (3×5 mL). The combined organic phases were dried (MgSO$_4$), filtered, concentrated and diluted with toluene/tert-butanol (1:1, 2 mL). Molecular sieves 4 Å (100 mg) were added and the resulting mixture was heated to 100° C. for 1½ h. Filtration, absorption onto silica and purification by chromatography (silica) to afforded the title compound (88 mg, 52%). [M-H]⁻=675.

Step B

To a solution of the title compound from Step a above (88 mg) in ᵗBuOAc (1 mL) was added concentrated H₂SO₄ (35 mL). The resulting mixture was stirred at room temperature for 1 h and then diluted with saturated aqueous NaHCO₃ (4 mL) and EtOAc (2 mL). The aqueous phase was separated and extracted with EtOAc (2×) and CH₂Cl₂ (2×). The combined organic phases were dried (MgSO₄), filtered, absorbed onto silica and purified by chromatography (silica) to afford the title compound (36 mg, 50%). [MH]⁺=577.

Example 1855

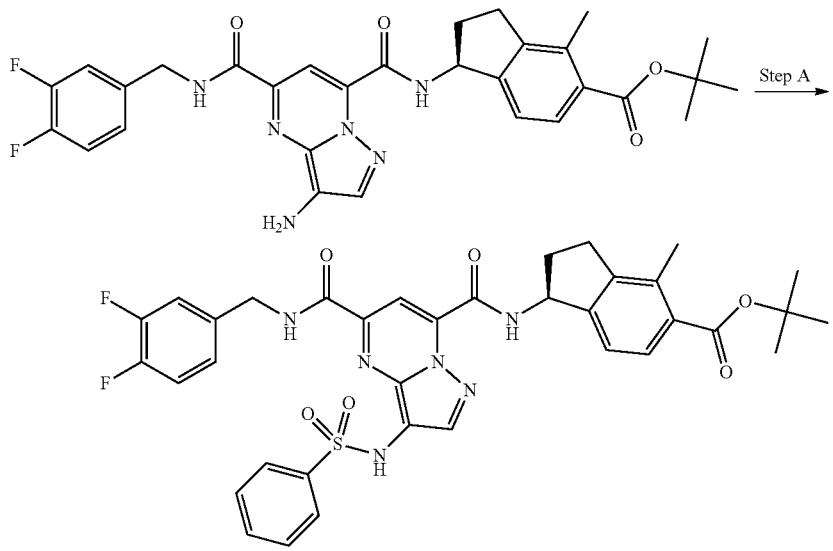

Step A

To an ice cooled (0-5° C.) solution of commercially available benzenesulfonyl chloride (3.5 μL) in CH₂Cl₂ (100 μL) were added NEt₃ (6 μL) and a solution of the title compound from the Example 1854, Step B (12 mg) in CH₂Cl₂ (100 μL). The ice bath was removed and the mixture was stirred at room temperature for 18 h and then concentrated. The remaining residue was purified by preparative thin layer chromatography (silica) to afford the title compound (3.1 mg, 21%). [M-H]'=715.

Example 1856

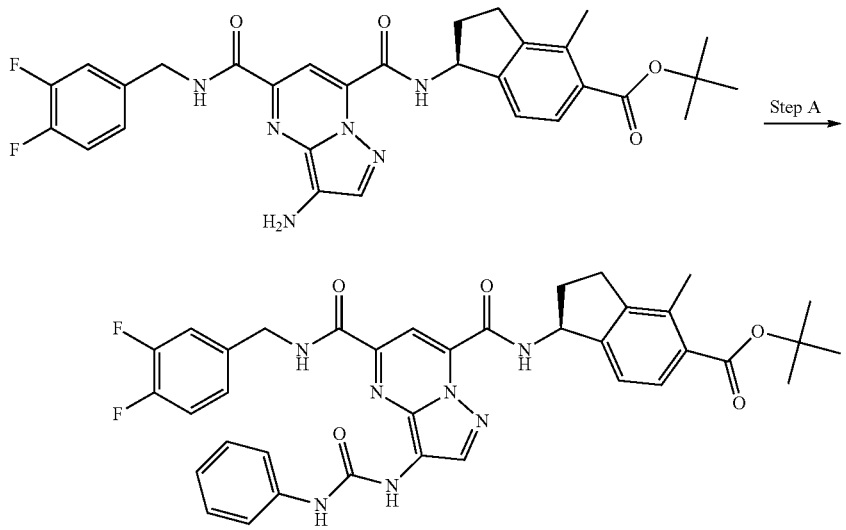

Step A

A mixture of the title compound from the Example 1854, Step B (12 mg) and commercially available phenyl isocyanate (3 μL) in CH₂Cl₂ (200 μL) was stirred at room temperature for 3 d, concentrated and purified by chromatography (silica) to afford the title compound (11 mg, 76%). [M-H]⁻=694.

Example 1857

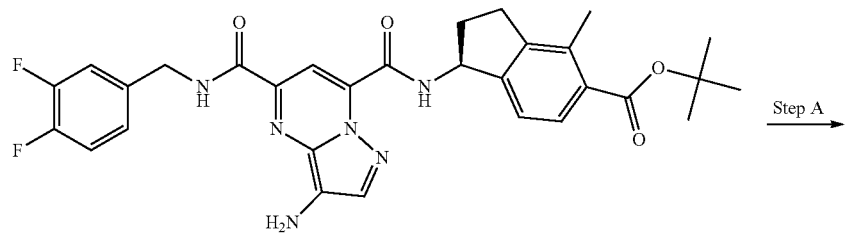

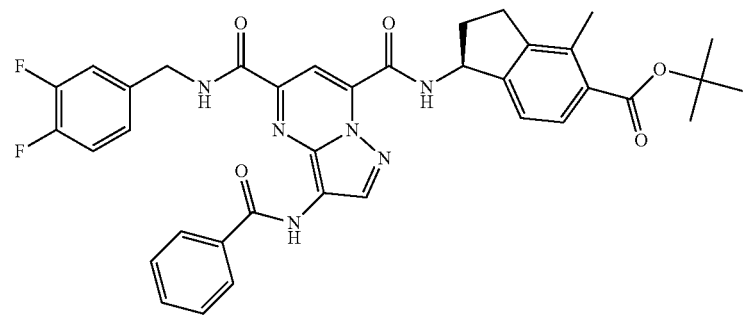

Step A

To an ice cooled (0-5° C.) solution of commercially available benzoyl chloride (3 μL) in CH₂Cl₂ (100 μL) were added NEt₃ (6 μL) and a solution of the title compound from the Example 1854, Step B (12 mg) in CH₂Cl₂ (100 μL). The ice bath was removed and the mixture was stirred at room temperature for 18 h and then concentrated. The remaining residue was purified by preparative thin layer chromatography (silica) to afford the title compound (11.2 mg, 79%). [M-H]⁻= 679.

Example 1858

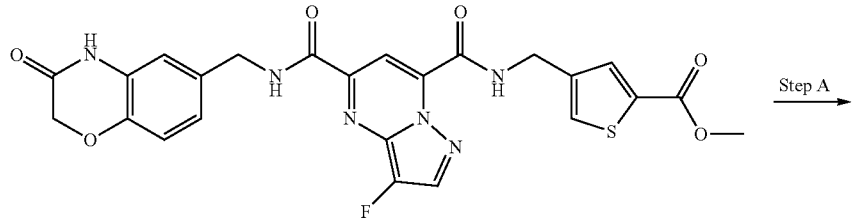

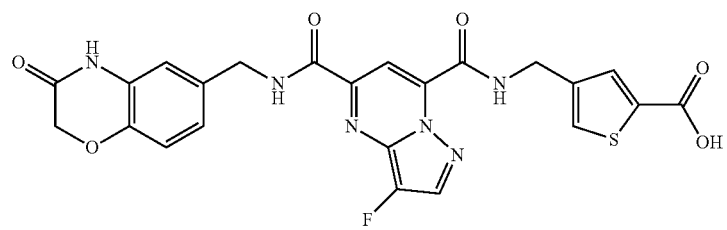

Step A

To a solution of the title compound from the Example HK119 (36 mg) in THF/H₂O (3:1, 2.4 mL) was added a 1M aqueous KOH (210 μL). The mixture was stirred at room temperature for 3 h, concentrated and diluted with EtOAc (150 mL) and 10% aqueous citric acid (40 mL). The organic phase was separated, dried (MgSO₄), filtered, concentrated and purified by chromatography (silica, CH₂Cl₂/MeOH) to afford the title compound as a yellow solid (20.9 mg, 56%). [MH]⁺=525.

Example 1859

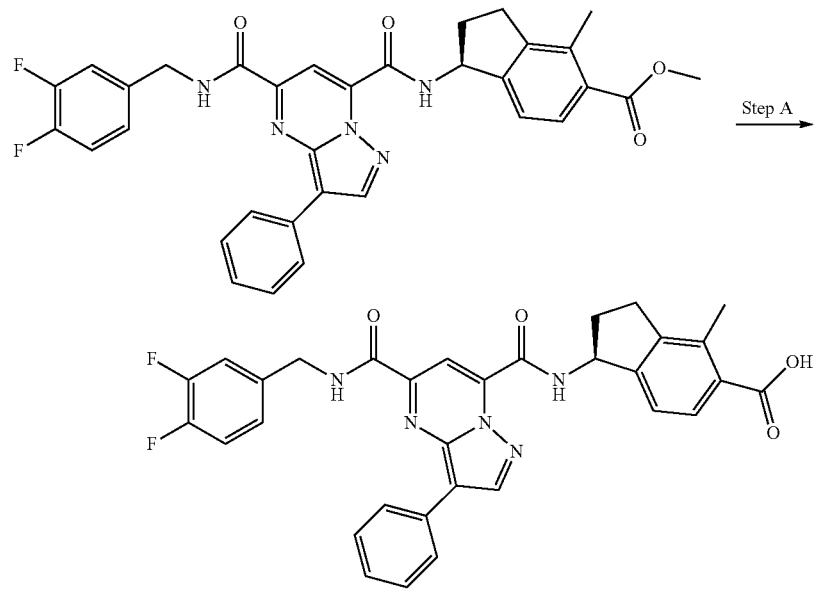

Step A

A solution of the title compound from the Example 1835, Step A (6 mg) and AlBr₃ (7 mg) in tetrahydrothiophene was stirred at room temperature for 16 h, absorbed onto silica and purified by chromatography (silica) to afford the title compound (3 mg, 52%). [M-H]⁻=580.

Examples 1860-1879

Following similar procedures as described in the Examples 314 (method A), 315 (method B), 1858 (method C) or 1859 (method D), except using the esters indicated in Table II-41 below, the following compounds were prepared.

TABLE II-41

| Ex. # | ester |
|---|---|
| 1860 | |
| 1861 | |

TABLE II-41-continued
| 1862 | 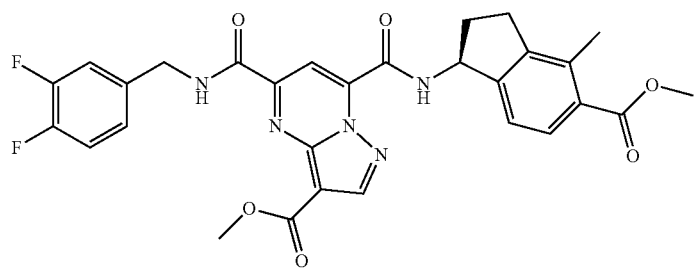 [SMILES: COC(=O)c1ccc2c(c1C)CC[C@@H]2NC(=O)c1cc(C(=O)NCc2ccc(F)c(F)c2)nc2c(C(=O)OC)cnn12] |
| 1863 | 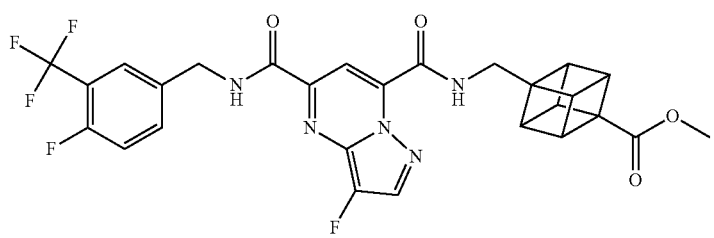 [SMILES: COC(=O)C12C3C4C1C1C2C3C41CNC(=O)c1cc(C(=O)NCc2ccc(F)c(C(F)(F)F)c2)nc2c(F)cnn12] |
| 1864 | 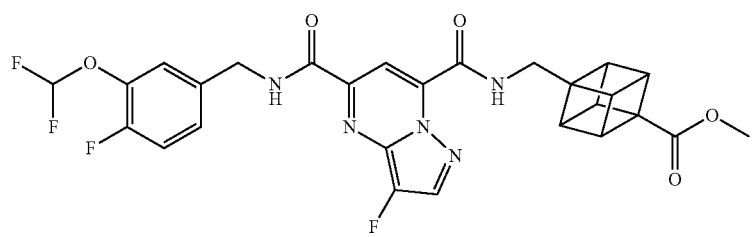 [SMILES: COC(=O)C12C3C4C1C1C2C3C41CNC(=O)c1cc(C(=O)NCc2ccc(F)c(OC(F)F)c2)nc2c(F)cnn12] |
| 1865 | 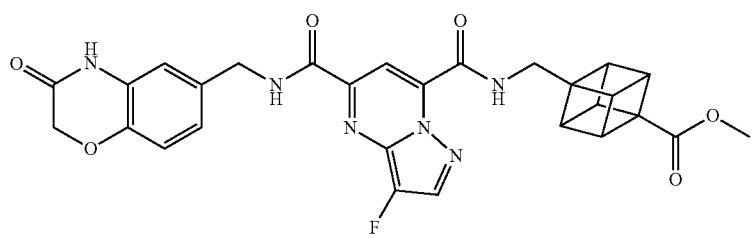 [SMILES: COC(=O)C12C3C4C1C1C2C3C41CNC(=O)c1cc(C(=O)NCc2ccc3c(c2)NC(=O)CO3)nc2c(F)cnn12] |
| 1866 | 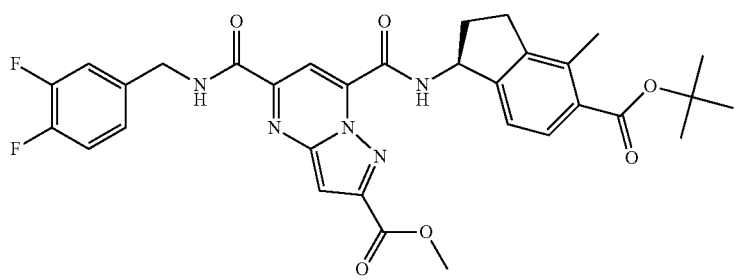 [SMILES: COC(=O)c1cc2nc(C(=O)NCc3ccc(F)c(F)c3)cc(C(=O)N[C@H]3CCc4c3ccc(C(=O)OC(C)(C)C)c4C)n2n1] |
| 1867 | 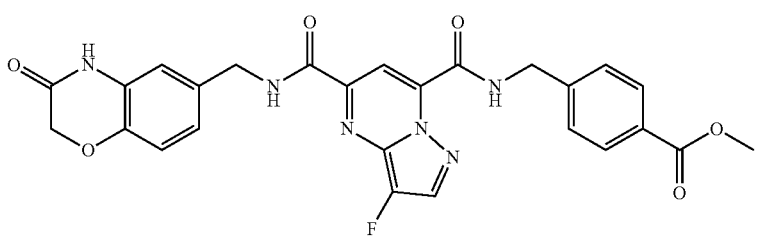 [SMILES: COC(=O)c1ccc(CNC(=O)c2cc(C(=O)NCc3ccc4c(c3)NC(=O)CO4)nc3c(F)cnn23)cc1] |

TABLE II-41-continued
| 1868 | 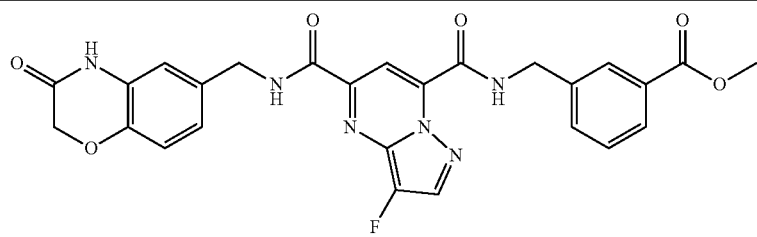 |
| --- | --- |
| 1869 | 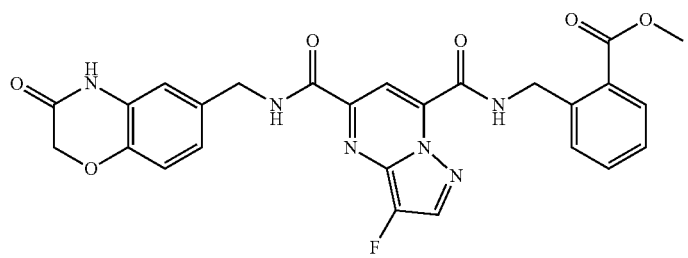 [SMILES: COC(=O)c1ccccc1CNC(=O)c1cc(C(=O)NCc2ccc3c(c2)NC(=O)CO3)nc2c(F)cnn12] |
| 1870 | 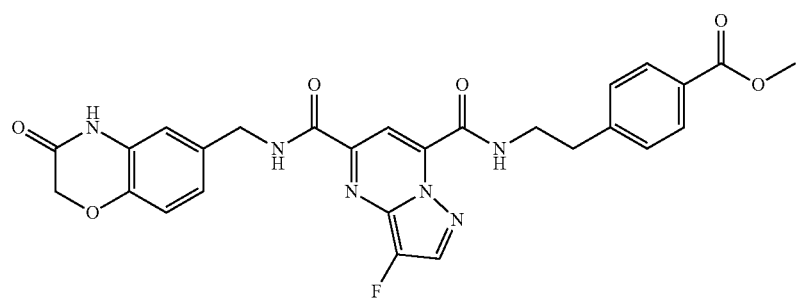 [SMILES: COC(=O)c1ccc(CCNC(=O)c2cc(C(=O)NCc3ccc4c(c3)NC(=O)CO4)nc3c(F)cnn23)cc1] |
| 1871 | 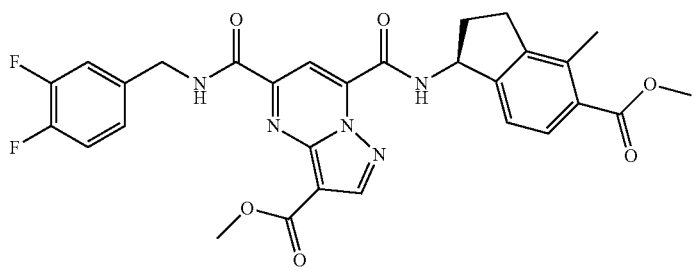 [SMILES: COC(=O)c1ccc2c(c1C)CC[C@@H]2NC(=O)c1cc(C(=O)NCc2ccc(F)c(F)c2)nc2c(C(=O)OC)cnn12] |
| 1872 | 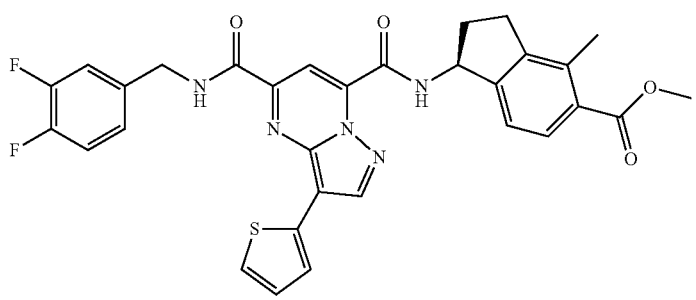 [SMILES: COC(=O)c1ccc2c(c1C)CC[C@@H]2NC(=O)c1cc(C(=O)NCc2ccc(F)c(F)c2)nc2c(-c3cccs3)cnn12] |
| 1873 | 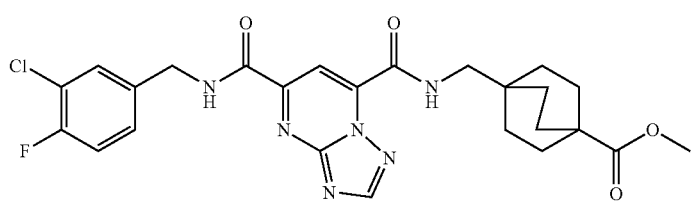 |

TABLE II-41-continued
1874 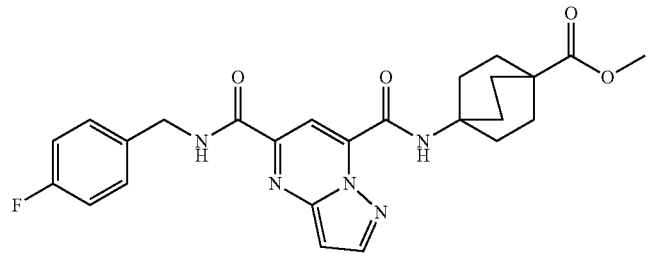 [SMILES: COC(=O)C12CCC(NC(=O)c3cc(C(=O)NCc4ccc(F)cc4)nc4ccnn34)(CC1)CC2]
1875 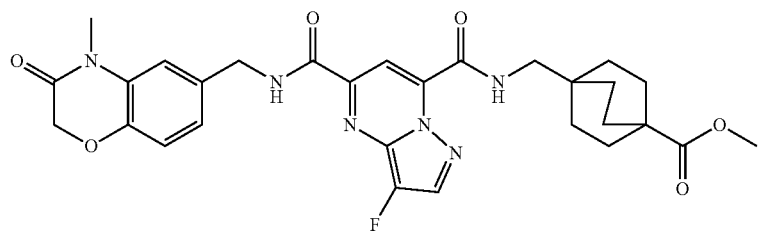 [SMILES: COC(=O)C12CCC(CNC(=O)c3cc(C(=O)NCc4ccc5c(c4)N(C)C(=O)CO5)nc4c(F)cnn34)(CC1)CC2]
1876 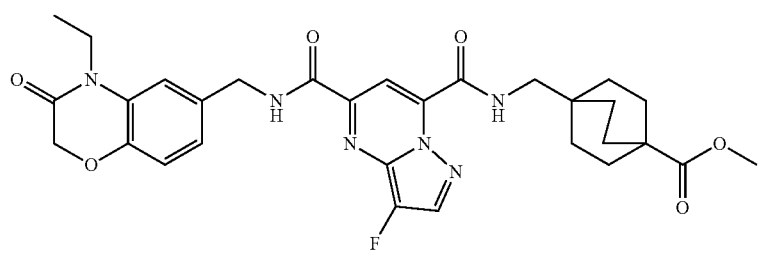 [SMILES: CCN1C(=O)COc2ccc(CNC(=O)c3cc(C(=O)NCC45CCC(C(=O)OC)(CC4)CC5)n4ncc(F)c4n3)cc21]
1877 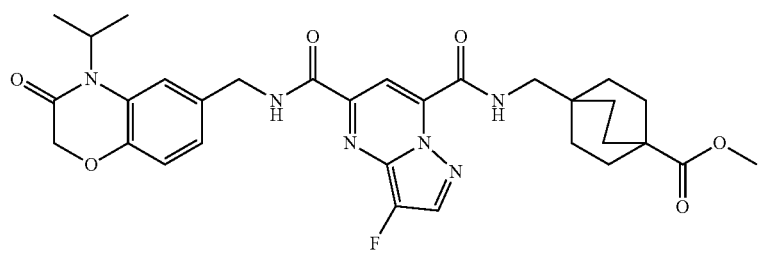 [SMILES: COC(=O)C12CCC(CNC(=O)c3cc(C(=O)NCc4ccc5c(c4)N(C(C)C)C(=O)CO5)nc4c(F)cnn34)(CC1)CC2]
1878 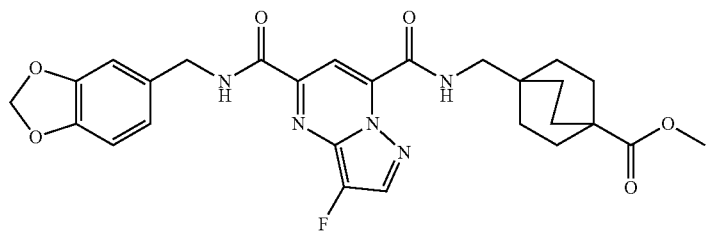 [SMILES: COC(=O)C12CCC(CNC(=O)c3cc(C(=O)NCc4ccc5c(c4)OCO5)nc4c(F)cnn34)(CC1)CC2]
1879 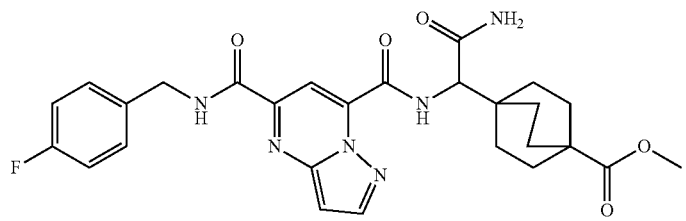 [SMILES: COC(=O)C12CCC(C(NC(=O)c3cc(C(=O)NCc4ccc(F)cc4)nc4ccnn34)C(N)=O)(CC1)CC2]

TABLE II-41-continued

| Ex. # | product | method, yield |
|---|---|---|
| 1860 | | B, 50%<br>[M − H]⁻ = 490 |
| 1861 | | A, n.d.<br>[MH]⁺ = 533 |
| 1862 | | B, 90%<br>[MH]⁺ = 570 |
| 1863 | | B, 43%<br>[MH]⁺ = 560 |
| 1864 | | B, 66%<br>[MH]⁺ = 554 |
| 1865 | | B, 20%<br>[MH]⁺ = 545 |

TABLE II-41-continued

| 1866 | (structure) | B, 86% [MNa]⁺ = 628 |
| 1867 | (structure) | C, 21% [MH]⁺ = 519 |
| 1868 | (structure) | C, 56% [MH]⁺ = 519 |
| 1869 | (structure) | C, 6% [MH]⁺ = 519 |
| 1870 | (structure) | C, 15% [MH]⁺ = 533 |
| 1871 | (structure) | D, 43% [M − H]⁻ = 562 |

TABLE II-41-continued
| | | |
|---|---|---|
| 1872 | 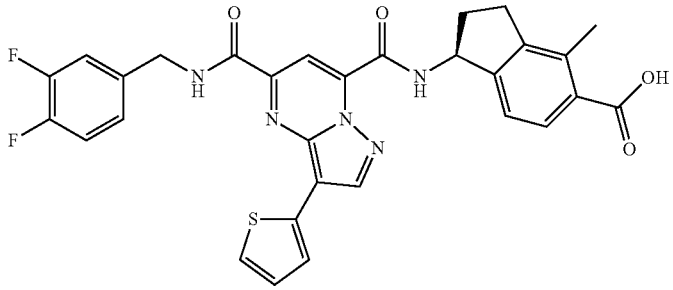 [SMILES: Cc1c(C(=O)O)ccc2c1CC[C@@H]2NC(=O)c1cc(C(=O)NCc2ccc(F)c(F)c2)nc2c(-c3cccs3)cnn12] | D, 28%<br>[M − H]⁻ = 586 |
| 1873 | 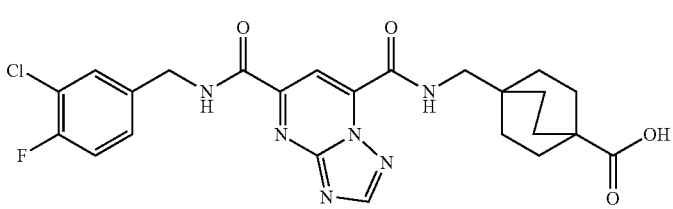 [SMILES: O=C(NCc1ccc(F)c(Cl)c1)c1cc(C(=O)NCC23CCC(C(=O)O)(CC2)CC3)n2ncnc2n1] | B, 17%<br>[MH]⁺ = 515 |
| 1874 | 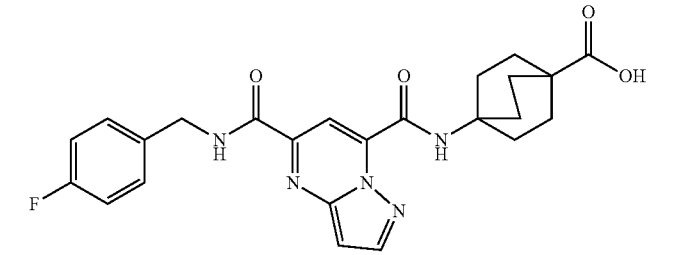 [SMILES: O=C(NCc1ccc(F)cc1)c1cc(C(=O)NC23CCC(C(=O)O)(CC2)CC3)n2nccc2n1] | A, 21%<br>[MH]⁺ = 466 |
| 1875 | 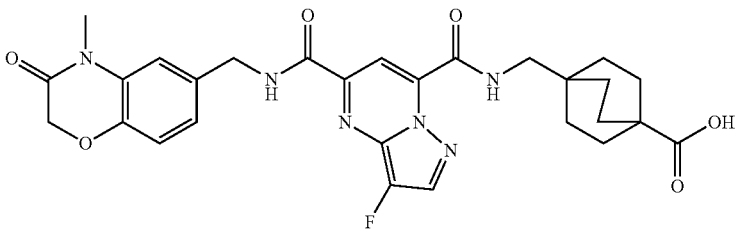 [SMILES: CN1C(=O)COc2ccc(CNC(=O)c3cc(C(=O)NCC45CCC(C(=O)O)(CC4)CC5)n4ncc(F)c4n3)cc21] | A, 12%<br>[MH]⁺ = 565 |
| 1876 | 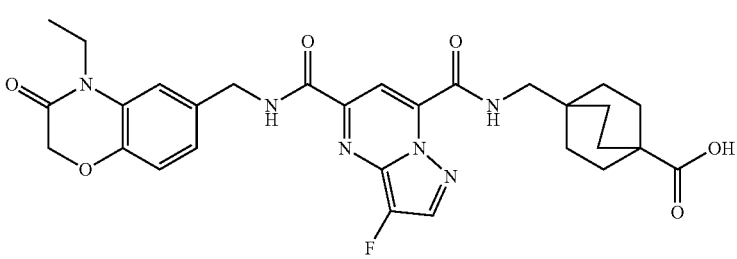 [SMILES: CCN1C(=O)COc2ccc(CNC(=O)c3cc(C(=O)NCC45CCC(C(=O)O)(CC4)CC5)n4ncc(F)c4n3)cc21] | A, 34%<br>[MH]⁺ = 579 |
| 1877 | 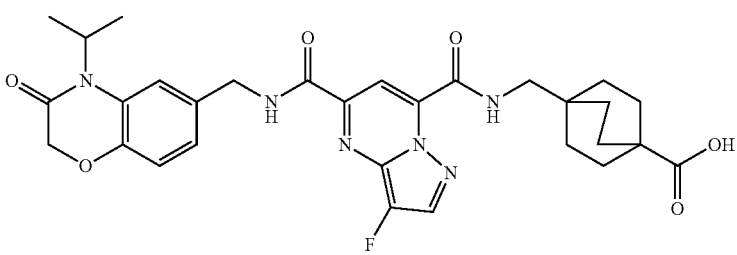 [SMILES: CC(C)N1C(=O)COc2ccc(CNC(=O)c3cc(C(=O)NCC45CCC(C(=O)O)(CC4)CC5)n4ncc(F)c4n3)cc21] | A, 19%<br>[MH]⁺ = 593 |

TABLE II-41-continued

| 1878 | [structure] | A, n.d. [MH]+ = 524 |
| 1879 | [structure] | A, 29% [MH]+ = 523 |

Examples 1880-1884

Following a similar procedure as described in the Example 362, except using the esters indicated in Table II-42 below, the following compounds were prepared.

TABLE II-42

| Ex. # | ester |
|---|---|
| 1880 | [structure] |
| 1881 | [structure] |
| 1882 | [structure] |

TABLE II-42-continued

| Ex. # | product | yield |
|---|---|---|
| 1880 | | 75%<br>[MH]⁺ = 532 |
| 1881 | | 43%<br>[MH]⁺ = 571 |
| 1882 | | 43%<br>[MH]⁺ = 574 |
| 1883 | | 19%<br>[MH]⁺ = 591 |

TABLE II-42-continued

| 1884 | 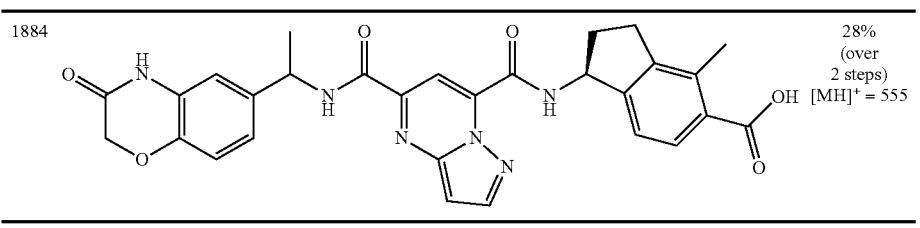 | 28% (over 2 steps) [MH]+ = 555 |

Example 1885

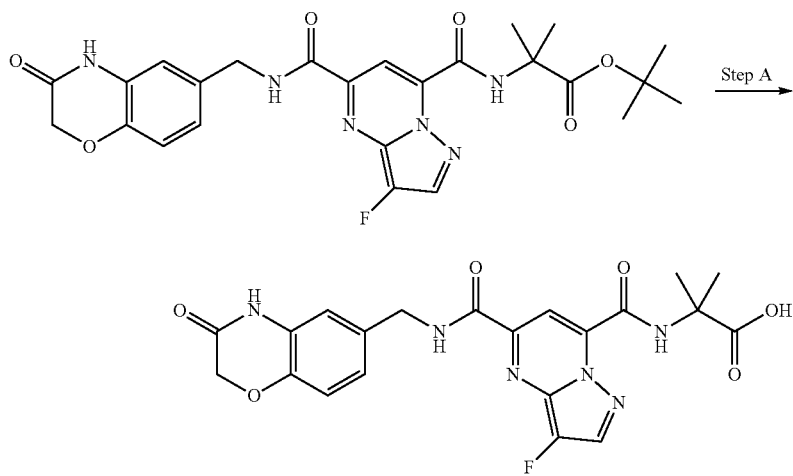

Step A

The title compound from the Example 1767 (27.5 mg) was stirred in formic acid (4 mL) at room temperature for 2 h and then concentrated to afford the title compound as a yellow solid (15.5 mg; 63%). [MH]+=471.

Examples 1886-1954

Following similar procedures as described in the Examples 436 (method A) or 1885 (method B), except using the esters as indicated in Table II-43 below, the following compounds were prepared.

TABLE II-43

| Ex. # | ester |
|---|---|
| 1886 | |
| 1887 | |

TABLE II-43-continued
1888 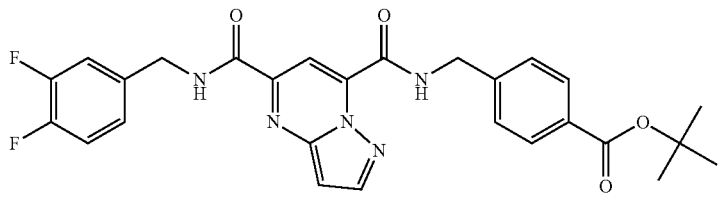 [SMILES: CC(C)(C)OC(=O)c1ccc(CNC(=O)c2cc(C(=O)NCc3ccc(F)c(F)c3)nc3ccnn23)cc1]
1889 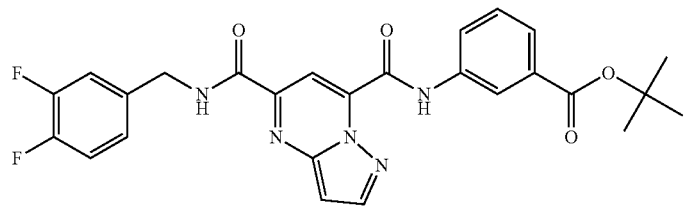 [SMILES: CC(C)(C)OC(=O)c1cccc(NC(=O)c2cc(C(=O)NCc3ccc(F)c(F)c3)nc3ccnn23)c1]
1890 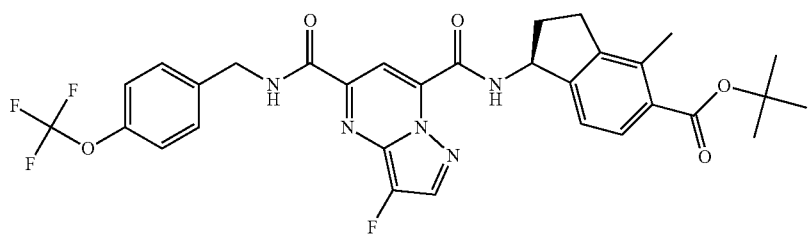 [SMILES: Cc1c(C(=O)OC(C)(C)C)ccc2c1CC[C@@H]2NC(=O)c1cc(C(=O)NCc2ccc(OC(F)(F)F)cc2)nc2c(F)cnn12]
1891 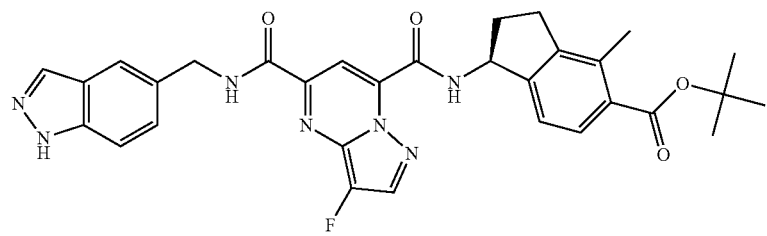 [SMILES: Cc1c(C(=O)OC(C)(C)C)ccc2c1CC[C@@H]2NC(=O)c1cc(C(=O)NCc2ccc3[nH]ncc3c2)nc2c(F)cnn12]
1892 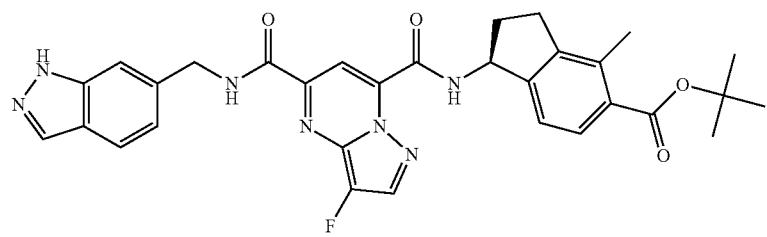 [SMILES: Cc1c(C(=O)OC(C)(C)C)ccc2c1CC[C@@H]2NC(=O)c1cc(C(=O)NCc2ccc3cn[nH]c3c2)nc2c(F)cnn12]
1893 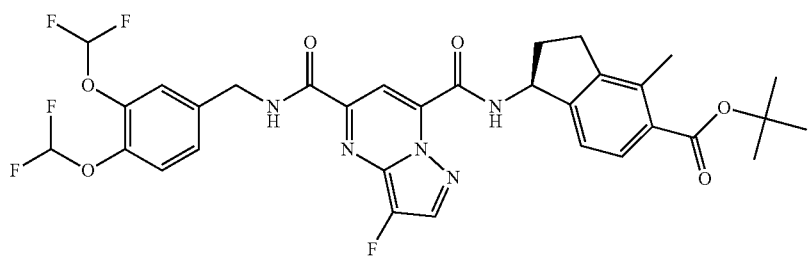 [SMILES: Cc1c(C(=O)OC(C)(C)C)ccc2c1CC[C@@H]2NC(=O)c1cc(C(=O)NCc2ccc(OC(F)F)c(OC(F)F)c2)nc2c(F)cnn12]
1894 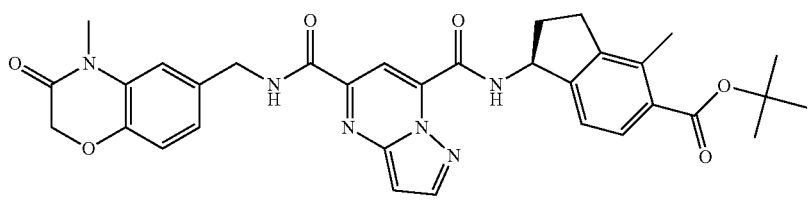 [SMILES: Cc1c(C(=O)OC(C)(C)C)ccc2c1CC[C@@H]2NC(=O)c1cc(C(=O)NCc2ccc3c(c2)N(C)C(=O)CO3)nc2ccnn12]

TABLE II-43-continued
1895 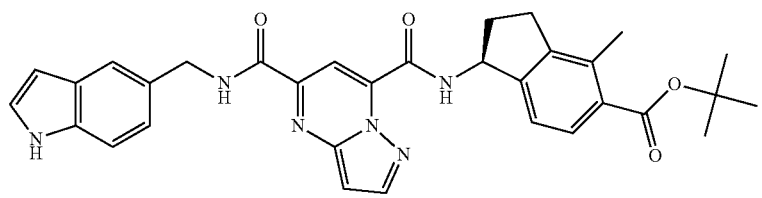 [SMILES: Cc1c(C(=O)OC(C)(C)C)ccc2c1CC[C@@H]2NC(=O)c1cc(C(=O)NCc2ccc3[nH]ccc3c2)nc2ccnn12]
1896 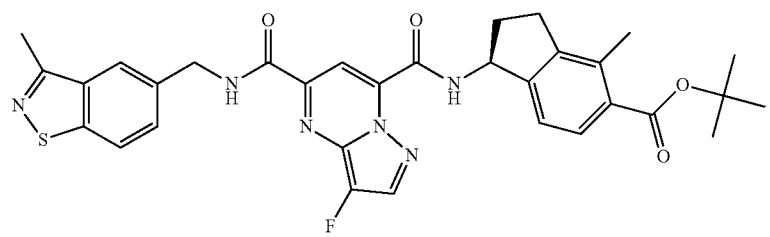 [SMILES: Cc1c(C(=O)OC(C)(C)C)ccc2c1CC[C@@H]2NC(=O)c1cc(C(=O)NCc2ccc3snc(C)c3c2)nc2c(F)cnn12]
1897 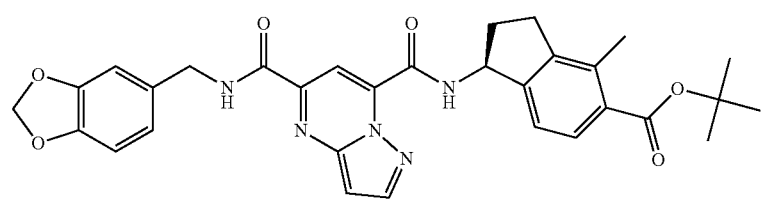
1898 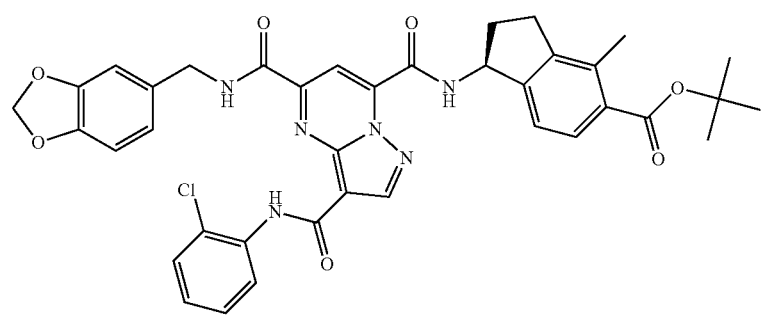 [SMILES: Cc1c(C(=O)OC(C)(C)C)ccc2c1CC[C@@H]2NC(=O)c1cc(C(=O)NCc2ccc3c(c2)OCO3)nc2c(C(=O)Nc3ccccc3Cl)cnn12]
1899 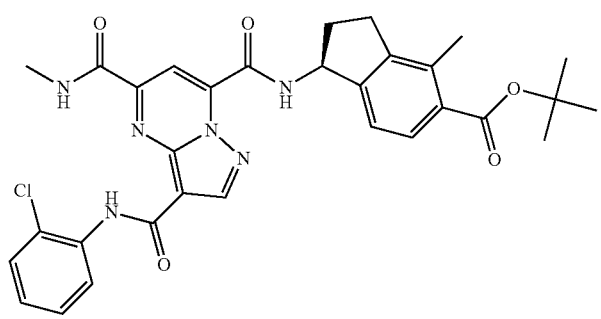 [SMILES: CNC(=O)c1cc(C(=O)N[C@H]2CCc3c2ccc(C(=O)OC(C)(C)C)c3C)n2ncc(C(=O)Nc3ccccc3Cl)c2n1]
1900 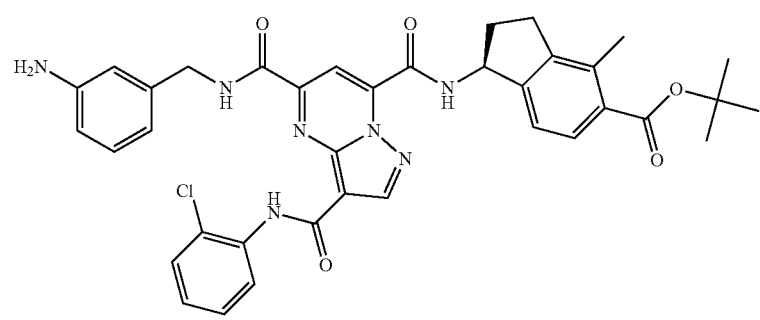 [SMILES: Cc1c(C(=O)OC(C)(C)C)ccc2c1CC[C@@H]2NC(=O)c1cc(C(=O)NCc2cccc(N)c2)nc2c(C(=O)Nc3ccccc3Cl)cnn12]

TABLE II-43-continued
1901
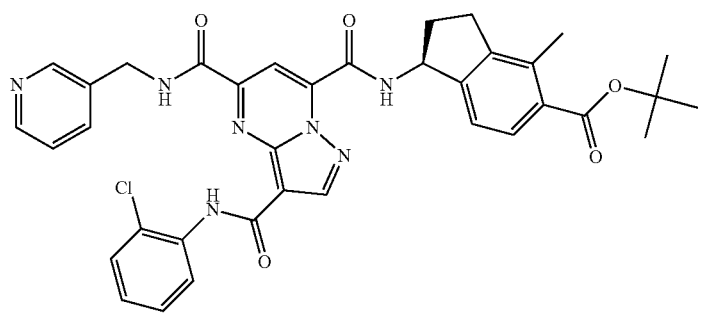 [SMILES: Cc1c(C(=O)OC(C)(C)C)ccc2c1CC[C@@H]2NC(=O)c1cc(C(=O)NCc2cccnc2)nc2c(C(=O)Nc3ccccc3Cl)cnn12]
1902
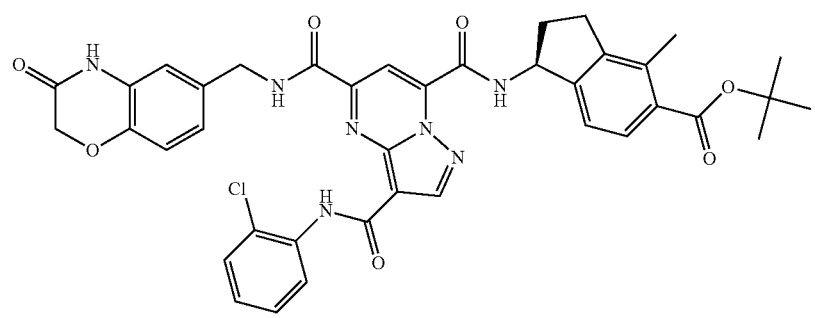 [SMILES: Cc1c(C(=O)OC(C)(C)C)ccc2c1CC[C@@H]2NC(=O)c1cc(C(=O)NCc2ccc3c(c2)NC(=O)CO3)nc2c(C(=O)Nc3ccccc3Cl)cnn12]
1903
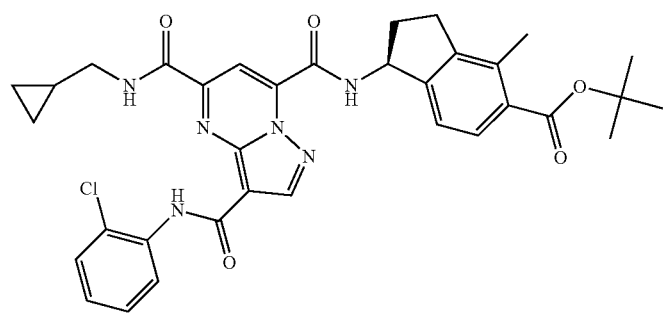 [SMILES: Cc1c(C(=O)OC(C)(C)C)ccc2c1CC[C@@H]2NC(=O)c1cc(C(=O)NCC2CC2)nc2c(C(=O)Nc3ccccc3Cl)cnn12]
1904
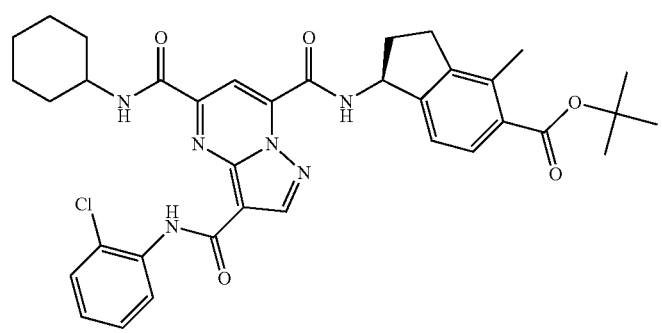 [SMILES: Cc1c(C(=O)OC(C)(C)C)ccc2c1CC[C@@H]2NC(=O)c1cc(C(=O)NC2CCCCC2)nc2c(C(=O)Nc3ccccc3Cl)cnn12]
1905
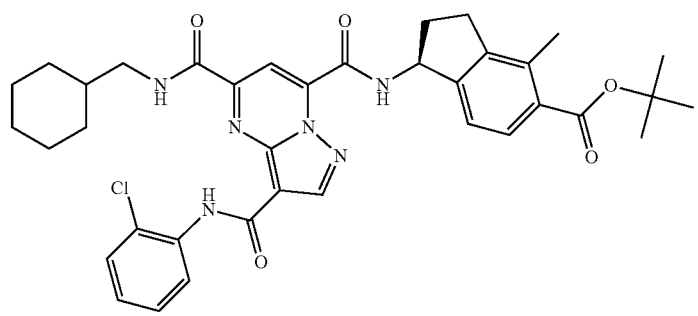 [SMILES: Cc1c(C(=O)OC(C)(C)C)ccc2c1CC[C@@H]2NC(=O)c1cc(C(=O)NCC2CCCCC2)nc2c(C(=O)Nc3ccccc3Cl)cnn12]

TABLE II-43-continued
1906 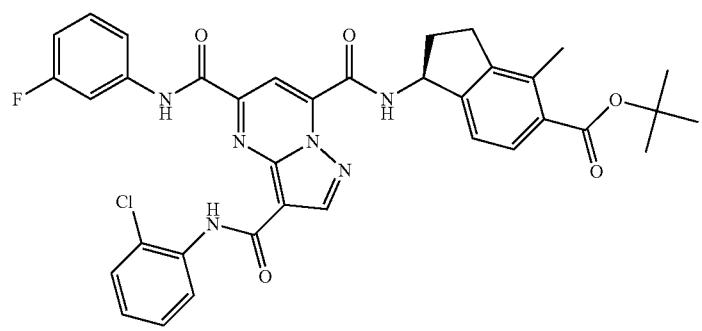 [SMILES: Cc1c(C(=O)OC(C)(C)C)ccc2c1CC[C@@H]2NC(=O)c1cc(C(=O)Nc2cccc(F)c2)nc2c(C(=O)Nc3ccccc3Cl)cnn12]
1907 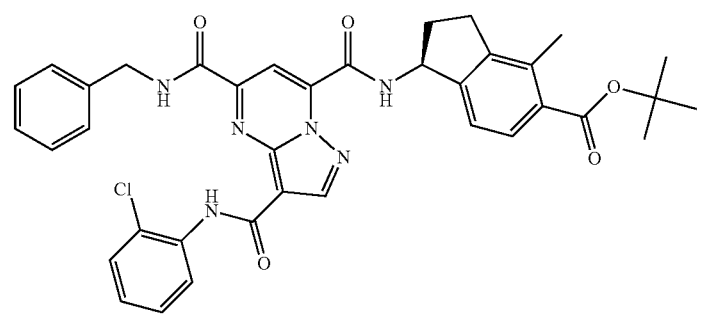 [SMILES: Cc1c(C(=O)OC(C)(C)C)ccc2c1CC[C@@H]2NC(=O)c1cc(C(=O)NCc2ccccc2)nc2c(C(=O)Nc3ccccc3Cl)cnn12]
1908 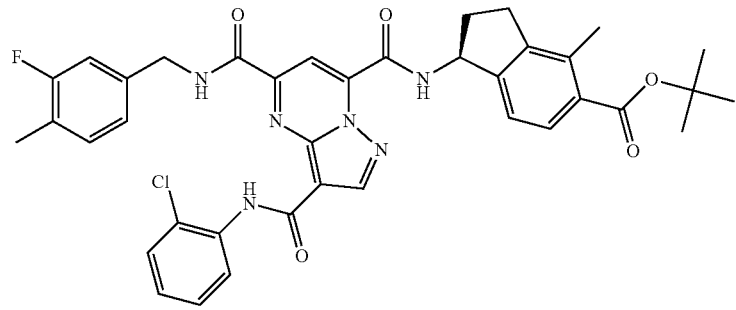 [SMILES: Cc1ccc(CNC(=O)c2cc(C(=O)N[C@H]3CCc4c3ccc(C(=O)OC(C)(C)C)c4C)n3ncc(C(=O)Nc4ccccc4Cl)c3n2)cc1F]
1909 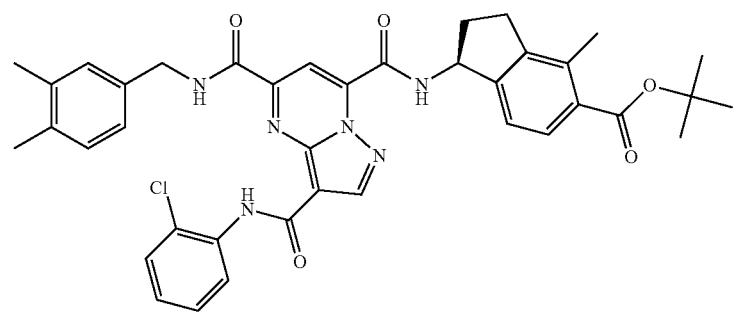 [SMILES: Cc1ccc(CNC(=O)c2cc(C(=O)N[C@H]3CCc4c3ccc(C(=O)OC(C)(C)C)c4C)n3ncc(C(=O)Nc4ccccc4Cl)c3n2)cc1C]
1910 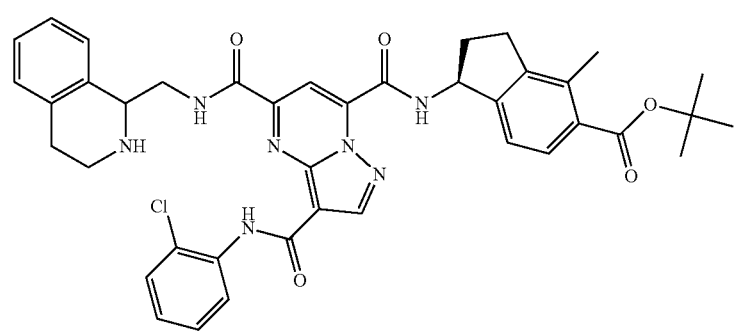 [SMILES: Cc1c(C(=O)OC(C)(C)C)ccc2c1CC[C@@H]2NC(=O)c1cc(C(=O)NCC2NCCc3ccccc32)nc2c(C(=O)Nc3ccccc3Cl)cnn12]

TABLE II-43-continued
1911
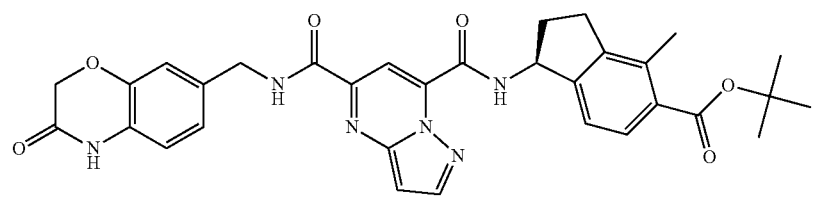 [SMILES: Cc1c(C(=O)OC(C)(C)C)ccc2c1CC[C@@H]2NC(=O)c1cc(C(=O)NCc2ccc3c(c2)OCC(=O)N3)nc2ccnn12]
1912
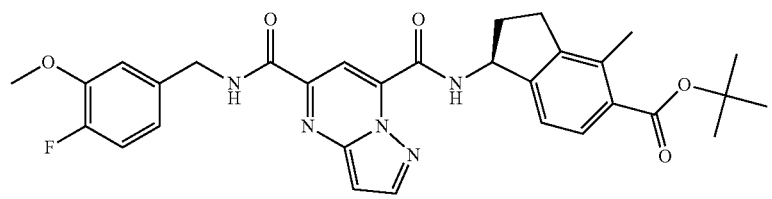 [SMILES: COc1cc(CNC(=O)c2cc(C(=O)N[C@H]3CCc4c3ccc(C(=O)OC(C)(C)C)c4C)n3nccc3n2)ccc1F]
1913
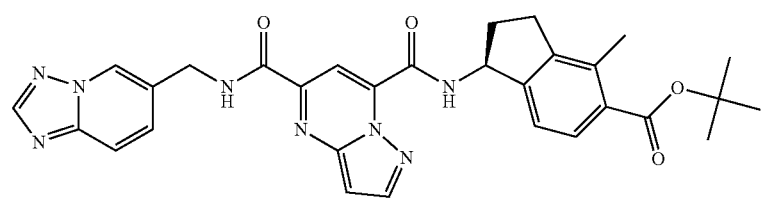 [SMILES: Cc1c(C(=O)OC(C)(C)C)ccc2c1CC[C@@H]2NC(=O)c1cc(C(=O)NCc2ccc3ncnn3c2)nc2ccnn12]
1914
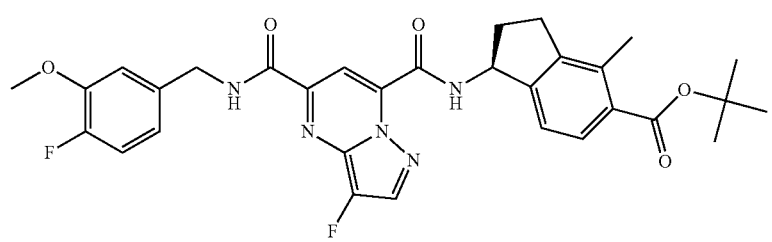 [SMILES: COc1cc(CNC(=O)c2cc(C(=O)N[C@H]3CCc4c3ccc(C(=O)OC(C)(C)C)c4C)n3ncc(F)c3n2)ccc1F]
1915
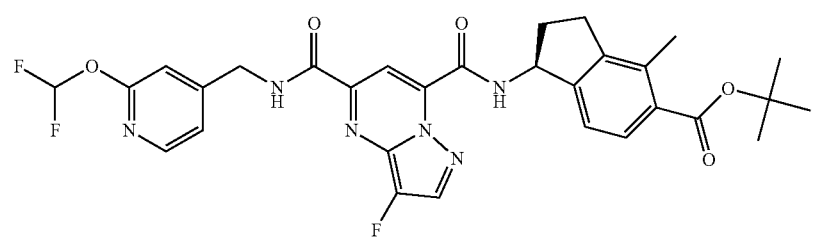 [SMILES: Cc1c(C(=O)OC(C)(C)C)ccc2c1CC[C@@H]2NC(=O)c1cc(C(=O)NCc2ccnc(OC(F)F)c2)nc2c(F)cnn12]
1916
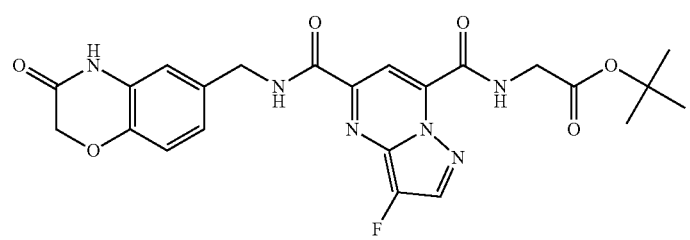
1917
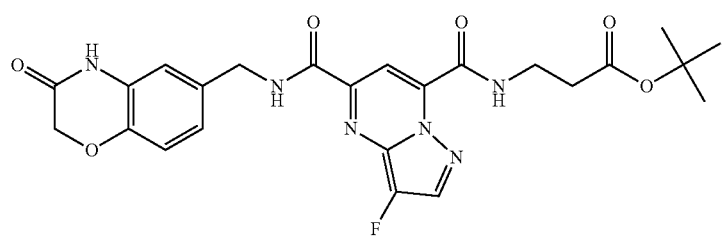 [SMILES: CC(C)(C)OC(=O)CCNC(=O)c1cc(C(=O)NCc2ccc3c(c2)NC(=O)CO3)nc2c(F)cnn12]

TABLE II-43-continued
| 1918 | 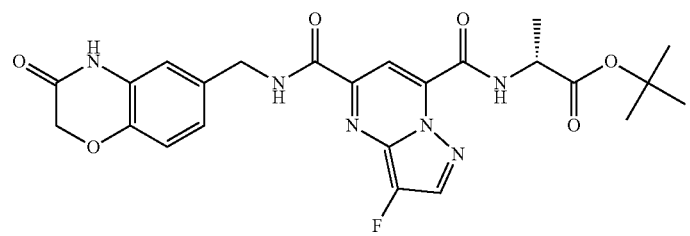 |
| 1919 | 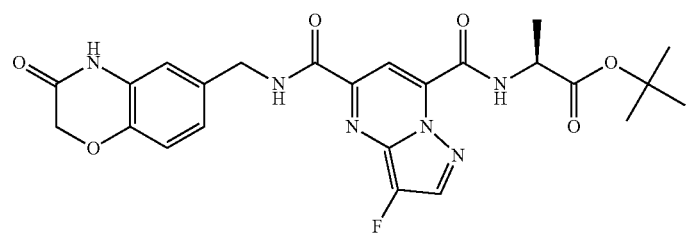 [SMILES: C[C@H](NC(=O)c1cc(C(=O)NCc2ccc3c(c2)NC(=O)CO3)nc2c(F)cnn12)C(=O)OC(C)(C)C] |
| 1920 | 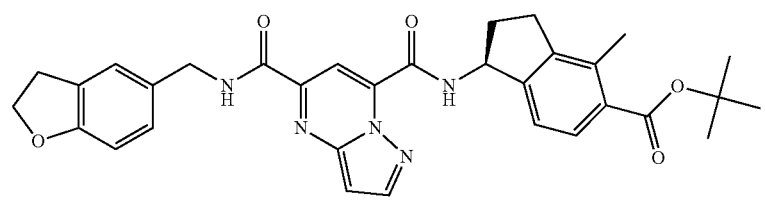 |
| 1921 | 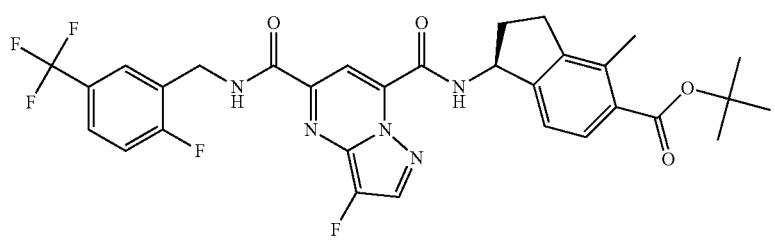 [SMILES: Cc1c(C(=O)OC(C)(C)C)ccc2c1CC[C@@H]2NC(=O)c1cc(C(=O)NCc2cc(C(F)(F)F)ccc2F)nc2c(F)cnn12] |
| 1922 | 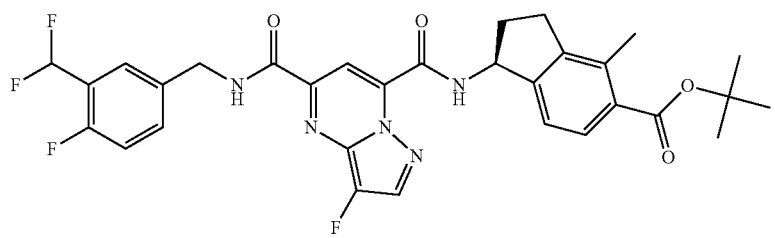 [SMILES: Cc1c(C(=O)OC(C)(C)C)ccc2c1CC[C@@H]2NC(=O)c1cc(C(=O)NCc2ccc(F)c(C(F)F)c2)nc2c(F)cnn12] |
| 1923 | 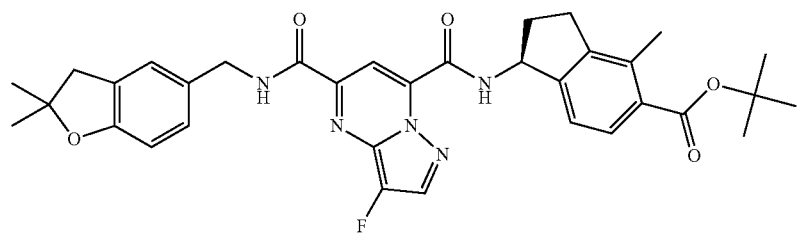 [SMILES: Cc1c(C(=O)OC(C)(C)C)ccc2c1CC[C@@H]2NC(=O)c1cc(C(=O)NCc2ccc3c(c2)CC(C)(C)O3)nc2c(F)cnn12] |
| 1924 | 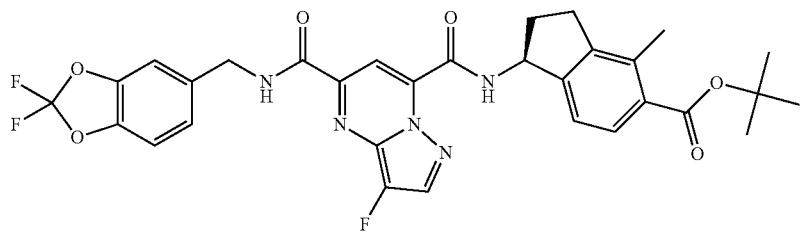 [SMILES: Cc1c(C(=O)OC(C)(C)C)ccc2c1CC[C@@H]2NC(=O)c1cc(C(=O)NCc2ccc3c(c2)OC(F)(F)O3)nc2c(F)cnn12] |

TABLE II-43-continued
1925 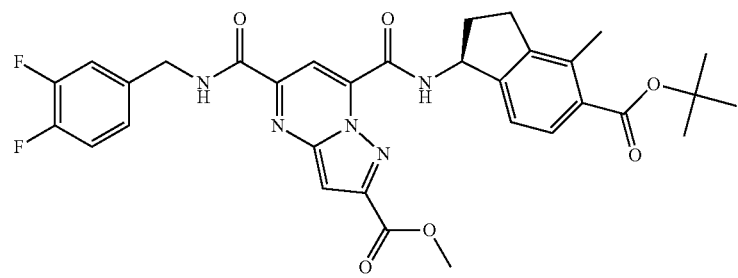 [SMILES: COC(=O)c1cc2nc(C(=O)NCc3ccc(F)c(F)c3)cc(C(=O)N[C@H]3CCc4c3ccc(C(=O)OC(C)(C)C)c4C)n2n1]
1926 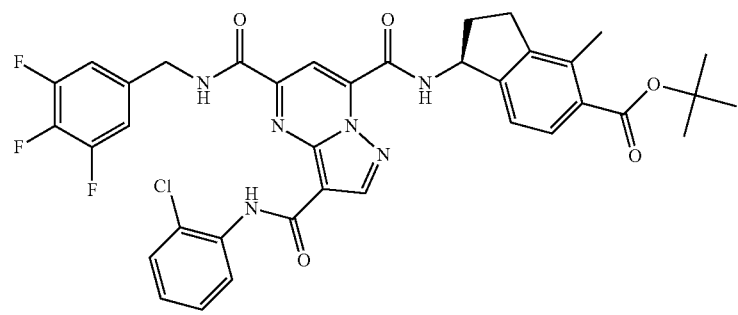 [SMILES: Cc1c(C(=O)OC(C)(C)C)ccc2c1CC[C@@H]2NC(=O)c1cc(C(=O)NCc2cc(F)c(F)c(F)c2)nc2c(C(=O)Nc3ccccc3Cl)cnn12]
1927 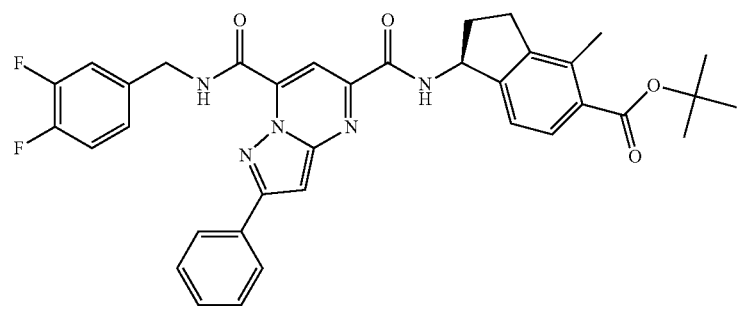 [SMILES: Cc1c(C(=O)OC(C)(C)C)ccc2c1CC[C@@H]2NC(=O)c1cc(C(=O)NCc2ccc(F)c(F)c2)n2nc(-c3ccccc3)cc2n1]
1928 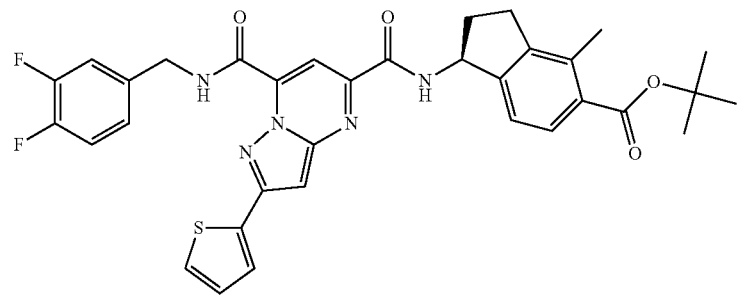 [SMILES: Cc1c(C(=O)OC(C)(C)C)ccc2c1CC[C@@H]2NC(=O)c1cc(C(=O)NCc2ccc(F)c(F)c2)n2nc(-c3cccs3)cc2n1]
1929 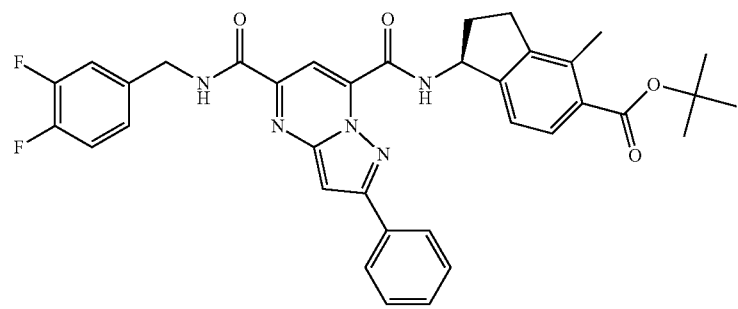 [SMILES: Cc1c(C(=O)OC(C)(C)C)ccc2c1CC[C@@H]2NC(=O)c1cc(C(=O)NCc2ccc(F)c(F)c2)nc2cc(-c3ccccc3)nn12]

TABLE II-43-continued
1930 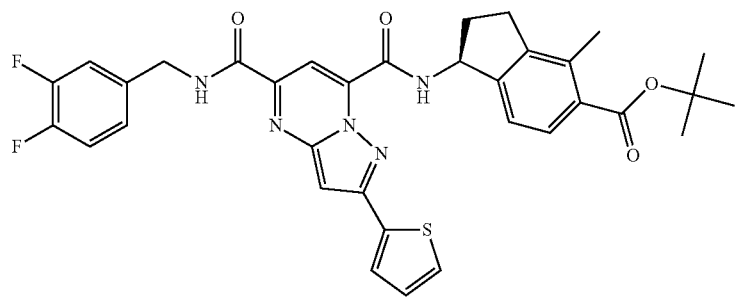 [SMILES: Cc1c(C(=O)OC(C)(C)C)ccc2c1CC[C@@H]2NC(=O)c1cc(C(=O)NCc2ccc(F)c(F)c2)nc2cc(-c3cccs3)nn12]
1931 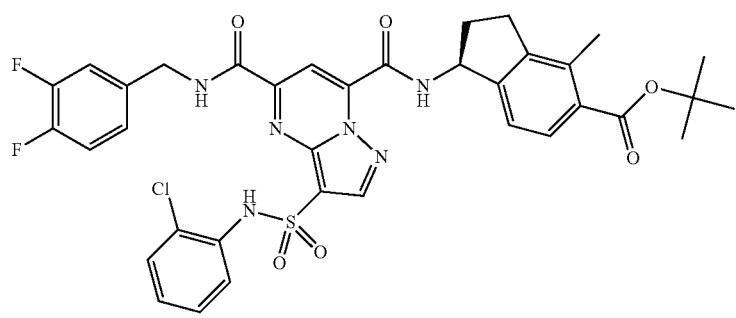 [SMILES: Cc1c(C(=O)OC(C)(C)C)ccc2c1CC[C@@H]2NC(=O)c1cc(C(=O)NCc2ccc(F)c(F)c2)nc2c(S(=O)(=O)Nc3ccccc3Cl)cnn12]
1932 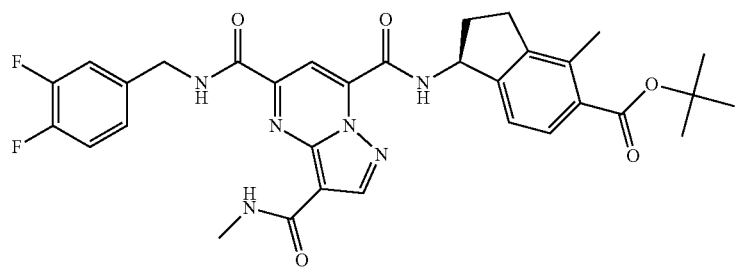 [SMILES: CNC(=O)c1cnn2c(C(=O)N[C@H]3CCc4c3ccc(C(=O)OC(C)(C)C)c4C)cc(C(=O)NCc3ccc(F)c(F)c3)nc12]
1933 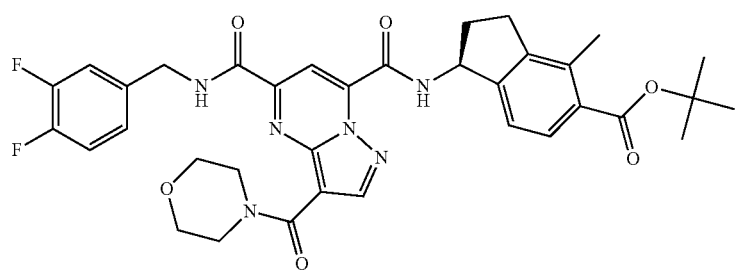 [SMILES: Cc1c(C(=O)OC(C)(C)C)ccc2c1CC[C@@H]2NC(=O)c1cc(C(=O)NCc2ccc(F)c(F)c2)nc2c(C(=O)N3CCOCC3)cnn12]
1934 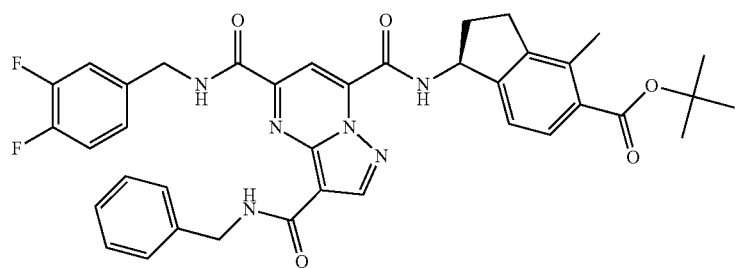 [SMILES: Cc1c(C(=O)OC(C)(C)C)ccc2c1CC[C@@H]2NC(=O)c1cc(C(=O)NCc2ccc(F)c(F)c2)nc2c(C(=O)NCc3ccccc3)cnn12]

TABLE II-43-continued
| 1935 | 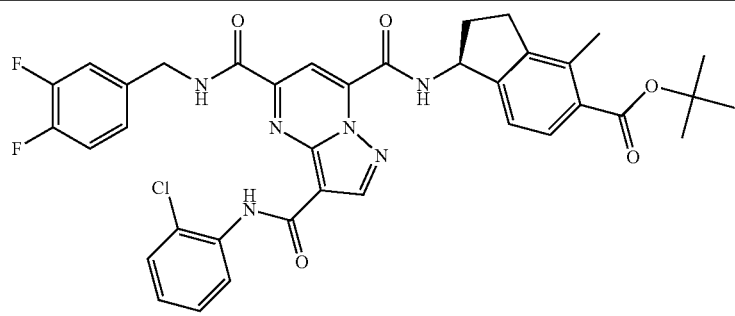 |
| --- | --- |
| 1936 | 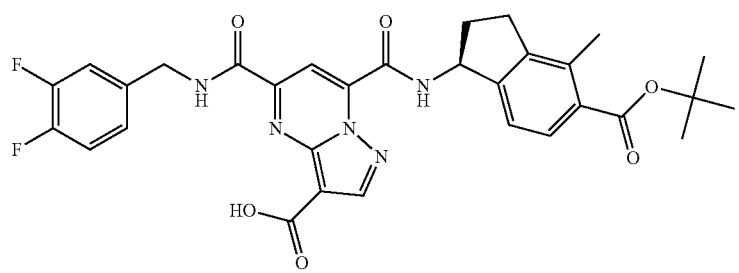 [SMILES: Cc1c(C(=O)OC(C)(C)C)ccc2c1CC[C@@H]2NC(=O)c1cc(C(=O)NCc2ccc(F)c(F)c2)nc2c(C(=O)O)cnn12] |
| 1937 | 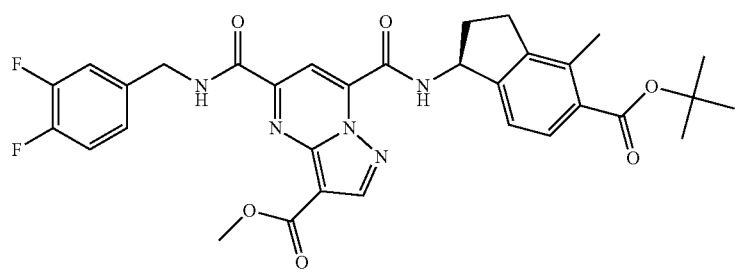 [SMILES: COC(=O)c1cnn2c(C(=O)N[C@H]3CCc4c3ccc(C(=O)OC(C)(C)C)c4C)cc(C(=O)NCc3ccc(F)c(F)c3)nc12] |
| 1938 | 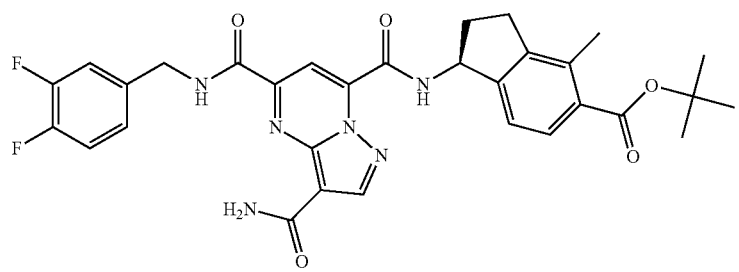 [SMILES: Cc1c(C(=O)OC(C)(C)C)ccc2c1CC[C@@H]2NC(=O)c1cc(C(=O)NCc2ccc(F)c(F)c2)nc2c(C(N)=O)cnn12] |
| 1939 | 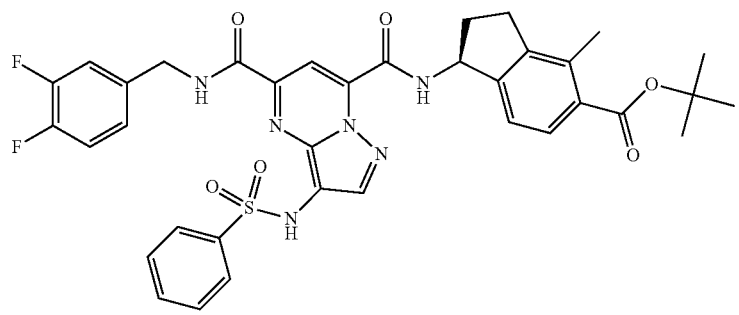 [SMILES: Cc1c(C(=O)OC(C)(C)C)ccc2c1CC[C@@H]2NC(=O)c1cc(C(=O)NCc2ccc(F)c(F)c2)nc2c(NS(=O)(=O)c3ccccc3)cnn12] |

TABLE II-43-continued
1940
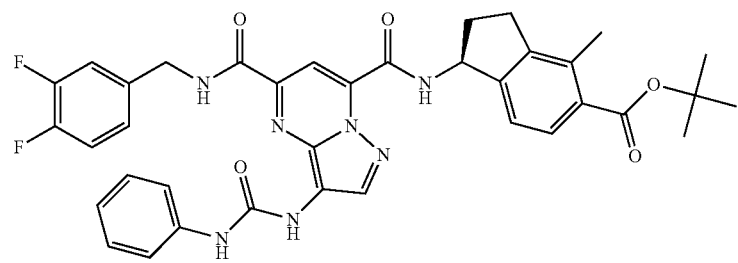 [SMILES: Cc1c(C(=O)OC(C)(C)C)ccc2c1CC[C@@H]2NC(=O)c1cc(C(=O)NCc2ccc(F)c(F)c2)nc2c(NC(=O)Nc3ccccc3)cnn12]
1941
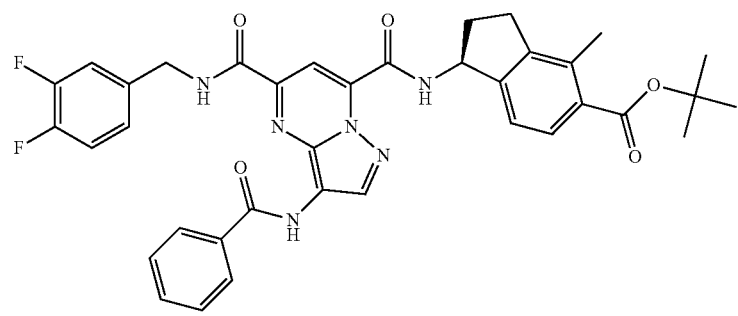 [SMILES: Cc1c(C(=O)OC(C)(C)C)ccc2c1CC[C@@H]2NC(=O)c1cc(C(=O)NCc2ccc(F)c(F)c2)nc2c(NC(=O)c3ccccc3)cnn12]
1942
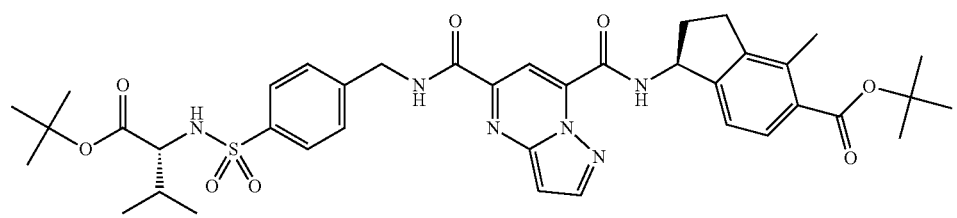 [SMILES: Cc1c(C(=O)OC(C)(C)C)ccc2c1CC[C@@H]2NC(=O)c1cc(C(=O)NCc2ccc(S(=O)(=O)N[C@@H](C(=O)OC(C)(C)C)C(C)C)cc2)nc2ccnn12]
1943
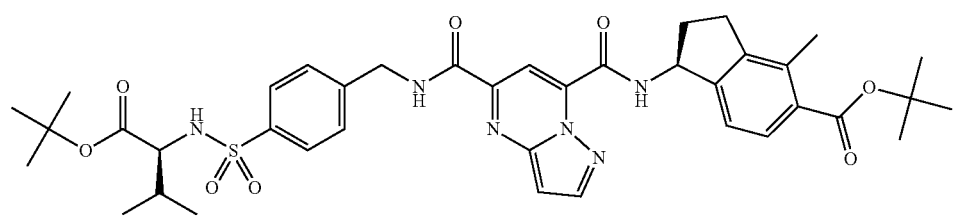 [SMILES: Cc1c(C(=O)OC(C)(C)C)ccc2c1CC[C@@H]2NC(=O)c1cc(C(=O)NCc2ccc(S(=O)(=O)N[C@H](C(=O)OC(C)(C)C)C(C)C)cc2)nc2ccnn12]
1944
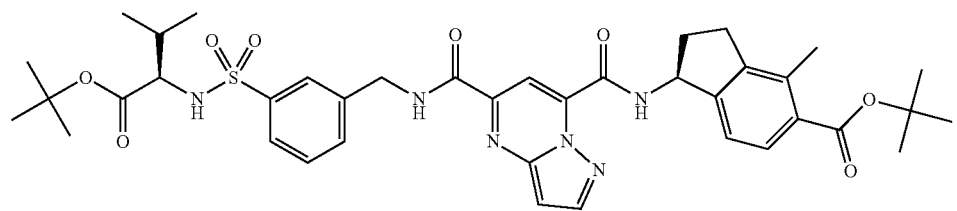 [SMILES: Cc1c(C(=O)OC(C)(C)C)ccc2c1CC[C@@H]2NC(=O)c1cc(C(=O)NCc2cccc(S(=O)(=O)N[C@@H](C(=O)OC(C)(C)C)C(C)C)c2)nc2ccnn12]
1945
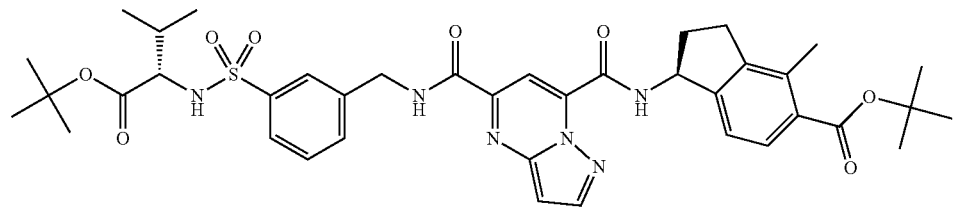 [SMILES: Cc1c(C(=O)OC(C)(C)C)ccc2c1CC[C@@H]2NC(=O)c1cc(C(=O)NCc2cccc(S(=O)(=O)N[C@H](C(=O)OC(C)(C)C)C(C)C)c2)nc2ccnn12]

TABLE II-43-continued
1946
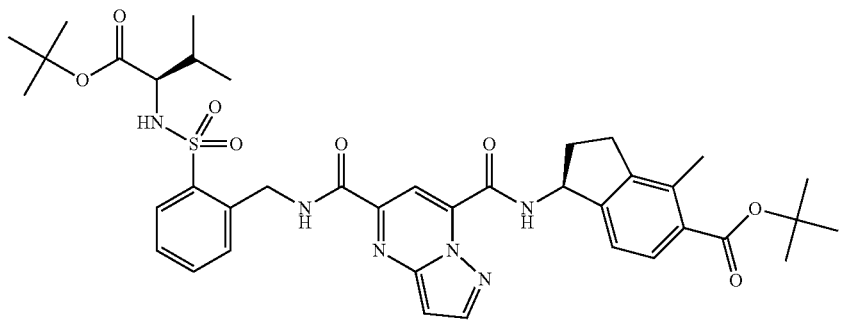 [SMILES: Cc1c(C(=O)OC(C)(C)C)ccc2c1CC[C@@H]2NC(=O)c1cc(C(=O)NCc2ccccc2S(=O)(=O)N[C@@H](C(=O)OC(C)(C)C)C(C)C)nc2ccnn12]
1947
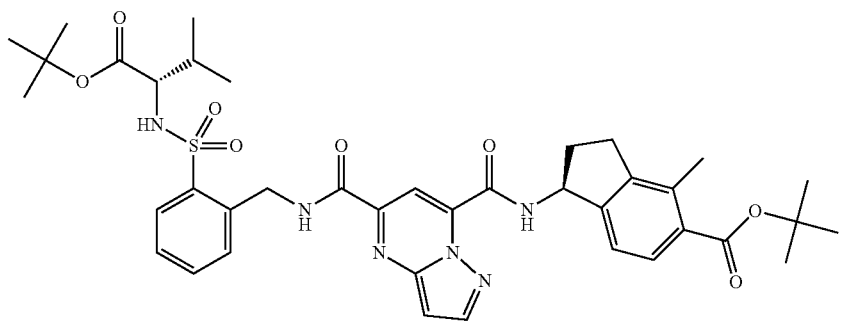 [SMILES: Cc1c(C(=O)OC(C)(C)C)ccc2c1CC[C@@H]2NC(=O)c1cc(C(=O)NCc2ccccc2S(=O)(=O)N[C@H](C(=O)OC(C)(C)C)C(C)C)nc2ccnn12]
1948
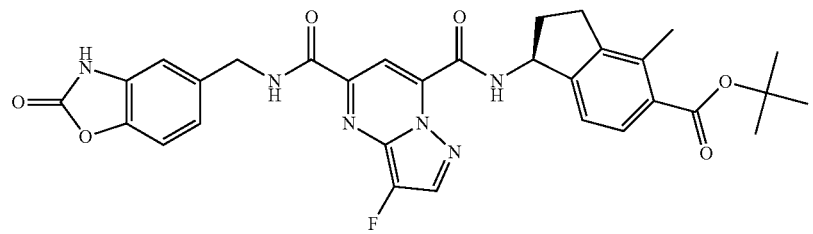 [SMILES: Cc1c(C(=O)OC(C)(C)C)ccc2c1CC[C@@H]2NC(=O)c1cc(C(=O)NCc2ccc3oc(=O)[nH]c3c2)nc2c(F)cnn12]
1949
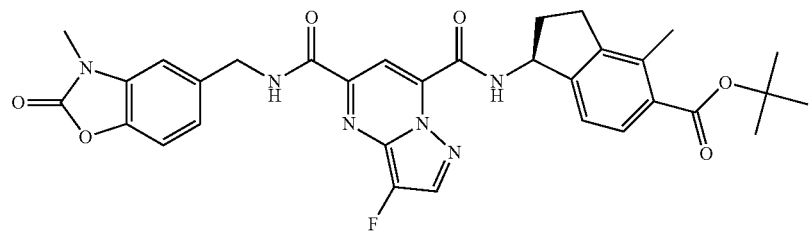 [SMILES: Cc1c(C(=O)OC(C)(C)C)ccc2c1CC[C@@H]2NC(=O)c1cc(C(=O)NCc2ccc3oc(=O)n(C)c3c2)nc2c(F)cnn12]
1950
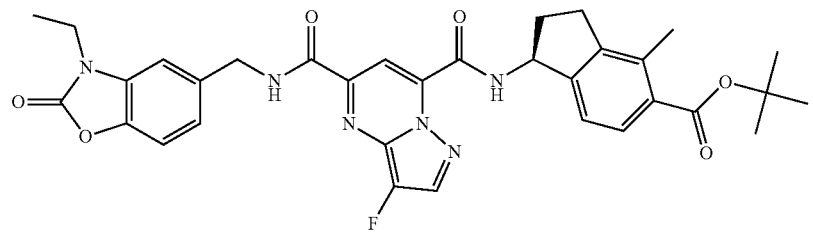 [SMILES: CCn1c(=O)oc2ccc(CNC(=O)c3cc(C(=O)N[C@H]4CCc5c4ccc(C(=O)OC(C)(C)C)c5C)n4ncc(F)c4n3)cc21]
1951
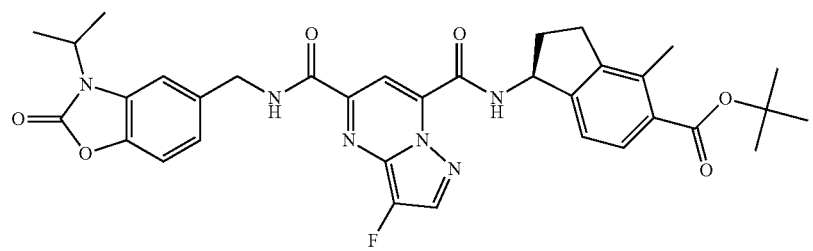 [SMILES: Cc1c(C(=O)OC(C)(C)C)ccc2c1CC[C@@H]2NC(=O)c1cc(C(=O)NCc2ccc3oc(=O)n(C(C)C)c3c2)nc2c(F)cnn12]

TABLE II-43-continued

| Ex. # | product | method, yield |
|---|---|---|
| 1952 | | |
| 1953 | | |
| 1954 | | |
| 1886 | | A, 95% [M − H]⁻ = 478 |
| 1887 | | A, 77% [M − H]⁻ = 388 |
| 1888 | | A, 16% (over 2 steps) [M − H]⁻ = 464 |
| 1889 | | A, 62% [M − H]⁻ = 450 |

TABLE II-43-continued
| 1890 | 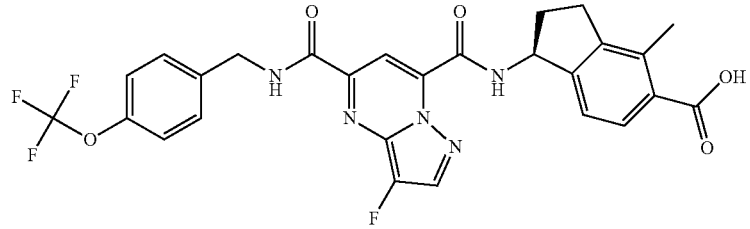 [SMILES: Cc1c(C(=O)O)ccc2c1CC[C@@H]2NC(=O)c1cc(C(=O)NCc2ccc(OC(F)(F)F)cc2)nc2c(F)cnn12] | A, >99%<br>[MH]⁺ = 554 |
|---|---|---|
| 1891 | 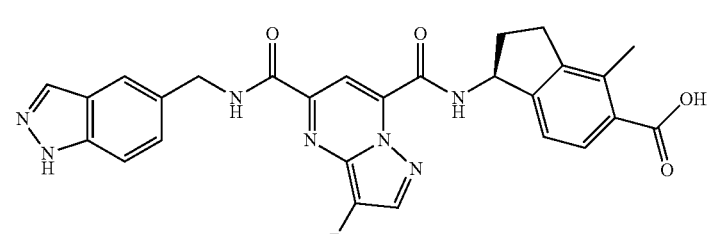 | A, >99%<br>[MH]⁺ = 528 |
| 1892 | 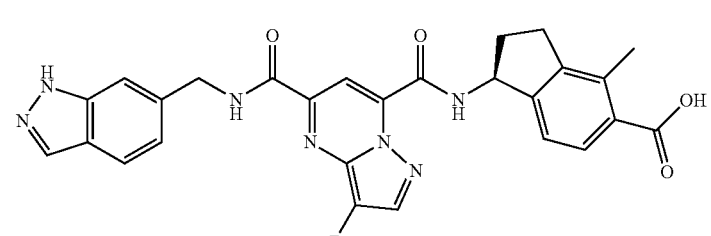 | A, >99%<br>[MH]⁺ = 528 |
| 1893 | 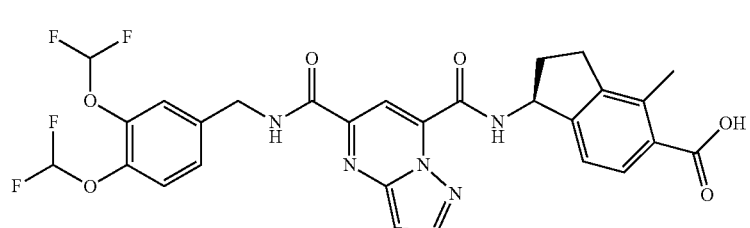 | A, >99%<br>[MH]⁺ = 620 |
| 1894 | 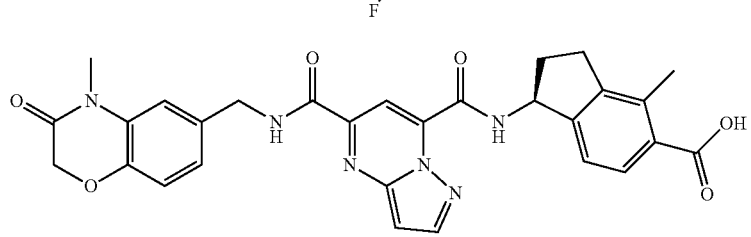 | A, >99%<br>[MH]⁺ = 555 |
| 1895 | 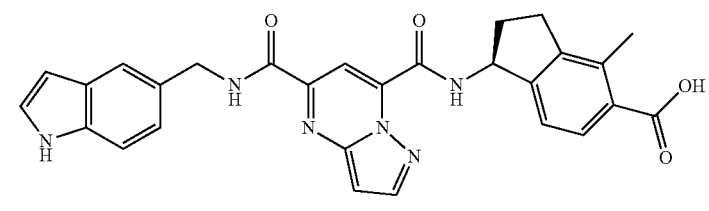 [SMILES: Cc1c(C(=O)O)ccc2c1CC[C@@H]2NC(=O)c1cc(C(=O)NCc2ccc3[nH]ccc3c2)nc2ccnn12] | A, 6%<br>(over 2 steps)<br>[MH]⁺ = 509 |
| 1896 | 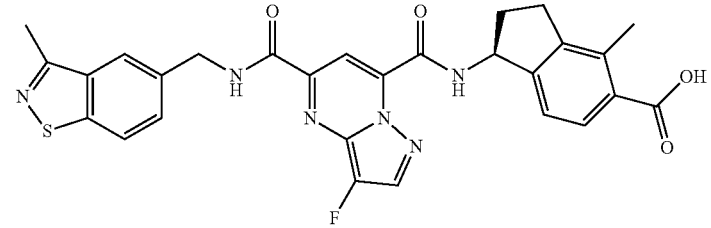 [SMILES: Cc1c(C(=O)O)ccc2c1CC[C@@H]2NC(=O)c1cc(C(=O)NCc2ccc3snc(C)c3c2)nc2c(F)cnn12] | A, >99%<br>[MH]⁺ = 559 |

TABLE II-43-continued
| 1897 | 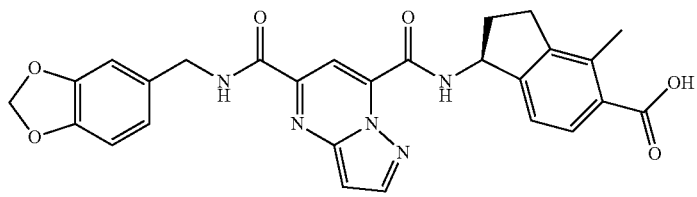 [SMILES: Cc1c(C(=O)O)ccc2c1CC[C@@H]2NC(=O)c1cc(C(=O)NCc2ccc3c(c2)OCO3)nc2ccnn12] | A, 99%<br>[MH]+ = 514 |
| --- | --- | --- |
| 1898 | 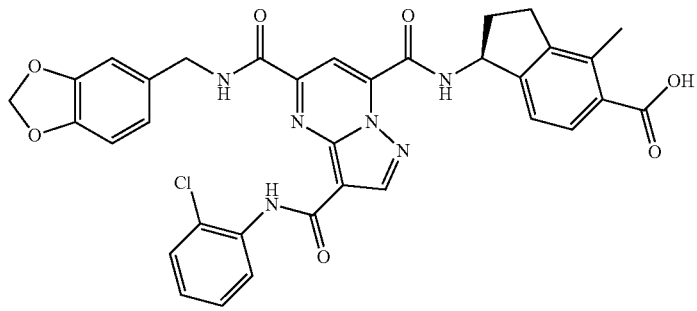 [SMILES: Cc1c(C(=O)O)ccc2c1CC[C@@H]2NC(=O)c1cc(C(=O)NCc2ccc3c(c2)OCO3)nc2c(C(=O)Nc3ccccc3Cl)cnn12] | A, 94%<br>[M − H]− = 665 |
| 1899 | 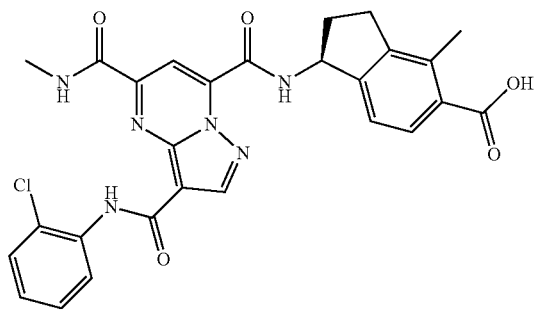 [SMILES: CNC(=O)c1cc(C(=O)N[C@H]2CCc3c2ccc(C(=O)O)c3C)n2ncc(C(=O)Nc3ccccc3Cl)c2n1] | A, >99%<br>[M − H]− = 601 |
| 1900 | 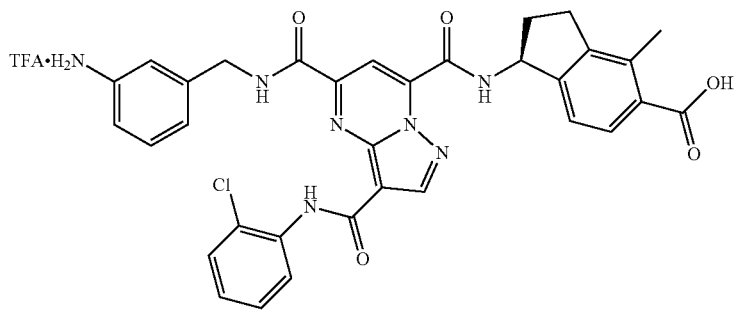 | A, >99%<br>[M − (TFA + H)]− = 636 |
| 1901 | 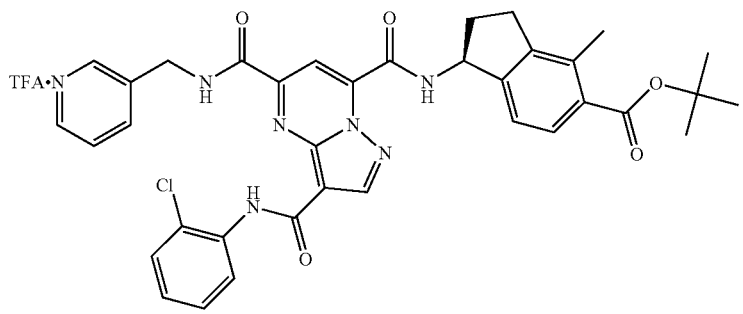 | A, >99%<br>[M − (TFA + H)]− = 622 |

TABLE II-43-continued
| 1902 | 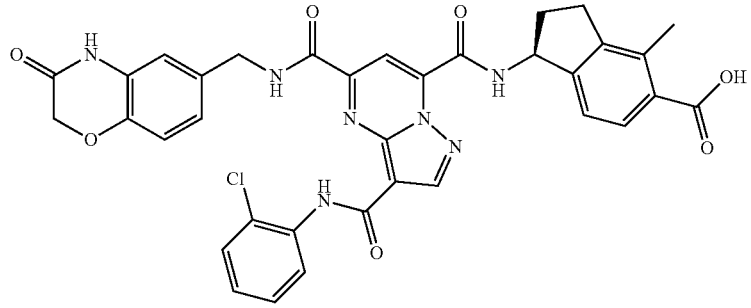 [SMILES: Cc1c(C(=O)O)ccc2c1CC[C@@H]2NC(=O)c1cc(C(=O)NCc2ccc3c(c2)NC(=O)CO3)nc2c(C(=O)Nc3ccccc3Cl)cnn12] | A, >99% [M − H]⁻ = 692 |
| 1903 | 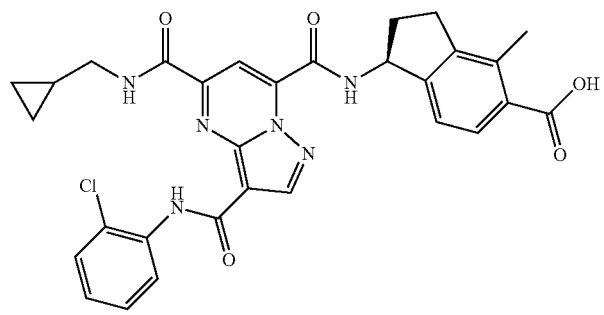 [SMILES: Cc1c(C(=O)O)ccc2c1CC[C@@H]2NC(=O)c1cc(C(=O)NCC2CC2)nc2c(C(=O)Nc3ccccc3Cl)cnn12] | A, >99% [M − H]⁻ = 585 |
| 1904 | 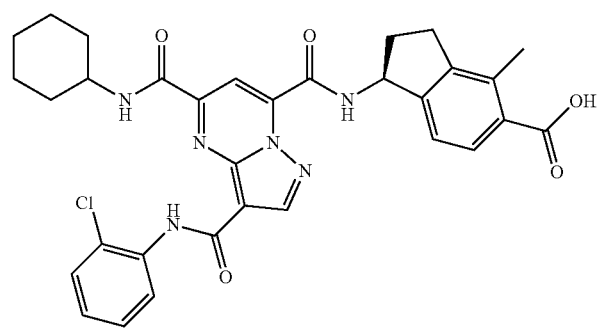 [SMILES: Cc1c(C(=O)O)ccc2c1CC[C@@H]2NC(=O)c1cc(C(=O)NC2CCCCC2)nc2c(C(=O)Nc3ccccc3Cl)cnn12] | A, >99% [M − H]⁻ = 613 |
| 1905 | 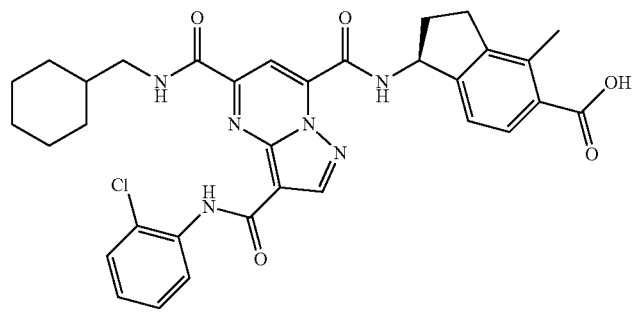 [SMILES: Cc1c(C(=O)O)ccc2c1CC[C@@H]2NC(=O)c1cc(C(=O)NCC2CCCCC2)nc2c(C(=O)Nc3ccccc3Cl)cnn12] | A, 94% [M − H]⁻ = 627 |
| 1906 | 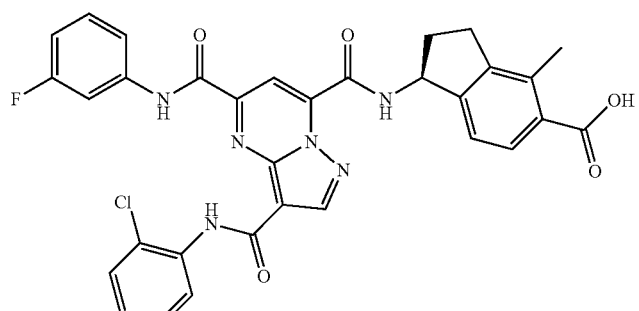 | A, >99% [M − H]⁻ = 625 |

TABLE II-43-continued
| 1907 | 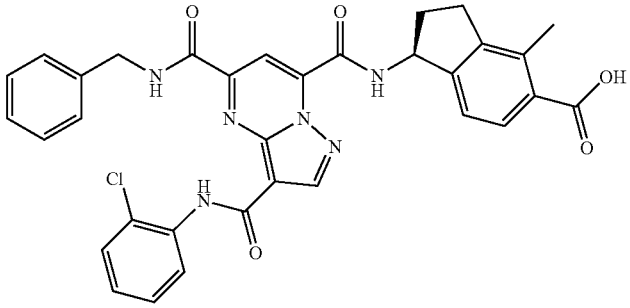 [SMILES: Cc1c(C(=O)O)ccc2c1CC[C@@H]2NC(=O)c1cc(C(=O)NCc2ccccc2)nc2c(C(=O)Nc3ccccc3Cl)cnn12] | A, 86% [M − H]⁻ = 621 |
| 1908 | 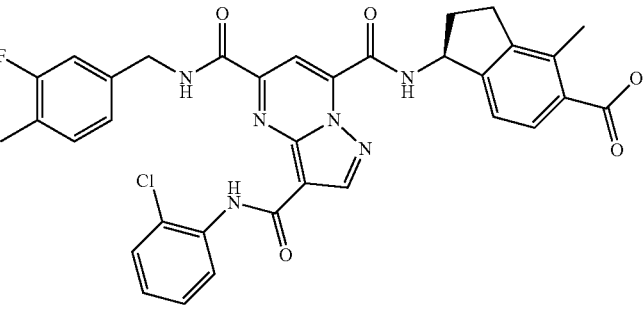 | A, 79% [M − H]⁻ = 653 |
| 1909 | 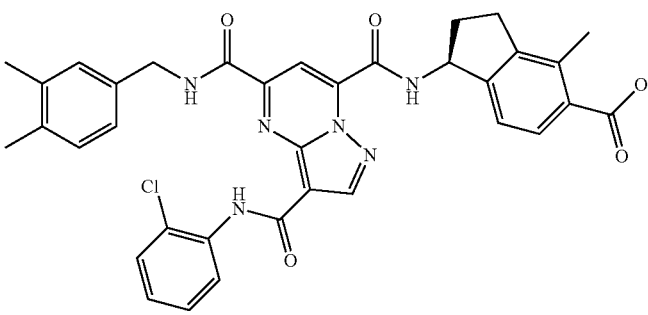 | A, 68% [M − H]⁻ = 649 |
| 1910 | 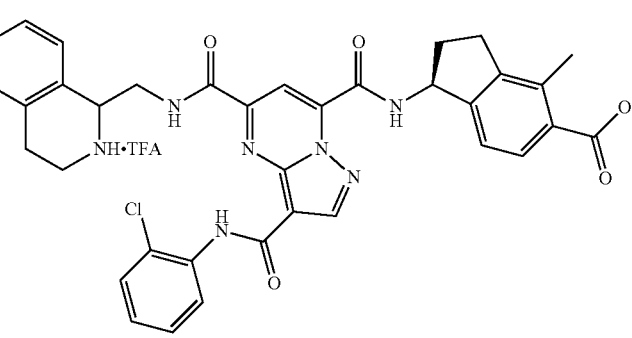 | A, >99% [M − (TFA + H)]⁻ = 676 |
| 1911 | 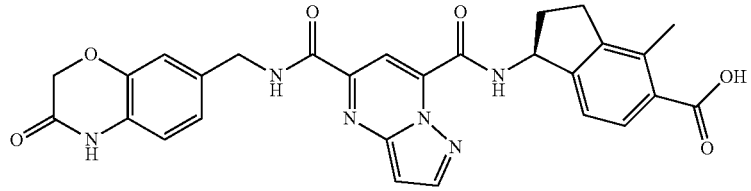 [SMILES: Cc1c(C(=O)O)ccc2c1CC[C@@H]2NC(=O)c1cc(C(=O)NCc2ccc3c(c2)OCC(=O)N3)nc2ccnn12] | A, 98% [MH]⁺ = 541 |

TABLE II-43-continued

| # | Structure | Data |
|---|---|---|
| 1912 | (structure) | A, 89%<br>[MH]⁺ = 518 |
| 1913 | (structure) | A, 13%<br>[MH]⁺ = 511 |
| 1914 | (structure) | A, 12%<br>(over 2 steps)<br>[MH]⁺ = 536 |
| 1915 | (structure) | A, 18%<br>(over 2 steps)<br>[MH]⁺ = 555 |
| 1916 | (structure) | B, 73%<br>[MH]⁺ = 443 |
| 1917 | (structure) | B, 87%<br>[MH]⁺ = 457 |
| 1918 | (structure) | B, 59%<br>[MH]⁺ = 457 |

TABLE II-43-continued

| # | Structure | Data |
|---|---|---|
| 1919 | 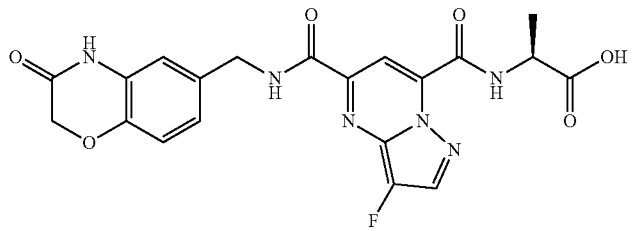 [SMILES: C[C@H](NC(=O)c1cc(C(=O)NCc2ccc3c(c2)NC(=O)CO3)nc2c(F)cnn12)C(=O)O] | B, 80%<br>[MH]⁺ = 457 |
| 1920 | 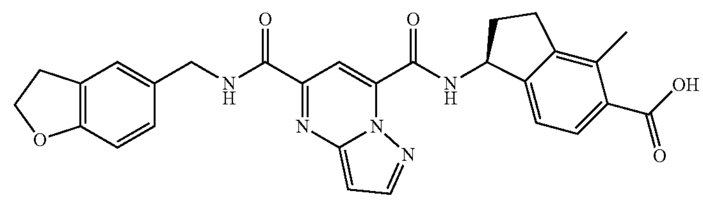 [SMILES: Cc1c(C(=O)O)ccc2c1CC[C@@H]2NC(=O)c1cc(C(=O)NCc2ccc3c(c2)CCO3)nc2ccnn12] | B, 74%<br>[MH]⁺ = 512 |
| 1921 | 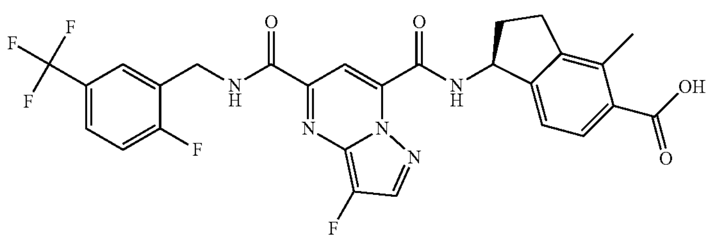 [SMILES: Cc1c(C(=O)O)ccc2c1CC[C@@H]2NC(=O)c1cc(C(=O)NCc2cc(C(F)(F)F)ccc2F)nc2c(F)cnn12] | B, 59%<br>(over 2 steps)<br>[MH]⁺ = 574 |
| 1922 | 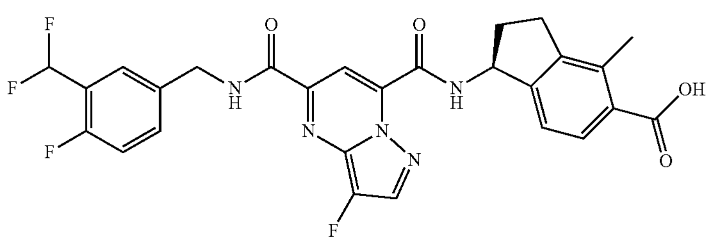 [SMILES: Cc1c(C(=O)O)ccc2c1CC[C@@H]2NC(=O)c1cc(C(=O)NCc2ccc(F)c(C(F)F)c2)nc2c(F)cnn12] | B, 56%<br>(over 2 steps)<br>[MH]⁺ = 556 |
| 1923 | 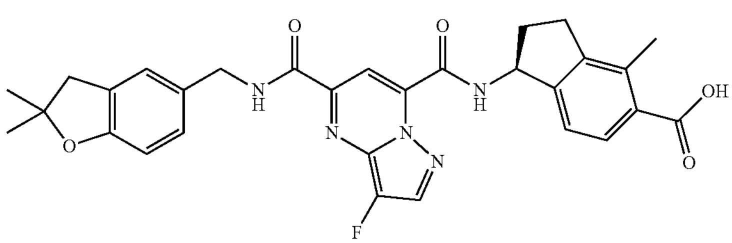 [SMILES: Cc1c(C(=O)O)ccc2c1CC[C@@H]2NC(=O)c1cc(C(=O)NCc2ccc3c(c2)CC(C)(C)O3)nc2c(F)cnn12] | B, 34%<br>(over 2 steps)<br>[MH]⁺ = 558 |
| 1924 | 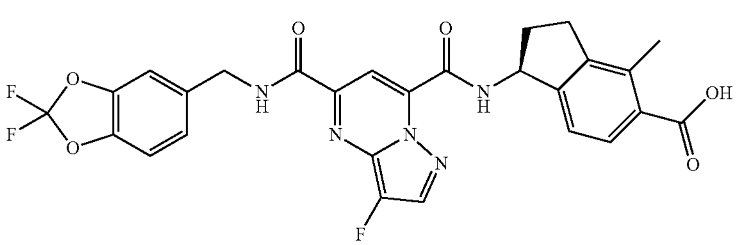 [SMILES: Cc1c(C(=O)O)ccc2c1CC[C@@H]2NC(=O)c1cc(C(=O)NCc2ccc3c(c2)OC(F)(F)O3)nc2c(F)cnn12] | B, 53%<br>(over 2 steps)<br>[MH]⁺ = 568 |

TABLE II-43-continued
| | | |
|---|---|---|
| 1925 | 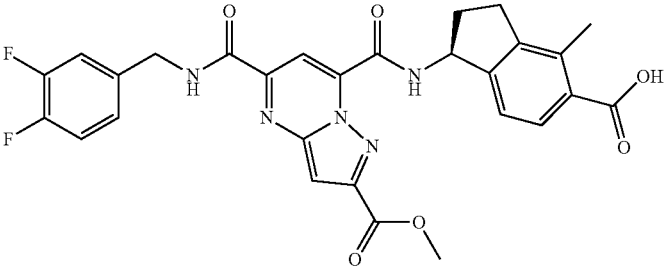 [SMILES: COC(=O)c1cc2nc(C(=O)NCc3ccc(F)c(F)c3)cc(C(=O)N[C@H]3CCc4c3ccc(C(=O)O)c4C)n2n1] | A, 99%<br>[MH]⁺ = 564 |
| 1926 | 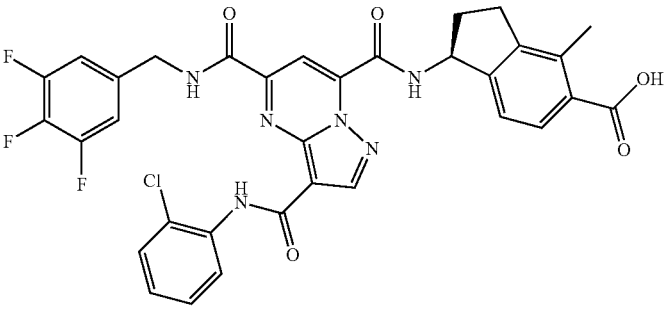 [SMILES: Cc1c(C(=O)O)ccc2c1CC[C@@H]2NC(=O)c1cc(C(=O)NCc2cc(F)c(F)c(F)c2)nc2c(C(=O)Nc3ccccc3Cl)cnn12] | A, n.d.<br>[MH]⁺ = 675 |
| 1927 | 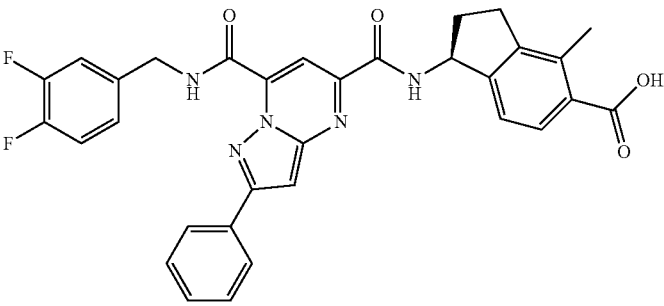 [SMILES: Cc1c(C(=O)O)ccc2c1CC[C@@H]2NC(=O)c1cc(C(=O)NCc2ccc(F)c(F)c2)n2nc(-c3ccccc3)cc2n1] | A, 78%<br>[M − H]⁻ = 580 |
| 1928 | 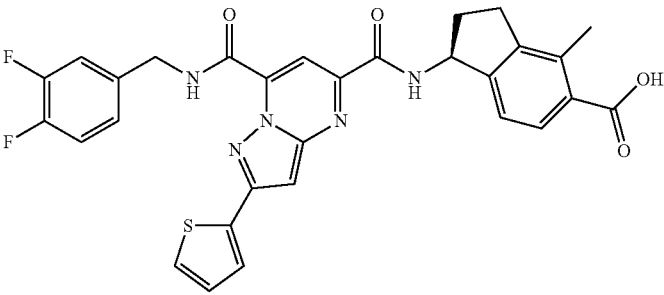 [SMILES: Cc1c(C(=O)O)ccc2c1CC[C@@H]2NC(=O)c1cc(C(=O)NCc2ccc(F)c(F)c2)n2nc(-c3cccs3)cc2n1] | A, 78%<br>[M − H]⁻ = 586 |
| 1929 | 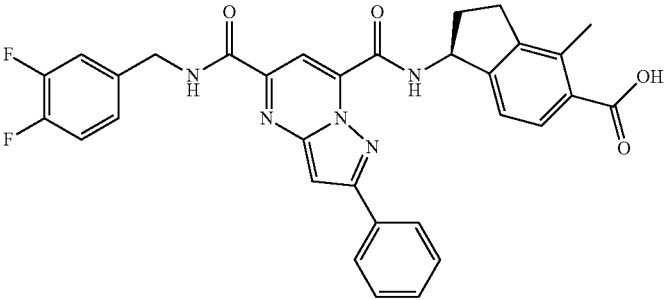 [SMILES: Cc1c(C(=O)O)ccc2c1CC[C@@H]2NC(=O)c1cc(C(=O)NCc2ccc(F)c(F)c2)nc2cc(-c3ccccc3)nn12] | A, 68%<br>[M − H]⁻ = 580 |

TABLE II-43-continued
| | | |
|---|---|---|
| 1930 | 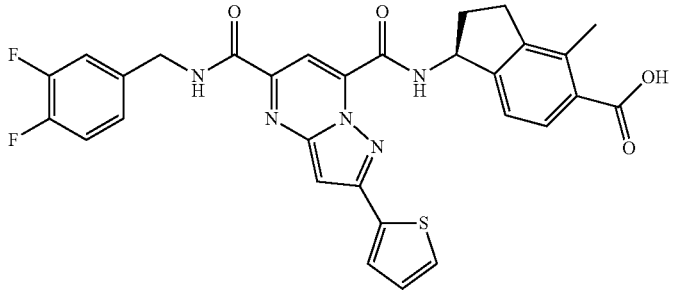 [SMILES: Cc1c(C(=O)O)ccc2c1CC[C@@H]2NC(=O)c1cc(C(=O)NCc2ccc(F)c(F)c2)nc2cc(-c3cccs3)nn12] | A, 62%<br>[M − H]⁻ = 586 |
| 1931 | 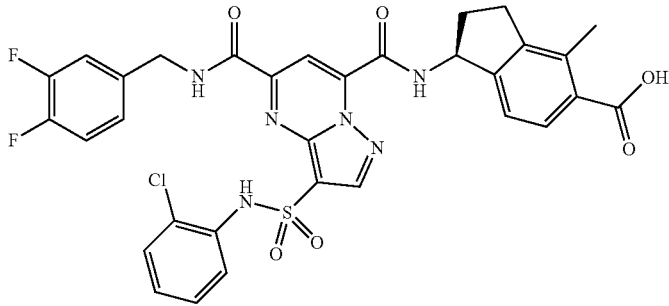 [SMILES: Cc1c(C(=O)O)ccc2c1CC[C@@H]2NC(=O)c1cc(C(=O)NCc2ccc(F)c(F)c2)nc2c(S(=O)(=O)Nc3ccccc3Cl)cnn12] | A, 25%<br>[M − H]⁻ = 693 |
| 1932 | 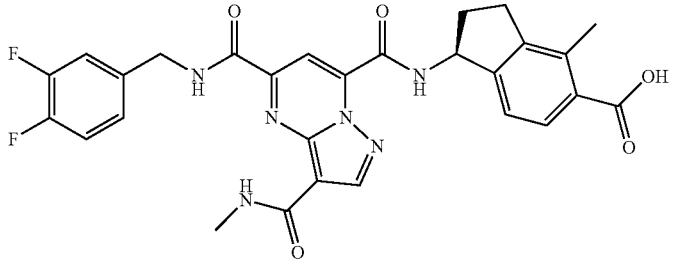 [SMILES: CNC(=O)c1cnn2c(C(=O)N[C@H]3CCc4c3ccc(C(=O)O)c4C)cc(C(=O)NCc3ccc(F)c(F)c3)nc12] | A, 99%<br>[M − H]⁻ = 561 |
| 1933 | 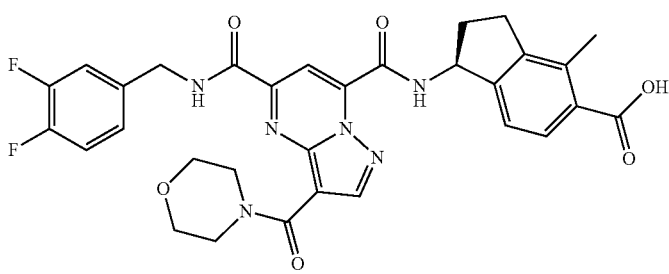 [SMILES: Cc1c(C(=O)O)ccc2c1CC[C@@H]2NC(=O)c1cc(C(=O)NCc2ccc(F)c(F)c2)nc2c(C(=O)N3CCOCC3)cnn12] | A, 82%<br>[M − H]⁻ = 617 |
| 1934 | 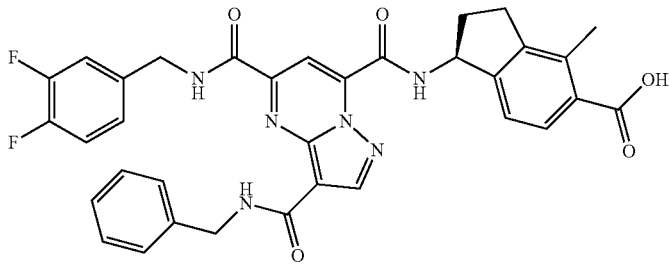 [SMILES: Cc1c(C(=O)O)ccc2c1CC[C@@H]2NC(=O)c1cc(C(=O)NCc2ccc(F)c(F)c2)nc2c(C(=O)NCc3ccccc3)cnn12] | A, 99%<br>[M − H]⁻ = 637 |

TABLE II-43-continued
1935 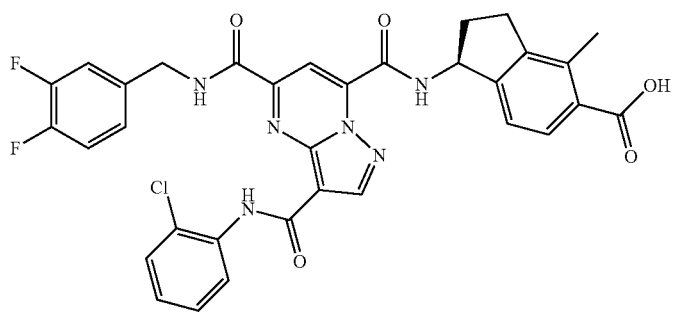 A, 99%
[M − H]⁻ = 657
1936 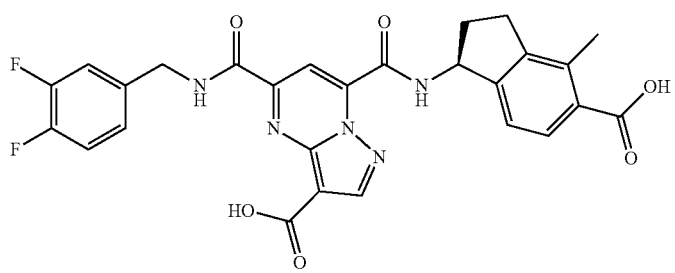 [SMILES: Cc1c(C(=O)O)ccc2c1CC[C@@H]2NC(=O)c1cc(C(=O)NCc2ccc(F)c(F)c2)nc2c(C(=O)O)cnn12] A, 99%
[M − H]⁻ = 548
1937 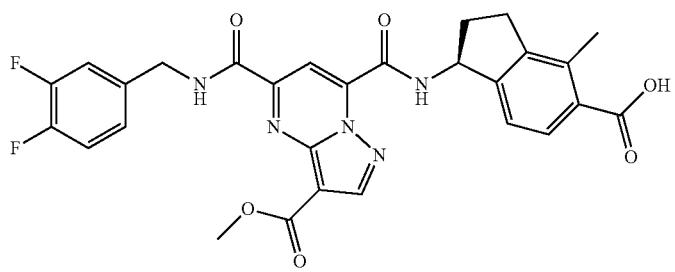 [SMILES: COC(=O)c1cnn2c(C(=O)N[C@H]3CCc4c3ccc(C(=O)O)c4C)cc(C(=O)NCc3ccc(F)c(F)c3)nc12] A, 99%
[M − H]⁻ = 562
1938 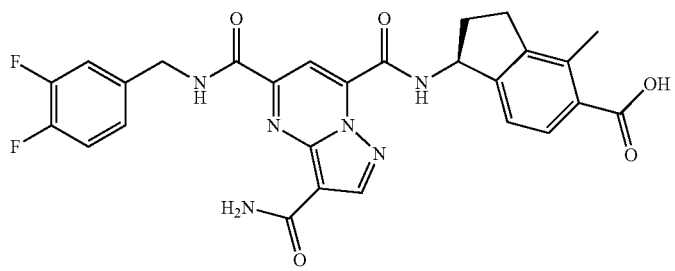 [SMILES: Cc1c(C(=O)O)ccc2c1CC[C@@H]2NC(=O)c1cc(C(=O)NCc2ccc(F)c(F)c2)nc2c(C(N)=O)cnn12] A, 99%
[M − H]⁻ = 547
1939 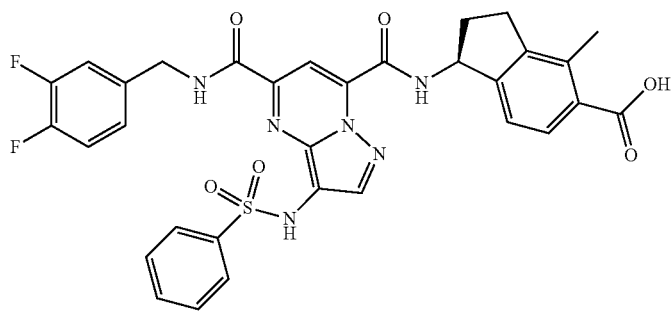 [SMILES: Cc1c(C(=O)O)ccc2c1CC[C@@H]2NC(=O)c1cc(C(=O)NCc2ccc(F)c(F)c2)nc2c(NS(=O)(=O)c3ccccc3)cnn12] A, 63%
[M − H]⁻ = 659

TABLE II-43-continued

| # | Structure | Result |
|---|---|---|
| 1940 | 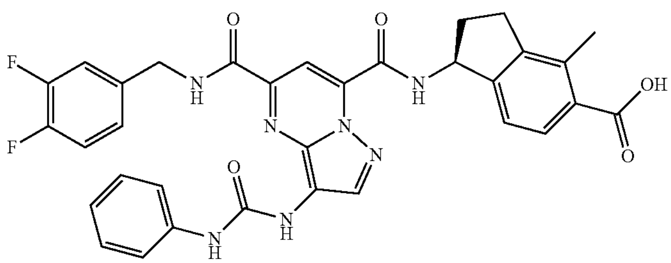 [SMILES: Cc1c(C(=O)O)ccc2c1CC[C@@H]2NC(=O)c1cc(C(=O)NCc2ccc(F)c(F)c2)nc2c(NC(=O)Nc3ccccc3)cnn12] | A, 94% [M − H]⁻ = 638 |
| 1941 | 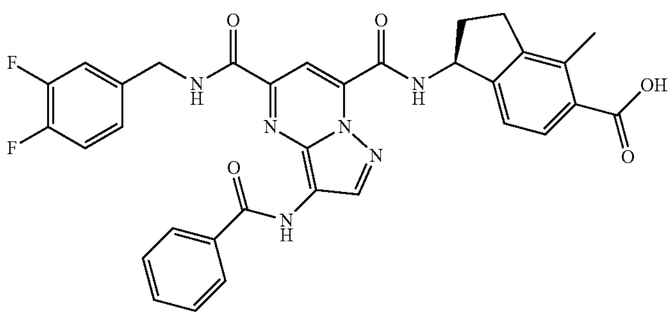 [SMILES: Cc1c(C(=O)O)ccc2c1CC[C@@H]2NC(=O)c1cc(C(=O)NCc2ccc(F)c(F)c2)nc2c(NC(=O)c3ccccc3)cnn12] | A, n.d. [M − H]⁻ = 623 |
| 1942 | 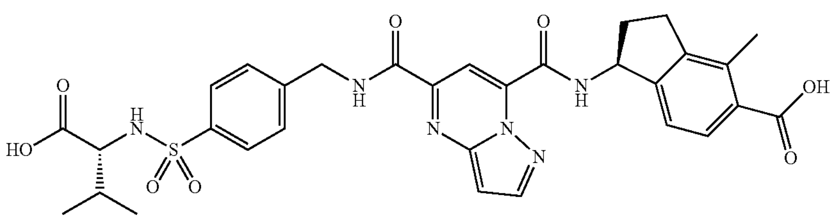 [SMILES: Cc1c(C(=O)O)ccc2c1CC[C@@H]2NC(=O)c1cc(C(=O)NCc2ccc(S(=O)(=O)N[C@@H](C(=O)O)C(C)C)cc2)nc2ccnn12] | B, 46% [MH]⁺ = 649 |
| 1943 | 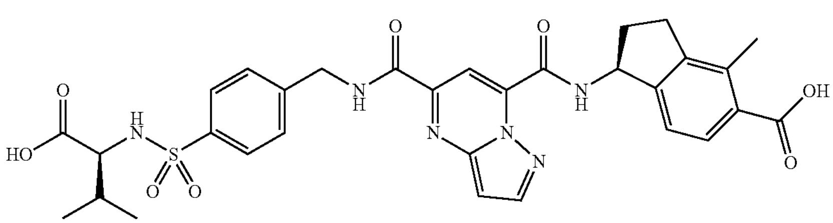 [SMILES: Cc1c(C(=O)O)ccc2c1CC[C@@H]2NC(=O)c1cc(C(=O)NCc2ccc(S(=O)(=O)N[C@H](C(=O)O)C(C)C)cc2)nc2ccnn12] | B, 53% [MH]⁺ = 649 |
| 1944 | 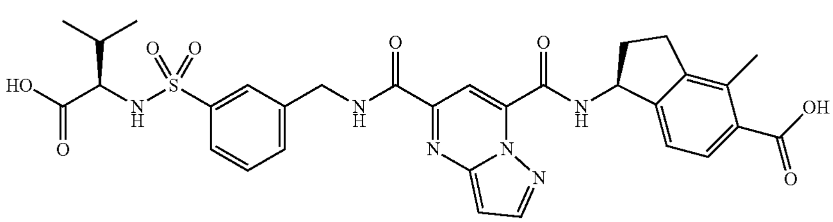 [SMILES: Cc1c(C(=O)O)ccc2c1CC[C@@H]2NC(=O)c1cc(C(=O)NCc2cccc(S(=O)(=O)N[C@@H](C(=O)O)C(C)C)c2)nc2ccnn12] | B, 39% [MH]⁺ = 649 |
| 1945 | 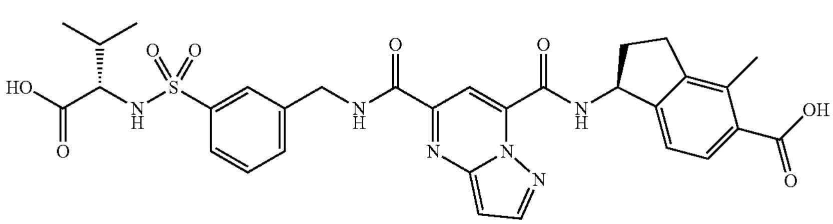 [SMILES: Cc1c(C(=O)O)ccc2c1CC[C@@H]2NC(=O)c1cc(C(=O)NCc2cccc(S(=O)(=O)N[C@H](C(=O)O)C(C)C)c2)nc2ccnn12] | B, 52% [MH]⁺ = 649 |

TABLE II-43-continued
| | | |
|---|---|---|
| 1946 | 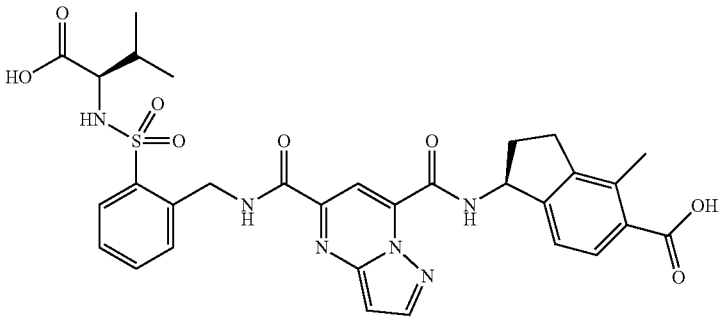 [SMILES: Cc1c(C(=O)O)ccc2c1CC[C@@H]2NC(=O)c1cc(C(=O)NCc2ccccc2S(=O)(=O)N[C@@H](C(=O)O)C(C)C)nc2ccnn12] | B, 62%<br>[MH]+ = 649 |
| 1947 | 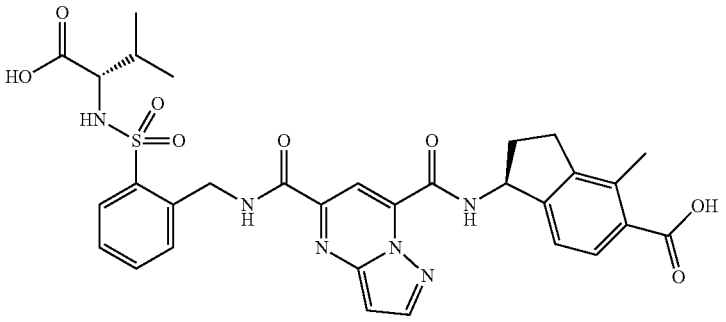 [SMILES: Cc1c(C(=O)O)ccc2c1CC[C@@H]2NC(=O)c1cc(C(=O)NCc2ccccc2S(=O)(=O)N[C@H](C(=O)O)C(C)C)nc2ccnn12] | B, 57%<br>[MH]+ = 649 |
| 1948 | 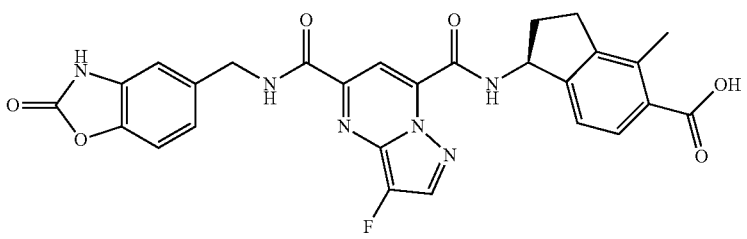 [SMILES: Cc1c(C(=O)O)ccc2c1CC[C@@H]2NC(=O)c1cc(C(=O)NCc2ccc3oc(=O)[nH]c3c2)nc2c(F)cnn12] | A, 99%<br>[MH]+ = 545 |
| 1949 | 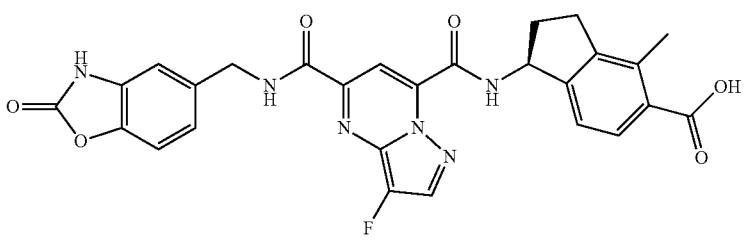 [SMILES: Cc1c(C(=O)O)ccc2c1CC[C@@H]2NC(=O)c1cc(C(=O)NCc2ccc3oc(=O)[nH]c3c2)nc2c(F)cnn12] | A, 90%<br>[MH]+ = 559 |
| 1950 | 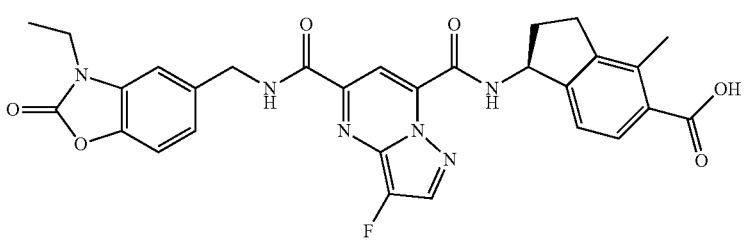 [SMILES: CCn1c(=O)oc2ccc(CNC(=O)c3cc(C(=O)N[C@H]4CCc5c4ccc(C(=O)O)c5C)n4ncc(F)c4n3)cc21] | A, 48%<br>[MH]+ = 573 |
| 1951 | 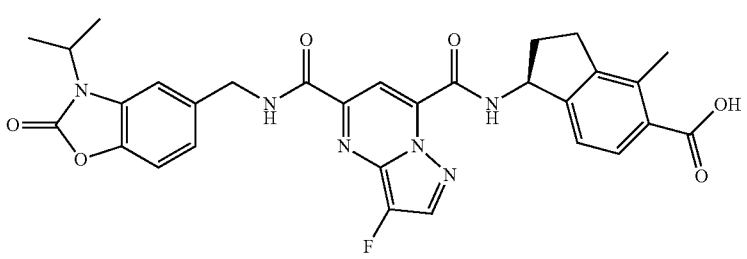 [SMILES: Cc1c(C(=O)O)ccc2c1CC[C@@H]2NC(=O)c1cc(C(=O)NCc2ccc3oc(=O)n(C(C)C)c3c2)nc2c(F)cnn12] | A, 34%<br>[MH]+ = 587 |

TABLE II-43-continued

| 1952 | [structure] | A, 90% [MH]+ = 563 |
| 1953 | [structure] | A, 99% [MH]+ = 599 |
| 1954 | [structure] | B, n.d. [MH]+ = 587 |

Example 1955

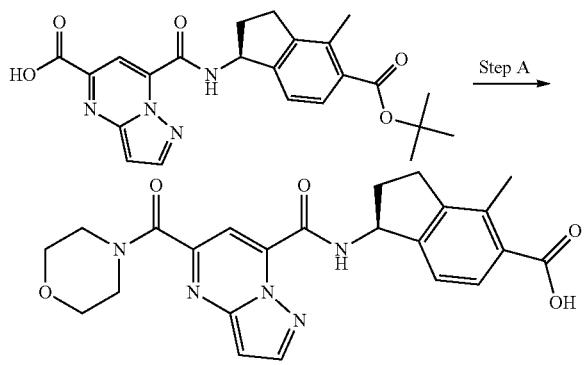

Step A

To a mixture of N-cyclohexyl-carbodiimide-N'-methyl-polystyrene (30 mg) in DMA (340 µL) were added a 0.2M solution of the title compound from the Preparative Example 337 in DMA (85 µL) and a 0.5M solution of HOBt in DMA (45 µL). The mixture was agitated for 15 min, then a 0.5M solution of morpholine in DMA (30 µL) was added and the mixture was heated in a sealed tube at 100° C. (microwave) for 5 min. (Plystyrylmethyl)-trimethylammonium bicarbonate (20 mg) was added and the mixture was agitated at room temperature for 3 h. Then the mixture was filtered, concentrated, diluted with formic acid (100 µL) and stirred at room temperature for 5 h. Concentration afforded the title compound as a pale yellow solid, which was used without further purification. [MH]+=450.

Examples 1956-2138

Following a similar procedure as described in the Example 1955, except using amines indicated in Table II-44 below, the following compounds were prepared.

TABLE II-44

| Ex. # | amine | product | yield |
|---|---|---|---|
| 1956 | [structure: H2N-CH2-CH(OH)-CH3] | [structure] | n.d. [MH]+ = 438 |

TABLE II-44-continued

| Ex. # | amine | product | yield |
|---|---|---|---|
| 1957 | piperonylamine (1,3-benzodioxol-5-ylmethanamine) | [structure] | n.d. [MH]+ = 514 |
| 1958 | isoamylamine (3-methylbutan-1-amine) | [structure] | n.d. [MH]+ = 550 |
| 1959 | furan-3-ylmethanamine | [structure] | n.d. [MH]+ = 460 |
| 1960 | (4-methoxyphenyl)methanamine | [structure] | n.d. [MH]+ = 500 |
| 1961 | (4-fluorophenyl)methanamine | [structure] | n.d. [MH]+ = 488 |
| 1962 | cyclopropylmethanamine | [structure] | n.d. [MH]+ = 434 |
| 1963 | (3-fluorophenyl)methanamine | [structure] | n.d. [MH]+ = 488 |
| 1964 | dicyclohexylamine | [structure] | n.d. [MH]+ = 544 |
| 1965 | piperidine | [structure] | n.d. [MH]+ = 448 |

TABLE II-44-continued

| Ex. # | amine | product | yield |
|---|---|---|---|
| 1966 | 3-aminopentane (H2N-CH(Et)2) | *sec*-pentyl amide product | n.d. [MH]+ = 450 |
| 1967 | isopropylamine | isopropyl amide product | n.d. [MH]+ = 422 |
| 1968 | cyclopentylamine | cyclopentyl amide product | n.d. [MH]+ = 448 |
| 1969 | benzylamine | benzyl amide product | n.d. [MH]+ = 470 |
| 1970 | cyclohexylmethylamine | cyclohexylmethyl amide product | n.d. [MH]+ = 476 |
| 1971 | L-valinamide·HCl | valinamide product | n.d. [MH]+ = 478 |
| 1972 | dimethylamine·HCl | N,N-dimethyl amide product | n.d. [MH]+ = 408 |
| 1973 | cyclohexylamine·HCl | cyclohexyl amide product | n.d. [MH]+ = 462 |

TABLE II-44-continued
| Ex. # | amine | product | yield |
|---|---|---|---|
| 1974 | 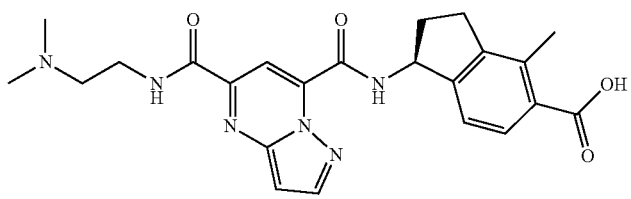 [SMILES: Cc1c(C(=O)O)ccc2c1CC[C@@H]2NC(=O)c1cc(C(=O)NCCN(C)C)nc2ccnn12] | 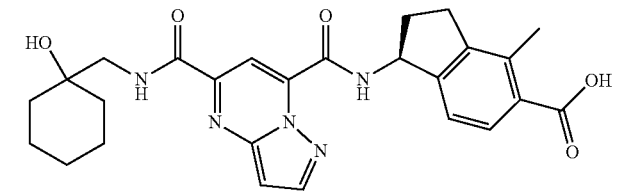 [SMILES: Cc1c(C(=O)O)ccc2c1CC[C@@H]2NC(=O)c1cc(C(=O)NCC2(O)CCCCC2)nc2ccnn12] | n.d. [MH]+ = 451 |
| 1975 | 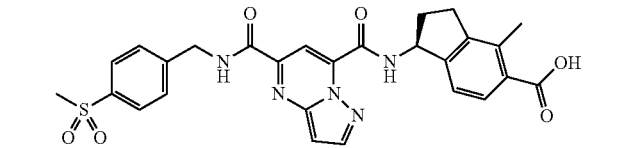 [SMILES: Cc1c(C(=O)O)ccc2c1CC[C@@H]2NC(=O)c1cc(C(=O)NCc2ccc(S(C)(=O)=O)cc2)nc2ccnn12] | 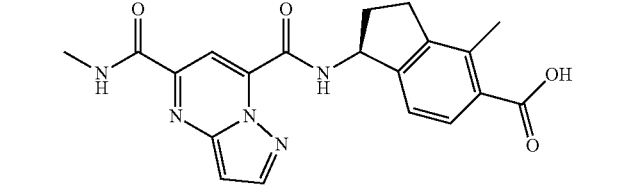 [SMILES: CNC(=O)c1cc(C(=O)N[C@H]2CCc3c2ccc(C(=O)O)c3C)n2nccc2n1] | n.d. [MH]+ = 492 |
| 1976 | 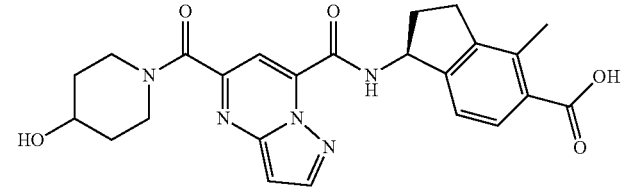 [SMILES: Cc1c(C(=O)O)ccc2c1CC[C@@H]2NC(=O)c1cc(C(=O)N2CCC(O)CC2)nc2ccnn12] | 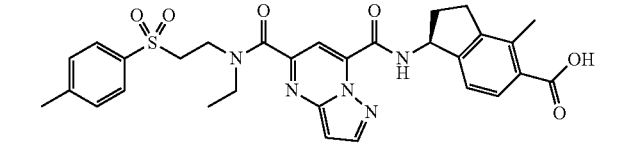 [SMILES: CCN(CCS(=O)(=O)c1ccc(C)cc1)C(=O)c1cc(C(=O)N[C@H]2CCc3c2ccc(C(=O)O)c3C)n2nccc2n1] | n.d. [MH]+ = 548 |
| 1977 | HCl·H2N— | 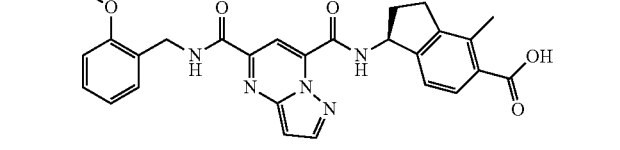 | n.d. [MH]+ = 394 |
| 1978 | 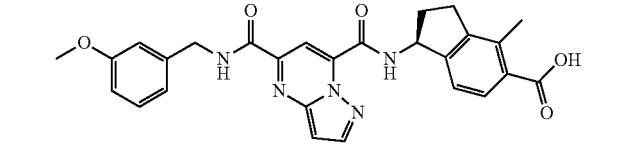 [SMILES: COc1cccc(CNC(=O)c2cc(C(=O)N[C@H]3CCc4c3ccc(C(=O)O)c4C)n3nccc3n2)c1] | | n.d. [MH]+ = 464 |
| 1979 | | | n.d. [MH]+ = 590 |
| 1980 | | | n.d. [MH]+ = 500 |
| 1981 | | | n.d. [MH]+ = 500 |

TABLE II-44-continued

| Ex. # | amine | product | yield |
|---|---|---|---|
| 1982 | (N-methylbenzylamine) | (product structure) | n.d. [MH]+ = 484 |
| 1983 | (N-ethylbutylamine) | (product structure) | n.d. [MH]+ = 464 |
| 1984 | (dipropylamine) | (product structure) | n.d. [MH]+ = 464 |
| 1985 | (N-ethylbenzylamine) | (product structure) | n.d. [MH]+ = 498 |
| 1986 | (2,5-diazabicyclic amine) | (product structure) | n.d. [MH]+ = 461 |
| 1987 | (2-amino-2-methyl-1-propanol) | (product structure) | n.d. [MH]+ = 452 |
| 1988 | (methyl 4-hydroxyprolinate HCl) | (product structure) | n.d. [MH]+ = 508 |
| 1989 | (decahydroisoquinoline) | (product structure) | n.d. [MH]+ = 502 |
| 1990 | (1-methylpiperazine) | (product structure) | n.d. [MH]+ = 463 |

TABLE II-44-continued

| Ex. # | amine | product | yield |
|---|---|---|---|
| 1991 | (piperidine-4-carboxylic acid ethyl ester) | (product structure) | n.d. [MH]+ = 520 |
| 1992 | (2-(benzylamino)cyclohexanol) | (product structure) | n.d. [MH]+ = 568 |
| 1993 | (threoninamide HCl) | (product structure) | n.d. [MH]+ = 481 |
| 1994 | (1-amino-2-indanol) | (product structure) | n.d. [MH]+ = 512 |
| 1995 | (thiazolidine-2-carboxylic acid methyl ester HCl) | (product structure) | n.d. [MH]+ = 510 |
| 1996 | (glycinamide HCl) | (product structure) | n.d. [MH]+ = 437 |
| 1997 | (3-(aminomethyl)pyridine) | (product structure) | n.d. [MH]+ = 471 |
| 1998 | ((R)-1-phenylethylamine) | (product structure) | n.d. [MH]+ = 484 |
| 1999 | ((S)-1-phenylethylamine) | (product structure) | n.d. [MH]+ = 484 |

TABLE II-44-continued

| Ex. # | amine | product | yield |
|---|---|---|---|
| 2000 | (piperazin-2-one) | (product structure) | n.d. [MH]+ = 463 |
| 2001 | (ethyl 2-(3-oxopiperazin-2-yl)acetate) | (product structure) | n.d. [MH]+ = 549 |
| 2002 | (piperidine-4-thiol) | (product structure) | n.d. [MH]+ = 480 |
| 2003 | (2-methylthiazolidine) | (product structure) | n.d. [MH]+ = 466 |
| 2004 | (4-fluoro-3-methylbenzylamine) | (product structure) | n.d. [MH]+ = 502 |
| 2005 | (2-benzyl-2,5-diazabicyclo[2.2.1]heptane HCl) | (product structure) | n.d. [MH]+ = 551 |
| 2006 | (2-azabicyclo[2.2.1]heptane) | (product structure) | n.d. [MH]+ = 460 |
| 2007 | (N,N-dimethyl-1,3-propanediamine) | (product structure) | n.d. [MH]+ = 465 |
| 2008 | (propargylamine HCl) | (product structure) | n.d. [MH]+ = 418 |

TABLE II-44-continued

| Ex. # | amine | product | yield |
|---|---|---|---|
| 2009 | 4-(aminomethyl)benzenesulfonamide | (structure) | n.d. [MH]+ = 549 |
| 2010 | 3-(trifluoromethoxy)benzylamine HCl | (structure) | n.d. [MH]+ = 554 |
| 2011 | methyl 3-(aminomethyl)benzoate | (structure) | n.d. [MH]+ = 528 |
| 2012 | isoindoline | (structure) | n.d. [MH]+ = 482 |
| 2013 | 1-[bis(4-fluorophenyl)methyl]piperazine | (structure) | n.d. [MH]+ = 651 |
| 2014 | 1-adamantanemethylamine | (structure) | n.d. [MH]+ = 527.622 |
| 2015 | (S)-1-(4-fluorophenyl)ethylamine | (structure) | n.d. [MH]+ = 502 |
| 2016 | (R)-1-(4-fluorophenyl)ethylamine | (structure) | n.d. [MH]+ = 502 |
| 2017 | 4-amino-1-hydroxyadamantane | (structure) | n.d. [MH]+ = 530 |

TABLE II-44-continued

| Ex. # | amine | product | yield |
|---|---|---|---|
| 2018 | (diphenylmethylamine) | (diphenylmethyl amide product) | n.d. [MH]⁺ = 546 |
| 2019 | (phenylglycinol HCl, one enantiomer) | (corresponding amide product) | n.d. [MH]⁺ = 500 |
| 2020 | (phenylglycinol HCl, other enantiomer) | (corresponding amide product) | n.d. [MH]⁺ = 500 |
| 2021 | 3-(3-fluorophenyl)pyrrolidine HCl | (corresponding amide product) | n.d. [MH]⁺ = 528 |
| 2022 | 3-(2-fluorophenyl)pyrrolidine HCl | (corresponding amide product) | n.d. [MH]⁺ = 528 |
| 2023 | 3-(4-fluorophenyl)pyrrolidine | (corresponding amide product) | n.d. [MH]⁺ = 528 |
| 2024 | 1-amino-tetralin (one enantiomer) | (corresponding amide product) | n.d. [MH]⁺ = 510 |
| 2025 | 2-aminocyclopentane-1-carboxamide | (corresponding amide product) | n.d. [MH]⁺ = 491 |
| 2026 | 1-amino-tetralin (other enantiomer) | (corresponding amide product) | n.d. [MH]⁺ = 510 |

TABLE II-44-continued
| Ex. # | amine | product | yield |
|---|---|---|---|
| 2027 | 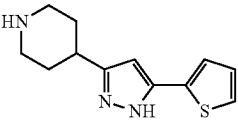 [SMILES: c1csc(-c2cc(C3CCNCC3)n[nH]2)c1] | 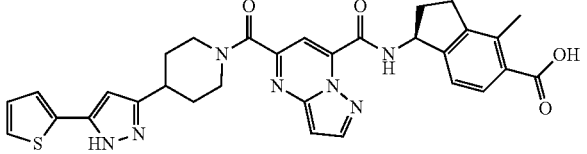 [SMILES: Cc1c(C(=O)O)ccc2c1CC[C@@H]2NC(=O)c1cc(C(=O)N2CCC(c3cc(-c4cccs4)[nH]n3)CC2)nc2ccnn12] | n.d. [MH]+ = 596 |
| 2028 | 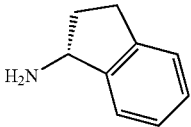 | 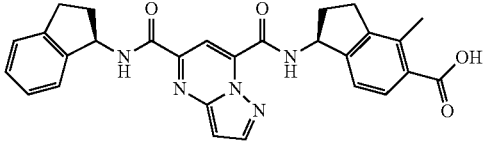 [SMILES: Cc1c(C(=O)O)ccc2c1CC[C@@H]2NC(=O)c1cc(C(=O)N[C@@H]2CCc3ccccc32)nc2ccnn12] | n.d. [MH]+ = 496 |
| 2029 | 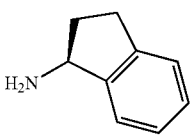 | 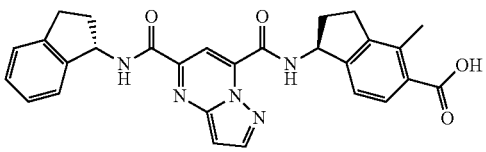 [SMILES: Cc1c(C(=O)O)ccc2c1CC[C@@H]2NC(=O)c1cc(C(=O)N[C@H]2CCc3ccccc32)nc2ccnn12] | n.d. [MH]+ = 496 |
| 2030 | 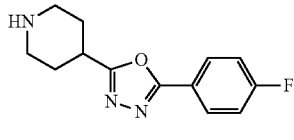 | 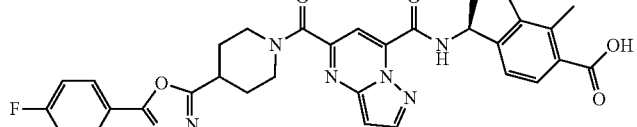 | n.d. [MH]+ = 610 |
| 2031 | 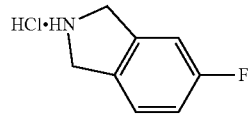 | 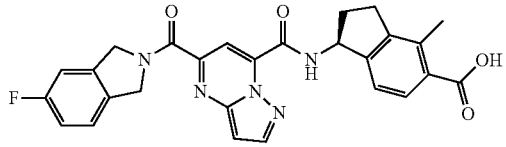 [SMILES: Cc1c(C(=O)O)ccc2c1CC[C@@H]2NC(=O)c1cc(C(=O)N2Cc3ccc(F)cc3C2)nc2ccnn12] | n.d. [MH]+ = 500 |
| 2032 |  | 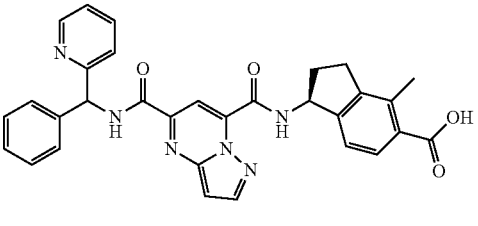 [SMILES: Cc1c(C(=O)O)ccc2c1CC[C@@H]2NC(=O)c1cc(C(=O)NC(c2ccccc2)c2ccccn2)nc2ccnn12] | n.d. [MH]+ = 547 |
| 2033 | 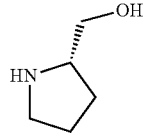 | 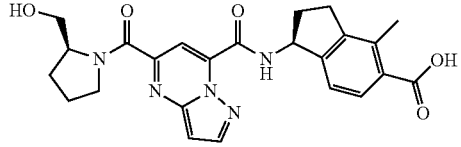 [SMILES: Cc1c(C(=O)O)ccc2c1CC[C@@H]2NC(=O)c1cc(C(=O)N2CCC[C@H]2CO)nc2ccnn12] | n.d. [MH]+ = 464 |
| 2034 | 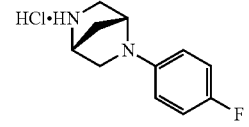 | 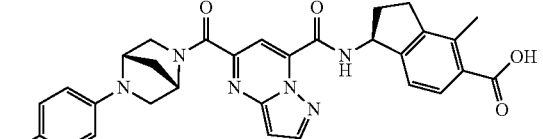 | n.d. [MH]+ = 555 |
| 2035 | 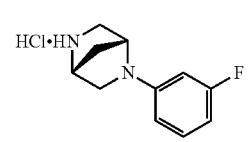 | 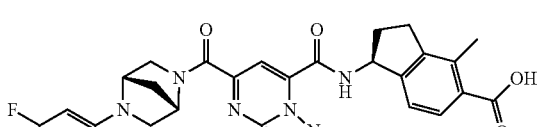 | n.d. [MH]+ = 555 |

TABLE II-44-continued

| Ex. # | amine | product | yield |
|---|---|---|---|
| 2036 | | | n.d.<br>[MH]⁺ = 511 |
| 2037 | | | n.d.<br>[MH]⁺ = 545 |
| 2038 | | | n.d.<br>[MH]⁺ = 516 |
| 2039 | | | n.d.<br>[MH]⁺ = 534 |
| 2040 | | | n.d.<br>[MH]⁺ = 492 |
| 2041 | | | n.d.<br>[MH]⁺ = 459 |
| 2042 | | | n.d.<br>[MH]⁺ = 477 |

TABLE II-44-continued

| Ex. # | amine | product | yield |
|---|---|---|---|
| 2043 | isobutylamine | isobutyl-NH-C(O)-pyrazolopyrimidine-C(O)-NH-(methyl-indanyl)-COOH | n.d. [MH]+ = 436 |
| 2044 | 2-(4-fluorophenyl)pyrrolidine | corresponding product | n.d. [MH]+ = 528 |
| 2045 | 2-(3-fluorophenyl)pyrrolidine | corresponding product | n.d. [MH]+ = 528 |
| 2046 | 7-cyano-1,2,3,4-tetrahydroisoquinoline | corresponding product | n.d. [MH]+ = 521 |
| 2047 | 4-fluoro-3-(trifluoromethoxy)benzylamine | corresponding product | n.d. [MH]+ = 572 |
| 2048 | benzo[b]thiophen-3-ylmethylamine·HCl | corresponding product | n.d. [MH]+ = 526 |
| 2049 | 4-(trifluoromethyl)benzylamine | corresponding product | n.d. [MH]+ = 538 |
| 2050 | 9H-fluoren-9-amine·HCl | corresponding product | n.d. [MH]+ = 544 |

TABLE II-44-continued

| Ex. # | amine | product | yield |
|---|---|---|---|
| 2051 | 3-(trifluoromethyl)benzylamine | product structure | n.d. [MH]+ = 538 |
| 2052 | 4-methylbenzylamine | product structure | n.d. [MH]+ = 484 |
| 2053 | 4-(dimethylamino)benzylamine | product structure | n.d. [MH]+ = 513 |
| 2054 | 1-naphthylmethylamine | product structure | n.d. [MH]+ = 520 |
| 2055 | 2-methylbenzylamine | product structure | n.d. [MH]+ = 484 |
| 2056 | 2-(trifluoromethyl)benzylamine | product structure | n.d. [MH]+ = 538 |
| 2057 | 2-fluorobenzylamine | product structure | n.d. [MH]+ = 488 |
| 2058 | (S)-1-cyclohexylethylamine | product structure | n.d. [MH]+ = 490 |
| 2059 | (R)-1-cyclohexylethylamine | product structure | n.d. [MH]+ = 490 |

TABLE II-44-continued

| Ex. # | amine | product | yield |
|---|---|---|---|
| 2060 | (S)-3,3-dimethylbutan-2-amine | indane carboxylic acid pyrazolopyrimidine diamide with (S)-3,3-dimethylbutan-2-yl group | n.d. [MH]+ = 464 |
| 2061 | 3-methylbutan-2-amine | corresponding diamide product | n.d. [MH]+ = 450 |
| 2062 | thiophen-3-ylmethanamine | corresponding diamide product | n.d. [MH]+ = 476 |
| 2063 | (4-morpholinophenyl)methanamine | corresponding diamide product | n.d. [MH]+ = 555 |
| 2064 | (5-cyanothiophen-2-yl)methanamine·HCl | corresponding diamide product | n.d. [MH]+ = 501 |
| 2065 | (2,2-difluorobenzo[d][1,3]dioxol-5-yl)methanamine·HCl | corresponding diamide product | n.d. [MH]+ = 550 |
| 2066 | (2-oxo-2,3-dihydro-1H-benzo[d]imidazol-5-yl)methanamine·HCl | corresponding diamide product | n.d. [MH]+ = 526 |
| 2067 | (2,2-dimethyl-2,3-dihydrobenzofuran-5-yl)methanamine·HCl | corresponding diamide product | n.d. [MH]+ = 540 |
| 2068 | (2-oxo-2,3-dihydrobenzo[d]oxazol-6-yl)methanamine·HCl | corresponding diamide product | n.d. [MH]+ = 527 |
| 2069 | (2-methylbenzo[d]thiazol-5-yl)methanamine·HCl | corresponding diamide product | n.d. [MH]+ = 541 |

TABLE II-44-continued

| Ex. # | amine | product | yield |
|---|---|---|---|
| 2070 | | | n.d. [MH]+ = 541 |
| 2071 | | | n.d. [MH]+ = 541 |
| 2072 | | | n.d. [MH]+ = 554 |
| 2073 | | | n.d. [MH]+ = 594 |
| 2074 | | | n.d. [MH]+ = 549 |
| 2075 | | | n.d. [MH]+ = 622 |
| 2076 | | | n.d. [MH]+ = 538 |
| 2077 | | | n.d. [MH]+ = 608 |
| 2078 | | | n.d. [MH]+ = 612 |

TABLE II-44-continued

| Ex. # | amine | product | yield |
|---|---|---|---|
| 2079 | | | n.d. [MH]⁺ = 626 |
| 2080 | | | n.d. [MH]⁺ = 626 |
| 2081 | | | n.d. [MH]⁺ = 620 |
| 2082 | | | n.d. [MH]⁺ = 560 |
| 2083 | | | n.d. [MH]⁺ = 512 |
| 2084 | | | n.d. [MH]⁺ = 498 |
| 2085 | | | n.d. [MH]⁺ = 498 |
| 2086 | | | n.d. [MH]⁺ = 498 |
| 2087 | | | n.d. [MH]⁺ = 450 |

TABLE II-44-continued

| Ex. # | amine | product | yield |
|---|---|---|---|
| 2088 | (S)-1-amino-2-mercaptopropane structure | product structure | n.d. [MH]+ = 468 |
| 2089 | (S)-sec-butylamine structure | product structure | n.d. [MH]+ = 436 |
| 2090 | (R)-sec-butylamine structure | product structure | n.d. [MH]+ = 436 |
| 2091 | cycloheptylamine | product structure | n.d. [MH]+ = 490 |
| 2092 | (S)-3,3-dimethyl-2-butylamine | product structure | n.d. [MH]+ = 464 |
| 2093 | 5-(aminomethyl)benzothiophene | product structure | n.d. [MH]+ = 526 |
| 2094 | 2-morpholinobenzylamine | product structure | n.d. [MH]+ = 555 |
| 2095 | 5-(aminomethyl)benzofuran | product structure | n.d. [MH]+ = 510 |
| 2096 | 4-(morpholinomethyl)benzylamine | product structure | n.d. [MH]+ = 569 |

TABLE II-44-continued

| Ex. # | amine | product | yield |
|---|---|---|---|
| 2097 | 2-(trifluoromethoxy)benzylamine | [product structure] | n.d. [MH]⁺ = 554 |
| 2098 | 4-(aminomethyl)pyridine | [product structure] | n.d. [MH]⁺ = 471 |
| 2099 | N-methyl-1-(pyridin-3-yl)methanamine | [product structure] | n.d. [MH]⁺ = 485 |
| 2100 | 3-morpholinobenzylamine | [product structure] | n.d. [MH]⁺ = 555 |
| 2101 | 3-(4-methylpiperazin-1-yl)benzylamine | [product structure] | n.d. [MH]⁺ = 568 |
| 2102 | 4-(trifluoromethoxy)benzylamine | [product structure] | n.d. [MH]⁺ = 554 |
| 2103 | (6,6-dimethylbicyclo[3.1.1]heptan-2-yl)methanamine | [product structure] | n.d. [MH]⁺ = 517 |
| 2104 | (tetrahydro-2H-pyran-4-yl)methanamine | [product structure] | n.d. [MH]⁺ = 478 |
| 2105 | 4-(aminomethyl)piperidine-1-carboxamidine | [product structure] | n.d. [MH]⁺ = 519 |

TABLE II-44-continued

| Ex. # | amine | product | yield |
|---|---|---|---|
| 2106 | HCl·H₂N-CH₂-(2,3-dihydrobenzofuran-2-yl) | (2,3-dihydrobenzofuran-2-yl-methyl)amide product | n.d. [MH]⁺ = 512 |
| 2107 | HCl·H₂N-CH(cyclohexyl)-C(=O)OMe | methyl ester product | n.d. [MH]⁺ = 534 |
| 2108 | H₂N-CH₂-(1-benzylpiperidin-4-yl) | 1-benzylpiperidin-4-ylmethyl product | n.d. [MH]⁺ = 567 |
| 2109 | HCl·H₂N-CH₂-(3-cyanophenyl) | 3-cyanobenzyl product | n.d. [MH]⁺ = 495 |
| 2110 | HCl·H₂N-CH₂-(1H-imidazol-2-yl) | (1H-imidazol-2-yl)methyl product | n.d. [MH]⁺ = 460 |
| 2111 | cycloheptyl-NH₂ | cycloheptyl product | n.d. [MH]⁺ = 476 |
| 2112 | azepane (HN-(CH₂)₆) | azepanyl product | n.d. [MH]⁺ = 462 |
| 2113 | HCl·H₂N-CH₂-(4-amidinophenyl) | 4-amidinobenzyl product | n.d. [MH]⁺ = 512 |
| 2114 | H₂N-CH₂-(5-methoxycarbonylthiophen-3-yl) | (5-methoxycarbonylthiophen-3-yl)methyl product | n.d. [MH]⁺ = 534 |

TABLE II-44-continued

| Ex. # | amine | product | yield |
|---|---|---|---|
| 2115 | 3-fluoro-5-(trifluoromethyl)benzylamine | | n.d. [MH]+ = 556 |
| 2116 | 4-fluoro-3-(trifluoromethyl)benzylamine | | n.d. [MH]+ = 556 |
| 2117 | (2,3-dihydro-1,4-benzodioxin-6-yl)methanamine | | n.d. [MH]+ = 528 |
| 2118 | methyl (R)-2-amino-2-(4-hydroxyphenyl)acetate HCl | | n.d. [MH]+ = 544 |
| 2119 | methyl (S)-2-amino-2-(4-hydroxyphenyl)acetate HCl | | n.d. [MH]+ = 544 |
| 2120 | 5-(aminomethyl)thiophene-2-sulfonamide | | n.d. [MH]+ = 555 |
| 2121 | 5,6-difluoro-2,3-dihydro-1H-inden-1-amine | | n.d. [MH]+ = 532 |
| 2122 | (6-(trifluoromethyl)pyridin-3-yl)methanamine | | n.d. [MH]+ = 539 |
| 2123 | (1S,2R)-1-amino-2,3-dihydro-1H-inden-2-ol | | n.d. [MH]+ = 512 |

TABLE II-44-continued

| Ex. # | amine | product | yield |
|---|---|---|---|
| 2124 | (S)-prolinamide | | n.d. [MH]+ = 477 |
| 2125 | 4-hydroxybenzylamine | | n.d. [MH]+ = 486 |
| 2126 | alanine ethyl ester HCl | | n.d. [MH]+ = 480 |
| 2127 | (1-acetylpiperidin-4-yl)methanamine HCl | | n.d. [MH]+ = 519 |
| 2128 | (1-acetylpiperidin-3-yl)methanamine HCl | | n.d. [MH]+ = 519 |
| 2129 | 6-(aminomethyl)-2,2-dimethyl-2H-benzo[b][1,4]oxazin-3(4H)-one HCl | | n.d. [MH]+ = 569 |
| 2130 | 7-(aminomethyl)-3,4-dihydroquinolin-2(1H)-one HCl | | n.d. [MH]+ = 539 |
| 2131 | 7-(aminomethyl)-3,4-dihydroquinolin-2(1H)-one HCl | | n.d. [MH]+ = 528 |
| 2132 | (2-methoxypyridin-4-yl)methanamine HCl | | n.d. [MH]+ = 501 |

TABLE II-44-continued
| Ex. # | amine | product | yield |
|---|---|---|---|
| 2133 | 3-methylbenzylamine | (structure) | n.d. [MH]+ = 484 |
| 2134 | 3-(methylsulfonamido)benzylamine HCl | (structure) | n.d. [MH]+ = 563 |
| 2135 | (S)-2-aminopropan-1-ol | (structure) | n.d. [MH]+ = 438 |
| 2136 | (R)-2-aminopropan-1-ol | (structure) | n.d. [MH]+ = 438 |
| 2137 | (S)-2-amino-2-phenylacetamide HCl | (structure) | n.d. [MH]+ = 513 |
| 2138 | (R)-2-amino-2-phenylacetamide HCl | (structure) | n.d. [MH]+ = 513 |
Example 2139
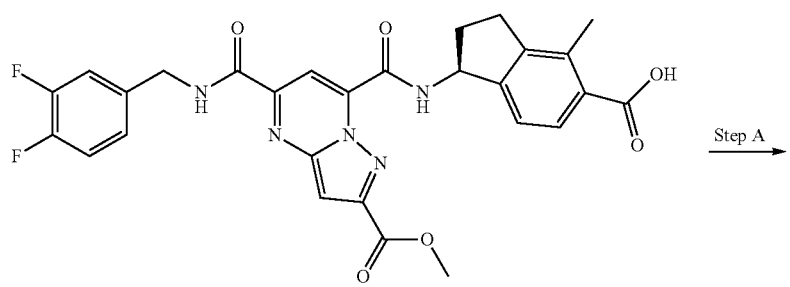
Step A -continued

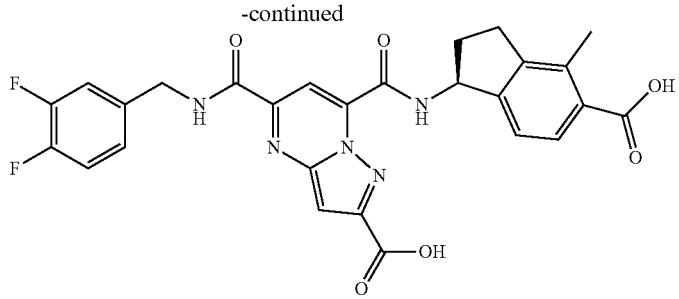

Step A

The title compound from the Example 1925 (3.6 mg) was treated similarly as described in the Example 314, except using NaOH instead of LiOH to afford the title compound as a yellow solid (2.2 mg, 60%). [MH]⁺=550.

Example 2140

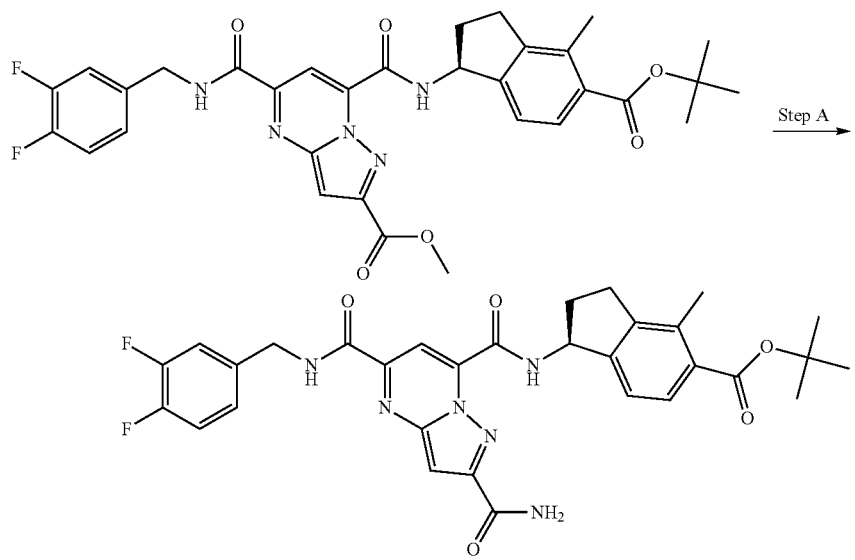

Step A

A solution of the title compound from the Example 1791 (5 mg) in a 7M solution of NH₃ in MeOH (1 mL) was heated to reflux overnight, concentrated and purified by chromatography (silica) to afford the title compound as a yellow solid (4.5 mg, 90%). [MH]⁺=605.

Example 2141

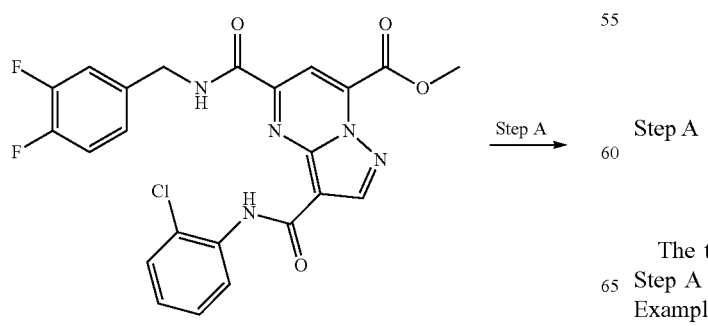

Step A →

-continued

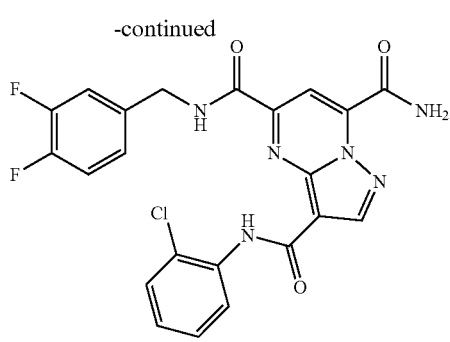

The title compound from the Preparative Example 974, Step A (6.4 mg) was treated similarly as described in the Example 2140, Step A to afford the title compound as a yellow solid (5.6 mg, 90%). [MH]⁺=485.

Example 2142

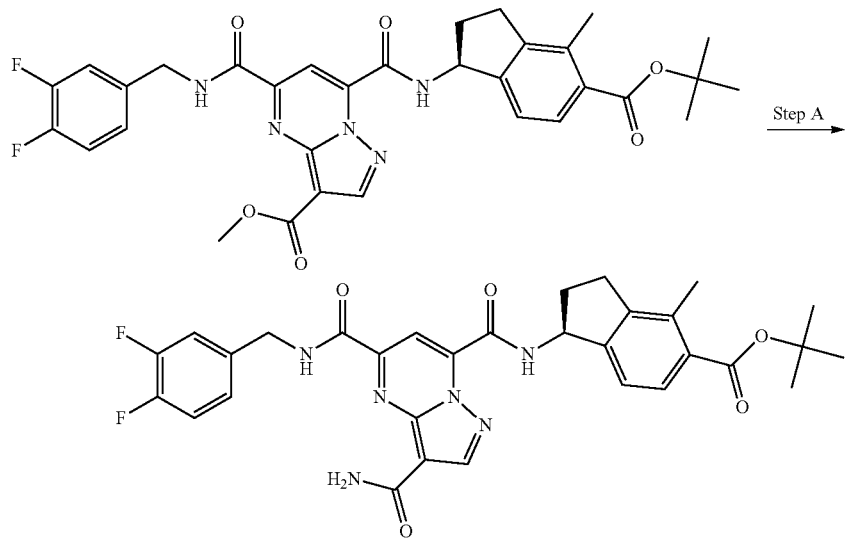

Step A

The title compound from the Example 1833, Step A (15 mg) was treated similarly as described in the Example 2140, Step A to afford the title compound (2.5 mg, 17%). [M-H]'= 603.

Examples 2143-2213

Following similar procedures as described in the Examples 1 (method A), 2 (method B), 3 (method C), 4 (method D), 5 (method E), 6 (method F) or 7 (method G), except using the acids and amines or alcohols indicated in Table II-45 below, the following compounds were prepared.

TABLE II-45

| Ex. # | acid, amine or alcohol |
|---|---|
| 2143 | |
| 2144 | |

TABLE II-45-continued
| 2145 | 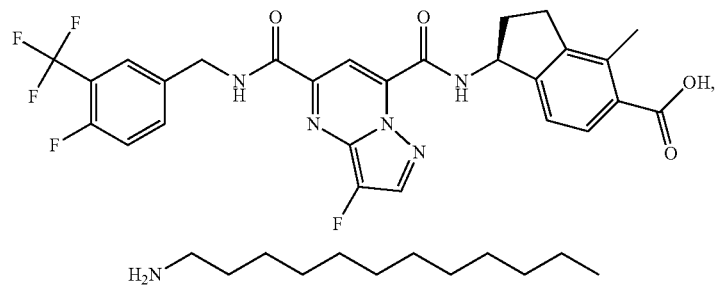 |
| 2146 | 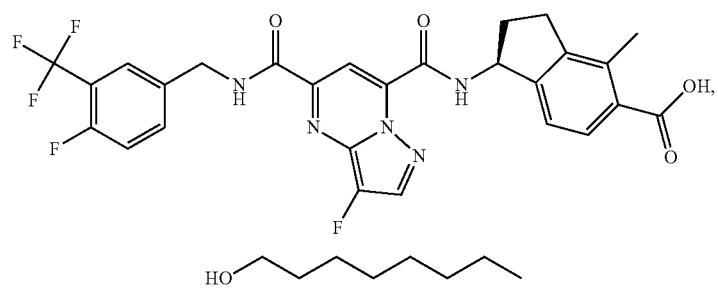 |
| 2147 | 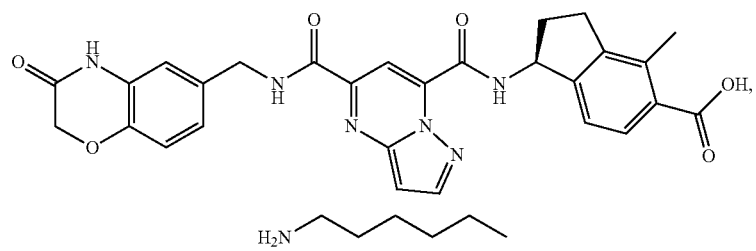 |
| 2148 | 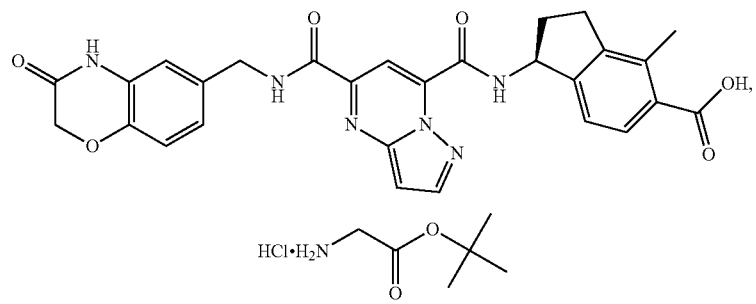 |
| 2149 | 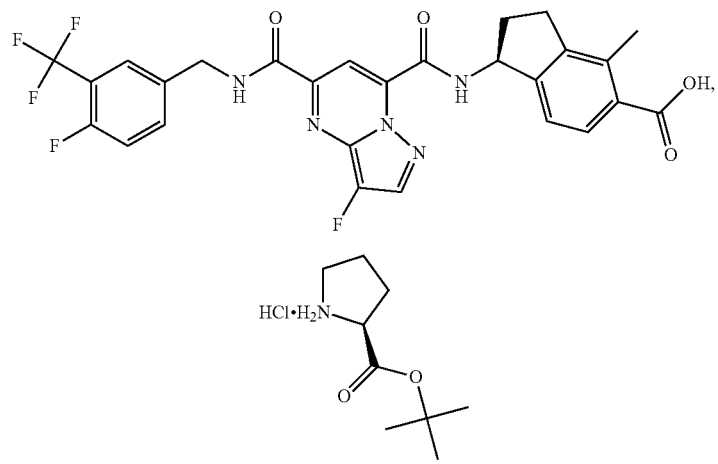 |

TABLE II-45-continued
2150
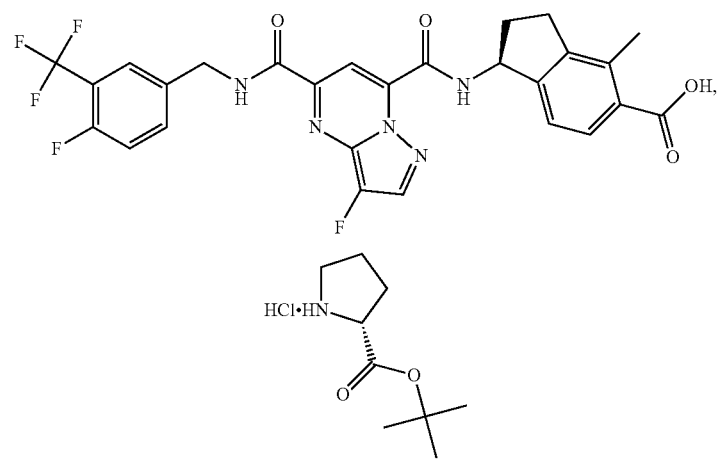
2151
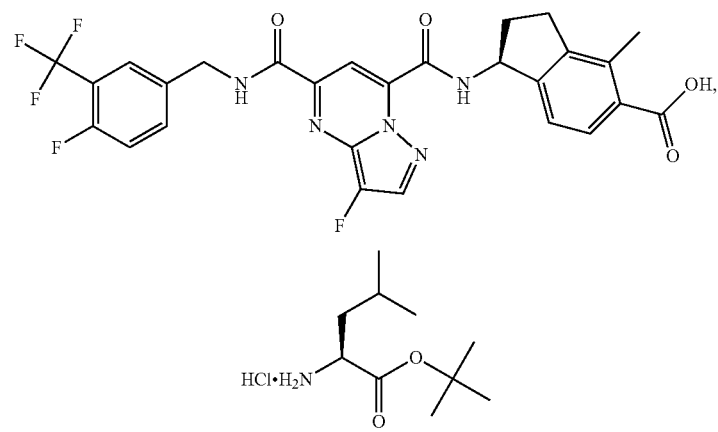
2152
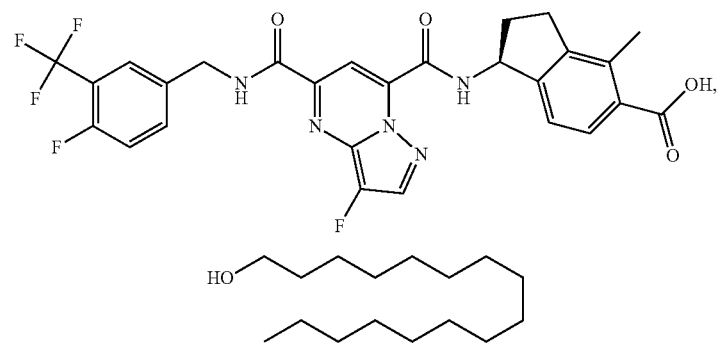
2153
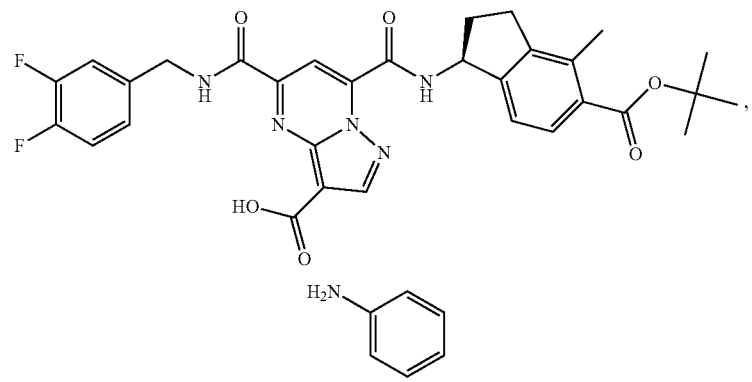

TABLE II-45-continued
| 2154 | 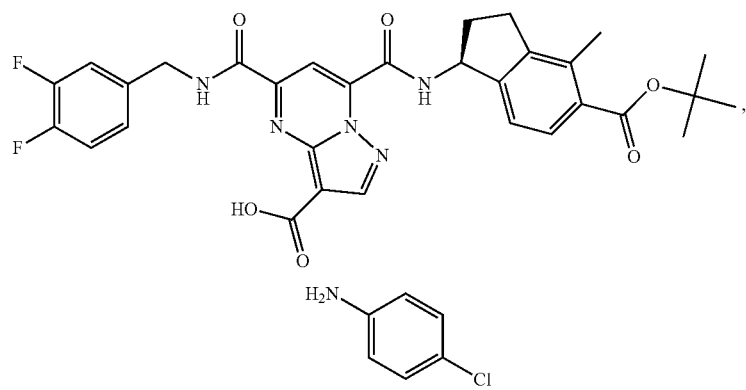 |
| 2155 | 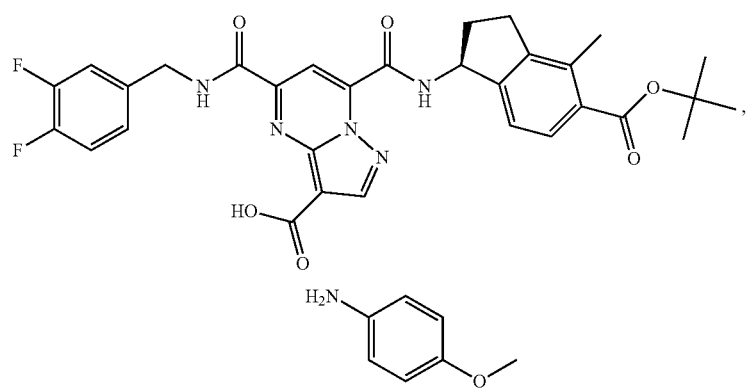 |
| 2156 | 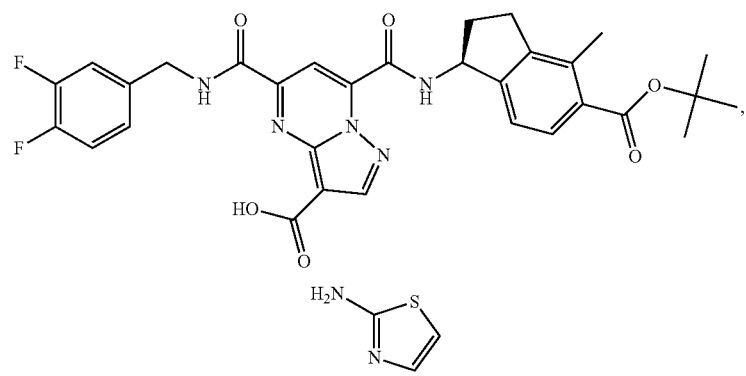 |
| 2157 | 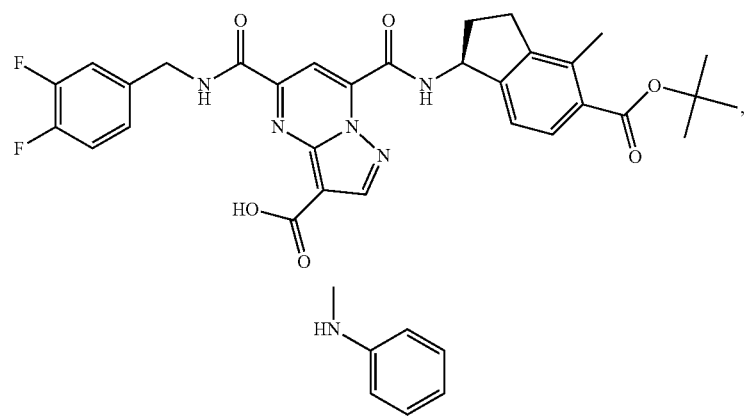 |

TABLE II-45-continued
| 2158 | 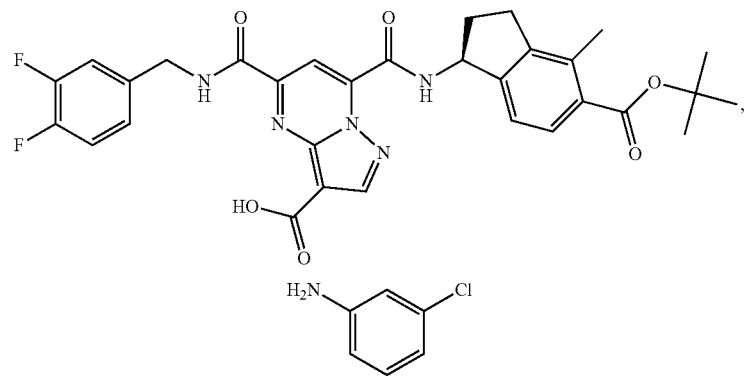 |
| 2159 | 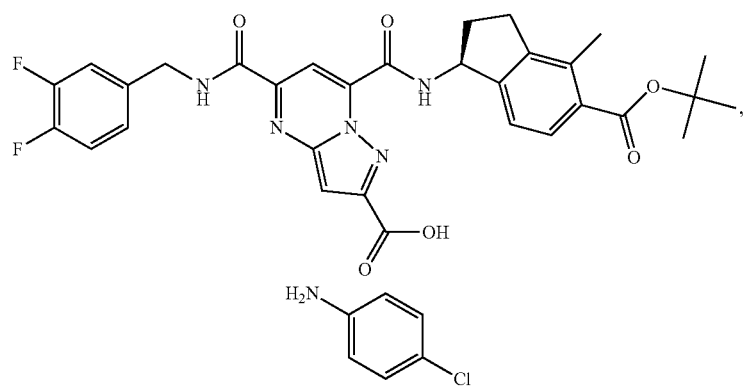 |
| 2160 | 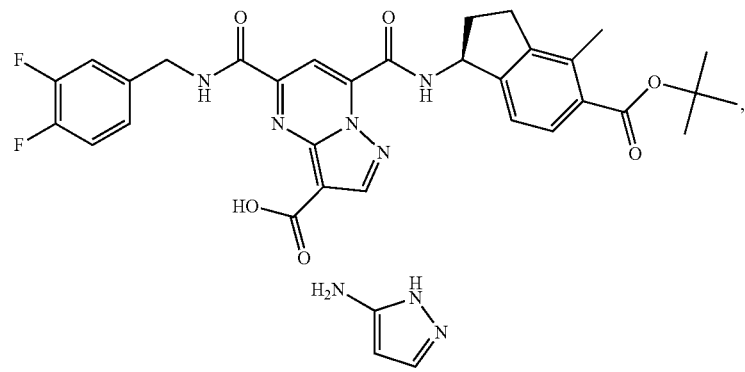 |
| 2161 | 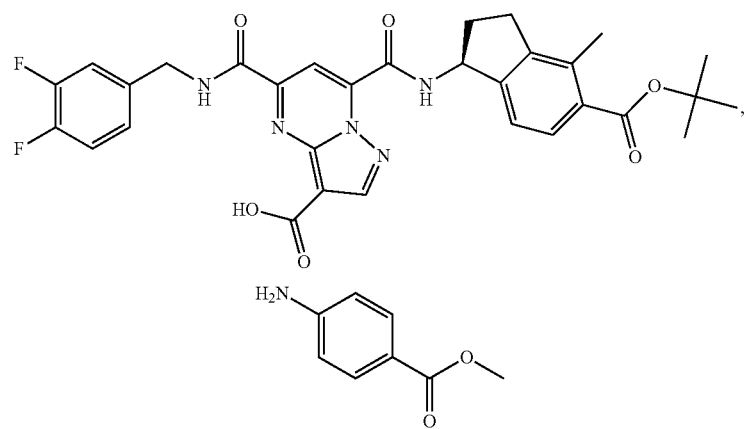 |

TABLE II-45-continued
| 2162 | 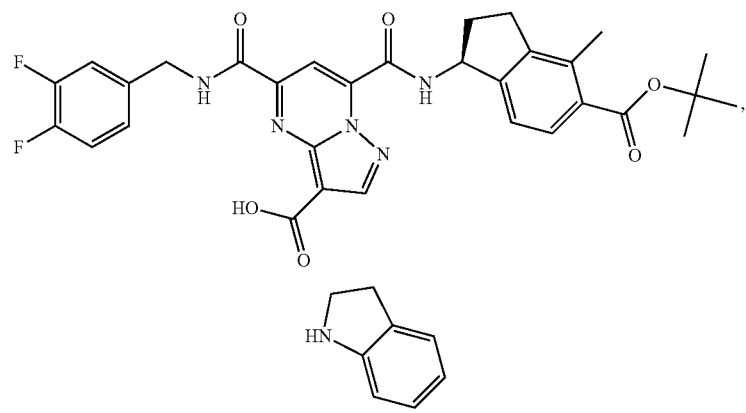 |
| 2163 | 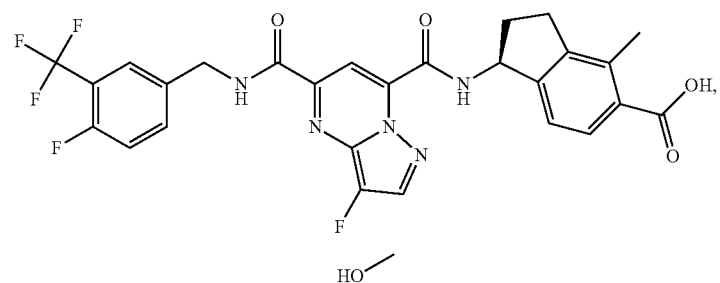 |
| 2164 | 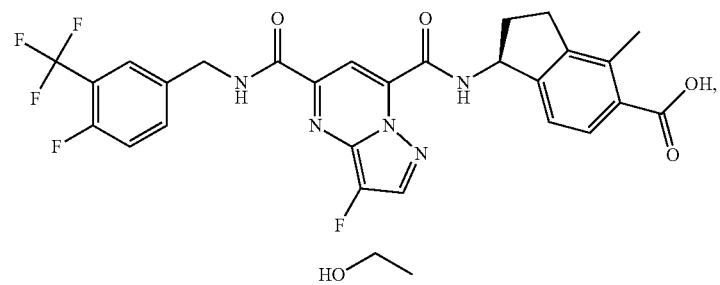 |
| 2165 | 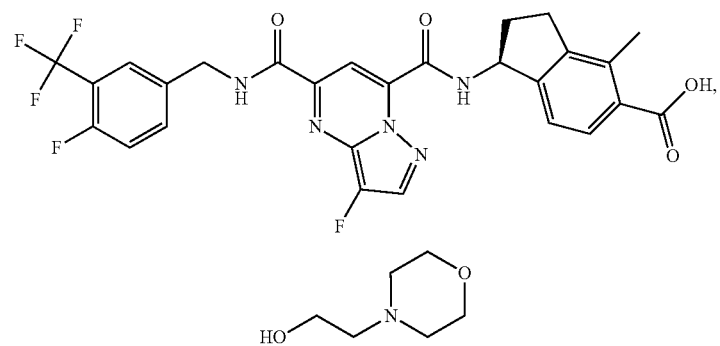 [SMILES: Cc1c(C(=O)O)ccc2c1CC[C@@H]2NC(=O)c1cc(C(=O)NCc2ccc(F)c(C(F)(F)F)c2)nc2c(F)cnn12 ; OCCN1CCOCC1] |

TABLE II-45-continued
| 2166 | 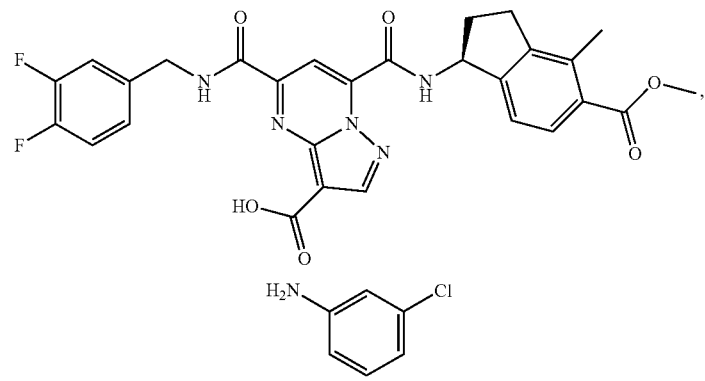 |
| 2167 | 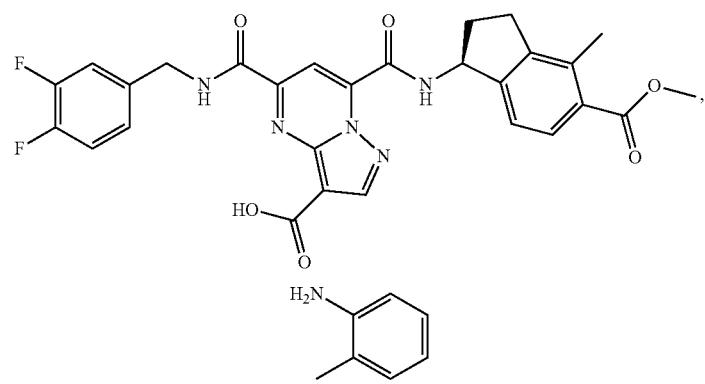 |
| 2168 | 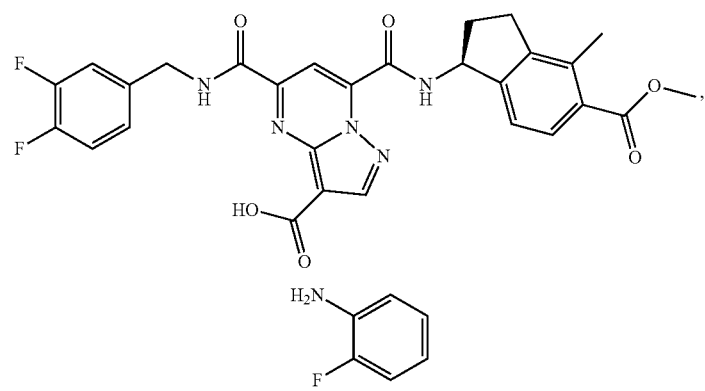 |
| 2169 | 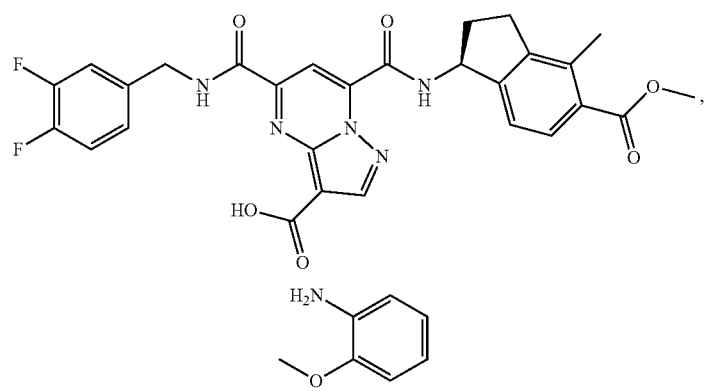 |

TABLE II-45-continued
2170 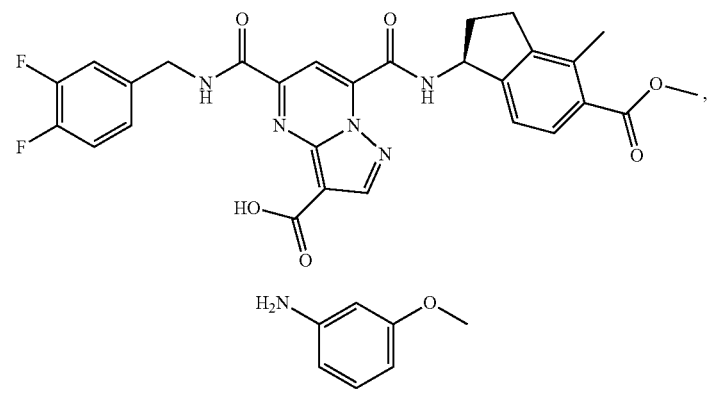
2171 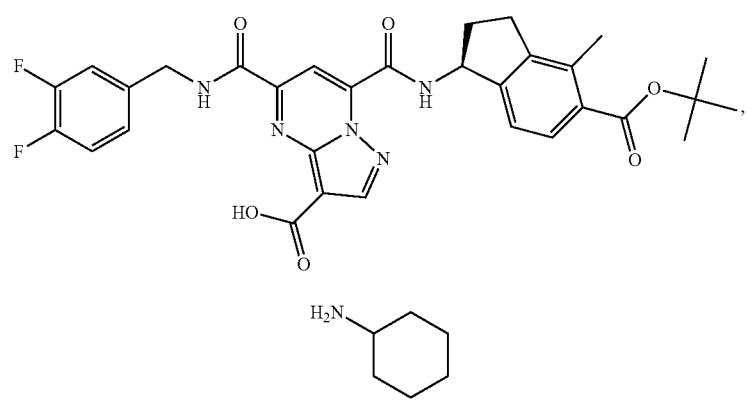
2172 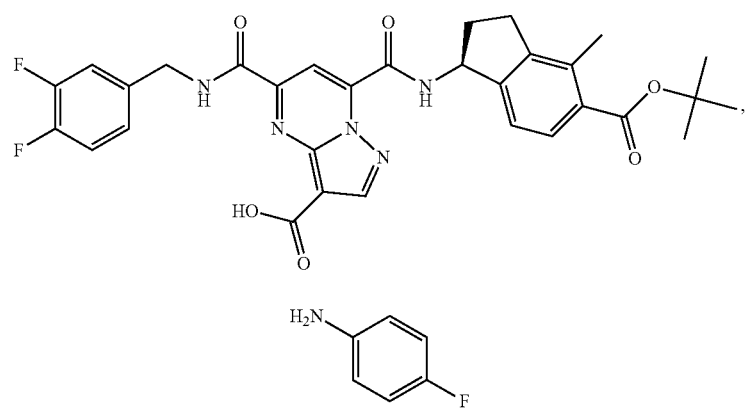
2173 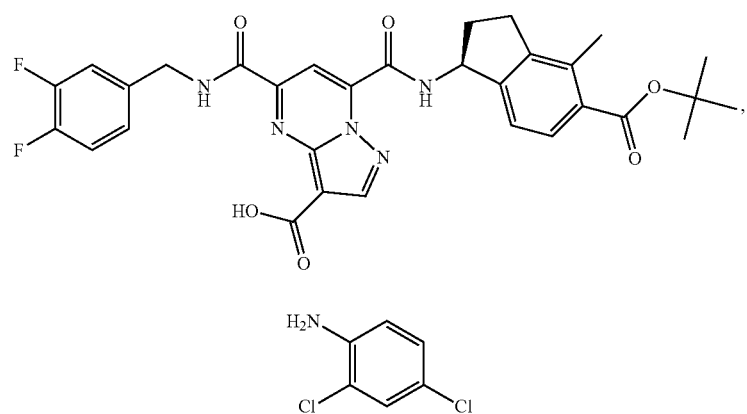

TABLE II-45-continued
| 2174 | 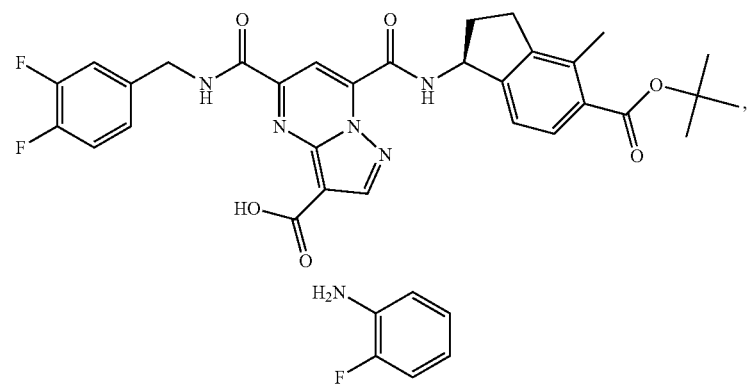 |
| --- | --- |
| 2175 | 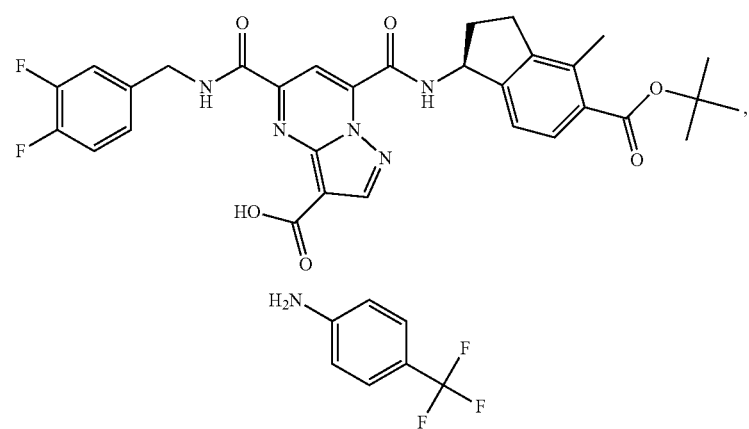 |
| 2176 | 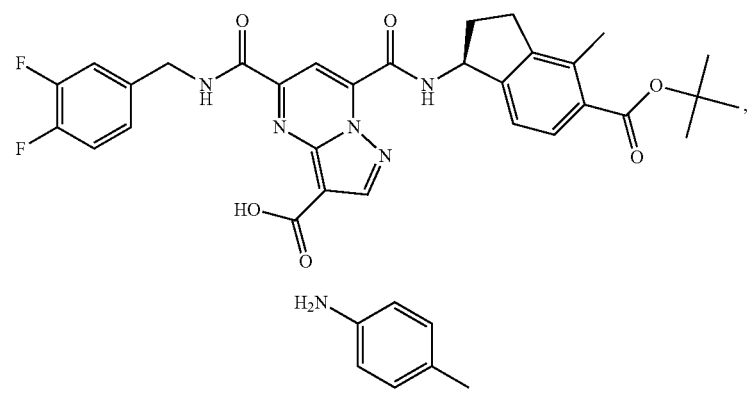 |
| 2177 | 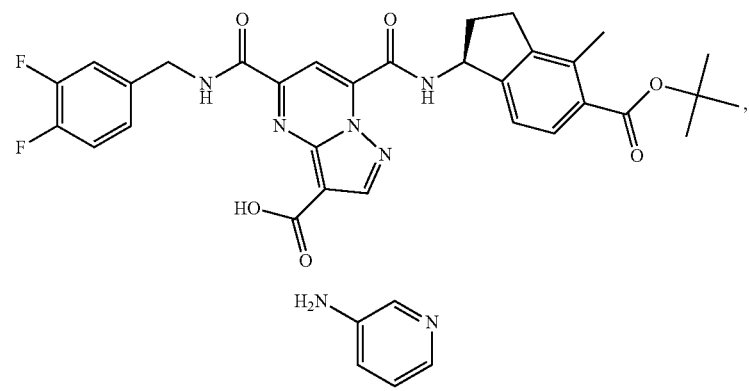 |

TABLE II-45-continued
2178 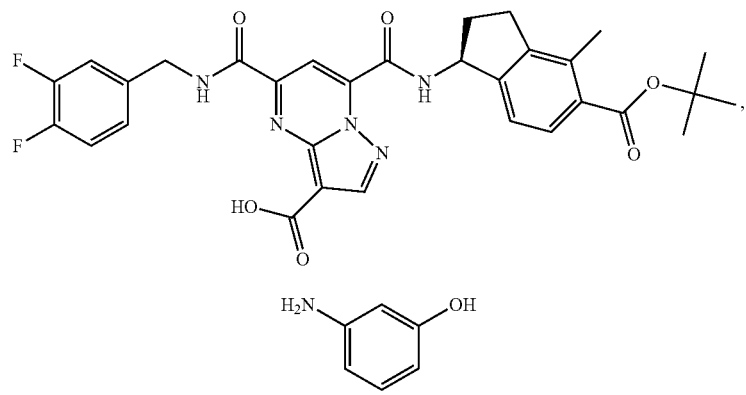
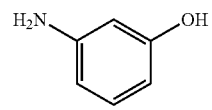
2179 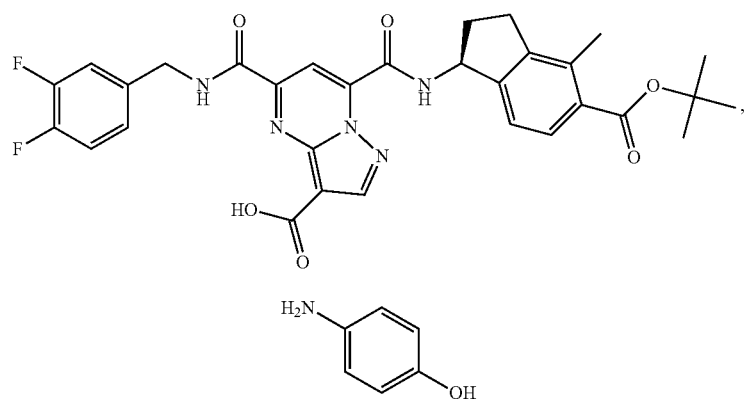
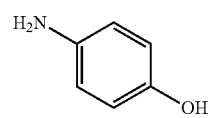
2180 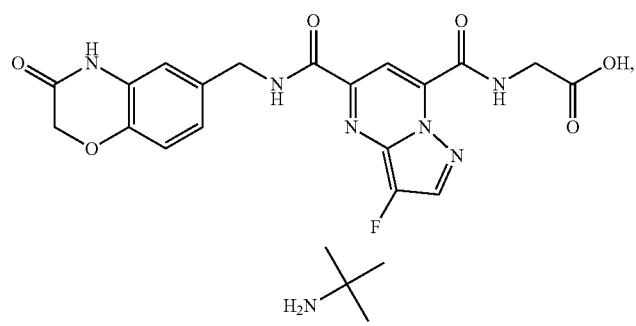
2181 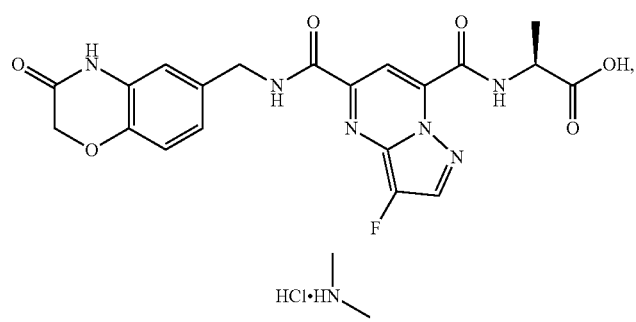

TABLE II-45-continued
| 2182 | 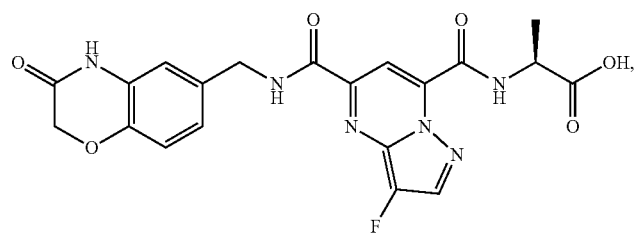 |
| --- | --- |
| 2183 | 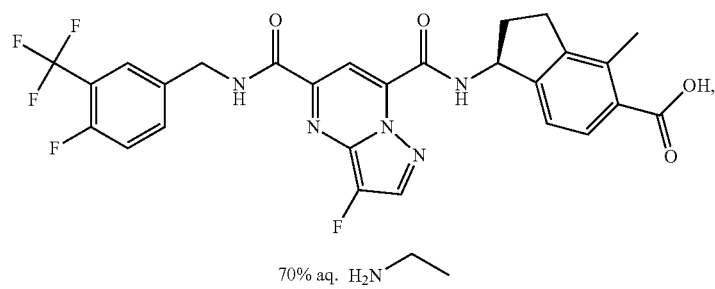 |
| 2184 | 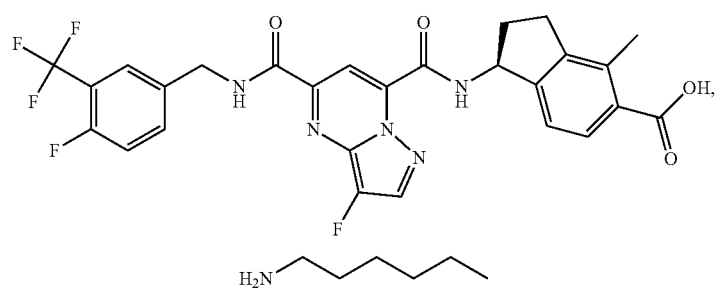 |
| 2185 | 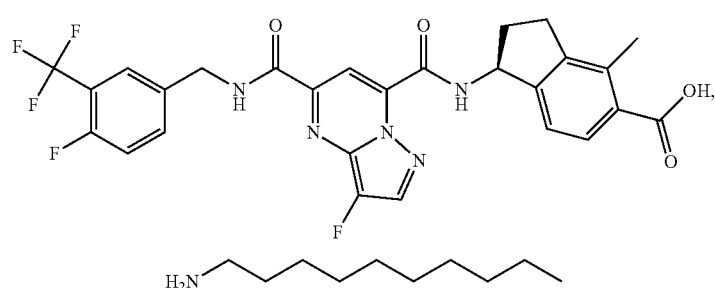 |
| 2186 | 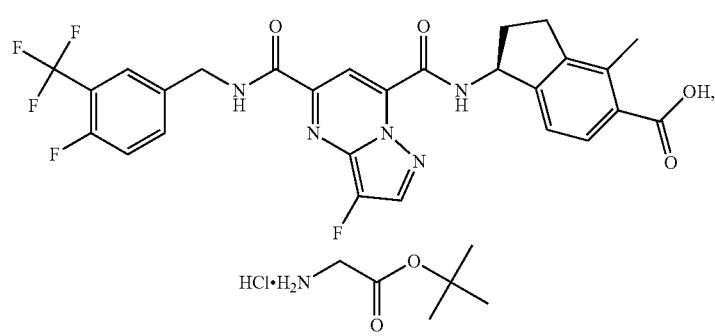 |

TABLE II-45-continued
2187 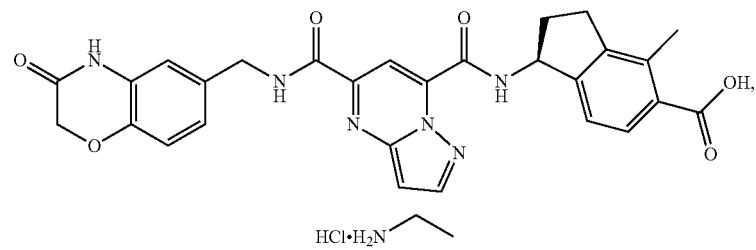
2188 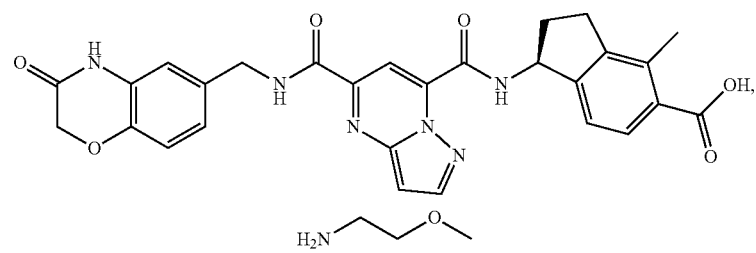
2189 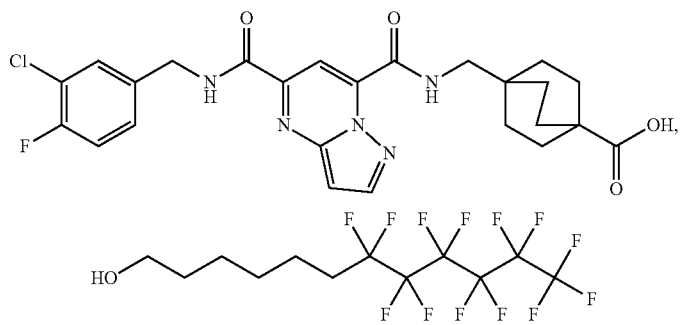
2190 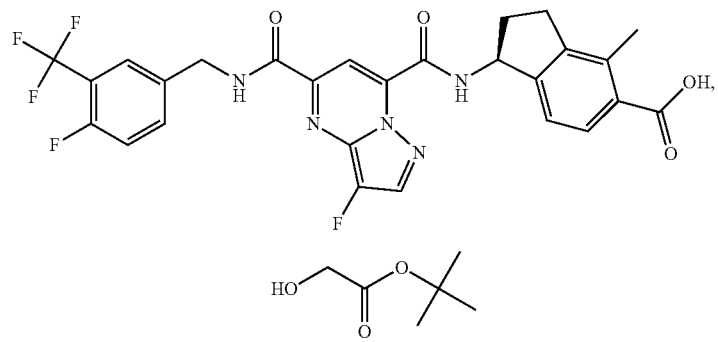
2191 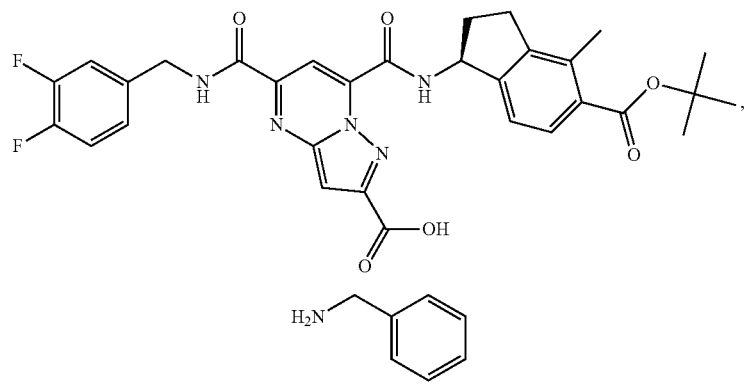

TABLE II-45-continued
2192 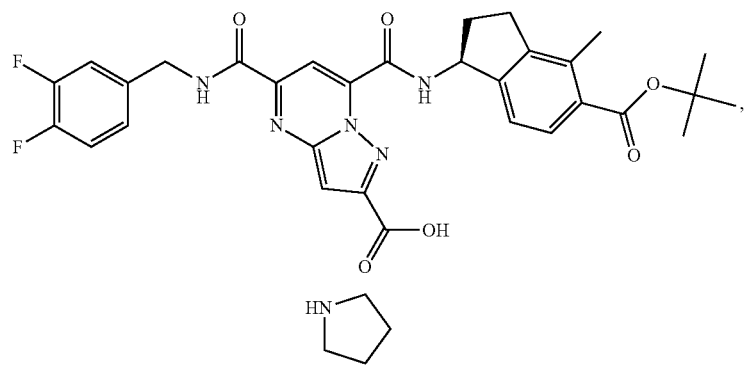
2193 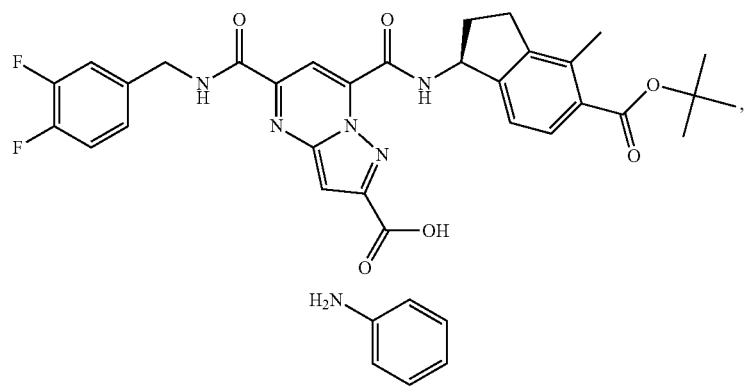
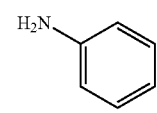
2194 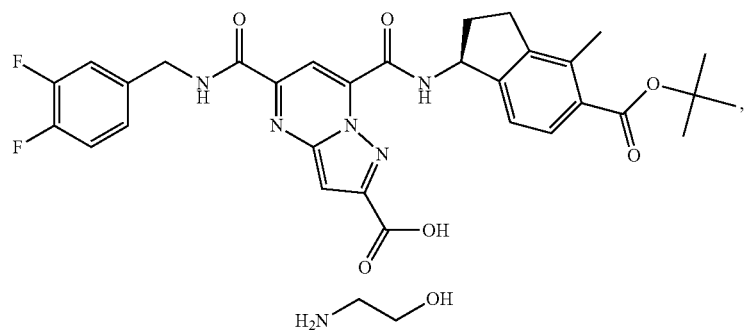
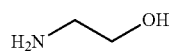
2195 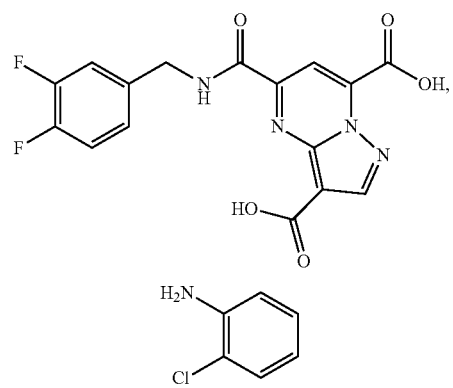
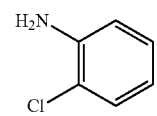

TABLE II-45-continued
2196 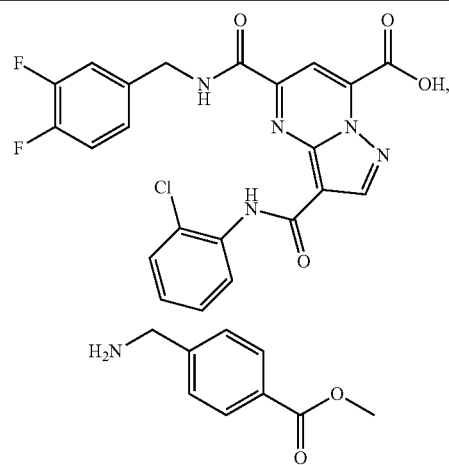
2197 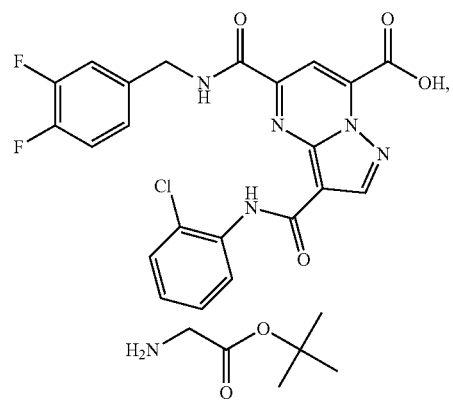
2198 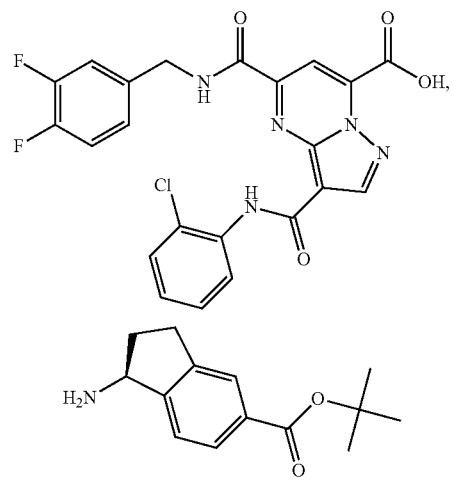

TABLE II-45-continued
2199 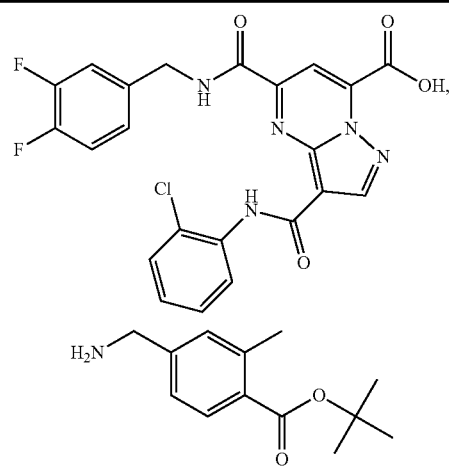
2200 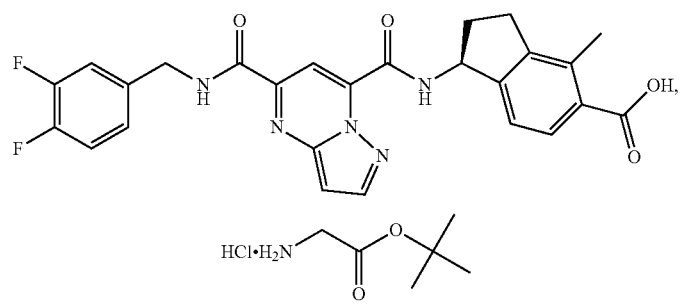
2201 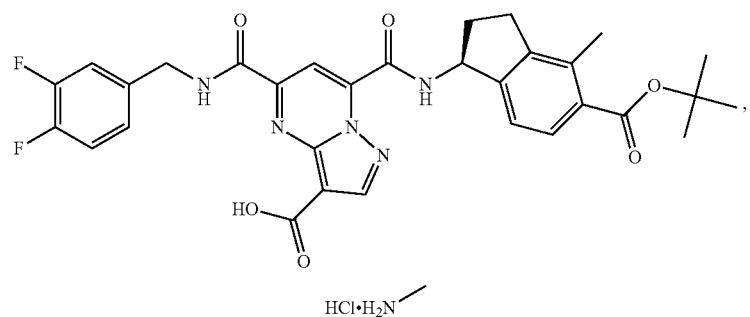
2202 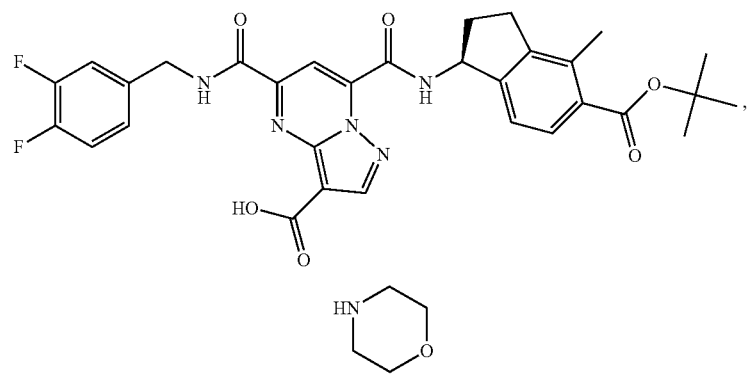 [SMILES: Cc1c(C(=O)OC(C)(C)C)ccc2c1CC[C@@H]2NC(=O)c1cc(C(=O)NCc2ccc(F)c(F)c2)nc2c(C(=O)O)cnn12 ; C1COCCN1]

TABLE II-45-continued
| 2203 | 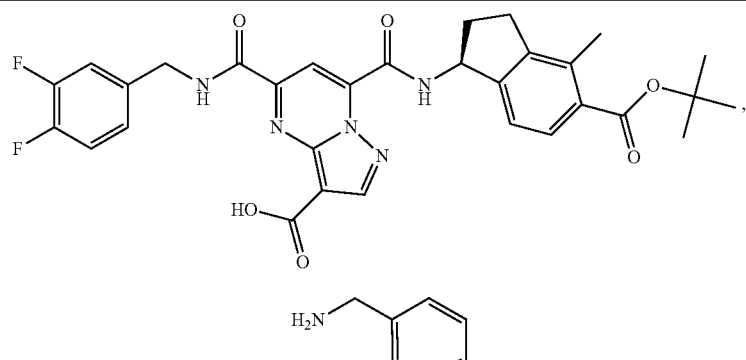 |
| --- | --- |
| | 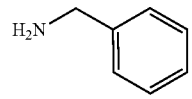 |
| 2204 | 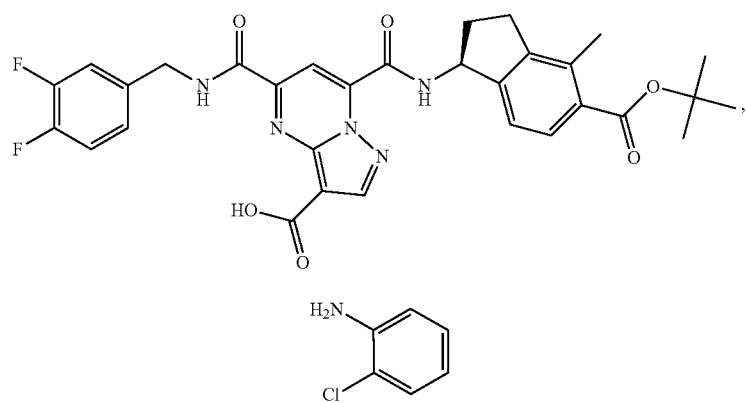 |
| | 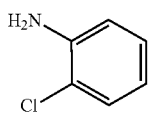 |
| 2205 | 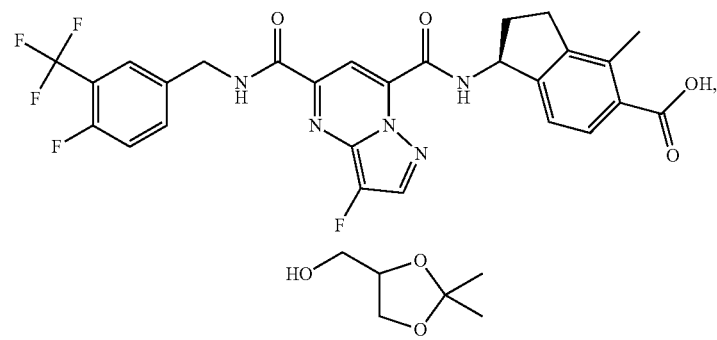 |
| | 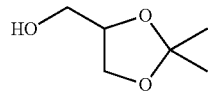 |
| 2206 | 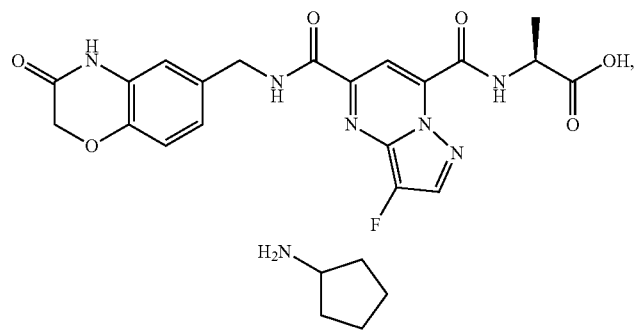 |
| | 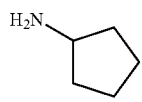 |

TABLE II-45-continued
2207
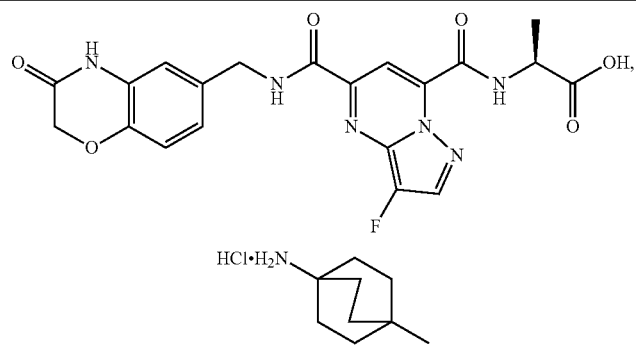
2208
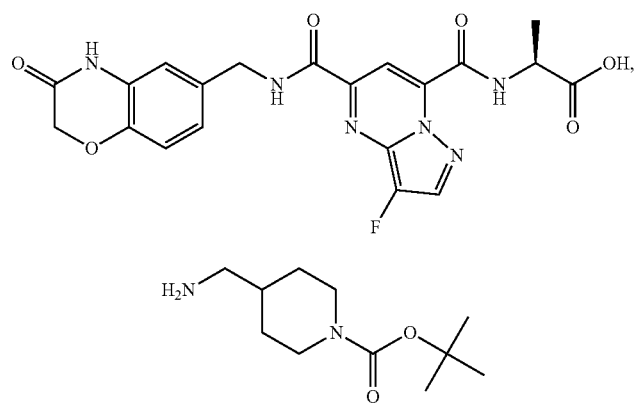 [SMILES: C[C@H](NC(=O)c1cc(C(=O)NCc2ccc3c(c2)NC(=O)CO3)nc2c(F)cnn12)C(=O)O ; CC(C)(C)OC(=O)N1CCC(CN)CC1]
2209
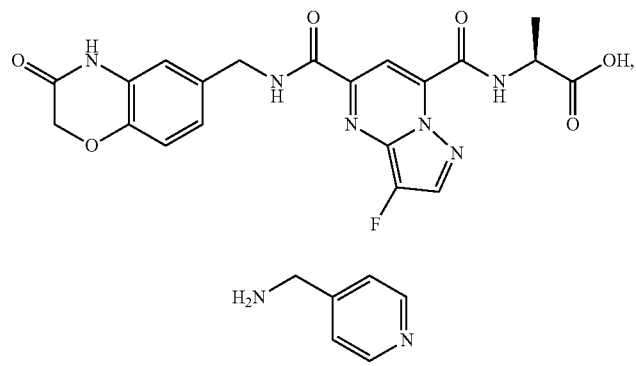
2210
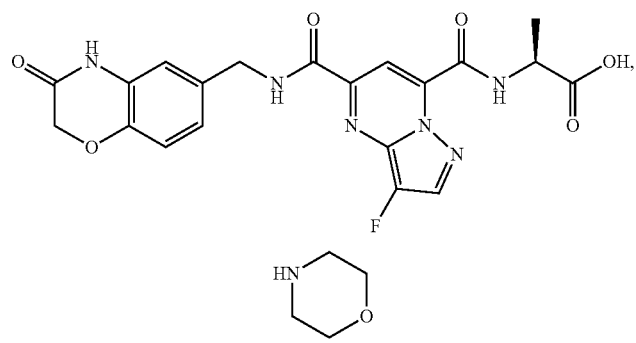

TABLE II-45-continued
| 2211 | 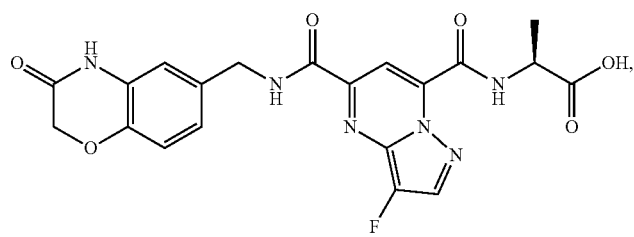 |
| --- | --- |
| | 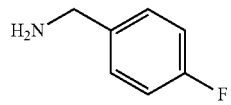 |
| 2212 | 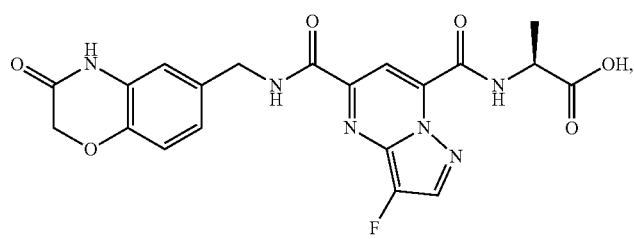 |
| | 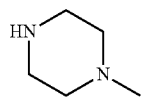 |
| 2213 | 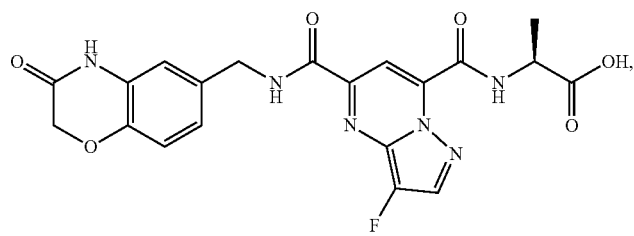 |
| | 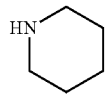 |
| Ex. # | product | method, yield |
| --- | --- | --- |
| 2143 | 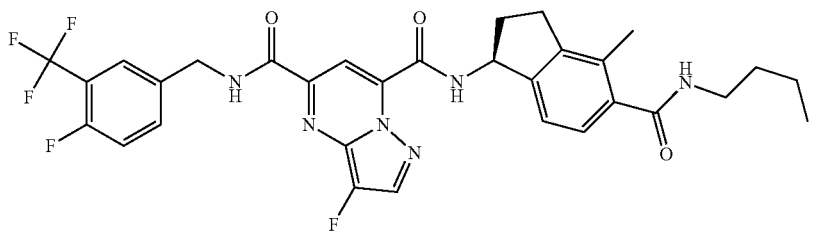 [SMILES: CCCCNC(=O)c1ccc2c(c1C)CC[C@@H]2NC(=O)c1cc(C(=O)NCc2ccc(F)c(C(F)(F)F)c2)nc2c(F)cnn12] | B, 74% [MH]⁺ = 629 |
| 2144 | 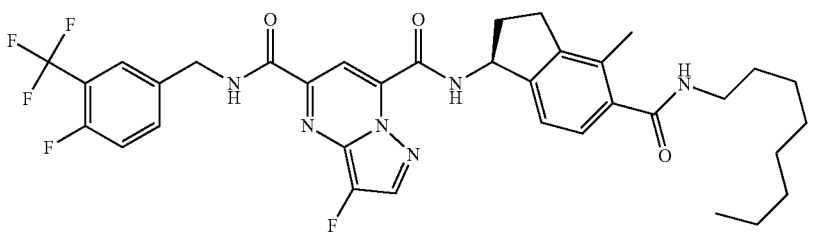 [SMILES: CCCCCCCCNC(=O)c1ccc2c(c1C)CC[C@@H]2NC(=O)c1cc(C(=O)NCc2ccc(F)c(C(F)(F)F)c2)nc2c(F)cnn12] | B, 79% [MH]⁺ = 685 |

TABLE II-45-continued

| # | Structure | Data |
|---|---|---|
| 2145 | 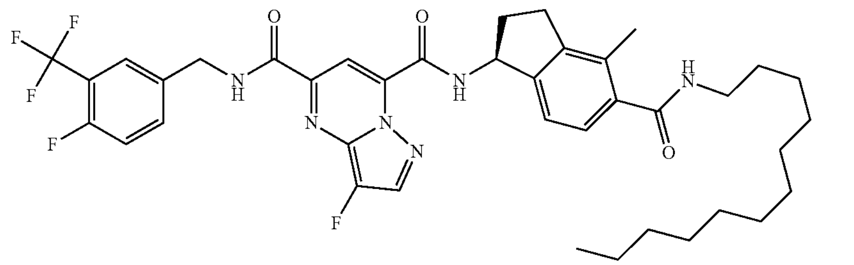 [SMILES: CCCCCCCCCCCCNC(=O)c1ccc2c(c1C)CC[C@@H]2NC(=O)c1cc(C(=O)NCc2ccc(F)c(C(F)(F)F)c2)nc2c(F)cnn12] | B, 77% [MH]⁺ = 741 |
| 2146 | 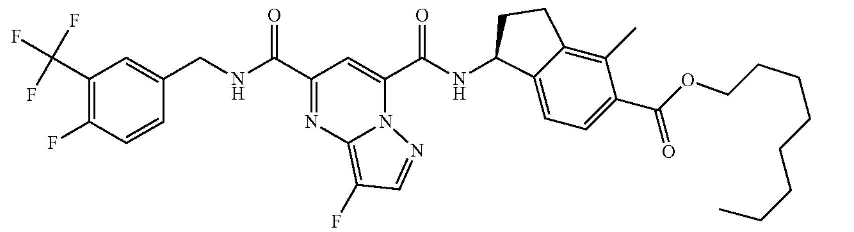 [SMILES: CCCCCCCCOC(=O)c1ccc2c(c1C)CC[C@@H]2NC(=O)c1cc(C(=O)NCc2ccc(F)c(C(F)(F)F)c2)nc2c(F)cnn12] | B, 54% [MH]⁺ = 686 |
| 2147 | 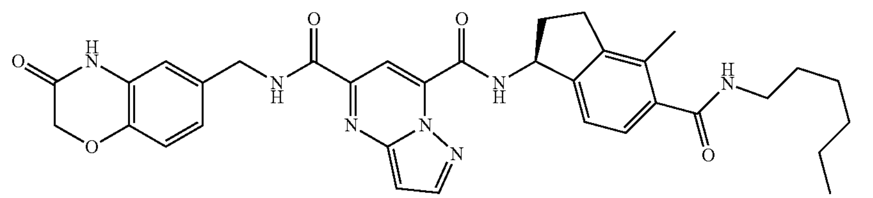 [SMILES: CCCCCCNC(=O)c1ccc2c(c1C)CC[C@@H]2NC(=O)c1cc(C(=O)NCc2ccc3c(c2)NC(=O)CO3)nc2ccnn12] | B, 95% [MH]⁺ = 624 |
| 2148 | 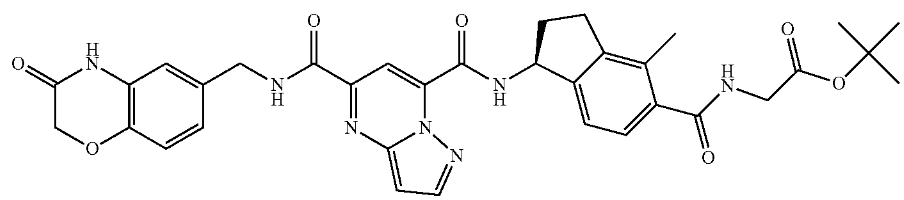 [SMILES: Cc1c(C(=O)NCC(=O)OC(C)(C)C)ccc2c1CC[C@@H]2NC(=O)c1cc(C(=O)NCc2ccc3c(c2)NC(=O)CO3)nc2ccnn12] | B, 92% [MH]⁺ = 654 |
| 2149 | 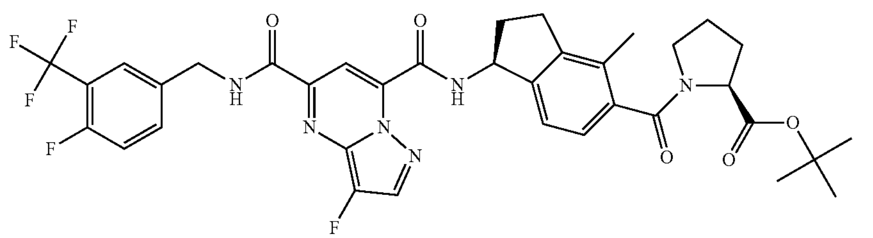 [SMILES: Cc1c(C(=O)N2CCC[C@H]2C(=O)OC(C)(C)C)ccc2c1CC[C@@H]2NC(=O)c1cc(C(=O)NCc2ccc(F)c(C(F)(F)F)c2)nc2c(F)cnn12] | B, 94% [MH]⁺ = 727 |
| 2150 | 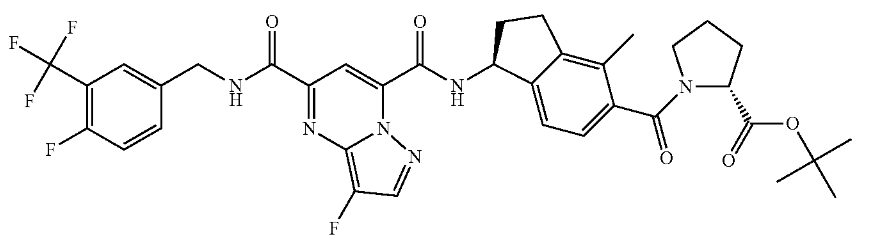 [SMILES: Cc1c(C(=O)N2CCC[C@@H]2C(=O)OC(C)(C)C)ccc2c1CC[C@@H]2NC(=O)c1cc(C(=O)NCc2ccc(F)c(C(F)(F)F)c2)nc2c(F)cnn12] | B, >99% [MH]⁺ = 572 |
| 2151 | 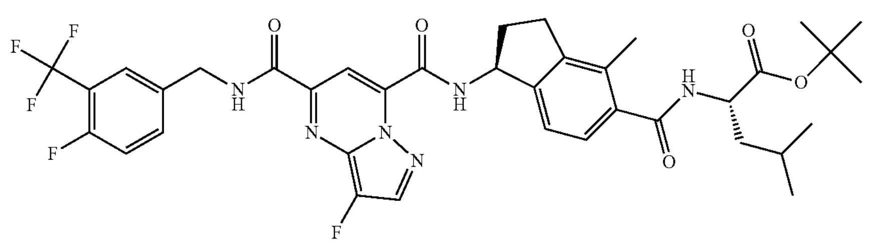 [SMILES: Cc1c(C(=O)N[C@@H](CC(C)C)C(=O)OC(C)(C)C)ccc2c1CC[C@@H]2NC(=O)c1cc(C(=O)NCc2ccc(F)c(C(F)(F)F)c2)nc2c(F)cnn12] | B, 78% [MH]⁺ = 743 |

TABLE II-45-continued

| | | |
|---|---|---|
| 2152 | [structure] | E, 68%<br>[(MH₂)/2]⁺ = 399 |
| 2153 | [structure] | E, n.d.<br>[M − H]⁻ = 679 |
| 2154 | [structure] | E, n.d.<br>[M − H]⁻ = 714 |
| 2155 | [structure] | E, n.d.<br>[M − H]⁻ = 709 |
| 2156 | [structure] | E, 40%<br>[M − H]⁻ = 686 |

TABLE II-45-continued
| 2157 | 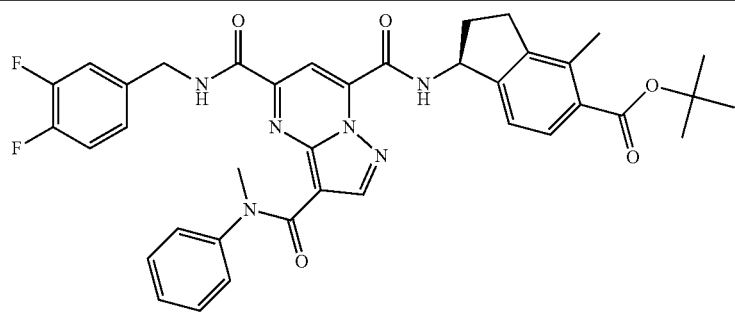 | E, 39%<br>[M − H]⁻ = 693 |
| --- | --- | --- |
| 2158 | 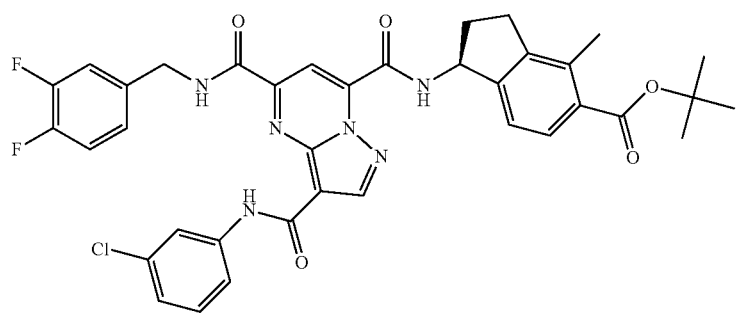 [SMILES: Cc1c(C(=O)OC(C)(C)C)ccc2c1CC[C@@H]2NC(=O)c1cc(C(=O)NCc2ccc(F)c(F)c2)nc2c(C(=O)Nc3cccc(Cl)c3)cnn12] | E, 25%<br>[M − H]⁻ = 714 |
| 2159 | 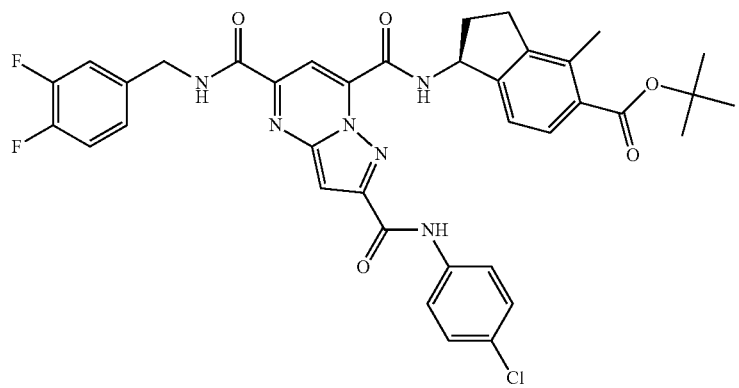 [SMILES: Cc1c(C(=O)OC(C)(C)C)ccc2c1CC[C@@H]2NC(=O)c1cc(C(=O)NCc2ccc(F)c(F)c2)nc2cc(C(=O)Nc3ccc(Cl)cc3)nn12] | E, 35%<br>[M − H]⁻ = 714 |
| 2160 | 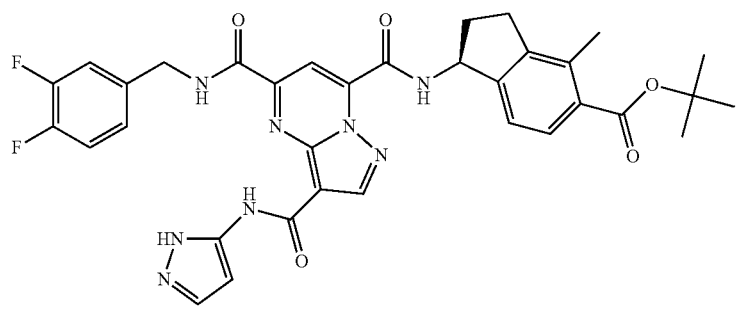 [SMILES: Cc1c(C(=O)OC(C)(C)C)ccc2c1CC[C@@H]2NC(=O)c1cc(C(=O)NCc2ccc(F)c(F)c2)nc2c(C(=O)Nc3ccn[nH]3)cnn12] | E, 41%<br>[M − H]⁻ = 669 |

TABLE II-45-continued
| | | |
|---|---|---|
| 2161 | 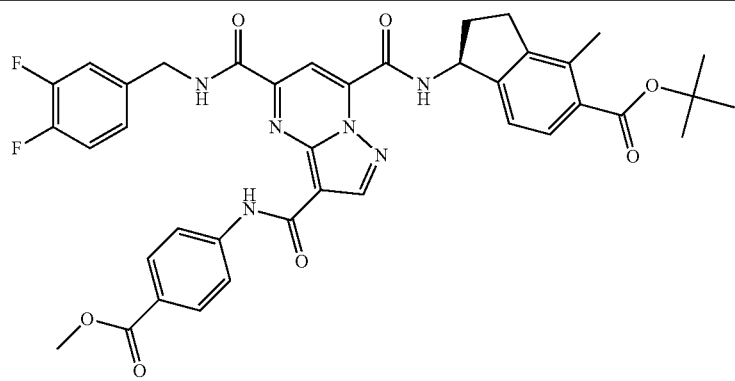 | E, 12%<br>[M − H]⁻ = 737 |
| 2162 | 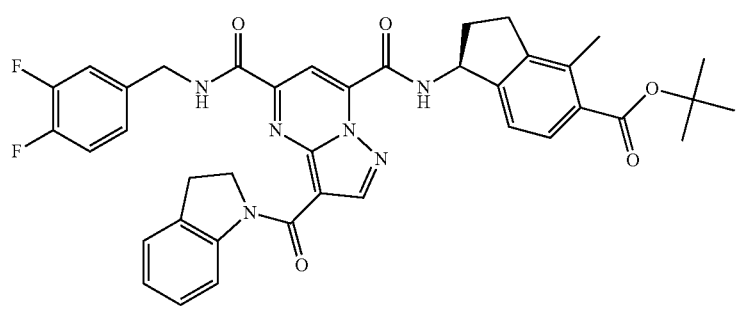 [SMILES: Cc1c(C(=O)OC(C)(C)C)ccc2c1CC[C@@H]2NC(=O)c1cc(C(=O)NCc2ccc(F)c(F)c2)nc2c(C(=O)N3CCc4ccccc43)cnn12] | E, 76%<br>[M − H]⁻ = 705 |
| 2163 | 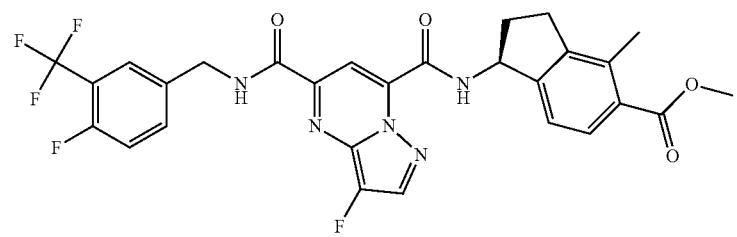 [SMILES: COC(=O)c1ccc2c(c1C)CC[C@@H]2NC(=O)c1cc(C(=O)NCc2ccc(F)c(C(F)(F)F)c2)nc2c(F)cnn12] | E, 40%<br>[MNa]⁺ = 610 |
| 2164 | 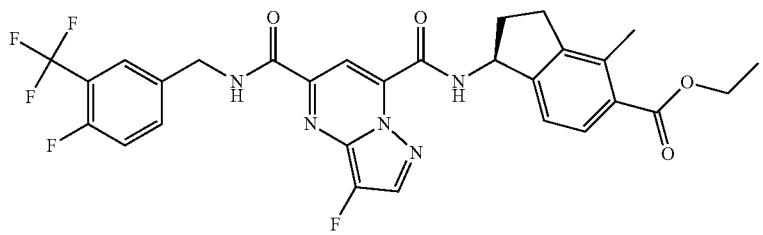 [SMILES: CCOC(=O)c1ccc2c(c1C)CC[C@@H]2NC(=O)c1cc(C(=O)NCc2ccc(F)c(C(F)(F)F)c2)nc2c(F)cnn12] | E, 41%<br>[MNa]⁺ = 624 |
| 2165 | 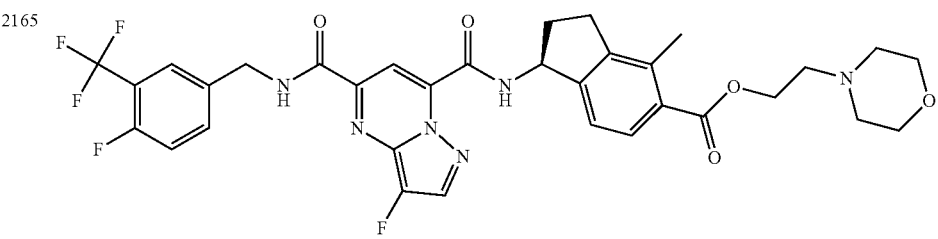 | E, 9%<br>[MH]⁺ = 687 |

TABLE II-45-continued
| 2166 | 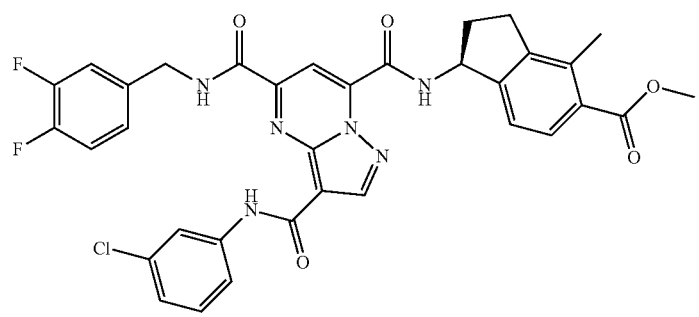 [SMILES: COC(=O)c1ccc2c(c1C)CC[C@@H]2NC(=O)c1cc(C(=O)NCc2ccc(F)c(F)c2)nc2c(C(=O)Nc3cccc(Cl)c3)cnn12] | E, 62% [M − H]⁻ = 671 |
| 2167 | 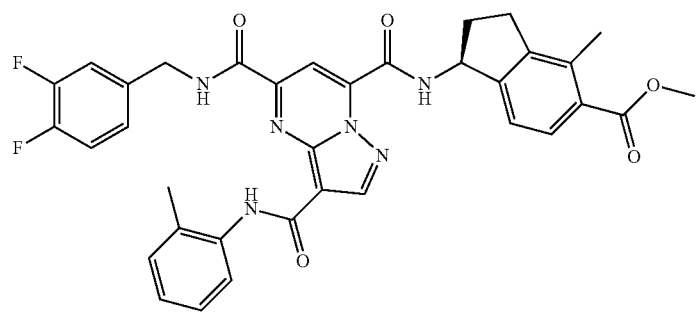 [SMILES: COC(=O)c1ccc2c(c1C)CC[C@@H]2NC(=O)c1cc(C(=O)NCc2ccc(F)c(F)c2)nc2c(C(=O)Nc3ccccc3C)cnn12] | E, 87% [M − H]⁻ = 651 |
| 2168 | 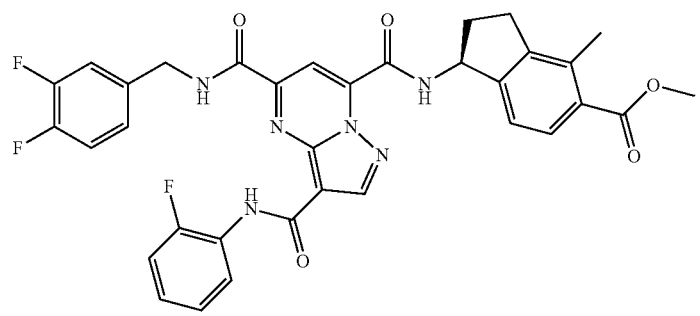 | E, 99% [M − H]⁻ = 655 |
| 2169 | 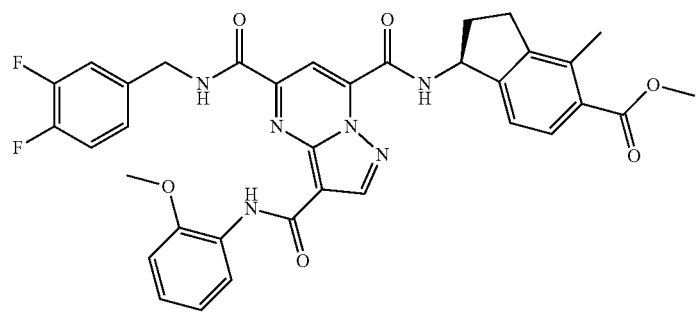 [SMILES: COC(=O)c1ccc2c(c1C)CC[C@@H]2NC(=O)c1cc(C(=O)NCc2ccc(F)c(F)c2)nc2c(C(=O)Nc3ccccc3OC)cnn12] | E, 78% [M − H]⁻ = 667 |
| 2170 | 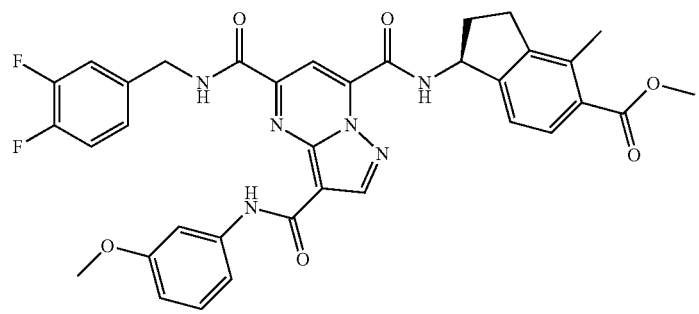 [SMILES: COC(=O)c1ccc2c(c1C)CC[C@@H]2NC(=O)c1cc(C(=O)NCc2ccc(F)c(F)c2)nc2c(C(=O)Nc3cccc(OC)c3)cnn12] | E, 65% [M − H]⁻ = 667 |

TABLE II-45-continued
| 2171 | 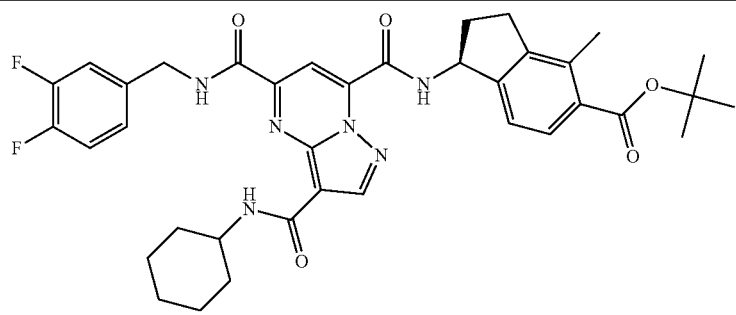 | E, 99% [M − H]⁻ = 685 |
| --- | --- | --- |
| 2172 | 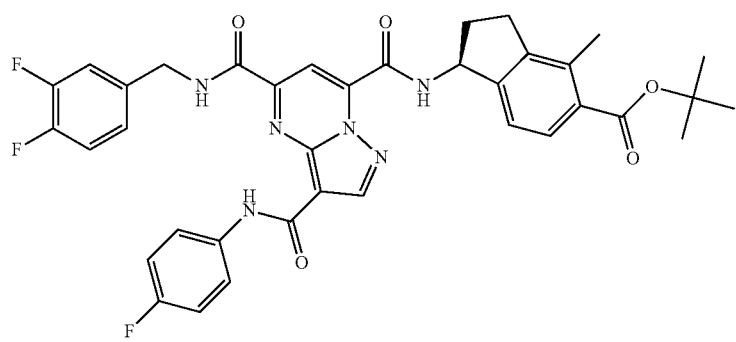 [SMILES: Cc1c(C(=O)OC(C)(C)C)ccc2c1CC[C@@H]2NC(=O)c1cc(C(=O)NCc2ccc(F)c(F)c2)nc2c(C(=O)Nc3ccc(F)cc3)cnn12] | E, 83% [M − H]⁻ = 697 |
| 2173 | 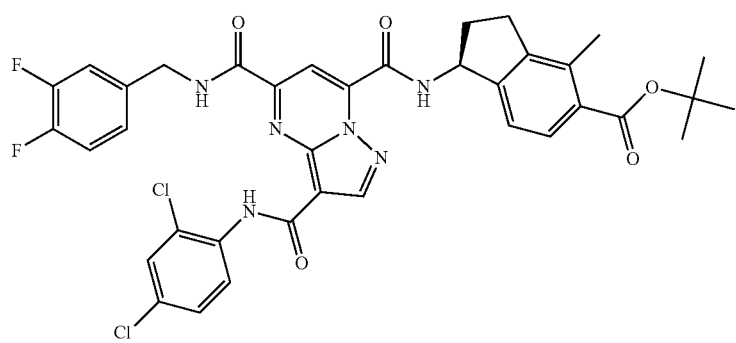 [SMILES: Cc1c(C(=O)OC(C)(C)C)ccc2c1CC[C@@H]2NC(=O)c1cc(C(=O)NCc2ccc(F)c(F)c2)nc2c(C(=O)Nc3ccc(Cl)cc3Cl)cnn12] | E, 80% [M − H]⁻ = 747 |
| 2174 | 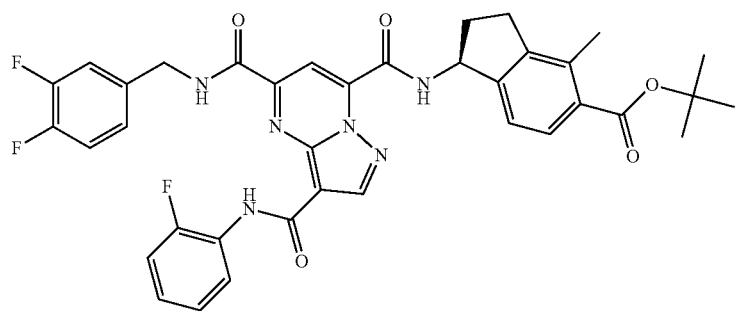 [SMILES: Cc1c(C(=O)OC(C)(C)C)ccc2c1CC[C@@H]2NC(=O)c1cc(C(=O)NCc2ccc(F)c(F)c2)nc2c(C(=O)Nc3ccccc3F)cnn12] | E, 77% [M − H]⁻ = 697 |

TABLE II-45-continued
| | | |
|---|---|---|
| 2175 | 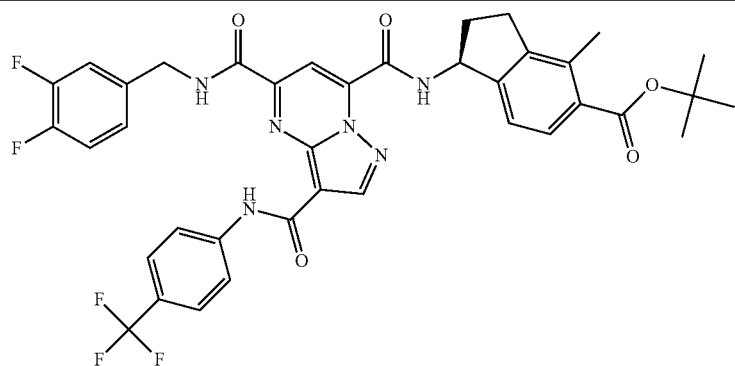 | E, 59%<br>[M − H]⁻ = 747 |
| 2176 | 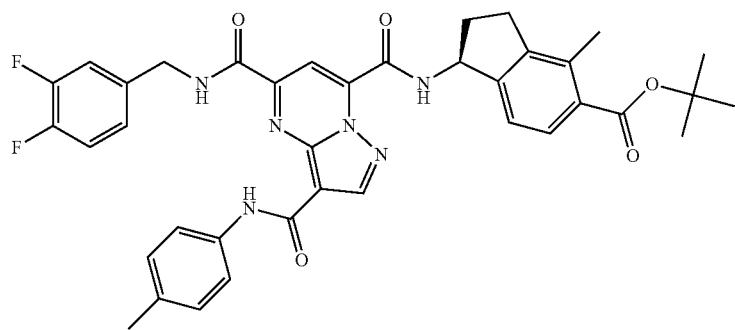 [SMILES: Cc1ccc(NC(=O)c2cnn3c(C(=O)N[C@H]4CCc5c4ccc(C(=O)OC(C)(C)C)c5C)cc(C(=O)NCc4ccc(F)c(F)c4)nc23)cc1] | E, 76%<br>[M − H]⁻ = 693 |
| 2177 | 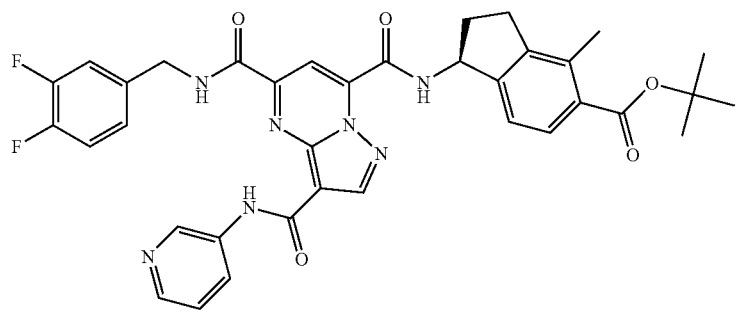 [SMILES: Cc1c(C(=O)OC(C)(C)C)ccc2c1CC[C@@H]2NC(=O)c1cc(C(=O)NCc2ccc(F)c(F)c2)nc2c(C(=O)Nc3cccnc3)cnn12] | E, 85%<br>[M − H]⁻ = 680 |
| 2178 | 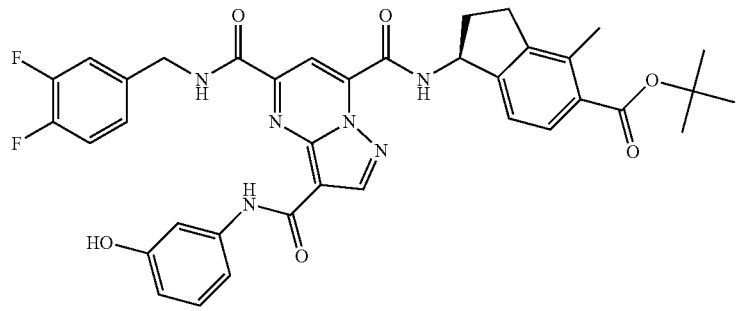 [SMILES: Cc1c(C(=O)OC(C)(C)C)ccc2c1CC[C@@H]2NC(=O)c1cc(C(=O)NCc2ccc(F)c(F)c2)nc2c(C(=O)Nc3cccc(O)c3)cnn12] | E, 65%<br>[M − H]⁻ = 695 |

TABLE II-45-continued
| 2179 | 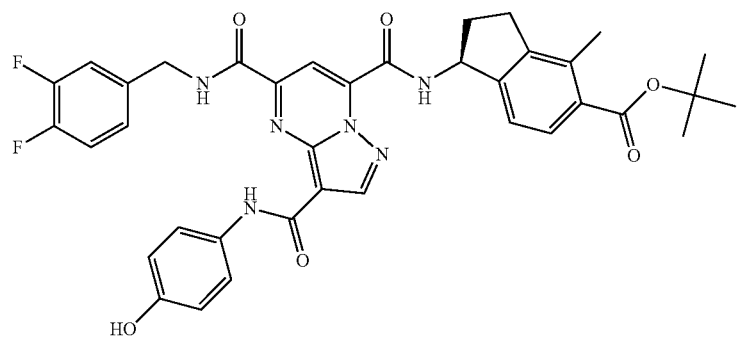 | E, 70%<br>[M − H]⁻ = 695 |
| 2180 | 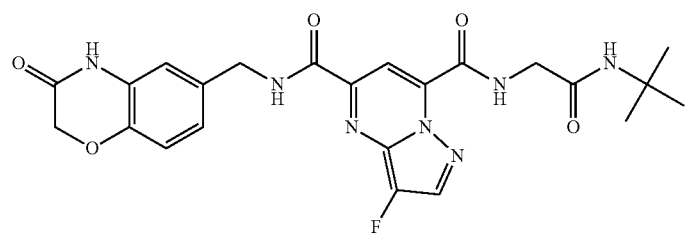 | B, 39%<br>[MH]⁺ = 498 |
| 2181 | 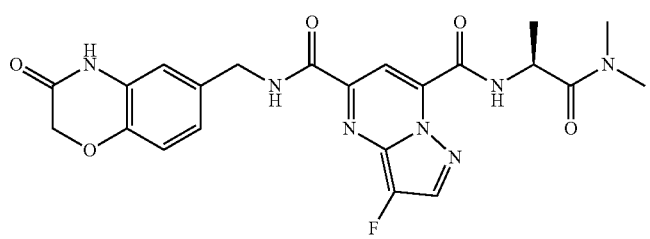 [SMILES: C[C@H](NC(=O)c1cc(C(=O)NCc2ccc3c(c2)NC(=O)CO3)nc2c(F)cnn12)C(=O)N(C)C] | B, 35%<br>[MH]⁺ = 484 |
| 2182 | 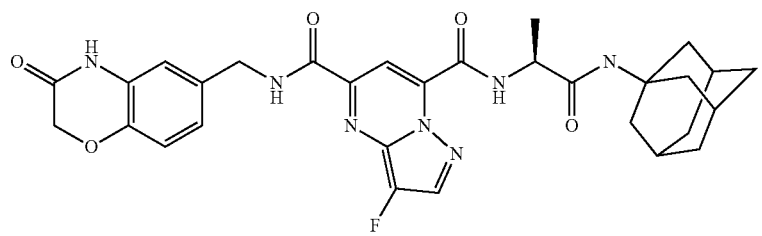 [SMILES: C[C@H](NC(=O)c1cc(C(=O)NCc2ccc3c(c2)NC(=O)CO3)nc2c(F)cnn12)C(=O)NC12CC3CC(CC(C3)C1)C2] | D, 40%<br>[MH]⁺ = 590 |
| 2183 | 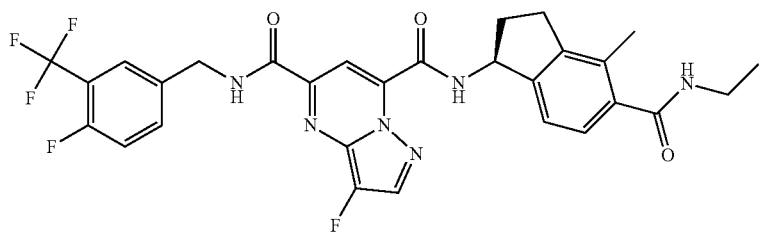 [SMILES: CCNC(=O)c1ccc2c(c1C)CC[C@@H]2NC(=O)c1cc(C(=O)NCc2ccc(F)c(C(F)(F)F)c2)nc2c(F)cnn12] | B, 11%<br>[MH]⁺ = 601 |
| 2184 | 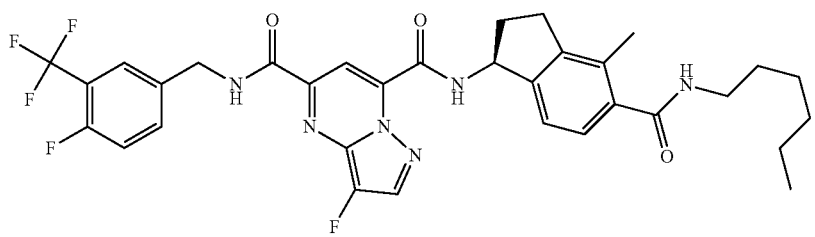 [SMILES: CCCCCCNC(=O)c1ccc2c(c1C)CC[C@@H]2NC(=O)c1cc(C(=O)NCc2ccc(F)c(C(F)(F)F)c2)nc2c(F)cnn12] | B, 22%<br>[MH]⁺ = 671 |

TABLE II-45-continued

| # | Structure | Data |
|---|---|---|
| 2185 | 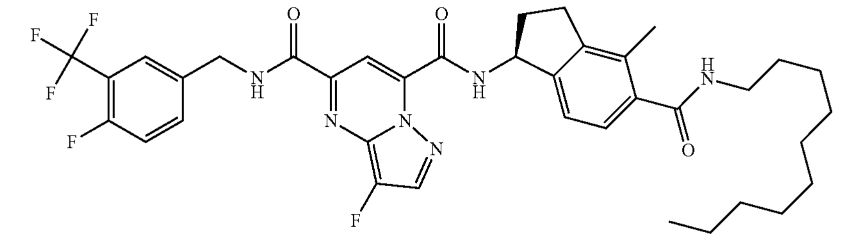 [SMILES: CCCCCCCCCCNC(=O)c1ccc2c(c1C)CC[C@@H]2NC(=O)c1cc(C(=O)NCc2ccc(F)c(C(F)(F)F)c2)nc2c(F)cnn12] | B, 10%<br>[MNa]⁺ = 713 |
| 2186 | 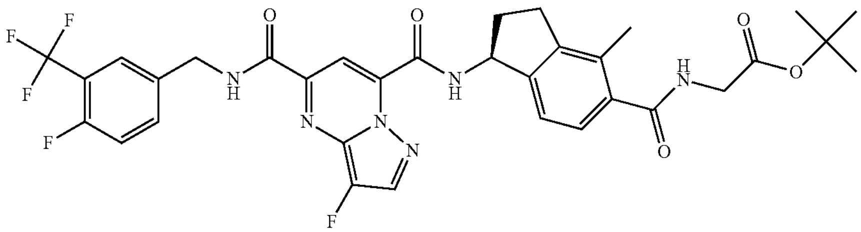 | B, 92%<br>[MH]⁺ = 687 |
| 2187 | 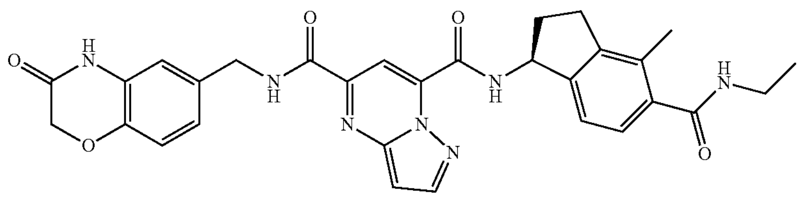 [SMILES: CCNC(=O)c1ccc2c(c1C)CC[C@@H]2NC(=O)c1cc(C(=O)NCc2ccc3c(c2)NC(=O)CO3)nc2ccnn12] | B, 76%<br>[MH]⁺ = 568 |
| 2188 | 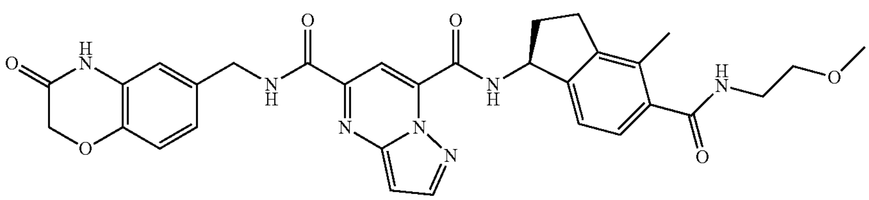 [SMILES: COCCNC(=O)c1ccc2c(c1C)CC[C@@H]2NC(=O)c1cc(C(=O)NCc2ccc3c(c2)NC(=O)CO3)nc2ccnn12] | B, 4%<br>[MH]⁺ = 598 |
| 2189 | 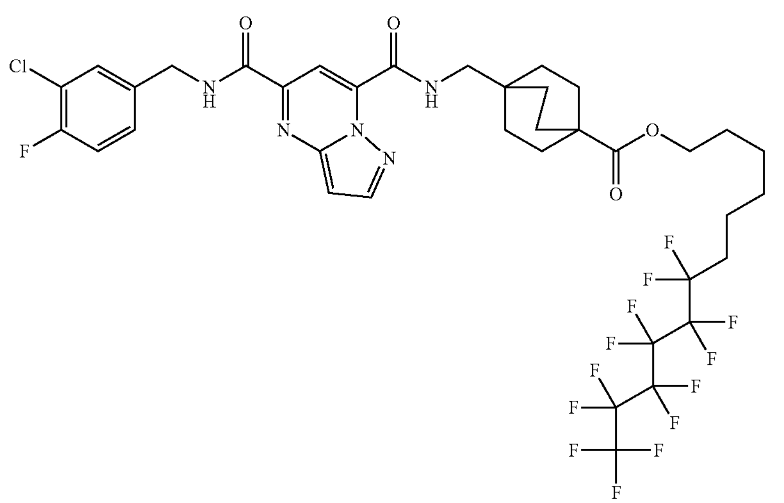 [SMILES: O=C(NCc1ccc(F)c(Cl)c1)c1cc(C(=O)NCC23CCC(C(=O)OCCCCCCC(F)(F)C(F)(F)C(F)(F)C(F)(F)C(F)(F)C(F)(F)F)(CC2)CC3)n2nccc2n1] | E, 4%<br>¹H-NMR (DMSO-d₆)<br>δ = 10.07 (t, 1 H), 9.73 (t, 1 H), 8.60 (d, 1 H), 8.11 (s, 1 H), 7.58 (d, 1 H), 7.39 (d, 2 H), 7.15 (d, 1 H), 4.52 (d, 2 H), 4.00 (t, 1 H), 3.29 (d, 2 H), 2.31-2.12 (m, 4 H), 1.75-1.12 (m, 20 H). |
| 2190 | 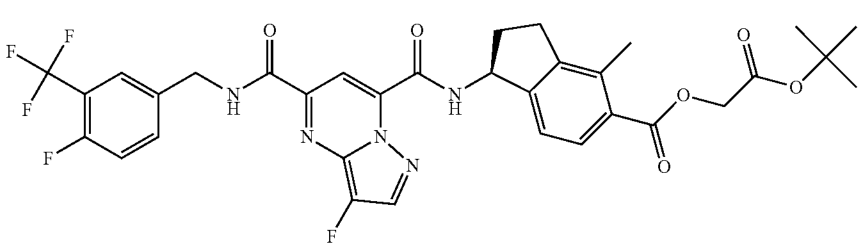 [SMILES: Cc1c(C(=O)OCC(=O)OC(C)(C)C)ccc2c1CC[C@@H]2NC(=O)c1cc(C(=O)NCc2ccc(F)c(C(F)(F)F)c2)nc2c(F)cnn12] | E, 73%<br>[MNA]⁺ = 710. |

TABLE II-45-continued
| | | |
|---|---|---|
| 2191 | 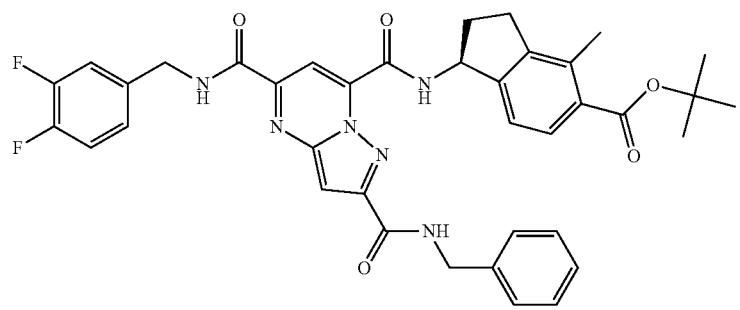 [SMILES: Cc1c(C(=O)OC(C)(C)C)ccc2c1CC[C@@H]2NC(=O)c1cc(C(=O)NCc2ccc(F)c(F)c2)nc2cc(C(=O)NCc3ccccc3)nn12] | A, 99%<br>[MH]⁺ = 695 |
| 2192 | 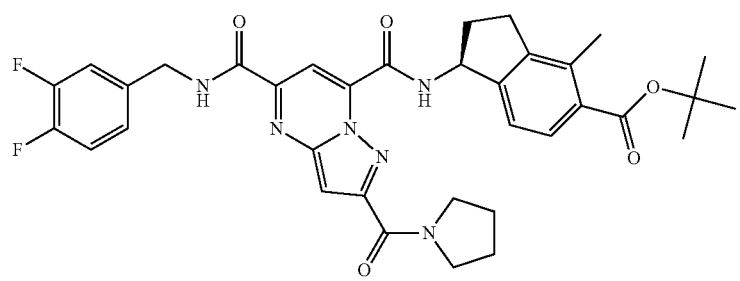 [SMILES: Cc1c(C(=O)OC(C)(C)C)ccc2c1CC[C@@H]2NC(=O)c1cc(C(=O)NCc2ccc(F)c(F)c2)nc2cc(C(=O)N3CCCC3)nn12] | E, 99%<br>[MH]⁺ = 659 |
| 2193 | 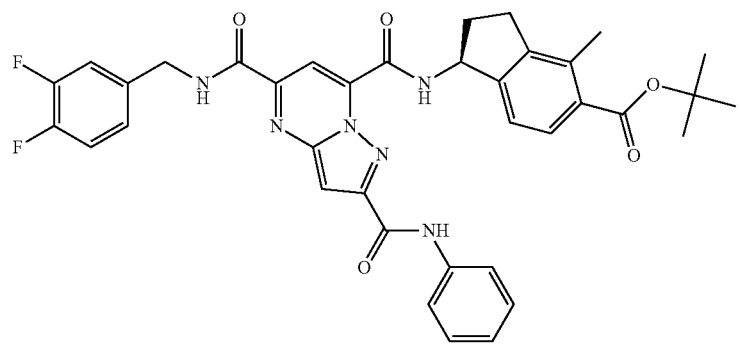 [SMILES: Cc1c(C(=O)OC(C)(C)C)ccc2c1CC[C@@H]2NC(=O)c1cc(C(=O)NCc2ccc(F)c(F)c2)nc2cc(C(=O)Nc3ccccc3)nn12] | E, n.d.<br>[MNa]⁺ = 681 |
| 2194 | 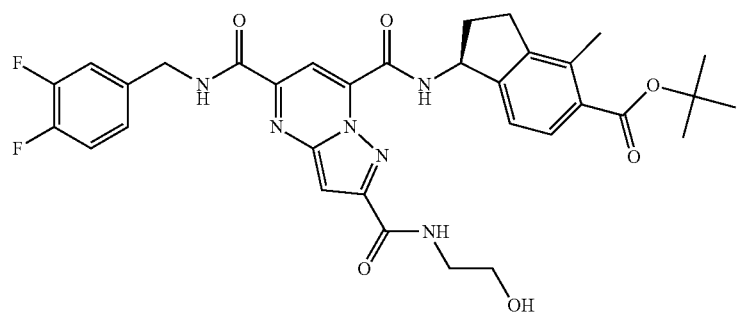 [SMILES: Cc1c(C(=O)OC(C)(C)C)ccc2c1CC[C@@H]2NC(=O)c1cc(C(=O)NCc2ccc(F)c(F)c2)nc2cc(C(=O)NCCO)nn12] | A, 67%<br>[MNa]⁺ = 671 |
| 2195 | 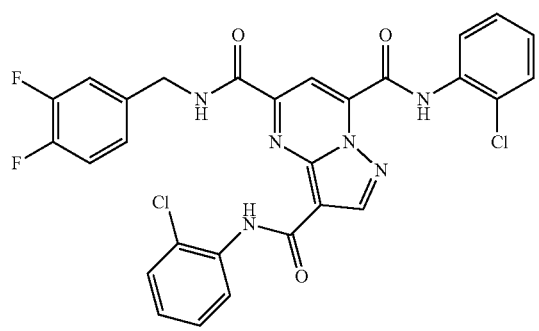 [SMILES: O=C(NCc1ccc(F)c(F)c1)c1cc(C(=O)Nc2ccccc2Cl)n2ncc(C(=O)Nc3ccccc3Cl)c2n1] | E, 20%<br>[MH]⁺ = 595 |

| | | |
|---|---|---|
| 2196 | 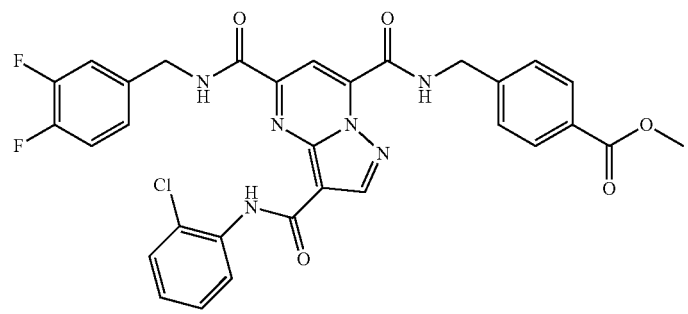 [SMILES: COC(=O)c1ccc(CNC(=O)c2cc(C(=O)NCc3ccc(F)c(F)c3)nc3c(C(=O)Nc4ccccc4Cl)cnn23)cc1] | E, 20%<br>[MH]+ = 633 |
| 2197 | 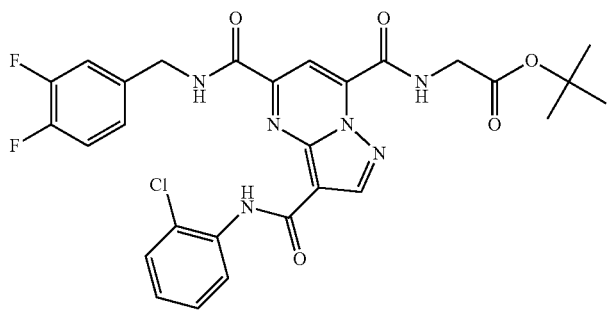 [SMILES: CC(C)(C)OC(=O)CNC(=O)c1cc(C(=O)NCc2ccc(F)c(F)c2)nc2c(C(=O)Nc3ccccc3Cl)cnn12] | E, 17%<br>[MH]+ = 599 |
| 2198 | 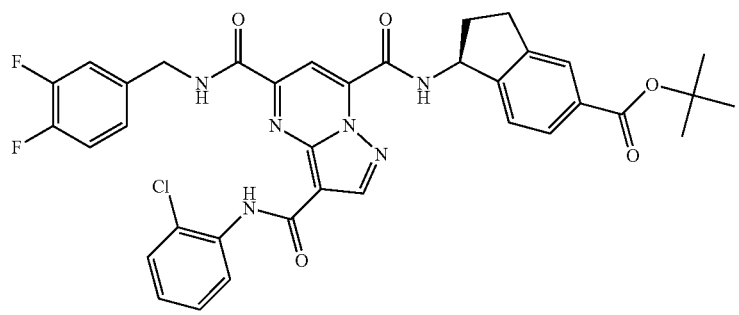 [SMILES: CC(C)(C)OC(=O)c1ccc2c(c1)CC[C@@H]2NC(=O)c1cc(C(=O)NCc2ccc(F)c(F)c2)nc2c(C(=O)Nc3ccccc3Cl)cnn12] | E, 75%<br>[MH]+ = 701 |
| 2199 | 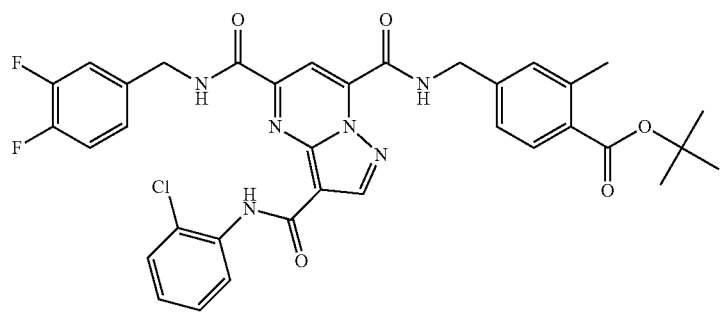 [SMILES: Cc1cc(CNC(=O)c2cc(C(=O)NCc3ccc(F)c(F)c3)nc3c(C(=O)Nc4ccccc4Cl)cnn23)ccc1C(=O)OC(C)(C)C] | E, 35%<br>[MH]+ = 689 |
| 2200 | 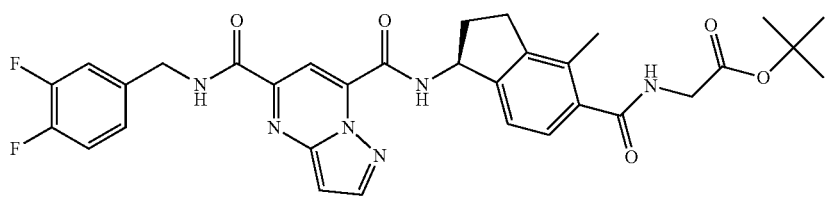 [SMILES: Cc1c(C(=O)NCC(=O)OC(C)(C)C)ccc2c1CC[C@@H]2NC(=O)c1cc(C(=O)NCc2ccc(F)c(F)c2)nc2ccnn12] | E, n.d.<br>[MH]+ = 619 |

TABLE II-45-continued
| 2201 | 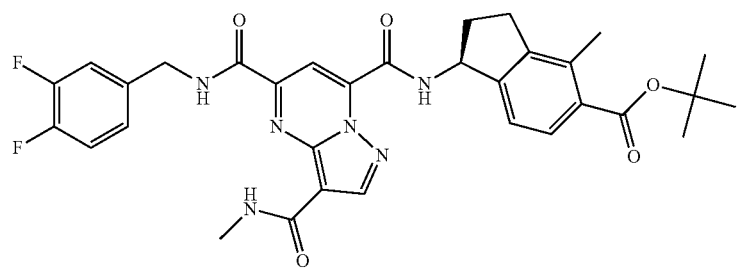 [SMILES: CNC(=O)c1cnn2c(C(=O)N[C@H]3CCc4c3ccc(C(=O)OC(C)(C)C)c4C)cc(C(=O)NCc3ccc(F)c(F)c3)nc12] | E, 66% [M − H]⁻ = 617 |
| 2202 | 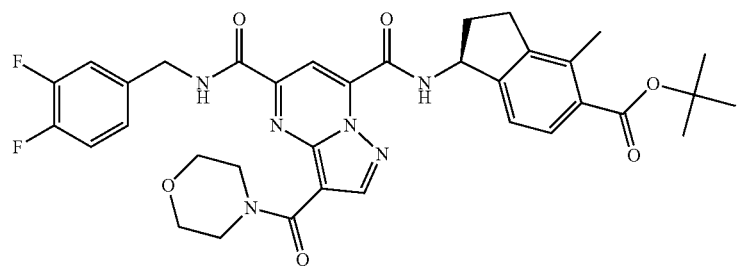 [SMILES: Cc1c(C(=O)OC(C)(C)C)ccc2c1CC[C@@H]2NC(=O)c1cc(C(=O)NCc2ccc(F)c(F)c2)nc2c(C(=O)N3CCOCC3)cnn12] | E, 73% [M − H]⁻ = 673 |
| 2203 | 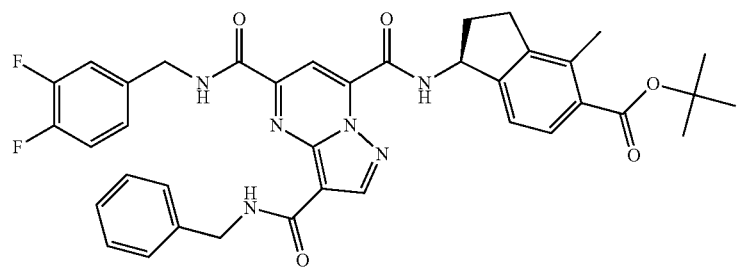 [SMILES: Cc1c(C(=O)OC(C)(C)C)ccc2c1CC[C@@H]2NC(=O)c1cc(C(=O)NCc2ccc(F)c(F)c2)nc2c(C(=O)NCc3ccccc3)cnn12] | E, 72% [M − H]⁻ = 693 |
| 2204 | 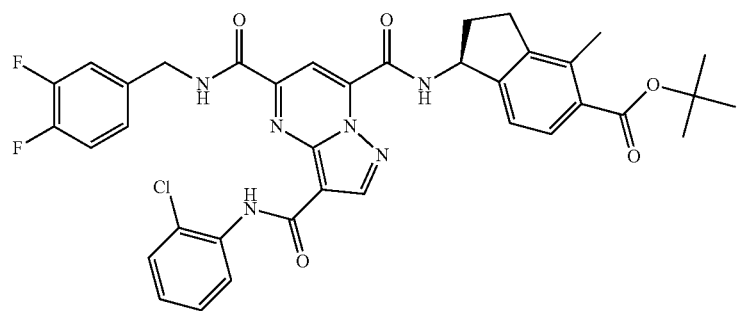 [SMILES: Cc1c(C(=O)OC(C)(C)C)ccc2c1CC[C@@H]2NC(=O)c1cc(C(=O)NCc2ccc(F)c(F)c2)nc2c(C(=O)Nc3ccccc3Cl)cnn12] | E, 65% [M − H]⁻ = 713 |
| 2205 | 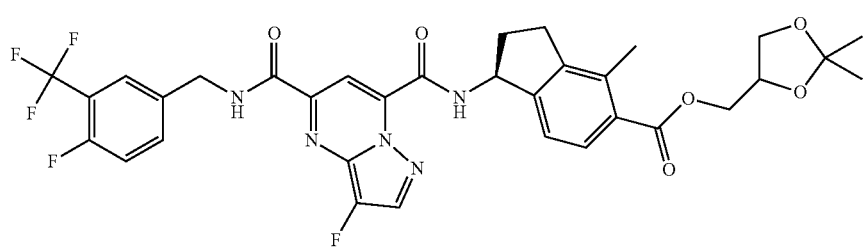 [SMILES: Cc1c(C(=O)OCC2COC(C)(C)O2)ccc2c1CC[C@@H]2NC(=O)c1cc(C(=O)NCc2ccc(F)c(C(F)(F)F)c2)nc2c(F)cnn12] | E, 23% [MNa]⁺ = 710 |
| 2206 | 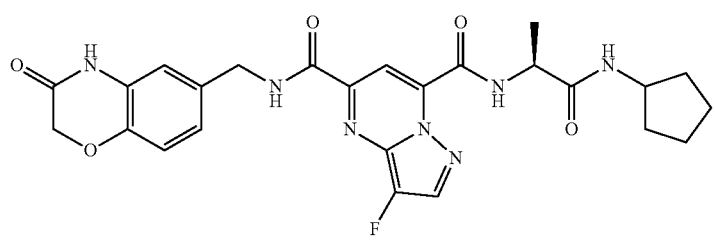 [SMILES: C[C@H](NC(=O)c1cc(C(=O)NCc2ccc3c(c2)NC(=O)CO3)nc2c(F)cnn12)C(=O)NC1CCCC1] | C, 30% [MH]⁺ = 524 |

TABLE II-45-continued
| 2207 | 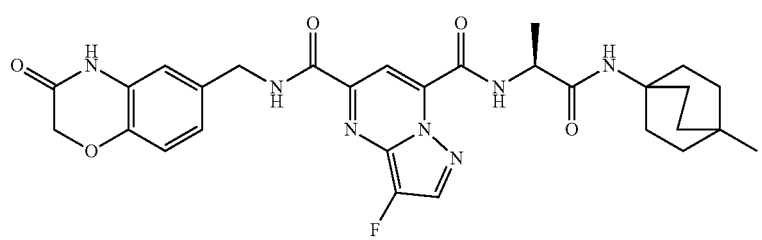 [SMILES: C[C@H](NC(=O)c1cc(C(=O)NCc2ccc3c(c2)NC(=O)CO3)nc2c(F)cnn12)C(=O)NC12CCC(C)(CC1)CC2] | C, 12%<br>[MH]⁺ = 578 |
| 2208 | 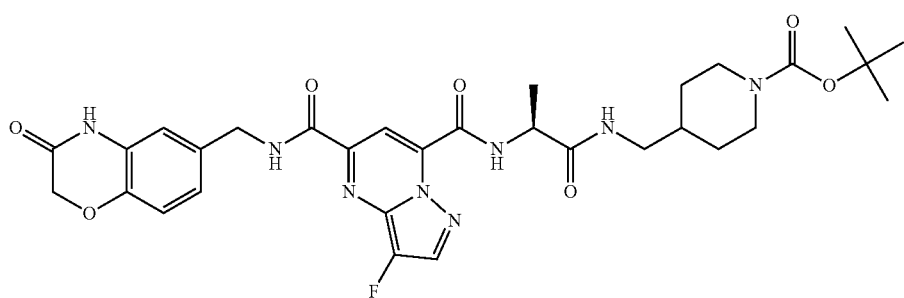 [SMILES: C[C@H](NC(=O)c1cc(C(=O)NCc2ccc3c(c2)NC(=O)CO3)nc2c(F)cnn12)C(=O)NCC1CCN(C(=O)OC(C)(C)C)CC1] | C, n.d.<br>[MNa]⁺ = 604 |
| 2209 | 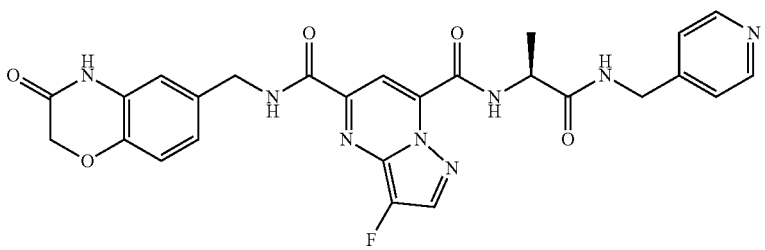 [SMILES: C[C@H](NC(=O)c1cc(C(=O)NCc2ccc3c(c2)NC(=O)CO3)nc2c(F)cnn12)C(=O)NCc1ccncc1] | C, 77%<br>[MH]⁺ = 476 |
| 2210 | 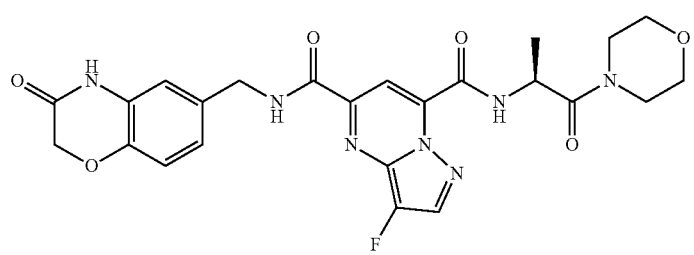 [SMILES: C[C@H](NC(=O)c1cc(C(=O)NCc2ccc3c(c2)NC(=O)CO3)nc2c(F)cnn12)C(=O)N1CCOCC1] | C, 46%<br>[MH]⁺ = 526 |
| 2211 | 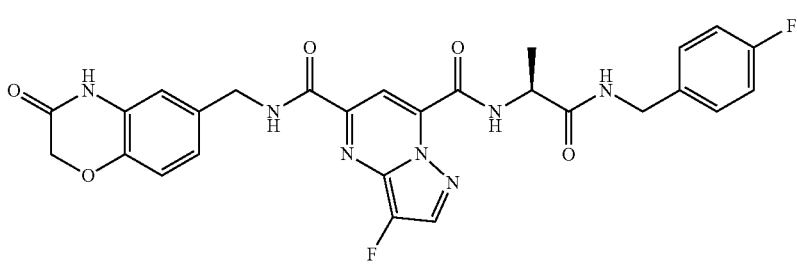 [SMILES: C[C@H](NC(=O)c1cc(C(=O)NCc2ccc3c(c2)NC(=O)CO3)nc2c(F)cnn12)C(=O)NCc1ccc(F)cc1] | C, 34%<br>[MH]⁺ = 564 |
| 2212 | 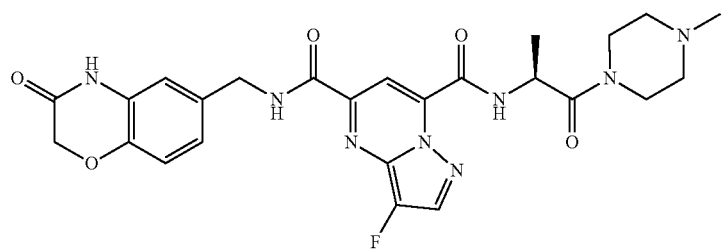 [SMILES: C[C@H](NC(=O)c1cc(C(=O)NCc2ccc3c(c2)NC(=O)CO3)nc2c(F)cnn12)C(=O)N1CCN(C)CC1] | C, 40%<br>[MH]⁺ = 539 |

TABLE II-45-continued
| 2213 | 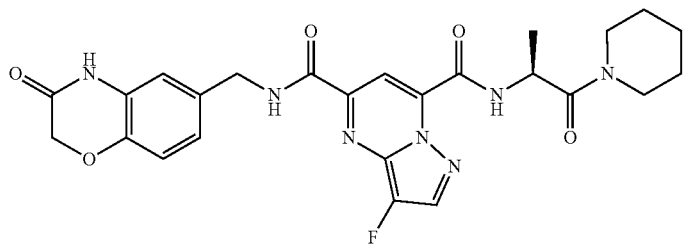 [SMILES: C[C@H](NC(=O)c1cc(C(=O)NCc2ccc3c(c2)NC(=O)CO3)nc2c(F)cnn12)C(=O)N1CCCCC1] | C, 91%<br>[MH]+ = 524 |
Example 2214
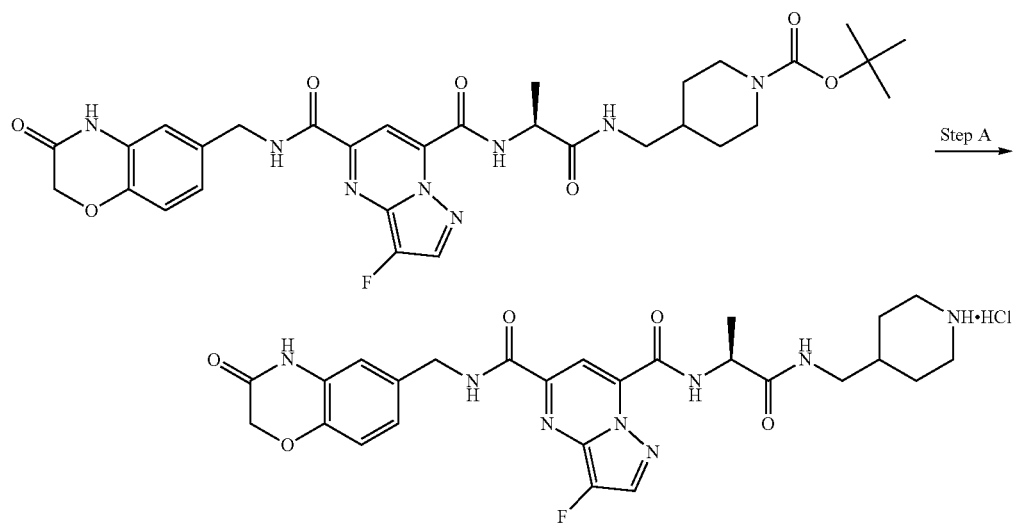
Step A  40
The title compound from the Example 2208 was treated similarly as described in the Example 296, Step B to afford the title compound. [M-Cl]+=482.
Example 2215

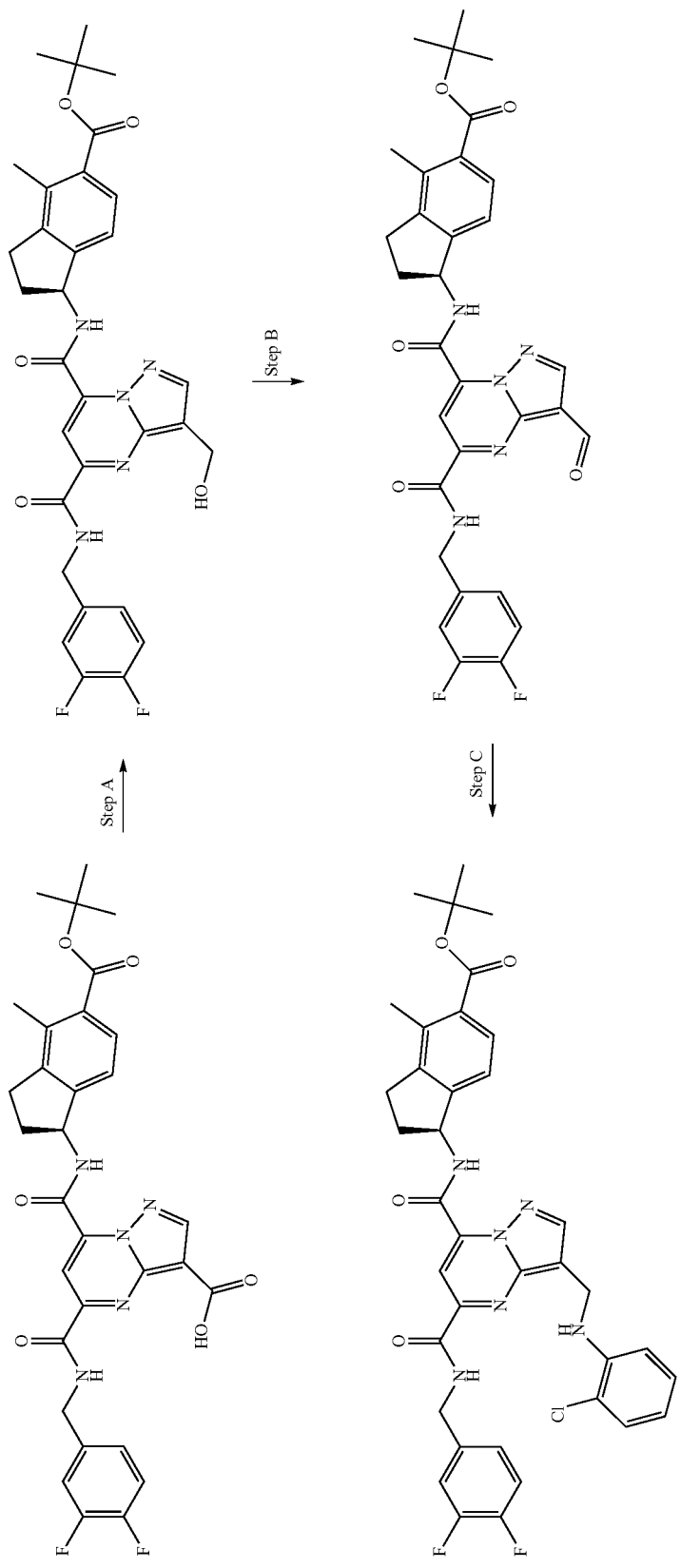

Step A

To an ice cooled (0-5° C.) solution of the title compound from the Example 1834 (25 mg) in THF (1 mL) was added BH$_3$.THF complex (120 μL). The resulting mixture was stirred for 24 h while warming to room temperature, cooled to 0-5° C. (ice bath), hydrolyzed with 1M aqueous HCl (2 mL) and extracted with CH$_2$Cl$_2$ (3×5 mL). The combined organic phases were dried (MgSO$_4$), filtered, concentrated and purified by chromatography (silica, hexanes/EtOAc) to afford the title compound as a yellow solid (5 mg, 23%). [MH]$^+$=592.

Step B

To a solution of the title compound from Step A above (5 mg) in CH$_2$Cl$_2$ (1 mL) were sequentially added molecular sieves 4A (100 mg), N-methylmorpholine N-oxide (2 mg) and TPAP (0.5 mg). The resulting black mixture was stirred at room temperature for 3 h, filtered through Celite® and concentrated to afford the title compound (5 mg, 98%). [MH]$^+$=590.

Step C

To a solution of the title compound from Step B above (5 mg) in MeOH (2 mL) were added NaBH$_3$CN (1.6 mg) and AcOH (50 μL). The resulting mixture was stirred at room temperature overnight, concentrated and purified by preparative thin layer chromatography (silica, hexanes/EtOAc) to afford the title compound as a yellow solid (2 mg, 35%). [MNa]$^+$=723.

Examples 2216-2220

Following a similar procedure as described in the Example 1859, except using the esters indicated in Table II-46 below, the following compounds were prepared.

TABLE II-46

| Ex. # | ester |
|---|---|
| 2216 | 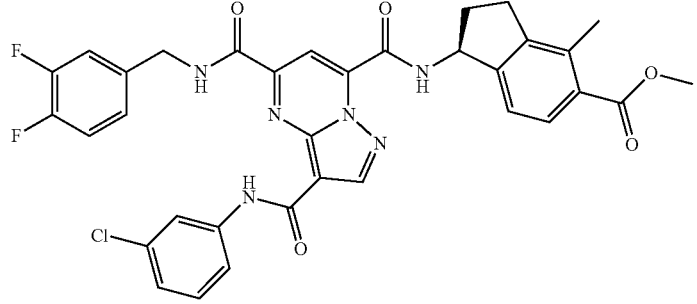 [SMILES: COC(=O)c1ccc2c(c1C)CC[C@@H]2NC(=O)c1cc(C(=O)NCc2ccc(F)c(F)c2)nc2c(C(=O)Nc3cccc(Cl)c3)cnn12] |
| 2217 | 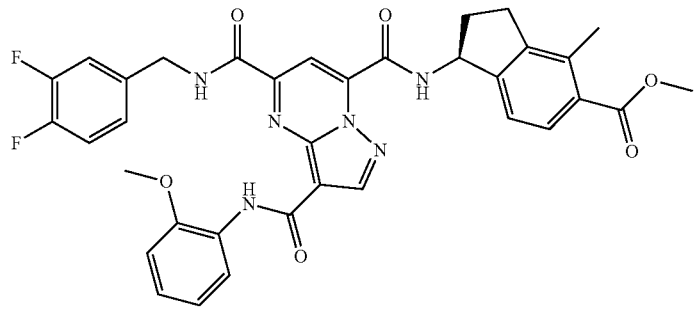 [SMILES: COC(=O)c1ccc2c(c1C)CC[C@@H]2NC(=O)c1cc(C(=O)NCc2ccc(F)c(F)c2)nc2c(C(=O)Nc3ccccc3OC)cnn12] |
| 2218 | 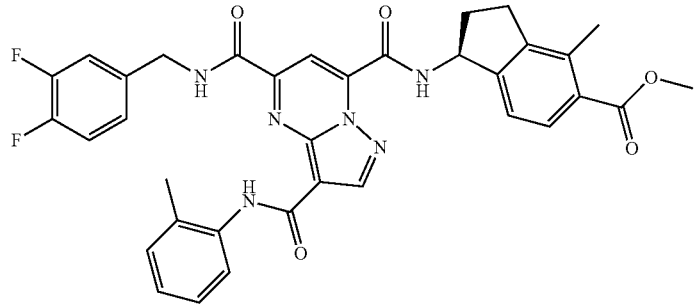 [SMILES: COC(=O)c1ccc2c(c1C)CC[C@@H]2NC(=O)c1cc(C(=O)NCc2ccc(F)c(F)c2)nc2c(C(=O)Nc3ccccc3C)cnn12] |

TABLE II-46-continued
| 2219 | 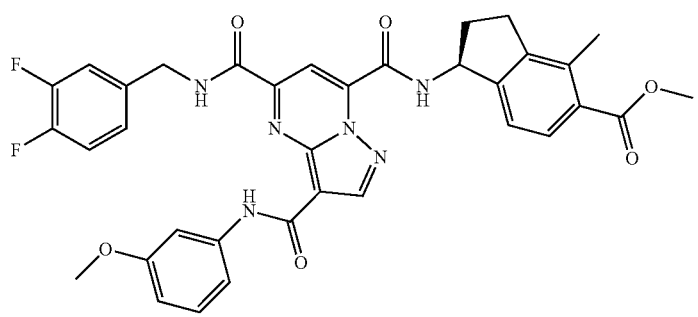 [SMILES: COC(=O)c1ccc2c(c1C)CC[C@@H]2NC(=O)c1cc(C(=O)NCc2ccc(F)c(F)c2)nc2c(C(=O)Nc3cccc(OC)c3)cnn12] |
| --- | --- |
| 2220 | 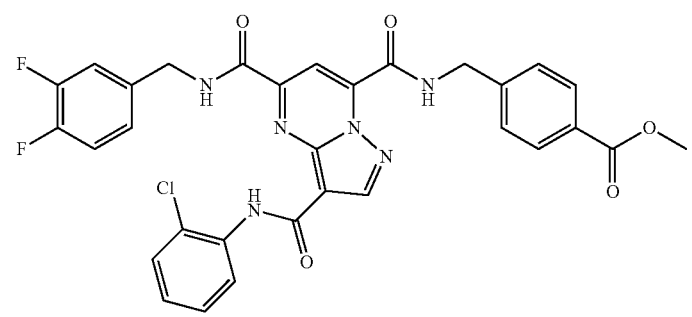 [SMILES: COC(=O)c1ccc(CNC(=O)c2cc(C(=O)NCc3ccc(F)c(F)c3)nc3c(C(=O)Nc4ccccc4Cl)cnn23)cc1] |
| Ex. # | product | yield |
| --- | --- | --- |
| 2216 | 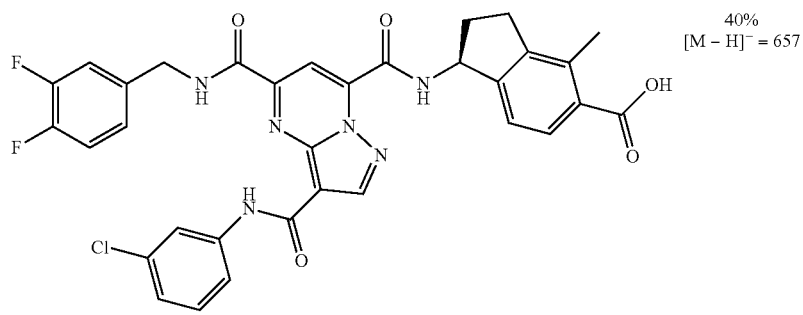 | 40%<br>[M − H]⁻ = 657 |
| 2217 | 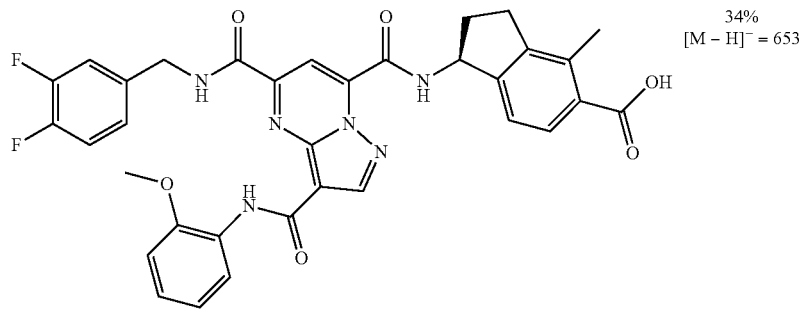 | 34%<br>[M − H]⁻ = 653 |
| 2218 | 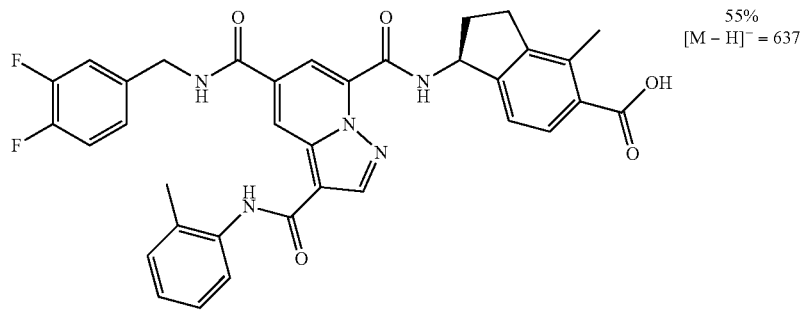 | 55%<br>[M − H]⁻ = 637 |

TABLE II-46-continued

| 2219 | [structure] | 40% [M − H]⁻ = 637 |
| 2220 | [structure] | B, 35% [MH]⁺ = 619 |

Examples 2221-2255

Following similar procedures as described in the Example 436 (method A) and the Example 1885 (method B), except using the esters as indicated in Table H-47 below, the following compounds were prepared.

TABLE II-47

| Ex. # | ester |
|---|---|
| 2221 | [structure] |
| 2222 | [structure] |
| 2223 | [structure] |

TABLE II-47-continued
| 2224 | 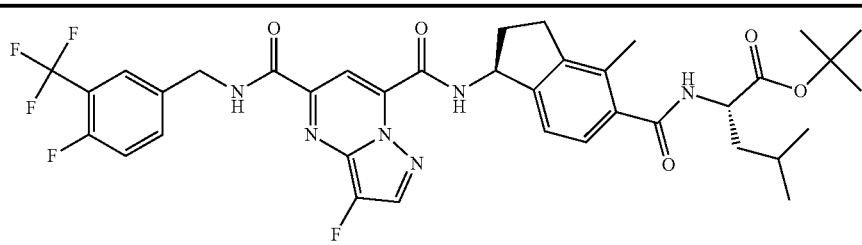 |
| 2225 | 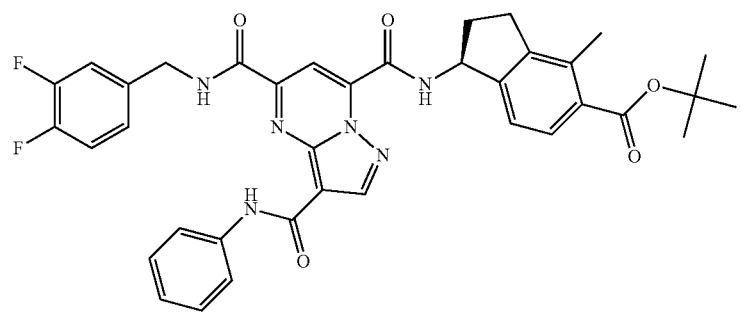 [SMILES: Cc1c(C(=O)OC(C)(C)C)ccc2c1CC[C@@H]2NC(=O)c1cc(C(=O)NCc2ccc(F)c(F)c2)nc2c(C(=O)Nc3ccccc3)cnn12] |
| 2226 | 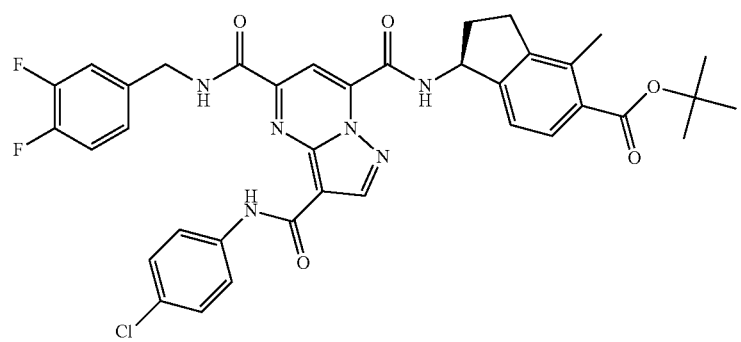 [SMILES: Cc1c(C(=O)OC(C)(C)C)ccc2c1CC[C@@H]2NC(=O)c1cc(C(=O)NCc2ccc(F)c(F)c2)nc2c(C(=O)Nc3ccc(Cl)cc3)cnn12] |
| 2227 | 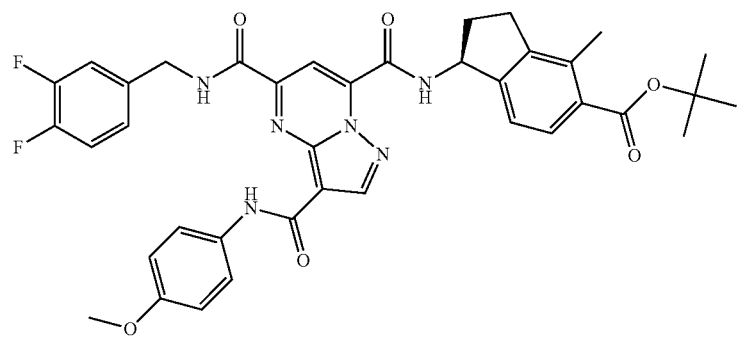 [SMILES: COc1ccc(NC(=O)c2cnn3c(C(=O)N[C@H]4CCc5c4ccc(C(=O)OC(C)(C)C)c5C)cc(C(=O)NCc4ccc(F)c(F)c4)nc23)cc1] |
| 2228 | 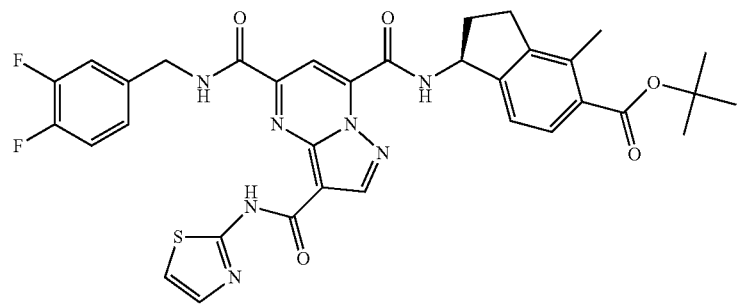 [SMILES: Cc1c(C(=O)OC(C)(C)C)ccc2c1CC[C@@H]2NC(=O)c1cc(C(=O)NCc2ccc(F)c(F)c2)nc2c(C(=O)Nc3nccs3)cnn12] |

TABLE II-47-continued
2229 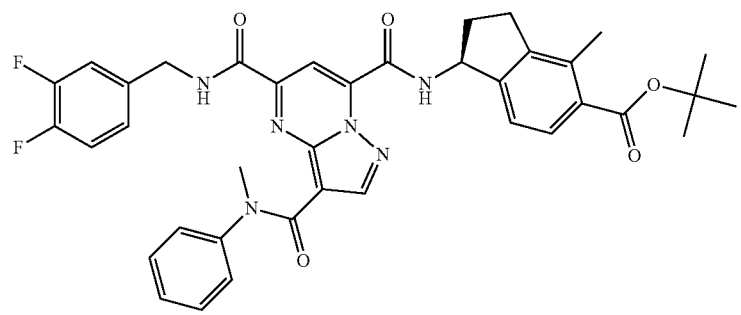 [SMILES: Cc1c(C(=O)OC(C)(C)C)ccc2c1CC[C@@H]2NC(=O)c1cc(C(=O)NCc2ccc(F)c(F)c2)nc2c(C(=O)N(C)c3ccccc3)cnn12]
2230 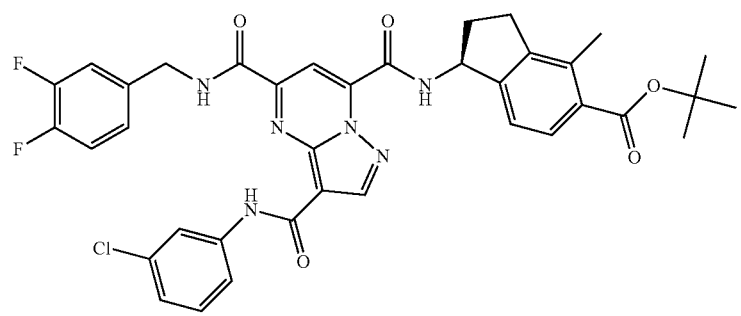 [SMILES: Cc1c(C(=O)OC(C)(C)C)ccc2c1CC[C@@H]2NC(=O)c1cc(C(=O)NCc2ccc(F)c(F)c2)nc2c(C(=O)Nc3cccc(Cl)c3)cnn12]
2231 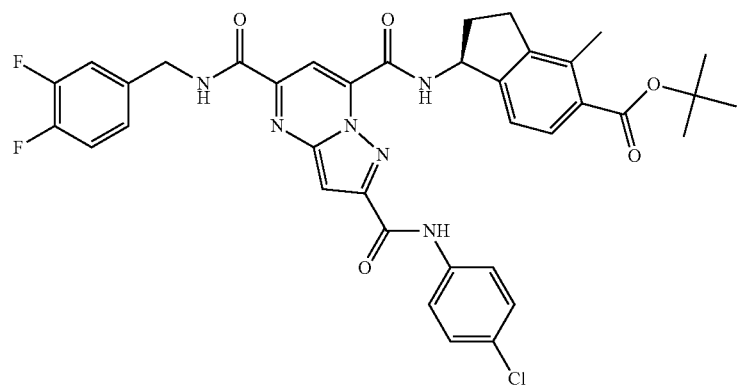 [SMILES: Cc1c(C(=O)OC(C)(C)C)ccc2c1CC[C@@H]2NC(=O)c1cc(C(=O)NCc2ccc(F)c(F)c2)nc2cc(C(=O)Nc3ccc(Cl)cc3)nn12]
2232 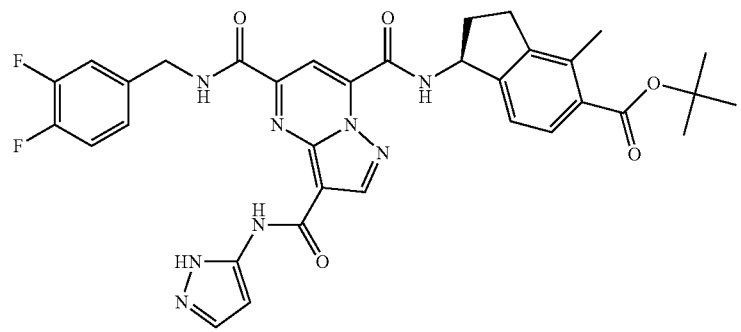 [SMILES: Cc1c(C(=O)OC(C)(C)C)ccc2c1CC[C@@H]2NC(=O)c1cc(C(=O)NCc2ccc(F)c(F)c2)nc2c(C(=O)Nc3ccn[nH]3)cnn12]

TABLE II-47-continued
| 2233 | 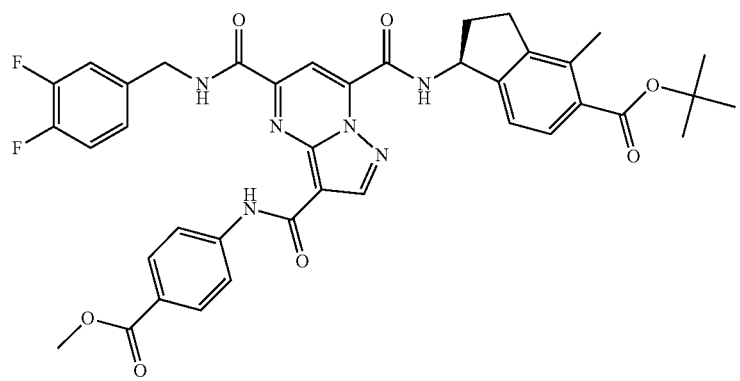 [SMILES: COC(=O)c1ccc(NC(=O)c2cnn3c(C(=O)N[C@H]4CCc5c4ccc(C(=O)OC(C)(C)C)c5C)cc(C(=O)NCc4ccc(F)c(F)c4)nc23)cc1] |
| 2234 | 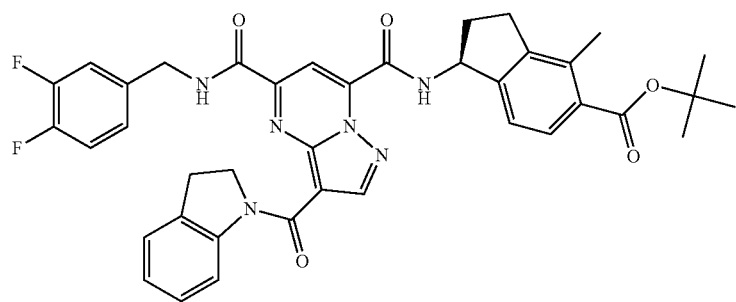 [SMILES: Cc1c(C(=O)OC(C)(C)C)ccc2c1CC[C@@H]2NC(=O)c1cc(C(=O)NCc2ccc(F)c(F)c2)nc2c(C(=O)N3CCc4ccccc43)cnn12] |
| 2235 | 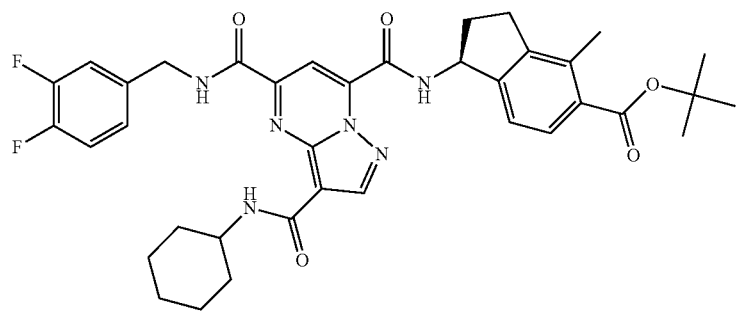 [SMILES: Cc1c(C(=O)OC(C)(C)C)ccc2c1CC[C@@H]2NC(=O)c1cc(C(=O)NCc2ccc(F)c(F)c2)nc2c(C(=O)NC3CCCCC3)cnn12] |
| 2236 | 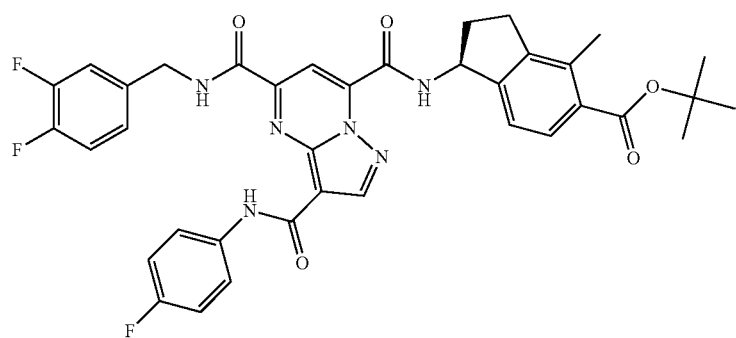 [SMILES: Cc1c(C(=O)OC(C)(C)C)ccc2c1CC[C@@H]2NC(=O)c1cc(C(=O)NCc2ccc(F)c(F)c2)nc2c(C(=O)Nc3ccc(F)cc3)cnn12] |

TABLE II-47-continued
| 2237 | 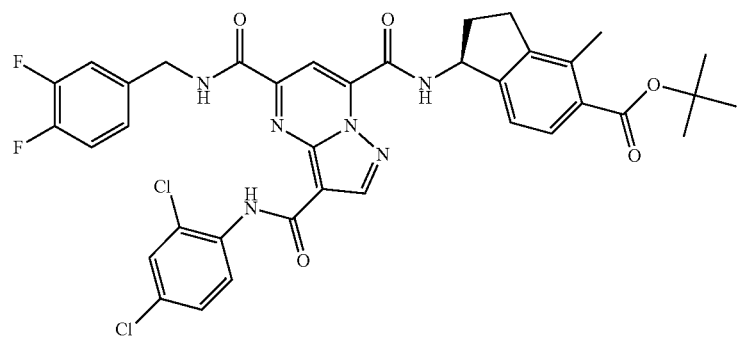 [SMILES: Cc1c(C(=O)OC(C)(C)C)ccc2c1CC[C@@H]2NC(=O)c1cc(C(=O)NCc2ccc(F)c(F)c2)nc2c(C(=O)Nc3ccc(Cl)cc3Cl)cnn12] |
| 2238 | 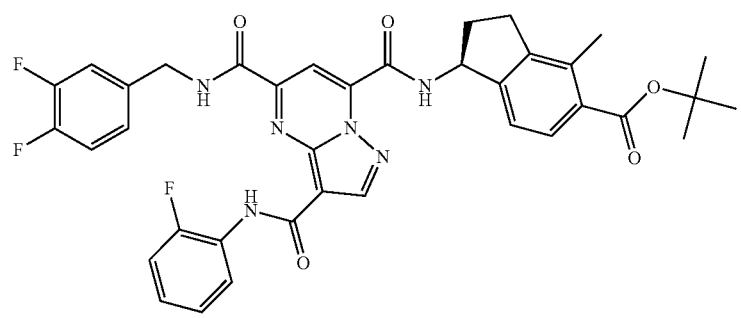 [SMILES: Cc1c(C(=O)OC(C)(C)C)ccc2c1CC[C@@H]2NC(=O)c1cc(C(=O)NCc2ccc(F)c(F)c2)nc2c(C(=O)Nc3ccccc3F)cnn12] |
| 2239 | 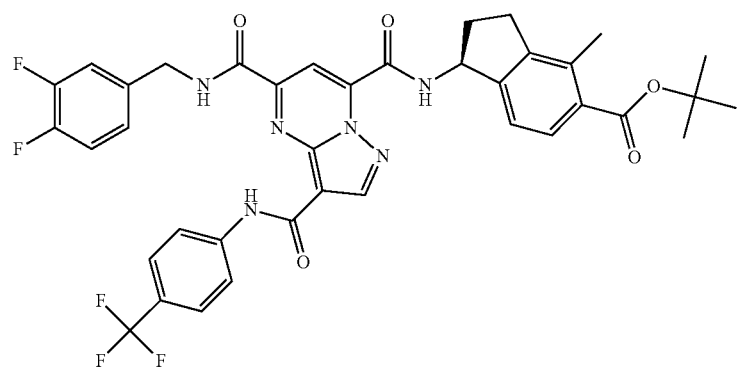 [SMILES: Cc1c(C(=O)OC(C)(C)C)ccc2c1CC[C@@H]2NC(=O)c1cc(C(=O)NCc2ccc(F)c(F)c2)nc2c(C(=O)Nc3ccc(C(F)(F)F)cc3)cnn12] |
| 2240 | 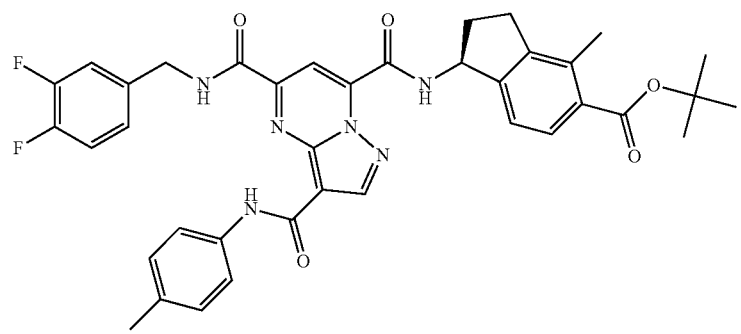 [SMILES: Cc1ccc(NC(=O)c2cnn3c(C(=O)N[C@H]4CCc5c4ccc(C(=O)OC(C)(C)C)c5C)cc(C(=O)NCc4ccc(F)c(F)c4)nc23)cc1] |

TABLE II-47-continued
| 2241 | 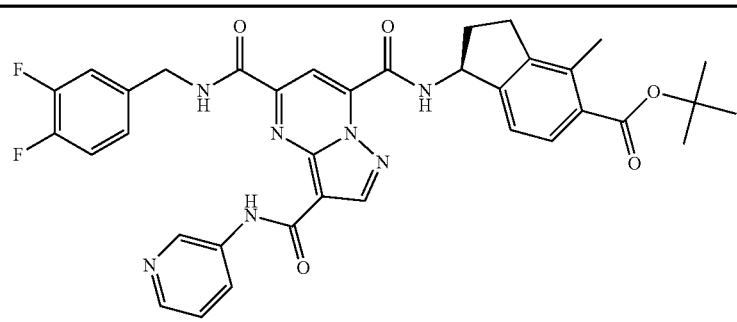 |
| 2242 | 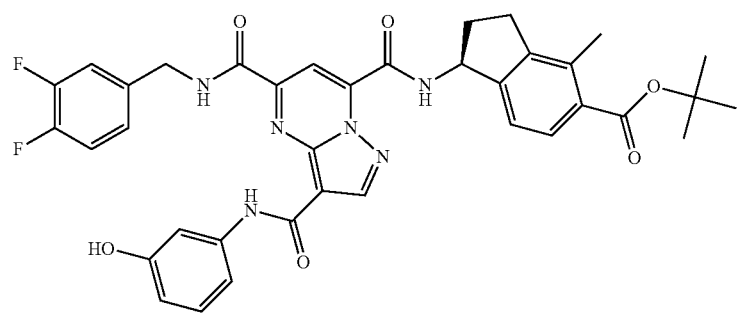 [SMILES: Cc1c(C(=O)OC(C)(C)C)ccc2c1CC[C@@H]2NC(=O)c1cc(C(=O)NCc2ccc(F)c(F)c2)nc2c(C(=O)Nc3cccc(O)c3)cnn12] |
| 2243 | 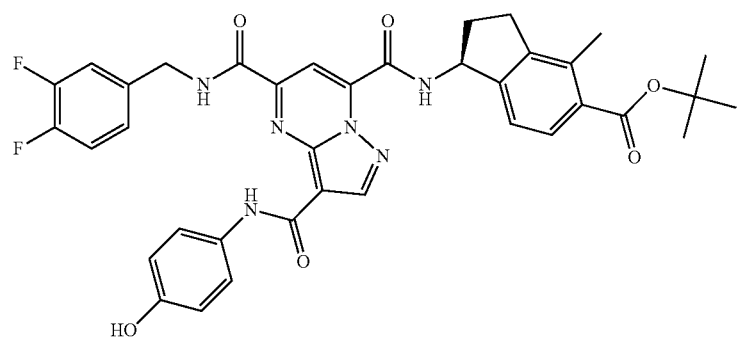 |
| 2244 | 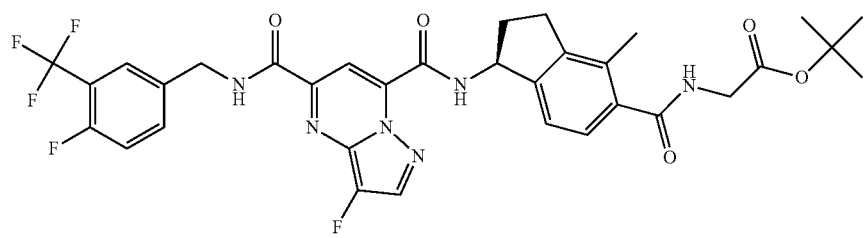 |
| 2245 | 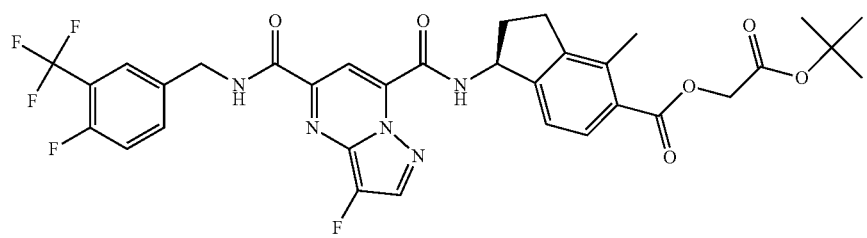 [SMILES: Cc1c(C(=O)OCC(=O)OC(C)(C)C)ccc2c1CC[C@@H]2NC(=O)c1cc(C(=O)NCc2ccc(F)c(C(F)(F)F)c2)nc2c(F)cnn12] |

TABLE II-47-continued
| 2246 | 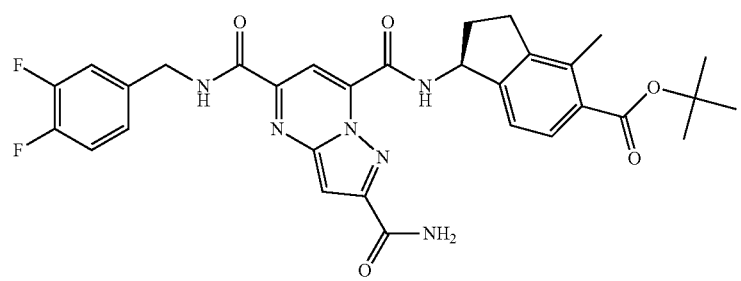 |
| --- | --- |
| 2247 | 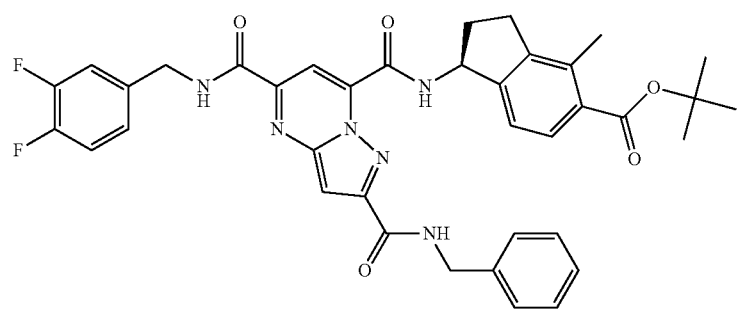 [SMILES: Cc1c(C(=O)OC(C)(C)C)ccc2c1CC[C@@H]2NC(=O)c1cc(C(=O)NCc2ccc(F)c(F)c2)nc2cc(C(=O)NCc3ccccc3)nn12] |
| 2248 | 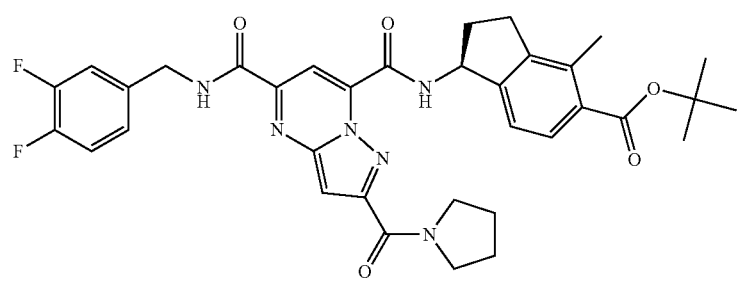 [SMILES: Cc1c(C(=O)OC(C)(C)C)ccc2c1CC[C@@H]2NC(=O)c1cc(C(=O)NCc2ccc(F)c(F)c2)nc2cc(C(=O)N3CCCC3)nn12] |
| 2249 | 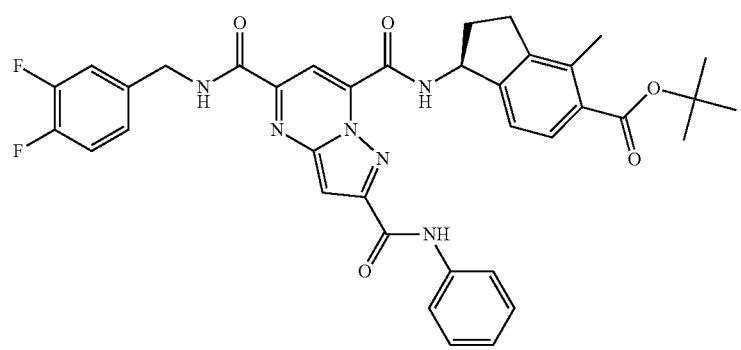 [SMILES: Cc1c(C(=O)OC(C)(C)C)ccc2c1CC[C@@H]2NC(=O)c1cc(C(=O)NCc2ccc(F)c(F)c2)nc2cc(C(=O)Nc3ccccc3)nn12] |
| 2250 | 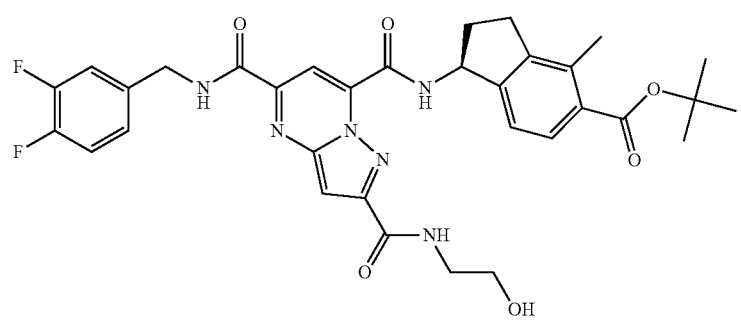 [SMILES: Cc1c(C(=O)OC(C)(C)C)ccc2c1CC[C@@H]2NC(=O)c1cc(C(=O)NCc2ccc(F)c(F)c2)nc2cc(C(=O)NCCO)nn12] |

TABLE II-47-continued
2251 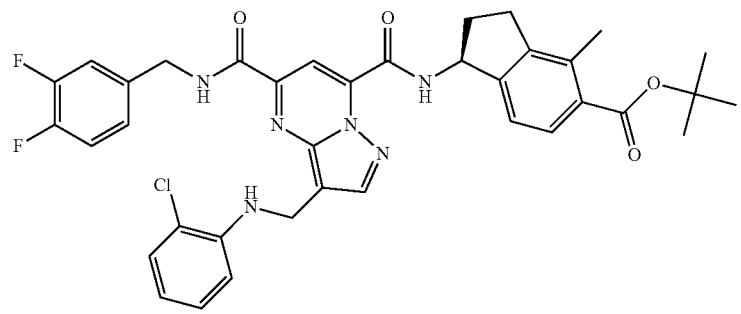 [SMILES: Cc1c(C(=O)OC(C)(C)C)ccc2c1CC[C@@H]2NC(=O)c1cc(C(=O)NCc2ccc(F)c(F)c2)nc2c(CNc3ccccc3Cl)cnn12]
2252 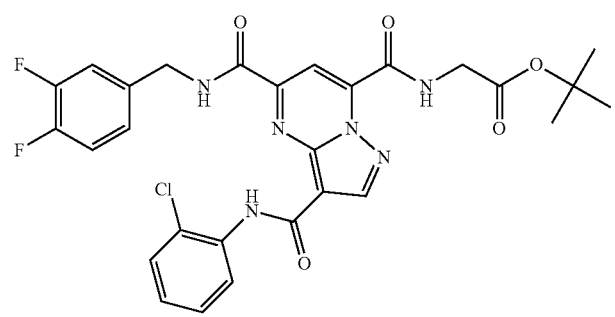 [SMILES: CC(C)(C)OC(=O)CNC(=O)c1cc(C(=O)NCc2ccc(F)c(F)c2)nc2c(C(=O)Nc3ccccc3Cl)cnn12]
2253 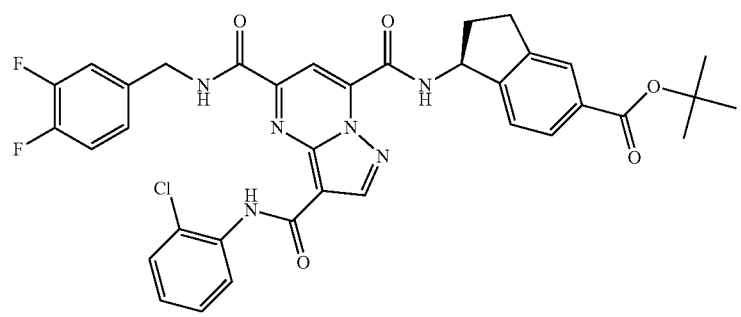 [SMILES: CC(C)(C)OC(=O)c1ccc2c(c1)CC[C@@H]2NC(=O)c1cc(C(=O)NCc2ccc(F)c(F)c2)nc2c(C(=O)Nc3ccccc3Cl)cnn12]
2254 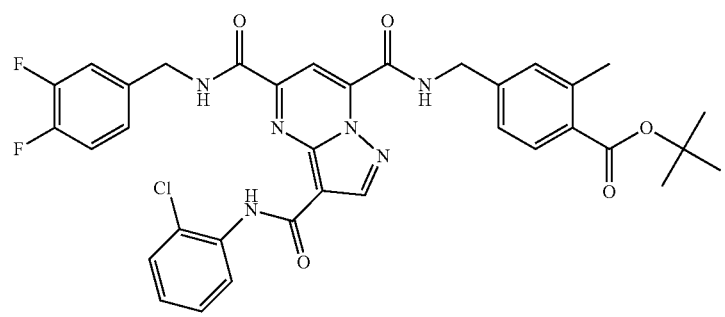 [SMILES: Cc1cc(CNC(=O)c2cc(C(=O)NCc3ccc(F)c(F)c3)nc3c(C(=O)Nc4ccccc4Cl)cnn23)ccc1C(=O)OC(C)(C)C]
2255 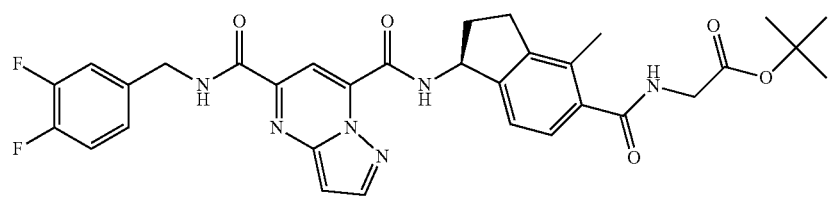 [SMILES: Cc1c(C(=O)NCC(=O)OC(C)(C)C)ccc2c1CC[C@@H]2NC(=O)c1cc(C(=O)NCc2ccc(F)c(F)c2)nc2ccnn12]

TABLE II-47-continued

| Ex. # | product | method, yield |
|---|---|---|
| 2221 | | B, 92% [MH]$^+$ = 598 |
| 2222 | | B, 96% [MH]$^+$ = 671 |
| 2223 | | B, >99% [MH]$^+$ = 671 |
| 2224 | | B, 93% [MH]$^+$ = 687 |
| 2225 | | A, 17% (over 2 steps) [M − H]$^-$ = 623 |
| 2226 | | A, 42% (over 2 steps) [M − H]$^-$ = 658 |

TABLE II-47-continued

| | | |
|---|---|---|
| 2227 | (structure) | A, 45% (over 2 steps) [M − H]⁻ = 653 |
| 2228 | (structure) | A, 91% [M − H]⁻ = 630 |
| 2229 | (structure) | A, 82% [M − H]⁻ = 637 |
| 2230 | (structure) | A, 50% [M − H]⁻ = 658 |

TABLE II-47-continued
| 2231 | 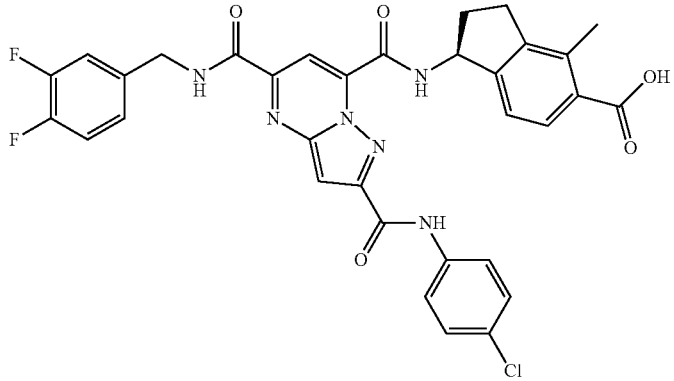 [SMILES: Cc1c(C(=O)O)ccc2c1CC[C@@H]2NC(=O)c1cc(C(=O)NCc2ccc(F)c(F)c2)nc2cc(C(=O)Nc3ccc(Cl)cc3)nn12] | A, 50%<br>[M − H]⁻ = 658 |
| 2232 | 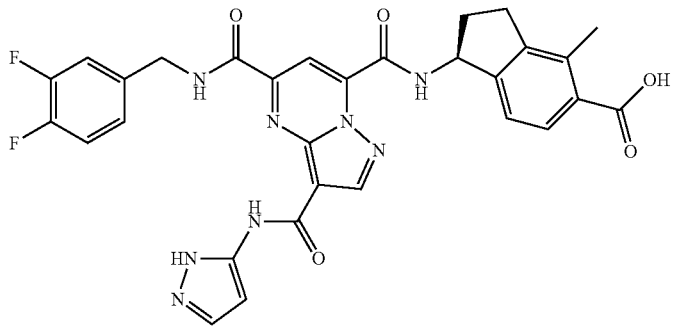 [SMILES: Cc1c(C(=O)O)ccc2c1CC[C@@H]2NC(=O)c1cc(C(=O)NCc2ccc(F)c(F)c2)nc2c(C(=O)Nc3ccn[nH]3)cnn12] | A, 95%<br>[M − H]⁻ = 613 |
| 2233 | 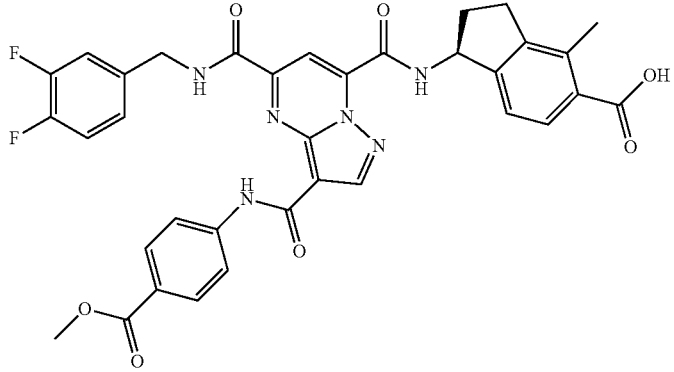 [SMILES: COC(=O)c1ccc(NC(=O)c2cnn3c(C(=O)N[C@H]4CCc5c4ccc(C(=O)O)c5C)cc(C(=O)NCc4ccc(F)c(F)c4)nc23)cc1] | A, 70%<br>[M − H]⁻ = 681 |
| 2234 | 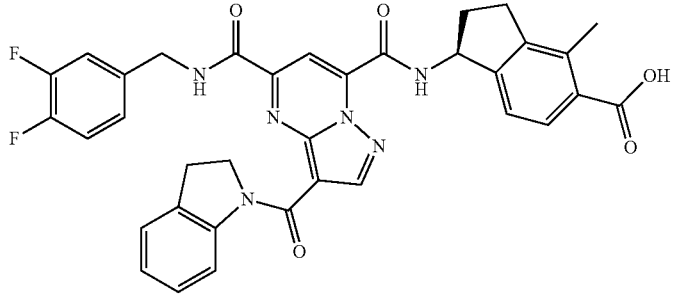 [SMILES: Cc1c(C(=O)O)ccc2c1CC[C@@H]2NC(=O)c1cc(C(=O)NCc2ccc(F)c(F)c2)nc2c(C(=O)N3CCc4ccccc43)cnn12] | A, 97%<br>[M − H]⁻ = 649 |

TABLE II-47-continued
| 2235 | 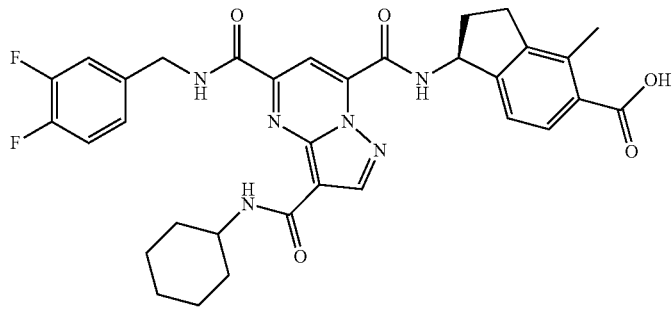 [SMILES: Cc1c(C(=O)O)ccc2c1CC[C@@H]2NC(=O)c1cc(C(=O)NCc2ccc(F)c(F)c2)nc2c(C(=O)NC3CCCCC3)cnn12] | A, 85%<br>[M − H]⁻ = 629 |
| --- | --- | --- |
| 2236 | 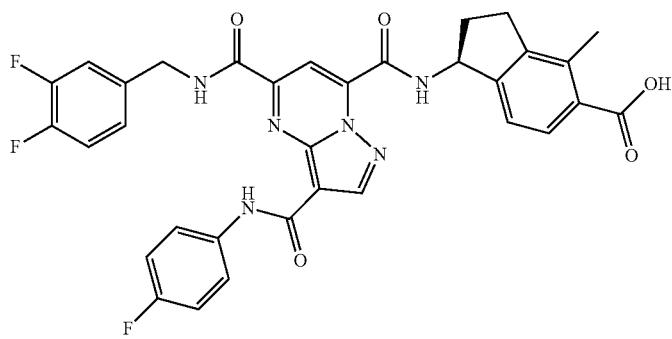 [SMILES: Cc1c(C(=O)O)ccc2c1CC[C@@H]2NC(=O)c1cc(C(=O)NCc2ccc(F)c(F)c2)nc2c(C(=O)Nc3ccc(F)cc3)cnn12] | A, >99%<br>[M − H]⁻ = 641 |
| 2237 | 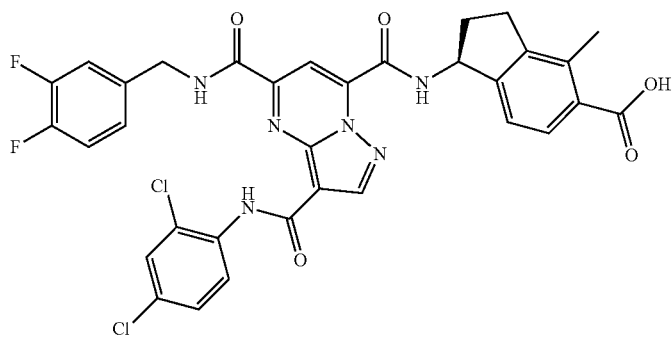 [SMILES: Cc1c(C(=O)O)ccc2c1CC[C@@H]2NC(=O)c1cc(C(=O)NCc2ccc(F)c(F)c2)nc2c(C(=O)Nc3ccc(Cl)cc3Cl)cnn12] | A, >99%<br>[M − H]⁻ = 691 |
| 2238 | 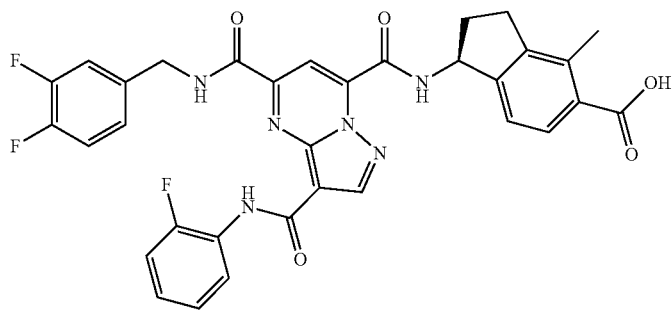 [SMILES: Cc1c(C(=O)O)ccc2c1CC[C@@H]2NC(=O)c1cc(C(=O)NCc2ccc(F)c(F)c2)nc2c(C(=O)Nc3ccccc3F)cnn12] | A, 69%<br>[M − H]⁻ = 641 |

TABLE II-47-continued

| 2239 | (structure) | A, 59% [M − H]⁻ = 691 |
| 2240 | (structure) | A, >99% [M − H]⁻ = 637 |
| 2241 | (structure) | A, 79% [M − (TFA + H)]⁻ = 624 |
| 2242 | (structure) | A, >99% [M − H]⁻ = 639 |

TABLE II-47-continued
| | | |
|---|---|---|
| 2243 | 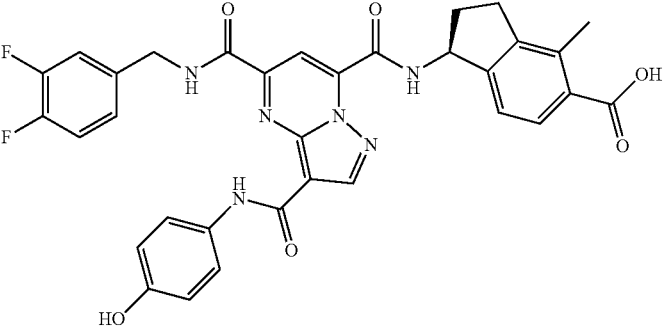 | A, >99%<br>[M − H]⁻ = 639 |
| 2244 | 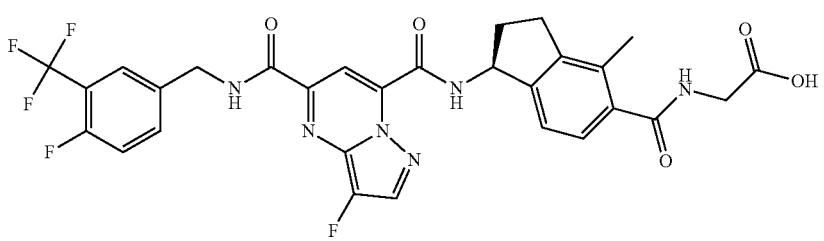 [SMILES: Cc1c(C(=O)NCC(=O)O)ccc2c1CC[C@@H]2NC(=O)c1cc(C(=O)NCc2ccc(F)c(C(F)(F)F)c2)nc2c(F)cnn12] | B, 68%<br>[MH]⁺ = 631 |
| 2245 | 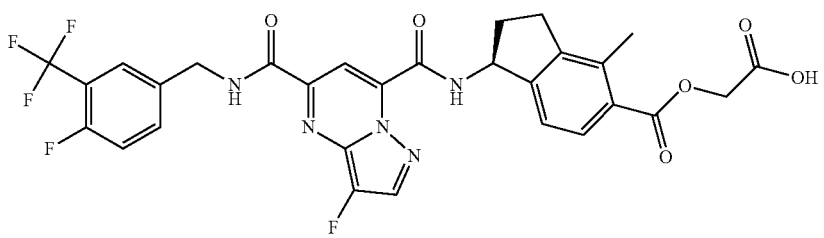 [SMILES: Cc1c(C(=O)OCC(=O)O)ccc2c1CC[C@@H]2NC(=O)c1cc(C(=O)NCc2ccc(F)c(C(F)(F)F)c2)nc2c(F)cnn12] | B, 83%<br>[MH]⁺ = 632 |
| 2246 | 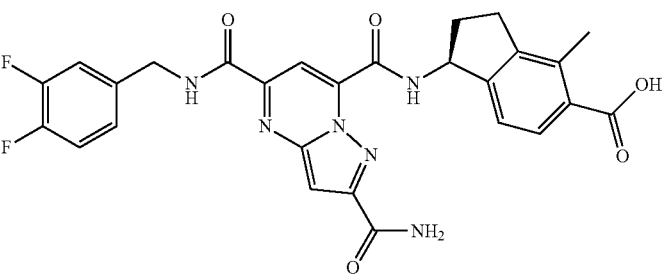 [SMILES: Cc1c(C(=O)O)ccc2c1CC[C@@H]2NC(=O)c1cc(C(=O)NCc2ccc(F)c(F)c2)nc2cc(C(N)=O)nn12] | A, 99%<br>[MH]⁺ = 549 |
| 2247 | 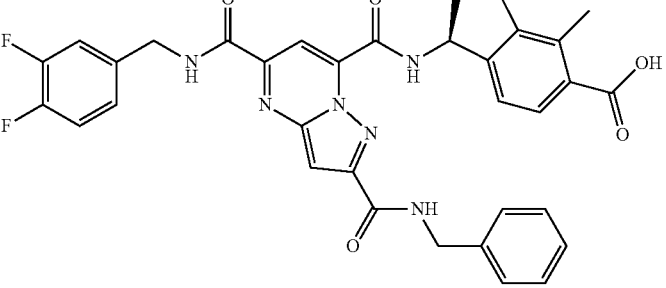 | A, 99%<br>[MH]⁺ = 639 |

TABLE II-47-continued
| 2248 | 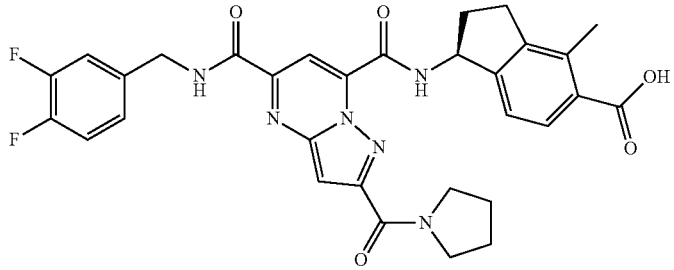 [SMILES: Cc1c(C(=O)O)ccc2c1CC[C@@H]2NC(=O)c1cc(C(=O)NCc2ccc(F)c(F)c2)nc2cc(C(=O)N3CCCC3)nn12] | A, 99% [MH]⁺ = 603 |
|---|---|---|
| 2249 | 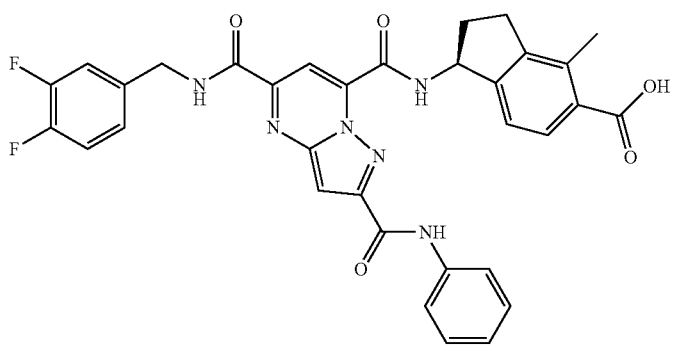 [SMILES: Cc1c(C(=O)O)ccc2c1CC[C@@H]2NC(=O)c1cc(C(=O)NCc2ccc(F)c(F)c2)nc2cc(C(=O)Nc3ccccc3)nn12] | A, 99% [MH]⁺ = 625 |
| 2250 | 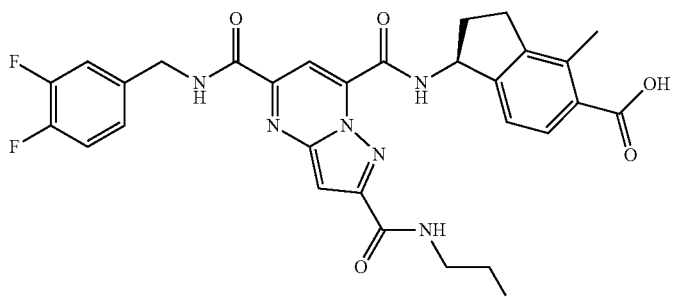 | A, 99% [M H]⁺ = 593 |
| 2251 | 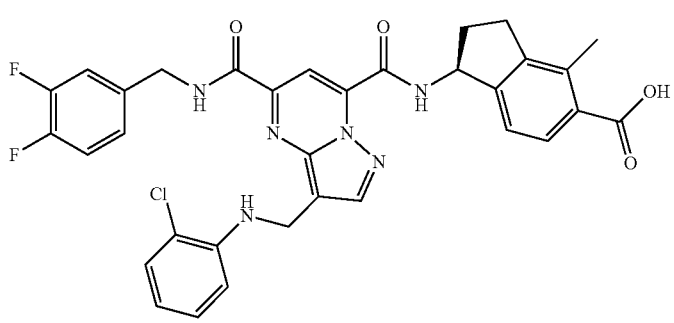 [SMILES: Cc1c(C(=O)O)ccc2c1CC[C@@H]2NC(=O)c1cc(C(=O)NCc2ccc(F)c(F)c2)nc2c(CNc3ccccc3Cl)cnn12] | A, 99% [MH]⁺ = 654 |
| 2252 | 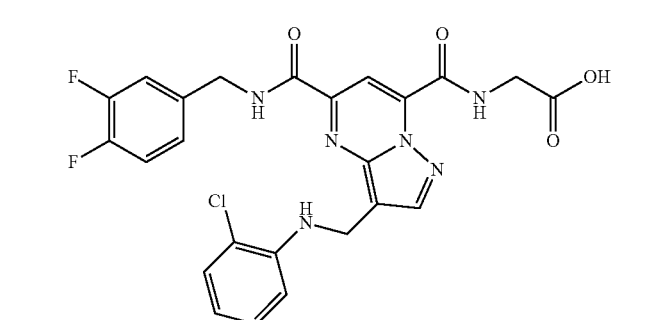 | A, 99% [MH]⁺ = 643 |

TABLE II-47-continued
| | | |
|---|---|---|
| 2253 | 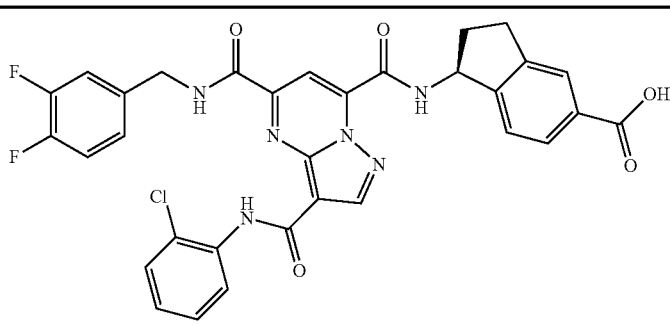 | A, 99%<br>[MH]+ = 645 |
| 2254 | 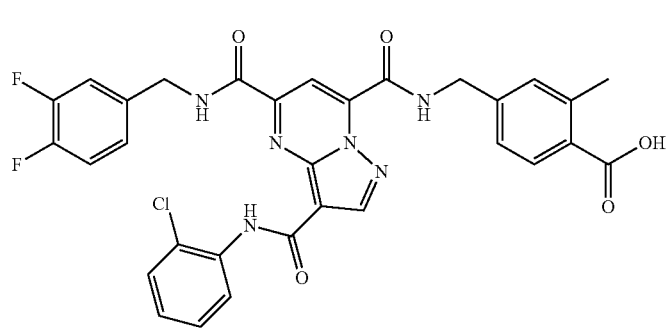 [SMILES: Cc1cc(CNC(=O)c2cc(C(=O)NCc3ccc(F)c(F)c3)nc3c(C(=O)Nc4ccccc4Cl)cnn23)ccc1C(=O)O] | A, 99%<br>[MH]+ = 633 |
| 2255 | 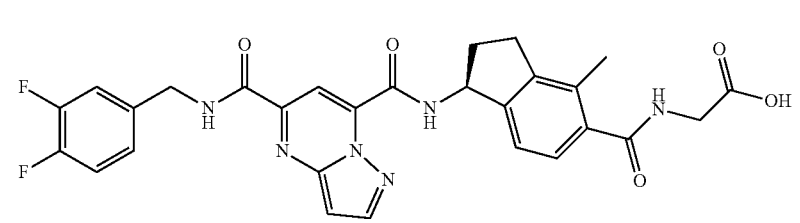 [SMILES: Cc1c(C(=O)NCC(=O)O)ccc2c1CC[C@@H]2NC(=O)c1cc(C(=O)NCc2ccc(F)c(F)c2)nc2ccnn12] | A, n.d.<br>[M − H]− = 561 |
Example 2256
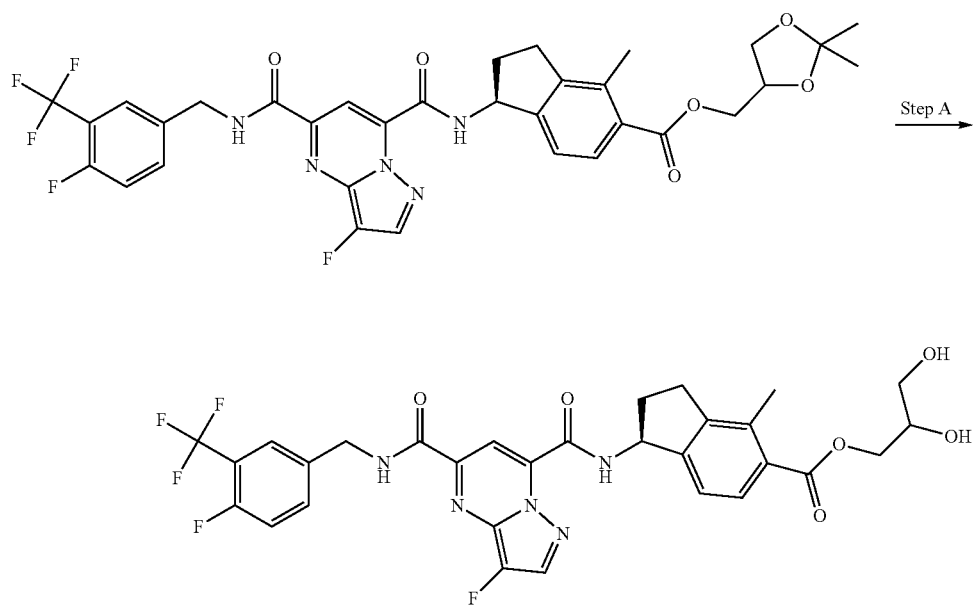

Step A

To a solution of the title compound from the Example 2205 (11 mg) in CH$_2$Cl$_2$ (1 mL) was added a 50% aqueous solution of trifluoroacetic acid (1 mL). The resulting mixture was stirred at room temperature for 6 h, diluted with CH$_2$Cl$_2$ (30 mL), washed with saturated aqueous NaHCO$_3$, dried (MgSO$_4$), filtered, concentrated and purified by chromatography (silica, CH$_2$Cl$_2$/MeOH) to afford the title compound (8.5 mg, 81%). [MNa]$^+$=670.

Example 2257

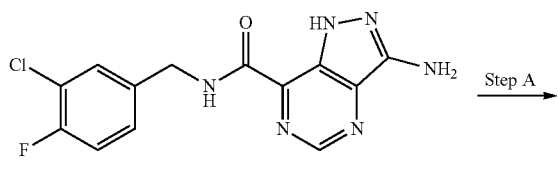

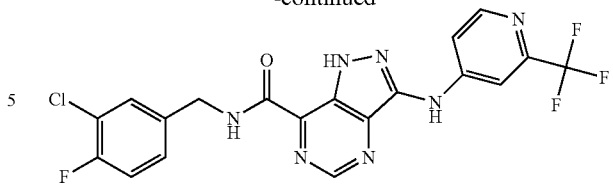

Step A

To a degassed solution of the title compound from the Preparative Example 377, Step E (30 mg) and the title compound from the Preparative Example 19, Step B (25 mg) in DMF (2 mL) were added Pd(OAc)$_2$ (1 mg), BINAP (3 mg) and KOtBu (10 mg). The resulting mixture was heated to 180° C. (microwave) for 30 min, cooled, concentrated, diluted with EtOAc, washed with 0.1M aqueous HCl and saturated aqueous NaCl, dried (MgSO$_4$), filtered, concentrated and purified by chromatography (silica, cyclohexane/EtOAc) to afford the title compound (6.5 mg, 15%). [MH]$^+$=466.

Examples 2258-2296

Following a similar procedure as described in the Example 479, except using the amines and carbonyl compounds indicated in Table II-48 below, the following compounds were prepared.

TABLE II-48

| Ex. # | amine, carbonyl compound | product | yield |
|---|---|---|---|
| 2258 | | | 13% [MH]$^+$ = 428 |
| 2259 | | | 53% [MH]$^+$ = 501 |
| 2260 | | | 14% [MH]$^+$ = 461 |

TABLE II-48-continued
| Ex. # | amine, carbonyl compound | product | yield |
|---|---|---|---|
| 2261 | 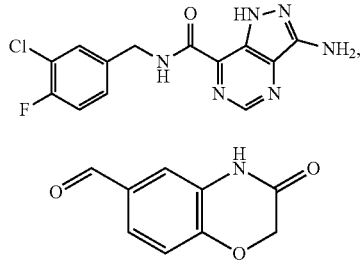 | 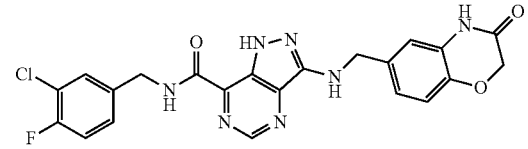 [SMILES: O=C1COc2ccc(CNc3n[nH]c4c(C(=O)NCc5ccc(F)c(Cl)c5)ncnc34)cc2N1] | 46% [MH]⁺ = 482 |
| 2262 | 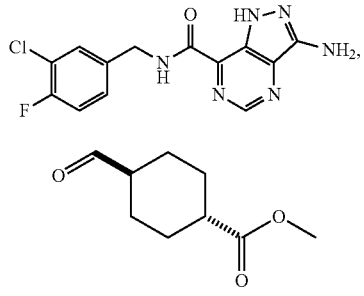 | 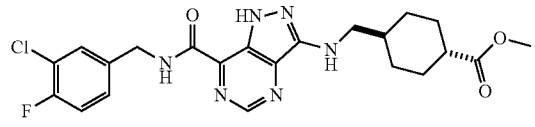 | 51% [MH]⁺ = 475 |
| 2263 | 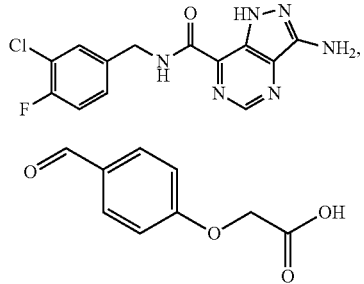 | 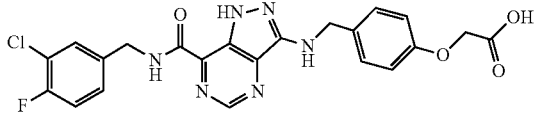 [SMILES: O=C(O)COc1ccc(CNc2n[nH]c3c(C(=O)NCc4ccc(F)c(Cl)c4)ncnc23)cc1] | 42% [MH]⁺ = 485 |
| 2264 | 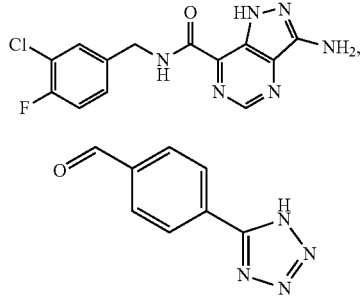 | 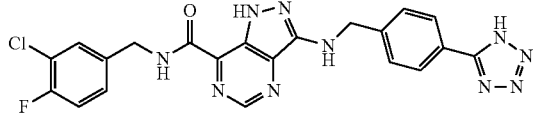 [SMILES: O=C(NCc1ccc(F)c(Cl)c1)c1ncnc2c(NCc3ccc(-c4nnn[nH]4)cc3)n[nH]c12] | 50% [MH]⁺ = 479 |
| 2265 | 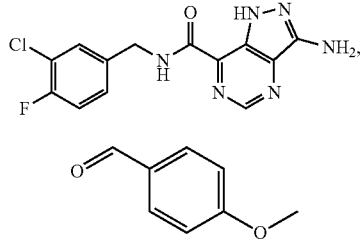 | 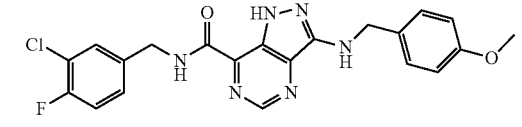 [SMILES: COc1ccc(CNc2n[nH]c3c(C(=O)NCc4ccc(F)c(Cl)c4)ncnc23)cc1] | 27% [MH]⁺ = 441 |

TABLE II-48-continued
| Ex. # | amine, carbonyl compound | product | yield |
|---|---|---|---|
| 2266 | 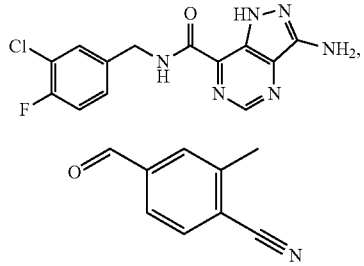 | 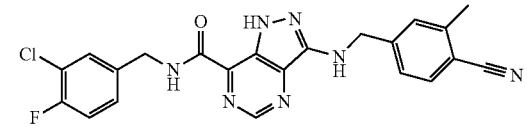 [SMILES: Cc1cc(CNc2n[nH]c3c(C(=O)NCc4ccc(F)c(Cl)c4)ncnc23)ccc1C#N] | 22% [MH]⁺ = 450 |
| 2267 | 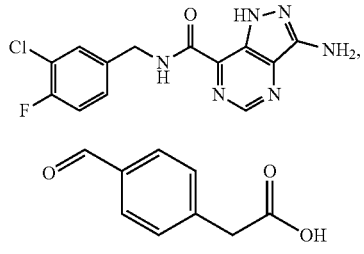 | 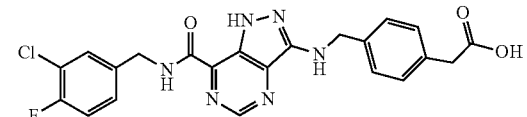 | 32% [MH]⁺ = 496 |
| 2268 | 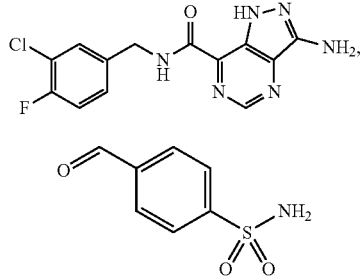 | 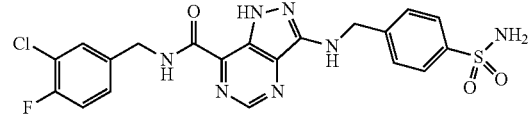 [SMILES: NS(=O)(=O)c1ccc(CNc2n[nH]c3c(C(=O)NCc4ccc(F)c(Cl)c4)ncnc23)cc1] | 95% [MH]⁺ = 490 |
| 2269 | 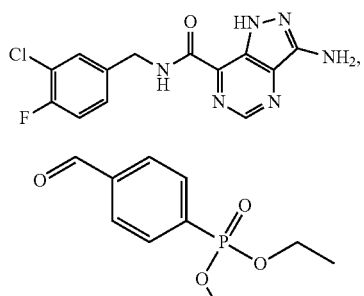 | 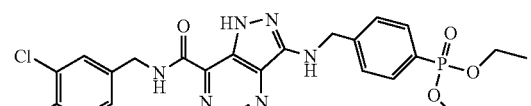 | 54% [MH]⁺ = 547 |
| 2270 | 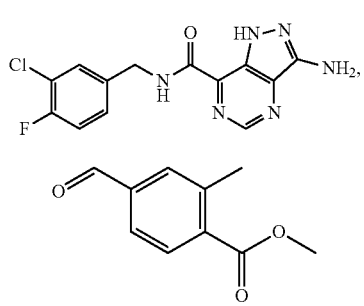 | 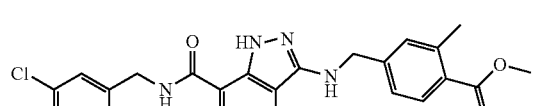 | n.d. [MH]⁺ = 483 |

TABLE II-48-continued
| Ex. # | amine, carbonyl compound | product | yield |
|---|---|---|---|
| 2271 | 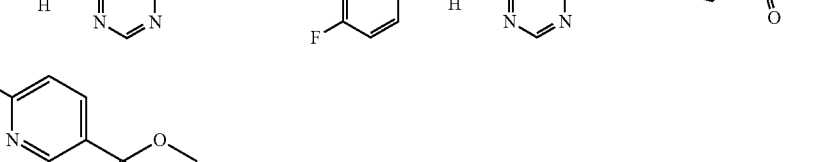 | 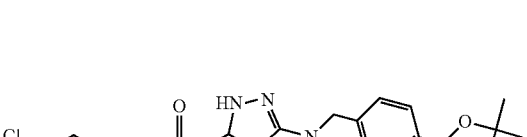 | n.d. [MH]⁺ = 469 |
| 2272 | 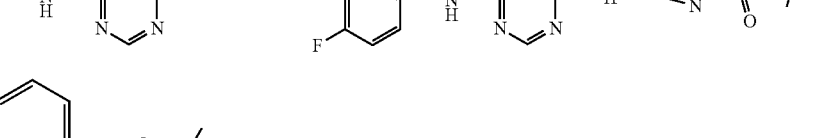 | 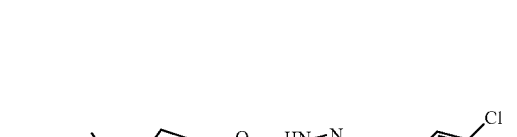 | n.d. [MH]⁺ = 534 |
| 2273 | 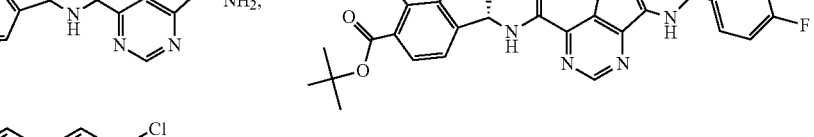 |  | n.d. [MNa]⁺ = 573 |
| 2274 | 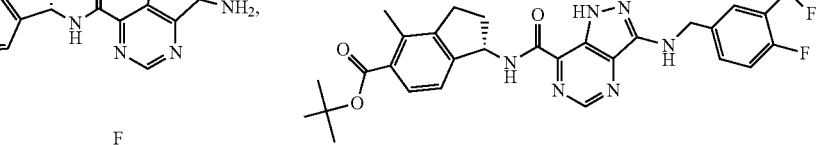 |  | n.d. [MNa]⁺ = 607 |
| 2275 | 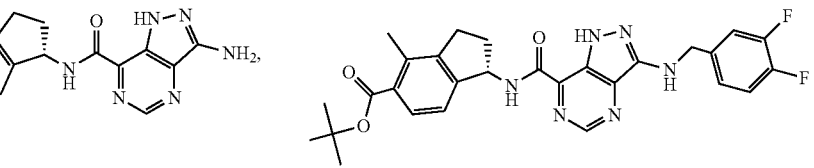 |  | n.d. [MNa]⁺ = 557 |

TABLE II-48-continued
| Ex. # | amine, carbonyl compound | product | yield |
|---|---|---|---|
| 2276 | 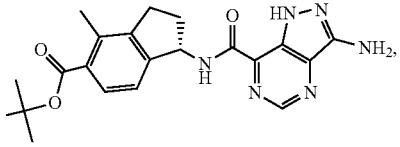 [SMILES: Cc1c(C(=O)OC(C)(C)C)ccc2c1CC[C@@H]2NC(=O)c1ncnc2c(N)n[nH]c12] | 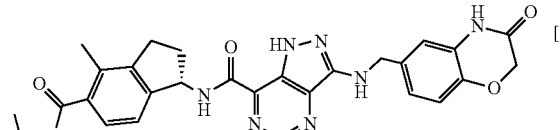 | n.d. [MNa]+ = 592 |
| 2277 | 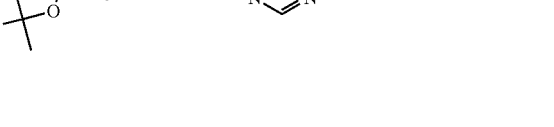 | 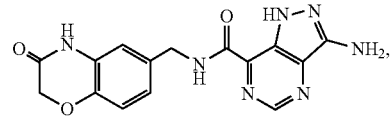 [SMILES: Nc1n[nH]c2c(C(=O)NCc3ccc4c(c3)NC(=O)CO4)ncnc12] | 73% [MH]+ = 474 |
| 2278 | 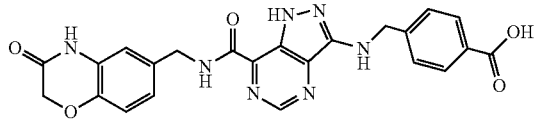 [SMILES: O=C1COc2ccc(CNC(=O)c3ncnc4c(NCc5ccc(C(=O)O)cc5)n[nH]c34)cc2N1] |  | 24% [MH]+ = 494 |
| 2279 | 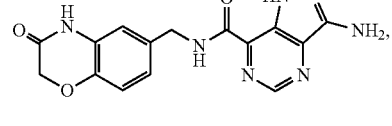 | 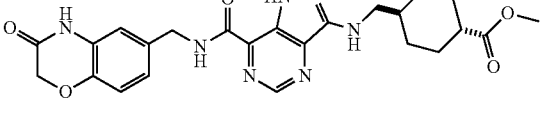 | n.d. [MH]+ = 520 |
| 2280 |  | 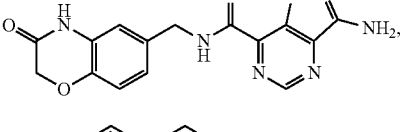 | 14% [MH]+ = 519 |

TABLE II-48-continued

| Ex. # | amine, carbonyl compound | product | yield |
|---|---|---|---|
| 2281 | | | 10% [MH]+ = 493 |
| 2282 | | | 89% [MH]+ = 489 |
| 2283 | | | 86% [MH]+ = 497 |
| 2284 | | | 15% [MH]+ = 535 |
| 2285 | | | 80% [MH]+ = 491 |

TABLE II-48-continued

| Ex. # | amine, carbonyl compound | product | yield |
|---|---|---|---|
| 2286 | | | 52% [MH]+ = 413 |
| 2287 | | | 82% [MH]+ = 463 |
| 2288 | | | 58% [MH]+ = 466 |
| 2289 | | | 82% [MH]+ = 379 |
| 2290 | | | 78% [MH]+ = 469 |

TABLE II-48-continued
| Ex. # | amine, carbonyl compound | product | yield |
|---|---|---|---|
| 2291 | 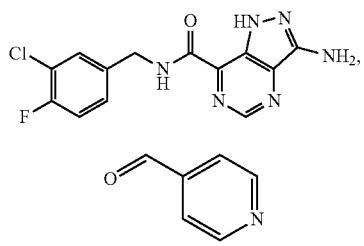 | 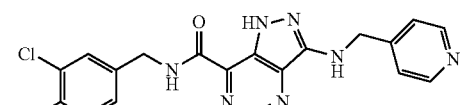 | 40% [MH]⁺ = 412 |
| 2292 |  (2 eq.) | 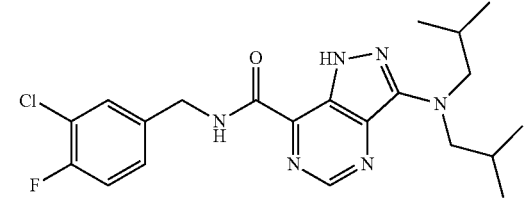 [SMILES: CC(C)CN(CC(C)C)c1n[nH]c2c(C(=O)NCc3ccc(F)c(Cl)c3)ncnc12] | 38% [MH]⁺ = 461 |
| 2293 | 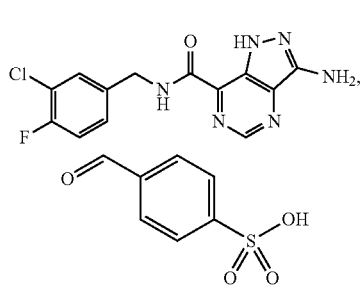 (2 eq.) | 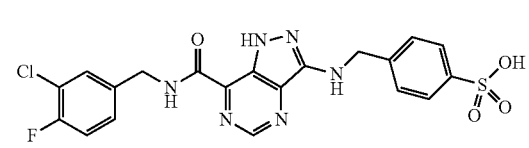 [SMILES: O=C(NCc1ccc(F)c(Cl)c1)c1ncnc2c(NCc3ccc(S(=O)(=O)O)cc3)n[nH]c12] | 67% [MH]⁺ = 433 |
| 2294 | 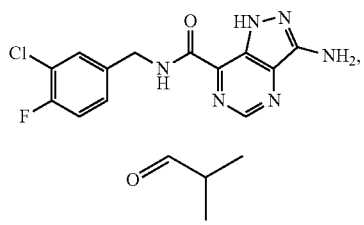 | 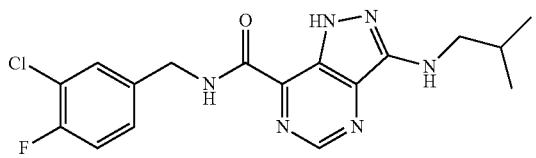 [SMILES: CC(C)CNc1n[nH]c2c(C(=O)NCc3ccc(F)c(Cl)c3)ncnc12] | 5% [MH]⁺ = 491 |
| 2295 | | | 7% [MH]⁺ = 377 |

TABLE II-48-continued
| Ex. # | amine, carbonyl compound | product | yield |
|---|---|---|---|
| 2296 | 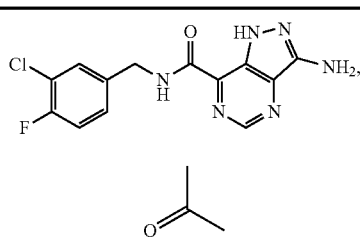 | 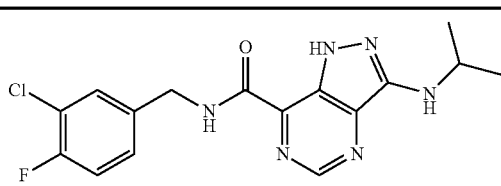 | 52% [MH]+ = 363 |
Example 2297
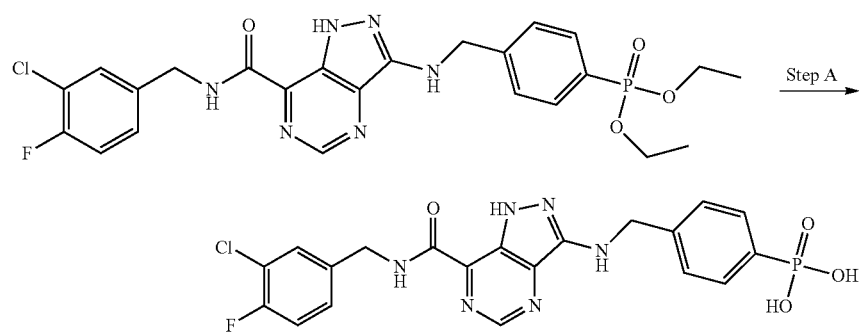
Step A
To a solution of the title compound from Example 2268 (10 mg) in anhydrous CH₃CN (1.5 mL) was added trimethylsilyl bromide (2.6 μL) at 25° C. The resulting mixture was stirred at room temperature for 24 h, concentrated and purified by HPLC (RP-C18, AcCN/H₂O) to afford the title compound (1.0 mg, 11%). [MH]⁺=491.
Example 2298
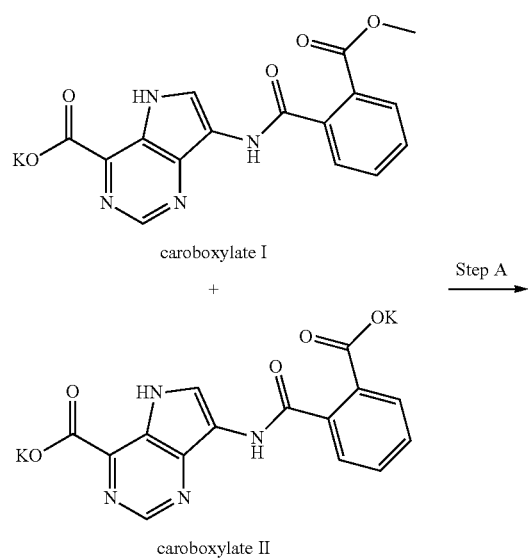

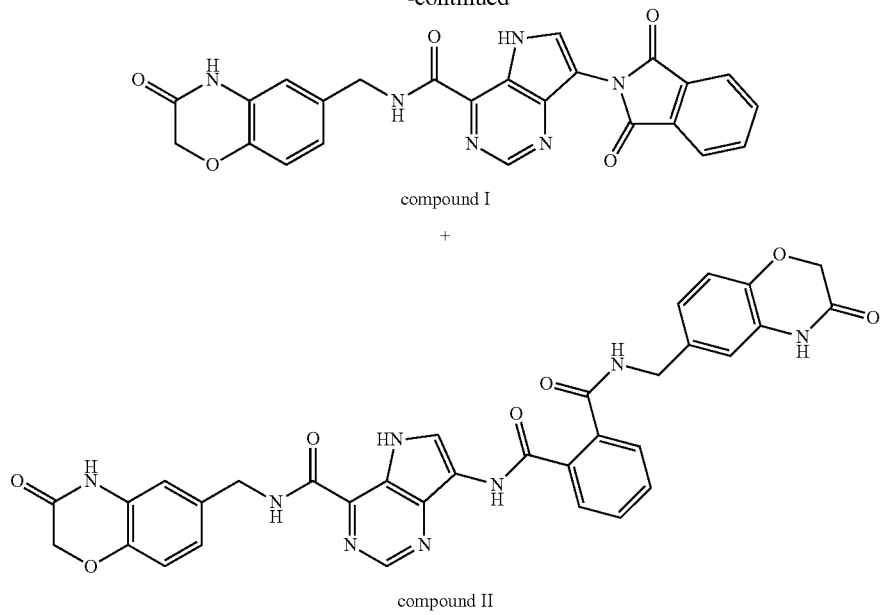

compound I

+ compound II

Step A

The crude ~1:1 mixture of the carboxylate I and the carboxylate II from the Preparative Example 1047 was treated similarly as described in the Example 2 to afford the title compound I (5.3 mg, 16%, [MH]⁺=468) and the title compound II (4.8 mg, 11%, [MH]⁺=647).

Examples 2299-2312

Following similar procedures as described in the Examples 1 (method A), 2 (method B), 3 (method C), 4 (method D), 5 (method E), 6 (method F) or 7 (method G), except using the acids and amines indicated in Table II-49 below, the following compounds were prepared.

TABLE II-49

| Ex. # | acid, amine | product | method, yield |
|---|---|---|---|
| 2299 | | | B, 50% (over 2 steps) [MH]⁺ = 460 |
| 2300 | | | B, 34% (over 2 steps) [MH]⁺ = 354 |

TABLE II-49-continued
| Ex. # | acid, amine | product | method, yield |
|---|---|---|---|
| 2301 | 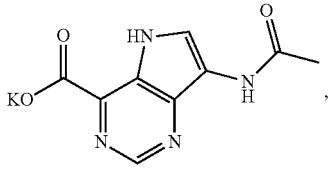 | 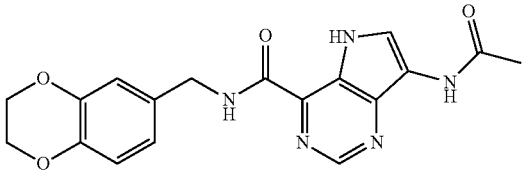 [SMILES: CC(=O)Nc1c[nH]c2c(C(=O)NCc3ccc4c(c3)OCCO4)ncnc12] | B, 31% (over 2 steps) [MH]+ = 368 |
| 2302 | 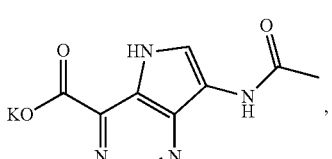 | 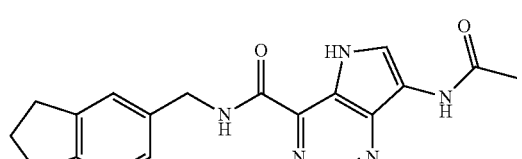 | B, 46% (over 2 steps) [MH]+ = 352 |
| 2303 | 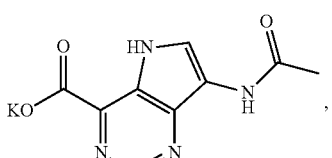 | 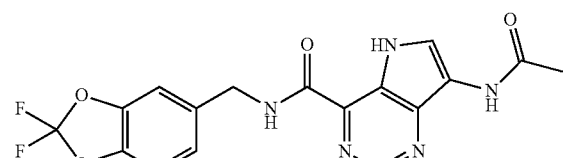 | B, 47% (over 2 steps) [MH]+ = 390 |
| 2304 | 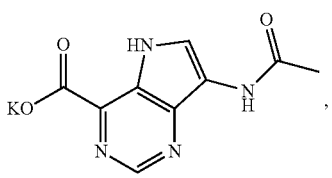 | 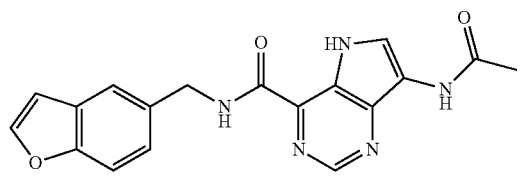 [SMILES: CC(=O)Nc1c[nH]c2c(C(=O)NCc3ccc4occc4c3)ncnc12] | B, 40% (over 2 steps) [MH]+ = 350 |
| 2305 | 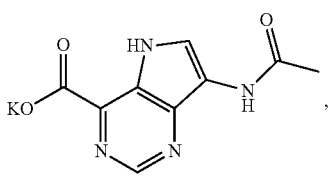 | 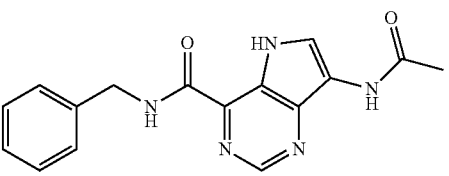 [SMILES: CC(=O)Nc1c[nH]c2c(C(=O)NCc3ccccc3)ncnc12] | B, 32% (over 2 steps) [MH]+ = 310 |

TABLE II-49-continued
| Ex. # | acid, amine | product | method, yield |
|---|---|---|---|
| 2306 | 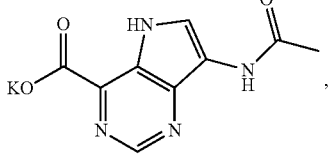 | 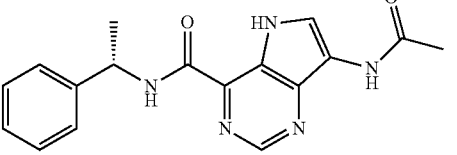 | B, 24% (over 2 steps) [MH]+ = 323 |
| 2307 | 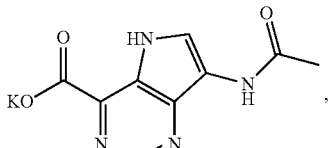 | 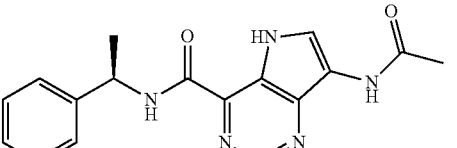 | B, 30% (over 2 steps) [MH]+ = 323 |
| 2308 | 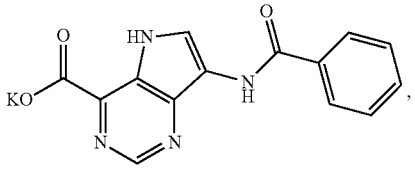 | 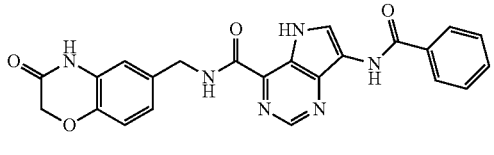 [SMILES: O=C1COc2ccc(CNC(=O)c3ncnc4c(NC(=O)c5ccccc5)c[nH]c34)cc2N1] | B, 8.8% (over 2 steps) [MH]+ = 297 |
| 2309 | 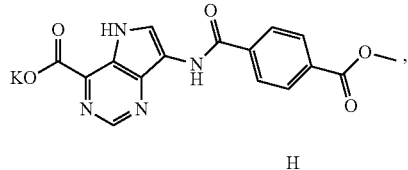 | 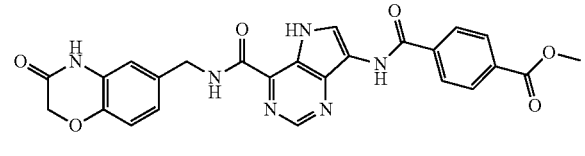 [SMILES: COC(=O)c1ccc(C(=O)Nc2c[nH]c3c(C(=O)NCc4ccc5c(c4)NC(=O)CO5)ncnc23)cc1] | B, 20% (over 2 steps) [MH]+ = 335 |
| 2310 | 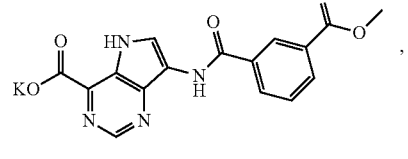 |  | B, 37% (over 2 steps) [MH]+ = 335 |

TABLE II-49-continued

| Ex. # | acid, amine | product | method, yield |
|---|---|---|---|
| 2311 | | | B, 88% [MH]+ = 439 |
| 2312 | | | B, 95% (over 2 steps) [MH]+ = 561/563 |

Example 2313

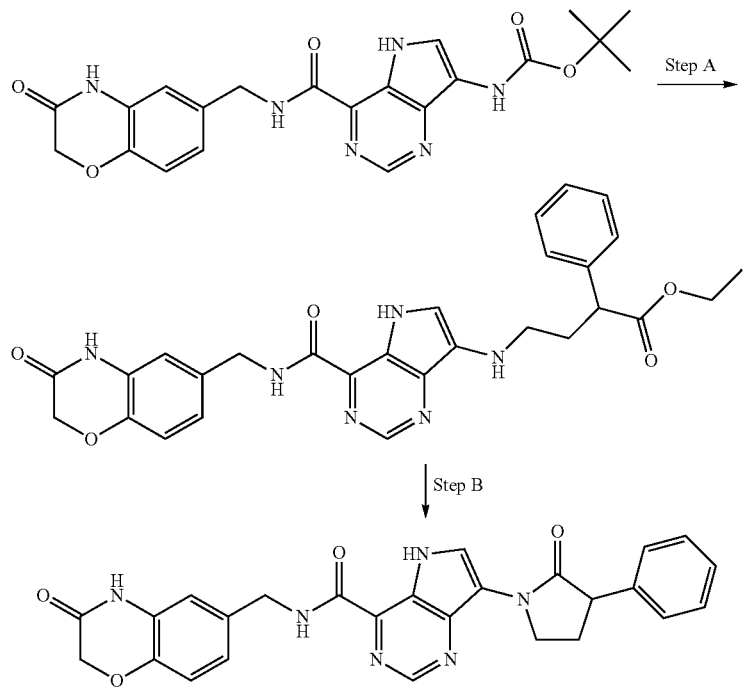

Step A

A mixture of the title compound from the Example 2311 (53 mg) in a 4M solution of HCl in 1,4-dioxane (3 mL) was stirred at room temperature for 3 h and then concentrated. The remaining residue was added to solution of NaBH$_3$CN (16 mg) in MeOH (2 mL). To the resulting solution was slowly added a solution of the title compound from the Preparative Example 1031, Step A (25 mg) in THF/MeOH (1:1, 1 mL) over a period of 7 h. Then the mixture was concentrated, diluted with saturated aqueous NaHCO$_3$ and extracted with EtOAc (3×). The combined organic phases were dried (MgSO$_4$), filtered, absorbed onto silica and purified by chromatography (silica) to afford the title compound (23 mg, 36%). [MH]+=529.

Step B

To an ice cooled (0-5° C.) solution of the title compound from Step A above (9 mg) in THF (2 mL) was added a 1M solution of tert.-butyl magnesium chloride (60 µL). The resulting mixture was stirred at 0-5° C. (ice bath) for 1½ h, diluted with saturated aqueous NaHCO$_3$ and extracted with EtOAc (3×). The combined organic phases were dried (MgSO$_4$), filtered, concentrated and purified by preparative thin layer chromatography (silica, EtOAc) to afford the title compound as a light yellow solid (1.7 mg, 20%). [MH]$^+$=483.

Example 2314

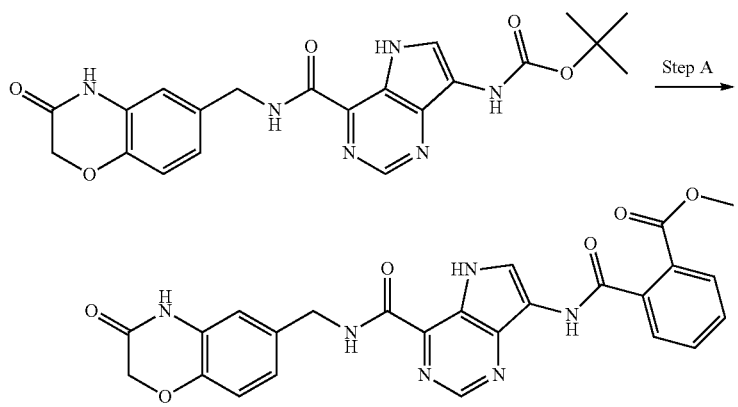

Step A

To the title compound from the Example 2311 (23.2 mg) was added a 4M solution of HCl in 1,4-dioxane (940 µL). The resulting mixture was stirred at room temperature for 3 h and then concentrated. The obtained residue was suspended in pyridine (800 µL), the title compound from Preparative Example 1022 (10.5 µL) was added and the resulting mixture was stirred at room temperature for 3 h. The mixture was concentrated, diluted with 10% aqueous citric acid (5 mL), sonicated for ~1 min and allowed to stand at room temperature for 30 min. The formed precipitate was collected by filtration, washed with H$_2$O (5 mL) and dried in vacuo to afford the title compound as yellow solid (16.8 mg, 63%). [MH]$^+$=501.

Examples 2315-2322

Following a similar procedure as described in the Example 2314, except using the acid chlorides indicated in Table II-50 below, the following compounds were prepared.

TABLE II-50

| Ex. # | acid chloride | Product | yield |
|---|---|---|---|
| 2315 | (structure) | (structure) | 96% [MH]$^+$ = 407 |
| 2316 | (structure) | (structure) | 14% [MH]$^+$ = 439 |
| 2317 | (structure) | (structure) | 24% [MH]$^+$ = 453 |

TABLE II-50-continued

| Ex. # | acid chloride | Product | yield |
|---|---|---|---|
| 2318 | | | 52% [MH]⁺ = 467 |
| 2319 | | | 45% [MH]⁺ = 465 |
| 2320 | | | 47% [MH]⁺ = 465 |
| 2321 | | | 35% [MH]⁺ = 423 |
| 2322 | | | 50% [MH]⁺ = 479 |

Example 2323

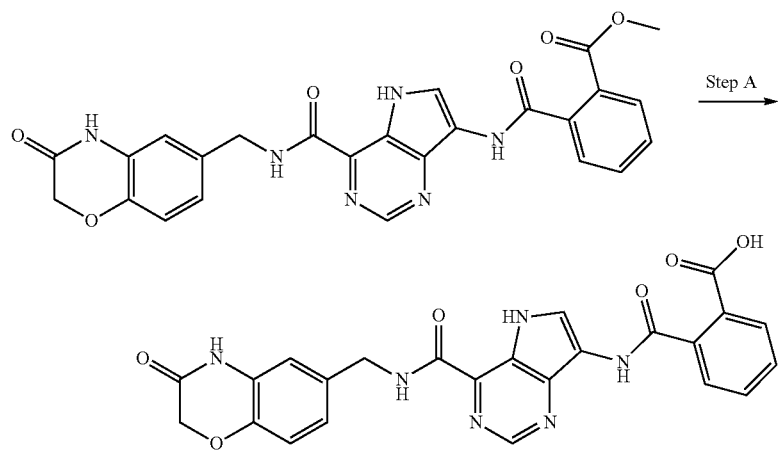

Step A

To a solution of the title compound from the Example 2314, Step A (13 mg) in THF/H₂O (1:1, 2 mL) was added a 1M aqueous KOH (140 μL). The mixture was stirred at room temperature for 2 h, concentrated, diluted with a 0.1M aqueous HCl (3 mL), sonicated for ~1 min and allowed to stand at room temperature for 30 min. The formed precipitate was collected by filtration, washed with H₂O (5 mL) and dried in vacuo to afford the title compound (11.7 mg, 92%). [MH]⁺= 487.

Examples 2324-2336

Following similar procedures as described in the Examples 314 (method A), 315 (method B) or 2314 (method C), except using the esters indicated in Table II-51 below, the following compounds were prepared.

TABLE II-51

| Ex. # | ester | product | method, yield |
|---|---|---|---|
| 2324 | | | A, 57% (over 2 step) [MH]+ = 456 |
| 2325 | | | A, 32% (over 2 step) [MH]+ = 469 |
| 2326 | | | A, 100% [MH]+ = 487 |
| 2327 | | | B, 78% [MH]+ = 487 |
| 2328 | | | A, 98% [MH]+ = 480 |
| 2329 | | | A, 18% (over 2 step) [MH]+ = 506, |
| 2330 | | | C, 29% [MH]+ = 487 |
| 2331 | | | C, 9% [MH]+ = 487 |
| 2332 | | | C, 98% [MH]+ = 439 |

TABLE II-51-continued

| Ex. # | ester | product | method, yield |
|---|---|---|---|
| 2333 | | | C, 69% [MH]+ = 453 |
| 2334 | | | C, 91% [MH]+ = 451 |
| 2335 | | | C, 92% [MH]+ = 465 |
| 2336 | | | A, >99% [MH]+ = 521 |

Examples 2337-2341

Following a similar procedure as described in the Example 436, except using the esters indicated in Table II-52 below, the following compounds were prepared.

TABLE II-52

| Ex. # | ester | Product | yield |
|---|---|---|---|
| 2337 | | | 66% (over 2 steps) [MH]+ = 456 |
| 2338 | | | 23% (over 2 steps) [MH]+ = 495 |
| 2339 | | | 18% (over 2 steps) [MH]+ = 529 |

TABLE II-52-continued

| Ex. # | ester | Product | yield |
|---|---|---|---|
| 2340 | | | 52% (over 2 steps) [MH]+ = 479 |
| 2341 | | | 32% (over 2 steps) [MH]+ = 514 |

Example 2342

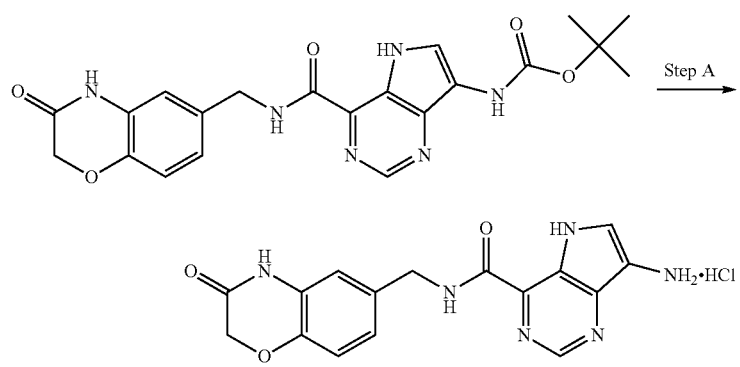

Step A

To a suspension of the title compound from the Example 2311 (939 mg) in EtOAc (17.1 mL) was added a 4M solution of HCl in 1,4-dioxane (17.1 mL). The reaction mixture was stirred at room temperature for 20 h and concentrated to afford the title compound (850 mg, >99%). [M-Cl]+=339.

Example 2343

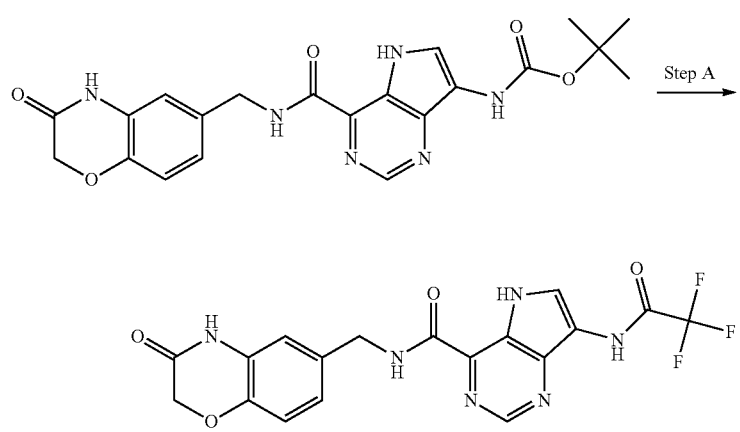 [SMILES: CC(C)(C)OC(=O)Nc1c[nH]c2c(C(=O)NCc3ccc4c(c3)NC(=O)CO4)ncnc12 ; O=C1COc2ccc(CNC(=O)c3ncnc4c(NC(=O)C(F)(F)F)c[nH]c34)cc2N1]

Step A

To a solution of the title compound from the Example 2311 (22.5 mg) in CHCl₃ (500 µL) was added and a 1:1 mixture of trifluoroacetic acid and CHCl₃ (500 µL). The mixture was stirred at room temperature for 3 h, concentrated and dried in vacuo. The obtained residue was dissolved in DMF (500 µL) and ⁱPr₂NEt (10.2 µL) was added. The mixture was stirred at room temperature overnight, concentrated and diluted with EtOAc and 10% aqueous citric acid. The organic phase was separated, washed with 10% aqueous citric acid, saturated aqueous NaHCO₃ and saturated aqueous NaCl, dried (MgSO₄), filtered, concentrated and purified by preparative thin layer chromatography (silica, CH₂Cl₂/MeOH) to afford the title compound as pale yellow solid (12.5 mg; 56%). [MH]⁺=435.

Example 2344

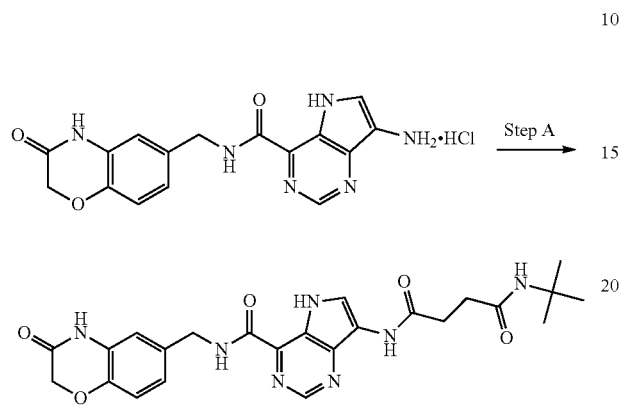

Step A

To a solution of the title compound from the Preparative Example 1028 (4.5 mg) in THF (1 mL) was added 1,1'-carbonyldiimidazole (5.4 mg). The resulting solution was stirred at room temperature for 90 min, then a solution of the title compound from the Example 2342, Step A (8.1 mg) in DMF (1 mL) and ⁱPr₂NEt (5 μL) were added and stirring at room temperature was continued overnight. Additional 1,1'-carbonyldiimidazole (5.4 mg) was added and stirring at room temperature was continued for 8 h. The mixture was concentrated, diluted with a 0.1M aqueous HCl (3 mL) and H₂O (15 mL) and extracted with EtOAc (3×30 mL). The combined organic phases were washed with saturated aqueous NaCl, dried (MgSO₄), filtered, concentrated and purified by preparative thin layer chromatography (silica, CH₂Cl₂/MeOH) to afford the title compound (1.1 mg; 9%). [MH]⁺=494.

Example 2345

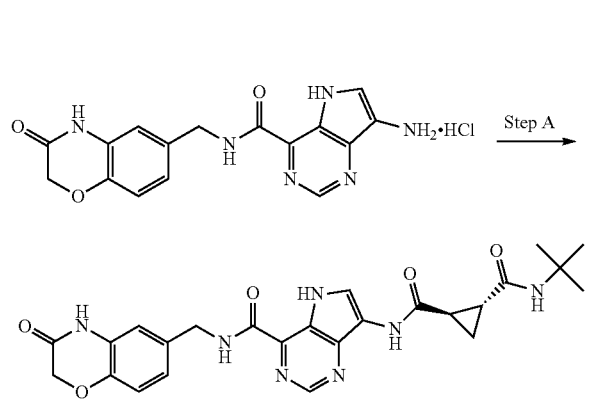

Step A

The title compound from the Example 2342, Step A (10.2 mg) was treated similarly as described in the Example 2344, Step A, except using the title compound from the Preparative Example 1029 instead of the title compound from the Preparative Example 1028 to afford the title compound (1.1 mg, 7.9%). [MH]⁺=506.

Example 2346

Step A

Using a microwave, a mixture of the title compound from Preparative Example 1049, Step E (3 mg), CsCO₃ (9 mg) and acetyl chloride (3 μL) in 1,4-dioxane/CH₃CN (1:1, 1 ml) was heated at 110° C. for 20 min and then cooled to room temperature. The formed precipitate was collected by filtration, washed with MeOH/H₂O (1:1) and then dried in vacuo to afford the title compound as orange solid (1.6 mg, 47%). [MH]⁺=382.

Example 2347

Step A

To a suspension of the title compound from the Example 2342, Step A (2.8 mg) in dry pyridine (75 μL) was added a 0.1M solution of thiophene-2-carbonyl chloride in 1,2-dichlorethane (75 μL). The resulting mixture was agitated (~800 rpm) at room temperature for 15 h, concentrated and dried in vacuo for 12 h to afford the crude title compound. [MH]⁺=449.

Examples 2348-2387

Following similar procedures as described in the Example 2346 (method A) or 2347 (method B), except using the amines and acid chlorides indicated in Table II-53 below, the following compounds were prepared.

TABLE II-53

| Ex. # | amine, acid chloride | product | yield |
|---|---|---|---|
| 2348 | | | A, 31% [MH]+ = 469 |
| 2349 | | | A, 61% [MH]+ = 363 |
| 2350 | | | B, n.d. [MH]+ = 533 |
| 2351 | | | B, n.d. [MH]+ = 493 |
| 2352 | | | B, n.d. [MH]+ = 409 |

TABLE II-53-continued

| Ex. # | amine, acid chloride | product | yield |
|---|---|---|---|
| 2353 | | | B, n.d. [MH]+ = 471 |
| 2354 | | | B, n.d. [MH]+ = 457 |
| 2355 | | | B, n.d. [MH]+ = 487 |
| 2356 | | | B, n.d. [MH]+ = 473 |
| 2357 | | | B, n.d. [MH]+ = 487 |

TABLE II-53-continued

| Ex. # | amine, acid chloride | product | yield |
|---|---|---|---|
| 2358 | | | B, n.d. [MH]⁺ = 468 |
| 2359 | | | B, n.d. [MH]⁺ = 527 |
| 2360 | | | B, n.d. [MH]⁺ = 489 |
| 2361 | | | B, n.d. [MH]⁺ = 486 |
| 2362 | | | B, n.d. [MH]⁺ = 395 |

TABLE II-53-continued

| Ex. # | amine, acid chloride | product | yield |
|---|---|---|---|
| 2363 | | | B, n.d. [MH]+ = 461 |
| 2364 | | | B, n.d. [MH]+ = 475 |
| 2365 | | | B, n.d. [MH]+ = 491 |
| 2366 | | | B, n.d. [MH]+ = 463 |
| 2367 | | | B, n.d. [MH]+ = 425 |

TABLE II-53-continued

| Ex. # | amine, acid chloride | product | yield |
|---|---|---|---|
| 2368 | | | B, n.d. [MH]+ = 519 |
| 2369 | | | B, n.d. [MH]+ = 449 |
| 2370 | | | B, n.d. [MH]+ = 461 |
| 2371 | | | B, n.d. [MH]+ = 421 |
| 2372 | | | B, n.d. [MH]+ = 463 |

TABLE II-53-continued

| Ex. # | amine, acid chloride | product | yield |
|---|---|---|---|
| 2373 | | | B, n.d. [MH]+ = 467 |
| 2374 | | | B, n.d. [MH]+ = 483 |
| 2375 | | | B, n.d. [MH]+ = 473 |
| 2376 | | | B, n.d. [MH]+ = 435 |
| 2377 | | | B, n.d. [MH]+ = 449 |

TABLE II-53-continued
| Ex. # | amine, acid chloride | product | yield |
|---|---|---|---|
| 2378 | 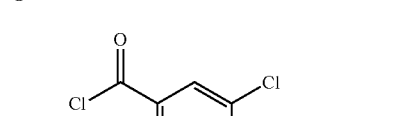 | 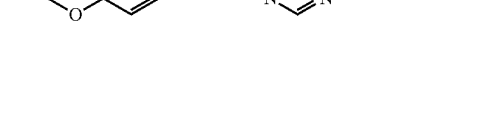 | B, n.d. [MH]+ = 478 |
| 2379 | 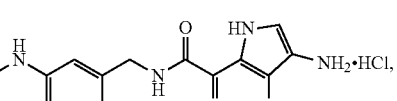 | 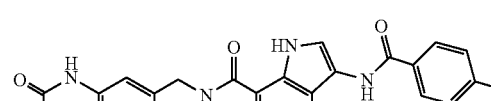 | B, n.d. [MH]+ = 499 |
| 2380 | 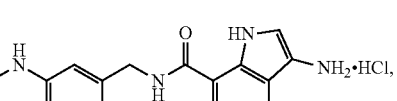 | 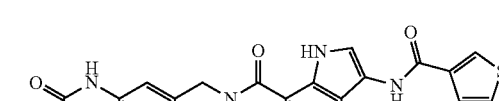 | B, n.d. [MH]+ = 449 |
| 2381 | 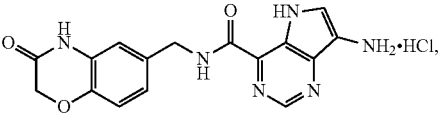 | 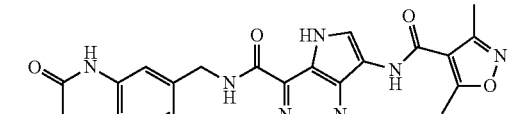 | B, n.d. [MH]+ = 462 |
| 2382 | 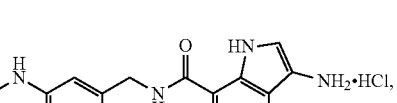 | 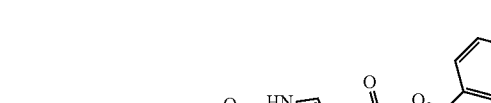 | B, n.d. [MH]+ = 487 |

TABLE II-53-continued

| Ex. # | amine, acid chloride | product | yield |
|---|---|---|---|
| 2383 | | | B, n.d. [MH]+ = 468 |
| 2384 | | | B, n.d. [MH]+ = 465 |
| 2385 | | | B, n.d. [MH]+ = 499 |
| 2386 | | | B, n.d. [MH]+ = 478 |
| 2387 | | | B, n.d. [MH]+ = 445 |

Example 2388

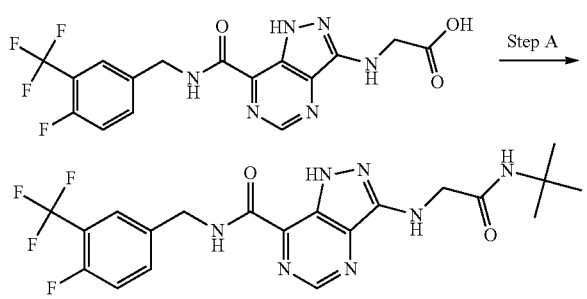

Step A

The title compound from the Example 2286 (4.5 mg) was treated similarly as described in the Example 2, Step A, except using commercially available tert-butylamine instead of the title compound from the Preparative Example 228, Step A to afford the title compound (1.9 mg, 37%). [MH]⁺=468.

Example 2389

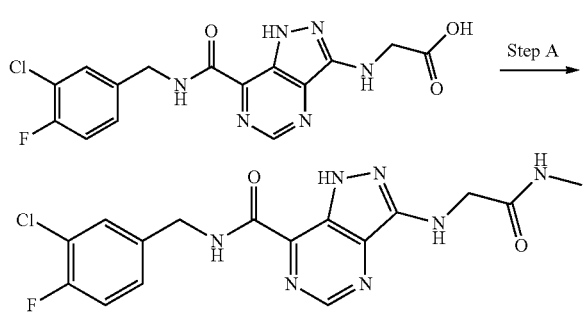

Step A

To a solution of the title compound from the Example 2289 (20 mg) in anhydrous THF (2 mL) was added 1,1'-carbonyldiimidazole (35 mg). The resulting mixture was stirred at room temperature for 1 h and then cooled to 0-5° C. (ice bath). A 2M solution of methylamine in THF (1 mL) was added and the ice bath was removed. The mixture was stirred at room temperature for 3 h, concentrated, diluted with $H_2O$ and 10% aqueous citric acid and extracted with EtOAc (3×). The combined organic phases were washed saturated aqueous NaCl (200 mL), dried ($MgSO_4$), filtered, concentrated and purified by preparative thin layer chromatography (silica, $CH_2Cl_2$/MeOH) to afford the title compound (14 mg, 85%). [α]⁺=392.

Example 2390

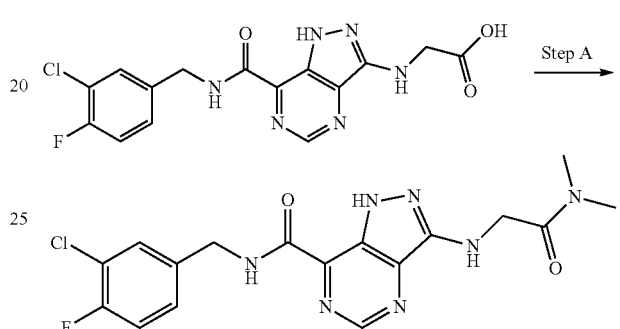

Step A

The title compound from the Example 2289 (20 mg) was treated similarly as described in the Example 2389, Step A, except using a 2M solution of dimethylamine in THF instead of a 2M solution of methylamine in THF to afford the title compound (17.9 mg, 83%). [MH]⁺=406.

Example 2391

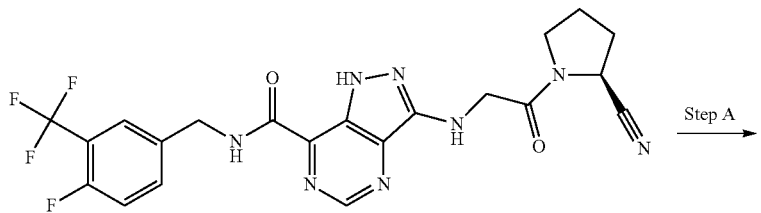

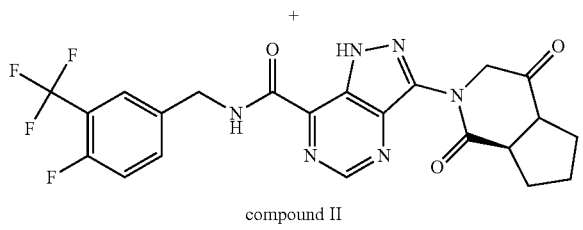

compound I

+ compound II

Step A

A mixture of the title compound from the Example 2285 (8.5 mg) and conc. HCl (4.5 mL) in THF (3 mL) was stirred at room temperature for 6 h, concentrated, absorbed on silica and purified by chromatography (silica, $CH_2Cl_2$/MeOH) to afford the title compound I (1.3 mg, 15%, $[MH]^+$=509) and title compound II (4 mg, 47%, $[MH]^+$=492).

Example 2392

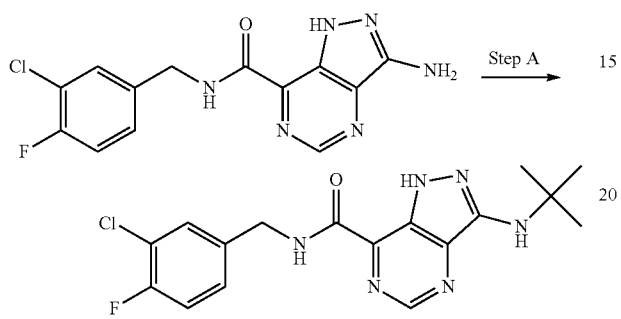

Step A

To a suspension of the Preparative Example 377, Step E (30 mg) in cyclohexane (5 mL) were added tert-butyl 2,2,2-trichloroacetimidate (44 mg) and $BF_3 \cdot Et_2O$ (2 drops). The resulting mixture was stirred at room temperature overnight, concentrated, absorbed on silica and purified by chromatography (silica, $CH_2Cl_2$/MeOH) to afford the title compound (10.2 mg, 34%). $[MH]^+$=377.

What is claimed is:

1. A compound having Formula

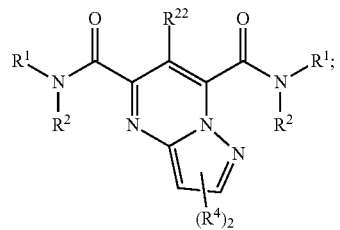

wherein:
$R^1$ is selected from the group consisting of cycloalkylalkyl, bicycloalkylalkyl, heterobicycloalkylalkyl, arylalkyl, and 5- to 10-membered heteroarylalkyl,
wherein $R^1$ is optionally substituted by one $R^{16}$ group and by one or more $R^9$ groups;
$R^2$ is hydrogen;
$R^4$ in each occurrence is independently selected from the group consisting of $R^{10}$, hydrogen, alkyl, cycloalkyl, 3- to 10-membered heterocycloalkyl, aryl, 5- to 10-membered heteroaryl, halo, haloalkyl, $CF_3$, $(C_0-C_6)$-alkyl-$COR^{10}$, $(C_0-C_6)$-alkyl-$OR^{10}$, $(C_0-C_6)$-alkyl-$NR^{10}R^{11}$, $(C_0-C_6)$-alkyl-$NO_2$, $(C_0-C_6)$-alkyl-CN, $(C_0-C_6)$-alkyl-$S(O)_yOR^{10}$, $(C_0-C_6)$-alkyl-$S(O)_yNR^{10}R^{11}$, $(C_0-C_6)$-alkyl-$NR^{10}CONR^{11}SO_2R^{30}$, $(C_0-C_6)$-alkyl-$S(O)_xR^{10}$, $(C_0-C_6)$-alkyl-$OC(O)R^{10}$, $(C_0-C_6)$-alkyl-$OC(O)NR^{10}R^{11}$, $(C_0-C_6)$-alkyl-$C(=NR^{10})NR^{10}R^{11}$, $(C_0-C_6)$-alkyl-$NR^{10}C(=NR^{11})NR^{10}R^{11}$, $(C_0-C_6)$-alkyl-$C(O)OR^{10}$, $(C_0-C_6)$-alkyl-$C(O)NR^{10}R^{11}$, $(C_0-C_6)$-alkyl-$C(O)NR^{10}SO_2R^{11}$, $(C_0-C_6)$-alkyl-$C(O)$—$NR^{11}$—CN, O—$(C_0-C_6)$-alkyl-$C(O)NR^{10}R^{11}$, $S(O)_x$—$(C_0-C_6)$-alkyl-$C(O)OR^{10}$, $S(O)_x$—$(C_0-C_6)$-alkyl-$C(O)NR^{10}R^{11}$, $(C_0-C_6)$-alkyl-$C(O)NR^{10}$—$(C_0-C_6)$-alkyl-$NR^{10}R^{11}$, $(C_0-C_6)$-alkyl-$NR^{10}$—$C(O)R^{10}$, $(C_0-C_6)$-alkyl-$NR^{10}$—$C(O)OR^{10}$, $(C_0-C_6)$-alkyl-$NR^{10}$—$C(O)$—$NR^{10}R^{11}$, $(C_0-C_6)$-alkyl-$NR^{10}$—$S(O)_yNR^{10}R^{11}$, $(C_0-C_6)$-alkyl-$NR^{10}$—$S(O)_yR^{10}$, O—$(C_0-C_6)$-alkyl-aryl and O—$(C_0-C_6)$-alkyl-5- to 10-membered heteroaryl,
wherein each $R^4$ group is optionally substituted by one or more $R^{14}$ groups;
$R^9$ in each occurrence is independently selected from the group consisting of $R^{10}$, hydrogen, alkyl, cycloalkyl, 3- to 10-membered heterocycloalkyl, aryl, 5- to 10-membered heteroaryl, halo, $CHF_2$, $CF_3$, $OR^{10}$, $SR^{10}$, $COOR^{10}$, $CH(CH_3)CO_2H$, $(C_0-C_6)$-alkyl-$COR^{10}$, $(C_0-C_6)$-alkyl-$OR^{10}$, $(C_0-C_6)$-alkyl-$NR^{10}R^{11}$, $(C_0-C_6)$-alkyl-$NO_2$, $(C_0-C_6)$-alkyl-CN, $(C_0-C_6)$-alkyl-$S(O)_yOR^{10}$, $(C_0-C_6)$-alkyl-$P(O)_2OH$, $(C_0-C_6)$-alkyl-$S(O)_yNR^{10}R^{11}$, $(C_0-C_6)$-alkyl-$NR^{10}CONR^{11}SO_2R^{30}$, $(C_0-C_6)$-alkyl-$S(O)_xR^{10}$, $(C_0-C_6)$-alkyl-$OC(O)R^{10}$, $(C_0-C_6)$-alkyl-$OC(O)NR^{10}R^{11}$, $(C_0-C_6)$-alkyl-$C(=NR^{10})NR^{10}R^{11}$, $(C_0-C_6)$-alkyl-$NR^{10}C(=NR^{11})NR^{10}R^{11}$, $(C_0-C_6)$-alkyl-$NR^{10}C(=N$—CN$)NR^{10}R^{11}$, $(C_0-C_6)$-alkyl-$C(=N$—CN$)NR^{10}R^{11}$, $(C_0-C_6)$-alkyl-$NR^{10}C(=N$—$NO_2)NR^{10}R^{11}$, $(C_0-C_6)$-alkyl-$C(=N$—$NO_2)NR^{10}R^{11}$, $(C_0-C_6)$-alkyl-$C(O)OR^{10}$, $(C_0-C_6)$-alkyl-$C(O)NR^{10}R^{11}$, $(C_0-C_6)$-alkyl-$C(O)NR^{10}SO_2R^{11}$, $C(O)NR^{10}$—$(C_0-C_6)$-alkyl-5- to 10-membered heteroaryl, $C(O)NR^{10}$—$(C_0-C_6)$-alkyl-aryl, $S(O)_2NR^{10}$—$(C_0-C_6)$-alkyl-aryl, $S(O)_2NR^{10}$—$(C_0-C_6)$-alkyl-5- to 10-membered heteroaryl, $S(O)_2NR^{10}$-alkyl, $S(O)_2$—$(C_0-C_6)$-alkyl-aryl, $S(O)_2$—$(C_0-C_6)$-alkyl-5- to 10-membered heteroaryl, $(C_0-C_6)$-alkyl-$C(O)$—$NR^{11}$—CN, O—$(C_0-C_6)$-alkyl-$C(O)NR^{10}R^{11}$, $S(O)_x$—$(C_0-C_6)$-alkyl-$C(O)OR^{10}$, $S(O)_x$—$(C_0-C_6)$-alkyl-$C(O)NR^{10}R^{11}$, $(C_0-C_6)$-alkyl-$C(O)NR^{10}$—$(C_0-C_6)$-alkyl-$NR^{10}R^{11}$, $(C_0-C_6)$-alkyl-$NR^{10}$—$C(O)R^{10}$, $(C_0-C_6)$-alkyl-$NR^{10}$—$C(O)OR^{10}$, $(C_0-C_6)$-alkyl-$NR^{10}$—$C(O)$—$NR^{10}R^{11}$, $(C_0-C_6)$-alkyl-$NR^{10}$—$S(O)_yNR^{10}R^{11}$, $(C_0-C_6)$-alkyl-$NR^{10}$—$S(O)_yR^{11}$, O—$(C_0-C_6)$-alkyl-aryl and O—$(C_0-C_6)$-alkyl-5- to 10-membered heteroaryl,
wherein each $R^9$ group is optionally substituted by one or more $R^{14}$ groups;
$R^{10}$ and $R^{11}$ in each occurrence are independently selected from the group consisting of hydrogen, alkyl, alkenyl, alkynyl, cycloalkyl, cycloalkylalkyl, 3- to 10-membered heterocycloalkyl, bicycloalkyl, heterobicycloalkyl, spiroalkyl, spiroheteroalkyl, fluoroalkyl, 3- to 10-membered heterocycloalkylalkyl, haloalkyl, alkenyl, alkynyl, aryl, 5- to 10-membered heteroaryl, arylalkyl, 5- to 10-membered heteroarylalkyl and aminoalkyl, wherein alkyl, cycloalkyl, cycloalkylalkyl, bicycloalkyl, heterobicycloalkyl, spiroalkyl, spiroheteroalkyl, 3- to 10-membered heterocycloalkyl, fluoroalkyl, 3- to 10-membered heterocycloalkylalkyl, alkenyl, alkynyl, aryl, 5- to 10-membered heteroaryl, arylalkyl, 5- to 10-membered heteroarylalkyl and aminoalkyl are optionally substituted one or more times, or $R^{10}$ and $R^{11}$ when taken together with the nitrogen to which they are attached complete a 3- to 8-membered ring containing carbon atoms and optionally containing a heteroatom selected from O, $S(O)_x$, or $NR^{50}$ and which is optionally substituted one or more times;
$R^{14}$ is independently selected from the group consisting of hydrogen, alkyl, arylalkyl, cycloalkylalkyl, 5- to 10-membered heteroarylalkyl, heterocyclylalkyl and halo, wherein alkyl, arylalkyl, cycloalkylalkyl, 5- to 10-membered heteroarylalkyl and heterocyclylalkyl are optionally substituted one or more times;

$R^{16}$ is selected from the group consisting of cycloalkyl, 3- to 10-membered heterocycloalkyl, bicycloalkyl, heterobicycloalkyl, spiroalkyl, spiroheteroalkyl, aryl, 5- to 10-membered heteroaryl, cycloalkyl fused aryl, 3- to 10-membered heterocycloalkyl fused aryl, cycloalkyl fused 5- to 10-membered heteroaryl, 3- to 10-membered heterocycloalkyl fused 5- to 10-membered heteroaryl, cycloalkylalkyl, 3- to 10-membered heterocycloalkylalkyl, bicycloalkylalkyl, heterobicycloalkylalkyl, spiroalkylalkyl, spiroheteroalkylalkyl, arylalkyl, 5- to 10-membered heteroarylalkyl, cycloalkyl fused arylalkyl, 3- to 10-membered heterocycloalkyl fused arylalkyl, cycloalkyl fused 5- to 10-membered heteroarylalkyl, 3- to 10-membered heterocycloalkyl fused 5- to 10-membered heteroarylalkyl, wherein said cycloalkyl, 3- to 10-membered heterocycloalkyl, bicycloalkyl, heterobicycloalkyl, spiroalkyl, spiroheteroalkyl, aryl, 5- to 10-membered heteroaryl, cycloalkyl fused aryl, 3- to 10-membered heterocycloalkyl fused aryl, cycloalkyl fused 5- to 10-membered heteroaryl, 3- to 10-membered heterocycloalkyl fused 5- to 10-membered heteroaryl, cycloalkylalkyl, 3- to 10-membered heterocycloalkylalkyl, bicycloalkylalkyl, heterobicycloalkylalkyl, spiroalkylalkyl, spiroheteroalkylalkyl, arylalkyl, 5- to 10-membered heteroarylalkyl, cycloalkyl fused arylalkyl, 3- to 10-membered heterocycloalkyl fused arylalkyl, cycloalkyl fused 5- to 10-membered heteroarylalkyl, and 3- to 10-membered heterocycloalkyl fused 5- to 10-membered heteroarylalkyl are optionally substituted one or more times;

$R^{22}$ is hydrogen;

$R^{30}$ is selected from the group consisting of alkyl and $(C_0$-$C_6)$-alkyl-aryl, wherein alkyl and aryl are optionally substituted;

$R^{50}$ in each occurrence is independently selected from the group consisting of hydrogen, alkyl, aryl, heteroaryl, $C(O)R^{80}$, $C(O)NR^{80}R^{81}$, $SO_2R^{80}$ and $SO_2NR^{80}R^{81}$, wherein alkyl, aryl, and heteroaryl are optionally substituted one or more times;

$R^{80}$ and $R^{81}$ in each occurrence are independently selected from the group consisting of hydrogen, alkyl, cycloalkyl, cycloalkylalkyl, 3- to 10-membered heterocycloalkyl, fluoroalkyl, 3- to 10-membered heterocycloalkylalkyl, haloalkyl, alkenyl, alkynyl, aryl, 5- to 10-membered heteroaryl, arylalkyl, 5- to 10-membered heteroarylalkyl and aminoalkyl, wherein alkyl, cycloalkyl, cycloalkylalkyl, 3- to 10-membered heterocycloalkyl, fluoroalkyl, 3- to 10-membered heterocycloalkylalkyl, alkenyl, alkynyl, aryl, 5- to 10-membered heteroaryl, arylalkyl, 5- to 10-membered heteroarylalkyl and aminoalkyl are optionally substituted, or $R^{80}$ and $R^{81}$ when taken together with the nitrogen to which they are attached complete a 3- to 8-membered ring containing carbon atoms and optionally a heteroatom selected from O, $S(O)_x$, —NH, and —N(alkyl) and which is optionally substituted one or more times;

$R^{51}$ is independently selected from the group consisting of hydrogen, alkyl, aryl, heteroaryl, arylalkyl, cycloalkylalkyl, heteroarylalkyl and haloalkyl, wherein alkyl, aryl, heteroaryl, arylalkyl, cycloalkylalkyl, heteroarylalkyl and haloalkyl are optionally substituted one or more time;

x is selected from 0 to 2;

y is selected from 1 and 2; and wherein each of said optional substitution is selected from the group consisting of $C_1$-$C_4$ alkyl; $C_2$-$C_4$ alkenyl; $C_2$-$C_4$ alkynyl; $CF_3$; halo; OH; O—$(C_1$-$C_4$ alkyl); $OCH_2F$; $OCHF_2$; $OCF_3$; $ONO_2$; OC(O)—$(C_1$-$C_4$ alkyl); OC(O)—$(C_1$-$C_4$ alkyl); OC(O)NH—$(C_1$-$C_4$ alkyl); OC(O)N$(C_1$-$C_4$ alkyl)$_2$; OC(S)NH—$(C_1$-$C_4$ alkyl); OC(S)N$(C_1$-$C_4$ alkyl)$_2$; SH; S—$(C_1$-$C_4$ alkyl); S(O)—$(C_1$-$C_4$ alkyl); S(O)$_2$—$(C_1$-$C_4$ alkyl); SC(O)—$(C_1$-$C_4$ alkyl); SC(O)O—$(C_1$-$C_4$ alkyl); NH$_2$; N(H)—$(C_1$-$C_4$ alkyl); N$(C_1$-$C_4$ alkyl)$_2$; N(H)C(O)—$(C_1$-$C_4$ alkyl); $(CH_3)$C(O)—$(C_1$-$C_4$ alkyl); N(H)C(O)—$CF_3$; N$(CH_3)$C(O)—$CF_3$; N(H)C(S)—$(C_1$-$C_4$ alkyl); N$(CH_3)$C(S)—$(C_1$-$C_4$ alkyl); N(H)S(O)$_2$—$(C_1$-$C_4$ alkyl); N(H)C(O)NH$_2$; N(H)C(O)NH—$(C_1$-$C_4$ alkyl); N$(CH_3)$C(O)NH—$(C_1$-$C_4$ alkyl); N(H)C(O)N$(C_1$-$C_4$ alkyl)$_2$; N$(CH_3)$C(O)N$(C_1$-$C_4$ alkyl)$_2$; N(H)S(O)$_2$NH$_2$; N(H)S(O)$_2$NH—$(C_1$-$C_4$ alkyl); N$(CH_3)$S(O)$_2$NH—$(C_1$-$C_4$ alkyl); N(H)S(O)$_2$N$(C_1$-$C_4$ alkyl)$_2$; N$(CH_3)$S(O)$_2$N$(C_1$-$C_4$ alkyl)$_2$; N(H)C(O)O—$(C_1$-$C_4$ alkyl); N$(CH_3)$C(O)O—$(C_1$-$C_4$ alkyl); N(H)S(O)$_2$O—$(C_1$-$C_4$ alkyl); N$(CH_3)$S(O)$_2$O—$(C_1$-$C_4$ alkyl); N$(CH_3)$C(S)NH—$(C_1$-$C_4$ alkyl); N$(CH_3)$C(S)N$(C_1$-$C_4$ alkyl)$_2$; N$(CH_3)$C(S)O—$(C_1$-$C_4$ alkyl); N(H)C(S)NH$_2$; NO$_2$; CO$_2$H; CO$_2$—$(C_1$-$C_4$ alkyl); C(O)N(H)OH; C(O)N$(CH_3)$OH: C(O)N$(CH_3)$OH; C(O)N$(CH_3)$O—$(C_1$-$C_4$ alkyl); C(O)N(H)—$(C_1$-$C_4$ alkyl); C(O)N$(C_1$-$C_4$ alkyl)$_2$; C(S)N(H)—$(C_1$-$C_4$ alkyl); C(S)N$(C_1$-$C_4$ alkyl)$_2$; C(NH)N(H)—$(C_1$-$C_4$ alkyl); C(H)N$(C_1$-$C_4$ alkyl)$_2$; C$(NCH_3)$N(H)—$(C_1$-$C_4$ alkyl); C$(NCH_3)$N$(C_1$-$C_4$ alkyl)$_2$; C(O)—$(C_1$-$C_4$ alkyl); C(NH)—$(C_1$-$C_4$ alkyl); C$(NCH_3)$—$(C_1$-$C_4$ alkyl); C(NOH)—$(C_1$-$C_4$ alkyl); C$(NOCH_3)$—$(C_1$-$C_4$ alkyl); CN; CHO; $CH_2OH$; $CH_2O$—$(C_1$-$C_4$ alkyl); $CH_2NH_2$; $CH_2N(H)$—$(C_1$-$C_4$ alkyl); $CH_2N(C_1$-$C_4$ alkyl)$_2$; aryl; 5- to 10-membered heteroaryl; cycloalkyl; and heterocyclyl; or a pharmaceutically acceptable salt, racemic mixture or stereoisomer thereof.

2. The compound of claim 1, which is:

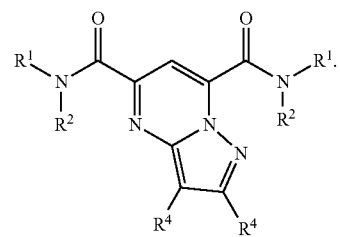

3. The compound of claim 2, selected from the group consisting of:

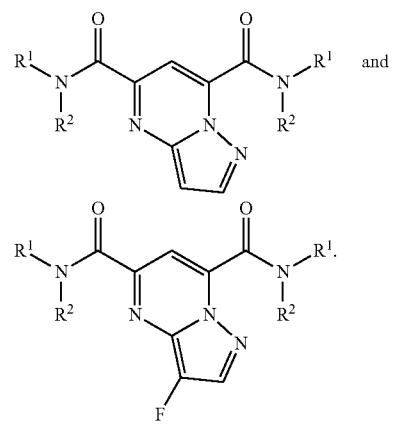

4. The compound of claim 3, wherein at least one $R^1$ is selected from the group consisting of:

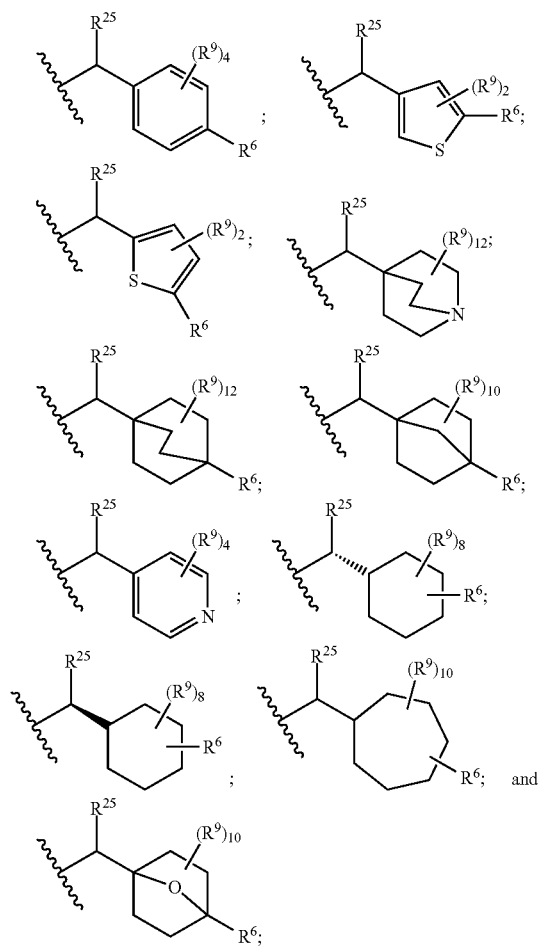

wherein:
$R^6$ is selected from the group consisting of hydrogen, halo, CN, OH, $CH_2OH$, $CF_3$, $CHF_2$, $OCF_3$, $OCHF_2$, $COCH_3$, $SO_2CH_3$, $SO_2CF_3$, $SO_2NH_2$, $SO_2NHCH_3$, $SO_2N(CH_3)_2$, $NH_2$, $NHCOCH_3$, $N(COCH_3)_2$, $NHCONH_2$, $NHSO_2CH_3$, alkoxy, alkyl, cycloalkyl, heterocycloalkyl, bicycloalkyl, $CO_2H$,

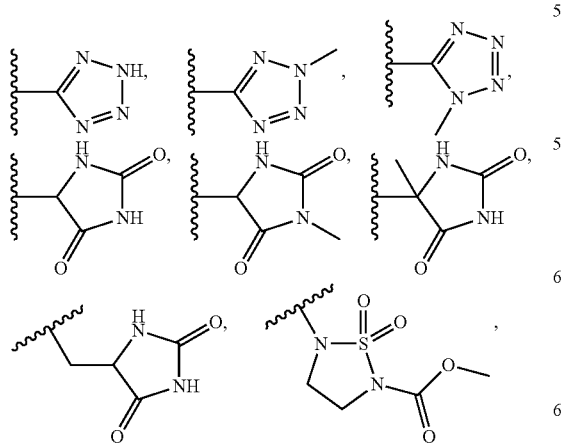

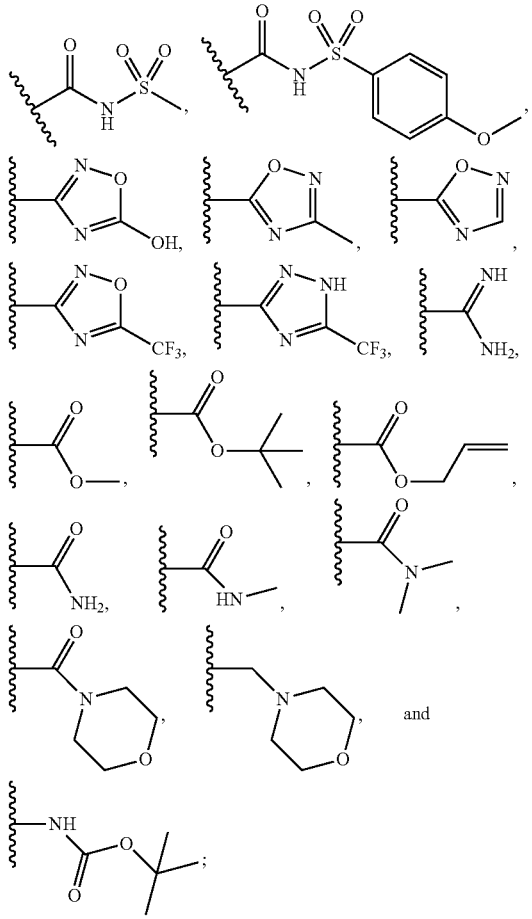

$R^9$ is independently selected from the group consisting of hydrogen, fluoro, chloro, $CH_3$, $CF_3$, $CHF_2$, $OCF_3$, and $OCHF_2$;

$R^{25}$ is selected from the group consisting of hydrogen, $CH_3$, $COOCH_3$, $COOH$, and $CONH_2$.

5. The compound of claim 3, wherein at least one $R^1$ is selected from the group consisting of:

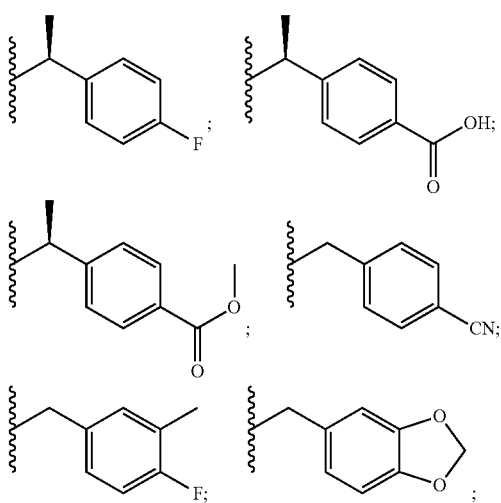

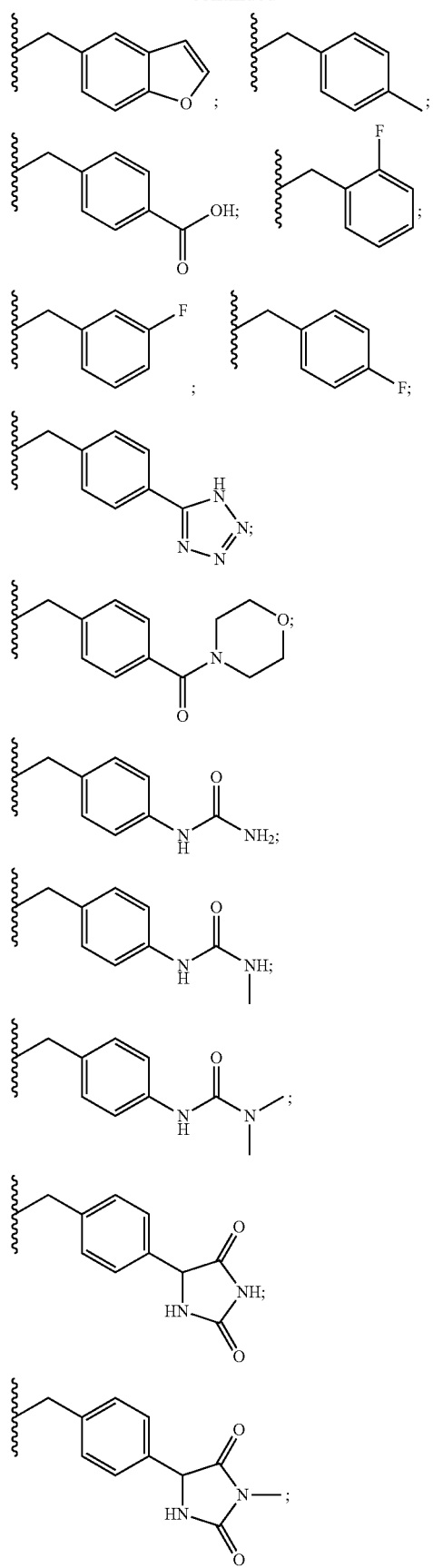
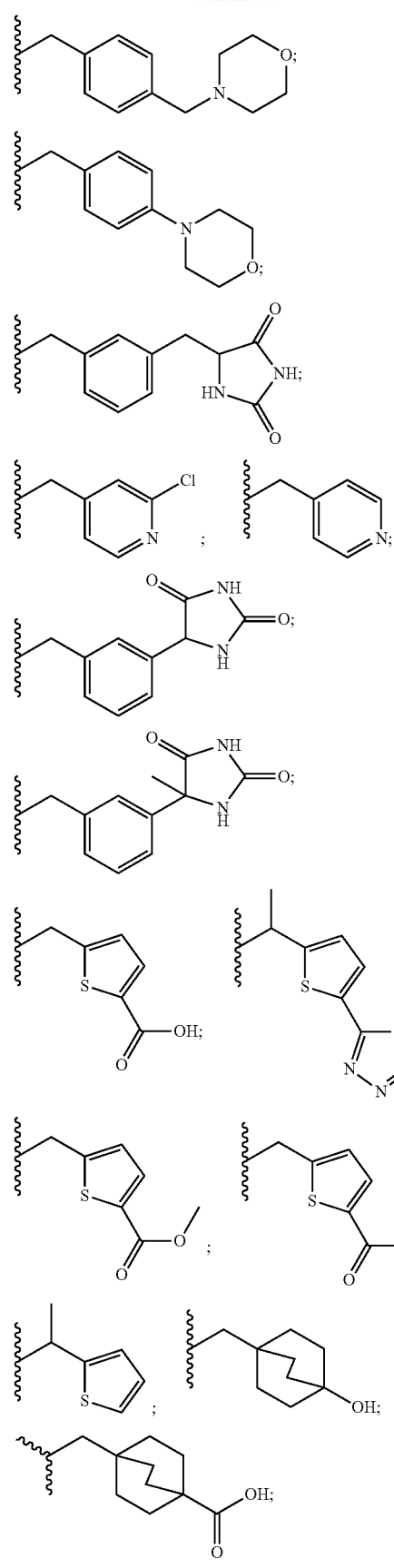

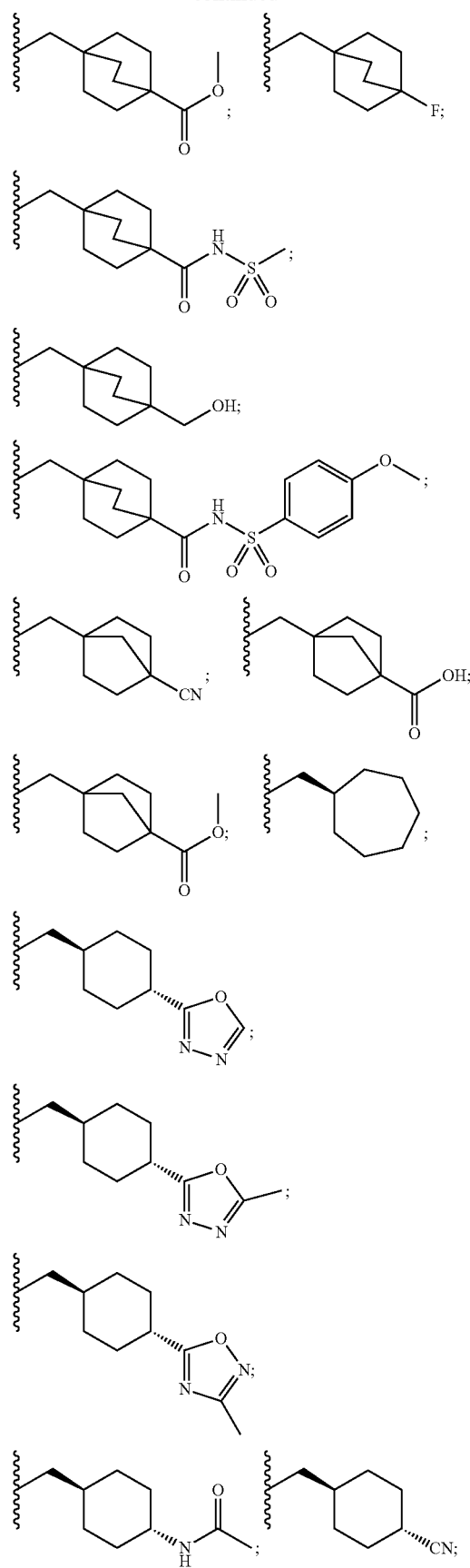
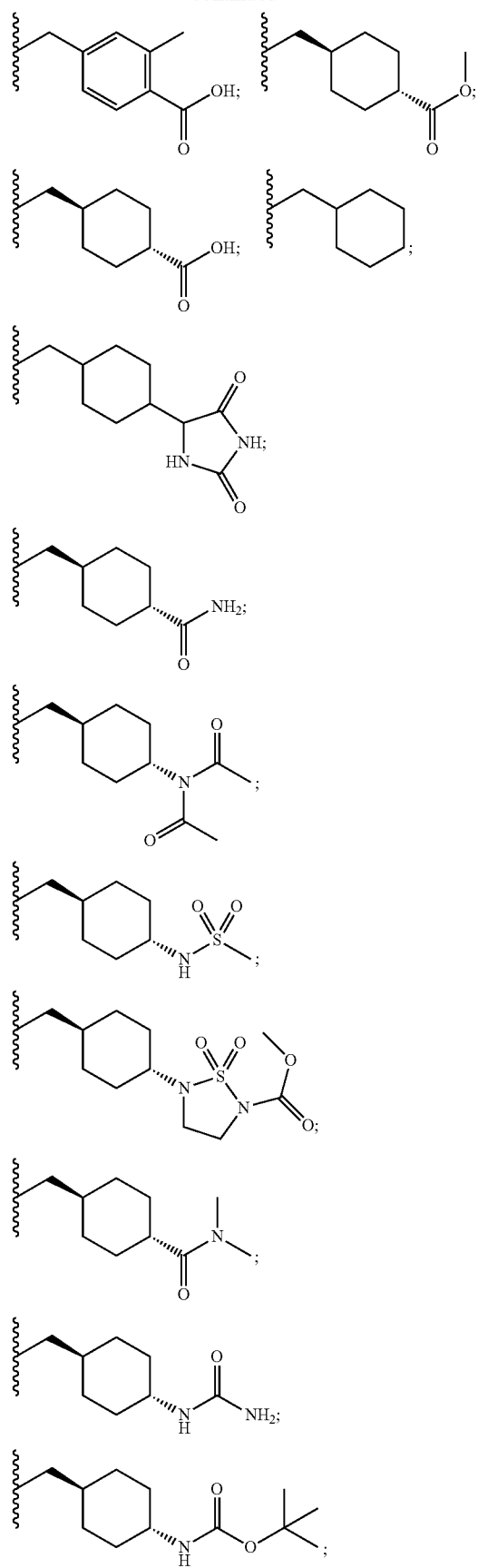

1587
-continued
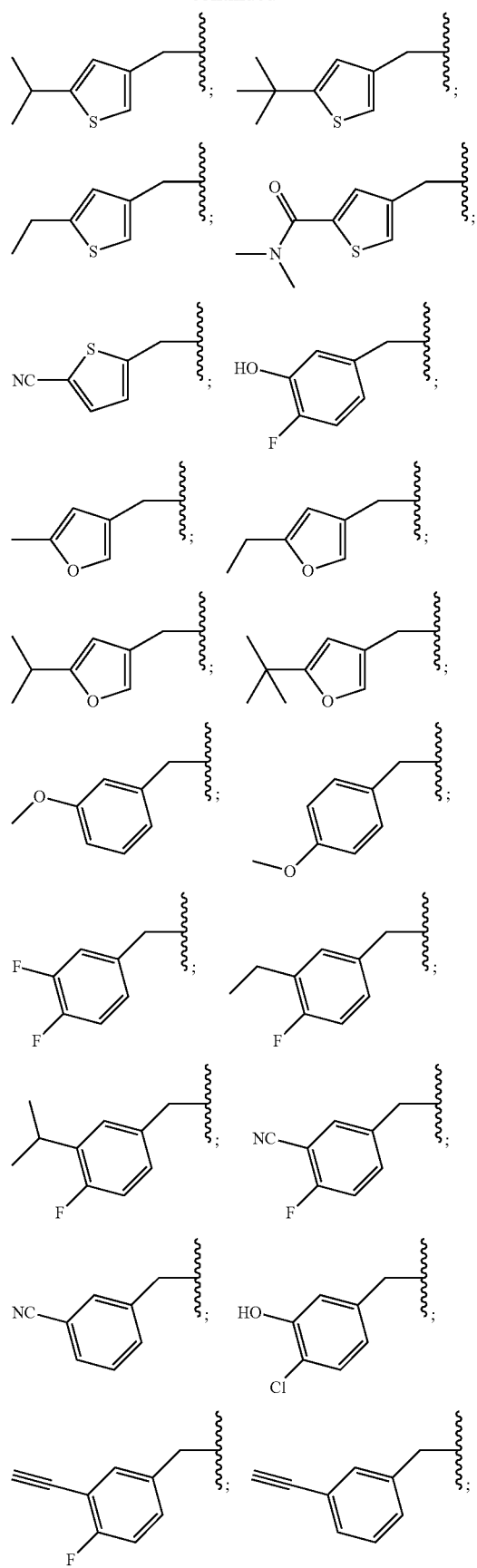
1588
-continued
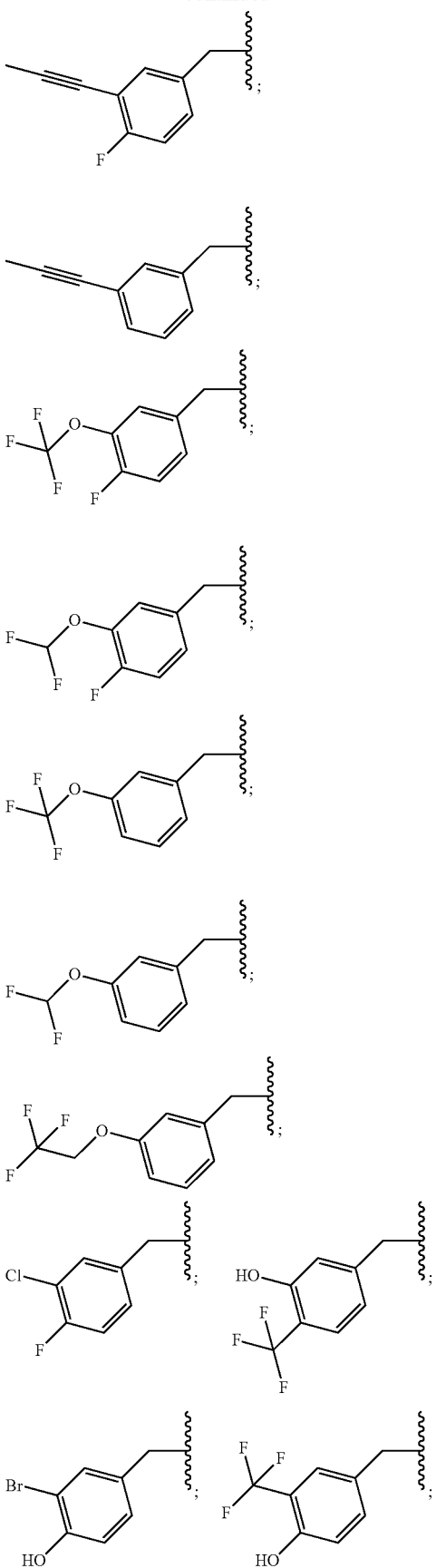

1589
-continued
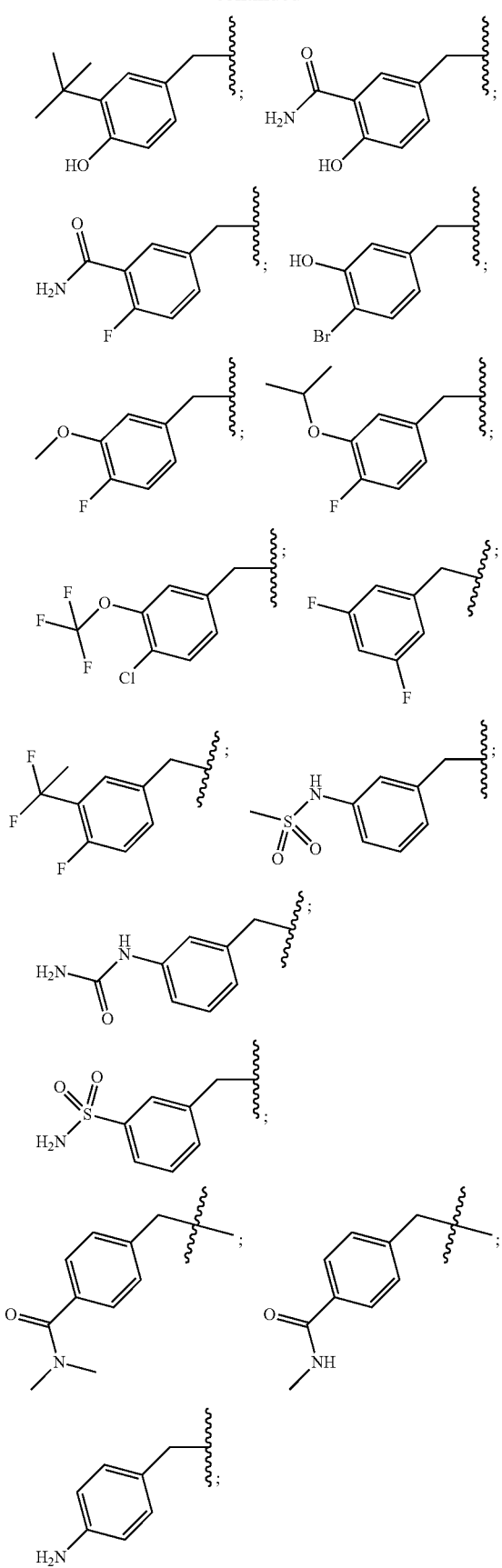
1590
-continued
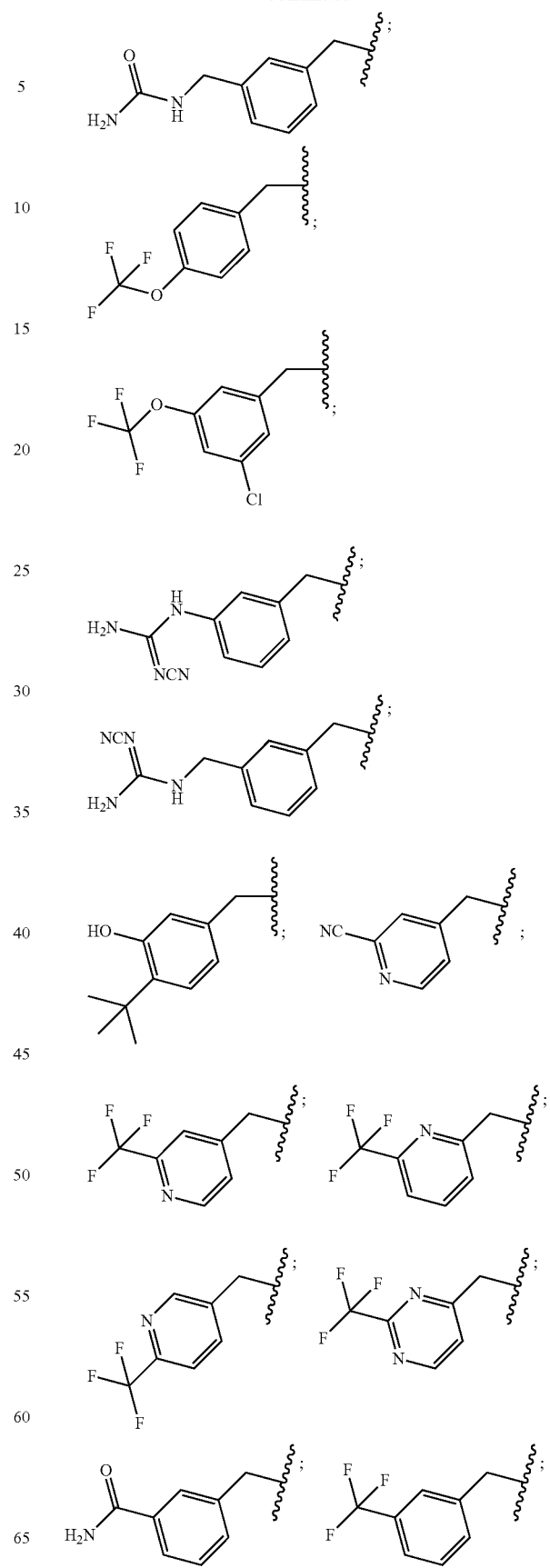

1591
-continued
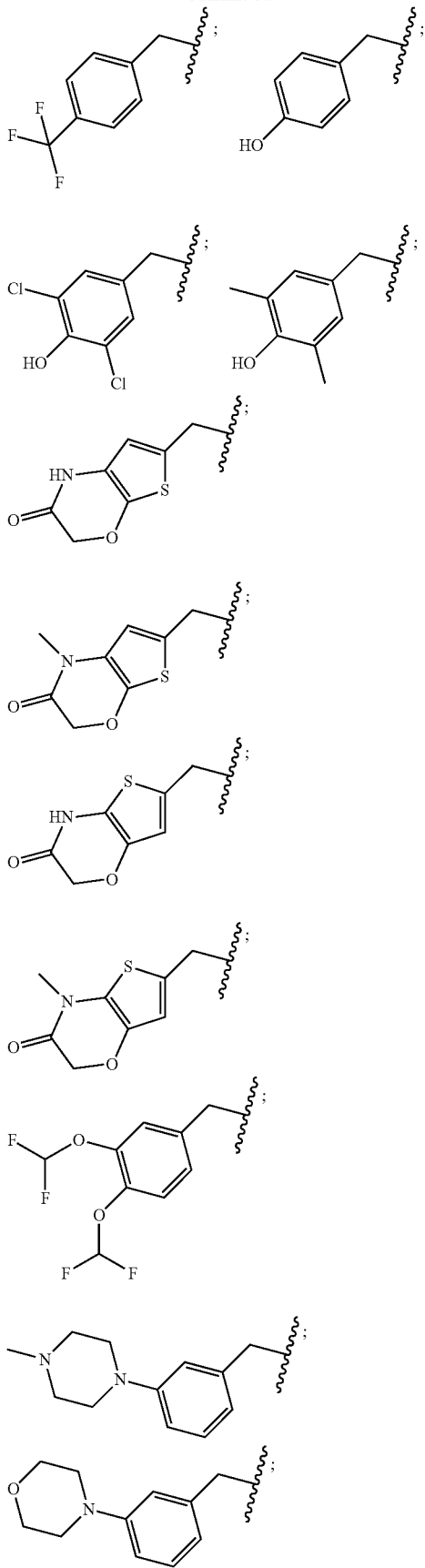
1592
-continued
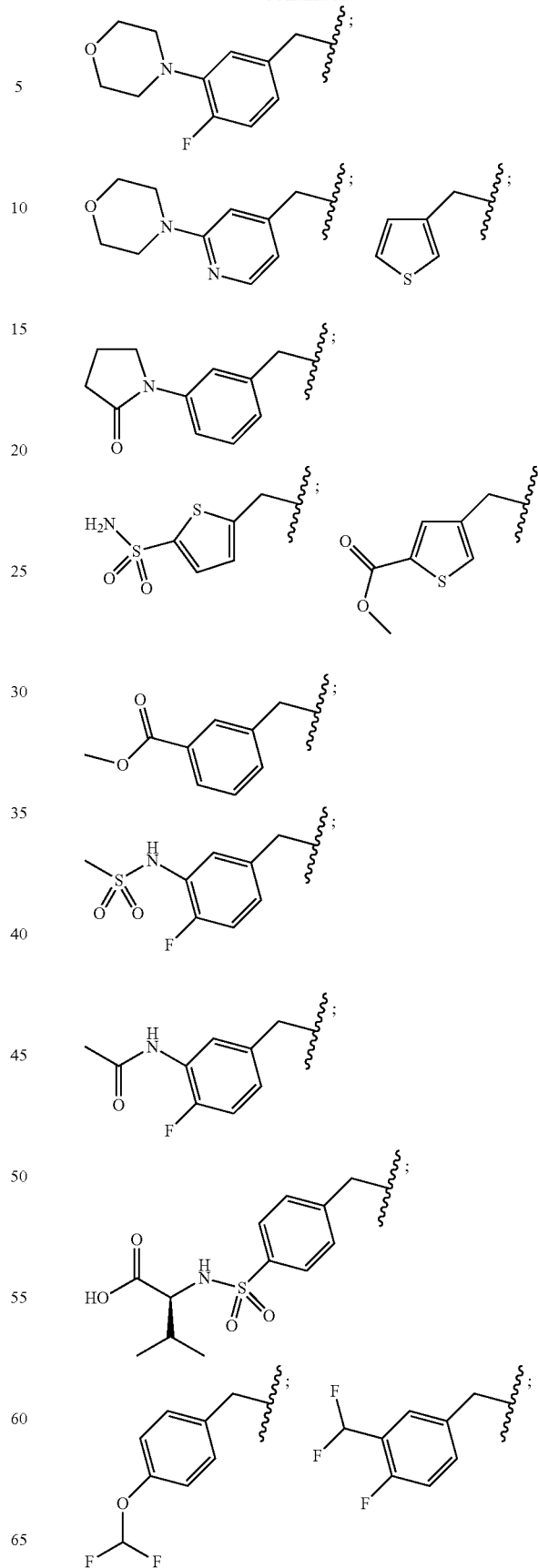

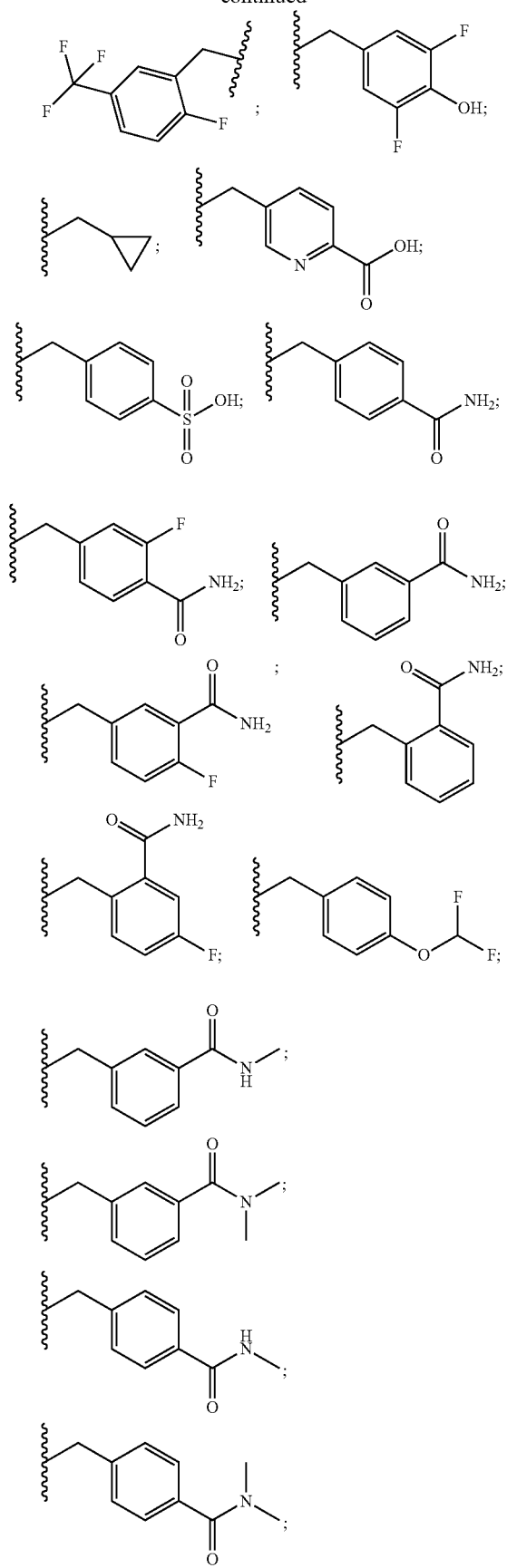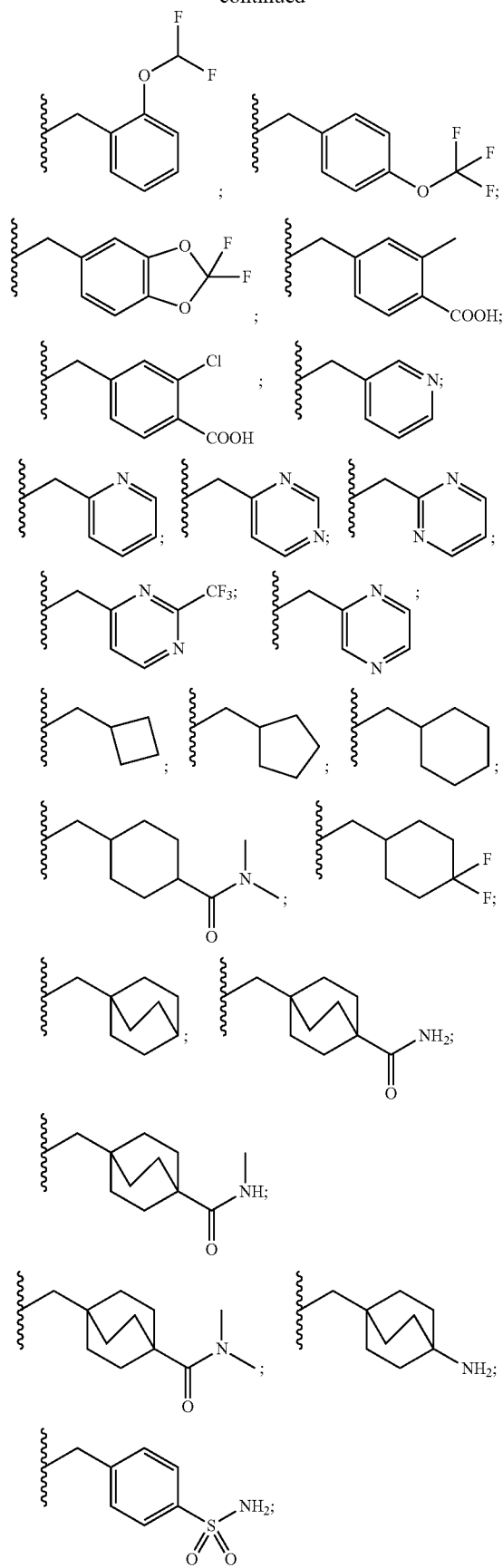

-continued
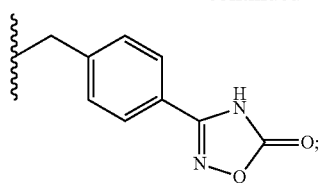
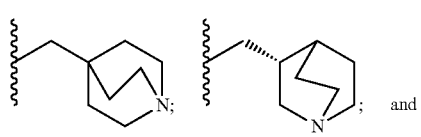 and
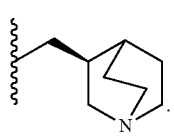
6. The compound of claim 1, wherein at least one R¹ is selected from the group consisting of:
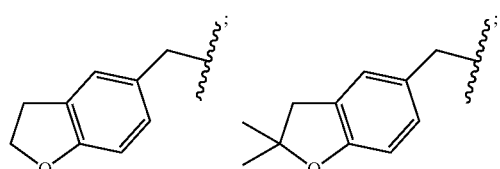
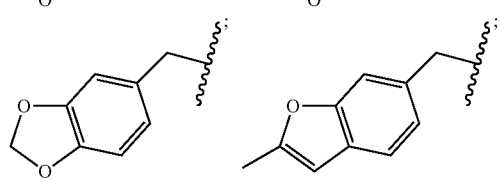
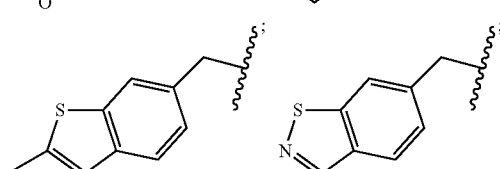
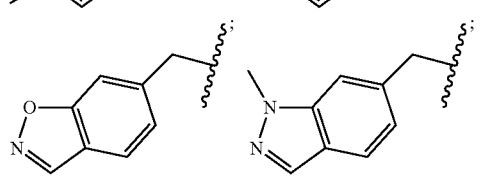
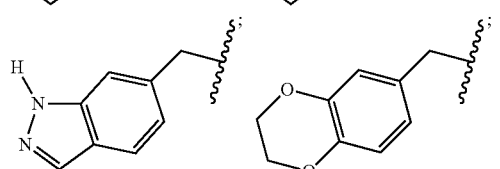
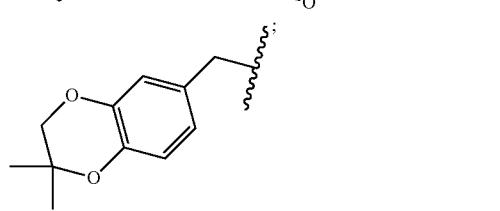
-continued
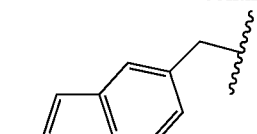
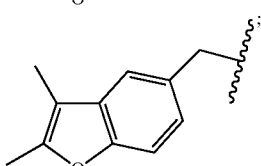
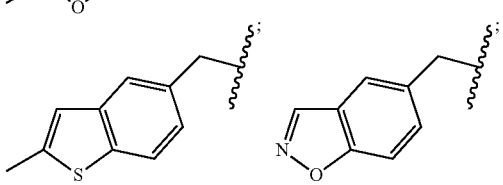
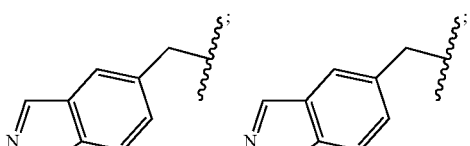

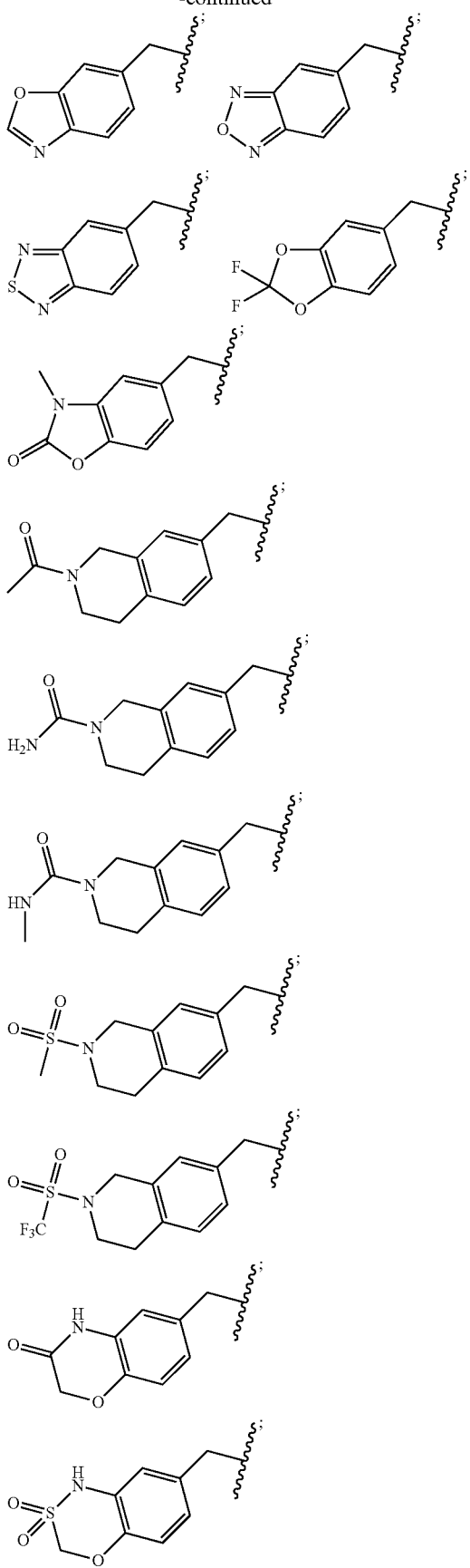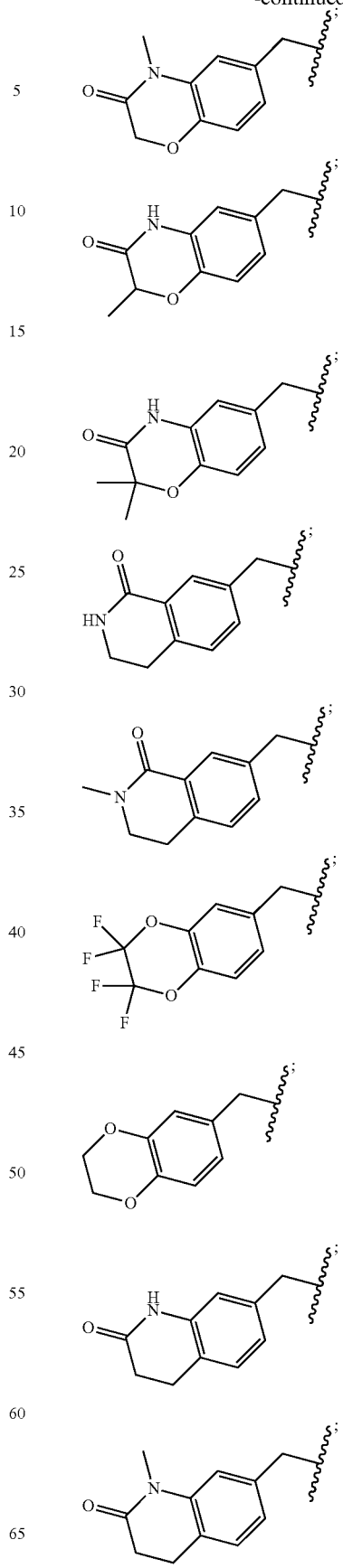

1599
-continued
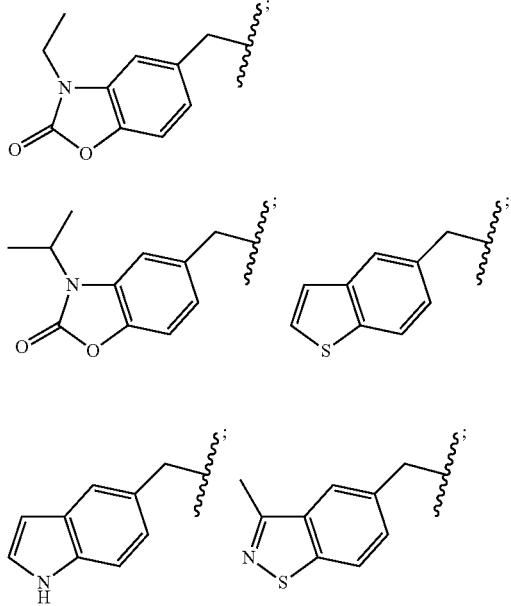
1600
-continued
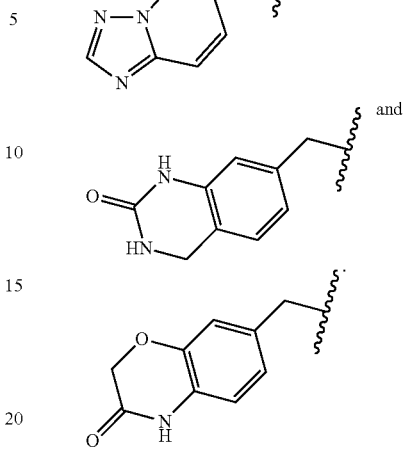
7. A compound according to claim 1, selected from the group consisting of:
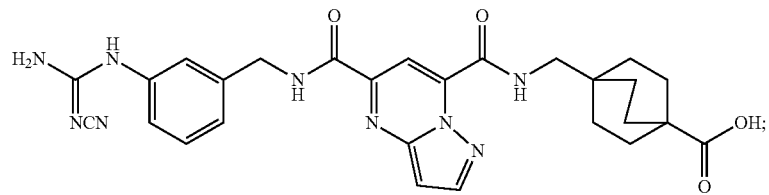
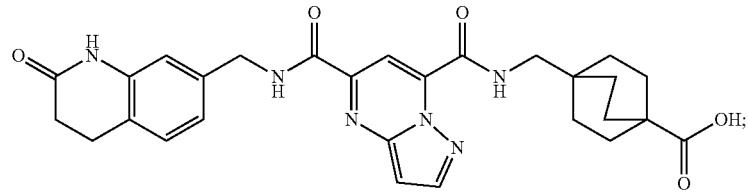
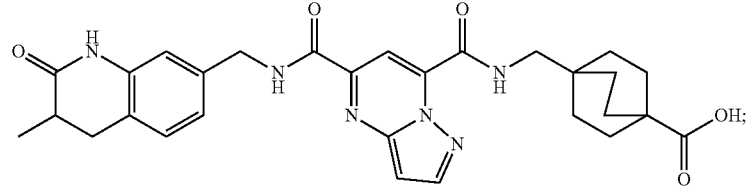
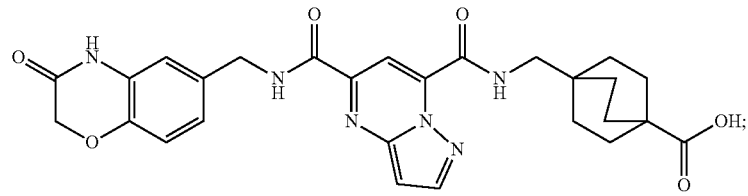
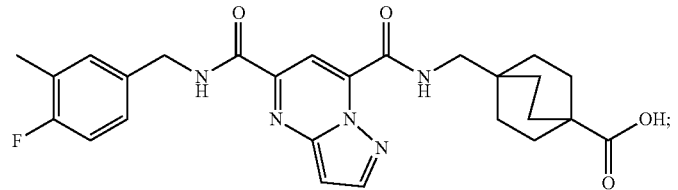

1601                                                                    1602
-continued
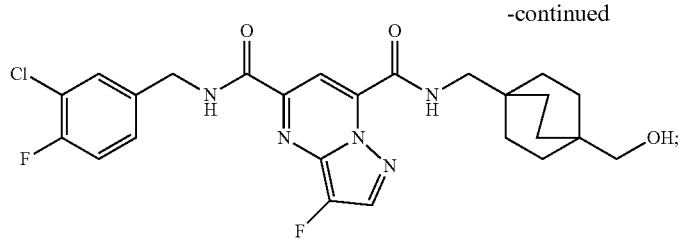
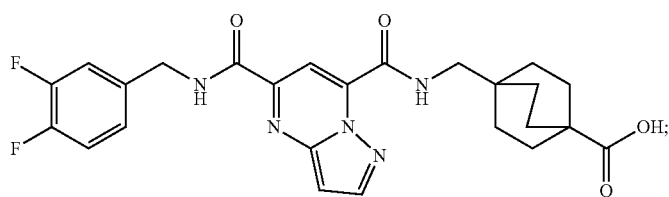
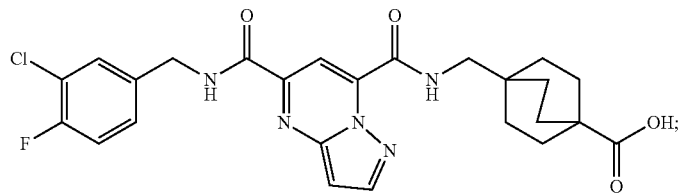
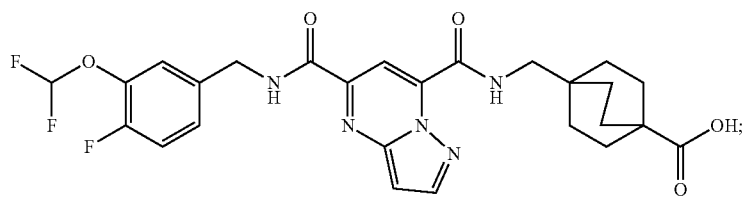
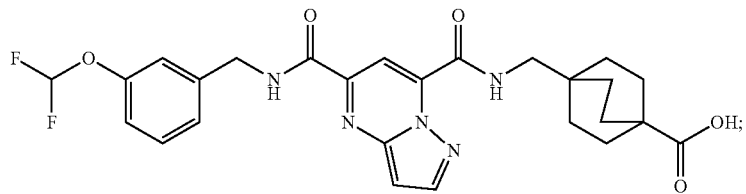
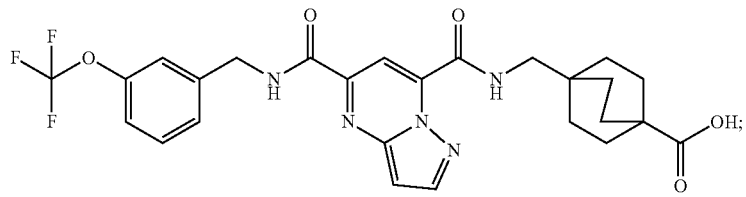
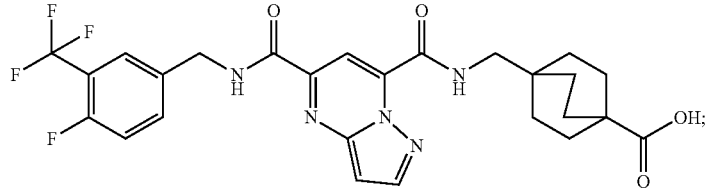
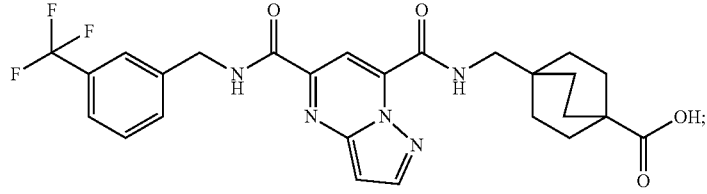

-continued
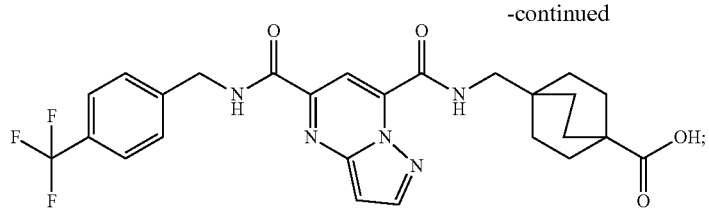
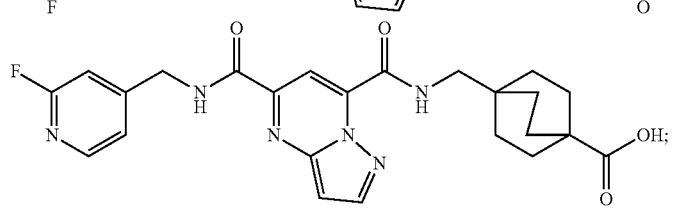
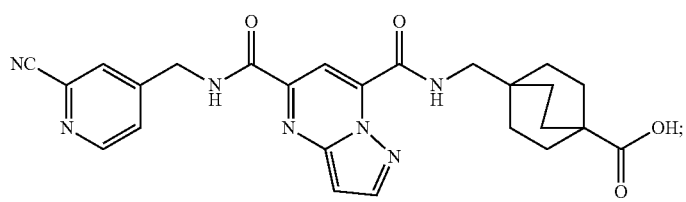
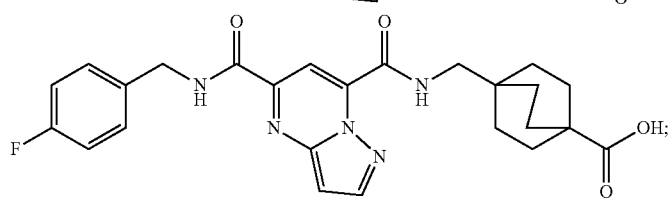
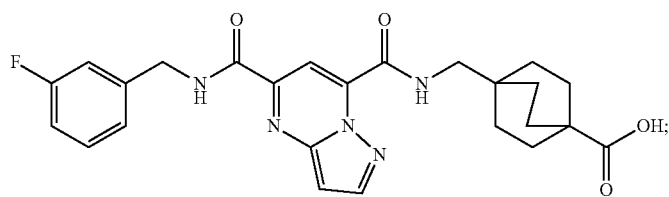
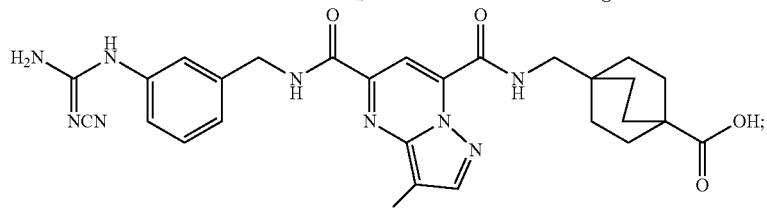
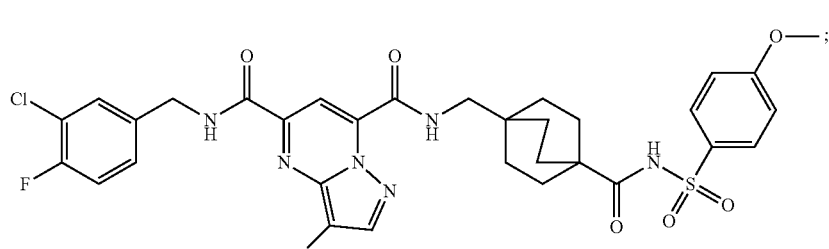
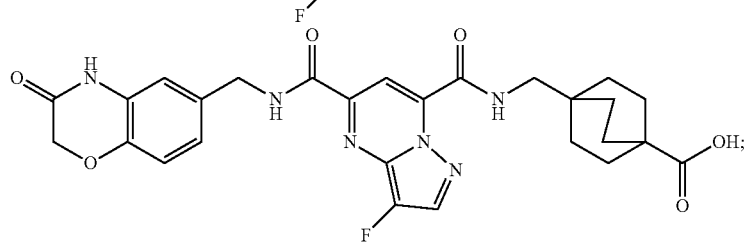

1605
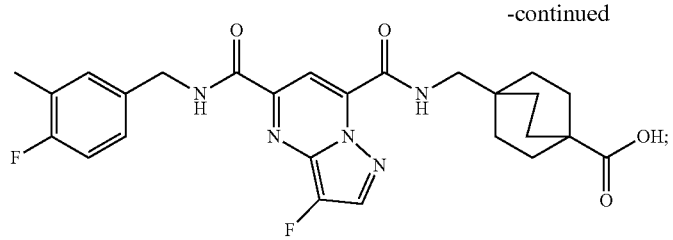
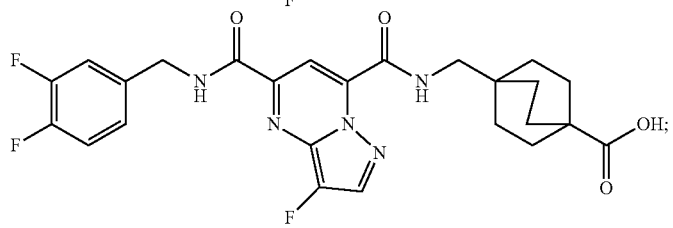
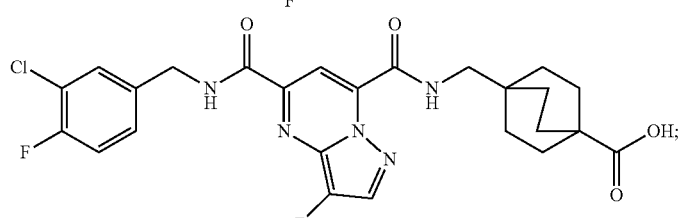
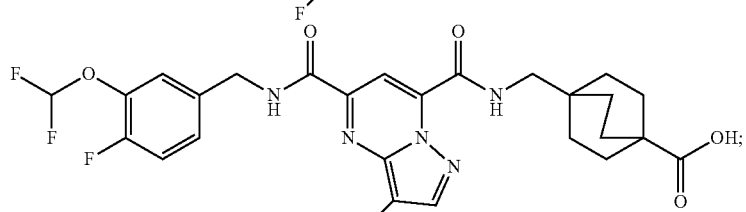
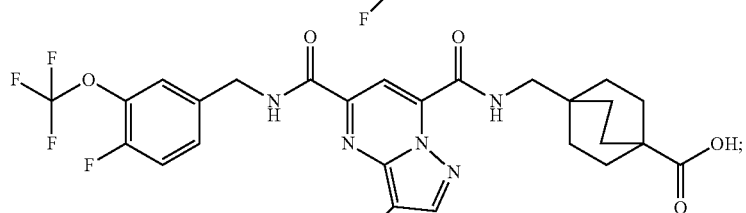
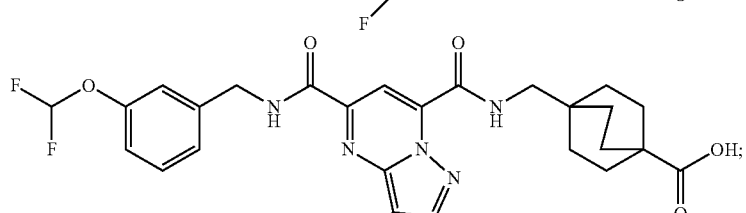
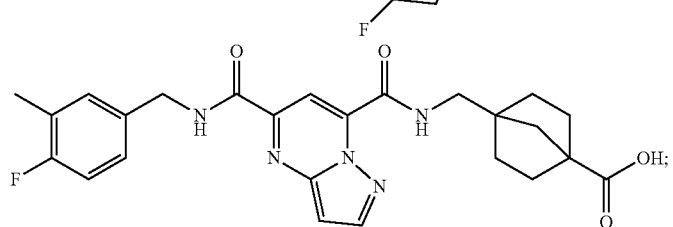
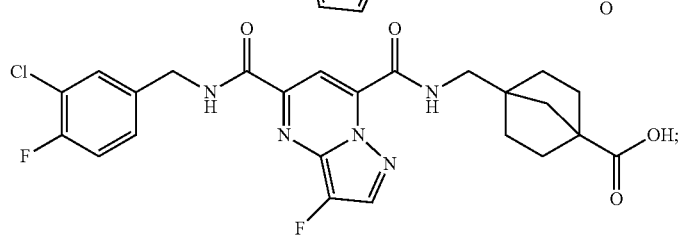

-continued
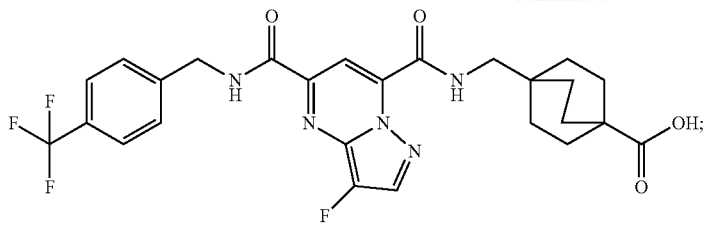
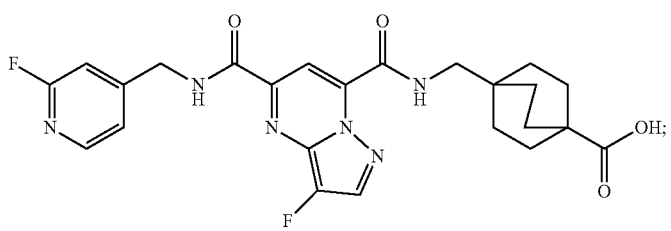
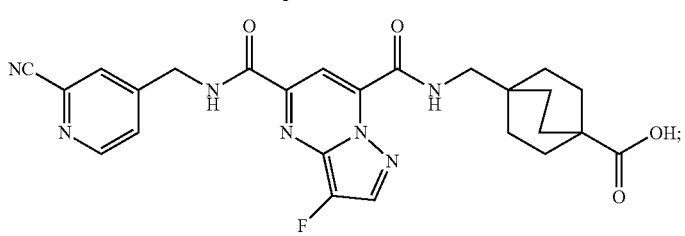
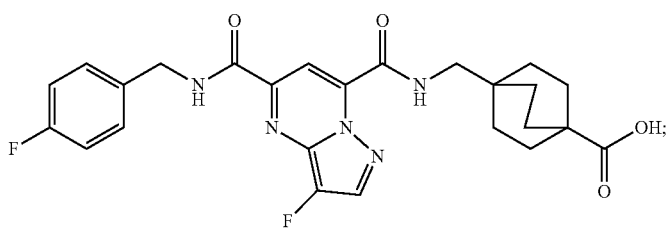
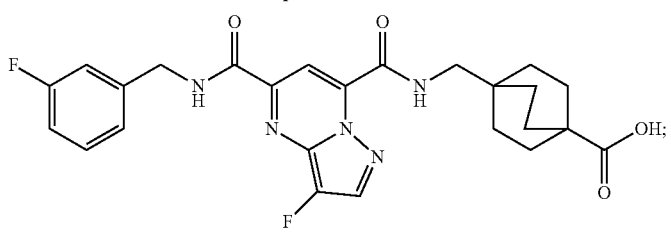
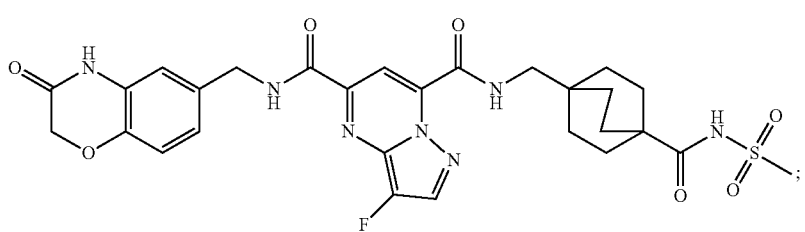
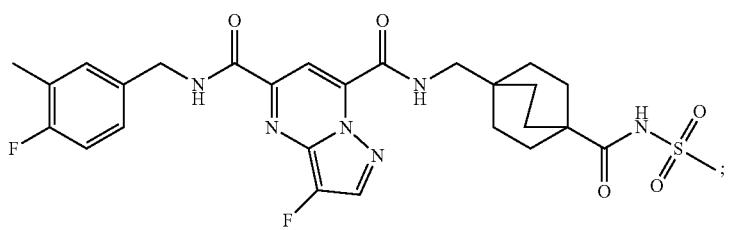

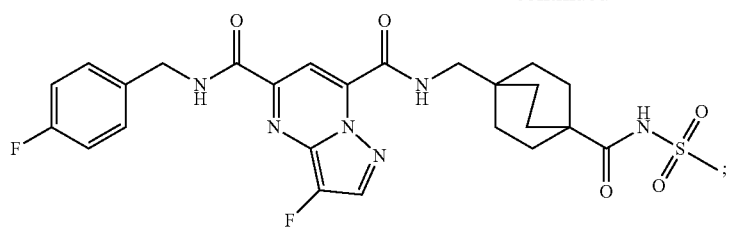
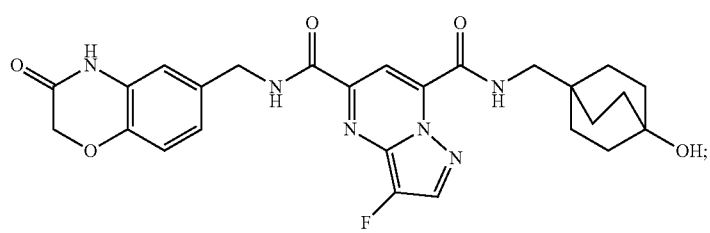
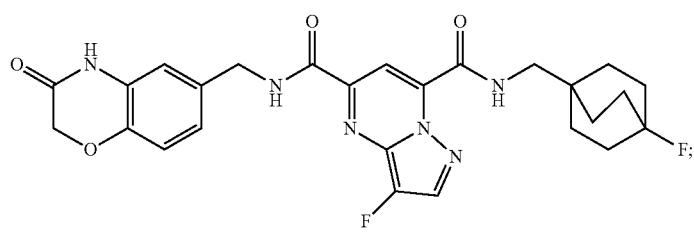
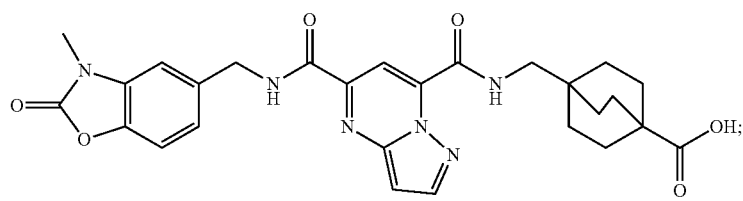
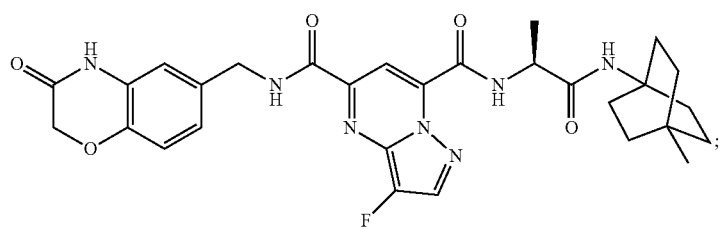
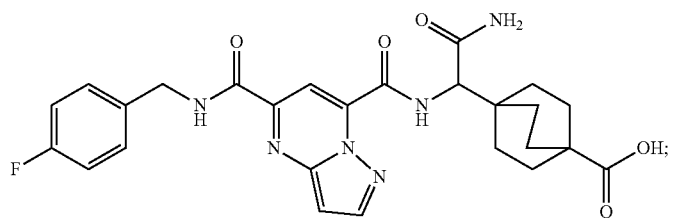
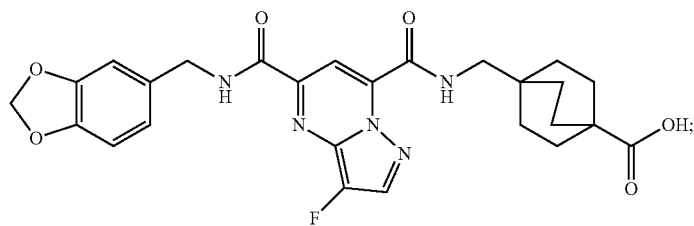

-continued

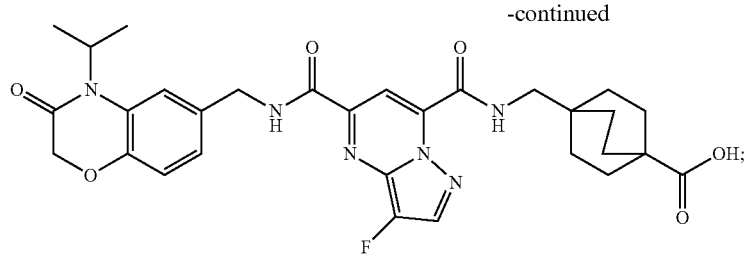

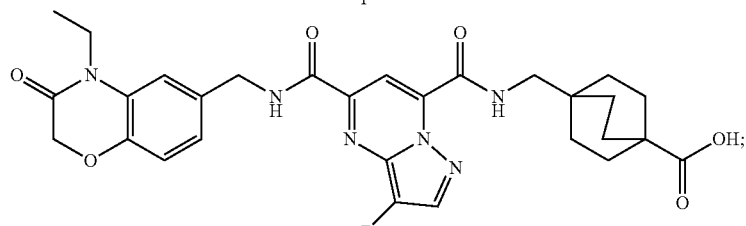

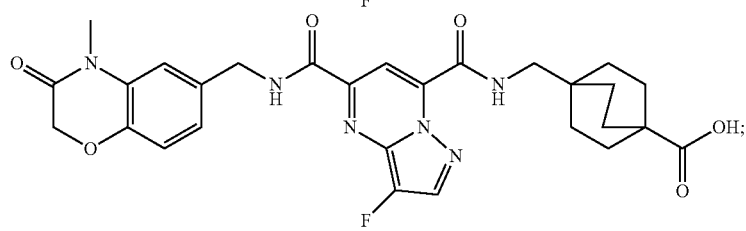

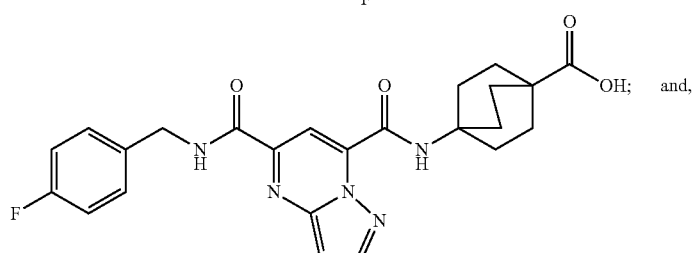

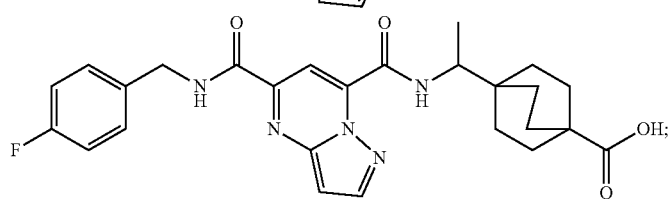

or a pharmaceutically acceptable salt thereof.

8. A compound, which is

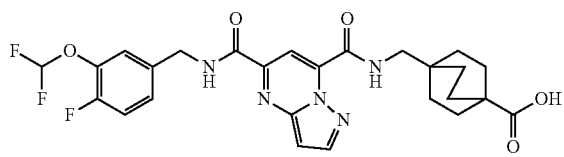 [SMILES: O=C(NCc1ccc(F)c(OC(F)F)c1)c1cc(C(=O)NCC23CCC(C(=O)O)(CC2)CC3)n2nccc2n1]

or a pharmaceutically acceptable salt thereof.

9. A pharmaceutical composition comprising:
a) an effective amount of a compound according to claim 1;
b) a pharmaceutically acceptable carrier; and
c) a member selected from the group consisting of: (a) a disease modifying antirheumatic drug; (b) a nonsteroidal anti-inflammatory drug; (c) a COX-2 selective inhibitor; (d) a COX-1 inhibitor; (e) an immunosuppressive; (f) a steroid; (g) a biological response modifier; and (h) a small molecule inhibitor of pro-inflammatory cytokine production.

10. A pharmaceutical composition according to claim 9 comprising at least one compound selected from the group consisting of:

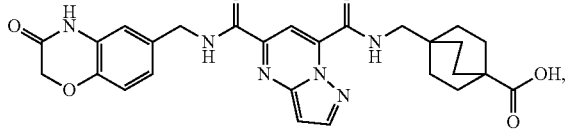

1613
-continued
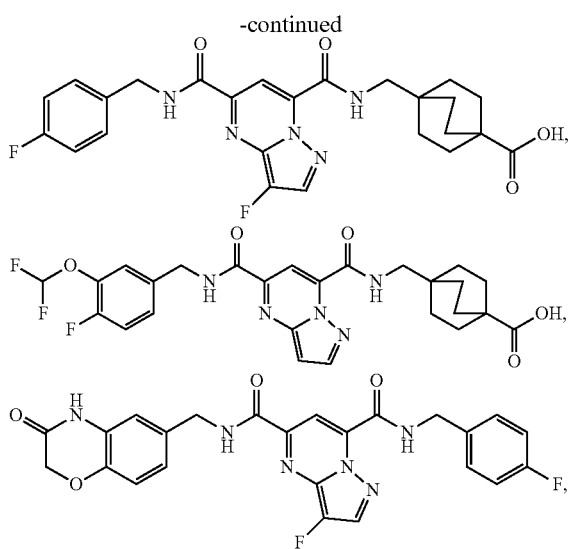
1614
-continued
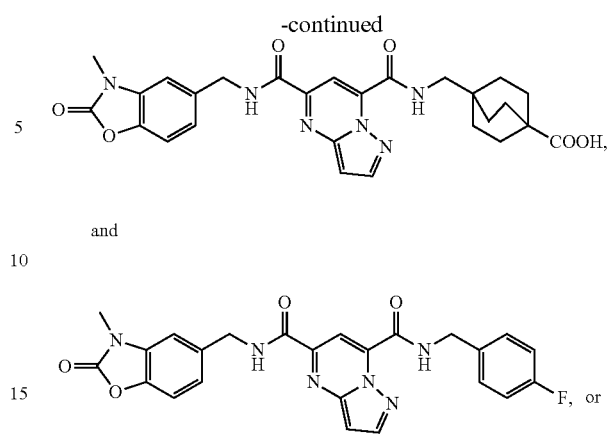
and
a pharmaceutically acceptable salt, racemic mixture or stereoisomer thereof, and a pharmaceutically acceptable carrier.
* * * * *